US009193723B2

(12) United States Patent
Clark et al.

(10) Patent No.: US 9,193,723 B2
(45) Date of Patent: Nov. 24, 2015

(54) NAMPT INHIBITORS

(71) Applicant: AbbVie Inc., North Chicago, IL (US)

(72) Inventors: Richard F. Clark, Gurnee, IL (US);
Bryan Sorensen, Antioch, IL (US);
Augustine T. Osuma, Lindenhurst, IL (US); Robin Frey, Liberyville, IL (US);
Kenton Longenecker, Grayslake, IL (US); George Doherty, Libertyville, IL (US); Michael L. Curtin, Pleasant Prairie, WI (US); Michael R. Michaelides, Libertyville, IL (US);
Ramzi F. Sweis, Lake Bluff, IL (US);
Marina A. Pliushchev, Vernon Hills, IL (US); Andy Judd, Grayslake, IL (US);
Todd M. Hansen, Grayslake, IL (US);
Howard R. Heyman, Deerfield, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/891,349

(22) Filed: May 10, 2013

(65) Prior Publication Data
US 2013/0303508 A1 Nov. 14, 2013

Related U.S. Application Data

(60) Provisional application No. 61/779,626, filed on Mar. 13, 2013, provisional application No. 61/718,998, filed on Oct. 26, 2012, provisional application No. 61/645,679, filed on May 11, 2012.

(51) Int. Cl.
*A61K 31/437* (2006.01)
*A61K 31/4985* (2006.01)
*A61K 45/06* (2006.01)
*A61K 31/5377* (2006.01)
*C07D 471/04* (2006.01)
*C07D 487/04* (2006.01)
*A61K 31/4545* (2006.01)
*A61K 31/4725* (2006.01)
*A61K 31/496* (2006.01)
*A61K 31/55* (2006.01)
*A61K 31/407* (2006.01)

(52) U.S. Cl.
CPC ............ *C07D 471/04* (2013.01); *A61K 31/407* (2013.01); *A61K 31/437* (2013.01); *A61K 31/4545* (2013.01); *A61K 31/4725* (2013.01); *A61K 31/496* (2013.01); *A61K 31/4985* (2013.01); *A61K 31/5377* (2013.01); *A61K 31/55* (2013.01); *A61K 45/06* (2013.01); *C07D 487/04* (2013.01)

(58) Field of Classification Search
USPC ..................... 546/121; 514/210.18
See application file for complete search history.

(56) References Cited

U.S. PATENT DOCUMENTS

| | | | |
|---|---|---|---|
| 7,504,412 B2 * | 3/2009 | Kishino et al. | 514/300 |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2008/0051409 A1 * | 2/2008 | Gmeiner et al. | 514/252.02 |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2013/0303511 A1 * | 11/2013 | Clark et al. | 514/210.18 |

FOREIGN PATENT DOCUMENTS

| | | | |
|---|---|---|---|
| EP | 1657242 A1 | 5/2006 | |
| WO | 9507271 A1 | 3/1995 | |
| WO | 9710223 A1 | 3/1997 | |
| WO | 9748397 A1 | 12/1997 | |
| WO | 9748696 A1 | 12/1997 | |
| WO | 03080054 A1 | 10/2003 | |
| WO | 2005085252 A1 | 9/2005 | |
| WO | 2005099353 A2 | 10/2005 | |
| WO | 2006008754 A1 | 1/2006 | |
| WO | 2008025857 A2 | 3/2008 | |
| WO | 2009109610 A1 | 9/2009 | |
| WO | 2012031197 A1 | 3/2012 | |
| WO | WO 2012031196 | * 3/2012 | |
| WO | WO 2012137089 | * 10/2012 | |

(Continued)

OTHER PUBLICATIONS

Gentile; Bioorganic and Medicinal Chemistry Letters 2012, 22, 1989-1994.*
Adya R., et al., "Nuclear Factor-kappaB Induction by Visfatin in Human Vascular Endothelial Cells: Its Role in MMP-2/9 Production and Activation," Diabetes Care, 2008, vol. 31 (4), pp. 758-760.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.

(Continued)

*Primary Examiner* — John Mabry
*Assistant Examiner* — Daniel Carcanague
(74) *Attorney, Agent, or Firm* — Glen J. Gesicki

(57) ABSTRACT

Disclosed are compounds which inhibit the activity of NAMPT, compositions containing the compounds and methods of treating diseases during which NAMPT is expressed.

18 Claims, No Drawings

(56) References Cited

FOREIGN PATENT DOCUMENTS

| WO | 2012154194 A1 | | 11/2012 |
|---|---|---|---|
| WO | WO 2013091011 | * | 6/2013 |
| WO | WO 2013130935 | * | 9/2013 |
| WO | WO 2013130943 | * | 9/2013 |

OTHER PUBLICATIONS

Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Bruzzone S., et al., "Catastrophic NAD+ Depletion in Activated T Lymphocytes through Nampt Inhibition Reduces Demyelination and Disability in EAE," PLoS One, 2009, vol. 4 (11), pp. e7897.
Busso N., et al., "Pharmacological Inhibition of Nicotinamide Phosphoribosyltransferase/visfatin Enzymatic Activity Identifies a New Inflammatory Pathway Linked to NAD," PLoS One, 2008, vol. 3 (5), pp. e2267.
Czajka, D. M. et al., "Effect of Deuterium Oxide on the Reproductive Potential of Mice," Annals of the New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Foster, A. B. et al., "Deuterium Isotope Effects in the Metabolism of Drugs and Xenobiotics: Implications for Drug Design," Advances in Drug Research, 1985, vol. 14, pp. 2-36.
Galli M., et al., "The Nicotinamide Phosphoribosyltransferase: A Molecular Link Between Metabolism, Inflammation, and Cancer," Cancer Research, 2010, vol. 70 (1), pp. 8-11.
Garten A., et al., "Nampt: Linking NAD Biology, Metabolism and Cancer," Trends in Endocrinology and Metabolism, 2009, vol. 20 (3), pp. 130-138.
Hansen C.M., et al., "Cyanoguanidine CHS 828 Induces Programmed Cell Death with Apoptotic Features in Human Breast Cancer Cells in Vitro," Anticancer Research, 2000, vol. 20 (6B), pp. 4211-4220.
Kato, S. et al., "Synthesis of Deuterated Mosapride Citrate," Journal of Labelled Compounds and Radiopharmaceuticals, 1995, vol. 36 (10), pp. 927-932.
Kim S.R., et al., "Visfatin Promotes Angiogenesis by Activation of Extracellular Signal-regulated Kinase 1/2," Biochemical and Biophysical Research Communications, 2007, vol. 357 (1), pp. 150-156.
Kushner, et al., "Pharmacological uses and perspectives of heavy water and deuterated compounds," Canadian Journal of Physiology and Pharmacology, 1999, vol. 77 (2), pp. 79-88.
Lizondo, J. et al., "Linezolid: Oxazolidinone antibacterial," Drugs of the Future, 1996, vol. 21 (11), pp. 1116-1123.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Olesen U.H., et al., "A Preclinical Study on the Rescue of Normal Tissue by Nicotinic Acid in High-dose Treatment with APO866, a Specific Nicotinamide Phosphoribosyltransferase Inhibitor," Molecular Cancer Therapeutics, 2010, vol. 9 (6), pp. 1609-1617.
Partial International Search Report for Application No. PCT/US2013/040476 mailed date Jul. 12, 2013, 3 pages.
Thomson, J.F., "Physiological Effects of D20 in Mammals," Annals of the New York Academy of Sciences, 1960, vol. 84, pp. 736-744.
Van Beijnum J.R., et al., "Target Validation for Genomics Using Peptide-specific Phage Antibodies: A Study of Five Gene Products Overexpressed in Colorectal Cancer," International Journal of Cancer, 2002, vol. 101 (2), pp. 118-127.
Ziegler M., "New Functions of a Long-known Molecule. Emerging Roles of NAD in Cellular Signaling," European Journal of Biochemistry, 2000, vol. 267 (6), pp. 1550-1564.
International Search Report for Application No. PCT/US2013/040476, mailed on Oct. 15, 2013, 5 pages.

* cited by examiner

NAMPT INHIBITORS

This application claims priority to U.S. Provisional Application Ser. No. 61/645,679, filed May 11, 2012, U.S. Provisional Application Ser. No. 61/718,998, filed Oct. 26, 2012, and U.S. Provisional Application Ser. No. 61/779,626, filed Mar. 13, 2013, which are incorporated by reference in their entirety.

FIELD OF THE INVENTION

This invention pertains to compounds which inhibit the activity of NAMPT, compositions containing the compounds, and methods of treating diseases during which NAMPT is expressed.

BACKGROUND OF THE INVENTION

NAD+ (nicotinamide adenine dinucleotide) is a coenzyme that plays a critical role in many physiologically essential processes (Ziegkel, M. Eur. J. Biochem. 267, 1550-1564, 2000). NAD is necessary for several signaling pathways including among others poly ADP-ribosylation in DNA repair, mono-ADP-ribosylation in both the immune system and G-protein-coupled signaling, and NAD is also required by sirtuins for their deacetylase activity (Garten, A. et al Trends in Endocrinology and Metabolism, 20, 130-138, 2008).

NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD.

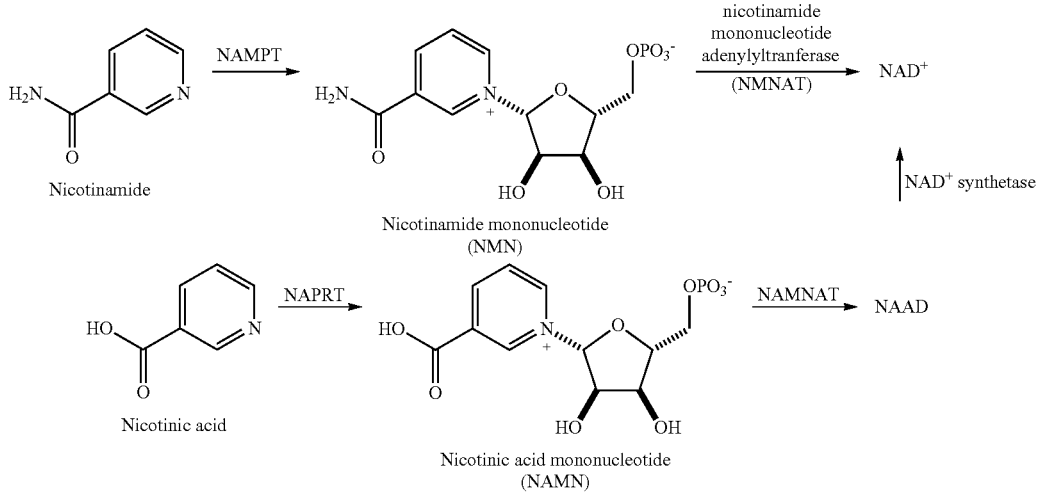

Increasing evidence suggests that NAMPT inhibitors have potential as anticancer agents. Cancer cells have a higher basal turnover of NAD and also display higher energy requirements compared with normal cells. Additionally, increased NAMPT expression has been reported in colorectal cancer (Van Beijnum, J. R. et al Int. J. Cancer 101, 118-127, 2002) and NAMPT is involved in angiogenesis (Kim, S. R. et al. Biochem. Biophys. Res. Commun. 357, 150-156, 2007). Small-molecule inhibitors of NAMPT have been shown to cause depletion of intracellular NAD+ levels and ultimately induce tumor cell death (Hansen, C M et al. Anticancer Res. 20, 42111-4220, 2000) as well as inhibit tumor growth in xenograft models (Olese, U. H. et al. Mol Cancer Ther. 9, 1609-1617, 2010).

NAMPT inhibitors also have potential as therapeutic agents in inflammatory and metabolic disorders (Galli, M. et al Cancer Res. 70, 8-11, 2010). For example, NAMPT is the predominant enzyme in T and B lymphocytes. Selective inhibition of NAMPT leads to NAD+ depletion in lymphocytes blocking the expansion that accompanies autoimmune disease progression whereas cell types expressing the other NAD+ generating pathways might be spared. A small molecule NAMPT inhibitor (FK866) has been shown to selectively block proliferation and induce apoptosis of activated T cells and was efficacious in animal models of arthritis (collagen-induced arthritis) (Busso, N. et al. Plos One 3, e2267, 2008). FK866 ameliorated the manifestations of experimental autoimmune encephalomyelitis (EAE), a model of T-cell mediated autoimmune disorders. (Bruzzone, S et al. Plos One 4, e7897, 2009). NaMPT activity increases NF-kB transcriptional activity in human vascular endothelial cell, resulting in MMP-2 and MMP-9 activation, suggesting a role for NAMPT inhibitors in the prevention of inflammatory mediated complications of obesity and type 2 diabetes (Adya, R. et. Al. Diabetes Care, 31, 758-760, 2008).

SUMMARY OF THE INVENTION

One embodiment, therefore, pertains to compounds or pharmaceutically acceptable salts thereof, which are useful as inhibitors of NAMPT, the compounds having Formula (IA)

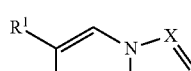

Formula (IA)

or a therapeutically acceptable salt thereof, wherein

X is N or $CY^1$;

$Y^1$ is independently selected from the group consisting of hydrogen, alkyl, alkoxy, haloalkyl, hydroxyalkyl, OH, CN, F, Cl, Br, and I;

$R^1$ is independently selected from the group consisting of $NHC(O)NHR^3$, $NHC(O)NH(CH_2)_mR^{3x}$, $CH_2NHC(O)NHR^3$, $NHC(O)R^3$, $NHC(O)(CH_2)_nR^3$, $C(O)NH(CH_2)_nR^3$, $NHC(O)(CH_2)_mR^{3x}$, $C(O)NH(CH_2)_mR^{3x}$, $CH_2C(O)NHR^3$, and $CH_2NHC(O)R^3$; and Z is CH, C—F, C—Cl, C—Br, C—I or N; or X is N or $CY^1$;

$Y^1$ is independently selected from the group consisting of hydrogen, alkyl, alkoxy, haloalkyl, hydroxyalkyl, OH, CN, F, Cl, Br, and I;

$R^1$ is hydrogen, F, Cl, Br, or I;

Z is $CR^2$; and $R^2$ is independently selected from the group consisting of $NHC(O)NHR^3$, $NHC(O)NH(CH_2)_mR^{3x}$, $CH_2NHC(O)NHR^3$, $NHC(O)R^3$, $NHC(O)(CH_2)_nR^3$, $C(O)NH(CH_2)_nR^3$, $NHC(O)(CH_2)_mR^{3x}$, $C(O)NH(CH_2)_mR^{3x}$, $CH_2C(O)NHR^3$, and $CH_2NHC(O)R^3$; and $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^{3x}$ is independently selected from the group consisting of phenyl and heterocyclyl; wherein each $R^{3x}$ phenyl and heterocyclyl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$ at each occurrence, is independently selected from the group consisting of aryl, heterocyclyl, cycloalkyl, cycloalkenyl, alkyl, alkenyl, and alkynyl; wherein each R$^{10}$ alkyl, alkenyl, and alkynyl is optionally substituted with one, two, three or four substituents independently selected from the group consisting of alkoxy, F, Cl, Br and I;

R$^{11}$ at each occurrence, is independently selected from the group consisting of aryl, heterocyclyl, cycloalkyl, cycloalkenyl, alkyl, alkenyl, and alkynyl;

m is 4, 5, or 6; and n is 1 or 2;

with the provisos that when X is CY$^1$ and Y$^1$ is hydrogen; and R$^3$ is thiazolyl; the R$^3$ thiazolyl is substituted with one substituent;

when X is CY$^1$ and Y$^1$ is hydrogen; R$^1$ is NHC(O)R$^3$; R$^2$ is hydrogen; and R$^3$ is phenyl; the R$^3$ phenyl is not substituted at the para position with phenyl;

when X is CY$^1$ and Y$^1$ is hydrogen; R$^1$ is C(O)NH(CH$_2$)$_n$R$^3$; n is 1; R$^2$ is hydrogen; and R$^3$ is phenyl; the R$^3$ phenyl is not substituted at the para position with phenylmethoxy or 3-fluorophenoxy;

when X is CY$^1$ and Y$^1$ is hydrogen; R$^1$ is C(O)NH(CH$_2$)$_n$R$^3$; n is 1; R$^2$ is hydrogen; and R$^3$ is furanyl; the R$^3$ furanyl is not substituted with benzyl, or 3-fluorophenyl methyl;

when X is CY$^1$ and Y$^1$ is hydrogen; R$^1$ is C(O)NH(CH$_2$)$_n$R$^3$; n is 1; R$^2$ is hydrogen; and R$^3$ is thienyl; the R$^3$ thienyl is not substituted with phenoxy, 3-fluorophenoxy, or 3-chlorophenoxy; and when X is CY$^1$ and Y$^1$ is hydrogen; R$^1$ is C(O)NH(CH$_2$)$_n$R$^3$; n is 1; R$^2$ is hydrogen; and R$^3$ is R$^3$ phenyl; the phenyl is not substituted at the para position with SO$_2$R$^4$ or SO$_2$NHR$^4$.

In another embodiment of Formula (IA), R$^1$ is NHC(O)NHR$^3$; and R$^2$ is hydrogen. In another embodiment of Formula (IA), R$^1$ is CH$_2$NHC(O)R$^3$; and R$^2$ is hydrogen. In another embodiment of Formula (IA), R$^1$ is hydrogen; and R$^2$ is CH$_2$NHC(O)NHR$^3$. In another embodiment of Formula (IA), R$^1$ is hydrogen; and R$^2$ is CH$_2$NHC(O)R$^3$. In one embodiment of Formula (IA), R$^3$ is phenyl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In one embodiment of Formula (IA), R$^1$ is NHC(O)NHR$^3$; R$^2$ is hydrogen; and R$^3$ is phenyl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In one embodiment of Formula (IA), R$^1$ is CH$_2$NHC(O)R$^3$; R$^2$ is hydrogen; and R$^3$ is phenyl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In one embodiment of Formula (IA), R$^1$ is hydrogen; R$^2$ is CH$_2$NHC(O)NHR$^3$; and R$^3$ is phenyl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In one embodiment of Formula (IA), R$^1$ is hydrogen; R$^2$ is CH$_2$NHC(O)R$^3$; and R$^3$ is phenyl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In another embodiment of Formula (IA), R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I. In another embodiment of Formula (IA), R$^1$ is NHC(O)NHR$^3$; R$^2$ is hydrogen; and R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I. In another embodiment of Formula (IA), R$^1$ is CH$_2$NHC(O)R$^3$; R$^2$ is hydrogen; and R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I. In another embodiment of Formula (IA), R$^1$ is hydrogen; R$^2$ is CH$_2$NHC(O)NHR$^3$; and R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I. In another embodiment of Formula (IA), R$^1$ is hydrogen; R$^2$ is CH$_2$NHC(O)R$^3$; and R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I.

Still another embodiment pertains to compounds, which are

4-[(imidazo[1,2-a]pyridin-6-ylcarbamoyl)amino]-N-(3-methylbutyl)benzamide;
4-[(imidazo[1,2-a]pyridin-7-ylcarbamoyl)amino]-N-(3-methylbutyl)benzamide;
2-cyclopentyl-N-{4-[(imidazo[1,2-a]pyridin-6-ylcarbamoyl)amino]phenyl}acetamide;
4-[(imidazo[1,2-a]pyridin-6-ylcarbamoyl)amino]-N-(2-phenylethyl)benzamide;
4-[(imidazo[1,2-a]pyridin-6-ylcarbamoyl)amino]-N-[2-(morpholin-4-yl)ethyl]benzamide;
N-(1-hydroxy-2-methylpropan-2-yl)-4-[(imidazo[1,2-a]pyridin-6-ylcarbamoyl)amino]benzamide;
N-benzyl-4-[(imidazo[1,2-a]pyridin-6-ylcarbamoyl)amino]benzamide;
N-(cyclopentylmethyl)-4-[(imidazo[1,2-a]pyridin-6-ylcarbamoyl)amino]benzamide;
4-[(imidazo[1,2-a]pyridin-6-ylcarbamoyl)amino]-N-[3-(piperidin-1-yl)propyl]benzamide;
4-[(imidazo[1,2-a]pyridin-6-ylcarbamoyl)amino]-N-(2-phenoxyethyl)benzamide;
4-[(imidazo[1,2-a]pyridin-6-ylcarbamoyl)amino]-N-[2-(pyrrolidin-1-yl)ethyl]benzamide;
4-[(imidazo[1,2-a]pyridin-6-ylcarbamoyl)amino]-N-[2-(propan-2-yloxy)ethyl]benzamide;
N-(2-hydroxy-2-methylpropyl)-4-[(imidazo[1,2-a]pyridin-6-ylcarbamoyl)amino]benzamide;
N-[2-hydroxy-1-(4-methoxyphenyl)ethyl]-4-[(imidazo[1,2-a]pyridin-6-ylcarbamoyl)amino]benzamide;
4-[(imidazo[1,2-a]pyridin-6-ylcarbamoyl)amino]-N-[2-(2-oxopyrrolidin-1-yl)ethyl]benzamide;
4-[(imidazo[1,2-a]pyridin-6-ylcarbamoyl)amino]-N-(tetrahydrofuran-2-ylmethyl)benzamide;
4-[(imidazo[1,2-a]pyridin-6-ylcarbamoyl)amino]-N-propylbenzamide;
4-[(imidazo[1,2-a]pyridin-6-ylcarbamoyl)amino]-N-[3-(morpholin-4-yl)propyl]benzamide;
4-[(imidazo[1,2-a]pyridin-6-ylcarbamoyl)amino]-N-phenylbenzamide;
4-[(imidazo[1,2-a]pyridin-6-ylcarbamoyl)amino]-N-(2-methylbutyl)benzamide;
4-[(imidazo[1,2-a]pyridin-6-ylcarbamoyl)amino]-N-[3-(2-oxopyrrolidin-1-yl)propyl]benzamide;
4-[(imidazo[1,2-a]pyridin-6-ylcarbamoyl)amino]-N-(tetrahydro-2H-pyran-4-ylmethyl)benzamide;
4-[(imidazo[1,2-a]pyridin-6-ylcarbamoyl)amino]-N-(tetrahydro-2H-pyran-2-ylmethyl)benzamide;
N-[(1,1-dioxidotetrahydrothiophen-3-yl)methyl]-4-[(imidazo[1,2-a]pyridin-6-ylcarbamoyl)amino]benzamide;
tert-butyl 4-{4-[(imidazo[1,2-a]pyridin-6-ylcarbamoyl)amino]phenyl}-3,6-dihydropyridine-1(2H)-carboxylate;
N-{4-[(imidazo[1,2-a]pyridin-6-ylcarbamoyl)amino]phenyl}-2-(tetrahydrofuran-3-yl)acetamide;
N-{4-[(imidazo[1,2-a]pyridin-6-ylcarbamoyl)amino]phenyl}acetamide;
1-imidazo[1,2-a]pyridin-6-yl-3-{4-[1-(tetrahydrofuran-3-ylacetyl)-1,2,3,6-tetrahydropyridin-4-yl]phenyl}urea;
1-{4-[1-(2-hydroxy-2-methylpropanoyl)-1,2,3,6-tetrahydropyridin-4-yl]phenyl}-3-imidazo[1,2-a]pyridin-6-ylurea;
1-imidazo[1,2-a]pyridin-6-yl-3-{4-[1-(morpholin-4-ylacetyl)-1,2,3,6-tetrahydropyridin-4-yl]phenyl}urea;
1-{4-[1-(ethoxyacetyl)-1,2,3,6-tetrahydropyridin-4-yl]phenyl}-3-imidazo[1,2-a]pyridin-6-ylurea;
1-imidazo[1,2-a]pyridin-6-yl-3-(4-{1-[(2-methoxyethoxy)acetyl]-1,2,3,6-tetrahydropyridin-4-yl}phenyl)urea;
1-imidazo[1,2-a]pyridin-6-yl-3-{4-[1-(tetrahydrofuran-2-ylcarbonyl)-1,2,3,6-tetrahydropyridin-4-yl]phenyl}urea;
1-imidazo[1,2-a]pyridin-6-yl-3-{4-[1-(tetrahydro-2H-pyran-4-ylcarbonyl)-1,2,3,6-tetrahydropyridin-4-yl]phenyl}urea;
1-{4-[1-(1,4-dioxan-2-ylcarbonyl)-1,2,3,6-tetrahydropyridin-4-yl]phenyl}-3-imidazo[1,2-a]pyridin-6-ylurea;
1-imidazo[1,2-a]pyridin-6-yl-3-(4-{1-[(1-methylpiperidin-4-yl)carbonyl]-1,2,3,6-tetrahydropyridin-4-yl}phenyl)urea;
1-(4-{1-[(1,1-dioxidotetrahydro-2H-thiopyran-4-yl)carbonyl]-1,2,3,6-tetrahydropyridin-4-yl}phenyl)-3-imidazo[1,2-a]pyridin-6-ylurea;
1-imidazo[1,2-a]pyridin-6-yl-3-{4-[1-(2-methylpropanoyl)-1,2,3,6-tetrahydropyridin-4-yl]phenyl}urea;
2-ethoxy-N-{4-[(imidazo[1,2-a]pyridin-6-ylcarbamoyl)amino]phenyl}acetamide;
N-{4-[(imidazo[1,2-a]pyridin-6-ylcarbamoyl)amino]phenyl}-2-(tetrahydro-2H-pyran-4-yl)acetamide;
N-{4-[(imidazo[1,2-a]pyridin-6-ylcarbamoyl)amino]phenyl}-2-(morpholin-4-yl)acetamide;
N-{4-[(imidazo[1,2-a]pyridin-6-ylcarbamoyl)amino]phenyl}-2-(2-methoxyethoxy)acetamide;
N-{4-[(imidazo[1,2-a]pyridin-6-ylcarbamoyl)amino]phenyl}-3-methoxy-2-methylpropanamide;
N-{4-[(imidazo[1,2-a]pyridin-6-ylcarbamoyl)amino]phenyl}butanamide;
4,4,4-trifluoro-N-{4-[(imidazo[1,2-a]pyridin-6-ylcarbamoyl)amino]phenyl}butanamide;
N-{4-[(imidazo[1,2-a]pyridin-6-ylcarbamoyl)amino]phenyl}tetrahydro-2H-pyran-4-carboxamide;
N-{4-[(imidazo[1,2-a]pyridin-6-ylcarbamoyl)amino]phenyl}-4-methylpentanamide;
N-{4-[(imidazo[1,2-a]pyridin-6-ylcarbamoyl)amino]phenyl}-1-methylpiperidine-4-carboxamide;
N-{4-[(imidazo[1,2-a]pyridin-6-ylcarbamoyl)amino]phenyl}tetrahydro-2H-thiopyran-4-carboxamide 1,1-dioxide;
N-{4-[(imidazo[1,2-a]pyridin-6-ylcarbamoyl)amino]phenyl}-1,4-dioxane-2-carboxamide;
1-imidazo[1,2-a]pyridin-6-yl-3-{4-[1-(2-methylpropyl)-1H-pyrazol-4-yl]phenyl}urea;
4-[(cyclopentylacetyl)amino]-N-(imidazo[1,2-a]pyridin-6-ylmethyl)benzamide;
2-[(4-cyanobenzyl)(3-methylbutanoyl)amino]-N-(imidazo[1,2-a]pyridin-6-yl)-1,3-thiazole-5-carboxamide;
2-[(4-cyanobenzyl)(3-methoxypropanoyl)amino]-N-(imidazo[1,2-a]pyridin-6-yl)-1,3-thiazole-5-carboxamide;
2-[(4-cyanobenzyl)(3-methylbutanoyl)amino]-N-(imidazo[1,2-a]pyridin-6-ylmethyl)-1,3-thiazole-5-carboxamide;
2-[(4-cyanobenzyl)(3-methoxypropanoyl)amino]-N-(imidazo[1,2-a]pyridin-6-ylmethyl)-1,3-thiazole-5-carboxamide;
2-[(4-cyanobenzyl)(3-methoxypropanoyl)amino]-N-(imidazo[1,2-a]pyridin-7-ylmethyl)-1,3-thiazole-5-carboxamide;
tert-butyl 4-{4-[(imidazo[1,2-a]pyridin-6-ylcarbamoyl)amino]butyl}piperidine-1-carboxylate;
4-{[(imidazo[1,2-a]pyridin-6-ylmethyl)carbamoyl]amino}-N-(3-methylbutyl)benzamide;
2-cyclopentyl-N-(4-{[(imidazo[1,2-a]pyridin-6-ylmethyl)carbamoyl]amino}phenyl)acetamide;
N-(imidazo[1,2-a]pyridin-6-ylmethyl)-2-[(3-methoxypropanoyl)(3-methylbutyl)amino]-1,3-thiazole-5-carboxamide;
1-imidazo[1,2-a]pyridin-6-yl-3-(4-{1-[(propan-2-yloxy)acetyl]piperidin-4-yl}butyl)urea;
1-{4-[1-(1,4-dioxan-2-ylcarbonyl)piperidin-4-yl]butyl}-3-imidazo[1,2-a]pyridin-6-ylurea;

1-{4-[1-(cyclopropylacetyl)piperidin-4-yl]butyl}-3-imidazo[1,2-a]pyridin-6-ylurea;
1-imidazo[1,2-a]pyridin-6-yl-3-{4-[1-(4,4-trifluorobutanoyl)piperidin-4-yl]butyl}urea;
1-imidazo[1,2-a]pyridin-6-yl-3-{4-[1-(tetrahydro-2H-pyran-4-ylacetyl)piperidin-4-yl]butyl}urea;
1-imidazo[1,2-a]pyridin-6-yl-3-{4-[1-(tetrahydrofuran-2-ylacetyl)piperidin-4-yl]butyl}urea;
1-{4-[1-(cyclopentylcarbonyl)piperidin-4-yl]butyl}-3-imidazo[1,2-a]pyridin-6-ylurea;
1-imidazo[1,2-a]pyridin-6-yl-3-{4-[1-(tetrahydro-2H-pyran-4-ylcarbonyl)piperidin-4-yl]butyl}urea;
1-imidazo[1,2-a]pyridin-6-yl-3-(4-{1-[(2-methoxyethoxy)acetyl]piperidin-4-yl}butyl)urea;
1-imidazo[1,2-a]pyridin-6-yl-3-{4-[1-(morpholin-4-ylacetyl)piperidin-4-yl]butyl}urea;
1-imidazo[1,2-a]pyridin-6-yl-3-{4-[1-(tetrahydrofuran-3-ylcarbonyl)piperidin-4-yl]butyl}urea;
1-imidazo[1,2-a]pyridin-6-yl-3-{4-[1-(tetrahydrofuran-3-ylacetyl)piperidin-4-yl]butyl}urea;
1-imidazo[1,2-a]pyridin-6-yl-3-{4-[1-(tetrahydrofuran-2-ylcarbonyl)piperidin-4-yl]butyl}urea;
N-(imidazo[1,2-a]pyridin-6-ylmethyl)-5-[1-(2-methylpropyl)-1H-pyrazol-4-yl]thiophene-2-carboxamide;
2-cyclopentyl-N-{4-[2-(imidazo[1,2-a]pyridin-6-ylamino)-2-oxoethyl]phenyl}acetamide;
N-(imidazo[1,2-a]pyridin-6-ylmethyl)-4-[(tetrahydrofuran-2-ylacetyl)amino]benzamide;
N-(imidazo[1,2-a]pyridin-6-ylmethyl)-4-[(tetrahydrofuran-3-ylacetyl)amino]benzamide;
N-(imidazo[1,2-a]pyridin-6-ylmethyl)-4-[(tetrahydro-2H-pyran-4-ylacetyl)amino]benzamide;
N-(imidazo[1,2-a]pyridin-6-ylmethyl)-4-[(morpholin-4-ylacetyl)amino]benzamide;
4-[(3-cyclopentylpropanoyl)amino]-N-(imidazo[1,2-a]pyridin-6-ylmethyl)benzamide;
N-(imidazo[1,2-a]pyridin-6-ylmethyl)-4-{[(propan-2-yloxy)acetyl]amino}benzamide;
tert-butyl 4-{4-[(imidazo[1,2-a]pyridin-6-ylmethyl)carbamoyl]phenyl}-3,6-dihydropyridine-1(2H)-carboxylate;
N-{4-[(cyclopentylacetyl)amino]benzyl}imidazo[1,2-a]pyridine-6-carboxamide;
N-(imidazo[1,2-a]pyridin-6-ylmethyl)-2-(1,2,4,5-tetrahydro-3H-3-benzazepin-3-yl)-1,3-thiazole-5-carboxamide;
N-(imidazo[1,2-a]pyridin-6-ylmethyl)-2-(3-phenylpyrrolidin-1-yl)-1,3-thiazole-5-carboxamide;
N-(imidazo[1,2-a]pyridin-6-ylmethyl)-2-[(3-methylbutyl)amino]-1,3-thiazole-5-carboxamide;
2-(1,3-dihydro-2H-isoindol-2-yl)-N-(imidazo[1,2-a]pyridin-6-ylmethyl)-1,3-thiazole-5-carboxamide;
tert-butyl 4-{4-[(imidazo[1,2-a]pyridin-6-ylcarbamoyl)amino]phenyl}piperidine-1-carboxylate;
N-(imidazo[1,2-a]pyridin-6-ylmethyl)-4-[1-(2-methylpropanoyl)-1,2,3,6-tetrahydropyridin-4-yl]benzamide;
4-[1-(2-hydroxy-2-methylpropanoyl)-1,2,3,6-tetrahydropyridin-4-yl]-N-(imidazo[1,2-a]pyridin-6-ylmethyl)benzamide;
N-(imidazo[1,2-a]pyridin-6-ylmethyl)-4-[1-(morpholin-4-ylacetyl)-1,2,3,6-tetrahydropyridin-4-yl]benzamide;
N-(imidazo[1,2-a]pyridin-6-ylmethyl)-4-[1-(tetrahydro-2H-pyran-4-ylacetyl)-1,2,3,6-tetrahydropyridin-4-yl]benzamide;
N-(imidazo[1,2-a]pyridin-6-ylmethyl)-4-[1-(tetrahydrofuran-3-ylacetyl)-1,2,3,6-tetrahydropyridin-4-yl]benzamide;
N-(imidazo[1,2-a]pyridin-6-ylmethyl)-4-[1-(tetrahydrofuran-2-ylacetyl)-1,2,3,6-tetrahydropyridin-4-yl]benzamide;
N-(imidazo[1,2-a]pyridin-6-ylmethyl)-4-{1-[3-(tetrahydrofuran-2-yl)propanoyl]-1,2,3,6-tetrahydropyridin-4-yl}benzamide;
4-[1-(cyclopentylacetyl)-1,2,3,6-tetrahydropyridin-4-yl]-N-(imidazo[1,2-a]pyridin-6-ylmethyl)benzamide;
N-(imidazo[1,2-a]pyridin-6-ylmethyl)-4-{1-[(propan-2-yloxy)acetyl]-1,2,3,6-tetrahydropyridin-4-yl}benzamide;
N-(imidazo[1,2-a]pyridin-6-ylmethyl)-4-[1-(tetrahydrofuran-2-ylcarbonyl)-1,2,3,6-tetrahydropyridin-4-yl]benzamide;
N-(imidazo[1,2-a]pyridin-6-ylmethyl)-4-[1-(tetrahydrofuran-3-ylcarbonyl)-1,2,3,6-tetrahydropyridin-4-yl]benzamide;
N-(imidazo[1,2-a]pyridin-6-ylmethyl)-4-[1-(tetrahydro-2H-pyran-4-ylcarbonyl)-1,2,3,6-tetrahydropyridin-4-yl]benzamide;
4-[1-(1,4-dioxan-2-ylcarbonyl)-1,2,3,6-tetrahydropyridin-4-yl]-N-(imidazo[1,2-a]pyridin-6-ylmethyl)benzamide;
N-(imidazo[1,2-a]pyridin-6-ylmethyl)-4-{1-[(2-methoxyethoxy)acetyl]-1,2,3,6-tetrahydropyridin-4-yl}benzamide;
4-(1-benzoyl-1,2,3,6-tetrahydropyridin-4-yl)-N-(imidazo[1,2-a]pyridin-6-ylmethyl)benzamide;
4-{1-[(4,4-difluorocyclohexyl)carbonyl]-1,2,3,6-tetrahydropyridin-4-yl}-N-(imidazo[1,2-a]pyridin-6-ylmethyl)benzamide;
1-imidazo[1,2-a]pyridin-6-yl-3-{4-[1-(2-methylpropanoyl)piperidin-4-yl]phenyl}urea;
1-[4-(1-benzoylpiperidin-4-yl)butyl]-3-imidazo[1,2-a]pyridin-6-ylurea;
2-(3,4-dihydroisoquinolin-2(1H)-yl)-N-(imidazo[1,2-a]pyridin-6-ylmethyl)-1,3-thiazole-5-carboxamide;
1-imidazo[1,2-a]pyridin-6-yl-3-{4-[1-(tetrahydro-2H-pyran-4-ylcarbonyl)piperidin-4-yl]phenyl}urea;
1-imidazo[1,2-a]pyridin-6-yl-3-{4-[1-(tetrahydrofuran-3-ylacetyl)piperidin-4-yl]phenyl}urea;
1-imidazo[1,2-a]pyridin-6-yl-3-{4-[1-(tetrahydrofuran-2-ylacetyl)piperidin-4-yl]phenyl}urea;
1-[4-(1-benzoylpiperidin-4-yl)phenyl]-3-imidazo[1,2-a]pyridin-6-ylurea;
1-imidazo[1,2-a]pyridin-6-yl-3-{4-[1-(tetrahydrofuran-2-ylcarbonyl)piperidin-4-yl]phenyl}urea;
tert-butyl 4-{4-[(imidazo[1,2-a]pyridin-6-ylmethyl)carbamoyl]phenoxy}piperidine-1-carboxylate;
N-(imidazo[1,2-a]pyridin-6-ylmethyl)-2-[{[2-(propan-2-yloxy)ethyl]carbamoyl}(tetrahydrofuran-2-ylmethyl)amino]-1,3-thiazole-5-carboxamide;
N-(imidazo[1,2-a]pyridin-6-ylmethyl)-2-[2-oxo-4-(tetrahydrofuran-3-yl)-1,3-oxazolidin-3-yl]-1,3-thiazole-5-carboxamide;
4-[(cyclopentylacetyl)amino]-N-(imidazo[1,2-a]pyridin-7-ylmethyl)benzamide;
2-cyclopentyl-N-(4-{[(imidazo[1,2-a]pyridin-7-ylmethyl)carbamoyl]amino}phenyl)acetamide;
N-(imidazo[1,2-a]pyridin-6-ylmethyl)-4-[1-(2-methylpropyl)-1H-pyrazol-4-yl]benzamide;
N-(imidazo[1,2-a]pyridin-6-ylmethyl)-5-[1-(2-methylpropyl)-1H-pyrazol-4-yl]furan-2-carboxamide;
N-(imidazo[1,2-a]pyridin-7-ylmethyl)-2-[3-methoxypropanoyl)(tetrahydrofuran-2-ylmethyl)amino]-1,3-thiazole-5-carboxamide;
N-(imidazo[1,2-a]pyridin-6-ylmethyl)-2-(2-oxo-5-phenyl-1,3-oxazolidin-3-yl)-1,3-thiazole-5-carboxamide;

N-(imidazo[1,2-a]pyridin-6-ylmethyl)-2-{[(2-methyl-1,3-thiazol-5-yl)acetyl](tetrahydrofuran-2-ylmethyl)amino}-1,3-thiazole-5-carboxamide;

N-(imidazo[1,2-a]pyridin-6-ylmethyl)-2-{[(2-methyl-1,3-thiazol-4-yl)acetyl](tetrahydrofuran-2-ylmethyl)amino}-1,3-thiazole-5-carboxamide;

N-(imidazo[1,2-a]pyridin-6-ylmethyl)-2-{[(3-methyl-1,2-oxazol-5-yl)acetyl](tetrahydrofuran-2-ylmethyl)amino}-1,3-thiazole-5-carboxamide;

2-{[3-(3-chloro-1,2-oxazol-5-yl)propanoyl](tetrahydrofuran-2-ylmethyl)amino}-N-(imidazo[1,2-a]pyridin-6-ylmethyl)-1,3-thiazole-5-carboxamide;

N-(imidazo[1,2-a]pyridin-6-ylmethyl)-2-{[3-(3-methoxy-1,2-oxazol-5-yl)propanoyl](tetrahydrofuran-2-ylmethyl)amino}-1,3-thiazole-5-carboxamide;

2-{[(3,5-dimethyl-1,2-oxazol-4-yl)acetyl](tetrahydrofuran-2-ylmethyl)amino}-N-(imidazo[1,2-a]pyridin-6-ylmethyl)-1,3-thiazole-5-carboxamide;

2-{[3-(3,5-dimethyl-1,2-oxazol-4-yl)propanoyl](tetrahydrofuran-2-ylmethyl)amino}-N-(imidazo[1,2-a]pyridin-6-ylmethyl)-1,3-thiazole-5-carboxamide;

N-(imidazo[1,2-a]pyridin-6-ylmethyl)-2-{[3-(1-methyl-1H-pyrazol-4-yl)propanoyl](tetrahydrofuran-2-ylmethyl)amino}-1,3-thiazole-5-carboxamide;

N-(imidazo[1,2-a]pyridin-6-ylmethyl)-2-{[3-(4-methyl-1,3-thiazol-5-yl)propanoyl](tetrahydrofuran-2-ylmethyl)amino}-1,3-thiazole-5-carboxamide;

N-(imidazo[1,2-a]pyridin-6-ylmethyl)-2-[(tetrahydrofuran-2-ylmethyl)(1H-tetrazol-5-ylacetyl)amino]-1,3-thiazole-5-carboxamide;

N-(imidazo[1,2-a]pyridin-6-ylmethyl)-2-{[3-(1,2-oxazol-5-yl)propanoyl](tetrahydrofuran-2-ylmethyl)amino}-1,3-thiazole-5-carboxamide;

N-(imidazo[1,2-a]pyridin-6-ylmethyl)-2-[(1,2-oxazol-3-ylacetyl)(tetrahydrofuran-2-ylmethyl)amino]-1,3-thiazole-5-carboxamide;

N-(imidazo[1,2-a]pyridin-6-ylmethyl)-2-{[3-(1,2-oxazol-4-yl)propanoyl](tetrahydrofuran-2-ylmethyl)amino}-1,3-thiazole-5-carboxamide;

N-(imidazo[1,2-a]pyridin-6-ylmethyl)-2-{(tetrahydrofuran-2-ylmethyl)[3-(1,3-thiazol-2-yl)propanoyl]amino}-1,3-thiazole-5-carboxamide;

N-(imidazo[1,2-a]pyridin-6-ylmethyl)-2-[3-methylbutanoyl)amino]-1,3-thiazole-5-carboxamide;

N-(imidazo[1,2-a]pyridin-7-ylmethyl)-2-{[(2-methoxyethyl)carbamoyl](tetrahydrofuran-2-ylmethyl)amino}-1,3-thiazole-5-carboxamide;

N-(imidazo[1,2-a]pyridin-6-ylmethyl)-2-[3-methoxypropanoyl)(tetrahydrofuran-3-ylmethyl)amino]-1,3-thiazole-5-carboxamide;

N-(imidazo[1,2-a]pyridin-6-ylmethyl)-2-[(tetrahydrofuran-3-ylmethyl)(tetrahydro-2H-pyran-4-ylcarbonyl)amino]-1,3-thiazole-5-carboxamide;

N-(imidazo[1,2-a]pyridin-6-ylmethyl)-2-{[(2-methoxyethyl)carbamoyl](tetrahydrofuran-3-ylmethyl)amino}-1,3-thiazole-5-carboxamide;

N-(imidazo[1,2-a]pyridin-6-ylmethyl)-2-[(3-methoxypropanoyl)(tetrahydro-2H-pyran-4-ylmethyl)amino]-1,3-thiazole-5-carboxamide;

N-(imidazo[1,2-a]pyridin-6-ylmethyl)-2-[(tetrahydrofuran-3-ylcarbonyl)(tetrahydro-2H-pyran-4-ylmethyl)amino]-1,3-thiazole-5-carboxamide;

N-(imidazo[1,2-a]pyridin-6-ylmethyl)-2-[(tetrahydro-2H-pyran-4-ylcarbonyl)(tetrahydro-2H-pyran-4-ylmethyl)amino]-1,3-thiazole-5-carboxamide;

N-(imidazo[1,2-a]pyridin-6-ylmethyl)-2-{(3-methoxypropanoyl)[(2R)-tetrahydrofuran-2-ylmethyl]amino}-1,3-thiazole-5-carboxamide;

N-(imidazo[1,2-a]pyridin-6-ylmethyl)-2-{(tetrahydrofuran-3-ylcarbonyl)[(2R)-tetrahydrofuran-2-ylmethyl]amino}-1,3-thiazole-5-carboxamide;

N-(imidazo[1,2-a]pyridin-6-ylmethyl)-2-{[(2R)-tetrahydrofuran-2-ylmethyl](tetrahydro-2H-pyran-4-ylcarbonyl)amino}-1,3-thiazole-5-carboxamide;

N-(imidazo[1,2-a]pyridin-6-ylmethyl)-2-{(3-methoxypropanoyl)[(2S)-tetrahydrofuran-2-ylmethyl]amino}-1,3-thiazole-5-carboxamide;

N-(imidazo[1,2-a]pyridin-6-ylmethyl)-2-{(tetrahydrofuran-3-ylcarbonyl)[(2S)-tetrahydrofuran-2-ylmethyl]amino}-1,3-thiazole-5-carboxamide;

N-(imidazo[1,2-a]pyridin-6-ylmethyl)-2-{[(2S)-tetrahydrofuran-2-ylmethyl](tetrahydro-2H-pyran-4-ylcarbonyl)amino}-1,3-thiazole-5-carboxamide;

N-(imidazo[1,2-a]pyridin-6-ylmethyl)-2-{[(2-methoxyethyl)carbamoyl](tetrahydro-2H-pyran-4-ylmethyl)amino}-1,3-thiazole-5-carboxamide;

N-(imidazo[1,2-a]pyridin-6-ylmethyl)-2-[{[2-(propan-2-yloxy)ethyl]carbamoyl}(tetrahydro-2H-pyran-4-ylmethyl)amino]-1,3-thiazole-5-carboxamide;

N-(imidazo[1,2-a]pyridin-6-ylmethyl)-2-{[(2-methoxyethyl)carbamoyl][(2R)-tetrahydrofuran-2-ylmethyl]amino}-1,3-thiazole-5-carboxamide;

N-(imidazo[1,2-a]pyridin-6-ylmethyl)-2-({[2-(propan-2-yloxy)ethyl]carbamoyl}[(2R)-tetrahydrofuran-2-ylmethyl]amino)-1,3-thiazole-5-carboxamide;

N-(imidazo[1,2-a]pyridin-6-ylmethyl)-2-{[(2-methoxyethyl)carbamoyl][(2S)-tetrahydrofuran-2-ylmethyl]amino}-1,3-thiazole-5-carboxamide;

N-(imidazo[1,2-a]pyridin-6-ylmethyl)-2-({[2-(propan-2-yloxy)ethyl]carbamoyl}[(2S)-tetrahydrofuran-2-ylmethyl]amino)-1,3-thiazole-5-carboxamide;

N-(imidazo[1,2-a]pyridin-6-ylmethyl)-2-[{[2-(propan-2-yloxy)ethyl]carbamoyl}(tetrahydrofuran-3-ylmethyl)amino]-1,3-thiazole-5-carboxamide;

2-[5-(4-chlorophenyl)-2-oxo-1,3-oxazolidin-3-yl]-N-(imidazo[1,2-a]pyridin-6-ylmethyl)-1,3-thiazole-5-carboxamide;

N-(imidazo[1,2-a]pyridin-6-ylmethyl)-4-{[1-(2-methylpropanoyl)piperidin-4-yl]oxy}benzamide;

4-[(1-acetylpiperidin-4-yl)oxy]-N-(imidazo[1,2-a]pyridin-6-ylmethyl)benzamide;

4-{[1-(cyclopropylcarbonyl)piperidin-4-yl]oxy}-N-(imidazo[1,2-a]pyridin-6-ylmethyl)benzamide;

N-(imidazo[1,2-a]pyridin-6-ylmethyl)-4-{[1-(tetrahydro-2H-pyran-4-ylcarbonyl)piperidin-4-yl]oxy}benzamide;

4-{[1-(1,4-dioxan-2-ylcarbonyl)piperidin-4-yl]oxy}-N-(imidazo[1,2-a]pyridin-6-ylmethyl)benzamide;

N-(imidazo[1,2-a]pyridin-6-ylmethyl)-4-({1-[(2S)-tetrahydrofuran-2-ylcarbonyl]piperidin-4-yl}oxy)benzamide;

N-(imidazo[1,2-a]pyridin-6-ylmethyl)-4-({1-[(2R)-tetrahydrofuran-2-ylcarbonyl]piperidin-4-yl}oxy)benzamide;

4-{[1-(2-hydroxy-2-methylpropanoyl)piperidin-4-yl]oxy}-N-(imidazo[1,2-a]pyridin-6-ylmethyl)benzamide;

N-(imidazo[1,2-a]pyridin-6-ylmethyl)-4-({1-[(propan-2-yloxy)acetyl]piperidin-4-yl}oxy)benzamide;

4-[(1-butanoylpiperidin-4-yl)oxy]-N-(imidazo[1,2-a]pyridin-6-ylmethyl)benzamide;

N-(imidazo[1,2-a]pyridin-6-ylmethyl)-4-{[1-(3-methoxy-2-methylpropanoyl)piperidin-4-yl]oxy}benzamide;

N-(imidazo[1,2-a]pyridin-6-ylmethyl)-4-{[1-(3,3,3-trifluoropropanoyl)piperidin-4-yl]oxy}benzamide;

N-(imidazo[1,2-a]pyridin-6-ylmethyl)-4-{[1-(tetrahydro-2H-pyran-4-ylacetyl)piperidin-4-yl]oxy}benzamide;
4-{[1-(cyclopropylacetyl)piperidin-4-yl]oxy}-N-(imidazo[1,2-a]pyridin-6-ylmethyl)benzamide;
N-(imidazo[1,2-a]pyridin-6-ylmethyl)-4-{[1-(tetrahydrofuran-2-ylacetyl)piperidin-4-yl]oxy}benzamide;
N-(imidazo[1,2-a]pyridin-7-ylmethyl)-5-[1-(2-methylpropyl)-1H-pyrazol-4-yl]thiophene-2-carboxamide;
N-(imidazo[1,2-a]pyridin-6-ylmethyl)-5-[1-(2-methylpropanoyl)-1H-pyrazol-4-yl]thiophene-2-carboxamide;
5-[1-(2-hydroxy-2-methylpropyl)-1H-pyrazol-4-yl]-N-(imidazo[1,2-a]pyridin-6-ylmethyl)thiophene-2-carboxamide;
N-(imidazo[1,2-a]pyridin-6-ylmethyl)-5-{1-[(3-methyloxetan-3-yl)methyl]-1H-pyrazol-4-yl}thiophene-2-carboxamide;
5-[1-(cyclobutylmethyl)-1H-pyrazol-4-yl]-N-(imidazo[1,2-a]pyridin-6-ylmethyl)thiophene-2-carboxamide;
5-[1-(cyclohexylmethyl)-1H-pyrazol-4-yl]-N-(imidazo[1,2-a]pyridin-6-ylmethyl)thiophene-2-carboxamide;
5-{1-[(2R)-2-hydroxybutyl]-1H-pyrazol-4-yl}-N-(imidazo[1,2-a]pyridin-6-ylmethyl)thiophene-2-carboxamide;
N-(imidazo[1,2-a]pyridin-7-ylmethyl)-2-[(4R)-2-oxo-4-(propan-2-yl)-1,3-oxazolidin-3-yl]-1,3-thiazole-5-carboxamide;
5-[1-(2-hydroxy-2-methylpropyl)-1H-pyrazol-4-yl]-N-(imidazo[1,2-a]pyridin-7-ylmethyl)thiophene-2-carboxamide;
N-(imidazo[1,2-a]pyridin-6-ylmethyl)-2-{[(1-methyl-1H-pyrazol-4-yl)acetyl](tetrahydrofuran-2-ylmethyl)amino}-1,3-thiazole-5-carboxamide;
2-{[(1,3-dimethyl-1H-pyrazol-4-yl)acetyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-7-ylmethyl)-2-[(4S)-2-oxo-4-(propan-2-yl)-1,3-oxazolidin-3-yl]-1,3-thiazole-5-carboxamide;
N-(imidazo[1,2-a]pyridin-6-ylmethyl)-5-[1-(tetrahydro-2H-pyran-2-ylmethyl)-1H-pyrazol-4-yl]thiophene-2-carboxamide;
2-{(4R)-4-[(benzyloxy)methyl]-2-oxo-1,3-oxazolidin-3-yl}-N-(imidazo[1,2-a]pyridin-7-ylmethyl)-1,3-thiazole-5-carboxamide;
2-{(4S)-4-[(benzyloxy)methyl]-2-oxo-1,3-oxazolidin-3-yl}-N-(imidazo[1,2-a]pyridin-7-ylmethyl)-1,3-thiazole-5-carboxamide;
N-(imidazo[1,2-a]pyridin-6-ylmethyl)-2-{3-(1-methyl-1H-pyrrol-2-yl)propanoyl](tetrahydrofuran-2-ylmethyl)amino}-1,3-thiazole-5-carboxamide;
2-{[(1,5-dimethyl-1H-pyrazol-3-yl)acetyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-[(tetrahydrofuran-2-ylmethyl)(1,3-thiazol-4-ylacetyl)amino]-1,3-thiazole-5-carboxamide;
N-(imidazo[1,2-a]pyridin-7-ylmethyl)-2-{(1,2-oxazol-3-ylacetyl)[(2R)-tetrahydrofuran-2-ylmethyl]amino}-1,3-thiazole-5-carboxamide;
N-(imidazo[1,2-a]pyridin-7-ylmethyl)-2-{[(5-methyl-1,2-oxazol-3-yl)acetyl][(2R)-tetrahydrofuran-2-ylmethyl]amino}-1,3-thiazole-5-carboxamide;
N-(imidazo[1,2-a]pyridin-7-ylmethyl)-2-{[3-(1,2-oxazol-5-yl)propanoyl][(2R)-tetrahydrofuran-2-ylmethyl]amino}-1,3-thiazole-5-carboxamide;
N-(imidazo[1,2-a]pyridin-7-ylmethyl)-2-{[3-(1,2-oxazol-4-yl)propanoyl][(2R)-tetrahydrofuran-2-ylmethyl]amino}-1,3-thiazole-5-carboxamide;
N-(imidazo[1,2-a]pyridin-7-ylmethyl)-2-{[(2R)-tetrahydrofuran-2-ylmethyl](1,3-thiazol-4-ylacetyl)amino}-1,3-thiazole-5-carboxamide;
2-{[(1,5-dimethyl-1H-pyrazol-3-yl)acetyl][(2R)-tetrahydrofuran-2-ylmethyl]amino}-N-(imidazo[1,2-a]pyridin-7-ylmethyl)-1,3-thiazole-5-carboxamide;
N-(imidazo[1,2-a]pyridin-7-ylmethyl)-2-{[3-(1-methyl-1H-pyrazol-4-yl)propanoyl][(2R)-tetrahydrofuran-2-ylmethyl]amino}-1,3-thiazole-5-carboxamide;
2-{[(3,5-dimethyl-1,2-oxazol-4-yl)acetyl][(2R)-tetrahydrofuran-2-ylmethyl]amino}-N-(imidazo[1,2-a]pyridin-7-ylmethyl)-1,3-thiazole-5-carboxamide;
N-(imidazo[1,2-a]pyridin-6-ylmethyl)-5-[1-(tetrahydrofuran-3-ylmethyl)-1H-pyrazol-4-yl]thiophene-2-carboxamide;
N-(imidazo[1,2-a]pyridin-6-ylmethyl)-5-[1-(tetrahydro-2H-pyran-4-ylmethyl)-1H-pyrazol-4-yl]thiophene-2-carboxamide;
N-(imidazo[1,2-a]pyridin-7-ylmethyl)-2-{[(1-methyl-1H-pyrazol-4-yl)acetyl][(2R)-tetrahydrofuran-2-ylmethyl]amino}-1,3-thiazole-5-carboxamide;
N-(imidazo[1,2-a]pyridin-7-ylmethyl)-2-{[3-(1-methyl-1H-pyrrol-2-yl)propanoyl][(2R)-tetrahydrofuran-2-ylmethyl]amino}-1,3-thiazole-5-carboxamide;
2-[1-(2-hydroxy-2-methylpropyl)-1H-pyrazol-4-yl]-N-(imidazo[1,2-a]pyridin-7-ylmethyl)-1,3-thiazole-5-carboxamide;
N-(imidazo[1,2-a]pyridin-7-ylmethyl)-2-[1-(2-methylpropyl)-1H-pyrazol-4-yl]-1,3-thiazole-5-carboxamide;
N-(imidazo[1,2-a]pyridin-6-ylmethyl)-5-[1-(tetrahydro-2H-pyran-3-ylmethyl)-1H-pyrazol-4-yl]thiophene-2-carboxamide;
tert-butyl {4-[(imidazo[1,2-a]pyridin-7-ylmethyl)carbamoyl]phenyl}carbamate;
N-(imidazo[1,2-a]pyridin-7-ylmethyl)-4-[(tetrahydro-2H-pyran-4-ylacetyl)amino]benzamide;
N-(imidazo[1,2-a]pyridin-7-ylmethyl)-4-[(tetrahydrofuran-2-ylacetyl)amino]benzamide;
N-(imidazo[1,2-a]pyridin-7-ylmethyl)-4-{[3-(tetrahydrofuran-2-yl)propanoyl]amino}benzamide;
N-(imidazo[1,2-a]pyridin-7-ylmethyl)-4-{[(propan-2-yloxy)acetyl]amino}benzamide;
4-[(3-cyclopentylpropanoyl)amino]-N-(imidazo[1,2-a]pyridin-7-ylmethyl)benzamide;
N-(imidazo[1,2-a]pyridin-7-ylmethyl)-4-[(4-methylpentanoyl)amino]benzamide;
N-(imidazo[1,2-a]pyridin-7-ylmethyl)-4-[(tetrahydrofuran-3-ylacetyl)amino]benzamide;
4-[(4-cyanobenzyl)(cyclopentylacetyl)amino]-N-(imidazo[1,2-a]pyridin-6-ylmethyl)benzamide;
tert-butyl 4-(4-{[(imidazo[1,2-a]pyridin-7-ylmethyl)carbamoyl]amino}phenyl)piperidine-1-carboxylate;
tert-butyl 4-{4-[(imidazo[1,2-a]pyridin-7-ylmethyl)carbamoyl]phenyl}piperidine-1-carboxylate;
2-{5-[(benzyloxy)methyl]-2-oxo-1,3-oxazolidin-3-yl}-N-(imidazo[1,2-a]pyridin-7-ylmethyl)-1,3-thiazole-5-carboxamide;
N-(imidazo[1,2-a]pyridin-6-ylmethyl)-5-[1-(tetrahydrofuran-2-ylmethyl)-1H-pyrazol-4-yl]thiophene-2-carboxamide;
1-(imidazo[1,2-a]pyridin-7-ylmethyl)-3-{4-[1-(tetrahydrofuran-2-ylcarbonyl)piperidin-4-yl]phenyl}urea;
1-(imidazo[1,2-a]pyridin-7-ylmethyl)-3-{4-[1-(tetrahydro-2H-pyran-4-ylcarbonyl)piperidin-4-yl]phenyl}urea;
1-{4-[1-(1,4-dioxan-2-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(tetrahydro-2H-pyran-4-ylacetyl)piperidin-4-yl]phenyl}urea;

1-(imidazo[1,2-a]pyridin-7-ylmethyl)-3-{4-[1-(morpholin-4-ylacetyl)piperidin-4-yl]phenyl}urea;

1-(imidazo[1,2-a]pyridin-7-ylmethyl)-3-{4-[1-(tetrahydrofuran-2-ylacetyl)piperidin-4-yl]phenyl}urea;

1-{4-[1-(3-hydroxy-3-methylbutanoyl)piperidin-4-yl]phenyl}-3-(imidazo[1,2-a]pyridin-7-ylmethyl)urea;

1-{4-[1-(2-hydroxy-2-methylpropanoyl)piperidin-4-yl]phenyl}-3-(imidazo[1,2-a]pyridin-7-ylmethyl)urea;

1-(imidazo[1,2-a]pyridin-7-ylmethyl)-3-{4-[1-(2-methylpropanoyl)piperidin-4-yl]phenyl}urea;

1-[4-(1-benzoylpiperidin-4-yl)phenyl]-3-(imidazo[1,2-a]pyridin-7-ylmethyl)urea;

4-[1-(2-hydroxy-2-methylpropanoyl)piperidin-4-yl]-N-(imidazo[1,2-a]pyridin-7-ylmethyl)benzamide;

N-(imidazo[1,2-a]pyridin-7-ylmethyl)-4-[1-(tetrahydrofuran-3-ylcarbonyl)piperidin-4-yl]benzamide;

N-(imidazo[1,2-a]pyridin-7-ylmethyl)-4-[1-(tetrahydro-2H-pyran-4-ylcarbonyl)piperidin-4-yl]benzamide;

4-[1-(1,4-dioxan-2-ylcarbonyl)piperidin-4-yl]-N-(imidazo[1,2-a]pyridin-7-ylmethyl)benzamide;

4-{1-[(1,1-dioxidotetrahydro-2H-thiopyran-4-yl)carbonyl]piperidin-4-yl}-N-(imidazo[1,2-a]pyridin-7-ylmethyl)benzamide;

N-(imidazo[1,2-a]pyridin-7-ylmethyl)-4-[1-(tetrahydrofuran-2-ylacetyl)piperidin-4-yl]benzamide;

N-(imidazo[1,2-a]pyridin-7-ylmethyl)-4-[1-(tetrahydro-2H-pyran-4-ylacetyl)piperidin-4-yl]benzamide;

N-(imidazo[1,2-a]pyridin-7-ylmethyl)-4-{1-[(propan-2-yloxy)acetyl]piperidin-4-yl}benzamide;

N-(imidazo[1,2-a]pyridin-7-ylmethyl)-4-{1-[(2S)-2-methylbutanoyl]piperidin-4-yl}benzamide;

N-(imidazo[1,2-a]pyridin-7-ylmethyl)-4-[1-(2-methylpropanoyl)piperidin-4-yl]benzamide;

4-[(4-cyanobenzyl)(3-methoxypropanoyl)amino]-N-(imidazo[1,2-a]pyridin-6-ylmethyl)benzamide;

5-(1-acetyl-1,2,3,6-tetrahydropyridin-4-yl)-N-(imidazo[1,2-a]pyridin-7-ylmethyl)thiophene-2-carboxamide;

N-(imidazo[1,2-a]pyridin-7-ylmethyl)-5-[1-(methylsulfonyl)-1,2,3,6-tetrahydropyridin-4-yl]thiophene-2-carboxamide;

1-(4-{1-[(1,1-dioxidotetrahydro-2H-thiopyran-4-yl)carbonyl]piperidin-4-yl}phenyl)-3-(imidazo[1,2-a]pyridin-7-ylmethyl)urea;

2-[(2S)-2-(hydroxymethyl)-5-oxopyrrolidin-1-yl]-N-(imidazo[1,2-a]pyridin-7-ylmethyl)-1,3-thiazole-5-carboxamide;

N-(imidazo[1,2-a]pyridin-7-ylmethyl)-2-[(4R)-4-methyl-2-oxo-1,3-oxazolidin-3-yl]-1,3-thiazole-5-carboxamide;

5-[1-(cyclopropylsulfonyl)-1,2,3,6-tetrahydropyridin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydro-2H-pyran-2-ylmethyl)-1H-pyrazol-4-yl]thiophene-2-carboxamide;

N-(imidazo[1,2-a]pyridin-7-ylmethyl)-5-[1-(tetrahydrofuran-2-ylmethyl)-1H-pyrazol-4-yl]thiophene-2-carboxamide;

N-(imidazo[1,2-a]pyridin-7-ylmethyl)-2-{2-oxo-5-[(propan-2-yloxy)methyl]-1,3-oxazolidin-3-yl}-1,3-thiazole-5-carboxamide;

N-(imidazo[1,2-a]pyridin-7-ylmethyl)-5-[(4R)-2-oxo-4-(propan-2-yl)-1,3-oxazolidin-3-yl]thiophene-2-carboxamide;

2-[5-(hydroxymethyl)-2-oxo-1,3-oxazolidin-3-yl]-N-(imidazo[1,2-a]pyridin-7-ylmethyl)-1,3-thiazole-5-carboxamide;

N-(imidazo[1,2-a]pyridin-7-ylmethyl)-5-[1-(tetrahydrofuran-3-ylmethyl)-1H-pyrazol-4-yl]thiophene-2-carboxamide;

N-(imidazo[1,2-a]pyridin-7-ylmethyl)-5-[1-(tetrahydro-2H-pyran-3-ylmethyl)-1H-pyrazol-4-yl]thiophene-2-carboxamide;

N-(imidazo[1,2-a]pyridin-7-ylmethyl)-5-{1-[(3-methyloxetan-3-yl)methyl]-1H-pyrazol-4-yl}thiophene-2-carboxamide;

N-(imidazo[1,2-a]pyridin-7-ylmethyl)-2-{(5S)-2-oxo-5-[(propan-2-yloxy)methyl]-1,3-oxazolidin-3-yl}-1,3-thiazole-5-carboxamide;

N-(imidazo[1,2-a]pyridin-7-ylmethyl)-2-{(5R)-2-oxo-5-[(propan-2-yloxy)methyl]-1,3-oxazolidin-3-yl}-1,3-thiazole-5-carboxamide;

N-(imidazo[1,2-a]pyridin-7-ylmethyl)-5-[1-(methoxyacetyl)piperidin-4-yl]thiophene-2-carboxamide;

5-(1-acetylpiperidin-4-yl)-N-(imidazo[1,2-a]pyridin-7-ylmethyl)thiophene-2-carboxamide;

N-(imidazo[1,2-a]pyridin-7-ylmethyl)-5-[1-(2-methylpropanoyl)piperidin-4-yl]thiophene-2-carboxamide;

5-[1-(cyclopropylcarbonyl)piperidin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydrofuran-3-ylcarbonyl)piperidin-4-yl]thiophene-2-carboxamide;

N-(imidazo[1,2-a]pyridin-7-ylmethyl)-5-[1-(tetrahydro-2H-pyran-4-ylacetyl)piperidin-4-yl]thiophene-2-carboxamide;

N-(imidazo[1,2-a]pyridin-7-ylmethyl)-5-[1-(3-methylbutanoyl)piperidin-4-yl]thiophene-2-carboxamide;

N-(imidazo[1,2-a]pyridin-7-ylmethyl)-5-[1-(1,2-oxazol-5-ylcarbonyl)piperidin-4-yl]thiophene-2-carboxamide;

N-(imidazo[1,2-a]pyridin-7-ylmethyl)-5-[1-(tetrahydro-2H-pyran-4-ylmethyl)-1H-pyrazol-4-yl]thiophene-2-carboxamide;

5-[5-(hydroxymethyl)-2-oxo-1,3-oxazolidin-3-yl]-N-(imidazo[1,2-a]pyridin-7-ylmethyl)thiophene-2-carboxamide;

5-[(4R)-4-hydroxy-2-oxopyrrolidin-1-yl]-N-(imidazo[1,2-a]pyridin-7-ylmethyl)thiophene-2-carboxamide;

5-[(4S)-4-hydroxy-2-oxopyrrolidin-1-yl]-N-(imidazo[1,2-a]pyridin-7-ylmethyl)thiophene-2-carboxamide;

N-(imidazo[1,2-a]pyridin-7-ylmethyl)-5-[1-(2-methoxyethyl)-1H-pyrazol-4-yl]thiophene-2-carboxamide;

1-[4-(1-benzoylpiperidin-4-yl)butyl]-3-imidazo[1,2-a]pyridin-7-ylurea;

N-(imidazo[1,2-a]pyridin-7-ylmethyl)-5-[1-(methylsulfonyl)piperidin-4-yl]thiophene-2-carboxamide;

5-[1-(cyclohexylmethyl)-5-ethyl-1H-pyrazol-4-yl]-N-(imidazo[1,2-a]pyridin-7-ylmethyl)thiophene-2-carboxamide;

N-(imidazo[1,2-a]pyridin-7-ylmethyl)-5-{1-[(1-methoxy-3,3-dimethylcyclohexyl)methyl]-5-methyl-1H-pyrazol-4-yl}thiophene-2-carboxamide;

N-(4-{[(imidazo[1,2-a]pyridin-6-ylmethyl)carbamoyl]amino}phenyl)-4-methylpentanamide;

3-cyclopentyl-N-(4-{[(imidazo[1,2-a]pyridin-6-ylmethyl)carbamoyl]amino}phenyl)propanamide;

N-(4-{[(imidazo[1,2-a]pyridin-6-ylmethyl)carbamoyl]amino}phenyl)-2-(propan-2-yloxy)acetamide;

N-(4-{[(imidazo[1,2-a]pyridin-6-ylmethyl)carbamoyl]amino}phenyl)-2-(tetrahydrofuran-2-yl)acetamide;

N-(4-{[(imidazo[1,2-a]pyridin-6-ylmethyl)carbamoyl] amino}phenyl)-2-(tetrahydro-2H-pyran-4-yl)acetamide;

N-(4-{[(imidazo[1,2-a]pyridin-6-ylmethyl)carbamoyl] amino}phenyl)-3-phenylpropanamide;

N-(4-{[(imidazo[1,2-a]pyridin-7-ylmethyl)carbamoyl] amino}phenyl)-4-methylpentanamide;

3-cyclopentyl-N-(4-{[(imidazo[1,2-a]pyridin-7-ylmethyl) carbamoyl]amino}phenyl)propanamide;

N-(4-{[(imidazo[1,2-a]pyridin-7-ylmethyl)carbamoyl] amino}phenyl)-2-(propan-2-yloxy)acetamide;

N-(4-{[(imidazo[1,2-a]pyridin-7-ylmethyl)carbamoyl] amino}phenyl)-2-(tetrahydrofuran-2-yl)acetamide;

N-(4-{[(imidazo[1,2-a]pyridin-7-ylmethyl)carbamoyl] amino}phenyl)-2-(tetrahydro-2H-pyran-4-yl)acetamide;

N-(4-{[(imidazo[1,2-a]pyridin-7-ylmethyl)carbamoyl] amino}phenyl)-3-phenylpropanamide;

1-(imidazo[1,2-a]pyridin-7-ylmethyl)-3-(4-{1-[(3S)-tetrahydrofuran-3-ylcarbonyl]piperidin-4-yl}phenyl)urea;

1-(imidazo[1,2-a]pyridin-7-ylmethyl)-3-(4-{1-[(3R)-tetrahydrofuran-3-ylcarbonyl]piperidin-4-yl}phenyl)urea;

1-(imidazo[1,2-a]pyridin-7-ylmethyl)-3-(4-{1-[(2S)-tetrahydrofuran-2-ylcarbonyl]piperidin-4-yl}phenyl)urea;

1-(imidazo[1,2-a]pyridin-7-ylmethyl)-3-(4-{1-[(2R)-tetrahydrofuran-2-ylcarbonyl]piperidin-4-yl}phenyl)urea;

tert-butyl 4-(3-fluoro-4-{[(imidazo[1,2-a]pyridin-7-ylmethyl)carbamoyl]amino}phenyl)-3,6-dihydropyridine-1 (2H)-carboxylate;

tert-butyl (3R)-3-(4-{[(imidazo[1,2-a]pyridin-7-ylmethyl) carbamoyl]amino}phenoxy)pyrrolidine-1-carboxylate;

tert-butyl {2-fluoro-4-[(imidazo[1,2-a]pyridin-7-ylmethyl) carbamoyl]phenyl}carbamate;

N-(imidazo[1,2-a]pyridin-7-ylmethyl)-5-(1-propyl-1H-pyrazol-4-yl)thiophene-2-carboxamide;

N-(imidazo[1,2-a]pyridin-7-ylmethyl)-5-{1-[2-(morpholin-4-yl)ethyl]-1H-pyrazol-4-yl}thiophene-2-carboxamide;

5-(1-ethyl-1H-pyrazol-4-yl)-N-(imidazo[1,2-a]pyridin-7-ylmethyl)thiophene-2-carboxamide;

5-[1-(1,1-dioxidotetrahydrothiophen-3-yl)-1H-pyrazol-4-yl]-N-(imidazo[1,2-a]pyridin-7-ylmethyl)thiophene-2-carboxamide;

2-(1-benzoyl-1,2,3,6-tetrahydropyridin-4-yl)-N-(imidazo[1,2-a]pyridin-7-ylmethyl)-1,3-thiazole-5-carboxamide;

4-[1-(2-hydroxy-2-methylpropyl)-1H-pyrazol-4-yl]-N-(imidazo[1,2-a]pyridin-7-ylmethyl)benzamide;

N-(imidazo[1,2-a]pyridin-7-ylmethyl)-5-phenylthiophene-2-carboxamide;

N-(imidazo[1,2-a]pyridin-7-ylmethyl)-5-{1-[2-(methylsulfonyl)ethyl]-1H-pyrazol-4-yl}thiophene-2-carboxamide;

tert-butyl 3-{4-[(imidazo[1,2-a]pyridin-7-ylmethyl)carbamoyl]phenyl}pyrrolidine-1-carboxylate;

tert-butyl 3-(4-{[(imidazo[1,2-a]pyridin-7-ylmethyl)carbamoyl]amino}phenyl)pyrrolidine-1-carboxylate;

N-(4-{[(imidazo[1,2-a]pyridin-7-ylmethyl)carbamoyl] amino}phenyl)biphenyl-2-sulfonamide;

5-{1-[(2R)-2-hydroxypropyl]-1H-pyrazol-4-yl}-N-(imidazo[1,2-a]pyridin-7-ylmethyl)thiophene-2-carboxamide;

4-[(cyclopentylacetyl)amino]-3-fluoro-N-(imidazo[1,2-a]pyridin-7-ylmethyl)benzamide;

1-{2-fluoro-4-[1-(2-methylpropanoyl)-1,2,3,6-tetrahydropyridin-4-yl]phenyl}-3-(imidazo[1,2-a]pyridin-7-ylmethyl)urea;

1-{2-fluoro-4-[1-(tetrahydrofuran-2-ylcarbonyl)-1,2,3,6-tetrahydropyridin-4-yl]phenyl}-3-(imidazo[1,2-a]pyridin-7-ylmethyl)urea;

N-(imidazo[1,2-a]pyridin-7-ylmethyl)-4-{1-[(3S)-tetrahydrofuran-3-ylcarbonyl]piperidin-4-yl}benzamide;

N-(imidazo[1,2-a]pyridin-7-ylmethyl)-4-{1-[(3R)-tetrahydrofuran-3-ylcarbonyl]piperidin-4-yl}benzamide;

N-(imidazo[1,2-a]pyridin-7-ylmethyl)-4-{1-[(2R)-tetrahydrofuran-2-ylcarbonyl]piperidin-4-yl}benzamide;

N-(imidazo[1,2-a]pyridin-7-ylmethyl)-4-{1-[(2S)-tetrahydrofuran-2-ylcarbonyl]piperidin-4-yl}benzamide;

4-[1-(cyclopropylacetyl)piperidin-4-yl]-N-(imidazo[1,2-a] pyridin-7-ylmethyl)benzamide;

4-(1-acetylpiperidin-4-yl)-N-(imidazo[1,2-a]pyridin-7-ylmethyl)benzamide;

tert-butyl 4-{4-[2-(imidazo[1,2-a]pyridin-6-ylamino)-2-oxoethyl]phenyl}-3,6-dihydropyridine-1(2H)-carboxylate;

N-(imidazo[1,2-a]pyridin-7-ylmethyl)-4-[1-(2-methylpropyl)-1H-pyrazol-4-yl]benzamide;

5-[1-(1,4-dioxan-2-ylmethyl)-1H-pyrazol-4-yl]-N-(imidazo [1,2-a]pyridin-7-ylmethyl)thiophene-2-carboxamide;

5-[1-(2-hydroxyethyl)-1H-pyrazol-4-yl]-N-(imidazo[1,2-a] pyridin-7-ylmethyl)thiophene-2-carboxamide;

N-(imidazo[1,2-a]pyridin-7-ylmethyl)-5-[3-(propan-2-yloxy)phenyl]thiophene-2-carboxamide;

N-(imidazo[1,2-a]pyridin-7-ylmethyl)-2-[1-(tetrahydro-2H-pyran-4-ylcarbonyl)-1,2,3,6-tetrahydropyridin-4-yl]-1,3-thiazole-5-carboxamide;

N-(imidazo[1,2-a]pyridin-7-ylmethyl)-2-[1-(2-methylpropanoyl)-1,2,3,6-tetrahydropyridin-4-yl]-1,3-thiazole-5-carboxamide;

N-(imidazo[1,2-a]pyridin-7-ylmethyl)-4-({(3S)-1-[(2S)-2-methylbutanoyl]pyrrolidin-3-yl}oxy)benzamide;

tert-butyl 4-[4-(imidazo[1,2-a]pyridin-7-ylcarbamoyl)phenyl]piperidine-1-carboxylate;

tert-butyl 4-[4-(imidazo[1,2-a]pyridin-6-ylcarbamoyl)phenyl]piperidine-1-carboxylate;

N-(imidazo[1,2-a]pyridin-7-ylmethyl)-5-{3-[(2-methylpropanoyl)amino]oxetan-3-yl}thiophene-2-carboxamide;

5-[3-(benzoylamino)oxetan-3-yl]-N-(imidazo[1,2-a]pyridin-7-ylmethyl)thiophene-2-carboxamide;

N-(imidazo[1,2-a]pyridin-7-ylmethyl)-5-{3-[(tetrahydrofuran-3-ylacetyl)amino]oxetan-3-yl}thiophene-2-carboxamide;

N-(imidazo[1,2-a]pyridin-7-ylmethyl)-5-[3-(pentanoylamino)oxetan-3-yl]thiophene-2-carboxamide;

1-(imidazo[1,2-a]pyridin-7-ylmethyl)-3-[4-({(3R)-1-[(2S)-2-methylbutanoyl]pyrrolidin-3-yl}oxy)phenyl]urea;

1-(4-{[(3R)-1-benzoylpyrrolidin-3-yl]oxy}phenyl)-3-(imidazo[1,2-a]pyridin-7-ylmethyl)urea;

1-(imidazo[1,2-a]pyridin-7-ylmethyl)-3-(4-{[(3R)-1-(2-methylpropanoyl)pyrrolidin-3-yl]oxy}phenyl)urea;

1-(4-{[(3R)-1-(cyclopropylcarbonyl)pyrrolidin-3-yl] oxy}phenyl)-3-(imidazo[1,2-a]pyridin-7-ylmethyl)urea;

1-(4-{[(3R)-1-(cyclopropylacetyl)pyrrolidin-3-yl] oxy}phenyl)-3-(imidazo[1,2-a]pyridin-7-ylmethyl)urea;

1-(imidazo[1,2-a]pyridin-7-ylmethyl)-3-(4-{[(3R)-1-(tetrahydro-2H-pyran-4-ylcarbonyl)pyrrolidin-3-yl] oxy}phenyl)urea;

1-(4-{[(3R)-1-(2-hydroxy-2-methylpropanoyl)pyrrolidin-3-yl]oxy}phenyl)-3-(imidazo[1,2-a]pyridin-7-ylmethyl) urea;

1-(imidazo[1,2-a]pyridin-7-ylmethyl)-3-[4-({(3R)-1-[(2R)-tetrahydrofuran-2-ylcarbonyl]pyrrolidin-3-yl] oxy}phenyl)urea;

1-(imidazo[1,2-a]pyridin-7-ylmethyl)-3-[4-({(3R)-1-[(2S)-tetrahydrofuran-2-ylcarbonyl]pyrrolidin-3-yl] oxy}phenyl)urea;

1-(imidazo[1,2-a]pyridin-7-ylmethyl)-3-(4-{[(3R)-1-(tetrahydrofuran-3-ylcarbonyl)pyrrolidin-3-yl]oxy}phenyl) urea;

1-(imidazo[1,2-a]pyridin-7-ylmethyl)-3-(4-{[(3R)-1-(tetrahydro-2H-pyran-4-ylacetyl)pyrrolidin-3-yl]oxy}phenyl)urea;

N-(imidazo[1,2-a]pyridin-7-ylmethyl)-4-({(3S)-1-[(3R)-tetrahydrofuran-3-ylcarbonyl]pyrrolidin-3-yl}oxy)benzamide;

N-(imidazo[1,2-a]pyridin-7-ylmethyl)-4-({(3S)-1-[(2R)-tetrahydrofuran-2-ylcarbonyl]pyrrolidin-3-yl}oxy)benzamide;

N-(imidazo[1,2-a]pyridin-7-ylmethyl)-4-({(3S)-1-[(2S)-tetrahydrofuran-2-ylcarbonyl]pyrrolidin-3-yl}oxy)benzamide;

N-(imidazo[1,2-a]pyridin-7-ylmethyl)-4-{[(3S)-1-(tetrahydro-2H-pyran-4-ylcarbonyl)pyrrolidin-3-yl]oxy}benzamide;

N-(imidazo[1,2-a]pyridin-7-ylmethyl)-4-{[(3S)-1-(tetrahydro-2H-pyran-4-ylacetyl)pyrrolidin-3-yl]oxy}benzamide;

5-{1-[(1,1-dioxidotetrahydro-2H-thiopyran-3-yl)methyl]-1H-pyrazol-4-yl}-N-(imidazo[1,2-a]pyridin-7-ylmethyl)thiophene-2-carboxamide;

N-(imidazo[1,2-a]pyridin-7-ylmethyl)-5-(1-methyl-1H-pyrazol-4-yl)thiophene-2-carboxamide;

N-(imidazo[1,2-a]pyridin-7-ylmethyl)-4-({(3S)-1-[(3S)-tetrahydrofuran-3-ylcarbonyl]pyrrolidin-3-yl}oxy)benzamide;

4-{[(3S)-1-(cyclopropylacetyl)pyrrolidin-3-yl]oxy}-N-(imidazo[1,2-a]pyridin-7-ylmethyl)benzamide;

4-{[(3S)-1-(2-hydroxy-2-methylpropanoyl)pyrrolidin-3-yl]oxy}-N-(imidazo[1,2-a]pyridin-7-ylmethyl)benzamide;

N-(imidazo[1,2-a]pyridin-7-ylmethyl)-4-{[(3S)-1-(3-methoxy-2-methylpropanoyl)pyrrolidin-3-yl]oxy}benzamide;

4-{[(3S)-1-butanoylpyrrolidin-3-yl]oxy}-N-(imidazo[1,2-a]pyridin-7-ylmethyl)benzamide;

N-(imidazo[1,2-a]pyridin-7-ylmethyl)-4-{[(3S)-1-(2-methylpropanoyl)pyrrolidin-3-yl]oxy}benzamide;

4-{[(3S)-1-(cyclopropylcarbonyl)pyrrolidin-3-yl]oxy}-N-(imidazo[1,2-a]pyridin-7-ylmethyl)benzamide;

4-{[(3S)-1-benzoylpyrrolidin-3-yl]oxy}-N-(imidazo[1,2-a]pyridin-7-ylmethyl)benzamide;

4-{[(3S)-1-(3-hydroxy-3-methylbutanoyl)pyrrolidin-3-yl]oxy}-N-(imidazo[1,2-a]pyridin-7-ylmethyl)benzamide;

2-(4-benzoylpiperazin-1-yl)-N-(imidazo[1,2-a]pyridin-7-ylmethyl)-1,3-thiazole-5-carboxamide;

N-(imidazo[1,2-a]pyridin-7-ylmethyl)-2-[4-(propan-2-yl)piperazin-1-yl]-1,3-thiazole-5-carboxamide;

N-(imidazo[1,2-a]pyridin-7-ylmethyl)-2-[4-(2-methoxyethyl)piperazin-1-yl]-1,3-thiazole-5-carboxamide;

N-(imidazo[1,2-a]pyridin-6-ylmethyl)-N'-(3-methylbutyl)benzene-1,4-dicarboxamide;

N-(imidazo[1,2-a]pyridin-6-ylmethyl)-N'-[(3S)-tetrahydrofuran-3-ylmethyl]benzene-1,4-dicarboxamide;

1-(imidazo[1,2-a]pyridin-6-ylmethyl)-3-[4-(1-propyl-1H-pyrazol-4-yl)phenyl]urea;

N-(imidazo[1,2-a]pyridin-7-ylmethyl)-2-phenyl-1,3-thiazole-5-carboxamide;

1-(imidazo[1,2-a]pyridin-6-ylmethyl)-3-{4-[1-(2-methylpropyl)-1H-pyrazol-4-yl]phenyl}urea;

N-(imidazo[1,2-a]pyridin-7-ylmethyl)-5-(1-methyl-1H-pyrazol-5-yl)thiophene-2-carboxamide;

tert-butyl 3-(4-{[(imidazo[1,2-a]pyridin-7-ylmethyl)carbamoyl]amino}phenyl)azetidine-1-carboxylate;

tert-butyl 4-{4-[(imidazo[1,2-a]pyridin-7-ylmethyl)carbamoyl]phenoxy}piperidine-1-carboxylate;

tert-butyl 4-(4-{[(imidazo[1,2-a]pyridin-7-ylmethyl)carbamoyl]amino}phenoxy)piperidine-1-carboxylate;

N-(imidazo[1,2-a]pyridin-7-ylmethyl)-4-[1-(2-methylpropanoyl)pyrrolidin-3-yl]benzamide;

N-(imidazo[1,2-a]pyridin-7-ylmethyl)-4-{1-[(2S)-2-methylbutanoyl]pyrrolidin-3-yl}benzamide;

4-[1-(cyclopropylacetyl)pyrrolidin-3-yl]-N-(imidazo[1,2-a]pyridin-7-ylmethyl)benzamide;

4-(1-benzoylpyrrolidin-3-yl)-N-(imidazo[1,2-a]pyridin-7-ylmethyl)benzamide;

N-(imidazo[1,2-a]pyridin-7-ylmethyl)-4-{1-[(propan-2-yloxy)acetyl]pyrrolidin-3-yl}benzamide;

4-[1-(2-hydroxy-2-methylpropanoyl)pyrrolidin-3-yl]-N-(imidazo[1,2-a]pyridin-7-ylmethyl)benzamide;

N-(imidazo[1,2-a]pyridin-7-ylmethyl)-4-{1-[(2R)-tetrahydrofuran-2-ylcarbonyl]pyrrolidin-3-yl}benzamide;

N-(imidazo[1,2-a]pyridin-7-ylmethyl)-4-{1-[(2S)-tetrahydrofuran-2-ylcarbonyl]pyrrolidin-3-yl}benzamide;

N-(imidazo[1,2-a]pyridin-7-ylmethyl)-4-{1-[(3S)-tetrahydrofuran-3-ylcarbonyl]pyrrolidin-3-yl}benzamide;

N-(imidazo[1,2-a]pyridin-7-ylmethyl)-4-[1-(tetrahydro-2H-pyran-4-ylcarbonyl)pyrrolidin-3-yl]benzamide;

4-[1-(1,4-dioxan-2-ylcarbonyl)pyrrolidin-3-yl]-N-(imidazo[1,2-a]pyridin-7-ylmethyl)benzamide;

N-(imidazo[1,2-a]pyridin-7-ylmethyl)-4-[1-(tetrahydro-2H-pyran-4-ylacetyl)pyrrolidin-3-yl]benzamide;

1-[4-(1-acetylpyrrolidin-3-yl)phenyl]-3-(imidazo[1,2-a]pyridin-7-ylmethyl)urea;

1-(imidazo[1,2-a]pyridin-7-ylmethyl)-3-{4-[1-(2-methylpropanoyl)pyrrolidin-3-yl]phenyl}urea;

1-(imidazo[1,2-a]pyridin-7-ylmethyl)-3-(4-{1-[(2S)-2-methylbutanoyl]pyrrolidin-3-yl}phenyl)urea;

1-{4-[1-(cyclopropylacetyl)pyrrolidin-3-yl]phenyl}-3-(imidazo[1,2-a]pyridin-7-ylmethyl)urea;

1-[4-(1-benzoylpyrrolidin-3-yl)phenyl]-3-(imidazo[1,2-a]pyridin-7-ylmethyl)urea;

1-(imidazo[1,2-a]pyridin-7-ylmethyl)-3-(4-{1-[(propan-2-yloxy)acetyl]pyrrolidin-3-yl}phenyl)urea;

1-{4-[1-(2-hydroxy-2-methylpropanoyl)pyrrolidin-3-yl]phenyl}-3-(imidazo[1,2-a]pyridin-7-ylmethyl)urea;

1-(imidazo[1,2-a]pyridin-7-ylmethyl)-3-(4-{1-[(2R)-tetrahydrofuran-2-ylcarbonyl]pyrrolidin-3-yl}phenyl)urea;

1-(imidazo[1,2-a]pyridin-7-ylmethyl)-3-(4-{1-[(2S)-tetrahydrofuran-2-ylcarbonyl]pyrrolidin-3-yl}phenyl)urea;

1-(imidazo[1,2-a]pyridin-7-ylmethyl)-3-(4-{1-[(3S)-tetrahydrofuran-3-ylcarbonyl]pyrrolidin-3-yl}phenyl)urea;

1-(imidazo[1,2-a]pyridin-7-ylmethyl)-3-{4-[1-(tetrahydro-2H-pyran-4-ylcarbonyl)pyrrolidin-3-yl]phenyl}urea;

1-{4-[1-(1,4-dioxan-2-ylcarbonyl)pyrrolidin-3-yl]phenyl}-3-(imidazo[1,2-a]pyridin-7-ylmethyl)urea;

1-(imidazo[1,2-a]pyridin-7-ylmethyl)-3-{4-[1-(tetrahydro-2H-pyran-4-ylacetyl)pyrrolidin-3-yl]phenyl}urea;

1-(imidazo[1,2-a]pyridin-7-ylmethyl)-3-{4-[1-(morpholin-4-ylacetyl)pyrrolidin-3-yl]phenyl}urea;

N-(imidazo[1,2-a]pyridin-7-ylmethyl)-N'-(3-methylbutyl)benzene-1,4-dicarboxamide;

N-(imidazo[1,2-a]pyridin-7-ylmethyl)-N'-[(3S)-tetrahydrofuran-3-ylmethyl]benzene-1,4-dicarboxamide;

N-(imidazo[1,2-a]pyridin-7-ylmethyl)-5-{1-[(2R)-tetrahydrofuran-2-ylmethyl]-1H-pyrazol-4-yl}thiophene-2-carboxamide;

4-{[(3-chloroimidazo[1,2-a]pyridin-6-yl)carbamoyl]amino}-N-(tetrahydro-2H-pyran-2-ylmethyl)benzamide;

N-(imidazo[1,2-a]pyridin-7-ylmethyl)-5-{1-[(2S)-tetrahydrofuran-2-ylmethyl]-1H-pyrazol-4-yl}thiophene-2-carboxamide;

N-[(3-chloroimidazo[1,2-a]pyridin-6-yl)methyl]-4-[(tetrahydrofuran-3-ylacetyl)amino]benzamide;

5-(4-hydroxytetrahydro-2H-pyran-4-yl)-N-(imidazo[1,2-a]pyridin-7-ylmethyl)thiophene-2-carboxamide;
5-[3-hydroxy-1-(2-methylpropanoyl)azetidin-3-yl]-N-(imidazo[1,2-a]pyridin-7-ylmethyl)thiophene-2-carboxamide;
5-(1-benzoyl-3-hydroxyazetidin-3-yl)-N-(imidazo[1,2-a]pyridin-7-ylmethyl)thiophene-2-carboxamide;
tert-butyl 3-{4-[(imidazo[1,2-a]pyridin-7-ylmethyl)carbamoyl]phenyl}azetidine-1-carboxylate;
tert-butyl 4-hydroxy-4-{5-[(imidazo[1,2-a]pyridin-7-ylmethyl)carbamoyl]thiophen-2-yl}piperidine-1-carboxylate;
1-(imidazo[1,2-a]pyridin-7-ylmethyl)-3-[5-(piperidin-1-ylcarbonyl)-1,3-thiazol-2-yl]urea;
5-{3-hydroxy-1-[(2S)-2-methylbutanoyl]azetidin-3-yl}-N-(imidazo[1,2-a]pyridin-7-ylmethyl)thiophene-2-carboxamide;
5-[3-hydroxy-1-(tetrahydro-2H-pyran-4-ylacetyl)azetidin-3-yl]-N-(imidazo[1,2-a]pyridin-7-ylmethyl)thiophene-2-carboxamide;
2-{[(imidazo[1,2-a]pyridin-7-ylmethyl)carbamoyl]amino}-N-(3-methylbutyl)-1,3-thiazole-5-carboxamide;
N-(imidazo[1,2-a]pyridin-7-ylmethyl)-5-(3-{[(2S)-2-methylbutanoyl]amino}oxetan-3-yl)thiophene-2-carboxamide;
N-(imidazo[1,2-a]pyridin-7-ylmethyl)-1-[1-(3-methylbutanoyl)piperidin-4-yl]-1H-pyrazole-3-carboxamide;
N-(imidazo[1,2-a]pyridin-7-ylmethyl)-5-[1-(tetrahydro-2H-pyran-4-yl)-1H-pyrazol-4-yl]thiophene-2-carboxamide;
4-[(1-acetylpiperidin-4-yl)oxy]-N-(imidazo[1,2-a]pyridin-7-ylmethyl)benzamide;
N-(imidazo[1,2-a]pyridin-7-ylmethyl)-4-{[1-(2-methylpropanoyl)piperidin-4-yl]oxy}benzamide;
N-(imidazo[1,2-a]pyridin-7-ylmethyl)-4-({1-[(2S)-2-methylbutanoyl]piperidin-4-yl}oxy)benzamide;
4-{[1-(cyclopropylacetyl)piperidin-4-yl]oxy}-N-(imidazo[1,2-a]pyridin-7-ylmethyl)benzamide;
4-[(1-benzoylpiperidin-4-yl)oxy]-N-(imidazo[1,2-a]pyridin-7-ylmethyl)benzamide;
N-(imidazo[1,2-a]pyridin-7-ylmethyl)-4-({1-[(propan-2-yloxy)acetyl]piperidin-4-yl}oxy)benzamide;
4-{[1-(2-hydroxy-2-methylpropanoyl)piperidin-4-yl]oxy}-N-(imidazo[1,2-a]pyridin-7-ylmethyl)benzamide;
N-(imidazo[1,2-a]pyridin-7-ylmethyl)-4-({1-[(2R)-tetrahydrofuran-2-ylcarbonyl]piperidin-4-yl}oxy)benzamide;
N-(imidazo[1,2-a]pyridin-7-ylmethyl)-4-({1-[(2S)-tetrahydrofuran-2-ylcarbonyl]piperidin-4-yl}oxy)benzamide;
N-(imidazo[1,2-a]pyridin-7-ylmethyl)-4-{[1-(tetrahydro-2H-pyran-4-ylcarbonyl)piperidin-4-yl]oxy}benzamide;
4-{[1-(1,4-dioxan-2-ylcarbonyl)piperidin-4-yl]oxy}-N-(imidazo[1,2-a]pyridin-7-ylmethyl)benzamide;
N-(imidazo[1,2-a]pyridin-7-ylmethyl)-4-{[1-(tetrahydro-2H-pyran-4-ylacetyl)piperidin-4-yl]oxy}benzamide;
N-(imidazo[1,2-a]pyridin-7-ylmethyl)-4-{[1-(morpholin-4-ylacetyl)piperidin-4-yl]oxy}benzamide;
1-{4-[(1-acetylazetidin-3-yl)oxy]phenyl}-3-(imidazo[1,2-a]pyridin-7-ylmethyl)urea;
1-(imidazo[1,2-a]pyridin-7-ylmethyl)-3-(4-{[1-(2-methylpropanoyl)azetidin-3-yl]oxy}phenyl)urea;
1-(imidazo[1,2-a]pyridin-7-ylmethyl)-3-[4-({1-[(2S)-2-methylbutanoyl]azetidin-3-yl}oxy)phenyl]urea;
1-(4-{[1-(cyclopropylacetyl)azetidin-3-yl]oxy}phenyl)-3-(imidazo[1,2-a]pyridin-7-ylmethyl)urea;
1-{4-[(1-benzoylazetidin-3-yl)oxy]phenyl}-3-(imidazo[1,2-a]pyridin-7-ylmethyl)urea;
1-(imidazo[1,2-a]pyridin-7-ylmethyl)-3-[4-({1-[(propan-2-yloxy)acetyl]azetidin-3-yl}oxy)phenyl]urea;
1-(4-{[1-(2-hydroxy-2-methylpropanoyl)azetidin-3-yl]oxy}phenyl)-3-(imidazo[1,2-a]pyridin-7-ylmethyl)urea;
1-(imidazo[1,2-a]pyridin-7-ylmethyl)-3-[4-({1-[(2R)-tetrahydrofuran-2-ylcarbonyl]azetidin-3-yl}oxy)phenyl]urea;
1-(imidazo[1,2-a]pyridin-7-ylmethyl)-3-[4-({1-[(2S)-tetrahydrofuran-2-ylcarbonyl]azetidin-3-yl}oxy)phenyl]urea;
1-(imidazo[1,2-a]pyridin-7-ylmethyl)-3-(4-{[1-(tetrahydro-2H-pyran-4-ylcarbonyl)azetidin-3-yl]oxy}phenyl)urea;
1-(4-{[1-(1,4-dioxan-2-ylcarbonyl)azetidin-3-yl]oxy}phenyl)-3-(imidazo[1,2-a]pyridin-7-ylmethyl)urea;
1-(imidazo[1,2-a]pyridin-7-ylmethyl)-3-(4-{[1-(tetrahydro-2H-pyran-4-ylacetyl)azetidin-3-yl]oxy}phenyl)urea;
tert-butyl (3R)-3-{4-[(imidazo[1,2-a]pyridin-7-ylmethyl)carbamoyl]phenoxy}pyrrolidine-1-carboxylate;
4-(1-benzoylpiperidin-4-yl)-N-(imidazo[1,2-a]pyridin-7-ylmethyl)benzamide;
1-[4-(1-benzoyl-1,2,3,6-tetrahydropyridin-4-yl)-2-fluorophenyl]-3-(imidazo[1,2-a]pyridin-7-ylmethyl)urea;
1-{2-fluoro-4-[1-(tetrahydro-2H-pyran-4-ylacetyl)-1,2,3,6-tetrahydropyridin-4-yl]phenyl}-3-(imidazo[1,2-a]pyridin-7-ylmethyl)urea;
4-{1-[(3,3-difluorocyclobutyl)carbonyl]piperidin-4-yl}-N-(imidazo[1,2-a]pyridin-7-ylmethyl)benzamide;
4-{1-[(4,4-difluorocyclohexyl)carbonyl]piperidin-4-yl}-N-(imidazo[1,2-a]pyridin-7-ylmethyl)benzamide;
1-(imidazo[1,2-a]pyridin-7-ylmethyl)-3-(4-{[1-(2-methylpropanoyl)piperidin-4-yl]oxy}phenyl)urea;
1-(imidazo[1,2-a]pyridin-7-ylmethyl)-3-[4-({1-[(2S)-2-methylbutanoyl]piperidin-4-yl}oxy)phenyl]urea;
1-(4-{[1-(cyclopropylacetyl)piperidin-4-yl]oxy}phenyl)-3-(imidazo[1,2-a]pyridin-7-ylmethyl)urea;
1-{4[(1-benzoylpiperidin-4-yl)oxy]phenyl}-3-(imidazo[1,2-a]pyridin-7-ylmethyl)urea;
1-(imidazo[1,2-a]pyridin-7-ylmethyl)-3-[4-({1-[(propan-2-yloxy)acetyl]piperidin-4-yl}oxy)phenyl]urea;
1-(4-{[1-(2-hydroxy-2-methylpropanoyl)piperidin-4-yl]oxy}phenyl)-3-(imidazo[1,2-a]pyridin-7-ylmethyl)urea;
1-(imidazo[1,2-a]pyridin-7-ylmethyl)-3-[4-({1-[(2R)-tetrahydrofuran-2-ylcarbonyl]piperidin-4-yl}oxy)phenyl]urea;
1-(imidazo[1,2-a]pyridin-7-ylmethyl)-3-[4-({1-[(2S)-tetrahydrofuran-2-ylcarbonyl]piperidin-4-yl}oxy)phenyl]urea;
1-(imidazo[1,2-a]pyridin-7-ylmethyl)-3-(4-{[1-(tetrahydro-2H-pyran-4-ylcarbonyl)piperidin-4-yl]oxy}phenyl)urea;
1-(imidazo[1,2-a]pyridin-7-ylmethyl)-3-(4-{[1-(tetrahydro-2H-pyran-4-ylacetyl)piperidin-4-yl]oxy}phenyl)urea;
1-(imidazo[1,2-a]pyridin-7-ylmethyl)-3-{4-[1-(2-methylpropanoyl)azetidin-3-yl]phenyl}urea;
1-(imidazo[1,2-a]pyridin-7-ylmethyl)-3-(4-{1-[(2S)-2-methylbutanoyl]azetidin-3-yl}phenyl)urea;
1-{4-[1-(cyclopropylacetyl)azetidin-3-yl]phenyl}-3-(imidazo[1,2-a]pyridin-7-ylmethyl)urea;
1-[4-(1-benzoylazetidin-3-yl)phenyl]-3-(imidazo[1,2-a]pyridin-7-ylmethyl)urea;
1-(imidazo[1,2-a]pyridin-7-ylmethyl)-3-(4-{1-[(propan-2-yloxy)acetyl]azetidin-3-yl}phenyl)urea;
1-{4-[1-(2-hydroxy-2-methylpropanoyl)azetidin-3-yl]phenyl}-3-(imidazo[1,2-a]pyridin-7-ylmethyl)urea;
1-(imidazo[1,2-a]pyridin-7-ylmethyl)-3-(4-{1-[(2R)-tetrahydrofuran-2-ylcarbonyl]azetidin-3-yl}phenyl)urea;
1-(imidazo[1,2-a]pyridin-7-ylmethyl)-3-(4-{1-[(2S)-tetrahydrofuran-2-ylcarbonyl]azetidin-3-yl}phenyl)urea;
1-(imidazo[1,2-a]pyridin-7-ylmethyl)-3-{4-[1-(tetrahydro-2H-pyran-4-ylcarbonyl)azetidin-3-yl]phenyl}urea;

1-(imidazo[1,2-a]pyridin-7-ylmethyl)-3-{4-[1-(tetrahydro-2H-pyran-4-ylacetyl)azetidin-3-yl]phenyl}urea;

4-[(cyclopentylacetyl)amino]-2-fluoro-N-(imidazo[1,2-a]pyridin-6-ylmethyl)benzamide;

4-[(cyclopentylacetyl)amino]-2-fluoro-N-(imidazo[1,2-a]pyridin-7-ylmethyl)benzamide;

N-(imidazo[1,2-a]pyridin-7-ylmethyl)-5-[6-(morpholin-4-yl)pyridin-3-yl]thiophene-2-carboxamide;

N-(imidazo[1,2-a]pyridin-7-ylmethyl)-5-{1-[(2-methyltetrahydro-2H-pyran-2-yl)methyl]-1H-pyrazol-4-yl}thiophene-2-carboxamide;

tert-butyl 4-[(4-{5-[(imidazo[1,2-a]pyridin-7-ylmethyl)carbamoyl]thiophen-2-yl}-1H-pyrazol-1-yl)methyl]piperidine-1-carboxylate;

N-(imidazo[1,2-a]pyridin-7-ylmethyl)-5-[1-(3-methylbutanoyl)pyrrolidin-3-yl]thiophene-2-carboxamide;

N-(imidazo[1,2-a]pyridin-7-ylmethyl)-5-{1-[(2-methylpropanoyl)amino]cyclobutyl}thiophene-2-carboxamide;

N-(imidazo[1,2-a]pyridin-7-ylmethyl)-5-{1-[(3-methylbutanoyl)amino]cyclobutyl}thiophene-2-carboxamide;

N-(imidazo[1,2-a]pyridin-7-ylmethyl)-5-(1-{[(2S)-2-methylbutanoyl]amino}cyclobutyl)thiophene-2-carboxamide;

5-[1-(benzoylamino)cyclobutyl]-N-(imidazo[1,2-a]pyridin-7-ylmethyl)thiophene-2-carboxamide;

N-(imidazo[1,2-a]pyridin-7-ylmethyl)-5-{1-[3,3,3-trifluoropropanoyl)amino]cyclobutyl}thiophene-2-carboxamide;

N-(1-{5-[(imidazo[1,2-a]pyridin-7-ylmethyl)carbamoyl]thiophen-2-yl}cyclobutyl)tetrahydro-2H-pyran-4-carboxamide;

tert-butyl 3-{4-[(imidazo[1,2-a]pyridin-7-ylmethyl)carbamoyl]phenoxy}azetidine-1-carboxylate;

5-[1-(cyclobutylmethyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[1-(tetrahydrofuran-2-ylmethyl)-1H-pyrazol-4-yl]furan-2-carboxamide;

N-(imidazo[1,2-a]pyridin-7-ylmethyl)-5-[1-(tetrahydro-2H-pyran-2-ylmethyl)-1H-pyrazol-4-yl]furan-2-carboxamide;

N-(imidazo[1,2-a]pyridin-7-ylmethyl)-5-[1-(tetrahydrofuran-3-ylmethyl)-1H-pyrazol-4-yl]furan-2-carboxamide;

N-(imidazo[1,2-a]pyridin-7-ylmethyl)-5-[1-(tetrahydro-2H-pyran-3-ylmethyl)-1H-pyrazol-4-yl]furan-2-carboxamide;

N-(imidazo[1,2-a]pyridin-7-ylmethyl)-5-[1-(tetrahydro-2H-pyran-4-ylmethyl)-1H-pyrazol-4-yl]furan-2-carboxamide;

5-[1-(cyclobutylmethyl)-1H-pyrazol-4-yl]-N-(imidazo[1,2-a]pyridin-7-ylmethyl)furan-2-carboxamide;

N-(imidazo[1,2-a]pyridin-7-ylmethyl)-5-{1-[(3-methyloxetan-3-yl)methyl]-1H-pyrazol-4-yl}furan-2-carboxamide;

5-[1-(2-hydroxy-2-methylpropyl)-1H-pyrazol-4-yl]-N-(imidazo[1,2-a]pyridin-7-ylmethyl)furan-2-carboxamide;

4-[1-(furan-2-ylcarbonyl)piperidin-4-yl]-N-(imidazo[1,2-a]pyridin-7-ylmethyl)benzamide;

N-(imidazo[1,2-a]pyridin-7-ylmethyl)-5-[1-(piperidin-4-ylmethyl)-1H-pyrazol-4-yl]thiophene-2-carboxamide;

1-(imidazo[1,2-a]pyridin-7-ylmethyl)-3-{4-[1-(2-methylpropyl)-1H-pyrazol-4-yl]phenyl}urea;

1-(imidazo[1,2-a]pyridin-7-ylmethyl)-3-[4-(1-propyl-1H-pyrazol-4-yl)phenyl]urea;

N-(imidazo[1,2-a]pyridin-7-ylmethyl)-4-[1-(thiophen-2-ylcarbonyl)pyrrolidin-3-yl]benzamide;

N-(imidazo[1,2-a]pyridin-7-ylmethyl)-4-phenoxybenzamide;

N-(imidazo[1,2-a]pyridin-7-ylmethyl)-4-[1-(2-methylpropanoyl)azetidin-3-yl]benzamide;

tert-butyl 4-{4-[(3-chloroimidazo[1,2-a]pyridin-6-yl)carbamoyl]phenyl}piperidine-1-carboxylate;

N-(imidazo[1,2-a]pyridin-7-ylmethyl)-4-{[(3R)-1-(2-methylpropanoyl)pyrrolidin-3-yl]oxy}benzamide;

4-{[(3R)-1-benzoylpyrrolidin-3-yl]oxy}-N-(imidazo[1,2-a]pyridin-7-ylmethyl)benzamide;

N-(imidazo[1,2-a]pyridin-7-ylmethyl)-4-({(3R)-1-[(3S)-tetrahydrofuran-3-ylcarbonyl]pyrrolidin-3-yl}oxy)benzamide;

N-(imidazo[1,2-a]pyridin-7-ylmethyl)-4-({(3R)-1-[(2S)-2-methylbutanoyl]pyrrolidin-3-yl}oxy)benzamide;

1-(imidazo[1,2-a]pyridin-7-ylmethyl)-3-(4-phenoxyphenyl)urea;

5-[1-(2-methylpropyl)-1H-pyrazol-4-yl]-N-([1,2,4]triazolo[1,5-a]pyridin-7-ylmethyl)thiophene-2-carboxamide;

N-(imidazo[1,2-a]pyridin-7-ylmethyl)-4-[1-(pyridin-2-ylcarbonyl)piperidin-4-yl]benzamide;

4-[1-(3,3-dimethylbutanoyl)piperidin-4-yl]-N-(imidazo[1,2-a]pyridin-7-ylmethyl)benzamide;

N-(imidazo[1,2-a]pyridin-7-ylmethyl)-4-[1-(4-methylbenzoyl)piperidin-4-yl]benzamide;

4-[1-(2,2-dimethylbutanoyl)piperidin-4-yl]-N-(imidazo[1,2-a]pyridin-7-ylmethyl)benzamide;

4-[1-(cyclohexylcarbonyl)piperidin-4-yl]-N-(imidazo[1,2-a]pyridin-7-ylmethyl)benzamide;

N-(imidazo[1,2-a]pyridin-7-ylmethyl)-4-[1-(thiophen-2-ylcarbonyl)piperidin-4-yl]benzamide;

N-(imidazo[1,2-a]pyridin-7-ylmethyl)-4-[1-(3,3,3-trifluoropropanoyl)piperidin-4-yl]benzamide;

4-(1-butanoylpiperidin-4-yl)-N-(imidazo[1,2-a]pyridin-7-ylmethyl)benzamide;

4-[1-(2,4-difluorobenzoyl)piperidin-4-yl]-N-(imidazo[1,2-a]pyridin-7-ylmethyl)benzamide;

N-(imidazo[1,2-a]pyridin-7-ylmethyl)-4-[1-(2-methylbenzoyl)piperidin-4-yl]benzamide;

4-[1-(4-fluorobenzoyl)piperidin-4-yl]-N-(imidazo[1,2-a]pyridin-7-ylmethyl)benzamide;

4-[1-(2,2-dimethylpropanoyl)piperidin-4-yl]-N-(imidazo[1,2-a]pyridin-7-ylmethyl)benzamide;

N-(imidazo[1,2-a]pyridin-7-ylmethyl)-4-{1-[(2E)-2-methylpent-2-enoyl]piperidin-4-yl}benzamide;

N-(imidazo[1,2-a]pyridin-7-ylmethyl)-4-{1-[(1-methyl-1H-pyrazol-5-yl)carbonyl]piperidin-4-yl}benzamide;

N-(imidazo[1,2-a]pyridin-7-ylmethyl)-4-{1-[(3-methyloxetan-3-yl)carbonyl]piperidin-4-yl}benzamide;

4-[1-(2-fluorobenzoyl)piperidin-4-yl]-N-(imidazo[1,2-a]pyridin-7-ylmethyl)benzamide;

4-{1-[(1-cyanocyclopropyl)carbonyl]piperidin-4-yl}-N-(imidazo[1,2-a]pyridin-7-ylmethyl)benzamide;

4-[1-(cyclopentylcarbonyl)piperidin-4-yl]-N-(imidazo[1,2-a]pyridin-7-ylmethyl)benzamide;

4-[1-(3-fluorobenzoyl)piperidin-4-yl]-N-(imidazo[1,2-a]pyridin-7-ylmethyl)benzamide;

N-(imidazo[1,2-a]pyridin-7-ylmethyl)-4-{1-[(1-methyl-1H-pyrazol-4-yl)carbonyl]piperidin-4-yl}benzamide;

N-(imidazo[1,2-a]pyridin-7-ylmethyl)-4-[1-(2-oxobutanoyl)piperidin-4-yl]benzamide;

4-{1-[(2,5-dimethylfuran-3-yl)carbonyl]piperidin-4-yl}-N-(imidazo[1,2-a]pyridin-7-ylmethyl)benzamide;

4-[1-(4-cyanobenzoyl)piperidin-4-yl]-N-(imidazo[1,2-a]pyridin-7-ylmethyl)benzamide;

4-[1-(3-cyanobenzoyl)piperidin-4-yl]-N-(imidazo[1,2-a]pyridin-7-ylmethyl)benzamide;

4-[1-(2,5-difluorobenzoyl)piperidin-4-yl]-N-(imidazo[1,2-a]pyridin-7-ylmethyl)benzamide;

N-(imidazo[1,2-a]pyridin-7-ylmethyl)-4-[1-(pyrazin-2-yl-carbonyl)piperidin-4-yl]benzamide;
N-(imidazo[1,2-a]pyridin-7-ylmethyl)-4-{1-[(3-methylth-iophen-2-yl)carbonyl]piperidin-4-yl}benzamide;
4-{1-[(3,5-dimethyl-1,2-oxazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(3-methoxyben-zoyl)piperidin-4-yl]benzamide;
4-[1-(3-chlorobenzoyl)piperidin-4-yl]-N-(imidazo[1,2-a]pyridin-7-ylmethyl)benzamide;
N-(imidazo[1,2-a]pyridin-7-ylmethyl)-4-[1-(4-methoxyben-zoyl)piperidin-4-yl]benzamide;
4-[1-(4-chlorobenzoyl)piperidin-4-yl]-N-(imidazo[1,2-a]pyridin-7-ylmethyl)benzamide;
4-[1-(3,5-difluorobenzoyl)piperidin-4-yl]-N-(imidazo[1,2-a]pyridin-7-ylmethyl)benzamide;
4-[1-(cyclopropylcarbonyl)piperidin-4-yl]-N-(imidazo[1,2-a]pyridin-7-ylmethyl)benzamide;
N-(imidazo[1,2-a]pyridin-7-ylmethyl)-4-(1-propanoylpip-eridin-4-yl)benzamide;
N-(imidazo[1,2-a]pyridin-7-ylmethyl)-4-{1-[(1-methyl-1H-pyrrol-2-yl)carbonyl]piperidin-4-yl}benzamide;
N-(imidazo[1,2-a]pyridin-7-ylmethyl)-4-[1-(3-methylbu-tanoyl)piperidin-4-yl]benzamide;
N-(imidazo[1,2-a]pyridin-7-ylmethyl)-4-[1-(pyridin-4-yl-carbonyl)piperidin-4-yl]benzamide;
4-[1-(2,3-dimethylbutanoyl)piperidin-4-yl]-N-(imidazo[1,2-a]pyridin-7-ylmethyl)benzamide;
N-(imidazo[1,2-a]pyridin-7-ylmethyl)-4-[1-(pyridin-3-yl-carbonyl)piperidin-4-yl]benzamide;
N-(imidazo[1,2-a]pyridin-7-ylmethyl)-4-{1-[(1-methylcy-clopropyl)carbonyl]piperidin-4-yl}benzamide;
N-(imidazo[1,2-a]pyridin-7-ylmethyl)-4-[1-(2-methoxyben-zoyl)piperidin-4-yl]benzamide;
N-(imidazo[1,2-a]pyridin-7-ylmethyl)-5-[1-(3,3,3-trifluoro-propanoyl)pyrrolidin-3-yl]thiophene-2-carboxamide;
N-(imidazo[1,2-a]pyridin-7-ylmethyl)-5-[1-(2-methylpro-panoyl)pyrrolidin-3-yl]thiophene-2-carboxamide;
5-(1-benzoylpyrrolidin-3-yl)-N-(imidazo[1,2-a]pyridin-7-ylmethyl)thiophene-2-carboxamide;
N-(imidazo[1,2-a]pyridin-7-ylmethyl)-2-[1-(2-methylpro-panoyl)piperidin-4-yl]-1,3-thiazole-5-carboxamide;
N-(imidazo[1,2-a]pyridin-7-ylmethyl)-2-[1-(3-methylbu-tanoyl)piperidin-4-yl]-1,3-thiazole-5-carboxamide;
2-(1-benzoylpiperidin-4-yl)-N-(imidazo[1,2-a]pyridin-7-yl-methyl)-1,3-thiazole-5-carboxamide;
4-[(cyclopentylacetyl)amino]-N-([1,2,4]triazolo[1,5-a]pyri-din-7-ylmethyl)benzamide;
N-(imidazo[1,2-a]pyridin-7-ylmethyl)-4-{1-[(2S)-2-meth-ylbutanoyl]azetidin-3-yl}benzamide;
4-[1-(cyclopropylacetyl)azetidin-3-yl]-N-(imidazo[1,2-a]pyridin-7-ylmethyl)benzamide;
4-(1-benzoylazetidin-3-yl)-N-(imidazo[1,2-a]pyridin-7-yl-methyl)benzamide;
4-[1-(2-hydroxy-2-methylpropanoyl)azetidin-3-yl]-N-(imi-dazo[1,2-a]pyridin-7-ylmethyl)benzamide;
N-(imidazo[1,2-a]pyridin-7-ylmethyl)-4-[1-(tetrahydro-2H-pyran-4-ylacetyl)azetidin-3-yl]benzamide;
N-(imidazo[1,2-a]pyridin-7-ylmethyl)-4-[1-(thiophen-2-yl-carbonyl)azetidin-3-yl]benzamide;
5-[4-hydroxy-1-(3-methylbutanoyl)piperidin-4-yl]-N-(imi-dazo[1,2-a]pyridin-7-ylmethyl)thiophene-2-carboxam-ide;
5-[4-hydroxy-1-(2-methylpropanoyl)piperidin-4-yl]-N-(imidazo[1,2-a]pyridin-7-ylmethyl)thiophene-2-carboxa-mide;
5-[1-(3,3-dimethylbutanoyl)-4-hydroxypiperidin-4-yl]-N-(imidazo[1,2-a]pyridin-7-ylmethyl)thiophene-2-carboxa-mide;
5-(1-benzoyl-4-hydroxypiperidin-4-yl)-N-(imidazo[1,2-a]pyridin-7-ylmethyl)thiophene-2-carboxamide;
N-(imidazo[1,2-a]pyridin-7-ylmethyl)-4-[1-(propan-2-yl-sulfonyl)azetidin-3-yl]benzamide;
N-(imidazo[1,2-a]pyridin-7-ylmethyl)-4-{[1-(2-methylpro-panoyl)azetidin-3-yl]oxy}benzamide;
N-(imidazo[1,2-a]pyridin-7-ylmethyl)-4-({1-[(2S)-2-meth-ylbutanoyl]azetidin-3-yl}oxy)benzamide;
4-{[1-(cyclopropylacetyl)azetidin-3-yl]oxy}-N-(imidazo[1,2-a]pyridin-7-ylmethyl)benzamide;
4-[(1-benzoylazetidin-3-yl)oxy]-N-(imidazo[1,2-a]pyridin-7-ylmethyl)benzamide;
4-[1-(4-fluorobenzoyl)pyrrolidin-3-yl]-N-(imidazo[1,2-a]pyridin-7-ylmethyl)benzamide;
tert-butyl 4-{4-[([1,2,4]triazolo[1,5-a]pyridin-7-ylmethyl)carbamoyl]phenyl}piperidine-1-carboxylate;
2-cyclopentyl-N-(4-{[([1,2,4]triazolo[1,5-a]pyridin-7-ylm-ethyl)carbamoyl]amino}phenyl)acetamide;
tert-butyl 4-(4-{[([1,2,4]triazolo[1,5-a]pyridin-7-ylmethyl)carbamoyl]amino}phenyl)piperidine-1-carboxylate;
N-(imidazo[1,2-a]pyridin-7-ylmethyl)-4-(piperidin-1-ylcar-bonyl)benzamide;
4-[1-(ethylsulfonyl)azetidin-3-yl]-N-(imidazo[1,2-a]pyri-din-7-ylmethyl)benzamide;
4-[1-(cyclopropylsulfonyl)azetidin-3-yl]-N-(imidazo[1,2-a]pyridin-7-ylmethyl)benzamide;
N-(imidazo[1,2-a]pyridin-7-ylmethyl)-4-[1-(phenylsulfo-nyl)azetidin-3-yl]benzamide;
propan-2-yl 4-{5-[(imidazo[1,2-a]pyridin-7-ylmethyl)car-bamoyl]thiophen-2-yl}piperidine-1-carboxylate;
2-methylpropyl 4-{5-[(imidazo[1,2-a]pyridin-7-ylmethyl)carbamoyl]thiophen-2-yl}piperidine-1-carboxylate;
N-(imidazo[1,2-a]pyridin-7-ylmethyl)-5-[1-(3,3,3-trifluoro-propanoyl)piperidin-4-yl]thiophene-2-carboxamide;
N-(imidazo[1,2-a]pyridin-7-ylmethyl)-5-{1-[(2-methylpro-pyl)sulfonyl]piperidin-4-yl}thiophene-2-carboxamide;
N-(imidazo[1,2-a]pyridin-7-ylmethyl)-5-[1-(4,4,4-trifluo-robutanoyl)piperidin-4-yl]thiophene-2-carboxamide;
N-[(3-chloroimidazo[1,2-a]pyridin-7-yl)methyl]-4-[1-(2-methylpropanoyl)piperidin-4-yl]benzamide;
N-(imidazo[1,2-a]pyridin-7-ylmethyl)-5-{1-[(4-methyltet-rahydro-2H-pyran-4-yl)methyl]-1H-pyrazol-4-yl}thiophene-2-carboxamide;
5-[1-(2-cyano-2-methylpropyl)-1H-pyrazol-4-yl]-N-(imi-dazo[1,2-a]pyridin-7-ylmethyl)thiophene-2-carboxam-ide;
4-chloro-N-(imidazo[1,2-a]pyridin-7-ylmethyl)-5-[1-(2-me-thylpropyl)-1H-pyrazol-4-yl]thiophene-2-carboxamide;
4-chloro-N-(imidazo[1,2-a]pyridin-7-ylmethyl)-5-{1-[(3R)-tetrahydrofuran-3-ylmethyl]-1H-pyrazol-4-yl}thiophene-2-carboxamide;
N-(imidazo[1,2-a]pyridin-7-ylmethyl)-4-{1-[(2-methylcy-clopropyl)carbonyl]pyrrolidin-3-yl}benzamide;
4-[1-(cyclopentylacetyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylpen-tanoyl)pyrrolidin-3-yl]benzamide;
4-[1-(cyclopentylcarbonyl)pyrrolidin-3-yl]-N-(imidazo[1,2-a]pyridin-7-ylmethyl)benzamide;
N-(imidazo[1,2-a]pyridin-7-ylmethyl)-4-{1-[(1-methylcy-clopropyl)carbonyl]pyrrolidin-3-yl}benzamide;
4-[1-(2,2-dimethylpropanoyl)pyrrolidin-3-yl]-N-(imidazo[1,2-a]pyridin-7-ylmethyl)benzamide;

N-(imidazo[1,2-a]pyridin-7-ylmethyl)-4-[1-(1,3-thiazol-5-ylcarbonyl)pyrrolidin-3-yl]benzamide;
N-(imidazo[1,2-a]pyridin-7-ylmethyl)-4-[1-(2-methoxybenzoyl)pyrrolidin-3-yl]benzamide;
N-(imidazo[1,2-a]pyridin-7-ylmethyl)-4-[1-(1,3-thiazol-4-ylcarbonyl)pyrrolidin-3-yl]benzamide;
4-[1-(2-fluorobenzoyl)pyrrolidin-3-yl]-N-(imidazo[1,2-a]pyridin-7-ylmethyl)benzamide;
4-[1-(furan-2-ylcarbonyl)pyrrolidin-3-yl]-N-(imidazo[1,2-a]pyridin-7-ylmethyl)benzamide;
4-[1-(3-fluorobenzoyl)pyrrolidin-3-yl]-N-(imidazo[1,2-a]pyridin-7-ylmethyl)benzamide;
4-[1-(2,4-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-[(1-methyl-1H-pyrazol-3-yl)carbonyl]pyrrolidin-3-yl]benzamide;
4-[1-(2-chlorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(2-methylbenzoyl)pyrrolidin-3-yl]benzamide;
4-[1-(4-chlorobenzoyl)pyrrolidin-3-yl]-N-(imidazo[1,2-a]pyridin-7-ylmethyl)benzamide;
4-[1-(3-chlorobenzoyl)pyrrolidin-3-yl]-N-(imidazo[1,2-a]pyridin-7-ylmethyl)benzamide;
4-[1-(2,2-dimethylbutanoyl)pyrrolidin-3-yl]-N-(imidazo[1,2-a]pyridin-7-ylmethyl)benzamide;
4-[1-(3,5-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(4-methylbenzoyl)pyrrolidin-3-yl]benzamide;
N-(imidazo[1,2-a]pyridin-7-ylmethyl)-4-[1-(3-methylbutanoyl)pyrrolidin-3-yl]benzamide;
4-[1-(3,3-dimethylbutanoyl)pyrrolidin-3-yl]-N-(imidazo[1,2-a]pyridin-7-ylmethyl)benzamide;
4-[1-(3-cyanobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)pyrrolidin-3-yl]benzamide;
N-(imidazo[1,2-a]pyridin-7-ylmethyl)-4-[1-(4-methoxybenzoyl)pyrrolidin-3-yl]benzamide;
N-(imidazo[1,2-a]pyridin-7-ylmethyl)-4-{1-[(1-methyl-1H-pyrrol-2-yl)carbonyl]pyrrolidin-3-yl}benzamide;
4-[1-(cyclohexylacetyl)pyrrolidin-3-yl]-N-(imidazo[1,2-a]pyridin-7-ylmethyl)benzamide;
N-(imidazo[1,2-a]pyridin-7-ylmethyl)-4-[1-(pyridin-4-ylcarbonyl)pyrrolidin-3-yl]benzamide;
N-(imidazo[1,2-a]pyridin-7-ylmethyl)-4-[1-(pyridin-3-ylcarbonyl)pyrrolidin-3-yl]benzamide;
4-[1-(cyclohexylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)pyrrolidin-3-yl]benzamide;
4-[1-(furan-3-ylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(1,3-thiazol-2-ylcarbonyl)pyrrolidin-3-yl]benzamide;
N-(imidazo[1,2-a]pyridin-7-ylmethyl)-4-{1-[(1-methylcyclohexyl)carbonyl]pyrrolidin-3-yl}benzamide;
4-[1-(2,3-dimethylbutanoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylbenzoyl)pyrrolidin-3-yl]benzamide;
N-(imidazo[1,2-a]pyridin-7-ylmethyl)-4-[1-(thiophen-3-ylcarbonyl)pyrrolidin-3-yl]benzamide;
N-(imidazo[1,2-a]pyridin-7-ylmethyl)-4-{1-[3-(trifluoromethoxy)benzoyl]pyrrolidin-3-yl}benzamide;
N-(imidazo[1,2-a]pyridin-7-ylmethyl)-4-{1-[(3-methylthiophen-2-yl)carbonyl]pyrrolidin-3-yl}benzamide;
N-(imidazo[1,2-a]pyridin-7-ylmethyl)-4-{1-[3-(trifluoromethyl)benzoyl]pyrrolidin-3-yl}benzamide;
5-[1-(2-hydroxy-2-methylpropyl)-1H-pyrazol-4-yl]-N-([1,2,4]triazolo[1,5-a]pyridin-6-ylmethyl)thiophene-2-carboxamide;
5-{1-[(4-methyltetrahydro-2H-pyran-4-yl)methyl]-1H-pyrazol-4-yl}-N-([1,2,4]triazolo[1,5-a]pyridin-6-ylmethyl)thiophene-2-carboxamide;
N-(imidazo[1,2-a]pyridin-7-ylmethyl)-4-[1-(methylsulfonyl)azetidin-3-yl]benzamide;
N-(imidazo[1,2-a]pyridin-7-ylmethyl)-4-[1-(methylsulfonyl)pyrrolidin-3-yl]benzamide;
4-[1-(ethylsulfonyl)pyrrolidin-3-yl]-N-(imidazo[1,2-a]pyridin-7-ylmethyl)benzamide;
4-[1-(cyclopropylsulfonyl)pyrrolidin-3-yl]-N-(imidazo[1,2-a]pyridin-7-ylmethyl)benzamide;
N-(imidazo[1,2-a]pyridin-7-ylmethyl)-4-[1-(phenylsulfonyl)pyrrolidin-3-yl]benzamide;
N-(imidazo[1,2-a]pyridin-7-ylmethyl)-4-{1-[(2-methylcyclopropyl)carbonyl]azetidin-3-yl}benzamide;
4-[1-(cyclopentylacetyl)azetidin-3-yl]-N-(imidazo[1,2-a]pyridin-7-ylmethyl)benzamide;
N-(imidazo[1,2-a]pyridin-7-ylmethyl)-4-[1-(3-methylpentanoyl)azetidin-3-yl]benzamide;
4-[1-(cyclopentylcarbonyl)azetidin-3-yl]-N-(imidazo[1,2-a]pyridin-7-ylmethyl)benzamide;
N-(imidazo[1,2-a]pyridin-7-ylmethyl)-4-{1-[(1-methylcyclopropyl)carbonyl]azetidin-3-yl}benzamide;
4-[1-(2,2-dimethylpropanoyl)azetidin-3-yl]-N-(imidazo[1,2-a]pyridin-7-ylmethyl)benzamide;
N-(imidazo[1,2-a]pyridin-7-ylmethyl)-4-[1-(1,3-thiazol-5-ylcarbonyl)azetidin-3-yl]benzamide;
N-(imidazo[1,2-a]pyridin-7-ylmethyl)-4-[1-(pyrazin-2-ylcarbonyl)azetidin-3-yl]benzamide;
N-(imidazo[1,2-a]pyridin-7-ylmethyl)-4-[1-(2-methoxybenzoyl)azetidin-3-yl]benzamide;
N-(imidazo[1,2-a]pyridin-7-ylmethyl)-4-[1-(1,3-thiazol-4-ylcarbonyl)azetidin-3-yl]benzamide;
4-[1-(2-fluorobenzoyl)azetidin-3-yl]-N-(imidazo[1,2-a]pyridin-7-ylmethyl)benzamide;
4-[1-(furan-2-ylcarbonyl)azetidin-3-yl]-N-(imidazo[1,2-a]pyridin-7-ylmethyl)benzamide;
4-[1-(3-fluorobenzoyl)azetidin-3-yl]-N-(imidazo[1,2-a]pyridin-7-ylmethyl)benzamide;
4-[1-(2,4-difluorobenzoyl)azetidin-3-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-3-yl)carbonyl]azetidin-3-yl}benzamide;
4-[1-(2-chlorobenzoyl)azetidin-3-yl]-N-(imidazo[1,2-a]pyridin-7-ylmethyl)benzamide;
N-(imidazo[1,2-a]pyridin-7-ylmethyl)-4-[1-(2-methylbenzoyl)azetidin-3-yl]benzamide;
4-[1-(4-chlorobenzoyl)azetidin-3-yl]-N-(imidazo[1,2-a]pyridin-7-ylmethyl)benzamide;
4-[1-(3-chlorobenzoyl)azetidin-3-yl]-N-(imidazo[1,2-a]pyridin-7-ylmethyl)benzamide;
4-[1-(2,2-dimethylbutanoyl)azetidin-3-yl]-N-(imidazo[1,2-a]pyridin-7-ylmethyl)benzamide;
4-[1-(3,5-difluorobenzoyl)azetidin-3-yl]-N-(imidazo[1,2-a]pyridin-7-ylmethyl)benzamide;
4-[1-(4-fluorobenzoyl)azetidin-3-yl]-N-(imidazo[1,2-a]pyridin-7-ylmethyl)benzamide;
N-(imidazo[1,2-a]pyridin-7-ylmethyl)-4-[1-(4-methylbenzoyl)azetidin-3-yl]benzamide;

N-(imidazo[1,2-a]pyridin-7-ylmethyl)-4-[1-(3-methylbutanoyl)azetidin-3-yl]benzamide;
4-[1-(3,3-dimethylbutanoyl)azetidin-3-yl]-N-(imidazo[1,2-a]pyridin-7-ylmethyl)benzamide;
4-[1-(3-cyanobenzoyl)azetidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)azetidin-3-yl]benzamide;
N-(imidazo[1,2-a]pyridin-7-ylmethyl)-4-[1-(4-methoxybenzoyl)azetidin-3-yl]benzamide;
N-(imidazo[1,2-a]pyridin-7-ylmethyl)-4-{1-[(1-methyl-1H-pyrrol-2-yl)carbonyl]azetidin-3-yl}benzamide;
4-[1-(cyclohexylacetyl)azetidin-3-yl]-N-(imidazo[1,2-a]pyridin-7-ylmethyl)benzamide;
N-(imidazo[1,2-a]pyridin-7-ylmethyl)-4-[1-(pyridin-4-ylcarbonyl)azetidin-3-yl]benzamide;
N-(imidazo[1,2-a]pyridin-7-ylmethyl)-4-[1-(pyridin-3-ylcarbonyl)azetidin-3-yl]benzamide;
4-[1-(cyclohexylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)azetidin-3-yl]benzamide;
4-[1-(furan-3-ylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyrimidin-4-ylcarbonyl)azetidin-3-yl]benzamide;
N-(imidazo[1,2-a]pyridin-7-ylmethyl)-4-[1-(1,3-thiazol-2-ylcarbonyl)azetidin-3-yl]benzamide;
N-(imidazo[1,2-a]pyridin-7-ylmethyl)-4-{1-[(1-methylcyclohexyl)carbonyl]azetidin-3-yl}benzamide;
4-[1-(2,3-dimethylbutanoyl)azetidin-3-yl]-N-(imidazo[1,2-a]pyridin-7-ylmethyl)benzamide;
N-(imidazo[1,2-a]pyridin-7-ylmethyl)-4-[1-(3-methylbenzoyl)azetidin-3-yl]benzamide;
N-(imidazo[1,2-a]pyridin-7-ylmethyl)-4-[1-(thiophen-3-ylcarbonyl)azetidin-3-yl]benzamide;
N-(imidazo[1,2-a]pyridin-7-ylmethyl)-4-{1-[3-(trifluoromethoxy)benzoyl]azetidin-3-yl}benzamide;
N-(imidazo[1,2-a]pyridin-7-ylmethyl)-4-{1-[(3-methylthiophen-2-yl)carbonyl]azetidin-3-yl}benzamide;
N-(imidazo[1,2-a]pyridin-7-ylmethyl)-4-{1-[3-(trifluoromethyl)benzoyl]azetidin-3-yl}benzamide;
N-(imidazo[1,2-a]pyridin-7-ylmethyl)-4-[1-(propan-2-ylsulfonyl)pyrrolidin-3-yl]benzamide;
1-(imidazo[1,2-a]pyridin-7-ylmethyl)-3-{4-[1-(2-methoxyethyl)-1H-pyrazol-4-yl]phenyl}urea;
1-(imidazo[1,2-a]pyridin-7-ylmethyl)-3-{4-[1-(tetrahydrofuran-2-ylmethyl)-1H-pyrazol-4-yl]phenyl}urea;
1-(imidazo[1,2-a]pyridin-7-ylmethyl)-3-{4-[1-(tetrahydro-2H-pyran-4-ylmethyl)-1H-pyrazol-4-yl]phenyl}urea;
5-[1-(1,4-dioxan-2-ylmethyl)-1H-pyrazol-4-yl]-N-([1,2,4]triazolo[1,5-a]pyridin-6-ylmethyl)thiophene-2-carboxamide;
5-[1-(2-fluorobenzoyl)piperidin-4-yl]-N-(imidazo[1,2-a]pyridin-7-ylmethyl)thiophene-2-carboxamide;
tert-butyl 4-{4-[(imidazo[1,2-a]pyrazin-6-ylmethyl)carbamoyl]phenyl}piperidine-1-carboxylate;
4-[(cyclopentylacetyl)amino]-N-(imidazo[1,2-a]pyrazin-6-ylmethyl)benzamide;
tert-butyl 4-(4-{[(imidazo[1,2-a]pyrazin-6-ylmethyl)carbamoyl]amino}phenyl)piperidine-1-carboxylate;
2-cyclopentyl-N-(4-{[(imidazo[1,2-a]pyrazin-6-ylmethyl)carbamoyl]amino}phenyl)acetamide;
N-(imidazo[1,2-a]pyridin-7-ylmethyl)-4-[1-(phenylsulfonyl)piperidin-4-yl]benzamide;
N-(imidazo[1,2-a]pyridin-7-ylmethyl)-4-[1-(propan-2-ylsulfonyl)piperidin-4-yl]benzamide;
4-[1-(cyclopropylsulfonyl)piperidin-4-yl]-N-(imidazo[1,2-a]pyridin-7-ylmethyl)benzamide;
5-{(1R)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-5-{(1R)-3-methyl-1-[(tetrahydrofuran-3-ylacetyl)amino]butyl}thiophene-2-carboxamide;
5-{(1S)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-2-(1-phenylpiperidin-4-yl)-1,3-thiazole-5-carboxamide;
1-(4-{[(3R)-1-(2-fluorobenzoyl)pyrrolidin-3-yl]oxy}phenyl)-3-(imidazo[1,2-a]pyridin-7-ylmethyl)urea;
1-(4-{[(3R)-1-(3-fluorobenzoyl)pyrrolidin-3-yl]oxy}phenyl)-3-(imidazo[1,2-a]pyridin-7-ylmethyl)urea;
1-(4-{[(3R)-1-(4-fluorobenzoyl)pyrrolidin-3-yl]oxy}phenyl)-3-(imidazo[1,2-a]pyridin-7-ylmethyl)urea;
1-(4-{[(3R)-1-(2,4-difluorobenzoyl)pyrrolidin-3-yl]oxy}phenyl)-3-(imidazo[1,2-a]pyridin-7-ylmethyl)urea;
1-(imidazo[1,2-a]pyridin-7-ylmethyl)-3-[4-({(3R)-1-[4-(trifluoromethyl)benzoyl]pyrrolidin-3-yl}oxy)phenyl]urea;
1-(4-{[(3R)-1-(3,5-difluorobenzoyl)pyrrolidin-3-yl]oxy}phenyl)-3-(imidazo[1,2-a]pyridin-7-ylmethyl)urea;
1-(4-{[(3R)-1-(2-chlorobenzoyl)pyrrolidin-3-yl]oxy}phenyl)-3-(imidazo[1,2-a]pyridin-7-ylmethyl)urea;
1-(4-{[(3R)-1-(4-chlorobenzoyl)pyrrolidin-3-yl]oxy}phenyl)-3-(imidazo[1,2-a]pyridin-7-ylmethyl)urea;
N-(imidazo[1,2-a]pyridin-7-ylmethyl)-2-[1-(pyridin-2-yl)piperidin-4-yl]-1,3-thiazole-5-carboxamide;
5-{1-[(4-fluorotetrahydro-2H-pyran-4-yl)methyl]-1H-pyrazol-4-yl}-N-(imidazo[1,2-a]pyridin-7-ylmethyl)thiophene-2-carboxamide;
4-[1-(2-chlorobenzoyl)piperidin-4-yl]-N-(imidazo[1,2-a]pyridin-7-ylmethyl)benzamide;
4-[1-(2,6-difluorobenzoyl)piperidin-4-yl]-N-(imidazo[1,2-a]pyridin-7-ylmethyl)benzamide;
4-[1-(3,4-difluorobenzoyl)piperidin-4-yl]-N-(imidazo[1,2-a]pyridin-7-ylmethyl)benzamide;
N-(imidazo[1,2-a]pyridin-7-ylmethyl)-4-{1-[3-(trifluoromethyl)benzoyl]piperidin-4-yl}benzamide;
N-(imidazo[1,2-a]pyridin-7-ylmethyl)-4-{1-[3-(trifluoromethoxy)benzoyl]piperidin-4-yl}benzamide;
N-(imidazo[1,2-a]pyridin-7-ylmethyl)-4-{1-[4-(trifluoromethoxy)benzoyl]piperidin-4-yl}benzamide;
N-(imidazo[1,2-a]pyridin-7-ylmethyl)-4-{1-[4-(trifluoromethyl)benzoyl]piperidin-4-yl}benzamide;
N-(imidazo[1,2-a]pyridin-7-ylmethyl)-4-{1-[2-(trifluoromethoxy)benzoyl]piperidin-4-yl}benzamide;
N-(imidazo[1,2-a]pyridin-7-ylmethyl)-4-[1-(phenylacetyl)piperidin-4-yl]benzamide;
N-(imidazo[1,2-a]pyridin-7-ylmethyl)-4-{1-[2-(trifluoromethyl)benzoyl]piperidin-4-yl}benzamide;
1-[4-(1-butanoylpiperidin-4-yl)phenyl]-3-(imidazo[1,2-a]pyridin-7-ylmethyl)urea;
1-(imidazo[1,2-a]pyridin-7-ylmethyl)-3-(4-{1-[(2S)-2-methylbutanoyl]piperidin-4-yl}phenyl)urea;
1-(imidazo[1,2-a]pyridin-7-ylmethyl)-3-(4-{1-[(2-methylcyclopropyl)carbonyl]piperidin-4-yl}phenyl)urea;
1-{4-[1-(cyclopropylacetyl)piperidin-4-yl]phenyl}-3-(imidazo[1,2-a]pyridin-7-ylmethyl)urea;
1-(imidazo[1,2-a]pyridin-7-ylmethyl)-3-{4-[1-(3,3,3-trifluoropropanoyl)piperidin-4-yl]phenyl}urea;
1-(imidazo[1,2-a]pyridin-7-ylmethyl)-3-{4-[1-(4,4,4-trifluorobutanoyl)piperidin-4-yl]phenyl}urea;

1-(4-{1-[(4,4-difluorocyclohexyl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(phenylacetyl)piperidin-4-yl]phenyl}urea;
5-[1-(cyclopropylcarbonyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(4-methylbenzoyl)pyrrolidin-3-yl]thiophene-2-carboxamide;
1-{4-[1-(2-fluorobenzoyl)piperidin-4-yl]phenyl}-3-(imidazo[1,2-a]pyridin-7-ylmethyl)urea;
1-{4-[1-(3-fluorobenzoyl)piperidin-4-yl]phenyl}-3-(imidazo[1,2-a]pyridin-7-ylmethyl)urea;
1-{4-[1-(4-fluorobenzoyl)piperidin-4-yl]phenyl}-3-(imidazo[1,2-a]pyridin-7-ylmethyl)urea;
1-{4-[1-(2,4-difluorobenzoyl)piperidin-4-yl]phenyl}-3-(imidazo[1,2-a]pyridin-7-ylmethyl)urea;
1-{4-[1-(3,4-difluorobenzoyl)piperidin-4-yl]phenyl}-3-(imidazo[1,2-a]pyridin-7-ylmethyl)urea;
1-{4-[1-(3,5-difluorobenzoyl)piperidin-4-yl]phenyl}-3-(imidazo[1,2-a]pyridin-7-ylmethyl)urea;
1-{4-[1-(2,5-difluorobenzoyl)piperidin-4-yl]phenyl}-3-(imidazo[1,2-a]pyridin-7-ylmethyl)urea;
1-(4-{[1-(3-fluorobenzoyl)piperidin-4-yl]oxy}phenyl)-3-(imidazo[1,2-a]pyridin-7-ylmethyl)urea;
1-(4-{[1-(2,4-difluorobenzoyl)piperidin-4-yl]oxy}phenyl)-3-(imidazo[1,2-a]pyridin-7-ylmethyl)urea;
1-(4-{[1-(2,5-difluorobenzoyl)piperidin-4-yl]oxy}phenyl)-3-(imidazo[1,2-a]pyridin-7-ylmethyl)urea;
1-(4-{[1-(3,4-difluorobenzoyl)piperidin-4-yl]oxy}phenyl)-3-(imidazo[1,2-a]pyridin-7-ylmethyl)urea;
1-(4-{[1-(3,5-difluorobenzoyl)piperidin-4-yl]oxy}phenyl)-3-(imidazo[1,2-a]pyridin-7-ylmethyl)urea;
N-(imidazo[1,2-a]pyridin-7-ylmethyl)-4-[1-(phenylacetyl)pyrrolidin-3-yl]benzamide;
N-(imidazo[1,2-a]pyridin-7-ylmethyl)-4-[1-(2-methyl-2-phenylpropanoyl)pyrrolidin-3-yl]benzamide;
4-{1-[difluoro(phenyl)acetyl]pyrrolidin-3-yl}-N-(imidazo[1,2-a]pyridin-7-ylmethyl)benzamide;
N-(imidazo[1,2-a]pyridin-7-ylmethyl)-5-{1-[(4-methyltetrahydro-2H-pyran-4-yl)methyl]-1H-pyrazol-4-yl}furan-2-carboxamide;
5-[1-(2-fluorobenzoyl)piperidin-4-yl]-N-(imidazo[1,2-a]pyridin-7-ylmethyl)furan-2-carboxamide;
N-(imidazo[1,2-a]pyridin-7-ylmethyl)-5-[1-(2-methylpropanoyl)piperidin-4-yl]furan-2-carboxamide;
4-[1-(2-cyanobenzoyl)piperidin-4-yl]-N-(imidazo[1,2-a]pyridin-7-ylmethyl)benzamide;
N-(imidazo[1,2-a]pyridin-7-ylmethyl)-5-[1-(2,2,2-trifluoroethyl)-1H-pyrazol-4-yl]furan-2-carboxamide;
2-cyclopentyl-N-{4-[(imidazo[1,2-a]pyridin-7-ylacetyl)amino]phenyl}acetamide;
N-(imidazo[1,2-a]pyridin-7-ylmethyl)-5-[1-(2-methylpropyl)-1H-pyrazol-4-yl]furan-2-carboxamide;
5-(1-benzyl-1H-pyrazol-4-yl)-N-(imidazo[1,2-a]pyridin-7-ylmethyl)furan-2-carboxamide;
N-(imidazo[1,2-a]pyridin-7-ylmethyl)-5-{1-[(2S)-tetrahydrofuran-2-ylmethyl]-1H-pyrazol-4-yl}furan-2-carboxamide;
N-(imidazo[1,2-a]pyridin-7-ylmethyl)-5-{1-[(2R)-tetrahydrofuran-2-ylmethyl]-1H-pyrazol-4-yl}furan-2-carboxamide;
N-(imidazo[1,2-a]pyridin-7-ylmethyl)-5-[1-(2-methylpropanoyl)-1,2,3,6-tetrahydropyridin-4-yl]furan-2-carboxamide;
N-(imidazo[1,2-a]pyridin-7-ylmethyl)-5-[1-(3-methylbutanoyl)-1,2,3,6-tetrahydropyridin-4-yl]furan-2-carboxamide;
5-(1-benzoyl-1,2,3,6-tetrahydropyridin-4-yl)-N-(imidazo[1,2-a]pyridin-7-ylmethyl)furan-2-carboxamide;
N-(imidazo[1,2-a]pyridin-7-ylmethyl)-5-[4-(2-methylpropyl)phenyl]furan-2-carboxamide;
N-(imidazo[1,2-a]pyridin-7-ylmethyl)-5-{1-[(2S)-2-methylbutanoyl]-1,2,3,6-tetrahydropyridin-4-yl}furan-2-carboxamide;
5-[1-(3,3-dimethylbutanoyl)-1,2,3,6-tetrahydropyridin-4-yl]-N-(imidazo[1,2-a]pyridin-7-ylmethyl)furan-2-carboxamide;
5-[1-(cyclopropylacetyl)-1,2,3,6-tetrahydropyridin-4-yl]-N-(imidazo[1,2-a]pyridin-7-ylmethyl)furan-2-carboxamide;
N-(imidazo[1,2-a]pyridin-7-ylmethyl)-2-{1[(2-methylpropyl)sulfonyl]pyrrolidin-3-yl}-1,3-thiazole-5-carboxamide;
N-(imidazo[1,2-a]pyridin-7-ylmethyl)-2-[1-(phenylsulfonyl)pyrrolidin-3-yl]-1,3-thiazole-5-carboxamide;
N-(imidazo[1,2-a]pyridin-7-ylmethyl)-5-{1-[(2-methylpropyl)sulfonyl]-1,2,3,6-tetrahydropyridin-4-yl}furan-2-carboxamide;
N-(imidazo[1,2-a]pyrazin-6-ylmethyl)-5-[1-(2-methylpropyl)-1H-pyrazol-4-yl]thiophene-2-carboxamide;
tert-butyl 4-{(4-{5-[(imidazo[1,2-a]pyridin-7-ylmethyl)carbamoyl]thiophen-2-yl}-1H-pyrazol-1-yl)methyl]-4-methylpiperidine-1-carboxylate;
5-[1-(cyclopropylacetyl)pyrrolidin-3-yl]-N-(imidazo[1,2-a]pyridin-7-ylmethyl)thiophene-2-carboxamide;
5-[1-(2-chlorobenzoyl)pyrrolidin-3-yl]-N-(imidazo[1,2-a]pyridin-7-ylmethyl)thiophene-2-carboxamide;
5-{1-[(4-fluorophenyl)acetyl]pyrrolidin-3-yl}-N-(imidazo[1,2-a]pyridin-7-ylmethyl)thiophene-2-carboxamide;
N-(imidazo[1,2-a]pyridin-7-ylmethyl)-5-[1-(3-methoxybenzoyl)pyrrolidin-3-yl]thiophene-2-carboxamide;
N-(imidazo[1,2-a]pyridin-7-ylmethyl)-5-[1-(2-methoxybenzoyl)pyrrolidin-3-yl]thiophene-2-carboxamide;
5-{1-[(3-fluorophenyl)acetyl]pyrrolidin-3-yl}-N-(imidazo[1,2-a]pyridin-7-ylmethyl)thiophene-2-carboxamide;
5-[1-(3-fluorobenzoyl)pyrrolidin-3-yl]-N-(imidazo[1,2-a]pyridin-7-ylmethyl)thiophene-2-carboxamide;
5-[1-(4-fluorobenzoyl)pyrrolidin-3-yl]-N-(imidazo[1,2-a]pyridin-7-ylmethyl)thiophene-2-carboxamide;
5-{1-[(3,5-difluorophenyl)acetyl]pyrrolidin-3-yl}-N-(imidazo[1,2-a]pyridin-7-ylmethyl)thiophene-2-carboxamide;
5-{1-[(2-fluorophenyl)acetyl]pyrrolidin-3-yl}-N-(imidazo[1,2-a]pyridin-7-ylmethyl)thiophene-2-carboxamide;
5-[1-(4-cyanobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(3-methyloxetan-3-yl)carbonyl]pyrrolidin-3-yl}thiophene-2-carboxamide;
5-[1-(3,5-difluorobenzoyl)pyrrolidin-3-yl]-N-(imidazo[1,2-a]pyridin-7-ylmethyl)thiophene-2-carboxamide;
5-[1-(cyclopentylcarbonyl)pyrrolidin-3-yl]-N-(imidazo[1,2-a]pyridin-7-ylmethyl)thiophene-2-carboxamide;
5-[1-(4-chlorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(1-methyl-1H-pyrrol-2-yl)carbonyl]pyrrolidin-3-yl}thiophene-2-carboxamide;
5-[1-(2,4-difluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(pyridin-4-ylcarbonyl)pyrrolidin-3-yl]thiophene-2-carboxamide;
N-(imidazo[1,2-a]pyridin-7-ylmethyl)-5-[1-(pyridin-2-ylcarbonyl)pyrrolidin-3-yl]thiophene-2-carboxamide;

N-(imidazo[1,2-a]pyridin-7-ylmethyl)-5-{1-[(1-methyl-1H-pyrazol-4-yl)carbonyl]pyrrolidin-3-yl}thiophene-2-carboxamide;

5-[1-(2-fluorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(2E)-2-methylpent-2-enoyl]pyrrolidin-3-yl}thiophene-2-carboxamide;

5-{1-[(2,5-dimethylfuran-3-yl)carbonyl]pyrrolidin-3-yl}-N-(imidazo[1,2-a]pyridin-7-ylmethyl)thiophene-2-carboxamide;

5-[1-(3-chlorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-(1-propanoylpyrrolidin-3-yl)thiophene-2-carboxamide;

5-{1-[(1-cyanocyclopropyl)carbonyl]pyrrolidin-3-yl}-N-(imidazo[1,2-a]pyridin-7-ylmethyl)thiophene-2-carboxamide;

5-(1-butanoylpyrrolidin-3-yl)-N-(imidazo[1,2-a]pyridin-7-ylmethyl)thiophene-2-carboxamide;

5-[1-(furan-2-ylcarbonyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(4-methoxybenzoyl)pyrrolidin-3-yl]thiophene-2-carboxamide;

5-[1-(2,5-difluorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(thiophen-2-ylcarbonyl)pyrrolidin-3-yl]thiophene-2-carboxamide;

5-[1-(2,2-dimethylpropanoyl)pyrrolidin-3-yl]-N-(imidazo[1,2-a]pyridin-7-ylmethyl)thiophene-2-carboxamide;

5-[1-(3,3-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(4-methylpiperidin-4-yl)methyl]-1H-pyrazol-4-yl}thiophene-2-carboxamide;

5-{1-[(4-fluorotetrahydro-2H-pyran-4-yl)methyl]-1H-pyrazol-4-yl}-N-(imidazo[1,2-a]pyridin-7-ylmethyl)furan-2-carboxamide;

5-[1-(2,2-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(pyrazin-2-ylcarbonyl)pyrrolidin-3-yl]thiophene-2-carboxamide;

N-(imidazo[1,2-a]pyridin-7-ylmethyl)-5-{1-[(3-methylthiophen-2-yl)carbonyl]pyrrolidin-3-yl}thiophene-2-carboxamide;

N-(imidazo[1,2-a]pyridin-7-ylmethyl)-5-[1-(2-methylbenzoyl)pyrrolidin-3-yl]thiophene-2-carboxamide;

N-(imidazo[1,2-a]pyridin-7-ylmethyl)-5-{1-[(1-methylcyclopropyl)carbonyl]pyrrolidin-3-yl}thiophene-2-carboxamide;

N-(imidazo[1,2-a]pyridin-7-ylmethyl)-5-[1-(4,4,4-trifluorobutanoyl)pyrrolidin-3-yl]thiophene-2-carboxamide;

5-{1-[(3,5-dimethyl-1,2-oxazol-4-yl)carbonyl]pyrrolidin-3-yl}-N-(imidazo[1,2-a]pyridin-7-ylmethyl)thiophene-2-carboxamide;

N-(imidazo[1,2-a]pyridin-7-ylmethyl)-5-[1-(pyridin-3-ylcarbonyl)pyrrolidin-3-yl]thiophene-2-carboxamide;

N-(imidazo[1,2-a]pyridin-7-ylmethyl)-5-{1-[(1-methyl-1H-pyrazol-5-yl)carbonyl]pyrrolidin-3-yl}thiophene-2-carboxamide;

5-[1-(2,3-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(phenylsulfonyl)-1,2,3,6-tetrahydropyridin-4-yl]furan-2-carboxamide;

2-[1-(2-fluorobenzoyl)piperidin-4-yl]-N-(imidazo[1,2-a]pyridin-7-ylmethyl)-1,3-thiazole-5-carboxamide;

5-[1-(2-fluorobenzoyl)-1,2,3,6-tetrahydropyridin-4-yl]-N-(imidazo[1,2-a]pyridin-7-ylmethyl)furan-2-carboxamide;

2-[1-(2-fluorobenzoyl)pyrrolidin-3-yl]-N-(imidazo[1,2-a]pyridin-7-ylmethyl)-1,3-thiazole-5-carboxamide;

N-(imidazo[1,2-a]pyridin-7-ylmethyl)-2-[1-(2-methylpropanoyl)pyrrolidin-3-yl]-1,3-thiazole-5-carboxamide;

N-(imidazo[1,2-a]pyridin-7-ylmethyl)-2-[1-(3-methylbutanoyl)pyrrolidin-3-yl]-1,3-thiazole-5-carboxamide;

2-(1-benzoylpyrrolidin-3-yl)-N-(imidazo[1,2-a]pyridin-7-ylmethyl)-1,3-thiazole-5-carboxamide;

tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate;

N-(imidazo[1,2-a]pyridin-7-ylmethyl)-5-{1-[2-(piperazin-1-yl)ethyl]-1H-pyrazol-4-yl}thiophene-2-carboxamide;

5-{1-[(4-fluorotetrahydro-2H-pyran-4-yl)methyl]-1H-pyrazol-4-yl}-N-([1,2,4]triazolo[1,5-a]pyridin-6-ylmethyl)furan-2-carboxamide;

N-(imidazo[1,2-a]pyrazin-6-ylmethyl)-4-[1-(2-methylpropanoyl)piperidin-4-yl]benzamide;

4-[1-(4-fluorobenzoyl)piperidin-4-yl]-N-(imidazo[1,2-a]pyrazin-6-ylmethyl)benzamide;

4-[1-(2,5-difluorobenzoyl)piperidin-4-yl]-N-(imidazo[1,2-a]pyrazin-6-ylmethyl)benzamide;

N-(imidazo[1,2-a]pyrazin-6-ylmethyl)-4-{1-[(1-methylcyclopropyl)carbonyl]piperidin-4-yl}benzamide;

N-(imidazo[1,2-a]pyrazin-6-ylmethyl)-4-[1-(3,3,3-trifluoropropanoyl)piperidin-4-yl]benzamide;

N-(imidazo[1,2-a]pyrazin-6-ylmethyl)-4-[1-(3-methylbutanoyl)piperidin-4-yl]benzamide;

N-(imidazo[1,2-a]pyrazin-6-ylmethyl)-4-[1-(propan-2-ylsulfonyl)piperidin-4-yl]benzamide;

N-(imidazo[1,2-a]pyridin-7-ylmethyl)-5-[1-(2-methylpropyl)-1H-pyrazol-5-yl]furan-2-carboxamide;

N-(imidazo[1,2-a]pyrazin-6-ylmethyl)-5-[1-(2-methylpropyl)-1H-pyrazol-4-yl]furan-2-carboxamide;

5-[1-(2-methylpropyl)-1H-pyrazol-4-yl]-N-([1,2,4]triazolo[1,5-a]pyridin-6-ylmethyl)furan-2-carboxamide;

N-(imidazo[1,2-a]pyridin-7-ylmethyl)-5-[1-(3-methylbutyl)-1H-pyrazol-5-yl]furan-2-carboxamide;

5-{1-[(4-methyltetrahydro-2H-pyran-4-yl)methyl]-1H-pyrazol-4-yl}-N-([1,2,4]triazolo[1,5-a]pyridin-6-ylmethyl)furan-2-carboxamide;

N-(imidazo[1,2-a]pyridin-7-ylmethyl)-5-{[(2R)-2-(methoxymethyl)pyrrolidin-1-yl]carbonyl}thiophene-2-carboxamide;

N-(imidazo[1,2-a]pyridin-7-ylmethyl)-5-{[2-(2-methylpropyl)pyrrolidin-1-yl]carbonyl}thiophene-2-carboxamide;

5-[1-(2,2-dimethylpropyl)-1H-pyrazol-4-yl]-N-(imidazo[1,2-a]pyridin-7-ylmethyl)furan-2-carboxamide;

4-[1-(2-fluorobenzoyl)piperidin-4-yl]-N-(imidazo[1,2-a]pyrazin-6-ylmethyl)benzamide;

5-[1-(2-fluorobenzoyl)piperidin-4-yl]-N-(imidazo[1,2-a]pyrazin-6-ylmethyl)thiophene-2-carboxamide;

5-[1-(4-fluorobenzoyl)piperidin-4-yl]-N-(imidazo[1,2-a]pyrazin-6-ylmethyl)thiophene-2-carboxamide;

5-[1-(2,4-difluorobenzoyl)piperidin-4-yl]-N-(imidazo[1,2-a]pyrazin-6-ylmethyl)thiophene-2-carboxamide;

5-[1-(2,5-difluorobenzoyl)piperidin-4-yl]-N-(imidazo[1,2-a]pyrazin-6-ylmethyl)thiophene-2-carboxamide;

5-[1-(2-fluorobenzoyl)piperidin-4-yl]-N-([1,2,4]triazolo[1,5-a]pyridin-6-ylmethyl)thiophene-2-carboxamide;

5-[1-(3-fluorobenzoyl)piperidin-4-yl]-N-([1,2,4]triazolo[1,5-a]pyridin-6-ylmethyl)thiophene-2-carboxamide;

5-[1-(4-fluorobenzoyl)piperidin-4-yl]-N-([1,2,4]triazolo[1,5-a]pyridin-6-ylmethyl)thiophene-2-carboxamide;

5-[1-(2,4-difluorobenzoyl)piperidin-4-yl]-N-([1,2,4]triazolo[1,5-a]pyridin-6-ylmethyl)thiophene-2-carboxamide;
5-[1-(2,5-difluorobenzoyl)piperidin-4-yl]-N-([1,2,4]triazolo[1,5-a]pyridin-6-ylmethyl)thiophene-2-carboxamide;
5-[1-(3,5-difluorobenzoyl)piperidin-4-yl]-N-([1,2,4]triazolo[1,5-a]pyridin-6-ylmethyl)thiophene-2-carboxamide;
N-(imidazo[1,2-a]pyrazin-6-ylmethyl)-5-[1-(2-methylpropanoyl)piperidin-4-yl]thiophene-2-carboxamide;
N-(imidazo[1,2-a]pyrazin-6-ylmethyl)-5-[1-(3-methylbutanoyl)piperidin-4-yl]thiophene-2-carboxamide;
N-(imidazo[1,2-a]pyrazin-6-ylmethyl)-5-{1-[(1-methylcyclopropyl)carbonyl]piperidin-4-yl}thiophene-2-carboxamide;
N-(imidazo[1,2-a]pyrazin-6-ylmethyl)-5-[1-(4,4,4-trifluorobutanoyl)piperidin-4-yl]thiophene-2-carboxamide;
N-(imidazo[1,2-a]pyrazin-6-ylmethyl)-5-[1-(tetrahydro-2H-pyran-4-ylcarbonyl)piperidin-4-yl]thiophene-2-carboxamide;
5-[1-(2-methylpropanoyl)piperidin-4-yl]-N-([1,2,4]triazolo[1,5-a]pyridin-6-ylmethyl)thiophene-2-carboxamide;
5-[1-(3-methylbutanoyl)piperidin-4-yl]-N-([1,2,4]triazolo[1,5-a]pyridin-6-ylmethyl)thiophene-2-carboxamide;
5-{1-[(2S)-2-methylbutanoyl]piperidin-4-yl}-N-([1,2,4]triazolo[1,5-a]pyridin-6-ylmethyl)thiophene-2-carboxamide;
5-{1-[(1-methylcyclopropyl)carbonyl]piperidin-4-yl}-N-([1,2,4]triazolo[1,5-a]pyridin-6-ylmethyl)thiophene-2-carboxamide;
N-([1,2,4]triazolo[1,5-a]pyridin-6-ylmethyl)-5-[1-(3,3,3-trifluoropropanoyl)piperidin-4-yl]thiophene-2-carboxamide;
N-([1,2,4]triazolo[1,5-a]pyridin-6-ylmethyl)-5-[1-(4,4,4-trifluorobutanoyl)piperidin-4-yl]thiophene-2-carboxamide;
5-{1-[(4,4-difluorocyclohexyl)carbonyl]piperidin-4-yl}-N-([1,2,4]triazolo[1,5-a]pyridin-6-ylmethyl)thiophene-2-carboxamide;
5-[1-(tetrahydro-2H-pyran-4-ylcarbonyl)piperidin-4-yl]-N-([1,2,4]triazolo[1,5-a]pyridin-6-ylmethyl)thiophene-2-carboxamide;
5-[1-(2-hydroxy-2-methylpropanoyl)piperidin-4-yl]-N-([1,2,4]triazolo[1,5-a]pyridin-6-ylmethyl)thiophene-2-carboxamide;
5-{1-[(1-methylpiperidin-4-yl)carbonyl]piperidin-4-yl}-N-([1,2,4]triazolo[1,5-a]pyridin-6-ylmethyl)thiophene-2-carboxamide;
5-[1-(2-cyanobenzoyl)piperidin-4-yl]-N-([1,2,4]triazolo[1,5-a]pyridin-6-ylmethyl)thiophene-2-carboxamide;
5-[1-(pyridin-2-ylcarbonyl)piperidin-4-yl]-N-([1,2,4]triazolo[1,5-a]pyridin-6-ylmethyl)thiophene-2-carboxamide;
2-cyclopentyl-N-{4-[(imidazo[1,2-a]pyridin-6-ylacetyl)amino]phenyl}acetamide;
tert-butyl 4-{4-[(imidazo[1,2-b]pyridazin-6-ylmethyl)carbamoyl]phenyl}piperidine-1-carboxylate;
4-[(cyclopentylacetyl)amino]-N-(imidazo[1,2-b]pyridazin-6-ylmethyl)benzamide;
5-(1-benzyl-3-cyclopropyl-1H-pyrazol-5-yl)-N-(imidazo[1,2-a]pyridin-7-ylmethyl)thiophene-2-carboxamide;
5-[1-(2,2-dimethylpropyl)-1H-pyrazol-4-yl]-N-(imidazo[1,2-a]pyrazin-6-ylmethyl)thiophene-2-carboxamide;
5-[1-(propan-2-ylsulfonyl)piperidin-4-yl]-N-([1,2,4]triazolo[1,5-a]pyridin-6-ylmethyl)thiophene-2-carboxamide;
5-[1-(phenylsulfonyl)piperidin-4-yl]-N-([1,2,4]triazolo[1,5-a]pyridin-6-ylmethyl)thiophene-2-carboxamide;
N-(imidazo[1,2-a]pyrazin-6-ylmethyl)-5-{1-[(4-methyltetrahydro-2H-pyran-4-yl)methyl]-1H-pyrazol-4-yl}thiophene-2-carboxamide;
tert-butyl 4-{4-[(imidazo[1,2-a]pyridin-6-ylacetyl)amino]phenyl}piperidine-1-carboxylate;
N-{4-[1-(2-fluorobenzoyl)piperidin-4-yl]phenyl}-2-(imidazo[1,2-a]pyridin-6-yl)acetamide;
N-(imidazo[1,2-a]pyrazin-6-ylmethyl)-4-[1-(phenylsulfonyl)piperidin-4-yl]benzamide;
2-(imidazo[1,2-a]pyridin-6-yl)-N-{4-[1-(2-methylpropanoyl)piperidin-4-yl]phenyl}acetamide;
N-{4-[1-(2,4-difluorobenzoyl)piperidin-4-yl]phenyl}-2-(imidazo[1,2-a]pyridin-6-yl)acetamide;
N-(imidazo[1,2-a]pyridin-7-ylmethyl)-4-{[(2-methoxyphenyl)acetyl]amino}benzamide;
N-(imidazo[1,2-a]pyridin-7-ylmethyl)-4-[(phenylacetyl)amino]benzamide;
4-(benzoylamino)-N-(imidazo[1,2-a]pyridin-7-ylmethyl)benzamide;
2,5-difluoro-N-{4-[(imidazo[1,2-a]pyridin-7-ylmethyl)carbamoyl]phenyl}benzamide;
3,5-difluoro-N-{4-[(imidazo[1,2-a]pyridin-7-ylmethyl)carbamoyl]phenyl}benzamide;
3,4-difluoro-N-{4-[(imidazo[1,2-a]pyridin-7-ylmethyl)carbamoyl]phenyl}benzamide;
2,4-difluoro-N-{4-[(imidazo[1,2-a]pyridin-7-ylmethyl)carbamoyl]phenyl}benzamide;
2-fluoro-N-{4-[(imidazo[1,2-a]pyridin-7-ylmethyl)carbamoyl]phenyl}benzamide;
N-{4-[(imidazo[1,2-a]pyridin-7-ylmethyl)carbamoyl]phenyl}-3-methoxybenzamide;
4-{[(2-fluorophenyl)acetyl]amino}-N-(imidazo[1,2-a]pyridin-7-ylmethyl)benzamide;
N-(imidazo[1,2-a]pyridin-7-ylmethyl)-4-{[2-(2-methylpropyl)pyrrolidin-1-yl]carbonyl}benzamide;
N-(imidazo[1,2-a]pyridin-7-ylmethyl)-4-{[(2R)-2-(methoxymethyl)pyrrolidin-1-yl]carbonyl}benzamide;
N-(imidazo[1,2-a]pyridin-7-ylmethyl)-5-{1-[2-methyl-2-(piperazin-1-yl)propanoyl]piperidin-4-yl}thiophene-2-carboxamide;
N-{4-[(imidazo[1,2-a]pyridin-7-ylmethyl)carbamoyl]phenyl}-2-methoxybenzamide;
N-(imidazo[1,2-a]pyridin-7-ylmethyl)-4-(phenylsulfonyl)benzamide;
4-(phenylsulfonyl)-N-([1,2,4]triazolo[1,5-a]pyridin-6-ylmethyl)benzamide;
5-[1-(2,2-dimethylpropyl)-1H-pyrazol-4-yl]-N-(imidazo[1,2-a]pyridin-7-ylmethyl)thiophene-2-carboxamide;
N-(imidazo[1,2-a]pyridin-7-ylmethyl)-5-[1-(tricyclo[3.3.1.1~3,7~]dec-1-ylmethyl)-1H-pyrazol-4-yl]thiophene-2-carboxamide;
5-(1-benzyl-1H-pyrazol-4-yl)-N-(imidazo[1,2-a]pyridin-7-ylmethyl)thiophene-2-carboxamide;
N-(imidazo[1,2-a]pyridin-7-ylmethyl)-5-[1-(2-oxatricyclo[3.3.1.1~3,7~]dec-1-ylmethyl)-1H-pyrazol-4-yl]thiophene-2-carboxamide;
5-[1-(2,5-difluorobenzoyl)piperidin-4-yl]-N-(imidazo[1,2-a]pyridin-7-ylmethyl)thiophene-2-carboxamide;
5-[1-(2,4-difluorobenzoyl)piperidin-4-yl]-N-(imidazo[1,2-a]pyridin-7-ylmethyl)thiophene-2-carboxamide;
N-(imidazo[1,2-a]pyridin-7-ylmethyl)-5-{1-[2-(piperazin-1-yl)ethyl]-1H-pyrazol-4-yl}furan-2-carboxamide;
4-{[(2,5-difluorophenyl)acetyl]amino}-N-(imidazo[1,2-a]pyridin-7-ylmethyl)benzamide;
4-{[(2,4-difluorophenyl)acetyl]amino}-N-(imidazo[1,2-a]pyridin-7-ylmethyl)benzamide;
5-(3-cyclopropyl-1-methyl-1H-pyrazol-5-yl)-N-(imidazo[1,2-a]pyridin-7-ylmethyl)thiophene-2-carboxamide;

5-[3-cyclopropyl-1-(2-methoxyethyl)-1H-pyrazol-5-yl]-N-(imidazo[1,2-a]pyridin-7-ylmethyl)thiophene-2-carboxamide;

N-(imidazo[1,2-a]pyrazin-6-ylmethyl)-5-{1-[2-(piperazin-1-yl)ethyl]-1H-pyrazol-4-yl}thiophene-2-carboxamide;

4-{[difluoro(phenyl)acetyl]amino}-N-(imidazo[1,2-a]pyridin-7-ylmethyl)benzamide;

N-(imidazo[1,2-a]pyridin-7-ylmethyl)-4-[(2-methyl-2-phenylpropanoyl)amino]benzamide;

N-(imidazo[1,2-a]pyrazin-6-ylmethyl)-4-(phenylsulfonyl)benzamide;

N-(imidazo[1,2-a]pyridin-6-ylmethyl)-4-(phenylsulfonyl)benzamide;

N-(imidazo[1,2-a]pyridin-7-ylmethyl)-5-[1-(2-methylpropyl)-1H-pyrazol-5-yl]thiophene-2-carboxamide;

tert-butyl 4-{4-[(imidazo[1,2-a]pyridin-7-ylacetyl)amino]phenyl}piperidine-1-carboxylate;

N-[(3-chloroimidazo[1,2-a]pyrazin-6-yl)methyl]-4-[(cyclopentylacetyl)amino]benzamide;

N-{4-[1-(2,4-difluorobenzoyl)piperidin-4-yl]phenyl}-2-(imidazo[1,2-a]pyridin-7-yl)acetamide;

2-(imidazo[1,2-a]pyridin-7-yl)-N-{4-[1-(2-methylpropanoyl)piperidin-4-yl]phenyl}acetamide;

1-[(3-chloroimidazo[1,2-a]pyridin-7-yl)methyl]-3-{4-[1-(2-methylpropanoyl)piperidin-4-yl]phenyl}urea;

N-{4-[1-(2-fluorobenzoyl)piperidin-4-yl]phenyl}-2-(imidazo[1,2-a]pyridin-7-yl)acetamide;

N-(imidazo[1,2-a]pyridin-7-ylmethyl)-5-[1-methyl-3-(2-methylpropyl)-1H-pyrazol-5-yl]thiophene-2-carboxamide;

5-[1-benzyl-3-(2-methylpropyl)-1H-pyrazol-5-yl]-N-(imidazo[1,2-a]pyridin-7-ylmethyl)thiophene-2-carboxamide;

4-[(cyclopentylacetyl)amino]-2-fluoro-N-(imidazo[1,2-a]pyrazin-6-ylmethyl)benzamide;

N-(2,5-difluorobenzyl)-N'-(imidazo[1,2-a]pyridin-7-ylmethyl)benzene-1,4-dicarboxamide;

N-(imidazo[1,2-a]pyridin-7-ylmethyl)-4-{[2-(propan-2-yl)pyrrolidin-1-yl]carbonyl}benzamide;

N-{4-[5-(2,2-dimethylpropyl)-1,3,4-oxadiazol-2-yl]phenyl}-2-(imidazo[1,2-a]pyridin-7-yl)acetamide;

tert-butyl 4-(3-fluoro-4-{[(imidazo[1,2-a]pyridin-7-ylmethyl)carbamoyl]amino}phenyl)piperidine-1-carboxylate;

4-{1-[(2-chloropyridin-3-yl)carbonyl]piperidin-4-yl}-N-(imidazo[1,2-a]pyridin-7-ylmethyl)benzamide;

N-(imidazo[1,2-a]pyridin-7-ylmethyl)-4-[1-(3-methylbut-2-enoyl)piperidin-4-yl]benzamide;

4-[1-(3-fluoro-4-methoxybenzoyl)piperidin-4-yl]-N-(imidazo[1,2-a]pyridin-7-ylmethyl)benzamide;

N-(imidazo[1,2-a]pyridin-7-ylmethyl)-4-{1-[(2-methylcyclopent-1-en-1-yl)carbonyl]piperidin-4-yl}benzamide;

4-[1-(2-ethylbutanoyl)piperidin-4-yl]-N-(imidazo[1,2-a]pyridin-7-ylmethyl)benzamide;

4-{1-[(4-fluorophenoxy)acetyl]piperidin-4-yl}-N-(imidazo[1,2-a]pyridin-7-ylmethyl)benzamide;

4-[1-(3,5-dimethoxybenzoyl)piperidin-4-yl]-N-(imidazo[1,2-a]pyridin-7-ylmethyl)benzamide;

4-[1-(cyclohex-3-en-1-ylcarbonyl)piperidin-4-yl]-N-(imidazo[1,2-a]pyridin-7-ylmethyl)benzamide;

N-(imidazo[1,2-a]pyridin-7-ylmethyl)-4-{1-[(2-methoxyphenyl)acetyl]piperidin-4-yl}benzamide;

4-[1-(3-hydroxy-2-phenylpropanoyl)piperidin-4-yl]-N-(imidazo[1,2-a]pyridin-7-ylmethyl)benzamide;

N-(imidazo[1,2-a]pyridin-7-ylmethyl)-4-[1-(3-methylbenzoyl)piperidin-4-yl]benzamide;

4-[1-(2-acetylbenzoyl)piperidin-4-yl]-N-(imidazo[1,2-a]pyridin-7-ylmethyl)benzamide;

N-(imidazo[1,2-a]pyridin-7-ylmethyl)-4-{1-[2-(methoxymethyl)benzoyl]piperidin-4-yl}benzamide;

N-(imidazo[1,2-a]pyridin-7-ylmethyl)-4-[1-(2-phenylpropanoyl)piperidin-4-yl]benzamide;

4-[1-(2,6-dimethoxybenzoyl)piperidin-4-yl]-N-(imidazo[1,2-a]pyridin-7-ylmethyl)benzamide;

4-[1-(N,N-diethyl-beta-alanyl)piperidin-4-yl]-N-(imidazo[1,2-a]pyridin-7-ylmethyl)benzamide;

N-(imidazo[1,2-a]pyridin-7-ylmethyl)-4-(1-{[(2-methylpropyl)sulfonyl]acetyl}piperidin-4-yl)benzamide;

N-(imidazo[1,2-a]pyridin-7-ylmethyl)-4-[1-(2-phenoxypropanoyl)piperidin-4-yl]benzamide;

N-(imidazo[1,2-a]pyridin-7-ylmethyl)-4-[1-({[(1R,2S)-2-methylcyclohexyl]oxy}acetyl)piperidin-4-yl]benzamide;

4-{1-[(2-chloro-6-methylpyridin-4-yl)carbonyl]piperidin-4-yl}-N-(imidazo[1,2-a]pyridin-7-ylmethyl)benzamide;

N-(imidazo[1,2-a]pyridin-7-ylmethyl)-4-{1-[(3-methoxyphenyl)acetyl]piperidin-4-yl}benzamide;

4-[1-(2-chloro-4-cyanobenzoyl)piperidin-4-yl]-N-(imidazo[1,2-a]pyridin-7-ylmethyl)benzamide;

N-(imidazo[1,2-a]pyridin-7-ylmethyl)-4-{1-[(2E)-2-methylbut-2-enoyl]piperidin-4-yl}benzamide;

N-(imidazo[1,2-a]pyridin-7-ylmethyl)-4-{1-[(2-methoxy-5-methylphenyl)acetyl]piperidin-4-yl}benzamide;

4-[1-(2-hydroxy-3-methylbenzoyl)piperidin-4-yl]-N-(imidazo[1,2-a]pyridin-7-ylmethyl)benzamide;

1-(4-{1-[(2-chloropyridin-3-yl)carbonyl]piperidin-4-yl}phenyl)-3-(imidazo[1,2-a]pyridin-7-ylmethyl)urea;

1-(imidazo[1,2-a]pyridin-7-ylmethyl)-3-{4-[1-(3-methylbut-2-enoyl)piperidin-4-yl]phenyl}urea;

1-{4-[1-(3,3-dimethylbutanoyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(2-methylcyclopent-1-en-1-yl)carbonyl]piperidin-4-yl}phenyl)urea;

1-{4-[1-(2-ethylbutanoyl)piperidin-4-yl]phenyl}-3-(imidazo[1,2-a]pyridin-7-ylmethyl)urea;

1-(4-{1-[(4-fluorophenoxy)acetyl]piperidin-4-yl}phenyl)-3-(imidazo[1,2-a]pyridin-7-ylmethyl)urea;

1-{4-[1-(2,4-dimethoxybenzoyl)piperidin-4-yl]phenyl}-3-(imidazo[1,2-a]pyridin-7-ylmethyl)urea;

1-{4-[1-(cyclohex-3-en-1-ylcarbonyl)piperidin-4-yl]phenyl}-3-(imidazo[1,2-a]pyridin-7-ylmethyl)urea;

1-{4-[1-(2,5-dimethoxybenzoyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(2-methoxyphenyl)acetyl]piperidin-4-yl}phenyl)urea;

1-{4-[1-(3-hydroxy-2-phenylpropanoyl)piperidin-4-yl]phenyl}-3-(imidazo[1,2-a]pyridin-7-ylmethyl)urea;

1-{4-[1-(2,6-dimethoxybenzoyl)piperidin-4-yl]phenyl}-3-(imidazo[1,2-a]pyridin-7-ylmethyl)urea;

1-{4-[1-(N,N-diethyl-beta-alanyl)piperidin-4-yl]phenyl}-3-(imidazo[1,2-a]pyridin-7-ylmethyl)urea;

1-(4-{1-[(2-chloro-6-methylpyridin-4-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(3-methoxyphenyl)acetyl]piperidin-4-yl}phenyl)urea;

1-(imidazo[1,2-a]pyridin-7-ylmethyl)-3-(4-{1-[(1-oxo-2,3-dihydro-1H-inden-4-yl)carbonyl]piperidin-4-yl}phenyl)urea;

1-{4-[1-(2-chloro-4-cyanobenzoyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(2E)-2-methylbut-2-enoyl]piperidin-4-yl}phenyl)urea;

1-(imidazo[1,2-a]pyridin-7-ylmethyl)-3-{4-[1-(1H-indol-3-ylacetyl)piperidin-4-yl]phenyl}urea;
1-{4-[1-(2-hydroxy-3-methylbenzoyl)piperidin-4-yl]phenyl}-3-(imidazo[1,2-a]pyridin-7-ylmethyl)urea;
N-(imidazo[1,2-a]pyridin-7-ylmethyl)-4-[1-(pyrrolidin-1-ylcarbonyl)piperidin-4-yl]benzamide;
N-(imidazo[1,2-a]pyridin-7-ylmethyl)-4-(1-{[1-(propan-2-yl)-1H-pyrazol-3-yl]carbonyl}piperidin-4-yl)benzamide;
4-{1-[(3-cyclopropyl-1-methyl-1H-pyrazol-5-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-4,5,6,7-tetrahydro-2H-indazol-3-yl)carbonyl]piperidin-4-yl}benzamide;
N-(imidazo[1,2-a]pyridin-7-ylmethyl)-4-[1-(4,5,6,7-tetrahydro-2,1-benzoxazol-3-ylcarbonyl)piperidin-4-yl]benzamide;
4-{1-[(3-fluoro-6-methylpyridin-2-yl)carbonyl]piperidin-4-yl}-N-(imidazo[1,2-a]pyridin-7-ylmethyl)benzamide;
4-{1-[(2-chloro-3-fluoropyridin-4-yl)carbonyl]piperidin-4-yl}-N-(imidazo[1,2-a]pyridin-7-ylmethyl)benzamide;
4-{1-[(3-chloropyridin-2-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[1-(pyridin-2-yl)cyclopropyl]carbonyl}piperidin-4-yl)benzamide;
4-{1-[(1-cyclopentyl-1H-pyrazol-3-yl)carbonyl]piperidin-4-yl}-N-(imidazo[1,2-a]pyridin-7-ylmethyl)benzamide;
4-{1-[2-(3-fluorophenoxy)propanoyl]piperidin-4-yl}-N-(imidazo[1,2-a]pyridin-7-ylmethyl)benzamide;
4-(1-{[1-(difluoromethyl)-1H-pyrazol-5-yl]carbonyl}piperidin-4-yl)-N-(imidazo[1,2-a]pyridin-7-ylmethyl)benzamide;
4-[1-(3,4-dihydro-2H-chromen-6-ylcarbonyl)piperidin-4-yl]-N-(imidazo[1,2-a]pyridin-7-ylmethyl)benzamide;
4-{1-[(cyclohexyloxy)acetyl]piperidin-4-yl}-N-(imidazo[1,2-a]pyridin-7-ylmethyl)benzamide;
4-{1-[(2-chloropyridin-3-yl)acetyl]piperidin-4-yl}-N-(imidazo[1,2-a]pyridin-7-ylmethyl)benzamide;
4-{1-[(5-cyclopropyl-1,2-oxazol-3-yl)carbonyl]piperidin-4-yl}-N-(imidazo[1,2-a]pyridin-7-ylmethyl)benzamide;
4-[1-(2H-chromen-3-ylcarbonyl)piperidin-4-yl]-N-(imidazo[1,2-a]pyridin-7-ylmethyl)benzamide;
4-{1-[(3,5-difluoropyridin-2-yl)carbonyl]piperidin-4-yl}-N-(imidazo[1,2-a]pyridin-7-ylmethyl)benzamide;
4-[1-(2,3-dihydro-1,4-benzodioxin-2-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(4-methoxycyclohexyl)carbonyl]piperidin-4-yl}benzamide;
4-[1-(2,3-dihydro-1,4-benzodioxin-5-ylcarbonyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-4-ylcarbonyl)piperidin-4-yl]benzamide;
N-(imidazo[1,2-a]pyridin-7-ylmethyl)-4-{1-[(2-methyl-1,3-benzoxazol-6-yl)carbonyl]piperidin-4-yl}benzamide;
4-{1-[(1-tert-butyl-3-methyl-1H-pyrazol-5-yl)carbonyl]piperidin-4-yl}-N-(imidazo[1,2-a]pyridin-7-ylmethyl)benzamide;
4-{1-[(1-cyanocyclopentyl)carbonyl]piperidin-4-yl}-N-(imidazo[1,2-a]pyridin-7-ylmethyl)benzamide;
N-(imidazo[1,2-a]pyridin-7-ylmethyl)-4-[1-(thieno[3,2-b]pyridin-2-ylcarbonyl)piperidin-4-yl]benzamide;
N-(imidazo[1,2-a]pyridin-7-ylmethyl)-4-[1-(quinolin-7-ylcarbonyl)piperidin-4-yl]benzamide;
4-[1-(5-cyano-2-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(5,6,7,8-tetrahydroquinolin-3-ylcarbonyl)piperidin-4-yl]benzamide;
4-[1-(3,4-dihydro-2H-pyrano[2,3-b]pyridin-6-ylcarbonyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-7-ylcarbonyl)piperidin-4-yl]benzamide;
N-(imidazo[1,2-a]pyridin-7-ylmethyl)-4-[1-(quinoxalin-2-ylcarbonyl)piperidin-4-yl]benzamide;
N-(imidazo[1,2-a]pyridin-7-ylmethyl)-4-{1-[(2E)-3-(2-methoxypyridin-3-yl)prop-2-enoyl]piperidin-4-yl}benzamide;
N-(imidazo[1,2-a]pyridin-7-ylmethyl)-4-{1-[(2E)-3-(pyridin-2-yl)prop-2-enoyl]piperidin-4-yl}benzamide;
N-(imidazo[1,2-a]pyridin-7-ylmethyl)-4-{1-[(8-methylimidazo[1,2-a]pyridin-2-yl)carbonyl]piperidin-4-yl}benzamide;
4-{1-[(2-ethoxypyridin-4-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(1-methyl-4,5,6,7-tetrahydro-1H-indazol-3-yl)carbonyl]piperidin-4-yl}benzamide;
N-(imidazo[1,2-a]pyridin-7-ylmethyl)-4-{1-[(4-methyl-4H-furo[3,2-b]pyrrol-5-yl)carbonyl]piperidin-4-yl}benzamide;
4-[1-(3-cyano-5-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-8-ylcarbonyl)piperidin-4-yl]benzamide;
4-{1-[(4-cyanophenyl)acetyl]piperidin-4-yl}-N-(imidazo[1,2-a]pyridin-7-ylmethyl)benzamide;
4-[1-(3-cyano-4-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(4,5,6,7-tetrahydro-1,3-benzothiazol-2-ylcarbonyl)piperidin-4-yl]benzamide;
4-[1-(1,3-benzothiazol-2-ylcarbonyl)piperidin-4-yl]-N-(imidazo[1,2-a]pyridin-7-ylmethyl)benzamide;
4-{1-[(3-ethyl-1,2-oxazol-5-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[3-methyl-1-(prop-2-en-1-yl)-1H-pyrazol-5-yl]carbonyl}piperidin-4-yl)benzamide;
4-[1-(1,2,3-benzothiadiazol-5-ylcarbonyl)piperidin-4-yl]-N-(imidazo[1,2-a]pyridin-7-ylmethyl)benzamide;
4-{1-[(2-ethyl-1,3-thiazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[2-(propan-2-yl)pyrimidin-4-yl]carbonyl}piperidin-4-yl)benzamide;
4-{1-[(5,6-dimethylpyridin-3-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[2-(propan-2-yl)tetrahydro-2H-pyran-4-yl]carbonyl}piperidin-4-yl)benzamide;
N-(imidazo[1,2-a]pyridin-7-ylmethyl)-4-[1-(2-methoxy-6-methylbenzoyl)piperidin-4-yl]benzamide;
4-[1-(1,3-benzothiazol-7-ylcarbonyl)piperidin-4-yl]-N-(imidazo[1,2-a]pyridin-7-ylmethyl)benzamide;
1-(imidazo[1,2-a]pyridin-7-ylmethyl)-3-[4-(1-{[1-(propan-2-yl)-1H-pyrazol-3-yl]carbonyl}piperidin-4-yl)phenyl]urea;
1-(4-{1-[(2S)-2,3-dihydro-1,4-benzodioxin-2-ylcarbonyl]piperidin-4-yl}phenyl)-3-(imidazo[1,2-a]pyridin-7-ylmethyl)urea;
1-(4-{1-[(3-cyclopropyl-1-methyl-1H-pyrazol-5-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(2-methyl-4,5,6,7-tetrahydro-2H-indazol-3-yl)carbonyl]piperidin-4-yl}phenyl)urea;

1-(imidazo[1,2-a]pyridin-7-ylmethyl)-3-{4-[1-(4,5,6,7-tetrahydro-2,1-benzoxazol-3-ylcarbonyl)piperidin-4-yl]phenyl}urea;

1-(4-{1-[(2-chloro-5-fluoropyridin-4-yl)carbonyl]piperidin-4-yl}phenyl)-3-(imidazo[1,2-a]pyridin-7-ylmethyl)urea;

1-(4-{1-[(3-fluoro-6-methylpyridin-2-yl)carbonyl]piperidin-4-yl}phenyl)-3-(imidazo[1,2-a]pyridin-7-ylmethyl)urea;

1-(4-{1-[(2-chloro-3-fluoropyridin-4-yl)carbonyl]piperidin-4-yl}phenyl)-3-(imidazo[1,2-a]pyridin-7-ylmethyl)urea;

1-(4-{1-[(3-chloropyridin-2-yl)carbonyl]piperidin-4-yl}phenyl)-3-(imidazo[1,2-a]pyridin-7-ylmethyl)urea;

1-(imidazo[1,2-a]pyridin-7-ylmethyl)-3-[4-(1-{[1-(pyridin-2-yl)cyclopropyl]carbonyl}piperidin-4-yl)phenyl]urea;

1-(4-{1-[(1-cyclopentyl-1H-pyrazol-3-yl)carbonyl]piperidin-4-yl}phenyl)-3-(imidazo[1,2-a]pyridin-7-ylmethyl)urea;

1-[4-(1-{[1-(difluoromethyl)-1H-pyrazol-5-yl]carbonyl}piperidin-4-yl)phenyl]-3-(imidazo[1,2-a]pyridin-7-ylmethyl)urea;

1-{4-[1-(2,3-dihydro-1,4-benzodioxin-2-ylcarbonyl)piperidin-4-yl]phenyl}-3-(imidazo[1,2-a]pyridin-7-ylmethyl)urea;

1-{4-[1-(2,3-dihydro-1-benzofuran-2-ylcarbonyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(4-methoxycyclohexyl)carbonyl]piperidin-4-yl}phenyl)urea;

1-{4-[1-(2,3-dihydro-1,4-benzodioxin-5-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(isoquinolin-4-ylcarbonyl)piperidin-4-yl]phenyl}urea;

1-(imidazo[1,2-a]pyridin-7-ylmethyl)-3-(4-{1-[(2-methyl-1,3-benzoxazol-6-yl)carbonyl]piperidin-4-yl}phenyl)urea;

1-(4-{1-[(1-tert-butyl-3-methyl-1H-pyrazol-5-yl)carbonyl]piperidin-4-yl}phenyl)-3-(imidazo[1,2-a]pyridin-7-ylmethyl)urea;

1-(4-{1-[(1-cyanocyclopentyl)carbonyl]piperidin-4-yl}phenyl)-3-(imidazo[1,2-a]pyridin-7-ylmethyl)urea;

1-{4-[1-(cinnolin-4-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(quinolin-7-ylcarbonyl)piperidin-4-yl]phenyl}urea;

1-{4-[1-(5-cyano-2-fluorobenzoyl)piperidin-4-yl]phenyl}-3-(imidazo[1,2-a]pyridin-7-ylmethyl)urea;

1-(4-{1-[(3-cyclopropyl-1,2-oxazol-5-yl)carbonyl]piperidin-4-yl}phenyl)-3-(imidazo[1,2-a]pyridin-7-ylmethyl)urea;

1-(imidazo[1,2-a]pyridin-7-ylmethyl)-3-{4-[1-(5,6,7,8-tetrahydroquinolin-3-ylcarbonyl)piperidin-4-yl]phenyl}urea;

1-{4-[1-(3,4-dihydro-2H-pyrano[2,3-b]pyridin-6-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(isoquinolin-7-ylcarbonyl)piperidin-4-yl]phenyl}urea;

1-(imidazo[1,2-a]pyridin-7-ylmethyl)-3-{4-[1-(quinoxalin-2-ylcarbonyl)piperidin-4-yl]phenyl}urea;

1-(imidazo[1,2-a]pyridin-7-ylmethyl)-3-(4-{1-[(2E)-3-(2-methoxypyridin-3-yl)prop-2-enoyl]piperidin-4-yl}phenyl)urea;

1-(imidazo[1,2-a]pyridin-7-ylmethyl)-3-(4-{1-[(2E)-3-(pyridin-2-yl)prop-2-enoyl]piperidin-4-yl}phenyl)urea;

1-(4-{1-[(4-chloro-2,6-dimethylpyridin-3-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(8-methylimidazo[1,2-a]pyridin-2-yl)carbonyl]piperidin-4-yl}phenyl)urea;

1-(4-{1-[(2-ethoxypyridin-4-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(1-methyl-4,5,6,7-tetrahydro-1H-indazol-3-yl)carbonyl]piperidin-4-yl}phenyl)urea;

1-(imidazo[1,2-a]pyridin-7-ylmethyl)-3-(4-{1-[(4-methyl-4H-furo[3,2-b]pyrrol-5-yl)carbonyl]piperidin-4-yl}phenyl)urea;

1-(imidazo[1,2-a]pyridin-7-ylmethyl)-3-(4-{1-[(2-methyl-2,3-dihydro-1-benzofuran-5-yl)carbonyl]piperidin-4-yl}phenyl)urea;

1-(4-{1-[(4-chloro-1-ethyl-1H-pyrazol-5-yl)carbonyl]piperidin-4-yl}phenyl)-3-(imidazo[1,2-a]pyridin-7-ylmethyl)urea;

1-{4-[1-(3-cyano-5-fluorobenzoyl)piperidin-4-yl]phenyl}-3-(imidazo[1,2-a]pyridin-7-ylmethyl)urea;

1-(imidazo[1,2-a]pyridin-7-ylmethyl)-3-{4-[1-(isoquinolin-8-ylcarbonyl)piperidin-4-yl]phenyl}urea;

1-(4-{1-[(4-cyanophenyl)acetyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(3-methoxythiophen-2-yl)carbonyl]piperidin-4-yl}phenyl)urea;

1-{4-[1-(3-cyano-4-fluorobenzoyl)piperidin-4-yl]phenyl}-3-(imidazo[1,2-a]pyridin-7-ylmethyl)urea;

1-(imidazo[1,2-a]pyridin-7-ylmethyl)-3-{4-[1-(4,5,6,7-tetrahydro-1,3-benzothiazol-2-ylcarbonyl)piperidin-4-yl]phenyl}urea;

1-{4-[1-(1,3-benzothiazol-2-ylcarbonyl)piperidin-4-yl]phenyl}-3-(imidazo[1,2-a]pyridin-7-ylmethyl)urea;

1-(4-{1-[(3-ethyl-1,2-oxazol-5-yl)carbonyl]piperidin-4-yl}phenyl)-3-(imidazo[1,2-a]pyridin-7-ylmethyl)urea;

1-(imidazo[1,2-a]pyridin-7-ylmethyl)-3-[4-(1-{[3-methyl-1-(prop-2-en-1-yl)-1H-pyrazol-5-yl]carbonyl}piperidin-4-yl)phenyl]urea;

1-{4-[1-(1,2,3-benzothiadiazol-5-ylcarbonyl)piperidin-4-yl]phenyl}-3-(imidazo[1,2-a]pyridin-7-ylmethyl)urea;

1-(4-{1-[(2-ethyl-1,3-thiazol-4-yl)carbonyl]piperidin-4-yl}phenyl)-3-(imidazo[1,2-a]pyridin-7-ylmethyl)urea;

1-(4-{1-[(5,6-dimethylpyridin-3-yl)carbonyl]piperidin-4-yl}phenyl)-3-(imidazo[1,2-a]pyridin-7-ylmethyl)urea;

1-{4-[1-(1,3-benzothiazol-7-ylcarbonyl)piperidin-4-yl]phenyl}-3-(imidazo[1,2-a]pyridin-7-ylmethyl)urea;

4-{1-[(2-chloro-5-fluoropyridin-4-yl)carbonyl]piperidin-4-yl}-N-(imidazo[1,2-a]pyridin-7-ylmethyl)benzamide;

4-{1-[(3-cyclopropyl-1,2-oxazol-5-yl)carbonyl]piperidin-4-yl}-N-(imidazo[1,2-a]pyridin-7-ylmethyl)benzamide;

N-(imidazo[1,2-a]pyridin-7-ylmethyl)-4-{1-[(3-methoxythiophen-2-yl)carbonyl]piperidin-4-yl}benzamide;

N-(imidazo[1,2-a]pyridin-7-ylmethyl)-4-(1-{[2-methyl-5-(propan-2-yl)furan-3-yl]carbonyl}piperidin-4-yl)benzamide;

1-(4-{1-[2-(3-fluorophenoxy)propanoyl]piperidin-4-yl}phenyl)-3-(imidazo[1,2-a]pyridin-7-ylmethyl)urea;

1-(4-{1-[(3,5-difluoropyridin-2-yl)carbonyl]piperidin-4-yl}phenyl)-3-(imidazo[1,2-a]pyridin-7-ylmethyl)urea;

tert-butyl 4-{3-fluoro-4-[(imidazo[1,2-a]pyridin-7-ylacetyl)amino]phenyl}piperidine-1-carboxylate;

N-(imidazo[1,2-a]pyridin-7-ylmethyl)-4-[1-(piperidin-1-ylcarbonyl)piperidin-4-yl]benzamide;

1-[4-(1-benzoylpiperidin-4-yl)-2-fluorophenyl]-3-(imidazo[1,2-a]pyridin-7-ylmethyl)urea;

1-{4-[1-(2,2-dimethylpropanoyl)piperidin-4-yl]-2-fluorophenyl}-3-(imidazo[1,2-a]pyridin-7-ylmethyl)urea;
1-{4-[1-(3,3-dimethylbutanoyl)piperidin-4-yl]-2-fluorophenyl}-3-(imidazo[1,2-a]pyridin-7-ylmethyl)urea;
1-{2-fluoro-4-[1-(4-methylpentanoyl)piperidin-4-yl]phenyl}-3-(imidazo[1,2-a]pyridin-7-ylmethyl)urea;
1-(2-fluoro-4-{1-[(2S)-2-methylbutanoyl]piperidin-4-yl}phenyl)-3-(imidazo[1,2-a]pyridin-7-ylmethyl)urea;
1-{2-fluoro-4-[1-(tetrahydro-2H-pyran-4-ylcarbonyl)piperidin-4-yl]phenyl}-3-(imidazo[1,2-a]pyridin-7-ylmethyl)urea;
1-{2-fluoro-4-[1-(pyridin-2-ylcarbonyl)piperidin-4-yl]phenyl}-3-(imidazo[1,2-a]pyridin-7-ylmethyl)urea;
1-{4-[1-(2-cyanobenzoyl)piperidin-4-yl]-2-fluorophenyl}-3-(imidazo[1,2-a]pyridin-7-ylmethyl)urea;
4-{4-[(imidazo[1,2-a]pyridin-7-ylmethyl)carbamoyl]phenyl}-N,N-dimethylpiperidine-1-carboxamide;
1-{2-fluoro-4-[1-(2-methylpropanoyl)piperidin-4-yl]phenyl}-3-(imidazo[1,2-a]pyridin-7-ylmethyl)urea;
4-[(cyclopentylacetyl)amino]-N-[(7-fluoroimidazo[1,2-a]pyridin-6-yl)methyl]benzamide;
N-[(7-fluoroimidazo[1,2-a]pyridin-6-yl)methyl]-5-[1-(2-methylpropyl)-1H-pyrazol-4-yl]thiophene-2-carboxamide;
N-[4-(1-benzoylpiperidin-4-yl)-2-fluorophenyl]-2-(imidazo[1,2-a]pyridin-7-yl)acetamide;
5-{1-[2,2-dimethyl-3-(piperazin-1-yl)propyl]-1H-pyrazol-4-yl}-N-(imidazo[1,2-a]pyridin-7-ylmethyl)thiophene-2-carboxamide;
5-[1-(3-amino-2,2-dimethylpropyl)-1H-pyrazol-4-yl]-N-(imidazo[1,2-a]pyridin-7-ylmethyl)thiophene-2-carboxamide;
4-{1-[(2-cyclopropyl-1,3-thiazol-5-yl)carbonyl]piperidin-4-yl}-N-(imidazo[1,2-a]pyridin-7-ylmethyl)benzamide;
4-[1-(1,3-benzothiazol-5-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(1-methyl-1H-indazol-6-yl)carbonyl]piperidin-4-yl}benzamide;
4-{1-[(4-chloro-1,3-dimethyl-1H-pyrazol-5-yl)carbonyl]piperidin-4-yl}-N-(imidazo[1,2-a]pyridin-7-ylmethyl)benzamide;
4-{1-[(5-ethylpyridin-2-yl)carbonyl]piperidin-4-yl}-N-(imidazo[1,2-a]pyridin-7-ylmethyl)benzamide;
4-{1-[(3-chloro-5-cyanopyridin-2-yl)carbonyl]piperidin-4-yl}-N-(imidazo[1,2-a]pyridin-7-ylmethyl)benzamide;
4-{1-[(1-cyano-3-methylcyclobutyl)carbonyl]piperidin-4-yl}-N-(imidazo[1,2-a]pyridin-7-ylmethyl)benzamide;
4-{1-[(1,5-diethyl-1H-1,2,3-triazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(4-methoxythiophen-2-yl)carbonyl]piperidin-4-yl}benzamide;
4-{1-[(5-cyanothiophen-2-yl)carbonyl]piperidin-4-yl}-N-(imidazo[1,2-a]pyridin-7-ylmethyl)benzamide;
4-{1-[(5-cyclopropylpyridin-2-yl)carbonyl]piperidin-4-yl}-N-(imidazo[1,2-a]pyridin-7-ylmethyl)benzamide;
4-[1-(4-cyano-2,6-difluorobenzoyl)piperidin-4-yl]-N-(imidazo[1,2-a]pyridin-7-ylmethyl)benzamide;
4-(1-{[1-ethyl-3-(propan-2-yl)-1H-pyrazol-4-yl]carbonyl}piperidin-4-yl)-N-(imidazo[1,2-a]pyridin-7-ylmethyl)benzamide;
N-(imidazo[1,2-a]pyridin-7-ylmethyl)-4-(1-{[1-(propan-2-yl)-1H-pyrazol-3-yl]acetyl}piperidin-4-yl)benzamide;
4-[1-(1-benzofuran-3-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(3-methyl-5,6,7,8-tetrahydroimidazo[1,5-a]pyridin-1-yl)carbonyl]piperidin-4-yl}benzamide;
N-(imidazo[1,2-a]pyridin-7-ylmethyl)-4-{1-[(4-methoxy-5-methylpyridin-2-yl)carbonyl]piperidin-4-yl}benzamide;
4-{1-[(1-cyclopentyl-1H-pyrazol-5-yl)carbonyl]piperidin-4-yl}-N-(imidazo[1,2-a]pyridin-7-ylmethyl)benzamide;
4-{1-[(4-chloro-1,3-thiazol-5-yl)carbonyl]piperidin-4-yl}-N-(imidazo[1,2-a]pyridin-7-ylmethyl)benzamide;
4-{1-[(3-cyanothiophen-2-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[4-(propan-2-yl)pyrimidin-5-yl]carbonyl}piperidin-4-yl)benzamide;
N-(imidazo[1,2-a]pyridin-7-ylmethyl)-4-{1-[(1-methyl-5-propyl-1H-pyrazol-4-yl)carbonyl]piperidin-4-yl}benzamide;
4-{1-[2-(3-cyclopropyl-1H-pyrazol-1-yl)propanoyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2,3-dihydro-1-benzofuran-7-yl)carbonyl]piperidin-4-yl}benzamide;
N-(imidazo[1,2-a]pyridin-7-ylmethyl)-4-(1-{[2-(propan-2-yl)-1,3-thiazol-4-yl]carbonyl}piperidin-4-yl)benzamide;
4-(1-{[1-(difluoromethyl)-5-methyl-1H-pyrazol-3-yl]carbonyl}piperidin-4-yl)-N-(imidazo[1,2-a]pyridin-7-ylmethyl)benzamide;
4-{1-[(4-cyanothiophen-2-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(pyrazolo[1,5-a]pyridin-2-ylcarbonyl)piperidin-4-yl]benzamide;
4-[1-(1-benzofuran-5-ylcarbonyl)piperidin-4-yl]-N-(imidazo[1,2-a]pyridin-7-ylmethyl)benzamide;
N-(imidazo[1,2-a]pyridin-7-ylmethyl)-4-(1-{[2-(propan-2-yl)-1,3-oxazol-4-yl]carbonyl}piperidin-4-yl)benzamide;
N-(imidazo[1,2-a]pyridin-7-ylmethyl)-4-{1-[(2-methoxy-5-methylpyridin-3-yl)carbonyl]piperidin-4-yl}benzamide;
4-{1-[(5,6-dimethoxypyridin-2-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2H-indazol-4-yl)carbonyl]piperidin-4-yl}benzamide;
4-{1-[(2-ethylpiperidin-1-yl)(oxo)acetyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2H-indazol-6-yl)carbonyl]piperidin-4-yl}benzamide;
N-(imidazo[1,2-a]pyridin-7-ylmethyl)-4-{1-[(1-methyl-1H-indazol-4-yl)carbonyl]piperidin-4-yl}benzamide;
N-(imidazo[1,2-a]pyridin-7-ylmethyl)-4-(1-{[2-(trifluoromethyl)furan-3-yl]carbonyl}piperidin-4-yl)benzamide;
1-(4-{1-[(2-cyclopropyl-1,3-thiazol-5-yl)carbonyl]piperidin-4-yl}phenyl)-3-(imidazo[1,2-a]pyridin-7-ylmethyl)urea;
1-{4-[1-(1,3-benzothiazol-5-ylcarbonyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(1-methyl-1H-indazol-6-yl)carbonyl]piperidin-4-yl}phenyl)urea;
1-(4-{1-[(4-chloro-1,3-dimethyl-1H-pyrazol-5-yl)carbonyl]piperidin-4-yl}phenyl)-3-(imidazo[1,2-a]pyridin-7-ylmethyl)urea;
1-(4-{1-[(5-ethylpyridin-2-yl)carbonyl]piperidin-4-yl}phenyl)-3-(imidazo[1,2-a]pyridin-7-ylmethyl)urea;
1-(4-{1-[(3-chloro-5-cyanopyridin-2-yl)carbonyl]piperidin-4-yl}phenyl)-3-(imidazo[1,2-a]pyridin-7-ylmethyl)urea;
1-(4-{1-[(1-cyano-3-methylcyclobutyl)carbonyl]piperidin-4-yl}phenyl)-3-(imidazo[1,2-a]pyridin-7-ylmethyl)urea;
1-(4-{1-[(1,5-diethyl-1H-1,2,3-triazol-4-yl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(thieno[3,2-b]furan-5-ylcarbonyl)piperidin-4-yl]phenyl}urea;

1-(imidazo[1,2-a]pyridin-7-ylmethyl)-3-(4-{1-[(4-methoxythiophen-2-yl)carbonyl]piperidin-4-yl}phenyl)urea;
1-(4-{1-[(5-cyanothiophen-2-yl)carbonyl]piperidin-4-yl}phenyl)-3-(imidazo[1,2-a]pyridin-7-ylmethyl)urea;
1-(4-{1-[(5-cyclopropylpyridin-2-yl)carbonyl]piperidin-4-yl}phenyl)-3-(imidazo[1,2-a]pyridin-7-ylmethyl)urea;
1-{4-[1-(4-cyano-2,6-difluorobenzoyl)piperidin-4-yl]phenyl}-3-(imidazo[1,2-a]pyridin-7-ylmethyl)urea;
1-[4-(1-{[1-ethyl-3-(propan-2-yl)-1H-pyrazol-4-yl]carbonyl}piperidin-4-yl)phenyl]-3-(imidazo[1,2-a]pyridin-7-ylmethyl)urea;
1-{4-[1-(1-benzofuran-3-ylcarbonyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(4-methoxy-5-methylpyridin-2-yl)carbonyl]piperidin-4-yl}phenyl)urea;
1-(4-{1-[(1-cyclopentyl-1H-pyrazol-5-yl)carbonyl]piperidin-4-yl}phenyl)-3-(imidazo[1,2-a]pyridin-7-ylmethyl)urea;
1-(4-{1-[(4-chloro-1,3-thiazol-5-yl)carbonyl]piperidin-4-yl}phenyl)-3-(imidazo[1,2-a]pyridin-7-ylmethyl)urea;
1-(4-{1-[(3-cyanothiophen-2-yl)carbonyl]piperidin-4-yl}phenyl)-3-(imidazo[1,2-a]pyridin-7-ylmethyl)urea;
1-(imidazo[1,2-a]pyridin-7-ylmethyl)-3-[4-(1-{[4-(propan-2-yl)pyrimidin-5-yl]carbonyl}piperidin-4-yl)phenyl]urea;
1-(imidazo[1,2-a]pyridin-7-ylmethyl)-3-(4-{1-[(1-methyl-5-propyl-1H-pyrazol-4-yl)carbonyl]piperidin-4-yl}phenyl)urea;
1-(4-{1-[2-(3-cyclopropyl-1H-pyrazol-1-yl)propanoyl]piperidin-4-yl}phenyl)-3-(imidazo[1,2-a]pyridin-7-ylmethyl)urea;
1-(imidazo[1,2-a]pyridin-7-ylmethyl)-3-{4-[1-(pyrazolo[1,5-a]pyridin-2-ylcarbonyl)piperidin-4-yl]phenyl}urea;
1-{4-[1-(1-benzofuran-5-ylcarbonyl)piperidin-4-yl]phenyl}-3-(imidazo[1,2-a]pyridin-7-ylmethyl)urea;
1-(imidazo[1,2-a]pyridin-7-ylmethyl)-3-[4-(1-{[2-(propan-2-yl)-1,3-oxazol-4-yl]carbonyl}piperidin-4-yl)phenyl]urea;
1-(imidazo[1,2-a]pyridin-7-ylmethyl)-3-(4-{1-[(1-methyl-1H-indazol-7-yl)carbonyl]piperidin-4-yl}phenyl)urea;
1-(imidazo[1,2-a]pyridin-7-ylmethyl)-3-(4-{1-[(2-methoxy-5-methylpyridin-3-yl)carbonyl]piperidin-4-yl}phenyl)urea;
1-(4-{1-[(5,6-dimethoxypyridin-2-yl)carbonyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(2-methyl-2H-indazol-4-yl)carbonyl]piperidin-4-yl}phenyl)urea;
1-(4-{1-[(2-ethylpiperidin-1-yl)(oxo)acetyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(2-methyl-2H-indazol-6-yl)carbonyl]piperidin-4-yl}phenyl)urea;
1-(imidazo[1,2-a]pyridin-7-ylmethyl)-3-(4-{1-[(1-methyl-1H-indazol-4-yl)carbonyl]piperidin-4-yl}phenyl)urea;
1-(imidazo[1,2-a]pyridin-7-ylmethyl)-3-[4-(1-{[2-(trifluoromethyl)furan-3-yl]carbonyl}piperidin-4-yl)phenyl]urea; and pharmaceutically acceptable salts thereof.

Still another embodiment pertains to compounds of Formula (IA), selected from the group consisting of
4-(1-benzoylpiperidin-4-yl)-N-(imidazo[1,2-a]pyridin-7-ylmethyl)benzamide;
4-[1-(4-fluorobenzoyl)piperidin-4-yl]-N-(imidazo[1,2-a]pyridin-7-ylmethyl)benzamide;
4-[1-(2-fluorobenzoyl)piperidin-4-yl]-N-(imidazo[1,2-a]pyridin-7-ylmethyl)benzamide;
4-[1-(3-fluorobenzoyl)piperidin-4-yl]-N-(imidazo[1,2-a]pyridin-7-ylmethyl)benzamide;
4-[1-(3-chlorobenzoyl)piperidin-4-yl]-N-(imidazo[1,2-a]pyridin-7-ylmethyl)benzamide;
4-[1-(4-chlorobenzoyl)piperidin-4-yl]-N-(imidazo[1,2-a]pyridin-7-ylmethyl)benzamide;
4-[1-(2-chlorobenzoyl)piperidin-4-yl]-N-(imidazo[1,2-a]pyridin-7-ylmethyl)benzamide;
4-[1-(3-fluoro-4-methoxybenzoyl)piperidin-4-yl]-N-(imidazo[1,2-a]pyridin-7-ylmethyl)benzamide;
4-[1-(3,5-dimethoxybenzoyl)piperidin-4-yl]-N-(imidazo[1,2-a]pyridin-7-ylmethyl)benzamide;
N-(imidazo[1,2-a]pyridin-7-ylmethyl)-4-[1-(3-methylbenzoyl)piperidin-4-yl]benzamide;
4-[1-(2-acetylbenzoyl)piperidin-4-yl]-N-(imidazo[1,2-a]pyridin-7-ylmethyl)benzamide;
N-(imidazo[1,2-a]pyridin-7-ylmethyl)-4-{1-[2-(methoxymethyl)benzoyl]piperidin-4-yl}benzamide;
4-[1-(2,6-dimethoxybenzoyl)piperidin-4-yl]-N-(imidazo[1,2-a]pyridin-7-ylmethyl)benzamide;
4-[1-(2-chloro-4-cyanobenzoyl)piperidin-4-yl]-N-(imidazo[1,2-a]pyridin-7-ylmethyl)benzamide;
4-[1-(2-hydroxy-3-methylbenzoyl)piperidin-4-yl]-N-(imidazo[1,2-a]pyridin-7-ylmethyl)benzamide;
4-[1-(5-cyano-2-fluorobenzoyl)piperidin-4-yl]-N-(imidazo[1,2-a]pyridin-7-ylmethyl)benzamide;
4-[1-(3-cyano-5-fluorobenzoyl)piperidin-4-yl]-N-(imidazo[1,2-a]pyridin-7-ylmethyl)benzamide;
4-[1-(3-cyano-4-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(2-methoxy-6-methylbenzoyl)piperidin-4-yl]benzamide;
4-[1-(4-cyano-2,6-difluorobenzoyl)piperidin-4-yl]-N-(imidazo[1,2-a]pyridin-7-ylmethyl)benzamide; and pharmaceutically acceptable salts thereof.

Another embodiment pertains to a composition for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic upus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said composition comprising an excipient and a therapeutically effective amount of a compound of Formula (IA), or pharmaceutically acceptable salts thereof.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said method comprising administering to the patient a therapeutically effective amount of a compound of Formula (IA), or pharmaceutically acceptable salts thereof.

Another embodiment pertains to a method of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia or spleen cancer in a patient, said method comprising administering to the patient therapeutically effective amount of the compound of Formula (IA), or pharmaceutically acceptable salts thereof; and a therapeutically effective amount of one additional therapeutic agent or more than one additional therapeutic agent.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include 1,2,3,6-tetrahydropyridine, thiomorpholinyl, tetrahydropyranyl, furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, pyrrolidin-2-only, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused-ring heterocyclyls include hexahydro-furo[3,4-c]pyrrole, hexahydro-furo[3,4-b]pyrrole, octahydro-pyrrolo[3,4-b]pyridine, octahydro-pyrrolo[3,4-c]pyridine, (3aR,6aR)-5-methyl-octahydro-pyrrolo[3,4-b]pyrrole, (3aR,6aR)-octahydro-pyrrolo[3,4-b]pyrrole, 6-methyl-2,6-diaza-bicyclo[3.2.0]heptane, (3aS,6aR)-2-methyl-octahydro-pyrrolo[3,4-c]pyrrole, decahydro-[1,5]naphthyridine, 2,3-dihydrobenzofuranyl, 2,3,4,9-tetrahydro-1H-pyrido[3,4-b]indolyl, thieno[3,2-c]pyridinyl, furo[3,2-c]pyridinyl, phthalazin-1(2H)-onyl, isoquinolinyl, isoquinolin-1(2H)-onyl, 5,6,7,8-tetrahydrophthalazin-1(2H)-onyl, fluorophthalazin-1(2H)-onyl, (Z)-3H-benzo[d][1,2]diazepin-4(5H)-onyl, (trifluoromethyl)phthalazin-1(2H)-onyl, pyrrolo[1,2-d][1,2,4]triazin-1(2H)-onyl, 1,2,3,4-tetrahydroisoquinolinyl, 2,3-dihydrobenzo[b][1,4]dioxinyl, 5,6,7,8-tetrahydrophthalazin-1(2H)-onyl, 5,6,7,8-tetrahydro-[1,2,4]triazolo[4,3-a]pyrazinyl, 5,6,7,8-tetrahydroimidazo[1,5-a]pyrazinyl, thieno[3,2-c]pyridinyl, furo[3,2-c]pyridinyl, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as benzimidazolyl, benzo[d][1,3]dioxolyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl). Examples of spirocyclic heterocyclyls include 1,4-dioxa-8-azaspiro[4.5]decanyl.

The term "5-6 membered heteroaryl" (alone or in combination with another term(s)) means aromatic heterocyclyl containing a total of 5 to 6 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, and purinyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$- prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to NAMPT activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for X, $R^1$, and Z in compounds of Formula (I) are independently selected. The described embodiments of the present invention may be combined. Such combination is contemplated and within the scope of the present invention. For example, it is contemplated that embodiments for any of X, $R^1$, and Z can be combined with embodiments defined for any other of X, $R^1$, and Z.

Embodiments of Formula (I)

One embodiment, therefore, pertains to compounds or pharmaceutically acceptable salts thereof, which are useful as inhibitors of NAMPT, the compounds having Formula (I)

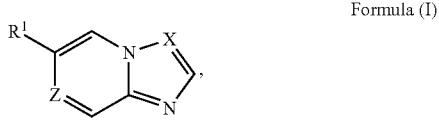

Formula (I)

wherein

X is N or $CY^1$;

$Y^1$ is independently selected from the group consisting of hydrogen, alkyl, alkoxy, haloalkyl, hydroxyalkyl, OH, CN, F, Cl, Br, and I;

$R^1$ is independently selected from the group consisting of $NHC(O)NHR^3$, $NHC(O)NH(CH_2)_mR^{3x}$, $CH_2NHC(O)NHR^3$, $NHC(O)R^3$, $NHC(O)(CH_2)_nR^3$, $C(O)NH(CH_2)_nR^3$, $NHC(O)(CH_2)_mR^{3x}$, $C(O)NH(CH_2)_mR^{3x}$, $CH_2C(O)NHR^3$; and $CH_2NHC(O)R^3$; and Z is CH or N; or X is N or $CY^1$;

$Y^1$ is independently selected from the group consisting of hydrogen, alkyl, alkoxy, haloalkyl, hydroxyalkyl, OH, CN, F, Cl, Br, and I;

$R^1$ is hydrogen;

Z is $CR^2$; and $R^2$ is independently selected from the group consisting of $NHC(O)NHR^3$, $NHC(O)NH(CH_2)_mR^{3x}$, $CH_2NHC(O)NHR^3$, $NHC(O)R^3$, $NHC(O)(CH_2)_nR^3$, $C(O)NH(CH_2)_nR^3$, $NHC(O)(CH_2)_mR^{3x}$, $C(O)NH(CH_2)_mR^{3x}$, $CH_2C(O)NHR^3$; and $CH_2NHC(O)R^3$; and $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^{3x}$ is independently selected from the group consisting of phenyl and heterocyclyl; wherein each $R^{3x}$ phenyl and heterocyclyl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)$ OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$ at each occurrence, is independently selected from the group consisting of haloalkyl, alkyl, alkenyl, and alkynyl;

R$^{11}$ at each occurrence, is independently selected from the group consisting of alkyl, alkenyl, and alkynyl;

m is 4, 5, or 6; and n is 1 or 2;

with the provisos that when X is CY$^1$ and Y$^1$ is hydrogen; and R$^3$ is thiazolyl; the R$^3$ thiazolyl is substituted with one substituent;

when X is CY$^1$ and Y$^1$ is hydrogen; R$^1$ is NHC(O)R$^3$; R$^2$ is hydrogen; and R$^3$ is phenyl; the R$^3$ phenyl is not substituted at the para position with phenyl;

when X is CY$^1$ and Y$^1$ is hydrogen; R$^1$ is C(O)NH(CH$_2$)$_n$R$^3$; n is 1; R$^2$ is hydrogen; and R$^3$ is phenyl; the R$^3$ phenyl is not substituted at the para position with phenylmethoxy or 3-fluorophenoxy;

when X is CY$^1$ and Y$^1$ is hydrogen; R$^1$ is C(O)NH(CH$_2$)$_n$R$^3$; n is 1; R$^2$ is hydrogen; and R$^3$ is furanyl; the R$^3$ furanyl is not substituted with benzyl, or 3-fluorophenyl methyl;

when X is CY$^1$ and Y$^1$ is hydrogen; R$^1$ is C(O)NH(CH$_2$)$_n$R$^3$; n is 1; R$^2$ is hydrogen; and R$^3$ is thienyl; the R$^3$ thienyl is not substituted with phenoxy, 3-fluorophenoxy, or 3-chlorophenoxy; and when X is CY$^1$ and Y$^1$ is hydrogen; R$^1$ is C(O)NH(CH$_2$)$_n$R$^3$; n is 1; R$^2$ is hydrogen; and R$^3$ is R$^3$ phenyl; the phenyl is not substituted at the para position with SO$_2$R$^4$ or SO$_2$NHR$^4$.

In one embodiment of Formula (I), X is N or CY$^1$. In another embodiment of Formula (I), X is N. In another embodiment of Formula (I), X is CY$^1$.

In one embodiment of Formula (I), X is CY$^1$; and Y$^1$ is independently selected from the group consisting of hydrogen, alkyl, alkoxy, haloalkyl, hydroxyalkyl, OH, CN, F, Cl, Br, and I. In another embodiment of Formula (I), X is CY$^1$; and Y$^1$ is independently selected from the group consisting of hydrogen, Cl, Br, and I. In another embodiment of Formula (I), X is CY$^1$; and Y$^1$ is Cl. In another embodiment of Formula (I), X is CY$^1$; and Y$^1$ is hydrogen.

In one embodiment of Formula (I), Z is CH or N; R$^1$ is independently selected from the group consisting of NHC(O)NHR$^3$, NHC(O)NH(CH$_2$)$_m$R$^{3x}$, CH$_2$NHC(O)NHR$^3$, NHC(O)R$^3$, NHC(O)(CH$_2$)$_n$R$^3$, C(O)NH(CH$_2$)$_n$R$^3$, NHC(O)(CH$_2$)$_m$R$^{3x}$, C(O)NH(CH$_2$)$_m$R$^{3x}$, CH$_2$C(O)NHR$^3$, and CH$_2$NHC(O)R$^3$; and R$^2$ is hydrogen. In another embodiment of Formula (I), Z is CH or N; R$^1$ is NHC(O)NHR$^3$; and R$^2$ is hydrogen. In another embodiment of Formula (I), Z is CH or N; R$^1$ is NHC(O)NH(CH$_2$)$_m$R$^{3x}$; and R$^2$ is hydrogen. In another embodiment of Formula (I), Z is CH or N; R$^1$ is CH$_2$NHC(O)NHR$^3$; and R$^2$ is hydrogen. In another embodiment of Formula (I), Z is CH or N; R$^1$ is NHC(O)R$^3$; and R$^2$ is hydrogen. In another embodiment of Formula (I), Z is CH or N; R$^1$ is NHC(O)(CH$_2$)$_n$R$^3$; and R$^2$ is hydrogen. In another embodiment of Formula (I), Z is CH or N; R$^1$ is C(O)NH(CH$_2$)$_n$R$^3$; and R$^2$ is hydrogen. In another embodiment of Formula (I), Z is CH or N; R$^1$ is NHC(O)(CH$_2$)$_m$R$^{3x}$; and R$^2$ is hydrogen. In another embodiment of Formula (I), Z is CH or N; R$^1$ is C(O)NH(CH$_2$)$_m$R$^{3x}$; and R$^2$ is hydrogen. In another embodiment of Formula (I), Z is CH or N; R$^1$ is CH$_2$C(O)NHR$^3$; and R$^2$ is hydrogen. In another embodiment of Formula (I), Z is CH or N; R$^1$ is CH$_2$NHC(O)R$^3$; and R$^2$ is hydrogen.

In one embodiment of Formula (I), Z is CH; R$^1$ is independently selected from the group consisting of NHC(O)NHR$^3$, NHC(O)NH(CH$_2$)$_m$R$^{3x}$, CH$_2$NHC(O)NHR$^3$, NHC(O)R$^3$, NHC(O)(CH$_2$)$_n$R$^3$, C(O)NH(CH$_2$)$_n$R$^3$, NHC(O)(CH$_2$)$_m$R$^{3x}$, C(O)NH(CH$_2$)$_m$R$^{3x}$, CH$_2$C(O)NHR$^3$, and CH$_2$NHC(O)R$^3$; and R$^2$ is hydrogen. In another embodiment of Formula (I), Z is CH; R$^1$ is NHC(O)NHR$^3$; and R$^2$ is hydrogen. In another embodiment of Formula (I), Z is CH; R$^1$ is NHC(O)NH(CH$_2$)$_m$R$^{3x}$; and R$^2$ is hydrogen. In another embodiment of Formula (I), Z is CH; R$^1$ is CH$_2$NHC(O)NHR$^3$; and R$^2$ is hydrogen. In another embodiment of Formula (I), Z is CH; R$^1$ is NHC(O)R$^3$; and R$^2$ is hydrogen. In another embodiment of Formula (I), Z is CH; R$^1$ is NHC(O)(CH$_2$)$_n$R$^3$; and R$^2$ is hydrogen. In another embodiment of Formula (I), Z is CH; R$^1$ is C(O)NH(CH$_2$)$_n$R$^3$; and R$^2$ is hydrogen. In another embodiment of Formula (I), Z is CH; R$^1$ is NHC(O)(CH$_2$)$_m$R$^{3x}$; and R$^2$ is hydrogen. In another embodiment of Formula (I), Z is CH; R$^1$ is C(O)NH(CH$_2$)$_m$R$^{3x}$; and R$^2$ is hydrogen. In another embodiment of Formula (I), Z is CH; R$^1$ is CH$_2$C(O)NHR$^3$;

and R² is hydrogen. In another embodiment of Formula (I), Z is CH; R¹ is CH₂NHC(O)R³; and R² is hydrogen.

In one embodiment of Formula (I), Z is N; R¹ is independently selected from the group consisting of NHC(O)NHR³, NHC(O)NH(CH₂)$_m$R$^{3x}$, CH₂NHC(O)NHR³, NHC(O)R³, NHC(O)(CH₂)$_n$R³, C(O)NH(CH₂)$_n$R³, NHC(O)(CH₂)$_m$R$^{3x}$, C(O)NH(CH₂)$_m$R$^{3x}$, CH₂C(O)NHR³, and CH₂NHC(O)R³; and R² is hydrogen. In another embodiment of Formula (I), Z is N; R¹ is NHC(O)NHR³; and R² is hydrogen. In another embodiment of Formula (I), Z is N; R¹ is NHC(O)NH(CH₂)$_m$R$^{3x}$; and R² is hydrogen. In another embodiment of Formula (I), Z is N; R¹ is CH₂NHC(O)NHR³; and R² is hydrogen. In another embodiment of Formula (I), Z is N; R¹ is NHC(O)R³; and R² is hydrogen. In another embodiment of Formula (I), Z is N; R¹ is NHC(O)(CH₂)$_n$R³; and R² is hydrogen. In another embodiment of Formula (I), Z is N; R¹ is C(O)NH(CH₂)$_n$R³; and R² is hydrogen. In another embodiment of Formula (I), Z is N; R¹ is NHC(O)(CH₂)$_m$R$^{3x}$; and R² is hydrogen. In another embodiment of Formula (I), Z is N; R¹ is C(O)NH(CH₂)$_m$R$^{3x}$; and R² is hydrogen. In another embodiment of Formula (I), Z is N; R¹ is CH₂C(O)NHR³; and R² is hydrogen. In another embodiment of Formula (I), Z is N; R¹ is CH₂NHC(O)R³; and R² is hydrogen.

In one embodiment of Formula (I), R¹ is hydrogen; Z is CR²; and R² is independently selected from the group consisting of NHC(O)NHR³, NHC(O)NH(CH₂)$_m$R$^{3x}$, CH₂NHC(O)NHR³, NHC(O)R³, NHC(O)(CH₂)$_n$R³, C(O)NH(CH₂)$_n$R³, NHC(O)(CH₂)$_m$R$^{3x}$, C(O)NH(CH₂)$_m$R$^{3x}$, CH₂C(O)NHR³, and CH₂NHC(O)R³. In another embodiment of Formula (I), R¹ is hydrogen; Z is CR²; and R² is NHC(O)NHR³. In another embodiment of Formula (I), R¹ is hydrogen; Z is CR²; and R² is NHC(O)NH(CH₂)$_m$R$^{3x}$. In another embodiment of Formula (I), R¹ is hydrogen; Z is CR²; and R² is CH₂NHC(O)NHR³. In another embodiment of Formula (I), R¹ is hydrogen; Z is CR²; and R² is NHC(O)R³. In another embodiment of Formula (I), R¹ is hydrogen; Z is CR²; and R² is NHC(O)(CH₂)$_n$R³. In another embodiment of Formula (I), R¹ is hydrogen; Z is CR²; and R² is C(O)NH(CH₂)$_n$R³. In another embodiment of Formula (I), R¹ is hydrogen; Z is CR²; and R² is NHC(O)(CH₂)$_m$R$^{3x}$. In another embodiment of Formula (I), R¹ is hydrogen; Z is CR²; and R² is C(O)NH(CH₂)$_m$R$^{3x}$. In another embodiment of Formula (I), R¹ is hydrogen; Z is CR²; and R² is CH₂C(O)NHR³. In another embodiment of Formula (I), R¹ is hydrogen; Z is CR²; and R² is CH₂NHC(O)R³.

In one embodiment of Formula (I), m is 4, 5, or 6. In another embodiment of Formula (I), m is 4. In another embodiment of Formula (I), m is 5. In another embodiment of Formula (I), m is 6.

In one embodiment of Formula (I), n is 1 or 2. In another embodiment of Formula (I), n is 1. In another embodiment of Formula (I), n is 2.

In one embodiment of Formula (I), R³ is independently selected from the group consisting of phenyl and 5-6 membered heteroaryl; wherein each R³ phenyl is substituted at the para position with one substituent independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I; wherein each R³ phenyl is optionally additionally substituted with one substituent independently selected from the group consisting of alkyl, haloalkyl, alkoxyalkyl, hydroxyalkyl, C(O)H, C(O)OH, C(N)NH₂, OH, CN, N₃, NO₂, F, Cl, Br and I; wherein each R³ 5-6 membered heteroaryl is substituted with one, two, three or four substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I. In another embodiment of Formula (I), R³ is independently selected from the group consisting of phenyl and 5-6 membered heteroaryl; wherein each R³ phenyl is substituted at the para position with one substituent independently selected from the group consisting of R⁴, OR⁴, C(O)R⁴, NHC(O)R⁴, NR⁴C(O)R⁴, NHS(O)₂R⁴, NHC(O)OR⁴, and C(O)NHR⁴; wherein each R³ phenyl is optionally additionally substituted with one substituent independently selected from the group consisting of F, Cl, Br and I; wherein each R³ 5-6 membered heteroaryl is substituted with one, two, three or four substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I.

In one embodiment of Formula (I), R³ is phenyl; wherein each R³ phenyl is substituted at the para position with one substituent independently selected from the group consisting of R⁴, OR⁴, C(O)R⁴, NHC(O)R⁴, NR⁴C(O)R⁴, NHS(O)₂R⁴, NHC(O)OR⁴, and C(O)NHR⁴; and wherein each R³ phenyl is optionally additionally substituted with one substituent independently selected from the group consisting of F, Cl, Br and I. In another embodiment of Formula (I), R³ is 5-6 membered heteroaryl; wherein each R³ 5-6 membered heteroaryl is substituted with one, two, three or four substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I. In another embodiment of Formula (I), R³ is thienyl; wherein each R³ thienyl is substituted with one, two, or three substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I.

In one embodiment of Formula (I), R$^{3x}$ is independently selected from the group consisting of phenyl and heterocyclyl; wherein each R$^{3x}$ phenyl and heterocycyl is substituted with one, two, three or four substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I. In another embodiment of Formula (I), R$^{3x}$ is heterocyclyl; wherein each R$^{3x}$ heterocycyl is substituted with C(O)R⁴, or CO(O)R⁴.

In one embodiment of Formula (I), R⁴, at each occurrence, is independently selected from the group consisting of alkyl, alkenyl, alkynyl, aryl, cycloalkyl, cycloalkenyl, and 3-12 membered heterocyclyl; wherein each R⁴ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $CN$, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, F, Cl, Br and I. In another embodiment of Formula (I), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and OH.

In another embodiment of Formula (I), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, F, Cl, Br and I. In another embodiment of Formula (I), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (I), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I. In another embodiment of Formula (I), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (I), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (I), $R^7$, at each occurrence, is alkyl or heterocyclyl.

In one embodiment of Formula (I), $R^8$ at each occurrence, is independently selected from the group consisting of alkyl, alkenyl, and alkynyl. In another embodiment of Formula (I), $R^8$ at each occurrence, is independently alkyl.

In one embodiment of Formula (I), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, $COH$, $CN$, $NO_2$, F, Cl, Br and I. In another embodiment of Formula (I), $R^9$ at each occurrence, is independently selected from the group consisting of alkyl, aryl, heterocyclyl, and cycloalkyl; wherein each R⁹ alkyl is optionally substituted with one, two, three or four substituents independently selected from the group consisting of aryl, and alkoxy; wherein each R⁹ aryl, cycloalkyl, and heterocyclyl is optionally substituted with one, two, three or four substituents independently selected from the group consisting of R¹¹, OR¹¹, CO(O)R¹¹, and F.

In one embodiment of Formula (I), R¹⁰ at each occurrence, is independently selected from the group consisting of haloalkyl, alkyl, alkenyl, and alkynyl. In another embodiment of Formula (I), R¹⁰ at each occurrence, is independently haloalkyl or alkyl.

In one embodiment of Formula (I), R¹¹ at each occurrence, is independently selected from the group consisting of alkyl, alkenyl, and alkynyl. In another embodiment of Formula (I), R¹¹ at each occurrence, is independently alkyl.

One embodiment pertains to compounds or pharmaceutically acceptable salts thereof, which are useful as inhibitors of NAMPT, the compounds having Formula (I)

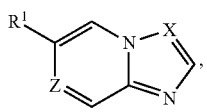

Formula (I)

wherein
X is N or CY¹;
Y¹ is independently selected from the group consisting of hydrogen, F, Cl, Br, and I;
R¹ is independently selected from the group consisting of NHC(O)NHR³, NHC(O)NH(CH₂)ₘR³ˣ, CH₂NHC(O)NHR³, NHC(O)R³, NHC(O)(CH₂)ₙR³, C(O)NH(CH₂)ₙR³, NHC(O)(CH₂)ₘR³ˣ, C(O)NH(CH₂)ₘR³ˣ, CH₂C(O)NHR³; and CH₂NHC(O)R³; and
Z is CH or N; or
X is N or CY¹;
Y¹ is independently selected from the group consisting of hydrogenF, Cl, Br, and I;
R¹ is hydrogen;
Z is CR²; and
R² is independently selected from the group consisting of NHC(O)NHR³, NHC(O)NH(CH₂)ₘR³ˣ, CH₂NHC(O)NHR³, NHC(O)R³, CH₂C(O)NHR³; and CH₂NHC(O)R³; and
R³ is independently selected from the group consisting of phenyl and 5-6 membered heteroaryl; wherein each R³ phenyl is substituted at the para position with one substituent independently selected from the group consisting of R⁴, OR⁴, C(O)R⁴, NHC(O)R⁴, NR⁴C(O)R⁴, NHS(O)₂R⁴, NHC(O)OR⁴, F, Cl, Br and I; wherein each R³ phenyl is optionally additionally substituted with one substituent independently selected from the group consisting of F, Cl, Br and I; wherein each R³ 5-6 membered heteroaryl is substituted with one, two, three or four substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I;
R³ˣ is independently heterocyclyl; wherein each R³ˣ heterocyclyl is substituted with one substituents independently selected from the group consisting of C(O)R⁴, CO(O)R⁴, F, Cl, Br and I;
R⁴, at each occurrence, is independently selected from the group consisting of alkyl, aryl, cycloalkyl, and 3-12 membered heterocyclyl; wherein each R⁴ alkyl is optionally substituted with one, two, three or four substituents independently selected from the group consisting of R⁵, OR⁵, C(O)R⁵, NHC(O)R⁵, OH, F, Cl, Br and I; wherein each R⁴ aryl, cycloalkyl and 3-12 membered heterocyclyl is optionally substituted with one, or two substituents independently selected from the group consisting of R⁶, OR⁶, SO₂R⁶, C(O)R⁶, CO(O)R⁶, C(O)C(O)R⁶, NHC(O)R⁶, OH, F, Cl, Br and I;

R⁵, at each occurrence, is independently selected from the group consisting of alkyl, aryl, heterocyclyl, and cycloalkyl; wherein each R⁵ alkyl is optionally substituted with one, substituent independently selected from the group consisting of R⁷, OR⁷, OH, F, Cl, Br and I; wherein each R⁵ aryl and heterocyclyl is optionally substituted with one, or two substituents independently selected from the group consisting of R⁸, OR⁸, CNF, Cl, Br and I;

R⁶, at each occurrence, is independently selected from the group consisting of alkyl, alkenyl, aryl, heterocyclyl, and cycloalkyl; wherein each R⁶ alkyl is optionally substituted with one, two, three or four substituents independently selected from the group consisting of R⁹, OR⁹, SO₂R⁹, OH, F, Cl, Br and I; wherein each R⁶ aryl, cycloalkyl, cycloalkenyl, and heterocyclyl is optionally substituted with one, two, three or four substituents independently selected from the group consisting of R¹⁰, OR¹⁰, CN, F, Cl, Br and I;

R⁷, at each occurrence, is independently selected from the group consisting of alkyl, and heterocyclyl;

R⁸, at each occurrence, is alkyl;

R⁹, at each occurrence, is independently selected from the group consisting of alkyl, aryl, heterocyclyl, and cycloalkyl; wherein each R⁹ alkyl is optionally substituted with one, substituent independently selected from the group consisting of aryl, alkoxy, F, Cl, Br and I; wherein each R⁹ aryl, cycloalkyl, and heterocyclyl is optionally substituted with one, two, or three substituents independently selected from the group consisting of R¹¹, OR¹¹, CO(O)R¹¹, F, Cl, Br and I;

R¹⁰ at each occurrence, is independently selected from the group consisting of haloalkyl, and alkyl;

R¹¹ at each occurrence, is alkyl;

m is 4, or 5; and n is 1;

with the provisos that
when X is CY¹ and Y¹ is hydrogen; and R³ is thiazolyl; the R³ thiazolyl is substituted with one substituent;
when X is CY¹ and Y¹ is hydrogen; R¹ is NHC(O)R³; R² is hydrogen; and R³ is phenyl; the R³ phenyl is not substituted at the para position with phenyl;
when X is CY¹ and Y¹ is hydrogen; R¹ is C(O)NH(CH₂)ₙR³; n is 1; R² is hydrogen; and R³ is phenyl; the R³ phenyl is not substituted at the para position with phenylmethoxy or 3-fluorophenoxy;
when X is CY¹ and Y¹ is hydrogen; R¹ is C(O)NH(CH₂)ₙR³; n is 1; R² is hydrogen; and R³ is furanyl; the R³ furanyl is not substituted with benzyl, or 3-fluorophenyl methyl;
when X is CY¹ and Y¹ is hydrogen; R¹ is C(O)NH(CH₂)ₙR³; n is 1; R² is hydrogen; and R³ is thienyl; the R³ thienyl is not substituted with phenoxy, 3-fluorophenoxy, or 3-chlorophenoxy; and
when X is CY¹ and Y¹ is hydrogen; R¹ is C(O)NH(CH₂)ₙR³; n is 1; R² is hydrogen; and R³ is R³ phenyl; the phenyl is not substituted at the para position with SO₂R⁴ or SO₂NHR⁴.

Still another embodiment pertains to compounds having Formula (I), which includes Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, and pharmaceutically acceptable salts thereof.

Embodiments of Formula (II)

In another aspect, the present invention provides compounds of Formula (II)

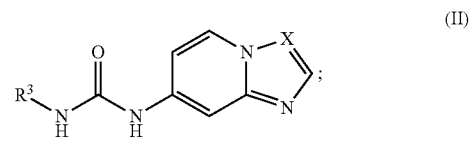

(II)

and pharmaceutically acceptable salts thereof; wherein X and $R^3$ are as described herein for Formula (I).

One embodiment pertains to compounds of Formula (II) or pharmaceutically acceptable salts thereof;
wherein X is N or $CY^1$;

$Y^1$ is independently selected from the group consisting of hydrogen, alkyl, alkoxy, haloalkyl, hydroxyalkyl, OH, CN, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, $COH$, $CN$, $NO_2$, F, Cl, Br and I;

$R^{10}$ at each occurrence, is independently selected from the group consisting of haloalkyl, alkyl, alkenyl, and alkynyl; and $R^{11}$ at each occurrence, is independently selected from the group consisting of alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (II), X is N or $CY^1$. In another embodiment of Formula (II), X is N. In another embodiment of Formula (II), X is $CY^1$.

In one embodiment of Formula (II), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (II), X is $CY^1$; and $Y^1$ is independently selected from the group consisting of hydrogen, Cl, Br, and I. In another embodiment of Formula (II), X is $CY^1$; and $Y^1$ is Cl. In another embodiment of Formula (II), X is $CY^1$; and $Y^1$ is hydrogen.

In one embodiment of Formula (II), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I. In another embodiment of Formula (II), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (II), $R^3$ is phenyl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (II), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (II), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (II), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (II), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and OH.

In another embodiment of Formula (II), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (II), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (II), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (II), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (II), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (II), $R^7$, at each occurrence, is alkyl or heterocyclyl.

In one embodiment of Formula (II), $R^8$ at each occurrence, is independently selected from the group consisting of alkyl, alkenyl, and alkynyl. In another embodiment of Formula (II), $R^8$ at each occurrence, is independently alkyl.

In one embodiment of Formula (II), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^1$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, C(O)H, C(O)OH, COH, CN, $NO_2$, F, Cl, Br and I. In another embodiment of Formula (II), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (II), $R^{10}$ at each occurrence, is independently selected from the group consisting of haloalkyl, alkyl, alkenyl, and alkynyl. In another embodiment of Formula (II), $R^{10}$ at each occurrence, is independently haloalkyl or alkyl.

In one embodiment of Formula (II), $R^{11}$ at each occurrence, is independently selected from the group consisting of alkyl, alkenyl, and alkynyl. In another embodiment of Formula (II), $R^{11}$ at each occurrence, is independently alkyl.

One embodiment pertains to compounds or pharmaceutically acceptable salts thereof, which are useful as inhibitors of NAMPT, the compounds having Formula (II)

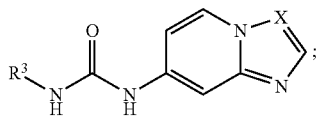

Formula (II)

wherein
X is N or $CY^1$;
$Y^1$ is independently selected from the group consisting of hydrogen, F, Cl, Br, and I;
$R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHR^4$, $NR^4C(O)R^4$, $NHS(O)_2R^4$, NHC(O)$OR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, C(O)$R^5$, NHC(O)$R^5$, OH, F, Cl, Br and I; wherein each $R^4$ aryl, cycloalkyl and 3-12 membered heterocyclyl is optionally substituted with one, or two substituents independently selected from the group consisting of $R^6$, $OR^6$, $SO_2R^6$, C(O)$R^6$, CO(O)$R^6$, C(O)C(O)$R^6$, NHC(O)$R^6$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, substituent independently selected from the group consisting of $R^7$, $OR^7$, OH, F, Cl, Br and I; wherein each $R^5$ aryl and heterocyclyl is optionally substituted with one, or two substituents independently selected from the group consisting of $R^8$, $OR^8$, CNF, Cl, Br and I;

$R^6$, at each occurrence, is independently selected from the group consisting of alkyl, alkenyl, aryl, heterocyclyl, and cycloalkyl; wherein each $R^6$ alkyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I;

$R^7$, at each occurrence, is independently selected from the group consisting of alkyl, and heterocyclyl;

$R^8$, at each occurrence, is alkyl;

$R^9$, at each occurrence, is independently selected from the group consisting of alkyl, aryl, heterocyclyl, and cycloalkyl; wherein each $R^9$ alkyl is optionally substituted with one, substituent independently selected from the group consisting of aryl, alkoxy, F, Cl, Br and I; wherein each $R^9$ aryl, cycloalkyl, and heterocyclyl is optionally substituted with one, two, or three substituents independently selected from the group consisting of $R^{11}$, $OR^{11}$, $CO(O)R^{11}$, F, Cl, Br and I;

$R^{10}$ at each occurrence, is independently selected from the group consisting of haloalkyl, and alkyl; and $R^{11}$ at each occurrence, is alkyl;
with the proviso that
when X is $CY^1$ and $Y^1$ is hydrogen; and $R^3$ is thiazolyl; the $R^3$ thiazolyl is substituted with one substituent.

Still another embodiment pertains to compounds having Formula (II), which includes Example 2; and pharmaceutically acceptable salts thereof.

Embodiments of Formula (III)
In another aspect, the present invention provides compounds of Formula (III)

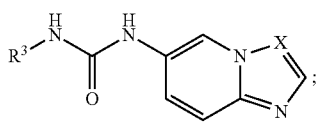

(III)

and pharmaceutically acceptable salts thereof; wherein X and R³ are as described in Formula (I) herein.

One embodiment pertains to compounds of Formula (III) or pharmaceutically acceptable salts thereof;
wherein
X is N or CY¹;
Y¹ is independently selected from the group consisting of hydrogen, alkyl, alkoxy, haloalkyl, hydroxyalkyl, OH, CN, F, Cl, Br, and I;
R³ is independently selected from the group consisting of phenyl and 5-6 membered heteroaryl; wherein each R³ phenyl is substituted at the para position with one substituent independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I; wherein each R³ phenyl is optionally additionally substituted with one substituent independently selected from the group consisting of alkyl, haloalkyl, alkoxyalkyl, hydroxyalkyl, C(O)H, C(O)OH, C(N)NH₂, OH, CN, N₃, NO₂, F, Cl, Br and I; wherein each R³ 5-6 membered heteroaryl is substituted with one, two, three or four substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I;

R⁴, at each occurrence, is independently selected from the group consisting of alkyl, alkenyl, alkynyl, aryl, cycloalkyl, cycloalkenyl, and 3-12 membered heterocyclyl; wherein each R⁴ alkyl, alkenyl, and alkynyl is optionally substituted with one, two, three or four substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC(O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, C(O)H, C(O)OH, C(N)NH₂, C(N)NHR⁵, C(N)N(R⁵)₂, CNOH, CNOCH₃, OH, CN, N₃, NO₂, F, Cl, Br and I; wherein each R⁴ aryl, cycloalkyl, cycloalkenyl, and 3-12 membered heterocyclyl is optionally substituted with one, two, three or four substituents independently selected from the group consisting of R⁶, OR⁶, SR⁶, S(O)R⁶, SO₂R⁶, C(O)R⁶, CO(O)R⁶, C(O)C(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, SO₂NH₂, SO₂NHR⁶, SO₂N(R⁶)₂, C(O)H, C(O)OH, C(N)NH₂, C(N)NHR⁶, C(N)N(R⁶)₂, CNOH, CNOCH₃, OH, CN, N₃, NO₂, F, Cl, Br and I;

R⁵, at each occurrence, is independently selected from the group consisting of alkyl, alkenyl, alkynyl, aryl, heterocyclyl, cycloalkyl, and cycloalkenyl; wherein each R⁵ alkyl, alkenyl, and alkynyl is optionally substituted with one, two, three or four substituents independently selected from the group consisting of R⁷, OR⁷, SR⁷, S(O)R⁷, SO₂R⁷, C(O)R⁷, CO(O)R⁷, OC(O)R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N(R⁷)₂, C(O)H, C(O)OH, C(N)NH₂, C(N)NHR⁷, C(N)N(R⁷)₂, CNOH, CNOCH₃, OH, CN, N₃, NO₂, F, Cl, Br and I; wherein each R⁵ aryl, cycloalkyl, cycloalkenyl, and heterocyclyl is optionally substituted with one, two, three or four substituents independently selected from the group consisting of R⁸, OR⁸, SR⁸, S(O)R⁸, SO₂R⁸, C(O)R⁸, CO(O)R⁸, OC(O)R⁸, OC(O)OR⁸, NH₂, NHR⁸, N(R⁸)₂, NHC(O)R⁸, NR⁸C(O)R⁸, NHS(O)₂R⁸, NR⁸S(O)₂R⁸, NHC(O)OR⁸, NR⁸C(O)OR⁸, NHC(O)NH₂, NHC(O)NHR⁸, NHC(O)N(R⁸)₂, NR⁸C(O)NHR⁸, NR⁸C(O)N(R⁸)₂, C(O)NH₂, C(O)NHR⁸, C(O)N(R⁸)₂, C(O)NHOH, C(O)NHOR⁸, C(O)NHSO₂R⁸, C(O)NR⁸SO₂R⁸, SO₂NH₂, SO₂NHR⁸, SO₂N(R⁸)₂, C(O)H, C(O)OH, C(N)NH₂, C(N)NHR⁸, C(N)N(R⁸)₂, CNOH, CNOCH₃, OH, CN, N₃, NO₂, F, Cl, Br and I;

R⁶, at each occurrence, is independently selected from the group consisting of alkyl, alkenyl, alkynyl, aryl, heterocyclyl, cycloalkyl, and cycloalkenyl; wherein each R⁶ alkyl, alkenyl, and alkynyl is optionally substituted with one, two, three or four substituents independently selected from the group consisting of R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R⁹, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O)N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₂NHR⁹, SO₂N(R⁹)₂, C(O)H, C(O)OH, C(N)NH₂, C(N)NHR⁹, C(N)N(R⁹)₂, CNOH, CNOCH₃, OH, CN, N₃, NO₂, F, Cl, Br and I; wherein each R⁶ aryl, cycloalkyl, cycloalkenyl, and heterocyclyl is optionally substituted with one, two, three or four substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R¹⁰)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, C(N)NH₂, C(N)NHR¹⁰, C(N)N(R¹⁰)₂, CNOH, CNOCH₃, OH, CN, N₃, NO₂, F, Cl, Br and I;

R⁷, at each occurrence, is independently selected from the group consisting of alkyl, alkenyl, alkynyl, aryl, heterocyclyl, cycloalkyl, and cycloalkenyl; wherein each R⁷ alkyl, alkenyl, and alkynyl is optionally substituted with one, two, three or four substituents independently selected from the group consisting of aryl, alkoxy, OH, CN, N₃, NO₂, F, Cl, Br and I; wherein each R⁷ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, C(O)H, C(O)OH, COH, CN, $NO_2$, F, Cl, Br and I;

$R^{10}$ at each occurrence, is independently selected from the group consisting of haloalkyl, alkyl, alkenyl, and alkynyl; and $R^{11}$ at each occurrence, is independently selected from the group consisting of alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (III), X is N or $CY^1$. In another embodiment of Formula (III), X is N. In another embodiment of Formula (III), X is $CY^1$.

In one embodiment of Formula (III), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (III), X is $CY^1$; and $Y^1$ is independently selected from the group consisting of hydrogen, Cl, Br, and I. In another embodiment of Formula (III), X is $CY^1$; and $Y^1$ is Cl. In another embodiment of Formula (III), X is $CY^1$; and $Y^1$ is hydrogen.

In one embodiment of Formula (III), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, C(O)NHOR^4, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, C(O)NHOR^4, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I. In another embodiment of Formula (III), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (III), $R^3$ is phenyl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (III), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (III), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (III), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, C(O)NHOH, C(O)NHOR^5, $C(O)NHSO_2R^5$, $C(O)NR^5SO_2R^5$, $SO_2NH_2$, $SO_2NHR^5$, $SO_2N(R^5)_2$, C(O)H, C(O)OH, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, C(O)NHOH, C(O)NHOR^6, $C(O)NHSO_2R^6$, $C(O)NR^6SO_2R^6$, $SO_2NH_2$, $SO_2NHR^6$, $SO_2N(R^6)_2$, C(O)H, C(O)OH, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (III), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and OH.

In another embodiment of Formula (III), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, OH, CN, $N_3$, $NO_2$, F, Cl, Br and I. In another embodiment of Formula (III), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (III), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, OH, CN, $N_3$, $NO_2$, F, Cl, Br and I. In another embodiment of Formula (III), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (III), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (III), $R^7$, at each occurrence, is alkyl or heterocyclyl.

In one embodiment of Formula (III), $R^8$ at each occurrence, is independently selected from the group consisting of alkyl, alkenyl, and alkynyl. In another embodiment of Formula (III), $R^8$ at each occurrence, is independently alkyl.

In one embodiment of Formula (III), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (III), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (III), $R^{10}$ at each occurrence, is independently selected from the group consisting of haloalkyl, alkyl, alkenyl, and alkynyl. In another embodiment of Formula (III), $R^{10}$ at each occurrence, is independently haloalkyl or alkyl.

In one embodiment of Formula (III), $R^{11}$ at each occurrence, is independently selected from the group consisting of alkyl, alkenyl, and alkynyl. In another embodiment of Formula (III), $R^{11}$ at each occurrence, is independently alkyl.

One embodiment pertains to compounds or pharmaceutically acceptable salts thereof, which are useful as inhibitors of NAMPT, the compounds having Formula (III)

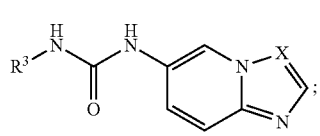

Formula (III)

wherein

X is N or CY$^1$;

Y$^1$ is independently selected from the group consisting of hydrogen, F, Cl, Br, and I;

R$^3$ is independently selected from the group consisting of phenyl and 5-6 membered heteroaryl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, F, Cl, Br and I; wherein each R$^3$ phenyl is optionally additionally substituted with one substituent independently selected from the group consisting of F, Cl, Br and I; wherein each R$^3$ 5-6 membered heteroaryl is substituted with one, two, three or four substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I;

R$^4$, at each occurrence, is independently selected from the group consisting of alkyl, aryl, cycloalkyl, and 3-12 membered heterocyclyl; wherein each R$^4$ alkyl is optionally substituted with one, two, three or four substituents independently selected from the group consisting of R$^5$, OR$^5$, C(O)R$^5$, NHC(O)R$^5$, OH, F, Cl, Br and I; wherein each R$^4$ aryl, cycloalkyl and 3-12 membered heterocyclyl is optionally substituted with one, or two substituents independently selected from the group consisting of R$^6$, OR$^6$, SO$_2$R$^6$, C(O)R$^6$, CO(O)R$^6$, C(O)C(O)R$^6$, NHC(O)R$^6$, OH, F, Cl, Br and I;

R$^5$, at each occurrence, is independently selected from the group consisting of alkyl, aryl, heterocyclyl, and cycloalkyl; wherein each R$^5$ alkyl is optionally substituted with one, substituent independently selected from the group consisting of R$^7$, OR$^7$, OH, F, Cl, Br and I; wherein each R$^5$ aryl and heterocyclyl is optionally substituted with one, or two substituents independently selected from the group consisting of R$^8$, OR$^8$, CNF, Cl, Br and I;

R$^6$, at each occurrence, is independently selected from the group consisting of alkyl, alkenyl, aryl, heterocyclyl, and cycloalkyl; wherein each R$^6$ alkyl is optionally substituted with one, two, three or four substituents independently selected from the group consisting of R$^9$, OR$^9$, SO$_2$R$^9$, OH, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, CN, F, Cl, Br and I;

R$^7$, at each occurrence, is independently selected from the group consisting of alkyl, and heterocyclyl;

R$^8$, at each occurrence, is alkyl;

R$^9$, at each occurrence, is independently selected from the group consisting of alkyl, aryl, heterocyclyl, and cycloalkyl; wherein each R$^9$ alkyl is optionally substituted with one, substituent independently selected from the group consisting of aryl, alkoxy, F, Cl, Br and I; wherein each R$^9$ aryl, cycloalkyl, and heterocyclyl is optionally substituted with one, two, or three substituents independently selected from the group consisting of R$^{11}$, OR$^{11}$, CO(O)R$^{11}$, F, Cl, Br and I;

R$^{10}$ at each occurrence, is independently selected from the group consisting of haloalkyl, and alkyl; and R$^{11}$ at each occurrence, is alkyl;

with the proviso that when X is CY$^1$ and Y$^1$ is hydrogen; and R$^3$ is thiazolyl; the R$^3$ thiazolyl is substituted with one substituent.

Still another embodiment pertains to compounds having Formula (III), which includes Examples 1, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 89, 106, 109, 110, 111, 112, 113, 396, and pharmaceutically acceptable salts thereof.

Embodiments of Formula (IV)

In another aspect, the present invention provides compounds of Formula (IV)

(IV)

and pharmaceutically acceptable salts thereof; wherein X and R$^3$ are as described herein for Formula (I).

One embodiment pertains to compounds of Formula (IV) or pharmaceutically acceptable salts thereof;

wherein

X is N or CY$^1$;

Y$^1$ is independently selected from the group consisting of hydrogen, alkyl, alkoxy, haloalkyl, hydroxyalkyl, OH, CN, F, Cl, Br, and I;

R$^3$ is independently selected from the group consisting of phenyl and 5-6 membered heteroaryl; wherein each R$^3$ phenyl is substituted at the para position with one substituent independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I; wherein each R$^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, $COH$, $CN$, $NO_2$, F, Cl, Br and I;

$R^{10}$ at each occurrence, is independently selected from the group consisting of haloalkyl, alkyl, alkenyl, and alkynyl; and $R^{11}$ at each occurrence, is independently selected from the group consisting of alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (IV), X is N or $CY^1$. In another embodiment of Formula (IV), X is N. In another embodiment of Formula (IV), X is $CY^1$.

In one embodiment of Formula (IV), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (IV), X is $CY^1$; and $Y^1$ is independently selected from the group consisting of hydrogen, Cl, Br, and I. In another embodiment of Formula (IV), X is $CY^1$; and $Y^1$ is Cl. In another embodiment of Formula (IV), X is $CY^1$; and $Y^1$ is hydrogen.

In one embodiment of Formula (IV), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I. In another embodiment of Formula (IV), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IV), $R^3$ is phenyl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (IV), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (IV), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IV), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $CN$, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, F, Cl, Br and I. In another embodiment of Formula (IV), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, $OH$, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and $OH$.

In another embodiment of Formula (IV), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, F, Cl, Br and I. In another embodiment of Formula (IV), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and $OH$; wherein each $R^5$ aryl and heterocyclyl is optionally substituted with one, two, three or four substituents independently selected from the group consisting of $R^8$, $OR^8$, $CN$, F, Cl, Br and I.

In one embodiment of Formula (IV), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I. In another embodiment of Formula (IV), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (IV), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (IV), $R^7$, at each occurrence, is alkyl or heterocyclyl.

In one embodiment of Formula (IV), $R^8$ at each occurrence, is independently selected from the group consisting of alkyl, alkenyl, and alkynyl. In another embodiment of Formula (IV), $R^8$ at each occurrence, is independently alkyl.

In one embodiment of Formula (IV), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, C(O)$R^{11}$, CO(O)$R^{11}$, OC(O)$R^{11}$, $NH_2$, $NHR^{11}$, $N(R^{11})_2$, NHC(O)$R^{11}$, $NR^{11}C(O)R^{11}$, $C(O)NH_2$, $C(O)NHR^{11}$, $C(O)N(R^{11})_2$, C(O)H, C(O)OH, COH, CN, $NO_2$, F, Cl, Br and I. In another embodiment of Formula (IV), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, CO(O)$R^{11}$, and F.

In one embodiment of Formula (IV), $R^{10}$ at each occurrence, is independently selected from the group consisting of haloalkyl, alkyl, alkenyl, and alkynyl. In another embodiment of Formula (IV), $R^{10}$ at each occurrence, is independently haloalkyl or alkyl.

In one embodiment of Formula (IV), $R^{11}$ at each occurrence, is independently selected from the group consisting of alkyl, alkenyl, and alkynyl. In another embodiment of Formula (IV), $R^{11}$ at each occurrence, is independently alkyl.

One embodiment pertains to compounds or pharmaceutically acceptable salts thereof, which are useful as inhibitors of NAMPT, the compounds having Formula (IV)

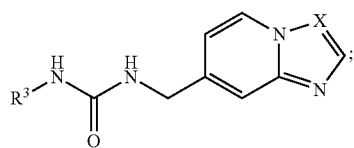

Formula (IV)

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, NHC(O)$OR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, NHC(O)$R^4$, $NR^4C(O)R^4$, NHC(O)$OR^4$, $NR^4C(O)NHR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, C(O)$R^5$, NHC(O)$R^5$, OH, F, Cl, Br and I; wherein each $R^4$ aryl, cycloalkyl and 3-12 membered heterocyclyl is optionally substituted with one, or two substituents independently selected from the group consisting of $R^6$, $OR^6$, $SO_2R^6$, C(O)$R^6$, CO(O)$R^6$, C(O)C(O)$R^6$, NHC(O)$R^6$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, substituent independently selected from the group consisting of $R^7$, $OR^7$, OH, F, Cl, Br and I; wherein each $R^5$ aryl and heterocyclyl is optionally substituted with one, or two substituents independently selected from the group consisting of $R^8$, $OR^8$, CNF, Cl, Br and I;

$R^6$, at each occurrence, is independently selected from the group consisting of alkyl, alkenyl, aryl, heterocyclyl, and cycloalkyl; wherein each $R^6$ alkyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I;

$R^7$, at each occurrence, is independently selected from the group consisting of alkyl, and heterocyclyl;

$R^8$, at each occurrence, is alkyl;

$R^9$, at each occurrence, is independently selected from the group consisting of alkyl, aryl, heterocyclyl, and cycloalkyl; wherein each $R^9$ alkyl is optionally substituted with one, substituent independently selected from the group consisting of aryl, alkoxy, F, Cl, Br and I; wherein each $R^9$ aryl, cycloalkyl, and heterocyclyl is optionally substituted with one, two, or three substituents independently selected from the group consisting of $R^{11}$, $OR^{11}$, CO(O)$R^{11}$, F, Cl, Br and I;

$R^{10}$ at each occurrence, is independently selected from the group consisting of haloalkyl, and alkyl; and $R^{11}$ at each occurrence, is alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (IV), which includes Examples 118, 216, 220, 221, 222, 223, 224, 225, 226, 227, 228, 229, 243, 280, 281, 282, 283, 284, 285, 286, 287, 288, 289, 290, 291, 302, 303, 306, 307, 328, 329, 330, 331, 332, 333, 334, 335, 336, 337, 338, 364, 366, 379, 380, 381, 382, 383, 384, 385, 386, 387, 388, 389, 390, 391, 392, 404, 407, 424, 425, 426, 427, 428, 429, 430, 431, 432, 433, 434, 435, 438, 439, 442, 443, 444, 445, 446, 447, 448, 449, 450, 451, 452, 453, 454, 455, 456, 457, 458, 459, 460, 461, 486, 487, 496, 564, 565, 673, 674, 675, 689, 690, 691, 692, 693, 694, 695, 696, 709, 710, 711, 712, 713, 714, 715, 716, 719, 720, 721, 722, 723, 724, 725, 726, 727, 728, 729, 730, and pharmaceutically acceptable salts thereof.

Embodiments of Formula (V)

In another aspect, the present invention provides compounds of Formula (V)

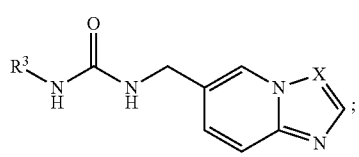

(V)

and pharmaceutically acceptable salts thereof; wherein X and $R^3$ are as described herein for Formula (I).

One embodiment pertains to compounds of Formula (V) or pharmaceutically acceptable salts thereof;
wherein X is N or $CY^1$;

$Y^1$ is independently selected from the group consisting of hydrogen, alkyl, alkoxy, haloalkyl, hydroxyalkyl, OH, CN, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, $F$, $Cl$, $Br$ and $I$;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, $OH$, $CN$, $N_3$, $NO_2$, $F$, $Cl$, $Br$ and $I$; wherein each $R^7$ aryl, cycloalkyl, cycloalkenyl, and heterocyclyl is optionally substituted with one, two, three or four substituents independently selected from the group consisting of $OH$, $CN$, $N_3$, $NO_2$, $F$, $Cl$, $Br$ and $I$;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, $OH$, $CN$, $NO_2$, $F$, $Cl$, $Br$ and $I$; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, $COH$, $CN$, $NO_2$, $F$, $Cl$, $Br$ and $I$;

$R^{10}$ at each occurrence, is independently selected from the group consisting of haloalkyl, alkyl, alkenyl, and alkynyl;

$R^{11}$ at each occurrence, is independently selected from the group consisting of alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (V), X is N or $CY^1$. In another embodiment of Formula (V), X is N. In another embodiment of Formula (V), X is $CY^1$.

In one embodiment of Formula (V), X is $CY^1$; and $Y^1$ is independently selected from the group consisting of hydrogen, alkyl, alkoxy, haloalkyl, hydroxyalkyl, $OH$, $CN$, $F$, $Cl$, $Br$, and $I$. In another embodiment of Formula (V), X is $CY^1$; and $Y^1$ is independently selected from the group consisting of hydrogen, $Cl$, $Br$, and $I$. In another embodiment of Formula (V), X is $CY^1$; and $Y^1$ is $Cl$. In another embodiment of Formula (V), X is $CY^1$; and $Y^1$ is hydrogen.

In one embodiment of Formula (V), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, $F$, $Cl$, $Br$ and $I$; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, $OH$, $CN$, $N_3$, $NO_2$, $F$, $Cl$, $Br$ and $I$; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)$ $OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $NR^4C(O)N(R^4)_2$, $C(O)NH_2$, $C(O)NHR^4$, $C(O)N(R^4)_2$, $C(O)$ $NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)$ $NH_2$, $C(N)NHR^4$, $C(N)N(R^4)_2$, $CNOH$, $CNOCH_3$, $OH$, $CN$, $N_3$, $NO_2$, $F$, $Cl$, $Br$ and $I$. In another embodiment of Formula (V), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)$ $OR^4$, and $C(O)NHR^4$; wherein each $R^3$ phenyl is optionally additionally substituted with one substituent independently selected from the group consisting of $F$, $Cl$, $Br$ and $I$; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, $F$, $Cl$, $Br$ and $I$.

In one embodiment of Formula (V), $R^3$ is phenyl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of $F$, $Cl$, $Br$ and $I$. In another embodiment of Formula (V), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)$ $NHR^4$, $C(O)NHR^4$, $F$, $Cl$, $Br$ and $I$. In another embodiment of Formula (V), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, $F$, $Cl$, $Br$ and $I$.

In one embodiment of Formula (V), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N$ $(R^5)_2$, $NR^5C(O)NHR^5$, $NR^5C(O)N(R^5)_2$, $C(O)NH_2$, $C(O)$ $NHR^5$, $C(O)N(R^5)_2$, $C(O)NHOH$, $C(O)NHOR^5$, $C(O)$ $NHSO_2R^5$, $C(O)NR^5SO_2R^5$, $SO_2NH_2$, $SO_2NHR^5$, $SO_2N$ $(R^5)_2$, $C(O)H$, $C(O)OH$, $C(N)NH_2$, $C(N)NHR^5$, $C(N)N(R^5)_2$, $CNOH$, $CNOCH_3$, $OH$, $CN$, $N_3$, $NO_2$, $F$, $Cl$, $Br$ and $I$; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N$ $(R^6)_2$, $NR^6C(O)NHR^6$, $NR^6C(O)N(R^6)_2$, $C(O)NH_2$, $C(O)$ $NHR^6$, $C(O)N(R^6)_2$, $C(O)NHOH$, $C(O)NHOR^6$, $C(O)$ $NHSO_2R^6$, $C(O)NR^6SO_2R^6$, $SO_2NH_2$, $SO_2NHR^6$, $SO_2N$ $(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, $F$, $Cl$, $Br$ and $I$. In another embodiment of Formula (V), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and OH.

In another embodiment of Formula (V), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, CNOCH$_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, CNOCH$_3$, OH, CN, $N_3$, $NO_2$, F, Cl, Br and I. In another embodiment of Formula (V), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (V), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, CNOCH$_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, CNOCH$_3$, OH, CN, $N_3$, $NO_2$, F, Cl, Br and I. In another embodiment of Formula (V), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (V), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (V), $R^7$, at each occurrence, is alkyl or heterocyclyl.

In one embodiment of Formula (V), $R^8$ at each occurrence, is independently selected from the group consisting of alkyl, alkenyl, and alkynyl. In another embodiment of Formula (V), $R^8$ at each occurrence, is independently alkyl.

In one embodiment of Formula (V), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (V), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (V), $R^{10}$ at each occurrence, is independently selected from the group consisting of haloalkyl, alkyl, alkenyl, and alkynyl. In another embodiment of Formula (V), $R^{10}$ at each occurrence, is independently haloalkyl or alkyl.

In one embodiment of Formula (V), $R^{11}$ at each occurrence, is independently selected from the group consisting of alkyl, alkenyl, and alkynyl. In another embodiment of Formula (V), $R^{11}$ at each occurrence, is independently alkyl.

One embodiment pertains to compounds or pharmaceutically acceptable salts thereof, which are useful as inhibitors of NAMPT, the compounds having Formula (V)

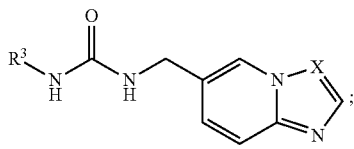

Formula (V)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, or two substituents independently selected from the group consisting of $R^6$, $OR^6$, $SO_2R^6$, $C(O)R^6$, $CO(O)R^6$, $C(O)C(O)R^6$, $NHC(O)R^6$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, substituent independently selected from the group consisting of $R^7$, $OR^7$, OH, F, Cl, Br and I; wherein each $R^5$ aryl and heterocyclyl is optionally substituted with one, or two substituents independently selected from the group consisting of $R^8$, $OR^8$, CN F, Cl, Br and I;

$R^6$, at each occurrence, is independently selected from the group consisting of alkyl, alkenyl, aryl, heterocyclyl, and cycloalkyl; wherein each $R^6$ alkyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I;

$R^7$, at each occurrence, is independently selected from the group consisting of alkyl, and heterocyclyl;

$R^8$, at each occurrence, is alkyl;

$R^9$, at each occurrence, is independently selected from the group consisting of alkyl, aryl, heterocyclyl, and cycloalkyl; wherein each $R^9$ alkyl is optionally substituted with one, substituent independently selected from the group consisting of aryl, alkoxy, F, Cl, Br and I; wherein each $R^9$ aryl, cycloalkyl, and heterocyclyl is optionally substituted with one, two, or three substituents independently selected from the group consisting of $R^{11}$, $OR^{11}$, $CO(O)R^{11}$, F, Cl, Br and I;

$R^{10}$ at each occurrence, is independently selected from the group consisting of haloalkyl, and alkyl; and $R^{11}$ at each occurrence, is alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (V), which include Examples 59, 60, 274, 275, 276, 277, 278, 279, 360, 362, and pharmaceutically acceptable salts thereof.

Embodiments of Formula (VI)

In another aspect, the present invention provides compounds of Formula (VI)

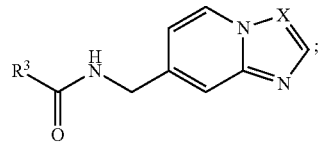

(VI)

and pharmaceutically acceptable salts thereof; wherein X and $R^3$ are as described herein for Formula (I).

One embodiment pertains to compounds of Formula (VI) or pharmaceutically acceptable salts thereof;

wherein

X is N or $CY^1$;

$Y^1$ is independently selected from the group consisting of hydrogen, alkyl, alkoxy, haloalkyl, hydroxyalkyl, OH, CN, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, C(O)C(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^8$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$ at each occurrence, is independently selected from the group consisting of haloalkyl, alkyl, alkenyl, and alkynyl; and R$^{11}$ at each occurrence, is independently selected from the group consisting of alkyl, alkenyl, and alkynyl;

with the proviso that when X is CY$^1$ and Y$^1$ is hydrogen; and R$^3$ is thiazolyl; the R$^3$ thiazolyl is substituted with one substituent.

In one embodiment of Formula (VI), X is N or CY$^1$. In another embodiment of Formula (VI), X is N. In another embodiment of Formula (VI), X is CY$^1$.

In one embodiment of Formula (VI), X is CY$^1$; and Y$^1$ is independently selected from the group consisting of hydrogen, alkyl, alkoxy, haloalkyl, hydroxyalkyl, OH, CN, F, Cl, Br, and I. In another embodiment of Formula (VI), X is CY$^1$; and Y$^1$ is independently selected from the group consisting of hydrogen, Cl, Br, and I. In another embodiment of Formula (VI), X is CY$^1$; and Y$^1$ is Cl. In another embodiment of Formula (VI), X is CY$^1$; and Y$^1$ is hydrogen.

In one embodiment of Formula (VI), R$^3$ is independently selected from the group consisting of phenyl and 5-6 membered heteroaryl; wherein each R$^3$ phenyl is substituted at the para position with one substituent independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I; wherein each R$^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS (O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I. In another embodiment of Formula (VI), R$^3$ is independently selected from the group consisting of phenyl and 5-6 membered heteroaryl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; wherein each R$^3$ phenyl is optionally additionally substituted with one substituent independently selected from the group consisting of F, Cl, Br and I; wherein each R$^3$ 5-6 membered heteroaryl is substituted with one, two, three or four substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I.

In one embodiment of Formula (VI), R$^3$ is phenyl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In another embodiment of Formula (VI), R$^3$ is 5-6 membered heteroaryl; wherein each R$^3$ 5-6 membered heteroaryl is substituted with one, two, three or four substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I. In another embodiment of Formula (VI), R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I.

In one embodiment of Formula (VI), R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I. In another embodiment of Formula (VI), R$^4$, at each occurrence, is independently selected from the group consisting of alkyl, aryl, cycloalkyl, and 3-12 membered heterocyclyl; wherein each R$^4$ alkyl is optionally substituted with one, two, three or four substituents independently selected from the group consisting of R$^5$, OR$^5$, C(O)R$^5$, NHC(O)R$^5$, OH, F, Cl, Br and I; wherein each R$^4$ aryl, cycloalkyl and 3-12 membered heterocyclyl is optionally substituted with one, two, three or four substituents independently selected from the group consisting of R$^6$, OR$^6$, SO$_2$R$^6$, C(O)R$^6$, CO(O)R$^6$, C(O)C(O)R$^6$, NHC(O)R$^6$, and OH.

In another embodiment of Formula (VI), R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I. In another embodiment of Formula (VI), R$^5$, at each occurrence, is independently selected from the group consisting of alkyl, aryl, heterocyclyl, and cycloalkyl; wherein each R$^5$ alkyl is optionally substituted with one, two, three or four substituents independently selected from the group consisting of R$^7$, OR$^7$, and OH; wherein each R$^5$ aryl and heterocyclyl is optionally substituted with one, two, three or four substituents independently selected from the group consisting of R$^8$, OR$^8$, CN, F, Cl, Br and I.

In one embodiment of Formula (VI), R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)

NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I. In another embodiment of Formula (VI), R$^6$, at each occurrence, is independently selected from the group consisting of alkyl, alkenyl, aryl, heterocyclyl, and cycloalkyl; wherein each R$^6$ alkyl and alkenyl is optionally substituted with one, two, three or four substituents independently selected from the group consisting of R$^9$, OR$^9$, SO$_2$R$^9$, OH, F, Cl, Br and I; wherein each R$^6$ aryl, cycloalkyl, and heterocyclyl is optionally substituted with one, two, three or four substituents independently selected from the group consisting of R$^{10}$, OR$^{10}$, CN, F, Cl, Br and I.

In one embodiment of Formula (VI), R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I. In another embodiment of Formula (VI), R$^7$, at each occurrence, is alkyl or heterocyclyl.

In one embodiment of Formula (VI), R$^8$ at each occurrence, is independently selected from the group consisting of alkyl, alkenyl, and alkynyl. In another embodiment of Formula (VI), R$^8$ at each occurrence, is independently alkyl.

In one embodiment of Formula (VI), R$^9$ at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I. In another embodiment of Formula (VI), R$^9$ at each occurrence, is independently selected from the group consisting of alkyl, aryl, heterocyclyl, and cycloalkyl; wherein each R$^9$ alkyl is optionally substituted with one, two, three or four substituents independently selected from the group consisting of aryl, and alkoxy; wherein each R$^9$ aryl, cycloalkyl, and heterocyclyl is optionally substituted with one, two, three or four substituents independently selected from the group consisting of R$^{11}$, OR$^{11}$, CO(O)R$^{11}$, and F.

In one embodiment of Formula (VI), R$^{10}$ at each occurrence, is independently selected from the group consisting of haloalkyl, alkyl, alkenyl, and alkynyl. In another embodiment of Formula (VI), R$^{10}$ at each occurrence, is independently haloalkyl or alkyl.

In one embodiment of Formula (VI), R$^{11}$ at each occurrence, is independently selected from the group consisting of alkyl, alkenyl, and alkynyl. In another embodiment of Formula (VI), R$^{11}$ at each occurrence, is independently alkyl.

One embodiment pertains to compounds or pharmaceutically acceptable salts thereof, which are useful as inhibitors of NAMPT, the compounds having Formula (VI)

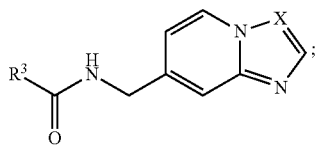

Formula (VI)

wherein
X is N or CY$^1$;
Y$^1$ is independently selected from the group consisting of hydrogen, F, Cl, Br, and I;
R$^3$ is independently selected from the group consisting of phenyl and 5-6 membered heteroaryl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, F, Cl, Br and I; wherein each R$^3$ phenyl is optionally additionally substituted with one substituent independently selected from the group consisting of F, Cl, Br and I; wherein each R$^3$ 5-6 membered heteroaryl is substituted with one, two, three or four substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I;
R$^4$, at each occurrence, is independently selected from the group consisting of alkyl, aryl, cycloalkyl, and 3-12 membered heterocyclyl; wherein each R$^4$ alkyl is optionally substituted with one, two, three or four substituents independently selected from the group consisting of R$^5$, OR$^5$, C(O)R$^5$, NHC(O)R$^5$, OH, F, Cl, Br and I; wherein each R$^4$ aryl, cycloalkyl and 3-12 membered heterocyclyl is optionally substituted with one, or two substituents independently selected from the group consisting of R$^6$, OR$^6$, SO$_2$R$^6$, C(O)R$^6$, CO(O)R$^6$, C(O)C(O)R$^6$, NHC(O)R$^6$, OH, F, Cl, Br and I;
R$^5$, at each occurrence, is independently selected from the group consisting of alkyl, aryl, heterocyclyl, and cycloalkyl; wherein each R$^5$ alkyl is optionally substituted with one, substituent independently selected from the group consisting of R$^7$, OR$^7$, OH, F, Cl, Br and I; wherein each R$^5$ aryl and heterocyclyl is optionally substituted with one, or two substituents independently selected from the group consisting of R$^8$, OR$^8$, CNF, Cl, Br and I;
R$^6$, at each occurrence, is independently selected from the group consisting of alkyl, alkenyl, aryl, heterocyclyl, and cycloalkyl; wherein each R$^6$ alkyl is optionally substituted with one, two, three or four substituents independently selected from the group consisting of R$^9$, OR$^9$, SO$_2$R$^9$, OH, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, CN, F, Cl, Br and I;
R$^7$, at each occurrence, is independently selected from the group consisting of alkyl, and heterocyclyl;
R$^8$, at each occurrence, is alkyl;
R$^9$, at each occurrence, is independently selected from the group consisting of alkyl, aryl, heterocyclyl, and cycloalkyl; wherein each R$^9$ alkyl is optionally substituted with one, substituent independently selected from the group consisting of aryl, alkoxy, F, Cl, Br and I; wherein each R$^9$ aryl, cycloalkyl, and heterocyclyl is optionally substituted with one, two, or three substituents independently selected from the group consisting of R$^{11}$, OR$^{11}$, CO(O)R$^{11}$, F, Cl, Br and I;
R$^{10}$ at each occurrence, is independently selected from the group consisting of haloalkyl, and alkyl; and
R$^{11}$ at each occurrence, is alkyl;

with the proviso that
when X is CY¹ and Y¹ is hydrogen; and R³ is thiazolyl; the R³ thiazolyl is substituted with one substituent.

Still another embodiment pertains to compounds having Formula (VI), which includes Examples 57, 117, 121, 138, 174, 181, 182, 185, 187, 188, 192, 193, 194, 195, 196, 197, 198, 199, 202, 203, 204, 205, 207, 208, 209, 210, 211, 212, 213, 214, 217, 218, 230, 231, 232, 233, 234, 235, 236, 237, 238, 239, 241, 242, 244, 245, 246, 247, 248, 249, 250, 251, 252, 253, 254, 255, 256, 257, 258, 259, 260, 261, 262, 263, 264, 265, 266, 267, 268, 269, 271, 272, 273, 292, 293, 294, 295, 296, 297, 298, 299, 300, 301, 304, 305, 308, 309, 310, 311, 312, 313, 315, 316, 317, 318, 319, 320, 321, 324, 325, 326, 327, 339, 340, 341, 342, 343, 344, 345, 346, 347, 348, 349, 350, 351, 352, 353, 354, 355, 356, 357, 361, 363, 365, 367, 368, 369, 370, 371, 372, 373, 374, 375, 376, 377, 378, 393, 394, 395, 397, 399, 400, 401, 402, 403, 405, 406, 408, 409, 410, 411, 412, 413, 414, 415, 416, 417, 418, 419, 420, 421, 422, 423, 436, 437, 440, 441, 463, 464, 465, 466, 467, 468, 469, 470, 471, 472, 473, 474, 475, 476, 477, 478, 479, 480, 481, 482, 483, 484, 485, 488, 489, 490, 492, 493, 494, 495, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 677, 682, 683, 684, 685, 686, 687, 688, 697, 698, 699, 700, 701, 702, 703, 704, 705, 706, 707, 708, 717, 718, 731, 732, 733, 734, 735, 736, 737, 738, 740, 741, 742, 743, 744, 745, 746, 747, 748, 749, 750, 751, 752, 753, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 818, 821, 823, 824, 825, and pharmaceutically acceptable salts thereof.

Embodiments of Formula (VII)

In another aspect, the present invention provides compounds of Formula (VII)

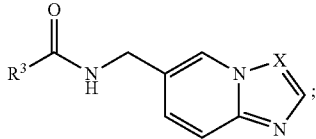

(VII)

and pharmaceutically acceptable salts thereof; wherein X and R³ are as described herein for Formula (I).

One embodiment pertains to compounds of Formula (VII) or pharmaceutically acceptable salts thereof;
wherein
X is N or CY¹;
Y¹ is independently selected from the group consisting of hydrogen, alkyl, alkoxy, haloalkyl, hydroxyalkyl, OH, CN, F, Cl, Br, and I;

R³ is independently selected from the group consisting of phenyl and 5-6 membered heteroaryl; wherein each R³ phenyl is substituted at the para position with one substituent independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I; wherein each R³ phenyl is optionally additionally substituted with one substituent independently selected from the group consisting of alkyl, haloalkyl, alkoxyalkyl, hydroxyalkyl, C(O)H, C(O)OH, C(N)NH₂, OH, CN, N₃, NO₂, F, Cl, Br and I; wherein each R³ 5-6 membered heteroaryl is substituted with one, two, three or four substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I;

R⁴, at each occurrence, is independently selected from the group consisting of alkyl, alkenyl, alkynyl, aryl, cycloalkyl, cycloalkenyl, and 3-12 membered heterocyclyl; wherein each R⁴ alkyl, alkenyl, and alkynyl is optionally substituted with one, two, three or four substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC(O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, C(O)H, C(O)OH, C(N)NH₂, C(N)NHR⁵, C(N)N(R⁵)₂, CNOH, CNOCH₃, OH, CN, N₃, NO₂, F, Cl, Br and I; wherein each R⁴ aryl, cycloalkyl, cycloalkenyl, and 3-12 membered heterocyclyl is optionally substituted with one, two, three or four substituents independently selected from the group consisting of R⁶, OR⁶, SR⁶, S(O)R⁶, SO₂R⁶, C(O)R⁶, CO(O)R⁶, C(O)C(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, NR⁶C(O)N(R⁶)₂, C(O)NH₂, C(O)NHR⁶, C(O)N(R⁶)₂, C(O)NHOH, C(O)NHOR⁶, C(O)NHSO₂R⁶, C(O)NR⁶SO₂R⁶, SO₂NH₂, SO₂NHR⁶, SO₂N(R⁶)₂, C(O)H, C(O)OH, C(N)NH₂, C(N)NHR⁶, C(N)N(R⁶)₂, CNOH, CNOCH₃, OH, CN, N₃, NO₂, F, Cl, Br and I;

R⁵, at each occurrence, is independently selected from the group consisting of alkyl, alkenyl, alkynyl, aryl, heterocyclyl, cycloalkyl, and cycloalkenyl; wherein each R⁵ alkyl, alkenyl, and alkynyl is optionally substituted with one, two, three or four substituents independently selected from the group consisting of R⁷, OR⁷, SR⁷, S(O)R⁷, SO₂R⁷, C(O)R⁷, CO(O)R⁷, OC(O)R⁷, OC(O)OR⁷, NH₂, NHR⁷, N(R⁷)₂, NHC(O)R⁷, NR⁷C(O)R⁷, NHS(O)₂R⁷, NR⁷S(O)₂R⁷, NHC(O)OR⁷, NR⁷C(O)OR⁷, NHC(O)NH₂, NHC(O)NHR⁷, NHC(O)N(R⁷)₂, NR⁷C(O)NHR⁷, NR⁷C(O)N(R⁷)₂, C(O)NH₂, C(O)NHR⁷, C(O)N(R⁷)₂, C(O)NHOH, C(O)NHOR⁷, C(O)NHSO₂R⁷, C(O)NR⁷SO₂R⁷, SO₂NH₂, SO₂NHR⁷, SO₂N $(R^7)_2$, C(O)H, C(O)OH, C(N)NH$_2$, C(N)NHR$^7$, C(N)N(R$^7)_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8)_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8)_2$, NR$^8$C(O)NHR$^8$, NR$^8$C(O)N(R$^8)_2$, C(O)NH$_2$, C(O)NHR$^8$, C(O)N(R$^8)_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8)_2$, C(O)H, C(O)OH, C(N)NH$_2$, C(N)NHR$^8$, C(N)N(R$^8)_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9)_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9)_2$, NR$^9$C(O)NHR$^9$, NR$^9$C(O)N(R$^9)_2$, C(O)NH$_2$, C(O)NHR$^9$, C(O)N(R$^9)_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9)_2$, C(O)H, C(O)OH, C(N)NH$_2$, C(N)NHR$^9$, C(N)N(R$^9)_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10})_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10})_2$, NR$^{10}$C(O)NHR$^{10}$, NR$^{10}$C(O)N(R$^{10})_2$, C(O)NH$_2$, C(O)NHR$^{10}$, C(O)N(R$^{10})_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10})_2$, C(O)H, C(O)OH, C(N)NH$_2$, C(N)NHR$^{10}$, C(N)N(R$^{10})_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11})_2$, NHC(O)R$^{11}$, NR$^{11}$C(O)R$^{11}$, C(O)NH$_2$, C(O)NHR$^{11}$, C(O)N(R$^{11})_2$, C(O)H, C(O)OH, COH, CN, NO$_2$, F, Cl, Br and I;

R$^{10}$ at each occurrence, is independently selected from the group consisting of haloalkyl, alkyl, alkenyl, and alkynyl; and R$^{11}$ at each occurrence, is independently selected from the group consisting of alkyl, alkenyl, and alkynyl;

with the proviso that when X is CY$^1$ and Y$^1$ is hydrogen; and R$^3$ is thiazolyl; the R$^3$ thiazolyl is substituted with one substituent.

In one embodiment of Formula (VII), X is N or CY$^1$. In another embodiment of Formula (VII), X is N. In another embodiment of Formula (VII), X is CY$^1$.

In one embodiment of Formula (VII), X is CY$^1$; and Y$^1$ is independently selected from the group consisting of hydrogen, alkyl, alkoxy, haloalkyl, hydroxyalkyl, OH, CN, F, Cl, Br, and I. In another embodiment of Formula (VII), X is CY$^1$; and Y$^1$ is independently selected from the group consisting of hydrogen, Cl, Br, and I. In another embodiment of Formula (VII), X is CY$^1$; and Y$^1$ is Cl. In another embodiment of Formula (VII), X is CY$^1$; and Y$^1$ is hydrogen.

In one embodiment of Formula (VII), R$^3$ is independently selected from the group consisting of phenyl and 5-6 membered heteroaryl; wherein each R$^3$ phenyl is substituted at the para position with one substituent independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4)_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4)_2$, NR$^4$C(O)NHR$^4$, NR$^4$C(O)N(R$^4)_2$, C(O)NH$_2$, C(O)NHR$^4$, C(O)N(R$^4)_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4)_2$, C(O)H, C(O)OH, C(N)NH$_2$, C(N)NHR$^4$, C(N)N(R$^4)_2$, CNOH, CNOCH$_3$, OH, CN, N$_3$, NO$_2$, F, Cl, Br and I; wherein each R$^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4)_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4)_2$, NR$^4$C(O)NHR$^4$, NR$^4$C(O)N(R$^4)_2$, C(O)NH$_2$, C(O)NHR$^4$, C(O)N(R$^4)_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4)_2$, C(O)H, C(O)OH, C(N)NH$_2$, C(N)NHR$^4$, C(N)N(R$^4)_2$, CNOH, CNOCH$_3$, OH, CN, N$_3$, NO$_2$, F, Cl, Br and I. In another embodiment of Formula (VII), R$^3$ is independently selected from the group consisting of phenyl and 5-6 membered heteroaryl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; wherein each R$^3$ phenyl is optionally additionally substituted with one substituent independently selected from the group consisting of F, Cl, Br and I; wherein each R$^3$ 5-6 membered heteroaryl is substituted with one, two, three or four substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I.

In one embodiment of Formula (VII), R$^3$ is phenyl; wherein each R$^3$ phenyl is substituted at the para position with one substituent independently selected from the group consisting of R$^4$, OR$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In another embodiment of Formula (VII), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (VII), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VII), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (VII), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and OH.

In another embodiment of Formula (VII), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (VII), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (VII), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (VII), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (VII), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (VII), $R^7$, at each occurrence, is alkyl or heterocyclyl.

In one embodiment of Formula (VII), $R^8$ at each occurrence, is independently selected from the group consisting of alkyl, alkenyl, and alkynyl. In another embodiment of Formula (VII), $R^8$ at each occurrence, is independently alkyl.

In one embodiment of Formula (VII), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, $COH$, CN, $NO_2$, F, Cl, Br and I. In another embodiment of Formula (VII), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (VII), $R^{10}$ at each occurrence, is independently selected from the group consisting of haloalkyl, alkyl, alkenyl, and alkynyl. In another embodiment of Formula (VII), $R^{10}$ at each occurrence, is independently haloalkyl or alkyl.

In one embodiment of Formula (VII), $R^{11}$ at each occurrence, is independently selected from the group consisting of alkyl, alkenyl, and alkynyl. In another embodiment of Formula (VII), $R^{11}$ at each occurrence, is independently alkyl.

One embodiment pertains to compounds or pharmaceutically acceptable salts thereof, which are useful as inhibitors of NAMPT, the compounds having Formula (VII)

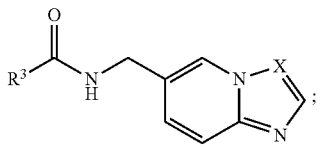

Formula (VII)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, or two substituents independently selected from the group consisting of $R^6$, $OR^6$, $SO_2R^6$, $C(O)R^6$, $CO(O)R^6$, $C(O)C(O)R^6$, $NHC(O)R^6$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, substituent independently selected from the group consisting of $R^7$, $OR^7$, OH, F, Cl, Br and I; wherein each $R^5$ aryl and heterocyclyl is optionally substituted with one, or two substituents independently selected from the group consisting of $R^8$, $OR^8$, CNF, Cl, Br and I;

$R^6$, at each occurrence, is independently selected from the group consisting of alkyl, alkenyl, aryl, heterocyclyl, and cycloalkyl; wherein each $R^6$ alkyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I;

$R^7$, at each occurrence, is independently selected from the group consisting of alkyl, and heterocyclyl;

$R^8$, at each occurrence, is alkyl;

$R^9$, at each occurrence, is independently selected from the group consisting of alkyl, aryl, heterocyclyl, and cycloalkyl; wherein each $R^9$ alkyl is optionally substituted with one, substituent independently selected from the group consisting of aryl, alkoxy, F, Cl, Br and I; wherein each $R^9$ aryl, cycloalkyl, and heterocyclyl is optionally substituted with one, two, or three substituents independently selected from the group consisting of $R^{11}$, $OR^{11}$, $CO(O)R^{11}$, F, Cl, Br and I;

$R^{10}$ at each occurrence, is independently selected from the group consisting of haloalkyl, and alkyl; and $R^{11}$ at each occurrence, is alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (VII), which includes Examples 52, 55, 56, 61, 75, 77, 78, 79, 80, 81, 82, 83, 85, 86, 87, 88, 90, 91, 92, 93, 94, 95, 96, 97, 98, 99, 100, 101, 102, 103, 104, 105, 108, 114, 115, 116, 119, 120, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 175, 176, 177, 178, 179, 180, 183, 184, 186, 189, 190, 191, 200, 201, 206, 215, 219, 240, 358, 359, 398, 462, 621, 622, 676, 810, 820, 822, 831, 832, 833, 834, 835, 836, 842, 843, 844, 845, 846, 847, 848, 849, 850, 851, 852, 853, and pharmaceutically acceptable salts thereof.

Embodiments of Formula (VIII)

In another aspect, the present invention provides compounds of Formula (VIII)

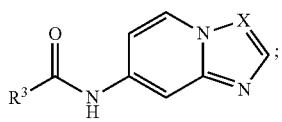

(VIII)

and pharmaceutically acceptable salts thereof; wherein X and $R^3$ are as described herein for Formula (I).

One embodiment pertains to compounds of Formula (VIII) or pharmaceutically acceptable salts thereof;
wherein
X is N or $CY^1$;
$Y^1$ is independently selected from the group consisting of hydrogen, alkyl, alkoxy, haloalkyl, hydroxyalkyl, OH, CN, F, Cl, Br, and I;
$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, C(O)H, C(O)OH, COH, CN, $NO_2$, F, Cl, Br and I;

$R^{10}$ at each occurrence, is independently selected from the group consisting of haloalkyl, alkyl, alkenyl, and alkynyl; and $R^{11}$ at each occurrence, is independently selected from the group consisting of alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (VIII), X is N or $CY^1$. In another embodiment of Formula (VIII), X is N. In another embodiment of Formula (VIII), X is $CY^1$.

In one embodiment of Formula (VIII), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (VIII), X is $CY^1$; and $Y^1$ is independently selected from the group consisting of hydrogen, Cl, Br, and I. In another embodiment of Formula (VIII), X is $CY^1$; and $Y^1$ is Cl. In another embodiment of Formula (VIII), X is $CY^1$; and $Y^1$ is hydrogen.

In one embodiment of Formula (VIII), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, C(O)NHOR^4, C(O)NHSO_2R^4, C(O)NR^4SO_2R^4, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, C(O)NHOR^4, C(O)NHSO_2R^4, C(O)NR^4SO_2R^4, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I. In another embodiment of Formula (VIII), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VIII), $R^3$ is phenyl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (VIII), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (VIII), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VIII), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, C(O)NHOH, C(O)NHOR^5, C(O)NHSO_2R^5, C(O)NR^5SO_2R^5, $SO_2NH_2$, $SO_2NHR^5$, $SO_2N(R^5)_2$, C(O)H, C(O)OH, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, C(O)NHOH, C(O)NHOR^6, C(O)NHSO_2R^6, C(O)NR^6SO_2R^6, $SO_2NH_2$, $SO_2NHR^6$, $SO_2N(R^6)_2$, C(O)H, C(O)OH, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (VIII), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and OH.

In another embodiment of Formula (VIII), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (VIII), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (VIII), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (VIII), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (VIII), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (VIII), $R^7$, at each occurrence, is alkyl or heterocyclyl.

In one embodiment of Formula (VIII), $R^8$ at each occurrence, is independently selected from the group consisting of alkyl, alkenyl, and alkynyl. In another embodiment of Formula (VIII), $R^8$ at each occurrence, is independently alkyl.

In one embodiment of Formula (VIII), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (VIII), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (VIII), $R^{10}$ at each occurrence, is independently selected from the group consisting of haloalkyl, alkyl, alkenyl, and alkynyl. In another embodiment of Formula (VIII), $R^{10}$ at each occurrence, is independently haloalkyl or alkyl.

In one embodiment of Formula (VIII), $R^{11}$ at each occurrence, is independently selected from the group consisting of alkyl, alkenyl, and alkynyl. In another embodiment of Formula (VIII), $R^{11}$ at each occurrence, is independently alkyl.

One embodiment pertains to compounds or pharmaceutically acceptable salts thereof, which are useful as inhibitors of NAMPT, the compounds having Formula (VIII)

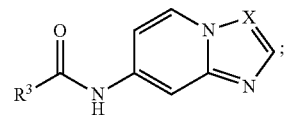

Formula (VIII)

wherein
X is N or CY¹;
Y¹ is independently selected from the group consisting of hydrogen, F, Cl, Br, and I;
R³ is independently selected from the group consisting of phenyl and 5-6 membered heteroaryl; wherein each R³ phenyl is substituted at the para position with one substituent independently selected from the group consisting of R⁴, OR⁴, C(O)R⁴, NHC(O)R⁴, NR⁴C(O)R⁴, NHS(O)₂R⁴, NHC(O)OR⁴, F, Cl, Br and I; wherein each R³ phenyl is optionally additionally substituted with one substituent independently selected from the group consisting of F, Cl, Br and I; wherein each R³ 5-6 membered heteroaryl is substituted with one, two, three or four substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I;

R⁴, at each occurrence, is independently selected from the group consisting of alkyl, aryl, cycloalkyl, and 3-12 membered heterocyclyl; wherein each R⁴ alkyl is optionally substituted with one, two, three or four substituents independently selected from the group consisting of R⁵, OR⁵, C(O)R⁵, NHC(O)R⁵, OH, F, Cl, Br and I; wherein each R⁴ aryl, cycloalkyl and 3-12 membered heterocyclyl is optionally substituted with one, or two substituents independently selected from the group consisting of R⁶, OR⁶, SO₂R⁶, C(O)R⁶, CO(O)R⁶, C(O)C(O)R⁶, NHC(O)R⁶, OH, F, Cl, Br and I;

R⁵, at each occurrence, is independently selected from the group consisting of alkyl, aryl, heterocyclyl, and cycloalkyl; wherein each R⁵ alkyl is optionally substituted with one, substituent independently selected from the group consisting of R⁷, OR⁷, OH, F, Cl, Br and I; wherein each R⁵ aryl and heterocyclyl is optionally substituted with one, or two substituents independently selected from the group consisting of R⁸, OR⁸, CN F, Cl, Br and I;

R⁶, at each occurrence, is independently selected from the group consisting of alkyl, alkenyl, aryl, heterocyclyl, and cycloalkyl; wherein each R⁶ alkyl is optionally substituted with one, two, three or four substituents independently selected from the group consisting of R⁹, OR⁹, SO₂R⁹, OH, F, Cl, Br and I; wherein each R⁶ aryl, cycloalkyl, cycloalkenyl, and heterocyclyl is optionally substituted with one, two, three or four substituents independently selected from the group consisting of R¹⁰, OR¹⁰, CN, F, Cl, Br and I;

R⁷, at each occurrence, is independently selected from the group consisting of alkyl, and heterocyclyl;

R⁸, at each occurrence, is alkyl;

R⁹, at each occurrence, is independently selected from the group consisting of alkyl, aryl, heterocyclyl, and cycloalkyl; wherein each R⁹ alkyl is optionally substituted with one, substituent independently selected from the group consisting of aryl, alkoxy, F, Cl, Br and I; wherein each R⁹ aryl, cycloalkyl, and heterocyclyl is optionally substituted with one, two, or three substituents independently selected from the group consisting of R¹¹, OR¹¹, CO(O)R¹¹, F, Cl, Br and I;

R¹⁰ at each occurrence, is independently selected from the group consisting of haloalkyl, and alkyl; and R¹¹ at each occurrence, is alkyl;
with the proviso that
when X is CY¹ and Y¹ is hydrogen; and R³ is thiazolyl; the R³ thiazolyl is substituted with one substituent.

Still another embodiment pertains to compounds having Formula (VIII), which includes Example 322, and pharmaceutically acceptable salts thereof.

Embodiments of Formula (IX)

In another aspect, the present invention provides compounds of Formula (IX)

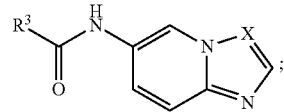

(IX)

and pharmaceutically acceptable salts thereof; wherein X and R³ are as described herein for Formula (I).

One embodiment pertains to compounds of Formula (IX) or pharmaceutically acceptable salts thereof;
wherein
X is N or CY¹;
Y¹ is independently selected from the group consisting of hydrogen, alkyl, alkoxy, haloalkyl, hydroxyalkyl, OH, CN, F, Cl, Br, and I;

R³ is independently selected from the group consisting of phenyl and 5-6 membered heteroaryl; wherein each R³ phenyl is substituted at the para position with one substituent independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I; wherein each R³ phenyl is optionally additionally substituted with one substituent independently selected from the group consisting of alkyl, haloalkyl, alkoxyalkyl, hydroxyalkyl, C(O)H, C(O)OH, C(N)NH₂, OH, CN, N₃, NO₂, F, Cl, Br and I; wherein each R³ 5-6 membered heteroaryl is substituted with one, two, three or four substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I;

R⁴, at each occurrence, is independently selected from the group consisting of alkyl, alkenyl, alkynyl, aryl, cycloalkyl, cycloalkenyl, and 3-12 membered heterocyclyl; wherein each R⁴ alkyl, alkenyl, and alkynyl is optionally substituted with one, two, three or four substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC(O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N(R⁵)₂, C(O)H, C(O)OH, C(N)NH₂, C(N)NHR⁵, C(N)N(R⁵)₂, CNOH, CNOCH₃, OH, CN, N₃, NO₂, F, Cl, Br and I; wherein each R⁴ aryl, cycloalkyl, cycloalkenyl, and 3-12 membered heterocyclyl is optionally substituted with one, two, three or four substituents independently selected from the group consisting of R⁶, OR⁶, SR⁶, S(O)R⁶, SO₂R⁶, C(O)R⁶, CO(O)R⁶, C(O)C(O)R⁶, OC(O)R⁶, OC(O)OR⁶, NH₂, NHR⁶, N(R⁶)₂, NHC(O)R⁶, NR⁶C(O)R⁶, NHS(O)₂R⁶, NR⁶S(O)₂R⁶, NHC(O)OR⁶, NR⁶C(O)OR⁶, NHC(O)NH₂, NHC(O)NHR⁶, NHC(O)N(R⁶)₂, NR⁶C(O)NHR⁶, $NR^6C(O)N(R^6)_2$, $C(O)NH_2$, $C(O)NHR^6$, $C(O)N(R^6)_2$, $C(O)$ $NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)$ $NH_2$, $C(N)NHR^6$, $C(N)N(R^6)_2$, $CNOH$, $CNOCH_3$, $OH$, $CN$, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I;

$R^{10}$ at each occurrence, is independently selected from the group consisting of haloalkyl, alkyl, alkenyl, and alkynyl; and $R^{11}$ at each occurrence, is independently selected from the group consisting of alkyl, alkenyl, and alkynyl;

with the provisos that when X is $CY^1$ and $Y^1$ is hydrogen; and $R^3$ is thiazolyl; the $R^3$ thiazolyl is substituted with one substituent; and when X is $CY^1$ and $Y^1$ is hydrogen; and $R^3$ is phenyl; the $R^3$ phenyl is not substituted at the para position with phenyl.

In one embodiment of Formula (IX), X is N or $CY^1$. In another embodiment of Formula (IX), X is N. In another embodiment of Formula (IX), X is $CY^1$.

In one embodiment of Formula (IX), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (IX), X is $CY^1$; and $Y^1$ is independently selected from the group consisting of hydrogen, Cl, Br, and I. In another embodiment of Formula (IX), X is $CY^1$; and $Y^1$ is Cl. In another embodiment of Formula (IX), X is $CY^1$; and $Y^1$ is hydrogen.

In one embodiment of Formula (IX), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I. In another embodiment of Formula (IX), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IX), $R^3$ is phenyl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (IX), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (IX), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IX), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (IX), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, and OH.

In another embodiment of Formula (IX), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (IX), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (IX), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (IX), $R^6$, at each occurrence, is independently selected from the group consisting of alkyl, alkenyl, aryl, heterocyclyl, and cycloalkyl; wherein each $R^6$ alkyl and alkenyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, and heterocyclyl is optionally substituted with one, two, three or four substituents independently selected from the group consisting of $R^{10}$, $OR^{10}$, CN, F, Cl, Br and I.

In one embodiment of Formula (IX), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (IX), $R^7$, at each occurrence, is alkyl or heterocyclyl.

In one embodiment of Formula (IX), $R^8$ at each occurrence, is independently selected from the group consisting of alkyl, alkenyl, and alkynyl. In another embodiment of Formula (IX), $R^8$ at each occurrence, is independently alkyl.

In one embodiment of Formula (IX), $R^9$ at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, $COH$, CN, $NO_2$, F, Cl, Br and I. In another embodiment of Formula (IX), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (IX), $R^{10}$ at each occurrence, is independently selected from the group consisting of haloalkyl, alkyl, alkenyl, and alkynyl. In another embodiment of Formula (IX), $R^{10}$ at each occurrence, is independently haloalkyl or alkyl.

In one embodiment of Formula (IX), $R^{11}$ at each occurrence, is independently selected from the group consisting of alkyl, alkenyl, and alkynyl. In another embodiment of Formula (IX), $R^{11}$ at each occurrence, is independently alkyl.

One embodiment pertains to compounds or pharmaceutically acceptable salts thereof, which are useful as inhibitors of NAMPT, the compounds having Formula (IX)

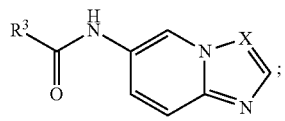

Formula (IX)

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $C(O)R^4$, $NHC(O)R^4$, $NR^4C(O)R^4$, $NHS(O)_2R^4$, $NHC(O)OR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, or two substituents independently selected from the group consisting of $R^6$, $OR^6$, $SO_2R^6$, $C(O)R^6$, $CO(O)R^6$, $C(O)C(O)R^6$, $NHC(O)R^6$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, substituent independently selected from the group consisting of $R^7$, $OR^7$, OH, F, Cl, Br and I; wherein each $R^5$ aryl and heterocyclyl is optionally substituted with one, or two substituents independently selected from the group consisting of $R^8$, $OR^8$, CNF, Cl, Br and I;

$R^6$, at each occurrence, is independently selected from the group consisting of alkyl, alkenyl, aryl, heterocyclyl, and cycloalkyl; wherein each $R^6$ alkyl is optionally substituted with one, two, three or four substituents independently selected from the group consisting of $R^9$, $OR^9$, $SO_2R^9$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I;

$R^7$, at each occurrence, is independently selected from the group consisting of alkyl, and heterocyclyl;

$R^8$, at each occurrence, is alkyl;

$R^9$, at each occurrence, is independently selected from the group consisting of alkyl, aryl, heterocyclyl, and cycloalkyl; wherein each $R^9$ alkyl is optionally substituted with one, substituent independently selected from the group consisting of aryl, alkoxy, F, Cl, Br and I; wherein each $R^9$ aryl, cycloalkyl, and heterocyclyl is optionally substituted with one, two, or three substituents independently selected from the group consisting of $R^{11}$, $OR^{11}$, $CO(O)R^{11}$, F, Cl, Br and I;

$R^{10}$ at each occurrence, is independently selected from the group consisting of haloalkyl, and alkyl; and $R^{11}$ at each occurrence, is alkyl;

with the provisos that when X is $CY^1$ and $Y^1$ is hydrogen; and $R^3$ is thiazolyl; the $R^3$ thiazolyl is substituted with one substituent; and when X is $CY^1$ and $Y^1$ is hydrogen; and $R^3$ is phenyl; the $R^3$ phenyl is not substituted at the para position with phenyl.

Still another embodiment pertains to compounds having Formula (IX), which includes Examples 53, 54, 76, 314, 323, 491, and pharmaceutically acceptable salts thereof.

Embodiments of Formula (IA)

One embodiment, therefore, pertains to compounds or pharmaceutically acceptable salts thereof, which are useful as inhibitors of NAMPT, the compounds having Formula (IA)

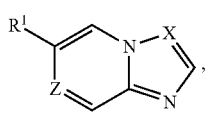

Formula (IA)

wherein

X is N or CY$^1$;

Y$^1$ is independently selected from the group consisting of hydrogen, alkyl, alkoxy, haloalkyl, hydroxyalkyl, OH, CN, F, Cl, Br, and I;

R$^1$ is independently selected from the group consisting of NHC(O)NHR$^3$, NHC(O)NH(CH$_2$)$_m$R$^{3x}$, CH$_2$NHC(O)NHR$^3$, NHC(O)R$^3$, NHC(O)(CH$_2$)$_n$R$^3$, C(O)NH(CH$_2$)$_n$R$^3$, NHC(O)(CH$_2$)$_m$R$^{3x}$, C(O)NH(CH$_2$)$_m$R$^{3x}$, CH$_2$C(O)NHR$^3$, and CH$_2$NHC(O)R$^3$; and Z is CH, C—F, C—Cl, C—Br, C—I or N; or X is N or CY$^1$;

Y$^1$ is independently selected from the group consisting of hydrogen, alkyl, alkoxy, haloalkyl, hydroxyalkyl, OH, CN, F, Cl, Br, and I;

R$^1$ is hydrogen, F, Cl, Br, or I;

Z is CR$^2$; and

R$^2$ is independently selected from the group consisting of NHC(O)NHR$^3$, NHC(O)NH(CH$_2$)$_m$R$^{3x}$, CH$_2$NHC(O)NHR$^3$, NHC(O)R$^3$, NHC(O)(CH$_2$)$_n$R$^3$, C(O)NH(CH$_2$)$_n$R$^3$, NHC(O)(CH$_2$)$_m$R$^{3x}$, C(O)NH(CH$_2$)$_m$R$^{3x}$, CH$_2$C(O)NHR$^3$, and CH$_2$NHC(O)R$^3$; and R$^3$ is independently selected from the group consisting of phenyl and 5-6 membered heteroaryl; wherein each R$^3$ phenyl is substituted at the para position with one substituent independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NHC(O)N(R$^4$)$_2$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I; wherein each R$^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^{3x}$ is independently selected from the group consisting of phenyl and heterocyclyl; wherein each R$^{3x}$ phenyl and heterocyclyl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, C(O)C(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I;

$R^{10}$ at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I;

$R^{11}$ at each occurrence, is independently selected from the group consisting of aryl, heterocyclyl, cycloalkyl, cycloalkenyl, alkyl, alkenyl, and alkynyl;

m is 4, 5, or 6; and n is 1 or 2;

with the provisos that when X is $CY^1$ and $Y^1$ is hydrogen; and $R^3$ is thiazolyl; the $R^3$ thiazolyl is substituted with one substituent;

when X is $CY^1$ and $Y^1$ is hydrogen; $R^1$ is $NHC(O)R^3$; $R^2$ is hydrogen; and $R^3$ is phenyl; the $R^3$ phenyl is not substituted at the para position with phenyl;

when X is $CY^1$ and $Y^1$ is hydrogen; $R^1$ is $C(O)NH(CH_2)_n R^3$; n is 1; $R^2$ is hydrogen; and $R^3$ is phenyl; the $R^3$ phenyl is not substituted at the para position with phenylmethoxy or 3-fluorophenoxy;

when X is $CY^1$ and $Y^1$ is hydrogen; $R^1$ is $C(O)NH(CH_2)_n R^3$; n is 1; $R^2$ is hydrogen; and $R^3$ is furanyl; the $R^3$ furanyl is not substituted with benzyl, or 3-fluorophenyl methyl;

when X is $CY^1$ and $Y^1$ is hydrogen; $R^1$ is $C(O)NH(CH_2)_n R^3$; n is 1; $R^2$ is hydrogen; and $R^3$ is thienyl; the $R^3$ thienyl is not substituted with phenoxy, 3-fluorophenoxy, or 3-chlorophenoxy; and when X is $CY^1$ and $Y^1$ is hydrogen; $R^1$ is $C(O)NH(CH_2)_n R^3$; n is 1; $R^2$ is hydrogen; and $R^3$ is $R^3$ phenyl; the phenyl is not substituted at the para position with $SO_2R^4$ or $SO_2NHR^4$.

In one embodiment of Formula (IA), X is N or $CY^1$. In another embodiment of Formula (IA), X is N. In another embodiment of Formula (IA), X is $CY^1$.

In one embodiment of Formula (IA), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (IA), X is $CY^1$; and $Y^1$ is independently selected from the group consisting of hydrogen, Cl, Br, and I. In another embodiment of Formula (IA), X is $CY^1$; and $Y^1$ is Cl. In another embodiment of Formula (IA), X is $CY^1$; and $Y^1$ is hydrogen.

In one embodiment of Formula (IA), Z is CH, C—F, C—Cl, C—Br, C—I or N; and $R^1$ is independently selected from the group consisting of $NHC(O)NHR^3$, $NHC(O)NH(CH_2)_m R^{3x}$, $CH_2NHC(O)NHR^3$, $NHC(O)R^3$, $NHC(O)(CH_2)_n R^3$, $C(O)NH(CH_2)_n R^3$, $NHC(O)(CH_2)_m R^{3x}$, $C(O)NH(CH_2)_m R^{3x}$, $CH_2C(O)NHR^3$, and $CH_2NHC(O)R^3$. In another embodiment of Formula (IA), Z is CH or N; and $R^1$ is $NHC(O)NHR^3$. In another embodiment of Formula (IA), Z is CH or N; and $R^1$ is $NHC(O)NH(CH_2)_m R^{3x}$. In another embodiment of Formula (IA), Z is CH or N; and $R^1$ is $CH_2NHC(O)NHR^3$. In another embodiment of Formula (IA), Z is CH or N; and $R^1$ is $NHC(O)R^3$. In another embodiment of Formula (IA), Z is CH or N; and $R^1$ is $NHC(O)(CH_2)_n R^3$. In another embodiment of Formula (IA), Z is CH or N; and $R^1$ is $C(O)NH(CH_2)_n R^3$. In another embodiment of Formula (IA), Z is CH or N; and $R^1$ is $NHC(O)(CH_2)_m R^{3x}$. In another embodiment of Formula (IA), Z is CH or N; and $R^1$ is $C(O)NH(CH_2)_m R^{3x}$. In another embodiment of Formula (IA), Z is CH or N; and $R^1$ is $CH_2C(O)NHR^3$. In another embodiment of Formula (IA), Z is CH or N; and $R^1$ is $CH_2NHC(O)R^3$.

In one embodiment of Formula (IA), Z is CH; and $R^1$ is independently selected from the group consisting of $NHC(O)NHR^3$, $NHC(O)NH(CH_2)_m R^{3x}$, $CH_2NHC(O)NHR^3$, $NHC(O)R^3$, $NHC(O)(CH_2)_n R^3$, $C(O)NH(CH_2)_n R^3$, $NHC(O)(CH_2)_m R^{3x}$, $C(O)NH(CH_2)_m R^{3x}$, $CH_2C(O)NHR^3$, and $CH_2NHC(O)R^3$. In another embodiment of Formula (IA), Z is CH; and $R^1$ is $NHC(O)NHR^3$. In another embodiment of Formula (IA), Z is CH; and $R^1$ is $NHC(O)NH(CH_2)_m R^{3x}$. In another embodiment of Formula (IA), Z is CH; and $R^1$ is $CH_2NHC(O)NHR^3$. In another embodiment of Formula (IA), Z is CH; and $R^1$ is $NHC(O)R^3$. In another embodiment of Formula (IA), Z is CH; and $R^1$ is $NHC(O)(CH_2)_n R^3$. In another embodiment of Formula (IA), Z is CH; and $R^1$ is $C(O)NH(CH_2)_n R^3$. In another embodiment of Formula (IA), Z is CH; and $R^1$ is $NHC(O)(CH_2)_m R^{3x}$. In another embodiment of Formula (IA), Z is CH; and $R^1$ is $C(O)NH(CH_2)_m R^{3x}$. In another embodiment of Formula (IA), Z is CH; and $R^1$ is $CH_2C(O)NHR^3$. In another embodiment of Formula (IA), Z is CH; and $R^1$ is $CH_2NHC(O)R^3$.

In one embodiment of Formula (IA), Z is N; and $R^1$ is independently selected from the group consisting of $NHC(O)NHR^3$, $NHC(O)NH(CH_2)_m R^{3x}$, $CH_2NHC(O)NHR^3$, NHC (O)R³, NHC(O)(CH₂)ₙR³, C(O)NH(CH₂)ₙR³, NHC(O)(CH₂)ₘR³ˣ, C(O)NH(CH₂)ₘR³ˣ, CH₂C(O)NHR³, and CH₂NHC(O)R³. In another embodiment of Formula (IA), Z is N; and R¹ is NHC(O)NHR³. In another embodiment of Formula (IA), Z is N; and R¹ is NHC(O)NH(CH₂)ₘR³ˣ. In another embodiment of Formula (IA), Z is N; and R¹ is CH₂NHC(O)NHR³. In another embodiment of Formula (IA), Z is N; and R¹ is NHC(O)R³. In another embodiment of Formula (IA), Z is N; and R¹ is NHC(O)(CH₂)ₙR³. In another embodiment of Formula (IA), Z is N; and R¹ is C(O)NH(CH₂)ₙR³. In another embodiment of Formula (IA), Z is N; and R¹ is NHC(O)(CH₂)ₘR³ˣ. In another embodiment of Formula (IA), Z is N; and R¹ is C(O)NH(CH₂)ₘR³ˣ. In another embodiment of Formula (IA), Z is N; and R¹ is CH₂C(O)NHR³. In another embodiment of Formula (IA), Z is N; and R¹ is CH₂NHC(O)R³.

In one embodiment of Formula (IA), R¹ is hydrogen; Z is CR²; and R² is independently selected from the group consisting of NHC(O)NHR³, NHC(O)NH(CH₂)ₘR³ˣ, CH₂NHC(O)NHR³, NHC(O)R³, NHC(O)(CH₂)ₙR³, C(O)NH(CH₂)ₙR³, NHC(O)(CH₂)ₘR³ˣ, C(O)NH(CH₂)ₘR³ˣ, CH₂C(O)NHR³, and CH₂NHC(O)R³. In another embodiment of Formula (IA), R¹ is hydrogen; Z is CR²; and R² is NHC(O)NHR³. In another embodiment of Formula (IA), R¹ is hydrogen; Z is CR²; and R² is NHC(O)NH(CH₂)ₘR³ˣ. In another embodiment of Formula (IA), R¹ is hydrogen; Z is CR²; and R² is CH₂NHC(O)NHR³. In another embodiment of Formula (IA), R¹ is hydrogen; Z is CR²; and R² is NHC(O)R³. In another embodiment of Formula (IA), R¹ is hydrogen; Z is CR²; and R² is NHC(O)(CH₂)ₙR³. In another embodiment of Formula (IA), R¹ is hydrogen; Z is CR²; and R² is C(O)NH(CH₂)ₙR³. In another embodiment of Formula (IA), R¹ is hydrogen; Z is CR²; and R² is NHC(O)(CH₂)ₘR³ˣ. In another embodiment of Formula (IA), R¹ is hydrogen; Z is CR²; and R² is C(O)NH(CH₂)ₘR³ˣ. In another embodiment of Formula (IA), R¹ is hydrogen; Z is CR²; and R² is CH₂C(O)NHR³. In another embodiment of Formula (IA), R¹ is hydrogen; Z is CR²; and R² is CH₂NHC(O)R³.

In one embodiment of Formula (IA), m is 4, 5, or 6. In another embodiment of Formula (IA), m is 4. In another embodiment of Formula (IA), m is 5. In another embodiment of Formula (IA), m is 6.

In one embodiment of Formula (IA), n is 1 or 2. In another embodiment of Formula (IA), n is 1. In another embodiment of Formula (IA), n is 2.

In one embodiment of Formula (IA), R³ is independently selected from the group consisting of phenyl and 5-6 membered heteroaryl; wherein each R³ phenyl is substituted at the para position with one substituent independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I; wherein each R³ phenyl is optionally additionally substituted with one substituent independently selected from the group consisting of alkyl, haloalkyl, alkoxyalkyl, hydroxyalkyl, C(O)H, C(O)OH, C(N)NH₂, OH, CN, N₃, NO₂, F, Cl, Br and I; wherein each R³ 5-6 membered heteroaryl is substituted with one, two, three or four substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I. In another embodiment of Formula (IA), R³ is independently selected from the group consisting of phenyl and 5-6 membered heteroaryl; wherein each R³ phenyl is substituted at the para position with one substituent independently selected from the group consisting of R⁴, SO₂R⁴, OR⁴, C(O)R⁴, NHC(O)R⁴, NR⁴C(O)R⁴, NHS(O)₂R⁴, NHC(O)OR⁴, and C(O)NHR⁴; wherein each R³ phenyl is optionally additionally substituted with one substituent independently selected from the group consisting of F, Cl, Br and I; wherein each R³ 5-6 membered heteroaryl is substituted with one, two, three or four substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I.

In one embodiment of Formula (IA), R³ is phenyl; wherein each R³ phenyl is substituted at the para position with one substituent independently selected from the group consisting of R⁴, SO₂R⁴, OR⁴, C(O)R⁴, NHC(O)R⁴, NR⁴C(O)R⁴, NHS(O)₂R⁴, NHC(O)OR⁴, and C(O)NHR⁴; and wherein each R³ phenyl is optionally additionally substituted with one substituent independently selected from the group consisting of F, Cl, Br and I. In another embodiment of Formula (IA), R³ is 5-6 membered heteroaryl; wherein each R³ 5-6 membered heteroaryl is substituted with one, two, three or four substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I. In another embodiment of Formula (IA), R³ is thienyl; wherein each R³ thienyl is substituted with one, two, or three substituents independently selected from the group consisting of R⁴, C(O)R⁴, NHR⁴, NHC(O)R⁴, NR⁴C(O)R⁴, NHC(O)OR⁴, NR⁴C(O)NHR⁴, C(O)NHR⁴, F, Cl, Br and I.

In one embodiment of Formula (IA), R³ˣ is independently selected from the group consisting of phenyl and heterocyclyl; wherein each R³ˣ phenyl and heterocyclyl is substituted with one, two, three or four substituents independently selected from the group consisting of R⁴, OR⁴, SR⁴, S(O)R⁴, SO₂R⁴, C(O)R⁴, CO(O)R⁴, OC(O)R⁴, OC(O)OR⁴, NH₂, NHR⁴, N(R⁴)₂, NHC(O)R⁴, NR⁴C(O)R⁴, NHS(O)₂R⁴, NR⁴S(O)₂R⁴, NHC(O)OR⁴, NR⁴C(O)OR⁴, NHC(O)NH₂, NHC(O)NHR⁴, NHC(O)N(R⁴)₂, NR⁴C(O)NHR⁴, NR⁴C(O)N(R⁴)₂, C(O)NH₂, C(O)NHR⁴, C(O)N(R⁴)₂, C(O)NHOH, C(O)NHOR⁴, C(O)NHSO₂R⁴, C(O)NR⁴SO₂R⁴, SO₂NH₂, SO₂NHR⁴, SO₂N(R⁴)₂, C(O)H, C(O)OH, C(N)NH₂, C(N)NHR⁴, C(N)N(R⁴)₂, CNOH, CNOCH₃, OH, CN, N₃, NO₂, F, Cl, Br and I. In another embodiment of Formula (IA), R³ˣ is heterocyclyl; wherein each R³ˣ heterocyclyl is substituted with C(O)R⁴, or CO(O)R⁴.

In one embodiment of Formula (IA), R⁴, at each occurrence, is independently selected from the group consisting of alkyl, alkenyl, alkynyl, aryl, cycloalkyl, cycloalkenyl, and 3-12 membered heterocyclyl; wherein each R⁴ alkyl, alkenyl, and alkynyl is optionally substituted with one, two, three or four substituents independently selected from the group consisting of R⁵, OR⁵, SR⁵, S(O)R⁵, SO₂R⁵, C(O)R⁵, CO(O)R⁵, OC(O)R⁵, OC(O)OR⁵, NH₂, NHR⁵, N(R⁵)₂, NHC(O)R⁵, NR⁵C(O)R⁵, NHS(O)₂R⁵, NR⁵S(O)₂R⁵, NHC(O)OR⁵, NR⁵C(O)OR⁵, NHC(O)NH₂, NHC(O)NHR⁵, NHC(O)N(R⁵)₂, NR⁵C(O)NHR⁵, NR⁵C(O)N(R⁵)₂, C(O)NH₂, C(O)NHR⁵, C(O)N(R⁵)₂, C(O)NHOH, C(O)NHOR⁵, C(O)NHSO₂R⁵, C(O)NR⁵SO₂R⁵, SO₂NH₂, SO₂NHR⁵, SO₂N $(R^5)_2$, C(O)H, C(O)OH, C(N)NH$_2$, C(N)NHR$^5$, C(N)N(R$^5)_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, OC(O)R$^6$, OC(O)OR$^6$, NH$_2$, NHR$^6$, N(R$^6)_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6)_2$, NR$^6$C(O)NHR$^6$, NR$^6$C(O)N(R$^6)_2$, C(O)NH$_2$, C(O)NHR$^6$, C(O)N(R$^6)_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6)_2$, C(O)H, C(O)OH, C(N)NH$_2$, C(N)NHR$^6$, C(N)N(R$^6)_2$, CNOH, CNOCH$_3$, OH, CN, N$_3$, NO$_2$, F, Cl, Br and I. In another embodiment of Formula (IA), R$^4$, at each occurrence, is independently selected from the group consisting of alkyl, aryl, cycloalkyl, and 3-12 membered heterocyclyl; wherein each R$^4$ alkyl is optionally substituted with one, two, three or four substituents independently selected from the group consisting of R$^5$, OR$^5$, C(O)R$^5$, NHC(O)R$^5$, OH, F, Cl, Br and I; wherein each R$^4$ aryl, cycloalkyl and 3-12 membered heterocyclyl is optionally substituted with one, two, three or four substituents independently selected from the group consisting of R$^6$, OR$^6$, SO$_2$R$^6$, C(O)R$^6$, CO(O)R$^6$, C(O)C(O)R$^6$, NHC(O)R$^6$, C(O)N(R$^6)_2$, OH, and F.

In another embodiment of Formula (IA), R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7)_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7)_2$, NR$^7$C(O)NHR$^7$, NR$^7$C(O)N(R$^7)_2$, C(O)NH$_2$, C(O)NHR$^7$, C(O)N(R$^7)_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7)_2$, C(O)H, C(O)OH, C(N)NH$_2$, C(N)NHR$^7$, C(N)N(R$^7)_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8)_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8)_2$, NR$^8$C(O)NHR$^8$, NR$^8$C(O)N(R$^8)_2$, C(O)NH$_2$, C(O)NHR$^8$, C(O)N(R$^8)_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8)_2$, C(O)H, C(O)OH, C(N)NH$_2$, C(N)NHR$^8$, C(N)N(R$^8)_2$, CNOH, CNOCH$_3$, OH, CN, N$_3$, NO$_2$, F, Cl, Br and I. In another embodiment of Formula (IA), R$^5$, at each occurrence, is independently selected from the group consisting of alkyl, aryl, heterocyclyl, and cycloalkyl; wherein each R$^5$ alkyl is optionally substituted with one, two, three or four substituents independently selected from the group consisting of R$^7$, OR$^7$, and OH; wherein each R$^5$ aryl and heterocyclyl is optionally substituted with one, two, three or four substituents independently selected from the group consisting of R$^8$, OR$^8$, CN, F, Cl, Br and I.

In one embodiment of Formula (IA), R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9)_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9)_2$, NR$^9$C(O)NHR$^9$, NR$^9$C(O)N(R$^9)_2$, C(O)NH$_2$, C(O)NHR$^9$, C(O)N(R$^9)_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9)_2$, C(O)H, C(O)OH, C(N)NH$_2$, C(N)NHR$^9$, C(N)N(R$^9)_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10})_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10})_2$, NR$^{10}$C(O)NHR$^{10}$, NR$^{10}$C(O)N(R$^{10})_2$, C(O)NH$_2$, C(O)NHR$^{10}$, C(O)N(R$^{10})_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10})_2$, C(O)H, C(O)OH, C(N)NH$_2$, C(N)NHR$^{10}$, C(N)N(R$^{10})_2$, CNOH, CNOCH$_3$, OH, CN, N$_3$, NO$_2$, F, Cl, Br and I. In another embodiment of Formula (IA), R$^6$, at each occurrence, is independently selected from the group consisting of alkyl, alkenyl, aryl, heterocyclyl, cycloalkyl, and cycloalkenyl; wherein each R$^6$ alkyl and alkenyl is optionally substituted with one, two, three or four substituents independently selected from the group consisting of R$^9$, OR$^9$, SO$_2$R$^9$, NH$_2$, N(R$^9)_2$, OH, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, CN, F, Cl, Br and I.

In one embodiment of Formula (IA), R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I. In another embodiment of Formula (IA), R$^7$, at each occurrence, is alkyl or heterocyclyl.

In one embodiment of Formula (IA), R$^8$, at each occurrence, is independently selected from the group consisting of alkyl, alkenyl, and alkynyl. In another embodiment of Formula (IA), R$^8$, at each occurrence, is independently alkyl.

In one embodiment of Formula (IA), R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^1$, C(O)R$^{11}$, CO(O)R$^{11}$, OC(O)R$^{11}$, NH$_2$, NHR$^{11}$, N(R$^{11})_2$, NHC(O)R$^{11}$, NR$^{11}$C(O)R$^{11}$, C(O)NH$_2$, C(O)NHR$^{11}$, C(O)N(R$^{11})_2$, C(O)H, C(O)OH, COH, CN, NO$_2$, F, Cl, Br and I. In another embodiment of Formula (IA), R$^9$, at each occurrence, is independently selected from the group consisting of alkyl, aryl, heterocyclyl, and cycloalkyl; wherein each R$^9$ alkyl is optionally substituted with one, two, three or four substituents independently selected from the group consisting of aryl, and alkoxy; wherein each R$^9$ aryl, cycloalkyl, and heterocyclyl is optionally substituted with one, two, three or four substituents independently selected from the group consisting of $R^{11}$, $OR^{11}$, $CO(O)R^{11}$, CN, F, and Cl.

In one embodiment of Formula (IA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (IA), $R^{10}$ at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (IA), $R^{11}$, at each occurrence, is independently selected from the group consisting of aryl, heterocyclyl, cycloalkyl, cycloalkenyl, alkyl, alkenyl, and alkynyl. In another embodiment of Formula (IA), $R^{11}$, at each occurrence, is independently alkyl.

In another embodiment of Formula (IA), $R^{11}$, at each occurrence, is independently cycloalkyl.

One embodiment pertains to compounds or pharmaceutically acceptable salts thereof, which are useful as inhibitors of NAMPT, the compounds having Formula (IA)

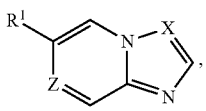

Formula (IA)

wherein
X is N or $CY^1$;
$Y^1$ is independently selected from the group consisting of hydrogen, F, Cl, Br, and I;
$R^1$ is independently selected from the group consisting of $NHC(O)NHR^3$, $NHC(O)NH(CH_2)_mR^{3x}$, $CH_2NHC(O)NHR^3$, $NHC(O)R^3$, $NHC(O)(CH_2)_nR^3$, $C(O)NH(CH_2)_nR^3$, $NHC(O)(CH_2)_mR^{3x}$, $C(O)NH(CH_2)_mR^{3x}$, $CH_2C(O)NHR^3$, and $CH_2NHC(O)R^3$; and
Z is CH, C—F, or N; or
X is N or $CY^1$;
$Y^1$ is independently selected from the group consisting of hydrogen, and Cl;
$R^1$ is hydrogen;
Z is $CR^2$; and
$R^2$ is independently selected from the group consisting of $NHC(O)NHR^3$, $NHC(O)NH(CH_2)_mR^{3x}$, $CH_2NHC(O)NHR^3$, $NHC(O)R^3$, $CH_2C(O)NHR^3$, and $CH_2NHC(O)R^3$; and
$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;
$R^{3x}$ is heterocyclyl; wherein the $R^{3x}$ heterocyclyl is substituted with one, two, three or four substituents independently selected from the group consisting of $C(O)R^4$, $CO(O)R^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$ at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F;

$R^{11}$ at each occurrence, is independently cycloalkyl or alkyl;

m is 4, or 5; and
n is 1;
with the provisos that
when X is $CY^1$ and $Y^1$ is hydrogen; and $R^3$ is thiazolyl; the $R^3$ thiazolyl is substituted with one substituent;
when X is $CY^1$ and $Y^1$ is hydrogen; $R^1$ is $NHC(O)R^3$; $R^2$ is hydrogen; and $R^3$ is phenyl; the $R^3$ phenyl is not substituted at the para position with phenyl;
when X is $CY^1$ and $Y^1$ is hydrogen; $R^1$ is $C(O)NH(CH_2)_n R^3$; n is 1; $R^2$ is hydrogen; and $R^3$ is phenyl; the $R^3$ phenyl is not substituted at the para position with phenylmethoxy or 3-fluorophenoxy;
when X is $CY^1$ and $Y^1$ is hydrogen; $R^1$ is $C(O)NH(CH_2)_n R^3$; n is 1; $R^2$ is hydrogen; and $R^3$ is furanyl; the $R^3$ furanyl is not substituted with benzyl, or 3-fluorophenyl methyl;
when X is $CY^1$ and $Y^1$ is hydrogen; $R^1$ is $C(O)NH(CH_2)_n R^3$; n is 1; $R^2$ is hydrogen; and $R^3$ is thienyl; the $R^3$ thienyl is not substituted with phenoxy, 3-fluorophenoxy, or 3-chlorophenoxy; and when X is CY¹ and Y¹ is hydrogen; R¹ is C(O)NH(CH$_2$)$_n$R³; n is 1; R² is hydrogen; and R³ is R³ phenyl; the phenyl is not substituted at the para position with SO$_2$R⁴ or SO$_2$NHR⁴.

Still another embodiment pertains to compounds having Formula (IA), which includes 4-[(imidazo[1,2-a]pyridin-6-ylcarbamoyl)amino]-N-(3-methylbutyl)benzamide;
4-[(imidazo[1,2-a]pyridin-7-ylcarbamoyl)amino]-N-(3-methylbutyl)benzamide;
2-cyclopentyl-N-{4-[(imidazo[1,2-a]pyridin-6-ylcarbamoyl)amino]phenyl}acetamide;
4-[(imidazo[1,2-a]pyridin-6-ylcarbamoyl)amino]-N-(2-phenylethyl)benzamide;
4-[(imidazo[1,2-a]pyridin-6-ylcarbamoyl)amino]-N-[2-(morpholin-4-yl)ethyl]benzamide;
N-(1-hydroxy-2-methylpropan-2-yl)-4-[(imidazo[1,2-a]pyridin-6-ylcarbamoyl)amino]benzamide;
N-benzyl-4-[(imidazo[1,2-a]pyridin-6-ylcarbamoyl)amino]benzamide;
N-(cyclopentylmethyl)-4-[(imidazo[1,2-a]pyridin-6-ylcarbamoyl)amino]benzamide;
4-[(imidazo[1,2-a]pyridin-6-ylcarbamoyl)amino]-N-[3-(piperidin-1-yl)propyl]benzamide;
4-[(imidazo[1,2-a]pyridin-6-ylcarbamoyl)amino]-N-(2-phenoxyethyl)benzamide;
4-[(imidazo[1,2-a]pyridin-6-ylcarbamoyl)amino]-N-[2-(pyrrolidin-1-yl)ethyl]benzamide;
4-[(imidazo[1,2-a]pyridin-6-ylcarbamoyl)amino]-N-[2-(propan-2-yloxy)ethyl]benzamide;
N-(2-hydroxy-2-methylpropyl)-4-[(imidazo[1,2-a]pyridin-6-ylcarbamoyl)amino]benzamide;
N-[2-hydroxy-1-(4-methoxyphenyl)ethyl]-4-[(imidazo[1,2-a]pyridin-6-ylcarbamoyl)amino]benzamide;
4-[(imidazo[1,2-a]pyridin-6-ylcarbamoyl)amino]-N-[2-(2-oxopyrrolidin-1-yl)ethyl]benzamide;
4-[(imidazo[1,2-a]pyridin-6-ylcarbamoyl)amino]-N-(tetrahydrofuran-2-ylmethyl)benzamide;
4-[(imidazo[1,2-a]pyridin-6-ylcarbamoyl)amino]-N-propylbenzamide;
4-[(imidazo[1,2-a]pyridin-6-ylcarbamoyl)amino]-N-[3-(morpholin-4-yl)propyl]benzamide;
4-[(imidazo[1,2-a]pyridin-6-ylcarbamoyl)amino]-N-phenylbenzamide;
4-[(imidazo[1,2-a]pyridin-6-ylcarbamoyl)amino]-N-(2-methylbutyl)benzamide;
4-[(imidazo[1,2-a]pyridin-6-ylcarbamoyl)amino]-N-[3-(2-oxopyrrolidin-1-yl)propyl]benzamide;
4-[(imidazo[1,2-a]pyridin-6-ylcarbamoyl)amino]-N-(tetrahydro-2H-pyran-4-ylmethyl)benzamide;
4-[(imidazo[1,2-a]pyridin-6-ylcarbamoyl)amino]-N-(tetrahydro-2H-pyran-2-ylmethyl)benzamide;
N-[(1,1-dioxidotetrahydrothiophen-3-yl)methyl]-4-[(imidazo[1,2-a]pyridin-6-ylcarbamoyl)amino]benzamide;
tert-butyl 4-{4-[(imidazo[1,2-a]pyridin-6-ylcarbamoyl)amino]phenyl}-3,6-dihydropyridine-1(2H)-carboxylate;
N-{4-[(imidazo[1,2-a]pyridin-6-ylcarbamoyl)amino]phenyl}-2-(tetrahydrofuran-3-yl)acetamide;
N-{4-[(imidazo[1,2-a]pyridin-6-ylcarbamoyl)amino]phenyl}acetamide;
1-imidazo[1,2-a]pyridin-6-yl-3-{4-[1-(tetrahydrofuran-3-ylacetyl)-1,2,3,6-tetrahydropyridin-4-yl]phenyl}urea;
1-{4-[1-(2-hydroxy-2-methylpropanoyl)-1,2,3,6-tetrahydropyridin-4-yl]phenyl}-3-imidazo[1,2-a]pyridin-6-ylurea;
1-imidazo[1,2-a]pyridin-6-yl-3-{4-[1-(morpholin-4-ylacetyl)-1,2,3,6-tetrahydropyridin-4-yl]phenyl}urea;
1-{4-[1-(ethoxyacetyl)-1,2,3,6-tetrahydropyridin-4-yl]phenyl}-3-imidazo[1,2-a]pyridin-6-ylurea;
1-imidazo[1,2-a]pyridin-6-yl-3-(4-{1-[(2-methoxyethoxy)acetyl]-1,2,3,6-tetrahydropyridin-4-yl}phenyl)urea;
1-imidazo[1,2-a]pyridin-6-yl-3-{4-[1-(tetrahydrofuran-2-ylcarbonyl)-1,2,3,6-tetrahydropyridin-4-yl]phenyl}urea;
1-imidazo[1,2-a]pyridin-6-yl-3-{4-[1-(tetrahydro-2H-pyran-4-ylcarbonyl)-1,2,3,6-tetrahydropyridin-4-yl]phenyl}urea;
1-{4-[1-(1,4-dioxan-2-ylcarbonyl)-1,2,3,6-tetrahydropyridin-4-yl]phenyl}-3-imidazo[1,2-a]pyridin-6-ylurea;
1-imidazo[1,2-a]pyridin-6-yl-3-(4-{1-[(1-methylpiperidin-4-yl)carbonyl]-1,2,3,6-tetrahydropyridin-4-yl}phenyl)urea;
1-(4-{1-[(1,1-dioxidotetrahydro-2H-thiopyran-4-yl)carbonyl]-1,2,3,6-tetrahydropyridin-4-yl}phenyl)-3-imidazo[1,2-a]pyridin-6-ylurea;
1-imidazo[1,2-a]pyridin-6-yl-3-{4-[1-(2-methylpropanoyl)-1,2,3,6-tetrahydropyridin-4-yl]phenyl}urea;
2-ethoxy-N-{4-[(imidazo[1,2-a]pyridin-6-ylcarbamoyl)amino]phenyl}acetamide;
N-{4-[(imidazo[1,2-a]pyridin-6-ylcarbamoyl)amino]phenyl}-2-(tetrahydro-2H-pyran-4-yl)acetamide;
N-{4-[(imidazo[1,2-a]pyridin-6-ylcarbamoyl)amino]phenyl}-2-(morpholin-4-yl)acetamide;
N-{4-[(imidazo[1,2-a]pyridin-6-ylcarbamoyl)amino]phenyl}-2-(2-methoxyethoxy)acetamide;
N-{4-[(imidazo[1,2-a]pyridin-6-ylcarbamoyl)amino]phenyl}-3-methoxy-2-methylpropanamide;
N-{4-[(imidazo[1,2-a]pyridin-6-ylcarbamoyl)amino]phenyl}butanamide;
4,4,4-trifluoro-N-{4-[(imidazo[1,2-a]pyridin-6-ylcarbamoyl)amino]phenyl}butanamide;
N-{4-[(imidazo[1,2-a]pyridin-6-ylcarbamoyl)amino]phenyl}tetrahydro-2H-pyran-4-carboxamide;
N-{4-[(imidazo[1,2-a]pyridin-6-ylcarbamoyl)amino]phenyl}-4-methylpentanamide;
N-{4-[(imidazo[1,2-a]pyridin-6-ylcarbamoyl)amino]phenyl}-1-methylpiperidine-4-carboxamide;
N-{4-[(imidazo[1,2-a]pyridin-6-ylcarbamoyl)amino]phenyl}tetrahydro-2H-thiopyran-4-carboxamide 1,1-dioxide;
N-{4-[(imidazo[1,2-a]pyridin-6-ylcarbamoyl)amino]phenyl}-1,4-dioxane-2-carboxamide;
1-imidazo[1,2-a]pyridin-6-yl-3-{4-[1-(2-methylpropyl)-1H-pyrazol-4-yl]phenyl}urea;
4-[(cyclopentylacetyl)amino]-N-(imidazo[1,2-a]pyridin-6-ylmethyl)benzamide;
2-[(4-cyanobenzyl)(3-methylbutanoyl)amino]-N-(imidazo[1,2-a]pyridin-6-yl)-1,3-thiazole-5-carboxamide;
2-[(4-cyanobenzyl)(3-methoxypropanoyl)amino]-N-(imidazo[1,2-a]pyridin-6-yl)-1,3-thiazole-5-carboxamide;
2-[(4-cyanobenzyl)(3-methylbutanoyl)amino]-N-(imidazo[1,2-a]pyridin-6-ylmethyl)-1,3-thiazole-5-carboxamide;
2-[(4-cyanobenzyl)(3-methoxypropanoyl)amino]-N-(imidazo[1,2-a]pyridin-6-ylmethyl)-1,3-thiazole-5-carboxamide;
2-[(4-cyanobenzyl)(3-methoxypropanoyl)amino]-N-(imidazo[1,2-a]pyridin-7-ylmethyl)-1,3-thiazole-5-carboxamide;
tert-butyl 4-{4-[(imidazo[1,2-a]pyridin-6-ylcarbamoyl)amino]butyl}piperidine-1-carboxylate;
4-{[(imidazo[1,2-a]pyridin-6-ylmethyl)carbamoyl]amino}-N-(3-methylbutyl)benzamide;
2-cyclopentyl-N-(4-{[(imidazo[1,2-a]pyridin-6-ylmethyl)carbamoyl]amino}phenyl)acetamide;
N-(imidazo[1,2-a]pyridin-6-ylmethyl)-2-[3-methoxypropanoyl)(3-methylbutyl)amino]-1,3-thiazole-5-carboxamide;

1-imidazo[1,2-a]pyridin-6-yl-3-(4-{1-[(propan-2-yloxy)acetyl]piperidin-4-yl}butyl)urea;
1-{4-[1-(1,4-dioxan-2-ylcarbonyl)piperidin-4-yl]butyl}-3-imidazo[1,2-a]pyridin-6-ylurea;
1-{4-[1-(cyclopropylacetyl)piperidin-4-yl]butyl}-3-imidazo[1,2-a]pyridin-6-ylurea;
1-imidazo[1,2-a]pyridin-6-yl-3-{4-[1-(4,4,4-trifluorobutanoyl)piperidin-4-yl]butyl}urea;
1-imidazo[1,2-a]pyridin-6-yl-3-{4-[1-(tetrahydro-2H-pyran-4-ylacetyl)piperidin-4-yl]butyl}urea;
1-imidazo[1,2-a]pyridin-6-yl-3-{4-[1-(tetrahydrofuran-2-ylacetyl)piperidin-4-yl]butyl}urea;
1-{4-[1-(cyclopentylcarbonyl)piperidin-4-yl]butyl}-3-imidazo[1,2-a]pyridin-6-ylurea;
1-imidazo[1,2-a]pyridin-6-yl-3-{4-[1-(tetrahydro-2H-pyran-4-ylcarbonyl)piperidin-4-yl]butyl}urea;
1-imidazo[1,2-a]pyridin-6-yl-3-(4-{1-[(2-methoxyethoxy)acetyl]piperidin-4-yl}butyl)urea;
1-imidazo[1,2-a]pyridin-6-yl-3-{4-[1-(morpholin-4-ylacetyl)piperidin-4-yl]butyl}urea;
1-imidazo[1,2-a]pyridin-6-yl-3-{4-[1-(tetrahydrofuran-3-ylcarbonyl)piperidin-4-yl]butyl}urea;
1-imidazo[1,2-a]pyridin-6-yl-3-{4-[1-(tetrahydrofuran-3-ylacetyl)piperidin-4-yl]butyl}urea;
1-imidazo[1,2-a]pyridin-6-yl-3-{4-[1-(tetrahydrofuran-2-ylcarbonyl)piperidin-4-yl]butyl}urea;
N-(imidazo[1,2-a]pyridin-6-ylmethyl)-5-[1-(2-methylpropyl)-1H-pyrazol-4-yl]thiophene-2-carboxamide;
2-cyclopentyl-N-{4-[2-(imidazo[1,2-a]pyridin-6-ylamino)-2-oxoethyl]phenyl}acetamide;
N-(imidazo[1,2-a]pyridin-6-ylmethyl)-4-[(tetrahydrofuran-2-ylacetyl)amino]benzamide;
N-(imidazo[1,2-a]pyridin-6-ylmethyl)-4-[(tetrahydrofuran-3-ylacetyl)amino]benzamide;
N-(imidazo[1,2-a]pyridin-6-ylmethyl)-4-[(tetrahydro-2H-pyran-4-ylacetyl)amino]benzamide;
N-(imidazo[1,2-a]pyridin-6-ylmethyl)-4-[(morpholin-4-ylacetyl)amino]benzamide;
4-[(3-cyclopentylpropanoyl)amino]-N-(imidazo[1,2-a]pyridin-6-ylmethyl)benzamide;
N-(imidazo[1,2-a]pyridin-6-ylmethyl)-4-{[(propan-2-yloxy)acetyl]amino}benzamide;
tert-butyl 4-{4-[(imidazo[1,2-a]pyridin-6-ylmethyl)carbamoyl]phenyl}-3,6-dihydropyridine-1(2H)-carboxylate;
N-{4-[(cyclopentylacetyl)amino]benzyl}imidazo[1,2-a]pyridine-6-carboxamide;
N-(imidazo[1,2-a]pyridin-6-ylmethyl)-2-(1,2,4,5-tetrahydro-3H-3-benzazepin-3-yl)-1,3-thiazole-5-carboxamide;
N-(imidazo[1,2-a]pyridin-6-ylmethyl)-2-(3-phenylpyrrolidin-1-yl)-1,3-thiazole-5-carboxamide;
N-(imidazo[1,2-a]pyridin-6-ylmethyl)-2-[3-methylbutyl)amino]-1,3-thiazole-5-carboxamide;
2-(1,3-dihydro-2H-isoindol-2-yl)-N-(imidazo[1,2-a]pyridin-6-ylmethyl)-1,3-thiazole-5-carboxamide;
tert-butyl 4-{4-[(imidazo[1,2-a]pyridin-6-ylcarbamoyl)amino]phenyl}piperidine-1-carboxylate;
N-(imidazo[1,2-a]pyridin-6-ylmethyl)-4-[1-(2-methylpropanoyl)-1,2,3,6-tetrahydropyridin-4-yl]benzamide;
4-[1-(2-hydroxy-2-methylpropanoyl)-1,2,3,6-tetrahydropyridin-4-yl]-N-(imidazo[1,2-a]pyridin-6-ylmethyl)benzamide;
N-(imidazo[1,2-a]pyridin-6-ylmethyl)-4-[1-(morpholin-4-ylacetyl)-1,2,3,6-tetrahydropyridin-4-yl]benzamide;
N-(imidazo[1,2-a]pyridin-6-ylmethyl)-4-[1-(tetrahydro-2H-pyran-4-ylacetyl)-1,2,3,6-tetrahydropyridin-4-yl]benzamide;
N-(imidazo[1,2-a]pyridin-6-ylmethyl)-4-[1-(tetrahydrofuran-3-ylacetyl)-1,2,3,6-tetrahydropyridin-4-yl]benzamide;
N-(imidazo[1,2-a]pyridin-6-ylmethyl)-4-[1-(tetrahydrofuran-2-ylacetyl)-1,2,3,6-tetrahydropyridin-4-yl]benzamide;
N-(imidazo[1,2-a]pyridin-6-ylmethyl)-4-{1-[3-(tetrahydrofuran-2-yl)propanoyl]-1,2,3,6-tetrahydropyridin-4-yl}benzamide;
4-[1-(cyclopentylacetyl)-1,2,3,6-tetrahydropyridin-4-yl]-N-(imidazo[1,2-a]pyridin-6-ylmethyl)benzamide;
N-(imidazo[1,2-a]pyridin-6-ylmethyl)-4-{1-[(propan-2-yloxy)acetyl]-1,2,3,6-tetrahydropyridin-4-yl}benzamide;
N-(imidazo[1,2-a]pyridin-6-ylmethyl)-4-[1-(tetrahydrofuran-2-ylcarbonyl)-1,2,3,6-tetrahydropyridin-4-yl]benzamide;
N-(imidazo[1,2-a]pyridin-6-ylmethyl)-4-[1-(tetrahydrofuran-3-ylcarbonyl)-1,2,3,6-tetrahydropyridin-4-yl]benzamide;
N-(imidazo[1,2-a]pyridin-6-ylmethyl)-4-[1-(tetrahydro-2H-pyran-4-ylcarbonyl)-1,2,3,6-tetrahydropyridin-4-yl]benzamide;
4-[1-(1,4-dioxan-2-ylcarbonyl)-1,2,3,6-tetrahydropyridin-4-yl]-N-(imidazo[1,2-a]pyridin-6-ylmethyl)benzamide;
N-(imidazo[1,2-a]pyridin-6-ylmethyl)-4-{1-[(2-methoxyethoxy)acetyl]-1,2,3,6-tetrahydropyridin-4-yl}benzamide;
4-(1-benzoyl-1,2,3,6-tetrahydropyridin-4-yl)-N-(imidazo[1,2-a]pyridin-6-ylmethyl)benzamide;
4-{1-[(4,4-difluorocyclohexyl)carbonyl]-1,2,3,6-tetrahydropyridin-4-yl}-N-(imidazo[1,2-a]pyridin-6-ylmethyl)benzamide;
1-imidazo[1,2-a]pyridin-6-yl-3-{4-[1-(2-methylpropanoyl)piperidin-4-yl]phenyl}urea;
1-[4-(1-benzoylpiperidin-4-yl)butyl]-3-imidazo[1,2-a]pyridin-6-ylurea;
2-(3,4-dihydroisoquinolin-2(1H)-yl)-N-(imidazo[1,2-a]pyridin-6-ylmethyl)-1,3-thiazole-5-carboxamide;
1-imidazo[1,2-a]pyridin-6-yl-3-{4-[1-(tetrahydro-2H-pyran-4-ylcarbonyl)piperidin-4-yl]phenyl}urea;
1-imidazo[1,2-a]pyridin-6-yl-3-{4-[1-(tetrahydrofuran-3-ylacetyl)piperidin-4-yl]phenyl}urea;
1-imidazo[1,2-a]pyridin-6-yl-3-{4-[1-(tetrahydrofuran-2-ylacetyl)piperidin-4-yl]phenyl}urea;
1-[4-(1-benzoylpiperidin-4-yl)phenyl]-3-imidazo[1,2-a]pyridin-6-ylurea;
1-imidazo[1,2-a]pyridin-6-yl-3-{4-[1-(tetrahydrofuran-2-ylcarbonyl)piperidin-4-yl]phenyl}urea;
tert-butyl 4-{4-[(imidazo[1,2-a]pyridin-6-ylmethyl)carbamoyl]phenoxy}piperidine-1-carboxylate;
N-(imidazo[1,2-a]pyridin-6-ylmethyl)-2-[{[2-(propan-2-yloxy)ethyl]carbamoyl}(tetrahydrofuran-2-ylmethyl)amino]-1,3-thiazole-5-carboxamide;
N-(imidazo[1,2-a]pyridin-6-ylmethyl)-2-[2-oxo-4-(tetrahydrofuran-3-yl)-1,3-oxazolidin-3-yl]-1,3-thiazole-5-carboxamide;
4-[(cyclopentylacetyl)amino]-N-(imidazo[1,2-a]pyridin-7-ylmethyl)benzamide;
2-cyclopentyl-N-(4-{[(imidazo[1,2-a]pyridin-7-ylmethyl)carbamoyl]amino}phenyl)acetamide;
N-(imidazo[1,2-a]pyridin-6-ylmethyl)-4-[1-(2-methylpropyl)-1H-pyrazol-4-yl]benzamide;
N-(imidazo[1,2-a]pyridin-6-ylmethyl)-5-[1-(2-methylpropyl)-1H-pyrazol-4-yl]furan-2-carboxamide;
N-(imidazo[1,2-a]pyridin-7-ylmethyl)-2-[3-methoxypropanoyl)(tetrahydrofuran-2-ylmethyl)amino]-1,3-thiazole-5-carboxamide;

N-(imidazo[1,2-a]pyridin-6-ylmethyl)-2-(2-oxo-5-phenyl-1,3-oxazolidin-3-yl)-1,3-thiazole-5-carboxamide;
N-(imidazo[1,2-a]pyridin-6-ylmethyl)-2-{[(2-methyl-1,3-thiazol-5-yl)acetyl](tetrahydrofuran-2-ylmethyl)amino}-1,3-thiazole-5-carboxamide;
N-(imidazo[1,2-a]pyridin-6-ylmethyl)-2-{[(2-methyl-1,3-thiazol-4-yl)acetyl](tetrahydrofuran-2-ylmethyl)amino}-1,3-thiazole-5-carboxamide;
N-(imidazo[1,2-a]pyridin-6-ylmethyl)-2-{[(3-methyl-1,2-oxazol-5-yl)acetyl](tetrahydrofuran-2-ylmethyl)amino}-1,3-thiazole-5-carboxamide;
2-{[3-(3-chloro-1,2-oxazol-5-yl)propanoyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-{[3-(3-methoxy-1,2-oxazol-5-yl)propanoyl](tetrahydrofuran-2-ylmethyl)amino}-1,3-thiazole-5-carboxamide;
2-{[(3,5-dimethyl-1,2-oxazol-4-yl)acetyl](tetrahydrofuran-2-ylmethyl)amino}-N-(imidazo[1,2-a]pyridin-6-ylmethyl)-1,3-thiazole-5-carboxamide;
2-{[3-(3,5-dimethyl-1,2-oxazol-4-yl)propanoyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-{[3-(1-methyl-1H-pyrazol-4-yl)propanoyl](tetrahydrofuran-2-ylmethyl)amino}-1,3-thiazole-5-carboxamide;
N-(imidazo[1,2-a]pyridin-6-ylmethyl)-2-{[3-(4-methyl-1,3-thiazol-5-yl)propanoyl](tetrahydrofuran-2-ylmethyl)amino}-1,3-thiazole-5-carboxamide;
N-(imidazo[1,2-a]pyridin-6-ylmethyl)-2-[(tetrahydrofuran-2-ylmethyl)(1H-tetrazol-5-ylacetyl)amino]-1,3-thiazole-5-carboxamide;
N-(imidazo[1,2-a]pyridin-6-ylmethyl)-2-{[3-(1,2-oxazol-5-yl)propanoyl](tetrahydrofuran-2-ylmethyl)amino}-1,3-thiazole-5-carboxamide;
N-(imidazo[1,2-a]pyridin-6-ylmethyl)-2-[(1,2-oxazol-3-ylacetyl)(tetrahydrofuran-2-ylmethyl)amino]-1,3-thiazole-5-carboxamide;
N-(imidazo[1,2-a]pyridin-6-ylmethyl)-2-{[3-(1,2-oxazol-4-yl)propanoyl](tetrahydrofuran-2-ylmethyl)amino}-1,3-thiazole-5-carboxamide;
N-(imidazo[1,2-a]pyridin-6-ylmethyl)-2-{(tetrahydrofuran-2-ylmethyl)[3-(1,3-thiazol-2-yl)propanoyl]amino}-1,3-thiazole-5-carboxamide;
N-(imidazo[1,2-a]pyridin-6-ylmethyl)-2-[3-methylbutanoyl)amino]-1,3-thiazole-5-carboxamide;
N-(imidazo[1,2-a]pyridin-7-ylmethyl)-2-{[(2-methoxyethyl)carbamoyl](tetrahydrofuran-2-ylmethyl)amino}-1,3-thiazole-5-carboxamide;
N-(imidazo[1,2-a]pyridin-6-ylmethyl)-2-[3-methoxypropanoyl)(tetrahydrofuran-3-ylmethyl)amino]-1,3-thiazole-5-carboxamide;
N-(imidazo[1,2-a]pyridin-6-ylmethyl)-2-[(tetrahydrofuran-3-ylmethyl)(tetrahydro-2H-pyran-4-ylcarbonyl)amino]-1,3-thiazole-5-carboxamide;
N-(imidazo[1,2-a]pyridin-6-ylmethyl)-2-{[(2-methoxyethyl)carbamoyl](tetrahydrofuran-3-ylmethyl)amino}-1,3-thiazole-5-carboxamide;
N-(imidazo[1,2-a]pyridin-6-ylmethyl)-2-[(3-methoxypropanoyl)(tetrahydro-2H-pyran-4-ylmethyl)amino]-1,3-thiazole-5-carboxamide;
N-(imidazo[1,2-a]pyridin-6-ylmethyl)-2-[(tetrahydrofuran-3-ylcarbonyl)(tetrahydro-2H-pyran-4-ylmethyl)amino]-1,3-thiazole-5-carboxamide;
N-(imidazo[1,2-a]pyridin-6-ylmethyl)-2-[(tetrahydro-2H-pyran-4-ylcarbonyl)(tetrahydro-2H-pyran-4-ylmethyl)amino]-1,3-thiazole-5-carboxamide;
N-(imidazo[1,2-a]pyridin-6-ylmethyl)-2-{(3-methoxypropanoyl)[(2R)-tetrahydrofuran-2-ylmethyl]amino}-1,3-thiazole-5-carboxamide;
N-(imidazo[1,2-a]pyridin-6-ylmethyl)-2-{(tetrahydrofuran-3-ylcarbonyl)[(2R)-tetrahydrofuran-2-ylmethyl]amino}-1,3-thiazole-5-carboxamide;
N-(imidazo[1,2-a]pyridin-6-ylmethyl)-2-{[(2R)-tetrahydrofuran-2-ylmethyl](tetrahydro-2H-pyran-4-ylcarbonyl)amino}-1,3-thiazole-5-carboxamide;
N-(imidazo[1,2-a]pyridin-6-ylmethyl)-2-{(3-methoxypropanoyl)[(2S)-tetrahydrofuran-2-ylmethyl]amino}-1,3-thiazole-5-carboxamide;
N-(imidazo[1,2-a]pyridin-6-ylmethyl)-2-{(tetrahydrofuran-3-ylcarbonyl)[(2S)-tetrahydrofuran-2-ylmethyl]amino}-1,3-thiazole-5-carboxamide;
N-(imidazo[1,2-a]pyridin-6-ylmethyl)-2-{[(2S)-tetrahydrofuran-2-ylmethyl](tetrahydro-2H-pyran-4-ylcarbonyl)amino}-1,3-thiazole-5-carboxamide;
N-(imidazo[1,2-a]pyridin-6-ylmethyl)-2-{[(2-methoxyethyl)carbamoyl](tetrahydro-2H-pyran-4-ylmethyl)amino}-1,3-thiazole-5-carboxamide;
N-(imidazo[1,2-a]pyridin-6-ylmethyl)-2-[{[2-(propan-2-yloxy)ethyl]carbamoyl}(tetrahydro-2H-pyran-4-ylmethyl)amino]-1,3-thiazole-5-carboxamide;
N-(imidazo[1,2-a]pyridin-6-ylmethyl)-2-{[(2-methoxyethyl)carbamoyl][(2R)-tetrahydrofuran-2-ylmethyl]amino}-1,3-thiazole-5-carboxamide;
N-(imidazo[1,2-a]pyridin-6-ylmethyl)-2-({[2-(propan-2-yloxy)ethyl]carbamoyl}[(2R)-tetrahydrofuran-2-ylmethyl]amino)-1,3-thiazole-5-carboxamide;
N-(imidazo[1,2-a]pyridin-6-ylmethyl)-2-{[(2-methoxyethyl)carbamoyl][(2S)-tetrahydrofuran-2-ylmethyl]amino}-1,3-thiazole-5-carboxamide;
N-(imidazo[1,2-a]pyridin-6-ylmethyl)-2-({[2-(propan-2-yloxy)ethyl]carbamoyl}[(2S)-tetrahydrofuran-2-ylmethyl]amino)-1,3-thiazole-5-carboxamide;
N-(imidazo[1,2-a]pyridin-6-ylmethyl)-2-[{[2-(propan-2-yloxy)ethyl]carbamoyl}(tetrahydrofuran-3-ylmethyl)amino]-1,3-thiazole-5-carboxamide;
2-[5-(4-chlorophenyl)-2-oxo-1,3-oxazolidin-3-yl]-N-(imidazo[1,2-a]pyridin-6-ylmethyl)-1,3-thiazole-5-carboxamide;
N-(imidazo[1,2-a]pyridin-6-ylmethyl)-4-{[1-(2-methylpropanoyl)piperidin-4-yl]oxy}benzamide;
4-[(1-acetylpiperidin-4-yl)oxy]-N-(imidazo[1,2-a]pyridin-6-ylmethyl)benzamide;
4-{[1-(cyclopropylcarbonyl)piperidin-4-yl]oxy}-N-(imidazo[1,2-a]pyridin-6-ylmethyl)benzamide;
N-(imidazo[1,2-a]pyridin-6-ylmethyl)-4-{[1-(tetrahydro-2H-pyran-4-ylcarbonyl)piperidin-4-yl]oxy}benzamide;
4-{[1-(1,4-dioxan-2-ylcarbonyl)piperidin-4-yl]oxy}-N-(imidazo[1,2-a]pyridin-6-ylmethyl)benzamide;
N-(imidazo[1,2-a]pyridin-6-ylmethyl)-4-({1-[(2S)-tetrahydrofuran-2-ylcarbonyl]piperidin-4-yl}oxy)benzamide;
N-(imidazo[1,2-a]pyridin-6-ylmethyl)-4-({1-[(2R)-tetrahydrofuran-2-ylcarbonyl]piperidin-4-yl}oxy)benzamide;
4-{[1-(2-hydroxy-2-methylpropanoyl)piperidin-4-yl]oxy}-N-(imidazo[1,2-a]pyridin-6-ylmethyl)benzamide;
N-(imidazo[1,2-a]pyridin-6-ylmethyl)-4-({1-[(propan-2-yloxy)acetyl]piperidin-4-yl}oxy)benzamide;
4-[(1-butanoylpiperidin-4-yl)oxy]-N-(imidazo[1,2-a]pyridin-6-ylmethyl)benzamide;
N-(imidazo[1,2-a]pyridin-6-ylmethyl)-4-{[1-(3-methoxy-2-methylpropanoyl)piperidin-4-yl]oxy}benzamide;
N-(imidazo[1,2-a]pyridin-6-ylmethyl)-4-{[1-(3,3,3-trifluoropropanoyl)piperidin-4-yl]oxy}benzamide;

N-(imidazo[1,2-a]pyridin-6-ylmethyl)-4-{[1-(tetrahydro-2H-pyran-4-ylacetyl)piperidin-4-yl]oxy}benzamide;
4-{[1-(cyclopropylacetyl)piperidin-4-yl]oxy}-N-(imidazo[1,2-a]pyridin-6-ylmethyl)benzamide;
N-(imidazo[1,2-a]pyridin-6-ylmethyl)-4-{[1-(tetrahydrofuran-2-ylacetyl)piperidin-4-yl]oxy}benzamide;
N-(imidazo[1,2-a]pyridin-7-ylmethyl)-5-[1-(2-methylpropyl)-1H-pyrazol-4-yl]thiophene-2-carboxamide;
N-(imidazo[1,2-a]pyridin-6-ylmethyl)-5-[1-(2-methylpropanoyl)-1H-pyrazol-4-yl]thiophene-2-carboxamide;
5-[1-(2-hydroxy-2-methylpropyl)-1H-pyrazol-4-yl]-N-(imidazo[1,2-a]pyridin-6-ylmethyl)thiophene-2-carboxamide;
N-(imidazo[1,2-a]pyridin-6-ylmethyl)-5-{1-[(3-methyloxetan-3-yl)methyl]-1H-pyrazol-4-yl}thiophene-2-carboxamide;
5-[1-(cyclobutylmethyl)-1H-pyrazol-4-yl]-N-(imidazo[1,2-a]pyridin-6-ylmethyl)thiophene-2-carboxamide;
5-[1-(cyclohexylmethyl)-1H-pyrazol-4-yl]-N-(imidazo[1,2-a]pyridin-6-ylmethyl)thiophene-2-carboxamide;
5-{1-[(2R)-2-hydroxybutyl]-1H-pyrazol-4-yl}-N-(imidazo[1,2-a]pyridin-6-ylmethyl)thiophene-2-carboxamide;
N-(imidazo[1,2-a]pyridin-7-ylmethyl)-2-[(4R)-2-oxo-4-(propan-2-yl)-1,3-oxazolidin-3-yl]-1,3-thiazole-5-carboxamide;
5-[1-(2-hydroxy-2-methylpropyl)-1H-pyrazol-4-yl]-N-(imidazo[1,2-a]pyridin-7-ylmethyl)thiophene-2-carboxamide;
N-(imidazo[1,2-a]pyridin-6-ylmethyl)-2-{[(1-methyl-1H-pyrazol-4-yl)acetyl](tetrahydrofuran-2-ylmethyl)amino}-1,3-thiazole-5-carboxamide;
2-{[(1,3-dimethyl-1H-pyrazol-4-yl)acetyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-7-ylmethyl)-2-[(4S)-2-oxo-4-(propan-2-yl)-1,3-oxazolidin-3-yl]-1,3-thiazole-5-carboxamide;
N-(imidazo[1,2-a]pyridin-6-ylmethyl)-5-[1-(tetrahydro-2H-pyran-2-ylmethyl)-1H-pyrazol-4-yl]thiophene-2-carboxamide;
2-{(4R)-4-[(benzyloxy)methyl]-2-oxo-1,3-oxazolidin-3-yl}-N-(imidazo[1,2-a]pyridin-7-ylmethyl)-1,3-thiazole-5-carboxamide;
2-{(4S)-4-[(benzyloxy)methyl]-2-oxo-1,3-oxazolidin-3-yl}-N-(imidazo[1,2-a]pyridin-7-ylmethyl)-1,3-thiazole-5-carboxamide;
N-(imidazo[1,2-a]pyridin-6-ylmethyl)-2-{[3-(1-methyl-1H-pyrrol-2-yl)propanoyl](tetrahydrofuran-2-ylmethyl)amino}-1,3-thiazole-5-carboxamide;
2-{[(1,5-dimethyl-1H-pyrazol-3-yl)acetyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-[(tetrahydrofuran-2-ylmethyl)(1,3-thiazol-4-ylacetyl)amino]-1,3-thiazole-5-carboxamide;
N-(imidazo[1,2-a]pyridin-7-ylmethyl)-2-{(1,2-oxazol-3-ylacetyl) [(2R)-tetrahydrofuran-2-ylmethyl]amino}-1,3-thiazole-5-carboxamide;
N-(imidazo[1,2-a]pyridin-7-ylmethyl)-2-{[(5-methyl-1,2-oxazol-3-yl)acetyl][(2R)-tetrahydrofuran-2-ylmethyl]amino}-1,3-thiazole-5-carboxamide;
N-(imidazo[1,2-a]pyridin-7-ylmethyl)-2-{[3-(1,2-oxazol-5-yl)propanoyl][(2R)-tetrahydrofuran-2-ylmethyl]amino}-1,3-thiazole-5-carboxamide;
N-(imidazo[1,2-a]pyridin-7-ylmethyl)-2-{[3-(1,2-oxazol-4-yl)propanoyl][(2R)-tetrahydrofuran-2-ylmethyl]amino}-1,3-thiazole-5-carboxamide;
N-(imidazo[1,2-a]pyridin-7-ylmethyl)-2-{[(2R)-tetrahydrofuran-2-ylmethyl](1,3-thiazol-4-ylacetyl)amino}-1,3-thiazole-5-carboxamide;
2-{[(1,5-dimethyl-1H-pyrazol-3-yl)acetyl][(2R)-tetrahydrofuran-2-ylmethyl]amino}-N-(imidazo[1,2-a]pyridin-7-ylmethyl)-1,3-thiazole-5-carboxamide;
N-(imidazo[1,2-a]pyridin-7-ylmethyl)-2-{[3-(1-methyl-1H-pyrazol-4-yl)propanoyl][(2R)-tetrahydrofuran-2-ylmethyl]amino}-1,3-thiazole-5-carboxamide;
2-{[(3,5-dimethyl-1,2-oxazol-4-yl)acetyl][(2R)-tetrahydrofuran-2-ylmethyl]amino}-N-(imidazo[1,2-a]pyridin-7-ylmethyl)-1,3-thiazole-5-carboxamide;
N-(imidazo[1,2-a]pyridin-6-ylmethyl)-5-[1-(tetrahydrofuran-3-ylmethyl)-1H-pyrazol-4-yl]thiophene-2-carboxamide;
N-(imidazo[1,2-a]pyridin-6-ylmethyl)-5-[1-(tetrahydro-2H-pyran-4-ylmethyl)-1H-pyrazol-4-yl]thiophene-2-carboxamide;
N-(imidazo[1,2-a]pyridin-7-ylmethyl)-2-{[(1-methyl-1H-pyrazol-4-yl)acetyl][(2R)-tetrahydrofuran-2-ylmethyl]amino}-1,3-thiazole-5-carboxamide;
N-(imidazo[1,2-a]pyridin-7-ylmethyl)-2-{[3-(1-methyl-1H-pyrrol-2-yl)propanoyl][(2R)-tetrahydrofuran-2-ylmethyl]amino}-1,3-thiazole-5-carboxamide;
2-[1-(2-hydroxy-2-methylpropyl)-1H-pyrazol-4-yl]-N-(imidazo[1,2-a]pyridin-7-ylmethyl)-1,3-thiazole-5-carboxamide;
N-(imidazo[1,2-a]pyridin-7-ylmethyl)-2-[1-(2-methylpropyl)-1H-pyrazol-4-yl]-1,3-thiazole-5-carboxamide;
N-(imidazo[1,2-a]pyridin-6-ylmethyl)-5-[1-(tetrahydro-2H-pyran-3-ylmethyl)-1H-pyrazol-4-yl]thiophene-2-carboxamide;
tert-butyl {4-[(imidazo[1,2-a]pyridin-7-ylmethyl)carbamoyl]phenyl}carbamate;
N-(imidazo[1,2-a]pyridin-7-ylmethyl)-4-[(tetrahydro-2H-pyran-4-ylacetyl)amino]benzamide;
N-(imidazo[1,2-a]pyridin-7-ylmethyl)-4-[(tetrahydrofuran-2-ylacetyl)amino]benzamide;
N-(imidazo[1,2-a]pyridin-7-ylmethyl)-4-{[3-(tetrahydrofuran-2-yl)propanoyl]amino}benzamide;
N-(imidazo[1,2-a]pyridin-7-ylmethyl)-4-{[(propan-2-yloxy)acetyl]amino}benzamide;
4-[(3-cyclopentylpropanoyl)amino]-N-(imidazo[1,2-a]pyridin-7-ylmethyl)benzamide;
N-(imidazo[1,2-a]pyridin-7-ylmethyl)-4-[(4-methylpentanoyl)amino]benzamide;
N-(imidazo[1,2-a]pyridin-7-ylmethyl)-4-[(tetrahydrofuran-3-ylacetyl)amino]benzamide;
4-[(4-cyanobenzyl)(cyclopentylacetyl)amino]-N-(imidazo[1,2-a]pyridin-6-ylmethyl)benzamide;
tert-butyl 4-(4-{[(imidazo[1,2-a]pyridin-7-ylmethyl)carbamoyl]amino}phenyl)piperidine-1-carboxylate;
tert-butyl 4-{4-[(imidazo[1,2-a]pyridin-7-ylmethyl)carbamoyl]phenyl}piperidine-1-carboxylate;
2-{5-[(benzyloxy)methyl]-2-oxo-1,3-oxazolidin-3-yl}-N-(imidazo[1,2-a]pyridin-7-ylmethyl)-1,3-thiazole-5-carboxamide;
N-(imidazo[1,2-a]pyridin-6-ylmethyl)-5-[1-(tetrahydrofuran-2-ylmethyl)-1H-pyrazol-4-yl]thiophene-2-carboxamide;
1-(imidazo[1,2-a]pyridin-7-ylmethyl)-3-{4-[1-(tetrahydrofuran-2-ylcarbonyl)piperidin-4-yl]phenyl}urea;
1-(imidazo[1,2-a]pyridin-7-ylmethyl)-3-{4-[1-(tetrahydro-2H-pyran-4-ylcarbonyl)piperidin-4-yl]phenyl}urea;
1-{4-[1-(1,4-dioxan-2-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(tetrahydro-2H-pyran-4-ylacetyl)piperidin-4-yl]phenyl}urea;

1-(imidazo[1,2-a]pyridin-7-ylmethyl)-3-{4-[1-(morpholin-4-ylacetyl)piperidin-4-yl]phenyl}urea;

1-(imidazo[1,2-a]pyridin-7-ylmethyl)-3-{4-[1-(tetrahydrofuran-2-ylacetyl)piperidin-4-yl]phenyl}urea;

1-{4-[1-(3-hydroxy-3-methylbutanoyl)piperidin-4-yl]phenyl}-3-(imidazo[1,2-a]pyridin-7-ylmethyl)urea;

1-{4-[1-(2-hydroxy-2-methylpropanoyl)piperidin-4-yl]phenyl}-3-(imidazo[1,2-a]pyridin-7-ylmethyl)urea;

1-(imidazo[1,2-a]pyridin-7-ylmethyl)-3-{4-[1-(2-methylpropanoyl)piperidin-4-yl]phenyl}urea;

1-[4-(1-benzoylpiperidin-4-yl)phenyl]-3-(imidazo[1,2-a]pyridin-7-ylmethyl)urea;

4-[1-(2-hydroxy-2-methylpropanoyl)piperidin-4-yl]-N-(imidazo[1,2-a]pyridin-7-ylmethyl)benzamide;

N-(imidazo[1,2-a]pyridin-7-ylmethyl)-4-[1-(tetrahydrofuran-3-ylcarbonyl)piperidin-4-yl]benzamide;

N-(imidazo[1,2-a]pyridin-7-ylmethyl)-4-[1-(tetrahydro-2H-pyran-4-ylcarbonyl)piperidin-4-yl]benzamide;

4-[1-(1,4-dioxan-2-ylcarbonyl)piperidin-4-yl]-N-(imidazo[1,2-a]pyridin-7-ylmethyl)benzamide;

4-{1-[(1,1-dioxidotetrahydro-2H-thiopyran-4-yl)carbonyl]piperidin-4-yl}-N-(imidazo[1,2-a]pyridin-7-ylmethyl)benzamide;

N-(imidazo[1,2-a]pyridin-7-ylmethyl)-4-[1-(tetrahydrofuran-2-ylacetyl)piperidin-4-yl]benzamide;

N-(imidazo[1,2-a]pyridin-7-ylmethyl)-4-[1-(tetrahydro-2H-pyran-4-ylacetyl)piperidin-4-yl]benzamide;

N-(imidazo[1,2-a]pyridin-7-ylmethyl)-4-{1-[(propan-2-yloxy)acetyl]piperidin-4-yl}benzamide;

N-(imidazo[1,2-a]pyridin-7-ylmethyl)-4-{1-[(2S)-2-methylbutanoyl]piperidin-4-yl}benzamide;

N-(imidazo[1,2-a]pyridin-7-ylmethyl)-4-[1-(2-methylpropanoyl)piperidin-4-yl]benzamide;

4-[(4-cyanobenzyl)(3-methoxypropanoyl)amino]-N-(imidazo[1,2-a]pyridin-6-ylmethyl)benzamide;

5-(1-acetyl-1,2,3,6-tetrahydropyridin-4-yl)-N-(imidazo[1,2-a]pyridin-7-ylmethyl)thiophene-2-carboxamide;

N-(imidazo[1,2-a]pyridin-7-ylmethyl)-5-[1-(methylsulfonyl)-1,2,3,6-tetrahydropyridin-4-yl]thiophene-2-carboxamide;

1-(4-{1-[(1,1-dioxidotetrahydro-2H-thiopyran-4-yl)carbonyl]piperidin-4-yl}phenyl)-3-(imidazo[1,2-a]pyridin-7-ylmethyl)urea;

2-[(2S)-2-(hydroxymethyl)-5-oxopyrrolidin-1-yl]-N-(imidazo[1,2-a]pyridin-7-ylmethyl)-1,3-thiazole-5-carboxamide;

N-(imidazo[1,2-a]pyridin-7-ylmethyl)-2-[(4R)-4-methyl-2-oxo-1,3-oxazolidin-3-yl]-1,3-thiazole-5-carboxamide;

5-[1-(cyclopropylsulfonyl)-1,2,3,6-tetrahydropyridin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydro-2H-pyran-2-ylmethyl)-1H-pyrazol-4-yl]thiophene-2-carboxamide;

N-(imidazo[1,2-a]pyridin-7-ylmethyl)-5-[1-(tetrahydrofuran-2-ylmethyl)-1H-pyrazol-4-yl]thiophene-2-carboxamide;

N-(imidazo[1,2-a]pyridin-7-ylmethyl)-2-{2-oxo-5-[(propan-2-yloxy)methyl]-1,3-oxazolidin-3-yl}-1,3-thiazole-5-carboxamide;

N-(imidazo[1,2-a]pyridin-7-ylmethyl)-5-[(4R)-2-oxo-4-(propan-2-yl)-1,3-oxazolidin-3-yl]thiophene-2-carboxamide;

2-[5-(hydroxymethyl)-2-oxo-1,3-oxazolidin-3-yl]-N-(imidazo[1,2-a]pyridin-7-ylmethyl)-1,3-thiazole-5-carboxamide;

N-(imidazo[1,2-a]pyridin-7-ylmethyl)-5-[1-(tetrahydrofuran-3-ylmethyl)-1H-pyrazol-4-yl]thiophene-2-carboxamide;

N-(imidazo[1,2-a]pyridin-7-ylmethyl)-5-[1-(tetrahydro-2H-pyran-3-ylmethyl)-1H-pyrazol-4-yl]thiophene-2-carboxamide;

N-(imidazo[1,2-a]pyridin-7-ylmethyl)-5-{1-[(3-methyloxetan-3-yl)methyl]-1H-pyrazol-4-yl}thiophene-2-carboxamide;

N-(imidazo[1,2-a]pyridin-7-ylmethyl)-2-{(5S)-2-oxo-5-[(propan-2-yloxy)methyl]-1,3-oxazolidin-3-yl}-1,3-thiazole-5-carboxamide;

N-(imidazo[1,2-a]pyridin-7-ylmethyl)-2-{(5R)-2-oxo-5-[(propan-2-yloxy)methyl]-1,3-oxazolidin-3-yl}-1,3-thiazole-5-carboxamide;

N-(imidazo[1,2-a]pyridin-7-ylmethyl)-5-[1-(methoxyacetyl)piperidin-4-yl]thiophene-2-carboxamide;

5-(1-acetylpiperidin-4-yl)-N-(imidazo[1,2-a]pyridin-7-ylmethyl)thiophene-2-carboxamide;

N-(imidazo[1,2-a]pyridin-7-ylmethyl)-5-[1-(2-methylpropanoyl)piperidin-4-yl]thiophene-2-carboxamide;

5-[1-(cyclopropylcarbonyl)piperidin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydrofuran-3-ylcarbonyl)piperidin-4-yl]thiophene-2-carboxamide;

N-(imidazo[1,2-a]pyridin-7-ylmethyl)-5-[1-(tetrahydro-2H-pyran-4-ylacetyl)piperidin-4-yl]thiophene-2-carboxamide;

N-(imidazo[1,2-a]pyridin-7-ylmethyl)-5-[1-(3-methylbutanoyl)piperidin-4-yl]thiophene-2-carboxamide;

N-(imidazo[1,2-a]pyridin-7-ylmethyl)-5-[1-(1,2-oxazol-5-ylcarbonyl)piperidin-4-yl]thiophene-2-carboxamide;

N-(imidazo[1,2-a]pyridin-7-ylmethyl)-5-[1-(tetrahydro-2H-pyran-4-ylmethyl)-1H-pyrazol-4-yl]thiophene-2-carboxamide;

5-[5-(hydroxymethyl)-2-oxo-1,3-oxazolidin-3-yl]-N-(imidazo[1,2-a]pyridin-7-ylmethyl)thiophene-2-carboxamide;

5-[(4R)-4-hydroxy-2-oxopyrrolidin-1-yl]-N-(imidazo[1,2-a]pyridin-7-ylmethyl)thiophene-2-carboxamide;

5-[(4S)-4-hydroxy-2-oxopyrrolidin-1-yl]-N-(imidazo[1,2-a]pyridin-7-ylmethyl)thiophene-2-carboxamide;

N-(imidazo[1,2-a]pyridin-7-ylmethyl)-5-[1-(2-methoxyethyl)-1H-pyrazol-4-yl]thiophene-2-carboxamide;

1-[4-(1-benzoylpiperidin-4-yl)butyl]-3-imidazo[1,2-a]pyridin-7-ylurea;

N-(imidazo[1,2-a]pyridin-7-ylmethyl)-5-[1-(methylsulfonyl)piperidin-4-yl]thiophene-2-carboxamide;

5-[1-(cyclohexylmethyl)-5-ethyl-1H-pyrazol-4-yl]-N-(imidazo[1,2-a]pyridin-7-ylmethyl)thiophene-2-carboxamide;

N-(imidazo[1,2-a]pyridin-7-ylmethyl)-5-{1-[(1-methoxy-3,3-dimethylcyclohexyl)methyl]-5-methyl-1H-pyrazol-4-yl}thiophene-2-carboxamide;

N-(4-{[(imidazo[1,2-a]pyridin-6-ylmethyl)carbamoyl]amino}phenyl)-4-methylpentanamide;

3-cyclopentyl-N-(4-{[(imidazo[1,2-a]pyridin-6-ylmethyl)carbamoyl]amino}phenyl)propanamide;

N-(4-{[(imidazo[1,2-a]pyridin-6-ylmethyl)carbamoyl]amino}phenyl)-2-(propan-2-yloxy)acetamide;

N-(4-{[(imidazo[1,2-a]pyridin-6-ylmethyl)carbamoyl]amino}phenyl)-2-(tetrahydrofuran-2-yl)acetamide;

N-(4-{[(imidazo[1,2-a]pyridin-6-ylmethyl)carbamoyl] amino}phenyl)-2-(tetrahydro-2H-pyran-4-yl)acetamide;
N-(4-{[(imidazo[1,2-a]pyridin-6-ylmethyl)carbamoyl] amino}phenyl)-3-phenylpropanamide;
N-(4-{[(imidazo[1,2-a]pyridin-7-ylmethyl)carbamoyl] amino}phenyl)-4-methylpentanamide;
3-cyclopentyl-N-(4-{[(imidazo[1,2-a]pyridin-7-ylmethyl) carbamoyl]amino}phenyl)propanamide;
N-(4-{[(imidazo[1,2-a]pyridin-7-ylmethyl)carbamoyl] amino}phenyl)-2-(propan-2-yloxy)acetamide;
N-(4-{[(imidazo[1,2-a]pyridin-7-ylmethyl)carbamoyl] amino}phenyl)-2-(tetrahydrofuran-2-yl)acetamide;
N-(4-{[(imidazo[1,2-a]pyridin-7-ylmethyl)carbamoyl] amino}phenyl)-2-(tetrahydro-2H-pyran-4-yl)acetamide;
N-(4-{[(imidazo[1,2-a]pyridin-7-ylmethyl)carbamoyl] amino}phenyl)-3-phenylpropanamide;
1-(imidazo[1,2-a]pyridin-7-ylmethyl)-3-(4-{1-[(3S)-tetrahydrofuran-3-ylcarbonyl]piperidin-4-yl}phenyl)urea;
1-(imidazo[1,2-a]pyridin-7-ylmethyl)-3-(4-{1-[(3R)-tetrahydrofuran-3-ylcarbonyl]piperidin-4-yl}phenyl)urea;
1-(imidazo[1,2-a]pyridin-7-ylmethyl)-3-(4-{1-[(2S)-tetrahydrofuran-2-ylcarbonyl]piperidin-4-yl}phenyl)urea;
1-(imidazo[1,2-a]pyridin-7-ylmethyl)-3-(4-{1-[(2R)-tetrahydrofuran-2-ylcarbonyl]piperidin-4-yl}phenyl)urea;
tert-butyl 4-(3-fluoro-4-{[(imidazo[1,2-a]pyridin-7-ylmethyl)carbamoyl]amino}phenyl)-3,6-dihydropyridine-1 (2H)-carboxylate;
tert-butyl (3R)-3-(4-{[(imidazo[1,2-a]pyridin-7-ylmethyl) carbamoyl]amino}phenoxy)pyrrolidine-1-carboxylate;
tert-butyl {2-fluoro-4-[(imidazo[1,2-a]pyridin-7-ylmethyl) carbamoyl]phenyl}carbamate;
N-(imidazo[1,2-a]pyridin-7-ylmethyl)-5-(1-propyl-1H-pyrazol-4-yl)thiophene-2-carboxamide;
N-(imidazo[1,2-a]pyridin-7-ylmethyl)-5-{1-[2-(morpholin-4-yl)ethyl]-1H-pyrazol-4-yl}thiophene-2-carboxamide;
5-(1-ethyl-1H-pyrazol-4-yl)-N-(imidazo[1,2-a]pyridin-7-ylmethyl)thiophene-2-carboxamide;
5-[1-(1,1-dioxidotetrahydrothiophen-3-yl)-1H-pyrazol-4-yl]-N-(imidazo[1,2-a]pyridin-7-ylmethyl)thiophene-2-carboxamide;
2-(1-benzoyl-1,2,3,6-tetrahydropyridin-4-yl)-N-(imidazo[1,2-a]pyridin-7-ylmethyl)-1,3-thiazole-5-carboxamide;
4-[1-(2-hydroxy-2-methylpropyl)-1H-pyrazol-4-yl]-N-(imidazo[1,2-a]pyridin-7-ylmethyl)benzamide;
N-(imidazo[1,2-a]pyridin-7-ylmethyl)-5-phenylthiophene-2-carboxamide;
N-(imidazo[1,2-a]pyridin-7-ylmethyl)-5-{1-[2-(methylsulfonyl)ethyl]-1H-pyrazol-4-yl}thiophene-2-carboxamide;
tert-butyl 3-{4-[(imidazo[1,2-a]pyridin-7-ylmethyl)carbamoyl]phenyl}pyrrolidine-1-carboxylate;
tert-butyl 3-(4-{[(imidazo[1,2-a]pyridin-7-ylmethyl)carbamoyl]amino}phenyl)pyrrolidine-1-carboxylate;
N-(4-{[(imidazo[1,2-a]pyridin-7-ylmethyl)carbamoyl] amino}phenyl)biphenyl-2-sulfonamide;
5-{1-[(2R)-2-hydroxypropyl]-1H-pyrazol-4-yl}-N-(imidazo[1,2-a]pyridin-7-ylmethyl)thiophene-2-carboxamide;
4-[(cyclopentylacetyl)amino]-3-fluoro-N-(imidazo[1,2-a] pyridin-7-ylmethyl)benzamide;
1-{2-fluoro-4-[1-(2-methylpropanoyl)-1,2,3,6-tetrahydropyridin-4-yl]phenyl}-3-(imidazo[1,2-a]pyridin-7-ylmethyl)urea;
1-{2-fluoro-4-[1-(tetrahydrofuran-2-ylcarbonyl)-1,2,3,6-tetrahydropyridin-4-yl]phenyl}-3-(imidazo[1,2-a]pyridin-7-ylmethyl)urea;
N-(imidazo[1,2-a]pyridin-7-ylmethyl)-4-{1-[(3S)-tetrahydrofuran-3-ylcarbonyl]piperidin-4-yl}benzamide;
N-(imidazo[1,2-a]pyridin-7-ylmethyl)-4-{1-[(3R)-tetrahydrofuran-3-ylcarbonyl]piperidin-4-yl}benzamide;
N-(imidazo[1,2-a]pyridin-7-ylmethyl)-4-{1-[(2R)-tetrahydrofuran-2-ylcarbonyl]piperidin-4-yl}benzamide;
N-(imidazo[1,2-a]pyridin-7-ylmethyl)-4-{1-[(2S)-tetrahydrofuran-2-ylcarbonyl]piperidin-4-yl}benzamide;
4-[1-(cyclopropylacetyl)piperidin-4-yl]-N-(imidazo[1,2-a] pyridin-7-ylmethyl)benzamide;
4-(1-acetylpiperidin-4-yl)-N-(imidazo[1,2-a]pyridin-7-ylmethyl)benzamide;
tert-butyl 4-{4-[2-(imidazo[1,2-a]pyridin-6-ylamino)-2-oxoethyl]phenyl}-3,6-dihydropyridine-1(2H)-carboxylate;
N-(imidazo[1,2-a]pyridin-7-ylmethyl)-4-[1-(2-methylpropyl)-1H-pyrazol-4-yl]benzamide;
5-[1-(1,4-dioxan-2-ylmethyl)-1H-pyrazol-4-yl]-N-(imidazo [1,2-a]pyridin-7-ylmethyl)thiophene-2-carboxamide;
5-[1-(2-hydroxyethyl)-1H-pyrazol-4-yl]-N-(imidazo[1,2-a] pyridin-7-ylmethyl)thiophene-2-carboxamide;
N-(imidazo[1,2-a]pyridin-7-ylmethyl)-5-[3-(propan-2-yloxy)phenyl]thiophene-2-carboxamide;
N-(imidazo[1,2-a]pyridin-7-ylmethyl)-2-[1-(tetrahydro-2H-pyran-4-ylcarbonyl)-1,2,3,6-tetrahydropyridin-4-yl]-1,3-thiazole-5-carboxamide;
N-(imidazo[1,2-a]pyridin-7-ylmethyl)-2-[1-(2-methylpropanoyl)-1,2,3,6-tetrahydropyridin-4-yl]-1,3-thiazole-5-carboxamide;
N-(imidazo[1,2-a]pyridin-7-ylmethyl)-4-({(3S)-1-[(2S)-2-methylbutanoyl]pyrrolidin-3-yl}oxy)benzamide;
tert-butyl 4-[4-(imidazo[1,2-a]pyridin-7-ylcarbamoyl)phenyl]piperidine-1-carboxylate;
tert-butyl 4-[4-(imidazo[1,2-a]pyridin-6-ylcarbamoyl)phenyl]piperidine-1-carboxylate;
N-(imidazo[1,2-a]pyridin-7-ylmethyl)-5-{3-[(2-methylpropanoyl)amino]oxetan-3-yl}thiophene-2-carboxamide;
5-[3-(benzoylamino)oxetan-3-yl]-N-(imidazo[1,2-a]pyridin-7-ylmethyl)thiophene-2-carboxamide;
N-(imidazo[1,2-a]pyridin-7-ylmethyl)-5-{3-[(tetrahydrofuran-3-ylacetyl)amino]oxetan-3-yl}thiophene-2-carboxamide;
N-(imidazo[1,2-a]pyridin-7-ylmethyl)-5-[3-(pentanoylamino)oxetan-3-yl]thiophene-2-carboxamide;
1-(imidazo[1,2-a]pyridin-7-ylmethyl)-3-[4-({(3R)-1-[(2S)-2-methylbutanoyl]pyrrolidin-3-yl}oxy)phenyl]urea;
1-(4-{[(3R)-1-benzoylpyrrolidin-3-yl]oxy}phenyl)-3-(imidazo[1,2-a]pyridin-7-ylmethyl)urea;
1-(imidazo[1,2-a]pyridin-7-ylmethyl)-3-(4-{[(3R)-1-(2-methylpropanoyl)pyrrolidin-3-yl]oxy}phenyl)urea;
1-(4-{[(3R)-1-(cyclopropylcarbonyl)pyrrolidin-3-yl] oxy}phenyl)-3-(imidazo[1,2-a]pyridin-7-ylmethyl)urea;
1-(4-{[(3R)-1-(cyclopropylacetyl)pyrrolidin-3-yl] oxy}phenyl)-3-(imidazo[1,2-a]pyridin-7-ylmethyl)urea;
1-(imidazo[1,2-a]pyridin-7-ylmethyl)-3-(4-{[(3R)-1-(tetrahydro-2H-pyran-4-ylcarbonyl)pyrrolidin-3-yl] oxy}phenyl)urea;
1-(4-{[(3R)-1-(2-hydroxy-2-methylpropanoyl)pyrrolidin-3-yl]oxy}phenyl)-3-(imidazo[1,2-a]pyridin-7-ylmethyl) urea;
1-(imidazo[1,2-a]pyridin-7-ylmethyl)-3-[4-({(3R)-1-[(2R)-tetrahydrofuran-2-ylcarbonyl]pyrrolidin-3-yl}oxy)phenyl]urea;
1-(imidazo[1,2-a]pyridin-7-ylmethyl)-3-[4-({(3R)-1-[(2S)-tetrahydrofuran-2-ylcarbonyl]pyrrolidin-3-yl}oxy)phenyl]urea;
1-(imidazo[1,2-a]pyridin-7-ylmethyl)-3-(4-{[(3R)-1-(tetrahydrofuran-3-ylcarbonyl)pyrrolidin-3-yl]oxy}phenyl) urea;

1-(imidazo[1,2-a]pyridin-7-ylmethyl)-3-(4-{[(3R)-1-(tetrahydro-2H-pyran-4-ylacetyl)pyrrolidin-3-yl]oxy}phenyl)urea;
N-(imidazo[1,2-a]pyridin-7-ylmethyl)-4-({(3S)-1-[(3R)-tetrahydrofuran-3-ylcarbonyl]pyrrolidin-3-yl}oxy)benzamide;
N-(imidazo[1,2-a]pyridin-7-ylmethyl)-4-({(3S)-1-[(2R)-tetrahydrofuran-2-ylcarbonyl]pyrrolidin-3-yl}oxy)benzamide;
N-(imidazo[1,2-a]pyridin-7-ylmethyl)-4-({(3S)-1-[(2S)-tetrahydrofuran-2-ylcarbonyl]pyrrolidin-3-yl}oxy)benzamide;
N-(imidazo[1,2-a]pyridin-7-ylmethyl)-4-{[(3S)-1-(tetrahydro-2H-pyran-4-ylcarbonyl)pyrrolidin-3-yl]oxy}benzamide;
N-(imidazo[1,2-a]pyridin-7-ylmethyl)-4-{[(3S)-1-(tetrahydro-2H-pyran-4-ylacetyl)pyrrolidin-3-yl]oxy}benzamide;
5-{1-[(1,1-dioxidotetrahydro-2H-thiopyran-3-yl)methyl]-1H-pyrazol-4-yl}-N-(imidazo[1,2-a]pyridin-7-ylmethyl)thiophene-2-carboxamide;
N-(imidazo[1,2-a]pyridin-7-ylmethyl)-5-(1-methyl-1H-pyrazol-4-yl)thiophene-2-carboxamide;
N-(imidazo[1,2-a]pyridin-7-ylmethyl)-4-({(3S)-1-[(3S)-tetrahydrofuran-3-ylcarbonyl]pyrrolidin-3-yl}oxy)benzamide;
4-{[(3S)-1-(cyclopropylacetyl)pyrrolidin-3-yl]oxy}-N-(imidazo[1,2-a]pyridin-7-ylmethyl)benzamide;
4-{[(3S)-1-(2-hydroxy-2-methylpropanoyl)pyrrolidin-3-yl]oxy}-N-(imidazo[1,2-a]pyridin-7-ylmethyl)benzamide;
N-(imidazo[1,2-a]pyridin-7-ylmethyl)-4-{[(3S)-1-(3-methoxy-2-methylpropanoyl)pyrrolidin-3-yl]oxy}benzamide;
4-{[(3S)-1-butanoylpyrrolidin-3-yl]oxy}-N-(imidazo[1,2-a]pyridin-7-ylmethyl)benzamide;
N-(imidazo[1,2-a]pyridin-7-ylmethyl)-4-{[(3S)-1-(2-methylpropanoyl)pyrrolidin-3-yl]oxy}benzamide;
4-{[(3S)-1-(cyclopropylcarbonyl)pyrrolidin-3-yl]oxy}-N-(imidazo[1,2-a]pyridin-7-ylmethyl)benzamide;
4-{[(3S)-1-benzoylpyrrolidin-3-yl]oxy}-N-(imidazo[1,2-a]pyridin-7-ylmethyl)benzamide;
4-{[(3S)-1-(3-hydroxy-3-methylbutanoyl)pyrrolidin-3-yl]oxy}-N-(imidazo[1,2-a]pyridin-7-ylmethyl)benzamide;
2-(4-benzoylpiperazin-1-yl)-N-(imidazo[1,2-a]pyridin-7-ylmethyl)-1,3-thiazole-5-carboxamide;
N-(imidazo[1,2-a]pyridin-7-ylmethyl)-2-[4-(propan-2-yl)piperazin-1-yl]-1,3-thiazole-5-carboxamide;
N-(imidazo[1,2-a]pyridin-7-ylmethyl)-2-[4-(2-methoxyethyl)piperazin-1-yl]-1,3-thiazole-5-carboxamide;
N-(imidazo[1,2-a]pyridin-6-ylmethyl)-N'-(3-methylbutyl)benzene-1,4-dicarboxamide;
N-(imidazo[1,2-a]pyridin-6-ylmethyl)-N'-[(3S)-tetrahydrofuran-3-ylmethyl]benzene-1,4-dicarboxamide;
1-(imidazo[1,2-a]pyridin-6-ylmethyl)-3-[4-(1-propyl-1H-pyrazol-4-yl)phenyl]urea;
N-(imidazo[1,2-a]pyridin-7-ylmethyl)-2-phenyl-1,3-thiazole-5-carboxamide;
1-(imidazo[1,2-a]pyridin-6-ylmethyl)-3-{4-[1-(2-methylpropyl)-1H-pyrazol-4-yl]phenyl}urea;
N-(imidazo[1,2-a]pyridin-7-ylmethyl)-5-(1-methyl-1H-pyrazol-5-yl)thiophene-2-carboxamide;
tert-butyl 3-(4-{[(imidazo[1,2-a]pyridin-7-ylmethyl)carbamoyl]amino}phenyl)azetidine-1-carboxylate;
tert-butyl 4-{4-[(imidazo[1,2-a]pyridin-7-ylmethyl)carbamoyl]phenoxy}piperidine-1-carboxylate;
tert-butyl 4-(4-{[(imidazo[1,2-a]pyridin-7-ylmethyl)carbamoyl]amino}phenoxy)piperidine-1-carboxylate;
N-(imidazo[1,2-a]pyridin-7-ylmethyl)-4-[1-(2-methylpropanoyl)pyrrolidin-3-yl]benzamide;
N-(imidazo[1,2-a]pyridin-7-ylmethyl)-4-{1-[(2S)-2-methylbutanoyl]pyrrolidin-3-yl}benzamide;
4-[1-(cyclopropylacetyl)pyrrolidin-3-yl]-N-(imidazo[1,2-a]pyridin-7-ylmethyl)benzamide;
4-(1-benzoylpyrrolidin-3-yl)-N-(imidazo[1,2-a]pyridin-7-ylmethyl)benzamide;
N-(imidazo[1,2-a]pyridin-7-ylmethyl)-4-{1-[(propan-2-yloxy)acetyl]pyrrolidin-3-yl}benzamide;
4-[1-(2-hydroxy-2-methylpropanoyl)pyrrolidin-3-yl]-N-(imidazo[1,2-a]pyridin-7-ylmethyl)benzamide;
N-(imidazo[1,2-a]pyridin-7-ylmethyl)-4-{1-[(2R)-tetrahydrofuran-2-ylcarbonyl]pyrrolidin-3-yl}benzamide;
N-(imidazo[1,2-a]pyridin-7-ylmethyl)-4-{1-[(2S)-tetrahydrofuran-2-ylcarbonyl]pyrrolidin-3-yl}benzamide;
N-(imidazo[1,2-a]pyridin-7-ylmethyl)-4-{1-[(3S)-tetrahydrofuran-3-ylcarbonyl]pyrrolidin-3-yl}benzamide;
N-(imidazo[1,2-a]pyridin-7-ylmethyl)-4-[1-(tetrahydro-2H-pyran-4-ylcarbonyl)pyrrolidin-3-yl]benzamide;
4-[1-(1,4-dioxan-2-ylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(tetrahydro-2H-pyran-4-ylacetyl)pyrrolidin-3-yl]benzamide;
1-[4-(1-acetylpyrrolidin-3-yl)phenyl]-3-(imidazo[1,2-a]pyridin-7-ylmethyl)urea;
1-(imidazo[1,2-a]pyridin-7-ylmethyl)-3-{4-[1-(2-methylpropanoyl)pyrrolidin-3-yl]phenyl}urea;
1-(imidazo[1,2-a]pyridin-7-ylmethyl)-3-(4-{1-[(2S)-2-methylbutanoyl]pyrrolidin-3-yl}phenyl)urea;
1-{4-[1-(cyclopropylacetyl)pyrrolidin-3-yl]phenyl}-3-(imidazo[1,2-a]pyridin-7-ylmethyl)urea;
1-[4-(1-benzoylpyrrolidin-3-yl)phenyl]-3-(imidazo[1,2-a]pyridin-7-ylmethyl)urea;
1-(imidazo[1,2-a]pyridin-7-ylmethyl)-3-(4-{1-[(propan-2-yloxy)acetyl]pyrrolidin-3-yl}phenyl)urea;
1-{4-[1-(2-hydroxy-2-methylpropanoyl)pyrrolidin-3-yl]phenyl}-3-(imidazo[1,2-a]pyridin-7-ylmethyl)urea;
1-(imidazo[1,2-a]pyridin-7-ylmethyl)-3-(4-{1-[(2R)-tetrahydrofuran-2-ylcarbonyl]pyrrolidin-3-yl}phenyl)urea;
1-(imidazo[1,2-a]pyridin-7-ylmethyl)-3-(4-{1-[(2S)-tetrahydrofuran-2-ylcarbonyl]pyrrolidin-3-yl}phenyl)urea;
1-(imidazo[1,2-a]pyridin-7-ylmethyl)-3-(4-{1-[(3S)-tetrahydrofuran-3-ylcarbonyl]pyrrolidin-3-yl}phenyl)urea;
1-(imidazo[1,2-a]pyridin-7-ylmethyl)-3-{4-[1-(tetrahydro-2H-pyran-4-ylcarbonyl)pyrrolidin-3-yl]phenyl}urea;
1-{4-[1-(1,4-dioxan-2-ylcarbonyl)pyrrolidin-3-yl]phenyl}-3-(imidazo[1,2-a]pyridin-7-ylmethyl)urea;
1-(imidazo[1,2-a]pyridin-7-ylmethyl)-3-{4-[1-(tetrahydro-2H-pyran-4-ylacetyl)pyrrolidin-3-yl]phenyl}urea;
1-(imidazo[1,2-a]pyridin-7-ylmethyl)-3-{4-[1-(morpholin-4-ylacetyl)pyrrolidin-3-yl]phenyl}urea;
N-(imidazo[1,2-a]pyridin-7-ylmethyl)-N'-(3-methylbutyl)benzene-1,4-dicarboxamide;
N-(imidazo[1,2-a]pyridin-7-ylmethyl)-N'-[(3S)-tetrahydrofuran-3-ylmethyl]benzene-1,4-dicarboxamide;
N-(imidazo[1,2-a]pyridin-7-ylmethyl)-5-{1-[(2R)-tetrahydrofuran-2-ylmethyl]-1H-pyrazol-4-yl}thiophene-2-carboxamide;
4-{[(3-chloroimidazo[1,2-a]pyridin-6-yl)carbamoyl]amino}-N-(tetrahydro-2H-pyran-2-ylmethyl)benzamide;
N-(imidazo[1,2-a]pyridin-7-ylmethyl)-5-{1-[(2S)-tetrahydrofuran-2-ylmethyl]-1H-pyrazol-4-yl}thiophene-2-carboxamide;
N-[(3-chloroimidazo[1,2-a]pyridin-6-yl)methyl]-4-[(tetrahydrofuran-3-ylacetyl)amino]benzamide;

5-(4-hydroxytetrahydro-2H-pyran-4-yl)-N-(imidazo[1,2-a]pyridin-7-ylmethyl)thiophene-2-carboxamide;
5-[3-hydroxy-1-(2-methylpropanoyl)azetidin-3-yl]-N-(imidazo[1,2-a]pyridin-7-ylmethyl)thiophene-2-carboxamide;
5-(1-benzoyl-3-hydroxyazetidin-3-yl)-N-(imidazo[1,2-a]pyridin-7-ylmethyl)thiophene-2-carboxamide;
tert-butyl 3-{4-[(imidazo[1,2-a]pyridin-7-ylmethyl)carbamoyl]phenyl}azetidine-1-carboxylate;
tert-butyl 4-hydroxy-4-{5-[(imidazo[1,2-a]pyridin-7-ylmethyl)carbamoyl]thiophen-2-yl}piperidine-1-carboxylate;
1-(imidazo[1,2-a]pyridin-7-ylmethyl)-3-[5-(piperidin-1-ylcarbonyl)-1,3-thiazol-2-yl]urea;
5-{3-hydroxy-1-[(2S)-2-methylbutanoyl]azetidin-3-yl}-N-(imidazo[1,2-a]pyridin-7-ylmethyl)thiophene-2-carboxamide;
5-[3-hydroxy-1-(tetrahydro-2H-pyran-4-ylacetyl)azetidin-3-yl]-N-(imidazo[1,2-a]pyridin-7-ylmethyl)thiophene-2-carboxamide;
2-{[(imidazo[1,2-a]pyridin-7-ylmethyl)carbamoyl]amino}-N-(3-methylbutyl)-1,3-thiazole-5-carboxamide;
N-(imidazo[1,2-a]pyridin-7-ylmethyl)-5-(3-{[(2S)-2-methylbutanoyl]amino}oxetan-3-yl)thiophene-2-carboxamide;
N-(imidazo[1,2-a]pyridin-7-ylmethyl)-1-[1-(3-methylbutanoyl)piperidin-4-yl]-1H-pyrazole-3-carboxamide;
N-(imidazo[1,2-a]pyridin-7-ylmethyl)-5-[1-(tetrahydro-2H-pyran-4-yl)-1H-pyrazol-4-yl]thiophene-2-carboxamide;
4-[(1-acetylpiperidin-4-yl)oxy]-N-(imidazo[1,2-a]pyridin-7-ylmethyl)benzamide;
N-(imidazo[1,2-a]pyridin-7-ylmethyl)-4-{[1-(2-methylpropanoyl)piperidin-4-yl]oxy}benzamide;
N-(imidazo[1,2-a]pyridin-7-ylmethyl)-4-({1-[(2S)-2-methylbutanoyl]piperidin-4-yl}oxy)benzamide;
4-{[1-(cyclopropylacetyl)piperidin-4-yl]oxy}-N-(imidazo[1,2-a]pyridin-7-ylmethyl)benzamide;
4-[(1-benzoylpiperidin-4-yl)oxy]-N-(imidazo[1,2-a]pyridin-7-ylmethyl)benzamide;
N-(imidazo[1,2-a]pyridin-7-ylmethyl)-4-({1-[(propan-2-yloxy)acetyl]piperidin-4-yl}oxy)benzamide;
4-{[1-(2-hydroxy-2-methylpropanoyl)piperidin-4-yl]oxy}-N-(imidazo[1,2-a]pyridin-7-ylmethyl)benzamide;
N-(imidazo[1,2-a]pyridin-7-ylmethyl)-4-({1-[(2R)-tetrahydrofuran-2-ylcarbonyl]piperidin-4-yl}oxy)benzamide;
N-(imidazo[1,2-a]pyridin-7-ylmethyl)-4-({1-[(2S)-tetrahydrofuran-2-ylcarbonyl]piperidin-4-yl}oxy)benzamide;
N-(imidazo[1,2-a]pyridin-7-ylmethyl)-4-{[1-(tetrahydro-2H-pyran-4-ylcarbonyl)piperidin-4-yl]oxy}benzamide;
4-{[1-(1,4-dioxan-2-ylcarbonyl)piperidin-4-yl]oxy}-N-(imidazo[1,2-a]pyridin-7-ylmethyl)benzamide;
N-(imidazo[1,2-a]pyridin-7-ylmethyl)-4-{[1-(tetrahydro-2H-pyran-4-ylacetyl)piperidin-4-yl]oxy}benzamide;
N-(imidazo[1,2-a]pyridin-7-ylmethyl)-4-{[1-(morpholin-4-ylacetyl)piperidin-4-yl]oxy}benzamide;
1-{4-[(1-acetylazetidin-3-yl)oxy]phenyl}-3-(imidazo[1,2-a]pyridin-7-ylmethyl)urea;
1-(imidazo[1,2-a]pyridin-7-ylmethyl)-3-(4-{[1-(2-methylpropanoyl)azetidin-3-yl]oxy}phenyl)urea;
1-(imidazo[1,2-a]pyridin-7-ylmethyl)-3-[4-({1-[(2S)-2-methylbutanoyl]azetidin-3-yl}oxy)phenyl]urea;
1-(4-{[1-(cyclopropylacetyl)azetidin-3-yl]oxy}phenyl)-3-(imidazo[1,2-a]pyridin-7-ylmethyl)urea;
1-{4-[(1-benzoylazetidin-3-yl)oxy]phenyl}-3-(imidazo[1,2-a]pyridin-7-ylmethyl)urea;
1-(imidazo[1,2-a]pyridin-7-ylmethyl)-3-[4-({1-[(propan-2-yloxy)acetyl]azetidin-3-yl}oxy)phenyl]urea;
1-(4-{[1-(2-hydroxy-2-methylpropanoyl)azetidin-3-yl]oxy}phenyl)-3-(imidazo[1,2-a]pyridin-7-ylmethyl)urea;
1-(imidazo[1,2-a]pyridin-7-ylmethyl)-3-[4-({1-[(2R)-tetrahydrofuran-2-ylcarbonyl]azetidin-3-yl}oxy)phenyl]urea;
1-(imidazo[1,2-a]pyridin-7-ylmethyl)-3-[4-({1-[(2S)-tetrahydrofuran-2-ylcarbonyl]azetidin-3-yl}oxy)phenyl]urea;
1-(imidazo[1,2-a]pyridin-7-ylmethyl)-3-(4-{[1-(tetrahydro-2H-pyran-4-ylcarbonyl)azetidin-3-yl]oxy}phenyl)urea;
1-(4-{[1-(1,4-dioxan-2-ylcarbonyl)azetidin-3-yl]oxy}phenyl)-3-(imidazo[1,2-a]pyridin-7-ylmethyl)urea;
1-(imidazo[1,2-a]pyridin-7-ylmethyl)-3-(4-{[1-(tetrahydro-2H-pyran-4-ylacetyl)azetidin-3-yl]oxy}phenyl)urea;
tert-butyl (3R)-3-{4-[(imidazo[1,2-a]pyridin-7-ylmethyl)carbamoyl]phenoxy}pyrrolidine-1-carboxylate;
4-(1-benzoylpiperidin-4-yl)-N-(imidazo[1,2-a]pyridin-7-ylmethyl)benzamide;
1-[4-(1-benzoyl-1,2,3,6-tetrahydropyridin-4-yl)-2-fluorophenyl]-3-(imidazo[1,2-a]pyridin-7-ylmethyl)urea;
1-{2-fluoro-4-[1-(tetrahydro-2H-pyran-4-ylacetyl)-1,2,3,6-tetrahydropyridin-4-yl]phenyl}-3-(imidazo[1,2-a]pyridin-7-ylmethyl)urea;
4-{1-[(3,3-difluorocyclobutyl)carbonyl]piperidin-4-yl}-N-(imidazo[1,2-a]pyridin-7-ylmethyl)benzamide;
4-{1-[(4,4-difluorocyclohexyl)carbonyl]piperidin-4-yl}-N-(imidazo[1,2-a]pyridin-7-ylmethyl)benzamide;
1-(imidazo[1,2-a]pyridin-7-ylmethyl)-3-(4-{[1-(2-methylpropanoyl)piperidin-4-yl]oxy}phenyl)urea;
1-(imidazo[1,2-a]pyridin-7-ylmethyl)-3-[4-({1-[(2S)-2-methylbutanoyl]piperidin-4-yl}oxy)phenyl]urea;
1-(4-{[1-(cyclopropylacetyl)piperidin-4-yl]oxy}phenyl)-3-(imidazo[1,2-a]pyridin-7-ylmethyl)urea;
1-{4[(1-benzoylpiperidin-4-yl)oxy]phenyl}-3-(imidazo[1,2-a]pyridin-7-ylmethyl)urea;
1-(imidazo[1,2-a]pyridin-7-ylmethyl)-3-[4-({1-[(propan-2-yloxy)acetyl]piperidin-4-yl}oxy)phenyl]urea;
1-(4-{[1-(2-hydroxy-2-methylpropanoyl)piperidin-4-yl]oxy}phenyl)-3-(imidazo[1,2-a]pyridin-7-ylmethyl)urea;
1-(imidazo[1,2-a]pyridin-7-ylmethyl)-3-[4-({1-[(2R)-tetrahydrofuran-2-ylcarbonyl]piperidin-4-yl}oxy)phenyl]urea;
1-(imidazo[1,2-a]pyridin-7-ylmethyl)-3-[4-({1-[(2S)-tetrahydrofuran-2-ylcarbonyl]piperidin-4-yl}oxy)phenyl]urea;
1-(imidazo[1,2-a]pyridin-7-ylmethyl)-3-(4-{[1-(tetrahydro-2H-pyran-4-ylcarbonyl)piperidin-4-yl]oxy}phenyl)urea;
1-(imidazo[1,2-a]pyridin-7-ylmethyl)-3-(4-{[1-(tetrahydro-2H-pyran-4-ylacetyl)piperidin-4-yl]oxy}phenyl)urea;
1-(imidazo[1,2-a]pyridin-7-ylmethyl)-3-{4-[1-(2-methylpropanoyl)azetidin-3-yl]phenyl}urea;
1-(imidazo[1,2-a]pyridin-7-ylmethyl)-3-(4-{1-[(2S)-2-methylbutanoyl]azetidin-3-yl}phenyl)urea;
1-{4-[1-(cyclopropylacetyl)azetidin-3-yl]phenyl}-3-(imidazo[1,2-a]pyridin-7-ylmethyl)urea;
1-[4-(1-benzoylazetidin-3-yl)phenyl]-3-(imidazo[1,2-a]pyridin-7-ylmethyl)urea;
1-(imidazo[1,2-a]pyridin-7-ylmethyl)-3-(4-{1-[(propan-2-yloxy)acetyl]azetidin-3-yl}phenyl)urea;
1-{4-[1-(2-hydroxy-2-methylpropanoyl)azetidin-3-yl]phenyl}-3-(imidazo[1,2-a]pyridin-7-ylmethyl)urea;
1-(imidazo[1,2-a]pyridin-7-ylmethyl)-3-(4-{1-[(2R)-tetrahydrofuran-2-ylcarbonyl]azetidin-3-yl}phenyl)urea;
1-(imidazo[1,2-a]pyridin-7-ylmethyl)-3-(4-{1-[(2S)-tetrahydrofuran-2-ylcarbonyl]azetidin-3-yl}phenyl)urea;
1-(imidazo[1,2-a]pyridin-7-ylmethyl)-3-{4-[1-(tetrahydro-2H-pyran-4-ylcarbonyl)azetidin-3-yl]phenyl}urea;

1-(imidazo[1,2-a]pyridin-7-ylmethyl)-3-{4-[1-(tetrahydro-2H-pyran-4-ylacetyl)azetidin-3-yl]phenyl}urea;

4-[(cyclopentylacetyl)amino]-2-fluoro-N-(imidazo[1,2-a]pyridin-6-ylmethyl)benzamide;

4-[(cyclopentylacetyl)amino]-2-fluoro-N-(imidazo[1,2-a]pyridin-7-ylmethyl)benzamide;

N-(imidazo[1,2-a]pyridin-7-ylmethyl)-5-[6-(morpholin-4-yl)pyridin-3-yl]thiophene-2-carboxamide;

N-(imidazo[1,2-a]pyridin-7-ylmethyl)-5-{1-[(2-methyltetrahydro-2H-pyran-2-yl)methyl]-1H-pyrazol-4-yl}thiophene-2-carboxamide;

tert-butyl 4-[(4-{5-[(imidazo[1,2-a]pyridin-7-ylmethyl)carbamoyl]thiophen-2-yl}-1H-pyrazol-1-yl)methyl]piperidine-1-carboxylate;

N-(imidazo[1,2-a]pyridin-7-ylmethyl)-5-[1-(3-methylbutanoyl)pyrrolidin-3-yl]thiophene-2-carboxamide;

N-(imidazo[1,2-a]pyridin-7-ylmethyl)-5-{1-[(2-methylpropanoyl)amino]cyclobutyl}thiophene-2-carboxamide;

N-(imidazo[1,2-a]pyridin-7-ylmethyl)-5-{1-[(3-methylbutanoyl)amino]cyclobutyl}thiophene-2-carboxamide;

N-(imidazo[1,2-a]pyridin-7-ylmethyl)-5-(1-{[(2S)-2-methylbutanoyl]amino}cyclobutyl)thiophene-2-carboxamide;

5-[1-(benzoylamino)cyclobutyl]-N-(imidazo[1,2-a]pyridin-7-ylmethyl)thiophene-2-carboxamide;

N-(imidazo[1,2-a]pyridin-7-ylmethyl)-5-{1-[(3,3,3-trifluoropropanoyl)amino]cyclobutyl}thiophene-2-carboxamide;

N-(1-{5-[(imidazo[1,2-a]pyridin-7-ylmethyl)carbamoyl]thiophen-2-yl}cyclobutyl)tetrahydro-2H-pyran-4-carboxamide;

tert-butyl 3-{4-[(imidazo[1,2-a]pyridin-7-ylmethyl)carbamoyl]phenoxy}azetidine-1-carboxylate;

5-[1-(cyclobutylmethyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[1-(tetrahydrofuran-2-ylmethyl)-1H-pyrazol-4-yl]furan-2-carboxamide;

N-(imidazo[1,2-a]pyridin-7-ylmethyl)-5-[1-(tetrahydro-2H-pyran-2-ylmethyl)-1H-pyrazol-4-yl]furan-2-carboxamide;

N-(imidazo[1,2-a]pyridin-7-ylmethyl)-5-[1-(tetrahydrofuran-3-ylmethyl)-1H-pyrazol-4-yl]furan-2-carboxamide;

N-(imidazo[1,2-a]pyridin-7-ylmethyl)-5-[1-(tetrahydro-2H-pyran-3-ylmethyl)-1H-pyrazol-4-yl]furan-2-carboxamide;

N-(imidazo[1,2-a]pyridin-7-ylmethyl)-5-[1-(tetrahydro-2H-pyran-4-ylmethyl)-1H-pyrazol-4-yl]furan-2-carboxamide;

5-[1-(cyclobutylmethyl)-1H-pyrazol-4-yl]-N-(imidazo[1,2-a]pyridin-7-ylmethyl)furan-2-carboxamide;

N-(imidazo[1,2-a]pyridin-7-ylmethyl)-5-{1-[(3-methyloxetan-3-yl)methyl]-1H-pyrazol-4-yl}furan-2-carboxamide;

5-[1-(2-hydroxy-2-methylpropyl)-1H-pyrazol-4-yl]-N-(imidazo[1,2-a]pyridin-7-ylmethyl)furan-2-carboxamide;

4-[1-(furan-2-ylcarbonyl)piperidin-4-yl]-N-(imidazo[1,2-a]pyridin-7-ylmethyl)benzamide;

N-(imidazo[1,2-a]pyridin-7-ylmethyl)-5-[1-(piperidin-4-ylmethyl)-1H-pyrazol-4-yl]thiophene-2-carboxamide;

1-(imidazo[1,2-a]pyridin-7-ylmethyl)-3-{4-[1-(2-methylpropyl)-1H-pyrazol-4-yl]phenyl}urea;

1-(imidazo[1,2-a]pyridin-7-ylmethyl)-3-[4-(1-propyl-1H-pyrazol-4-yl)phenyl]urea;

N-(imidazo[1,2-a]pyridin-7-ylmethyl)-4-[1-(thiophen-2-ylcarbonyl)pyrrolidin-3-yl]benzamide;

N-(imidazo[1,2-a]pyridin-7-ylmethyl)-4-phenoxybenzamide;

N-(imidazo[1,2-a]pyridin-7-ylmethyl)-4-[1-(2-methylpropanoyl)azetidin-3-yl]benzamide;

tert-butyl 4-{4-[(3-chloroimidazo[1,2-a]pyridin-6-yl)carbamoyl]phenyl}piperidine-1-carboxylate;

N-(imidazo[1,2-a]pyridin-7-ylmethyl)-4-{[(3R)-1-(2-methylpropanoyl)pyrrolidin-3-yl]oxy}benzamide;

4-{[(3R)-1-benzoylpyrrolidin-3-yl]oxy}-N-(imidazo[1,2-a]pyridin-7-ylmethyl)benzamide;

N-(imidazo[1,2-a]pyridin-7-ylmethyl)-4-({(3R)-1-[(3S)-tetrahydrofuran-3-ylcarbonyl]pyrrolidin-3-yl}oxy)benzamide;

N-(imidazo[1,2-a]pyridin-7-ylmethyl)-4-({(3R)-1-[(2S)-2-methylbutanoyl]pyrrolidin-3-yl}oxy)benzamide;

1-(imidazo[1,2-a]pyridin-7-ylmethyl)-3-(4-phenoxyphenyl)urea;

5-[1-(2-methylpropyl)-1H-pyrazol-4-yl]-N-([1,2,4]triazolo[1,5-a]pyridin-7-ylmethyl)thiophene-2-carboxamide;

N-(imidazo[1,2-a]pyridin-7-ylmethyl)-4-[1-(pyridin-2-ylcarbonyl)piperidin-4-yl]benzamide;

4-[1-(3,3-dimethylbutanoyl)piperidin-4-yl]-N-(imidazo[1,2-a]pyridin-7-ylmethyl)benzamide;

N-(imidazo[1,2-a]pyridin-7-ylmethyl)-4-[1-(4-methylbenzoyl)piperidin-4-yl]benzamide;

4-[1-(2,2-dimethylbutanoyl)piperidin-4-yl]-N-(imidazo[1,2-a]pyridin-7-ylmethyl)benzamide;

4-[1-(cyclohexylcarbonyl)piperidin-4-yl]-N-(imidazo[1,2-a]pyridin-7-ylmethyl)benzamide;

N-(imidazo[1,2-a]pyridin-7-ylmethyl)-4-[1-(thiophen-2-ylcarbonyl)piperidin-4-yl]benzamide;

N-(imidazo[1,2-a]pyridin-7-ylmethyl)-4-[1-(3,3,3-trifluoropropanoyl)piperidin-4-yl]benzamide;

4-(1-butanoylpiperidin-4-yl)-N-(imidazo[1,2-a]pyridin-7-ylmethyl)benzamide;

4-[1-(2,4-difluorobenzoyl)piperidin-4-yl]-N-(imidazo[1,2-a]pyridin-7-ylmethyl)benzamide;

N-(imidazo[1,2-a]pyridin-7-ylmethyl)-4-[1-(2-methylbenzoyl)piperidin-4-yl]benzamide;

4-[1-(4-fluorobenzoyl)piperidin-4-yl]-N-(imidazo[1,2-a]pyridin-7-ylmethyl)benzamide;

4-[1-(2,2-dimethylpropanoyl)piperidin-4-yl]-N-(imidazo[1,2-a]pyridin-7-ylmethyl)benzamide;

N-(imidazo[1,2-a]pyridin-7-ylmethyl)-4-{1-[(2E)-2-methylpent-2-enoyl]piperidin-4-yl}benzamide;

N-(imidazo[1,2-a]pyridin-7-ylmethyl)-4-{1-[(1-methyl-1H-pyrazol-5-yl)carbonyl]piperidin-4-yl}benzamide;

N-(imidazo[1,2-a]pyridin-7-ylmethyl)-4-{1-[(3-methyloxetan-3-yl)carbonyl]piperidin-4-yl}benzamide;

4-[1-(2-fluorobenzoyl)piperidin-4-yl]-N-(imidazo[1,2-a]pyridin-7-ylmethyl)benzamide;

4-{1-[(1-cyanocyclopropyl)carbonyl]piperidin-4-yl}-N-(imidazo[1,2-a]pyridin-7-ylmethyl)benzamide;

4-[1-(cyclopentylcarbonyl)piperidin-4-yl]-N-(imidazo[1,2-a]pyridin-7-ylmethyl)benzamide;

4-[1-(3-fluorobenzoyl)piperidin-4-yl]-N-(imidazo[1,2-a]pyridin-7-ylmethyl)benzamide;

N-(imidazo[1,2-a]pyridin-7-ylmethyl)-4-{1-[(1-methyl-1H-pyrazol-4-yl)carbonyl]piperidin-4-yl}benzamide;

N-(imidazo[1,2-a]pyridin-7-ylmethyl)-4-[1-(2-oxobutanoyl)piperidin-4-yl]benzamide;

4-{1-[(2,5-dimethylfuran-3-yl)carbonyl]piperidin-4-yl}-N-(imidazo[1,2-a]pyridin-7-ylmethyl)benzamide;

4-[1-(4-cyanobenzoyl)piperidin-4-yl]-N-(imidazo[1,2-a]pyridin-7-ylmethyl)benzamide;

4-[1-(3-cyanobenzoyl)piperidin-4-yl]-N-(imidazo[1,2-a]pyridin-7-ylmethyl)benzamide;

4-[1-(2,5-difluorobenzoyl)piperidin-4-yl]-N-(imidazo[1,2-a]pyridin-7-ylmethyl)benzamide;

N-(imidazo[1,2-a]pyridin-7-ylmethyl)-4-[1-(pyrazin-2-yl-carbonyl)piperidin-4-yl]benzamide;
N-(imidazo[1,2-a]pyridin-7-ylmethyl)-4-{1-[(3-methylthiophen-2-yl)carbonyl]piperidin-4-yl}benzamide;
4-{1-[(3,5-dimethyl-1,2-oxazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(3-methoxybenzoyl)piperidin-4-yl]benzamide;
4-[1-(3-chlorobenzoyl)piperidin-4-yl]-N-(imidazo[1,2-a]pyridin-7-ylmethyl)benzamide;
N-(imidazo[1,2-a]pyridin-7-ylmethyl)-4-[1-(4-methoxybenzoyl)piperidin-4-yl]benzamide;
4-[1-(4-chlorobenzoyl)piperidin-4-yl]-N-(imidazo[1,2-a]pyridin-7-ylmethyl)benzamide;
4-[1-(3,5-difluorobenzoyl)piperidin-4-yl]-N-(imidazo[1,2-a]pyridin-7-ylmethyl)benzamide;
4-[1-(cyclopropylcarbonyl)piperidin-4-yl]-N-(imidazo[1,2-a]pyridin-7-ylmethyl)benzamide;
N-(imidazo[1,2-a]pyridin-7-ylmethyl)-4-(1-propanoylpiperidin-4-yl)benzamide;
N-(imidazo[1,2-a]pyridin-7-ylmethyl)-4-{1-[(1-methyl-1H-pyrrol-2-yl)carbonyl]piperidin-4-yl}benzamide;
N-(imidazo[1,2-a]pyridin-7-ylmethyl)-4-[1-(3-methylbutanoyl)piperidin-4-yl]benzamide;
N-(imidazo[1,2-a]pyridin-7-ylmethyl)-4-[1-(pyridin-4-ylcarbonyl)piperidin-4-yl]benzamide;
4-[1-(2,3-dimethylbutanoyl)piperidin-4-yl]-N-(imidazo[1,2-a]pyridin-7-ylmethyl)benzamide;
N-(imidazo[1,2-a]pyridin-7-ylmethyl)-4-[1-(pyridin-3-ylcarbonyl)piperidin-4-yl]benzamide;
N-(imidazo[1,2-a]pyridin-7-ylmethyl)-4-{1-[(1-methylcyclopropyl)carbonyl]piperidin-4-yl}benzamide;
N-(imidazo[1,2-a]pyridin-7-ylmethyl)-4-[1-(2-methoxybenzoyl)piperidin-4-yl]benzamide;
N-(imidazo[1,2-a]pyridin-7-ylmethyl)-5-[1-(3,3,3-trifluoropropanoyl)pyrrolidin-3-yl]thiophene-2-carboxamide;
N-(imidazo[1,2-a]pyridin-7-ylmethyl)-5-[1-(2-methylpropanoyl)pyrrolidin-3-yl]thiophene-2-carboxamide;
5-(1-benzoylpyrrolidin-3-yl)-N-(imidazo[1,2-a]pyridin-7-ylmethyl)thiophene-2-carboxamide;
N-(imidazo[1,2-a]pyridin-7-ylmethyl)-2-[1-(2-methylpropanoyl)piperidin-4-yl]-1,3-thiazole-5-carboxamide;
N-(imidazo[1,2-a]pyridin-7-ylmethyl)-2-[1-(3-methylbutanoyl)piperidin-4-yl]-1,3-thiazole-5-carboxamide;
2-(1-benzoylpiperidin-4-yl)-N-(imidazo[1,2-a]pyridin-7-ylmethyl)-1,3-thiazole-5-carboxamide;
4-[(cyclopentylacetyl)amino]-N-([1,2,4]triazolo[1,5-a]pyridin-7-ylmethyl)benzamide;
N-(imidazo[1,2-a]pyridin-7-ylmethyl)-4-{1-[(2S)-2-methylbutanoyl]azetidin-3-yl}benzamide;
4-[1-(cyclopropylacetyl)azetidin-3-yl]-N-(imidazo[1,2-a]pyridin-7-ylmethyl)benzamide;
4-(1-benzoylazetidin-3-yl)-N-(imidazo[1,2-a]pyridin-7-ylmethyl)benzamide;
4-[1-(2-hydroxy-2-methylpropanoyl)azetidin-3-yl]-N-(imidazo[1,2-a]pyridin-7-ylmethyl)benzamide;
N-(imidazo[1,2-a]pyridin-7-ylmethyl)-4-[1-(tetrahydro-2H-pyran-4-ylacetyl)azetidin-3-yl]benzamide;
N-(imidazo[1,2-a]pyridin-7-ylmethyl)-4-[1-(thiophen-2-ylcarbonyl)azetidin-3-yl]benzamide;
5-[4-hydroxy-1-(3-methylbutanoyl)piperidin-4-yl]-N-(imidazo[1,2-a]pyridin-7-ylmethyl)thiophene-2-carboxamide;
5-[4-hydroxy-1-(2-methylpropanoyl)piperidin-4-yl]-N-(imidazo[1,2-a]pyridin-7-ylmethyl)thiophene-2-carboxamide;
5-[1-(3,3-dimethylbutanoyl)-4-hydroxypiperidin-4-yl]-N-(imidazo[1,2-a]pyridin-7-ylmethyl)thiophene-2-carboxamide;
5-(1-benzoyl-4-hydroxypiperidin-4-yl)-N-(imidazo[1,2-a]pyridin-7-ylmethyl)thiophene-2-carboxamide;
N-(imidazo[1,2-a]pyridin-7-ylmethyl)-4-[1-(propan-2-ylsulfonyl)azetidin-3-yl]benzamide;
N-(imidazo[1,2-a]pyridin-7-ylmethyl)-4-{[1-(2-methylpropanoyl)azetidin-3-yl]oxy}benzamide;
N-(imidazo[1,2-a]pyridin-7-ylmethyl)-4-({1-[(2S)-2-methylbutanoyl]azetidin-3-yl}oxy)benzamide;
4-{[1-(cyclopropylacetyl)azetidin-3-yl]oxy}-N-(imidazo[1,2-a]pyridin-7-ylmethyl)benzamide;
4-[(1-benzoylazetidin-3-yl)oxy]-N-(imidazo[1,2-a]pyridin-7-ylmethyl)benzamide;
4-[1-(4-fluorobenzoyl)pyrrolidin-3-yl]-N-(imidazo[1,2-a]pyridin-7-ylmethyl)benzamide;
tert-butyl 4-{4-[([1,2,4]triazolo[1,5-a]pyridin-7-ylmethyl)carbamoyl]phenyl}piperidine-1-carboxylate;
2-cyclopentyl-N-(4-{[([1,2,4]triazolo[1,5-a]pyridin-7-ylmethyl)carbamoyl]amino}phenyl)acetamide;
tert-butyl 4-(4-{[([1,2,4]triazolo[1,5-a]pyridin-7-ylmethyl)carbamoyl]amino}phenyl)piperidine-1-carboxylate;
N-(imidazo[1,2-a]pyridin-7-ylmethyl)-4-(piperidin-1-ylcarbonyl)benzamide;
4-[1-(ethylsulfonyl)azetidin-3-yl]-N-(imidazo[1,2-a]pyridin-7-ylmethyl)benzamide;
4-[1-(cyclopropylsulfonyl)azetidin-3-yl]-N-(imidazo[1,2-a]pyridin-7-ylmethyl)benzamide;
N-(imidazo[1,2-a]pyridin-7-ylmethyl)-4-[1-(phenylsulfonyl)azetidin-3-yl]benzamide;
propan-2-yl 4-{5-[(imidazo[1,2-a]pyridin-7-ylmethyl)carbamoyl]thiophen-2-yl}piperidine-1-carboxylate;
2-methylpropyl 4-{5-[(imidazo[1,2-a]pyridin-7-ylmethyl)carbamoyl]thiophen-2-yl}piperidine-1-carboxylate;
N-(imidazo[1,2-a]pyridin-7-ylmethyl)-5-[1-(3,3,3-trifluoropropanoyl)piperidin-4-yl]thiophene-2-carboxamide;
N-(imidazo[1,2-a]pyridin-7-ylmethyl)-5-{1-[(2-methylpropyl)sulfonyl]piperidin-4-yl}thiophene-2-carboxamide;
N-(imidazo[1,2-a]pyridin-7-ylmethyl)-5-[1-(4,4,4-trifluorobutanoyl)piperidin-4-yl]thiophene-2-carboxamide;
N-[(3-chloroimidazo[1,2-a]pyridin-7-yl)methyl]-4-[1-(2-methylpropanoyl)piperidin-4-yl]benzamide;
N-(imidazo[1,2-a]pyridin-7-ylmethyl)-5-{1-[(4-methyltetrahydro-2H-pyran-4-yl)methyl]-1H-pyrazol-4-yl}thiophene-2-carboxamide;
5-[1-(2-cyano-2-methylpropyl)-1H-pyrazol-4-yl]-N-(imidazo[1,2-a]pyridin-7-ylmethyl)thiophene-2-carboxamide;
4-chloro-N-(imidazo[1,2-a]pyridin-7-ylmethyl)-5-[1-(2-methylpropyl)-1H-pyrazol-4-yl]thiophene-2-carboxamide;
4-chloro-N-(imidazo[1,2-a]pyridin-7-ylmethyl)-5-{1-[(3R)-tetrahydrofuran-3-ylmethyl]-1H-pyrazol-4-yl}thiophene-2-carboxamide;
N-(imidazo[1,2-a]pyridin-7-ylmethyl)-4-{1-[(2-methylcyclopropyl)carbonyl]pyrrolidin-3-yl}benzamide;
4-[1-(cyclopentylacetyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylpentanoyl)pyrrolidin-3-yl]benzamide;
4-[1-(cyclopentylcarbonyl)pyrrolidin-3-yl]-N-(imidazo[1,2-a]pyridin-7-ylmethyl)benzamide;
N-(imidazo[1,2-a]pyridin-7-ylmethyl)-4-{1-[(1-methylcyclopropyl)carbonyl]pyrrolidin-3-yl}benzamide;
4-[1-(2,2-dimethylpropanoyl)pyrrolidin-3-yl]-N-(imidazo[1,2-a]pyridin-7-ylmethyl)benzamide;

N-(imidazo[1,2-a]pyridin-7-ylmethyl)-4-[1-(1,3-thiazol-5-ylcarbonyl)pyrrolidin-3-yl]benzamide;
N-(imidazo[1,2-a]pyridin-7-ylmethyl)-4-[1-(2-methoxybenzoyl)pyrrolidin-3-yl]benzamide;
N-(imidazo[1,2-a]pyridin-7-ylmethyl)-4-[1-(1,3-thiazol-4-ylcarbonyl)pyrrolidin-3-yl]benzamide;
4-[1-(2-fluorobenzoyl)pyrrolidin-3-yl]-N-(imidazo[1,2-a]pyridin-7-ylmethyl)benzamide;
4-[1-(furan-2-ylcarbonyl)pyrrolidin-3-yl]-N-(imidazo[1,2-a]pyridin-7-ylmethyl)benzamide;
4-[1-(3-fluorobenzoyl)pyrrolidin-3-yl]-N-(imidazo[1,2-a]pyridin-7-ylmethyl)benzamide;
4-[1-(2,4-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-3-yl)carbonyl]pyrrolidin-3-yl}benzamide;
4-[1-(2-chlorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(2-methylbenzoyl)pyrrolidin-3-yl]benzamide;
4-[1-(4-chlorobenzoyl)pyrrolidin-3-yl]-N-(imidazo[1,2-a]pyridin-7-ylmethyl)benzamide;
4-[1-(3-chlorobenzoyl)pyrrolidin-3-yl]-N-(imidazo[1,2-a]pyridin-7-ylmethyl)benzamide;
4-[1-(2,2-dimethylbutanoyl)pyrrolidin-3-yl]-N-(imidazo[1,2-a]pyridin-7-ylmethyl)benzamide;
4-[1-(3,5-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(4-methylbenzoyl)pyrrolidin-3-yl]benzamide;
N-(imidazo[1,2-a]pyridin-7-ylmethyl)-4-[1-(3-methylbutanoyl)pyrrolidin-3-yl]benzamide;
4-[1-(3,3-dimethylbutanoyl)pyrrolidin-3-yl]-N-(imidazo[1,2-a]pyridin-7-ylmethyl)benzamide;
4-[1-(3-cyanobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)pyrrolidin-3-yl]benzamide;
N-(imidazo[1,2-a]pyridin-7-ylmethyl)-4-[1-(4-methoxybenzoyl)pyrrolidin-3-yl]benzamide;
N-(imidazo[1,2-a]pyridin-7-ylmethyl)-4-{1-[(1-methyl-1H-pyrrol-2-yl)carbonyl]pyrrolidin-3-yl}benzamide;
4-[1-(cyclohexylacetyl)pyrrolidin-3-yl]-N-(imidazo[1,2-a]pyridin-7-ylmethyl)benzamide;
N-(imidazo[1,2-a]pyridin-7-ylmethyl)-4-[1-(pyridin-4-ylcarbonyl)pyrrolidin-3-yl]benzamide;
N-(imidazo[1,2-a]pyridin-7-ylmethyl)-4-[1-(pyridin-3-ylcarbonyl)pyrrolidin-3-yl]benzamide;
4-[1-(cyclohexylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)pyrrolidin-3-yl]benzamide;
4-[1-(furan-3-ylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(1,3-thiazol-2-ylcarbonyl)pyrrolidin-3-yl]benzamide;
N-(imidazo[1,2-a]pyridin-7-ylmethyl)-4-{1-[(1-methylcyclohexyl)carbonyl]pyrrolidin-3-yl}benzamide;
4-[1-(2,3-dimethylbutanoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylbenzoyl)pyrrolidin-3-yl]benzamide;
N-(imidazo[1,2-a]pyridin-7-ylmethyl)-4-[1-(thiophen-3-ylcarbonyl)pyrrolidin-3-yl]benzamide;
N-(imidazo[1,2-a]pyridin-7-ylmethyl)-4-{1-[3-(trifluoromethoxy)benzoyl]pyrrolidin-3-yl}benzamide;
N-(imidazo[1,2-a]pyridin-7-ylmethyl)-4-{1-[(3-methylthiophen-2-yl)carbonyl]pyrrolidin-3-yl}benzamide;
N-(imidazo[1,2-a]pyridin-7-ylmethyl)-4-{1-[3-(trifluoromethyl)benzoyl]pyrrolidin-3-yl}benzamide;
5-[1-(2-hydroxy-2-methylpropyl)-1H-pyrazol-4-yl]-N-([1,2,4]triazolo[1,5-a]pyridin-6-ylmethyl)thiophene-2-carboxamide;
5-{1-[(4-methyltetrahydro-2H-pyran-4-yl)methyl]-1H-pyrazol-4-yl}-N-([1,2,4]triazolo[1,5-a]pyridin-6-ylmethyl)thiophene-2-carboxamide;
N-(imidazo[1,2-a]pyridin-7-ylmethyl)-4-[1-(methylsulfonyl)azetidin-3-yl]benzamide;
N-(imidazo[1,2-a]pyridin-7-ylmethyl)-4-[1-(methylsulfonyl)pyrrolidin-3-yl]benzamide;
4-[1-(ethylsulfonyl)pyrrolidin-3-yl]-N-(imidazo[1,2-a]pyridin-7-ylmethyl)benzamide;
4-[1-(cyclopropylsulfonyl)pyrrolidin-3-yl]-N-(imidazo[1,2-a]pyridin-7-ylmethyl)benzamide;
N-(imidazo[1,2-a]pyridin-7-ylmethyl)-4-[1-(phenylsulfonyl)pyrrolidin-3-yl]benzamide;
N-(imidazo[1,2-a]pyridin-7-ylmethyl)-4-{1-[(2-methylcyclopropyl)carbonyl]azetidin-3-yl}benzamide;
4-[1-(cyclopentylacetyl)azetidin-3-yl]-N-(imidazo[1,2-a]pyridin-7-ylmethyl)benzamide;
N-(imidazo[1,2-a]pyridin-7-ylmethyl)-4-[1-(3-methylpentanoyl)azetidin-3-yl]benzamide;
4-[1-(cyclopentylcarbonyl)azetidin-3-yl]-N-(imidazo[1,2-a]pyridin-7-ylmethyl)benzamide;
N-(imidazo[1,2-a]pyridin-7-ylmethyl)-4-{1-[(1-methylcyclopropyl)carbonyl]azetidin-3-yl}benzamide;
4-[1-(2,2-dimethylpropanoyl)azetidin-3-yl]-N-(imidazo[1,2-a]pyridin-7-ylmethyl)benzamide;
N-(imidazo[1,2-a]pyridin-7-ylmethyl)-4-[1-(1,3-thiazol-5-ylcarbonyl)azetidin-3-yl]benzamide;
N-(imidazo[1,2-a]pyridin-7-ylmethyl)-4-[1-(pyrazin-2-ylcarbonyl)azetidin-3-yl]benzamide;
N-(imidazo[1,2-a]pyridin-7-ylmethyl)-4-[1-(2-methoxybenzoyl)azetidin-3-yl]benzamide;
N-(imidazo[1,2-a]pyridin-7-ylmethyl)-4-[1-(1,3-thiazol-4-ylcarbonyl)azetidin-3-yl]benzamide;
4-[1-(2-fluorobenzoyl)azetidin-3-yl]-N-(imidazo[1,2-a]pyridin-7-ylmethyl)benzamide;
4-[1-(furan-2-ylcarbonyl)azetidin-3-yl]-N-(imidazo[1,2-a]pyridin-7-ylmethyl)benzamide;
4-[1-(3-fluorobenzoyl)azetidin-3-yl]-N-(imidazo[1,2-a]pyridin-7-ylmethyl)benzamide;
4-[1-(2,4-difluorobenzoyl)azetidin-3-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-3-yl)carbonyl]azetidin-3-yl}benzamide;
4-[1-(2-chlorobenzoyl)azetidin-3-yl]-N-(imidazo[1,2-a]pyridin-7-ylmethyl)benzamide;
N-(imidazo[1,2-a]pyridin-7-ylmethyl)-4-[1-(2-methylbenzoyl)azetidin-3-yl]benzamide;
4-[1-(4-chlorobenzoyl)azetidin-3-yl]-N-(imidazo[1,2-a]pyridin-7-ylmethyl)benzamide;
4-[1-(3-chlorobenzoyl)azetidin-3-yl]-N-(imidazo[1,2-a]pyridin-7-ylmethyl)benzamide;
4-[1-(2,2-dimethylbutanoyl)azetidin-3-yl]-N-(imidazo[1,2-a]pyridin-7-ylmethyl)benzamide;
4-[1-(3,5-difluorobenzoyl)azetidin-3-yl]-N-(imidazo[1,2-a]pyridin-7-ylmethyl)benzamide;
4-[1-(4-fluorobenzoyl)azetidin-3-yl]-N-(imidazo[1,2-a]pyridin-7-ylmethyl)benzamide;
N-(imidazo[1,2-a]pyridin-7-ylmethyl)-4-[1-(4-methylbenzoyl)azetidin-3-yl]benzamide;

N-(imidazo[1,2-a]pyridin-7-ylmethyl)-4-[1-(3-methylbutanoyl)azetidin-3-yl]benzamide;
4-[1-(3,3-dimethylbutanoyl)azetidin-3-yl]-N-(imidazo[1,2-a]pyridin-7-ylmethyl)benzamide;
4-[1-(3-cyanobenzoyl)azetidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)azetidin-3-yl]benzamide;
N-(imidazo[1,2-a]pyridin-7-ylmethyl)-4-[1-(4-methoxybenzoyl)azetidin-3-yl]benzamide;
N-(imidazo[1,2-a]pyridin-7-ylmethyl)-4-{1-[(1-methyl-1H-pyrrol-2-yl)carbonyl]azetidin-3-yl}benzamide;
4-[1-(cyclohexylacetyl)azetidin-3-yl]-N-(imidazo[1,2-a]pyridin-7-ylmethyl)benzamide;
N-(imidazo[1,2-a]pyridin-7-ylmethyl)-4-[1-(pyridin-4-ylcarbonyl)azetidin-3-yl]benzamide;
N-(imidazo[1,2-a]pyridin-7-ylmethyl)-4-[1-(pyridin-3-ylcarbonyl)azetidin-3-yl]benzamide;
4-[1-(cyclohexylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)azetidin-3-yl]benzamide;
4-[1-(furan-3-ylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyrimidin-4-ylcarbonyl)azetidin-3-yl]benzamide;
N-(imidazo[1,2-a]pyridin-7-ylmethyl)-4-[1-(1,3-thiazol-2-ylcarbonyl)azetidin-3-yl]benzamide;
N-(imidazo[1,2-a]pyridin-7-ylmethyl)-4-{1-[(1-methylcyclohexyl)carbonyl]azetidin-3-yl}benzamide;
4-[1-(2,3-dimethylbutanoyl)azetidin-3-yl]-N-(imidazo[1,2-a]pyridin-7-ylmethyl)benzamide;
N-(imidazo[1,2-a]pyridin-7-ylmethyl)-4-[1-(3-methylbenzoyl)azetidin-3-yl]benzamide;
N-(imidazo[1,2-a]pyridin-7-ylmethyl)-4-[1-(thiophen-3-ylcarbonyl)azetidin-3-yl]benzamide;
N-(imidazo[1,2-a]pyridin-7-ylmethyl)-4-{1-[3-(trifluoromethoxy)benzoyl]azetidin-3-yl}benzamide;
N-(imidazo[1,2-a]pyridin-7-ylmethyl)-4-{1-[(3-methylthiophen-2-yl)carbonyl]azetidin-3-yl}benzamide;
N-(imidazo[1,2-a]pyridin-7-ylmethyl)-4-{1-[3-(trifluoromethyl)benzoyl]azetidin-3-yl}benzamide;
N-(imidazo[1,2-a]pyridin-7-ylmethyl)-4-[1-(propan-2-ylsulfonyl)pyrrolidin-3-yl]benzamide;
1-(imidazo[1,2-a]pyridin-7-ylmethyl)-3-{4-[1-(2-methoxyethyl)-1H-pyrazol-4-yl]phenyl}urea;
1-(imidazo[1,2-a]pyridin-7-ylmethyl)-3-{4-[1-(tetrahydrofuran-2-ylmethyl)-1H-pyrazol-4-yl]phenyl}urea;
1-(imidazo[1,2-a]pyridin-7-ylmethyl)-3-{4-[1-(tetrahydro-2H-pyran-4-ylmethyl)-1H-pyrazol-4-yl]phenyl}urea;
5-[1-(1,4-dioxan-2-ylmethyl)-1H-pyrazol-4-yl]-N-([1,2,4]triazolo[1,5-a]pyridin-6-ylmethyl)thiophene-2-carboxamide;
5-[1-(2-fluorobenzoyl)piperidin-4-yl]-N-(imidazo[1,2-a]pyridin-7-ylmethyl)thiophene-2-carboxamide;
tert-butyl 4-{4-[(imidazo[1,2-a]pyrazin-6-ylmethyl)carbamoyl]phenyl}piperidine-1-carboxylate;
4-[(cyclopentylacetyl)amino]-N-(imidazo[1,2-a]pyrazin-6-ylmethyl)benzamide;
tert-butyl 4-(4-{[(imidazo[1,2-a]pyrazin-6-ylmethyl)carbamoyl]amino}phenyl)piperidine-1-carboxylate;
2-cyclopentyl-N-(4-{[(imidazo[1,2-a]pyrazin-6-ylmethyl)carbamoyl]amino}phenyl)acetamide;
N-(imidazo[1,2-a]pyridin-7-ylmethyl)-4-[1-(phenylsulfonyl)piperidin-4-yl]benzamide;
N-(imidazo[1,2-a]pyridin-7-ylmethyl)-4-[1-(propan-2-ylsulfonyl)piperidin-4-yl]benzamide;
4-[1-(cyclopropylsulfonyl)piperidin-4-yl]-N-(imidazo[1,2-a]pyridin-7-ylmethyl)benzamide;
5-{(1R)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-5-{(1R)-3-methyl-1-[(tetrahydrofuran-3-ylacetyl)amino]butyl}thiophene-2-carboxamide;
5-{(1S)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-2-(1-phenylpiperidin-4-yl)-1,3-thiazole-5-carboxamide;
1-(4-{[(3R)-1-(2-fluorobenzoyl)pyrrolidin-3-yl]oxy}phenyl)-3-(imidazo[1,2-a]pyridin-7-ylmethyl)urea;
1-(4-{[(3R)-1-(3-fluorobenzoyl)pyrrolidin-3-yl]oxy}phenyl)-3-(imidazo[1,2-a]pyridin-7-ylmethyl)urea;
1-(4-{[(3R)-1-(4-fluorobenzoyl)pyrrolidin-3-yl]oxy}phenyl)-3-(imidazo[1,2-a]pyridin-7-ylmethyl)urea;
1-(4-{[(3R)-1-(2,4-difluorobenzoyl)pyrrolidin-3-yl]oxy}phenyl)-3-(imidazo[1,2-a]pyridin-7-ylmethyl)urea;
1-(imidazo[1,2-a]pyridin-7-ylmethyl)-3-[4-({(3R)-1-[4-(trifluoromethyl)benzoyl]pyrrolidin-3-yl}oxy)phenyl]urea;
1-(4-{[(3R)-1-(3,5-difluorobenzoyl)pyrrolidin-3-yl]oxy}phenyl)-3-(imidazo[1,2-a]pyridin-7-ylmethyl)urea;
1-(4-{[(3R)-1-(2-chlorobenzoyl)pyrrolidin-3-yl]oxy}phenyl)-3-(imidazo[1,2-a]pyridin-7-ylmethyl)urea;
1-(4-{[(3R)-1-(4-chlorobenzoyl)pyrrolidin-3-yl]oxy}phenyl)-3-(imidazo[1,2-a]pyridin-7-ylmethyl)urea;
N-(imidazo[1,2-a]pyridin-7-ylmethyl)-2-[1-(pyridin-2-yl)piperidin-4-yl]-1,3-thiazole-5-carboxamide;
5-{1-[(4-fluorotetrahydro-2H-pyran-4-yl)methyl]-1H-pyrazol-4-yl}-N-(imidazo[1,2-a]pyridin-7-ylmethyl)thiophene-2-carboxamide;
4-[1-(2-chlorobenzoyl)piperidin-4-yl]-N-(imidazo[1,2-a]pyridin-7-ylmethyl)benzamide;
4-[1-(2,6-difluorobenzoyl)piperidin-4-yl]-N-(imidazo[1,2-a]pyridin-7-ylmethyl)benzamide;
4-[1-(3,4-difluorobenzoyl)piperidin-4-yl]-N-(imidazo[1,2-a]pyridin-7-ylmethyl)benzamide;
N-(imidazo[1,2-a]pyridin-7-ylmethyl)-4-{1-[3-(trifluoromethyl)benzoyl]piperidin-4-yl}benzamide;
N-(imidazo[1,2-a]pyridin-7-ylmethyl)-4-{1-[3-(trifluoromethoxy)benzoyl]piperidin-4-yl}benzamide;
N-(imidazo[1,2-a]pyridin-7-ylmethyl)-4-{1-[4-(trifluoromethoxy)benzoyl]piperidin-4-yl}benzamide;
N-(imidazo[1,2-a]pyridin-7-ylmethyl)-4-{1-[4-(trifluoromethyl)benzoyl]piperidin-4-yl}benzamide;
N-(imidazo[1,2-a]pyridin-7-ylmethyl)-4-{1-[2-(trifluoromethoxy)benzoyl]piperidin-4-yl}benzamide;
N-(imidazo[1,2-a]pyridin-7-ylmethyl)-4-[1-(phenylacetyl)piperidin-4-yl]benzamide;
N-(imidazo[1,2-a]pyridin-7-ylmethyl)-4-{1-[2-(trifluoromethyl)benzoyl]piperidin-4-yl}benzamide;
1-[4-(1-butanoylpiperidin-4-yl)phenyl]-3-(imidazo[1,2-a]pyridin-7-ylmethyl)urea;
1-(imidazo[1,2-a]pyridin-7-ylmethyl)-3-(4-{1-[(2S)-2-methylbutanoyl]piperidin-4-yl}phenyl)urea;
1-(imidazo[1,2-a]pyridin-7-ylmethyl)-3-(4-{1-[(2-methylcyclopropyl)carbonyl]piperidin-4-yl}phenyl)urea;
1-{4-[1-(cyclopropylacetyl)piperidin-4-yl]phenyl}-3-(imidazo[1,2-a]pyridin-7-ylmethyl)urea;
1-(imidazo[1,2-a]pyridin-7-ylmethyl)-3-{4-[1-(3,3,3-trifluoropropanoyl)piperidin-4-yl]phenyl}urea;
1-(imidazo[1,2-a]pyridin-7-ylmethyl)-3-{4-[1-(4,4,4-trifluorobutanoyl)piperidin-4-yl]phenyl}urea;

1-(4-{1-[(4,4-difluorocyclohexyl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(phenylacetyl)piperidin-4-yl]phenyl}urea;
5-[1-(cyclopropylcarbonyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(4-methylbenzoyl)pyrrolidin-3-yl]thiophene-2-carboxamide;
1-{4-[1-(2-fluorobenzoyl)piperidin-4-yl]phenyl}-3-(imidazo[1,2-a]pyridin-7-ylmethyl)urea;
1-{4-[1-(3-fluorobenzoyl)piperidin-4-yl]phenyl}-3-(imidazo[1,2-a]pyridin-7-ylmethyl)urea;
1-{4-[1-(4-fluorobenzoyl)piperidin-4-yl]phenyl}-3-(imidazo[1,2-a]pyridin-7-ylmethyl)urea;
1-{4-[1-(2,4-difluorobenzoyl)piperidin-4-yl]phenyl}-3-(imidazo[1,2-a]pyridin-7-ylmethyl)urea;
1-{4-[1-(3,4-difluorobenzoyl)piperidin-4-yl]phenyl}-3-(imidazo[1,2-a]pyridin-7-ylmethyl)urea;
1-{4-[1-(3,5-difluorobenzoyl)piperidin-4-yl]phenyl}-3-(imidazo[1,2-a]pyridin-7-ylmethyl)urea;
1-{4-[1-(2,5-difluorobenzoyl)piperidin-4-yl]phenyl}-3-(imidazo[1,2-a]pyridin-7-ylmethyl)urea;
1-(4-{[1-(3-fluorobenzoyl)piperidin-4-yl]oxy}phenyl)-3-(imidazo[1,2-a]pyridin-7-ylmethyl)urea;
1-(4-{[1-(2,4-difluorobenzoyl)piperidin-4-yl]oxy}phenyl)-3-(imidazo[1,2-a]pyridin-7-ylmethyl)urea;
1-(4-{[1-(2,5-difluorobenzoyl)piperidin-4-yl]oxy}phenyl)-3-(imidazo[1,2-a]pyridin-7-ylmethyl)urea;
1-(4-{[1-(3,4-difluorobenzoyl)piperidin-4-yl]oxy}phenyl)-3-(imidazo[1,2-a]pyridin-7-ylmethyl)urea;
1-(4-{[1-(3,5-difluorobenzoyl)piperidin-4-yl]oxy}phenyl)-3-(imidazo[1,2-a]pyridin-7-ylmethyl)urea;
N-(imidazo[1,2-a]pyridin-7-ylmethyl)-4-[1-(phenylacetyl)pyrrolidin-3-yl]benzamide;
N-(imidazo[1,2-a]pyridin-7-ylmethyl)-4-[1-(2-methyl-2-phenylpropanoyl)pyrrolidin-3-yl]benzamide;
4-{1-[difluoro(phenyl)acetyl]pyrrolidin-3-yl}-N-(imidazo[1,2-a]pyridin-7-ylmethyl)benzamide;
N-(imidazo[1,2-a]pyridin-7-ylmethyl)-5-{1-[(4-methyltetrahydro-2H-pyran-4-yl)methyl]-1H-pyrazol-4-yl}furan-2-carboxamide;
5-[1-(2-fluorobenzoyl)piperidin-4-yl]-N-(imidazo[1,2-a]pyridin-7-ylmethyl)furan-2-carboxamide;
N-(imidazo[1,2-a]pyridin-7-ylmethyl)-5-[1-(2-methylpropanoyl)piperidin-4-yl]furan-2-carboxamide;
4-[1-(2-cyanobenzoyl)piperidin-4-yl]-N-(imidazo[1,2-a]pyridin-7-ylmethyl)benzamide;
N-(imidazo[1,2-a]pyridin-7-ylmethyl)-5-[1-(2,2,2-trifluoroethyl)-1H-pyrazol-4-yl]furan-2-carboxamide;
2-cyclopentyl-N-{4-[(imidazo[1,2-a]pyridin-7-ylacetyl)amino]phenyl}acetamide;
N-(imidazo[1,2-a]pyridin-7-ylmethyl)-5-[1-(2-methylpropyl)-1H-pyrazol-4-yl]furan-2-carboxamide;
5-(1-benzyl-1H-pyrazol-4-yl)-N-(imidazo[1,2-a]pyridin-7-ylmethyl)furan-2-carboxamide;
N-(imidazo[1,2-a]pyridin-7-ylmethyl)-5-{1-[(2S)-tetrahydrofuran-2-ylmethyl]-1H-pyrazol-4-yl}furan-2-carboxamide;
N-(imidazo[1,2-a]pyridin-7-ylmethyl)-5-{1-[(2R)-tetrahydrofuran-2-ylmethyl]-1H-pyrazol-4-yl}furan-2-carboxamide;
N-(imidazo[1,2-a]pyridin-7-ylmethyl)-5-[1-(2-methylpropanoyl)-1,2,3,6-tetrahydropyridin-4-yl]furan-2-carboxamide;
N-(imidazo[1,2-a]pyridin-7-ylmethyl)-5-[1-(3-methylbutanoyl)-1,2,3,6-tetrahydropyridin-4-yl]furan-2-carboxamide;
5-(1-benzoyl-1,2,3,6-tetrahydropyridin-4-yl)-N-(imidazo[1,2-a]pyridin-7-ylmethyl)furan-2-carboxamide;
N-(imidazo[1,2-a]pyridin-7-ylmethyl)-5-[4-(2-methylpropyl)phenyl]furan-2-carboxamide;
N-(imidazo[1,2-a]pyridin-7-ylmethyl)-5-{1-[(2S)-2-methylbutanoyl]-1,2,3,6-tetrahydropyridin-4-yl}furan-2-carboxamide;
5-[1-(3,3-dimethylbutanoyl)-1,2,3,6-tetrahydropyridin-4-yl]-N-(imidazo[1,2-a]pyridin-7-ylmethyl)furan-2-carboxamide;
5-[1-(cyclopropylacetyl)-1,2,3,6-tetrahydropyridin-4-yl]-N-(imidazo[1,2-a]pyridin-7-ylmethyl)furan-2-carboxamide;
N-(imidazo[1,2-a]pyridin-7-ylmethyl)-2-{1[(2-methylpropyl)sulfonyl]pyrrolidin-3-yl}-1,3-thiazole-5-carboxamide;
N-(imidazo[1,2-a]pyridin-7-ylmethyl)-2-[1-(phenylsulfonyl)pyrrolidin-3-yl]-1,3-thiazole-5-carboxamide;
N-(imidazo[1,2-a]pyridin-7-ylmethyl)-5-{1-[(2-methylpropyl)sulfonyl]-1,2,3,6-tetrahydropyridin-4-yl}furan-2-carboxamide;
N-(imidazo[1,2-a]pyrazin-6-ylmethyl)-5-[1-(2-methylpropyl)-1H-pyrazol-4-yl]thiophene-2-carboxamide;
tert-butyl 4-[(4-{5-[(imidazo[1,2-a]pyridin-7-ylmethyl)carbamoyl]thiophen-2-yl}-1H-pyrazol-1-yl)methyl]-4-methylpiperidine-1-carboxylate;
5-[1-(cyclopropylacetyl)pyrrolidin-3-yl]-N-(imidazo[1,2-a]pyridin-7-ylmethyl)thiophene-2-carboxamide;
5-[1-(2-chlorobenzoyl)pyrrolidin-3-yl]-N-(imidazo[1,2-a]pyridin-7-ylmethyl)thiophene-2-carboxamide;
5-{1-[(4-fluorophenyl)acetyl]pyrrolidin-3-yl}-N-(imidazo[1,2-a]pyridin-7-ylmethyl)thiophene-2-carboxamide;
N-(imidazo[1,2-a]pyridin-7-ylmethyl)-5-[1-(3-methoxybenzoyl)pyrrolidin-3-yl]thiophene-2-carboxamide;
N-(imidazo[1,2-a]pyridin-7-ylmethyl)-5-[1-(2-methoxybenzoyl)pyrrolidin-3-yl]thiophene-2-carboxamide;
5-{1-[(3-fluorophenyl)acetyl]pyrrolidin-3-yl}-N-(imidazo[1,2-a]pyridin-7-ylmethyl)thiophene-2-carboxamide;
5-[1-(3-fluorobenzoyl)pyrrolidin-3-yl]-N-(imidazo[1,2-a]pyridin-7-ylmethyl)thiophene-2-carboxamide;
5-[1-(4-fluorobenzoyl)pyrrolidin-3-yl]-N-(imidazo[1,2-a]pyridin-7-ylmethyl)thiophene-2-carboxamide;
5-{1-[(3,5-difluorophenyl)acetyl]pyrrolidin-3-yl}-N-(imidazo[1,2-a]pyridin-7-ylmethyl)thiophene-2-carboxamide;
5-{1-[(2-fluorophenyl)acetyl]pyrrolidin-3-yl}-N-(imidazo[1,2-a]pyridin-7-ylmethyl)thiophene-2-carboxamide;
5-[1-(4-cyanobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(3-methyloxetan-3-yl)carbonyl]pyrrolidin-3-yl}thiophene-2-carboxamide;
5-[1-(3,5-difluorobenzoyl)pyrrolidin-3-yl]-N-(imidazo[1,2-a]pyridin-7-ylmethyl)thiophene-2-carboxamide;
5-[1-(cyclopentylcarbonyl)pyrrolidin-3-yl]-N-(imidazo[1,2-a]pyridin-7-ylmethyl)thiophene-2-carboxamide;
5-[1-(4-chlorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(1-methyl-1H-pyrrol-2-yl)carbonyl]pyrrolidin-3-yl}thiophene-2-carboxamide;
5-[1-(2,4-difluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(pyridin-4-ylcarbonyl)pyrrolidin-3-yl]thiophene-2-carboxamide;
N-(imidazo[1,2-a]pyridin-7-ylmethyl)-5-[1-(pyridin-2-ylcarbonyl)pyrrolidin-3-yl]thiophene-2-carboxamide;

N-(imidazo[1,2-a]pyridin-7-ylmethyl)-5-{1-[(1-methyl-1H-pyrazol-4-yl)carbonyl]pyrrolidin-3-yl}thiophene-2-carboxamide;

5-[1-(2-fluorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(2E)-2-methylpent-2-enoyl]pyrrolidin-3-yl}thiophene-2-carboxamide;

5-{1-[(2,5-dimethylfuran-3-yl)carbonyl]pyrrolidin-3-yl}-N-(imidazo[1,2-a]pyridin-7-ylmethyl)thiophene-2-carboxamide;

5-[1-(3-chlorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-(1-propanoylpyrrolidin-3-yl)thiophene-2-carboxamide;

5-{1-[(1-cyanocyclopropyl)carbonyl]pyrrolidin-3-yl}-N-(imidazo[1,2-a]pyridin-7-ylmethyl)thiophene-2-carboxamide;

5-(1-butanoylpyrrolidin-3-yl)-N-(imidazo[1,2-a]pyridin-7-ylmethyl)thiophene-2-carboxamide;

5-[1-(furan-2-ylcarbonyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(4-methoxybenzoyl)pyrrolidin-3-yl]thiophene-2-carboxamide;

5-[1-(2,5-difluorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(thiophen-2-ylcarbonyl)pyrrolidin-3-yl]thiophene-2-carboxamide;

5-[1-(2,2-dimethylpropanoyl)pyrrolidin-3-yl]-N-(imidazo[1,2-a]pyridin-7-ylmethyl)thiophene-2-carboxamide;

5-[1-(3,3-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(4-methylpiperidin-4-yl)methyl]-1H-pyrazol-4-yl}thiophene-2-carboxamide;

5-{1-[(4-fluorotetrahydro-2H-pyran-4-yl)methyl]-1H-pyrazol-4-yl}-N-(imidazo[1,2-a]pyridin-7-ylmethyl)furan-2-carboxamide;

5-[1-(2,2-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(pyrazin-2-ylcarbonyl)pyrrolidin-3-yl]thiophene-2-carboxamide;

N-(imidazo[1,2-a]pyridin-7-ylmethyl)-5-{1-[(3-methylthiophen-2-yl)carbonyl]pyrrolidin-3-yl}thiophene-2-carboxamide;

N-(imidazo[1,2-a]pyridin-7-ylmethyl)-5-[1-(2-methylbenzoyl)pyrrolidin-3-yl]thiophene-2-carboxamide;

N-(imidazo[1,2-a]pyridin-7-ylmethyl)-5-{1-[(1-methylcyclopropyl)carbonyl]pyrrolidin-3-yl}thiophene-2-carboxamide;

N-(imidazo[1,2-a]pyridin-7-ylmethyl)-5-[1-(4,4,4-trifluorobutanoyl)pyrrolidin-3-yl]thiophene-2-carboxamide;

5-{1-[(3,5-dimethyl-1,2-oxazol-4-yl)carbonyl]pyrrolidin-3-yl}-N-(imidazo[1,2-a]pyridin-7-ylmethyl)thiophene-2-carboxamide;

N-(imidazo[1,2-a]pyridin-7-ylmethyl)-5-[1-(pyridin-3-ylcarbonyl)pyrrolidin-3-yl]thiophene-2-carboxamide;

N-(imidazo[1,2-a]pyridin-7-ylmethyl)-5-{1-[(1-methyl-1H-pyrazol-5-yl)carbonyl]pyrrolidin-3-yl}thiophene-2-carboxamide;

5-[1-(2,3-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(phenylsulfonyl)-1,2,3,6-tetrahydropyridin-4-yl]furan-2-carboxamide;

2-[1-(2-fluorobenzoyl)piperidin-4-yl]-N-(imidazo[1,2-a]pyridin-7-ylmethyl)-1,3-thiazole-5-carboxamide;

5-[1-(2-fluorobenzoyl)-1,2,3,6-tetrahydropyridin-4-yl]-N-(imidazo[1,2-a]pyridin-7-ylmethyl)furan-2-carboxamide;

2-[1-(2-fluorobenzoyl)pyrrolidin-3-yl]-N-(imidazo[1,2-a]pyridin-7-ylmethyl)-1,3-thiazole-5-carboxamide;

N-(imidazo[1,2-a]pyridin-7-ylmethyl)-2-[1-(2-methylpropanoyl)pyrrolidin-3-yl]-1,3-thiazole-5-carboxamide;

N-(imidazo[1,2-a]pyridin-7-ylmethyl)-2-[1-(3-methylbutanoyl)pyrrolidin-3-yl]-1,3-thiazole-5-carboxamide;

2-(1-benzoylpyrrolidin-3-yl)-N-(imidazo[1,2-a]pyridin-7-ylmethyl)-1,3-thiazole-5-carboxamide;

tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate;

N-(imidazo[1,2-a]pyridin-7-ylmethyl)-5-{1-[2-(piperazin-1-yl)ethyl]-1H-pyrazol-4-yl}thiophene-2-carboxamide;

5-{1-[(4-fluorotetrahydro-2H-pyran-4-yl)methyl]-1H-pyrazol-4-yl}-N-([1,2,4]triazolo[1,5-a]pyridin-6-ylmethyl)furan-2-carboxamide;

N-(imidazo[1,2-a]pyrazin-6-ylmethyl)-4-[1-(2-methylpropanoyl)piperidin-4-yl]benzamide;

4-[1-(4-fluorobenzoyl)piperidin-4-yl]-N-(imidazo[1,2-a]pyrazin-6-ylmethyl)benzamide;

4-[1-(2,5-difluorobenzoyl)piperidin-4-yl]-N-(imidazo[1,2-a]pyrazin-6-ylmethyl)benzamide;

N-(imidazo[1,2-a]pyrazin-6-ylmethyl)-4-{1-[(1-methylcyclopropyl)carbonyl]piperidin-4-yl}benzamide;

N-(imidazo[1,2-a]pyrazin-6-ylmethyl)-4-[1-(3,3,3-trifluoropropanoyl)piperidin-4-yl]benzamide;

N-(imidazo[1,2-a]pyrazin-6-ylmethyl)-4-[1-(3-methylbutanoyl)piperidin-4-yl]benzamide;

N-(imidazo[1,2-a]pyrazin-6-ylmethyl)-4-[1-(propan-2-ylsulfonyl)piperidin-4-yl]benzamide;

N-(imidazo[1,2-a]pyridin-7-ylmethyl)-5-[1-(2-methylpropyl)-1H-pyrazol-5-yl]furan-2-carboxamide;

N-(imidazo[1,2-a]pyrazin-6-ylmethyl)-5-[1-(2-methylpropyl)-1H-pyrazol-4-yl]furan-2-carboxamide;

5-[1-(2-methylpropyl)-1H-pyrazol-4-yl]-N-([1,2,4]triazolo[1,5-a]pyridin-6-ylmethyl)furan-2-carboxamide;

N-(imidazo[1,2-a]pyridin-7-ylmethyl)-5-[1-(3-methylbutyl)-1H-pyrazol-5-yl]furan-2-carboxamide;

5-{1-[(4-methyltetrahydro-2H-pyran-4-yl)methyl]-1H-pyrazol-4-yl}-N-([1,2,4]triazolo[1,5-a]pyridin-6-ylmethyl)furan-2-carboxamide;

N-(imidazo[1,2-a]pyridin-7-ylmethyl)-5-{[(2R)-2-(methoxymethyl)pyrrolidin-1-yl]carbonyl}thiophene-2-carboxamide;

N-(imidazo[1,2-a]pyridin-7-ylmethyl)-5-{[2-(2-methylpropyl)pyrrolidin-1-yl]carbonyl}thiophene-2-carboxamide;

5-[1-(2,2-dimethylpropyl)-1H-pyrazol-4-yl]-N-(imidazo[1,2-a]pyridin-7-ylmethyl)furan-2-carboxamide;

4-[1-(2-fluorobenzoyl)piperidin-4-yl]-N-(imidazo[1,2-a]pyrazin-6-ylmethyl)benzamide;

5-[1-(2-fluorobenzoyl)piperidin-4-yl]-N-(imidazo[1,2-a]pyrazin-6-ylmethyl)thiophene-2-carboxamide;

5-[1-(4-fluorobenzoyl)piperidin-4-yl]-N-(imidazo[1,2-a]pyrazin-6-ylmethyl)thiophene-2-carboxamide;

5-[1-(2,4-difluorobenzoyl)piperidin-4-yl]-N-(imidazo[1,2-a]pyrazin-6-ylmethyl)thiophene-2-carboxamide;

5-[1-(2,5-difluorobenzoyl)piperidin-4-yl]-N-(imidazo[1,2-a]pyrazin-6-ylmethyl)thiophene-2-carboxamide;

5-[1-(2-fluorobenzoyl)piperidin-4-yl]-N-([1,2,4]triazolo[1,5-a]pyridin-6-ylmethyl)thiophene-2-carboxamide;

5-[1-(3-fluorobenzoyl)piperidin-4-yl]-N-([1,2,4]triazolo[1,5-a]pyridin-6-ylmethyl)thiophene-2-carboxamide;

5-[1-(4-fluorobenzoyl)piperidin-4-yl]-N-([1,2,4]triazolo[1,5-a]pyridin-6-ylmethyl)thiophene-2-carboxamide;

5-[1-(2,4-difluorobenzoyl)piperidin-4-yl]-N-([1,2,4]triazolo[1,5-a]pyridin-6-ylmethyl)thiophene-2-carboxamide;
5-[1-(2,5-difluorobenzoyl)piperidin-4-yl]-N-([1,2,4]triazolo[1,5-a]pyridin-6-ylmethyl)thiophene-2-carboxamide;
5-[1-(3,5-difluorobenzoyl)piperidin-4-yl]-N-([1,2,4]triazolo[1,5-a]pyridin-6-ylmethyl)thiophene-2-carboxamide;
N-(imidazo[1,2-a]pyrazin-6-ylmethyl)-5-[1-(2-methylpropanoyl)piperidin-4-yl]thiophene-2-carboxamide;
N-(imidazo[1,2-a]pyrazin-6-ylmethyl)-5-[1-(3-methylbutanoyl)piperidin-4-yl]thiophene-2-carboxamide;
N-(imidazo[1,2-a]pyrazin-6-ylmethyl)-5-{1-[(1-methylcyclopropyl)carbonyl]piperidin-4-yl}thiophene-2-carboxamide;
N-(imidazo[1,2-a]pyrazin-6-ylmethyl)-5-[1-(4,4,4-trifluorobutanoyl)piperidin-4-yl]thiophene-2-carboxamide;
N-(imidazo[1,2-a]pyrazin-6-ylmethyl)-5-[1-(tetrahydro-2H-pyran-4-ylcarbonyl)piperidin-4-yl]thiophene-2-carboxamide;
5-[1-(2-methylpropanoyl)piperidin-4-yl]-N-([1,2,4]triazolo[1,5-a]pyridin-6-ylmethyl)thiophene-2-carboxamide;
5-[1-(3-methylbutanoyl)piperidin-4-yl]-N-([1,2,4]triazolo[1,5-a]pyridin-6-ylmethyl)thiophene-2-carboxamide;
5-{1-[(2S)-2-methylbutanoyl]piperidin-4-yl}-N-([1,2,4]triazolo[1,5-a]pyridin-6-ylmethyl)thiophene-2-carboxamide;
5-{1-[(1-methylcyclopropyl)carbonyl]piperidin-4-yl}-N-([1,2,4]triazolo[1,5-a]pyridin-6-ylmethyl)thiophene-2-carboxamide;
N-([1,2,4]triazolo[1,5-a]pyridin-6-ylmethyl)-5-[1-(3,3,3-trifluoropropanoyl)piperidin-4-yl]thiophene-2-carboxamide;
N-([1,2,4]triazolo[1,5-a]pyridin-6-ylmethyl)-5-[1-(4,4,4-trifluorobutanoyl)piperidin-4-yl]thiophene-2-carboxamide;
5-{1-[(4,4-difluorocyclohexyl)carbonyl]piperidin-4-yl}-N-([1,2,4]triazolo[1,5-a]pyridin-6-ylmethyl)thiophene-2-carboxamide;
5-[1-(tetrahydro-2H-pyran-4-ylcarbonyl)piperidin-4-yl]-N-([1,2,4]triazolo[1,5-a]pyridin-6-ylmethyl)thiophene-2-carboxamide;
5-[1-(2-hydroxy-2-methylpropanoyl)piperidin-4-yl]-N-([1,2,4]triazolo[1,5-a]pyridin-6-ylmethyl)thiophene-2-carboxamide;
5-{1-[(1-methylpiperidin-4-yl)carbonyl]piperidin-4-yl}-N-([1,2,4]triazolo[1,5-a]pyridin-6-ylmethyl)thiophene-2-carboxamide;
5-[1-(2-cyanobenzoyl)piperidin-4-yl]-N-([1,2,4]triazolo[1,5-a]pyridin-6-ylmethyl)thiophene-2-carboxamide;
5-[1-(pyridin-2-ylcarbonyl)piperidin-4-yl]-N-([1,2,4]triazolo[1,5-a]pyridin-6-ylmethyl)thiophene-2-carboxamide;
2-cyclopentyl-N-{4-[(imidazo[1,2-a]pyridin-6-ylacetyl)amino]phenyl}acetamide;
tert-butyl 4-{4-[(imidazo[1,2-b]pyridazin-6-ylmethyl)carbamoyl]phenyl}piperidine-1-carboxylate;
4-[(cyclopentylacetyl)amino]-N-(imidazo[1,2-b]pyridazin-6-ylmethyl)benzamide;
5-(1-benzyl-3-cyclopropyl-1H-pyrazol-5-yl)-N-(imidazo[1,2-a]pyridin-7-ylmethyl)thiophene-2-carboxamide;
5-[1-(2,2-dimethylpropyl)-1H-pyrazol-4-yl]-N-(imidazo[1,2-a]pyrazin-6-ylmethyl)thiophene-2-carboxamide;
5-[1-(propan-2-ylsulfonyl)piperidin-4-yl]-N-([1,2,4]triazolo[1,5-a]pyridin-6-ylmethyl)thiophene-2-carboxamide;
5-[1-(phenylsulfonyl)piperidin-4-yl]-N-([1,2,4]triazolo[1,5-a]pyridin-6-ylmethyl)thiophene-2-carboxamide;
N-(imidazo[1,2-a]pyrazin-6-ylmethyl)-5-{1-[(4-methyltetrahydro-2H-pyran-4-yl)methyl]-1H-pyrazol-4-yl}thiophene-2-carboxamide;
tert-butyl 4-{4-[(imidazo[1,2-a]pyridin-6-ylacetyl)amino]phenyl}piperidine-1-carboxylate;
N-{4-[1-(2-fluorobenzoyl)piperidin-4-yl]phenyl}-2-(imidazo[1,2-a]pyridin-6-yl)acetamide;
N-(imidazo[1,2-a]pyrazin-6-ylmethyl)-4-[1-(phenylsulfonyl)piperidin-4-yl]benzamide;
2-(imidazo[1,2-a]pyridin-6-yl)-N-{4-[1-(2-methylpropanoyl)piperidin-4-yl]phenyl}acetamide;
N-{4-[1-(2,4-difluorobenzoyl)piperidin-4-yl]phenyl}-2-(imidazo[1,2-a]pyridin-6-yl)acetamide;
N-(imidazo[1,2-a]pyridin-7-ylmethyl)-4-{[(2-methoxyphenyl)acetyl]amino}benzamide;
N-(imidazo[1,2-a]pyridin-7-ylmethyl)-4-[(phenylacetyl)amino]benzamide;
4-(benzoylamino)-N-(imidazo[1,2-a]pyridin-7-ylmethyl)benzamide;
2,5-difluoro-N-{4-[(imidazo[1,2-a]pyridin-7-ylmethyl)carbamoyl]phenyl}benzamide;
3,5-difluoro-N-{4-[(imidazo[1,2-a]pyridin-7-ylmethyl)carbamoyl]phenyl}benzamide;
3,4-difluoro-N-{4-[(imidazo[1,2-a]pyridin-7-ylmethyl)carbamoyl]phenyl}benzamide;
2,4-difluoro-N-{4-[(imidazo[1,2-a]pyridin-7-ylmethyl)carbamoyl]phenyl}benzamide;
2-fluoro-N-{4-[(imidazo[1,2-a]pyridin-7-ylmethyl)carbamoyl]phenyl}benzamide;
N-{4-[(imidazo[1,2-a]pyridin-7-ylmethyl)carbamoyl]phenyl}-3-methoxybenzamide;
4-{[(2-fluorophenyl)acetyl]amino}-N-(imidazo[1,2-a]pyridin-7-ylmethyl)benzamide;
N-(imidazo[1,2-a]pyridin-7-ylmethyl)-4-{[2-(2-methylpropyl)pyrrolidin-1-yl]carbonyl}benzamide;
N-(imidazo[1,2-a]pyridin-7-ylmethyl)-4-{[(2R)-2-(methoxymethyl)pyrrolidin-1-yl]carbonyl}benzamide;
N-(imidazo[1,2-a]pyridin-7-ylmethyl)-5-{1-[2-methyl-2-(piperazin-1-yl)propanoyl]piperidin-4-yl}thiophene-2-carboxamide;
N-{4-[(imidazo[1,2-a]pyridin-7-ylmethyl)carbamoyl]phenyl}-2-methoxybenzamide;
N-(imidazo[1,2-a]pyridin-7-ylmethyl)-4-(phenylsulfonyl)benzamide;
4-(phenylsulfonyl)-N-([1,2,4]triazolo[1,5-a]pyridin-6-ylmethyl)benzamide;
5-[1-(2,2-dimethylpropyl)-1H-pyrazol-4-yl]-N-(imidazo[1,2-a]pyridin-7-ylmethyl)thiophene-2-carboxamide;
N-(imidazo[1,2-a]pyridin-7-ylmethyl)-5-[1-(tricyclo[3.3.1.1~3,7~]dec-1-ylmethyl)-1H-pyrazol-4-yl]thiophene-2-carboxamide;
5-(1-benzyl-1H-pyrazol-4-yl)-N-(imidazo[1,2-a]pyridin-7-ylmethyl)thiophene-2-carboxamide;
N-(imidazo[1,2-a]pyridin-7-ylmethyl)-5-[1-(2-oxatricyclo[3.3.1.1~3,7~]dec-1-ylmethyl)-1H-pyrazol-4-yl]thiophene-2-carboxamide;
5-[1-(2,5-difluorobenzoyl)piperidin-4-yl]-N-(imidazo[1,2-a]pyridin-7-ylmethyl)thiophene-2-carboxamide;
5-[1-(2,4-difluorobenzoyl)piperidin-4-yl]-N-(imidazo[1,2-a]pyridin-7-ylmethyl)thiophene-2-carboxamide;
N-(imidazo[1,2-a]pyridin-7-ylmethyl)-5-{1-[2-(piperazin-1-yl)ethyl]-1H-pyrazol-4-yl}furan-2-carboxamide;
4-{[(2,5-difluorophenyl)acetyl]amino}-N-(imidazo[1,2-a]pyridin-7-ylmethyl)benzamide;
4-{[(2,4-difluorophenyl)acetyl]amino}-N-(imidazo[1,2-a]pyridin-7-ylmethyl)benzamide;
5-(3-cyclopropyl-1-methyl-1H-pyrazol-5-yl)-N-(imidazo[1,2-a]pyridin-7-ylmethyl)thiophene-2-carboxamide;

5-[3-cyclopropyl-1-(2-methoxyethyl)-1H-pyrazol-5-yl]-N-(imidazo[1,2-a]pyridin-7-ylmethyl)thiophene-2-carboxamide;

N-(imidazo[1,2-a]pyrazin-6-ylmethyl)-5-{1-[2-(piperazin-1-yl)ethyl]-1H-pyrazol-4-yl}thiophene-2-carboxamide;

4-{[difluoro(phenyl)acetyl]amino}-N-(imidazo[1,2-a]pyridin-7-ylmethyl)benzamide;

N-(imidazo[1,2-a]pyridin-7-ylmethyl)-4-[(2-methyl-2-phenylpropanoyl)amino]benzamide;

N-(imidazo[1,2-a]pyrazin-6-ylmethyl)-4-(phenylsulfonyl)benzamide;

N-(imidazo[1,2-a]pyridin-6-ylmethyl)-4-(phenylsulfonyl)benzamide;

N-(imidazo[1,2-a]pyridin-7-ylmethyl)-5-[1-(2-methylpropyl)-1H-pyrazol-5-yl]thiophene-2-carboxamide;

tert-butyl 4-{4-[(imidazo[1,2-a]pyridin-7-ylacetyl)amino]phenyl}piperidine-1-carboxylate;

N-[(3-chloroimidazo[1,2-a]pyrazin-6-yl)methyl]-4-[(cyclopentylacetyl)amino]benzamide;

N-{4-[1-(2,4-difluorobenzoyl)piperidin-4-yl]phenyl}-2-(imidazo[1,2-a]pyridin-7-yl)acetamide;

2-(imidazo[1,2-a]pyridin-7-yl)-N-{4-[1-(2-methylpropanoyl)piperidin-4-yl]phenyl}acetamide;

1-[(3-chloroimidazo[1,2-a]pyridin-7-yl)methyl]-3-{4-[1-(2-methylpropanoyl)piperidin-4-yl]phenyl}urea;

N-{4-[1-(2-fluorobenzoyl)piperidin-4-yl]phenyl}-2-(imidazo[1,2-a]pyridin-7-yl)acetamide;

N-(imidazo[1,2-a]pyridin-7-ylmethyl)-5-[1-methyl-3-(2-methylpropyl)-1H-pyrazol-5-yl]thiophene-2-carboxamide;

5-[1-benzyl-3-(2-methylpropyl)-1H-pyrazol-5-yl]-N-(imidazo[1,2-a]pyridin-7-ylmethyl)thiophene-2-carboxamide;

4-[(cyclopentylacetyl)amino]-2-fluoro-N-(imidazo[1,2-a]pyrazin-6-ylmethyl)benzamide;

N-(2,5-difluorobenzyl)-N'-(imidazo[1,2-a]pyridin-7-ylmethyl)benzene-1,4-dicarboxamide;

N-(imidazo[1,2-a]pyridin-7-ylmethyl)-4-{[2-(propan-2-yl)pyrrolidin-1-yl]carbonyl}benzamide;

N-{4-[5-(2,2-dimethylpropyl)-1,3,4-oxadiazol-2-yl]phenyl}-2-(imidazo[1,2-a]pyridin-7-yl)acetamide;

tert-butyl 4-(3-fluoro-4-{[(imidazo[1,2-a]pyridin-7-ylmethyl)carbamoyl]amino}phenyl)piperidine-1-carboxylate;

4-{1-[(2-chloropyridin-3-yl)carbonyl]piperidin-4-yl}-N-(imidazo[1,2-a]pyridin-7-ylmethyl)benzamide;

N-(imidazo[1,2-a]pyridin-7-ylmethyl)-4-[1-(3-methylbut-2-enoyl)piperidin-4-yl]benzamide;

4-[1-(3-fluoro-4-methoxybenzoyl)piperidin-4-yl]-N-(imidazo[1,2-a]pyridin-7-ylmethyl)benzamide;

N-(imidazo[1,2-a]pyridin-7-ylmethyl)-4-{1-[(2-methylcyclopent-1-en-1-yl)carbonyl]piperidin-4-yl}benzamide;

4-[1-(2-ethylbutanoyl)piperidin-4-yl]-N-(imidazo[1,2-a]pyridin-7-ylmethyl)benzamide;

4-{1-[(4-fluorophenoxy)acetyl]piperidin-4-yl}-N-(imidazo[1,2-a]pyridin-7-ylmethyl)benzamide;

4-[1-(3,5-dimethoxybenzoyl)piperidin-4-yl]-N-(imidazo[1,2-a]pyridin-7-ylmethyl)benzamide;

4-[1-(cyclohex-3-en-1-ylcarbonyl)piperidin-4-yl]-N-(imidazo[1,2-a]pyridin-7-ylmethyl)benzamide;

N-(imidazo[1,2-a]pyridin-7-ylmethyl)-4-{1-[(2-methoxyphenyl)acetyl]piperidin-4-yl}benzamide;

4-[1-(3-hydroxy-2-phenylpropanoyl)piperidin-4-yl]-N-(imidazo[1,2-a]pyridin-7-ylmethyl)benzamide;

N-(imidazo[1,2-a]pyridin-7-ylmethyl)-4-[1-(3-methylbenzoyl)piperidin-4-yl]benzamide;

4-[1-(2-acetylbenzoyl)piperidin-4-yl]-N-(imidazo[1,2-a]pyridin-7-ylmethyl)benzamide;

N-(imidazo[1,2-a]pyridin-7-ylmethyl)-4-{1-[2-(methoxymethyl)benzoyl]piperidin-4-yl}benzamide;

N-(imidazo[1,2-a]pyridin-7-ylmethyl)-4-[1-(2-phenylpropanoyl)piperidin-4-yl]benzamide;

4-[1-(2,6-dimethoxybenzoyl)piperidin-4-yl]-N-(imidazo[1,2-a]pyridin-7-ylmethyl)benzamide;

4-[1-(N,N-diethyl-beta-alanyl)piperidin-4-yl]-N-(imidazo[1,2-a]pyridin-7-ylmethyl)benzamide;

N-(imidazo[1,2-a]pyridin-7-ylmethyl)-4-(1-{[(2-methylpropyl)sulfonyl]acetyl}piperidin-4-yl)benzamide;

N-(imidazo[1,2-a]pyridin-7-ylmethyl)-4-[1-(2-phenoxypropanoyl)piperidin-4-yl]benzamide;

N-(imidazo[1,2-a]pyridin-7-ylmethyl)-4-[1-({[(1R,2S)-2-methylcyclohexyl]oxy}acetyl)piperidin-4-yl]benzamide;

4-{1-[(2-chloro-6-methylpyridin-4-yl)carbonyl]piperidin-4-yl}-N-(imidazo[1,2-a]pyridin-7-ylmethyl)benzamide;

N-(imidazo[1,2-a]pyridin-7-ylmethyl)-4-{1-[(3-methoxyphenyl)acetyl]piperidin-4-yl}benzamide;

4-[1-(2-chloro-4-cyanobenzoyl)piperidin-4-yl]-N-(imidazo[1,2-a]pyridin-7-ylmethyl)benzamide;

N-(imidazo[1,2-a]pyridin-7-ylmethyl)-4-{1-[(2E)-2-methylbut-2-enoyl]piperidin-4-yl}benzamide;

N-(imidazo[1,2-a]pyridin-7-ylmethyl)-4-{1-[(2-methoxy-5-methylphenyl)acetyl]piperidin-4-yl}benzamide;

4-[1-(2-hydroxy-3-methylbenzoyl)piperidin-4-yl]-N-(imidazo[1,2-a]pyridin-7-ylmethyl)benzamide;

1-(4-{1-[(2-chloropyridin-3-yl)carbonyl]piperidin-4-yl}phenyl)-3-(imidazo[1,2-a]pyridin-7-ylmethyl)urea;

1-(imidazo[1,2-a]pyridin-7-ylmethyl)-3-{4-[1-(3-methylbut-2-enoyl)piperidin-4-yl]phenyl}urea;

1-{4-[1-(3,3-dimethylbutanoyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(2-methylcyclopent-1-en-1-yl)carbonyl]piperidin-4-yl}phenyl)urea;

1-{4-[1-(2-ethylbutanoyl)piperidin-4-yl]phenyl}-3-(imidazo[1,2-a]pyridin-7-ylmethyl)urea;

1-(4-{1-[(4-fluorophenoxy)acetyl]piperidin-4-yl}phenyl)-3-(imidazo[1,2-a]pyridin-7-ylmethyl)urea;

1-{4-[1-(2,4-dimethoxybenzoyl)piperidin-4-yl]phenyl}-3-(imidazo[1,2-a]pyridin-7-ylmethyl)urea;

1-{4-[1-(cyclohex-3-en-1-ylcarbonyl)piperidin-4-yl]phenyl}-3-(imidazo[1,2-a]pyridin-7-ylmethyl)urea;

1-{4-[1-(2,5-dimethoxybenzoyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(2-methoxyphenyl)acetyl]piperidin-4-yl}phenyl)urea;

1-{4-[1-(3-hydroxy-2-phenylpropanoyl)piperidin-4-yl]phenyl}-3-(imidazo[1,2-a]pyridin-7-ylmethyl)urea;

1-{4-[1-(2,6-dimethoxybenzoyl)piperidin-4-yl]phenyl}-3-(imidazo[1,2-a]pyridin-7-ylmethyl)urea;

1-{4-[1-(N,N-diethyl-beta-alanyl)piperidin-4-yl]phenyl}-3-(imidazo[1,2-a]pyridin-7-ylmethyl)urea;

1-(4-{1-[(2-chloro-6-methylpyridin-4-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(3-methoxyphenyl)acetyl]piperidin-4-yl}phenyl)urea;

1-(imidazo[1,2-a]pyridin-7-ylmethyl)-3-(4-{1-[(1-oxo-2,3-dihydro-1H-inden-4-yl)carbonyl]piperidin-4-yl}phenyl)urea;

1-{4-[1-(2-chloro-4-cyanobenzoyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(2E)-2-methylbut-2-enoyl]piperidin-4-yl}phenyl)urea;

1-(imidazo[1,2-a]pyridin-7-ylmethyl)-3-{4-[1-(1H-indol-3-ylacetyl)piperidin-4-yl]phenyl}urea;
1-{4-[1-(2-hydroxy-3-methylbenzoyl)piperidin-4-yl]phenyl}-3-(imidazo[1,2-a]pyridin-7-ylmethyl)urea;
N-(imidazo[1,2-a]pyridin-7-ylmethyl)-4-[1-(pyrrolidin-1-ylcarbonyl)piperidin-4-yl]benzamide;
N-(imidazo[1,2-a]pyridin-7-ylmethyl)-4-(1-{[1-(propan-2-yl)-1H-pyrazol-3-yl]carbonyl}piperidin-4-yl)benzamide;
4-{1-[(3-cyclopropyl-1-methyl-1H-pyrazol-5-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-4,5,6,7-tetrahydro-2H-indazol-3-yl)carbonyl]piperidin-4-yl}benzamide;
N-(imidazo[1,2-a]pyridin-7-ylmethyl)-4-[1-(4,5,6,7-tetrahydro-2,1-benzoxazol-3-ylcarbonyl)piperidin-4-yl]benzamide;
4-{1-[(3-fluoro-6-methylpyridin-2-yl)carbonyl]piperidin-4-yl}-N-(imidazo[1,2-a]pyridin-7-ylmethyl)benzamide;
4-{1-[(2-chloro-3-fluoropyridin-4-yl)carbonyl]piperidin-4-yl}-N-(imidazo[1,2-a]pyridin-7-ylmethyl)benzamide;
4-{1-[(3-chloropyridin-2-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[1-(pyridin-2-yl)cyclopropyl]carbonyl}piperidin-4-yl)benzamide;
4-{1-[(1-cyclopentyl-1H-pyrazol-3-yl)carbonyl]piperidin-4-yl}-N-(imidazo[1,2-a]pyridin-7-ylmethyl)benzamide;
4-{1-[2-(3-fluorophenoxy)propanoyl]piperidin-4-yl}-N-(imidazo[1,2-a]pyridin-7-ylmethyl)benzamide;
4-(1-{[1-(difluoromethyl)-1H-pyrazol-5-yl]carbonyl}piperidin-4-yl)-N-(imidazo[1,2-a]pyridin-7-ylmethyl)benzamide;
4-[1-(3,4-dihydro-2H-chromen-6-ylcarbonyl)piperidin-4-yl]-N-(imidazo[1,2-a]pyridin-7-ylmethyl)benzamide;
4-{1-[(cyclohexyloxy)acetyl]piperidin-4-yl}-N-(imidazo[1,2-a]pyridin-7-ylmethyl)benzamide;
4-{1-[(2-chloropyridin-3-yl)acetyl]piperidin-4-yl}-N-(imidazo[1,2-a]pyridin-7-ylmethyl)benzamide;
4-{1-[(5-cyclopropyl-1,2-oxazol-3-yl)carbonyl]piperidin-4-yl}-N-(imidazo[1,2-a]pyridin-7-ylmethyl)benzamide;
4-[1-(2H-chromen-3-ylcarbonyl)piperidin-4-yl]-N-(imidazo[1,2-a]pyridin-7-ylmethyl)benzamide;
4-{1-[(3,5-difluoropyridin-2-yl)carbonyl]piperidin-4-yl}-N-(imidazo[1,2-a]pyridin-7-ylmethyl)benzamide;
4-[1-(2,3-dihydro-1,4-benzodioxin-2-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(4-methoxycyclohexyl)carbonyl]piperidin-4-yl}benzamide;
4-[1-(2,3-dihydro-1,4-benzodioxin-5-ylcarbonyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-4-ylcarbonyl)piperidin-4-yl]benzamide;
N-(imidazo[1,2-a]pyridin-7-ylmethyl)-4-{1-[(2-methyl-1,3-benzoxazol-6-yl)carbonyl]piperidin-4-yl}benzamide;
4-{1-[(1-tert-butyl-3-methyl-1H-pyrazol-5-yl)carbonyl]piperidin-4-yl}-N-(imidazo[1,2-a]pyridin-7-ylmethyl)benzamide;
4-{1-[(1-cyanocyclopentyl)carbonyl]piperidin-4-yl}-N-(imidazo[1,2-a]pyridin-7-ylmethyl)benzamide;
N-(imidazo[1,2-a]pyridin-7-ylmethyl)-4-[1-(thieno[3,2-b]pyridin-2-ylcarbonyl)piperidin-4-yl]benzamide;
N-(imidazo[1,2-a]pyridin-7-ylmethyl)-4-[1-(quinolin-7-ylcarbonyl)piperidin-4-yl]benzamide;
4-[1-(5-cyano-2-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(5,6,7,8-tetrahydroquinolin-3-ylcarbonyl)piperidin-4-yl]benzamide;
4-[1-(3,4-dihydro-2H-pyrano[2,3-b]pyridin-6-ylcarbonyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-7-ylcarbonyl)piperidin-4-yl]benzamide;
N-(imidazo[1,2-a]pyridin-7-ylmethyl)-4-[1-(quinoxalin-2-ylcarbonyl)piperidin-4-yl]benzamide;
N-(imidazo[1,2-a]pyridin-7-ylmethyl)-4-{1-[(2E)-3-(2-methoxypyridin-3-yl)prop-2-enoyl]piperidin-4-yl}benzamide;
N-(imidazo[1,2-a]pyridin-7-ylmethyl)-4-{1-[(2E)-3-(pyridin-2-yl)prop-2-enoyl]piperidin-4-yl}benzamide;
N-(imidazo[1,2-a]pyridin-7-ylmethyl)-4-{1-[(8-methylimidazo[1,2-a]pyridin-2-yl)carbonyl]piperidin-4-yl}benzamide;
4-{1-[(2-ethoxypyridin-4-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(1-methyl-4,5,6,7-tetrahydro-1H-indazol-3-yl)carbonyl]piperidin-4-yl}benzamide;
N-(imidazo[1,2-a]pyridin-7-ylmethyl)-4-{1-[(4-methyl-4H-furo[3,2-b]pyrrol-5-yl)carbonyl]piperidin-4-yl}benzamide;
4-[1-(3-cyano-5-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-8-ylcarbonyl)piperidin-4-yl]benzamide;
4-{1-[(4-cyanophenyl)acetyl]piperidin-4-yl}-N-(imidazo[1,2-a]pyridin-7-ylmethyl)benzamide;
4-[1-(3-cyano-4-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(4,5,6,7-tetrahydro-1,3-benzothiazol-2-ylcarbonyl)piperidin-4-yl]benzamide;
4-[1-(1,3-benzothiazol-2-ylcarbonyl)piperidin-4-yl]-N-(imidazo[1,2-a]pyridin-7-ylmethyl)benzamide;
4-{1-[(3-ethyl-1,2-oxazol-5-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[3-methyl-1-(prop-2-en-1-yl)-1H-pyrazol-5-yl]carbonyl}piperidin-4-yl)benzamide;
4-[1-(1,2,3-benzothiadiazol-5-ylcarbonyl)piperidin-4-yl]-N-(imidazo[1,2-a]pyridin-7-ylmethyl)benzamide;
4-{1-[(2-ethyl-1,3-thiazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[2-(propan-2-yl)pyrimidin-4-yl]carbonyl}piperidin-4-yl)benzamide;
4-{1-[(5,6-dimethylpyridin-3-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[2-(propan-2-yl)tetrahydro-2H-pyran-4-yl]carbonyl}piperidin-4-yl)benzamide;
N-(imidazo[1,2-a]pyridin-7-ylmethyl)-4-[1-(2-methoxy-6-methylbenzoyl)piperidin-4-yl]benzamide;
4-[1-(1,3-benzothiazol-7-ylcarbonyl)piperidin-4-yl]-N-(imidazo[1,2-a]pyridin-7-ylmethyl)benzamide;
1-(imidazo[1,2-a]pyridin-7-ylmethyl)-3-[4-(1-{[1-(propan-2-yl)-1H-pyrazol-3-yl]carbonyl}piperidin-4-yl)phenyl]urea;
1-(4-{1-[(2S)-2,3-dihydro-1,4-benzodioxin-2-ylcarbonyl]piperidin-4-yl}phenyl)-3-(imidazo[1,2-a]pyridin-7-ylmethyl)urea;
1-(4-{1-[(3-cyclopropyl-1-methyl-1H-pyrazol-5-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(2-methyl-4,5,6,7-tetrahydro-2H-indazol-3-yl)carbonyl]piperidin-4-yl}phenyl)urea;

1-(imidazo[1,2-a]pyridin-7-ylmethyl)-3-{4-[1-(4,5,6,7-tetrahydro-2,1-benzoxazol-3-ylcarbonyl)piperidin-4-yl]phenyl}urea;

1-(4-{1-[(2-chloro-5-fluoropyridin-4-yl)carbonyl]piperidin-4-yl}phenyl)-3-(imidazo[1,2-a]pyridin-7-ylmethyl)urea;

1-(4-{1-[(3-fluoro-6-methylpyridin-2-yl)carbonyl]piperidin-4-yl}phenyl)-3-(imidazo[1,2-a]pyridin-7-ylmethyl)urea;

1-(4-{1-[(2-chloro-3-fluoropyridin-4-yl)carbonyl]piperidin-4-yl}phenyl)-3-(imidazo[1,2-a]pyridin-7-ylmethyl)urea;

1-(4-{1-[(3-chloropyridin-2-yl)carbonyl]piperidin-4-yl}phenyl)-3-(imidazo[1,2-a]pyridin-7-ylmethyl)urea;

1-(imidazo[1,2-a]pyridin-7-ylmethyl)-3-[4-(1-{[1-(pyridin-2-yl)cyclopropyl]carbonyl}piperidin-4-yl)phenyl]urea;

1-(4-{1-[(1-cyclopentyl-1H-pyrazol-3-yl)carbonyl]piperidin-4-yl}phenyl)-3-(imidazo[1,2-a]pyridin-7-ylmethyl)urea;

1-[4-(1-{[1-(difluoromethyl)-1H-pyrazol-5-yl]carbonyl}piperidin-4-yl)phenyl]-3-(imidazo[1,2-a]pyridin-7-ylmethyl)urea;

1-{4-[1-(2,3-dihydro-1,4-benzodioxin-2-ylcarbonyl)piperidin-4-yl]phenyl}-3-(imidazo[1,2-a]pyridin-7-ylmethyl)urea;

1-{4-[1-(2,3-dihydro-1-benzofuran-2-ylcarbonyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(4-methoxycyclohexyl)carbonyl]piperidin-4-yl}phenyl)urea;

1-{4-[1-(2,3-dihydro-1,4-benzodioxin-5-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(isoquinolin-4-ylcarbonyl)piperidin-4-yl]phenyl}urea;

1-(imidazo[1,2-a]pyridin-7-ylmethyl)-3-(4-{1-[(2-methyl-1,3-benzoxazol-6-yl)carbonyl]piperidin-4-yl}phenyl)urea;

1-(4-{1-[(1-tert-butyl-3-methyl-1H-pyrazol-5-yl)carbonyl]piperidin-4-yl}phenyl)-3-(imidazo[1,2-a]pyridin-7-ylmethyl)urea;

1-(4-{1-[(1-cyanocyclopentyl)carbonyl]piperidin-4-yl}phenyl)-3-(imidazo[1,2-a]pyridin-7-ylmethyl)urea;

1-{4-[1-(cinnolin-4-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(quinolin-7-ylcarbonyl)piperidin-4-yl]phenyl}urea;

1-{4-[1-(5-cyano-2-fluorobenzoyl)piperidin-4-yl]phenyl}-3-(imidazo[1,2-a]pyridin-7-ylmethyl)urea;

1-(4-{1-[(3-cyclopropyl-1,2-oxazol-5-yl)carbonyl]piperidin-4-yl}phenyl)-3-(imidazo[1,2-a]pyridin-7-ylmethyl)urea;

1-(imidazo[1,2-a]pyridin-7-ylmethyl)-3-{4-[1-(5,6,7,8-tetrahydroquinolin-3-ylcarbonyl)piperidin-4-yl]phenyl}urea;

1-{4-[1-(3,4-dihydro-2H-pyrano[2,3-b]pyridin-6-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(isoquinolin-7-ylcarbonyl)piperidin-4-yl]phenyl}urea;

1-(imidazo[1,2-a]pyridin-7-ylmethyl)-3-{4-[1-(quinoxalin-2-ylcarbonyl)piperidin-4-yl]phenyl}urea;

1-(imidazo[1,2-a]pyridin-7-ylmethyl)-3-(4-{1-[(2E)-3-(2-methoxypyridin-3-yl)prop-2-enoyl]piperidin-4-yl}phenyl)urea;

1-(imidazo[1,2-a]pyridin-7-ylmethyl)-3-(4-{1-[(2E)-3-(pyridin-2-yl)prop-2-enoyl]piperidin-4-yl}phenyl)urea;

1-(4-{1-[(4-chloro-2,6-dimethylpyridin-3-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(8-methylimidazo[1,2-a]pyridin-2-yl)carbonyl]piperidin-4-yl}phenyl)urea;

1-(4-{1-[(2-ethoxypyridin-4-yl)carbonyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(1-methyl-4,5,6,7-tetrahydro-1H-indazol-3-yl)carbonyl]piperidin-4-yl}phenyl)urea;

1-(imidazo[1,2-a]pyridin-7-ylmethyl)-3-(4-{1-[(4-methyl-4H-furo[3,2-b]pyrrol-5-yl)carbonyl]piperidin-4-yl}phenyl)urea;

1-(imidazo[1,2-a]pyridin-7-ylmethyl)-3-(4-{1-[(2-methyl-2,3-dihydro-1-benzofuran-5-yl)carbonyl]piperidin-4-yl}phenyl)urea;

1-(4-{1-[(4-chloro-1-ethyl-1H-pyrazol-5-yl)carbonyl]piperidin-4-yl}phenyl)-3-(imidazo[1,2-a]pyridin-7-ylmethyl)urea;

1-{4-[1-(3-cyano-5-fluorobenzoyl)piperidin-4-yl]phenyl}-3-(imidazo[1,2-a]pyridin-7-ylmethyl)urea;

1-(imidazo[1,2-a]pyridin-7-ylmethyl)-3-{4-[1-(isoquinolin-8-ylcarbonyl)piperidin-4-yl]phenyl}urea;

1-(4-{1-[(4-cyanophenyl)acetyl]piperidin-4-yl}phenyl)-3-(imidazo[1,2-a]pyridin-7-ylmethyl)urea;

1-(imidazo[1,2-a]pyridin-7-ylmethyl)-3-(4-{1-[(3-methoxythiophen-2-yl)carbonyl]piperidin-4-yl}phenyl)urea;

1-{4-[1-(3-cyano-4-fluorobenzoyl)piperidin-4-yl]phenyl}-3-(imidazo[1,2-a]pyridin-7-ylmethyl)urea;

1-(imidazo[1,2-a]pyridin-7-ylmethyl)-3-{4-[1-(4,5,6,7-tetrahydro-1,3-benzothiazol-2-ylcarbonyl)piperidin-4-yl]phenyl}urea;

1-{4-[1-(1,3-benzothiazol-2-ylcarbonyl)piperidin-4-yl]phenyl}-3-(imidazo[1,2-a]pyridin-7-ylmethyl)urea;

1-(4-{1-[(3-ethyl-1,2-oxazol-5-yl)carbonyl]piperidin-4-yl}phenyl)-3-(imidazo[1,2-a]pyridin-7-ylmethyl)urea;

1-(imidazo[1,2-a]pyridin-7-ylmethyl)-3-[4-(1-{[3-methyl-1-(prop-2-en-1-yl)-1H-pyrazol-5-yl]carbonyl}piperidin-4-yl)phenyl]urea;

1-{4-[1-(1,2,3-benzothiadiazol-5-ylcarbonyl)piperidin-4-yl]phenyl}-3-(imidazo[1,2-a]pyridin-7-ylmethyl)urea;

1-(4-{1-[(2-ethyl-1,3-thiazol-4-yl)carbonyl]piperidin-4-yl}phenyl)-3-(imidazo[1,2-a]pyridin-7-ylmethyl)urea;

1-(4-{1-[(5,6-dimethylpyridin-3-yl)carbonyl]piperidin-4-yl}phenyl)-3-(imidazo[1,2-a]pyridin-7-ylmethyl)urea;

1-{4-[1-(1,3-benzothiazol-7-ylcarbonyl)piperidin-4-yl]phenyl}-3-(imidazo[1,2-a]pyridin-7-ylmethyl)urea;

4-{1-[(2-chloro-5-fluoropyridin-4-yl)carbonyl]piperidin-4-yl}-N-(imidazo[1,2-a]pyridin-7-ylmethyl)benzamide;

4-{1-[(3-cyclopropyl-1,2-oxazol-5-yl)carbonyl]piperidin-4-yl}-N-(imidazo[1,2-a]pyridin-7-ylmethyl)benzamide;

N-(imidazo[1,2-a]pyridin-7-ylmethyl)-4-{1-[(3-methoxythiophen-2-yl)carbonyl]piperidin-4-yl}benzamide;

N-(imidazo[1,2-a]pyridin-7-ylmethyl)-4-(1-{[2-methyl-5-(propan-2-yl)furan-3-yl]carbonyl}piperidin-4-yl)benzamide;

1-(4-{1-[2-(3-fluorophenoxy)propanoyl]piperidin-4-yl}phenyl)-3-(imidazo[1,2-a]pyridin-7-ylmethyl)urea;

1-(4-{1-[(3,5-difluoropyridin-2-yl)carbonyl]piperidin-4-yl}phenyl)-3-(imidazo[1,2-a]pyridin-7-ylmethyl)urea;

tert-butyl 4-{3-fluoro-4-[(imidazo[1,2-a]pyridin-7-ylacetyl)amino]phenyl}piperidine-1-carboxylate;

N-(imidazo[1,2-a]pyridin-7-ylmethyl)-4-[1-(piperidin-1-ylcarbonyl)piperidin-4-yl]benzamide;

1-[4-(1-benzoylpiperidin-4-yl)-2-fluorophenyl]-3-(imidazo[1,2-a]pyridin-7-ylmethyl)urea;

1-{4-[1-(2,2-dimethylpropanoyl)piperidin-4-yl]-2-fluorophenyl}-3-(imidazo[1,2-a]pyridin-7-ylmethyl)urea;
1-{4-[1-(3,3-dimethylbutanoyl)piperidin-4-yl]-2-fluorophenyl}-3-(imidazo[1,2-a]pyridin-7-ylmethyl)urea;
1-{2-fluoro-4-[1-(4-methylpentanoyl)piperidin-4-yl]phenyl}-3-(imidazo[1,2-a]pyridin-7-ylmethyl)urea;
1-(2-fluoro-4-{1-[(2S)-2-methylbutanoyl]piperidin-4-yl}phenyl)-3-(imidazo[1,2-a]pyridin-7-ylmethyl)urea;
1-{2-fluoro-4-[1-(tetrahydro-2H-pyran-4-ylcarbonyl)piperidin-4-yl]phenyl}-3-(imidazo[1,2-a]pyridin-7-ylmethyl)urea;
1-{2-fluoro-4-[1-(pyridin-2-ylcarbonyl)piperidin-4-yl]phenyl}-3-(imidazo[1,2-a]pyridin-7-ylmethyl)urea;
1-{4-[1-(2-cyanobenzoyl)piperidin-4-yl]-2-fluorophenyl}-3-(imidazo[1,2-a]pyridin-7-ylmethyl)urea;
4-{4-[(imidazo[1,2-a]pyridin-7-ylmethyl)carbamoyl]phenyl}-N,N-dimethylpiperidine-1-carboxamide;
1-{2-fluoro-4-[1-(2-methylpropanoyl)piperidin-4-yl]phenyl}-3-(imidazo[1,2-a]pyridin-7-ylmethyl)urea;
4-[(cyclopentylacetyl)amino]-N-[(7-fluoroimidazo[1,2-a]pyridin-6-yl)methyl]benzamide;
N-[(7-fluoroimidazo[1,2-a]pyridin-6-yl)methyl]-5-[1-(2-methylpropyl)-1H-pyrazol-4-yl]thiophene-2-carboxamide;
N-[4-(1-benzoylpiperidin-4-yl)-2-fluorophenyl]-2-(imidazo[1,2-a]pyridin-7-yl)acetamide;
5-{1-[2,2-dimethyl-3-(piperazin-1-yl)propyl]-1H-pyrazol-4-yl}-N-(imidazo[1,2-a]pyridin-7-ylmethyl)thiophene-2-carboxamide;
5-[1-(3-amino-2,2-dimethylpropyl)-1H-pyrazol-4-yl]-N-(imidazo[1,2-a]pyridin-7-ylmethyl)thiophene-2-carboxamide;
4-{1-[(2-cyclopropyl-1,3-thiazol-5-yl)carbonyl]piperidin-4-yl}-N-(imidazo[1,2-a]pyridin-7-ylmethyl)benzamide;
4-[1-(1,3-benzothiazol-5-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(1-methyl-1H-indazol-6-yl)carbonyl]piperidin-4-yl}benzamide;
4-{1-[(4-chloro-1,3-dimethyl-1H-pyrazol-5-yl)carbonyl]piperidin-4-yl}-N-(imidazo[1,2-a]pyridin-7-ylmethyl)benzamide;
4-{1-[(5-ethylpyridin-2-yl)carbonyl]piperidin-4-yl}-N-(imidazo[1,2-a]pyridin-7-ylmethyl)benzamide;
4-{1-[(3-chloro-5-cyanopyridin-2-yl)carbonyl]piperidin-4-yl}-N-(imidazo[1,2-a]pyridin-7-ylmethyl)benzamide;
4-{1-[(1-cyano-3-methylcyclobutyl)carbonyl]piperidin-4-yl}-N-(imidazo[1,2-a]pyridin-7-ylmethyl)benzamide;
4-{1-[(1,5-diethyl-1H-1,2,3-triazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(4-methoxythiophen-2-yl)carbonyl]piperidin-4-yl}benzamide;
4-{1-[(5-cyanothiophen-2-yl)carbonyl]piperidin-4-yl}-N-(imidazo[1,2-a]pyridin-7-ylmethyl)benzamide;
4-{1-[(5-cyclopropylpyridin-2-yl)carbonyl]piperidin-4-yl}-N-(imidazo[1,2-a]pyridin-7-ylmethyl)benzamide;
4-[1-(4-cyano-2,6-difluorobenzoyl)piperidin-4-yl]-N-(imidazo[1,2-a]pyridin-7-ylmethyl)benzamide;
4-(1-{[1-ethyl-3-(propan-2-yl)-1H-pyrazol-4-yl]carbonyl}piperidin-4-yl)-N-(imidazo[1,2-a]pyridin-7-ylmethyl)benzamide;
N-(imidazo[1,2-a]pyridin-7-ylmethyl)-4-(1-{[1-(propan-2-yl)-1H-pyrazol-3-yl]acetyl}piperidin-4-yl)benzamide;
4-[1-(1-benzofuran-3-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(3-methyl-5,6,7,8-tetrahydroimidazo[1,5-a]pyridin-1-yl)carbonyl]piperidin-4-yl}benzamide;
N-(imidazo[1,2-a]pyridin-7-ylmethyl)-4-{1-[(4-methoxy-5-methylpyridin-2-yl)carbonyl]piperidin-4-yl}benzamide;
4-{1-[(1-cyclopentyl-1H-pyrazol-5-yl)carbonyl]piperidin-4-yl}-N-(imidazo[1,2-a]pyridin-7-ylmethyl)benzamide;
4-{1-[(4-chloro-1,3-thiazol-5-yl)carbonyl]piperidin-4-yl}-N-(imidazo[1,2-a]pyridin-7-ylmethyl)benzamide;
4-{1-[(3-cyanothiophen-2-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[4-(propan-2-yl)pyrimidin-5-yl]carbonyl}piperidin-4-yl)benzamide;
N-(imidazo[1,2-a]pyridin-7-ylmethyl)-4-{1-[(1-methyl-5-propyl-1H-pyrazol-4-yl)carbonyl]piperidin-4-yl}benzamide;
4-{1-[2-(3-cyclopropyl-1H-pyrazol-1-yl)propanoyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2,3-dihydro-1-benzofuran-7-yl)carbonyl]piperidin-4-yl}benzamide;
N-(imidazo[1,2-a]pyridin-7-ylmethyl)-4-(1-{[2-(propan-2-yl)-1,3-thiazol-4-yl]carbonyl}piperidin-4-yl)benzamide;
4-(1-{[1-(difluoromethyl)-5-methyl-1H-pyrazol-3-yl]carbonyl}piperidin-4-yl)-N-(imidazo[1,2-a]pyridin-7-ylmethyl)benzamide;
4-{1-[(4-cyanothiophen-2-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(pyrazolo[1,5-a]pyridin-2-ylcarbonyl)piperidin-4-yl]benzamide;
4-[1-(1-benzofuran-5-ylcarbonyl)piperidin-4-yl]-N-(imidazo[1,2-a]pyridin-7-ylmethyl)benzamide;
N-(imidazo[1,2-a]pyridin-7-ylmethyl)-4-(1-{[2-(propan-2-yl)-1,3-oxazol-4-yl]carbonyl}piperidin-4-yl)benzamide;
N-(imidazo[1,2-a]pyridin-7-ylmethyl)-4-{1-[(2-methoxy-5-methylpyridin-3-yl)carbonyl]piperidin-4-yl}benzamide;
4-{1-[(5,6-dimethoxypyridin-2-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2H-indazol-4-yl)carbonyl]piperidin-4-yl}benzamide;
4-{1-[(2-ethylpiperidin-1-yl)(oxo)acetyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2H-indazol-6-yl)carbonyl]piperidin-4-yl}benzamide;
N-(imidazo[1,2-a]pyridin-7-ylmethyl)-4-{1-[(1-methyl-1H-indazol-4-yl)carbonyl]piperidin-4-yl}benzamide;
N-(imidazo[1,2-a]pyridin-7-ylmethyl)-4-(1-{[2-(trifluoromethyl)furan-3-yl]carbonyl}piperidin-4-yl)benzamide;
1-(4-{1-[(2-cyclopropyl-1,3-thiazol-5-yl)carbonyl]piperidin-4-yl}phenyl)-3-(imidazo[1,2-a]pyridin-7-ylmethyl)urea;
1-{4-[1-(1,3-benzothiazol-5-ylcarbonyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(1-methyl-1H-indazol-6-yl)carbonyl]piperidin-4-yl}phenyl)urea;
1-(4-{1-[(4-chloro-1,3-dimethyl-1H-pyrazol-5-yl)carbonyl]piperidin-4-yl}phenyl)-3-(imidazo[1,2-a]pyridin-7-ylmethyl)urea;
1-(4-{1-[(5-ethylpyridin-2-yl)carbonyl]piperidin-4-yl}phenyl)-3-(imidazo[1,2-a]pyridin-7-ylmethyl)urea;
1-(4-{1-[(3-chloro-5-cyanopyridin-2-yl)carbonyl]piperidin-4-yl}phenyl)-3-(imidazo[1,2-a]pyridin-7-ylmethyl)urea;
1-(4-{1-[(1-cyano-3-methylcyclobutyl)carbonyl]piperidin-4-yl}phenyl)-3-(imidazo[1,2-a]pyridin-7-ylmethyl)urea;
1-(4-{1-[(1,5-diethyl-1H-1,2,3-triazol-4-yl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(thieno[3,2-b]furan-5-ylcarbonyl)piperidin-4-yl]phenyl}urea;

1-(imidazo[1,2-a]pyridin-7-ylmethyl)-3-(4-{1-[(4-methoxythiophen-2-yl)carbonyl]piperidin-4-yl}phenyl)urea;
1-(4-{1-[(5-cyanothiophen-2-yl)carbonyl]piperidin-4-yl}phenyl)-3-(imidazo[1,2-a]pyridin-7-ylmethyl)urea;
1-(4-{1-[(5-cyclopropylpyridin-2-yl)carbonyl]piperidin-4-yl}phenyl)-3-(imidazo[1,2-a]pyridin-7-ylmethyl)urea;
1-{4-[1-(4-cyano-2,6-difluorobenzoyl)piperidin-4-yl]phenyl}-3-(imidazo[1,2-a]pyridin-7-ylmethyl)urea;
1-[4-(1-{[1-ethyl-3-(propan-2-yl)-1H-pyrazol-4-yl]carbonyl}piperidin-4-yl)phenyl]-3-(imidazo[1,2-a]pyridin-7-ylmethyl)urea;
1-{4-[1-(1-benzofuran-3-ylcarbonyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(4-methoxy-5-methylpyridin-2-yl)carbonyl]piperidin-4-yl}phenyl)urea;
1-(4-{1-[(1-cyclopentyl-1H-pyrazol-5-yl)carbonyl]piperidin-4-yl}phenyl)-3-(imidazo[1,2-a]pyridin-7-ylmethyl)urea;
1-(4-{1-[(4-chloro-1,3-thiazol-5-yl)carbonyl]piperidin-4-yl}phenyl)-3-(imidazo[1,2-a]pyridin-7-ylmethyl)urea;
1-(4-{1-[(3-cyanothiophen-2-yl)carbonyl]piperidin-4-yl}phenyl)-3-(imidazo[1,2-a]pyridin-7-ylmethyl)urea;
1-(imidazo[1,2-a]pyridin-7-ylmethyl)-3-[4-(1-{[4-(propan-2-yl)pyrimidin-5-yl]carbonyl}piperidin-4-yl)phenyl]urea;
1-(imidazo[1,2-a]pyridin-7-ylmethyl)-3-(4-{1-[(1-methyl-5-propyl-1H-pyrazol-4-yl)carbonyl]piperidin-4-yl}phenyl)urea;
1-(4-{1-[2-(3-cyclopropyl-1H-pyrazol-1-yl)propanoyl]piperidin-4-yl}phenyl)-3-(imidazo[1,2-a]pyridin-7-ylmethyl)urea;
1-(imidazo[1,2-a]pyridin-7-ylmethyl)-3-{4-[1-(pyrazolo[1,5-a]pyridin-2-ylcarbonyl)piperidin-4-yl]phenyl}urea;
1-{4-[1-(1-benzofuran-5-ylcarbonyl)piperidin-4-yl]phenyl}-3-(imidazo[1,2-a]pyridin-7-ylmethyl)urea;
1-(imidazo[1,2-a]pyridin-7-ylmethyl)-3-[4-(1-{[2-(propan-2-yl)-1,3-oxazol-4-yl]carbonyl}piperidin-4-yl)phenyl]urea;
1-(imidazo[1,2-a]pyridin-7-ylmethyl)-3-(4-{1-[(1-methyl-1H-indazol-7-yl)carbonyl]piperidin-4-yl}phenyl)urea;
1-(imidazo[1,2-a]pyridin-7-ylmethyl)-3-(4-{1-[(2-methoxy-5-methylpyridin-3-yl)carbonyl]piperidin-4-yl}phenyl)urea;
1-(4-{1-[(5,6-dimethoxypyridin-2-yl)carbonyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(2-methyl-2H-indazol-4-yl)carbonyl]piperidin-4-yl}phenyl)urea;
1-(4-{1-[(2-ethylpiperidin-1-yl)(oxo)acetyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(2-methyl-2H-indazol-6-yl)carbonyl]piperidin-4-yl}phenyl)urea;
1-(imidazo[1,2-a]pyridin-7-ylmethyl)-3-(4-{1-[(1-methyl-1H-indazol-4-yl)carbonyl]piperidin-4-yl}phenyl)urea;
1-(imidazo[1,2-a]pyridin-7-ylmethyl)-3-[4-(1-{[2-(trifluoromethyl)furan-3-yl]carbonyl}piperidin-4-yl)phenyl]urea; and pharmaceutically acceptable salts thereof.

Still another embodiment pertains to compounds of Formula (IA) selected from the group consisting of
4-(1-benzoylpiperidin-4-yl)-N-(imidazo[1,2-a]pyridin-7-ylmethyl)benzamide;
4-[1-(4-fluorobenzoyl)piperidin-4-yl]-N-(imidazo[1,2-a]pyridin-7-ylmethyl)benzamide;
4-[1-(2-fluorobenzoyl)piperidin-4-yl]-N-(imidazo[1,2-a]pyridin-7-ylmethyl)benzamide;
4-[1-(3-fluorobenzoyl)piperidin-4-yl]-N-(imidazo[1,2-a]pyridin-7-ylmethyl)benzamide;
4-[1-(3-chlorobenzoyl)piperidin-4-yl]-N-(imidazo[1,2-a]pyridin-7-ylmethyl)benzamide;
4-[1-(4-chlorobenzoyl)piperidin-4-yl]-N-(imidazo[1,2-a]pyridin-7-ylmethyl)benzamide;
4-[1-(2-chlorobenzoyl)piperidin-4-yl]-N-(imidazo[1,2-a]pyridin-7-ylmethyl)benzamide;
4-[1-(3-fluoro-4-methoxybenzoyl)piperidin-4-yl]-N-(imidazo[1,2-a]pyridin-7-ylmethyl)benzamide;
4-[1-(3,5-dimethoxybenzoyl)piperidin-4-yl]-N-(imidazo[1,2-a]pyridin-7-ylmethyl)benzamide;
N-(imidazo[1,2-a]pyridin-7-ylmethyl)-4-[1-(3-methylbenzoyl)piperidin-4-yl]benzamide;
4-[1-(2-acetylbenzoyl)piperidin-4-yl]-N-(imidazo[1,2-a]pyridin-7-ylmethyl)benzamide;
N-(imidazo[1,2-a]pyridin-7-ylmethyl)-4-{1-[2-(methoxymethyl)benzoyl]piperidin-4-yl}benzamide;
4-[1-(2,6-dimethoxybenzoyl)piperidin-4-yl]-N-(imidazo[1,2-a]pyridin-7-ylmethyl)benzamide;
4-[1-(2-chloro-4-cyanobenzoyl)piperidin-4-yl]-N-(imidazo[1,2-a]pyridin-7-ylmethyl)benzamide;
4-[1-(2-hydroxy-3-methylbenzoyl)piperidin-4-yl]-N-(imidazo[1,2-a]pyridin-7-ylmethyl)benzamide;
4-[1-(5-cyano-2-fluorobenzoyl)piperidin-4-yl]-N-(imidazo[1,2-a]pyridin-7-ylmethyl)benzamide;
4-[1-(3-cyano-5-fluorobenzoyl)piperidin-4-yl]-N-(imidazo[1,2-a]pyridin-7-ylmethyl)benzamide;
4-[1-(3-cyano-4-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(2-methoxy-6-methylbenzoyl)piperidin-4-yl]benzamide;
4-[1-(4-cyano-2,6-difluorobenzoyl)piperidin-4-yl]-N-(imidazo[1,2-a]pyridin-7-ylmethyl)benzamide; and pharmaceutically acceptable salts thereof.

Embodiments of Formula (IIA)

In another aspect, the present invention provides compounds of Formula (IIA)

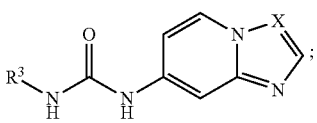

(IIA)

and pharmaceutically acceptable salts thereof; wherein X and $R^3$ are as described herein for Formula (IA).

One embodiment pertains to compounds of Formula (IIA) or pharmaceutically acceptable salts thereof;
wherein
X is N or $CY^1$;
$Y^1$ is independently selected from the group consisting of hydrogen, alkyl, alkoxy, haloalkyl, hydroxyalkyl, OH, CN, F, Cl, Br, and I;
$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, C(O)C(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$, at each occurrence, is independently selected from the group consisting of aryl, heterocyclyl, cycloalkyl, cycloalkenyl, alkyl, alkenyl, and alkynyl; wherein each R$^{10}$ alkyl, alkenyl, and alkynyl is optionally substituted with one, two, three or four substituents independently selected from the group consisting of alkoxy, F, Cl, Br and I; and R$^{11}$, at each occurrence, is independently selected from the group consisting of aryl, heterocyclyl, cycloalkyl, cycloalkenyl, alkyl, alkenyl, and alkynyl;

with the proviso that when X is CY$^1$ and Y$^1$ is hydrogen; and R$^3$ is thiazolyl; the R$^3$ thiazolyl is substituted with one substituent.

In one embodiment of Formula (IIA), X is N or $CY^1$. In another embodiment of Formula (IIA), X is N. In another embodiment of Formula (IIA), X is $CY^1$.

In one embodiment of Formula (IIA), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (IIA), X is $CY^1$; and $Y^1$ is independently selected from the group consisting of hydrogen, Cl, Br, and I. In another embodiment of Formula (IIA), X is $CY^1$; and $Y^1$ is Cl. In another embodiment of Formula (IIA), X is $CY^1$; and $Y^1$ is hydrogen.

In one embodiment of Formula (IIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, Br and I. In another embodiment of Formula (IIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IIA), $R^3$ is phenyl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (IIA), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (IIA), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IIA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, OH, CN, $N_3$, $NO_2$, F, Cl, Br and I. In another embodiment of Formula (IIA), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, OH, and F.

In another embodiment of Formula (IIA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)$ NHR⁸, C(N)N(R⁸)₂, CNOH, CNOCH₃, OH, CN, N₃, NO₂, F, Cl, Br and I. In another embodiment of Formula (IIA), R⁵, at each occurrence, is independently selected from the group consisting of alkyl, aryl, heterocyclyl, and cycloalkyl; wherein each R⁵ alkyl is optionally substituted with one, two, three or four substituents independently selected from the group consisting of R⁷, OR⁷, and OH; wherein each R⁵ aryl and heterocyclyl is optionally substituted with one, two, three or four substituents independently selected from the group consisting of R⁸, OR⁸, CN, F, Cl, Br and I.

In one embodiment of Formula (IIA), R⁶, at each occurrence, is independently selected from the group consisting of alkyl, alkenyl, alkynyl, aryl, heterocyclyl, cycloalkyl, and cycloalkenyl; wherein each R⁶ alkyl, alkenyl, and alkynyl is optionally substituted with one, two, three or four substituents independently selected from the group consisting of R⁹, OR⁹, SR⁹, S(O)R⁹, SO₂R⁹, C(O)R⁹, CO(O)R⁹, OC(O)R⁹, OC(O)OR⁹, NH₂, NHR⁹, N(R⁹)₂, NHC(O)R⁹, NR⁹C(O)R⁹, NHS(O)₂R⁹, NR⁹S(O)₂R⁹, NHC(O)OR⁹, NR⁹C(O)OR⁹, NHC(O)NH₂, NHC(O)NHR⁹, NHC(O)N(R⁹)₂, NR⁹C(O)NHR⁹, NR⁹C(O)N(R⁹)₂, C(O)NH₂, C(O)NHR⁹, C(O)N(R⁹)₂, C(O)NHOH, C(O)NHOR⁹, C(O)NHSO₂R⁹, C(O)NR⁹SO₂R⁹, SO₂NH₂, SO₂NHR⁹, SO₂N(R⁹)₂, C(O)H, C(O)OH, C(N)NH₂, C(N)NHR⁹, C(N)N(R⁹)₂, CNOH, CNOCH₃, OH, CN, N₃, NO₂, F, Cl, Br and I; wherein each R⁶ aryl, cycloalkyl, cycloalkenyl, and heterocyclyl is optionally substituted with one, two, three or four substituents independently selected from the group consisting of R¹⁰, OR¹⁰, SR¹⁰, S(O)R¹⁰, SO₂R¹⁰, C(O)R¹⁰, CO(O)R¹⁰, OC(O)R¹⁰, OC(O)OR¹⁰, NH₂, NHR¹⁰, N(R¹⁰)₂, NHC(O)R¹⁰, NR¹⁰C(O)R¹⁰, NHS(O)₂R¹⁰, NR¹⁰S(O)₂R¹⁰, NHC(O)OR¹⁰, NR¹⁰C(O)OR¹⁰, NHC(O)NH₂, NHC(O)NHR¹⁰, NHC(O)N(R¹⁰)₂, NR¹⁰C(O)NHR¹⁰, NR¹⁰C(O)N(R¹⁰)₂, C(O)NH₂, C(O)NHR¹⁰, C(O)N(R)₂, C(O)NHOH, C(O)NHOR¹⁰, C(O)NHSO₂R¹⁰, C(O)NR¹⁰SO₂R¹⁰, SO₂NH₂, SO₂NHR¹⁰, SO₂N(R¹⁰)₂, C(O)H, C(O)OH, C(N)NH₂, C(N)NHR¹⁰, C(N)N(R¹⁰)₂, CNOH, CNOCH₃, OH, CN, N₃, NO₂, F, Cl, Br and I. In another embodiment of Formula (IIA), R⁶, at each occurrence, is independently selected from the group consisting of alkyl, alkenyl, aryl, heterocyclyl, cycloalkyl, and cycloalkenyl; wherein each R⁶ alkyl and alkenyl is optionally substituted with one, two, three or four substituents independently selected from the group consisting of R⁹, OR⁹, SO₂R⁹, NH₂, N(R⁹)₂, OH, F, Cl, Br and I; wherein each R⁶ aryl, cycloalkyl, cycloalkenyl, and heterocyclyl is optionally substituted with one, two, three or four substituents independently selected from the group consisting of R¹⁰, OR¹⁰, CN, F, Cl, Br and I.

In one embodiment of Formula (IIA), R⁷, at each occurrence, is independently selected from the group consisting of alkyl, alkenyl, alkynyl, aryl, heterocyclyl, cycloalkyl, and cycloalkenyl; wherein each R⁷ alkyl, alkenyl, and alkynyl is optionally substituted with one, two, three or four substituents independently selected from the group consisting of aryl, alkoxy, OH, CN, N₃, NO₂, F, Cl, Br and I; wherein each R⁷ aryl, cycloalkyl, cycloalkenyl, and heterocyclyl is optionally substituted with one, two, three or four substituents independently selected from the group consisting of OH, CN, N₃, NO₂, F, Cl, Br and I. In another embodiment of Formula (IIA), R⁷, at each occurrence, is alkyl or heterocyclyl.

In one embodiment of Formula (IIA), R⁸, at each occurrence, is independently selected from the group consisting of alkyl, alkenyl, and alkynyl. In another embodiment of Formula (IIA), R⁸, at each occurrence, is independently alkyl.

In one embodiment of Formula (IIA), R⁹, at each occurrence, is independently selected from the group consisting of alkyl, alkenyl, alkynyl, aryl, heterocyclyl, cycloalkyl, and cycloalkenyl; wherein each R⁹ alkyl, alkenyl, and alkynyl is optionally substituted with one, two, three or four substituents independently selected from the group consisting of aryl, alkoxy, OH, CN, NO₂, F, Cl, Br and I; wherein each R⁹ aryl, cycloalkyl, cycloalkenyl, and heterocyclyl is optionally substituted with one, two, three or four substituents independently selected from the group consisting of R¹¹, OR¹¹, C(O)R¹¹, CO(O)R¹¹, OC(O)R¹¹, NH₂, NHR¹¹, N(R¹¹)₂, NHC(O)R¹¹, NR¹¹C(O)R¹¹, C(O)NH₂, C(O)NHR¹¹, C(O)N(R¹¹)₂, C(O)H, C(O)OH, COH, CN, NO₂, F, Cl, Br and I. In another embodiment of Formula (IIA), R⁹, at each occurrence, is independently selected from the group consisting of alkyl, aryl, heterocyclyl, and cycloalkyl; wherein each R⁹ alkyl is optionally substituted with one, two, three or four substituents independently selected from the group consisting of aryl, and alkoxy; wherein each R⁹ aryl, cycloalkyl, and heterocyclyl is optionally substituted with one, two, three or four substituents independently selected from the group consisting of R¹¹, OR¹¹, CO(O)R¹¹, and F.

In one embodiment of Formula (IIA), R¹⁰, at each occurrence, is independently selected from the group consisting of aryl, heterocyclyl, cycloalkyl, cycloalkenyl, alkyl, alkenyl, and alkynyl; wherein each R¹⁰ alkyl, alkenyl, and alkynyl is optionally substituted with one, two, three or four substituents independently selected from the group consisting of alkoxy, F, Cl, Br and I. In another embodiment of Formula (IIA), R¹⁰, at each occurrence, is independently heterocyclyl, cycloalkyl, alkyl, or alkenyl; wherein each R¹⁰ alkyl is optionally substituted with one, two, three or four substituents independently selected from the group consisting of alkoxy, and F.

In one embodiment of Formula (IIA), R¹¹, at each occurrence, is independently selected from the group consisting of aryl, heterocyclyl, cycloalkyl, cycloalkenyl, alkyl, alkenyl, and alkynyl. In another embodiment of Formula (IIA), R¹¹, at each occurrence, is independently alkyl. In another embodiment of Formula (IIA), R¹¹, at each occurrence, is independently cycloalkyl.

One embodiment pertains to compounds or pharmaceutically acceptable salts thereof, which are useful as inhibitors of NAMPT, the compounds having Formula (IIA)

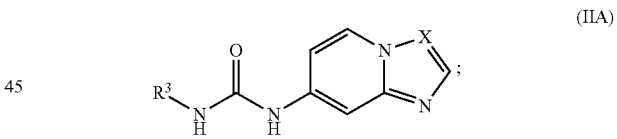

(IIA)

wherein

X is N or CY¹;

Y¹ is independently selected from the group consisting of hydrogen, F, Cl, Br, and I;

R³ is independently selected from the group consisting of phenyl and 5-6 membered heteroaryl; wherein each R³ phenyl is substituted at the para position with one substituent independently selected from the group consisting of R⁴, OR⁴, SO₂R⁴, C(O)R⁴, NHC(O)R⁴, NR⁴C(O)R⁴, NHS(O)₂R⁴, NHC(O)OR⁴, C(O)NHR⁴, F, Cl, Br and I; wherein each R³ phenyl is optionally additionally substituted with one substituent independently selected from the group consisting of F, Cl, Br and I; wherein each R³ 5-6 membered heteroaryl is substituted with one, two, three or four substituents independently selected from the group consisting of R⁴, C(O)R⁴, NHR⁴, NHC(O)R⁴, NR⁴C(O)R⁴, NHC(O)OR⁴, NR⁴C(O)OR⁴, C(O)NHR⁴, F, Cl, Br and I;

R⁴, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$, at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F; and $R^{11}$, at each occurrence, is independently cycloalkyl or alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (IIA), which include 4-[(imidazo[1,2-a]pyridin-7-ylcarbamoyl)amino]-N-(3-methylbutyl)benzamide; and pharmaceutically acceptable salts thereof.

Embodiments of Formula (IIIA)

In another aspect, the present invention provides compounds of Formula (IIIA)

(IIIA)

and pharmaceutically acceptable salts thereof; wherein X and $R^3$ are as described in Formula (IA) herein.

One embodiment pertains to compounds of Formula (IIIA) or pharmaceutically acceptable salts thereof;

wherein

X is N or $CY^1$;

$Y^1$ is independently selected from the group consisting of hydrogen, alkyl, alkoxy, haloalkyl, hydroxyalkyl, OH, CN, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I;

$R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I; and $R^{11}$, at each occurrence, is independently selected from the group consisting of aryl, heterocyclyl, cycloalkyl, cycloalkenyl, alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (IIIA), X is N or $CY^1$. In another embodiment of Formula (IIIA), X is N. In another embodiment of Formula (IIIA), X is $CY^1$.

In one embodiment of Formula (IIIA), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (IIIA), X is $CY^1$; and $Y^1$ is independently selected from the group consisting of hydrogen, Cl, Br, and I. In another embodiment of Formula (IIIA), X is $CY^1$; and $Y^1$ is Cl. In another embodiment of Formula (IIIA), X is $CY^1$; and $Y^1$ is hydrogen.

In one embodiment of Formula (IIIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I. In another embodiment of Formula (IIIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IIIA), $R^3$ is phenyl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (IIIA), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (IIIA), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IIIA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (IIIA), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, OH, and F.

In another embodiment of Formula (IIIA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (IIIA), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (IIIA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (IIIA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (IIIA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (IIIA), $R^7$, at each occurrence, is alkyl or heterocyclyl.

In one embodiment of Formula (IIIA), $R^8$, at each occurrence, is independently selected from the group consisting of alkyl, alkenyl, and alkynyl. In another embodiment of Formula (IIIA), $R^8$, at each occurrence, is independently alkyl.

In one embodiment of Formula (IIIA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (IIIA), $R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (IIIA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (IIIA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (IIIA), $R^{11}$, at each occurrence, is independently selected from the group consisting of aryl, heterocyclyl, cycloalkyl, cycloalkenyl, alkyl, alkenyl, and alkynyl. In another embodiment of Formula (IIIA), $R^{11}$, at each occurrence, is independently alkyl. In another embodiment of Formula (IIIA), $R^{11}$, at each occurrence, is independently cycloalkyl.

One embodiment pertains to compounds or pharmaceutically acceptable salts thereof, which are useful as inhibitors of NAMPT, the compounds having Formula (IIIA)

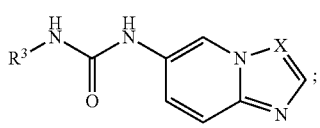

Formula (IIIA)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$, at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F; and $R^{11}$, at each occurrence, is independently cycloalkyl or alkyl;

with the proviso that
when X is CY$^1$ and Y$^1$ is hydrogen; and R$^3$ is thiazolyl; the R$^3$ thiazolyl is substituted with one substituent.

Still another embodiment pertains to compounds having Formula (IIIA), which include
4-[(imidazo[1,2-a]pyridin-6-ylcarbamoyl)amino]-N-(3-methylbutyl)benzamide;
2-cyclopentyl-N-{4-[(imidazo[1,2-a]pyridin-6-ylcarbamoyl)amino]phenyl}acetamide;
4-[(imidazo[1,2-a]pyridin-6-ylcarbamoyl)amino]-N-(2-phenylethyl)benzamide;
4-[(imidazo[1,2-a]pyridin-6-ylcarbamoyl)amino]-N-[2-(morpholin-4-yl)ethyl]benzamide;
N-(1-hydroxy-2-methylpropan-2-yl)-4-[(imidazo[1,2-a]pyridin-6-ylcarbamoyl)amino]benzamide;
N-benzyl-4-[(imidazo[1,2-a]pyridin-6-ylcarbamoyl)amino]benzamide;
N-(cyclopentylmethyl)-4-[(imidazo[1,2-a]pyridin-6-ylcarbamoyl)amino]benzamide;
4-[(imidazo[1,2-a]pyridin-6-ylcarbamoyl)amino]-N-[3-(piperidin-1-yl)propyl]benzamide;
4-[(imidazo[1,2-a]pyridin-6-ylcarbamoyl)amino]-N-(2-phenoxyethyl)benzamide;
4-[(imidazo[1,2-a]pyridin-6-ylcarbamoyl)amino]-N-[2-(pyrrolidin-1-yl)ethyl]benzamide;
4-[(imidazo[1,2-a]pyridin-6-ylcarbamoyl)amino]-N-[2-(propan-2-yloxy)ethyl]benzamide;
N-(2-hydroxy-2-methylpropyl)-4-[(imidazo[1,2-a]pyridin-6-ylcarbamoyl)amino]benzamide;
N-[2-hydroxy-1-(4-methoxyphenyl)ethyl]-4-[(imidazo[1,2-a]pyridin-6-ylcarbamoyl)amino]benzamide;
4-[(imidazo[1,2-a]pyridin-6-ylcarbamoyl)amino]-N-[2-(2-oxopyrrolidin-1-yl)ethyl]benzamide;
4-[(imidazo[1,2-a]pyridin-6-ylcarbamoyl)amino]-N-(tetrahydrofuran-2-ylmethyl)benzamide;
4-[(imidazo[1,2-a]pyridin-6-ylcarbamoyl)amino]-N-propylbenzamide;
4-[(imidazo[1,2-a]pyridin-6-ylcarbamoyl)amino]-N-[3-(morpholin-4-yl)propyl]benzamide;
4-[(imidazo[1,2-a]pyridin-6-ylcarbamoyl)amino]-N-phenylbenzamide;
4-[(imidazo[1,2-a]pyridin-6-ylcarbamoyl)amino]-N-(2-methylbutyl)benzamide;
4-[(imidazo[1,2-a]pyridin-6-ylcarbamoyl)amino]-N-[3-(2-oxopyrrolidin-1-yl)propyl]benzamide;
4-[(imidazo[1,2-a]pyridin-6-ylcarbamoyl)amino]-N-(tetrahydro-2H-pyran-4-ylmethyl)benzamide;
4-[(imidazo[1,2-a]pyridin-6-ylcarbamoyl)amino]-N-(tetrahydro-2H-pyran-2-ylmethyl)benzamide;
N-[(1,1-dioxidotetrahydrothiophen-3-yl)methyl]-4-[(imidazo[1,2-a]pyridin-6-ylcarbamoyl)amino]benzamide;
tert-butyl 4-{4-[(imidazo[1,2-a]pyridin-6-ylcarbamoyl)amino]phenyl}-3,6-dihydropyridine-1(2H)-carboxylate;
N-{4-[(imidazo[1,2-a]pyridin-6-ylcarbamoyl)amino]phenyl}-2-(tetrahydrofuran-3-yl)acetamide;
N-{4-[(imidazo[1,2-a]pyridin-6-ylcarbamoyl)amino]phenyl}acetamide;
1-imidazo[1,2-a]pyridin-6-yl-3-{4-[1-(tetrahydrofuran-3-ylacetyl)-1,2,3,6-tetrahydropyridin-4-yl]phenyl}urea;
1-{4-[1-(2-hydroxy-2-methylpropanoyl)-1,2,3,6-tetrahydropyridin-4-yl]phenyl}-3-imidazo[1,2-a]pyridin-6-ylurea;
1-imidazo[1,2-a]pyridin-6-yl-3-{4-[1-(morpholin-4-ylacetyl)-1,2,3,6-tetrahydropyridin-4-yl]phenyl}urea;
1-{4-[1-(ethoxyacetyl)-1,2,3,6-tetrahydropyridin-4-yl]phenyl}-3-imidazo[1,2-a]pyridin-6-ylurea;
1-imidazo[1,2-a]pyridin-6-yl-3-(4-{1-[(2-methoxyethoxy)acetyl]-1,2,3,6-tetrahydropyridin-4-yl}phenyl)urea;
1-imidazo[1,2-a]pyridin-6-yl-3-{4-[1-(tetrahydrofuran-2-ylcarbonyl)-1,2,3,6-tetrahydropyridin-4-yl]phenyl}urea;
1-imidazo[1,2-a]pyridin-6-yl-3-{4-[1-(tetrahydro-2H-pyran-4-ylcarbonyl)-1,2,3,6-tetrahydropyridin-4-yl]phenyl}urea;
1-{4-[1-(1,4-dioxan-2-ylcarbonyl)-1,2,3,6-tetrahydropyridin-4-yl]phenyl}-3-imidazo[1,2-a]pyridin-6-ylurea;
1-imidazo[1,2-a]pyridin-6-yl-3-(4-{1-[(1-methylpiperidin-4-yl)carbonyl]-1,2,3,6-tetrahydropyridin-4-yl}phenyl)urea;
1-(4-{1-[(1,1-dioxidotetrahydro-2H-thiopyran-4-yl)carbonyl]-1,2,3,6-tetrahydropyridin-4-yl}phenyl)-3-imidazo[1,2-a]pyridin-6-ylurea;
1-imidazo[1,2-a]pyridin-6-yl-3-{4-[1-(2-methylpropanoyl)-1,2,3,6-tetrahydropyridin-4-yl]phenyl}urea;
2-ethoxy-N-{4-[(imidazo[1,2-a]pyridin-6-ylcarbamoyl)amino]phenyl}acetamide;
N-{4-[(imidazo[1,2-a]pyridin-6-ylcarbamoyl)amino]phenyl}-2-(tetrahydro-2H-pyran-4-yl)acetamide;
N-{4-[(imidazo[1,2-a]pyridin-6-ylcarbamoyl)amino]phenyl}-2-(morpholin-4-yl)acetamide;
N-{4-[(imidazo[1,2-a]pyridin-6-ylcarbamoyl)amino]phenyl}-2-(2-methoxyethoxy)acetamide;
N-{4-[(imidazo[1,2-a]pyridin-6-ylcarbamoyl)amino]phenyl}-3-methoxy-2-methylpropanamide;
N-{4-[(imidazo[1,2-a]pyridin-6-ylcarbamoyl)amino]phenyl}butanamide;
4,4,4-trifluoro-N-{4-[(imidazo[1,2-a]pyridin-6-ylcarbamoyl)amino]phenyl}butanamide;
N-{4-[(imidazo[1,2-a]pyridin-6-ylcarbamoyl)amino]phenyl}tetrahydro-2H-pyran-4-carboxamide;
N-{4-[(imidazo[1,2-a]pyridin-6-ylcarbamoyl)amino]phenyl}-4-methylpentanamide;
N-{4-[(imidazo[1,2-a]pyridin-6-ylcarbamoyl)amino]phenyl}-1-methylpiperidine-4-carboxamide;
N-{4-[(imidazo[1,2-a]pyridin-6-ylcarbamoyl)amino]phenyl}tetrahydro-2H-thiopyran-4-carboxamide 1,1-dioxide;
N-{4-[(imidazo[1,2-a]pyridin-6-ylcarbamoyl)amino]phenyl}-1,4-dioxane-2-carboxamide;
1-imidazo[1,2-a]pyridin-6-yl-3-{4-[1-(2-methylpropyl)-1H-pyrazol-4-yl]phenyl}urea;
tert-butyl 4-{4-[(imidazo[1,2-a]pyridin-6-ylcarbamoyl)amino]phenyl}piperidine-1-carboxylate;
1-imidazo[1,2-a]pyridin-6-yl-3-{4-[1-(2-methylpropanoyl)piperidin-4-yl]phenyl}urea;
1-imidazo[1,2-a]pyridin-6-yl-3-{4-[1-(tetrahydro-2H-pyran-4-ylcarbonyl)piperidin-4-yl]phenyl}urea;
1-imidazo[1,2-a]pyridin-6-yl-3-{4-[1-(tetrahydrofuran-3-ylacetyl)piperidin-4-yl]phenyl}urea;
1-imidazo[1,2-a]pyridin-6-yl-3-{4-[1-(tetrahydrofuran-2-ylacetyl)piperidin-4-yl]phenyl}urea;
1-[4-(1-benzoylpiperidin-4-yl)phenyl]-3-imidazo[1,2-a]pyridin-6-ylurea;
1-imidazo[1,2-a]pyridin-6-yl-3-{4-[1-(tetrahydrofuran-2-ylcarbonyl)piperidin-4-yl]phenyl}urea;
4-{[(3-chloroimidazo[1,2-a]pyridin-6-yl)carbamoyl]amino}-N-(tetrahydro-2H-pyran-2-ylmethyl)benzamide; and pharmaceutically acceptable salts thereof.

Embodiments of Formula (IVA)

In another aspect, the present invention provides compounds of Formula (IVA)

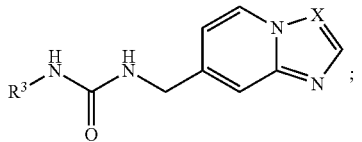

(IVA)

and pharmaceutically acceptable salts thereof; wherein X and $R^3$ are as described herein for Formula (IA).

One embodiment pertains to compounds of Formula (IVA) or pharmaceutically acceptable salts thereof;
wherein
X is N or $CY^1$;
$Y^1$ is independently selected from the group consisting of hydrogen, alkyl, alkoxy, haloalkyl, hydroxyalkyl, OH, CN, F, Cl, Br, and I;
$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, OH, CN, $N_3$, $NO_2$, F, Cl, Br and I;
$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, OH, CN, $N_3$, $NO_2$, F, Cl, Br and I;
$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, OH, CN, $N_3$, $NO_2$, F, Cl, Br and I;
$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, OH, CN, $N_3$, $NO_2$, F, Cl, Br and I;
$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, C(O)H, C(O)OH, COH, CN, $NO_2$, F, Cl, Br and I;

$R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I; and $R^{11}$, at each occurrence, is independently selected from the group consisting of aryl, heterocyclyl, cycloalkyl, cycloalkenyl, alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (IVA), X is N or $CY^1$. In another embodiment of Formula (IVA), X is N. In another embodiment of Formula (IVA), X is $CY^1$.

In one embodiment of Formula (IVA), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (IVA), X is $CY^1$; and $Y^1$ is independently selected from the group consisting of hydrogen, Cl, Br, and I. In another embodiment of Formula (IVA), X is $CY^1$; and $Y^1$ is Cl. In another embodiment of Formula (IVA), X is $CY^1$; and $Y^1$ is hydrogen.

In one embodiment of Formula (IVA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, C(N)$NH_2$, $C(N)NHR^4$, $C(N)N(R^4)_2$, CNOH, $CNOCH_3$, OH, CN, $N_3$, $NO_2$, F, Cl, Br and I. In another embodiment of Formula (IVA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IVA), $R^3$ is phenyl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (IVA), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (IVA), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (IVA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, C(O)NHOH, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, C(O)NHOH, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (IVA), $R^4$, at each occurrence, is independently selected from the group consisting of alkyl, aryl, cycloalkyl, and 3-12 membered heterocyclyl;

wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, OH, and F.

In another embodiment of Formula (IVA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (IVA), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (IVA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (IVA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (IVA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (IVA), $R^7$, at each occurrence, is alkyl or heterocyclyl.

In one embodiment of Formula (IVA), $R^8$, at each occurrence, is independently selected from the group consisting of alkyl, alkenyl, and alkynyl. In another embodiment of Formula (IVA), $R^8$, at each occurrence, is independently alkyl.

In one embodiment of Formula (IVA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (IVA), $R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (IVA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (IVA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (IVA), $R^{11}$, at each occurrence, is independently selected from the group consisting of aryl, heterocyclyl, cycloalkyl, cycloalkenyl, alkyl, alkenyl, and alkynyl. In another embodiment of Formula (IVA), $R^{11}$, at each occurrence, is independently alkyl. In another embodiment of Formula (IVA), $R^{11}$, at each occurrence, is independently cycloalkyl.

One embodiment pertains to compounds or pharmaceutically acceptable salts thereof, which are useful as inhibitors of NAMPT, the compounds having Formula (IVA)

Formula (IVA)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl;

wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$, at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F; and $R^{11}$, at each occurrence, is independently cycloalkyl or alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (IVA), which include 2-cyclopentyl-N-(4-{[(imidazo[1,2-a]pyridin-7-ylmethyl)carbamoyl]amino}phenyl)acetamide;

tert-butyl 4-(4-{[(imidazo[1,2-a]pyridin-7-ylmethyl)carbamoyl]amino}phenyl)piperidine-1-carboxylate;

1-(imidazo[1,2-a]pyridin-7-ylmethyl)-3-{4-[1-(tetrahydrofuran-2-ylcarbonyl)piperidin-4-yl]phenyl}urea;

1-(imidazo[1,2-a]pyridin-7-ylmethyl)-3-{4-[1-(tetrahydro-2H-pyran-4-ylcarbonyl)piperidin-4-yl]phenyl}urea;

1-{4-[1-(1,4-dioxan-2-ylcarbonyl)piperidin-4-yl]phenyl}-3-(imidazo[1,2-a]pyridin-7-ylmethyl)urea;

1-(imidazo[1,2-a]pyridin-7-ylmethyl)-3-{4-[1-(tetrahydro-2H-pyran-4-ylacetyl)piperidin-4-yl]phenyl}urea;

1-(imidazo[1,2-a]pyridin-7-ylmethyl)-3-{4-[1-(morpholin-4-ylacetyl)piperidin-4-yl]phenyl}urea;

1-(imidazo[1,2-a]pyridin-7-ylmethyl)-3-{4-[1-(tetrahydrofuran-2-ylacetyl)piperidin-4-yl]phenyl}urea;

1-{4-[1-(3-hydroxy-3-methylbutanoyl)piperidin-4-yl]phenyl}-3-(imidazo[1,2-a]pyridin-7-ylmethyl)urea;

1-{4-[1-(2-hydroxy-2-methylpropanoyl)piperidin-4-yl]phenyl}-3-(imidazo[1,2-a]pyridin-7-ylmethyl)urea;

1-(imidazo[1,2-a]pyridin-7-ylmethyl)-3-{4-[1-(2-methylpropanoyl)piperidin-4-yl]phenyl}urea;

1-[4-(1-benzoylpiperidin-4-yl)phenyl]-3-(imidazo[1,2-a]pyridin-7-ylmethyl)urea;

1-(4-{1-[(1,1-dioxidotetrahydro-2H-thiopyran-4-yl)carbonyl]piperidin-4-yl}phenyl)-3-(imidazo[1,2-a]pyridin-7-ylmethyl)urea;

N-(4-{[(imidazo[1,2-a]pyridin-7-ylmethyl)carbamoyl]amino}phenyl)-4-methylpentanamide;

3-cyclopentyl-N-(4-{[(imidazo[1,2-a]pyridin-7-ylmethyl)carbamoyl]amino}phenyl)propanamide;

N-(4-{[(imidazo[1,2-a]pyridin-7-ylmethyl)carbamoyl]amino}phenyl)-2-(propan-2-yloxy)acetamide;

N-(4-{[(imidazo[1,2-a]pyridin-7-ylmethyl)carbamoyl]amino}phenyl)-2-(tetrahydrofuran-2-yl)acetamide;

N-(4-{[(imidazo[1,2-a]pyridin-7-ylmethyl)carbamoyl]amino}phenyl)-2-(tetrahydro-2H-pyran-4-yl)acetamide;

N-(4-{[(imidazo[1,2-a]pyridin-7-ylmethyl)carbamoyl]amino}phenyl)-3-phenylpropanamide;

1-(imidazo[1,2-a]pyridin-7-ylmethyl)-3-(4-{1-[(3S)-tetrahydrofuran-3-ylcarbonyl]piperidin-4-yl}phenyl)urea;

1-(imidazo[1,2-a]pyridin-7-ylmethyl)-3-(4-{1-[(3R)-tetrahydrofuran-3-ylcarbonyl]piperidin-4-yl}phenyl)urea;

1-(imidazo[1,2-a]pyridin-7-ylmethyl)-3-(4-{1-[(2S)-tetrahydrofuran-2-ylcarbonyl]piperidin-4-yl}phenyl)urea;

1-(imidazo[1,2-a]pyridin-7-ylmethyl)-3-(4-{1-[(2R)-tetrahydrofuran-2-ylcarbonyl]piperidin-4-yl}phenyl)urea;

tert-butyl 4-(3-fluoro-4-{[(imidazo[1,2-a]pyridin-7-ylmethyl)carbamoyl]amino}phenyl)-3,6-dihydropyridine-1(2H)-carboxylate;
tert-butyl (3R)-3-(4-{[(imidazo[1,2-a]pyridin-7-ylmethyl)carbamoyl]amino}phenoxy)pyrrolidine-1-carboxylate;
tert-butyl 3-(4-{[(imidazo[1,2-a]pyridin-7-ylmethyl)carbamoyl]amino}phenyl)pyrrolidine-1-carboxylate;
N-(4-{[(imidazo[1,2-a]pyridin-7-ylmethyl)carbamoyl]amino}phenyl)biphenyl-2-sulfonamide;
1-{2-fluoro-4-[1-(2-methylpropanoyl)-1,2,3,6-tetrahydropyridin-4-yl]phenyl}-3-(imidazo[1,2-a]pyridin-7-ylmethyl)urea;
1-{2-fluoro-4-[1-(tetrahydrofuran-2-ylcarbonyl)-1,2,3,6-tetrahydropyridin-4-yl]phenyl}-3-(imidazo[1,2-a]pyridin-7-ylmethyl)urea;
1-(imidazo[1,2-a]pyridin-7-ylmethyl)-3-[4-({(3R)-1-[(2S)-2-methylbutanoyl]pyrrolidin-3-yl}oxy)phenyl]urea;
1-(4-{[(3R)-1-benzoylpyrrolidin-3-yl]oxy}phenyl)-3-(imidazo[1,2-a]pyridin-7-ylmethyl)urea;
1-(imidazo[1,2-a]pyridin-7-ylmethyl)-3-(4-{[(3R)-1-(2-methylpropanoyl)pyrrolidin-3-yl]oxy}phenyl)urea;
1-(4-{[(3R)-1-(cyclopropylcarbonyl)pyrrolidin-3-yl]oxy}phenyl)-3-(imidazo[1,2-a]pyridin-7-ylmethyl)urea;
1-(4-{[(3R)-1-(cyclopropylacetyl)pyrrolidin-3-yl]oxy}phenyl)-3-(imidazo[1,2-a]pyridin-7-ylmethyl)urea;
1-(imidazo[1,2-a]pyridin-7-ylmethyl)-3-(4-{[(3R)-1-(tetrahydro-2H-pyran-4-ylcarbonyl)pyrrolidin-3-yl]oxy}phenyl)urea;
1-(4-{[(3R)-1-(2-hydroxy-2-methylpropanoyl)pyrrolidin-3-yl]oxy}phenyl)-3-(imidazo[1,2-a]pyridin-7-ylmethyl)urea;
1-(imidazo[1,2-a]pyridin-7-ylmethyl)-3-[4-({(3R)-1-[(2R)-tetrahydrofuran-2-ylcarbonyl]pyrrolidin-3-yl}oxy)phenyl]urea;
1-(imidazo[1,2-a]pyridin-7-ylmethyl)-3-[4-({(3R)-1-[(2S)-tetrahydrofuran-2-ylcarbonyl]pyrrolidin-3-yl}oxy)phenyl]urea;
1-(imidazo[1,2-a]pyridin-7-ylmethyl)-3-(4-{[(3R)-1-(tetrahydrofuran-3-ylcarbonyl)pyrrolidin-3-yl]oxy}phenyl)urea;
1-(imidazo[1,2-a]pyridin-7-ylmethyl)-3-(4-{[(3R)-1-(tetrahydro-2H-pyran-4-ylacetyl)pyrrolidin-3-yl]oxy}phenyl)urea;
tert-butyl 3-(4-{[(imidazo[1,2-a]pyridin-7-ylmethyl)carbamoyl]amino}phenyl)azetidine-1-carboxylate;
tert-butyl 4-(4-{[(imidazo[1,2-a]pyridin-7-ylmethyl)carbamoyl]amino}phenoxy)piperidine-1-carboxylate;
1-[4-(1-acetylpyrrolidin-3-yl)phenyl]-3-(imidazo[1,2-a]pyridin-7-ylmethyl)urea;
1-(imidazo[1,2-a]pyridin-7-ylmethyl)-3-{4-[1-(2-methylpropanoyl)pyrrolidin-3-yl]phenyl}urea;
1-(imidazo[1,2-a]pyridin-7-ylmethyl)-3-(4-{1-[(2S)-2-methylbutanoyl]pyrrolidin-3-yl}phenyl)urea;
1-{4-[1-(cyclopropylacetyl)pyrrolidin-3-yl]phenyl}-3-(imidazo[1,2-a]pyridin-7-ylmethyl)urea;
1-[4-(1-benzoylpyrrolidin-3-yl)phenyl]-3-(imidazo[1,2-a]pyridin-7-ylmethyl)urea;
1-(imidazo[1,2-a]pyridin-7-ylmethyl)-3-(4-{1-[(propan-2-yloxy)acetyl]pyrrolidin-3-yl}phenyl)urea;
1-{4-[1-(2-hydroxy-2-methylpropanoyl)pyrrolidin-3-yl]phenyl}-3-(imidazo[1,2-a]pyridin-7-ylmethyl)urea;
1-(imidazo[1,2-a]pyridin-7-ylmethyl)-3-(4-{1-[(2R)-tetrahydrofuran-2-ylcarbonyl]pyrrolidin-3-yl}phenyl)urea;
1-(imidazo[1,2-a]pyridin-7-ylmethyl)-3-(4-{1-[(2S)-tetrahydrofuran-2-ylcarbonyl]pyrrolidin-3-yl}phenyl)urea;
1-(imidazo[1,2-a]pyridin-7-ylmethyl)-3-(4-{1-[(3S)-tetrahydrofuran-3-ylcarbonyl]pyrrolidin-3-yl}phenyl)urea;
1-(imidazo[1,2-a]pyridin-7-ylmethyl)-3-{4-[1-(tetrahydro-2H-pyran-4-ylcarbonyl)pyrrolidin-3-yl]phenyl}urea;
1-{4-[1-(1,4-dioxan-2-ylcarbonyl)pyrrolidin-3-yl]phenyl}-3-(imidazo[1,2-a]pyridin-7-ylmethyl)urea;
1-(imidazo[1,2-a]pyridin-7-ylmethyl)-3-{4-[1-(tetrahydro-2H-pyran-4-ylacetyl)pyrrolidin-3-yl]phenyl}urea;
1-(imidazo[1,2-a]pyridin-7-ylmethyl)-3-{4-[1-(morpholin-4-ylacetyl)pyrrolidin-3-yl]phenyl}urea;
1-(imidazo[1,2-a]pyridin-7-ylmethyl)-3-[5-(piperidin-1-ylcarbonyl)-1,3-thiazol-2-yl]urea;
2-{[(imidazo[1,2-a]pyridin-7-ylmethyl)carbamoyl]amino}-N-(3-methylbutyl)-1,3-thiazole-5-carboxamide;
1-{4-[(1-acetylazetidin-3-yl)oxy]phenyl}-3-(imidazo[1,2-a]pyridin-7-ylmethyl)urea;
1-(imidazo[1,2-a]pyridin-7-ylmethyl)-3-(4-{[1-(2-methylpropanoyl)azetidin-3-yl]oxy}phenyl)urea;
1-(imidazo[1,2-a]pyridin-7-ylmethyl)-3-[4-({1-[(2S)-2-methylbutanoyl]azetidin-3-yl}oxy)phenyl]urea;
1-(4-{[1-(cyclopropylacetyl)azetidin-3-yl]oxy}phenyl)-3-(imidazo[1,2-a]pyridin-7-ylmethyl)urea;
1-{4-[(1-benzoylazetidin-3-yl)oxy]phenyl}-3-(imidazo[1,2-a]pyridin-7-ylmethyl)urea;
1-(imidazo[1,2-a]pyridin-7-ylmethyl)-3-[4-({1-[(propan-2-yloxy)acetyl]azetidin-3-yl}oxy)phenyl]urea;
1-(4-{[1-(2-hydroxy-2-methylpropanoyl)azetidin-3-yl]oxy}phenyl)-3-(imidazo[1,2-a]pyridin-7-ylmethyl)urea;
1-(imidazo[1,2-a]pyridin-7-ylmethyl)-3-[4-({1-[(2R)-tetrahydrofuran-2-ylcarbonyl]azetidin-3-yl}oxy)phenyl]urea;
1-(imidazo[1,2-a]pyridin-7-ylmethyl)-3-[4-({1-[(2S)-tetrahydrofuran-2-ylcarbonyl]azetidin-3-yl}oxy)phenyl]urea;
1-(imidazo[1,2-a]pyridin-7-ylmethyl)-3-(4-{[1-(tetrahydro-2H-pyran-4-ylcarbonyl)azetidin-3-yl]oxy}phenyl)urea;
1-(4-{[1-(1,4-dioxan-2-ylcarbonyl)azetidin-3-yl]oxy}phenyl)-3-(imidazo[1,2-a]pyridin-7-ylmethyl)urea;
1-(imidazo[1,2-a]pyridin-7-ylmethyl)-3-(4-{[1-(tetrahydro-2H-pyran-4-ylacetyl)azetidin-3-yl]oxy}phenyl)urea;
1-[4-(1-benzoyl-1,2,3,6-tetrahydropyridin-4-yl)-2-fluorophenyl]-3-(imidazo[1,2-a]pyridin-7-ylmethyl)urea;
1-{2-fluoro-4-[1-(tetrahydro-2H-pyran-4-ylacetyl)-1,2,3,6-tetrahydropyridin-4-yl]phenyl}-3-(imidazo[1,2-a]pyridin-7-ylmethyl)urea;
1-(imidazo[1,2-a]pyridin-7-ylmethyl)-3-(4-{[1-(2-methylpropanoyl)piperidin-4-yl]oxy}phenyl)urea;
1-(imidazo[1,2-a]pyridin-7-ylmethyl)-3-[4-({1-[(2S)-2-methylbutanoyl]piperidin-4-yl}oxy)phenyl]urea;
1-(4-{[1-(cyclopropylacetyl)piperidin-4-yl]oxy}phenyl)-3-(imidazo[1,2-a]pyridin-7-ylmethyl)urea;
1-{4[(1-benzoylpiperidin-4-yl)oxy]phenyl}-3-(imidazo[1,2-a]pyridin-7-ylmethyl)urea;
1-(imidazo[1,2-a]pyridin-7-ylmethyl)-3-[4-({1-[(propan-2-yloxy)acetyl]piperidin-4-yl}oxy)phenyl]urea;
1-(4-{[1-(2-hydroxy-2-methylpropanoyl)piperidin-4-yl]oxy}phenyl)-3-(imidazo[1,2-a]pyridin-7-ylmethyl)urea;
1-(imidazo[1,2-a]pyridin-7-ylmethyl)-3-[4-({1-[(2R)-tetrahydrofuran-2-ylcarbonyl]piperidin-4-yl}oxy)phenyl]urea;
1-(imidazo[1,2-a]pyridin-7-ylmethyl)-3-[4-({1-[(2S)-tetrahydrofuran-2-ylcarbonyl]piperidin-4-yl}oxy)phenyl]urea;
1-(imidazo[1,2-a]pyridin-7-ylmethyl)-3-(4-{[1-(tetrahydro-2H-pyran-4-ylcarbonyl)piperidin-4-yl]oxy}phenyl)urea;
1-(imidazo[1,2-a]pyridin-7-ylmethyl)-3-(4-{[1-(tetrahydro-2H-pyran-4-ylacetyl)piperidin-4-yl]oxy}phenyl)urea;
1-(imidazo[1,2-a]pyridin-7-ylmethyl)-3-{4-[1-(2-methylpropanoyl)azetidin-3-yl]phenyl}urea;

1-(imidazo[1,2-a]pyridin-7-ylmethyl)-3-(4-{1-[(2S)-2-methylbutanoyl]azetidin-3-yl}phenyl)urea;
1-{4-[1-(cyclopropylacetyl)azetidin-3-yl]phenyl}-3-(imidazo[1,2-a]pyridin-7-ylmethyl)urea;
1-[4-(1-benzoylazetidin-3-yl)phenyl]-3-(imidazo[1,2-a]pyridin-7-ylmethyl)urea;
1-(imidazo[1,2-a]pyridin-7-ylmethyl)-3-(4-{1-[(propan-2-yloxy)acetyl]azetidin-3-yl}phenyl)urea;
1-{4-[1-(2-hydroxy-2-methylpropanoyl)azetidin-3-yl]phenyl}-3-(imidazo[1,2-a]pyridin-7-ylmethyl)urea;
1-(imidazo[1,2-a]pyridin-7-ylmethyl)-3-(4-{1-[(2R)-tetrahydrofuran-2-ylcarbonyl]azetidin-3-yl}phenyl)urea;
1-(imidazo[1,2-a]pyridin-7-ylmethyl)-3-(4-{1-[(2S)-tetrahydrofuran-2-ylcarbonyl]azetidin-3-yl}phenyl)urea;
1-(imidazo[1,2-a]pyridin-7-ylmethyl)-3-{4-[1-(tetrahydro-2H-pyran-4-ylcarbonyl)azetidin-3-yl]phenyl}urea;
1-(imidazo[1,2-a]pyridin-7-ylmethyl)-3-{4-[1-(tetrahydro-2H-pyran-4-ylacetyl)azetidin-3-yl]phenyl}urea;
1-(imidazo[1,2-a]pyridin-7-ylmethyl)-3-{4-[1-(2-methylpropyl)-1H-pyrazol-4-yl]phenyl}urea;
1-(imidazo[1,2-a]pyridin-7-ylmethyl)-3-[4-(1-propyl-1H-pyrazol-4-yl)phenyl]urea;
1-(imidazo[1,2-a]pyridin-7-ylmethyl)-3-(4-phenoxyphenyl)urea;
2-cyclopentyl-N-(4-{[([1,2,4]triazolo[1,5-a]pyridin-7-ylmethyl)carbamoyl]amino}phenyl)acetamide;
tert-butyl 4-(4-{[([1,2,4]triazolo[1,5-a]pyridin-7-ylmethyl)carbamoyl]amino}phenyl)piperidine-1-carboxylate;
1-(imidazo[1,2-a]pyridin-7-ylmethyl)-3-{4-[1-(2-methoxyethyl)-1H-pyrazol-4-yl]phenyl}urea;
1-(imidazo[1,2-a]pyridin-7-ylmethyl)-3-{4-[1-(tetrahydrofuran-2-ylmethyl)-1H-pyrazol-4-yl]phenyl}urea;
1-(imidazo[1,2-a]pyridin-7-ylmethyl)-3-{4-[1-(tetrahydro-2H-pyran-4-ylmethyl)-1H-pyrazol-4-yl]phenyl}urea;
1-(4-{[(3R)-1-(2-fluorobenzoyl)pyrrolidin-3-yl]oxy}phenyl)-3-(imidazo[1,2-a]pyridin-7-ylmethyl)urea;
1-(4-{[(3R)-1-(3-fluorobenzoyl)pyrrolidin-3-yl]oxy}phenyl)-3-(imidazo[1,2-a]pyridin-7-ylmethyl)urea;
1-(4-{[(3R)-1-(4-fluorobenzoyl)pyrrolidin-3-yl]oxy}phenyl)-3-(imidazo[1,2-a]pyridin-7-ylmethyl)urea;
1-(4-{[(3R)-1-(2,4-difluorobenzoyl)pyrrolidin-3-yl]oxy}phenyl)-3-(imidazo[1,2-a]pyridin-7-ylmethyl)urea;
1-(imidazo[1,2-a]pyridin-7-ylmethyl)-3-[4-({(3R)-1-[4-(trifluoromethyl)benzoyl]pyrrolidin-3-yl}oxy)phenyl]urea;
1-(4-{[(3R)-1-(3,5-difluorobenzoyl)pyrrolidin-3-yl]oxy}phenyl)-3-(imidazo[1,2-a]pyridin-7-ylmethyl)urea;
1-(4-{[(3R)-1-(2-chlorobenzoyl)pyrrolidin-3-yl]oxy}phenyl)-3-(imidazo[1,2-a]pyridin-7-ylmethyl)urea;
1-(4-{[(3R)-1-(4-chlorobenzoyl)pyrrolidin-3-yl]oxy}phenyl)-3-(imidazo[1,2-a]pyridin-7-ylmethyl)urea;
1-[4-(1-butanoylpiperidin-4-yl)phenyl]-3-(imidazo[1,2-a]pyridin-7-ylmethyl)urea;
1-(imidazo[1,2-a]pyridin-7-ylmethyl)-3-(4-{1-[(2S)-2-methylbutanoyl]piperidin-4-yl}phenyl)urea;
1-(imidazo[1,2-a]pyridin-7-ylmethyl)-3-(4-{1-[(2-methylcyclopropyl)carbonyl]piperidin-4-yl}phenyl)urea;
1-{4-[1-(cyclopropylacetyl)piperidin-4-yl]phenyl}-3-(imidazo[1,2-a]pyridin-7-ylmethyl)urea;
1-(imidazo[1,2-a]pyridin-7-ylmethyl)-3-{4-[1-(3,3,3-trifluoropropanoyl)piperidin-4-yl]phenyl}urea;
1-(imidazo[1,2-a]pyridin-7-ylmethyl)-3-{4-[1-(4,4,4-trifluorobutanoyl)piperidin-4-yl]phenyl}urea;
1-(4-{1-[(4,4-difluorocyclohexyl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(phenylacetyl)piperidin-4-yl]phenyl}urea;
1-{4-[1-(2-fluorobenzoyl)piperidin-4-yl]phenyl}-3-(imidazo[1,2-a]pyridin-7-ylmethyl)urea;
1-{4-[1-(3-fluorobenzoyl)piperidin-4-yl]phenyl}-3-(imidazo[1,2-a]pyridin-7-ylmethyl)urea;
1-{4-[1-(4-fluorobenzoyl)piperidin-4-yl]phenyl}-3-(imidazo[1,2-a]pyridin-7-ylmethyl)urea;
1-{4-[1-(2,4-difluorobenzoyl)piperidin-4-yl]phenyl}-3-(imidazo[1,2-a]pyridin-7-ylmethyl)urea;
1-{4-[1-(3,4-difluorobenzoyl)piperidin-4-yl]phenyl}-3-(imidazo[1,2-a]pyridin-7-ylmethyl)urea;
1-{4-[1-(3,5-difluorobenzoyl)piperidin-4-yl]phenyl}-3-(imidazo[1,2-a]pyridin-7-ylmethyl)urea;
1-{4-[1-(2,5-difluorobenzoyl)piperidin-4-yl]phenyl}-3-(imidazo[1,2-a]pyridin-7-ylmethyl)urea;
1-(4-{[1-(3-fluorobenzoyl)piperidin-4-yl]oxy}phenyl)-3-(imidazo[1,2-a]pyridin-7-ylmethyl)urea;
1-(4-{[1-(2,4-difluorobenzoyl)piperidin-4-yl]oxy}phenyl)-3-(imidazo[1,2-a]pyridin-7-ylmethyl)urea;
1-(4-{[1-(2,5-difluorobenzoyl)piperidin-4-yl]oxy}phenyl)-3-(imidazo[1,2-a]pyridin-7-ylmethyl)urea;
1-(4-{[1-(3,4-difluorobenzoyl)piperidin-4-yl]oxy}phenyl)-3-(imidazo[1,2-a]pyridin-7-ylmethyl)urea;
1-(4-{[1-(3,5-difluorobenzoyl)piperidin-4-yl]oxy}phenyl)-3-(imidazo[1,2-a]pyridin-7-ylmethyl)urea;
1-[(3-chloroimidazo[1,2-a]pyridin-7-yl)methyl]-3-{4-[1-(2-methylpropanoyl)piperidin-4-yl]phenyl}urea;
tert-butyl 4-(3-fluoro-4-{[(imidazo[1,2-a]pyridin-7-ylmethyl)carbamoyl]amino}phenyl)piperidine-1-carboxylate;
1-(4-{1-[(2-chloropyridin-3-yl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(3-methylbut-2-enoyl)piperidin-4-yl]phenyl}urea;
1-{4-[1-(3,3-dimethylbutanoyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(2-methylcyclopent-1-en-1-yl)carbonyl]piperidin-4-yl}phenyl)urea;
1-{4-[1-(2-ethylbutanoyl)piperidin-4-yl]phenyl}-3-(imidazo[1,2-a]pyridin-7-ylmethyl)urea;
1-(4-{1-[(4-fluorophenoxy)acetyl]piperidin-4-yl}phenyl)-3-(imidazo[1,2-a]pyridin-7-ylmethyl)urea;
1-{4-[1-(2,4-dimethoxybenzoyl)piperidin-4-yl]phenyl}-3-(imidazo[1,2-a]pyridin-7-ylmethyl)urea;
1-{4-[1-(cyclohex-3-en-1-ylcarbonyl)piperidin-4-yl]phenyl}-3-(imidazo[1,2-a]pyridin-7-ylmethyl)urea;
1-{4-[1-(2,5-dimethoxybenzoyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(2-methoxyphenyl)acetyl]piperidin-4-yl}phenyl)urea;
1-{4-[1-(3-hydroxy-2-phenylpropanoyl)piperidin-4-yl]phenyl}-3-(imidazo[1,2-a]pyridin-7-ylmethyl)urea;
1-{4-[1-(2,6-dimethoxybenzoyl)piperidin-4-yl]phenyl}-3-(imidazo[1,2-a]pyridin-7-ylmethyl)urea;
1-{4-[1-(N,N-diethyl-beta-alanyl)piperidin-4-yl]phenyl}-3-(imidazo[1,2-a]pyridin-7-ylmethyl)urea;
1-(4-{1-[(2-chloro-6-methylpyridin-4-yl)carbonyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(3-methoxyphenyl)acetyl]piperidin-4-yl}phenyl)urea;
1-(imidazo[1,2-a]pyridin-7-ylmethyl)-3-(4-{1-[(1-oxo-2,3-dihydro-1H-inden-4-yl)carbonyl]piperidin-4-yl}phenyl)urea;
1-{4-[1-(2-chloro-4-cyanobenzoyl)piperidin-4-yl]phenyl}-3-(imidazo[1,2-a]pyridin-7-ylmethyl)urea;

1-(imidazo[1,2-a]pyridin-7-ylmethyl)-3-(4-{1-[(2E)-2-methylbut-2-enoyl]piperidin-4-yl}phenyl)urea;
1-(imidazo[1,2-a]pyridin-7-ylmethyl)-3-{4-[1-(1H-indol-3-ylacetyl)piperidin-4-yl]phenyl}urea;
1-{4-[1-(2-hydroxy-3-methylbenzoyl)piperidin-4-yl]phenyl}-3-(imidazo[1,2-a]pyridin-7-ylmethyl)urea;
1-(imidazo[1,2-a]pyridin-7-ylmethyl)-3-[4-(1-{[1-(propan-2-yl)-1H-pyrazol-3-yl]carbonyl}piperidin-4-yl)phenyl]urea;
1-(4-{1-[(2S)-2,3-dihydro-1,4-benzodioxin-2-ylcarbonyl]piperidin-4-yl}phenyl)-3-(imidazo[1,2-a]pyridin-7-ylmethyl)urea;
1-(4-{1-[(3-cyclopropyl-1-methyl-1H-pyrazol-5-yl)carbonyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(2-methyl-4,5,6,7-tetrahydro-2H-indazol-3-yl)carbonyl]piperidin-4-yl}phenyl)urea;
1-(imidazo[1,2-a]pyridin-7-ylmethyl)-3-{4-[1-(4,5,6,7-tetrahydro-2,1-benzoxazol-3-ylcarbonyl)piperidin-4-yl]phenyl}urea;
1-(4-{1-[(2-chloro-5-fluoropyridin-4-yl)carbonyl]piperidin-4-yl}phenyl)-3-(imidazo[1,2-a]pyridin-7-ylmethyl)urea;
1-(4-{1-[(3-fluoro-6-methylpyridin-2-yl)carbonyl]piperidin-4-yl}phenyl)-3-(imidazo[1,2-a]pyridin-7-ylmethyl)urea;
1-(4-{1-[(2-chloro-3-fluoropyridin-4-yl)carbonyl]piperidin-4-yl}phenyl)-3-(imidazo[1,2-a]pyridin-7-ylmethyl)urea;
1-(4-{1-[(3-chloropyridin-2-yl)carbonyl]piperidin-4-yl}phenyl)-3-(imidazo[1,2-a]pyridin-7-ylmethyl)urea;
1-(imidazo[1,2-a]pyridin-7-ylmethyl)-3-[4-(1-{[1-(pyridin-2-yl)cyclopropyl]carbonyl}piperidin-4-yl)phenyl]urea;
1-(4-{1-[(1-cyclopentyl-1H-pyrazol-3-yl)carbonyl]piperidin-4-yl}phenyl)-3-(imidazo[1,2-a]pyridin-7-ylmethyl)urea;
1-[4-(1-{[1-(difluoromethyl)-1H-pyrazol-5-yl]carbonyl}piperidin-4-yl)phenyl]-3-(imidazo[1,2-a]pyridin-7-ylmethyl)urea;
1-{4-[1-(2,3-dihydro-1,4-benzodioxin-2-ylcarbonyl)piperidin-4-yl]phenyl}-3-(imidazo[1,2-a]pyridin-7-ylmethyl)urea;
1-{4-[1-(2,3-dihydro-1-benzofuran-2-ylcarbonyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(4-methoxycyclohexyl)carbonyl]piperidin-4-yl}phenyl)urea;
1-{4-[1-(2,3-dihydro-1,4-benzodioxin-5-ylcarbonyl)piperidin-4-yl]phenyl}-3-(imidazo[1,2-a]pyridin-7-ylmethyl)urea;
1-(imidazo[1,2-a]pyridin-7-ylmethyl)-3-{4-[1-(isoquinolin-4-ylcarbonyl)piperidin-4-yl]phenyl}urea;
1-(imidazo[1,2-a]pyridin-7-ylmethyl)-3-(4-{1-[(2-methyl-1,3-benzoxazol-6-yl)carbonyl]piperidin-4-yl}phenyl)urea;
1-(4-{1-[(1-tert-butyl-3-methyl-1H-pyrazol-5-yl)carbonyl]piperidin-4-yl}phenyl)-3-(imidazo[1,2-a]pyridin-7-ylmethyl)urea;
1-(4-{1-[(1-cyanocyclopentyl)carbonyl]piperidin-4-yl}phenyl)-3-(imidazo[1,2-a]pyridin-7-ylmethyl)urea;
1-{4-[1-(cinnolin-4-ylcarbonyl)piperidin-4-yl]phenyl}-3-(imidazo[1,2-a]pyridin-7-ylmethyl)urea;
1-(imidazo[1,2-a]pyridin-7-ylmethyl)-3-{4-[1-(quinolin-7-ylcarbonyl)piperidin-4-yl]phenyl}urea;
1-{4-[1-(5-cyano-2-fluorobenzoyl)piperidin-4-yl]phenyl}-3-(imidazo[1,2-a]pyridin-7-ylmethyl)urea;
1-(4-{1-[(3-cyclopropyl-1,2-oxazol-5-yl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(5,6,7,8-tetrahydroquinolin-3-ylcarbonyl)piperidin-4-yl]phenyl}urea;
1-{4-[1-(3,4-dihydro-2H-pyrano[2,3-b]pyridin-6-ylcarbonyl)piperidin-4-yl]phenyl}-3-(imidazo[1,2-a]pyridin-7-ylmethyl)urea;
1-(imidazo[1,2-a]pyridin-7-ylmethyl)-3-{4-[1-(isoquinolin-7-ylcarbonyl)piperidin-4-yl]phenyl}urea;
1-(imidazo[1,2-a]pyridin-7-ylmethyl)-3-{4-[1-(quinoxalin-2-ylcarbonyl)piperidin-4-yl]phenyl}urea;
1-(imidazo[1,2-a]pyridin-7-ylmethyl)-3-(4-{1-[(2E)-3-(2-methoxypyridin-3-yl)prop-2-enoyl]piperidin-4-yl}phenyl)urea;
1-(imidazo[1,2-a]pyridin-7-ylmethyl)-3-(4-{1-[(2E)-3-(pyridin-2-yl)prop-2-enoyl]piperidin-4-yl}phenyl)urea;
1-(4-{1-[(4-chloro-2,6-dimethylpyridin-3-yl)carbonyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(8-methylimidazo[1,2-a]pyridin-2-yl)carbonyl]piperidin-4-yl}phenyl)urea;
1-(4-{1-[(2-ethoxypyridin-4-yl)carbonyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(1-methyl-4,5,6,7-tetrahydro-1H-indazol-3-yl)carbonyl]piperidin-4-yl}phenyl)urea;
1-(imidazo[1,2-a]pyridin-7-ylmethyl)-3-(4-{1-[(4-methyl-4H-furo[3,2-b]pyrrol-5-yl)carbonyl]piperidin-4-yl}phenyl)urea;
1-(imidazo[1,2-a]pyridin-7-ylmethyl)-3-(4-{1-[(2-methyl-2,3-dihydro-1-benzofuran-5-yl)carbonyl]piperidin-4-yl}phenyl)urea;
1-(4-{1-[(4-chloro-1-ethyl-1H-pyrazol-5-yl)carbonyl]piperidin-4-yl}phenyl)-3-(imidazo[1,2-a]pyridin-7-ylmethyl)urea;
1-{4-[1-(3-cyano-5-fluorobenzoyl)piperidin-4-yl]phenyl}-3-(imidazo[1,2-a]pyridin-7-ylmethyl)urea;
1-(imidazo[1,2-a]pyridin-7-ylmethyl)-3-{4-[1-(isoquinolin-8-ylcarbonyl)piperidin-4-yl]phenyl}urea;
1-(4-{1-[(4-cyanophenyl)acetyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(3-methoxythiophen-2-yl)carbonyl]piperidin-4-yl}phenyl)urea;
1-{4-[1-(3-cyano-4-fluorobenzoyl)piperidin-4-yl]phenyl}-3-(imidazo[1,2-a]pyridin-7-ylmethyl)urea;
1-(imidazo[1,2-a]pyridin-7-ylmethyl)-3-{4-[1-(4,5,6,7-tetrahydro-1,3-benzothiazol-2-ylcarbonyl)piperidin-4-yl]phenyl}urea;
1-{4-[1-(1,3-benzothiazol-2-ylcarbonyl)piperidin-4-yl]phenyl}-3-(imidazo[1,2-a]pyridin-7-ylmethyl)urea;
1-(4-{1-[(3-ethyl-1,2-oxazol-5-yl)carbonyl]piperidin-4-yl}phenyl)-3-(imidazo[1,2-a]pyridin-7-ylmethyl)urea;
1-(imidazo[1,2-a]pyridin-7-ylmethyl)-3-[4-(1-{[3-methyl-1-(prop-2-en-1-yl)-1H-pyrazol-5-yl]carbonyl}piperidin-4-yl)phenyl]urea;
1-{4-[1-(1,2,3-benzothiadiazol-5-ylcarbonyl)piperidin-4-yl]phenyl}-3-(imidazo[1,2-a]pyridin-7-ylmethyl)urea;
1-(4-{1-[(2-ethyl-1,3-thiazol-4-yl)carbonyl]piperidin-4-yl}phenyl)-3-(imidazo[1,2-a]pyridin-7-ylmethyl)urea;
1-(4-{1-[(5,6-dimethylpyridin-3-yl)carbonyl]piperidin-4-yl}phenyl)-3-(imidazo[1,2-a]pyridin-7-ylmethyl)urea;
1-{4-[1-(1,3-benzothiazol-7-ylcarbonyl)piperidin-4-yl]phenyl}-3-(imidazo[1,2-a]pyridin-7-ylmethyl)urea;
1-(4-{1-[2-(3-fluorophenoxy)propanoyl]piperidin-4-yl}phenyl)-3-(imidazo[1,2-a]pyridin-7-ylmethyl)urea;
1-(4-{1-[(3,5-difluoropyridin-2-yl)carbonyl]piperidin-4-yl}phenyl)-3-(imidazo[1,2-a]pyridin-7-ylmethyl)urea;

1-[4-(1-benzoylpiperidin-4-yl)-2-fluorophenyl]-3-(imidazo[1,2-a]pyridin-7-ylmethyl)urea;
1-{4-[1-(2,2-dimethylpropanoyl)piperidin-4-yl]-2-fluorophenyl}-3-(imidazo[1,2-a]pyridin-7-ylmethyl)urea;
1-{4-[1-(3,3-dimethylbutanoyl)piperidin-4-yl]-2-fluorophenyl}-3-(imidazo[1,2-a]pyridin-7-ylmethyl)urea;
1-{2-fluoro-4-[1-(4-methylpentanoyl)piperidin-4-yl]phenyl}-3-(imidazo[1,2-a]pyridin-7-ylmethyl)urea;
1-(2-fluoro-4-{1-[(2S)-2-methylbutanoyl]piperidin-4-yl}phenyl)-3-(imidazo[1,2-a]pyridin-7-ylmethyl)urea;
1-{2-fluoro-4-[1-(tetrahydro-2H-pyran-4-ylcarbonyl)piperidin-4-yl]phenyl}-3-(imidazo[1,2-a]pyridin-7-ylmethyl)urea;
1-{2-fluoro-4-[1-(pyridin-2-ylcarbonyl)piperidin-4-yl]phenyl}-3-(imidazo[1,2-a]pyridin-7-ylmethyl)urea;
1-{4-[1-(2-cyanobenzoyl)piperidin-4-yl]-2-fluorophenyl}-3-(imidazo[1,2-a]pyridin-7-ylmethyl)urea;
1-{2-fluoro-4-[1-(2-methylpropanoyl)piperidin-4-yl]phenyl}-3-(imidazo[1,2-a]pyridin-7-ylmethyl)urea;
1-(4-{1-[(2-cyclopropyl-1,3-thiazol-5-yl)carbonyl]piperidin-4-yl}phenyl)-3-(imidazo[1,2-a]pyridin-7-ylmethyl)urea;
1-{4-[1-(1,3-benzothiazol-5-ylcarbonyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(1-methyl-1H-indazol-6-yl)carbonyl]piperidin-4-yl}phenyl)urea;
1-(4-{1-[(4-chloro-1,3-dimethyl-1H-pyrazol-5-yl)carbonyl]piperidin-4-yl}phenyl)-3-(imidazo[1,2-a]pyridin-7-ylmethyl)urea;
1-(4-{1-[(5-ethylpyridin-2-yl)carbonyl]piperidin-4-yl}phenyl)-3-(imidazo[1,2-a]pyridin-7-ylmethyl)urea;
1-(4-{1-[(3-chloro-5-cyanopyridin-2-yl)carbonyl]piperidin-4-yl}phenyl)-3-(imidazo[1,2-a]pyridin-7-ylmethyl)urea;
1-(4-{1-[(1-cyano-3-methylcyclobutyl)carbonyl]piperidin-4-yl}phenyl)-3-(imidazo[1,2-a]pyridin-7-ylmethyl)urea;
1-(4-{1-[(1,5-diethyl-1H-1,2,3-triazol-4-yl)carbonyl]piperidin-4-yl}phenyl)-3-(imidazo[1,2-a]pyridin-7-ylmethyl)urea;
1-(imidazo[1,2-a]pyridin-7-ylmethyl)-3-{4-[1-(thieno[3,2-b]furan-5-ylcarbonyl)piperidin-4-yl]phenyl}urea;
1-(imidazo[1,2-a]pyridin-7-ylmethyl)-3-(4-{1-[(4-methoxythiophen-2-yl)carbonyl]piperidin-4-yl}phenyl)urea;
1-(4-{1-[(5-cyanothiophen-2-yl)carbonyl]piperidin-4-yl}phenyl)-3-(imidazo[1,2-a]pyridin-7-ylmethyl)urea;
1-(4-{1-[(5-cyclopropylpyridin-2-yl)carbonyl]piperidin-4-yl}phenyl)-3-(imidazo[1,2-a]pyridin-7-ylmethyl)urea;
1-{4-[1-(4-cyano-2,6-difluorobenzoyl)piperidin-4-yl]phenyl}-3-(imidazo[1,2-a]pyridin-7-ylmethyl)urea;
1-[4-(1-{[1-ethyl-3-(propan-2-yl)-1H-pyrazol-4-yl]carbonyl}piperidin-4-yl)phenyl]-3-(imidazo[1,2-a]pyridin-7-ylmethyl)urea;
1-{4-[1-(1-benzofuran-3-ylcarbonyl)piperidin-4-yl]phenyl}-3-(imidazo[1,2-a]pyridin-7-ylmethyl)urea;
1-(imidazo[1,2-a]pyridin-7-ylmethyl)-3-(4-{1-[(4-methoxy-5-methylpyridin-2-yl)carbonyl]piperidin-4-yl}phenyl)urea;
1-(4-{1-[(1-cyclopentyl-1H-pyrazol-5-yl)carbonyl]piperidin-4-yl}phenyl)-3-(imidazo[1,2-a]pyridin-7-ylmethyl)urea;
1-(4-{1-[(4-chloro-1,3-thiazol-5-yl)carbonyl]piperidin-4-yl}phenyl)-3-(imidazo[1,2-a]pyridin-7-ylmethyl)urea;
1-(4-{1-[(3-cyanothiophen-2-yl)carbonyl]piperidin-4-yl}phenyl)-3-(imidazo[1,2-a]pyridin-7-ylmethyl)urea;
1-(imidazo[1,2-a]pyridin-7-ylmethyl)-3-[4-(1-{[4-(propan-2-yl)pyrimidin-5-yl]carbonyl}piperidin-4-yl)phenyl]urea;
1-(imidazo[1,2-a]pyridin-7-ylmethyl)-3-(4-{1-[(1-methyl-5-propyl-1H-pyrazol-4-yl)carbonyl]piperidin-4-yl}phenyl)urea;
1-(4-{1-[2-(3-cyclopropyl-1H-pyrazol-1-yl)propanoyl]piperidin-4-yl}phenyl)-3-(imidazo[1,2-a]pyridin-7-ylmethyl)urea;
1-(imidazo[1,2-a]pyridin-7-ylmethyl)-3-{4-[1-(pyrazolo[1,5-a]pyridin-2-ylcarbonyl)piperidin-4-yl]phenyl}urea;
1-{4-[1-(1-benzofuran-5-ylcarbonyl)piperidin-4-yl]phenyl}-3-(imidazo[1,2-a]pyridin-7-ylmethyl)urea;
1-(imidazo[1,2-a]pyridin-7-ylmethyl)-3-[4-(1-{[2-(propan-2-yl)-1,3-oxazol-4-yl]carbonyl}piperidin-4-yl)phenyl]urea;
1-(imidazo[1,2-a]pyridin-7-ylmethyl)-3-(4-{1-[(1-methyl-1H-indazol-7-yl)carbonyl]piperidin-4-yl}phenyl)urea;
1-(imidazo[1,2-a]pyridin-7-ylmethyl)-3-(4-{1-[(2-methoxy-5-methylpyridin-3-yl)carbonyl]piperidin-4-yl}phenyl)urea;
1-(4-{1-[(5,6-dimethoxypyridin-2-yl)carbonyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(2-methyl-2H-indazol-4-yl)carbonyl]piperidin-4-yl}phenyl)urea;
1-(4-{1-[(2-ethylpiperidin-1-yl)(oxo)acetyl]piperidin-4-yl}phenyl)-3-(imidazo[1,2-a]pyridin-7-ylmethyl)urea;
1-(imidazo[1,2-a]pyridin-7-ylmethyl)-3-(4-{1-[(2-methyl-2H-indazol-6-yl)carbonyl]piperidin-4-yl}phenyl)urea;
1-(imidazo[1,2-a]pyridin-7-ylmethyl)-3-(4-{1-[(1-methyl-1H-indazol-4-yl)carbonyl]piperidin-4-yl}phenyl)urea;
1-(imidazo[1,2-a]pyridin-7-ylmethyl)-3-[4-(1-{[2-(trifluoromethyl)furan-3-yl]carbonyl}piperidin-4-yl)phenyl]urea; and pharmaceutically acceptable salts thereof.

Embodiments of Formula (VA)

In another aspect, the present invention provides compounds of Formula (VA)

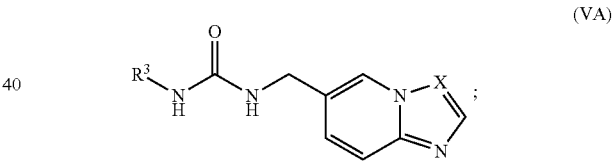

(VA)

and pharmaceutically acceptable salts thereof; wherein X and $R^3$ are as described herein for Formula (IA).

One embodiment pertains to compounds of Formula (VA) or pharmaceutically acceptable salts thereof;
wherein
X is N or $CY^1$;
$Y^1$ is independently selected from the group consisting of hydrogen, alkyl, alkoxy, haloalkyl, hydroxyalkyl, OH, CN, F, Cl, Br, and I;
$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, C(O)C(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$, at each occurrence, is independently selected from the group consisting of aryl, heterocyclyl, cycloalkyl, cycloalkenyl, alkyl, alkenyl, and alkynyl; wherein each R$^{10}$ alkyl, alkenyl, and alkynyl is optionally substituted with one, two, three or four substituents independently selected from the group consisting of alkoxy, F, Cl, Br and I; and R$^{11}$, at each occurrence, is independently selected from the group consisting of aryl, heterocyclyl, cycloalkyl, cycloalkenyl, alkyl, alkenyl, and alkynyl;

with the proviso that when X is CY$^1$ and Y$^1$ is hydrogen; and R$^3$ is thiazolyl; the R$^3$ thiazolyl is substituted with one substituent.

In one embodiment of Formula (VA), X is N or CY$^1$. In another embodiment of Formula (VA), X is N. In another embodiment of Formula (VA), X is CY$^1$.

In one embodiment of Formula (VA), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (VA), X is $CY^1$; and $Y^1$ is independently selected from the group consisting of hydrogen, Cl, Br, and I. In another embodiment of Formula (VA), X is $CY^1$; and $Y^1$ is Cl. In another embodiment of Formula (VA), X is $CY^1$; and $Y^1$ is hydrogen.

In one embodiment of Formula (VA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I. In another embodiment of Formula (VA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VA), $R^3$ is phenyl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (VA), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (VA), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (VA), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, OH, and F.

In another embodiment of Formula (VA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (VA), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (VA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (VA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (VA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (VA), $R^7$, at each occurrence, is alkyl or heterocyclyl.

In one embodiment of Formula (VA), $R^8$, at each occurrence, is independently selected from the group consisting of alkyl, alkenyl, and alkynyl. In another embodiment of Formula (VA), $R^8$, at each occurrence, is independently alkyl.

In one embodiment of Formula (VA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (VA), $R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (VA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (VA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (VA), $R^{11}$, at each occurrence, is independently selected from the group consisting of aryl, heterocyclyl, cycloalkyl, cycloalkenyl, alkyl, alkenyl, and alkynyl. In another embodiment of Formula (VA), $R^{11}$, at each occurrence, is independently alkyl. In another embodiment of Formula (VA), $R^{11}$, at each occurrence, is independently cycloalkyl.

One embodiment pertains to compounds or pharmaceutically acceptable salts thereof, which are useful as inhibitors of NAMPT, the compounds having Formula (VA)

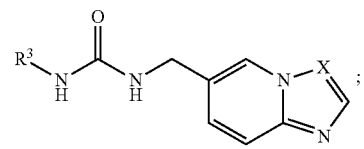

Formula (VA)

wherein
X is N or $CY^1$;
$Y^1$ is independently selected from the group consisting of hydrogen, F, Cl, Br, and I;
$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$, at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F; and $R^{11}$, at each occurrence, is independently cycloalkyl or alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (VA), which include 4-{[(imidazo[1,2-a]pyridin-6-ylmethyl)carbamoyl]amino}-N-(3-methylbutyl)benzamide;

2-cyclopentyl-N-(4-{[(imidazo[1,2-a]pyridin-6-ylmethyl)carbamoyl]amino}phenyl)acetamide;

N-(4-{[(imidazo[1,2-a]pyridin-6-ylmethyl)carbamoyl]amino}phenyl)-4-methylpentanamide;

3-cyclopentyl-N-(4-{[(imidazo[1,2-a]pyridin-6-ylmethyl)carbamoyl]amino}phenyl)propanamide;

N-(4-{[(imidazo[1,2-a]pyridin-6-ylmethyl)carbamoyl]amino}phenyl)-2-(propan-2-yloxy)acetamide;

N-(4-{[(imidazo[1,2-a]pyridin-6-ylmethyl)carbamoyl]amino}phenyl)-2-(tetrahydrofuran-2-yl)acetamide;

N-(4-{[(imidazo[1,2-a]pyridin-6-ylmethyl)carbamoyl]amino}phenyl)-2-(tetrahydro-2H-pyran-4-yl)acetamide;

N-(4-{[(imidazo[1,2-a]pyridin-6-ylmethyl)carbamoyl]amino}phenyl)-3-phenylpropanamide;

1-(imidazo[1,2-a]pyridin-6-ylmethyl)-3-[4-(1-propyl-1H-pyrazol-4-yl)phenyl]urea;

1-(imidazo[1,2-a]pyridin-6-ylmethyl)-3-{4-[1-(2-methylpropyl)-1H-pyrazol-4-yl]phenyl}urea; and pharmaceutically acceptable salts thereof Embodiments of Formula (VIA)

In another aspect, the present invention provides compounds of Formula (VIA)

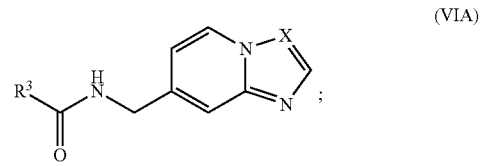

(VIA)

and pharmaceutically acceptable salts thereof; wherein X and $R^3$ are as described herein for Formula (IA).

One embodiment pertains to compounds of Formula (VIA) or pharmaceutically acceptable salts thereof;

wherein

X is N or $CY^1$;

$Y^1$ is independently selected from the group consisting of hydrogen, alkyl, alkoxy, haloalkyl, hydroxyalkyl, OH, CN, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $CN$, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, $COH$, $CN$, $NO_2$, F, Cl, Br and I;

$R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I; and $R^{11}$, at each occurrence, is independently selected from the group consisting of aryl, heterocyclyl, cycloalkyl, cycloalkenyl, alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (VIA), X is N or $CY^1$. In another embodiment of Formula (VIA), X is N. In another embodiment of Formula (VIA), X is $CY^1$.

In one embodiment of Formula (VIA), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (VIA), X is $CY^1$; and $Y^1$ is independently selected from the group consisting of hydrogen, Cl, Br, and I. In another embodiment of Formula (VIA), X is $CY^1$; and $Y^1$ is Cl. In another embodiment of Formula (VIA), X is $CY^1$; and $Y^1$ is hydrogen.

In one embodiment of Formula (VIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I. In another embodiment of Formula (VIA), R$^3$ is independently selected from the group consisting of phenyl and 5-6 membered heteroaryl; wherein each R$^3$ phenyl is substituted at the para position with one substituent independently selected from the group consisting of R$^4$, OR$^4$, SO$_2$R$^4$, C(O)R$^4$, NHC(O)R$^4$, NR$^4$C(O)R$^4$, NHS(O)$_2$R$^4$, NHC(O)OR$^4$, and C(O)NHR$^4$; wherein each R$^3$ phenyl is optionally additionally substituted with one substituent independently selected from the group consisting of F, Cl, Br and I; wherein each R$^3$ 5-6 membered heteroaryl is substituted with one, two, three or four substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I.

In one embodiment of Formula (VIA), R$^3$ is phenyl; wherein each R$^3$ phenyl is substituted at the para position with one substituent independently selected from the group consisting of R$^4$, OR$^4$, SO$_2$R$^4$, C(O)R$^4$, NHC(O)R$^4$, NR$^4$C(O)R$^4$, NHS(O)$_2$R$^4$, NHC(O)OR$^4$, and C(O)NHR$^4$; and wherein each R$^3$ phenyl is optionally additionally substituted with one substituent independently selected from the group consisting of F, Cl, Br and I. In another embodiment of Formula (VIA), R$^3$ is 5-6 membered heteroaryl; wherein each R$^3$ 5-6 membered heteroaryl is substituted with one, two, three or four substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I. In another embodiment of Formula (VIA), R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I.

In one embodiment of Formula (VIA), R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I. In another embodiment of Formula (VIA), R$^4$, at each occurrence, is independently selected from the group consisting of alkyl, aryl, cycloalkyl, and 3-12 membered heterocyclyl; wherein each R$^4$ alkyl is optionally substituted with one, two, three or four substituents independently selected from the group consisting of R$^5$, OR$^5$, C(O)R$^5$, NHC(O)R$^5$, OH, F, Cl, Br and I; wherein each R$^4$ aryl, cycloalkyl and 3-12 membered heterocyclyl is optionally substituted with one, two, three or four substituents independently selected from the group consisting of R$^6$, OR$^6$, SO$_2$R$^6$, C(O)R$^6$, CO(O)R$^6$, C(O)C(O)R$^6$, NHC(O)R$^6$, C(O)N(R$^6$)$_2$, OH, and F.

In another embodiment of Formula (VIA), R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I. In another embodiment of Formula (VIA), R$^5$, at each occurrence, is independently selected from the group consisting of alkyl, aryl, heterocyclyl, and cycloalkyl; wherein each R$^5$ alkyl is optionally substituted with one, two, three or four substituents independently selected from the group consisting of R$^7$, OR$^7$, and OH; wherein each R$^5$ aryl and heterocyclyl is optionally substituted with one, two, three or four substituents independently selected from the group consisting of R$^8$, OR$^8$, CN, F, Cl, Br and I.

In one embodiment of Formula (VIA), R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NH_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (VIA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (VIA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (VIA), $R^7$, at each occurrence, is alkyl or heterocyclyl.

In one embodiment of Formula (VIA), $R^8$, at each occurrence, is independently selected from the group consisting of alkyl, alkenyl, and alkynyl. In another embodiment of Formula (VIA), $R^8$, at each occurrence, is independently alkyl.

In one embodiment of Formula (VIA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (VIA), $R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (VIA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (VIA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (VIA), $R^{11}$, at each occurrence, is independently selected from the group consisting of aryl, heterocyclyl, cycloalkyl, cycloalkenyl, alkyl, alkenyl, and alkynyl. In another embodiment of Formula (VIA), $R^{11}$, at each occurrence, is independently alkyl. In another embodiment of Formula (VIA), $R^{11}$, at each occurrence, is independently cycloalkyl.

One embodiment pertains to compounds or pharmaceutically acceptable salts thereof, which are useful as inhibitors of NAMPT, the compounds having Formula (VIA)

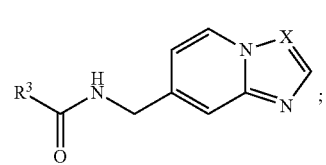

Formula (VIA)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$, at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F; and $R^{11}$, at each occurrence, is independently cycloalkyl or alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (VIA), which include 2-[(4-cyanobenzyl)(3-methoxypropanoyl)amino]-N-(imidazo[1,2-a]pyridin-7-ylmethyl)-1,3-thiazole-5-carboxamide;

4-[(cyclopentylacetyl)amino]-N-(imidazo[1,2-a]pyridin-7-ylmethyl)benzamide;

N-(imidazo[1,2-a]pyridin-7-ylmethyl)-2-[3-methoxypropanoyl)(tetrahydrofuran-2-ylmethyl)amino]-1,3-thiazole-5-carboxamide;

N-(imidazo[1,2-a]pyridin-7-ylmethyl)-2-{[(2-methoxyethyl)carbamoyl](tetrahydrofuran-2-ylmethyl)amino}-1,3-thiazole-5-carboxamide;

N-(imidazo[1,2-a]pyridin-7-ylmethyl)-5-[1-(2-methylpropyl)-1H-pyrazol-4-yl]thiophene-2-carboxamide;

N-(imidazo[1,2-a]pyridin-7-ylmethyl)-2-[(4R)-2-oxo-4-(propan-2-yl)-1,3-oxazolidin-3-yl]-1,3-thiazole-5-carboxamide;

5-[1-(2-hydroxy-2-methylpropyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-2-[(4S)-2-oxo-4-(propan-2-yl)-1,3-oxazolidin-3-yl]-1,3-thiazole-5-carboxamide;

2-{(4R)-4-[(benzyloxy)methyl]-2-oxo-1,3-oxazolidin-3-yl}-N-(imidazo[1,2-a]pyridin-7-ylmethyl)-1,3-thiazole-5-carboxamide;

2-{(4S)-4-[(benzyloxy)methyl]-2-oxo-1,3-oxazolidin-3-yl}-N-(imidazo[1,2-a]pyridin-7-ylmethyl)-1,3-thiazole-5-carboxamide;

N-(imidazo[1,2-a]pyridin-7-ylmethyl)-2-{(1,2-oxazol-3-ylacetyl)[(2R)-tetrahydrofuran-2-ylmethyl]amino}-1,3-thiazole-5-carboxamide;

N-(imidazo[1,2-a]pyridin-7-ylmethyl)-2-{[(5-methyl-1,2-oxazol-3-yl)acetyl][(2R)-tetrahydrofuran-2-ylmethyl]amino}-1,3-thiazole-5-carboxamide;

N-(imidazo[1,2-a]pyridin-7-ylmethyl)-2-{[3-(1,2-oxazol-5-yl)propanoyl][(2R)-tetrahydrofuran-2-ylmethyl]amino}-1,3-thiazole-5-carboxamide;

N-(imidazo[1,2-a]pyridin-7-ylmethyl)-2-{[3-(1,2-oxazol-4-yl)propanoyl][(2R)-tetrahydrofuran-2-ylmethyl]amino}-1,3-thiazole-5-carboxamide;

N-(imidazo[1,2-a]pyridin-7-ylmethyl)-2-{[(2R)-tetrahydrofuran-2-ylmethyl](1,3-thiazol-4-ylacetyl)amino}-1,3-thiazole-5-carboxamide;

2-{[(1,5-dimethyl-1H-pyrazol-3-yl)acetyl][(2R)-tetrahydrofuran-2-ylmethyl]amino}-N-(imidazo[1,2-a]pyridin-7-ylmethyl)-1,3-thiazole-5-carboxamide;

N-(imidazo[1,2-a]pyridin-7-ylmethyl)-2-{[3-(1-methyl-1H-pyrazol-4-yl)propanoyl][(2R)-tetrahydrofuran-2-ylmethyl]amino}-1,3-thiazole-5-carboxamide;

2-{[(3,5-dimethyl-1,2-oxazol-4-yl)acetyl][(2R)-tetrahydrofuran-2-ylmethyl]amino}-N-(imidazo[1,2-a]pyridin-7-ylmethyl)-1,3-thiazole-5-carboxamide;

N-(imidazo[1,2-a]pyridin-7-ylmethyl)-2-{[(1-methyl-1H-pyrazol-4-yl)acetyl][(2R)-tetrahydrofuran-2-ylmethyl]amino}-1,3-thiazole-5-carboxamide;

N-(imidazo[1,2-a]pyridin-7-ylmethyl)-2-{[3-(1-methyl-1H-pyrrol-2-yl)propanoyl][(2R)-tetrahydrofuran-2-ylmethyl]amino}-1,3-thiazole-5-carboxamide;

2-[1-(2-hydroxy-2-methylpropyl)-1H-pyrazol-4-yl]-N-(imidazo[1,2-a]pyridin-7-ylmethyl)-1,3-thiazole-5-carboxamide;

N-(imidazo[1,2-a]pyridin-7-ylmethyl)-2-[1-(2-methylpropyl)-1H-pyrazol-4-yl]-1,3-thiazole-5-carboxamide;

tert-butyl {4-[(imidazo[1,2-a]pyridin-7-ylmethyl)carbamoyl]phenyl}carbamate;

N-(imidazo[1,2-a]pyridin-7-ylmethyl)-4-[(tetrahydro-2H-pyran-4-ylacetyl)amino]benzamide;

N-(imidazo[1,2-a]pyridin-7-ylmethyl)-4-[(tetrahydrofuran-2-ylacetyl)amino]benzamide;

N-(imidazo[1,2-a]pyridin-7-ylmethyl)-4-{[3-(tetrahydrofuran-2-yl)propanoyl]amino}benzamide;

N-(imidazo[1,2-a]pyridin-7-ylmethyl)-4-{[(propan-2-yloxy)acetyl]amino}benzamide;

4-[(3-cyclopentylpropanoyl)amino]-N-(imidazo[1,2-a]pyridin-7-ylmethyl)benzamide;

N-(imidazo[1,2-a]pyridin-7-ylmethyl)-4-[(4-methylpentanoyl)amino]benzamide;

N-(imidazo[1,2-a]pyridin-7-ylmethyl)-4-[(tetrahydrofuran-3-ylacetyl)amino]benzamide;

tert-butyl 4-{4-[(imidazo[1,2-a]pyridin-7-ylmethyl)carbamoyl]phenyl}piperidine-1-carboxylate;

2-{5-[(benzyloxy)methyl]-2-oxo-1,3-oxazolidin-3-yl}-N-(imidazo[1,2-a]pyridin-7-ylmethyl)-1,3-thiazole-5-carboxamide;

4-[1-(2-hydroxy-2-methylpropanoyl)piperidin-4-yl]-N-(imidazo[1,2-a]pyridin-7-ylmethyl)benzamide;

N-(imidazo[1,2-a]pyridin-7-ylmethyl)-4-[1-(tetrahydrofuran-3-ylcarbonyl)piperidin-4-yl]benzamide;

N-(imidazo[1,2-a]pyridin-7-ylmethyl)-4-[1-(tetrahydro-2H-pyran-4-ylcarbonyl)piperidin-4-yl]benzamide;

4-[1-(1,4-dioxan-2-ylcarbonyl)piperidin-4-yl]-N-(imidazo[1,2-a]pyridin-7-ylmethyl)benzamide;

4-{1-[(1,1-dioxidotetrahydro-2H-thiopyran-4-yl)carbonyl]piperidin-4-yl}-N-(imidazo[1,2-a]pyridin-7-ylmethyl)benzamide;

N-(imidazo[1,2-a]pyridin-7-ylmethyl)-4-[1-(tetrahydrofuran-2-ylacetyl)piperidin-4-yl]benzamide;

N-(imidazo[1,2-a]pyridin-7-ylmethyl)-4-[1-(tetrahydro-2H-pyran-4-ylacetyl)piperidin-4-yl]benzamide;

N-(imidazo[1,2-a]pyridin-7-ylmethyl)-4-{1-[(propan-2-yloxy)acetyl]piperidin-4-yl}benzamide;

N-(imidazo[1,2-a]pyridin-7-ylmethyl)-4-{1-[(2S)-2-methylbutanoyl]piperidin-4-yl}benzamide;

N-(imidazo[1,2-a]pyridin-7-ylmethyl)-4-[1-(2-methylpropanoyl)piperidin-4-yl]benzamide;

5-(1-acetyl-1,2,3,6-tetrahydropyridin-4-yl)-N-(imidazo[1,2-a]pyridin-7-ylmethyl)thiophene-2-carboxamide;

N-(imidazo[1,2-a]pyridin-7-ylmethyl)-5-[1-(methylsulfonyl)-1,2,3,6-tetrahydropyridin-4-yl]thiophene-2-carboxamide;
2-[(2S)-2-(hydroxymethyl)-5-oxopyrrolidin-1-yl]-N-(imidazo[1,2-a]pyridin-7-ylmethyl)-1,3-thiazole-5-carboxamide;
N-(imidazo[1,2-a]pyridin-7-ylmethyl)-2-[(4R)-4-methyl-2-oxo-1,3-oxazolidin-3-yl]-1,3-thiazole-5-carboxamide;
5-[1-(cyclopropylsulfonyl)-1,2,3,6-tetrahydropyridin-4-yl]-N-(imidazo[1,2-a]pyridin-7-ylmethyl)thiophene-2-carboxamide;
N-(imidazo[1,2-a]pyridin-7-ylmethyl)-5-[1-(tetrahydro-2H-pyran-2-ylmethyl)-1H-pyrazol-4-yl]thiophene-2-carboxamide;
N-(imidazo[1,2-a]pyridin-7-ylmethyl)-5-[1-(tetrahydrofuran-2-ylmethyl)-1H-pyrazol-4-yl]thiophene-2-carboxamide;
N-(imidazo[1,2-a]pyridin-7-ylmethyl)-2-{2-oxo-5-[(propan-2-yloxy)methyl]-1,3-oxazolidin-3-yl}-1,3-thiazole-5-carboxamide;
N-(imidazo[1,2-a]pyridin-7-ylmethyl)-5-[(4R)-2-oxo-4-(propan-2-yl)-1,3-oxazolidin-3-yl]thiophene-2-carboxamide;
2-[5-(hydroxymethyl)-2-oxo-1,3-oxazolidin-3-yl]-N-(imidazo[1,2-a]pyridin-7-ylmethyl)-1,3-thiazole-5-carboxamide;
N-(imidazo[1,2-a]pyridin-7-ylmethyl)-5-[1-(tetrahydrofuran-3-ylmethyl)-1H-pyrazol-4-yl]thiophene-2-carboxamide;
N-(imidazo[1,2-a]pyridin-7-ylmethyl)-5-[1-(tetrahydro-2H-pyran-3-ylmethyl)-1H-pyrazol-4-yl]thiophene-2-carboxamide;
N-(imidazo[1,2-a]pyridin-7-ylmethyl)-5-{1-[(3-methyloxetan-3-yl)methyl]-1H-pyrazol-4-yl}thiophene-2-carboxamide;
N-(imidazo[1,2-a]pyridin-7-ylmethyl)-2-{(5S)-2-oxo-5-[(propan-2-yloxy)methyl]-1,3-oxazolidin-3-yl}-1,3-thiazole-5-carboxamide;
N-(imidazo[1,2-a]pyridin-7-ylmethyl)-2-{(5R)-2-oxo-5-[(propan-2-yloxy)methyl]-1,3-oxazolidin-3-yl}-1,3-thiazole-5-carboxamide;
N-(imidazo[1,2-a]pyridin-7-ylmethyl)-5-[1-(methoxyacetyl)piperidin-4-yl]thiophene-2-carboxamide;
5-(1-acetylpiperidin-4-yl)-N-(imidazo[1,2-a]pyridin-7-ylmethyl)thiophene-2-carboxamide;
N-(imidazo[1,2-a]pyridin-7-ylmethyl)-5-[1-(2-methylpropanoyl)piperidin-4-yl]thiophene-2-carboxamide;
5-[1-(cyclopropylcarbonyl)piperidin-4-yl]-N-(imidazo[1,2-a]pyridin-7-ylmethyl)thiophene-2-carboxamide;
N-(imidazo[1,2-a]pyridin-7-ylmethyl)-5-[1-(tetrahydrofuran-3-ylcarbonyl)piperidin-4-yl]thiophene-2-carboxamide;
N-(imidazo[1,2-a]pyridin-7-ylmethyl)-5-[1-(tetrahydro-2H-pyran-4-ylacetyl)piperidin-4-yl]thiophene-2-carboxamide;
N-(imidazo[1,2-a]pyridin-7-ylmethyl)-5-[1-(3-methylbutanoyl)piperidin-4-yl]thiophene-2-carboxamide;
N-(imidazo[1,2-a]pyridin-7-ylmethyl)-5-[1-(1,2-oxazol-5-ylcarbonyl)piperidin-4-yl]thiophene-2-carboxamide;
N-(imidazo[1,2-a]pyridin-7-ylmethyl)-5-[1-(tetrahydro-2H-pyran-4-ylmethyl)-1H-pyrazol-4-yl]thiophene-2-carboxamide;
5-[5-(hydroxymethyl)-2-oxo-1,3-oxazolidin-3-yl]-N-(imidazo[1,2-a]pyridin-7-ylmethyl)thiophene-2-carboxamide;
5-[(4R)-4-hydroxy-2-oxopyrrolidin-1-yl]-N-(imidazo[1,2-a]pyridin-7-ylmethyl)thiophene-2-carboxamide;
5-[(4S)-4-hydroxy-2-oxopyrrolidin-1-yl]-N-(imidazo[1,2-a]pyridin-7-ylmethyl)thiophene-2-carboxamide;
N-(imidazo[1,2-a]pyridin-7-ylmethyl)-5-[1-(2-methoxyethyl)-1H-pyrazol-4-yl]thiophene-2-carboxamide;
N-(imidazo[1,2-a]pyridin-7-ylmethyl)-5-[1-(methylsulfonyl)piperidin-4-yl]thiophene-2-carboxamide;
5-[1-(cyclohexylmethyl)-5-ethyl-1H-pyrazol-4-yl]-N-(imidazo[1,2-a]pyridin-7-ylmethyl)thiophene-2-carboxamide;
N-(imidazo[1,2-a]pyridin-7-ylmethyl)-5-{1-[(1-methoxy-3,3-dimethylcyclohexyl)methyl]-5-methyl-1H-pyrazol-4-yl}thiophene-2-carboxamide;
tert-butyl {2-fluoro-4-[(imidazo[1,2-a]pyridin-7-ylmethyl)carbamoyl]phenyl}carbamate;
N-(imidazo[1,2-a]pyridin-7-ylmethyl)-5-(1-propyl-1H-pyrazol-4-yl)thiophene-2-carboxamide;
N-(imidazo[1,2-a]pyridin-7-ylmethyl)-5-{1-[2-(morpholin-4-yl)ethyl]-1H-pyrazol-4-yl}thiophene-2-carboxamide;
5-(1-ethyl-1H-pyrazol-4-yl)-N-(imidazo[1,2-a]pyridin-7-ylmethyl)thiophene-2-carboxamide;
5-[1-(1,1-dioxidotetrahydrothiophen-3-yl)-1H-pyrazol-4-yl]-N-(imidazo[1,2-a]pyridin-7-ylmethyl)thiophene-2-carboxamide;
2-(1-benzoyl-1,2,3,6-tetrahydropyridin-4-yl)-N-(imidazo[1,2-a]pyridin-7-ylmethyl)-1,3-thiazole-5-carboxamide;
4-[1-(2-hydroxy-2-methylpropyl)-1H-pyrazol-4-yl]-N-(imidazo[1,2-a]pyridin-7-ylmethyl)benzamide;
N-(imidazo[1,2-a]pyridin-7-ylmethyl)-5-phenylthiophene-2-carboxamide;
N-(imidazo[1,2-a]pyridin-7-ylmethyl)-5-{1-[2-(methylsulfonyl)ethyl]-1H-pyrazol-4-yl}thiophene-2-carboxamide;
tert-butyl 3-{4-[(imidazo[1,2-a]pyridin-7-ylmethyl)carbamoyl]phenyl}pyrrolidine-1-carboxylate;
5-{1-[(2R)-2-hydroxypropyl]-1H-pyrazol-4-yl}-N-(imidazo[1,2-a]pyridin-7-ylmethyl)thiophene-2-carboxamide;
4-[(cyclopentylacetyl)amino]-3-fluoro-N-(imidazo[1,2-a]pyridin-7-ylmethyl)benzamide;
N-(imidazo[1,2-a]pyridin-7-ylmethyl)-4-{1-[(3S)-tetrahydrofuran-3-ylcarbonyl]piperidin-4-yl}benzamide;
N-(imidazo[1,2-a]pyridin-7-ylmethyl)-4-{1-[(3R)-tetrahydrofuran-3-ylcarbonyl]piperidin-4-yl}benzamide;
N-(imidazo[1,2-a]pyridin-7-ylmethyl)-4-{1-[(2R)-tetrahydrofuran-2-ylcarbonyl]piperidin-4-yl}benzamide;
N-(imidazo[1,2-a]pyridin-7-ylmethyl)-4-{1-[(2S)-tetrahydrofuran-2-ylcarbonyl]piperidin-4-yl}benzamide;
4-[1-(cyclopropylacetyl)piperidin-4-yl]-N-(imidazo[1,2-a]pyridin-7-ylmethyl)benzamide;
4-(1-acetylpiperidin-4-yl)-N-(imidazo[1,2-a]pyridin-7-ylmethyl)benzamide;
N-(imidazo[1,2-a]pyridin-7-ylmethyl)-4-[1-(2-methylpropyl)-1H-pyrazol-4-yl]benzamide;
5-[1-(1,4-dioxan-2-ylmethyl)-1H-pyrazol-4-yl]-N-(imidazo[1,2-a]pyridin-7-ylmethyl)thiophene-2-carboxamide;
5-[1-(2-hydroxyethyl)-1H-pyrazol-4-yl]-N-(imidazo[1,2-a]pyridin-7-ylmethyl)thiophene-2-carboxamide;
N-(imidazo[1,2-a]pyridin-7-ylmethyl)-5-[3-(propan-2-yloxy)phenyl]thiophene-2-carboxamide;
N-(imidazo[1,2-a]pyridin-7-ylmethyl)-2-[1-(tetrahydro-2H-pyran-4-ylcarbonyl)-1,2,3,6-tetrahydropyridin-4-yl]-1,3-thiazole-5-carboxamide;
N-(imidazo[1,2-a]pyridin-7-ylmethyl)-2-[1-(2-methylpropanoyl)-1,2,3,6-tetrahydropyridin-4-yl]-1,3-thiazole-5-carboxamide;
N-(imidazo[1,2-a]pyridin-7-ylmethyl)-4-({(3S)-1-[(2S)-2-methylbutanoyl]pyrrolidin-3-yl}oxy)benzamide;
N-(imidazo[1,2-a]pyridin-7-ylmethyl)-5-{3-[(2-methylpropanoyl)amino]oxetan-3-yl}thiophene-2-carboxamide;

5-[3-(benzoylamino)oxetan-3-yl]-N-(imidazo[1,2-a]pyridin-7-ylmethyl)thiophene-2-carboxamide;
N-(imidazo[1,2-a]pyridin-7-ylmethyl)-5-{3-[(tetrahydrofuran-3-ylacetyl)amino]oxetan-3-yl}thiophene-2-carboxamide;
N-(imidazo[1,2-a]pyridin-7-ylmethyl)-5-[3-(pentanoylamino)oxetan-3-yl]thiophene-2-carboxamide;
N-(imidazo[1,2-a]pyridin-7-ylmethyl)-4-({(3S)-1-[(3R)-tetrahydrofuran-2-ylcarbonyl]pyrrolidin-3-yl}oxy)benzamide;
N-(imidazo[1,2-a]pyridin-7-ylmethyl)-4-({(3S)-1-[(2R)-tetrahydrofuran-2-ylcarbonyl]pyrrolidin-3-yl}oxy)benzamide;
N-(imidazo[1,2-a]pyridin-7-ylmethyl)-4-({(3S)-1-[(2S)-tetrahydrofuran-2-ylcarbonyl]pyrrolidin-3-yl}oxy)benzamide;
N-(imidazo[1,2-a]pyridin-7-ylmethyl)-4-{[(3S)-1-(tetrahydro-2H-pyran-4-ylcarbonyl)pyrrolidin-3-yl]oxy}benzamide;
N-(imidazo[1,2-a]pyridin-7-ylmethyl)-4-{[(3S)-1-(tetrahydro-2H-pyran-4-ylacetyl)pyrrolidin-3-yl]oxy}benzamide;
5-{1-[(1,1-dioxidotetrahydro-2H-thiopyran-3-yl)methyl]-1H-pyrazol-4-yl}-N-(imidazo[1,2-a]pyridin-7-ylmethyl)thiophene-2-carboxamide;
N-(imidazo[1,2-a]pyridin-7-ylmethyl)-5-(1-methyl-1H-pyrazol-4-yl)thiophene-2-carboxamide;
N-(imidazo[1,2-a]pyridin-7-ylmethyl)-4-({(3S)-1-[(3S)-tetrahydrofuran-3-ylcarbonyl]pyrrolidin-3-yl}oxy)benzamide;
4-{[(3S)-1-(cyclopropylacetyl)pyrrolidin-3-yl]oxy}-N-(imidazo[1,2-a]pyridin-7-ylmethyl)benzamide;
4-{[(3S)-1-(2-hydroxy-2-methylpropanoyl)pyrrolidin-3-yl]oxy}-N-(imidazo[1,2-a]pyridin-7-ylmethyl)benzamide;
N-(imidazo[1,2-a]pyridin-7-ylmethyl)-4-{[(3S)-1-(3-methoxy-2-methylpropanoyl)pyrrolidin-3-yl]oxy}benzamide;
4-{[(3S)-1-butanoylpyrrolidin-3-yl]oxy}-N-(imidazo[1,2-a]pyridin-7-ylmethyl)benzamide;
N-(imidazo[1,2-a]pyridin-7-ylmethyl)-4-{[(3S)-1-(2-methylpropanoyl)pyrrolidin-3-yl]oxy}benzamide;
4-{[(3S)-1-(cyclopropylcarbonyl)pyrrolidin-3-yl]oxy}-N-(imidazo[1,2-a]pyridin-7-ylmethyl)benzamide;
4-{[(3S)-1-benzoylpyrrolidin-3-yl]oxy}-N-(imidazo[1,2-a]pyridin-7-ylmethyl)benzamide;
4-{[(3S)-1-(3-hydroxy-3-methylbutanoyl)pyrrolidin-3-yl]oxy}-N-(imidazo[1,2-a]pyridin-7-ylmethyl)benzamide;
2-(4-benzoylpiperazin-1-yl)-N-(imidazo[1,2-a]pyridin-7-ylmethyl)-1,3-thiazole-5-carboxamide;
N-(imidazo[1,2-a]pyridin-7-ylmethyl)-2-[4-(propan-2-yl)piperazin-1-yl]-1,3-thiazole-5-carboxamide;
N-(imidazo[1,2-a]pyridin-7-ylmethyl)-2-[4-(2-methoxyethyl)piperazin-1-yl]-1,3-thiazole-5-carboxamide;
N-(imidazo[1,2-a]pyridin-7-ylmethyl)-2-phenyl-1,3-thiazole-5-carboxamide;
N-(imidazo[1,2-a]pyridin-7-ylmethyl)-5-(1-methyl-1H-pyrazol-5-yl)thiophene-2-carboxamide;
tert-butyl 4-{4-[(imidazo[1,2-a]pyridin-7-ylmethyl)carbamoyl]phenoxy}piperidine-1-carboxylate;
N-(imidazo[1,2-a]pyridin-7-ylmethyl)-4-[1-(2-methylpropanoyl)pyrrolidin-3-yl]benzamide;
N-(imidazo[1,2-a]pyridin-7-ylmethyl)-4-{1-[(2S)-2-methylbutanoyl]pyrrolidin-3-yl}benzamide;
4-[1-(cyclopropylacetyl)pyrrolidin-3-yl]-N-(imidazo[1,2-a]pyridin-7-ylmethyl)benzamide;
4-(1-benzoylpyrrolidin-3-yl)-N-(imidazo[1,2-a]pyridin-7-ylmethyl)benzamide;
N-(imidazo[1,2-a]pyridin-7-ylmethyl)-4-{1-[(propan-2-yloxy)acetyl]pyrrolidin-3-yl}benzamide;
4-[1-(2-hydroxy-2-methylpropanoyl)pyrrolidin-3-yl]-N-(imidazo[1,2-a]pyridin-7-ylmethyl)benzamide;
N-(imidazo[1,2-a]pyridin-7-ylmethyl)-4-{1-[(2R)-tetrahydrofuran-2-ylcarbonyl]pyrrolidin-3-yl}benzamide;
N-(imidazo[1,2-a]pyridin-7-ylmethyl)-4-{1-[(2S)-tetrahydrofuran-2-ylcarbonyl]pyrrolidin-3-yl}benzamide;
N-(imidazo[1,2-a]pyridin-7-ylmethyl)-4-{1-[(3S)-tetrahydrofuran-3-ylcarbonyl]pyrrolidin-3-yl}benzamide;
N-(imidazo[1,2-a]pyridin-7-ylmethyl)-4-[1-(tetrahydro-2H-pyran-4-ylcarbonyl)pyrrolidin-3-yl]benzamide;
4-[1-(1,4-dioxan-2-ylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(tetrahydro-2H-pyran-4-ylacetyl)pyrrolidin-3-yl]benzamide;
N-(imidazo[1,2-a]pyridin-7-ylmethyl)-N'-(3-methylbutyl)benzene-1,4-dicarboxamide;
N-(imidazo[1,2-a]pyridin-7-ylmethyl)-N'-[(3S)-tetrahydrofuran-3-ylmethyl]benzene-1,4-dicarboxamide;
N-(imidazo[1,2-a]pyridin-7-ylmethyl)-5-{1-[(2R)-tetrahydrofuran-2-ylmethyl]-1H-pyrazol-4-yl}thiophene-2-carboxamide;
N-(imidazo[1,2-a]pyridin-7-ylmethyl)-5-{1-[(2S)-tetrahydrofuran-2-ylmethyl]-1H-pyrazol-4-yl}thiophene-2-carboxamide;
5-(4-hydroxytetrahydro-2H-pyran-4-yl)-N-(imidazo[1,2-a]pyridin-7-ylmethyl)thiophene-2-carboxamide;
5-[3-hydroxy-1-(2-methylpropanoyl)azetidin-3-yl]-N-(imidazo[1,2-a]pyridin-7-ylmethyl)thiophene-2-carboxamide;
5-(1-benzoyl-3-hydroxyazetidin-3-yl)-N-(imidazo[1,2-a]pyridin-7-ylmethyl)thiophene-2-carboxamide;
tert-butyl 3-{4-[(imidazo[1,2-a]pyridin-7-ylmethyl)carbamoyl]phenyl}azetidine-1-carboxylate;
tert-butyl 4-hydroxy-4-{5-[(imidazo[1,2-a]pyridin-7-ylmethyl)carbamoyl]thiophen-2-yl}piperidine-1-carboxylate;
5-{3-hydroxy-1-[(2S)-2-methylbutanoyl]azetidin-3-yl}-N-(imidazo[1,2-a]pyridin-7-ylmethyl)thiophene-2-carboxamide;
5-[3-hydroxy-1-(tetrahydro-2H-pyran-4-ylacetyl)azetidin-3-yl]-N-(imidazo[1,2-a]pyridin-7-ylmethyl)thiophene-2-carboxamide;
N-(imidazo[1,2-a]pyridin-7-ylmethyl)-5-(3-{[(2S)-2-methylbutanoyl]amino}oxetan-3-yl)thiophene-2-carboxamide;
N-(imidazo[1,2-a]pyridin-7-ylmethyl)-1-[1-(3-methylbutanoyl)piperidin-4-yl]-1H-pyrazole-3-carboxamide;
N-(imidazo[1,2-a]pyridin-7-ylmethyl)-5-[1-(tetrahydro-2H-pyran-4-yl)-1H-pyrazol-4-yl]thiophene-2-carboxamide;
4-[(1-acetylpiperidin-4-yl)oxy]-N-(imidazo[1,2-a]pyridin-7-ylmethyl)benzamide;
N-(imidazo[1,2-a]pyridin-7-ylmethyl)-4-{[1-(2-methylpropanoyl)piperidin-4-yl]oxy}benzamide;
N-(imidazo[1,2-a]pyridin-7-ylmethyl)-4-({1-[(2S)-2-methylbutanoyl]piperidin-4-yl}oxy)benzamide;
4-{[1-(cyclopropylacetyl)piperidin-4-yl]oxy}-N-(imidazo[1,2-a]pyridin-7-ylmethyl)benzamide;
4-[(1-benzoylpiperidin-4-yl)oxy]-N-(imidazo[1,2-a]pyridin-7-ylmethyl)benzamide;
N-(imidazo[1,2-a]pyridin-7-ylmethyl)-4-({1-[(propan-2-yloxy)acetyl]piperidin-4-yl}oxy)benzamide;
4-{[1-(2-hydroxy-2-methylpropanoyl)piperidin-4-yl]oxy}-N-(imidazo[1,2-a]pyridin-7-ylmethyl)benzamide;
N-(imidazo[1,2-a]pyridin-7-ylmethyl)-4-({1-[(2R)-tetrahydrofuran-2-ylcarbonyl]piperidin-4-yl}oxy)benzamide;

N-(imidazo[1,2-a]pyridin-7-ylmethyl)-4-({1-[(2S)-tetrahydrofuran-2-ylcarbonyl]piperidin-4-yl}oxy)benzamide;
N-(imidazo[1,2-a]pyridin-7-ylmethyl)-4-{[1-(tetrahydro-2H-pyran-4-ylcarbonyl)piperidin-4-yl]oxy}benzamide;
4-{[1-(1,4-dioxan-2-ylcarbonyl)piperidin-4-yl]oxy}-N-(imidazo[1,2-a]pyridin-7-ylmethyl)benzamide;
N-(imidazo[1,2-a]pyridin-7-ylmethyl)-4-{[1-(tetrahydro-2H-pyran-4-ylacetyl)piperidin-4-yl]oxy}benzamide;
N-(imidazo[1,2-a]pyridin-7-ylmethyl)-4-{[1-(morpholin-4-ylacetyl)piperidin-4-yl]oxy}benzamide;
tert-butyl (3R)-3-{4-[(imidazo[1,2-a]pyridin-7-ylmethyl)carbamoyl]phenoxy}pyrrolidine-1-carboxylate;
4-(1-benzoylpiperidin-4-yl)-N-(imidazo[1,2-a]pyridin-7-ylmethyl)benzamide;
4-{1-[(3,3-difluorocyclobutyl)carbonyl]piperidin-4-yl}-N-(imidazo[1,2-a]pyridin-7-ylmethyl)benzamide;
4-{1-[(4,4-difluorocyclohexyl)carbonyl]piperidin-4-yl}-N-(imidazo[1,2-a]pyridin-7-ylmethyl)benzamide;
4-[(cyclopentylacetyl)amino]-2-fluoro-N-(imidazo[1,2-a]pyridin-7-ylmethyl)benzamide;
N-(imidazo[1,2-a]pyridin-7-ylmethyl)-5-[6-(morpholin-4-yl)pyridin-3-yl]thiophene-2-carboxamide;
N-(imidazo[1,2-a]pyridin-7-ylmethyl)-5-{1-[(2-methyltetrahydro-2H-pyran-2-yl)methyl]-1H-pyrazol-4-yl}thiophene-2-carboxamide;
tert-butyl 4-[(4-{5-[(imidazo[1,2-a]pyridin-7-ylmethyl)carbamoyl]thiophen-2-yl}-1H-pyrazol-1-yl)methyl]piperidine-1-carboxylate;
N-(imidazo[1,2-a]pyridin-7-ylmethyl)-5-[1-(3-methylbutanoyl)pyrrolidin-3-yl]thiophene-2-carboxamide;
N-(imidazo[1,2-a]pyridin-7-ylmethyl)-5-{1-[(2-methylpropanoyl)amino]cyclobutyl}thiophene-2-carboxamide;
N-(imidazo[1,2-a]pyridin-7-ylmethyl)-5-{1-[(3-methylbutanoyl)amino]cyclobutyl}thiophene-2-carboxamide;
N-(imidazo[1,2-a]pyridin-7-ylmethyl)-5-(1-{[(2S)-2-methylbutanoyl]amino}cyclobutyl)thiophene-2-carboxamide;
5-[1-(benzoylamino)cyclobutyl]-N-(imidazo[1,2-a]pyridin-7-ylmethyl)thiophene-2-carboxamide;
N-(imidazo[1,2-a]pyridin-7-ylmethyl)-5-{1-[(3,3,3-trifluoropropanoyl)amino]cyclobutyl}thiophene-2-carboxamide;
N-(1-{5-[(imidazo[1,2-a]pyridin-7-ylmethyl)carbamoyl]thiophen-2-yl}cyclobutyl)tetrahydro-2H-pyran-4-carboxamide;
tert-butyl 3-{4-[(imidazo[1,2-a]pyridin-7-ylmethyl)carbamoyl]phenoxy}azetidine-1-carboxylate;
5-[1-(cyclobutylmethyl)-1H-pyrazol-4-yl]-N-(imidazo[1,2-a]pyridin-7-ylmethyl)thiophene-2-carboxamide;
N-(imidazo[1,2-a]pyridin-7-ylmethyl)-5-[1-(tetrahydrofuran-2-ylmethyl)-1H-pyrazol-4-yl]furan-2-carboxamide;
N-(imidazo[1,2-a]pyridin-7-ylmethyl)-5-[1-(tetrahydro-2H-pyran-2-ylmethyl)-1H-pyrazol-4-yl]furan-2-carboxamide;
N-(imidazo[1,2-a]pyridin-7-ylmethyl)-5-[1-(tetrahydrofuran-3-ylmethyl)-1H-pyrazol-4-yl]furan-2-carboxamide;
N-(imidazo[1,2-a]pyridin-7-ylmethyl)-5-[1-(tetrahydro-2H-pyran-3-ylmethyl)-1H-pyrazol-4-yl]furan-2-carboxamide;
N-(imidazo[1,2-a]pyridin-7-ylmethyl)-5-[1-(tetrahydro-2H-pyran-4-ylmethyl)-1H-pyrazol-4-yl]furan-2-carboxamide;
5-[1-(cyclobutylmethyl)-1H-pyrazol-4-yl]-N-(imidazo[1,2-a]pyridin-7-ylmethyl)furan-2-carboxamide;
N-(imidazo[1,2-a]pyridin-7-ylmethyl)-5-{1-[(3-methyloxetan-3-yl)methyl]-1H-pyrazol-4-yl}furan-2-carboxamide;
5-[1-(2-hydroxy-2-methylpropyl)-1H-pyrazol-4-yl]-N-(imidazo[1,2-a]pyridin-7-ylmethyl)furan-2-carboxamide;
4-[1-(furan-2-ylcarbonyl)piperidin-4-yl]-N-(imidazo[1,2-a]pyridin-7-ylmethyl)benzamide;
N-(imidazo[1,2-a]pyridin-7-ylmethyl)-5-[1-(piperidin-4-ylmethyl)-1H-pyrazol-4-yl]thiophene-2-carboxamide;
N-(imidazo[1,2-a]pyridin-7-ylmethyl)-4-[1-(thiophen-2-ylcarbonyl)pyrrolidin-3-yl]benzamide;
N-(imidazo[1,2-a]pyridin-7-ylmethyl)-4-phenoxybenzamide;
N-(imidazo[1,2-a]pyridin-7-ylmethyl)-4-[1-(2-methylpropanoyl)azetidin-3-yl]benzamide;
N-(imidazo[1,2-a]pyridin-7-ylmethyl)-4-{[(3R)-1-(2-methylpropanoyl)pyrrolidin-3-yl]oxy}benzamide;
4-{[(3R)-1-benzoylpyrrolidin-3-yl]oxy}-N-(imidazo[1,2-a]pyridin-7-ylmethyl)benzamide;
N-(imidazo[1,2-a]pyridin-7-ylmethyl)-4-({(3R)-1-[(3S)-tetrahydrofuran-3-ylcarbonyl]pyrrolidin-3-yl}oxy)benzamide;
N-(imidazo[1,2-a]pyridin-7-ylmethyl)-4-({(3R)-1-[(2S)-2-methylbutanoyl]pyrrolidin-3-yl}oxy)benzamide;
5-[1-(2-methylpropyl)-1H-pyrazol-4-yl]-N-([1,2,4]triazolo[1,5-a]pyridin-7-ylmethyl)thiophene-2-carboxamide;
N-(imidazo[1,2-a]pyridin-7-ylmethyl)-4-[1-(pyridin-2-ylcarbonyl)piperidin-4-yl]benzamide;
4-[1-(3,3-dimethylbutanoyl)piperidin-4-yl]-N-(imidazo[1,2-a]pyridin-7-ylmethyl)benzamide;
N-(imidazo[1,2-a]pyridin-7-ylmethyl)-4-[1-(4-methylbenzoyl)piperidin-4-yl]benzamide;
4-[1-(2,2-dimethylbutanoyl)piperidin-4-yl]-N-(imidazo[1,2-a]pyridin-7-ylmethyl)benzamide;
4-[1-(cyclohexylcarbonyl)piperidin-4-yl]-N-(imidazo[1,2-a]pyridin-7-ylmethyl)benzamide;
N-(imidazo[1,2-a]pyridin-7-ylmethyl)-4-[1-(thiophen-2-ylcarbonyl)piperidin-4-yl]benzamide;
N-(imidazo[1,2-a]pyridin-7-ylmethyl)-4-[1-(3,3,3-trifluoropropanoyl)piperidin-4-yl]benzamide;
4-(1-butanoylpiperidin-4-yl)-N-(imidazo[1,2-a]pyridin-7-ylmethyl)benzamide;
4-[1-(2,4-difluorobenzoyl)piperidin-4-yl]-N-(imidazo[1,2-a]pyridin-7-ylmethyl)benzamide;
N-(imidazo[1,2-a]pyridin-7-ylmethyl)-4-[1-(2-methylbenzoyl)piperidin-4-yl]benzamide;
4-[1-(4-fluorobenzoyl)piperidin-4-yl]-N-(imidazo[1,2-a]pyridin-7-ylmethyl)benzamide;
4-[1-(2,2-dimethylpropanoyl)piperidin-4-yl]-N-(imidazo[1,2-a]pyridin-7-ylmethyl)benzamide;
N-(imidazo[1,2-a]pyridin-7-ylmethyl)-4-{1-[(2E)-2-methylpent-2-enoyl]piperidin-4-yl}benzamide;
N-(imidazo[1,2-a]pyridin-7-ylmethyl)-4-{1-[(1-methyl-1H-pyrazol-5-yl)carbonyl]piperidin-4-yl}benzamide;
N-(imidazo[1,2-a]pyridin-7-ylmethyl)-4-{1-[(3-methyloxetan-3-yl)carbonyl]piperidin-4-yl}benzamide;
4-[1-(2-fluorobenzoyl)piperidin-4-yl]-N-(imidazo[1,2-a]pyridin-7-ylmethyl)benzamide;
4-{1-[(1-cyanocyclopropyl)carbonyl]piperidin-4-yl}-N-(imidazo[1,2-a]pyridin-7-ylmethyl)benzamide;
4-[1-(cyclopentylcarbonyl)piperidin-4-yl]-N-(imidazo[1,2-a]pyridin-7-ylmethyl)benzamide;
4-[1-(3-fluorobenzoyl)piperidin-4-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-4-yl)carbonyl]piperidin-4-yl}benzamide;
N-(imidazo[1,2-a]pyridin-7-ylmethyl)-4-[1-(2-oxobutanoyl)piperidin-4-yl]benzamide;
4-{1-[2,5-dimethylfuran-3-yl)carbonyl]piperidin-4-yl}-N-(imidazo[1,2-a]pyridin-7-ylmethyl)benzamide;

4-[1-(4-cyanobenzoyl)piperidin-4-yl]-N-(imidazo[1,2-a]pyridin-7-ylmethyl)benzamide;
4-[1-(3-cyanobenzoyl)piperidin-4-yl]-N-(imidazo[1,2-a]pyridin-7-ylmethyl)benzamide;
4-[1-(2,5-difluorobenzoyl)piperidin-4-yl]-N-(imidazo[1,2-a]pyridin-7-ylmethyl)benzamide;
N-(imidazo[1,2-a]pyridin-7-ylmethyl)-4-[1-(pyrazin-2-ylcarbonyl)piperidin-4-yl]benzamide;
N-(imidazo[1,2-a]pyridin-7-ylmethyl)-4-{1-[(3-methylthiophen-2-yl)carbonyl]piperidin-4-yl}benzamide;
4-{1-[(3,5-dimethyl-1,2-oxazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(3-methoxybenzoyl)piperidin-4-yl]benzamide;
4-[1-(3-chlorobenzoyl)piperidin-4-yl]-N-(imidazo[1,2-a]pyridin-7-ylmethyl)benzamide;
N-(imidazo[1,2-a]pyridin-7-ylmethyl)-4-[1-(4-methoxybenzoyl)piperidin-4-yl]benzamide;
4-[1-(4-chlorobenzoyl)piperidin-4-yl]-N-(imidazo[1,2-a]pyridin-7-ylmethyl)benzamide;
4-[1-(3,5-difluorobenzoyl)piperidin-4-yl]-N-(imidazo[1,2-a]pyridin-7-ylmethyl)benzamide;
4-[1-(cyclopropylcarbonyl)piperidin-4-yl]-N-(imidazo[1,2-a]pyridin-7-ylmethyl)benzamide;
N-(imidazo[1,2-a]pyridin-7-ylmethyl)-4-(1-propanoylpiperidin-4-yl)benzamide;
N-(imidazo[1,2-a]pyridin-7-ylmethyl)-4-{1-[(1-methyl-1H-pyrrol-2-yl)carbonyl]piperidin-4-yl}benzamide;
N-(imidazo[1,2-a]pyridin-7-ylmethyl)-4-[1-(3-methylbutanoyl)piperidin-4-yl]benzamide;
N-(imidazo[1,2-a]pyridin-7-ylmethyl)-4-[1-(pyridin-4-ylcarbonyl)piperidin-4-yl]benzamide;
4-[1-(2,3-dimethylbutanoyl)piperidin-4-yl]-N-(imidazo[1,2-a]pyridin-7-ylmethyl)benzamide;
N-(imidazo[1,2-a]pyridin-7-ylmethyl)-4-[1-(pyridin-3-ylcarbonyl)piperidin-4-yl]benzamide;
N-(imidazo[1,2-a]pyridin-7-ylmethyl)-4-{1-[(1-methylcyclopropyl)carbonyl]piperidin-4-yl}benzamide;
N-(imidazo[1,2-a]pyridin-7-ylmethyl)-4-[1-(2-methoxybenzoyl)piperidin-4-yl]benzamide;
N-(imidazo[1,2-a]pyridin-7-ylmethyl)-5-[1-(3,3,3-trifluoropropanoyl)pyrrolidin-3-yl]thiophene-2-carboxamide;
N-(imidazo[1,2-a]pyridin-7-ylmethyl)-5-[1-(2-methylpropanoyl)pyrrolidin-3-yl]thiophene-2-carboxamide;
5-(1-benzoylpyrrolidin-3-yl)-N-(imidazo[1,2-a]pyridin-7-ylmethyl)thiophene-2-carboxamide;
N-(imidazo[1,2-a]pyridin-7-ylmethyl)-2-[1-(2-methylpropanoyl)piperidin-4-yl]-1,3-thiazole-5-carboxamide;
N-(imidazo[1,2-a]pyridin-7-ylmethyl)-2-[1-(3-methylbutanoyl)piperidin-4-yl]-1,3-thiazole-5-carboxamide;
2-(1-benzoylpiperidin-4-yl)-N-(imidazo[1,2-a]pyridin-7-ylmethyl)-1,3-thiazole-5-carboxamide;
4-[(cyclopentylacetyl)amino]-N-([1,2,4]triazolo[1,5-a]pyridin-7-ylmethyl)benzamide;
N-(imidazo[1,2-a]pyridin-7-ylmethyl)-4-{1-[(2S)-2-methylbutanoyl]azetidin-3-yl}benzamide;
4-[1-(cyclopropylacetyl)azetidin-3-yl]-N-(imidazo[1,2-a]pyridin-7-ylmethyl)benzamide;
4-(1-benzoylazetidin-3-yl)-N-(imidazo[1,2-a]pyridin-7-ylmethyl)benzamide;
4-[1-(2-hydroxy-2-methylpropanoyl)azetidin-3-yl]-N-(imidazo[1,2-a]pyridin-7-ylmethyl)benzamide;
N-(imidazo[1,2-a]pyridin-7-ylmethyl)-4-[1-(tetrahydro-2H-pyran-4-ylacetyl)azetidin-3-yl]benzamide;
N-(imidazo[1,2-a]pyridin-7-ylmethyl)-4-[1-(thiophen-2-ylcarbonyl)azetidin-3-yl]benzamide;
5-[4-hydroxy-1-(3-methylbutanoyl)piperidin-4-yl]-N-(imidazo[1,2-a]pyridin-7-ylmethyl)thiophene-2-carboxamide;
5-[4-hydroxy-1-(2-methylpropanoyl)piperidin-4-yl]-N-(imidazo[1,2-a]pyridin-7-ylmethyl)thiophene-2-carboxamide;
5-[1-(3,3-dimethylbutanoyl)-4-hydroxypiperidin-4-yl]-N-(imidazo[1,2-a]pyridin-7-ylmethyl)thiophene-2-carboxamide;
5-(1-benzoyl-4-hydroxypiperidin-4-yl)-N-(imidazo[1,2-a]pyridin-7-ylmethyl)thiophene-2-carboxamide;
N-(imidazo[1,2-a]pyridin-7-ylmethyl)-4-[1-(propan-2-ylsulfonyl)azetidin-3-yl]benzamide;
N-(imidazo[1,2-a]pyridin-7-ylmethyl)-4-{[1-(2-methylpropanoyl)azetidin-3-yl]oxy}benzamide;
N-(imidazo[1,2-a]pyridin-7-ylmethyl)-4-({1-[(2S)-2-methylbutanoyl]azetidin-3-yl}oxy)benzamide;
4-{[1-(cyclopropylacetyl)azetidin-3-yl]oxy}-N-(imidazo[1,2-a]pyridin-7-ylmethyl)benzamide;
4-[(1-benzoylazetidin-3-yl)oxy]-N-(imidazo[1,2-a]pyridin-7-ylmethyl)benzamide;
4-[1-(4-fluorobenzoyl)pyrrolidin-3-yl]-N-(imidazo[1,2-a]pyridin-7-ylmethyl)benzamide;
tert-butyl 4-{4-[([1,2,4]triazolo[1,5-a]pyridin-7-ylmethyl)carbamoyl]phenyl}piperidine-1-carboxylate;
N-(imidazo[1,2-a]pyridin-7-ylmethyl)-4-(piperidin-1-ylcarbonyl)benzamide;
4-[1-(ethylsulfonyl)azetidin-3-yl]-N-(imidazo[1,2-a]pyridin-7-ylmethyl)benzamide;
4-[1-(cyclopropylsulfonyl)azetidin-3-yl]-N-(imidazo[1,2-a]pyridin-7-ylmethyl)benzamide;
N-(imidazo[1,2-a]pyridin-7-ylmethyl)-4-[1-(phenylsulfonyl)azetidin-3-yl]benzamide;
propan-2-yl 4-{5-[(imidazo[1,2-a]pyridin-7-ylmethyl)carbamoyl]thiophen-2-yl}piperidine-1-carboxylate;
2-methylpropyl 4-{5-[(imidazo[1,2-a]pyridin-7-ylmethyl)carbamoyl]thiophen-2-yl}piperidine-1-carboxylate;
N-(imidazo[1,2-a]pyridin-7-ylmethyl)-5-[1-(3,3,3-trifluoropropanoyl)piperidin-4-yl]thiophene-2-carboxamide;
N-(imidazo[1,2-a]pyridin-7-ylmethyl)-5-{1-[(2-methylpropyl)sulfonyl]piperidin-4-yl}thiophene-2-carboxamide;
N-(imidazo[1,2-a]pyridin-7-ylmethyl)-5-[1-(4,4,4-trifluorobutanoyl)piperidin-4-yl]thiophene-2-carboxamide;
N-[(3-chloroimidazo[1,2-a]pyridin-7-yl)methyl]-4-[1-(2-methylpropanoyl)piperidin-4-yl]benzamide;
N-(imidazo[1,2-a]pyridin-7-ylmethyl)-5-{1-[(4-methyltetrahydro-2H-pyran-4-yl)methyl]-1H-pyrazol-4-yl}thiophene-2-carboxamide;
5-[1-(2-cyano-2-methylpropyl)-1H-pyrazol-4-yl]-N-(imidazo[1,2-a]pyridin-7-ylmethyl)thiophene-2-carboxamide;
4-chloro-N-(imidazo[1,2-a]pyridin-7-ylmethyl)-5-[1-(2-methylpropyl)-1H-pyrazol-4-yl]thiophene-2-carboxamide;
4-chloro-N-(imidazo[1,2-a]pyridin-7-ylmethyl)-5-{1-[(3R)-tetrahydrofuran-3-ylmethyl]-1H-pyrazol-4-yl}thiophene-2-carboxamide;
N-(imidazo[1,2-a]pyridin-7-ylmethyl)-4-{1-[(2-methylcyclopropyl)carbonyl]pyrrolidin-3-yl}benzamide;
4-[1-(cyclopentylacetyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylpentanoyl)pyrrolidin-3-yl]benzamide;
4-[1-(cyclopentylcarbonyl)pyrrolidin-3-yl]-N-(imidazo[1,2-a]pyridin-7-ylmethyl)benzamide;
N-(imidazo[1,2-a]pyridin-7-ylmethyl)-4-{1-[(1-methylcyclopropyl)carbonyl]pyrrolidin-3-yl}benzamide;

4-[1-(2,2-dimethylpropanoyl)pyrrolidin-3-yl]-N-(imidazo[1,2-a]pyridin-7-ylmethyl)benzamide;
N-(imidazo[1,2-a]pyridin-7-ylmethyl)-4-[1-(1,3-thiazol-5-ylcarbonyl)pyrrolidin-3-yl]benzamide;
N-(imidazo[1,2-a]pyridin-7-ylmethyl)-4-[1-(2-methoxybenzoyl)pyrrolidin-3-yl]benzamide;
N-(imidazo[1,2-a]pyridin-7-ylmethyl)-4-[1-(1,3-thiazol-4-ylcarbonyl)pyrrolidin-3-yl]benzamide;
4-[1-(2-fluorobenzoyl)pyrrolidin-3-yl]-N-(imidazo[1,2-a]pyridin-7-ylmethyl)benzamide;
4-[1-(furan-2-ylcarbonyl)pyrrolidin-3-yl]-N-(imidazo[1,2-a]pyridin-7-ylmethyl)benzamide;
4-[1-(3-fluorobenzoyl)pyrrolidin-3-yl]-N-(imidazo[1,2-a]pyridin-7-ylmethyl)benzamide;
4-[1-(2,4-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-3-yl)carbonyl]pyrrolidin-3-yl}benzamide;
4-[1-(2-chlorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(2-methylbenzoyl)pyrrolidin-3-yl]benzamide;
4-[1-(4-chlorobenzoyl)pyrrolidin-3-yl]-N-(imidazo[1,2-a]pyridin-7-ylmethyl)benzamide;
4-[1-(3-chlorobenzoyl)pyrrolidin-3-yl]-N-(imidazo[1,2-a]pyridin-7-ylmethyl)benzamide;
4-[1-(2,2-dimethylbutanoyl)pyrrolidin-3-yl]-N-(imidazo[1,2-a]pyridin-7-ylmethyl)benzamide;
4-[1-(3,5-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(4-methylbenzoyl)pyrrolidin-3-yl]benzamide;
N-(imidazo[1,2-a]pyridin-7-ylmethyl)-4-[1-(3-methylbutanoyl)pyrrolidin-3-yl]benzamide;
4-[1-(3,3-dimethylbutanoyl)pyrrolidin-3-yl]-N-(imidazo[1,2-a]pyridin-7-ylmethyl)benzamide;
4-[1-(3-cyanobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)pyrrolidin-3-yl]benzamide;
N-(imidazo[1,2-a]pyridin-7-ylmethyl)-4-[1-(4-methoxybenzoyl)pyrrolidin-3-yl]benzamide;
N-(imidazo[1,2-a]pyridin-7-ylmethyl)-4-{1-[(1-methyl-1H-pyrrol-2-yl)carbonyl]pyrrolidin-3-yl}benzamide;
4-[1-(cyclohexylacetyl)pyrrolidin-3-yl]-N-(imidazo[1,2-a]pyridin-7-ylmethyl)benzamide;
N-(imidazo[1,2-a]pyridin-7-ylmethyl)-4-[1-(pyridin-4-ylcarbonyl)pyrrolidin-3-yl]benzamide;
N-(imidazo[1,2-a]pyridin-7-ylmethyl)-4-[1-(pyridin-3-ylcarbonyl)pyrrolidin-3-yl]benzamide;
4-[1-(cyclohexylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)pyrrolidin-3-yl]benzamide;
4-[1-(furan-3-ylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(1,3-thiazol-2-ylcarbonyl)pyrrolidin-3-yl]benzamide;
N-(imidazo[1,2-a]pyridin-7-ylmethyl)-4-{1-[(1-methylcyclohexyl)carbonyl]pyrrolidin-3-yl}benzamide;
4-[1-(2,3-dimethylbutanoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylbenzoyl)pyrrolidin-3-yl]benzamide;
N-(imidazo[1,2-a]pyridin-7-ylmethyl)-4-[1-(thiophen-3-ylcarbonyl)pyrrolidin-3-yl]benzamide;
N-(imidazo[1,2-a]pyridin-7-ylmethyl)-4-{1-[3-(trifluoromethoxy)benzoyl]pyrrolidin-3-yl}benzamide;
N-(imidazo[1,2-a]pyridin-7-ylmethyl)-4-{1-[(3-methylthiophen-2-yl)carbonyl]pyrrolidin-3-yl}benzamide;
N-(imidazo[1,2-a]pyridin-7-ylmethyl)-4-{1-[3-(trifluoromethyl)benzoyl]pyrrolidin-3-yl}benzamide;
N-(imidazo[1,2-a]pyridin-7-ylmethyl)-4-[1-(methylsulfonyl)azetidin-3-yl]benzamide;
N-(imidazo[1,2-a]pyridin-7-ylmethyl)-4-[1-(methylsulfonyl)pyrrolidin-3-yl]benzamide;
4-[1-(ethylsulfonyl)pyrrolidin-3-yl]-N-(imidazo[1,2-a]pyridin-7-ylmethyl)benzamide;
4-[1-(cyclopropylsulfonyl)pyrrolidin-3-yl]-N-(imidazo[1,2-a]pyridin-7-ylmethyl)benzamide;
N-(imidazo[1,2-a]pyridin-7-ylmethyl)-4-[1-(phenylsulfonyl)pyrrolidin-3-yl]benzamide;
N-(imidazo[1,2-a]pyridin-7-ylmethyl)-4-{1-[(2-methylcyclopropyl)carbonyl]azetidin-3-yl}benzamide;
4-[1-(cyclopentylacetyl)azetidin-3-yl]-N-(imidazo[1,2-a]pyridin-7-ylmethyl)benzamide;
N-(imidazo[1,2-a]pyridin-7-ylmethyl)-4-[1-(3-methylpentanoyl)azetidin-3-yl]benzamide;
4-[1-(cyclopentylcarbonyl)azetidin-3-yl]-N-(imidazo[1,2-a]pyridin-7-ylmethyl)benzamide;
N-(imidazo[1,2-a]pyridin-7-ylmethyl)-4-{1-[(1-methylcyclopropyl)carbonyl]azetidin-3-yl}benzamide;
4-[1-(2,2-dimethylpropanoyl)azetidin-3-yl]-N-(imidazo[1,2-a]pyridin-7-ylmethyl)benzamide;
N-(imidazo[1,2-a]pyridin-7-ylmethyl)-4-[1-(1,3-thiazol-5-ylcarbonyl)azetidin-3-yl]benzamide;
N-(imidazo[1,2-a]pyridin-7-ylmethyl)-4-[1-(pyrazin-2-ylcarbonyl)azetidin-3-yl]benzamide;
N-(imidazo[1,2-a]pyridin-7-ylmethyl)-4-[1-(2-methoxybenzoyl)azetidin-3-yl]benzamide;
N-(imidazo[1,2-a]pyridin-7-ylmethyl)-4-[1-(1,3-thiazol-4-ylcarbonyl)azetidin-3-yl]benzamide;
4-[1-(2-fluorobenzoyl)azetidin-3-yl]-N-(imidazo[1,2-a]pyridin-7-ylmethyl)benzamide;
4-[1-(furan-2-ylcarbonyl)azetidin-3-yl]-N-(imidazo[1,2-a]pyridin-7-ylmethyl)benzamide;
4-[1-(3-fluorobenzoyl)azetidin-3-yl]-N-(imidazo[1,2-a]pyridin-7-ylmethyl)benzamide;
4-[1-(2,4-difluorobenzoyl)azetidin-3-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-3-yl)carbonyl]azetidin-3-yl}benzamide;
4-[1-(2-chlorobenzoyl)azetidin-3-yl]-N-(imidazo[1,2-a]pyridin-7-ylmethyl)benzamide;
N-(imidazo[1,2-a]pyridin-7-ylmethyl)-4-[1-(2-methylbenzoyl)azetidin-3-yl]benzamide;
4-[1-(4-chlorobenzoyl)azetidin-3-yl]-N-(imidazo[1,2-a]pyridin-7-ylmethyl)benzamide;
4-[1-(3-chlorobenzoyl)azetidin-3-yl]-N-(imidazo[1,2-a]pyridin-7-ylmethyl)benzamide;
4-[1-(2,2-dimethylbutanoyl)azetidin-3-yl]-N-(imidazo[1,2-a]pyridin-7-ylmethyl)benzamide;
4-[1-(3,5-difluorobenzoyl)azetidin-3-yl]-N-(imidazo[1,2-a]pyridin-7-ylmethyl)benzamide;
4-[1-(4-fluorobenzoyl)azetidin-3-yl]-N-(imidazo[1,2-a]pyridin-7-ylmethyl)benzamide;
N-(imidazo[1,2-a]pyridin-7-ylmethyl)-4-[1-(4-methylbenzoyl)azetidin-3-yl]benzamide;
N-(imidazo[1,2-a]pyridin-7-ylmethyl)-4-[1-(3-methylbutanoyl)azetidin-3-yl]benzamide;
4-[1-(3,3-dimethylbutanoyl)azetidin-3-yl]-N-(imidazo[1,2-a]pyridin-7-ylmethyl)benzamide;

4-[1-(3-cyanobenzoyl)azetidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)azetidin-3-yl]benzamide;
N-(imidazo[1,2-a]pyridin-7-ylmethyl)-4-[1-(4-methoxybenzoyl)azetidin-3-yl]benzamide;
N-(imidazo[1,2-a]pyridin-7-ylmethyl)-4-{1-[(1-methyl-1H-pyrrol-2-yl)carbonyl]azetidin-3-yl}benzamide;
4-[1-(cyclohexylacetyl)azetidin-3-yl]-N-(imidazo[1,2-a]pyridin-7-ylmethyl)benzamide;
N-(imidazo[1,2-a]pyridin-7-ylmethyl)-4-[1-(pyridin-4-ylcarbonyl)azetidin-3-yl]benzamide;
N-(imidazo[1,2-a]pyridin-7-ylmethyl)-4-[1-(pyridin-3-ylcarbonyl)azetidin-3-yl]benzamide;
4-[1-(cyclohexylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)azetidin-3-yl]benzamide;
4-[1-(furan-3-ylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyrimidin-4-ylcarbonyl)azetidin-3-yl]benzamide;
N-(imidazo[1,2-a]pyridin-7-ylmethyl)-4-[1-(1,3-thiazol-2-ylcarbonyl)azetidin-3-yl]benzamide;
N-(imidazo[1,2-a]pyridin-7-ylmethyl)-4-{1-[(1-methylcyclohexyl)carbonyl]azetidin-3-yl}benzamide;
4-[1-(2,3-dimethylbutanoyl)azetidin-3-yl]-N-(imidazo[1,2-a]pyridin-7-ylmethyl)benzamide;
N-(imidazo[1,2-a]pyridin-7-ylmethyl)-4-[1-(3-methylbenzoyl)azetidin-3-yl]benzamide;
N-(imidazo[1,2-a]pyridin-7-ylmethyl)-4-[1-(thiophen-3-ylcarbonyl)azetidin-3-yl]benzamide;
N-(imidazo[1,2-a]pyridin-7-ylmethyl)-4-{1-[3-(trifluoromethoxy)benzoyl]azetidin-3-yl}benzamide;
N-(imidazo[1,2-a]pyridin-7-ylmethyl)-4-{1-[(3-methylthiophen-2-yl)carbonyl]azetidin-3-yl}benzamide;
N-(imidazo[1,2-a]pyridin-7-ylmethyl)-4-{1-[3-(trifluoromethyl)benzoyl]azetidin-3-yl}benzamide;
N-(imidazo[1,2-a]pyridin-7-ylmethyl)-4-[1-(propan-2-ylsulfonyl)pyrrolidin-3-yl]benzamide;
5-[1-(2-fluorobenzoyl)piperidin-4-yl]-N-(imidazo[1,2-a]pyridin-7-ylmethyl)thiophene-2-carboxamide;
N-(imidazo[1,2-a]pyridin-7-ylmethyl)-4-[1-(phenylsulfonyl)piperidin-4-yl]benzamide;
N-(imidazo[1,2-a]pyridin-7-ylmethyl)-4-[1-(propan-2-ylsulfonyl)piperidin-4-yl]benzamide;
4-[1-(cyclopropylsulfonyl)piperidin-4-yl]-N-(imidazo[1,2-a]pyridin-7-ylmethyl)benzamide;
5-{(1R)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-5-{(1R)-3-methyl-1-[(tetrahydrofuran-3-ylacetyl)amino]butyl}thiophene-2-carboxamide;
5-{(1S)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-2-(1-phenylpiperidin-4-yl)-1,3-thiazole-5-carboxamide;
N-(imidazo[1,2-a]pyridin-7-ylmethyl)-2-[1-(pyridin-2-yl)piperidin-4-yl]-1,3-thiazole-5-carboxamide;
5-{1-[(4-fluorotetrahydro-2H-pyran-4-yl)methyl]-1H-pyrazol-4-yl}-N-(imidazo[1,2-a]pyridin-7-ylmethyl)thiophene-2-carboxamide;
4-[1-(2-chlorobenzoyl)piperidin-4-yl]-N-(imidazo[1,2-a]pyridin-7-ylmethyl)benzamide;
4-[1-(2,6-difluorobenzoyl)piperidin-4-yl]-N-(imidazo[1,2-a]pyridin-7-ylmethyl)benzamide;
4-[1-(3,4-difluorobenzoyl)piperidin-4-yl]-N-(imidazo[1,2-a]pyridin-7-ylmethyl)benzamide;
N-(imidazo[1,2-a]pyridin-7-ylmethyl)-4-{1-[3-(trifluoromethyl)benzoyl]piperidin-4-yl}benzamide;
N-(imidazo[1,2-a]pyridin-7-ylmethyl)-4-{1-[3-(trifluoromethoxy)benzoyl]piperidin-4-yl}benzamide;
N-(imidazo[1,2-a]pyridin-7-ylmethyl)-4-{1-[4-(trifluoromethoxy)benzoyl]piperidin-4-yl}benzamide;
N-(imidazo[1,2-a]pyridin-7-ylmethyl)-4-{1-[4-(trifluoromethyl)benzoyl]piperidin-4-yl}benzamide;
N-(imidazo[1,2-a]pyridin-7-ylmethyl)-4-{1-[2-(trifluoromethoxy)benzoyl]piperidin-4-yl}benzamide;
N-(imidazo[1,2-a]pyridin-7-ylmethyl)-4-[1-(phenylacetyl)piperidin-4-yl]benzamide;
N-(imidazo[1,2-a]pyridin-7-ylmethyl)-4-{1-[2-(trifluoromethyl)benzoyl]piperidin-4-yl}benzamide;
5-[1-(cyclopropylcarbonyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(4-methylbenzoyl)pyrrolidin-3-yl]thiophene-2-carboxamide;
N-(imidazo[1,2-a]pyridin-7-ylmethyl)-4-[1-(phenylacetyl)pyrrolidin-3-yl]benzamide;
N-(imidazo[1,2-a]pyridin-7-ylmethyl)-4-[1-(2-methyl-2-phenylpropanoyl)pyrrolidin-3-yl]benzamide;
4-{1-[difluoro(phenyl)acetyl]pyrrolidin-3-yl}-N-(imidazo[1,2-a]pyridin-7-ylmethyl)benzamide;
N-(imidazo[1,2-a]pyridin-7-ylmethyl)-5-{1-[(4-methyltetrahydro-2H-pyran-4-yl)methyl]-1H-pyrazol-4-yl}furan-2-carboxamide;
5-[1-(2-fluorobenzoyl)piperidin-4-yl]-N-(imidazo[1,2-a]pyridin-7-ylmethyl)furan-2-carboxamide;
N-(imidazo[1,2-a]pyridin-7-ylmethyl)-5-[1-(2-methylpropanoyl)piperidin-4-yl]furan-2-carboxamide;
4-[1-(2-cyanobenzoyl)piperidin-4-yl]-N-(imidazo[1,2-a]pyridin-7-ylmethyl)benzamide;
N-(imidazo[1,2-a]pyridin-7-ylmethyl)-5-[1-(2,2,2-trifluoroethyl)-1H-pyrazol-4-yl]furan-2-carboxamide;
N-(imidazo[1,2-a]pyridin-7-ylmethyl)-5-[1-(2-methylpropyl)-1H-pyrazol-4-yl]furan-2-carboxamide;
5-(1-benzyl-1H-pyrazol-4-yl)-N-(imidazo[1,2-a]pyridin-7-ylmethyl)furan-2-carboxamide;
N-(imidazo[1,2-a]pyridin-7-ylmethyl)-5-{1-[(2S)-tetrahydrofuran-2-ylmethyl]-1H-pyrazol-4-yl}furan-2-carboxamide;
N-(imidazo[1,2-a]pyridin-7-ylmethyl)-5-{1-[(2R)-tetrahydrofuran-2-ylmethyl]-1H-pyrazol-4-yl}furan-2-carboxamide;
N-(imidazo[1,2-a]pyridin-7-ylmethyl)-5-[1-(2-methylpropanoyl)-1,2,3,6-tetrahydropyridin-4-yl]furan-2-carboxamide;
N-(imidazo[1,2-a]pyridin-7-ylmethyl)-5-[1-(3-methylbutanoyl)-1,2,3,6-tetrahydropyridin-4-yl]furan-2-carboxamide;
5-(1-benzoyl-1,2,3,6-tetrahydropyridin-4-yl)-N-(imidazo[1,2-a]pyridin-7-ylmethyl)furan-2-carboxamide;
N-(imidazo[1,2-a]pyridin-7-ylmethyl)-5-[4-(2-methylpropyl)phenyl]furan-2-carboxamide;
N-(imidazo[1,2-a]pyridin-7-ylmethyl)-5-{1-[(2S)-2-methylbutanoyl]-1,2,3,6-tetrahydropyridin-4-yl}furan-2-carboxamide;
5-[1-(3,3-dimethylbutanoyl)-1,2,3,6-tetrahydropyridin-4-yl]-N-(imidazo[1,2-a]pyridin-7-ylmethyl)furan-2-carboxamide;
5-[1-(cyclopropylacetyl)-1,2,3,6-tetrahydropyridin-4-yl]-N-(imidazo[1,2-a]pyridin-7-ylmethyl)furan-2-carboxamide;

N-(imidazo[1,2-a]pyridin-7-ylmethyl)-2-{1-[(2-methylpropyl)sulfonyl]pyrrolidin-3-yl}-1,3-thiazole-5-carboxamide;
N-(imidazo[1,2-a]pyridin-7-ylmethyl)-2-[1-(phenylsulfonyl)pyrrolidin-3-yl]-1,3-thiazole-5-carboxamide;
N-(imidazo[1,2-a]pyridin-7-ylmethyl)-5-{1-[(2-methylpropyl)sulfonyl]-1,2,3,6-tetrahydropyridin-4-yl}furan-2-carboxamide;
tert-butyl 4-[(4-{5-[(imidazo[1,2-a]pyridin-7-ylmethyl)carbamoyl]thiophen-2-yl}-1H-pyrazol-1-yl)methyl]-4-methylpiperidine-1-carboxylate;
5-[1-(cyclopropylacetyl)pyrrolidin-3-yl]-N-(imidazo[1,2-a]pyridin-7-ylmethyl)thiophene-2-carboxamide;
5-[1-(2-chlorobenzoyl)pyrrolidin-3-yl]-N-(imidazo[1,2-a]pyridin-7-ylmethyl)thiophene-2-carboxamide;
5-{1-[(4-fluorophenyl)acetyl]pyrrolidin-3-yl}-N-(imidazo[1,2-a]pyridin-7-ylmethyl)thiophene-2-carboxamide;
N-(imidazo[1,2-a]pyridin-7-ylmethyl)-5-[1-(3-methoxybenzoyl)pyrrolidin-3-yl]thiophene-2-carboxamide;
N-(imidazo[1,2-a]pyridin-7-ylmethyl)-5-[1-(2-methoxybenzoyl)pyrrolidin-3-yl]thiophene-2-carboxamide;
5-{1-[(3-fluorophenyl)acetyl]pyrrolidin-3-yl}-N-(imidazo[1,2-a]pyridin-7-ylmethyl)thiophene-2-carboxamide;
5-[1-(3-fluorobenzoyl)pyrrolidin-3-yl]-N-(imidazo[1,2-a]pyridin-7-ylmethyl)thiophene-2-carboxamide;
5-[1-(4-fluorobenzoyl)pyrrolidin-3-yl]-N-(imidazo[1,2-a]pyridin-7-ylmethyl)thiophene-2-carboxamide;
5-{1-[(3,5-difluorophenyl)acetyl]pyrrolidin-3-yl}-N-(imidazo[1,2-a]pyridin-7-ylmethyl)thiophene-2-carboxamide;
5-{1-[(2-fluorophenyl)acetyl]pyrrolidin-3-yl}-N-(imidazo[1,2-a]pyridin-7-ylmethyl)thiophene-2-carboxamide;
5-[1-(4-cyanobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(3-methyloxetan-3-yl)carbonyl]pyrrolidin-3-yl}thiophene-2-carboxamide;
5-[1-(3,5-difluorobenzoyl)pyrrolidin-3-yl]-N-(imidazo[1,2-a]pyridin-7-ylmethyl)thiophene-2-carboxamide;
5-[1-(cyclopentylcarbonyl)pyrrolidin-3-yl]-N-(imidazo[1,2-a]pyridin-7-ylmethyl)thiophene-2-carboxamide;
5-[1-(4-chlorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(1-methyl-1H-pyrrol-2-yl)carbonyl]pyrrolidin-3-yl}thiophene-2-carboxamide;
5-[1-(2,4-difluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(pyridin-4-ylcarbonyl)pyrrolidin-3-yl]thiophene-2-carboxamide;
N-(imidazo[1,2-a]pyridin-7-ylmethyl)-5-[1-(pyridin-2-ylcarbonyl)pyrrolidin-3-yl]thiophene-2-carboxamide;
N-(imidazo[1,2-a]pyridin-7-ylmethyl)-5-{1-[(1-methyl-1H-pyrazol-4-yl)carbonyl]pyrrolidin-3-yl}thiophene-2-carboxamide;
5-[1-(2-fluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(2E)-2-methylpent-2-enoyl]pyrrolidin-3-yl}thiophene-2-carboxamide;
5-{1-[(2,5-dimethylfuran-3-yl)carbonyl]pyrrolidin-3-yl}-N-(imidazo[1,2-a]pyridin-7-ylmethyl)thiophene-2-carboxamide;
5-[1-(3-chlorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-(1-propanoylpyrrolidin-3-yl)thiophene-2-carboxamide;
5-{1-[(1-cyanocyclopropyl)carbonyl]pyrrolidin-3-yl}-N-(imidazo[1,2-a]pyridin-7-ylmethyl)thiophene-2-carboxamide;
5-(1-butanoylpyrrolidin-3-yl)-N-(imidazo[1,2-a]pyridin-7-ylmethyl)thiophene-2-carboxamide;
5-[1-(furan-2-ylcarbonyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(4-methoxybenzoyl)pyrrolidin-3-yl]thiophene-2-carboxamide;
5-[1-(2,5-difluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(thiophen-2-ylcarbonyl)pyrrolidin-3-yl]thiophene-2-carboxamide;
5-[1-(2,2-dimethylpropanoyl)pyrrolidin-3-yl]-N-(imidazo[1,2-a]pyridin-7-ylmethyl)thiophene-2-carboxamide;
5-[1-(3,3-dimethylbutanoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(4-methylpiperidin-4-yl)methyl]-1H-pyrazol-4-yl}thiophene-2-carboxamide;
5-{1-[(4-fluorotetrahydro-2H-pyran-4-yl)methyl]-1H-pyrazol-4-yl}-N-(imidazo[1,2-a]pyridin-7-ylmethyl)furan-2-carboxamide;
5-[1-(2,2-dimethylbutanoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(pyrazin-2-ylcarbonyl)pyrrolidin-3-yl]thiophene-2-carboxamide;
N-(imidazo[1,2-a]pyridin-7-ylmethyl)-5-{1-[(3-methylthiophen-2-yl)carbonyl]pyrrolidin-3-yl}thiophene-2-carboxamide;
N-(imidazo[1,2-a]pyridin-7-ylmethyl)-5-[1-(2-methylbenzoyl)pyrrolidin-3-yl]thiophene-2-carboxamide;
N-(imidazo[1,2-a]pyridin-7-ylmethyl)-5-{1-[(1-methylcyclopropyl)carbonyl]pyrrolidin-3-yl}thiophene-2-carboxamide;
N-(imidazo[1,2-a]pyridin-7-ylmethyl)-5-[1-(4,4,4-trifluorobutanoyl)pyrrolidin-3-yl]thiophene-2-carboxamide;
5-{1-[(3,5-dimethyl-1,2-oxazol-4-yl)carbonyl]pyrrolidin-3-yl}-N-(imidazo[1,2-a]pyridin-7-ylmethyl)thiophene-2-carboxamide;
N-(imidazo[1,2-a]pyridin-7-ylmethyl)-5-[1-(pyridin-3-ylcarbonyl)pyrrolidin-3-yl]thiophene-2-carboxamide;
N-(imidazo[1,2-a]pyridin-7-ylmethyl)-5-{1-[(1-methyl-1H-pyrazol-5-yl)carbonyl]pyrrolidin-3-yl}thiophene-2-carboxamide;
5-[1-(2,3-dimethylbutanoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(phenylsulfonyl)-1,2,3,6-tetrahydropyridin-4-yl]furan-2-carboxamide;
2-[1-(2-fluorobenzoyl)piperidin-4-yl]-N-(imidazo[1,2-a]pyridin-7-ylmethyl)-1,3-thiazole-5-carboxamide;
5-[1-(2-fluorobenzoyl)-1,2,3,6-tetrahydropyridin-4-yl]-N-(imidazo[1,2-a]pyridin-7-ylmethyl)furan-2-carboxamide;
2-[1-(2-fluorobenzoyl)pyrrolidin-3-yl]-N-(imidazo[1,2-a]pyridin-7-ylmethyl)-1,3-thiazole-5-carboxamide;
N-(imidazo[1,2-a]pyridin-7-ylmethyl)-2-[1-(2-methylpropanoyl)pyrrolidin-3-yl]-1,3-thiazole-5-carboxamide;
N-(imidazo[1,2-a]pyridin-7-ylmethyl)-2-[1-(3-methylbutanoyl)pyrrolidin-3-yl]-1,3-thiazole-5-carboxamide;
2-(1-benzoylpyrrolidin-3-yl)-N-(imidazo[1,2-a]pyridin-7-ylmethyl)-1,3-thiazole-5-carboxamide;
tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate;
N-(imidazo[1,2-a]pyridin-7-ylmethyl)-5-{1-[2-(piperazin-1-yl)ethyl]-1H-pyrazol-4-yl}thiophene-2-carboxamide;

N-(imidazo[1,2-a]pyridin-7-ylmethyl)-5-[1-(2-methylpropyl)-1H-pyrazol-5-yl]furan-2-carboxamide;
N-(imidazo[1,2-a]pyridin-7-ylmethyl)-5-[1-(3-methylbutyl)-1H-pyrazol-5-yl]furan-2-carboxamide;
N-(imidazo[1,2-a]pyridin-7-ylmethyl)-5-{[(2R)-2-(methoxymethyl)pyrrolidin-1-yl]carbonyl}thiophene-2-carboxamide;
N-(imidazo[1,2-a]pyridin-7-ylmethyl)-5-{[2-(2-methylpropyl)pyrrolidin-1-yl]carbonyl}thiophene-2-carboxamide;
5-[1-(2,2-dimethylpropyl)-1H-pyrazol-4-yl]-N-(imidazo[1,2-a]pyridin-7-ylmethyl)furan-2-carboxamide;
5-(1-benzyl-3-cyclopropyl-1H-pyrazol-5-yl)-N-(imidazo[1,2-a]pyridin-7-ylmethyl)thiophene-2-carboxamide;
N-(imidazo[1,2-a]pyridin-7-ylmethyl)-4-{[(2-methoxyphenyl)acetyl]amino}benzamide;
N-(imidazo[1,2-a]pyridin-7-ylmethyl)-4-[(phenylacetyl)amino]benzamide;
4-(benzoylamino)-N-(imidazo[1,2-a]pyridin-7-ylmethyl)benzamide;
2,5-difluoro-N-{4-[(imidazo[1,2-a]pyridin-7-ylmethyl)carbamoyl]phenyl}benzamide;
3,5-difluoro-N-{4-[(imidazo[1,2-a]pyridin-7-ylmethyl)carbamoyl]phenyl}benzamide;
3,4-difluoro-N-{4-[(imidazo[1,2-a]pyridin-7-ylmethyl)carbamoyl]phenyl}benzamide;
2,4-difluoro-N-{4-[(imidazo[1,2-a]pyridin-7-ylmethyl)carbamoyl]phenyl}benzamide;
2-fluoro-N-{4-[(imidazo[1,2-a]pyridin-7-ylmethyl)carbamoyl]phenyl}benzamide;
N-{4-[(imidazo[1,2-a]pyridin-7-ylmethyl)carbamoyl]phenyl}-3-methoxybenzamide;
4-{[(2-fluorophenyl)acetyl]amino}-N-(imidazo[1,2-a]pyridin-7-ylmethyl)benzamide;
N-(imidazo[1,2-a]pyridin-7-ylmethyl)-4-{[2-(2-methylpropyl)pyrrolidin-1-yl]carbonyl}benzamide;
N-(imidazo[1,2-a]pyridin-7-ylmethyl)-4-{[(2R)-2-(methoxymethyl)pyrrolidin-1-yl]carbonyl}benzamide;
N-(imidazo[1,2-a]pyridin-7-ylmethyl)-5-{1-[2-methyl-2-(piperazin-1-yl)propanoyl]piperidin-4-yl}thiophene-2-carboxamide;
N-{4-[(imidazo[1,2-a]pyridin-7-ylmethyl)carbamoyl]phenyl}-2-methoxybenzamide;
N-(imidazo[1,2-a]pyridin-7-ylmethyl)-4-(phenylsulfonyl)benzamide;
5-[1-(2,2-dimethylpropyl)-1H-pyrazol-4-yl]-N-(imidazo[1,2-a]pyridin-7-ylmethyl)thiophene-2-carboxamide;
N-(imidazo[1,2-a]pyridin-7-ylmethyl)-5-[1-(tricyclo[3.3.1.1~3,7~]dec-1-ylmethyl)-1H-pyrazol-4-yl]thiophene-2-carboxamide;
5-(1-benzyl-1H-pyrazol-4-yl)-N-(imidazo[1,2-a]pyridin-7-ylmethyl)thiophene-2-carboxamide;
N-(imidazo[1,2-a]pyridin-7-ylmethyl)-5-[1-(2-oxatricyclo[3.3.1.1~3,7~]dec-1-ylmethyl)-1H-pyrazol-4-yl]thiophene-2-carboxamide;
5-[1-(2,5-difluorobenzoyl)piperidin-4-yl]-N-(imidazo[1,2-a]pyridin-7-ylmethyl)thiophene-2-carboxamide;
5-[1-(2,4-difluorobenzoyl)piperidin-4-yl]-N-(imidazo[1,2-a]pyridin-7-ylmethyl)thiophene-2-carboxamide;
N-(imidazo[1,2-a]pyridin-7-ylmethyl)-5-{1-[2-(piperazin-1-yl)ethyl]-1H-pyrazol-4-yl}furan-2-carboxamide;
4-{[(2,5-difluorophenyl)acetyl]amino}-N-(imidazo[1,2-a]pyridin-7-ylmethyl)benzamide;
4-{[(2,4-difluorophenyl)acetyl]amino}-N-(imidazo[1,2-a]pyridin-7-ylmethyl)benzamide;
5-(3-cyclopropyl-1-methyl-1H-pyrazol-5-yl)-N-(imidazo[1,2-a]pyridin-7-ylmethyl)thiophene-2-carboxamide;
5-[3-cyclopropyl-1-(2-methoxyethyl)-1H-pyrazol-5-yl]-N-(imidazo[1,2-a]pyridin-7-ylmethyl)thiophene-2-carboxamide;
4-{[difluoro(phenyl)acetyl]amino}-N-(imidazo[1,2-a]pyridin-7-ylmethyl)benzamide;
N-(imidazo[1,2-a]pyridin-7-ylmethyl)-4-[(2-methyl-2-phenylpropanoyl)amino]benzamide;
N-(imidazo[1,2-a]pyridin-7-ylmethyl)-5-[1-(2-methylpropyl)-1H-pyrazol-5-yl]thiophene-2-carboxamide;
N-(imidazo[1,2-a]pyridin-7-ylmethyl)-5-[1-methyl-3-(2-methylpropyl)-1H-pyrazol-5-yl]thiophene-2-carboxamide;
5-[1-benzyl-3-(2-methylpropyl)-1H-pyrazol-5-yl]-N-(imidazo[1,2-a]pyridin-7-ylmethyl)thiophene-2-carboxamide;
N-(2,5-difluorobenzyl)-N'-(imidazo[1,2-a]pyridin-7-ylmethyl)benzene-1,4-dicarboxamide;
N-(imidazo[1,2-a]pyridin-7-ylmethyl)-4-{[2-(propan-2-yl)pyrrolidin-1-yl]carbonyl}benzamide;
4-{1-[(2-chloropyridin-3-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(3-methylbut-2-enoyl)piperidin-4-yl]benzamide;
4-[1-(3-fluoro-4-methoxybenzoyl)piperidin-4-yl]-N-(imidazo[1,2-a]pyridin-7-ylmethyl)benzamide;
N-(imidazo[1,2-a]pyridin-7-ylmethyl)-4-{1-[(2-methylcyclopent-1-en-1-yl)carbonyl]piperidin-4-yl}benzamide;
4-[1-(2-ethylbutanoyl)piperidin-4-yl]-N-(imidazo[1,2-a]pyridin-7-ylmethyl)benzamide;
4-{1-[(4-fluorophenoxy)acetyl]piperidin-4-yl}-N-(imidazo[1,2-a]pyridin-7-ylmethyl)benzamide;
4-[1-(3,5-dimethoxybenzoyl)piperidin-4-yl]-N-(imidazo[1,2-a]pyridin-7-ylmethyl)benzamide;
4-[1-(cyclohex-3-en-1-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(2-methoxyphenyl)acetyl]piperidin-4-yl}benzamide;
4-[1-(3-hydroxy-2-phenylpropanoyl)piperidin-4-yl]-N-(imidazo[1,2-a]pyridin-7-ylmethyl)benzamide;
N-(imidazo[1,2-a]pyridin-7-ylmethyl)-4-[1-(3-methylbenzoyl)piperidin-4-yl]benzamide;
4-[1-(2-acetylbenzoyl)piperidin-4-yl]-N-(imidazo[1,2-a]pyridin-7-ylmethyl)benzamide;
N-(imidazo[1,2-a]pyridin-7-ylmethyl)-4-{1-[2-(methoxymethyl)benzoyl]piperidin-4-yl}benzamide;
N-(imidazo[1,2-a]pyridin-7-ylmethyl)-4-[1-(2-phenylpropanoyl)piperidin-4-yl]benzamide;
4-[1-(2,6-dimethoxybenzoyl)piperidin-4-yl]-N-(imidazo[1,2-a]pyridin-7-ylmethyl)benzamide;
4-[1-(N,N-diethyl-beta-alanyl)piperidin-4-yl]-N-(imidazo[1,2-a]pyridin-7-ylmethyl)benzamide;
N-(imidazo[1,2-a]pyridin-7-ylmethyl)-4-(1-{[(2-methylpropyl)sulfonyl]acetyl}piperidin-4-yl)benzamide;
N-(imidazo[1,2-a]pyridin-7-ylmethyl)-4-[1-(2-phenoxypropanoyl)piperidin-4-yl]benzamide;
N-(imidazo[1,2-a]pyridin-7-ylmethyl)-4-[1-({[(1R,2S)-2-methylcyclohexyl]oxy}acetyl)piperidin-4-yl]benzamide;
4-{1-[(2-chloro-6-methylpyridin-4-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(3-methoxyphenyl)acetyl]piperidin-4-yl}benzamide;
4-[1-(2-chloro-4-cyanobenzoyl)piperidin-4-yl]-N-(imidazo[1,2-a]pyridin-7-ylmethyl)benzamide;
N-(imidazo[1,2-a]pyridin-7-ylmethyl)-4-{1-[(2E)-2-methylbut-2-enoyl]piperidin-4-yl}benzamide;
N-(imidazo[1,2-a]pyridin-7-ylmethyl)-4-{1-[(2-methoxy-5-methylphenyl)acetyl]piperidin-4-yl}benzamide;

4-[1-(2-hydroxy-3-methylbenzoyl)piperidin-4-yl]-N-(imidazo[1,2-a]pyridin-7-ylmethyl)benzamide;
N-(imidazo[1,2-a]pyridin-7-ylmethyl)-4-[1-(pyrrolidin-1-ylcarbonyl)piperidin-4-yl]benzamide;
N-(imidazo[1,2-a]pyridin-7-ylmethyl)-4-(1-{[1-(propan-2-yl)-1H-pyrazol-3-yl]carbonyl}piperidin-4-yl)benzamide;
4-{1-[(3-cyclopropyl-1-methyl-1H-pyrazol-5-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-4,5,6,7-tetrahydro-2H-indazol-3-yl)carbonyl]piperidin-4-yl}benzamide;
N-(imidazo[1,2-a]pyridin-7-ylmethyl)-4-[1-(4,5,6,7-tetrahydro-2,1-benzoxazol-3-ylcarbonyl)piperidin-4-yl]benzamide;
4-{1-[(3-fluoro-6-methylpyridin-2-yl)carbonyl]piperidin-4-yl}-N-(imidazo[1,2-a]pyridin-7-ylmethyl)benzamide;
4-{1-[(2-chloro-3-fluoropyridin-4-yl)carbonyl]piperidin-4-yl}-N-(imidazo[1,2-a]pyridin-7-ylmethyl)benzamide;
4-{1-[(3-chloropyridin-2-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[1-(pyridin-2-yl)cyclopropyl]carbonyl}piperidin-4-yl)benzamide;
4-{1-[(1-cyclopentyl-1H-pyrazol-3-yl)carbonyl]piperidin-4-yl}-N-(imidazo[1,2-a]pyridin-7-ylmethyl)benzamide;
4-{1-[2-(3-fluorophenoxy)propanoyl]piperidin-4-yl}-N-(imidazo[1,2-a]pyridin-7-ylmethyl)benzamide;
4-(1-{[1-(difluoromethyl)-1H-pyrazol-5-yl]carbonyl}piperidin-4-yl)-N-(imidazo[1,2-a]pyridin-7-ylmethyl)benzamide;
4-[1-(3,4-dihydro-2H-chromen-6-ylcarbonyl)piperidin-4-yl]-N-(imidazo[1,2-a]pyridin-7-ylmethyl)benzamide;
4-{1-[(cyclohexyloxy)acetyl]piperidin-4-yl}-N-(imidazo[1,2-a]pyridin-7-ylmethyl)benzamide;
4-{1-[(2-chloropyridin-3-yl)acetyl]piperidin-4-yl}-N-(imidazo[1,2-a]pyridin-7-ylmethyl)benzamide;
4-{1-[(5-cyclopropyl-1,2-oxazol-3-yl)carbonyl]piperidin-4-yl}-N-(imidazo[1,2-a]pyridin-7-ylmethyl)benzamide;
4-[1-(2H-chromen-3-ylcarbonyl)piperidin-4-yl]-N-(imidazo[1,2-a]pyridin-7-ylmethyl)benzamide;
4-{1-[(3,5-difluoropyridin-2-yl)carbonyl]piperidin-4-yl}-N-(imidazo[1,2-a]pyridin-7-ylmethyl)benzamide;
4-[1-(2,3-dihydro-1,4-benzodioxin-2-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(4-methoxycyclohexyl)carbonyl]piperidin-4-yl}benzamide;
4-[1-(2,3-dihydro-1,4-benzodioxin-5-ylcarbonyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-4-ylcarbonyl)piperidin-4-yl]benzamide;
N-(imidazo[1,2-a]pyridin-7-ylmethyl)-4-{1-[(2-methyl-1,3-benzoxazol-6-yl)carbonyl]piperidin-4-yl}benzamide;
4-{1-[(1-tert-butyl-3-methyl-1H-pyrazol-5-yl)carbonyl]piperidin-4-yl}-N-(imidazo[1,2-a]pyridin-7-ylmethyl)benzamide;
4-{1-[(1-cyanocyclopentyl)carbonyl]piperidin-4-yl}-N-(imidazo[1,2-a]pyridin-7-ylmethyl)benzamide;
N-(imidazo[1,2-a]pyridin-7-ylmethyl)-4-[1-(thieno[3,2-b]pyridin-2-ylcarbonyl)piperidin-4-yl]benzamide;
N-(imidazo[1,2-a]pyridin-7-ylmethyl)-4-[1-(quinolin-7-ylcarbonyl)piperidin-4-yl]benzamide;
4-[1-(5-cyano-2-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(5,6,7,8-tetrahydroquinolin-3-ylcarbonyl)piperidin-4-yl]benzamide;
4-[1-(3,4-dihydro-2H-pyrano[2,3-b]pyridin-6-ylcarbonyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-7-ylcarbonyl)piperidin-4-yl]benzamide;
N-(imidazo[1,2-a]pyridin-7-ylmethyl)-4-[1-(quinoxalin-2-ylcarbonyl)piperidin-4-yl]benzamide;
N-(imidazo[1,2-a]pyridin-7-ylmethyl)-4-{1-[(2E)-3-(2-methoxypyridin-3-yl)prop-2-enoyl]piperidin-4-yl}benzamide;
N-(imidazo[1,2-a]pyridin-7-ylmethyl)-4-{1-[(2E)-3-(pyridin-2-yl)prop-2-enoyl]piperidin-4-yl}benzamide;
N-(imidazo[1,2-a]pyridin-7-ylmethyl)-4-{1-[(8-methylimidazo[1,2-a]pyridin-2-yl)carbonyl]piperidin-4-yl}benzamide;
4-{1-[(2-ethoxypyridin-4-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(1-methyl-4,5,6,7-tetrahydro-1H-indazol-3-yl)carbonyl]piperidin-4-yl}benzamide;
N-(imidazo[1,2-a]pyridin-7-ylmethyl)-4-{1-[(4-methyl-4H-furo[3,2-b]pyrrol-5-yl)carbonyl]piperidin-4-yl}benzamide;
4-[1-(3-cyano-5-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(isoquinolin-8-ylcarbonyl)piperidin-4-yl]benzamide;
4-{1-[(4-cyanophenyl)acetyl]piperidin-4-yl}-N-(imidazo[1,2-a]pyridin-7-ylmethyl)benzamide;
4-[1-(3-cyano-4-fluorobenzoyl)piperidin-4-yl]-N-(imidazo[1,2-a]pyridin-7-ylmethyl)benzamide;
N-(imidazo[1,2-a]pyridin-7-ylmethyl)-4-[1-(4,5,6,7-tetrahydro-1,3-benzothiazol-2-ylcarbonyl)piperidin-4-yl]benzamide;
4-[1-(1,3-benzothiazol-2-ylcarbonyl)piperidin-4-yl]-N-(imidazo[1,2-a]pyridin-7-ylmethyl)benzamide;
4-{1-[(3-ethyl-1,2-oxazol-5-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[3-methyl-1-(prop-2-en-1-yl)-1H-pyrazol-5-yl]carbonyl}piperidin-4-yl)benzamide;
4-[1-(1,2,3-benzothiadiazol-5-ylcarbonyl)piperidin-4-yl]-N-(imidazo[1,2-a]pyridin-7-ylmethyl)benzamide;
4-{1-[(2-ethyl-1,3-thiazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[2-(propan-2-yl)pyrimidin-4-yl]carbonyl}piperidin-4-yl)benzamide;
4-{1-[(5,6-dimethylpyridin-3-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[2-(propan-2-yl)tetrahydro-2H-pyran-4-yl]carbonyl}piperidin-4-yl)benzamide;
N-(imidazo[1,2-a]pyridin-7-ylmethyl)-4-[1-(2-methoxy-6-methylbenzoyl)piperidin-4-yl]benzamide;
4-[1-(1,3-benzothiazol-7-ylcarbonyl)piperidin-4-yl]-N-(imidazo[1,2-a]pyridin-7-ylmethyl)benzamide;
4-{1-[(2-chloro-5-fluoropyridin-4-yl)carbonyl]piperidin-4-yl}-N-(imidazo[1,2-a]pyridin-7-ylmethyl)benzamide;
4-{1-[(3-cyclopropyl-1,2-oxazol-5-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(3-methoxythiophen-2-yl)carbonyl]piperidin-4-yl}benzamide;
N-(imidazo[1,2-a]pyridin-7-ylmethyl)-4-(1-{[2-methyl-5-(propan-2-yl)furan-3-yl]carbonyl}piperidin-4-yl)benzamide;
N-(imidazo[1,2-a]pyridin-7-ylmethyl)-4-[1-(piperidin-1-ylcarbonyl)piperidin-4-yl]benzamide;

4-{4-[(imidazo[1,2-a]pyridin-7-ylmethyl)carbamoyl]phenyl}-N,N-dimethylpiperidine-1-carboxamide;
5-{1-[2,2-dimethyl-3-(piperazin-1-yl)propyl]-1H-pyrazol-4-yl}-N-(imidazo[1,2-a]pyridin-7-ylmethyl)thiophene-2-carboxamide;
5-[1-(3-amino-2,2-dimethylpropyl)-1H-pyrazol-4-yl]-N-(imidazo[1,2-a]pyridin-7-ylmethyl)thiophene-2-carboxamide;
4-{1-[(2-cyclopropyl-1,3-thiazol-5-yl)carbonyl]piperidin-4-yl}-N-(imidazo[1,2-a]pyridin-7-ylmethyl)benzamide;
4-[1-(1,3-benzothiazol-5-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(1-methyl-1H-indazol-6-yl)carbonyl]piperidin-4-yl}benzamide;
4-{1-[(4-chloro-1,3-dimethyl-1H-pyrazol-5-yl)carbonyl]piperidin-4-yl}-N-(imidazo[1,2-a]pyridin-7-ylmethyl)benzamide;
4-{1-[(5-ethylpyridin-2-yl)carbonyl]piperidin-4-yl}-N-(imidazo[1,2-a]pyridin-7-ylmethyl)benzamide;
4-{1-[(3-chloro-5-cyanopyridin-2-yl)carbonyl]piperidin-4-yl}-N-(imidazo[1,2-a]pyridin-7-ylmethyl)benzamide;
4-{1-[(1-cyano-3-methylcyclobutyl)carbonyl]piperidin-4-yl}-N-(imidazo[1,2-a]pyridin-7-ylmethyl)benzamide;
4-{1-[(1,5-diethyl-1H-1,2,3-triazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(4-methoxythiophen-2-yl)carbonyl]piperidin-4-yl}benzamide;
4-{1-[(5-cyanothiophen-2-yl)carbonyl]piperidin-4-yl}-N-(imidazo[1,2-a]pyridin-7-ylmethyl)benzamide;
4-{1-[(5-cyclopropylpyridin-2-yl)carbonyl]piperidin-4-yl}-N-(imidazo[1,2-a]pyridin-7-ylmethyl)benzamide;
4-[1-(4-cyano-2,6-difluorobenzoyl)piperidin-4-yl]-N-(imidazo[1,2-a]pyridin-7-ylmethyl)benzamide;
4-(1-{[1-ethyl-3-(propan-2-yl)-1H-pyrazol-4-yl]carbonyl}piperidin-4-yl)-N-(imidazo[1,2-a]pyridin-7-ylmethyl)benzamide;
N-(imidazo[1,2-a]pyridin-7-ylmethyl)-4-(1-{[1-(propan-2-yl)-1H-pyrazol-3-yl]acetyl}piperidin-4-yl)benzamide;
4-[1-(1-benzofuran-3-ylcarbonyl)piperidin-4-yl]-N-(imidazo[1,2-a]pyridin-7-ylmethyl)benzamide;
N-(imidazo[1,2-a]pyridin-7-ylmethyl)-4-{1-[(3-methyl-5,6,7,8-tetrahydroimidazo[1,5-a]pyridin-1-yl)carbonyl]piperidin-4-yl}benzamide;
N-(imidazo[1,2-a]pyridin-7-ylmethyl)-4-{1-[(4-methoxy-5-methylpyridin-2-yl)carbonyl]piperidin-4-yl}benzamide;
4-{1-[(1-cyclopentyl-1H-pyrazol-5-yl)carbonyl]piperidin-4-yl}-N-(imidazo[1,2-a]pyridin-7-ylmethyl)benzamide;
4-{1-[(4-chloro-1,3-thiazol-5-yl)carbonyl]piperidin-4-yl}-N-(imidazo[1,2-a]pyridin-7-ylmethyl)benzamide;
4-{1-[(3-cyanothiophen-2-yl)carbonyl]piperidin-4-yl}-N-(imidazo[1,2-a]pyridin-7-ylmethyl)benzamide;
N-(imidazo[1,2-a]pyridin-7-ylmethyl)-4-(1-{[4-(propan-2-yl)pyrimidin-5-yl]carbonyl}piperidin-4-yl)benzamide;
N-(imidazo[1,2-a]pyridin-7-ylmethyl)-4-{1-[(1-methyl-5-propyl-1H-pyrazol-4-yl)carbonyl]piperidin-4-yl}benzamide;
4-{1-[2-(3-cyclopropyl-1H-pyrazol-1-yl)propanoyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2,3-dihydro-1-benzofuran-7-yl)carbonyl]piperidin-4-yl}benzamide;
N-(imidazo[1,2-a]pyridin-7-ylmethyl)-4-(1-{[2-(propan-2-yl)-1,3-thiazol-4-yl]carbonyl}piperidin-4-yl)benzamide;
4-(1-{[1-(difluoromethyl)-5-methyl-1H-pyrazol-3-yl]carbonyl}piperidin-4-yl)-N-(imidazo[1,2-a]pyridin-7-ylmethyl)benzamide;
4-{1-[(4-cyanothiophen-2-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(pyrazolo[1,5-a]pyridin-2-ylcarbonyl)piperidin-4-yl]benzamide;
4-[1-(1-benzofuran-5-ylcarbonyl)piperidin-4-yl]-N-(imidazo[1,2-a]pyridin-7-ylmethyl)benzamide;
N-(imidazo[1,2-a]pyridin-7-ylmethyl)-4-(1-{[2-(propan-2-yl)-1,3-oxazol-4-yl]carbonyl}piperidin-4-yl)benzamide;
N-(imidazo[1,2-a]pyridin-7-ylmethyl)-4-{1-[(2-methoxy-5-methylpyridin-3-yl)carbonyl]piperidin-4-yl}benzamide;
4-{1-[(5,6-dimethoxypyridin-2-yl)carbonyl]piperidin-4-yl}-N-(imidazo[1,2-a]pyridin-7-ylmethyl)benzamide;
N-(imidazo[1,2-a]pyridin-7-ylmethyl)-4-{1-[(2-methyl-2H-indazol-4-yl)carbonyl]piperidin-4-yl}benzamide;
4-{1-[(2-ethylpiperidin-1-yl)(oxo)acetyl]piperidin-4-yl}-N-(imidazo[1,2-a]pyridin-7-ylmethyl)benzamide;
N-(imidazo[1,2-a]pyridin-7-ylmethyl)-4-[1-[(2-methyl-2H-indazol-6-yl)carbonyl]piperidin-4-yl]benzamide;
N-(imidazo[1,2-a]pyridin-7-ylmethyl)-4-[1-[(1-methyl-1H-indazol-4-yl)carbonyl]piperidin-4-yl]benzamide;
N-(imidazo[1,2-a]pyridin-7-ylmethyl)-4-(1-{[2-(trifluoromethyl)furan-3-yl]carbonyl}piperidin-4-yl)benzamide; and
pharmaceutically acceptable salts thereof.

Embodiments of Formula (VII)

In another aspect, the present invention provides compounds of Formula (VIIA)

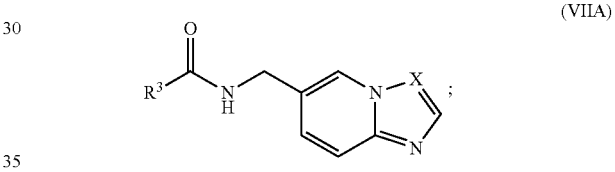

(VIIA)

and pharmaceutically acceptable salts thereof; wherein X and $R^3$ are as described herein for Formula (IA).

One embodiment pertains to compounds of Formula (VIIA) or pharmaceutically acceptable salts thereof;
wherein
X is N or CY$^1$;
Y$^1$ is independently selected from the group consisting of hydrogen, alkyl, alkoxy, haloalkyl, hydroxyalkyl, OH, CN, F, Cl, Br, and I;
R$^3$ is independently selected from the group consisting of phenyl and 5-6 membered heteroaryl; wherein each R$^3$ phenyl is substituted at the para position with one substituent independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I; wherein each R$^3$ phenyl is optionally additionally substituted with one substituent independently selected from the group consisting of alkyl, haloalkyl, alkoxyalkyl, hydroxyalkyl, C(O)H, C(O)OH, C(N)NH$_2$, OH, CN, N$_3$, NO$_2$, F, Cl, Br and I; wherein each R$^3$ 5-6 membered heteroaryl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, C(O)C(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$, at each occurrence, is independently selected from the group consisting of aryl, heterocyclyl, cycloalkyl, cycloalkenyl, alkyl, alkenyl, and alkynyl; wherein each R$^{10}$ alkyl, alkenyl, and alkynyl is optionally substituted with one, two, three or four substituents independently selected from the group consisting of alkoxy, F, Cl, Br and I; and R$^{11}$, at each occurrence, is independently selected from the group consisting of aryl, heterocyclyl, cycloalkyl, cycloalkenyl, alkyl, alkenyl, and alkynyl;

with the proviso that when X is CY$^1$ and Y$^1$ is hydrogen; and R$^3$ is thiazolyl; the R$^3$ thiazolyl is substituted with one substituent.

In one embodiment of Formula (VIIA), X is N or CY$^1$. In another embodiment of Formula (VIIA), X is N. In another embodiment of Formula (VIIA), X is CY$^1$.

In one embodiment of Formula (VIIA), X is CY$^1$; and Y$^1$ is independently selected from the group consisting of hydrogen, alkyl, alkoxy, haloalkyl, hydroxyalkyl, OH, CN, F, Cl, Br, and I. In another embodiment of Formula (VIIA), X is CY$^1$; and Y$^1$ is independently selected from the group consisting of hydrogen, Cl, Br, and I. In another embodiment of Formula (VIIA), X is CY$^1$; and Y$^1$ is Cl. In another embodiment of Formula (VIIA), X is CY$^1$; and Y$^1$ is hydrogen.

In one embodiment of Formula (VIIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, $OH$, $CN$, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, F, Cl, Br and I. In another embodiment of Formula (VIIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VIIA), $R^3$ is phenyl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (VIIA), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (VIIA), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VIIA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $CN$, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, F, Cl, Br and I. In another embodiment of Formula (VIIA), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, $OH$, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, $OH$, and F.

In another embodiment of Formula (VIIA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, F, Cl, Br and I. In another embodiment of Formula (VIIA), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and $OH$; wherein each $R^5$ aryl and heterocyclyl is optionally substituted with one, two, three or four substituents independently selected from the group consisting of $R^8$, $OR^8$, $CN$, F, Cl, Br and I.

In one embodiment of Formula (VIIA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, $OH$, $CN$, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, $OH$, $CN$, $N_3$, $NO_2$, F, Cl, Br and I. In another embodiment of Formula (VIIA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, $OH$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (VIIA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (VIIA), $R^7$, at each occurrence, is alkyl or heterocyclyl.

In one embodiment of Formula (VIIA), $R^8$, at each occurrence, is independently selected from the group consisting of alkyl, alkenyl, and alkynyl. In another embodiment of Formula (VIIA), $R^8$, at each occurrence, is independently alkyl.

In one embodiment of Formula (VIIA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (VIIA), $R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (VIIA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (VIIA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (VIIA), $R^{11}$, at each occurrence, is independently selected from the group consisting of aryl, heterocyclyl, cycloalkyl, cycloalkenyl, alkyl, alkenyl, and alkynyl. In another embodiment of Formula (VIIA), $R^{11}$, at each occurrence, is independently alkyl. In another embodiment of Formula (VIIA), $R^{11}$, at each occurrence, is independently cycloalkyl.

One embodiment pertains to compounds or pharmaceutically acceptable salts thereof, which are useful as inhibitors of NAMPT, the compounds having Formula (VIIA)

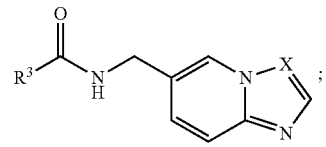

Formula (VIIA)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, C(O)R⁶, CO(O)R⁶, C(O)C(O)R⁶, NHC(O)R⁶, NHC(O)NHR⁶, C(O)N(R⁶)₂, OH, F, Cl, Br and I;

R⁵, at each occurrence, is independently selected from the group consisting of alkyl, aryl, heterocyclyl, and cycloalkyl; wherein each R⁵ alkyl is optionally substituted with one, two, three or four substituents independently selected from the group consisting of R⁷, OR⁷, OH, F, Cl, Br and I; wherein each R⁵ aryl, and heterocyclyl is optionally substituted with one, two, three or four substituents independently selected from the group consisting of R⁸, OR⁸, CN, F, Cl, Br and I;

R⁶, at each occurrence, is independently selected from the group consisting of alkyl, alkenyl, aryl, heterocyclyl, cycloalkyl, and cycloalkenyl; wherein each R⁶ alkyl and alkenyl is optionally substituted with one, two, three or four substituents independently selected from the group consisting of R⁹, OR⁹, SO₂R⁹, NH₂, N(R⁹)₂, OH, F, Cl, Br and I; wherein each R⁶ aryl, cycloalkyl, cycloalkenyl, and heterocyclyl is optionally substituted with one, two, three or four substituents independently selected from the group consisting of R¹⁰, OR¹⁰, C(O)R¹⁰, CN, F, and Cl;

R⁷, at each occurrence, is independently selected from the group consisting of alkyl, and heterocyclyl;

R⁸, at each occurrence, is independently alkyl;

R⁹, at each occurrence, is independently selected from the group consisting of alkyl, aryl, heterocyclyl, and cycloalkyl; wherein each R⁹ alkyl is optionally substituted with one, two, three or four substituents independently selected from the group consisting of aryl, alkoxy, F, Cl, Br and I; wherein each R⁹ aryl, cycloalkyl, and heterocyclyl is optionally substituted with one, two, three or four substituents independently selected from the group consisting of R¹¹, OR¹¹, CO(O)R¹¹, CN, F, Cl, Br and I;

R¹⁰, at each occurrence, is independently selected from the group consisting of aryl, heterocyclyl, cycloalkyl, alkyl, and alkenyl; wherein each R¹⁰ alkyl is optionally substituted with one, two, three or four substituents independently selected from the group consisting of alkoxy, and F; and R¹¹, at each occurrence, is independently cycloalkyl or alkyl;

with the proviso that when X is CY¹ and Y¹ is hydrogen; and R³ is thiazolyl; the R³ thiazolyl is substituted with one substituent.

Still another embodiment pertains to compounds having Formula (VIIA), which include 4-[(cyclopentylacetyl)amino]-N-(imidazo[1,2-a]pyridin-6-ylmethyl)benzamide;

2-[(4-cyanobenzyl)(3-methylbutanoyl)amino]-N-(imidazo[1,2-a]pyridin-6-ylmethyl)-1,3-thiazole-5-carboxamide;

2-[(4-cyanobenzyl)(3-methoxypropanoyl)amino]-N-(imidazo[1,2-a]pyridin-6-ylmethyl)-1,3-thiazole-5-carboxamide;

N-(imidazo[1,2-a]pyridin-6-ylmethyl)-2-[3-methoxypropanoyl)(3-methylbutyl)amino]-1,3-thiazole-5-carboxamide;

N-(imidazo[1,2-a]pyridin-6-ylmethyl)-5-[1-(2-methylpropyl)-1H-pyrazol-4-yl]thiophene-2-carboxamide;

N-(imidazo[1,2-a]pyridin-6-ylmethyl)-4-[(tetrahydrofuran-2-ylacetyl)amino]benzamide;

N-(imidazo[1,2-a]pyridin-6-ylmethyl)-4-[(tetrahydrofuran-3-ylacetyl)amino]benzamide;

N-(imidazo[1,2-a]pyridin-6-ylmethyl)-4-[(tetrahydro-2H-pyran-4-ylacetyl)amino]benzamide;

N-(imidazo[1,2-a]pyridin-6-ylmethyl)-4-[(morpholin-4-ylacetyl)amino]benzamide;

4-[(3-cyclopentylpropanoyl)amino]-N-(imidazo[1,2-a]pyridin-6-ylmethyl)benzamide;

N-(imidazo[1,2-a]pyridin-6-ylmethyl)-4-{[(propan-2-yloxy)acetyl]amino}benzamide;

tert-butyl 4-{4-[(imidazo[1,2-a]pyridin-6-ylmethyl)carbamoyl]phenyl}-3,6-dihydropyridine-1(2H)-carboxylate;

N-(imidazo[1,2-a]pyridin-6-ylmethyl)-2-(1,2,4,5-tetrahydro-3H-3-benzazepin-3-yl)-1,3-thiazole-5-carboxamide;

N-(imidazo[1,2-a]pyridin-6-ylmethyl)-2-(3-phenylpyrrolidin-1-yl)-1,3-thiazole-5-carboxamide;

N-(imidazo[1,2-a]pyridin-6-ylmethyl)-2-[(3-methylbutyl)amino]-1,3-thiazole-5-carboxamide;

2-(1,3-dihydro-2H-isoindol-2-yl)-N-(imidazo[1,2-a]pyridin-6-ylmethyl)-1,3-thiazole-5-carboxamide;

N-(imidazo[1,2-a]pyridin-6-ylmethyl)-4-[1-(2-methylpropanoyl)-1,2,3,6-tetrahydropyridin-4-yl]benzamide;

4-[1-(2-hydroxy-2-methylpropanoyl)-1,2,3,6-tetrahydropyridin-4-yl]-N-(imidazo[1,2-a]pyridin-6-ylmethyl)benzamide;

N-(imidazo[1,2-a]pyridin-6-ylmethyl)-4-[1-(morpholin-4-ylacetyl)-1,2,3,6-tetrahydropyridin-4-yl]benzamide;

N-(imidazo[1,2-a]pyridin-6-ylmethyl)-4-[1-(tetrahydro-2H-pyran-4-ylacetyl)-1,2,3,6-tetrahydropyridin-4-yl]benzamide;

N-(imidazo[1,2-a]pyridin-6-ylmethyl)-4-[1-(tetrahydrofuran-3-ylacetyl)-1,2,3,6-tetrahydropyridin-4-yl]benzamide;

N-(imidazo[1,2-a]pyridin-6-ylmethyl)-4-[1-(tetrahydrofuran-2-ylacetyl)-1,2,3,6-tetrahydropyridin-4-yl]benzamide;

N-(imidazo[1,2-a]pyridin-6-ylmethyl)-4-{1-[3-(tetrahydrofuran-2-yl)propanoyl]-1,2,3,6-tetrahydropyridin-4-yl}benzamide;

4-[1-(cyclopentylacetyl)-1,2,3,6-tetrahydropyridin-4-yl]-N-(imidazo[1,2-a]pyridin-6-ylmethyl)benzamide;

N-(imidazo[1,2-a]pyridin-6-ylmethyl)-4-{1-[(propan-2-yloxy)acetyl]-1,2,3,6-tetrahydropyridin-4-yl}benzamide;

N-(imidazo[1,2-a]pyridin-6-ylmethyl)-4-[1-(tetrahydrofuran-2-ylcarbonyl)-1,2,3,6-tetrahydropyridin-4-yl]benzamide;

N-(imidazo[1,2-a]pyridin-6-ylmethyl)-4-[1-(tetrahydrofuran-3-ylcarbonyl)-1,2,3,6-tetrahydropyridin-4-yl]benzamide;

N-(imidazo[1,2-a]pyridin-6-ylmethyl)-4-[1-(tetrahydro-2H-pyran-4-ylcarbonyl)-1,2,3,6-tetrahydropyridin-4-yl]benzamide;

4-[1-(1,4-dioxan-2-ylcarbonyl)-1,2,3,6-tetrahydropyridin-4-yl]-N-(imidazo[1,2-a]pyridin-6-ylmethyl)benzamide;

N-(imidazo[1,2-a]pyridin-6-ylmethyl)-4-{1-[(2-methoxyethyl)acetyl]-1,2,3,6-tetrahydropyridin-4-yl}benzamide;

4-(1-benzoyl-1,2,3,6-tetrahydropyridin-4-yl)-N-(imidazo[1,2-a]pyridin-6-ylmethyl)benzamide;

4-{1-[(4,4-difluorocyclohexyl)carbonyl]-1,2,3,6-tetrahydropyridin-4-yl}-N-(imidazo[1,2-a]pyridin-6-ylmethyl)benzamide;

2-(3,4-dihydroisoquinolin-2(1H)-yl)-N-(imidazo[1,2-a]pyridin-6-ylmethyl)-1,3-thiazole-5-carboxamide;

tert-butyl 4-{4-[(imidazo[1,2-a]pyridin-6-ylmethyl)carbamoyl]phenoxy}piperidine-1-carboxylate;

N-(imidazo[1,2-a]pyridin-6-ylmethyl)-2-[{[2-(propan-2-yloxy)ethyl]carbamoyl}(tetrahydrofuran-2-ylmethyl)amino]-1,3-thiazole-5-carboxamide;

N-(imidazo[1,2-a]pyridin-6-ylmethyl)-2-[2-oxo-4-(tetrahydrofuran-3-yl)-1,3-oxazolidin-3-yl]-1,3-thiazole-5-carboxamide;

N-(imidazo[1,2-a]pyridin-6-ylmethyl)-4-[1-(2-methylpropyl)-1H-pyrazol-4-yl]benzamide;

N-(imidazo[1,2-a]pyridin-6-ylmethyl)-5-[1-(2-methylpropyl)-1H-pyrazol-4-yl]furan-2-carboxamide;
N-(imidazo[1,2-a]pyridin-6-ylmethyl)-2-(2-oxo-5-phenyl-1,3-oxazolidin-3-yl)-1,3-thiazole-5-carboxamide;
N-(imidazo[1,2-a]pyridin-6-ylmethyl)-2-{[(2-methyl-1,3-thiazol-5-yl)acetyl](tetrahydrofuran-2-ylmethyl)amino}-1,3-thiazole-5-carboxamide;
N-(imidazo[1,2-a]pyridin-6-ylmethyl)-2-{[(2-methyl-1,3-thiazol-4-yl)acetyl](tetrahydrofuran-2-ylmethyl)amino}-1,3-thiazole-5-carboxamide;
N-(imidazo[1,2-a]pyridin-6-ylmethyl)-2-{[(3-methyl-1,2-oxazol-5-yl)acetyl](tetrahydrofuran-2-ylmethyl)amino}-1,3-thiazole-5-carboxamide;
2-{[3-(3-chloro-1,2-oxazol-5-yl)propanoyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-{[3-(3-methoxy-1,2-oxazol-5-yl)propanoyl](tetrahydrofuran-2-ylmethyl)amino}-1,3-thiazole-5-carboxamide;
2-{[(3,5-dimethyl-1,2-oxazol-4-yl)acetyl](tetrahydrofuran-2-ylmethyl)amino}-N-(imidazo[1,2-a]pyridin-6-ylmethyl)-1,3-thiazole-5-carboxamide;
2-{[3-(3,5-dimethyl-1,2-oxazol-4-yl)propanoyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-{[3-(1-methyl-1H-pyrazol-4-yl)propanoyl](tetrahydrofuran-2-ylmethyl)amino}-1,3-thiazole-5-carboxamide;
N-(imidazo[1,2-a]pyridin-6-ylmethyl)-2-{[3-(4-methyl-1,3-thiazol-5-yl)propanoyl](tetrahydrofuran-2-ylmethyl)amino}-1,3-thiazole-5-carboxamide;
N-(imidazo[1,2-a]pyridin-6-ylmethyl)-2-[(tetrahydrofuran-2-ylmethyl)(1H-tetrazol-5-ylacetyl)amino]-1,3-thiazole-5-carboxamide;
N-(imidazo[1,2-a]pyridin-6-ylmethyl)-2-{[3-(1,2-oxazol-5-yl)propanoyl](tetrahydrofuran-2-ylmethyl)amino}-1,3-thiazole-5-carboxamide;
N-(imidazo[1,2-a]pyridin-6-ylmethyl)-2-[(1,2-oxazol-3-ylacetyl)(tetrahydrofuran-2-ylmethyl)amino]-1,3-thiazole-5-carboxamide;
N-(imidazo[1,2-a]pyridin-6-ylmethyl)-2-{[3-(1,2-oxazol-4-yl)propanoyl](tetrahydrofuran-2-ylmethyl)amino}-1,3-thiazole-5-carboxamide;
N-(imidazo[1,2-a]pyridin-6-ylmethyl)-2-{(tetrahydrofuran-2-ylmethyl)[3-(1,3-thiazol-2-yl)propanoyl]amino}-1,3-thiazole-5-carboxamide;
N-(imidazo[1,2-a]pyridin-6-ylmethyl)-2-[3-methylbutanoyl)amino]-1,3-thiazole-5-carboxamide;
N-(imidazo[1,2-a]pyridin-6-ylmethyl)-2-[3-methoxypropanoyl)(tetrahydrofuran-3-ylmethyl)amino]-1,3-thiazole-5-carboxamide;
N-(imidazo[1,2-a]pyridin-6-ylmethyl)-2-[(tetrahydrofuran-3-ylmethyl)(tetrahydro-2H-pyran-4-ylcarbonyl)amino]-1,3-thiazole-5-carboxamide;
N-(imidazo[1,2-a]pyridin-6-ylmethyl)-2-{[(2-methoxyethyl)carbamoyl](tetrahydrofuran-3-ylmethyl)amino}-1,3-thiazole-5-carboxamide;
N-(imidazo[1,2-a]pyridin-6-ylmethyl)-2-[(3-methoxypropanoyl)(tetrahydro-2H-pyran-4-ylmethyl)amino]-1,3-thiazole-5-carboxamide;
N-(imidazo[1,2-a]pyridin-6-ylmethyl)-2-[(tetrahydrofuran-3-ylcarbonyl)(tetrahydro-2H-pyran-4-ylmethyl)amino]-1,3-thiazole-5-carboxamide;
N-(imidazo[1,2-a]pyridin-6-ylmethyl)-2-[(tetrahydro-2H-pyran-4-ylcarbonyl)(tetrahydro-2H-pyran-4-ylmethyl)amino]-1,3-thiazole-5-carboxamide;
N-(imidazo[1,2-a]pyridin-6-ylmethyl)-2-{(3-methoxypropanoyl)[(2R)-tetrahydrofuran-2-ylmethyl]amino}-1,3-thiazole-5-carboxamide;
N-(imidazo[1,2-a]pyridin-6-ylmethyl)-2-{(tetrahydrofuran-3-ylcarbonyl)[(2R)-tetrahydrofuran-2-ylmethyl]amino}-1,3-thiazole-5-carboxamide;
N-(imidazo[1,2-a]pyridin-6-ylmethyl)-2-{[(2R)-tetrahydrofuran-2-ylmethyl](tetrahydro-2H-pyran-4-ylcarbonyl)amino}-1,3-thiazole-5-carboxamide;
N-(imidazo[1,2-a]pyridin-6-ylmethyl)-2-{(3-methoxypropanoyl)[(2S)-tetrahydrofuran-2-ylmethyl]amino}-1,3-thiazole-5-carboxamide;
N-(imidazo[1,2-a]pyridin-6-ylmethyl)-2-{(tetrahydrofuran-3-ylcarbonyl)[(2S)-tetrahydrofuran-2-ylmethyl]amino}-1,3-thiazole-5-carboxamide;
N-(imidazo[1,2-a]pyridin-6-ylmethyl)-2-{[(2S)-tetrahydrofuran-2-ylmethyl](tetrahydro-2H-pyran-4-ylcarbonyl)amino}-1,3-thiazole-5-carboxamide;
N-(imidazo[1,2-a]pyridin-6-ylmethyl)-2-{[(2-methoxyethyl)carbamoyl](tetrahydro-2H-pyran-4-ylmethyl)amino}-1,3-thiazole-5-carboxamide;
N-(imidazo[1,2-a]pyridin-6-ylmethyl)-2-[{[2-(propan-2-yloxy)ethyl]carbamoyl}(tetrahydro-2H-pyran-4-ylmethyl)amino]-1,3-thiazole-5-carboxamide;
N-(imidazo[1,2-a]pyridin-6-ylmethyl)-2-{[(2-methoxyethyl)carbamoyl][(2R)-tetrahydrofuran-2-ylmethyl]amino}-1,3-thiazole-5-carboxamide;
N-(imidazo[1,2-a]pyridin-6-ylmethyl)-2-({[2-(propan-2-yloxy)ethyl]carbamoyl}[(2R)-tetrahydrofuran-2-ylmethyl]amino)-1,3-thiazole-5-carboxamide;
N-(imidazo[1,2-a]pyridin-6-ylmethyl)-2-{[(2-methoxyethyl)carbamoyl][(2S)-tetrahydrofuran-2-ylmethyl]amino}-1,3-thiazole-5-carboxamide;
N-(imidazo[1,2-a]pyridin-6-ylmethyl)-2-({[2-(propan-2-yloxy)ethyl]carbamoyl}[(2S)-tetrahydrofuran-2-ylmethyl]amino)-1,3-thiazole-5-carboxamide;
N-(imidazo[1,2-a]pyridin-6-ylmethyl)-2-[{[2-(propan-2-yloxy)ethyl]carbamoyl}(tetrahydrofuran-3-ylmethyl)amino]-1,3-thiazole-5-carboxamide;
2-[5-(4-chlorophenyl)-2-oxo-1,3-oxazolidin-3-yl]-N-(imidazo[1,2-a]pyridin-6-ylmethyl)-1,3-thiazole-5-carboxamide;
N-(imidazo[1,2-a]pyridin-6-ylmethyl)-4-{[1-(2-methylpropanoyl)piperidin-4-yl]oxy}benzamide;
4-[(1-acetylpiperidin-4-yl)oxy]-N-(imidazo[1,2-a]pyridin-6-ylmethyl)benzamide;
4-{[1-(cyclopropylcarbonyl)piperidin-4-yl]oxy}-N-(imidazo[1,2-a]pyridin-6-ylmethyl)benzamide;
N-(imidazo[1,2-a]pyridin-6-ylmethyl)-4-{[1-(tetrahydro-2H-pyran-4-ylcarbonyl)piperidin-4-yl]oxy}benzamide;
4-{[1-(1,4-dioxan-2-ylcarbonyl)piperidin-4-yl]oxy}-N-(imidazo[1,2-a]pyridin-6-ylmethyl)benzamide;
N-(imidazo[1,2-a]pyridin-6-ylmethyl)-4-({1-[(2S)-tetrahydrofuran-2-ylcarbonyl]piperidin-4-yl}oxy)benzamide;
N-(imidazo[1,2-a]pyridin-6-ylmethyl)-4-({1-[(2R)-tetrahydrofuran-2-ylcarbonyl]piperidin-4-yl}oxy)benzamide;
4-{[1-(2-hydroxy-2-methylpropanoyl)piperidin-4-yl]oxy}-N-(imidazo[1,2-a]pyridin-6-ylmethyl)benzamide;
N-(imidazo[1,2-a]pyridin-6-ylmethyl)-4-({1-[(propan-2-yloxy)acetyl]piperidin-4-yl}oxy)benzamide;
4-[(1-butanoylpiperidin-4-yl)oxy]-N-(imidazo[1,2-a]pyridin-6-ylmethyl)benzamide;
N-(imidazo[1,2-a]pyridin-6-ylmethyl)-4-{[1-(3-methoxy-2-methylpropanoyl)piperidin-4-yl]oxy}benzamide;
N-(imidazo[1,2-a]pyridin-6-ylmethyl)-4-{[1-(3,3,3-trifluoropropanoyl)piperidin-4-yl]oxy}benzamide;

N-(imidazo[1,2-a]pyridin-6-ylmethyl)-4-{[1-(tetrahydro-2H-pyran-4-ylacetyl)piperidin-4-yl]oxy}benzamide;
4-{[1-(cyclopropylacetyl)piperidin-4-yl]oxy}-N-(imidazo[1,2-a]pyridin-6-ylmethyl)benzamide;
N-(imidazo[1,2-a]pyridin-6-ylmethyl)-4-{[1-(tetrahydrofuran-2-ylacetyl)piperidin-4-yl]oxy}benzamide;
N-(imidazo[1,2-a]pyridin-6-ylmethyl)-5-[1-(2-methylpropanoyl)-1H-pyrazol-4-yl]thiophene-2-carboxamide;
5-[1-(2-hydroxy-2-methylpropyl)-1H-pyrazol-4-yl]-N-(imidazo[1,2-a]pyridin-6-ylmethyl)thiophene-2-carboxamide;
N-(imidazo[1,2-a]pyridin-6-ylmethyl)-5-{1-[(3-methyloxetan-3-yl)methyl]-1H-pyrazol-4-yl}thiophene-2-carboxamide;
5-[1-(cyclobutylmethyl)-1H-pyrazol-4-yl]-N-(imidazo[1,2-a]pyridin-6-ylmethyl)thiophene-2-carboxamide;
5-[1-(cyclohexylmethyl)-1H-pyrazol-4-yl]-N-(imidazo[1,2-a]pyridin-6-ylmethyl)thiophene-2-carboxamide;
5-{1-[(2R)-2-hydroxybutyl]-1H-pyrazol-4-yl}-N-(imidazo[1,2-a]pyridin-6-ylmethyl)thiophene-2-carboxamide;
N-(imidazo[1,2-a]pyridin-6-ylmethyl)-2-{[(1-methyl-1H-pyrazol-4-yl)acetyl](tetrahydrofuran-2-ylmethyl)amino}-1,3-thiazole-5-carboxamide;
2-{[(1,3-dimethyl-1H-pyrazol-4-yl)acetyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-5-[1-(tetrahydro-2H-pyran-2-ylmethyl)-1H-pyrazol-4-yl]thiophene-2-carboxamide;
N-(imidazo[1,2-a]pyridin-6-ylmethyl)-2-{[3-(1-methyl-1H-pyrrol-2-yl)propanoyl](tetrahydrofuran-2-ylmethyl)amino}-1,3-thiazole-5-carboxamide;
2-{[(1,5-dimethyl-1H-pyrazol-3-yl)acetyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-[(tetrahydrofuran-2-ylmethyl)(1,3-thiazol-4-ylacetyl)amino]-1,3-thiazole-5-carboxamide;
N-(imidazo[1,2-a]pyridin-6-ylmethyl)-5-[1-(tetrahydrofuran-3-ylmethyl)-1H-pyrazol-4-yl]thiophene-2-carboxamide;
N-(imidazo[1,2-a]pyridin-6-ylmethyl)-5-[1-(tetrahydro-2H-pyran-4-ylmethyl)-1H-pyrazol-4-yl]thiophene-2-carboxamide;
N-(imidazo[1,2-a]pyridin-6-ylmethyl)-5-[1-(tetrahydro-2H-pyran-3-ylmethyl)-1H-pyrazol-4-yl]thiophene-2-carboxamide;
4-[(4-cyanobenzyl)(cyclopentylacetyl)amino]-N-(imidazo[1,2-a]pyridin-6-ylmethyl)benzamide;
N-(imidazo[1,2-a]pyridin-6-ylmethyl)-5-[1-(tetrahydrofuran-2-ylmethyl)-1H-pyrazol-4-yl]thiophene-2-carboxamide;
4-[(4-cyanobenzyl)(3-methoxypropanoyl)amino]-N-(imidazo[1,2-a]pyridin-6-ylmethyl)benzamide;
N-(imidazo[1,2-a]pyridin-6-ylmethyl)-N'-(3-methylbutyl)benzene-1,4-dicarboxamide;
N-(imidazo[1,2-a]pyridin-6-ylmethyl)-N'-[(3S)-tetrahydrofuran-3-ylmethyl]benzene-1,4-dicarboxamide;
N-[(3-chloroimidazo[1,2-a]pyridin-6-yl)methyl]-4-[(tetrahydrofuran-3-ylacetyl)amino]benzamide;
4-[(cyclopentylacetyl)amino]-2-fluoro-N-(imidazo[1,2-a]pyridin-6-ylmethyl)benzamide;
5-[1-(2-hydroxy-2-methylpropyl)-1H-pyrazol-4-yl]-N-([1,2,4]triazolo[1,5-a]pyridin-6-ylmethyl)thiophene-2-carboxamide;
5-{1-[(4-methyltetrahydro-2H-pyran-4-yl)methyl]-1H-pyrazol-4-yl}-N-([1,2,4]triazolo[1,5-a]pyridin-6-ylmethyl)thiophene-2-carboxamide;
5-[1-(1,4-dioxan-2-ylmethyl)-1H-pyrazol-4-yl]-N-([1,2,4]triazolo[1,5-a]pyridin-6-ylmethyl)thiophene-2-carboxamide;
5-{1-[(4-fluorotetrahydro-2H-pyran-4-yl)methyl]-1H-pyrazol-4-yl}-N-([1,2,4]triazolo[1,5-a]pyridin-6-ylmethyl)furan-2-carboxamide;
5-[1-(2-methylpropyl)-1H-pyrazol-4-yl]-N-([1,2,4]triazolo[1,5-a]pyridin-6-ylmethyl)furan-2-carboxamide;
5-{1-[(4-methyltetrahydro-2H-pyran-4-yl)methyl]-1H-pyrazol-4-yl}-N-([1,2,4]triazolo[1,5-a]pyridin-6-ylmethyl)furan-2-carboxamide;
5-[1-(2-fluorobenzoyl)piperidin-4-yl]-N-([1,2,4]triazolo[1,5-a]pyridin-6-ylmethyl)thiophene-2-carboxamide;
5-[1-(3-fluorobenzoyl)piperidin-4-yl]-N-([1,2,4]triazolo[1,5-a]pyridin-6-ylmethyl)thiophene-2-carboxamide;
5-[1-(4-fluorobenzoyl)piperidin-4-yl]-N-([1,2,4]triazolo[1,5-a]pyridin-6-ylmethyl)thiophene-2-carboxamide;
5-[1-(2,4-difluorobenzoyl)piperidin-4-yl]-N-([1,2,4]triazolo[1,5-a]pyridin-6-ylmethyl)thiophene-2-carboxamide;
5-[1-(2,5-difluorobenzoyl)piperidin-4-yl]-N-([1,2,4]triazolo[1,5-a]pyridin-6-ylmethyl)thiophene-2-carboxamide;
5-[1-(3,5-difluorobenzoyl)piperidin-4-yl]-N-([1,2,4]triazolo[1,5-a]pyridin-6-ylmethyl)thiophene-2-carboxamide;
5-[1-(2-methylpropanoyl)piperidin-4-yl]-N-([1,2,4]triazolo[1,5-a]pyridin-6-ylmethyl)thiophene-2-carboxamide;
5-[1-(3-methylbutanoyl)piperidin-4-yl]-N-([1,2,4]triazolo[1,5-a]pyridin-6-ylmethyl)thiophene-2-carboxamide;
5-{1-[(2S)-2-methylbutanoyl]piperidin-4-yl}-N-([1,2,4]triazolo[1,5-a]pyridin-6-ylmethyl)thiophene-2-carboxamide;
5-{1-[(1-methylcyclopropyl)carbonyl]piperidin-4-yl}-N-([1,2,4]triazolo[1,5-a]pyridin-6-ylmethyl)thiophene-2-carboxamide;
N-([1,2,4]triazolo[1,5-a]pyridin-6-ylmethyl)-5-[1-(3,3,3-trifluoropropanoyl)piperidin-4-yl]thiophene-2-carboxamide;
N-([1,2,4]triazolo[1,5-a]pyridin-6-ylmethyl)-5-[1-(4,4,4-trifluorobutanoyl)piperidin-4-yl]thiophene-2-carboxamide;
5-{1-[(4,4-difluorocyclohexyl)carbonyl]piperidin-4-yl}-N-([1,2,4]triazolo[1,5-a]pyridin-6-ylmethyl)thiophene-2-carboxamide;
5-[1-(tetrahydro-2H-pyran-4-ylcarbonyl)piperidin-4-yl]-N-([1,2,4]triazolo[1,5-a]pyridin-6-ylmethyl)thiophene-2-carboxamide;
5-[1-(2-hydroxy-2-methylpropanoyl)piperidin-4-yl]-N-([1,2,4]triazolo[1,5-a]pyridin-6-ylmethyl)thiophene-2-carboxamide;
5-{1-[(1-methylpiperidin-4-yl)carbonyl]piperidin-4-yl}-N-([1,2,4]triazolo[1,5-a]pyridin-6-ylmethyl)thiophene-2-carboxamide;
5-[1-(2-cyanobenzoyl)piperidin-4-yl]-N-([1,2,4]triazolo[1,5-a]pyridin-6-ylmethyl)thiophene-2-carboxamide;
5-[1-(pyridin-2-ylcarbonyl)piperidin-4-yl]-N-([1,2,4]triazolo[1,5-a]pyridin-6-ylmethyl)thiophene-2-carboxamide;
5-[1-(propan-2-ylsulfonyl)piperidin-4-yl]-N-([1,2,4]triazolo[1,5-a]pyridin-6-ylmethyl)thiophene-2-carboxamide;
5-[1-(phenylsulfonyl)piperidin-4-yl]-N-([1,2,4]triazolo[1,5-a]pyridin-6-ylmethyl)thiophene-2-carboxamide;
4-(phenylsulfonyl)-N-([1,2,4]triazolo[1,5-a]pyridin-6-ylmethyl)benzamide;
N-(imidazo[1,2-a]pyridin-6-ylmethyl)-4-(phenylsulfonyl)benzamide; and
pharmaceutically acceptable salts thereof.

Embodiments of Formula (VIIIA)

In another aspect, the present invention provides compounds of Formula (VIII)

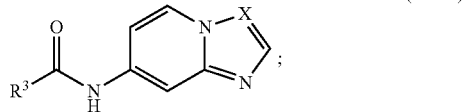

(VIIIA)

and pharmaceutically acceptable salts thereof; wherein X and $R^3$ are as described herein for Formula (I).

One embodiment pertains to compounds of Formula (VIIIA) or pharmaceutically acceptable salts thereof; wherein X is N or $CY^1$;

$Y^1$ is independently selected from the group consisting of hydrogen, alkyl, alkoxy, haloalkyl, hydroxyalkyl, OH, CN, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;

$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;

$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I;

wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, C(O)H, C(O)OH, COH, CN, $NO_2$, F, Cl, Br and I;

$R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I; and $R^{11}$, at each occurrence, is independently selected from the group consisting of aryl, heterocyclyl, cycloalkyl, cycloalkenyl, alkyl, alkenyl, and alkynyl;

with the proviso that when X is $CY^1$ and $Y^1$ is hydrogen; and $R^3$ is thiazolyl; the $R^3$ thiazolyl is substituted with one substituent.

In one embodiment of Formula (VIIIA), X is N or $CY^1$. In another embodiment of Formula (VIIIA), X is N. In another embodiment of Formula (VIIIA), X is $CY^1$.

In one embodiment of Formula (VIIIA), X is $CY^1$; and $Y^1$ is independently selected from the group consisting of hydrogen, alkyl, alkoxy, haloalkyl, hydroxyalkyl, OH, CN, F, Cl, Br, and I. In another embodiment of Formula (VIIIA), X is $CY^1$; and $Y^1$ is independently selected from the group consisting of hydrogen, Cl, Br, and I. In another embodiment of Formula (VIIIA), X is $CY^1$; and $Y^1$ is Cl. In another embodiment of Formula (VIIIA), X is $CY^1$; and $Y^1$ is hydrogen.

In one embodiment of Formula (VIIIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, C(O)NHOH, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I. In another embodiment of Formula (VIIIA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VIIIA), $R^3$ is phenyl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of F, Cl, Br and I. In another embodiment of Formula (VIIIA), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I. In another embodiment of Formula (VIIIA), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

In one embodiment of Formula (VIIIA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, C(O)NHOH, $C(O)NHOR^5$, $C(O)NHSO_2R^5$, $C(O)NR^5SO_2R^5$, $SO_2NH_2$, $SO_2NHR^5$, $SO_2N(R^5)_2$, C(O)H, C(O)OH, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, C(O)NHOH, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)H, C(O)OH, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (VIIIA), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, OH, and F.

In another embodiment of Formula (VIIIA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, CNOCH$_3$, OH, CN, N$_3$, NO$_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, CNOCH$_3$, OH, CN, N$_3$, NO$_2$, F, Cl, Br and I. In another embodiment of Formula (VIIIA), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (VIIIA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, CNOCH$_3$, OH, CN, N$_3$, NO$_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, CNOCH$_3$, OH, CN, N$_3$, NO$_2$, F, Cl, Br and I. In another embodiment of Formula (VIIIA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (VIIIA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each $R^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I. In another embodiment of Formula (VIIIA), $R^7$, at each occurrence, is alkyl or heterocyclyl.

In one embodiment of Formula (VIIIA), $R^8$, at each occurrence, is independently selected from the group consisting of alkyl, alkenyl, and alkynyl. In another embodiment of Formula (VIIIA), $R^8$, at each occurrence, is independently alkyl.

In one embodiment of Formula (VIIIA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, NO$_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, NO$_2$, F, Cl, Br and I. In another embodiment of Formula (VIIIA), $R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (VIIIA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (VIIIA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (VIIIA), $R^{11}$, at each occurrence, is independently selected from the group consisting of aryl, heterocyclyl, cycloalkyl, cycloalkenyl, alkyl, alkenyl, and alkynyl. In another embodiment of Formula (VIIIA), $R^{11}$, at each occurrence, is independently alkyl. In another embodiment of Formula (VIIIA), $R^{11}$, at each occurrence, is independently cycloalkyl.

One embodiment pertains to compounds or pharmaceutically acceptable salts thereof, which are useful as inhibitors of NAMPT, the compounds having Formula (VIIIA)

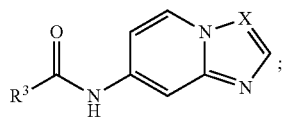

Formula (VIIIA)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$, at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F; and $R^{11}$, at each occurrence, is independently cycloalkyl or alkyl;

with the proviso that when X is $CY^1$ and $Y^1$ is hydrogen; and $R^3$ is thiazolyl; the $R^3$ thiazolyl is substituted with one substituent.

Still another embodiment pertains to compounds having Formula (VIIIA), which include tert-butyl 4-[4-(imidazo[1,2-a]pyridin-7-ylcarbamoyl)phenyl]piperidine-1-carboxylate; and pharmaceutically acceptable salts thereof Embodiments of Formula (IXA)

In another aspect, the present invention provides compounds of Formula (IXA)

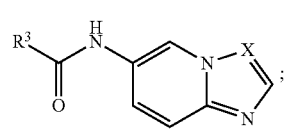

(IXA)

and pharmaceutically acceptable salts thereof; wherein X and $R^3$ are as described herein for Formula (I).

One embodiment pertains to compounds of Formula (IX) or pharmaceutically acceptable salts thereof;

wherein

X is N or $CY^1$;

$Y^1$ is independently selected from the group consisting of hydrogen, alkyl, alkoxy, haloalkyl, hydroxyalkyl, OH, CN, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, C(O)H, C(O)OH, $C(N)NH_2$, $C(N)NHR^4$, $C(N)N(R^4)_2$, CNOH, $CNOCH_3$, OH, CN, $N_3$, $NO_2$, F, Cl, Br and I; wherein each $R^3$ phenyl is optionally additionally substituted with one substituent independently selected from the group consisting of alkyl, haloalkyl, alkoxyalkyl, hydroxyalkyl, C(O)H, C(O)OH, $C(N)NH_2$, OH, CN, $N_3$, $NO_2$, F, Cl, Br and I; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, C(O)

NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, NR$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, C(O)C(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, NR$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$R$^8$, NR$^8$S(O)$_2$R$^8$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$)$_2$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$^{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$, at each occurrence, is independently selected from the group consisting of aryl, heterocyclyl, cycloalkyl, cycloalkenyl, alkyl, alkenyl, and alkynyl; wherein each R$^{10}$ alkyl, alkenyl, and alkynyl is optionally substituted with one, two, three or four substituents independently selected from the group consisting of alkoxy, F, Cl, Br and I; and R$^{11}$, at each occurrence, is independently selected from the group consisting of aryl, heterocyclyl, cycloalkyl, cycloalkenyl, alkyl, alkenyl, and alkynyl;

with the provisos that when X is CY$^1$ and Y$^1$ is hydrogen; and R$^3$ is thiazolyl; the R$^3$ thiazolyl is substituted with one substituent; and when X is CY$^1$ and Y$^1$ is hydrogen; and R$^3$ is phenyl; the R$^3$ phenyl is not substituted at the para position with phenyl.

In one embodiment of Formula (IXA), X is N or CY$^1$. In another embodiment of Formula (IXA), X is N. In another embodiment of Formula (IXA), X is CY$^1$.

In one embodiment of Formula (IXA), X is CY$^1$; and Y$^1$ is independently selected from the group consisting of hydrogen, alkyl, alkoxy, haloalkyl, hydroxyalkyl, OH, CN, F, Cl, Br, and I. In another embodiment of Formula (IXA), X is CY$^1$; and Y$^1$ is independently selected from the group consisting of hydrogen, Cl, Br, and I. In another embodiment of Formula (IXA), X is CY$^1$; and Y$^1$ is Cl. In another embodiment of Formula (IXA), X is CY$^1$; and Y$^1$ is hydrogen.

In one embodiment of Formula (IXA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, $F$, $Cl$, $Br$ and $I$; wherein each $R^3$ phenyl is optionally additionally substituted with one substituent independently selected from the group consisting of alkyl, haloalkyl, alkoxyalkyl, hydroxyalkyl, $C(O)H$, $C(O)OH$, $C(N)NH_2$, $OH$, $CN$, $N_3$, $NO_2$, $F$, $Cl$, $Br$ and $I$; wherein each $R^3$ 5-6 membered heteroaryl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, $CNOH$, $CNOCH_3$, $OH$, $CN$, $N_3$, $NO_2$, $F$, $Cl$, $Br$ and $I$. In another embodiment of Formula (IXA), $R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; wherein each $R^3$ phenyl is optionally additionally substituted with one substituent independently selected from the group consisting of $F$, $Cl$, $Br$ and $I$; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, $F$, $Cl$, $Br$ and $I$.

In one embodiment of Formula (IXA), $R^3$ is phenyl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, and $C(O)NHR^4$; and wherein each $R^3$ phenyl is optionally additionally substituted with one substituent independently selected from the group consisting of $F$, $Cl$, $Br$ and $I$. In another embodiment of Formula (IXA), $R^3$ is 5-6 membered heteroaryl; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, $F$, $Cl$, $Br$ and $I$. In another embodiment of Formula (IXA), $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, $F$, $Cl$, $Br$ and $I$.

In one embodiment of Formula (IXA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, $CNOH$, $CNOCH_3$, $OH$, $CN$, $N_3$, $NO_2$, $F$, $Cl$, $Br$ and $I$; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, $CNOH$, $CNOCH_3$, $OH$, $CN$, $N_3$, $NO_2$, $F$, $Cl$, $Br$ and $I$. In another embodiment of Formula (IXA), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, $OH$, $F$, $Cl$, $Br$ and $I$; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, $OH$, and $F$.

In another embodiment of Formula (IXA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, $CNOH$, $CNOCH_3$, $OH$, $CN$, $N_3$, $NO_2$, $F$, $Cl$, $Br$ and $I$; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, $CNOH$, $CNOCH_3$, $OH$, $CN$, $N_3$, $NO_2$, $F$, $Cl$, $Br$ and $I$. In another embodiment of Formula (IXA), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and $OH$; wherein each $R^5$ aryl and heterocyclyl is optionally substituted with one, two, three or four substituents independently selected from the group consisting of $R^8$, $OR^8$, $CN$, $F$, $Cl$, $Br$ and $I$.

In one embodiment of Formula (IXA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I. In another embodiment of Formula (IXA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (IXA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (IXA), $R^7$, at each occurrence, is alkyl or heterocyclyl.

In one embodiment of Formula (IXA), $R^8$, at each occurrence, is independently selected from the group consisting of alkyl, alkenyl, and alkynyl. In another embodiment of Formula (IXA), $R^8$, at each occurrence, is independently alkyl.

In one embodiment of Formula (IXA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (IXA), $R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (IXA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (IXA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (IXA), $R^{11}$, at each occurrence, is independently selected from the group consisting of aryl, heterocyclyl, cycloalkyl, cycloalkenyl, alkyl, alkenyl, and alkynyl. In another embodiment of Formula (IXA), $R^{11}$, at each occurrence, is independently alkyl. In another embodiment of Formula (IXA), $R^{11}$, at each occurrence, is independently cycloalkyl.

One embodiment pertains to compounds or pharmaceutically acceptable salts thereof, which are useful as inhibitors of NAMPT, the compounds having Formula (IXA)

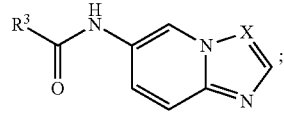

Formula (IXA)

wherein

X is N or $CY^1$;

$Y^1$ is independently selected from the group consisting of hydrogen, F, Cl, Br, and I;

$R^3$ is independently selected from the group consisting of phenyl and 5-6 membered heteroaryl; wherein each $R^3$ phenyl is substituted at the para position with one substituent independently selected from the group consisting of $R^4$, $OR^4$, $SO_2R^4$, $C(O)R^4$, $NHC(O)R^4$, $NR^4C(O)R^4$, $NHS(O)_2R^4$, $NHC(O)OR^4$, $C(O)NHR^4$, F, Cl, Br and I; wherein each $R^3$ phenyl is optionally additionally substituted with one substituent independently selected from the group consisting of F, Cl, Br and I; wherein each $R^3$ 5-6 membered heteroaryl is substituted with one, two, three or four substituents independently selected from the group consisting of $R^4$, $C(O)R^4$, $NHR^4$, $NHC(O)R^4$, $NR^4C(O)R^4$, $NHC(O)OR^4$, $NR^4C(O)OR^4$, $C(O)NHR^4$, F, Cl, Br and I;

$R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

R[5], at each occurrence, is independently selected from the group consisting of alkyl, aryl, heterocyclyl, and cycloalkyl; wherein each R[5] alkyl is optionally substituted with one, two, three or four substituents independently selected from the group consisting of R[7], OR[7], OH, F, Cl, Br and I; wherein each R[5] aryl, and heterocyclyl is optionally substituted with one, two, three or four substituents independently selected from the group consisting of R[8], OR[8], CN, F, Cl, Br and I;

R[6], at each occurrence, is independently selected from the group consisting of alkyl, alkenyl, aryl, heterocyclyl, cycloalkyl, and cycloalkenyl; wherein each R[6] alkyl and alkenyl is optionally substituted with one, two, three or four substituents independently selected from the group consisting of R[9], OR[9], SO$_2$R[9], NH$_2$, N(R[9])$_2$, OH, F, Cl, Br and I; wherein each R[6] aryl, cycloalkyl, cycloalkenyl, and heterocyclyl is optionally substituted with one, two, three or four substituents independently selected from the group consisting of R[10], OR[10], C(O)R[10], CN, F, and Cl;

R[7], at each occurrence, is independently selected from the group consisting of alkyl, and heterocyclyl;

R[8], at each occurrence, is independently alkyl;

R[9], at each occurrence, is independently selected from the group consisting of alkyl, aryl, heterocyclyl, and cycloalkyl; wherein each R[9] alkyl is optionally substituted with one, two, three or four substituents independently selected from the group consisting of aryl, alkoxy, F, Cl, Br and I; wherein each R[9] aryl, cycloalkyl, and heterocyclyl is optionally substituted with one, two, three or four substituents independently selected from the group consisting of R[11], OR[11], CO(O)R[11], CN, F, Cl, Br and I;

R[10], at each occurrence, is independently selected from the group consisting of aryl, heterocyclyl, cycloalkyl, alkyl, and alkenyl; wherein each R[10] alkyl is optionally substituted with one, two, three or four substituents independently selected from the group consisting of alkoxy, and F; and R[11], at each occurrence, is independently cycloalkyl or alkyl;

with the provisos that when X is CY[1] and Y[1] is hydrogen; and R[3] is thiazolyl; the R[3] thiazolyl is substituted with one substituent; and when X is CY[1] and Y[1] is hydrogen; and R[3] is phenyl; the R[3] phenyl is not substituted at the para position with phenyl.

Still another embodiment pertains to compounds having Formula (IXA), which include 2-[(4-cyanobenzyl)(3-methylbutanoyl)amino]-N-(imidazo[1,2-a]pyridin-6-yl)-1,3-thiazole-5-carboxamide;

2-[(4-cyanobenzyl)(3-methoxypropanoyl)amino]-N-(imidazo[1,2-a]pyridin-6-yl)-1,3-thiazole-5-carboxamide;

2-cyclopentyl-N-{4-[2-(imidazo[1,2-a]pyridin-6-ylamino)-2-oxoethyl]phenyl}acetamide;

tert-butyl 4-{4-[2-(imidazo[1,2-a]pyridin-6-ylamino)-2-oxoethyl]phenyl}-3,6-dihydropyridine-1(2H)-carboxylate;

tert-butyl 4-[4-(imidazo[1,2-a]pyridin-6-ylcarbamoyl)phenyl]piperidine-1-carboxylate;

tert-butyl 4-{4-[(3-chloroimidazo[1,2-a]pyridin-6-yl)carbamoyl]phenyl}piperidine-1-carboxylate; and pharmaceutically acceptable salts thereof.

Embodiments of Formula (XA)

In another aspect, the present invention provides compounds of Formula (XA)

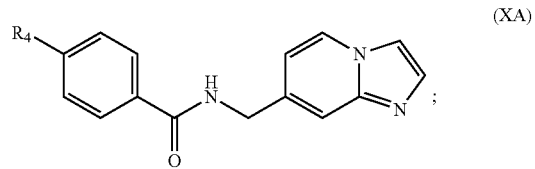

(XA)

and pharmaceutically acceptable salts thereof wherein R[4] is as described herein for Formula (IA).

One embodiment pertains to compounds of Formula (XA) or pharmaceutically acceptable salts thereof;

wherein

R[4], at each occurrence, is independently selected from the group consisting of alkyl, alkenyl, alkynyl, aryl, cycloalkyl, cycloalkenyl, and 3-12 membered heterocyclyl; wherein each R[4] alkyl, alkenyl, and alkynyl is optionally substituted with one, two, three or four substituents independently selected from the group consisting of R[5], OR[5], SR[5], S(O)R[5], SO$_2$R[5], C(O)R[5], CO(O)R[5], OC(O)R[5], OC(O)OR[5], NH$_2$, NHR[5], N(R[5])$_2$, NHC(O)R[5], NR[5]C(O)R[5], NHS(O)$_2$R[5], NR[5]S(O)$_2$R[5], NHC(O)OR[5], NR[5]C(O)OR[5], NHC(O)NH$_2$, NHC(O)NHR[5], NHC(O)N(R[5])$_2$, NR[5]C(O)NHR[5], NR[5]C(O)N(R[5])$_2$, C(O)NH$_2$, C(O)NHR[5], C(O)N(R[5])$_2$, C(O)NHOH, C(O)NHOR[5], C(O)NHSO$_2$R[5], C(O)NR[5]SO$_2$R[5], SO$_2$NH$_2$, SO$_2$NHR[5], SO$_2$N(R[5])$_2$, C(O)H, C(O)OH, C(N)NH$_2$, C(N)NHR[5], C(N)N(R[5])$_2$, CNOH, CNOCH$_3$, OH, CN, N$_3$, NO$_2$, F, Cl, Br and I; wherein each R[4] aryl, cycloalkyl, cycloalkenyl, and 3-12 membered heterocyclyl is optionally substituted with one, two, three or four substituents independently selected from the group consisting of R[6], OR[6], SR[6], S(O)R[6], SO$_2$R[6], C(O)R[6], CO(O)R[6], C(O)C(O)R[6], OC(O)R[6], OC(O)OR[6], NH$_2$, NHR[6], N(R[6])$_2$, NHC(O)R[6], NR[6]C(O)R[6], NHS(O)$_2$R[6], NR[6]S(O)$_2$R[6], NHC(O)OR[6], NR[6]C(O)OR[6], NHC(O)NH$_2$, NHC(O)NHR[6], NHC(O)N(R[6])$_2$, NR[6]C(O)NHR[6], NR[6]C(O)N(R[6])$_2$, C(O)NH$_2$, C(O)NHR[6], C(O)N(R[6])$_2$, C(O)NHOH, C(O)NHOR[6], C(O)NHSO$_2$R[6], C(O)NR[6]SO$_2$R[6], SO$_2$NH$_2$, SO$_2$NHR[6], SO$_2$N(R[6])$_2$, C(O)H, C(O)OH, C(N)NH$_2$, C(N)NHR[6], C(N)N(R[6])$_2$, CNOH, CNOCH$_3$, OH, CN, N$_3$, NO$_2$, F, Cl, Br and I;

R[5], at each occurrence, is independently selected from the group consisting of alkyl, alkenyl, alkynyl, aryl, heterocyclyl, cycloalkyl, and cycloalkenyl; wherein each R[5] alkyl, alkenyl, and alkynyl is optionally substituted with one, two, three or four substituents independently selected from the group consisting of R[7], OR[7], SR[7], S(O)R[7], SO$_2$R[7], C(O)R[7], CO(O)R[7], OC(O)R[7], OC(O)OR[7], NH$_2$, NHR[7], N(R[7])$_2$, NHC(O)R[7], NR[7]C(O)R[7], NHS(O)$_2$R[7], NR[7]S(O)$_2$R[7], NHC(O)OR[7], NR[7]C(O)OR[7], NHC(O)NH$_2$, NHC(O)NHR[7], NHC(O)N(R[7])$_2$, NR[7]C(O)NHR[7], NR[7]C(O)N(R[7])$_2$, C(O)NH$_2$, C(O)NHR[7], C(O)N(R[7])$_2$, C(O)NHOH, C(O)NHOR[7], C(O)NHSO$_2$R[7], C(O)NR[7]SO$_2$R[7], SO$_2$NH$_2$, SO$_2$NHR[7], SO$_2$N(R[7])$_2$, C(O)H, C(O)OH, C(N)NH$_2$, C(N)NHR[7], C(N)N(R[7])$_2$, CNOH, CNOCH$_3$, OH, CN, N$_3$, NO$_2$, F, Cl, Br and I; wherein each R[5] aryl, cycloalkyl, cycloalkenyl, and heterocyclyl is optionally substituted with one, two, three or four substituents independently selected from the group consisting of R[8], OR[8], SR[8], S(O)R[8], SO$_2$R[8], C(O)R[8], CO(O)R[8], OC(O)R[8], OC(O)OR[8], NH$_2$, NHR[8], N(R[8])$_2$, NHC(O)R[8], NR[8]C(O)R[8], NHS(O)$_2$R[8], NR[8]S(O)$_2$R[8], NHC(O)OR[8], NR[8]C(O)OR[8], NHC(O)NH$_2$, NHC(O)NHR[8], NHC(O)N(R[8])$_2$, NR[8]C(O)NHR[8], NR[8]C(O)N(R[8])$_2$, C(O)NH$_2$, C(O)NHR[8], C(O)N(R[8])$_2$, C(O)NHOH, C(O)NHOR[8], C(O)NHSO$_2$R[8], NR[8]SO$_2$R[8], SO$_2$NH$_2$, SO$_2$NHR[8], SO$_2$N(R[8])$_2$, C(O)H, C(O)OH, C(N)NH$_2$, C(N)NHR[8], C(N)N(R[8])$_2$, CNOH, CNOCH$_3$, OH, CN, N$_3$, NO$_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I; and $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I; and $R^{11}$, at each occurrence, is independently selected from the group consisting of aryl, heterocyclyl, cycloalkyl, cycloalkenyl, alkyl, alkenyl, and alkynyl.

In one embodiment of Formula (XA), $R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I. In another embodiment of Formula (XA), $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $C(O)N(R^6)_2$, OH, and F.

In another embodiment of Formula (XA), $R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $NR^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I. In another embodiment of Formula (XA), $R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, and OH; wherein each $R^5$ aryl and heterocyclyl is optionally substituted with one, two, three or four substituents independently selected from the group consisting of $R^8$, $OR^8$, CN, F, Cl, Br and I.

In one embodiment of Formula (XA), $R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, $CNOH$, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, OH, CN, $N_3$, $NO_2$, F, Cl, Br and I. In another embodiment of Formula (XA), $R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, CN, F, Cl, Br and I.

In one embodiment of Formula (XA), $R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I. In another embodiment of Formula (XA), $R^7$, at each occurrence, is alkyl or heterocyclyl.

In one embodiment of Formula (XA), $R^8$, at each occurrence, is independently selected from the group consisting of alkyl, alkenyl, and alkynyl. In another embodiment of Formula (XA), $R^8$, at each occurrence, is independently alkyl.

In one embodiment of Formula (XA), $R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $OC(O)R^{11}$, $NH_2$, $NHR^{11}$, $N(R^{11})_2$, $NHC(O)R^{11}$, $NR^{11}C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I. In another embodiment of Formula (XA), $R^9$ at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, and alkoxy; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, and F.

In one embodiment of Formula (XA), $R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I. In another embodiment of Formula (XA), $R^{10}$, at each occurrence, is independently heterocyclyl, cycloalkyl, alkyl, or alkenyl; wherein each $R^{10}$ alkyl is optionally substituted with one, two, three or four substituents independently selected from the group consisting of alkoxy, and F.

In one embodiment of Formula (XA), $R^{11}$, at each occurrence, is independently selected from the group consisting of aryl, heterocyclyl, cycloalkyl, cycloalkenyl, alkyl, alkenyl, and alkynyl. In another embodiment of Formula (XA), $R^{11}$, at each occurrence, is independently alkyl. In another embodiment of Formula (XA), $R^{11}$, at each occurrence, is independently cycloalkyl.

One embodiment pertains to compounds or pharmaceutically acceptable salts thereof, which are useful as inhibitors of NAMPT, the compounds having Formula (XA)

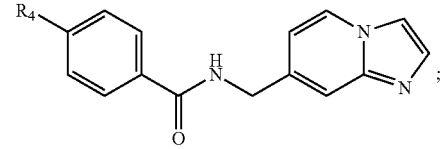

Formula (XA)

wherein $R^4$, at each occurrence, is independently selected from the group consisting of alkyl, aryl, cycloalkyl, and 3-12 membered heterocyclyl; wherein each $R^4$ alkyl is optionally substituted with one, two, three or four substituents independently selected from the group consisting of $R^5$, $OR^5$, $C(O)R^5$, $NHC(O)R^5$, OH, F, Cl, Br and I; wherein each $R^4$ aryl, cycloalkyl, and 3-12 membered heterocyclyl is optionally substituted with one, two, three or four substituents independently selected from the group consisting of $R^6$, $OR^6$, $SO_2R^6$, $C(O)R^6$, $CO(O)R^6$, $C(O)C(O)R^6$, $NHC(O)R^6$, $NHC(O)NHR^6$, $C(O)N(R^6)_2$, OH, F, Cl, Br and I;

$R^5$, at each occurrence, is independently selected from the group consisting of alkyl, aryl, heterocyclyl, and cycloalkyl; wherein each $R^5$ alkyl is optionally substituted with one, two, three or four substituents independently selected from the group consisting of $R^7$, $OR^7$, OH, F, Cl, Br and I; wherein each $R^5$ aryl, and heterocyclyl is optionally substituted with one, two, three or four substituents independently selected from the group consisting of $R^8$, $OR^8$, CN, F, Cl, Br and I;

$R^6$, at each occurrence, is independently selected from the group consisting of alkyl, alkenyl, aryl, heterocyclyl, cycloalkyl, and cycloalkenyl; wherein each $R^6$ alkyl and alkenyl is optionally substituted with one, two, three or four substituents independently selected from the group consisting of $R^9$, $OR^9$, $SO_2R^9$, $NH_2$, $N(R^9)_2$, OH, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $C(O)R^{10}$, CN, F, and Cl;

$R^7$, at each occurrence, is independently selected from the group consisting of alkyl, and heterocyclyl;

$R^8$, at each occurrence, is independently alkyl;

$R^9$, at each occurrence, is independently selected from the group consisting of alkyl, aryl, heterocyclyl, and cycloalkyl; wherein each $R^9$ alkyl is optionally substituted with one, two, three or four substituents independently selected from the group consisting of aryl, alkoxy, F, Cl, Br and I; wherein each $R^9$ aryl, cycloalkyl, and heterocyclyl is optionally substituted with one, two, three or four substituents independently selected from the group consisting of $R^{11}$, $OR^{11}$, $CO(O)R^{11}$, CN, F, Cl, Br and I;

$R^{10}$, at each occurrence, is independently selected from the group consisting of aryl, heterocyclyl, cycloalkyl, alkyl, and alkenyl; wherein each $R^{10}$ alkyl is optionally substituted with one, two, three or four substituents independently selected from the group consisting of alkoxy, and F; and $R^{11}$, at each occurrence, is independently cycloalkyl or alkyl.

Still another embodiment pertains to compounds having Formula (XA), which include tert-butyl 4-{4-[(imidazo[1,2-a]pyridin-7-ylmethyl)carbamoyl]phenyl}piperidine-1-carboxylate;

4-[1-(2-hydroxy-2-methylpropanoyl)piperidin-4-yl]-N-(imidazo[1,2-a]pyridin-7-ylmethyl)benzamide;

N-(imidazo[1,2-a]pyridin-7-ylmethyl)-4-[1-(tetrahydrofuran-3-ylcarbonyl)piperidin-4-yl]benzamide;

N-(imidazo[1,2-a]pyridin-7-ylmethyl)-4-[1-(tetrahydro-2H-pyran-4-ylcarbonyl)piperidin-4-yl]benzamide;

4-[1-(1,4-dioxan-2-ylcarbonyl)piperidin-4-yl]-N-(imidazo[1,2-a]pyridin-7-ylmethyl)benzamide;

4-[1-[(1,1-dioxidotetrahydro-2H-thiopyran-4-yl)carbonyl]piperidin-4-yl]-N-(imidazo[1,2-a]pyridin-7-ylmethyl)benzamide;

N-(imidazo[1,2-a]pyridin-7-ylmethyl)-4-[1-(tetrahydrofuran-2-ylacetyl)piperidin-4-yl]benzamide;

N-(imidazo[1,2-a]pyridin-7-ylmethyl)-4-[1-(tetrahydro-2H-pyran-4-ylacetyl)piperidin-4-yl]benzamide;

N-(imidazo[1,2-a]pyridin-7-ylmethyl)-4-{1-[(propan-2-yloxy)acetyl]piperidin-4-yl}benzamide;

N-(imidazo[1,2-a]pyridin-7-ylmethyl)-4-{1-[(2S)-2-methylbutanoyl]piperidin-4-yl}benzamide;

N-(imidazo[1,2-a]pyridin-7-ylmethyl)-4-[1-(2-methylpropanoyl)piperidin-4-yl]benzamide;

4-[1-(2-hydroxy-2-methylpropyl)-1H-pyrazol-4-yl]-N-(imidazo[1,2-a]pyridin-7-ylmethyl)benzamide;

N-(imidazo[1,2-a]pyridin-7-ylmethyl)-5-phenylthiophene-2-carboxamide;

N-(imidazo[1,2-a]pyridin-7-ylmethyl)-5-{1-[2-(methylsulfonyl)ethyl]-1H-pyrazol-4-yl}thiophene-2-carboxamide;

tert-butyl 3-{4-[(imidazo[1,2-a]pyridin-7-ylmethyl)carbamoyl]phenyl}pyrrolidine-1-carboxylate;

5-{1-[(2R)-2-hydroxypropyl]-1H-pyrazol-4-yl}-N-(imidazo[1,2-a]pyridin-7-ylmethyl)thiophene-2-carboxamide;

4-[(cyclopentylacetyl)amino]-3-fluoro-N-(imidazo[1,2-a]pyridin-7-ylmethyl)benzamide;

N-(imidazo[1,2-a]pyridin-7-ylmethyl)-4-{1-[(3S)-tetrahydrofuran-3-ylcarbonyl]piperidin-4-yl}benzamide;

N-(imidazo[1,2-a]pyridin-7-ylmethyl)-4-{1-[(3R)-tetrahydrofuran-3-ylcarbonyl]piperidin-4-yl}benzamide;

N-(imidazo[1,2-a]pyridin-7-ylmethyl)-4-{1-[(2R)-tetrahydrofuran-2-ylcarbonyl]piperidin-4-yl}benzamide;

N-(imidazo[1,2-a]pyridin-7-ylmethyl)-4-{1-[(2S)-tetrahydrofuran-2-ylcarbonyl]piperidin-4-yl}benzamide;

4-[1-(cyclopropylacetyl)piperidin-4-yl]-N-(imidazo[1,2-a]pyridin-7-ylmethyl)benzamide;

4-(1-acetylpiperidin-4-yl)-N-(imidazo[1,2-a]pyridin-7-ylmethyl)benzamide;

N-(imidazo[1,2-a]pyridin-7-ylmethyl)-4-[1-(2-methylpropyl)-1H-pyrazol-4-yl]benzamide;

5-[1-(1,4-dioxan-2-ylmethyl)-1H-pyrazol-4-yl]-N-(imidazo[1,2-a]pyridin-7-ylmethyl)thiophene-2-carboxamide;

5-[1-(2-hydroxyethyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[3-(propan-2-yloxy)phenyl]thiophene-2-carboxamide;

N-(imidazo[1,2-a]pyridin-7-ylmethyl)-2-[1-(tetrahydro-2H-pyran-4-ylcarbonyl)-1,2,3,6-tetrahydropyridin-4-yl]-1,3-thiazole-5-carboxamide;

N-(imidazo[1,2-a]pyridin-7-ylmethyl)-2-[1-(2-methylpropanoyl)-1,2,3,6-tetrahydropyridin-4-yl]-1,3-thiazole-5-carboxamide;

N-(imidazo[1,2-a]pyridin-7-ylmethyl)-4-({(3S)-1-[(2S)-2-methylbutanoyl]pyrrolidin-3-yl}oxy)benzamide;

N-(imidazo[1,2-a]pyridin-7-ylmethyl)-5-{3-[(2-methylpropanoyl)amino]oxetan-3-yl}thiophene-2-carboxamide;

5-[3-(benzoylamino)oxetan-3-yl]-N-(imidazo[1,2-a]pyridin-7-ylmethyl)thiophene-2-carboxamide;

N-(imidazo[1,2-a]pyridin-7-ylmethyl)-5-{3-[(tetrahydrofuran-3-ylacetyl)amino]oxetan-3-yl}thiophene-2-carboxamide;

N-(imidazo[1,2-a]pyridin-7-ylmethyl)-5-[3-(pentanoylamino)oxetan-3-yl]thiophene-2-carboxamide;

N-(imidazo[1,2-a]pyridin-7-ylmethyl)-4-({(3S)-1-[(3R)-tetrahydrofuran-3-ylcarbonyl]pyrrolidin-3-yl}oxy)benzamide;

N-(imidazo[1,2-a]pyridin-7-ylmethyl)-4-({(3S)-1-[(2R)-tetrahydrofuran-2-ylcarbonyl]pyrrolidin-3-yl}oxy)benzamide;

N-(imidazo[1,2-a]pyridin-7-ylmethyl)-4-({(3S)-1-[(2S)-tetrahydrofuran-2-ylcarbonyl]pyrrolidin-3-yl}oxy)benzamide;

N-(imidazo[1,2-a]pyridin-7-ylmethyl)-4-{[(3S)-1-(tetrahydro-2H-pyran-4-ylcarbonyl)pyrrolidin-3-yl]oxy}benzamide;

N-(imidazo[1,2-a]pyridin-7-ylmethyl)-4-{[(3S)-1-(tetrahydro-2H-pyran-4-ylacetyl)pyrrolidin-3-yl]oxy}benzamide;

5-{1-[(1,1-dioxidotetrahydro-2H-thiopyran-3-yl)methyl]-1H-pyrazol-4-yl}-N-(imidazo[1,2-a]pyridin-7-ylmethyl)thiophene-2-carboxamide;

N-(imidazo[1,2-a]pyridin-7-ylmethyl)-5-(1-methyl-1H-pyrazol-4-yl)thiophene-2-carboxamide;

N-(imidazo[1,2-a]pyridin-7-ylmethyl)-4-({(3S)-1-[(3S)-tetrahydrofuran-3-ylcarbonyl]pyrrolidin-3-yl}oxy)benzamide;

4-{[(3S)-1-(cyclopropylacetyl)pyrrolidin-3-yl]oxy}-N-(imidazo[1,2-a]pyridin-7-ylmethyl)benzamide;

4-{[(3S)-1-(2-hydroxy-2-methylpropanoyl)pyrrolidin-3-yl]oxy}-N-(imidazo[1,2-a]pyridin-7-ylmethyl)benzamide;

N-(imidazo[1,2-a]pyridin-7-ylmethyl)-4-{[(3S)-1-(3-methoxy-2-methylpropanoyl)pyrrolidin-3-yl]oxy}benzamide;

4-{[(3S)-1-butanoylpyrrolidin-3-yl]oxy}-N-(imidazo[1,2-a]pyridin-7-ylmethyl)benzamide;

N-(imidazo[1,2-a]pyridin-7-ylmethyl)-4-{[(3S)-1-(2-methylpropanoyl)pyrrolidin-3-yl]oxy}benzamide;

4-{[(3S)-1-(cyclopropylcarbonyl)pyrrolidin-3-yl]oxy}-N-(imidazo[1,2-a]pyridin-7-ylmethyl)benzamide;

4-{[(3S)-1-benzoylpyrrolidin-3-yl]oxy}-N-(imidazo[1,2-a]pyridin-7-ylmethyl)benzamide;

4-{[(3S)-1-(3-hydroxy-3-methylbutanoyl)pyrrolidin-3-yl]oxy}-N-(imidazo[1,2-a]pyridin-7-ylmethyl)benzamide;
2-(4-benzoylpiperazin-1-yl)-N-(imidazo[1,2-a]pyridin-7-ylmethyl)-1,3-thiazole-5-carboxamide;
N-(imidazo[1,2-a]pyridin-7-ylmethyl)-2-[4-(propan-2-yl)piperazin-1-yl]-1,3-thiazole-5-carboxamide;
N-(imidazo[1,2-a]pyridin-7-ylmethyl)-2-[4-(2-methoxyethyl)piperazin-1-yl]-1,3-thiazole-5-carboxamide;
N-(imidazo[1,2-a]pyridin-7-ylmethyl)-2-phenyl-1,3-thiazole-5-carboxamide;
N-(imidazo[1,2-a]pyridin-7-ylmethyl)-5-(1-methyl-1H-pyrazol-5-yl)thiophene-2-carboxamide;
tert-butyl 4-{4-[(imidazo[1,2-a]pyridin-7-ylmethyl)carbamoyl]phenoxy}piperidine-1-carboxylate;
N-(imidazo[1,2-a]pyridin-7-ylmethyl)-4-[1-(2-methylpropanoyl)pyrrolidin-3-yl]benzamide;
N-(imidazo[1,2-a]pyridin-7-ylmethyl)-4-{1-[(2S)-2-methylbutanoyl]pyrrolidin-3-yl}benzamide;
4-[1-(cyclopropylacetyl)pyrrolidin-3-yl]-N-(imidazo[1,2-a]pyridin-7-ylmethyl)benzamide;
4-(1-benzoylpyrrolidin-3-yl)-N-(imidazo[1,2-a]pyridin-7-ylmethyl)benzamide;
N-(imidazo[1,2-a]pyridin-7-ylmethyl)-4-{1-[(propan-2-yloxy)acetyl]pyrrolidin-3-yl}benzamide;
4-[1-(2-hydroxy-2-methylpropanoyl)pyrrolidin-3-yl]-N-(imidazo[1,2-a]pyridin-7-ylmethyl)benzamide;
N-(imidazo[1,2-a]pyridin-7-ylmethyl)-4-{1-[(2R)-tetrahydrofuran-2-ylcarbonyl]pyrrolidin-3-yl}benzamide;
N-(imidazo[1,2-a]pyridin-7-ylmethyl)-4-{1-[(2S)-tetrahydrofuran-2-ylcarbonyl]pyrrolidin-3-yl}benzamide;
N-(imidazo[1,2-a]pyridin-7-ylmethyl)-4-{1-[(3S)-tetrahydrofuran-3-ylcarbonyl]pyrrolidin-3-yl}benzamide;
N-(imidazo[1,2-a]pyridin-7-ylmethyl)-4-[1-(tetrahydro-2H-pyran-4-ylcarbonyl)pyrrolidin-3-yl]benzamide;
4-[1-(1,4-dioxan-2-ylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(tetrahydro-2H-pyran-4-ylacetyl)pyrrolidin-3-yl]benzamide;
N-(imidazo[1,2-a]pyridin-7-ylmethyl)-N'-(3-methylbutyl)benzene-1,4-dicarboxamide;
N-(imidazo[1,2-a]pyridin-7-ylmethyl)-N'-[(3S)-tetrahydrofuran-3-ylmethyl]benzene-1,4-dicarboxamide;
N-(imidazo[1,2-a]pyridin-7-ylmethyl)-5-{1-[(2R)-tetrahydrofuran-2-ylmethyl]-1H-pyrazol-4-yl}thiophene-2-carboxamide;
N-(imidazo[1,2-a]pyridin-7-ylmethyl)-5-{1-[(2S)-tetrahydrofuran-2-ylmethyl]-1H-pyrazol-4-yl}thiophene-2-carboxamide;
5-(4-hydroxytetrahydro-2H-pyran-4-yl)-N-(imidazo[1,2-a]pyridin-7-ylmethyl)thiophene-2-carboxamide;
5-[3-hydroxy-1-(2-methylpropanoyl)azetidin-3-yl]-N-(imidazo[1,2-a]pyridin-7-ylmethyl)thiophene-2-carboxamide;
5-(1-benzoyl-3-hydroxyazetidin-3-yl)-N-(imidazo[1,2-a]pyridin-7-ylmethyl)thiophene-2-carboxamide;
tert-butyl 3-{4-[(imidazo[1,2-a]pyridin-7-ylmethyl)carbamoyl]phenyl}azetidine-1-carboxylate;
tert-butyl 4-hydroxy-4-{5-[(imidazo[1,2-a]pyridin-7-ylmethyl)carbamoyl]thiophen-2-yl}piperidine-1-carboxylate;
5-{3-hydroxy-1-[(2S)-2-methylbutanoyl]azetidin-3-yl}-N-(imidazo[1,2-a]pyridin-7-ylmethyl)thiophene-2-carboxamide;
5-[3-hydroxy-1-(tetrahydro-2H-pyran-4-ylacetyl)azetidin-3-yl]-N-(imidazo[1,2-a]pyridin-7-ylmethyl)thiophene-2-carboxamide;
N-(imidazo[1,2-a]pyridin-7-ylmethyl)-5-(3-{[(2S)-2-methylbutanoyl]amino}oxetan-3-yl)thiophene-2-carboxamide;
N-(imidazo[1,2-a]pyridin-7-ylmethyl)-1-[1-(3-methylbutanoyl)piperidin-4-yl]-1H-pyrazole-3-carboxamide;
N-(imidazo[1,2-a]pyridin-7-ylmethyl)-5-[1-(tetrahydro-2H-pyran-4-yl)-1H-pyrazol-4-yl]thiophene-2-carboxamide;
4-[(1-acetylpiperidin-4-yl)oxy]-N-(imidazo[1,2-a]pyridin-7-ylmethyl)benzamide;
N-(imidazo[1,2-a]pyridin-7-ylmethyl)-4-{[1-(2-methylpropanoyl)piperidin-4-yl]oxy}benzamide;
N-(imidazo[1,2-a]pyridin-7-ylmethyl)-4-({1-[(2S)-2-methylbutanoyl]piperidin-4-yl}oxy)benzamide;
4-{[1-(cyclopropylacetyl)piperidin-4-yl]oxy}-N-(imidazo[1,2-a]pyridin-7-ylmethyl)benzamide;
4-[(1-benzoylpiperidin-4-yl)oxy]-N-(imidazo[1,2-a]pyridin-7-ylmethyl)benzamide;
N-(imidazo[1,2-a]pyridin-7-ylmethyl)-4-({1-[(propan-2-yloxy)acetyl]piperidin-4-yl}oxy)benzamide;
4-{[1-(2-hydroxy-2-methylpropanoyl)piperidin-4-yl]oxy}-N-(imidazo[1,2-a]pyridin-7-ylmethyl)benzamide;
N-(imidazo[1,2-a]pyridin-7-ylmethyl)-4-({1-[(2R)-tetrahydrofuran-2-ylcarbonyl]piperidin-4-yl}oxy)benzamide;
N-(imidazo[1,2-a]pyridin-7-ylmethyl)-4-({1-[(2S)-tetrahydrofuran-2-ylcarbonyl]piperidin-4-yl}oxy)benzamide;
N-(imidazo[1,2-a]pyridin-7-ylmethyl)-4-{[1-(tetrahydro-2H-pyran-4-ylcarbonyl)piperidin-4-yl]oxy}benzamide;
4-{[1-(1,4-dioxan-2-ylcarbonyl)piperidin-4-yl]oxy}-N-(imidazo[1,2-a]pyridin-7-ylmethyl)benzamide;
N-(imidazo[1,2-a]pyridin-7-ylmethyl)-4-{[1-(tetrahydro-2H-pyran-4-ylacetyl)piperidin-4-yl]oxy}benzamide;
N-(imidazo[1,2-a]pyridin-7-ylmethyl)-4-{[1-(morpholin-4-ylacetyl)piperidin-4-yl]oxy}benzamide;
tert-butyl (3R)-3-{4-[(imidazo[1,2-a]pyridin-7-ylmethyl)carbamoyl]phenoxy}pyrrolidine-1-carboxylate;
4-(1-benzoylpiperidin-4-yl)-N-(imidazo[1,2-a]pyridin-7-ylmethyl)benzamide;
4-{1-[(3,3-difluorocyclobutyl)carbonyl]piperidin-4-yl}-N-(imidazo[1,2-a]pyridin-7-ylmethyl)benzamide;
4-{1-[(4,4-difluorocyclohexyl)carbonyl]piperidin-4-yl}-N-(imidazo[1,2-a]pyridin-7-ylmethyl)benzamide;
4-[(cyclopentylacetyl)amino]-2-fluoro-N-(imidazo[1,2-a]pyridin-7-ylmethyl)benzamide;
N-(imidazo[1,2-a]pyridin-7-ylmethyl)-5-[6-(morpholin-4-yl)pyridin-3-yl]thiophene-2-carboxamide;
N-(imidazo[1,2-a]pyridin-7-ylmethyl)-5-{1-[(2-methyltetrahydro-2H-pyran-2-yl)methyl]-1H-pyrazol-4-yl}thiophene-2-carboxamide;
tert-butyl 4-[(4-{5-[(imidazo[1,2-a]pyridin-7-ylmethyl)carbamoyl]thiophen-2-yl}-1H-pyrazol-1-yl)methyl]piperidine-1-carboxylate;
N-(imidazo[1,2-a]pyridin-7-ylmethyl)-5-[1-(3-methylbutanoyl)pyrrolidin-3-yl]thiophene-2-carboxamide;
N-(imidazo[1,2-a]pyridin-7-ylmethyl)-5-{1-[(2-methylpropanoyl)amino]cyclobutyl}thiophene-2-carboxamide;
N-(imidazo[1,2-a]pyridin-7-ylmethyl)-5-{1-[(3-methylbutanoyl)amino]cyclobutyl}thiophene-2-carboxamide;
N-(imidazo[1,2-a]pyridin-7-ylmethyl)-5-(1-{[(2S)-2-methylbutanoyl]amino}cyclobutyl)thiophene-2-carboxamide;
5-[1-(benzoylamino)cyclobutyl]-N-(imidazo[1,2-a]pyridin-7-ylmethyl)thiophene-2-carboxamide;
N-(imidazo[1,2-a]pyridin-7-ylmethyl)-5-{1-[(3,3,3-trifluoropropanoyl)amino]cyclobutyl}thiophene-2-carboxamide;
N-(1-{5-[(imidazo[1,2-a]pyridin-7-ylmethyl)carbamoyl]thiophen-2-yl}cyclobutyl)tetrahydro-2H-pyran-4-carboxamide;

tert-butyl 3-{4-[(imidazo[1,2-a]pyridin-7-ylmethyl)carbamoyl]phenoxy}azetidine-1-carboxylate;
5-[1-(cyclobutylmethyl)-1H-pyrazol-4-yl]-N-(imidazo[1,2-a]pyridin-7-ylmethyl)thiophene-2-carboxamide;
N-(imidazo[1,2-a]pyridin-7-ylmethyl)-5-[1-(tetrahydrofuran-2-ylmethyl)-1H-pyrazol-4-yl]furan-2-carboxamide;
N-(imidazo[1,2-a]pyridin-7-ylmethyl)-5-[1-(tetrahydro-2H-pyran-2-ylmethyl)-1H-pyrazol-4-yl]furan-2-carboxamide;
N-(imidazo[1,2-a]pyridin-7-ylmethyl)-5-[1-(tetrahydrofuran-3-ylmethyl)-1H-pyrazol-4-yl]furan-2-carboxamide;
N-(imidazo[1,2-a]pyridin-7-ylmethyl)-5-[1-(tetrahydro-2H-pyran-3-ylmethyl)-1H-pyrazol-4-yl]furan-2-carboxamide;
N-(imidazo[1,2-a]pyridin-7-ylmethyl)-5-[1-(tetrahydro-2H-pyran-4-ylmethyl)-1H-pyrazol-4-yl]furan-2-carboxamide;
5-[1-(cyclobutylmethyl)-1H-pyrazol-4-yl]-N-(imidazo[1,2-a]pyridin-7-ylmethyl)furan-2-carboxamide;
N-(imidazo[1,2-a]pyridin-7-ylmethyl)-5-{1-[(3-methyloxetan-3-yl)methyl]-1H-pyrazol-4-yl}furan-2-carboxamide;
5-[1-(2-hydroxy-2-methylpropyl)-1H-pyrazol-4-yl]-N-(imidazo[1,2-a]pyridin-7-ylmethyl)furan-2-carboxamide;
4-[1-(furan-2-ylcarbonyl)piperidin-4-yl]-N-(imidazo[1,2-a]pyridin-7-ylmethyl)benzamide;
N-(imidazo[1,2-a]pyridin-7-ylmethyl)-5-[1-(piperidin-4-ylmethyl)-1H-pyrazol-4-yl]thiophene-2-carboxamide;
N-(imidazo[1,2-a]pyridin-7-ylmethyl)-4-[1-(thiophen-2-ylcarbonyl)pyrrolidin-3-yl]benzamide;
N-(imidazo[1,2-a]pyridin-7-ylmethyl)-4-phenoxybenzamide;
N-(imidazo[1,2-a]pyridin-7-ylmethyl)-4-[1-(2-methylpropanoyl)azetidin-3-yl]benzamide;
N-(imidazo[1,2-a]pyridin-7-ylmethyl)-4-{[(3R)-1-(2-methylpropanoyl)pyrrolidin-3-yl]oxy}benzamide;
4-{[(3R)-1-benzoylpyrrolidin-3-yl]oxy}-N-(imidazo[1,2-a]pyridin-7-ylmethyl)benzamide;
N-(imidazo[1,2-a]pyridin-7-ylmethyl)-4-({(3R)-1-[(3S)-tetrahydrofuran-3-ylcarbonyl]pyrrolidin-3-yl}oxy)benzamide;
N-(imidazo[1,2-a]pyridin-7-ylmethyl)-4-({(3R)-1-[(2S)-2-methylbutanoyl]pyrrolidin-3-yl}oxy)benzamide;
5-[1-(2-methylpropyl)-1H-pyrazol-4-yl]-N-([1,2,4]triazolo[1,5-a]pyridin-7-ylmethyl)thiophene-2-carboxamide;
N-(imidazo[1,2-a]pyridin-7-ylmethyl)-4-[1-(pyridin-2-ylcarbonyl)piperidin-4-yl]benzamide;
4-[1-(3,3-dimethylbutanoyl)piperidin-4-yl]-N-(imidazo[1,2-a]pyridin-7-ylmethyl)benzamide;
N-(imidazo[1,2-a]pyridin-7-ylmethyl)-4-[1-(4-methylbenzoyl)piperidin-4-yl]benzamide;
4-[1-(2,2-dimethylbutanoyl)piperidin-4-yl]-N-(imidazo[1,2-a]pyridin-7-ylmethyl)benzamide;
4-[1-(cyclohexylcarbonyl)piperidin-4-yl]-N-(imidazo[1,2-a]pyridin-7-ylmethyl)benzamide;
N-(imidazo[1,2-a]pyridin-7-ylmethyl)-4-[1-(thiophen-2-ylcarbonyl)piperidin-4-yl]benzamide;
N-(imidazo[1,2-a]pyridin-7-ylmethyl)-4-[1-(3,3,3-trifluoropropanoyl)piperidin-4-yl]benzamide;
4-(1-butanoylpiperidin-4-yl)-N-(imidazo[1,2-a]pyridin-7-ylmethyl)benzamide;
4-[1-(2,4-difluorobenzoyl)piperidin-4-yl]-N-(imidazo[1,2-a]pyridin-7-ylmethyl)benzamide;
N-(imidazo[1,2-a]pyridin-7-ylmethyl)-4-[1-(2-methylbenzoyl)piperidin-4-yl]benzamide;
4-[1-(4-fluorobenzoyl)piperidin-4-yl]-N-(imidazo[1,2-a]pyridin-7-ylmethyl)benzamide;
4-[1-(2,2-dimethylpropanoyl)piperidin-4-yl]-N-(imidazo[1,2-a]pyridin-7-ylmethyl)benzamide;
N-(imidazo[1,2-a]pyridin-7-ylmethyl)-4-{1-[(2E)-2-methylpent-2-enoyl]piperidin-4-yl}benzamide;
N-(imidazo[1,2-a]pyridin-7-ylmethyl)-4-{1-[(1-methyl-1H-pyrazol-5-yl)carbonyl]piperidin-4-yl}benzamide;
N-(imidazo[1,2-a]pyridin-7-ylmethyl)-4-{1-[(3-methyloxetan-3-yl)carbonyl]piperidin-4-yl}benzamide;
4-[1-(2-fluorobenzoyl)piperidin-4-yl]-N-(imidazo[1,2-a]pyridin-7-ylmethyl)benzamide;
4-{1-[(1-cyanocyclopropyl)carbonyl]piperidin-4-yl}-N-(imidazo[1,2-a]pyridin-7-ylmethyl)benzamide;
4-[1-(cyclopentylcarbonyl)piperidin-4-yl]-N-(imidazo[1,2-a]pyridin-7-ylmethyl)benzamide;
4-[1-(3-fluorobenzoyl)piperidin-4-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-4-yl)carbonyl]piperidin-4-yl}benzamide;
N-(imidazo[1,2-a]pyridin-7-ylmethyl)-4-[1-(2-oxobutanoyl)piperidin-4-yl]benzamide;
4-{1-[(2,5-dimethylfuran-3-yl)carbonyl]piperidin-4-yl}-N-(imidazo[1,2-a]pyridin-7-ylmethyl)benzamide;
4-[1-(4-cyanobenzoyl)piperidin-4-yl]-N-(imidazo[1,2-a]pyridin-7-ylmethyl)benzamide;
4-[1-(3-cyanobenzoyl)piperidin-4-yl]-N-(imidazo[1,2-a]pyridin-7-ylmethyl)benzamide;
4-[1-(2,5-difluorobenzoyl)piperidin-4-yl]-N-(imidazo[1,2-a]pyridin-7-ylmethyl)benzamide;
N-(imidazo[1,2-a]pyridin-7-ylmethyl)-4-[1-(pyrazin-2-ylcarbonyl)piperidin-4-yl]benzamide;
N-(imidazo[1,2-a]pyridin-7-ylmethyl)-4-{1-[(3-methylthiophen-2-yl)carbonyl]piperidin-4-yl}benzamide;
4-{1-[(3,5-dimethyl-1,2-oxazol-4-yl)carbonyl]piperidin-4-yl}-N-(imidazo[1,2-a]pyridin-7-ylmethyl)benzamide;
N-(imidazo[1,2-a]pyridin-7-ylmethyl)-4-[1-(3-methoxybenzoyl)piperidin-4-yl]benzamide;
4-[1-(3-chlorobenzoyl)piperidin-4-yl]-N-(imidazo[1,2-a]pyridin-7-ylmethyl)benzamide;
N-(imidazo[1,2-a]pyridin-7-ylmethyl)-4-[1-(4-methoxybenzoyl)piperidin-4-yl]benzamide;
4-[1-(4-chlorobenzoyl)piperidin-4-yl]-N-(imidazo[1,2-a]pyridin-7-ylmethyl)benzamide;
4-[1-(3,5-difluorobenzoyl)piperidin-4-yl]-N-(imidazo[1,2-a]pyridin-7-ylmethyl)benzamide;
4-[1-(cyclopropylcarbonyl)piperidin-4-yl]-N-(imidazo[1,2-a]pyridin-7-ylmethyl)benzamide;
N-(imidazo[1,2-a]pyridin-7-ylmethyl)-4-(1-propanoylpiperidin-4-yl)benzamide;
N-(imidazo[1,2-a]pyridin-7-ylmethyl)-4-{1-[(1-methyl-1H-pyrrol-2-yl)carbonyl]piperidin-4-yl}benzamide;
N-(imidazo[1,2-a]pyridin-7-ylmethyl)-4-[1-(3-methylbutanoyl)piperidin-4-yl]benzamide;
N-(imidazo[1,2-a]pyridin-7-ylmethyl)-4-[1-(pyridin-4-ylcarbonyl)piperidin-4-yl]benzamide;
4-[1-(2,3-dimethylbutanoyl)piperidin-4-yl]-N-(imidazo[1,2-a]pyridin-7-ylmethyl)benzamide;
N-(imidazo[1,2-a]pyridin-7-ylmethyl)-4-[1-(pyridin-3-ylcarbonyl)piperidin-4-yl]benzamide;
N-(imidazo[1,2-a]pyridin-7-ylmethyl)-4-{1-[(1-methylcyclopropyl)carbonyl]piperidin-4-yl}benzamide;
N-(imidazo[1,2-a]pyridin-7-ylmethyl)-4-[1-(2-methoxybenzoyl)piperidin-4-yl]benzamide;
N-(imidazo[1,2-a]pyridin-7-ylmethyl)-5-[1-(3,3,3-trifluoropropanoyl)pyrrolidin-3-yl]thiophene-2-carboxamide;
N-(imidazo[1,2-a]pyridin-7-ylmethyl)-5-[1-(2-methylpropanoyl)pyrrolidin-3-yl]thiophene-2-carboxamide;

5-(1-benzoylpyrrolidin-3-yl)-N-(imidazo[1,2-a]pyridin-7-ylmethyl)thiophene-2-carboxamide;
N-(imidazo[1,2-a]pyridin-7-ylmethyl)-2-[1-(2-methylpropanoyl)piperidin-4-yl]-1,3-thiazole-5-carboxamide;
N-(imidazo[1,2-a]pyridin-7-ylmethyl)-2-[1-(3-methylbutanoyl)piperidin-4-yl]-1,3-thiazole-5-carboxamide;
2-(1-benzoylpiperidin-4-yl)-N-(imidazo[1,2-a]pyridin-7-ylmethyl)-1,3-thiazole-5-carboxamide;
4-[(cyclopentylacetyl)amino]-N-([1,2,4]triazolo[1,5-a]pyridin-7-ylmethyl)benzamide;
N-(imidazo[1,2-a]pyridin-7-ylmethyl)-4-{1-[(2S)-2-methylbutanoyl]azetidin-3-yl}benzamide;
4-[1-(cyclopropylacetyl)azetidin-3-yl]-N-(imidazo[1,2-a]pyridin-7-ylmethyl)benzamide;
4-(1-benzoylazetidin-3-yl)-N-(imidazo[1,2-a]pyridin-7-ylmethyl)benzamide;
4-[1-(2-hydroxy-2-methylpropanoyl)azetidin-3-yl]-N-(imidazo[1,2-a]pyridin-7-ylmethyl)benzamide;
N-(imidazo[1,2-a]pyridin-7-ylmethyl)-4-[1-(tetrahydro-2H-pyran-4-ylacetyl)azetidin-3-yl]benzamide;
N-(imidazo[1,2-a]pyridin-7-ylmethyl)-4-[1-(thiophen-2-ylcarbonyl)azetidin-3-yl]benzamide;
5-[4-hydroxy-1-(3-methylbutanoyl)piperidin-4-yl]-N-(imidazo[1,2-a]pyridin-7-ylmethyl)thiophene-2-carboxamide;
5-[4-hydroxy-1-(2-methylpropanoyl)piperidin-4-yl]-N-(imidazo[1,2-a]pyridin-7-ylmethyl)thiophene-2-carboxamide;
5-[1-(3,3-dimethylbutanoyl)-4-hydroxypiperidin-4-yl]-N-(imidazo[1,2-a]pyridin-7-ylmethyl)thiophene-2-carboxamide;
5-(1-benzoyl-4-hydroxypiperidin-4-yl)-N-(imidazo[1,2-a]pyridin-7-ylmethyl)thiophene-2-carboxamide;
N-(imidazo[1,2-a]pyridin-7-ylmethyl)-4-[1-(propan-2-ylsulfonyl)azetidin-3-yl]benzamide;
N-(imidazo[1,2-a]pyridin-7-ylmethyl)-4-{[1-(2-methylpropanoyl)azetidin-3-yl]oxy}benzamide;
N-(imidazo[1,2-a]pyridin-7-ylmethyl)-4-({1-[(2S)-2-methylbutanoyl]azetidin-3-yl}oxy)benzamide;
4-{[1-(cyclopropylacetyl)azetidin-3-yl]oxy}-N-(imidazo[1,2-a]pyridin-7-ylmethyl)benzamide;
4-[(1-benzoylazetidin-3-yl)oxy]-N-(imidazo[1,2-a]pyridin-7-ylmethyl)benzamide;
4-[1-(4-fluorobenzoyl)pyrrolidin-3-yl]-N-(imidazo[1,2-a]pyridin-7-ylmethyl)benzamide;
tert-butyl 4-{4-[([1,2,4]triazolo[1,5-a]pyridin-7-ylmethyl)carbamoyl]phenyl}piperidine-1-carboxylate;
N-(imidazo[1,2-a]pyridin-7-ylmethyl)-4-(piperidin-1-ylcarbonyl)benzamide;
4-[1-(ethylsulfonyl)azetidin-3-yl]-N-(imidazo[1,2-a]pyridin-7-ylmethyl)benzamide;
4-[1-(cyclopropylsulfonyl)azetidin-3-yl]-N-(imidazo[1,2-a]pyridin-7-ylmethyl)benzamide;
N-(imidazo[1,2-a]pyridin-7-ylmethyl)-4-[1-(phenylsulfonyl)azetidin-3-yl]benzamide;
propan-2-yl 4-{5-[(imidazo[1,2-a]pyridin-7-ylmethyl)carbamoyl]thiophen-2-yl}piperidine-1-carboxylate;
2-methylpropyl 4-{5-[(imidazo[1,2-a]pyridin-7-ylmethyl)carbamoyl]thiophen-2-yl}piperidine-1-carboxylate;
N-(imidazo[1,2-a]pyridin-7-ylmethyl)-5-[1-(3,3,3-trifluoropropanoyl)piperidin-4-yl]thiophene-2-carboxamide;
N-(imidazo[1,2-a]pyridin-7-ylmethyl)-5-{1-[(2-methylpropyl)sulfonyl]piperidin-4-yl}thiophene-2-carboxamide;
N-(imidazo[1,2-a]pyridin-7-ylmethyl)-5-[1-(4,4,4-trifluorobutanoyl)piperidin-4-yl]thiophene-2-carboxamide;
N-[(3-chloroimidazo[1,2-a]pyridin-7-yl)methyl]-4-[1-(2-methylpropanoyl)piperidin-4-yl]benzamide;
N-(imidazo[1,2-a]pyridin-7-ylmethyl)-5-{1-[(4-methyltetrahydro-2H-pyran-4-yl)methyl]-1H-pyrazol-4-yl}thiophene-2-carboxamide;
5-[1-(2-cyano-2-methylpropyl)-1H-pyrazol-4-yl]-N-(imidazo[1,2-a]pyridin-7-ylmethyl)thiophene-2-carboxamide;
4-chloro-N-(imidazo[1,2-a]pyridin-7-ylmethyl)-5-[1-(2-methylpropyl)-1H-pyrazol-4-yl]thiophene-2-carboxamide;
4-chloro-N-(imidazo[1,2-a]pyridin-7-ylmethyl)-5-{1-[(3R)-tetrahydrofuran-3-ylmethyl]-1H-pyrazol-4-yl}thiophene-2-carboxamide;
N-(imidazo[1,2-a]pyridin-7-ylmethyl)-4-{1-[(2-methylcyclopropyl)carbonyl]pyrrolidin-3-yl}benzamide;
4-[1-(cyclopentylacetyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylpentanoyl)pyrrolidin-3-yl]benzamide;
4-[1-(cyclopentylcarbonyl)pyrrolidin-3-yl]-N-(imidazo[1,2-a]pyridin-7-ylmethyl)benzamide;
N-(imidazo[1,2-a]pyridin-7-ylmethyl)-4-{1-[(1-methylcyclopropyl)carbonyl]pyrrolidin-3-yl}benzamide;
4-[1-(2,2-dimethylpropanoyl)pyrrolidin-3-yl]-N-(imidazo[1,2-a]pyridin-7-ylmethyl)benzamide;
N-(imidazo[1,2-a]pyridin-7-ylmethyl)-4-[1-(1,3-thiazol-5-ylcarbonyl)pyrrolidin-3-yl]benzamide;
N-(imidazo[1,2-a]pyridin-7-ylmethyl)-4-[1-(2-methoxybenzoyl)pyrrolidin-3-yl]benzamide;
N-(imidazo[1,2-a]pyridin-7-ylmethyl)-4-[1-(1,3-thiazol-4-ylcarbonyl)pyrrolidin-3-yl]benzamide;
4-[1-(2-fluorobenzoyl)pyrrolidin-3-yl]-N-(imidazo[1,2-a]pyridin-7-ylmethyl)benzamide;
4-[1-(furan-2-ylcarbonyl)pyrrolidin-3-yl]-N-(imidazo[1,2-a]pyridin-7-ylmethyl)benzamide;
4-[1-(3-fluorobenzoyl)pyrrolidin-3-yl]-N-(imidazo[1,2-a]pyridin-7-ylmethyl)benzamide;
4-[1-(2,4-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-3-yl)carbonyl]pyrrolidin-3-yl}benzamide;
4-[1-(2-chlorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(2-methylbenzoyl)pyrrolidin-3-yl]benzamide;
4-[1-(4-chlorobenzoyl)pyrrolidin-3-yl]-N-(imidazo[1,2-a]pyridin-7-ylmethyl)benzamide;
4-[1-(3-chlorobenzoyl)pyrrolidin-3-yl]-N-(imidazo[1,2-a]pyridin-7-ylmethyl)benzamide;
4-[1-(2,2-dimethylbutanoyl)pyrrolidin-3-yl]-N-(imidazo[1,2-a]pyridin-7-ylmethyl)benzamide;
4-[1-(3,5-difluorobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(4-methylbenzoyl)pyrrolidin-3-yl]benzamide;
N-(imidazo[1,2-a]pyridin-7-ylmethyl)-4-[1-(3-methylbutanoyl)pyrrolidin-3-yl]benzamide;
4-[1-(3,3-dimethylbutanoyl)pyrrolidin-3-yl]-N-(imidazo[1,2-a]pyridin-7-ylmethyl)benzamide;
4-[1-(3-cyanobenzoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)pyrrolidin-3-yl]benzamide;
N-(imidazo[1,2-a]pyridin-7-ylmethyl)-4-[1-(4-methoxybenzoyl)pyrrolidin-3-yl]benzamide;
N-(imidazo[1,2-a]pyridin-7-ylmethyl)-4-{1-[(1-methyl-1H-pyrrol-2-yl)carbonyl]pyrrolidin-3-yl}benzamide;
4-[1-(cyclohexylacetyl)pyrrolidin-3-yl]-N-(imidazo[1,2-a]pyridin-7-ylmethyl)benzamide;

N-(imidazo[1,2-a]pyridin-7-ylmethyl)-4-[1-(pyridin-4-ylcarbonyl)pyrrolidin-3-yl]benzamide;
N-(imidazo[1,2-a]pyridin-7-ylmethyl)-4-[1-(pyridin-3-ylcarbonyl)pyrrolidin-3-yl]benzamide;
4-[1-(cyclohexylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)pyrrolidin-3-yl]benzamide;
4-[1-(furan-3-ylcarbonyl)pyrrolidin-3-yl]-N-(imidazo[1,2-a]pyridin-7-ylmethyl)benzamide;
N-(imidazo[1,2-a]pyridin-7-ylmethyl)-4-[1-(1,3-thiazol-2-ylcarbonyl)pyrrolidin-3-yl]benzamide;
N-(imidazo[1,2-a]pyridin-7-ylmethyl)-4-{1-[(1-methylcyclohexyl)carbonyl]pyrrolidin-3-yl}benzamide;
4-[1-(2,3-dimethylbutanoyl)pyrrolidin-3-yl]-N-(imidazo[1,2-a]pyridin-7-ylmethyl)benzamide;
N-(imidazo[1,2-a]pyridin-7-ylmethyl)-4-[1-(3-methylbenzoyl)pyrrolidin-3-yl]benzamide;
N-(imidazo[1,2-a]pyridin-7-ylmethyl)-4-[1-(thiophen-3-ylcarbonyl)pyrrolidin-3-yl]benzamide;
N-(imidazo[1,2-a]pyridin-7-ylmethyl)-4-{1-[3-(trifluoromethoxy)benzoyl]pyrrolidin-3-yl}benzamide;
N-(imidazo[1,2-a]pyridin-7-ylmethyl)-4-{1-[(3-methylthiophen-2-yl)carbonyl]pyrrolidin-3-yl}benzamide;
N-(imidazo[1,2-a]pyridin-7-ylmethyl)-4-{1-[3-(trifluoromethyl)benzoyl]pyrrolidin-3-yl}benzamide;
N-(imidazo[1,2-a]pyridin-7-ylmethyl)-4-[1-(methylsulfonyl)azetidin-3-yl]benzamide;
N-(imidazo[1,2-a]pyridin-7-ylmethyl)-4-[1-(methylsulfonyl)pyrrolidin-3-yl]benzamide;
4-[1-(ethylsulfonyl)pyrrolidin-3-yl]-N-(imidazo[1,2-a]pyridin-7-ylmethyl)benzamide;
4-[1-(cyclopropylsulfonyl)pyrrolidin-3-yl]-N-(imidazo[1,2-a]pyridin-7-ylmethyl)benzamide;
N-(imidazo[1,2-a]pyridin-7-ylmethyl)-4-[1-(phenylsulfonyl)pyrrolidin-3-yl]benzamide;
N-(imidazo[1,2-a]pyridin-7-ylmethyl)-4-{1-[(2-methylcyclopropyl)carbonyl]azetidin-3-yl}benzamide;
4-[1-(cyclopentylacetyl)azetidin-3-yl]-N-(imidazo[1,2-a]pyridin-7-ylmethyl)benzamide;
N-(imidazo[1,2-a]pyridin-7-ylmethyl)-4-[1-(3-methylpentanoyl)azetidin-3-yl]benzamide;
4-[1-(cyclopentylcarbonyl)azetidin-3-yl]-N-(imidazo[1,2-a]pyridin-7-ylmethyl)benzamide;
N-(imidazo[1,2-a]pyridin-7-ylmethyl)-4-{1-[(1-methylcyclopropyl)carbonyl]azetidin-3-yl}benzamide;
4-[1-(2,2-dimethylpropanoyl)azetidin-3-yl]-N-(imidazo[1,2-a]pyridin-7-ylmethyl)benzamide;
N-(imidazo[1,2-a]pyridin-7-ylmethyl)-4-[1-(1,3-thiazol-5-ylcarbonyl)azetidin-3-yl]benzamide;
N-(imidazo[1,2-a]pyridin-7-ylmethyl)-4-[1-(pyrazin-2-ylcarbonyl)azetidin-3-yl]benzamide;
N-(imidazo[1,2-a]pyridin-7-ylmethyl)-4-[1-(2-methoxybenzoyl)azetidin-3-yl]benzamide;
N-(imidazo[1,2-a]pyridin-7-ylmethyl)-4-[1-(1,3-thiazol-4-ylcarbonyl)azetidin-3-yl]benzamide;
4-[1-(2-fluorobenzoyl)azetidin-3-yl]-N-(imidazo[1,2-a]pyridin-7-ylmethyl)benzamide;
4-[1-(furan-2-ylcarbonyl)azetidin-3-yl]-N-(imidazo[1,2-a]pyridin-7-ylmethyl)benzamide;
4-[1-(3-fluorobenzoyl)azetidin-3-yl]-N-(imidazo[1,2-a]pyridin-7-ylmethyl)benzamide;
4-[1-(2,4-difluorobenzoyl)azetidin-3-yl]-N-(imidazo[1,2-a]pyridin-7-ylmethyl)benzamide;
N-(imidazo[1,2-a]pyridin-7-ylmethyl)-4-{1-[(1-methyl-1H-pyrazol-3-yl)carbonyl]azetidin-3-yl}benzamide;
4-[1-(2-chlorobenzoyl)azetidin-3-yl]-N-(imidazo[1,2-a]pyridin-7-ylmethyl)benzamide;
N-(imidazo[1,2-a]pyridin-7-ylmethyl)-4-[1-(2-methylbenzoyl)azetidin-3-yl]benzamide;
4-[1-(4-chlorobenzoyl)azetidin-3-yl]-N-(imidazo[1,2-a]pyridin-7-ylmethyl)benzamide;
4-[1-(3-chlorobenzoyl)azetidin-3-yl]-N-(imidazo[1,2-a]pyridin-7-ylmethyl)benzamide;
4-[1-(2,2-dimethylbutanoyl)azetidin-3-yl]-N-(imidazo[1,2-a]pyridin-7-ylmethyl)benzamide;
4-[1-(3,5-difluorobenzoyl)azetidin-3-yl]-N-(imidazo[1,2-a]pyridin-7-ylmethyl)benzamide;
4-[1-(4-fluorobenzoyl)azetidin-3-yl]-N-(imidazo[1,2-a]pyridin-7-ylmethyl)benzamide;
N-(imidazo[1,2-a]pyridin-7-ylmethyl)-4-[1-(4-methylbenzoyl)azetidin-3-yl]benzamide;
N-(imidazo[1,2-a]pyridin-7-ylmethyl)-4-[1-(3-methylbutanoyl)azetidin-3-yl]benzamide;
4-[1-(3,3-dimethylbutanoyl)azetidin-3-yl]-N-(imidazo[1,2-a]pyridin-7-ylmethyl)benzamide;
4-[1-(3-cyanobenzoyl)azetidin-3-yl]-N-(imidazo[1,2-a]pyridin-7-ylmethyl)benzamide;
N-(imidazo[1,2-a]pyridin-7-ylmethyl)-4-[1-(3-methoxybenzoyl)azetidin-3-yl]benzamide;
N-(imidazo[1,2-a]pyridin-7-ylmethyl)-4-[1-(4-methoxybenzoyl)azetidin-3-yl]benzamide;
N-(imidazo[1,2-a]pyridin-7-ylmethyl)-4-{1-[(1-methyl-1H-pyrrol-2-yl)carbonyl]azetidin-3-yl}benzamide;
4-[1-(cyclohexylacetyl)azetidin-3-yl]-N-(imidazo[1,2-a]pyridin-7-ylmethyl)benzamide;
N-(imidazo[1,2-a]pyridin-7-ylmethyl)-4-[1-(pyridin-4-ylcarbonyl)azetidin-3-yl]benzamide;
N-(imidazo[1,2-a]pyridin-7-ylmethyl)-4-[1-(pyridin-3-ylcarbonyl)azetidin-3-yl]benzamide;
4-[1-(cyclohexylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyridin-2-ylcarbonyl)azetidin-3-yl]benzamide;
4-[1-(furan-ylcarbonyl)azetidin-3-yl]-N-(imidazo[1,2-a]pyridin-7-ylmethyl)benzamide;
N-(imidazo[1,2-a]pyridin-7-ylmethyl)-4-[1-(pyrimidin-4-ylcarbonyl)azetidin-3-yl]benzamide;
N-(imidazo[1,2-a]pyridin-7-ylmethyl)-4-[1-(1,3-thiazol-2-ylcarbonyl)azetidin-3-yl]benzamide;
N-(imidazo[1,2-a]pyridin-7-ylmethyl)-4-{1-[(1-methylcyclohexyl)carbonyl]azetidin-3-yl}benzamide;
4-[1-(2,3-dimethylbutanoyl)azetidin-3-yl]-N-(imidazo[1,2-a]pyridin-7-ylmethyl)benzamide;
N-(imidazo[1,2-a]pyridin-7-ylmethyl)-4-[1-(3-methylbenzoyl)azetidin-3-yl]benzamide;
N-(imidazo[1,2-a]pyridin-7-ylmethyl)-4-[1-(thiophen-3-ylcarbonyl)azetidin-3-yl]benzamide;
N-(imidazo[1,2-a]pyridin-7-ylmethyl)-4-{1-[3-(trifluoromethoxy)benzoyl]azetidin-3-yl}benzamide;
N-(imidazo[1,2-a]pyridin-7-ylmethyl)-4-{1-[(3-methylthiophen-2-yl)carbonyl]azetidin-3-yl}benzamide;
N-(imidazo[1,2-a]pyridin-7-ylmethyl)-4-{1-[3-(trifluoromethyl)benzoyl]azetidin-3-yl}benzamide;
N-(imidazo[1,2-a]pyridin-7-ylmethyl)-4-[1-(propan-2-ylsulfonyl)pyrrolidin-3-yl]benzamide;
5-[1-(2-fluorobenzoyl)piperidin-4-yl]-N-(imidazo[1,2-a]pyridin-7-ylmethyl)thiophene-2-carboxamide;
N-(imidazo[1,2-a]pyridin-7-ylmethyl)-4-[1-(phenylsulfonyl)piperidin-4-yl]benzamide;
N-(imidazo[1,2-a]pyridin-7-ylmethyl)-4-[1-(propan-2-ylsulfonyl)piperidin-4-yl]benzamide;

4-[1-(cyclopropylsulfonyl)piperidin-4-yl]-N-(imidazo[1,2-a]pyridin-7-ylmethyl)benzamide;
5-{(1R)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-5-{(1R)-3-methyl-1-[(tetrahydrofuran-3-ylacetyl)amino]butyl}thiophene-2-carboxamide;
5-{(1S)-1-[(cyclopropylcarbonyl)amino]-3-methylbutyl}-N-(imidazo[1,2-a]pyridin-7-ylmethyl)thiophene-2-carboxamide;
N-(imidazo[1,2-a]pyridin-7-ylmethyl)-2-(1-phenylpiperidin-4-yl)-1,3-thiazole-5-carboxamide;
N-(imidazo[1,2-a]pyridin-7-ylmethyl)-2-[1-(pyridin-2-yl)piperidin-4-yl]-1,3-thiazole-5-carboxamide;
5-{1-[(4-fluorotetrahydro-2H-pyran-4-yl)methyl]-1H-pyrazol-4-yl}-N-(imidazo[1,2-a]pyridin-7-ylmethyl)thiophene-2-carboxamide;
4-[1-(2-chlorobenzoyl)piperidin-4-yl]-N-(imidazo[1,2-a]pyridin-7-ylmethyl)benzamide;
4-[1-(2,6-difluorobenzoyl)piperidin-4-yl]-N-(imidazo[1,2-a]pyridin-7-ylmethyl)benzamide;
4-[1-(3,4-difluorobenzoyl)piperidin-4-yl]-N-(imidazo[1,2-a]pyridin-7-ylmethyl)benzamide;
N-(imidazo[1,2-a]pyridin-7-ylmethyl)-4-{1-[3-(trifluoromethyl)benzoyl]piperidin-4-yl}benzamide;
N-(imidazo[1,2-a]pyridin-7-ylmethyl)-4-{1-[3-(trifluoromethoxy)benzoyl]piperidin-4-yl}benzamide;
N-(imidazo[1,2-a]pyridin-7-ylmethyl)-4-{1-[4-(trifluoromethoxy)benzoyl]piperidin-4-yl}benzamide;
N-(imidazo[1,2-a]pyridin-7-ylmethyl)-4-{1-[4-(trifluoromethyl)benzoyl]piperidin-4-yl}benzamide;
N-(imidazo[1,2-a]pyridin-7-ylmethyl)-4-{1-[2-(trifluoromethoxy)benzoyl]piperidin-4-yl}benzamide;
N-(imidazo[1,2-a]pyridin-7-ylmethyl)-4-[1-(phenylacetyl)piperidin-4-yl]benzamide;
N-(imidazo[1,2-a]pyridin-7-ylmethyl)-4-{1-[2-(trifluoromethyl)benzoyl]piperidin-4-yl}benzamide; and pharmaceutically acceptable salts thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment pertains to compositions for treating diseases during which NAMPT is expressed, said compositions comprising an excipient and a therapeutically effective amount of the compound having Formula (I).

Still another embodiment pertains to methods of treating disease in a patient during which NAMPT is expressed, said methods comprising administering to the patient a therapeutically effective amount of a compound having Formula (I).

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I).

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of a compound having Formula (I).

Still another embodiment pertains to compositions for treating diseases during which NAMPT is expressed, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which NAMPT is expressed, said methods comprising administering to the patient a therapeutically effective amount of a compound having Formula (I) and a therapeutically effective amount of one additional therapeutic agent or more than one additional therapeutic agent.

Still another embodiment pertains to compositions for treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia, said compositions comprising an excipient and a therapeutically effective amount of the compound having Formula (I) and a therapeutically effective amount of one additional therapeutic agent or more than one additional therapeutic agent.

Still another embodiment pertains to methods of treating inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukemia, lymphoma or Hodgkin's disease, cachexia, inflammation associated with infection and certain viral infections, including Acquired Immune Deficiency Syndrome (AIDS), adult respiratory distress syndrome, and ataxia telengiectasia in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with NAMPT.

Certain precursor compounds which may be metabolized in vitro or in vivo to form compounds having Formula (I) may also have utility for treating diseases associated with NAMPT.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of NAMPT was performed using Time-Resolved Fluorescence Resonance Energy Transfer (TR-FRET) binding assays.

Time-Resolved Fluorescence Resonance Energy Transfer (TR-FRET) Binding Assay of NAMPT Test compounds were serially diluted (typically 11 half log dilutions) in neat DMSO to 50× final concentrations prior to dilution with assay buffer (50 mM HEPES (NaOH), pH 7.5, 100 mM NaCl, 10 mM MgCl$_2$, 1 mM DTT, 1% Glycerol) to 3× and 6% DMSO. Six L were transferred to 384-well low-volume plates (Owens Corning #3673). To this, 12 L of a 1.5× solution containing enzyme, probe and antibody were added. Final concentrations in the 18 L reactions were 1× assay buffer, 2% DMSO, 6.8 nM NAMPT (human, recombinant, C-terminally His-tagged), 200 nM probe (a potent nicotinamide-competitive inhibitor conjugated to Oregon Green 488) and 1 nM Tb-anti-His antibody (Invitrogen # PV5895). Reactions were equilibrated at room temperature for 3 hours prior to reading on an Envision multi-label plate reader (Perkin Elmer; Ex=337 nm, Em=520 and 495 nm). Time-resolved FRET ratios ($Em_{520}/Em_{495}$) were normalized to controls, plotted as a function of compound concentration and fit with the four-parameter logistic equation to determine IC50s.

Time-Resolved Fluorescence Resonance Energy Transfer (TR-FRET) Binding Assay of NAMPT with PRPP Compound handling and data processing were identical to the assay in the absence of substrates (above). Final concentrations were 1× assay buffer, 2% DMSO, 2 nM NAMPT, 2 nM probe, 1 nM Tb-anti-His antibody (Invitrogen # PV5895), 200 M PRPP and 2.5 mM ATP. Reactions were equilibrated for 16 hours prior to measurement to allow for potential enzymatic modification of test compounds.

Table 1 shows the utility of compounds having Formula I to functionally inhibit NAMPT.

TABLE 1

| Example | TR-FRET Binding-IC50 (μM) | TR-FRET Binding-IC50 (with PRPP) (μM) | Example | TR-FRET Binding-IC50 (μM) | TR-FRET Binding-IC50 (with PRPP) (μM) |
| --- | --- | --- | --- | --- | --- |
| 1 | 0.0921 | 0.00072 | 414 | 2.63 | 0.000307 |
| 2 | 0.854 | 0.0398 | 415 | 1.62 | 0.000246 |
| 3 | 0.0316 | 0.000282 | 416 | 2.5 | 0.000318 |
| 4 | 0.413 | 0.000516 | 417 | 6.84 | 0.000264 |

TABLE 1-continued

| Example | TR-FRET Binding-IC50 (μM) | TR-FRET Binding-IC50 (with PRPP) (μM) |
|---|---|---|
| 5 | 2.5 | 0.000684 |
| 6 | 2.91 | 0.000964 |
| 7 | 0.183 | 0.000516 |
| 8 | 0.114 | 0.000702 |
| 9 | 1.72 | 0.000459 |
| 10 | 0.197 | 0.000457 |
| 11 | 7.6 | 0.000271 |
| 12 | 0.486 | 0.000292 |
| 13 | 0.653 | 0.000663 |
| 14 | 0.741 | 0.00122 |
| 15 | 1.76 | 0.000841 |
| 16 | 0.409 | 0.000396 |
| 17 | 2.96 | 0.000401 |
| 18 | 2.73 | 0.000418 |
| 19 | 2.68 | 0.000921 |
| 20 | 0.404 | 0.000169 |
| 21 | 0.433 | 0.000887 |
| 22 | 0.399 | 0.000277 |
| 23 | 0.281 | 0.000409 |
| 24 | 0.167 | 0.000363 |
| 25 | 0.508 | 0.000714 |
| 26 | 0.211 | 0.0011 |
| 27 | 0.756 | 0.000658 |
| 28 | 0.152 | 0.00019 |
| 29 | 0.168 | 0.000236 |
| 30 | 1.18 | 0.000785 |
| 31 | 0.739 | 0.000311 |
| 32 | 0.906 | 0.000169 |
| 33 | 0.369 | 0.000553 |
| 34 | 0.208 | 0.000377 |
| 35 | 0.387 | 0.000801 |
| 36 | 0.356 | 0.000444 |
| 37 | 0.129 | 0.000309 |
| 38 | 0.243 | 0.000266 |
| 39 | 0.814 | 0.00026 |
| 40 | 0.0409 | 0.000217 |
| 41 | 0.294 | 0.00115 |
| 42 | 0.697 | 0.000381 |
| 43 | 4.35 | 0.000169 |
| 44 | 0.396 | 0.000496 |
| 45 | 0.879 | 0.00119 |
| 46 | 0.773 | 0.000318 |
| 47 | 0.0575 | 0.00062 |
| 48 | >10 | 0.000169 |
| 49 | 0.442 | 0.000317 |
| 50 | 1.64 | 0.000817 |
| 51 | 0.264 | 0.000524 |
| 52 | 0.0186 | 0.00579 |
| 53 | 4.45 | 0.0144 |
| 54 | 0.363 | 0.00255 |
| 55 | 0.364 | 0.00137 |
| 56 | 0.158 | 0.00107 |
| 57 | 0.0058 | |
| 58 | 0.523 | 0.00143 |
| 59 | 0.222 | 0.000695 |
| 60 | 0.00861 | 0.00149 |
| 61 | 0.0782 | 0.000549 |
| 62 | 0.25 | 0.000456 |
| 63 | 0.636 | 0.000283 |
| 64 | 0.518 | 0.000495 |
| 65 | 0.773 | 0.000685 |
| 66 | 0.558 | 0.000326 |
| 67 | 0.53 | 0.000326 |
| 68 | 0.386 | 0.000476 |
| 69 | 0.676 | 0.000268 |
| 70 | 0.71 | 0.000616 |
| 71 | 0.754 | 0.000348 |
| 72 | 0.851 | 0.000536 |
| 73 | 0.605 | 0.000426 |
| 74 | 0.356 | 0.000222 |
| 75 | 0.0122 | 0.000445 |
| 76 | 0.993 | 0.000739 |
| 77 | 0.0561 | 0.00288 |
| 78 | 0.0565 | 0.0024 |
| 79 | 0.121 | 0.00697 |
| 80 | 0.228 | 0.00571 |
| 81 | 0.0155 | 0.00268 |
| 82 | 0.357 | 0.00642 |
| 83 | 0.899 | 0.0023 |
| 84 | 1.67 | 0.0109 |
| 85 | 4.07 | 0.00141 |
| 86 | 2.04 | 0.0119 |
| 87 | 2.05 | 0.00135 |
| 88 | 2.85 | 0.00855 |
| 89 | 0.667 | 0.000383 |
| 90 | 0.204 | 0.00063 |
| 91 | 0.174 | 0.00126 |
| 92 | 0.183 | 0.000881 |
| 93 | 0.389 | 0.00139 |
| 94 | 0.29 | 0.000593 |
| 95 | 0.201 | 0.000991 |
| 96 | 0.192 | 0.00156 |
| 97 | 0.109 | 0.000333 |
| 98 | 0.12 | 0.000367 |
| 99 | 0.119 | 0.000411 |
| 100 | 0.102 | 0.000169 |
| 101 | 0.332 | 0.00173 |
| 102 | 0.385 | 0.00121 |
| 103 | 0.84 | 0.00144 |
| 104 | 0.135 | 0.002 |
| 105 | 0.106 | 0.000476 |
| 106 | 0.247 | 0.000201 |
| 107 | 0.0451 | 0.000492 |
| 108 | 1.77 | 0.00105 |
| 109 | 0.34 | 0.000209 |
| 110 | 0.423 | 0.000174 |
| 111 | 0.263 | 0.000209 |
| 112 | 0.0465 | 0.000169 |
| 113 | 0.356 | 0.000169 |
| 114 | 0.818 | 0.00111 |
| 115 | 0.243 | 0.000676 |
| 116 | 0.863 | 0.00069 |
| 117 | 0.392 | 0.000436 |
| 118 | 0.0352 | 0.000234 |
| 119 | 0.942 | 0.000783 |
| 120 | 0.0739 | 0.000367 |
| 121 | 0.486 | 0.000234 |
| 122 | 0.255 | 0.00476 |
| 123 | 0.133 | 0.00257 |
| 124 | 1.1 | 0.00212 |
| 125 | 0.547 | 0.00209 |
| 126 | 0.102 | 0.000963 |
| 127 | 0.0522 | 0.000522 |
| 128 | 0.0307 | 0.000873 |
| 129 | 0.0116 | 0.000634 |
| 130 | 0.0532 | 0.000981 |
| 131 | 0.0152 | 0.00167 |
| 132 | 0.155 | 0.0133 |
| 133 | 0.067 | 0.000709 |
| 134 | 0.303 | 0.00149 |
| 135 | 0.0738 | 0.00127 |
| 136 | 0.0727 | 0.000512 |
| 137 | 0.315 | 0.00721 |
| 138 | 0.0807 | 0.000424 |
| 139 | 0.582 | 0.000173 |
| 140 | 1.34 | 0.000927 |
| 141 | 2.11 | 0.000757 |
| 142 | 1.43 | 0.00305 |
| 143 | 8.71 | 0.00203 |
| 144 | 9.49 | 0.00292 |
| 145 | 0.191 | 0.00108 |
| 146 | 0.261 | 0.000403 |
| 147 | 0.251 | 0.00063 |
| 148 | 6.23 | 0.00135 |
| 149 | >10 | 0.00486 |
| 150 | 6.11 | 0.00349 |
| 151 | 7.15 | 0.00554 |
| 152 | 3.6 | 0.00691 |
| 153 | 0.118 | 0.00188 |
| 154 | 0.194 | 0.0026 |
| 418 | 4.75 | 0.000233 |
| 419 | 2.43 | 0.000197 |
| 420 | 2.71 | 0.000226 |
| 421 | 2.45 | 0.000271 |
| 422 | 1.72 | 0.000212 |
| 423 | 8.26 | 0.000338 |
| 424 | 0.988 | 0.000494 |
| 425 | 0.153 | 0.000227 |
| 426 | 0.0256 | 0.000169 |
| 427 | 0.15 | 0.00027 |
| 428 | 0.0871 | 0.000258 |
| 429 | 0.129 | 0.000369 |
| 430 | 0.292 | 0.000264 |
| 431 | 0.301 | 0.000276 |
| 432 | 0.304 | 0.00033 |
| 433 | 0.2 | 0.000248 |
| 434 | 0.102 | 0.000169 |
| 435 | 0.163 | 0.000191 |
| 436 | 1.59 | 0.000416 |
| 437 | 0.0291 | 0.000169 |
| 438 | 0.145 | 0.000427 |
| 439 | 0.453 | 0.000641 |
| 440 | 0.295 | 0.00049 |
| 441 | 0.338 | 0.000324 |
| 442 | 0.301 | 0.0002 |
| 443 | 0.138 | 0.000274 |
| 444 | 0.156 | 0.000244 |
| 445 | 0.11 | 0.000212 |
| 446 | 0.388 | 0.000253 |
| 447 | 0.261 | 0.000232 |
| 448 | 0.175 | 0.000176 |
| 449 | 0.256 | 0.000169 |
| 450 | 0.422 | 0.000244 |
| 451 | 0.4 | 0.000373 |
| 452 | 0.293 | 0.000285 |
| 453 | 0.152 | 0.000258 |
| 454 | 0.405 | 0.00034 |
| 455 | 0.0167 | 0.000194 |
| 456 | 0.389 | 0.000169 |
| 457 | 1.14 | 0.000487 |
| 458 | 0.94 | 0.000382 |
| 459 | 0.381 | 0.00041 |
| 460 | 0.569 | 0.000307 |
| 461 | 0.459 | 0.000169 |
| 462 | 0.0591 | 0.000266 |
| 463 | 0.314 | 0.000529 |
| 464 | 0.0634 | 0.000169 |
| 465 | 0.0138 | 0.000169 |
| 466 | 0.0749 | 0.000287 |
| 467 | 0.0911 | 0.000278 |
| 468 | >10 | 0.000985 |
| 469 | 10 | 0.000432 |
| 470 | 5.58 | 0.000456 |
| 471 | 3.44 | 0.000471 |
| 472 | 2.86 | 0.000334 |
| 473 | 10 | 0.00101 |
| 474 | 1.98 | 0.000362 |
| 475 | 0.00976 | 0.000169 |
| 476 | 0.0708 | 0.000194 |
| 477 | 0.0729 | 0.000235 |
| 478 | 0.192 | 0.00024 |
| 479 | 0.063 | 0.000243 |
| 480 | 0.181 | 0.000342 |
| 481 | 0.0572 | 0.000176 |
| 482 | 0.0763 | 0.000259 |
| 483 | 0.13 | 0.000575 |
| 484 | 0.0795 | 0.00019 |
| 485 | 0.0956 | 0.000205 |
| 486 | 0.0917 | 0.000232 |
| 487 | 0.143 | 0.000334 |
| 488 | 0.138 | 0.000544 |
| 489 | 1.22 | 0.000263 |
| 490 | 0.753 | 0.000267 |
| 491 | 10 | 0.0019 |
| 492 | 10 | 0.000863 |
| 493 | 1.29 | 0.000455 |
| 494 | 7.56 | 0.000712 |
| 495 | 1.47 | 0.000399 |
| 496 | 0.199 | 0.00114 |
| 497 | 0.0242 | 0.00286 |
| 498 | 0.309 | 0.000169 |
| 499 | 0.113 | 0.00038 |
| 500 | 0.181 | 0.000169 |
| 501 | 0.104 | 0.000483 |
| 502 | 0.169 | 0.000385 |
| 503 | 0.0532 | 0.000277 |
| 504 | 0.185 | 0.000361 |
| 505 | 0.253 | 0.000355 |
| 506 | 0.245 | 0.000407 |
| 507 | 0.121 | 0.000359 |
| 508 | 0.257 | 0.000481 |
| 509 | 0.163 | 0.000384 |
| 510 | 0.142 | 0.000284 |
| 511 | 0.0653 | 0.000286 |
| 512 | 0.631 | 0.000209 |
| 513 | 0.0239 | 0.000188 |
| 514 | 0.368 | 0.000249 |
| 515 | 0.18 | 0.000268 |
| 516 | 0.117 | 0.000266 |
| 517 | 0.33 | 0.000264 |
| 518 | 0.234 | 0.000169 |
| 519 | 0.218 | 0.000338 |
| 520 | 0.565 | 0.000301 |
| 521 | 0.413 | 0.000292 |
| 522 | 0.0581 | 0.000199 |
| 523 | 0.343 | 0.000422 |
| 524 | 0.0247 | 0.000169 |
| 525 | 0.0864 | 0.000213 |
| 526 | 0.126 | 0.000275 |
| 527 | 0.141 | 0.000265 |
| 528 | 0.126 | 0.000276 |
| 529 | 0.248 | 0.000283 |
| 530 | 0.378 | 0.000791 |
| 531 | 0.333 | 0.000253 |
| 532 | 0.338 | 0.000178 |
| 533 | 0.101 | 0.000169 |
| 534 | 0.145 | 0.000251 |
| 535 | 0.297 | 0.000325 |
| 536 | 0.0776 | 0.000202 |
| 537 | 0.461 | 0.0023 |
| 538 | 0.275 | 0.000514 |
| 539 | 0.0985 | 0.00031 |
| 540 | 0.266 | 0.000305 |
| 541 | 0.175 | 0.000448 |
| 542 | 0.0351 | 0.000337 |
| 543 | 1.48 | 0.000383 |
| 544 | 0.871 | 0.000437 |
| 545 | 0.109 | 0.000403 |
| 546 | 0.237 | 0.0232 |
| 547 | 0.498 | 0.000423 |
| 548 | 0.397 | 0.000471 |
| 549 | 0.0812 | 0.000224 |
| 550 | 0.762 | 0.000427 |
| 551 | 0.713 | 0.000392 |
| 552 | 0.184 | 0.000543 |
| 553 | 0.478 | 0.000592 |
| 554 | 0.451 | 0.000837 |
| 555 | 0.427 | 0.000749 |
| 556 | 0.00543 | 0.000407 |
| 557 | 0.167 | 0.000359 |
| 558 | 1.41 | 0.000352 |
| 559 | 0.681 | 0.000223 |
| 560 | 0.969 | 0.000312 |
| 561 | 0.869 | 0.000335 |
| 562 | 0.218 | 0.000607 |
| 563 | 0.322 | 0.00419 |
| 564 | 0.0238 | 0.00343 |
| 565 | 0.215 | 0.00538 |
| 566 | >10 | 0.216 |
| 567 | 0.403 | 0.00111 |

TABLE 1-continued

| Example | TR-FRET Binding-IC50 (μM) | TR-FRET Binding-IC50 (with PRPP) (μM) | Example | TR-FRET Binding-IC50 (μM) | TR-FRET Binding-IC50 (with PRPP) (μM) |
|---|---|---|---|---|---|
| 155 | 3.37 | 0.0023 | 568 | 0.375 | 0.000723 |
| 156 | 3.27 | 0.00318 | 569 | 0.217 | 0.000669 |
| 157 | 4.14 | 0.0011 | 570 | 0.0704 | 0.000751 |
| 158 | 0.341 | 0.00639 | 571 | 0.0417 | 0.000494 |
| 159 | 2.49 | 0.00216 | 572 | 0.0516 | 0.000403 |
| 160 | 3.22 | 0.00126 | 573 | 0.0242 | 0.000403 |
| 161 | 1.31 | 0.00289 | 574 | 0.0975 | 0.000505 |
| 162 | 2.57 | 0.00209 | 575 | 3.25 | 0.0108 |
| 163 | 2.1 | 0.00629 | 576 | 0.016 | 0.000783 |
| 164 | 2.46 | 0.00346 | 577 | 0.0189 | 0.000361 |
| 165 | 1.53 | 0.00161 | 578 | 0.682 | 0.000775 |
| 166 | 1.43 | 0.00181 | 579 | 0.488 | 0.000634 |
| 167 | 1.73 | 0.00252 | 580 | 1.47 | 0.000798 |
| 168 | 1.11 | 0.000951 | 581 | 0.945 | 0.00109 |
| 169 | 0.375 | 0.00425 | 582 | 0.711 | 0.000911 |
| 170 | 3.36 | 0.00225 | 583 | 1.12 | 0.000799 |
| 171 | 2.17 | 0.00251 | 584 | 0.811 | 0.000756 |
| 172 | 2.21 | 0.00355 | 585 | 0.641 | 0.000648 |
| 173 | 1.51 | 0.00124 | 586 | 0.842 | 0.00109 |
| 174 | 0.0283 | 0.000169 | 587 | 0.236 | 0.000917 |
| 175 | 0.697 | 0.0009 | 588 | 0.684 | 0.000623 |
| 176 | 0.0606 | 0.000414 | 589 | 0.0161 | 0.000887 |
| 177 | 0.0201 | 0.000169 | 590 | 0.666 | 0.000734 |
| 178 | 0.0143 | 0.000169 | 591 | 0.138 | 0.000761 |
| 179 | 0.0581 | 0.000445 | 592 | 0.0388 | 0.000603 |
| 180 | 0.584 | 0.000266 | 593 | 0.767 | 0.000544 |
| 181 | 0.349 | 0.000283 | 594 | 0.0227 | 0.000682 |
| 182 | 0.139 | 0.0004 | 595 | 0.133 | 0.000746 |
| 183 | 1.05 | 0.0018 | 596 | 0.691 | 0.000909 |
| 184 | 4.34 | 0.00254 | 597 | 0.232 | 0.000862 |
| 185 | >10 | 0.00186 | 598 | 0.457 | 0.000804 |
| 186 | 0.0657 | 0.000347 | 599 | 0.527 | 0.000786 |
| 187 | 0.549 | 0.000172 | 600 | 0.51 | 0.000169 |
| 188 | >10 | 0.00509 | 601 | 0.712 | 0.000682 |
| 189 | 0.192 | 0.0111 | 602 | 0.786 | 0.000887 |
| 190 | 0.4 | 0.00457 | 603 | 1.03 | 0.00101 |
| 191 | 0.821 | 0.00609 | 604 | 0.151 | 0.000843 |
| 192 | 0.238 | 0.000242 | 605 | 0.559 | 0.000886 |
| 193 | 0.516 | 0.000266 | 606 | 0.281 | 0.000169 |
| 194 | 0.0323 | 0.00024 | 607 | 0.478 | 0.000796 |
| 195 | 0.0247 | 0.000251 | 608 | 0.481 | 0.00051 |
| 196 | 0.358 | 0.000169 | 609 | 0.598 | 0.00062 |
| 197 | 1.57 | 0.000505 | 610 | 0.751 | 0.000762 |
| 198 | 0.0325 | 0.000225 | 611 | 0.288 | 0.000621 |
| 199 | 0.00976 | 0.000311 | 612 | 0.706 | 0.000919 |
| 200 | 0.063 | 0.000482 | 613 | 0.347 | 0.000916 |
| 201 | 0.0466 | 0.000281 | 614 | 0.216 | 0.00067 |
| 202 | 0.216 | 0.000355 | 615 | 0.544 | 0.00079 |
| 203 | 0.0137 | 0.00021 | 616 | 0.174 | 0.00049 |
| 204 | 4.83 | 0.000773 | 617 | 0.164 | 0.000645 |
| 205 | 1.06 | 0.000358 | 618 | 0.5 | 0.000751 |
| 206 | 0.0257 | 0.000263 | 619 | 0.0793 | 0.000616 |
| 207 | 1.51 | 0.000282 | 620 | 0.71 | 0.001 |
| 208 | 0.404 | 0.000169 | 621 | 0.114 | 0.00542 |
| 209 | 0.811 | 0.000988 | 622 | 0.0294 | 0.00236 |
| 210 | 0.469 | 0.000363 | 623 | 1.01 | 0.0016 |
| 211 | 1.66 | 0.000453 | 624 | 0.261 | 0.000627 |
| 212 | 0.0448 | 0.00021 | 625 | 0.795 | 0.00076 |
| 213 | 0.116 | 0.000271 | 626 | 0.645 | 0.000793 |
| 214 | 0.641 | 0.00128 | 627 | 0.211 | 0.00071 |
| 215 | 2.01 | 0.00304 | 628 | 0.706 | 0.000978 |
| 216 | 0.118 | 0.00019 | 629 | 0.23 | 0.000643 |
| 217 | 0.22 | 0.0002 | 630 | 0.266 | 0.000563 |
| 218 | 0.123 | 0.000169 | 631 | 0.616 | 0.00126 |
| 219 | 0.0794 | 0.000903 | 632 | 0.27 | 0.000698 |
| 220 | 0.0742 | 0.000278 | 633 | 0.335 | 0.000707 |
| 221 | 0.12 | 0.000352 | 634 | 0.353 | 0.000648 |
| 222 | 0.112 | 0.000192 | 635 | 0.462 | 0.000975 |
| 223 | 0.109 | 0.000354 | 636 | 0.238 | 0.000915 |
| 224 | 0.233 | 0.000555 | 637 | 0.36 | 0.000421 |
| 225 | 0.155 | 0.000673 | 638 | 0.0166 | 0.000545 |
| 226 | 0.113 | 0.000608 | 639 | 0.215 | 0.000713 |
| 227 | 0.0162 | 0.000273 | 640 | 0.17 | 0.000817 |
| 228 | 0.0494 | 0.000238 | 641 | 0.0748 | 0.000684 |
| 229 | 0.0136 | 0.000398 | 642 | 0.454 | 0.000532 |
| 230 | 0.294 | 0.000169 | 643 | 0.028 | 0.000552 |
| 231 | 0.817 | 0.000546 | 644 | 0.0817 | 0.00069 |
| 232 | 0.396 | 0.000277 | 645 | 0.091 | 0.000474 |
| 233 | 0.495 | 0.000401 | 646 | 0.195 | 0.00051 |
| 234 | 0.904 | 0.000736 | 647 | 0.173 | 0.000672 |
| 235 | 0.494 | 0.000369 | 648 | 0.661 | 0.00106 |
| 236 | 0.604 | 0.000243 | 649 | 0.203 | 0.000749 |
| 237 | 0.451 | 0.000285 | 650 | 0.153 | 0.00111 |
| 238 | 0.123 | 0.000187 | 651 | 0.276 | 0.000715 |
| 239 | 0.308 | 0.000771 | 652 | 0.535 | 0.00116 |
| 240 | 7.35 | 0.00875 | 653 | 0.831 | 0.000893 |
| 241 | 0.0674 | 0.000169 | 654 | 0.213 | 0.000945 |
| 242 | 0.0571 | 0.000169 | 655 | 0.23 | 0.000998 |
| 243 | 0.169 | 0.000169 | 656 | 0.218 | 0.000738 |
| 244 | >10 | 0.00169 | 657 | 0.232 | 0.000589 |
| 245 | 2.89 | 0.000502 | 658 | 0.137 | 0.00076 |
| 246 | 0.0732 | 0.00022 | 659 | 0.646 | 0.00071 |
| 247 | 0.0627 | 0.000275 | 660 | 0.282 | 0.000693 |
| 248 | 0.0658 | 0.000169 | 661 | 0.462 | 0.000641 |
| 249 | 0.817 | 0.00072 | 662 | 0.318 | 0.000671 |
| 250 | 0.0205 | 0.00023 | 663 | 0.653 | 0.00107 |
| 251 | 2.2 | 0.00063 | 664 | 0.214 | 0.000733 |
| 252 | 0.0374 | 0.000274 | 665 | 0.123 | 0.000357 |
| 253 | 0.0144 | 0.000229 | 666 | 0.193 | 0.000855 |
| 254 | 0.0313 | 0.000306 | 667 | 0.226 | 0.000798 |
| 255 | 8.19 | 0.00222 | 668 | 0.263 | 0.0011 |
| 256 | 0.126 | 0.000266 | 669 | 0.407 | 0.000807 |
| 257 | 0.101 | 0.000344 | 670 | 0.062 | 0.000545 |
| 258 | 0.113 | 0.000558 | 671 | 0.611 | 0.00106 |
| 259 | 0.0266 | 0.000169 | 672 | 0.313 | 0.000504 |
| 260 | 0.0465 | 0.000351 | 673 | 0.452 | 0.000697 |
| 261 | 0.0627 | 0.000231 | 674 | 0.297 | 0.000535 |
| 262 | 0.00367 | 0.000221 | 675 | 0.376 | 0.0007 |
| 263 | 0.0486 | 0.000247 | 676 | 0.126 | 0.00698 |
| 264 | 0.0404 | 0.000412 | 677 | 0.00177 | 0.000796 |
| 265 | 0.0331 | 0.000266 | 678 | 0.0412 | 0.00023 |
| 266 | 0.12 | 0.000333 | 679 | 0.0228 | 0.00174 |
| 267 | 0.0543 | 0.000291 | 680 | 0.0371 | 0.00238 |
| 268 | 0.755 | 0.000169 | 681 | 0.0276 | 0.002 |
| 269 | 0.0412 | 0.000169 | 682 | 0.607 | 0.00158 |
| 270 | 0.0609 | 0.000991 | 683 | 0.154 | 0.0119 |
| 271 | 0.0517 | 0.000169 | 684 | 0.481 | 0.00134 |
| 272 | 0.0272 | 0.000417 | 685 | 1.25 | 0.00136 |
| 273 | 0.0493 | 0.000555 | 686 | 0.959 | 0.0013 |
| 274 | 0.0178 | 0.000196 | 687 | 0.0973 | 0.00116 |
| 275 | 0.0123 | 0.00043 | 688 | 1.11 | 0.00266 |
| 276 | 0.107 | 0.000468 | 689 | 0.016 | 0.00132 |
| 277 | 0.103 | 0.000667 | 690 | 0.0643 | 0.00122 |
| 278 | 0.102 | 0.000621 | 691 | 0.169 | 0.00067 |
| 279 | 0.0688 | 0.000437 | 692 | 0.0839 | 0.00119 |
| 280 | 0.0113 | 0.000213 | 693 | 0.781 | 0.00142 |
| 281 | 0.0055 | 0.000214 | 694 | 0.163 | 0.00112 |
| 282 | 0.0765 | 0.000297 | 695 | 0.0137 | 0.000621 |
| 283 | 0.0632 | 0.000264 | 696 | 0.272 | 0.000725 |
| 284 | 0.00796 | 0.000169 | 697 | 0.735 | 0.000802 |
| 285 | 0.0826 | 0.000593 | 698 | 0.0364 | 0.000629 |
| 286 | 0.12 | 0.000412 | 699 | 0.0411 | 0.000721 |
| 287 | 0.0673 | 0.000351 | 700 | 0.0684 | 0.00103 |
| 288 | 0.0495 | 0.000568 | 701 | 0.367 | 0.000856 |
| 289 | 0.155 | 0.000286 | 702 | 0.568 | 0.00129 |
| 290 | 0.415 | 0.00096 | 703 | 0.559 | 0.000824 |
| 291 | 0.159 | 0.000449 | 704 | 0.503 | 0.000777 |
| 292 | 1.54 | 0.00115 | 705 | 0.876 | 0.00163 |
| 293 | 0.0273 | 0.000169 | 706 | 0.0841 | 0.000937 |
| 294 | 0.0447 | 0.000169 | 707 | 0.277 | 0.000624 |
| 295 | 0.0561 | 0.000292 | 708 | 0.06 | 0.0009 |
| 296 | 0.067 | 0.000226 | 709 | 0.0194 | 0.000473 |
| 297 | 0.177 | 0.000286 | 710 | 0.0491 | 0.00125 |
| 298 | 3.41 | 0.000557 | 711 | 0.0885 | 0.00111 |
| 299 | 0.172 | 0.000283 | 712 | 0.0911 | 0.000907 |
| 300 | 0.0614 | 0.000169 | 713 | 0.0443 | 0.000689 |
| 301 | 0.288 | 0.000301 | 714 | 0.168 | 0.000991 |
| 302 | 0.16 | 0.000435 | 715 | 0.0659 | 0.000771 |
| 303 | 0.00999 | 0.000169 | 716 | 0.0502 | 0.000607 |
| 304 | 0.0662 | 0.000169 | 717 | 0.186 | 0.000428 |

TABLE 1-continued

| Example | TR-FRET Binding-IC50 (μM) | TR-FRET Binding-IC50 (with PRPP) (μM) | Example | TR-FRET Binding-IC50 (μM) | TR-FRET Binding-IC50 (with PRPP) (μM) |
|---|---|---|---|---|---|
| 305 | 0.494 | 0.000449 | 718 | 0.0236 | 0.000755 |
| 306 | 0.144 | 0.000169 | 719 | 0.00632 | 0.000835 |
| 307 | 0.0508 | 0.000169 | 720 | 0.0367 | 0.000181 |
| 308 | 0.306 | 0.000169 | 721 | 0.125 | 0.00121 |
| 309 | 0.117 | 0.000169 | 722 | 0.0394 | 0.00101 |
| 310 | 0.564 | 0.000217 | 723 | 0.154 | 0.000932 |
| 311 | 0.289 | 0.000274 | 724 | 0.161 | 0.000992 |
| 312 | 0.165 | 0.000243 | 725 | 0.0196 | 0.000747 |
| 313 | 0.531 | 0.00036 | 726 | 0.251 | 0.000534 |
| 314 | 1.98 | 0.000581 | 727 | 0.166 | 0.000783 |
| 315 | 0.231 | 0.00032 | 728 | 0.14 | 0.000496 |
| 316 | 0.0421 | 0.000169 | 729 | 0.428 | 0.000765 |
| 317 | 0.317 | 0.000282 | 730 | 0.489 | 0.000847 |
| 318 | 0.0416 | 0.000228 | 731 | 0.223 | 0.000391 |
| 319 | 0.466 | 0.000192 | 732 | 0.0213 | 0.000471 |
| 320 | 0.0963 | 0.000208 | 733 | 0.119 | 0.000712 |
| 321 | 3.16 | 0.000792 | 734 | 0.0142 | 0.000605 |
| 322 | 6.04 | 0.0341 | 735 | 0.646 | 0.000864 |
| 323 | 1.4 | 0.000232 | 736 | 3.09 | 0.00073 |
| 324 | 0.981 | 0.000752 | 737 | 0.0704 | 0.000612 |
| 325 | 0.18 | 0.000278 | 738 | 0.364 | 0.000705 |
| 326 | 2.35 | 0.0013 | 739 | 0.0377 | 0.000672 |
| 327 | 1.32 | 0.000558 | 740 | 0.0701 | 0.000403 |
| 328 | 0.068 | 0.000169 | 741 | 0.068 | 0.000647 |
| 329 | 0.0308 | 0.000169 | 742 | 0.241 | 0.000526 |
| 330 | 0.32 | 0.000432 | 743 | 0.0633 | 0.000691 |
| 331 | 0.383 | 0.000416 | 744 | 1.08 | 0.000806 |
| 332 | 0.18 | 0.000297 | 745 | 0.994 | 0.000783 |
| 333 | 0.583 | 0.000346 | 746 | 0.795 | 0.000839 |
| 334 | 0.0809 | 0.000345 | 747 | 0.435 | 0.00175 |
| 335 | 0.632 | 0.000354 | 748 | 0.558 | 0.000648 |
| 336 | 0.334 | 0.000264 | 749 | 0.392 | 0.00079 |
| 337 | 0.497 | 0.000205 | 750 | 1.53 | 0.00154 |
| 338 | 0.609 | 0.000394 | 751 | 1.24 | 0.001 |
| 339 | >10 | 0.000797 | 752 | 5.19 | 0.00077 |
| 340 | >10 | 0.000817 | 753 | 0.403 | 0.000783 |
| 341 | >10 | 0.000719 | 754 | 0.00492 | 0.00051 |
| 342 | >10 | 0.000454 | 755 | 0.013 | 0.00057 |
| 343 | >10 | 0.000456 | 756 | 0.123 | 0.000609 |
| 344 | 0.036 | 0.000169 | 757 | 0.0156 | 0.000705 |
| 345 | 0.201 | 0.00027 | 758 | 0.132 | 0.00061 |
| 346 | 3.11 | 0.000548 | 759 | 0.0285 | 0.000799 |
| 347 | 4.73 | 0.000667 | 760 | 0.0289 | 0.00071 |
| 348 | >10 | 0.00152 | 761 | 0.0944 | 0.000394 |
| 349 | 4.11 | 0.000736 | 762 | 0.0301 | 0.000506 |
| 350 | >10 | 0.000795 | 763 | 0.0485 | 0.000478 |
| 351 | 8.39 | 0.000792 | 764 | 0.135 | 0.000465 |
| 352 | >10 | 0.00106 | 765 | 0.0365 | 0.000782 |
| 353 | 3.17 | 0.00047 | 766 | 0.0615 | 0.000581 |
| 354 | >10 | 0.000526 | 767 | 0.265 | 0.00064 |
| 355 | 0.831 | 0.000169 | 768 | 0.0281 | 0.000672 |
| 356 | >10 | 0.000169 | 769 | 0.0984 | 0.000705 |
| 357 | >10 | 0.000291 | 770 | 0.0388 | 0.000735 |
| 358 | 1.84 | 0.00219 | 771 | 0.0708 | 0.000573 |
| 359 | >10 | 0.0025 | 772 | 0.0615 | 0.000828 |
| 360 | 0.291 | 0.000717 | 773 | 0.0726 | 0.000773 |
| 361 | 5.03 | 0.00194 | 774 | 0.103 | 0.00046 |
| 362 | 0.143 | 0.000256 | 775 | 0.0519 | 0.000538 |
| 363 | 0.588 | 0.000305 | 776 | 0.0215 | 0.000169 |
| 364 | 0.135 | 0.000172 | 777 | 0.0394 | 0.00092 |
| 365 | 1.34 | 0.000171 | 778 | 0.0276 | 0.000414 |
| 366 | 0.146 | 0.000435 | 779 | 0.0142 | 0.000603 |
| 367 | 0.65 | 0.00018 | 780 | 0.25 | 0.000382 |
| 368 | 0.602 | 0.000317 | 781 | 0.0875 | 0.000839 |
| 369 | 0.429 | 0.000337 | 782 | 0.134 | 0.000466 |
| 370 | 0.0476 | 0.000175 | 783 | 0.0644 | 0.000907 |
| 371 | 1.44 | 0.000298 | 784 | 0.0226 | 0.000455 |
| 372 | 2.44 | 0.00046 | 785 | 0.0236 | 0.000638 |
| 373 | 3.04 | 0.00036 | 786 | 0.0444 | 0.000484 |
| 374 | 1.67 | 0.000292 | 787 | 0.055 | 0.000474 |
| 375 | 0.986 | 0.000241 | 788 | 0.082 | 0.000674 |
| 376 | 1.05 | 0.000305 | 789 | 0.0217 | 0.000434 |
| 377 | 1.67 | 0.000275 | 790 | 0.0795 | 0.000586 |
| 378 | 0.897 | 0.000169 | 791 | 0.0471 | 0.00115 |
| 379 | 0.279 | 0.00029 | 792 | 0.116 | 0.0005 |
| 380 | 0.179 | 0.000251 | 793 | 0.0231 | 0.000398 |
| 381 | 0.0841 | 0.000259 | 794 | 0.029 | 0.000465 |
| 382 | 0.119 | 0.000204 | 795 | 0.0896 | 0.000764 |
| 383 | 0.0495 | 0.000225 | 796 | 0.0917 | 0.00049 |
| 384 | 0.406 | 0.000375 | 797 | 0.0972 | 0.000671 |
| 385 | 0.491 | 0.000539 | 798 | 0.0957 | 0.00047 |
| 386 | 0.283 | 0.000254 | 799 | 0.102 | 0.000406 |
| 387 | 0.419 | 0.000467 | 800 | 0.0821 | 0.000925 |
| 388 | 0.388 | 0.000506 | 801 | 0.866 | 0.001 |
| 389 | 0.584 | 0.000617 | 802 | 0.0359 | 0.000533 |
| 390 | 0.133 | 0.000445 | 803 | 0.314 | 0.00101 |
| 391 | 0.171 | 0.000227 | 804 | 0.289 | 0.000445 |
| 392 | 0.814 | 0.000465 | 805 | 3.92 | 0.00112 |
| 393 | >10 | 0.00437 | 806 | 2.74 | 0.000543 |
| 394 | >10 | 0.00308 | 807 | 0.628 | 0.000509 |
| 395 | 0.0125 | 0.000193 | 808 | 0.0944 | 0.000568 |
| 396 | 0.0226 | 0.00036 | 809 | 0.0953 | 0.00063 |
| 397 | 0.0177 | 0.000169 | 810 | 0.481 | 0.0126 |
| 398 | 0.21 | 0.000792 | 811 | 0.0998 | 0.00286 |
| 399 | 9.5 | 0.00154 | 812 | 0.08 | 0.00257 |
| 400 | 0.0812 | 0.000298 | 813 | 0.0112 | 0.00153 |
| 401 | 0.0126 | 0.000292 | 814 | 0.0687 | 0.00163 |
| 402 | 0.0548 | 0.000327 | 815 | 0.053 | 0.00193 |
| 403 | 1.55 | 0.000847 | 816 | 0.0461 | 0.00158 |
| 404 | 2.55 | 0.00088 | 817 | 0.0658 | 0.0016 |
| 405 | 0.0784 | 0.000214 | 818 | 1.52 | 0.000644 |
| 406 | 1.14 | 0.000505 | 819 | 0.0199 | 0.000624 |
| 407 | 0.22 | 0.000659 | 820 | 0.499 | 0.00928 |
| 408 | 0.276 | 0.000725 | 821 | 0.663 | 0.000284 |
| 409 | >10 | 0.48 | 822 | 0.104 | 0.00346 |
| 410 | 0.0207 | 0.000169 | 823 | 0.189 | 0.000356 |
| 411 | 1.87 | 0.000556 | 824 | 0.118 | 0.000566 |
| 412 | 1.25 | 0.000424 | 825 | 0.0261 | 0.000538 |
| 413 | 0.805 | 0.000279 | 826 | 0.00779 | 0.000897 |

NAMPT Cell Proliferation Assay

PC3 cells were seeded in 96-well black plates (Corning #3904) at 500 cells/well in 90 l of RPMI media containing 10% heat-inactivated FBS and incubated overnight at 37° C. and 5% $CO_2$ to allow cells to attach to wells. The following day, test compounds were serially diluted in neat DMSO to 1000× final concentrations prior to dilution with RPMI media to 10× and 1% DMSO. Ten L of the 10× compounds were then transferred to wells containing cells to produce a dose response of 10-fold dilutions from 10 M to $1 \times 10^{-5}$ M. Cells were incubated for 5 days at 37° C. and 5% $CO_2$, then cell viability was measured using Cell Titer Glo reagent (Promega #G7571). Percent inhibition values were calculated and fitted to a sigmoidal dose response curves using Assay Explorer software to determine IC50s. To assess whether inhibition of cell viability was due to NAMPT inhibition, the proliferation assay was also performed in the presence of 0.3 mM nicotinamide mononucleotide.

Table 2 shows the results of the cell proliferation assay.

TABLE 2

| Example | Cell Titer-Glo-IC50 (M) | Example | Cell Titer-Glo-IC50 (M) | Example | Cell Titer-Glo-IC50 (M) | Example | Cell Titer-Glo-IC50 (M) |
|---|---|---|---|---|---|---|---|
| 1 | 0.0609 | 290 | 0.0722 | 579 | 0.758 | 868 | 0.0869 |
| 2 | >10 | 291 | 0.0261 | 580 | 0.212 | 869 | 6.87 |
| 3 | 0.0367 | 292 | 7.22 | 581 | 0.0812 | 870 | 0.994 |
| 4 | 0.935 | 293 | 0.00774 | 582 | 0.0332 | 871 | 7.3 |
| 5 | 0.74 | 294 | 0.00188 | 583 | 0.189 | 872 | >10 |
| 6 | 6.65 | 295 | 0.0242 | 584 | 0.0587 | 873 | 3.87 |
| 7 | 0.527 | 296 | 0.0115 | 585 | 0.0346 | 874 | 6.65 |
| 8 | 0.0702 | 297 | 0.0358 | 586 | 0.301 | 875 | 1.14 |
| 9 | 0.649 | 298 | 2.37 | 587 | 0.00754 | 876 | 0.0477 |
| 10 | 0.331 | 299 | 8.64 | 588 | 0.181 | 877 | >10 |
| 11 | 4.53 | 300 | 0.0287 | 589 | 0.00131 | 878 | >10 |
| 12 | 0.213 | 301 | 0.0258 | 590 | 0.189 | 879 | 0.0633 |
| 13 | 1.17 | 302 | 0.0193 | 591 | 0.0193 | 880 | 0.75 |
| 14 | 0.644 | 303 | 0.00179 | 592 | 0.00375 | 881 | 8.49 |
| 15 | 3.97 | 304 | 0.0188 | 593 | 0.677 | 882 | >10 |
| 16 | 0.325 | 305 | 1.17 | 594 | 0.00111 | 883 | 0.000220 |
| 17 | 4.96 | 306 | 0.0219 | 595 | 0.00693 | 884 | 0.000968 |
| 18 | 0.36 | 307 | 0.0136 | 596 | 0.257 | 885 | 0.005333 |
| 19 | 6.63 | 308 | 0.0295 | 597 | 0.0335 | 886 | 0.000194 |
| 20 | 0.102 | 309 | 0.0548 | 598 | 0.0166 | 887 | 0.000214 |
| 21 | 0.899 | 310 | 0.0244 | 599 | 0.0523 | 888 | 0.000494 |
| 22 | 0.142 | 311 | 0.0191 | 600 | 0.11 | 889 | 0.651 |
| 23 | 0.0415 | 312 | 0.065 | 601 | 0.0567 | 890 | 0.0318 |
| 24 | 0.691 | 313 | 0.82 | 602 | 0.0486107 | 891 | 0.0872 |
| 25 | 0.146 | 314 | 0.395 | 603 | 0.695 | 892 | 0.00676 |
| 26 | 0.261 | 315 | 0.72 | 604 | 0.0101 | 893 | 0.000662 |
| 27 | 7.54 | 316 | 0.00634 | 605 | 0.0661 | 894 | 0.202 |
| 28 | 0.0142 | 317 | 0.542 | 606 | 0.0348 | 895 | 0.73 |
| 29 | 0.0439 | 318 | 0.0421 | 607 | 0.0744 | 896 | 1.58 |
| 30 | 0.0384 | 319 | 0.0293 | 608 | 0.148 | 897 | 0.716 |
| 31 | 0.107 | 320 | 0.171 | 609 | 0.142 | 898 | 0.223 |
| 32 | 0.284 | 321 | 1.13 | 610 | 0.0744 | 899 | 0.181 |
| 33 | 0.0673 | 322 | >10 | 611 | 0.0709 | 900 | 0.0174 |
| 34 | 0.0383 | 323 | 0.175 | 612 | 0.695 | 901 | 0.865 |
| 35 | 0.0586 | 324 | 0.0547 | 613 | 0.14 | 902 | 0.0108 |
| 36 | 0.0514 | 325 | 0.0329 | 614 | 0.00572 | 903 | 0.0352 |
| 37 | 0.0347 | 326 | 0.457 | 615 | 0.0188 | 904 | 0.282 |
| 38 | 0.0659 | 327 | 0.638 | 616 | 0.0326 | 905 | 0.000994 |
| 39 | 7.28 | 328 | 0.0089 | 617 | 0.0826 | 906 | 0.00417 |
| 40 | 0.0708 | 329 | 0.0124 | 618 | 0.125 | 907 | 0.00709 |
| 41 | 0.138 | 330 | 0.0229 | 619 | 0.0033 | 908 | 0.0112 |
| 42 | 1.59 | 331 | 0.227 | 620 | 0.131 | 909 | 7.21 |
| 43 | 7.45 | 332 | 0.0643 | 621 | 0.0253 | 910 | >10 |
| 44 | 1.58 | 333 | 0.116 | 622 | 0.00706 | 911 | 0.0425 |
| 45 | 2.07 | 334 | 0.0219 | 623 | 0.446 | 912 | 0.008725 |
| 46 | 6.28 | 335 | 0.0976 | 624 | 0.329 | 913 | 0.0144 |
| 47 | 0.0648 | 336 | 0.139 | 625 | 0.226 | 914 | 0.0772 |
| 48 | 5.32 | 337 | 0.533 | 626 | 0.0807 | 915 | 0.174 |
| 49 | 7.04 | 338 | 0.081 | 627 | 0.0175 | 916 | 0.00673 |
| 50 | 6.14 | 339 | 9.18 | 628 | 0.0436 | 917 | 0.00679 |
| 51 | 0.083 | 340 | >10 | 629 | 0.0652 | 918 | 0.233 |
| 52 | 0.00407 | 341 | 8.3 | 630 | 0.0404 | 919 | 0.101 |
| 53 | 3.3 | 342 | 6.73 | 631 | 0.0772 | 920 | 0.00794 |
| 54 | 0.303 | 343 | 6.53 | 632 | 0.0323 | 921 | 0.157 |
| 55 | 0.0146 | 344 | 0.00746 | 633 | 0.012 | 922 | 0.00995 |
| 56 | 0.00886 | 345 | 0.281 | 634 | 0.0835 | 923 | 0.00458 |
| 57 | 0.00576 | 346 | 7.02 | 635 | 0.05 | 924 | 0.018 |
| 58 | 0.0526 | 347 | 8.08 | 636 | 0.0184 | 925 | 0.00206 |
| 59 | 0.143 | 348 | >10 | 637 | 0.0811 | 926 | 0.00969 |
| 60 | 0.00958 | 349 | 5.51 | 638 | 0.00261 | 927 | 0.00713 |
| 61 | 0.00601 | 350 | 8.17 | 639 | 0.0581 | 928 | 0.106 |
| 62 | 0.0165 | 351 | 8.11 | 640 | 0.05 | 929 | 0.0247 |
| 63 | 0.0168 | 352 | 9.8 | 641 | 0.00999 | 930 | 0.00209 |
| 64 | 0.0198 | 353 | 7.51 | 642 | 0.0949 | 931 | 0.00677 |
| 65 | 0.0656 | 354 | 7.49 | 643 | 0.0069 | 932 | 0.0303 |
| 66 | 0.0115 | 355 | 1.94 | 644 | 0.00408 | 933 | 0.0717 |
| 67 | 0.0119 | 356 | 1.02 | 645 | 0.034 | 934 | 0.00638 |
| 68 | 0.0538 | 357 | 6.74 | 646 | 0.13 | 935 | 0.0103 |
| 69 | 0.0166 | 358 | 2.26 | 647 | 0.00699 | 936 | 0.0325 |
| 70 | 0.0278 | 359 | 8.77 | 648 | 0.203 | 937 | 0.0809 |
| 71 | 0.0667 | 360 | 0.663 | 649 | 0.0706 | 938 | 0.00627 |
| 72 | 0.0659 | 361 | >10 | 650 | 0.0583 | 939 | >10 |
| 73 | 0.0595 | 362 | 0.106 | 651 | 0.0648 | 940 | 0.000691 |
| 74 | 0.014 | 363 | 7.66 | 652 | 0.0346 | 941 | 0.000519 |

TABLE 2-continued

| Example | Cell Titer-Glo-IC50 (M) | Example | Cell Titer-Glo-IC50 (M) | Example | Cell Titer-Glo-IC50 (M) | Example | Cell Titer-Glo-IC50 (M) |
|---|---|---|---|---|---|---|---|
| 75 | 0.00149 | 364 | 0.031 | 653 | 0.715 | 942 | 0.00102 |
| 76 | 0.185 | 365 | 0.332 | 654 | 0.0679 | 943 | 0.0244 |
| 77 | 0.0142 | 366 | 0.0215 | 655 | 0.0688 | 944 | 0.00336 |
| 78 | 0.0407 | 367 | 0.601 | 656 | 0.0385 | 945 | 0.00238 |
| 79 | 0.00745 | 368 | 0.0484 | 657 | 0.036 | 946 | 0.00594 |
| 80 | 0.0194 | 369 | 0.738 | 658 | 0.0608 | 947 | 0.00328 |
| 81 | 0.0071 | 370 | 0.00993 | 659 | 0.223 | 948 | 0.00539 |
| 82 | 0.0679 | 371 | 0.82 | 660 | 0.0709 | 949 | 0.0254 |
| 83 | 0.0243 | 372 | 0.868 | 661 | 0.0672 | 950 | 0.634 |
| 84 | 0.762 | 373 | 0.585 | 662 | 0.0934 | 951 | 0.0639 |
| 85 | 2.61 | 374 | 0.792 | 663 | 0.09 | 952 | 0.0103 |
| 86 | 5.72 | 375 | >10 | 664 | 0.0715 | 953 | 0.00235 |
| 87 | 6.58 | 376 | >10 | 665 | 0.00728 | 954 | 0.00276 |
| 88 | 8.11 | 377 | >10 | 666 | 0.00518 | 955 | 0.00256 |
| 89 | 0.113 | 378 | >10 | 667 | 0.0458 | 956 | 0.00883 |
| 90 | 0.0187 | 379 | 0.37 | 668 | 0.0803 | 957 | 0.00351 |
| 91 | 0.0139 | 380 | 0.04 | 669 | 0.686 | 958 | 0.0214 |
| 92 | 0.00948 | 381 | 0.0173 | 670 | 0.00992 | 959 | 0.00976 |
| 93 | 0.00713 | 382 | 0.0838 | 671 | 0.684 | 960 | 0.00613 |
| 94 | 0.0142 | 383 | 0.0133 | 672 | 0.08 | 961 | 0.00894 |
| 95 | 0.0106 | 384 | 0.0517 | 673 | 0.122 | 962 | 0.0161 |
| 96 | 0.00965 | 385 | 0.11 | 674 | 0.0324 | 963 | 0.0195 |
| 97 | 0.00455 | 386 | 0.0424 | 675 | 0.0698 | 964 | 0.00622 |
| 98 | 0.0194 | 387 | 0.0581 | 676 | 0.0787 | 965 | 0.00831 |
| 99 | 0.0264 | 388 | 0.122 | 677 | 6.13E-04 | 966 | 0.00209 |
| 100 | 0.0162 | 389 | 0.0783 | 678 | 0.0151 | 967 | 0.00396 |
| 101 | 0.00244 | 390 | 0.0803 | 679 | 0.0109 | 968 | 0.00177 |
| 102 | 0.013 | 391 | 0.0784 | 680 | 0.629 | 969 | 0.00636 |
| 103 | 0.0621 | 392 | 0.666 | 681 | 0.145 | 970 | 0.0109 |
| 104 | 0.00846 | 393 | >10 | 682 | 0.771 | 971 | 0.0226 |
| 105 | 0.00661 | 394 | >10 | 683 | 0.0361 | 972 | 0.0289 |
| 106 | 0.0787 | 395 | 0.00634 | 684 | 0.32 | 973 | 0.0218 |
| 107 | 0.0108 | 396 | 0.0324 | 685 | 0.074 | 974 | 0.0287 |
| 108 | 7.66 | 397 | 0.00712 | 686 | 0.0772 | 975 | 0.0503 |
| 109 | 0.0522 | 398 | 0.0736 | 687 | 0.00219 | 976 | 0.0349 |
| 110 | 0.202 | 399 | 7.68 | 688 | 5.48 | 977 | 0.00265 |
| 111 | 0.0755 | 400 | 0.712 | 689 | 0.00721 | 978 | 0.00202 |
| 112 | 0.00696 | 401 | 0.0559 | 690 | 0.0138 | 979 | 0.0757 |
| 113 | 0.0933 | 402 | 0.00671 | 691 | 0.0777 | 980 | 0.0294 |
| 114 | 0.142 | 403 | 0.0545 | 692 | 0.0198 | 981 | 0.00654 |
| 115 | 0.00638 | 404 | 9.41 | 693 | 0.652 | 982 | 0.1 |
| 116 | 0.0613 | 405 | 0.0221 | 694 | 0.0247 | 983 | 0.724 |
| 117 | 0.0639 | 406 | 0.347 | 695 | 0.00582 | 984 | 0.0554 |
| 118 | 0.0182 | 407 | 1.31 | 696 | 0.667 | 985 | 0.0283 |
| 119 | 0.146 | 408 | 0.0192 | 697 | 0.633 | 986 | 0.0214 |
| 120 | 0.0908 | 409 | 10 | 698 | 0.000670 | 987 | 0.543 |
| 121 | 0.00391 | 410 | nd | 699 | 0.00527 | 988 | 0.0601 |
| 122 | 0.172 | 411 | 4.72 | 700 | 0.00325 | 989 | 0.0682 |
| 123 | 0.00743 | 412 | 0.978 | 701 | 0.0761902 | 990 | 0.0179 |
| 124 | 0.0208 | 413 | 0.19 | 702 | 0.088 | 991 | 0.0669 |
| 125 | 0.023 | 414 | 0.853 | 703 | 0.0903 | 992 | 0.584 |
| 126 | 0.00396 | 415 | 0.234 | 704 | 0.0915 | 993 | 0.074 |
| 127 | 0.00234 | 416 | 0.659 | 705 | 0.0958 | 994 | 0.0121 |
| 128 | 0.00221 | 417 | 0.867 | 706 | 0.00654 | 995 | 0.0108 |
| 129 | 0.00274 | 418 | 0.866 | 707 | 0.0741 | 996 | 0.062 |
| 130 | 0.00655 | 419 | 0.365 | 708 | 0.00597 | 997 | 0.0194 |
| 131 | 0.00217 | 420 | 0.147 | 709 | 0.00336 | 998 | 0.123 |
| 132 | 0.523 | 421 | 0.317 | 710 | 0.00276 | 999 | 0.684 |
| 133 | 0.00216 | 422 | 0.109 | 711 | 0.00325 | 1000 | 0.0818 |
| 134 | 0.00654 | 423 | 0.187 | 712 | 0.0058 | 1001 | 0.0953 |
| 135 | 0.00636 | 424 | 0.521 | 713 | 0.00286 | 1002 | 0.154 |
| 136 | 0.00305 | 425 | 0.069 | 714 | 0.0174 | 1003 | 0.00496 |
| 137 | 0.225 | 426 | 0.0064 | 715 | 0.00349 | 1004 | 0.0567 |
| 138 | 0.00383 | 427 | 0.0622 | 716 | 0.021 | 1005 | 0.0747 |
| 139 | 0.0122 | 428 | 0.0675 | 717 | 0.0724 | 1006 | 0.0737 |
| 140 | 0.0655 | 429 | 0.0186 | 718 | 0.00125 | 1007 | 0.0373 |
| 141 | 0.0778 | 430 | 0.0886 | 719 | 0.00237 | 1008 | 0.00294 |
| 142 | 0.0182 | 431 | 0.0719 | 720 | 0.00582 | 1009 | 0.0012 |
| 143 | 0.0808 | 432 | 0.0363 | 721 | 0.0307 | 1010 | 0.0058 |
| 144 | 0.187 | 433 | 0.0644 | 722 | 0.00388 | 1011 | 0.00197 |
| 145 | 0.00601 | 434 | 0.00559 | 723 | 0.0716 | 1012 | 0.00836 |
| 146 | 0.00769 | 435 | 0.0204 | 724 | 0.0632 | 1013 | 0.00232 |
| 147 | 0.00669 | 436 | 0.762 | 725 | 0.006 | 1014 | 0.00207 |
| 148 | 0.0415 | 437 | 0.00702 | 726 | 0.0719 | 1015 | 0.00168 |

TABLE 2-continued

| Example | Cell Titer-Glo-IC50 (M) | Example | Cell Titer-Glo-IC50 (M) | Example | Cell Titer-Glo-IC50 (M) | Example | Cell Titer-Glo-IC50 (M) |
|---|---|---|---|---|---|---|---|
| 149 | 0.0266 | 438 | 0.0425 | 727 | 0.0582 | 1016 | 0.00219 |
| 150 | 0.0362 | 439 | 0.0375 | 728 | 0.021 | 1017 | 0.00229 |
| 151 | 0.0761 | 440 | | 729 | 0.0459 | 1018 | 0.00164 |
| 152 | 0.0283 | 441 | 0.0072 | 730 | 0.0295 | 1019 | 0.00198 |
| 153 | 0.00373 | 442 | 0.0707 | 731 | 0.05 | 1020 | 0.000901 |
| 154 | 0.00667 | 443 | 0.00896 | 732 | 0.0059 | 1021 | 0.00111 |
| 155 | 0.0176 | 444 | 0.0699 | 733 | 0.0202 | 1022 | 0.00293 |
| 156 | 0.028 | 445 | 0.0229 | 734 | 0.000553 | 1023 | 0.00687 |
| 157 | 0.0292 | 446 | 0.0612 | 735 | 0.688 | 1024 | 0.00352 |
| 158 | 0.191 | 447 | 0.0125 | 736 | 8.36 | 1025 | 0.000808 |
| 159 | 0.233 | 448 | 0.0678 | 737 | 0.00405 | 1026 | 0.00156 |
| 160 | 0.915 | 449 | 0.0236 | 738 | 0.0859 | 1027 | 0.00228 |
| 161 | 0.635 | 450 | 0.0701 | 739 | 0.0676 | 1028 | 0.00736 |
| 162 | 0.0436 | 451 | 0.0173 | 740 | 0.00813 | 1029 | 0.000272 |
| 163 | 0.0964 | 452 | 0.0592 | 741 | 0.0749 | 1030 | 0.002040 |
| 164 | 0.101 | 453 | 0.00921 | 742 | 0.0105 | 1031 | 0.00773 |
| 165 | 0.137 | 454 | 0.0422 | 743 | 0.00681 | 1032 | 0.00888 |
| 166 | 0.0971 | 455 | 0.0035 | 744 | 0.505 | 1033 | 0.00197 |
| 167 | 0.104 | 456 | 0.0496 | 745 | 0.632 | 1034 | 0.00629 |
| 168 | 0.208 | 457 | 0.194 | 746 | 0.116 | 1035 | 0.00304 |
| 169 | 0.0269 | 458 | 0.183 | 747 | 0.942 | 1036 | 0.016 |
| 170 | 0.604 | 459 | 0.0777 | 748 | 0.0507 | 1037 | 0.00776 |
| 171 | 0.0447 | 460 | 0.0509 | 749 | 0.077 | 1038 | 0.00784 |
| 172 | 0.223 | 461 | 0.0314 | 750 | 0.794 | 1039 | 0.00687 |
| 173 | 0.0501 | 462 | 0.00743 | 751 | 0.755 | 1040 | 0.0134 |
| 174 | 0.00112 | 463 | 0.234 | 752 | 6.66 | 1041 | 0.00241 |
| 175 | 0.313 | 464 | 0.00679 | 753 | 0.0746 | 1042 | 0.00359 |
| 176 | 0.00181 | 465 | 0.000319 | 754 | 0.00125 | 1043 | 0.0104 |
| 177 | 0.00169 | 466 | 0.00431 | 755 | 0.00249 | 1044 | 0.000892 |
| 178 | 0.00185 | 467 | 0.00402 | 756 | 0.0189 | 1045 | 0.00669 |
| 179 | 0.00218 | 468 | 2.93 | 757 | 0.000435 | 1046 | 0.00461 |
| 180 | 0.00912 | 469 | 3.38 | 758 | 0.0232 | 1047 | 0.000205 |
| 181 | 0.00775 | 470 | 0.936 | 759 | 0.00165 | 1048 | 0.00827 |
| 182 | 0.00137 | 471 | 6.51 | 760 | 0.00119 | 1049 | 0.00239 |
| 183 | 0.063 | 472 | 0.963 | 761 | 0.0277 | 1050 | 0.0234 |
| 184 | 0.0651 | 473 | 7.85 | 762 | 0.00112 | 1051 | 0.000313 |
| 185 | 5.05 | 474 | 0.879 | 763 | 0.00231 | 1052 | 0.0271 |
| 186 | 0.00236 | 475 | 0.00692 | 764 | 0.0687 | 1053 | 0.00341 |
| 187 | 0.0341 | 476 | 0.00942 | 765 | 0.00291 | 1054 | 0.026 |
| 188 | 6.29 | 477 | 0.00321 | 766 | 0.00636 | 1055 | 0.00438 |
| 189 | 0.0293 | 478 | 0.0312 | 767 | 0.0672 | 1056 | 0.0013 |
| 190 | 0.0149 | 479 | 0.00808 | 768 | 0.000905 | 1057 | 0.0258 |
| 191 | 0.0143 | 480 | 0.00743 | 769 | 0.00526 | 1058 | 0.00249 |
| 192 | 0.00185 | 481 | 0.00579 | 770 | 0.006 | 1059 | 0.0164 |
| 193 | 0.0199 | 482 | 0.00222 | 771 | 0.00347 | 1060 | 0.00229 |
| 194 | 0.000773 | 483 | 0.0124 | 772 | 0.0024 | 1061 | 0.00784 |
| 195 | 0.000966 | 484 | 0.00959 | 773 | 0.00953 | 1062 | 0.017 |
| 196 | 0.00675 | 485 | 0.0345 | 774 | 0.00707 | 1063 | 0.00189 |
| 197 | 0.0254 | 486 | 0.0233 | 775 | 0.0609 | 1064 | 0.00412 |
| 198 | 0.00184 | 487 | 0.0833 | 776 | 0.0021 | 1065 | 0.00143 |
| 199 | 0.000539 | 488 | 0.0983 | 777 | 0.00126 | 1066 | 0.0057 |
| 200 | 0.00572 | 489 | >10 | 778 | 0.000896 | 1067 | 0.37 |
| 201 | 0.00189 | 490 | 0.0899 | 779 | 0.000499 | 1068 | 0.00577 |
| 202 | 0.00488 | 491 | 7.83 | 780 | 0.0817 | 1069 | 0.00123 |
| 203 | 0.00239 | 492 | 1.27 | 781 | 0.00727 | 1070 | 0.000857 |
| 204 | 1.62 | 493 | 0.486 | 782 | 0.0247 | 1071 | 0.000473 |
| 205 | 0.483 | 494 | 1.22 | 783 | 0.0098 | 1072 | 0.00624 |
| 206 | 0.00131 | 495 | 0.127 | 784 | 0.00238 | 1073 | 0.00388 |
| 207 | 0.739 | 496 | 7.14 | 785 | 0.000839 | 1074 | 0.0144 |
| 208 | 0.0849 | 497 | 0.742 | 786 | 0.00751 | 1075 | 0.00762 |
| 209 | 0.693 | 498 | 0.0179 | 787 | 0.00675 | 1076 | 0.0057 |
| 210 | 0.398 | 499 | 0.00219 | 788 | 0.00544 | 1077 | 0.0691 |
| 211 | 0.95 | 500 | 0.0217 | 789 | 0.0694 | 1078 | 0.00761 |
| 212 | 0.0341 | 501 | 0.00596 | 790 | 0.0026 | 1079 | 0.0182 |
| 213 | 0.0397 | 502 | 0.0165 | 791 | 0.000898 | 1080 | 0.00341 |
| 214 | 0.289 | 503 | 0.00421 | 792 | 0.00957 | 1081 | 0.195 |
| 215 | 0.686 | 504 | 0.0154 | 793 | 0.00102 | 1082 | 0.00218 |
| 216 | 0.00659 | 505 | 0.0305 | 794 | 0.000883 | 1083 | 0.000920 |
| 217 | 0.00342 | 506 | 0.0180018 | 795 | 0.0062 | 1084 | 0.0148 |
| 218 | 0.0711 | 507 | 0.0032 | 796 | 0.00465 | 1085 | 0.0256 |
| 219 | 0.00559 | 508 | 0.0285902 | 797 | 0.00698 | 1086 | 0.00993 |
| 220 | 0.00573 | 509 | 0.00747 | 798 | 0.00963 | 1087 | 0.00168 |
| 221 | 0.00782 | 510 | 0.0121 | 799 | 0.00696 | 1088 | 0.0344 |
| 222 | 0.00408 | 511 | 0.00278 | 800 | 0.00621 | 1089 | 0.00827 |

TABLE 2-continued

| Example | Cell Titer-Glo-IC50 (M) | Example | Cell Titer-Glo-IC50 (M) | Example | Cell Titer-Glo-IC50 (M) | Example | Cell Titer-Glo-IC50 (M) |
|---|---|---|---|---|---|---|---|
| 223 | 0.00708 | 512 | 0.0179 | 801 | 0.0573 | 1090 | 0.00542 |
| 224 | 0.023 | 513 | 0.0011805 | 802 | 0.00583 | 1091 | 0.00419 |
| 225 | 0.00927 | 514 | 0.0308 | 803 | 0.0176 | 1092 | 0.0177 |
| 226 | 0.00726 | 515 | 0.0158 | 804 | 0.0497 | 1093 | 0.565 |
| 227 | 0.00628 | 516 | 0.021279 | 805 | 7.82 | 1094 | 0.0688 |
| 228 | 0.00856 | 517 | 0.0722 | 806 | 1.4 | 1095 | 0.00445 |
| 229 | 0.00106 | 518 | 0.0348 | 807 | 0.1 | 1096 | 0.00207 |
| 230 | 0.0072 | 519 | 0.0609 | 808 | 0.0011 | 1097 | 0.0647 |
| 231 | 0.0351 | 520 | 0.101 | 809 | 0.0332 | 1098 | 0.00955 |
| 232 | 0.00927 | 521 | 0.0935 | 810 | 0.327 | 1099 | 0.0156 |
| 233 | 0.00937 | 522 | 0.00673 | 811 | 0.0114 | 1100 | 0.0087 |
| 234 | 0.105 | 523 | 0.0171 | 812 | 0.0388 | 1101 | 0.00206 |
| 235 | 0.0555 | 524 | 0.00246 | 813 | 0.00221 | 1102 | 0.00177 |
| 236 | 0.0138 | 525 | 0.00677 | 814 | 0.0045 | 1103 | 0.00424 |
| 237 | 0.0372 | 526 | 0.0603 | 815 | 0.00589 | 1104 | 0.00696 |
| 238 | 0.00257 | 527 | 0.0598 | 816 | 0.00482 | 1105 | 0.0026 |
| 239 | 0.0177 | 528 | 0.024 | 817 | 0.00927 | 1106 | 0.0275 |
| 240 | 0.651 | 529 | 0.227 | 818 | 0.716 | 1107 | 0.00226 |
| 241 | 0.00848 | 530 | 0.0821 | 819 | 0.013 | 1108 | 0.0201 |
| 242 | 0.00756 | 531 | 0.0529 | 820 | 0.802 | 1109 | 0.00921 |
| 243 | 0.028 | 532 | 0.0927 | 821 | 0.192 | 1110 | 0.111 |
| 244 | 7.04 | 533 | 0.0174 | 822 | 0.0711 | 1111 | 0.062 |
| 245 | 5.5 | 534 | 0.00508 | 823 | 0.00462 | 1112 | 0.0164 |
| 246 | 0.00243 | 535 | 0.0285 | 824 | 0.0124 | 1113 | 0.0231 |
| 247 | 0.00134 | 536 | 0.00304 | 825 | 0.00106 | 1114 | 0.0218 |
| 248 | 0.00242 | 537 | 0.0431 | 826 | 0.00679 | 1115 | 0.0212 |
| 249 | 0.0665 | 538 | 0.00333 | 827 | 0.000625 | 1116 | 0.00619 |
| 250 | 0.000675 | 539 | 0.00347 | 828 | 0.00644 | 1117 | 0.0657 |
| 251 | 1.84 | 540 | 0.074 | 829 | 0.00177 | 1118 | 0.00418 |
| 252 | 0.00191 | 541 | 0.0645 | 830 | 0.000269 | 1119 | 0.00667 |
| 253 | 0.000702 | 542 | 0.00289 | 831 | 0.000886 | 1120 | 0.00237 |
| 254 | 0.000938 | 543 | 0.386 | 832 | 0.0101 | 1121 | 0.00842 |
| 255 | 4.29 | 544 | 0.647 | 833 | 0.07 | 1122 | 0.00996 |
| 256 | 0.00984 | 545 | 0.0287 | 834 | 0.0127 | 1123 | 0.00711 |
| 257 | 0.0152 | 546 | 2.45 | 835 | 0.00395 | 1124 | 0.000344 |
| 258 | 0.0325 | 547 | 0.0255558 | 836 | 0.0683 | 1125 | 0.00477 |
| 259 | 0.00254 | 548 | 0.0744613 | 837 | 0.00277 | 1126 | 0.00236 |
| 260 | 0.00806 | 549 | 0.009417 | 838 | 0.0027 | 1127 | 0.00299 |
| 261 | 0.0051 | 550 | 0.1741494 | 839 | 0.000607 | 1128 | 0.00605 |
| 262 | 0.00187 | 551 | 0.0550545 | 840 | 0.00275 | 1129 | 0.00805 |
| 263 | 0.00243 | 552 | 0.0425577 | 841 | 0.00613 | 1130 | 0.00296 |
| 264 | 0.00669 | 553 | 0.103 | 842 | 0.0714 | 1131 | 0.0344 |
| 265 | 0.00159 | 554 | 0.177 | 843 | 0.0172 | 1132 | 0.00896 |
| 266 | 0.606 | 555 | 0.0332 | 844 | 0.0148172 | 1133 | 0.001 |
| 267 | 0.665 | 556 | 0.00655 | 845 | 0.00389 | 1134 | 0.00551 |
| 268 | 5.54 | 557 | 0.0374 | 846 | 0.0744 | 1135 | 0.00423 |
| 269 | 0.0151 | 558 | 1.17 | 847 | 0.0936 | 1136 | 0.00302 |
| 270 | 0.973 | 559 | 0.0943 | 848 | 0.0292 | 1137 | 0.000277 |
| 271 | 0.00271 | 560 | 0.844 | 849 | 0.0636 | 1138 | 0.00385 |
| 272 | 0.0156 | 561 | 0.24 | 850 | 0.054 | 1139 | 0.00141 |
| 273 | 0.00235 | 562 | 0.0709 | 851 | 0.133 | 1140 | 0.00584 |
| 274 | 0.0104 | 563 | 5.14 | 852 | 0.00832 | 1141 | 0.0022 |
| 275 | 0.0239 | 564 | 0.211 | 853 | 0.00996 | 1142 | 0.0029 |
| 276 | 0.0381 | 565 | 0.891 | 854 | 0.000414 | 1143 | 0.0174 |
| 277 | 0.0832 | 566 | >10 | 855 | 0.111 | 1144 | 0.0096 |
| 278 | 0.0517 | 567 | 0.237 | 856 | 0.657 | 1145 | 0.00704 |
| 279 | 0.869 | 568 | 0.18 | 857 | 0.00155 | 1146 | 0.00188 |
| 280 | 0.013 | 569 | 0.226 | 858 | 0.00059 | 1147 | 0.00283 |
| 281 | 0.0248 | 570 | 0.00735 | 859 | 0.0104 | 1148 | 0.00272 |
| 282 | 0.0447 | 571 | 0.0229 | 860 | 0.00824 | 1149 | 0.00262 |
| 283 | 0.145 | 572 | 0.00666 | 861 | 0.000574 | 1150 | 0.0641 |
| 284 | 0.107 | 573 | 0.00372 | 862 | 0.000780 | 1151 | 0.00778 |
| 285 | 0.301 | 574 | 0.005201 | 863 | 0.000642 | 1152 | 0.00308 |
| 286 | 0.0194 | 575 | >10 | 864 | 0.0672 | 1153 | 0.00172 |
| 287 | 0.0241 | 576 | .000569 | 865 | 0.000861 | | |
| 288 | 0.00811 | 577 | 0.00215 | 866 | 0.000525 | | |
| 289 | 0.00933 | 578 | 4.6 | 867 | 0.0687 | | |

Compounds which inhibit NAMPT are useful for treating diseases in which activation of NF-KB is implicated. Such methods are useful in the treatment of a variety of diseases including inflammatory and tissue repair disorders; particularly rheumatoid arthritis, inflammatory bowel disease, asthma and COPD (chronic obstructive pulmonary disease), osteoarthritis, osteoporosis and fibrotic diseases; dermatosis, including psoriasis, atopic dermatitis and ultra-violet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukaemia, lymphoma or Hodgkin's disease, cachexia, inflammation associated with infection and certain viral infections, including Acquired Immune Deficiency Syndrome (AIDS), adult respiratory distress syndrome, and ataxia telengiectasia.

Involvement of NAMPT in the treatment of cancer is described in WO 97/48696. Involvement of NAMPT in immuno-suppression is described in WO 97/48397. Involvement of NAMPT for the treatment of diseases involving angiogenesis is described in WO 2003/80054. Involvement of NAMPT for the treatment of rheumatoid arthritis and septic shock is described in WO 2008/025857. Involvement of NAMPT for the prophlaxis and treatment of ischaemia is described in WO 2009/109610.

Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP\text{-}BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Schemes

Scheme 1

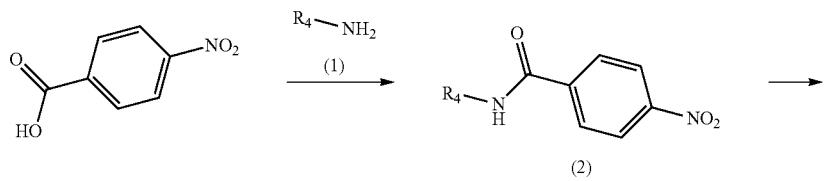

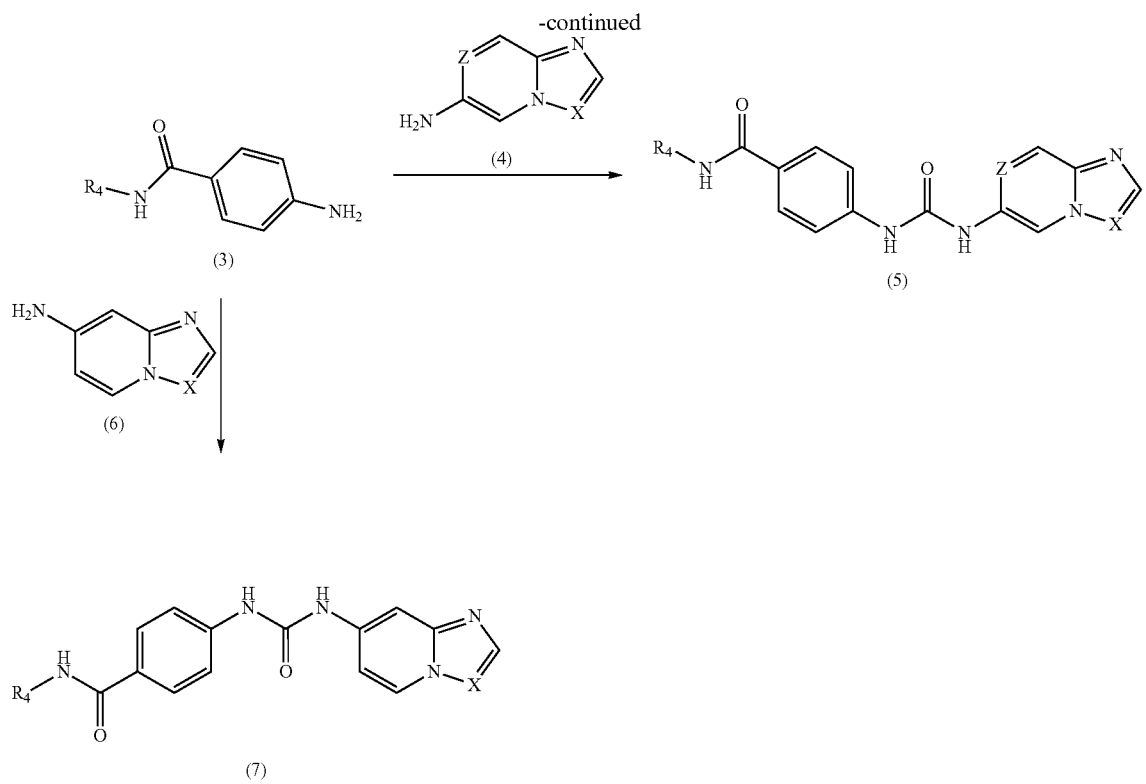

As shown in Scheme 1, compounds of formula (1), wherein $R^4$ is as described herein, can be reacted with 4-nitrobenzoic acid in the presence of a base such as but not limited to N-methylmorpholine, an ester activating agent such as but not limited to 1-hydroxybenzotriazole hydrate, and a carboxyl activating agent such as but not limited to N-(3-dimethylaminopropyl)-N'-ethylcarbodiimide hydrochloride, to provide compounds of formula (2). The reaction is typically performed at ambient temperature in a solvent such as but not limited to dimethylformamide. Compounds of formula (3) can be prepared by reacting compounds of formula (2) with hydrogen in the presence of palladium on carbon. The reaction is typically performed at ambient temperature in a solvent such as but not limited to methanol. Compounds of formula (3) can be reacted with compounds of formula (4) wherein X and Z are as described herein, to provide compounds of formula (5). The reaction is typically performed in the presence of bis(2,5-dioxopyrrolidin-1-yl) carbonate and a base such as but not limited to pyridine. The reaction is typically performed at ambient temperature in a solvent such as but not limited to N-methyl-2-pyrrolidinone.

Alternatively, Compounds of formula (3) can be reacted with compounds of formula (6) wherein X is as described herein, to provide compounds of formula (7). The reaction is typically performed in the presence of bis(2,5-dioxopyrrolidin-1-yl)carbonate and a base such as but not limited to pyridine. The reaction is typically performed at ambient temperature in a solvent such as but not limited to N-methyl-2-pyrrolidinone.

Scheme 2

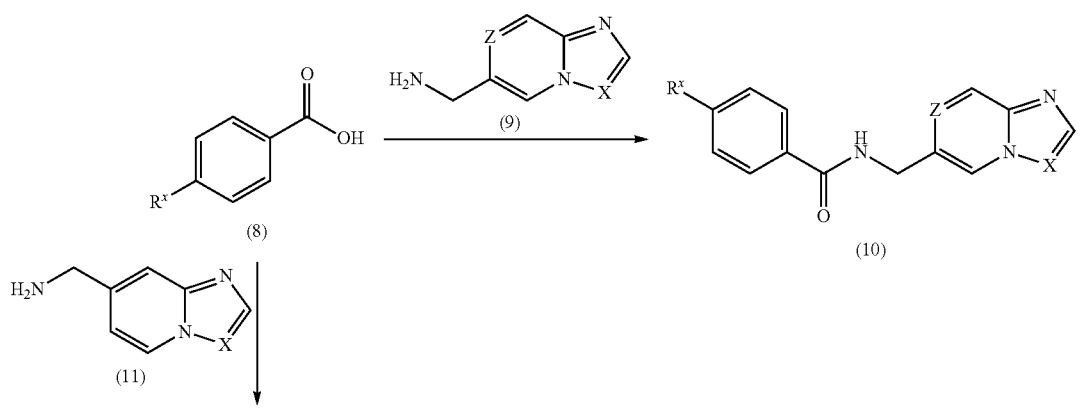

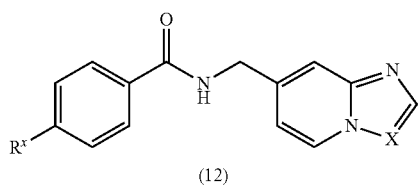

(12)

Compounds of formula (8), wherein $R^x$ is as described herein for substituents on the $R^3$ phenyl, can be reacted with compounds of formula (9), wherein X and Z are as described herein, to provide compounds of formula (10). The reaction is typically performed in the presence of a base such as but not limited to N-methylmorpholine, an ester activating agent such as but not limited to 1-hydroxybenzotriazole hydrate, and a carboxyl activating agent such as but not limited to N-(3-dimethylaminopropyl)-N'-ethylcarbodiimide hydrochloride. The reaction is typically performed at ambient temperature in a solvent such as but not limited to dimethylformamide.

Similarly, compounds of formula (8), wherein $R^x$ is as described herein for substituents on the $R^3$ phenyl, can be reacted with compounds of formula (11), wherein X is as described herein, to provide compounds of formula (12). The reaction is typically performed in the presence of a base such as but not limited to N-methylmorpholine, an ester activating agent such as but not limited to 1-hydroxybenzotriazole hydrate, and a carboxyl activating agent such as but not limited to N-(3-dimethylaminopropyl)-N'-ethylcarbodiimide hydrochloride. The reaction is typically performed at ambient temperature in a solvent such as but not limited to dimethylformamide.

As shown in Scheme 3, compounds of formula (13), wherein $R^3$ is as described herein, can be reacted with compounds of formula (11), wherein X is as described herein, in the presence of bis(2,5-dioxopyrrolidin-1-yl)carbonate and a base such as but not limited to pyridine to provide compounds of formula (14). The reaction is typically performed at ambient temperature in a solvent such as but not limited to N-methyl-2-pyrrolidinone.

Alternatively, compounds of formula (13), wherein $R^3$ is as described herein, can be reacted with compounds of formula (9), wherein X and Z are as described herein, in the presence of bis(2,5-dioxopyrrolidin-1-yl)carbonate and a base such as but not limited to pyridine to provide compounds of formula (14). The reaction is typically performed at ambient temperature in a solvent such as but not limited to N-methyl-2-pyrrolidinone.

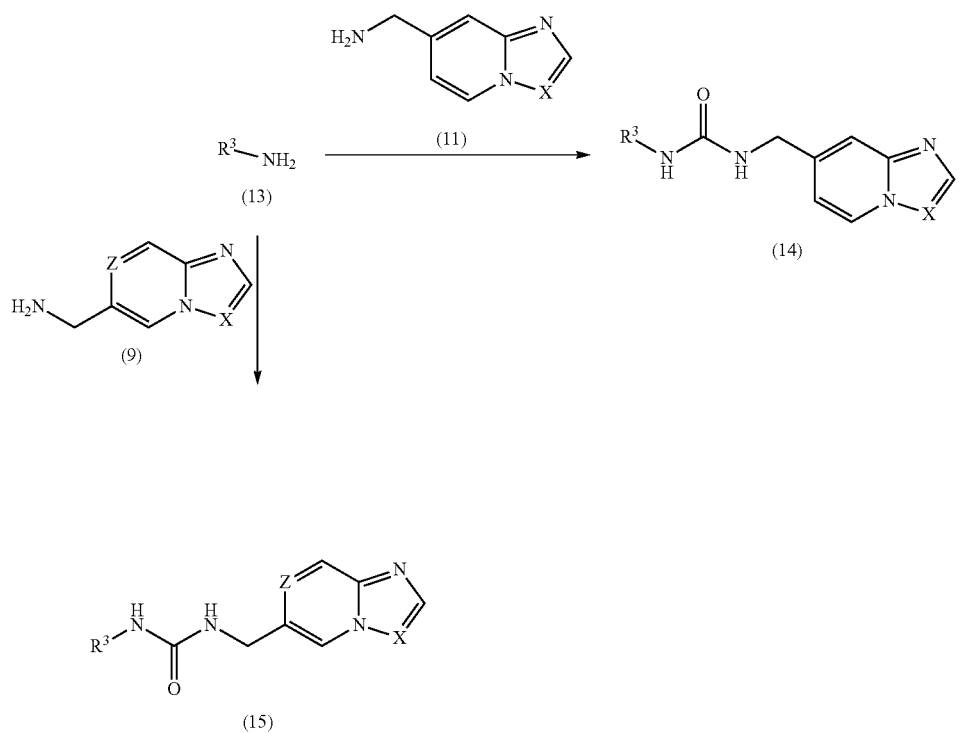

Scheme 4

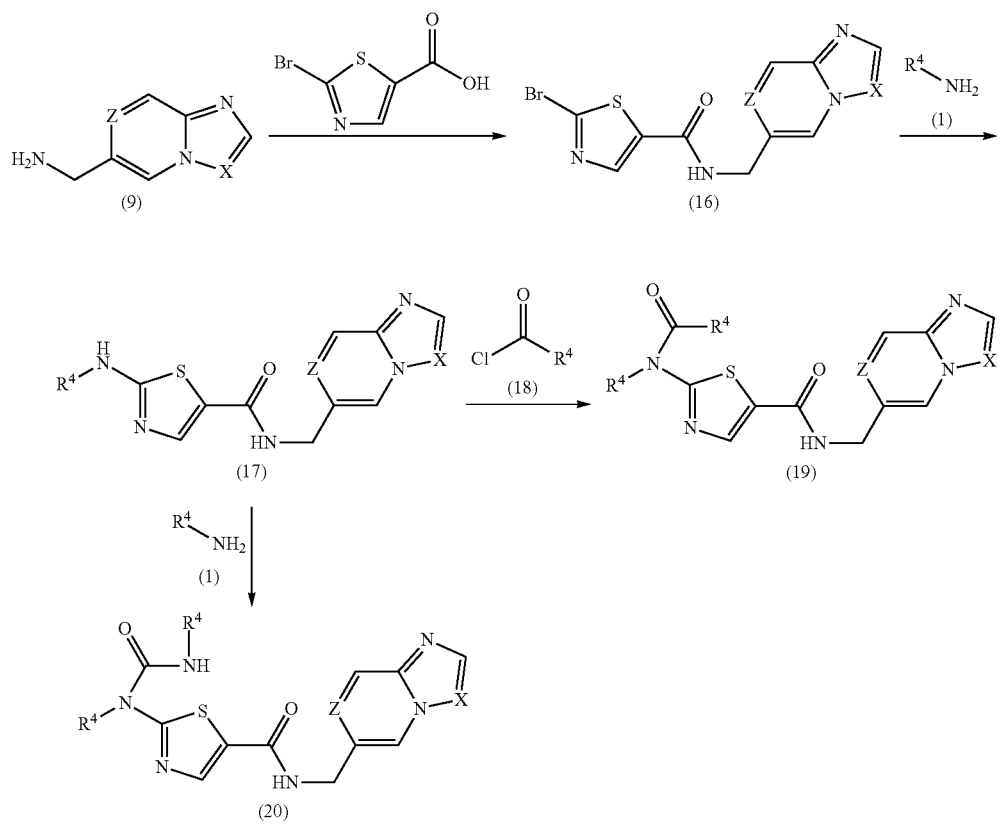

2-Bromo-5-thiazolecarboxylic acid can be reacted with compounds of formula (9), wherein X and Z are as described herein, in the presence of a base such as but not limited to N-methylmorpholine, an ester activating agent such as but not limited to 1-hydroxybenzotriazole hydrate, and a carboxyl activating agent such as but not limited to N-(3-dimethylaminopropyl)-N'-ethylcarbodiimide hydrochloride, to provide compounds of formula (16). The reaction is typically performed at ambient temperature in a solvent such as but not limited to dimethylformamide. Compounds of formula (16) can be reacted with amines of formula (1) wherein $R^4$ is as described herein, to provide compounds of formula (17). The reaction is typically performed at an elevated temperature in a solvent such as but not limited to acetonitrile and may be performed in a microwave oven. Compounds of formula (19), which are representative of the compounds of this invention, can be prepared by reacting compounds of formula (17) with compounds of formula (18), wherein $R^4$ is as described herein, in the presence of a base such as but not limited to diisopropylethylamine. The reaction is typically performed at ambient temperature in a solvent such as but not limited to tetrahydrofuran. Alternatively, compounds of formula (17) can be reacted with amines of formula (4), wherein $R^4$ is as described herein, to provide compounds of formula (20), which are representative of the compounds of Formula (I). The reaction is typically performed in the presence of bis(2,5-dioxopyrrolidin-1-yl)carbonate and a base such as but not limited to pyridine. The reaction is typically performed at ambient temperature in a solvent such as but not limited to N-methyl-2-pyrrolidinone.

Scheme 5

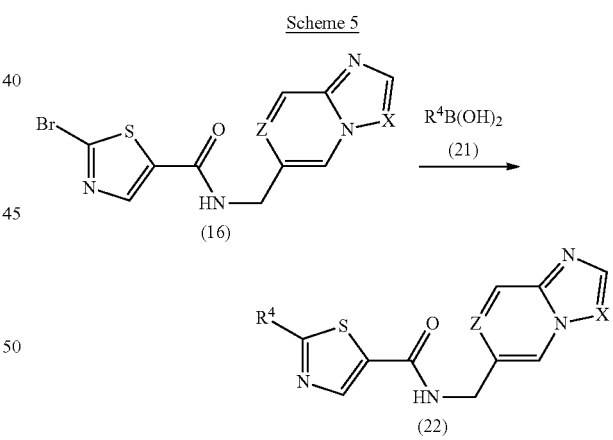

As shown in Scheme 5, compounds of formula (16), which can be prepared as described in Scheme 4 and wherein X and Z are as described herein, can be reacted with suitable boronic acids (or the equivalent boronic ester) of formula (21) wherein $R^4$ is as described herein, under Suzuki coupling conditions known to those skilled in the art and widely available in the literature, to provide compounds of formula (22), which are representative of the compounds of Formula (I).

EXAMPLES

The following examples are presented to provide what is believed to be the most useful and readily understood descrip-

Example 1

4-[(imidazo[1,2-a]pyridin-6-ylcarbamoyl)amino]-N-(3-methylbutyl)benzamide

Example 1A

N-isopentyl-4-nitrobenzamide

4-Nitrobenzoic acid (0.8 g, 4.79 mmol) and 1-hydroxybenzotriazole hydrate (1.1 g, 7.18 mmol) in dimethylformamide (20 mL) was treated with N-methylmorpholine (1.8 mL, 16.75 mmol) and 3-methylbutan-1-amine (0.724 mL, 6.22 mmol) followed by 1-(3-dimethylaminopropyl)-3-ethylcarbodiimide hydrochloride (1.38 g, 7.18 mmol). The reaction mixture was stirred at room temperature for 17 hours. Water was added and the resulting suspension was stirred for 2 hours. The suspension was filtered and the solid collected was washed with water and dried to provide the title compound.

Example 1B

4-amino-N-isopentylbenzamide

N-Isopentyl-4-nitrobenzamide (1 g, 4.23 mmol) and methanol (40 ml) were added to palladium on carbon (0.200 g, 1.879 mmol) in a 250 mL SS pressure bottle and the mixture was stirred for 6 hours with hydrogen at 30 psi and room temperature. The mixture was filtered through a nylon membrane and concentrated to provide the title compound.

Example 1C

4-[(imidazo[1,2-a]pyridin-6-ylcarbamoyl)amino]-N-(3-methylbutyl)benzamide

A solution of 4-amino-N-isopentylbenzamide (0.05 g, 0.242 mmol), bis(2,5-dioxopyrrolidin-1-yl)carbonate (0.078 g, 0.303 mmol) and pyridine (0.020 ml, 0.242 mmol) in N-methyl-2-pyrrolidinone (0.6 mL) was stirred at room temperature for 1 hour. Diisopropylethylamine (0.127 ml, 0.727 mmol) was added followed by addition of a solution of imidazo[1,2-a]pyridin-6-amine (0.041 g, 0.279 mmol) in N-methyl-2-pyrrolidinone (0.6 mL) dropwise by syringe over 5 minutes. The reaction mixture was stirred for 16 hours at room temperature and the mixture was treated with water. The resulting suspension was stirred for 5 minutes and filtered with water washes. Vacuum drying and reverse phase chromatography provided the title compound. $^1$H NMR (300 MHz, DMSO-$d_6$) δ ppm 9.04-8.93 (m, 2H), 8.76 (bs, 1H), 8.24 (t, J=5.5 Hz, 1H), 7.96 (s, 1H), 7.79 (d, J=8.7 Hz, 2H), 7.58-7.45 (m, 4H), 7.09 (dd, J=9.6, 2.0 Hz, 1H), 3.33-3.20 (m, 2H), 1.68-1.52 (m, 1H), 1.46-1.35 (m, 2H), 0.90 (d, J=6.6 Hz, 6H); MS (ESI(+)) m/e 366 (M+H)$^+$.

Example 2

4-[(imidazo[1,2-a]pyridin-7-ylcarbamoyl)amino]-N-(3-methylbutyl)benzamide

The title compound was prepared as described in Example 1C, substituting imidazo[1,2-a]pyridin-7-amine for imidazo[1,2-a]pyridin-6-amine $^1$H NMR (300 MHz, DMSO-$d_6$) δ ppm 9.04 (m, 2H), 8.42 (dd, J=7.5, 0.6 Hz, 1H), 8.25 (t, J=5.5 Hz, 1H), 7.78 (m, 4H), 7.53 (d, J=8.7 Hz, 2H), 7.42 (d, J=1.2 Hz, 1H), 6.90 (dd, J=7.3, 2.1 Hz, 1H), 3.30-3.21 (m, 2H), 1.69-1.54 (m, 1H), 1.47-2.36 (m, 2H), 0.91 (d, J=6.5 Hz, 6H); MS (ESI(+)) m/e 366 (M+H)$^+$.

Example 3

2-cyclopentyl-N-{4-[(imidazo[1,2-a]pyridin-6-ylcarbamoyl)amino]phenyl}acetamide

Example 3A

1-(imidazo[1,2-a]pyridin-6-yl)-3-(4-nitrophenyl)urea

A 0° C. solution of imidazo[1,2-a]pyridin-6-amine (1 g, 7.21 mmol), N-ethyl-N-isopropylpropan-2-amine (2.51 ml, 14.42 mmol) and dimethylformamide (21.85 ml) was treated with a solution of 1-isocyanato-4-nitrobenzene (1.313 g, 8.00 mmol) in tetrahydrofuran (10.92 ml) which was added dropwise via syringe over 5 minutes. The reaction mixture was allowed to stir at room temperature for 6 hours, and water was added. The suspension was filtered with water washes to give the title compound after vacuum drying.

Example 3B

1-(4-aminophenyl)-3-(imidazo[1,2-a]pyridin-6-yl)urea

The title compound was prepared as described in Example 1B, substituting 1-(imidazo[1,2-a]pyridin-6-yl)-3-(4-nitrophenyl)urea for N-isopentyl-4-nitrobenzamide.

Example 3C

2-cyclopentyl-N-{4-[(imidazo[1,2-a]pyridin-6-ylcarbamoyl)amino]phenyl}acetamide The title compound was prepared as described in Example 1A, substituting 1-(4-aminophenyl)-3-(imidazo[1,2-a]pyridin-6-yl)urea for 3-methylbutan-1-amine and 2-cyclopentylacetic acid for 4-nitrobenzoic acid. $^1$H NMR (300 MHz, DMSO-$d_6$, Temp=90° C.) δ ppm 9.73 (bs, 1H), 8.96 (m, 1H), 8.66 (s, 1H), 8.62 (s, 1H), 7.95 (s, 1H), 7.57-7.44 (m, 4H), 7.37 (d, J=8.9 Hz, 2H), 7.07 (dd, J=9.6, 2.0 Hz, 1H), 2.29-2.15 (m, 3H), 1.82-1.68 (m, 2H), 1.68-1.45 (m, 4H), 1.29-1.07 (m, 2H); MS (ESI(+)) m/e 378 (M+H)$^+$.

TABLE 1

The following Examples were prepared essentially as described in Example 3, substituting the appropriate carboxylic acid in Example 1C. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
| 26 | N-{4-[(imidazo[1,2-a]pyridin-6-ylcarbamoyl)amino]phenyl}-2-(tetrahydrofuran-3-yl)acetamide | $^1$H NMR (400 MHz, DMSO-$d_6$, Temp = 90° C.) δ ppm 9.49 (bs, 1H), 8.84 (m, 1H), 8.44 (m, 2H), 7.85 (s, 1H), 7.52-7.44 (m, 4H), 7.39-7.29 (m, 2H), 7.09 (dd, J = 9.6, 2.1 Hz, 1H), 3.83-3.72 (m, 2H), 3.68-3.62 (m, 1H), 3.38-3.33 (m, 1H), 2.57 (m, 1H), 2.40-2.33 (m, 2H), 2.08-1.95 (m, 1H), 1.62-1.52 (m, 1H) | (ESI(+)) m/e 380 (M + H)$^+$ |
| 27 | N-{4-[(imidazo[1,2-a]pyridin-6-ylcarbamoyl)amino]phenyl}acetamide | $^1$H NMR (300 MHz, DMSO-$d_6$) δ ppm δ 9.81 (s, 1H), 8.98-8.93 (m, 1H), 8.70-8.62 (m, 2H), 7.96-7.93 (m, 1H), 7.53-7.45 (m, 4H), 7.41-7.33 (m, 2H), 7.07 (dd, J = 9.5, 2.0 Hz, 1H), 2.01 (s, 3H) | (ESI(+)) m/e 310 (M + H)$^+$ |
| 39 | 2-ethoxy-N-{4-[(imidazo[1,2-a]pyridin-6-ylcarbamoyl)amino]phenyl}acetamide | $^1$H NMR (400 MHz, DMSO-$d_6$, Temp = 90° C.) δ ppm 9.57 (s, 1H), 8.96 (m, 1H), 8.69 (s, 1H), 8.64 (s, 1H), 7.95 (s, 1H), 7.60-7.48 (m, 4H), 7.42-7.37 (m, 2H), 7.07 (dd, J = 9.6, 2.0 Hz, 1H), 4.00 (s, 2H), 3.56 (q, J = 7.0 Hz, 2H), 1.19 (t, J = 7.0 Hz, 3H) | (ESI(+)) m/e 354 (M + H)$^+$ |
| 40 | N-{4-[(imidazo[1,2-a]pyridin-6-ylcarbamoyl)amino]phenyl}-2-(tetrahydro-2H-pyran-4-yl)acetamide | $^1$H NMR (400 MHz, DMSO-$d_6$,) δ ppm 9.79 (s, 1H), 8.98-8.93 (m, 1H), 8.67 (s, 1H), 8.63 (s, 1H), 7.97-7.93 (m, 1H), 7.54-7.46 (m, 4H), 7.40-7.34 (m, 2H), 7.07 (dd, J = 9.5, 2.0 Hz, 1H), 3.87-3.79 (m, 2H), 3.34-3.26 (m, 2H), 2.25-2.19 (m, 2H), 2.07-1.91 (m, 1H), 1.63-1.54 (m, 2H), 1.31-1.17 (m, 2H) | (ESI(+)) m/e 394 (M + H)$^+$ |
| 41 | N-{4-[(imidazo[1,2-a]pyridin-6-ylcarbamoyl)amino]phenyl}-2-(morpholin-4-yl)acetamide | $^1$H NMR (400 MHz, DMSO-$d_6$, Temp = 90° C.) δ ppm 9.35 (bs, 1H), 8.85 (m, 1H), 8.50-8.30 (M, 2H), 7.86 (s, 1H), 7.55-7.43 (m, 4H), 7.41-7.34 (m, 2H), 7.09 (dd, J = 9.5, 2.0 Hz, 1H), 3.68-3.60 (m, 4H), 3.09 (s, 2H), 2.56-2.51 (m, 4H) | (ESI(+)) m/e 395 (M + H)$^+$ |
| 42 | N-{4-[(imidazo[1,2-a]pyridin-6-ylcarbamoyl)amino]phenyl}-2-(2-methoxyethoxy)acetamide | | (ESI(+)) m/e 384 (M + H)$^+$ |
| 43 | N-{4-[(imidazo[1,2-a]pyridin-6-ylcarbamoyl)amino]phenyl}-3-methoxy-2-methylpropanamide | | (ESI(+)) m/e 368 (M + H)$^+$ |
| 44 | N-{4-[(imidazo[1,2-a]pyridin-6-ylcarbamoyl)amino]phenyl}butanamide | | (ESI(+)) m/e 338 (M + H)$^+$ |
| 45 | 4,4,4-trifluoro-N-{4-[(imidazo[1,2-a]pyridin-6-ylcarbamoyl)amino]phenyl}butanamide | | (ESI(+)) m/e 392 (M + H)$^+$ |
| 46 | -{4-[(imidazo[1,2-a]pyridin-6-ylcarbamoyl)amino]phenyl}tetrahydro-2H-pyran-4-carboxamide | | (ESI(+)) m/e 380 (M + H)$^+$ |
| 47 | N-{4-[(imidazo[1,2-a]pyridin-6-ylcarbamoyl)amino]phenyl}-4-methylpentanamide | | (ESI(+)) m/e 366 (M + H)$^+$ |
| 48 | N-{4-[(imidazo[1,2-a]pyridin-6-ylcarbamoyl)amino]phenyl}-1-methylpiperidine-4-carboxamide | | (ESI(+)) m/e 393 (M + H)$^+$ |

TABLE 1-continued

The following Examples were prepared essentially as described in Example 3, substituting the appropriate carboxylic acid in Example 1C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 49 | N-{4-[(imidazo[1,2-a]pyridin-6-ylcarbamoyl)amino]phenyl}tetrahydro-2H-thiopyran-4-carboxamide 1,1-dioxide | | (ESI(+)) m/e 428 (M + H)$^+$ |
| 50 | N-{4-[(imidazo[1,2-a]pyridin-6-ylcarbamoyl)amino]phenyl}-1,4-dioxane-2-carboxamide | | (ESI(+)) m/e 382 (M + H)$^+$ |

Example 4

4-[(imidazo[1,2-a]pyridin-6-ylcarbamoyl)amino]-N-(2-phenylethyl)benzamide

Example 4A methyl 4-(3-imidazo[1,2-a]pyridin-6-ylureido)benzoate

The title compound was prepared as described in Example 3A, substituting methyl 4-isocyanatobenzoate for 1-isocyanato-4-nitrobenzene.

Example 4B

4-(3-imidazo[1,2-a]pyridin-6-ylureido)benzoic acid

A solution of methyl 4-(3-imidazo[1,2-a]pyridin-6-ylureido)benzoate (2.1 g, 6.77 mmol) in tetrahydrofuran (18.05 ml) and methanol (9.02 ml) was treated with 2N lithium hydroxide (13.53 ml, 27.1 mmol) and the reaction was allowed to stir at room temperature for 16 hours. The mixture was concentrated, redissolved in 225 mL water and acidified to ~pH 4 with 3N hydrochloric acid. The suspension was filtered with water washes to give the title compound after vacuum drying.

Example 4C

4-[(imidazo[1,2-a]pyridin-6-ylcarbamoyl)amino]-N-(2-phenylethyl)benzamide

The title compound was prepared as described in Example 1A, substituting 2-phenylethanamine for 3-methylbutan-1-amine and 4-(3-imidazo[1,2-a]pyridin-6-ylureido)benzoic acid for 4-nitrobenzoic acid. $^1$H NMR (500 MHz, DMSO-d$_6$/D$_2$O, Temp=90° C.) δ ppm 9.33 (dd, J=1.9, 0.8 Hz, 1H), 8.32 (d, J=1.8 Hz, 1H), 8.05 (d, J=2.0 Hz, 1H), 7.90 (d, J=9.7 Hz, 1H), 7.85-7.74 (m, 3H), 7.61-7.51 (m, 2H), 7.35-7.20 (m, 5H), 3.49 (dd, J=8.1, 6.9 Hz, 2H), 2.94-2.79 (m, 2H); MS (ESI(+)) m/e 400 (M+H)$^+$.

TABLE 2

The following Examples were prepared essentially as described in Example 4, substituting the appropriate amine in Example 4C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 5 | 4-[(imidazo[1,2-a]pyridin-6-ylcarbamoyl)amino]-N-[2-(morpholin-4-yl)ethyl]benzamide | $^1$H NMR (500 MHz, DMSO-d$_6$/D$_2$O, Temp = 90° C.) δ ppm 9.37 (dd, J = 2.0, 0.9 Hz, 1H), 8.36 (d, J = 2.1 Hz, 1H), 8.10 (d, J = 2.1 Hz, 1H), 7.94 (d, J = 9.6 Hz, 1H), 7.88-7.78 (m, 3H), 7.71-7.57 (m, 2H), 4.02 (d, J = 11.3 Hz, 2H), 3.66 (dd, J = 16.1, 10.0 Hz, 4H), 3.56 (d, J = 11.3 Hz, 2H), 3.33 (t, J = 6.1 Hz, 2H), 3.17 (d, J = 13.5 Hz, 2H), 2.70 (s, 2H) | (ESI(+)) m/e 409 (M + H)$^+$ |
| 6 | N-(1-hydroxy-2-methylpropan-2-yl)-4-[(imidazo[1,2-a]pyridin-6-ylcarbamoyl)amino]benzamide | $^1$H NMR (500 MHz, DMSO-d$_6$/D$_2$O, Temp = 90° C.) δ ppm 9.36 (t, J = 6.6 Hz, 1H), 8.34 (d, J = 1.9 Hz, 1H), 8.09 (dd, J = 10.9, 5.4 Hz, 1H), 7.90 (t, J = 10.7 Hz, 1H), 7.85-7.73 (m, 3H), 7.56 (dd, J = 12.5, 5.6 Hz, 2H), 3.51 (s, 2H), 1.49-1.23 (m, 6H) | (ESI(+)) m/e 368 (M + H)$^+$ |
| 7 | N-benzyl-4-[(imidazo[1,2-a]pyridin-6-ylcarbamoyl)amino]benzamide | $^1$H NMR (500 MHz, DMSO-d$_6$/D$_2$O, Temp = 90° C.) δ ppm 9.38-9.29 (m, 1H), 8.33 (d, J = 2.0 Hz, 1H), 8.07 (d, J = 2.0 Hz, 1H), 7.96-7.85 (m, 3H), 7.77 (td, J = 9.4, 1.5 Hz, 1H), 7.66-7.51 (m, 2H), 7.38-7.31 (m, 4H), 7.32-7.19 (m, 1H), 4.48 (s, 2H) | (ESI(+)) m/e 386 (M + H)$^+$ |

TABLE 2-continued

The following Examples were prepared essentially as described in Example 4, substituting the appropriate amine in Example 4C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 8 | N-(cyclopentylmethyl)-4-[(imidazo[1,2-a]pyridin-6-ylcarbamoyl)amino]benzamide | $^1$H NMR (500 MHz, DMSO-$d_6$/D$_2$O, Temp = 90° C.) δ ppm 9.41-9.31 (m, 1H), 8.34 (d, J = 2.0 Hz, 1H), 8.07 (d, J = 2.0 Hz, 1H), 7.91 (d, J = 8.9 Hz, 1H), 7.86-7.73 (m, 3H), 7.63-7.51 (m, 2H), 3.19 (d, J = 7.4 Hz, 2H), 2.24-2.01 (m, 1H), 1.68 (dt, J = 11.6, 7.2 Hz, 2H), 1.64-1.57 (m, 2H), 1.57-1.42 (m, 2H), 1.37-1.14 (m, 2H) | (ESI(+)) m/e 378 (M + H)$^+$ |
| 9 | 4-[(imidazo[1,2-a]pyridin-6-ylcarbamoyl)amino]-N-[3-(piperidin-1-yl)propyl]benzamide | $^1$H NMR (500 MHz, DMSO-$d_6$/D$_2$O, Temp = 90° C.) δ ppm 9.36 (d, J = 1.4 Hz, 1H), 8.35 (d, J = 2.0 Hz, 1H), 8.10 (d, J = 2.1 Hz, 1H), 7.94 (d, J = 9.7 Hz, 1H), 7.88-7.80 (m, 3H), 7.66-7.53 (m, 2H), 3.44 (d, J = 12.2 Hz, 2H), 3.34 (t, J = 6.6 Hz, 2H), 3.12-3.02 (m, 2H), 2.97-2.85 (m, 2H), 2.02-1.81 (m, 4H), 1.81-1.58 (m, 4H), 1.51-1.31 (m, 1H) | (ESI(+)) m/e 421 (M + H)$^+$ |
| 10 | 4-[(imidazo[1,2-a]pyridin-6-ylcarbamoyl)amino]-N-(2-phenoxyethyl)benzamide | $^1$H NMR (500 MHz, DMSO-$d_6$/D$_2$O, Temp = 90° C.) δ ppm 9.36 (dd, J = 6.3, 5.4 Hz, 1H), 8.35 (d, J = 2.1 Hz, 1H), 8.09 (d, J = 2.0 Hz, 1H), 7.92 (d, J = 9.8 Hz, 1H), 7.89-7.80 (m, 3H), 7.63-7.55 (m, 2H), 7.30 (dd, J = 8.4, 7.4 Hz, 2H), 6.95 (dd, J = 11.9, 7.8 Hz, 3H), 4.12 (t, J = 5.8 Hz, 2H), 3.64 (t, J = 5.8 Hz, 2H) | (ESI(+)) m/e 411 (M + H)$^+$ |
| 11 | 4-[(imidazo[1,2-a]pyridin-6-ylcarbamoyl)amino]-N-[2-(pyrrolidin-1-yl)ethyl]benzamide | $^1$H NMR (500 MHz, DMSO-$d_6$/D$_2$O, Temp = 90° C.) δ ppm 9.34 (s, 1H), 8.34 (d, J = 2.0 Hz, 1H), 8.09 (d, J = 2.0 Hz, 1H), 7.92 (d, J = 9.1 Hz, 1H), 7.88-7.78 (m, 3H), 7.59 (dd, J = 16.4, 8.7 Hz, 2H), 3.59 (dd, J = 15.8, 9.8 Hz, 4H), 3.33 (t, J = 6.0 Hz, 2H), 3.07 (d, J = 11.0 Hz, 2H), 2.05 (s, 2H), 1.97-1.74 (m, 2H) | (ESI(+)) m/e 393 (M + H)$^+$ |
| 12 | -[(imidazo[1,2-a]pyridin-6-ylcarbamoyl)amino]-N-[2-(propan-2-yloxy)ethyl]benzamide | $^1$H NMR (500 MHz, DMSO-$d_6$/D$_2$O, Temp = 90° C.) δ ppm 9.35 (d, J = 1.3 Hz, 1H), 8.34 (d, J = 2.0 Hz, 1H), 8.08 (d, J = 2.0 Hz, 1H), 7.92 (d, J = 9.7 Hz, 1H), 7.88-7.77 (m, 3H), 7.63-7.52 (m, 2H), 3.64-3.55 (m, 1H), 3.51 (dd, J = 20.1, 13.7 Hz, 2H), 3.39 (t, J = 6.2 Hz, 2H), 1.09 (d, J = 6.1 Hz, 6H) | (ESI(+)) m/e 382 (M + H)$^+$ |
| 13 | N-(2-hydroxy-2-methylpropyl)-4-[(imidazo[1,2-a]pyridin-6-ylcarbamoyl)amino]benzamide | $^1$H NMR (500 MHz, DMSO-$d_6$/D$_2$O, Temp = 90° C.) δ ppm 9.37-9.31 (m, 1H), 8.33 (d, J = 1.9 Hz, 1H), 8.06 (d, J = 2.0 Hz, 1H), 7.96-7.88 (m, 1H), 7.88-7.81 (m, 2H), 7.76 (dd, J = 9.6, 1.9 Hz, 1H), 7.65-7.53 (m, 2H), 3.27 (s, 2H), 1.15 (d, J = 27.1 Hz, 6H) | (ESI(+)) m/e 368 (M + H)$^+$ |
| 14 | N-[2-hydroxy-1-(4-methoxyphenyl)ethyl]-4-[(imidazo[1,2-a]pyridin-6-ylcarbamoyl)amino]benzamide | $^1$H NMR (500 MHz, DMSO-$d_6$/D$_2$O, Temp = 90° C.) δ ppm 9.40-9.32 (m, 1H), 8.34 (d, J = 2.0 Hz, 1H), 8.08 (d, J = 2.1 Hz, 1H), 7.95-7.86 (m, 3H), 7.81-7.75 (m, 1H), 7.61-7.55 (m, 2H), 7.39-7.26 (m, 2H), 6.92-6.86 (m, 2H), 5.09-4.96 (m, 1H), 3.72-3.67 (m, 5H), 3.66-3.60 (m, 1H) | (ESI(+)) m/e 446 (M + H)$^+$ |
| 15 | 4-[(imidazo[1,2-a]pyridin-6-ylcarbamoyl)amino]-N-[2-(2-oxopyrrolidin-1-yl)ethyl]benzamide | $^1$H NMR (500 MHz, DMSO-$d_6$/D$_2$O, Temp = 90° C.) δ ppm 9.41-9.33 (m, 1H), 8.35 (d, J = 2.0 Hz, 1H), 8.09 (d, J = 2.1 Hz, 1H), 7.92 (d, J = 9.7 Hz, 1H), 7.82-7.72 (m, 3H), 7.63-7.51 (m, 2H), 3.50-3.30 (m, 6H), 2.20 (t, J = 8.1 Hz, 2H), 1.96-1.86 (m, 2H) | (ESI(+)) m/e 407 (M + H)$^+$ |
| 16 | 4-[(imidazo[1,2-a]pyridin-6-ylcarbamoyl)amino]-N-(tetrahydrofuran-2-ylmethyl)benzamide | NMR (500 MHz, DMSO-$d_6$/D$_2$O, Temp = 90° C.) δ ppm 9.39-9.29 (m, 1H), 8.34 (d, J = 2.0 Hz, 1H), 8.08 (d, J = 2.0 Hz, 1H), 7.92 (d, J = 9.5 Hz, 1H), 7.86-7.77 (m, 3H), 7.63-7.53 (m, 2H), 3.99 (p, J = 6.3 Hz, 1H), 3.64 (dd, J = 14.3, 7.5 Hz, 2H), 3.42-3.24 (m, 2H), 2.03-1.87 (m, 1H), 1.89-1.75 (m, 2H), 1.66-1.52 (m, 1H) | (ESI(+)) m/e 380 (M + H)$^+$ |
| 17 | 4-[(imidazo[1,2-a]pyridin-6- | $^1$H NMR (500 MHz, DMSO-$d_6$/D$_2$O, Temp = 90° C.) δ ppm 9.34 (d, J = 1.3 Hz, | (ESI(+)) m/e |

TABLE 2-continued

The following Examples were prepared essentially as described in Example 4, substituting the appropriate amine in Example 4C. Some products were purified by flash chromatography while others were purified by reverse-phase HPLC. Accordingly, some Examples were isolated as trifluoroacetic acid salts.

| Ex | Name | $^1$H NMR | MS |
|----|------|-----------|-----|
| | ylcarbamoyl)amino]-N-propylbenzamide | 1H), 8.34 (d, J = 2.0 Hz, 1H), 8.07 (d, J = 2.0 Hz, 1H), 7.91 (d, J = 9.6 Hz, 1H), 7.87-7.73 (m, 3H), 7.64-7.50 (m, 2H), 3.22 (t, J = 7.1 Hz, 2H), 1.61-1.45 (m, 2H), 0.89 (t, J = 7.4 Hz, 3H) | 338 (M + H)$^+$ |
| 18 | 4-[(imidazo[1,2-a]pyridin-6-ylcarbamoyl)amino]-N-[3-(morpholin-4-yl)propyl]benzamide | $^1$H NMR (500 MHz, DMSO-d$_6$/D$_2$O, Temp = 90° C.) δ ppm 9.35 (d, J = 1.2 Hz, 1H), 8.35 (d, J = 2.1 Hz, 1H), 8.10 (d, J = 2.1 Hz, 1H), 7.93 (d, J = 9.7 Hz, 1H), 7.85-7.78 (m, 3H), 7.65-7.56 (m, 2H), 4.07-3.96 (m, 2H), 3.66 (t, J = 12.1 Hz, 2H), 3.44 (d, J = 12.4 Hz, 2H), 3.35 (t, J = 6.6 Hz, 2H), 3.21-3.12 (m, 2H), 3.07 (d, J = 9.4 Hz, 2H), 2.03-1.83 (m, 2H) | (ESI(+)) m/e 423 (M + H)$^+$ |
| 19 | 4-[(imidazo[1,2-a]pyridin-6-ylcarbamoyl)amino]-N-phenylbenzamide | $^1$H NMR (500 MHz, DMSO-d$_6$/D$_2$O, Temp = 90° C.) δ ppm 9.30 (s, 1H), 8.29 (d, J = 1.6 Hz, 1H), 8.02-7.92 (m, 3H), 7.87 (d, J = 9.6 Hz, 1H), 7.79-7.66 (m, 3H), 7.65-7.58 (m, 2H), 7.42-7.33 (m, 2H), 7.20-7.05 (m, 1H) | (ESI(+)) m/e 372 (M + H)$^+$ |
| 20 | 4-[(imidazo[1,2-a]pyridin-6-ylcarbamoyl)amino]-N-(2-methylbutyl)benzamide | $^1$H NMR (500 MHz, DMSO-d$_6$/D$_2$O, Temp = 90° C.) δ ppm 9.39-9.29 (m, 1H), 8.43-8.29 (m, 1H), 8.09-8.03 (m, 1H), 7.96-7.89 (m, 1H), 7.87-7.75 (m, 3H), 7.66-7.50 (m, 2H), 3.25-3.16 (m, 1H), 3.14-3.03 (m, 1H), 1.70-1.58 (m, 1H), 1.48-1.36 (m, 1H), 1.23-1.05 (m, 1H), 0.97-0.79 (m, 6H) | (ESI(+)) m/e 366 (M + H)$^+$ |
| 21 | 4-[(imidazo[1,2-a]pyridin-6-ylcarbamoyl)amino]-N-[3-(2-oxopyrrolidin-1-yl)propyl]benzamide | $^1$H NMR (500 MHz, DMSO-d$_6$/D$_2$O, Temp = 90° C.) δ ppm 9.44-9.30 (m, 1H), 8.34 (t, J = 5.8 Hz, 1H), 8.13-8.05 (m, 1H), 7.92 (d, J = 9.7 Hz, 1H), 7.87-7.76 (m, 3H), 7.68-7.51 (m, 2H), 3.45-3.32 (m, 2H), 3.31-3.14 (m, 4H), 2.33-2.19 (m, 2H), 2.02-1.87 (m, 2H), 1.80-1.63 (m, 2H) | (ESI(+)) m/e 421 (M + H)$^+$ |
| 22 | 4-[(imidazo[1,2-a]pyridin-6-ylcarbamoyl)amino]-N-(tetrahydro-2H-pyran-4-ylmethyl)benzamide | $^1$H NMR (500 MHz, DMSO-d$_6$/D$_2$O, Temp = 90° C.) δ ppm 9.34 (d, J = 1.2 Hz, 1H), 8.33 (d, J = 2.0 Hz, 1H), 8.07 (d, J = 2.0 Hz, 1H), 7.91 (d, J = 9.6 Hz, 1H), 7.85-7.75 (m, 3H), 7.62-7.53 (m, 2H), 3.85 (dd, J = 11.4, 2.5 Hz, 2H), 3.27 (td, J = 11.7, 1.9 Hz, 2H), 3.16 (d, J = 6.9 Hz, 2H), 1.80 (tt, J = 11.3, 3.9 Hz, 1H), 1.59 (d, J = 11.0 Hz, 2H), 1.20 (qd, J = 12.0, 4.5 Hz, 2H) | (ESI(+)) m/e 394 (M + H)$^+$ |
| 23 | 4-[(imidazo[1,2-a]pyridin-6-ylcarbamoyl)amino]-N-(tetrahydro-2H-pyran-2-ylmethyl)benzamide | $^1$H NMR (500 MHz, DMSO-d$_6$/D$_2$O, Temp = 90° C.) δ ppm 9.43-9.28 (m, 1H), 8.34 (d, J = 2.0 Hz, 1H), 8.08 (d, J = 2.0 Hz, 1H), 7.92 (d, J = 9.7 Hz, 1H) 7.87-7.74 (m, 3H), 7.65-7.51 (m, 2H), 3.87 (dd, J = 10.6, 2.6 Hz, 1H), 3.48-3.41 (m, 1H), 3.33 (td, J = 11.1, 3.3 Hz, 1H), 3.29-3.21 (m, 2H), 1.78 (d, J = 5.1 Hz, 1H), 1.61 (d, J = 12.8 Hz, 1H), 1.54-1.38 (m, 3H), 1.18 (qd, J = 12.1, 3.7 Hz, 1H) | (ESI(+)) m/e 394 (M + H)$^+$ |
| 24 | N-[(1,1-dioxidotetrahydrothiophen-3-yl)methyl]-4-[(imidazo[1,2-a]pyridin-6-ylcarbamoyl)amino]benzamide | | (ESI(+)) m/e 428 (M + H)$^+$ |

Example 25 tert-butyl 4-{4-[(imidazo[1,2-a]pyridin-6-ylcarbamoyl)amino]phenyl}-3,6-dihydropyridine-1(2H)-carboxylate The title compound was prepared as described in Example 1C, substituting tert-butyl 4-(4-aminophenyl)-5,6-dihydropyridine-1(2H)-carboxylate for 4-amino-N-isopentylbenzamide. $^1$H NMR (300 MHz, DMSO-d$_6$) δ ppm 8.96 (m, 1H), 8.82-8.75 (m, 1H), 8.65 (m, 1H), 7.96 (s, 1H), 7.52-7.36 (m, 6H), 7.12-7.04 (m, 1H), 6.12-6.05 (m, 1H), 4.07-3.92 (m, 2H), 3.59-3.49 (m, 2H), 2.44 (m, 2H), 1.43 (s, 9H); MS (ESI(+)) m/e 434 (M+H)$^+$.

Example 28

1-imidazo[1,2-a]pyridin-6-yl-3-{4-[1-(tetrahydrofuran-3-ylacetyl)-1,2,3,6-tetrahydropyridin-4-yl]phenyl}urea

Example 28A

1-(imidazo[1,2-a]pyridin-6-yl)-3-(4-(1,2,3,6-tetrahydropyridin-4-yl)phenyl)urea A solution of tert-butyl 4-(4-(3-imidazo[1,2-a]pyridin-6-ylureido)phenyl)-5,6-dihydropyridine-1(2H)-carboxylate (0.57 g, 1.315 mmol) in dichloromethane (5 ml) was treated with trifluoroacetic acid (0.608 ml, 7.88 mmol) and the reaction mixture was stirred at room temperature for 4 hours. Concentration provided the title compound.

Example 28B

1-imidazo[1,2-a]pyridin-6-yl-3-{4-[1-(tetrahydrofuran-3-ylacetyl)-1,2,3,6-tetrahydropyridin-4-yl]phenyl}urea The title compound was prepared as described in Example 1A, substituting 1-(imidazo[1,2-a]pyridin-6-yl)-3-(4-(1,2,3,6-tetrahydropyridin-4-yl)phenyl)urea for 3-methylbutan-1-amine and 2-(tetrahydrofuran-3-yl)acetic acid for 4-nitrobenzoic acid. $^1$H NMR (300 MHz, DMSO-d$_6$) δ ppm 8.96 (m, 1H), 8.82 (bs, 1H), 8.70 (bs, 1H), 7.96 (s, 1H), 7.55-7.35 (m, 6H), 7.08 (dd, J=9.6, 2.0 Hz, 1H), 6.11 (m, 1H), 4.18-4.05 (m, 2H), 3.90-3.79 (m, 1H), 3.76-3.57 (m, 4H), 3.35-3.23 (m, 2H), 2.55-2.39 (m, 4H), 2.05-1.95 (m, 1H), 1.60-1.42 (m, 1H); MS (ESI(+)) m/e 446 (M+H)$^+$.

TABLE 3

The following Examples were prepared essentially as described in Example 28, substituting the appropriate carboxylic acid in Example 28B. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 29 | 1-{4-[1-(2-hydroxy-2-methylpropanoyl)-1,2,3,6-tetrahydropyridin-4-yl]phenyl}-3-imidazo[1,2-a]pyridin-6-ylurea | $^1$H NMR (300 MHz, DMSO-d$_6$,) δ ppm 9.01-8.93 (m, 1H), 8.84 (bs, 1H), 8.71 (bs, 1H), 7.95 (s, 1H), 7.53-7.35 (m, 6H), 7.12-7.04 (m, 1H), 6.13 (m, 1H), 5.43 (bs, 1H), 4.20-3.95 (m, 2H), 3.31 (m, 2H), 2.58-2.45 (m, 2H), 1.34 (s, 6H) | (ESI(+)) m/e 420 (M + H)$^+$ |
| 30 | 1-imidazo[1,2-a]pyridin-6-yl-3-{4-[1-(morpholin-4-ylacetyl)-1,2,3,6-tetrahydropyridin-4-yl]phenyl}urea | $^1$H NMR (300 MHz, methanol-d$_4$) δ ppm 9.01-8.81 (m, 1H), 7.82 (bs, 1H), 7.54-7.49 (m, 2H), 7.48-7.32 (m, 4H), 7.18 (dd, J = 9.6, 2.0 Hz, 1H), 6.09 (m, 1H), 4.31 (d, J = 2.8 Hz, 1H), 4.18 (d, J = 2.9 Hz, 1H), 3.89-3.76 (m, 2H), 3.71 (m, 4H), 3.38-3.25 (m, 2H), 2.65 (m, 1H), 2.61-2.49 (m, 5H) | (ESI(+)) m/e 461 (M + H)$^+$ |
| 31 | 1-{4-[1-(ethoxyacetyl)-1,2,3,6-tetrahydropyridin-4-yl]phenyl}-3-imidazo[1,2-a]pyridin-6-ylurea | $^1$H NMR (400 MHz, DMSO-d$_6$) δ ppm 8.85 (d, J = 1.9 Hz, 1H), 8.56 (s, 1H), 8.43 (s, 1H), 7.87 (s, 1H), 7.50-7.40 (m, 4H), 7.38-7.32 (m, 2H), 7.10 (dd, J = 9.4, 2.0 Hz, 1H), 6.09-6.04 (m, 1H), 4.13 (s, 2H), 4.13-4.08 (m, 2H), 3.66 (t, J = 5.7 Hz, 2H), 3.51 (q, J = 6.9 Hz, 2H), 2.50-2.45 (m, 2H), 1.14 (t, J = 6.9 Hz, 3H) | (ESI(+)) m/e 420 (M + H)$^+$ |
| 32 | 1-imidazo[1,2-a]pyridin-6-yl-3-(4-{1-[(2-methoxyethoxy)acetyl]-1,2,3,6-tetrahydropyridin-4-yl}phenyl)urea | $^1$H NMR (300 MHz, DMSO-d$_6$) δ ppm 8.96 (d, J = 1.9 Hz, 1H), 8.83 (s, 1H), 8.70 (s, 1H), 7.96 (s, 1H), 7.55-7.42 (m, 4H), 7.42-7.34 (m, 2H), 7.08 (dd, J = 9.6, 2.0 Hz, 1H), 6.15-6.05 (m, 1H), 4.24-4.17 (m, 2H), 4.12-4.05 (m, 2H), 3.70-3.54 (m, 4H), 3.51-3.43 (m, 2H), 3.25 (s, 3H), 2.57-2.41 (m, 2H) | (ESI(+)) m/e 450 (M + H)$^+$ |
| 33 | 1-imidazo[1,2-a]pyridin-6-yl-3-{4-[1-(tetrahydrofuran-2-ylcarbonyl)- | $^1$H NMR (400 MHz, DMSO-d$_6$, Temp = 90° C.) δ ppm 8.89-8.84 (m, 1H), 8.59 (s, 1H), 8.47 (s, 1H), 7.86 (s, 1H), 7.51-7.40 (m, 4H), 7.39-7.31 (m, 2H), 7.12-7.08 (m, 1H), 6.10-6.04 (m, 1H), | (ESI(+)) m/e 432 (M + H)$^+$ |

TABLE 3-continued

The following Examples were prepared essentially as described in Example 28, substituting the appropriate carboxylic acid in Example 28B. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | 1,2,3,6-tetrahydropyridin-4-yl]phenyl}urea | 4.71-4.64 (m, 1H), 4.15 (m, 2H), 3.84-3.68 (m, 4H), 2.54-2.44 (m, 2H), 2.15-1.96 (m, 2H), 1.92-1.81 (m, 2H) |  |
| 34 | 1-imidazo[1,2-a]pyridin-6-yl-3-{4-[1-(tetrahydro-2H-pyran-4-ylcarbonyl)-1,2,3,6-tetrahydropyridin-4-yl]phenyl}urea | $^1$H NMR (300 MHz, methanol-d$_4$) δ ppm 8.93 (dd, J = 2.0, 1.0 Hz, 1H), 7.82 (s, 1H), 7.56-7.47 (m, 2H), 7.47-7.35 (m, 4H), 7.22-7.14 (m, 1H), 6.13-6.07 (m, 1H), 4.32-4.16 (m, 2H), 4.03-3.92 (m, 2H), 3.86-3.77 (m, 2H), 3.61-3.46 (m, 2H), 3.12-2.92 (m, 1H), 2.66-2.49 (m, 2H), 1.92-1.71 (m, 2H), 1.72-1.59 (m, 2H) | (ESI(+)) m/e 446 (M + H)$^+$ |
| 35 | 1-{4-[1-(1,4-dioxan-2-ylcarbonyl)-1,2,3,6-tetrahydropyridin-4-yl]phenyl}-3-imidazo[1,2-a]pyridin-6-ylurea | $^1$H NMR (400 MHz, DMSO-d$_6$, Temp = 90° C.) δ ppm 8.86 (d, J = 1.2 Hz, 1H), 8.61 (bs, 1H), 8.49 (bs, 1H), 7.87 (s, 1H), 7.52-7.40 (m, 4H), 7.38-7.32 (m, 2H), 7.11 (dd, J = 9.6, 2.0 Hz, 1H), 6.10-6.04 (m, 1H), 4.37 (dd, J = 9.2, 2.9 Hz, 1H), 4.15 (m, 2H), 3.81-3.63 (m, 7H), 3.58-3.45 (m, 1H), 2.56-2.47 (m, 2H) | (ESI(+)) m/e 448 (M + H)$^+$ |
| 36 | 1-imidazo[1,2-a]pyridin-6-yl-3-(4-{1-[(1-methylpiperidin-4-yl)carbonyl]-1,2,3,6-tetrahydropyridin-4-yl}phenyl)urea | $^1$H NMR (400 MHz, DMSO-d$_6$, Temp = 90° C.) δ ppm 8.91-8.87 (m 1H), 8.68 (s, 1H), 8.56 (s, 1H), 7.90 (s, 1H), 7.53-7.44 (m, 4H), 7.41-7.35 (m, 2H), 7.14 (dd, J = 9.6, 2.1 Hz, 1H), 6.14-6.08 (m, 1H), 4.19-4.13 (m, 2H), 3.72 (t, J = 5.7 Hz, 2H), 3.17 (m, 1H), 2.85-2.77 (m, 2H), 2.64-2.48 (m, 2H), 2.20 (s, 3H), 2.06-1.94 (m, 2H), 1.76-1.60 (m, 4H) | (ESI(+)) m/e 459 (M + H)$^+$ |
| 37 | 1-(4-{1-[(1,1-dioxidotetrahydro-2H-thiopyran-4-yl)carbonyl]-1,2,3,6-tetrahydropyridin-4-yl}phenyl)-3-imidazo[1,2-a]pyridin-6-ylurea | $^1$H NMR (300 MHz, DMSO-d$_6$) δ 8.98-8.94 (m, 1H), 8.83 (bs, 1H), 8.70 (s, 1H), 7.97-7.94 (m, 1H), 7.55-7.35 (m, 6H), 7.09 (dd, J = 9.6, 2.0 Hz, 1H), 6.15-6.09 (m, 1H), 4.27-4.20 (m, 1H), 4.13-4.06 (m, 1H), 3.79-3.62 (m, 2H), 3.28-3.02 (m, 5H), 2.40-2.60 (m, 2H), 2.08-1.94 (m, 4H) | (ESI(+)) m/e 494 (M + H)$^+$ |
| 38 | 1-imidazo[1,2-a]pyridin-6-yl-3-{4-[1-(2-methylpropanoyl)-1,2,3,6-tetrahydropyridin-4-yl]phenyl}urea | $^1$H NMR (400 MHz, DMSO-d$_6$, Temp = 90° C.) δ ppm 8.88-8.83 (m, 1H), 8.59 (bs, 1H), 8.47 (bs, 1H), 7.87 (s, 1H), 7.50-7.41 (m, 4H), 7.39-7.33 (m, 2H), 7.11 (dd, J = 9.5, 2.0 Hz, 1H), 6.12-6.06 (m, 1H), 4.17-4.11 (m, 2H), 3.69 (t, J = 5.7 Hz, 2H), 2.95-2.86 (m, 1H), 2.50 (m, 2H), 1.05 (d, J = 6.7 Hz, 6H) | (ESI(+)) m/e 404 (M + H)$^+$ |

Example 51

1-imidazo[1,2-a]pyridin-6-yl-3-{4-[1-(2-methylpropyl)-1H-pyrazol-4-yl]phenyl}urea Example 51A 4-(1-isobutyl-1H-pyrazol-4-yl)aniline A suspension of 4-bromoaniline (406 mg, 2.362 mmol), 1-isobutyl-4-(4,4,5,5-tetramethyl-1,3,2-dioxaborolan-2-yl)-1H-pyrazole (650 mg, 2.60 mmol), [1,1'-bis(diphenylphosphino) ferrocene]dichloropalladium(II), complex with dichloromethane (57.9 mg, 0.071 mmol) and sodium carbonate (526 mg, 4.96 mmol) in a 6:2:1 mixture of tetrahydrofuran/water/methanol (12 ml) in a microwave vial was subjected to three vacuum/nitrogen purge cycles. The vial was sealed and heated in an oil bath at 85° C. overnight. The mixture was dissolved in a mixture of ethyl acetate (45 ml) and water (20 ml), and the separated aqueous layer was extracted with ethyl acetate (20 ml). The combined organic layers were washed with brine (20 ml), dried with magnesium sulfate, filtered and concentrated. Normal phase chromatography provided the title compound.

Example 51B 1-imidazo[1,2-a]pyridin-6-yl-3-{4-[1-(2-methylpropyl)-1H-pyrazol-4-yl]phenyl}urea The title compound was prepared as described in Example 1C, substituting 4-(1-isobutyl-1H-pyrazol-4-yl)aniline for 4-amino-N-isopentylbenzamide. $^1$H NMR (400 MHz, CDCl$_3$) δ 9.18 (s, 2H), 8.49 (s, 1H), 7.73 (s, 1H), 7.64 (d, J=10.3 Hz, 2H), 7.56 (s, 1H), 7.42-7.31 (m, 4H), 7.36 (d, J=9.5 Hz, 1H), 6.62 (dd, J=9.6, 1.7 Hz, 1H), 3.92 (d, J=7.3 Hz, 2H), 2.23 (hept, J=6.8 Hz, 1H), 0.93 (d, J=6.7 Hz, 6H). MS (ESI(+)) m/e 375 (M+H)$^+$.

Example 52

4-[(cyclopentylacetyl)amino]-N-(imidazo[1,2-a]pyridin-6-ylmethyl)benzamide

Example 52A methyl 4-(2-cyclopentylacetamido)benzoate

A solution of methyl 4-aminobenzoate (0.25 g, 1.654 mmol) in tetrahydrofuran (8.27 ml) was treated with diisopropylethylamine (0.433 ml, 2.481 mmol) and 2-cyclopentylacetyl chloride (0.279 g, 1.902 mmol) and the reaction mixture was stirred at ambient temperature for 2 hours. Concentration and normal phase chromatography provided the title compound.

Example 52B

4-(2-cyclopentylacetamido)benzoic acid

The title compound was prepared as described in Example 4B, substituting methyl 4-(2-cyclopentylacetamido)benzoate for methyl 4-(3-imidazo[1,2-a]pyridin-6-ylureido)benzoate.

Example 52C

4-[(cyclopentylacetyl)amino]-N-(imidazo[1,2-a]pyridin-6-ylmethyl)benzamide

The title compound was prepared as described in Example 1A, substituting imidazo[1,2-a]pyridin-6-ylmethanamine for 3-methylbutan-1-amine and 4-(2-cyclopentylacetamido)benzoic acid for 4-nitrobenzoic acid. $^1$H NMR (400 MHz, DMSO-$d_6$) δ ppm 10.08 (s, 1H), 8.93 (t, J=5.8 Hz, 1H), 8.47 (s, 1H), 7.96 (s, 1H), 7.87-7.81 (m, 2H), 7.70-7.64 (m, 2H), 7.57-7.50 (m, 2H), 7.24 (dd, J=9.2, 1.7 Hz, 1H), 4.45 (d, J=5.8 Hz, 2H), 2.36-2.30 (m, 2H), 2.29-2.15 (m, 1H), 1.81-1.65 (m, 2H), 1.67-1.38 (m, 4H), 1.39-0.95 (m, 2H); MS (ESI(+)) m/e 377 (M+H)$^+$.

Example 53

2-[(4-cyanobenzyl)(3-methylbutanoyl)amino]-N-(imidazo[1,2-a]pyridin-6-yl)-1,3-thiazole-5-carboxamide

Example 53A

2-bromo-N-(imidazo[1,2-a]pyridin-6-yl)thiazole-5-carboxamide

The title compound was prepared as described in Example 1A, substituting imidazo[1,2-A]pyridin-6-amine (0.768 g, 5.77 mmol) for 3-methylbutan-1-amine and 2-bromo-5-thiazolecarboxylic acid (1 g, 4.81 mmol) for 4-nitrobenzoic acid.

Example 53B

2-(4-cyanobenzylamino)-N-(imidazo[1,2-a]pyridin-6-yl)thiazole-5-carboxamide To a solution of 2-bromo-N-(imidazo[1,2-a]pyridin-6-yl)thiazole-5-carboxamide (165 mg, 0.511 mmol) in acetonitrile (2553 μl) was added 4-cyanobenzylamine (67.5 mg, 0.511 mmol). The mixture was heated in a microwave (Biotage Initiator) at 180° C. for 30 minutes. The heating was repeated again after another equivalent of 4-cyanobenzylamine was added. The reaction mixture was purified by normal phase chromatography to provide the title compound.

Example 53C

2-[(4-cyanobenzyl)(3-methylbutanoyl)amino]-N-(imidazo[1,2-a]pyridin-6-yl)-1,3-thiazole-5-carboxamide The title compound was prepared as described in Example 52A, substituting 3-methylbutanoyl chloride for 2-cyclopentylacetyl chloride and 2-(4-cyanobenzylamino)-N-(imidazo[1,2-a]pyridin-6-yl)thiazole-5-carboxamide for methyl 4-aminobenzoate. $^1$H NMR (400 MHz, DMSO-$d_6$) δ 10.75 (s, 1H), 9.62 (s, 1H), 8.43 (d, J=1.6 Hz, 1H), 8.32 (s, 1H), 8.11 (s, 1H), 7.99-7.89 (m, 2H), 7.82 (dd, J=18.8, 8.3 Hz, 2H), 7.38 (d, J=8.3 Hz, 2H), 5.63 (s, 2H), 2.14 (dt, J=13.4, 6.7 Hz, 1H), 0.88 (d, J=6.7 Hz, 6H); (APCI(+)) m/e 459 (M+H)$^+$.

TABLE 4

The following Examples were prepared essentially as described in Example 53, substituting the appropriate amine in Example 53A, the appropriate amine in 53B and the appropriate acid chloride in Example 53C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 54 | 2-[(4-cyanobenzyl)(3-methoxypropanoyl)amino]-N-(imidazo[1,2-a]pyridin-6-yl)-1,3-thiazole-5-carboxamide | $^1$H NMR (400 MHz, DMSO-$d_6$) δ 10.75 (s, 1H), 9.61 (s, 1H), 8.42 (s, 1H), 8.33 (s, 1H), 8.10 (s, 1H), 7.94 (s, 2H), 7.84 (d, J = 8.3 Hz, 3H), 7.40 (d, J = 8.3 Hz, 2H), 5.64 (s, 2H), 3.64 (t, J = 6.0 Hz, 2H), 3.20 (s, 3H), 2.89 (t, J = 6.1 Hz, 2H). | (APCI(+)) m/e 461 (M + H)$^+$ |
| 55 | 2-[(4-cyanobenzyl)(3-methylbutanoyl)amino]-N-(imidazo[1,2-a]pyridin-6-ylmethyl)-1,3-thiazole-5-carboxamide | $^1$H NMR (400 MHz, CDCl$_3$) δ 8.57 (s, 1H), 8.16 (d, J = 9.5 Hz, 1H), 7.96 (s, 1H), 7.86 (d, J = 1.8 Hz, 1H), 7.81 (d, J = 9.6 Hz, 1H), 7.75 (s, 1H), 7.63 (d, J = 8.3 Hz, 2H), 7.24 (d, J = 8.3 Hz, 2H), 5.54 (s, 2H), 4.69 (d, J = 6.1 Hz, 2H), 2.39 (d, J = 6.7 Hz, 2H), 2.30-2.24 (m, 1H), 0.94 (d, J = 6.6 Hz, 6H) | (APCI(+)) m/e 473 (M + H)$^+$ |

TABLE 4-continued

The following Examples were prepared essentially as described in Example 53, substituting the appropriate amine in Example 53A, the appropriate amine in 53B and the appropriate acid chloride in Example 53C. Some products were purified by flash chromatography while others were purified by reverse-phase HPLC. Accordingly, some Examples were isolated as trifluoroacetic acid salts.

| Ex | Name | $^1$H NMR | MS |
|----|------|-----------|-----|
| 56 | 2-[(4-cyanobenzyl)(3-methoxypropanoyl)amino]-N-(imidazo[1,2-a]pyridin-6-ylmethyl)-1,3-thiazole-5-carboxamide | $^1$H NMR (400 MHz, methanol-d$_4$) δ 8.78 (s, 1H), 8.20 (d, J = 2.1 Hz, 1H), 8.02 (d, J = 2.1 Hz, 1H), 8.01 (s, 1H), 8.00-7.96 (m, 1H), 7.90 (d, J = 9.3 Hz, 1H), 7.70 (d, J = 8.2 Hz, 2H), 7.38 (d, J = 8.2 Hz, 2H), 5.65 (s, 2H), 4.66 (s, 2H), 3.73 (t, J = 5.9 Hz, 2H), 2.87 (t, J = 5.9 Hz, 2H) | (APCI(+)) m/e 475 (M + H)$^+$ |
| 57 | 2-[(4-cyanobenzyl)(3-methoxypropanoyl)amino]-N-(imidazo[1,2-a]pyridin-7-ylmethyl)-1,3-thiazole-5-carboxamide | $^1$H NMR (400 MHz, methanol-d$_4$) δ 9.22 (td, J = 6.4, 1.2 Hz, 1H), 8.75 (d, J = 7.0 Hz, 1H), 8.18 (d, J = 2.0 Hz, 1H), 8.08-7.95 (m, 2H), 7.80 (s, 1H), 7.77-7.66 (m, 2H), 7.47 (dd, J = 7.1, 1.1 Hz, 1H), 7.39 (d, J = 8.2 Hz, 2H), 5.66 (s, 2H), 4.73 (d, J = 4.5 Hz, 2H), 3.74 (t, J = 5.9 Hz, 2H), 2.88 (t, J = 5.8 Hz, 2H) | (APCI(+)) m/e 475 (M + H)$^+$ |
| 61 | N-(imidazo[1,2-a]pyridin-6-ylmethyl)-2-[(3-methoxypropanoyl)(3-methylbutyl)amino]-1,3-thiazole-5-carboxamide | $^1$H NMR (400 MHz, methanol-d$_4$) δ 8.79 (s, 1H), 8.22 (d, J = 2.1 Hz, 1H), 8.08 (s, 1H), 8.05-7.96 (m, 2H), 7.90 (d, J = 9.3 Hz, 1H), 4.67 (d, J = 3.8 Hz, 2H), 4.27 (dd, J = 9.3, 7.0 Hz, 2H), 3.79 (t, J = 5.9 Hz, 2H), 3.36 (s, 3H), 2.98 (t, J = 5.9 Hz, 2H), 1.80-1.67 (m, 1H), 1.67-1.57 (m, 2H), 1.01 (d, J = 6.5 Hz, 6H) | (APCI(+)) m/e 430 (M + H)$^+$ |
| 121 | N-(imidazo[1,2-a]pyridin-7-ylmethyl)-2-[(3-methoxypropanoyl)(tetrahydrofuran-2-ylmethyl)amino]-1,3-thiazole-5-carboxamide | $^1$H NMR (400 MHz, DMSO-d$_6$) δ 9.11 (t, J = 5.9 Hz, 1H), 8.50 (d, J = 7.0 Hz, 1H), 8.17 (s, 1H), 7.90 (s, 1H), 7.53 (s, 1H), 7.41 (s, 1H), 6.85 (dd, J = 7.1, 1.5 Hz, 1H), 4.48 (d, J = 5.8 Hz, 2H), 4.39 (d, J = 12.5 Hz, 1H), 4.25-4.08 (m, 2H), 3.78 (dd, J = 14.8, 6.8 Hz, 1H), 3.66 (t, J = 6.4 Hz, 2H), 3.65-3.55 (m, 1H), 3.26 (s, 3H), 3.06 (ddd, J = 17.2, 13.9, 6.4 Hz, 2H), 1.99 (dd, J = 12.7, 7.4 Hz, 1H), 1.94-1.86 (m, 1H), 1.86-1.74 (m, 1H), 1.66-1.53 (m, 1H) | (APCI(+)) m/e 444 (M + H)$^+$ |
| 123 | N-(imidazo[1,2-a]pyridin-6-ylmethyl)-2-{[(2-methyl-1,3-thiazol-5-yl)acetyl](tetrahydrofuran-2-ylmethyl)amino}-1,3-thiazole-5-carboxamide | $^1$H NMR (400 MHz, DMSO-d$_6$/D$_2$O) ppm 8.76 (s, 1 H) 8.24 (d, J = 2.14 Hz, 1 H) 8.10 (s, 1 H) 8.02 (d, J = 2.14 Hz, 1 H) 7.89 (d, J = 1.22 Hz, 2 H) 7.45 (s, 1 H) 4.57 (s, 2 H) 4.50 (d, J = 12.21 Hz, 1 H) 4.42 (d, J = 5.80 Hz, 1 H) 4.19-4.31 (m, 2 H) 3.78-3.85 (m, 1 H) 3.63-3.69 (m, 1 H) 3.28-3.29 (m, 2 H) 2.62 (s, 3 H) 2.01 (s, 1 H) 1.81-1.95 (m, 2 H) 1.60-1.68 (m, 1 H) | (ESI(+)) m/e 496 (M + H)$^+$ |
| 124 | N-(imidazo[1,2-a]pyridin-6-ylmethyl)-2-{[(2-methyl-1,3-thiazol-4-yl)acetyl](tetrahydrofuran-2-ylmethyl)amino}-1,3-thiazole-5-carboxamide | $^1$H NMR (400 MHz, DMSO-d$_6$/D$_2$O) ppm 8.78 (s, 1 H) 8.26 (d, J = 1.83 Hz, 1 H) 8.10 (s, 1 H) 8.05 (d, J = 2.14 Hz, 1 H) 7.90-7.96 (m, 2 H) 7.24 (s, 1 H) 4.58 (s, 2 H) 4.47 (dd, 1 H) 4.18-4.37 (m, 4 H) 3.79-3.86 (m, 1 H) 3.62-3.69 (m, 1 H) 2.62 (s, 3 H) 1.97-2.06 (m, 1 H) 1.80-1.94 (m, 2 H) 1.56-1.69 (m, 1 H) | (ESI(+)) m/e 496 (M + H)$^+$ |
| 125 | N-(imidazo[1,2-a]pyridin-6-ylmethyl)-2-{[(3-methyl-1,2-oxazol-5-yl)acetyl](tetrahydrofuran-2-ylmethyl)amino}-1,3-thiazole-5-carboxamide | $^1$H NMR (400 MHz, DMSO-d$_6$/D$_2$O) ppm 8.70 (s, 1 H) 8.17 (d, J = 1.83 Hz, 1 H) 8.10 (s, 1 H) 7.92 (d, J = 1.83 Hz, 1 H) 7.79-7.84 (m, 1 H) 7.73-7.85 (m, 1 H) 6.27 (s, 1 H) 4.55 (s, 2 H) 4.35-4.52 (m, 3 H) 4.19-4.27 (m, 2 H) 3.77-3.85 (m, 1 H) 3.62-3.69 (m, 1 H) 2.23 (s, 3 H) 2.01 (d, J = 2.75 Hz, 1 H) 1.80-1.95 (m, 2 H) 1.56-1.67 (m, 1 H) | (ESI(+)) m/e 480 (M + H)$^+$ |
| 126 | 2-{[3-(3-chloro-1,2-oxazol-5-yl)propanoyl](tetrahydrofuran- | | (ESI(+) m/e 515 (M + H)$^+$ |

TABLE 4-continued

The following Examples were prepared essentially as described in Example 53, substituting the appropriate amine in Example 53A, the appropriate amine in 53B and the appropriate acid chloride in Example 53C. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
|  | 2-ylmethyl)amino}-N-(imidazo[1,2-a]pyridin-6-ylmethyl)-1,3-thiazole-5-carboxamide |  |  |
| 127 | N-(imidazo[1,2-a]pyridin-6-ylmethyl)-2-{[3-(3-methoxy-1,2-oxazol-5-yl)propanoyl](tetrahydrofuran-2-ylmethyl)amino}-1,3-thiazole-5-carboxamide |  | (ESI(+) m/e 510 (M + H)⁺ |
| 128 | 2-{[(3,5-dimethyl-1,2-oxazol-4-yl)acetyl](tetrahydrofuran-2-ylmethyl)amino}-N-(imidazo[1,2-a]pyridin-6-ylmethyl)-1,3-thiazole-5-carboxamide |  | (ESI(+)) m/e 495 (M + H)⁺ |
| 129 | 2-{[3-(3,5-dimethyl-1,2-oxazol-4-yl)propanoyl](tetrahydrofuran-2-ylmethyl)amino}-N-(imidazo[1,2-a]pyridin-6-ylmethyl)-1,3-thiazole-5-carboxamide |  | (ESI(+)) m/e 509 (M + H)⁺ |
| 130 | N-(imidazo[1,2-a]pyridin-6-ylmethyl)-2-{[3-(1-methyl-1H-pyrazol-4-yl)propanoyl](tetrahydrofuran-2-ylmethyl)amino}-1,3-thiazole-5-carboxamide |  | (ESI(+)) m/e 494 (M + H)⁺ |
| 131 | N-(imidazo[1,2-a]pyridin-6-ylmethyl)-2-{[3-(4-methyl-1,3-thiazol-5-yl)propanoyl](tetrahydrofuran-2-ylmethyl)amino}-1,3-thiazole-5-carboxamide |  | (ESI(+)) m/e 511 (M + H)⁺ |
| 132 | N-(imidazo[1,2-a]pyridin-6-ylmethyl)-2-[(tetrahydrofuran-2-ylmethyl)(1H-tetrazol-5-ylacetyl)amino]-1,3-thiazole-5-carboxamide |  | (ESI(+)) m/e 468 (M + H)⁺ |
| 133 | N-(imidazo[1,2-a]pyridin-6-ylmethyl)-2-{[3-(1,2-oxazol-5-yl)propanoyl](tetrahydrofuran- |  | (ESI(+)) m/e 481 (M + H)⁺ |

TABLE 4-continued

The following Examples were prepared essentially as described in Example 53, substituting the appropriate amine in Example 53A, the appropriate amine in 53B and the appropriate acid chloride in Example 53C. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | 2-ylmethyl)amino}-1,3-thiazole-5-carboxamide |  |  |
| 134 | N-(imidazo[1,2-a]pyridin-6-ylmethyl)-2-[(1,2-oxazol-3-ylacetyl)(tetrahydrofuran-2-ylmethyl)amino]-1,3-thiazole-5-carboxamide |  | (ESI(+)) m/e 467 (M + H)$^+$ |
| 135 | N-(imidazo[1,2-a]pyridin-6-ylmethyl)-2-{[3-(1,2-oxazol-4-yl)propanoyl](tetrahydrofuran-2-ylmethyl)amino}-1,3-thiazole-5-carboxamide |  | (ESI(+)) m/e 481 (M + H)$^+$ |
| 136 | N-(imidazo[1,2-a]pyridin-6-ylmethyl)-2-{(tetrahydrofuran-2-ylmethyl)[3-(1,3-thiazol-2-yl)propanoyl]amino}-1,3-thiazole-5-carboxamide |  | (ESI(+)) m/e 497 (M + H)$^+$ |
| 139 | N-(imidazo[1,2-a]pyridin-6-ylmethyl)-2-[(3-methoxypropanoyl)(tetrahydrofuran-3-ylmethyl)amino]-1,3-thiazole-5-carboxamide | $^1$H NMR (400 MHz, methanol-d$_4$) δ 8.79 (s, 1H), 8.22 (d, J = 2.1 Hz, 1H), 8.08 (s, 1H), 8.03 (d, J = 2.2 Hz, 1H), 7.98 (d, J = 1.4 Hz, 1H), 7.91 (d, J = 9.3 Hz, 1H), 4.66 (s, 2H), 4.31 (qd, J = 14.8, 7.7 Hz, 2H), 3.96 (td, J = 8.2, 5.7 Hz, 1H), 3.87-3.71 (m, 3H), 3.65 (qd, J = 8.9, 5.6 Hz, 2H), 3.36 (s, 3H), 3.02 (dd, J = 10.4, 5.6 Hz, 2H), 2.94-2.81 (m, 1H), 2.05 (dtd, J = 13.5, 8.0, 5.7 Hz, 1H), 1.75 (ddd, J = 12.6, 7.9, 6.5 Hz, 1H) | (APCI(+)) m/e 444 (M + H)$^+$ |
| 140 | N-(imidazo[1,2-a]pyridin-6-ylmethyl)-2-[(tetrahydrofuran-3-ylmethyl)(tetrahydro-2H-pyran-4-ylcarbonyl)amino]-1,3-thiazole-5-carboxamide | $^1$H NMR (500 MHz, methanol-d$_4$) δ 8.79 (s, 1H), 8.21 (d, J = 1.9 Hz, 1H), 8.09 (s, 1H), 8.03 (d, J = 2.0 Hz, 1H), 8.00 (d, J = 9.3 Hz, 1H), 7.91 (d, J = 9.2 Hz, 1H), 4.66 (s, 2H), 4.40 (dd, J = 14.8, 7.0 Hz, 1H), 4.28 (dd, J = 14.7, 8.5 Hz, 1H), 4.06-3.94 (m, 3H), 3.77 (dd, J = 15.0, 8.1 Hz, 1H), 3.68 (dd, J = 8.9, 6.3 Hz, 1H), 3.60 (dd, J = 8.9, 4.7 Hz, 1H), 3.55 (t, J = 11.7 Hz, 2H), 3.24 (tt, J = 11.1, 3.7 Hz, 1H), 2.85 (dt, J = 12.1, 3.5 Hz, 1H), 2.11-2.01 (m, 1H), 1.93 (ddd, J = 16.1, 12.7, 4.3 Hz, 1H), 1.89-1.82 (m, 1H), 1.75 (dt, J = 13.0, 9.9 Hz, 3H) | (APCI(+)) m/e 470 (M + H)$^+$ |
| 142 | N-(imidazo[1,2-a]pyridin-6-ylmethyl)-2-[(3-methoxypropanoyl)(tetrahydro-2H-pyran-4-ylmethyl)amino]-1,3-thiazole-5-carboxamide | $^1$H NMR (400 MHz, methanol-d$_4$) δ 8.79 (s, 1H), 8.22 (d, J = 2.1 Hz, 1H), 8.08 (s, 1H), 8.03 (d, J = 2.1 Hz, 1H), 8.00 (dd, J = 9.4, 1.4 Hz, 1H), 7.91 (d, J = 9.4 Hz, 1H), 4.66 (s, 2H), 4.23 (d, J = 7.3 Hz, 2H), 4.00-3.85 (m, 2H), 3.79 (t, J = 5.9 Hz, 2H), 3.36 (s, 3H), 3.02 (t, J = 5.9 Hz, 2H), 2.26-2.13 (m, 1H), 1.58-1.50 (m, 2H), 1.49-1.36 (m, 2H) | (APCI(+)) m/e 458 (M + H)$^+$ |
| 143 | N-(imidazo[1,2-a]pyridin-6-ylmethyl)-2-[(tetrahydrofuran-3-ylcarbonyl)(tetrahydro- | $^1$H NMR (500 MHz, methanol-d$_4$) δ 8.79 (s, 1H), 8.21 (d, J = 2.1 Hz, 1H), 8.09 (s, 1H), 8.03 (d, J = 2.0 Hz, 1H), 8.00 (d, J = 9.3 Hz, 1H), 7.91 (d, J = 9.3 Hz, 1H), 4.67 (s, 2H), 4.32-4.23 (m, 2H), 4.08 (t, J = 8.1 Hz, 1H), 3.94 (qd, J = 9.9, | (APCI(+)) m/e 470 (M + H)$^+$ |

TABLE 4-continued

The following Examples were prepared essentially as described in Example 53,
substituting the appropriate amine in Example 53A, the appropriate amine in 53B and the
appropriate acid chloride in Example 53C. Some products were purified by flash
chromatography while others were purified by reverse-phase HPLC. Accordingly, some
Examples were isolated as trifluoroacetic acid salts.

| Ex | Name | $^1$H NMR | MS |
|---|---|---|---|
|  | 2H-pyran-4-ylmethyl)amino]-1,3-thiazole-5-carboxamide | 3.8 Hz, 4H), 3.87 (dd, J = 14.8, 7.3 Hz, 1H), 3.83-3.74 (m, 1H), 3.35 (dd, J = 11.7, 1.9 Hz, 2H), 2.31 (dt, J = 15.4, 7.1 Hz, 1H), 2.18 (td, J = 12.9, 6.6 Hz, 2H), 1.53 (t, J = 10.9 Hz, 2H), 1.50-1.41 (m, 2H) |  |
| 144 | N-(imidazo[1,2-a]pyridin-6-ylmethyl)-2-[(tetrahydro-2H-pyran-4-ylcarbonyl)(tetrahydro-2H-pyran-4-ylmethyl)amino]-1,3-thiazole-5-carboxamide | $^1$H NMR (500 MHz, methanol-d$_4$) δ 8.79 (s, 1H), 8.21 (d, J = 2.0 Hz, 1H), 8.09 (s, 1H), 8.03 (d, J = 2.1 Hz, 1H), 8.00 (dd, J = 9.3, 1.4 Hz, 1H), 7.91 (d, J = 9.3 Hz, 1H), 4.66 (s, 2H), 4.27 (d, J = 7.3 Hz, 2H), 4.03-3.97 (m, 2H), 3.93 (dd, J = 11.4, 2.7 Hz, 2H), 3.62-3.52 (m, 2H), 3.35 (dd, J = 11.6, 2.2 Hz, 2H), 3.26 (dd, J = 9.3, 5.6 Hz, 1H), 2.21-2.10 (m, 1H), 1.89 (ddd, J = 16.0, 12.6, 4.4 Hz, 2H), 1.76 (dd, J = 13.0, 1.5 Hz, 2H), 1.54 (dt, J = 7.1, 3.0 Hz, 2H), 1.51-1.42 (m, 2H) | (APCI(+)) m/e 484 (M + H)$^+$ |
| 145 | N-(imidazo[1,2-a]pyridin-6-ylmethyl)-2-{(3-methoxypropanoyl)[(2R)-tetrahydrofuran-2-ylmethyl]amino}-1,3-thiazole-5-carboxamide | $^1$H NMR (500 MHz, methanol-d$_4$) δ 8.78 (s, 1H), 8.21 (s, 1H), 8.07 (s, 1H), 8.02 (s, 1H), 8.00 (d, J = 9.4 Hz, 1H), 7.91 (d, J = 9.4 Hz, 1H), 4.66 (s, 2H), 4.52 (d, J = 14.9 Hz, 1H), 4.29 (d, J = 6.8 Hz, 1H), 4.17 (dd, J = 14.9, 8.9 Hz, 1H), 3.88 (dd, J = 14.5, 7.2 Hz, 1H), 3.76 (dd, J = 14.0, 7.9 Hz, 2H), 3.74-3.69 (m, 1H), 3.36 (s, 3H), 3.13 (q, J = 6.1 Hz, 2H), 2.10 (td, J = 12.4, 7.4 Hz, 1H), 2.04-1.94 (m, 1H), 1.94-1.85 (m, 1H), 1.67 (dq, J = 15.3, 7.8 Hz, 1H) | (APCI(+)) m/e 444 (M + H)$^+$ |
| 146 | N-(imidazo[1,2-a]pyridin-6-ylmethyl)-2-{(tetrahydrofuran-3-ylcarbonyl)[(2R)-tetrahydrofuran-2-ylmethyl]amino}-1,3-thiazole-5-carboxamide | $^1$H NMR (500 MHz, methanol-d$_4$) δ 8.79 (s, 1H), 8.21 (s, 1H), 8.08 (s, 1H), 8.02 (d, J = 1.8 Hz, 1H), 8.00 (d, J = 9.4 Hz, 1H), 7.91 (d, J = 9.3 Hz, 1H), 4.66 (s, 2H), 4.61 (t, J = 13.7 Hz, 1H), 4.30-4.17 (m, 2H), 4.06 (ddd, J = 15.8, 14.9, 7.9 Hz, 1H), 3.99-3.91 (m, 2H), 3.90-3.79 (m, 3H), 3.76-3.68 (m, 1H), 2.32 (qd, J = 12.8, 6.7 Hz, 1H), 2.25-2.04 (m, 2H), 2.03-1.86 (m, 2H), 1.72-1.61 (m, 1H) | (APCI(+)) m/e 456 (M + H)$^+$ |
| 147 | N-(imidazo[1,2-a]pyridin-6-ylmethyl)-2-{[(2R)-tetrahydrofuran-2-ylmethyl](tetrahydro-2H-pyran-4-ylcarbonyl)amino}-1,3-thiazole-5-carboxamide | $^1$H NMR (500 MHz, methanol-d$_4$) δ 8.79 (s, 1H), 8.21 (d, J = 2.1 Hz, 1H), 8.07 (s, 1H), 8.02 (d, J = 2.1 Hz, 1H), 8.00 (dd, J = 9.3, 1.2 Hz, 1H), 7.91 (d, J = 9.3 Hz, 1H), 4.66 (s, 2H), 4.61 (d, J = 12.8 Hz, 1H), 4.29-4.19 (m, 2H), 4.06-3.96 (m, 2H), 3.85 (dd, J = 14.9, 6.9 Hz, 1H), 3.73 (dd, J = 13.9, 7.7 Hz, 1H), 3.57-3.47 (m, 2H), 3.43 (ddd, J = 14.8, 8.4, 3.9 Hz, 1H), 2.11 (dt, J = 12.1, 5.4 Hz, 1H), 2.05-1.87 (m, 3H), 1.83-1.73 (m, 3H), 1.73-1.64 (m, 1H) | (APCI(+)) m/e 470 (M + H)$^+$ |
| 148 | N-(imidazo[1,2-a]pyridin-6-ylmethyl)-2-{(3-methoxypropanoyl)[(2S)-tetrahydrofuran-2-ylmethyl]amino}-1,3-thiazole-5-carboxamide 2H), | $^1$H NMR (500 MHz, methanol-d$_4$) δ 8.78 (s, 1H), 8.21 (d, J = 1.8 Hz, 1H), 8.06 (s, 1H), 8.02 (d, J = 2.2 Hz, 1H), 8.00 (dd, J = 9.4, 1.5 Hz, 1H), 7.90 (d, J = 9.3 Hz, 1H), 4.66 (s, 2H), 4.52 (dd, J = 14.9, 2.5 Hz, 1H), 4.32-4.25 (m, 1H), 4.17 (dd, J = 14.8, 8.9 Hz, 1H), 3.92-3.83 (m, 1H), 3.81-3.74 (m, 2H), 3.71 (td, J = 7.7, 6.3 Hz, 1H), 3.36 (s, 3H), 3.21-3.05 (m, 2H), 2.15-2.05 (m, 1H), 2.04-1.95 (m, 1H), 1.91 (ddt, J = 7.5, 5.0, 1.9 Hz, 1H), 1.73-1.60 (m, 1H) | (APCI(+)) m/e 444 (M + H)$^+$ |
| 149 | N-(imidazo[1,2-a]pyridin-6-ylmethyl)-2-{(tetrahydrofuran-3- | $^1$H NMR (500 MHz, methanol-d$_4$) δ 8.79 (s, 1H), 8.21 (d, J = 2.2 Hz, 1H), 8.08 (d, J = 0.7 Hz, 1H), 8.02 (d, J = 2.1 Hz, 1H), 8.00 (dd, J = 9.3, 1.3 Hz, 1H), 7.91 (d, J = 9.3 Hz, 1H), 4.66 (s, 2H), | (APCI(+)) m/e 456 (M + H)$^+$ |

TABLE 4-continued

The following Examples were prepared essentially as described in Example 53, substituting the appropriate amine in Example 53A, the appropriate amine in 53B and the appropriate acid chloride in Example 53C. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
|  | ylcarbonyl)[(2S)-tetrahydrofuran-2-ylmethyl]amino}-1,3-thiazole-5-carboxamide | 4.61 (t, J = 13.2 Hz, 1H), 4.31-4.17 (m, 2H), 4.06 (ddd, J = 14.8, 14.3, 7.3 Hz, 1H), 4.00-3.92 (m, 2H), 3.90-3.79 (m, 3H), 3.71 (ddd, J = 10.8, 8.3, 3.1 Hz, 1H), 2.39-2.27 (m, 1H), 2.25-2.04 (m, 2H), 2.03-1.87 (m, 2H), 1.73-1.60 (m, 1H) |  |
| 150 | N-(imidazo[1,2-a]pyridin-6-ylmethyl)-2-{[(2S)-tetrahydrofuran-2-ylmethyl](tetrahydro-2H-pyran-4-ylcarbonyl)amino}-1,3-thiazole-5-carboxamide | ¹H NMR (500 MHz, methanol-d₄) δ 8.79 (s, 1H), 8.21 (d, J = 1.9 Hz, 1H), 8.07 (d, J = 3.1 Hz, 1H), 8.02 (d, J = 2.2 Hz, 1H), 8.00 (dd, J = 9.4, 1.5 Hz, 1H), 7.91 (d, J = 9.3 Hz, 1H), 4.66 (s, 2H), 4.61 (d, J = 12.7 Hz, 1H), 4.31-4.19 (m, 2H), 4.07-3.95 (m, 2H), 3.89-3.81 (m, 1H), 3.73 (td, J = 7.8, 6.1 Hz, 1H), 3.58-3.47 (m, 2H), 3.47-3.39 (m, 1H), 2.16-2.05 (m, 1H), 2.05-1.86 (m, 3H), 1.77 (ddd, J = 14.6, 6.0, 2.5 Hz, 3H), 1.73-1.65 (m, 1H) | (APCI(+)) m/e 470 (M + H)⁺ |
| 183 | N-(imidazo[1,2-a]pyridin-6-ylmethyl)-2-{[(1-methyl-1H-pyrazol-4-yl)acetyl](tetrahydrofuran-2-ylmethyl)amino}-1,3-thiazole-5-carboxamide |  | (ESI(+)) m/e 480 (M + H)⁺ |
| 184 | 2-{[(1,3-dimethyl-1H-pyrazol-4-yl)acetyl](tetrahydrofuran-2-ylmethyl)amino}-N-(imidazo[1,2-a]pyridin-6-ylmethyl)-1,3-thiazole-5-carboxamide |  | (ESI(+)) m/e 494 (M + H)⁺ |
| 189 | N-(imidazo[1,2-a]pyridin-6-ylmethyl)-2-{[3-(1-methyl-1H-pyrrol-2-yl)propanoyl](tetrahydrofuran-2-ylmethyl)amino}-1,3-thiazole-5-carboxamide |  | (ESI(+)) m/e 493 (M + H)⁺ |
| 190 | 2-{[(1,5-dimethyl-1H-pyrazol-3-yl)acetyl](tetrahydrofuran-2-ylmethyl)amino}-N-(imidazo[1,2-a]pyridin-6-ylmethyl)-1,3-thiazole-5-carboxamide |  | (ESI(+)) m/e 494 (M + H)⁺ |
| 191 | N-(imidazo[1,2-a]pyridin-6-ylmethyl)-2-[(tetrahydrofuran-2-ylmethyl)(1,3-thiazol-4-ylacetyl)amino]-1,3-thiazole-5-carboxamide |  | (ESI(+)) m/e 483 (M + H)⁺ |
| 192 | N-(imidazo[1,2-a]pyridin-7-ylmethyl)-2-{(1,2-oxazol-3- | ¹H NMR (400 MHz, methanol-d₄) δ 8.73 (d, J = 7.0 Hz, 1H), 8.64 (d, J = 1.5 Hz, 1H), 8.16 (d, J = 2.1 Hz, 1H), 8.12 (s, 1H), 7.98 (d, J = 2.2 Hz, 1H), 7.80 (s, | (APCI(+)) m/e 467 (M + H)⁺ |

TABLE 4-continued

The following Examples were prepared essentially as described in Example 53, substituting the appropriate amine in Example 53A, the appropriate amine in 53B and the appropriate acid chloride in Example 53C. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
|  | ylacetyl][(2R)-tetrahydrofuran-2-ylmethyl]amino}-1,3-thiazole-5-carboxamide | 1H), 7.46 (dd, J = 7.0, 1.4 Hz, 1H), 6.52 (d, J = 1.6 Hz, 1H), 4.72 (s, 2H), 4.65 (dd, J = 14.9, 1.9 Hz, 1H), 4.42 (d, J = 1.4 Hz, 2H), 4.32 (dd, J = 11.6, 4.4 Hz, 1H), 4.23 (dd, J = 14.8, 9.0 Hz, 1H), 3.94 (dd, J = 14.9, 6.8 Hz, 1H), 3.76 (dd, J = 14.2, 7.7 Hz, 1H), 2.21-2.07 (m, 1H), 2.08-1.87 (m, 2H), 1.69 (ddd, J = 15.8, 12.3, 7.6 Hz, 1H) |  |
| 193 | N-(imidazo[1,2-a]pyridin-7-ylmethyl)-2-{[(5-methyl-1,2-oxazol-3-yl)acetyl][(2R)-tetrahydrofuran-2-ylmethyl]amino}-1,3-thiazole-5-carboxamide | ¹H NMR (400 MHz, methanol-d₄) δ 8.74 (d, J = 7.0 Hz, 1H), 8.17 (d, J = 1.9 Hz, 1H), 8.11 (s, 1H), 7.99 (d, J = 2.1 Hz, 1H), 7.79 (s, 1H), 7.47 (d, J = 6.8 Hz, 1H), 6.16 (s, 1H), 4.72 (s, 2H), 4.63 (d, J = 12.8 Hz, 1H), 4.36-4.27 (m, 3H), 4.21 (dd, J = 14.6, 9.4 Hz, 1H), 3.94 (dd, J = 15.1, 6.8 Hz, 1H), 3.75 (dd, J = 14.3, 7.5 Hz, 1H), 2.43 (s, 3H), 2.13 (d, J = 8.1 Hz, 1H), 2.05-1.89 (m, 2H), 1.75-1.62 (m, 1H) | (APCI(+)) m/e 481 (M + H)⁺ |
| 194 | N-(imidazo[1,2-a]pyridin-7-ylmethyl)-2-{[3-(1,2-oxazol-5-yl)propanoyl][(2R)-tetrahydrofuran-2-ylmethyl]amino}-1,3-thiazole-5-carboxamide | ¹H NMR (400 MHz, methanol-d₄) δ 8.74 (d, J = 7.0 Hz, 1H), 8.27 (d, J = 1.6 Hz, 1H), 8.17 (d, J = 2.1 Hz, 1H), 8.10 (s, 1H), 7.99 (d, J = 2.1 Hz, 1H), 7.79 (s, 1H), 7.47 (d, J = 6.8 Hz, 1H), 6.23 (s, 1H), 4.72 (s, 2H), 4.55 (d, J = 12.6 Hz, 1H), 4.35-4.23 (m, 1H), 4.15 (dd, J = 14.8, 9.0 Hz, 1H), 3.87 (dd, J = 14.8, 6.9 Hz, 1H), 3.72 (dd, J = 14.0, 7.8 Hz, 1H), 3.46 (dd, J = 12.2, 6.1 Hz, 1H), 3.28-3.18 (m, 3H), 2.10 (dd, J = 12.6, 7.2 Hz, 1H), 1.94 (dd, J = 15.7, 8.4 Hz, 2H), 1.74-1.60 (m, 1H) | (APCI(+)) m/e 481 (M + H)⁺ |
| 195 | N-(imidazo[1,2-a]pyridin-7-ylmethyl)-2-{[3-(1,2-oxazol-4-yl)propanoyl][(2R)-tetrahydrofuran-2-ylmethyl]amino}-1,3-thiazole-5-carboxamide | ¹H NMR (400 MHz, methanol-d₄) δ 8.71 (d, J = 7.0 Hz, 1H), 8.51 (s, 1H), 8.36 (s, 1H), 8.11 (d, J = 17.0 Hz, 2H), 7.94 (d, J = 2.0 Hz, 1H), 7.76 (s, 1H), 7.42 (d, J = 6.8 Hz, 1H), 4.71 (s, 2H), 4.53 (d, J = 12.5 Hz, 1H), 4.27 (t, J = 6.7 Hz, 1H), 4.14 (dd, J = 14.9, 9.1 Hz, 1H), 3.83 (dd, J = 14.9, 6.8 Hz, 1H), 3.69 (dd, J = 13.8, 7.5 Hz, 1H), 3.26 (d, J = 7.1 Hz, 1H), 3.09 (dd, J = 17.6, 6.4 Hz, 1H), 2.91 (dd, J = 12.3, 6.4 Hz, 2H), 2.10 (dt, J = 12.3, 5.9 Hz, 1H), 2.03-1.84 (m, 2H), 1.74-1.58 (m, 1H) | (APCI(+)) m/e 481 (M + H)⁺ |
| 196 | N-(imidazo[1,2-a]pyridin-7-ylmethyl)-2-{[(2R)-tetrahydrofuran-2-ylmethyl](1,3-thiazol-4-ylacetyl)amino}-1,3-thiazole-5-carboxamide | ¹H NMR (400 MHz, methanol-d₄) δ 9.00 (s, 1H), 8.74 (d, J = 7.0 Hz, 1H), 8.17 (d, J = 1.9 Hz, 1H), 8.11 (s, 1H), 7.98 (d, J = 2.2 Hz, 1H), 7.79 (s, 1H), 7.51 (s, 1H), 7.47 (d, J = 7.0 Hz, 1H), 4.72 (s, 2H), 4.63 (d, J = 12.8 Hz, 1H), 4.49 (q, J = 16.9 Hz, 2H), 4.38-4.25 (m, 2H), 3.96 (dd, J = 14.9, 6.7 Hz, 1H), 3.76 (dd, J = 14.2, 7.6 Hz, 1H), 2.19-2.08 (m, 1H), 2.06-1.98 (m, 1H), 1.98-1.89 (m, 1H), 1.70 (td, J = 15.6, 7.6 Hz, 1H) | (APCI(+)) m/e 483 (M + H)⁺ |
| 197 | 2-{[(1,5-dimethyl-1H-pyrazol-3-yl)acetyl][(2R)-tetrahydrofuran-2-ylmethyl]amino}-N-(imidazo[1,2-a]pyridin-7-ylmethyl)-1,3-thiazole-5-carboxamide | ¹H NMR (400 MHz, methanol-d₄) δ 8.74 (d, J = 7.0 Hz, 1H), 8.17 (d, J = 2.1 Hz, 1H), 8.10 (s, 1H), 7.99 (d, J = 2.1 Hz, 1H), 7.79 (s, 1H), 7.47 (d, J = 7.0 Hz, 1H), 6.01 (s, 1H), 4.72 (s, 2H), 4.55 (d, J = 12.9 Hz, 1H), 4.30 (t, J = 7.9 Hz, 1H), 4.27-4.18 (m, 2H), 4.10 (t, J = 15.1 Hz, 1H), 3.94 (dd, J = 14.8, 6.8 Hz, 1H), 3.82-3.68 (m, 4H), 2.27 (s, 3H), 2.20-2.06 (m, 1H), 2.00 (dd, J = 13.5, 5.8 Hz, 1H), 1.97-1.87 (m, 1H), 1.76-1.58 (m, 1H) | (APCI(+)) m/e 494 (M + H)⁺ |
| 198 | N-(imidazo[1,2-a]pyridin-7- | ¹H NMR (400 MHz, methanol-d₄) δ 8.75 (d, J = 7.0 Hz, 1H), 8.17 (d, J = 2.1 Hz, | (APCI(+)) m/e |

TABLE 4-continued

The following Examples were prepared essentially as described in Example 53, substituting the appropriate amine in Example 53A, the appropriate amine in 53B and the appropriate acid chloride in Example 53C. Some products were purified by flash chromatography while others were purified by reverse-phase HPLC. Accordingly, some Examples were isolated as trifluoroacetic acid salts.

| Ex | Name | ¹H NMR | MS |
|---|---|---|---|
|  | ylmethyl)-2-{[3-(1-methyl-1H-pyrazol-4-yl)propanoyl][(2R)-tetrahydrofuran-2-ylmethyl]amino}-1,3-thiazole-5-carboxamide | 1H), 8.09 (s, 1H), 7.99 (d, J = 2.1 Hz, 1H), 7.80 (s, 1H), 7.47 (d, J = 8.2 Hz, 1H), 7.45 (s, 1H), 7.36 (s, 1H), 4.72 (s, 2H), 4.50 (dd, J = 14.9, 2.3 Hz, 1H), 4.27 (t, J = 6.9 Hz, 1H), 4.13 (dd, J = 14.9, 9.0 Hz, 1H), 3.89-3.76 (m, 4H), 3.70 (dd, J = 14.1, 7.6 Hz, 1H), 3.21 (dt, J = 17.0, 7.2 Hz, 1H), 3.05 (dt, J = 16.9, 6.9 Hz, 1H), 2.88 (t, J = 7.1 Hz, 2H), 2.09 (dt, J = 12.1, 7.6 Hz, 1H), 1.92 (ddd, J = 19.6, 13.4, 7.1 Hz, 2H), 1.65 (dt, J = 19.6, 7.6 Hz, 1H) | 494 (M + H)⁺ |
| 199 | 2-{[(3,5-dimethyl-1,2-oxazol-4-yl)acetyl][(2R)-tetrahydrofuran-2-ylmethyl]amino}-N-(imidazo[1,2-a]pyridin-7-ylmethyl)-1,3-thiazole-5-carboxamide | ¹H NMR (400 MHz, methanol-d₄) δ 8.74 (d, J = 7.0 Hz, 1H), 8.17 (d, J = 2.0 Hz, 1H), 8.11 (s, 1H), 7.99 (d, J = 2.2 Hz, 1H), 7.79 (s, 1H), 7.47 (d, J = 7.1 Hz, 1H), 4.72 (s, 2H), 4.68 (d, J = 13.1 Hz, 1H), 4.39-4.19 (m, 3H), 4.03-3.88 (m, 2H), 3.77 (dd, J = 13.8, 7.6 Hz, 1H), 2.32 (s, 3H), 2.23-2.11 (m, 4H), 2.09-1.91 (m, 2H), 1.77-1.63 (m, 1H) | (APCI(+)) m/e 495 (M + H)⁺ |
| 202 | N-(imidazo[1,2-a]pyridin-7-ylmethyl)-2-{[(1-methyl-1H-pyrazol-4-yl)acetyl][(2R)-tetrahydrofuran-2-ylmethyl]amino}-1,3-thiazole-5-carboxamide | ¹H NMR (400 MHz, methanol-d₄) δ 9.20 (s, 1H), 8.74 (d, J = 7.2 Hz, 1H), 8.17 (d, J = 2.0 Hz, 1H), 8.10 (s, 1H), 7.99 (d, J = 2.1 Hz, 1H), 7.79 (s, 1H), 7.57 (s, 1H), 7.47 (d, J = 5.9 Hz, 1H), 7.42 (s, 1H), 4.72 (s, 2H), 4.59 (d, J = 13.1 Hz, 1H), 4.31 (t, J = 7.1 Hz, 1H), 4.22 (dd, J = 14.7, 9.1 Hz, 1H), 4.11 (s, 2H), 3.92 (dd, J = 14.9, 6.9 Hz, 1H), 3.87 (s, 3H), 3.76 (dd, J = 14.2, 7.7 Hz, 1H), 2.19-2.06 (m, 1H), 2.00 (d, J = 7.3 Hz, 1H), 1.94 (dd, J = 13.4, 6.2 Hz, 1H), 1.69 (dt, J = 15.5, 7.5 Hz, 1H) | (APCI(+)) m/e 480 (M + H)⁺ |
| 203 | N-(imidazo[1,2-a]pyridin-7-ylmethyl)-2-{[3-(1-methyl-1H-pyrrol-2-yl)propanoyl][(2R)-tetrahydrofuran-2-ylmethyl]amino}-1,3-thiazole-5-carboxamide | ¹H NMR (400 MHz, methanol-d₄) δ 8.74 (d, J = 7.0 Hz, 1H), 8.17 (d, J = 2.0 Hz, 1H), 8.10 (s, 1H), 7.99 (d, J = 2.1 Hz, 1H), 7.80 (s, 1H), 7.47 (d, J = 7.0 Hz, 1H), 6.54 (d, J = 2.5 Hz, 1H), 5.91 (t, J = 3.1 Hz, 1H), 5.83 (s, 1H), 4.72 (s, 2H), 4.50 (dd, J = 14.9, 2.3 Hz, 1H), 4.28 (t, J = 6.8 Hz, 1H), 4.12 (dd, J = 14.8, 8.9 Hz, 1H), 3.85 (dd, J = 14.9, 6.8 Hz, 1H), 3.77-3.65 (m, 1H), 3.58 (s, 3H), 3.25 (t, J = 8.4 Hz, 1H), 3.16-3.02 (m, 1H), 2.96 (t, J = 7.4 Hz, 2H), 2.10 (dt, J = 12.0, 7.3 Hz, 1H), 2.04-1.81 (m, 2H), 1.66 (dt, J = 15.7, 7.4 Hz, 1H) | (APCI(+)) m/e 493 (M + H)⁺ |

Example 58 tert-butyl 4-{4-[(imidazo[1,2-a]pyridin-6-ylcarbamoyl)amino]butyl}piperidine-1-carboxylate The title compound was prepared as described in Example 1C, substituting tert-butyl 4-(4-aminobutyl)piperidine-1-carboxylate for 4-amino-N-isopentylbenzamide. ¹H NMR (500 MHz, DMSO-d₆, Temp=90° C.) δ ppm 8.79-8.76 (m, 1H), 8.10 (bs, 1H), 7.81-7.78 (m, 1H), 7.45-7.37 (m, 2H), 7.02 (dd, J=9.5, 2.1 Hz, 1H), 6.04-5.96 (m, 1H), 3.93-3.85 (m, 2H), 3.14-3.06 (m, 2H), 2.75-2.63 (m, 2H), 1.67-1.57 (m, 2H), 1.50-1.19 (m, 16H), 1.07-0.91 (m, 2H); MS (ESI(+)) m/e 416 (M+H)⁺.

Example 59

4-{[(imidazo[1,2-a]pyridin-6-ylmethyl)carbamoyl]amino}-N-(3-methylbutyl)benzamide The title compound was prepared as described in Example 1, substituting imidazo[1,2-a]pyridin-6-ylmethanamine for imidazo[1,2-a]pyridin-6-amine in Example 1C. ¹H NMR (500 MHz, DMSO-d₆) δ ppm 8.87 (s, 1H), 8.46-8.41 (m, 1H), 8.23-8.15 (m, 1H), 7.97-7.93 (m, 1H), 7.76-7.70 (m, 2H), 7.57-7.51 (m, 2H), 7.49-7.43 (m, 2H), 7.21 (dd, J=9.2, 1.7 Hz, 1H), 6.77 (t, J=5.9 Hz, 1H), 4.30 (d, J=5.8 Hz, 2H), 3.29-3.19 (m, 2H), 1.67-1.53 (m, 1H), 1.45-1.35 (m, 2H), 0.93-0.87 (m, 6H); MS (ESI(+)) m/e 380 (M+H)⁺.

Example 60

2-cyclopentyl-N-(4-{[(imidazo[1,2-a]pyridin-6-ylmethyl)carbamoyl]amino}phenyl)acetamide The title compound was prepared as described in Example 3, substituting imidazo[1,2-a]pyridin-6-ylmethanamine for imidazo[1,2-a]pyridin-6-amine in Example 3A. $^1$H NMR (400 MHz, DMSO-$d_6$, Temp=90° C.) δ 9.34 (bs, 1H), 8.71 (s, 1H), 8.38-8.33 (m, 1H), 8.23 (d, J=1.9 Hz, 1H), 7.97 (d, J=1.9 Hz, 1H), 7.86-7.75 (m, 2H), 7.44-7.38 (m, 2H), 7.32-7.26 (m, 2H), 6.69-6.62 (m, 1H), 4.43-4.38 (m, 2H), 2.29-2.18 (m, 3H), 1.81-1.68 (m, 2H), 1.67-1.45 (m, 4H), 1.29-1.15 (m, 2H); MS (ESI(+)) m/e 392 (M+H)$^+$.

Example 62

1-imidazo[1,2-a]pyridin-6-yl-3-(4-{1-[(propan-2-yloxy)acetyl]piperidin-4-yl}butyl)urea

Example 62A

4-{4-[(imidazo[1,2-a]pyridin-6-ylcarbamoyl)amino]butyl}piperidine

The title compound was prepared as described in Example 28A, substituting tert-butyl 4-{4-[(imidazo[1,2-a]pyridin-6-ylcarbamoyl)amino]butyl}piperidine-1-carboxylate for tert-butyl 4-(4-(3-imidazo[1,2-a]pyridin-6-ylureido)phenyl)-5,6-dihydropyridine-1(2H)-carboxylate.

Example 62B

1-imidazo[1,2-a]pyridin-6-yl-3-(4-{1-[(propan-2-yloxy)acetyl]piperidin-4-yl}butyl)urea The title compound was prepared as described in Example 1A, substituting 4-{4-[(imidazo[1,2-a]pyridin-6-ylcarbamoyl)amino]butyl}piperidine for 3-methylbutan-1-amine and 2-isopropoxyacetic acid for 4-nitrobenzoic acid. $^1$H NMR (400 MHz, DMSO-$d_6$/$D_2$O) δ ppm 9.18 (dd, J=1.9, 0.8 Hz, 1H), 8.30-8.19 (m, 1H), 7.98 (d, J=2.1 Hz, 1H), 7.84 (d, J=9.7 Hz, 1H), 7.76-7.72 (m, 1H), 4.03 (s, 4H), 3.72-3.52 (m, 1H), 3.14 (t, J=6.9 Hz, 2H), 2.77 (s, 2H), 1.69 (dd, J=12.9, 2.3 Hz, 2H), 1.58-1.40 (m, 4H), 1.41-1.31 (m, 2H), 1.31-1.21 (m, 2H), 1.11 (t, J=5.2 Hz, 6H), 1.03 (d, J=10.2 Hz, 2H); MS (ESI(+)) m/e 416 (M+H)$^+$.

TABLE 5

The following Examples were prepared essentially as described in Example 62, substituting the appropriate carboxylic acid in Example 62B. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 63 | 1-{4-[1-(1,4-dioxan-2-ylcarbonyl)piperidin-4-yl]butyl}-3-imidazo[1,2-a]pyridin-6-ylurea | $^1$H NMR (400 MHz, DMSO-$d_6$/$D_2$O, Temp = 90° C.) δ ppm 9.17 (dd, J = 2.0, 0.8 Hz, 1H), 8.23 (d, J = 1.7 Hz, 1H), 7.97 (d, J = 2.1 Hz, 1H), 7.83 (d, J = 9.7 Hz, 1H), 7.74 (dd, J = 9.7, 1.9 Hz, 1H), 4.27 (dt, J = 16.5, 8.3 Hz, 1H), 3.80 – 3.70 (m, 2H), 3.70 – 3.58 (m, 3H), 3.58 – 3.43 (m, 1H), 3.13 (q, J = 7.1 Hz, 2H), 1.69 (d, J = 11.6 Hz, 2H), 1.56 – 1.43 (m, 4H), 1.42 – 1.21 (m, 6H), 1.03 (s, 2H) | (ESI(+)) m/e 430 (M + H)$^+$ |
| 64 | 1-{4-[1-(cyclopropylacetyl)piperidin-4-yl]butyl}-3-imidazo[1,2-a]pyridin-6-ylurea | $^1$H NMR (400 MHz, DMSO-$d_6$/$D_2$O, Temp = 90° C.) δ ppm 9.25 – 9.11 (m, 1H), 8.24 (d, J = 1.8 Hz, 1H), 7.98 (d, J = 2.0 Hz, 1H), 7.84 (d, J = 9.7 Hz, 1H), 7.81 – 7.71 (m, 1H), 3.98 (s, 1H), 3.24 – 3.06 (m, 3H), 2.23 (d, J = 6.7 Hz, 2H), 1.68 (d, J = 12.9 Hz, 2H), 1.61 – 1.41 (m, 4H), 1.39 – 1.20 (m, 4H), 1.09 – 0.85 (m, 4H), 0.49 – 0.35 (m, 2H), 0.22 – 0.05 (m, 2H) | (ESI(+)) m/e 398 (M + H)$^+$ |
| 65 | 1-imidazo[1,2-a]pyridin-6-yl-3-{4-[1-(4,4,4-trifluorobutanoyl)piperidin-4-yl]butyl}urea | $^1$H NMR (400 MHz, DMSO-$d_6$/$D_2$O, Temp = 90° C.) δ ppm 9.24 – 9.11 (m, 1H), 8.23 (d, J = 2.1 Hz, 1H), 7.97 (d, J = 2.0 Hz, 1H), 7.83 (d, J = 9.7 Hz, 1H), 7.77 – 7.69 (m, 1H), 3.14 (t, J = 6.9 Hz, 2H), 2.56 (dd, J = 10.8, 4.4 Hz, 3H), 2.51 – 2.40 (m, 2H), 1.69 (d, J = 12.0 Hz, 2H), 1.63 – 1.43 (m, 4H), 1.41 – 1.22 (m, 4H), 0.98 (dd, J = 36.1, 8.5 Hz, 2H) | (ESI(+)) m/e 440 (M + H)$^+$ |
| 66 | 1-imidazo[1,2-a]pyridin-6-yl-3-{4-[1-(tetrahydro-2H-pyran-4-ylacetyl)piperidin-4-yl]butyl}urea | $^1$H NMR (400 MHz, DMSO-$d_6$/$D_2$O, Temp = 90° C.) δ ppm 9.17 (dd, J = 1.9, 0.8 Hz, 1H); 8.23 (d, J = 2.0 Hz, 1H), 7.97 (d, J = 2.1 Hz, 1H), 7.82 (d, J = 9.3 Hz, 1H), 7.73 (dd, J = 9.7, 1.9 Hz, 1H), 7.55 (dd, J = 8.4, 4.5 Hz, 2H), 4.46 (d, J = 12.6 Hz, 2H), 3.16 (dd, J = 18.1, 11.2 Hz, 2H), 2.78 (t, J = 12.3 Hz, 3H), 1.68 (d, J = 9.8 Hz, 2H), 1.54 – 1.42 (m, 4H), 1.33 (s, 8H), 1.26 (t, J = 7.0 Hz, 3H), 1.11 – 0.99 (m, 2H) | (ESI(+)) m/e 402 (M + H)$^+$ |
| 67 | 1-imidazo[1,2-a]pyridin-6-yl-3-{4-[1-(tetrahydrofuran-2- | $^1$H NMR (400 MHz, DMSO-$d_6$/$D_2$O, Temp = 90° C.) δ ppm 9.17 (dd, J = 1.9, 0.8 | (ESI(+)) m/e 442 |

TABLE 5-continued

The following Examples were prepared essentially as described in Example 62, substituting the appropriate carboxylic acid in Example 62B. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
|  | ylacetyl)piperidin-4-yl]butyl}urea | Hz, 1H), 8.30 – 8.19 (m, 1H), 7.98 (d, J = 2.1 Hz, 1H), 7.83 (d, J = 9.6 Hz, 1H), 7.75 (dd, J = 9.6, 1.9 Hz, 1H), 3.88 – 3.71 (m, 2H), 3.14 (t, J = 6.9 Hz, 2H), 2.23 (t, J = 6.9 Hz, 2H), 1.91 (ttd, J = 10.7, 6.9, 3.5 Hz, 1H), 1.68 (d, J = 12.1 Hz, 2H), 1.56 (t, J = 12.5 Hz, 2H), 1.53 – 1.42 (m, 4H), 1.42 – 1.28 (m, 2H), 1.22 (m, 4H), 0.99 (d, J = 10.1 Hz, 2H) | (M + H)$^+$ |
| 68 | 1-{4-[1-(cyclopentylcarbonyl)piperidin-4-yl]butyl}-3-imidazo[1,2-a]pyridin-6-ylurea | $^1$H NMR (400 MHz, DMSO-d$_6$/D$_2$O, Temp = 90° C.) δ ppm 9.23 – 9.13 (m, 1H), 8.23 (d, J = 2.1 Hz, 1H), 7.97 (d, J = 2.0 Hz, 1H), 7.83 (d, J = 9.7 Hz, 1H), 7.82 – 7.71 (m, 1H), 4.12 (s, 2H), 3.98 (s, 1H), 3.14 (t, J = 6.9 Hz, 2H), 3.04 – 2.89 (m, 2H), 2.77 (s, 2H), 1.87 – 1.59 (m, 8H), 1.51 – 1.33 (m, 6H), 1.40 – 1.10 (m, 4H), 1.08 – 0.91 (m, 2H) | (ESI(+)) m/e 412 (M + H)$^+$ |
| 69 | 1-imidazo[1,2-a]pyridin-6-yl-3-{4-[1-(tetrahydro-2H-pyran-4-ylcarbonyl)piperidin-4-yl]butyl}urea | $^1$H NMR (400 MHz, DMSO-d$_6$/D$_2$O, Temp = 90° C.) δ 9 ppm. 23 – 9.14 (m, 1H), 8.24 (d, J = 1.9 Hz, 1H), 7.98 (d, J = 2.1 Hz, 1H), 7.84 (d, J = 9.7 Hz, 1H), 7.79 – 7.68 (m, 1H), 4.11 (s, 2H), 3.88 – 3.77 (m, 2H), 3.51 – 3.36 (m, 2H), 3.21 – 3.09 (m, 2H), 2.92 – 2.73 (m, 2H), 1.76 – 1.56 (m, 4H), 1.56 – 1.42 (m, 6H), 1.45 – 1.18 (m, 4H), 1.04 – 0.87 (m, 2H) | (ESI(+)) m/e 428 (M + H)$^+$ |
| 70 | 1-imidazo[1,2-a]pyridin-6-yl-3-(4-{1-[(2-methoxyethoxy)acetyl]piperidin-4-yl}butyl)urea | $^1$H NMR (400 MHz, DMSO-d$_6$/D$_2$O, Temp = 90° C.) δ ppm 9.17 (dd, J = 1.9, 0.8 Hz, 1H), 8.24 (d, J = 1.9 Hz, 1H), 7.98 (d, J = 2.1 Hz, 1H), 7.84 (d, J = 9.7 Hz, 1H), 7.75 (dd, J = 9.7, 1.9 Hz, 1H), 4.09 (d, J = 7.6 Hz, 2H), 3.56 (dd, J = 6.0, 3.8 Hz, 2H), 3.47 (dd, J = 5.7, 3.7 Hz, 2H), 3.26 (s, 2H), 3.19 – 3.07 (m, 2H), 1.68 (dd, J = 13.0, 2.2 Hz, 2H), 1.48 (dt, J = 14.1, 7.0 Hz, 4H), 1.40 – 1.22 (m, 6H), 1.04 (d, J = 9.3 Hz, 2H) | (ESI(+)) m/e 432 (M + H)$^+$ |
| 71 | 1-imidazo[1,2-a]pyridin-6-yl-3-{4-[1-(morpholin-4-ylacetyl)piperidin-4-yl]butyl}urea | $^1$H NMR (400 MHz, DMSO-d$_6$/D$_2$O, Temp = 90° C.) δ ppm 9.26 – 9.11 (m, 1H), 8.23 (d, J = 1.8 Hz, 1H), 7.98 (d, J = 2.1 Hz, 1H), 7.83 (t, J = 8.1 Hz, 1H), 7.80 – 7.71 (m, 1H), 4.22 (s, 2H), 3.98 (s, 1H), 3.93 – 3.84 (m, 4H), 3.62 (s, 1H), 3.18 – 3.07 (m, 2H), 2.71 (s, 2H), 1.80 – 1.67 (m, 2H), 1.51 (dq, J = 21.7, 7.0 Hz, 4H), 1.42 – 1.20 (m, 6H), 1.07 (s, 2H) | (ESI(+)) m/e 443 (M + H)$^+$ |
| 72 | 1-imidazo[1,2-a]pyridin-6-yl-3-{4-[1-(tetrahydrofuran-3-ylcarbonyl)piperidin-4-yl]butyl}urea | $^1$H NMR (400 MHz, DMSO-d$_6$/D$_2$O, Temp = 90° C.) δ ppm 9.25 – 9.14 (m, 1H), 8.24 (d, J = 1.9 Hz, 1H), 7.98 (d, J = 2.0 Hz, 1H), 7.84 (d, J = 9.7 Hz, 1H), 7.79 – 7.69 (m, 1H), 3.85 (t, J = 8.1 Hz, 2H), 3.70 (h, J = 7.8 Hz, 4H), 3.20 – 3.08 (m, 2H), 2.09 – 1.91 (m, 2H), 1.70 (d, J = 12.1 Hz, 2H), 1.61 – 1.43 (m, 4H), 1.37 – 1.24 (m, 4H), 1.08 – 0.88 (m, 2H) | (ESI(+)) m/e 414 (M + H)$^+$ |
| 73 | 1-imidazo[1,2-a]pyridin-6-yl-3-{4-[1-(tetrahydrofuran-3-ylacetyl)piperidin-4-yl]butyl}urea | $^1$H NMR (400 MHz, DMSO-d$_6$/D$_2$O, Temp = 90° C.) δ ppm 9.22 – 9.12 (m, 1H), 8.24 (d, J = 2.1 Hz, 1H), 7.98 (d, J = 2.0 Hz, 1H), 7.84 (d, J = 9.7 Hz, 1H), 7.79 – 7.69 (m, 1H), 3.98 (s, 1H), 3.86 – 3.76 (m, 1H), 3.75 – 3.68 (m, 1H), 3.68 – 3.57 (m, 1H), 3.28 – 3.23 (m, 1H), 3.14 (t, J = 6.9 Hz, 2H), 2.50 – 2.43 (m, 1H), 2.43 – 2.30 (m, 2H), 2.09 – 1.92 (m, 1H), 1.68 (d, J = 13.3 Hz, 2H), 1.56 – 1.41 (m, 6H), 1.38 – 1.29 (m, 2H), 1.25 (dd, J = 14.2, 6.0 Hz, 2H), 1.00 (d, J = 10.2 Hz, 2H) | (ESI(+)) m/e 428 (M + H)$^+$ |
| 74 | 1-imidazo[1,2-a]pyridin-6-yl-3-{4-[1-(tetrahydrofuran-2-ylcarbonyl)piperidin-4-yl]butyl}urea | $^1$H NMR (400 MHz, DMSO-d$_6$/D$_2$O, Temp = 90° C.) δ ppm 9.18 (d, J = 1.1 Hz, 1H), 8.24 (d, J = 2.0 Hz, 1H), 7.98 (d, J = 2.0 Hz, 1H), 7.84 (d, J = 9.6 Hz, 1H), 7.79 – 7.65 (m, 1H), 4.59 (t, J = 6.7 Hz, 1H), | (ESI(+)) m/e 414 (M + H)$^+$ |

TABLE 5-continued

The following Examples were prepared essentially as described in Example 62, substituting the appropriate carboxylic acid in Example 62B. Some products were purified by flash chromatography while others were purified by reverse-phase HPLC. Accordingly, some Examples were isolated as trifluoroacetic acid salts.

| Ex | Name | $^1$H NMR | MS |
|---|---|---|---|
| 107 | 1-[4-(1-benzoylpiperidin-4-yl)butyl]-3-imidazo[1,2-a]pyridin-6-ylurea | 4.12 (s, 2H), 3.88 – 3.62 (m, 2H), 3.16 (dd, J = 18.1, 11.3 Hz, 2H), 2.02 – 1.93 (m, 2H), 1.93 – 1.72 (m, 2H), 1.69 (d, J = 12.7 Hz, 2H), 1.58 – 1.43 (m, 4H), 1.42 – 1.19 (m, 5H), 1.17 – 0.87 (m, 2H) $^1$H NMR (400 MHz, methanol-d$_4$) δ ppm 8.82 – 8.77 (m, 1H), 7.76 (s, 1H), 7.50 (s, 1H), 7.48 – 7.40 (m, 4H), 7.42 – 7.33 (m, 2H), 7.09 (dd, J = 9.5, 2.0 Hz, 1H), 4.65 – 4.57 (m, 1H), 3.74 – 3.65 (m, 1H), 3.21 (t, J = 6.9 Hz, 2H), 3.13 – 3.03 (m, 1H), 2.88 – 2.78 (m, 1H), 1.90 – 1.82 (m, 1H), 1.74 – 1.46 (m, 4H), 1.48 – 1.26 (m, 4H), 1.28 – 1.04 (m, 2H) | (ESI(+)) m/e 420 (M + H)$^+$ |
| 270 | 1-[4-(1-benzoylpiperidin-4-yl)butyl]-3-imidazo[1,2-a]pyridin-7-ylurea | | (ESI(+)) m/e 420 (M + H)$^+$ |

Example 75

N-(imidazo[1,2-a]pyridin-6-ylmethyl)-5-[1-(2-methylpropyl)-1H-pyrazol-4-yl]thiophene-2-carboxamide

Example 75A 5-bromo-N-(imidazo[1,2-a]pyridin-6-ylmethyl)thiophene-2-carboxamide The title compound was prepared as described in Example 1A, substituting imidazo[1,2-a]pyridin-6-ylmethanamine for 3-methylbutan-1-amine and 5-bromothiophene-2-carboxylic acid for 4-nitrobenzoic acid.

Example 75B

N-(imidazo[1,2-a]pyridin-6-ylmethyl)-5-[1-(2-methylpropyl)-1H-pyrazol-4-yl]thiophene-2-carboxamide The title compound was prepared as described in Example 51A, substituting 5-bromo-N-(imidazo[1,2-a]pyridin-6-ylmethyl)thiophene-2-carboxamide for 4-bromoaniline. $^1$H NMR (400 MHz, DMSO-d$_6$) δ ppm 8.99 (t, J=5.8 Hz, 1 H), 8.46 (s, 1 H), 8.14 (s, 1 H), 7.95 (s, 1 H), 7.79 (s, 1 H), 7.69 (d, J=3.9 Hz, 1 H), 7.49-7.58 (m, 2 H), 7.20 (d, J=4.0 Hz, 2 H), 4.43 (d, J=5.7 Hz, 2 H), 3.91 (d, J=7.2 Hz, 2 H), 2.11 (dq, J=13.6, 6.8 Hz, 1 H), 0.84 (d, J=6.7 Hz, 6 H); MS (ESI(+)) m/e 380 (M+H)$^+$.

TABLE 6

The following Examples were prepared essentially as described in Example 75, substituting the appropriate carboxylic acid and amine in Example 75A and the appropriate boronate in Example 75B. Some boronates were Boc-protected and required deprotection as in Example 28A.

| Ex | Name | $^1$H NMR | MS |
|---|---|---|---|
| 120 | N-(imidazo[1,2-a]pyridin-6-ylmethyl)-5-[1-(2-methylpropyl)-1H-pyrazol-4-yl]furan-2-carboxamide | $^1$H NMR (400 MHz, DMSO-d$_6$) ppm 8.87 (t, J = 6.0 Hz, 1 H), 8.46 (2, 1 H), 8.14 (s, 1 H), 7.96 (s, 1 H), 7.87 (s, 1 H), 7.53 (d, J = 6.8 Hz, 2 H), 7.21 (dd, J = 9.3, 1.4 Hz, 1 H), 7.14 (d, J = 3.6 Hz, 1 H), 6.64 (d, J = 3.5 Hz, 1 H), 4.44 (d, J = 6.0 Hz, 2 H), 3.94 (d, J = 7.2 Hz, 2 H), 2.11 (dq, J = 13.6, 6.8 Hz, 1 H), 0.83 (d, J = 6.7 Hz, 6 H) | (ESI(+)) m/e 364 (M + H)$^+$ |
| 174 | N-(imidazo[1,2-a]pyridin-7-ylmethyl)-5-[1-(2-methylpropyl)-1H-pyrazol-4-yl]thiophene-2-carboxamide | $^1$H NMR (400 MHz, DMSO-d$_6$) ppm 9.04 (t, J = 6.0 Hz, 1 H), 8.48 (d, J = 7.0 Hz, 1 H), 8.14 (s, 1 H), 7.88 (s, 1 H), 7.80 (s, 1 H), 7.73 (d, J = 3.8 Hz, 1 H), 7.51 (s, 1 H), 7.38 (s, 1 H), 7.21 (d, J = 3.9 Hz, 1 H), 6.84 (dd, J = 7.0, 1.5 Hz, 1 H), 4.46 (d, J = 5.9 Hz, 2 H), 3.91 (d, J = 7.3 Hz, 2 H), 2.11 (dq, J = 13.6, 6.7, 6.6 Hz, 1 H), 0.84 (d, J = 6.7 Hz, 6 H) | (ESI(+)) m/e 380 (M + H)$^+$ |
| 175 | N-(imidazo[1,2-a]pyridin-6-ylmethyl)-5-[1-(2-methylpropanoyl)-1H-pyrazol-4-yl]thiophene-2-carboxamide | $^1$H NMR (400 MHz, DMSO-d$_6$) ppm 9.09 (t, J = 5.9 Hz, 1 H), 8.81 (s, 1 H), 8.47 (s, 1 H), 8.31 (s, 1 H), 7.95 (s, 1 H), 7.76 (d, J = 3.9 Hz, 1 H), 7.54 (t, J = 4.6 Hz, 2 H), 7.50 (d, J = 3.9 Hz, 1 H), 7.20 (dd, J = 9.2, 1.5 Hz, 1 H), 4.44 (d, J = 5.9 Hz, 2 H), 3.77 (dq, J = 6.9 Hz, 1 H), 1.21 (d, J = 6.9 Hz, 6 H) | |

TABLE 6-continued

The following Examples were prepared essentially as described in Example 75, substituting the appropriate carboxylic acid and amine in Example 75A and the appropriate boronate in Example 75B. Some boronates were Boc-protected and required deprotection as in Example 28A.

| Ex | Name | $^1$H NMR | MS |
|---|---|---|---|
| 176 | 5-[1-(2-hydroxy-2-methylpropyl)-1H-pyrazol-4-yl]-N-(imidazo[1,2-a]pyridin-6-ylmethyl)thiophene-2-carboxamide | $^1$H NMR (400 MHz, DMSO-d$_6$) ppm 9.00 (t, J = 5.9 Hz, 1 H), 8.46 (s, 1 H), 8.03 (s, 1 H), 7.95 (s, 1 H), 7.78 (s, 1 H), 7.69 (d, J = 3.8 Hz, 1 H), 7.49 – 7.58 (m, 2 H), 7.16 – 7.25 (m, 2 H), 4.76 (s, 1 H), 4.42 (d, J = 5.7 Hz, 2 H), 4.01 (s, 2 H), 1.06 (s, 6 H) | (ESI(+)) m/e 396 (M + H)$^+$ |
| 177 | N-(imidazo[1,2-a]pyridin-6-ylmethyl)-5-{1-[(3-methyloxetan-3-yl)methyl]-1H-pyrazol-4-yl}thiophene-2-carboxamide | $^1$H NMR (400 MHz, DMSO-d$_6$) ppm 9.00 (t, J = 5.9 Hz, 1 H), 8.46, (s, 1 H), 8.19 (s, 1 H), 7.95 (s, 1 H), 7.83 (s, 1 H), 7.70 (d, J = 3.9 Hz, 1 H), 7.48 – 7.58 (m, 2 H). 7.15 – 7.24 (m, 2 H), 4.59 (d, J = 6.0 Hz, 2 H), 4.42 (d, J = 5.9 Hz, 2 H), 4.33 (s, 2 H), 4.22 (d, J = 6.0 Hz, 2 H), 1.13 (s, 3 H) | |
| 178 | 5-[1-(cyclobutylmethyl)-1H-pyrazol-4-yl]-N-(imidazo[1,2-a]pyridin-6-ylmethyl)thiophene-2-carboxamide | $^1$H NMR (400 MHz, DMSO-d$_6$) ppm 8.99 (t, J = 5.9 Hz, 1 H), 8.46 (s, 1 H), 8.13 (s, 1 H), 7.95 (s, 1 H), 7.77 (s, 1 H), 7.69 (d, J = 3.9 Hz, 1 H), 7.48 – 7.57 (m, 2 H), 7.16 – 7.23 (m, 2 H), 4.42 (d, J = 5.7 Hz, 2 H), 4.12 (d, J = 7.3 Hz, 2 H), 2.74 (dq, J = 7.5, 7.4 Hz, 1 H), 1.90 – 2.02 (m, 2 H), 1.67 – 1.90 (m, 4 H) | |
| 179 | 5-[1-(cyclohexylmethyl)-1H-pyrazol-4-yl]-N-(imidazo[1,2-a]pyridin-6-ylmethyl)thiophene-2-carboxamide | $^1$H NMR (400 MHz, DMSO-d$_6$) ppm 8.99 (t, J = 5.9 Hz, 1 H), 8.46 (s, 1 H), 8.12 (s, 1 H), 7.95 (s, 1 H), 7.78 (s, 1 H), 7.69 (d, J = 3.9 Hz, 1 H), 7.48 – 7.57 (m, 2 H), 7.14 – 7.26 (m, 2 H), 4.42 (d, J = 5.9 Hz, 2 H), 3.93 (d, J = 7.2 Hz, 2 H), 1.72 – 1.88 (m, 1 H), 1.54 - 1.70 (m, 3 H), 1.50 (d, J = 12.1 Hz, 2 H), 1.03 – 1.28 (m, 3 H), 0.85 – 1.01 (m, 2 H) | (ESI(+)) m/e 420 (M + H)$^+$ |
| 180 | 5-{1-[(2R)-2-hydroxybutyl]-1H-pyrazol-4-yl}-N-(imidazo[1,2-a]pyridin-6-ylmethyl)thiophene-2-carboxamide | $^1$H NMR (400 MHz, DMSO-d$_6$) ppm 8.99 (t, J = 5.8 Hz, 1 H), 8.46 (s, 1 H), 8.08 (s, 1 H), 7.95 (s, 1 H), 7.78 (s, 1 H), 7.69 (d, J = 3.9 Hz, 1 H), 7.50 – 7.58 (m, 2 H), 7.17 – 7.23 (m, 2 H), 4.92 (d, J = 5.4 Hz, 1 H), 4.42 (d, J = 5.7 Hz, 2 H), 4.03 – 4.12 (m, 1 H), 3.93 – 4.02 (m, 1 H), 3.66 – 3.76 (m, 1 H), 1.20 – 1.44 (m, 2 H), 0.88 (t, J = 7.4 Hz, 3 H) | |
| 182 | 5-[1-(2-hydroxy-2-methylpropyl)-1H-pyrazol-4-yl]-N-(imidazo[1,2-a]pyridin-7-ylmethyl)thiophene-2-carboxamide | $^1$H NMR (400 MHz, DMSO-d$_6$) ppm 9.04 (t, J = 5.9 Hz, 1 H), 8.48 (d, J = 7.0 Hz, 1 H), 8.04 (s, 1 H), 7.88 (s, 1 H), 7.79 (s, 1 H), 7.73 (d, J = 3.8 Hz, 1 H), 7.51 (s, 1 H), 7.38 (s, 1 H), 7.23 (d, J = 3.8 Hz, 1 H), 6.84 (dd, J = 7.0, 1.3 Hz, 1 H), 4.75 (s, 1 H), 4.46 (d, J = 5.9 Hz, 2 H), 4.01 (s, 2 H), 1.07 (s, 6 H) | |
| 186 | N-(imidazo[1,2-a]pyridin-6-ylmethyl)-5-[1-(tetrahydro-2H-pyran-2-ylmethyl)-1H-pyrazol-4-yl]thiophene-2-carboxamide | $^1$H NMR (400 MHz, DMSO-d$_6$) ppm 9.00 (t, J = 5.8 Hz, 1 H), 8.46 (s, 1 H), 8.07 (s, 1 H), 7.95 (s, 1 H), 7.78 (s, 1 H), 7.69 (d, J = 3.8 Hz, 1 H), 7.48 – 7.57 (m, 2 H), 7.14 – 7.27 (m, 2 H), 4.42 (d, J = 5.9 Hz, 2 H), 4.05 – 4.15 (m, 2 H), 3.83 (d, J = 11.1 Hz, 1 H), 3.55 – 3.71 (m, 1 H), 3.19 – 3.37 (m, 2 H), 1.68 – 1.85 (m, 1 H), 1.48 – 1.63 (m, 1 H), 1.32 – 1.50 (m, 2 H), 1.06 – 1.29 (m, 1 H) | (ESI(+)) m/e 422 (M + H)$^+$ |
| 200 | N-(imidazo[1,2-a]pyridin-6-ylmethyl)-5-[1-(tetrahydrofuran-3-ylmethyl)-1H-pyrazol-4-yl]thiophene-2-carboxamide | $^1$H NMR (400 MHz, DMSO-d$_6$) ppm 9.00 (t, J = 5.8 Hz, 1 H), 8.46 (s, 1 H), 8.20 (s, 1 H), 7.95 (s, 1 H), 7.81 (s, 1 H), 7.69 (d, J = 3.9 Hz, 1 H), 7.49 – 7.57 (m, 2 H), 7.15 – 7.24 (m, 2 H), 4.42 (d, J = 5.7 Hz, 2 H), 4.10 (d, J = 7.5 Hz, 2 H), 3.69 – 3.79 (m, 1 H), 3.56 – 3.70 (m, 2 H), 3.46 (dd, J = 8.7, 5.4 Hz, 2 H), 1.81 – 1.98 (m, 1 H), 1.52 – 1.65 (m, 1 H) | |
| 201 | N-(imidazo[1,2-a]pyridin-6-ylmethyl)-5-[1-(tetrahydro-2H-pyran-4-ylmethyl)-1H-pyrazol-4-yl]thiophene-2-carboxamide | $^1$H NMR (400 MHz, DMSO-d$_6$) ppm 8.99 (t, J = 5.8 Hz, 1 H), 8.46 (s, 1 H), 8.14 (s, 1 H), 7.95 (s, 1 H), 7.80 (s, 1 H), 7.69 (d, J = 3.9 Hz, 1 H), 7.48 – 7.58 (m, 2 H), 7.12 – 7.25 (m, 2 H), 4.43 (d, J = 5.7 Hz, 2 H), 4.00 (d, J = 7.2 Hz, 2 H), 3.81 (dd, J = 11.3, 2.9 Hz, 2 H), 3.24 (td, J = 11.6, 1.7 | |

TABLE 6-continued

The following Examples were prepared essentially as described in Example 75, substituting the appropriate carboxylic acid and amine in Example 75A and the appropriate boronate in Example 75B. Some boronates were Boc-protected and required deprotection as in Example 28A.

| Ex | Name | $^1$H NMR | MS |
|---|---|---|---|
| 206 | N-(imidazo[1,2-a]pyridin-6-ylmethyl)-5-[1-(tetrahydro-2H-pyran-3-ylmethyl)-1H-pyrazol-4-yl]thiophene-2-carboxamide | Hz, 2 H), 1.91 – 2.18 (m, 1 H), 1.39 (dd, J = 12.7, 1.4 Hz, 2 H), 1.14 – 1.30 (m, 2 H) $^1$H NMR (400 MHz, DMSO-d$_6$) ppm 8.99 (t, J = 5.8 Hz, 1 H), 8.46 (s, 1 H), 8.15 (s, 1 H), 7.95 (s, 1 H), 7.80 (s, 1 H), 7.69 (d, J = 3.9 Hz, 1 H), 7.53 (t, J = 4.6 Hz, 2 H), 7.15 – 7.26 (m, 2 H), 4.43 (d, J = 5.9 Hz, 2 H), 4.02 (dd, J = 7.2, 3.2 Hz, 2 H), 3.64 – 3.72 (m, 1 H), 3.61 (dd, J = 11.1, 3.3 Hz, 1 H), 3.15 (dd, J = 11.2, 8.8 Hz, 1 H), 1.96 – 2.18 (m, 1 H), 1.52 – 1.70 (m, 2 H), 1.34 – 1.51 (m, 1 H), 1.10 – 1.31 (m, 2 H) | |
| 219 | N-(imidazo[1,2-a]pyridin-6-ylmethyl)-5-[1-(tetrahydrofuran-2-ylmethyl)-1H-pyrazol-4-yl]thiophene-2-carboxamide | $^1$H NMR (400 MHz, DMSO-d$_6$) ppm 8.99 (t, J = 5.9 Hz, 1 H), 8.46 (s, 1 H), 8.10 (s, 1 H), 7.95 (s, 1 H), 7.79 (s, 1 H), 7.70 (d, J = 3.9 Hz, 1 H), 7.46 – 7.60 (m, 2 H), 7.11 – 7.26 (m, 2 H), 4.43 (d, J = 5.9 Hz, 2 H), 4.04 – 4.25 (m, 3 H), 3.69 – 3.80 (m, 1 H), 3.62 (q, J = 7.4 Hz, 1 H), 1.86 - 2.01 (m, 1 H), 1.68 - 1.84 (m, 2 H), 1.52 – 1.67 (m, 1 H) | |
| 247 | N-(imidazo[1,2-a]pyridin-7-ylmethyl)-5-[1-(tetrahydro-2H-pyran-2-ylmethyl)-1H-pyrazol-4-yl]thiophene-2-carboxamide | | (ESI(+)) m/e 422 (M + H)$^+$ |
| 248 | N-(imidazo[1,2-a]pyridin-7-ylmethyl)-5-[1-(tetrahydrofuran-2-ylmethyl)-1H-pyrazol-4-yl]thiophene-2-carboxamide | | (ESI(+)) m/e 408 (M + H)$^+$ |
| 252 | N-(imidazo[1,2-a]pyridin-7-ylmethyl)-5-[1-(tetrahydrofuran-3-ylmethyl)-1H-pyrazol-4-yl]thiophene-2-carboxamide | | (ESI(+)) m/e 408 (M + H)$^+$ |
| 253 | N-(imidazo[1,2-a]pyridin-7-ylmethyl)-5-[1-(tetrahydro-2H-pyran-3-ylmethyl)-1H-pyrazol-4-yl]thiophene-2-carboxamide | $^1$H NMR (300 MHz, DMSO-d$_6$) δ ppm 9.04 (t, J = 6.0 Hz, 1H), 8.49 (dd, J = 7.2, 1.1 Hz, 1H), 8.16 (s, 1H), 7.89 (t, J = 1.0 Hz, 1H), 7.82 (s, 1H), 7.74 (d, J = 3.9 Hz, 1H), 7.52 (d, J = 1.4 Hz, 1H), 7.40 (s, 1H), 7.22 (d, J = 3.8 Hz, 1H), 6.85 (dd, J = 7.0, 1.7 Hz, 1H), 4.48 (d, J = 5.7 Hz, 2H), 4.03 (dd, J = 7.3, 2.1 Hz, 2H), 3.76 – 3.57 (m, 2H), 3.42 – 3.32 (m, 1H), 3.17 (dd, J = 11.2, 8.7 Hz, 1H), 2.15 – 1.98 (m, 1H), 1.77 – 1.54 (m, 2H), 1.54 – 1.35 (m, 1H), 1.32 – 1.14 (m, 1H) | (ESI(+)) m/e 422 (M + H)$^+$ |
| 254 | N-(imidazo[1,2-a]pyridin-7-ylmethyl)-5-{1-[(3-methyloxetan-3-yl)methyl]-1H-pyrazol-4-yl}thiophene-2-carboxamide | | (ESI(+)) m/e 408 (M + H)$^+$ |
| 265 | N-(imidazo[1,2-a]pyridin-7-ylmethyl)-5-[1-(tetrahydro-2H-pyran-4-ylmethyl)-1H-pyrazol-4-yl]thiophene-2-carboxamide | | (ESI(+)) m/e 422 (M + H)$^+$ |
| 269 | N-(imidazo[1,2-a]pyridin-7-ylmethyl)-5-[1-(2-methoxyethyl)-1H-pyrazol-4-yl]thiophene-2-carboxamide | $^1$H NMR (300 MHz, DMSO-d$_6$) δ ppm 9.03 (t, J = 5.9 Hz, 1H), 8.53 – 8.45 (m, 1H), 8.13 (s, 1H), 7.89 (s, 1H), 7.81 (s, 1H), 7.74 (d, J = 3.9 Hz, 1H), 7.52 (d, J = 1.1 Hz, 1H), 7.40 (s, 1H), 7.22 (d, J = 3.8 Hz, 1H), 6.85 (dd, J = 7.0, 1.6 Hz, 1H), 4.48 (d, J = 5.9 Hz, 2H), 4.27 (t, J = 5.3 Hz, 2H), 3.70 (t, J = 5.3 Hz, 2H), 3.24 (s, 3H) | (ESI(+)) m/e 382 (M + H)$^+$ |
| 272 | 5-[1-(cyclohexylmethyl)-5-ethyl-1H-pyrazol-4-yl]-N-(imidazo[1,2-a]pyridin-7-ylmethyl)thiophene-2-carboxamide | $^1$H NMR (300 MHz, DMSO-d$_6$) 9.04 (t, J = 6.1 Hz, 1H), 8.49 (d, J = 7.8 Hz, 1H), 7.89 (s, 1H), 7.78 (d, J = 4.1 Hz, 1H), 7.72 (s, 1H), 7.52 (d, J = 1.0 Hz, 1H), 7.40 (s, 1H), 7.17 (d, J = 4.1 Hz, 1H), 6.85 (dd, J = 7.1, 1.7 Hz, 1H), 4.48 (d, J = 5.8 Hz, 2H), 3.90 (d, J = 7.5 Hz, 2H), 2.87 (q, J = 7.2 Hz, 2H), 1.79-1.95 (m, 1H), 1.59-1.73 (m, J = 3.4 Hz, 3H), 1.54 (d, J = 12.5 Hz, 2H), 1.09-1.25 (m, 6H), 0.93-1.08 (m, J = 11.9 Hz, 2H) | (ESI(+)) m/e 448 (M + H)$^+$ |
| 273 | N-(imidazo[1,2-a]pyridin-7-ylmethyl)-5-{1-[(1-methoxy-3,3-dimethylcyclohexyl)methyl]-5-methyl- | $^1$H NMR (300 MHz, DMSO-d$_6$) ppm 9.03 (t, J = 5.9 Hz, 1H), 8.49 (d, J = 7.1 Hz, 1H), 7.89 (s, 1H), 7.79 (d, J = 3.7 Hz, | (ESI(+)) m/e 492 (M + H)$^+$ |

TABLE 6-continued

The following Examples were prepared essentially as described in Example 75, substituting the appropriate carboxylic acid and amine in Example 75A and the appropriate boronate in Example 75B. Some boronates were Boc-protected and required deprotection as in Example 28A.

| Ex | Name | $^1$H NMR | MS |
|---|---|---|---|
|  | 1H-pyrazol-4-yl}thiophene-2-carboxamide | 1H), 7.74 (s, 1H), 7.52 (d, J = 1.0 Hz, 1H), 7.40 (s, 1H), 7.18 (d, J = 4.1 Hz, 1H), 6.85 (dd, J = 7.1, 1.7 Hz, 1H), 4.48 (d, J = 5.8 Hz, 2H), 3.97 – 4.16 (m, 2H), 3.20 (s, 3H), 2.45 (s, 3H), 1.64 – 1.78 (m, 1H), 1.27 – 1.59 (m, 4H), 0.99 – 1.24 (m, 3H), 0.96 (s, 3H), 0.85 (s, 3H) |  |
| 293 | N-(imidazo[1,2-a]pyridin-7-ylmethyl)-5-(1-propyl-1H-pyrazol-4-yl)thiophene-2-carboxamide | $^1$H NMR (300 MHz, DMSO-d$_6$) δ ppm 9.03 (s, 1H), 8.47 (t, J = 9.6 Hz, 1H), 8.17 (s, 1H), 7.89 (s, 1H), 7.80 (s, 1H), 7.74 (d, J = 3.9 Hz, 1H), 7.52 (d, J = 1.1 Hz, 1H), 7.40 (s, 1H), 7.22 (d, J = 3.8 Hz, 1H), 6.83 (dt, J = 14.9, 7.4 Hz, 1H), 4.48 (d, J = 5.9 Hz, 2H), 4.07 (t, J = 7.0 Hz, 2H), 1.81 (dd, J = 14.4, 7.2 Hz, 2H), 0.84 (t, J = 7.4 Hz, 3H) | (ESI(+)) m/e 366 (M + H)$^+$ |
| 294 | N-(imidazo[1,2-a]pyridin-7-ylmethyl)-5-{1-[2-(morpholin-4-yl)ethyl]-1H-pyrazol-4-yl}thiophene-2-carboxamide | $^1$H NMR (300 MHz, DMSO-d$_6$) δ ppm 9.03 (t, J = 5.9 Hz, 1H), 8.49 (d, J = 7.0 Hz, 1H), 8.17 (s, 1H), 7.89 (s, 1H), 7.80 (s, 1H), 7.74 (d, J = 3.9 Hz, 1H), 7.52 (d, J = 1.2 Hz, 1H), 7.40 (s, 1H), 7.22 (d, J = 3.8 Hz, 1H), 6.85 (dd, J = 7.0, 1.5 Hz, 1H), 4.48 (d, J = 5.9 Hz, 2H), 4.24 (t, J = 6.5 Hz, 2H), 3.59 – 3.49 (m, 4H), 2.72 (t, J = 6.5 Hz, 2H), 2.45 – 2.35 (m, 4H) | (ESI(+)) m/e 437 (M + H)$^+$ |
| 295 | 5-(1-ethyl-1H-pyrazol-4-yl)-N-(imidazo[1,2-a]pyridin-7-ylmethyl)thiophene-2-carboxamide | $^1$H NMR (300 MHz, DMSO-d$_6$) δ ppm 9.02 (t, J = 5.9 Hz, 1H), 8.49 (d, J = 7.0 Hz, 1H), 8.17 (s, 1H), 7.89 (s, 1H), 7.79 (s, 1H), 7.74 (d, J = 3.8 Hz, 1H), 7.52 (d, J = 1.2 Hz, 1H), 7.40 (s, 1H), 7.21 (d, J = 3.8 Hz, 1H), 6.85 (dd, J = 7.0, 1.6 Hz, 1H), 4.48 (d, J = 5.9 Hz, 2H), 4.15 (q, J = 7.3 Hz, 2H), 1.39 (t, J = 7.3 Hz, 3H) | (ESI(+)) m/e 352 (M + H)$^+$ |
| 296 | 5-[1-(1,1-dioxidotetrahydrothiophen-3-yl)-1H-pyrazol-4-yl]-N-(imidazo[1,2-a]pyridin-7-ylmethyl)thiophene-2-carboxamide | $^1$H NMR (300 MHz, DMSO-d$_6$) δ ppm 9.05 (t, J = 6.0 Hz, 1H), 8.49 (d, J = 6.9 Hz, 1H), 8.32 (s, 1H), 7.94 (s, 1H), 7.89 (s, 1H), 7.76 (d, J = 3.8 Hz, 1H), 7.52 (d, J = 1.1 Hz, 1H), 7.40 (s, 1H), 7.26 (d, J = 3.8 Hz, 1H), 6.85 (dd, J = 7.0, 1.6 Hz, 1H), 5.35 - 5.18 (m, 1H), 4.48 (d, J = 5.9 Hz, 2H), 3.75 (dd, J = 13.6, 8.2 Hz, 1H), 3.48 (m, 2H), 3.35 – 3.20 (m, 1H), 2.78 – 2.53 (m, 2H) | (ESI(+)) m/e 442 (M + H)$^+$ |
| 300 | N-(imidazo[1,2-a]pyridin-7-ylmethyl)-5-{1-[2-(methylsulfonyl)ethyl]-1H-pyrazol-4-yl}thiophene-2-carboxamide | $^1$H NMR (300 MHz, DMSO-d$_6$) δ ppm 9.04 (t, J = 6.0 Hz, 1H), 8.49 (dd, J = 7.0, 0.8 Hz, 1H), 8.25 (s, 1H), 7.89 (d, J = 1.4 Hz, 2H), 7.75 (d, J = 3.9 Hz, 1H), 7.52 (d, J = 1.2 Hz, 1H), 7.40 (s, 1H), 7.24 (d, J = 3.8 Hz, 1H), 6.85 (dd, J = 7.0, 1.7 Hz, 1H), 4.57 (t, J = 6.9 Hz, 2H), 4.48 (d, J = 5.9 Hz, 2H), 3.73 (t, J = 6.9 Hz, 2H), 2.93 (s, 3H) | (ESI(+)) m/e 430 (M + H)$^+$ |
| 304 | 5-{1-[(2R)-2-hydroxypropyl]-1H-pyrazol-4-yl}-N-(imidazo[1,2-a]pyridin-7-ylmethyl)thiophene-2-carboxamide | $^1$H NMR (300 MHz, DMSO-d$_6$) δ ppm 9.02 (t, J = 6.0 Hz, 1H), 8.49 (dd, J = 7.0, 0.7 Hz, 1H), 8.09 (s, 1H), 7.89 (s, 1H), 7.80 (d, J = 0.5 Hz, 1H), 7.74 (d, J = 3.9 Hz, 1H), 7.52 (d, J = 1.2 Hz, 1H), 7.40 (s, 1H), 7.22 (d, J = 3.8 Hz, 1H), 6.85 (dd, J = 7.0, 1.6 Hz, 1H), 4.93 (d, J = 4.7 Hz, 1H), 4.48 (d, J= 5.9 Hz, 2H), 4.11 – 3.93 (m, 3H), 1.12 – 0.98 (m, 3H) | (ESI(+)) m/e 382 (M + H)$^+$ |
| 316 | 5-[1-(1,4-dioxan-2-ylmethyl)-1H-pyrazol-4-yl]-N-(imidazo[1,2-a]pyridin-7-ylmethyl)thiophene-2-carboxamide | $^1$H NMR (300 MHz, DMSO-d$_6$) δ ppm 9.03 (t, J = 6.0 Hz, 1H), 8.49 (dd, J = 7.0, 0.7 Hz, 1H), 8.12 (s, 1H), 7.89 (s, 1H), 7.82 (s, 1H), 7.74 (d, J = 3.8 Hz, 1H), 7.52 (d, J = 1.2 Hz, 1H), 7.40 (s, 1H), 7.23 (d, J = 3.8 Hz, 1H), 6.85 (dd, J = 7.0, 1.6 Hz, 1H), 4.48 (d, J = 5.9 Hz, 2H), 4.20 – 4.14 (m, 2H), 3.96 – 3.83 (m, 1H), 3.79 – 3.70 (m, 2H), 3.68 – 3.39 (m, 3H), 3.29 – 3.21 (m, 1H) | (ESI(+)) m/e 424 (M + H)$^+$ |

TABLE 6-continued

The following Examples were prepared essentially as described in Example 75, substituting the appropriate carboxylic acid and amine in Example 75A and the appropriate boronate in Example 75B. Some boronates were Boc-protected and required deprotection as in Example 28A.

| Ex | Name | $^1$H NMR | MS |
|---|---|---|---|
| 317 | 5-[1-(2-hydroxyethyl)-1H-pyrazol-4-yl]-N-(imidazo[1,2-a]pyridin-7-ylmethyl)thiophene-2-carboxamide | $^1$H NMR (300 MHz, DMSO-d$_6$) δ ppm 9.02 (t, J = 5.9 Hz, 1H), 8.49 (dd, J = 7.0, 0.7 Hz, 1H), 8.12 (s, 1H), 7.89 (d, J = 0.8 Hz, 1H), 7.80 (d, J = 0.6 Hz, 1H), 7.74 (d, J = 3.8 Hz, 1H), 7.52 (d, J = 1.2 Hz, 1H), 7.40 (s, 1H), 7.22 (d, J = 3.9 Hz, 1H), 6.85 (dd, J = 7.0, 1.6 Hz, 1H), 4.92 (t, J = 5.3 Hz, 1H), 4.48 (d, J = 5.9 Hz, 2H), 4.15 (t, J = 5.6 Hz, 2H), 3.75 (q, J = 5.5 Hz, 2H) | (ESI(+)) m/e 368 (M + H)$^+$ |
| 344 | 5-{1-[(1,1-dioxidotetrahydro-2H-thiopyran-3-yl)methyl]-1H-pyrazol-4-yl}-N-(imidazo[1,2-a]pyridin-7-ylmethyl)thiophene-2-carboxamide | $^1$H NMR (300 MHz, DMSO-d$_6$) δ ppm 9.04 (t, J = 6.0 Hz, 1H), 8.49 (dd, J = 7.0, 0.8 Hz, 1H), 8.19 (d, J = 0.4 Hz, 1H), 7.89 (d, J = 0.8 Hz, 1H), 7.86 (d, J = 0.5 Hz, 1H), 7.75 (d, J = 3.9 Hz, 1H), 7.52 (d, J = 1.2 Hz, 1H), 7.40 (s, 1H), 7.24 (d, J = 3.9 Hz, 1H), 6.85 (dd, J = 7.0, 1.7 Hz, 1H), 4.48 (d, J = 5.8 Hz, 2H), 4.13 (d, J = 6.6 Hz, 2H), 3.09 – 2.83 (m, 4H), 2.47 – 2.40 (m, 1H), 2.14 – 1.96 (m, 1H), 1.88 – 1.69 (m, 1H), 1.69 – 1.54 (m, 1H), 1.37 – 1.14 (m, 1H) | (ESI(+)) m/e 470 (M + H)$^+$ |
| 345 | N-(imidazo[1,2-a]pyridin-7-ylmethyl)-5-(1-methyl-1H-pyrazol-4-yl)thiophene-2-carboxamide | $^1$H NMR (300 MHz, DMSO-d$_6$) δ ppm 9.03 (t, J = 6.0 Hz, 1H), 8.49 (d, J = 7.0 Hz, 1H), 8.12 (s, 1H), 7.89 (s, 1H), 7.79 (s, 1H), 7.74 (d, J = 3.8 Hz, 1H), 7.52 (d, J = 1.1 Hz, 1H), 7.40 (s, 1H), 7.21 (d, J = 3.8 Hz, 1H), 6.84 (dd, J = 7.0, 1.6 Hz, 1H), 4.48 (d, J = 5.9 Hz, 2H), 3.86 (s, 3H) | (ESI(+)) m/e 338 (M + H)$^+$ |
| 363 | N-(imidazo[1,2-a]pyridin-7-ylmethyl)-5-(1-methyl-1H-pyrazol-5-yl)thiophene-2-carboxamide | $^1$H NMR (300 MHz, DMSO-d$_6$) δ ppm 9.22 (t, J = 5.9 Hz, 1H), 8.50 (dd, J = 6.9, 0.8 Hz, 1H), 7.92 – 7.86 (m, 2H), 7.53 (d, J = 1.2 Hz, 1H), 7.48 (d, J = 2.0 Hz, 1H), 7.45 (d, J = 3.9 Hz, 1H), 7.41 (s, 1H), 6.86 (dd, J = 7.0, 1.7 Hz, 1H), 6.59 (d, J = 1.9 Hz, 1H), 4.51 (d, J = 5.9 Hz, 2H), 3.98 (s, 3H) | (ESI(+)) m/e 338 (M + H)$^+$ |
| 395 | N-(imidazo[1,2-a]pyridin-7-ylmethyl)-5-{1-[(2R)-tetrahydrofuran-2-ylmethyl]-1H-pyrazol-4-yl}thiophene-2-carboxamide | $^1$H NMR (300 MHz, DMSO-d$_6$) δ ppm 9.03 (t, J = 6.0 Hz, 1H), 8.49 (dd, J = 6.9, 1.0 Hz, 1H), 8.12 (s, 1H), 7.89 (t, J = 1.0 Hz, 1H), 7.81 (s, 1H), 7.74 (d, J = 4.0 Hz, 1H), 7.52 (d, J = 1.5 Hz, 1H), 7.40 (s, 1H), 7.23 (d, J = 4.0 Hz, 1H), 6.85 (dd, J = 7.0, 1.7 Hz, 1H), 4.48 (d, J = 5.9 Hz, 2H), 4.26 – 4.04 (m, 3H), 3.82 – 3.69 (m, 1H), 3.69 – 3.57 (m, 1H), 2.00 – 1.85 (m, 1H), 1.85 – 1.70 (m, 2H), 1.70 – 1.52 (m, 1H) | (ESI(+)) m/e 408 (M + H)$^+$ |
| 397 | N-(imidazo[1,2-a]pyridin-7-ylmethyl)-5-{1-[(2S)-tetrahydrofuran-2-ylmethyl]-1H-pyrazol-4-yl}thiophene-2-carboxamide | $^1$H NMR (300 MHz, DMSO-d$_6$) δ ppm 9.02 (t, J = 6.0 Hz, 1H), 8.49 (dd, J = 6.9, 1.0 Hz, 1H), 8.11 (d, J = 0.9 Hz, 1H), 7.89 (d, J = 0.9 Hz, 1H), 7.80 (d, J = 0.9 Hz, 1H), 7.74 (d, J = 3.9 Hz, 1H), 7.52 (d, J = 1.2 Hz, 1H), 7.43 – 7.37 (m, 1H), 7.23 (d, J = 3.9 Hz, 1H), 6.85 (dd, J = 7.1, 1.7 Hz, 1H), 4.48 (d, J = 5.7 Hz, 2H), 4.27 – 4.06 (m, 3H), 3.82 – 3.69 (m, 1H), 3.69 – 3.58 (m, 1H), 2.01 – 1.86 (m, 1H), 1.86 – 1.69 (m, 1H), 1.69 – 1.52 (m, 1H) | (ESI(+)) m/e 408 (M + H)$^+$ |
| 410 | N-(imidazo[1,2-a]pyridin-7-ylmethyl)-5-[1-(tetrahydro-2H-pyran-4-yl)-1H-pyrazol-4-yl]thiophene-2-carboxamide | $^1$H NMR (300 MHz, DMSO-d$_6$) δ ppm 9.03 (t, J = 6.0 Hz, 1H), 8.49 (d, J = 6.7 Hz, 1H), 8.24 (s, 1H), 7.89 (s, 1H), 7.82 (s, 1H), 7.75 (d, J = 3.9 Hz, 1H), 7.52 (d, J = 1.1 Hz, 1H), 7.40 (s, 1H), 7.23 (d, J = 3.9 Hz, 1H), 6.85 (dd, J = 7.0, 1.7 Hz, 1H), 4.54 – 4.34 (m, 3H), 4.04 – 3.88 (m, 2H), 3.47 (td, J = 11.3, 3.9 Hz, 2H), 2.06 – 1.86 (m, 4H) | (ESI(+)) m/e 408 (M + H)$^+$ |
| 465 | N-(imidazo[1,2-a]pyridin-7-ylmethyl)-5-{1-[(2-methyltetrahydro-2H-pyran-2-yl)methyl]-1H-pyrazol-4-yl}thiophene-2-carboxamide | $^1$H NMR (300 MHz, DMSO-d$_6$) δ ppm 9.05 (t, J = 6.0 Hz, 1H), 8.50 (d, J = 7.0 Hz, 1H), 8.03 (s, 1H), 7.90 (s, 1H), 7.80 (s, 1H), 7.75 (d, J = 3.8 Hz, 1H), 7.54 (d, J = 1.1 Hz, 1H), 7.41 (s, 1H), 7.25 (d, J = 3.9 Hz, 1H), 6.86 (dd, J = 7.0, 1.6 Hz, 1H), 4.49 (d, J = 5.9 Hz, 2H), 4.24 (d, J = 14.1 Hz, 1H), 4.10 (d, J = 14.0 Hz, 1H), | (ESI(+)) m/e 436 (M + H)$^+$ |

TABLE 6-continued

The following Examples were prepared essentially as described in Example 75, substituting the appropriate carboxylic acid and amine in Example 75A and the appropriate boronate in Example 75B. Some boronates were Boc-protected and required deprotection as in Example 28A.

| Ex | Name | ¹H NMR | MS |
|---|---|---|---|
| 466 | tert-butyl 4-[(4-{5-[(imidazo[1,2-a]pyridin-7-ylmethyl)carbamoyl]thiophen-2-yl}-1H-pyrazol-1-yl)methyl]piperidine-1-carboxylate | 3.81 – 3.67 (m, 1H), 3.65 – 3.52 (m, 1H), 1.71 – 1.55 (m, 2H), 1.52 – 1.31 (m, 4H), 1.07 (s, 3H) ¹H NMR (300 MHz, DMSO-d₆) δ ppm 9.02 (t, J = 6.0 Hz, 1H), 8.49 (dd, J = 7.1, 1.0 Hz, 1H), 8.14 (d, J = 0.8 Hz, 1H), 7.89 (s, 1H), 7.81 (d, J = 0.9 Hz, 1H), 7.74 (d, J = 3.8 Hz, 1H), 7.52 (d, J = 1.3 Hz, 1H), 7.40 (s, 1H), 7.22 (d, J = 3.9 Hz, 1H), 6.84 (dd, J = 7.1, 1.7 Hz, 1H), 4.48 (d, J = 5.7 Hz, 2H), 4.02 (d, J = 7.0 Hz, 2H), 3.92 (d, J = 13.2 Hz, 2H), 2.81 – 2.57 (m, 2H), 2.16 – 1.90 (m, 1H), 1.56 – 1.42 (m, 2H), 1.38 (s, 9H), 1.22 – 0.94 (m, 2H) | (ESI(+)) m/e 521 (M + H)⁺ |
| 475 | 5-[1-(cyclobutylmethyl)-1H-pyrazol-4-yl]-N-(imidazo[1,2-a]pyridin-7-ylmethyl)thiophene-2-carboxamide | | (ESI(+)) m/e 392 (M + H)⁺ |
| 476 | N-(imidazo[1,2-a]pyridin-7-ylmethyl)-5-[1-(tetrahydrofuran-2-ylmethyl)-1H-pyrazol-4-yl]furan-2-carboxamide | | (ESI(+)) m/e 392 (M + H)⁺ |
| 477 | N-(imidazo[1,2-a]pyridin-7-ylmethyl)-5-[1-(tetrahydro-2H-pyran-2-ylmethyl)-1H-pyrazol-4-yl]furan-2-carboxamide | | (ESI(+)) m/e 406 (M + H)⁺ |
| 478 | N-(imidazo[1,2-a]pyridin-7-ylmethyl)-5-[1-(tetrahydrofuran-3-ylmethyl)-1H-pyrazol-4-yl]furan-2-carboxamide | | (ESI(+)) m/e 392 (M + H)⁺ |
| 479 | N-(imidazo[1,2-a]pyridin-7-ylmethyl)-5-[1-(tetrahydro-2H-pyran-3-ylmethyl)-1H-pyrazol-4-yl]furan-2-carboxamide | | (ESI(+)) m/e 406 (M + H)⁺ |
| 480 | N-(imidazo[1,2-a]pyridin-7-ylmethyl)-5-[1-(tetrahydro-2H-pyran-4-ylmethyl)-1H-pyrazol-4-yl]furan-2-carboxamide | | (ESI(+)) m/e 406 (M + H)⁺ |
| 481 | 5-[1-(cyclobutylmethyl)-1H-pyrazol-4-yl]-N-(imidazo[1,2-a]pyridin-7-ylmethyl)furan-2-carboxamide | | (ESI(+)) m/e 376 (M + H)⁺ |
| 482 | N-(imidazo[1,2-a]pyridin-7-ylmethyl)-5-{1-[(3-methyloxetan-3-yl)methyl]-1H-pyrazol-4-yl}furan-2-carboxamide | | (ESI(+)) m/e 392 (M + H)⁺ |
| 483 | 5-[1-(2-hydroxy-2-methylpropyl)-1H-pyrazol-4-yl]-N-(imidazo[1,2-a]pyridin-7-ylmethyl)furan-2-carboxamide | | (ESI(+)) m/e 380 (M + H)⁺ |
| 883 | 5-[1-(2,2-dimethylpropyl)-1H-pyrazol-4-yl]-N-(imidazo[1,2-a]pyridin-7-ylmethyl)thiophene-2-carboxamide | | (ESI(+)) m/e 394 (M + H)⁺ |
| 884 | N-(imidazo[1,2-a]pyridin-7-ylmethyl)-5-[1-(tricyclo[3.3.1.1~3.7~]dec-1-ylmethyl)-1H-pyrazol-4-yl]thiophene-2-carboxamide | | (ESI(+)) m/e 472 (M + H)⁺ |
| 885 | 5-(1-benzyl-1H-pyrazol-4-yl)-N-(imidazo[1,2-a]pyridin-7-ylmethyl)thiophene-2-carboxamide | | (ESI(+)) m/e 414 (M + H)⁺ |
| 886 | N-(imidazo[1,2-a]pyridin-7-ylmethyl)-5-[1-(2-oxatricyclo[3.3.1.1~3,7~]dec-1-ylmethyl)-1H-pyrazol-4-yl]thiophene-2-carboxamide | | (ESI(+)) m/e 474 (M + H)⁺ |
| 1082 | 5-{1-[2,2-dimethyl-3-(piperazin-1-yl)propyl]-1H-pyrazol-4-yl}-N-(imidazo[1,2-a]pyridin-7-ylmethyl)thiophene-2-carboxamide | | (ESI(+)) m/e 478 (M + H)⁺ |
| 1083 | 5-[1-(3-amino-2,2-dimethylpropyl)-1H-pyrazol-4-yl]-N-(imidazo[1,2-a]pyridin-7-ylmethyl)thiophene-2-carboxamide | | (ESI(+)) m/e 409 (M + H)⁺ |

Example 76

2-cyclopentyl-N-{4-[2-(imidazo[1,2-a]pyridin-6-ylamino)-2-oxoethyl]phenyl}acetamide

Example 76A

N-(imidazo[1,2-a]pyridin-6-yl)-2-(4-nitrophenyl)acetamide

The title compound was prepared as described in Example 1A, substituting imidazo[1,2-a]pyridin-6-amine for 3-methylbutan-1-amine and 2-(4-nitrophenyl)acetic acid for 4-nitrobenzoic acid.

Example 76B 2-(4-aminophenyl)-N-(imidazo[1,2-a]pyridin-6-yl)acetamide

The title compound was prepared as described in Example 1B, substituting N-(imidazo[1,2-a]pyridin-6-yl)-2-(4-nitrophenyl)acetamide for N-isopentyl-4-nitrobenzamide.

Example 76C 2-cyclopentyl-N-{4-[2-(imidazo[1,2-a]pyridin-6-ylamino)-2-oxoethyl]phenyl}acetamide The title compound was prepared as described in Example 52A, substituting 2-(4-aminophenyl)-N-(imidazo[1,2-a]pyridin-6-yl)acetamide for methyl 4-aminobenzoate. $^1$H NMR (400 MHz, DMSO-$d_6$) δ ppm 10.71 (s, 1H), 9.83 (s, 1H), 9.55 (m, 1H), 8.38 (d, J=2.0 Hz, 1H), 8.08 (d, J=2.0 Hz, 1H), 7.96-7.88 (m, 1H), 7.80-7.73 (m, 1H), 7.58-7.51 (m, 2H), 7.29-7.23 (m, 2H), 3.67 (bs, 2H), 2.34-2.15 (m, 3H), 1.82-1.65 (m, 2H), 1.67-1.41 (m, 4H), 1.26-1.10 (m, 2H); MS (ESI(+)) m/e 377 (M+H)$^+$.

Example 77

N-(imidazo[1,2-a]pyridin-6-ylmethyl)-4-[(tetrahydrofuran-2-ylacetyl)amino]benzamide

Example 77A tert-butyl 4-(imidazo[1,2-a]pyridin-6-ylmethylcarbamoyl)phenylcarbamate The title compound was prepared as described in Example 1A, substituting imidazo[1,2-a]pyridin-6-ylmethanamine for 3-methylbutan-1-amine and 4-(tert-butoxycarbonylamino)benzoic acid for 4-nitrobenzoic acid.

Example 77B 4-amino-N-(imidazo[1,2-a]pyridin-6-ylmethyl)benzamide

The title compound was prepared as described in Example 28A, substituting tert-butyl 4-(imidazo[1,2-a]pyridin-6-ylmethylcarbamoyl)phenylcarbamate for tert-butyl 4-(4-(3-imidazo[1,2-a]pyridin-6-ylureido)phenyl)-5,6-dihydropyridine-1(2H)-carboxylate.

Example 77C

N-(imidazo[1,2-a]pyridin-6-ylmethyl)-4-[(tetrahydrofuran-2-ylacetyl)amino]benzamide The title compound was prepared as described in Example 1A, substituting 4-amino-N-(imidazo[1,2-a]pyridin-6-ylmethyl)benzamide for 3-methylbutan-1-amine and 2-(tetrahydrofuran-2-yl)acetic acid for 4-nitrobenzoic acid. $^1$H NMR (400 MHz, DMSO-$d_6$) δ ppm 10.14 (s, 1H), 8.93 (t, J=5.8 Hz, 1H), 8.48-8.45 (m, 1H), 7.95 (s, 1H), 7.88-7.82 (m, 2H), 7.71-7.64 (m, 2H), 7.53 (m, 7.55-7.48, 2H), 7.22 (dd, J=9.2, 1.7 Hz, 1H), 4.45 (d, J=5.8 Hz, 2H), 4.23-4.12 (m, 1H), 3.82-3.72 (m, 1H), 3.66-3.56 (m, 1H), 2.59-2.44 (m, 2H), 2.07-1.95 (m, 1H), 1.92-1.77 (m, 2H), 1.60-1.47 (m, 1H); MS (ESI(+)) m/e 379 (M+H)$^+$.

Example 78

N-(imidazo[1,2-a]pyridin-6-ylmethyl)-4-[(tetrahydrofuran-3-ylacetyl)amino]benzamide The title compound was prepared as described in Example 77, substituting 2-(tetrahydrofuran-3-yl)acetic acid for 2-(tetrahydrofuran-2-yl)acetic acid in Example 77C. $^1$H NMR (500 MHz, DMSO-$d_6$, Temp=90° C.) δ ppm 9.87 (bs, 1H), 8.65-8.59 (m, 1H), 8.42 (s, 1H), 7.87 (s, 1H), 7.84-7.79 (m, 2H), 7.66-7.61 (m, 2H), 7.52-7.45 (m, 2H), 7.21 (dd, J=9.2, 1.7 Hz, 1H), 4.45 (d, J=5.8 Hz, 2H), 3.85-3.78 (m, 1H), 3.77-3.69 (m, 1H), 3.68-3.60 (m, 1H), 3.38-3.31 (m, 1H), 2.64-2.54 (m, 1H), 2.45-2.40 (m, 2H), 2.09-1.98 (m, 1H), 1.63-1.51 (m, 1H); MS (ESI(+)) m/e 379 (M+H)$^+$.

Example 79

N-(imidazo[1,2-a]pyridin-6-ylmethyl)-4-[(tetrahydro-2H-pyran-4-ylacetyl)amino]benzamide The title compound was prepared as described in Example 77, substituting 2-(tetrahydro-2H-pyran-4-yl)acetic acid for 2-(tetrahydrofuran-2-yl)acetic acid in Example 77C. $^1$H NMR (500 MHz, DMSO-$d_6$, Temp=90° C.) δ ppm 9.84 (bs, 1H), 8.67-8.60 (m, 1H), 8.42 (s, 1H), 7.87 (s, 1H), 7.85-7.79 (m, 2H), 7.67-7.61 (m, 2H), 7.52-7.45 (m, 2H), 7.21 (dd, J=9.2, 1.7 Hz, 1H), 4.45 (d, J=5.8 Hz, 2H), 3.85-3.77 (m, 2H), 3.35-3.26 (m, 2H), 2.28 (d, J=7.0 Hz, 2H), 2.07-1.96 (m, 1H), 1.65-1.57 (m, 2H), 1.31-1.22 (m, 2H); MS (ESI(+)) m/e 393 (M+H)$^+$.

Example 80

N-(imidazo[1,2-a]pyridin-6-ylmethyl)-4-[(morpholin-4-ylacetyl)amino]benzamide

The title compound was prepared as described in Example 77, substituting 2-morpholinoacetic acid for 2-(tetrahydrofuran-2-yl)acetic acid in Example 77C. $^1$H NMR (500 MHz, DMSO-$d_6$, Temp=90° C.) δ ppm 9.70 (bs, 1H), 8.69-8.63 (m, 1H), 8.42 (s, 1H), 7.90-7.81 (m, 3H), 7.70-7.65 (m, 2H), 7.53-7.45 (m, 2H), 7.21 (dd, J=9.3, 1.7 Hz, 1H), 4.46 (d, J=5.8 Hz, 2H), 3.67-3.61 (m, 4H), 3.14 (s, 2H), 2.56-2.52 (m, 4H); MS (ESI(+)) m/e 394 (M+H)$^+$.

Example 81

4-[(3-cyclopentylpropanoyl)amino]-N-(imidazo[1,2-a]pyridin-6-ylmethyl)benzamide

The title compound was prepared as described in Example 77, substituting 4-cyclopentylbutanoic acid for 2-(tetrahydrofuran-2-yl)acetic acid in Example 77C. $^1$H NMR (400 MHz, DMSO-$d_6$) δ ppm 10.10 (s, 1H), 8.92 (t, J=5.8 Hz, 1H), 8.46 (dd, J=1.9, 0.9 Hz, 1H), 7.95 (dd, J=1.2, 0.6 Hz, 1H), 7.87-7.81 (m, 2H), 7.70-7.64 (m, 2H), 7.55-7.49 (m, 2H), 7.22 (dd, J=9.2, 1.7 Hz, 1H), 4.45 (d, J=5.8 Hz, 2H), 2.37-2.30 (m, 2H), 1.81-1.68 (m, 3H), 1.64-1.41 (m, 6H), 1.19-1.02 (m, 2H); MS (ESI(+)) m/e 391 (M+H)$^+$.

Example 82

N-(imidazo[1,2-a]pyridin-6-ylmethyl)-4-{[(propan-2-yloxy)acetyl]amino}benzamide

The title compound was prepared as described in Example 77, substituting 2-isopropoxyacetic acid for 2-(tetrahydrofuran-2-yl)acetic acid in Example 77C. $^1$H NMR (400 MHz, DMSO-$d_6$) δ ppm 9.78 (s, 1H), 8.95 (t, J=5.8 Hz, 1H), 8.49-8.44 (m, 1H), 7.97-7.93 (m, 1H), 7.89-7.83 (m, 2H), 7.78-7.72 (m, 2H), 7.56-7.50 (m, 2H), 7.22 (dd, J=9.2, 1.7 Hz, 1H), 4.46 (d, J=5.8 Hz, 2H), 4.04 (s, 2H), 3.75-3.64 (m, 1H), 1.17 (d, J=6.1 Hz, 6H); MS (ESI(+)) m/e 367 391 (M+H)$^+$.

Example 83 tert-butyl 4-{4-[(imidazo[1,2-a]pyridin-6-ylmethyl)carbamoyl]phenyl}-3,6-dihydropyridine-1(2H)-carboxylate

Example 83A 4-bromo-N-(imidazo[1,2-a]pyridin-6-ylmethyl)benzamide

The title compound was prepared as described in Example 1A, substituting imidazo[1,2-a]pyridin-6-ylmethanamine for 3-methylbutan-1-amine and 4-bromobenzoic acid for 4-nitrobenzoic acid.

Example 83B tert-butyl 4-{4-[(imidazo[1,2-a]pyridin-6-ylmethyl)carbamoyl]phenyl}-3,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 4-bromo-N-(imidazo[1,2-a]pyridin-6-ylmethyl)benzamide for 4-bromoaniline. $^1$H NMR (300 MHz, DMSO-$d_6$) δ ppm 9.03 (t, J=5.9 Hz, 1H), 8.49-8.45 (m, 1H), 7.97-7.93 (m, 1H), 7.91-7.84 (m, 2H), 7.61-7.48 (m, 4H), 7.22 (dd, J=9.3, 1.7 Hz, 1H), 6.32-6.25 (m, 1H), 4.47 (d, J=5.8 Hz, 2H), 4.05-3.99 (m, 2H), 3.58-3.50 (m, 2H), 2.55-2.44 (m, 2H), 1.43 (s, 9H); MS (ESI(+)) m/e 433 (M+H)$^+$.

Example 84

N-{4-[(cyclopentylacetyl)amino]benzyl}imidazo[1,2-a]pyridine-6-carboxamide

Example 84A

N-(4-nitrobenzyl)imidazo[1,2-a]pyridine-6-carboxamide

The title compound was prepared as described in Example 1A, substituting (4-nitrophenyl)methanamine for 3-methylbutan-1-amine and imidazo[1,2-a]pyridine-6-carboxylic acid for 4-nitrobenzoic acid.

Example 84B

N-(4-aminobenzyl)imidazo[1,2-a]pyridine-6-carboxamide

The title compound was prepared as described in Example 1B, substituting N-(4-nitrobenzyl)imidazo[1,2-a]pyridine-6-carboxamide for N-isopentyl-4-nitrobenzamide.

Example 84C

N-{4-[(cyclopentylacetyl)amino]benzyl}imidazo[1,2-a]pyridine-6-carboxamide

The title compound was prepared as described in Example 1A, substituting N-(4-aminobenzyl)imidazo[1,2-a]pyridine-6-carboxamide for 3-methylbutan-1-amine and 2-cyclopentylacetic acid for 4-nitrobenzoic acid. $^1$H NMR (300 MHz, DMSO-$d_6$) δ ppm 9.80 (s, 1H), 9.16-9.11 (m, 1H), 9.04 (t, J=5.9 Hz, 1H), 8.08-8.03 (m, 1H), 7.76-7.57 (m, 3H), 7.58-7.50 (m, 2H), 7.29-7.22 (m, 2H), 4.44 (d, J=5.8 Hz, 2H), 2.33-2.14 (m, 3H), 1.81-1.67 (m, 2H), 1.66-1.42 (m, 4H), 1.27-1.09 (m, 2H); MS (ESI(+)) m/e 377 (M+H)$^+$.

Example 85

N-(imidazo[1,2-a]pyridin-6-ylmethyl)-2-(1,2,4,5-tetrahydro-3H-3-benzazepin-3-yl)-1,3-thiazole-5-carboxamide

Example 85A 2-bromo-N-(imidazo[1,2-a]pyridin-6-ylmethyl)thiazole-5-carboxamide The title compound was prepared as described in Example 1A, substituting imidazo[1,2-a]pyridin-6-ylmethanamine for 3-methylbutan-1-amine and 2-bromothiazole-5-carboxamide for 4-nitrobenzoic acid.

Example 85B

N-(imidazo[1,2-a]pyridin-6-ylmethyl)-2-(1,2,4,5-tetrahydro-3H-3-benzazepin-3-yl)-1,3-thiazole-5-carboxamide The title compound was prepared as in Example 53B, substituting 2,3,4,5-tetrahydro-1H-benzo[d]azepine for 4-cyanobenzylamine and 2-bromo-N-(imidazo[1,2-a]pyridin-6-ylmethyl)thiazole-5-carboxamide for 2-bromo-N-(imidazo[1,2-a]pyridin-6-yl)thiazole-5-carboxamide. $^1$H NMR (400 MHz, DMSO-$d_6$) ppm 8.78 (t, J=5.8 Hz, 1 H), 8.44 (s, 1 H), 7.95 (s, 1 H), 7.86 (s, 1 H), 7.48-7.56 (m, 2 H), 7.08-7.22 (m, 5 H), 4.38 (d, J=5.9 Hz, 2 H), 3.67-3.78 (m, 4 H), 2.89-3.01 (m, 4 H); MS (ESI(+)) m/e 402 (M+H)$^+$.

Example 86

N-(imidazo[1,2-a]pyridin-6-ylmethyl)-2-(3-phenylpyrrolidin-1-yl)-1,3-thiazole-5-carboxamide The title compound was prepared as in Example 85, substituting 3-phenylpyrrolidine for 2,3,4,5-tetrahydro-1H-benzo[d]azepine in Example 85B. $^1$H NMR (400 MHz, DMSO-d$_6$) δ 8.75 (dd, J=5.8, 5.6 Hz, 1H), 8.44 (s, 1H), 7.95 (s, 1H), 7.86 (s, 1H), 7.56-7.50 (m, 2H), 7.35-7.31 (m, 2H), 7.29-7.21 (m, 2H), 7.18 (dd, J=8.4, 4.7 Hz, 1H), 4.45 (s, 1H), 4.38 (d, J=5.8 Hz, 2H), 3.92-3.83 (m, 2H), 3.62-3.45 (m, 2H), 2.68-2.62 (m, 1H), 2.42-2.30 (m, 1H), 2.20-2.07 (m, 1H). MS (ESI)(+)) m/e 404 (M+H)$^+$.

Example 87

N-(imidazo[1,2-a]pyridin-6-ylmethyl)-2-[(3-methylbutyl)amino]-1,3-thiazole-5-carboxamide The title compound was prepared as in Example 85, substituting 3-methylbutan-1-amine for 2,3,4,5-tetrahydro-1H-benzo[d]azepine in Example 85B. $^1$H NMR (400 MHz, DMSO-d$_6$) ppm 8.67 (t, J=5.9 Hz, 1H), 8.42 (s, 1 H), 8.08 (t, J=5.4 Hz, 1 H), 7.94 (s, 1 H), 7.71 (s, 1 H), 7.49-7.55 (m, 2 H), 7.16 (dd, J=9.3, 1.6 Hz, 1 H), 4.36 (d, J=5.9 Hz, 2 H), 3.17-3.26 (m, 2 H), 1.61 (dq, J=6.7 Hz, 1 H), 1.41 (q, J=7.0 Hz, 2 H), 0.87 (d, J=6.6 Hz, 6 H); MS (ESI(+)) m/e 344 (M+H)$^+$.

Example 88

2-(1,3-dihydro-2H-isoindol-2-yl)-N-(imidazo[1,2-a]pyridin-6-ylmethyl)-1,3-thiazole-5-carboxamide The title compound was prepared as in Example 85, substituting isoindoline for 2,3,4,5-tetrahydro-1H-benzo[d] azepine in Example 85B. $^1$H NMR (400 MHz, DMSO-d$_6$) ppm 8.81 (t, J=5.9 Hz, 1 H), 8.45 (s, 1 H), 7.89-7.99 (m, 2 H), 7.49-7.56 (m, 2 H), 7.37-7.45 (m, 2 H), 7.30-7.37 (m, 2 H), 7.19 (dd, J=9.3, 1.5 Hz, 1 H), 4.76 (s, 4 H), 4.40 (d, J=5.7 Hz, 2 H); MS (ESI(+)) m/e 376 (M+H)$^+$.

Example 89 tert-butyl 4-{4-[(imidazo[1,2-a]pyridin-6-ylcarbamoyl)amino]phenyl}piperidine-1-carboxylate The title compound was prepared as described in Example 1C, substituting tert-butyl 4-(4-aminophenyl)piperidine-1-carboxylate for 4-amino-N-isopentylbenzamide. $^1$H NMR (400 MHz, DMSO-d$_6$) δ ppm 8.98-8.94 (m, 1H), 8.67 (s, 1H), 8.64 (s, 1H), 7.97-7.93 (m, 1H), 7.54-7.48 (m, 2H), 7.42-7.36 (m, 2H), 7.19-7.12 (m, 2H), 7.08 (dd, J=9.5, 2.1 Hz, 1H), 4.14-3.99 (m, 2H), 2.89-2.56 (m, 3H), 1.77-1.69 (m, 2H), 1.52-1.36 (m, 11H); MS (ESI(+)) m/e 436 (M+H)$^+$.

Example 90

N-(imidazo[1,2-a]pyridin-6-ylmethyl)-4-[1-(2-methylpropanoyl)-1,2,3,6-tetrahydropyridin-4-yl]benzamide

Example 90A

N-(imidazo[1,2-a]pyridin-6-ylmethyl)-4-(1,2,3,6-tetrahydropyridin-4-yl)benzamide The title compound was prepared as described in Example 28A, substituting tert-butyl 4-{4-[(imidazo[1,2-a]pyridin-6-ylmethyl)carbamoyl]phenyl}-3,6-dihydropyridine-1(2H)-carboxylate for tert-butyl 4-(4-(3-imidazo[1,2-a]pyridin-6-ylureido)phenyl)-5,6-dihydropyridine-1(2H)-carboxylate.

Example 90B

N-(imidazo[1,2-a]pyridin-6-ylmethyl)-4-[1-(2-methylpropanoyl)-1,2,3,6-tetrahydropyridin-4-yl]benzamide The title compound was prepared as described in Example 1A, substituting N-(imidazo[1,2-a]pyridin-6-ylmethyl)-4-(1,2,3,6-tetrahydropyridin-4-yl)benzamide for 3-methylbutan-1-amine and isobutyric acid for 4-nitrobenzoic acid. $^1$H NMR (400 MHz, DMSO-d$_6$, Temp=90° C.) δ ppm 8.75-8.67 (m, 1H), 8.43 (s, 1H), 7.89-7.83 (m, 3H), 7.54-7.43 (m, 4H), 7.21 (dd, J=9.2, 1.7 Hz, 1H), 6.29-6.23 (m, 1H), 4.47 (d, J=5.8 Hz, 2H), 4.19-4.13 (m, 2H), 3.70 (t, J=5.7 Hz, 2H), 2.95-2.84 (m, 1H), 2.57-2.49 (m, 2H), 1.04 (d, J=6.7 Hz, 6H); MS (ESI(+)) m/e 403 (M+H)$^+$.

TABLE 7

The following Examples were prepared essentially as described in Example 90, substituting the appropriate carboxylic acid for isobutyric acid in Example 90B.

| Ex | Name | $^1$H NMR | MS |
|---|---|---|---|
| 91 | 4-[1-(2-hydroxy-2-methylpropanoyl)-1,2,3,6-tetrahydropyridin-4-yl]-N-(imidazo[1,2-a]pyridin-6-ylmethyl)benzamide | | (ESI(+)) m/e 419 (M + H)$^+$ |
| 92 | N-(imidazo[1,2-a]pyridin-6-ylmethyl)-4-[1-(morpholin-4-ylacetyl)-1,2,3,6-tetrahydropyridin-4-yl]benzamide | | (ESI(+)) m/e 460 (M + H)$^+$ |
| 93 | N-(imidazo[1,2-a]pyridin-6-ylmethyl)-4-[1-(tetrahydro-2H-pyran-4-ylacetyl)-1,2,3,6-tetrahydropyridin-4-yl]benzamide | | (ESI(+)) m/e 459 (M + H)$^+$ |
| 94 | N-(imidazo[1,2-a]pyridin-6-ylmethyl)-4-[1-(tetrahydrofuran-3-ylacetyl)-1,2,3,6-tetrahydropyridin-4-yl]benzamide | | (ESI(+)) m/e 445 (M + H)$^+$ |
| 95 | N-(imidazo[1,2-a]pyridin-6-ylmethyl)-4-[1-(tetrahydrofuran-2-ylacetyl)-1,2,3,6-tetrahydropyridin-4-yl]benzamide | | (ESI(+)) m/e 445 (M + H)$^+$ |

TABLE 7-continued

The following Examples were prepared essentially as described in Example 90, substituting the appropriate carboxylic acid for isobutyric acid in Example 90B.

| Ex | Name | $^1$H NMR | MS |
|---|---|---|---|
| 96 | N-(imidazo[1,2-a]pyridin-6-ylmethyl)-4-(tetrahydrofuran-2-yl)propanoyl]-1,2,3,6-tetrahydropyridin-4-yl}benzamide | | (ESI(+)) m/e 459 (M + H)$^+$ |
| 97 | 4-[1-(cyclopentylacetyl)-1,2,3,6-tetrahydropyridin-4-yl]-N-(imidazo[1,2-a]pyridin-6-ylmethyl)benzamide | $^1$H NMR (300 MHz, methanol-d$_4$) δ ppm 8.81 – 8.76 (m, 1H), 8.21 (m, 1H), 8.05 – 7.98 (m, 2H), 7.97 – 7.79 (m, 3H), 7.59 – 7.53 (m, 2H), 6.31 – 6.23 (m, 1H), 4.74 – 4.65 (m, 2H), 4.29 – 4.19 (m, 2H), 3.85 – 3.75 (m, 2H), 2.71 – 2.41 (m, 4H), 2.33 – 2.14 (m, 1H), 1.92 – 1.74 (m, 2H), 1.76 – 1.49 (m, 4H), 1.32 – 1.13 (m, 2H) | (ESI(+)) m/e 443 (M + H)$^+$ |
| 98 | N-(imidazo[1,2-a]pyridin-6-ylmethyl)-4-{1-[(propan-2-yloxy)acetyl]-1,2,3,6-tetrahydropyridin-4-yl}benzamide | $^1$H NMR (300 MHz, methanol-d$_4$) δ ppm 8.81 – 8.76 (m, 1H), 8.21 (m, 1H), 8.05 – 7.98 (m, 2H), 7.95 – 7.83 (m, 3H), 7.61 – 7.51 (m, 2H), 6.31 – 6.22 (m, 1H), 4.74 – 4.68 (m, 2H), 4.32 – 4.17 (m, 2H), 3.90 – 3.64 (m, 3H), 2.73 – 2.53 (m, 2H), 1.25 – 1.16 (m, 6H) | (ESI(+)) m/e 443 (M + H)$^+$ |
| 99 | N-(imidazo[1,2-a]pyridin-6-ylmethyl)-4-[1-(tetrahydrofuran-2-ylcarbonyl)-1,2,3,6-tetrahydropyridin-4-yl]benzamide | $^1$H NMR (300 MHz, methanol-d$_4$) δ ppm 8.81 – 8.77 (m, 1H), 8.22 – 8.20 (m, 1H), 8.02 – 7.99 (m, 2H), 7.97 – 7.82 (m, 3H), 7.59 – 7.53 (m, 2H), 6.31 – 6.23 (m, 1H), 4.82 – 4.74 (m, 1H), 4.70 (s, 2H), 4.40 – 4.11 (m, 2H), 4.01 – 3.71 (m, 4H), 2.74 – 2.52 (m, 2H), 2.30 – 2.17 (m, 1H), 2.17 – 1.84 (m, 3H) | (ESI(+)) m/e 431 (M + H)$^+$ |
| 100 | N-(imidazo[1,2-a]pyridin-6-ylmethyl)-4-[1-(tetrahydrofuran-3-ylcarbonyl)-1,2,3,6-tetrahydropyridin-4-yl]benzamide | $^1$H NMR (300 MHz, methanol-d$_4$) δ ppm 8.81 – 8.77 (m, 1H), 8.24 – 8.17 (m, 1H), 8.05 – 7.97 (m, 2H), 7.97 – 7.82 (m, 3H), 7.59 – 7.53 (m, 2H), 6.31 – 6.25 (m, 1H), 4.72 (s, 2H), 4.35 – 4.21 (m, 2H), 4.06 – 3.93 (m, 1H), 3.95 – 3.76 (m, 5H), 3.60 – 3.42 (m, 1H), 2.71 – 2.52 (m, 2H), 2.27 – 2.02 (m, 2H) | (ESI(+)) m/e 431 (M + H)$^+$ |
| 101 | N-(imidazo[1,2-a]pyridin-6-ylmethyl)-4-[1-(tetrahydro-2H-pyran-4-ylcarbonyl)-1,2,3,6-tetrahydropyridin-4-yl]benzamide | $^1$H NMR (400 MHz, methanol-d$_4$) δ ppm 8.81 – 8.78 (m, 1H), 8.23 – 8.19 (m, 1H), 8.05 – 7.98 (m, 2H), 7.93 – 7.84 (m, 3H), 7.59 – 7.53 (m, 2H), 6.31 – 6.25 (m, 1H), 4.70 (s, 2H), 4.36 – 4.30 (m, 1H), 4.25 – 4.19 (m, 1H), 4.02 – 3.93 (m, 2H), 3.87 – 3.78 (m, 1H), 3.59 – 3.46 (m, 2H), 3.10 – 2.92 (m, 1H), 2.70 – 2.53 (m, 2H), 1.91 – 1.72 (m, 2H), 1.73 – 1.57 (m, 2H) | (ESI(+)) m/e 828 (M + H)$^+$ |
| 102 | 4-[1-(1,4-dioxan-2-ylcarbonyl)-1,2,3,6-tetrahydropyridin-4-yl]-N-(imidazo[1,2-a]pyridin-6-ylmethyl)benzamide | $^1$H NMR (400 MHz, methanol-d$_4$) δ ppm 8.79 (s, 1H), 8.23 – 8.20 (m, 1H), 8.04 – 7.99 (m, 2H), 7.93 – 7.84 (m, 3H), 7.59 – 7.53 (m, 2H), 6.29 – 6.23 (m, 1H), 4.73 – 4.67 (m, 2H), 4.53 – 4.06 (m, 3H), 3.96 – 3.59 (m, 8H), 2.76 – 2.53 (m, 2H) | (ESI(+)) m/e 447 (M + H)$^+$ |
| 103 | N-(imidazo[1,2-a]pyridin-6-ylmethyl)-4-{1-[(2-methoxyethoxy)acetyl]-1,2,3,6-tetrahydropyridin-4-yl}benzamide | $^1$H NMR (400 MHz, methanol-d$_4$) δ ppm 8.79 (s, 1H), 8.24 – 8.19 (m, 1H), 8.01 (m, 2H), 7.97 – 7.82 (m, 3H), 7.59 – 7.53 (m, 2H), 6.31 – 6.23 (m, 1H), 4.76 – 4.69 (m, 2H), 4.35 – 4.26 (m, 2H), 4.25 – 4.19 (m, 2H), 3.86 – 3.62 (m, 4H), 3.61 – 3.54 (m, 2H), 3.35 (s, 3H), 2.72 – 2.54 (m, 2H) | (ESI(+)) m/e 449 (M + H)$^+$ |
| 104 | 4-(1-benzoyl-1,2,3,6-tetrahydropyridin-4-yl)-N-(imidazo[1,2-a]pyridin-6-ylmethyl)benzamide | $^1$H NMR (400 MHz, DMSO-d$_6$, Temp = 90° C.) δ ppm 8.89 – 8.82 (m, 1H), 8.73 (s, 1H), 8.22 (d, J = 1.9 Hz, 1H), 7.96 (d, J = 1.9 Hz, 1H), 7.90 – 7.75 (m, 4H), 7.56 – 7.49 (m, 2H), 7.49 – 7.37 (m, 5H), 6.27 (bs, 1H), 4.58 (d, J = 5.8 Hz, 2H), 4.23 – 4.17 (m, 2H), 3.72 – 3.65 (m, 2H), 2.61 – 2.53 (m, 2H) | (ESI(+)) m/e 437 (M + H)$^+$ |
| 105 | 4-{1-[(4,4-difluorocyclohexyl)carbonyl]-1,2,3,6-tetrahydropyridin-4-yl}-N-(imidazo[1,2-a]pyridin-6-ylmethyl)benzamide | $^1$H NMR (400 MHz, DMSO-d$_6$, Temp = 90° C.) δ ppm 8.90 – 8.83 (m, 1H), 8.74 (s, 1H), 8.22 (d, J = 1.9 Hz, 1H), 7.97 (d, J = 1.9 Hz, 1H), 7.90 – 7.75 (m, 4H), 7.54 – 7.48 (m, 2H), 6.30 – 6.24 (m, 1H), 4.58 (d, J = 5.8 Hz, 2H), 4.21 – 4.15 (m, 2H), 3.77 – 3.69 (m, 2H), 2.91 – 2.79 (m, 1H), 2.58 – 2.51 (m, 2H), 2.12 – 2.00 (m, 2H), 2.00 – 1.59 (m, 6H) | (ESI(+)) m/e 479 (M + H)$^+$ |

Example 106

1-imidazo[1,2-a]pyridin-6-yl-3-{4-[1-(2-methylpropanoyl)piperidin-4-yl]phenyl}urea

Example 106A 1-(imidazo[1,2-a]pyridin-6-yl)-3-(4-(piperidin-4-yl)phenyl)urea The title compound was prepared as described in Example 28A, substituting tert-butyl 4-(4-(3-imidazo[1,2-a]pyridin-6-ylureido)phenyl)piperidine-1-carboxylate for tert-butyl 4-(4-(3-imidazo[1,2-a]pyridin-6-ylureido)phenyl)-5,6-dihydropyridine-1(2H)-carboxylate.

Example 106B 1-imidazo[1,2-a]pyridin-6-yl-3-{4-[1-(2-methylpropanoyl)piperidin-4-yl]phenyl}urea The title compound was prepared as described in Example 1A, substituting 1-(imidazo[1,2-a]pyridin-6-yl)-3-(4-(piperidin-4-yl)phenyl)urea for 3-methylbutan-1-amine and isobutyric acid for 4-nitrobenzoic acid. $^1$H NMR (400 MHz, DMSO-d$_6$, Temp=90° C.) δ ppm 8.86-8.81 (m, 1H), 8.41 (s, 1H), 8.38 (s, 1H), 7.86 (s, 1H), 7.50-7.42 (m, 2H), 7.40-7.34 (m, 2H), 7.18-7.12 (m, 2H), 7.12-7.06 (m, 1H), 4.41-4.18 (m, 2H), 2.95-2.64 (m, 4H), 1.87-1.78 (m, 2H), 1.56-1.38 (m, 2H), 1.03 (d, J=6.7 Hz, 6H); MS (ESI(+)) m/e 406 (M+H)$^+$.

Example 108

2-(3,4-dihydroisoquinolin-2(1H)-yl)-N-(imidazo[1,2-a]pyridin-6-ylmethyl)-1,3-thiazole-5-carboxamide The title compound was prepared as in Example 85, substituting 1,2,3,4-tetrahydroisoquinoline for 2,3,4,5-tetrahydro-1H-benzo[d]azepine in Example 85B. $^1$H NMR (400 MHz, DMSO-d$_6$) ppm 8.81 (t, J=5.8 Hz, 1 H), 8.47 (s, 1 H), 7.98 (s, 1 H), 7.89 (s, 1 H), 7.48-7.63 (m, 2 H), 7.13-7.32 (m, 5 H), 4.65 (s, 2 H), 4.39 (d, J=5.9 Hz, 2 H), 3.73 (t, J=6.0 Hz, 2 H), 2.94 (t, J=6.0 Hz, 2 H); MS (ESI(+)) m/e 390 (M+H)$^+$.

Example 109

1-imidazo[1,2-a]pyridin-6-yl-3-{4-[1-(tetrahydro-2H-pyran-4-ylcarbonyl)piperidin-4-yl]phenyl}urea The title compound was prepared as described in Example 106, substituting tetrahydro-2H-pyran-4-carboxylic acid for isobutyric acid in Example 106B. $^1$H NMR (400 MHz, methanol-d$_4$) δ ppm 9.37-9.33 (m, 1H), 8.22-8.17 (m, 1H), 7.97 (d, J=2.1 Hz, 1H), 7.89-7.77 (m, 2H), 7.44-7.38 (m, 2H), 7.24-7.18 (m, 2H), 4.73-4.64 (m, 1H), 4.25-4.15 (m, 1H), 4.01-3.93 (m, 2H), 3.57-3.46 (m, 2H), 3.27-3.17 (m, 1H), 3.06-2.95 (m, 1H), 2.87-2.66 (m, 2H), 2.00-1.70 (m, 4H), 1.70-1.48 (m, 4H); MS (ESI(+)) m/e 448 (M+H)$^+$.

Example 110

1-imidazo[1,2-a]pyridin-6-yl-3-{4-[1-(tetrahydrofuran-3-ylacetyl)piperidin-4-yl]phenyl}urea The title compound was prepared as described in Example 106, substituting 2-(tetrahydrofuran-3-yl)acetic acid for isobutyric acid in Example 106B. $^1$H NMR (400 MHz, methanol-d$_4$) δ ppm 9.37-9.32 (m, 1H), 8.21-8.17 (m, 1H), 7.97 (d, J=2.1 Hz, 1H), 7.88-7.76 (m, 2H), 7.44-7.38 (m, 2H), 7.23-7.18 (m, 2H), 4.71-4.62 (m, 1H), 4.14-4.05 (m, 1H), 3.95-3.82 (m, 2H), 3.81-3.70 (m, 1H), 3.47-3.35 (m, 1H), 3.25-3.12 (m, 1H), 2.86-2.48 (m, 5H), 2.22-2.07 (m, 1H), 1.95-1.83 (m, 2H), 1.74-1.46 (m, 3H); MS (ESI(+) m/e 448 (M+H)$^+$.

Example 111

1-imidazo[1,2-a]pyridin-6-yl-3-{4-[1-(tetrahydrofuran-2-ylacetyl)piperidin-4-yl]phenyl}urea The title compound was prepared as described in Example 106, substituting 2-(tetrahydrofuran-2-yl)acetic acid for isobutyric acid in Example 106B. $^1$H NMR (400 MHz, methanol-d$_4$) δ ppm 9.37-9.32 (m, 1H), 8.21-8.17 (m, 1H), 7.99-7.95 (m, 1H), 7.88-7.77 (m, 2H), 7.44-7.38 (m, 2H), 7.23-7.17 (m, 2H), 4.73-4.63 (m, 1H), 4.33-4.20 (m, 1H), 4.19-4.10 (m, 1H), 3.92-3.83 (m, 1H), 3.79-3.69 (m, 1H), 3.26-3.14 (m, 1H), 2.87-2.65 (m, 3H), 2.63-2.47 (m, 1H), 2.19-2.06 (m, 1H), 2.01-1.81 (m, 4H), 1.77-1.50 (m, 3H); MS (ESI(+)) m/e 448 (M+H)$^+$.

Example 112

1-[4-(1-benzoylpiperidin-4-yl)phenyl]-3-imidazo[1,2-a]pyridin-6-ylurea

The title compound was prepared as described in Example 106, substituting benzoic acid for isobutyric acid in Example 106B. $^1$H NMR (400 MHz, DMSO-d$_6$) δ ppm 8.87-8.81 (m, 1H), 8.38 (bs, 1H), 8.38 (bs, 1H), 7.86 (s, 1H), 7.51-7.34 (m, 9H), 7.21-7.14 (m, 2H), 7.09 (dd, J=9.5, 2.0 Hz, 1H), 4.34-3.97 (m, 2H), 3.08-2.95 (m, 2H), 2.83-2.71 (m, 1H), 1.85-1.77 (m, 2H), 1.66-1.50 (m, 2H); MS (ESI(+)) m/e 440 (M+H)$^+$.

Example 113

1-imidazo[1,2-a]pyridin-6-yl-3-{4-[1-(tetrahydrofuran-2-ylcarbonyl)piperidin-4-yl]phenyl}urea The title compound was prepared as described in Example 106, substituting tetrahydrofuran-2-carboxylic acid for isobutyric acid in Example 106B. $^1$H NMR (400 MHz, methanol-d$_4$) δ ppm 9.38-9.33 (m, 1H), 8.21-8.16 (m, 1H), 8.00-7.95 (m, 1H), 7.88-7.77 (m, 2H), 7.44-7.38 (m, 2H), 7.23-7.17 (m, 2H), 4.83-4.73 (m, 1H), 4.69-4.60 (m, 1H), 4.22-4.11 (m, 1H), 4.01-3.90 (m, 1H), 3.91-3.82 (m, 1H), 3.26-3.12 (m, 1H), 2.87-2.68 (m, 2H), 2.31-2.14 (m, 1H), 2.12-1.75 (m, 5H), 1.77-1.50 (m, 2H); MS (ESI(+)) m/e 434 (M+H)$^+$.

Example 114 tert-butyl 4-{4-[(imidazo[1,2-a]pyridin-6-ylmethyl)carbamoyl]phenoxy}piperidine-1-carboxylate The title compound was prepared as described in Example 1A, substituting imidazo[1,2-a]pyridin-6-ylmethanamine for 3-methylbutan-1-amine and 4-(1-(tert-butoxycarbonyl)piperidin-4-yloxy)benzoic acid for 4-nitrobenzoic acid. $^1$H NMR (400 MHz, methanol-d$_4$) δ ppm 8.40 (s, 1H), 7.86-7.79 (m, 3H), 7.52 (t, J=5.4 Hz, 2H), 7.34 (dd, J=9.3, 1.7 Hz, 1H), 7.06-6.99 (m, 2H), 4.72-4.60 (m, 1H), 4.56 (s, 2H), 3.77-3.65

(m, 2H), 3.41-3.30 (m, 2H), 2.03-1.90 (m, 2H), 1.76-1.59 (m, 2H), 1.46 (s, 9H); MS (ESI(+)) m/e 451 (M+H)+.

Example 115

N-(imidazo[1,2-a]pyridin-6-ylmethyl)-2-[{[2-(propan-2-yloxy)ethyl]carbamoyl}(tetrahydrofuran-2-ylmethyl)amino]-1,3-thiazole-5-carboxamide Example 115A 2-bromo-N-(imidazo[1,2-a]pyridin-6-ylmethyl)thiazole-5-carboxamide The title compound was prepared as described in Example 1A, substituting imidazo[1,2-a]pyridin-6-ylmethanamine for 3-methylbutan-1-amine and 2-bromothiazole-5-carboxylic acid for 4-nitrobenzoic acid.

Example 115B

N-(imidazo[1,2-a]pyridin-6-ylmethyl)-2-((tetrahydrofuran-2-yl)methylamino)thiazole-5-carboxamide The title compound was prepared as in Example 53B, substituting (tetrahydrofuran-2-yl)methanamine for 4-cyanobenzylamine and 2-bromo-N-(imidazo[1,2-a]pyridin-6-ylmethyl)thiazole-5-carboxamide for 2-bromo-N-(imidazo[1,2-a]pyridin-6-yl)thiazole-5-carboxamide.

Example 115C

N-(imidazo[1,2-a]pyridin-6-ylmethyl)-2-[{[2-(propan-2-yloxy)ethyl]carbamoyl}(tetrahydrofuran-2-ylmethyl)amino]-1,3-thiazole-5-carboxamide The title compound was prepared as described in Example 1C, substituting 2-isopropoxyethanamine for 4-amino-N-isopentylbenzamide and N-(imidazo[1,2-a]pyridin-6-ylmethyl)-2-((tetrahydrofuran-2-yl)methylamino)thiazole-5-carboxamide for imidazo[1,2-a]pyridin-6-amine $^1$H NMR (400 MHz, CDCl$_3$) δ ppm 8.52 (s, 1H), 8.21 (d, J=9.0 Hz, 1H), 7.96 (s, 1H), 7.89 (d, J=1.5 Hz, 1H), 7.86-7.80 (m, 1H), 7.78 (d, J=9.5 Hz, 1H), 7.73 (s, 1H), 6.96-6.86 (m, 1H), 4.74-4.60 (m, 2H), 4.50-4.38 (m, 1H), 4.26 (ddd, J=4.4, 2.2, 0.6 Hz, 1H), 4.07-3.90 (m, 2H), 3.85-3.74 (m, 1H), 3.63 (dd, J=12.2, 6.1 Hz, 1H), 3.60-3.53 (m, 2H), 3.53-3.41 (m, 2H), 1.95 (dd, J=7.8, 6.9 Hz, 3H), 1.63-1.56 (m, 1H), 1.18 (dd, J=6.1, 1.2 Hz, 6H); (APCI(+)) m/e 487 (M+H)+.

TABLE 8

The following Examples were prepared essentially as described in Example 115, substituting the appropriate amine in Example 115B and the appropriate amine for 2-isopropoxyethanamine in Example 115C.

| Ex | Name | $^1$H NMR | MS |
|---|---|---|---|
| 138 | N-(imidazo[1,2-a]pyridin-7-ylmethyl)-2-{[(2-methoxyethyl)carbamoyl](tetrahydrofuran-2-ylmethyl)amino}-1,3-thiazole-5-carboxamide | $^1$H NMR (400 MHz, CDCl$_3$) δ ppm 8.09 (d, J = 7.0 Hz, 1H), 7.86 (d, J = 14.0 Hz, 2H), 7.62 (d, J = 0.8 Hz, 1H), 7.54 (d, J = 9.1 Hz, 2H), 6.84 (dd, J = 7.0, 1.4 Hz, 1H), 6.27 (t, J = 5.8 Hz, 1H), 4.63 (d, J = 6.0 Hz, 2H), 4.44 (d, J = 14.3 Hz, 1H), 4.29 (q, J = 7.3 Hz, 1H), 4.05 (dd, J = 15.4, 7.2 Hz, 1H), 3.92 (dd, J = 15.2, 7.2 Hz, 1H), 3.86-3.72 (m, 1H), 3.58-3.51 (m, 2H), 3.48 (dd, J = 9.2, 3.8 Hz, 3H), 3.39 (s, 3H), 2.14 (dt, J = 12.4, 6.3 Hz, 1H), 2.05-1.86 (m, 2H) | (APCI(+)) m/e 459 (M + H)+ |
| 141 | N-(imidazo[1,2-a]pyridin-6-ylmethyl)-2-{[(2-methoxyethyl)carbamoyl](tetrahydrofuran-3-ylmethyl)amino}-1,3-thiazole-5-carboxamide | $^1$H NMR (400 MHz, methanol-d$_4$) δ ppm 8.78 (s, 1H), 8.22 (d, J = 2.1 Hz, 1H), 8.03 (d, J = 2.1 Hz, 1H), 7.99 (d, J = 9.8 Hz, 2H), 7.91 (d, J = 9.3 Hz, 1H), 4.65 (s, 2H), 4.24 (dd, J = 15.2, 7.6 Hz, 1H), 4.12 (dd, J = 15.2, 7.9 Hz, 1H), 3.93 (td, J = 8.1, 5.8 Hz, 1H), 3.79-3.67 (m, 2H), 3.60 (dd, J = 8.7, 5.2 Hz, 1H), 3.55-3.45 (m, 4H), 3.36 (s, 3H), 2.85-2.75 (m, 1H), 2.00 (td, J = 13.4, 7.8 Hz, 1H), 1.72 (dt, J = 20.1, 6.3 Hz, 1H) | (APCI(+)) m/e 459 (M + H)+ |
| 151 | N-(imidazo[1,2-a]pyridin-6-ylmethyl)-2-{[(2-methoxyethyl)carbamoyl](tetrahydro-2H-pyran-4-ylmethyl)amino}-1,3-thiazole-5-carboxamide | $^1$H NMR (500 MHz, methanol-d$_4$) δ ppm 8.77 (s, 1H), 8.21 (d, J = 2.0 Hz, 1H), 8.02 (d, J = 2.1 Hz, 1H), 7.99 (dd, J = 9.3, 1.4 Hz, 1H), 7.97 (s, 1H), 7.90 (d, J = 9.3 Hz, 1H), 4.65 (s, 2H), 4.07 (d, J = 7.6 Hz, 2H), 3.92 (dd, J = 11.5, 3.0 Hz, 2H), 3.52 (dd, J = 8.3, 3.1 Hz, 2H), 3.47 (dd, J = 8.1, 3.0 Hz, 2H), 3.36 (s, 3H), 3.36-3.32 (m, 2H), 2.14 (ddd, J = 15.4, 7.7, 3.8 Hz, 1H), 1.54 (d, J = 11.2 Hz, 2H), 1.42 (qd, J = 12.1, 4.4 Hz, 2H) | (APCI(+)) m/e 473 (M + H)+ |
| 152 | N-(imidazo[1,2-a]pyridin-6-ylmethyl)-2-[{[2-(propan-2-yloxy)ethyl]carbamoyl}(tetrahydro-2H-pyran-4-ylmethyl)amino]- | $^1$H NMR (400 MHz, methanol-d$_4$) δ ppm 8.78 (s, 1H), 8.22 (d, J = 2.1 Hz, 1H), 8.03 (d, J = 2.1 Hz, 1H), 8.01-7.97 (m, 2H), 7.91 (d, J = 9.3 Hz, 1H), 4.65 (s, 2H), 4.06 (d, J = 7.6 Hz, 2H), 3.92 (dd, J = 11.4, 3.0 Hz, 2H), 3.63 (dt, J = 12.2, 6.1 Hz, 1H), 3.57 (dd, J = 10.1, | (APCI(+)) m/e 501 (M + H)+ |

TABLE 8-continued

The following Examples were prepared essentially as described in Example 115, substituting the appropriate amine in Example 115B and the appropriate amine for 2-isopropoxyethanamine in Example 115C.

| Ex | Name | ¹H NMR | MS |
|---|---|---|---|
|  | 1,3-thiazole-5-carboxamide | 4.5 Hz, 2H), 3.45 (t, J = 5.5 Hz, 2H), 3.35 (dd, J = 11.6, 1.7 Hz, 2H), 2.16 (ddd, J = 11.4, 7.6, 3.8 Hz, 1H), 1.55 (dd, J = 12.6, 1.5 Hz, 2H), 1.42 (qd, J = 12.1, 4.4 Hz, 2H), 1.16 (d, J = 6.1 Hz, 6H) |  |
| 153 | N-(imidazo[1,2-a]pyridin-6-ylmethyl)-2-{[(2-methoxyethyl)carbamoyl][(2R)-tetrahydrofuran-2-ylmethyl]amino}-1,3-thiazole-5-carboxamide | ¹H NMR (400 MHz, methanol-d₄) δ ppm 8.70 (s, 1H), 8.14 (d, J = 2.1 Hz, 1H), 7.95 (d, J = 2.2 Hz, 1H), 7.91 (dd, J = 9.4, 1.5 Hz, 1H), 7.88 (s, 1H), 7.82 (d, J = 9.3 Hz, 1H), 4.57 (s, 2H), 4.33 (dd, J = 15.4, 1.8 Hz, 1H), 4.17 (dd, J = 11.3, 4.9 Hz, 1H), 4.00 (dd, J = 15.4, 7.7 Hz, 1H), 3.86 (dd, J = 15.2, 7.0 Hz, 1H), 3.71 (td, J = 7.8, 5.8 Hz, 1H), 3.52-3.39 (m, 2H), 3.38-3.32 (m, 2H), 3.30 (s, 3H), 2.11-1.95 (m, 1H), 1.95-1.77 (m, 2H), 1.66-1.48 (m, 1H), 0.99-0.87 (m, 1H) | (APCI(+)) m/e 459 (M + H)⁺ |
| 154 | N-(imidazo[1,2-a]pyridin-6-ylmethyl)-2-({[2-(propan-2-yloxy)ethyl]carbamoyl}[(2R)-tetrahydrofuran-2-ylmethyl]amino)-1,3-thiazole-5-carboxamide | ¹H NMR (400 MHz, methanol-d₄) δ ppm 8.77 (s, 1H), 8.21 (d, J = 2.1 Hz, 1H), 8.02 (d, J = 2.1 Hz, 1H), 7.98 (dd, J = 9.4, 1.2 Hz, 1H), 7.96 (s, 1H), 7.90 (d, J = 9.3 Hz, 1H), 4.64 (s, 2H), 4.41 (dd, J = 15.4, 1.6 Hz, 1H), 4.29-4.21 (m, 1H), 4.07 (dd, J = 15.4, 7.6 Hz, 1H), 3.96 (dd, J = 15.0, 7.1 Hz, 1H), 3.77 (dd, J = 14.0, 7.7 Hz, 1H), 3.64 (dt, J = 12.2, 6.1 Hz, 1H), 3.57 (t, J = 5.0 Hz, 2H), 3.41 (t, J = 5.3 Hz, 2H), 2.15-2.03 (m, 1H), 2.00-1.87 (m, 2H), 1.64 (dq, J = 12.4, 8.2 Hz, 1H), 1.16 (d, J = 6.1 Hz, 6H) | (APCI(+)) m/e 487 (M + H)⁺ |
| 155 | N-(imidazo[1,2-a]pyridin-6-ylmethyl)-2-{[(2-methoxyethyl)carbamoyl][(2S)-tetrahydrofuran-2-ylmethyl]amino}-1,3-thiazole-5-carboxamide | ¹H NMR (400 MHz, methanol-d₄) δ ppm 8.78 (s, 1H), 8.21 (d, J = 2.1 Hz, 1H), 8.03 (d, J = 2.1 Hz, 1H), 8.01-7.97 (m, 1H), 7.96 (s, 1H), 7.90 (d, J = 9.3 Hz, 1H), 4.64 (s, 2H), 4.41 (d, J = 15.4 Hz, 1H), 4.26 (q, J = 6.4 Hz, 1H), 4.08 (dd, J = 15.4, 7.7 Hz, 1H), 3.94 (dd, J = 15.1, 7.1 Hz, 1H), 3.79 (dd, J = 13.7, 7.7 Hz, 1H), 3.53 (dt, J = 7.4, 4.5 Hz, 2H), 3.43 (t, J = 5.2 Hz, 2H), 3.38 (s, 3H), 2.11 (td, J = 12.3, 7.2 Hz, 1H), 2.01-1.85 (m, 2H), 1.65 (dq, J = 12.2, 8.2 Hz, 1H) | (APCI(+)) m/e 459 (M + H)⁺ |
| 156 | N-(imidazo[1,2-a]pyridin-6-ylmethyl)-2-({[2-(propan-2-yloxy)ethyl]carbamoyl}[(2S)-tetrahydrofuran-2-ylmethyl]amino)-1,3-thiazole-5-carboxamide | ¹H NMR (400 MHz, methanol-d₄) δ ppm 8.78 (s, 1H), 8.22 (d, J = 2.1 Hz, 1H), 8.03 (d, J = 2.1 Hz, 1H), 7.99 (dd, J = 9.3, 1.4 Hz, 1H), 7.96 (s, 1H), 7.91 (d, J = 9.3 Hz, 1H), 4.65 (s, 2H), 4.41 (dd, J = 15.4, 1.8 Hz, 1H), 4.31-4.22 (m, 1H), 4.08 (dd, J = 15.4, 7.6 Hz, 1H), 3.96 (dd, J = 15.1, 7.0 Hz, 1H), 3.78 (dd, J = 14.0, 7.7 Hz, 1H), 3.65 (dt, J = 12.1, 6.1 Hz, 1H), 3.57 (t, J = 4.9 Hz, 2H), 3.41 (t, J = 5.3 Hz, 2H), 2.11 (td, J = 12.2, 7.1 Hz, 1H), 2.01-1.85 (m, 2H), 1.65 (dq, J = 12.3, 8.2 Hz, 1H), 1.17 (d, J = 6.1 Hz, 6H) | (APCI(+)) m/e 487 (M + H)⁺ |
| 157 | N-(imidazo[1,2-a]pyridin-6-ylmethyl)-2-[{[2-(propan-2-yloxy)ethyl]carbamoyl}(tetrahydrofuran-3-ylmethyl)amino]-1,3-thiazole-5-carboxamide | ¹H NMR (400 MHz, methanol-d₄) δ ppm 8.78 (s, 1H), 8.21 (d, J = 2.0 Hz, 1H), 8.03 (d, J = 2.1 Hz, 1H), 7.99 (d, J = 11.6 Hz, 2H), 7.90 (d, J = 9.4 Hz, 1H), 4.65 (d, J = 3.9 Hz, 2H), 4.24 (dd, J = 15.2, 7.6 Hz, 1H), 4.12 (dd, J = 15.1, 8.0 Hz, 1H), 3.94 (td, J = 8.1, 5.7 Hz, 1H), 3.79-3.67 (m, 2H), 3.63 (dt, J = 8.2, 4.7 Hz, 2H), 3.57 (t, J = 5.8 Hz, 2H), 3.51-3.41 (m, 2H), 2.89-2.76 (m, 1H), 2.00 (td, J = 13.3, 7.9 Hz, 1H), 1.73 (dt, J = 20.3, 6.4 Hz, 1H), 1.15 (d, J = 6.1 Hz, 6H) | (APCI(+)) m/e 487 (M + H)⁺ |

Example 116

N-(imidazo[1,2-a]pyridin-6-ylmethyl)-2-[2-oxo-4-(tetrahydrofuran-3-yl)-1,3-oxazolidin-3-yl]-1,3-thiazole-5-carboxamide

Example 116A 2-bromo-N-(imidazo[1,2-a]pyridin-6-ylmethyl)thiazole-5-carboxamide The title compound was prepared as described in Example 1A, substituting imidazo[1,2-a]pyridin-6-ylmethanamine for 3-methylbutan-1-amine and 2-bromothiazole-5-carboxylic acid for 4-nitrobenzoic acid.

Example 116B

N-(imidazo[1,2-a]pyridin-6-ylmethyl)-2-[2-oxo-4-(tetrahydrofuran-3-yl)-1,3-oxazolidin-3-yl]-1,3-thiazole-5-carboxamide The title compound was prepared as in Example 53B, substituting 4-(tetrahydrofuran-3-yl)oxazolidin-2-one for 4-cyanobenzylamine and 2-bromo-N-(imidazo[1,2-a]pyridin-6-ylmethyl)thiazole-5-carboxamide for 2-bromo-N-(imidazo[1,2-a]pyridin-6-yl)thiazole-5-carboxamide. $^1$H NMR (400 MHz, methanol-$d_4$) δ 8.79 (s, 1H), 8.22 (d, J=1.9 Hz, 1H), 8.03 (s, 2H), 8.01-7.97 (m, 1H), 7.91 (d, J=9.5 Hz, 1H), 4.98-4.92 (m, 1H), 4.64 (dt, J=8.6, 4.5 Hz, 3H), 4.57-4.49 (m, 1H), 3.97 (td, J=8.5, 3.9 Hz, 1H), 3.81-3.71 (m, 1H), 3.71-3.59 (m, 2H), 2.26-2.02 (m, 1H), 1.96-1.85 (m, 1H), 1.78-1.65 (m, 1H); (APCI(+)) m/e 414 (M+H)$^+$.

TABLE 9

The following Examples were prepared essentially as described in Example 116, substituting the appropriate amine in Example 116A and the appropriate amine in Example 116B.

| Ex | Name | $^1$H NMR | MS |
|---|---|---|---|
| 122 | N-(imidazo[1,2-a]pyridin-6-ylmethyl)-2-(2-oxo-5-phenyl-1,3-oxazolidin-3-yl)-1,3-thiazole-5-carboxamide | | (ESI(+)) m/e 420 (M + H)$^+$ |
| 158 | 2-[5-(4-chlorophenyl)-2-oxo-1,3-oxazolidin-3-yl]-N-(imidazo[1,2-a]pyridin-6-ylmethyl)-1,3-thiazole-5-carboxamide | | (ESI(+)) m/e 454 (M + H)$^+$ |
| 181 | N-(imidazo[1,2-a]pyridin-7-ylmethyl)-2-[(4R)-2-oxo-4-(propan-2-yl)-1,3-oxazolidin-3-yl]-1,3-thiazole-5-carboxamide | $^1$H NMR (400 MHz, methanol-$d_4$) δ ppm 8.39 (d, J = 7.0 Hz, 1H), 8.04 (s, 1H), 7.80 (s, 1H), 7.53 (s, 1H), 7.45 (s, 1H), 6.97-6.87 (m, 1H), 4.75 (dt, J = 7.7, 3.8 Hz, 1H), 4.52 (dd, J = 9.5, 6.3 Hz, 2H), 2.85-2.65 (m, 1H), 0.99 (d, J = 7.1 Hz, 3H), 0.84 (d, J = 6.9 Hz, 3H) | (APCI(+)) m/e 386 (M + H)$^+$ |
| 185 | N-(imidazo[1,2-a]pyridin-7-ylmethyl)-2-[(4S)-2-oxo-4-(propan-2-yl)-1,3-oxazolidin-3-yl]-1,3-thiazole-5-carboxamide | $^1$H NMR (400 MHz, methanol-$d_4$) δ ppm 9.26 (t, J = 5.5 Hz, 1H), 8.75 (d, J = 7.0 Hz, 1H), 8.18 (d, J = 2.1 Hz, 1H), 8.07 (s, 1H), 8.00 (d, J = 2.1 Hz, 1H), 7.81 (s, 1H), 7.48 (d, J = 7.0 Hz, 1H), 4.77 (dd, J = 7.7, 3.9 Hz, 1H), 4.55 (dd, J = 10.7, 6.3 Hz, 2H), 2.76 (qd, J = 10.6, 7.1 Hz, 1H), 1.00 (d, J = 7.1 Hz, 3H), 0.84 (d, J = 6.9 Hz, 3H) | (APCI(+)) m/e 386 (M + H)$^+$ |
| 187 | 2-{(4R)-4-[(benzyloxy)methyl]-2-oxo-1,3-oxazolidin-3-yl}-N-(imidazo[1,2-a]pyridin-7-ylmethyl)-1,3-thiazole-5-carboxamide | $^1$H NMR (400 MHz, methanol-$d_4$) δ ppm 8.40 (d, J = 7.0 Hz, 1H), 7.91 (s, 1H), 7.80 (s, 1H), 7.53 (s, 1H), 7.46 (s, 1H), 7.20 (ddd, J = 15.4, 11.1, 5.1 Hz, 5H), 6.93 (dd, J = 7.0, 1.3 Hz, 1H), 4.85 (dd, J = 6.1, 2.6 Hz, 1H), 4.67-4.52 (m, 5H), 4.41 (d, J = 12.2 Hz, 1H), 4.12 (dd, J = 10.2, 3.2 Hz, 1H), 3.63 (dd, J = 10.2, 1.6 Hz, 1H) | (APCI(+)) m/e 464 (M + H)$^+$ |
| 188 | 2-{(4S)-4-[(benzyloxy)methyl]-2-oxo-1,3-oxazolidin-3-yl}-N-(imidazo[1,2-a]pyridin-7-ylmethyl)-1,3-thiazole-5-carboxamide | $^1$H NMR (400 MHz, methanol-$d_4$) δ ppm 8.35 (d, J = 7.0 Hz, 1H), 7.87 (s, 1H), 7.75 (s, 1H), 7.48 (s, 1H), 7.42 (s, 1H), 7.16 (ddd, J = 19.3, 11.3, 5.0 Hz, 5H), 6.88 (dd, J = 7.0, 1.3 Hz, 1H), 4.83-4.75 (m, 1H), 4.62-4.47 (m, 5H), 4.36 (d, J = 12.2 Hz, 1H), 4.07 (dd, J = 10.2, 3.2 Hz, 1H), 3.59 (dd, J = 10.2, 1.6 Hz, 1H) | (APCI(+)) m/e 464 (M + H)$^+$ |

TABLE 9-continued

The following Examples were prepared essentially as described in Example 116, substituting the appropriate amine in Example 116A and the appropriate amine in Example 116B.

| Ex | Name | ¹H NMR | MS |
|---|---|---|---|
| 218 | 2-{5-[(benzyloxy)methyl]-2-oxo-1,3-oxazolidin-3-yl}-N-(imidazo[1,2-a]pyridin-7-ylmethyl)-1,3-thiazole-5-carboxamide | ¹H NMR (400 MHz, methanol-$d_4$) δ ppm 8.39 (d, J = 7.0 Hz, 1H), 8.03 (s, 1H), 7.79 (s, 1H), 7.53 (s, 1H), 7.45 (s, 1H), 7.36-7.18 (m, 5H), 6.92 (d, J = 5.6 Hz, 1H), 5.02-4.99 (m, 2H), 4.59 (d, J = 2.3 Hz, 6H), 3.76 (ddd, J = 14.8, 11.2, 3.2 Hz, 1H) | (APCI(+)) m/e 464 (M + H)⁺ |
| 244 | 2-[(2S)-2-(hydroxymethyl)-5-oxopyrrolidin-1-yl]-N-(imidazo[1,2-a]pyridin-7-ylmethyl)-1,3-thiazole-5-carboxamide | ¹H NMR (400 MHz, methanol-$d_4$) δ ppm 9.25 (t, J = 5.7 Hz, 1H), 8.75 (d, J = 7.0 Hz, 1H), 8.18 (d, J = 1.9 Hz, 1H), 8.10 (s, 1H), 8.00 (d, J = 2.1 Hz, 1H), 7.81 (s, 1H), 7.48 (dd, J = 7.1, 1.3 Hz, 1H), 4.75-4.69 (m, 3H), 4.17 (dd, J = 11.7, 3.4 Hz, 1H), 3.75 (dd, J = 11.7, 2.2 Hz, 1H), 2.88 (dt, J = 17.8, 10.1 Hz, 1H), 2.57 (ddd, J = 17.7, 10.1, 2.3 Hz, 1H), 2.48-2.33 (m, 1H), 2.33-2.18 (m, 1H) | (APCI(+)) m/e 372 (M + H)⁺ |
| 245 | N-(imidazo[1,2-a]pyridin-7-ylmethyl)-2-[(4R)-4-methyl-2-oxo-1,3-oxazolidin-3-yl]-1,3-thiazole-5-carboxamide | ¹H NMR (400 MHz, methanol-$d_4$) δ ppm 8.75 (d, J = 7.0 Hz, 1H), 8.18 (d, J = 2.0 Hz, 1H), 8.07 (s, 1H), 8.00 (t, J = 2.4 Hz, 1H), 7.81 (s, 1H), 7.48 (dd, J = 7.0, 1.4 Hz, 1H), 4.87-4.78 (m, 1H), 4.73 (s, 2H), 4.69 (t, J = 8.5 Hz, 1H), 4.25 (dd, J = 8.7, 3.9 Hz, 1H), 1.57 (d, J = 6.3 Hz, 3H) | (APCI(+)) m/e 358 (M + H)⁺ |
| 249 | N-(imidazo[1,2-a]pyridin-7-ylmethyl)-2-{2-oxo-5-[(propan-2-yloxy)methyl]-1,3-oxazolidin-3-yl}-1,3-thiazole-5-carboxamide | ¹H NMR (400 MHz, methanol-$d_4$) δ ppm 9.26 (t, J = 5.9 Hz, 1H), 8.75 (d, J = 7.0 Hz, 1H), 8.18 (d, J = 2.0 Hz, 1H), 8.06 (s, 1H), 8.00 (d, J = 2.1 Hz, 1H), 7.81 (s, 1H), 7.48 (d, J = 7.0 Hz, 1H), 4.98 (ddd, J = 9.1, 5.8, 2.9 Hz, 1H), 4.73 (s, 2H), 4.31 (t, J = 9.5 Hz, 1H), 4.14 (dd, J = 9.9, 5.6 Hz, 1H), 3.78 (dd, J = 11.2, 2.9 Hz, 1H), 3.73-3.60 (m, 2H), 1.13 (d, J = 6.1 Hz, 6H) | (APCI(+)) m/e 416 (M + H)⁺ |
| 251 | 2-[5-(hydroxymethyl)-2-oxo-1,3-oxazolidin-3-yl]-N-(imidazo[1,2-a]pyridin-7-ylmethyl)-1,3-thiazole-5-carboxamide | ¹H NMR (400 MHz, DMSO-$d_6$) δ ppm 9.17 (t, J = 6.2 Hz, 1H), 8.50 (d, J = 6.9 Hz, 1H), 8.14 (s, 1H), 7.90 (s, 1H), 7.53 (s, 1H), 7.41 (s, 1H), 6.85 (d, J = 6.9 Hz, 1H), 5.29 (t, J = 5.6 Hz, 1H), 4.93-4.84 (m, 1H), 4.47 (d, J = 5.8 Hz, 2H), 4.24 (t, J = 9.4 Hz, 1H), 4.00 (dd, J = 9.8, 5.8 Hz, 1H), 3.76-3.66 (m, 1H), 3.66-3.56 (m, 1H) | (APCI(+)) m/e 374 (M + H)⁺ |
| 255 | N-(imidazo[1,2-a]pyridin-7-ylmethyl)-2-{(5S)-2-oxo-5-[(propan-2-yloxy)methyl]-1,3-oxazolidin-3-yl}-1,3-thiazole-5-carboxamide | ¹H NMR (400 MHz, methanol-$d_4$) δ 8.40 (d, J = 7.0 Hz, 1H), 8.04 (s, 1H), 7.80 (s, 1H), 7.53 (s, 1H), 7.45 (s, 1H), 6.92 (d, J = 6.3 Hz, 1H), 5.01-4.94 (m, 1H), 4.59 (s, 2H), 4.31 (t, J = 9.5 Hz, 1H), 4.13 (dd, J = 9.9, 5.6 Hz, 1H), 3.77 (dd, J = 11.2, 3.0 Hz, 1H), 3.72-3.58 (m, 2H), 1.13 (d, J = 6.1 Hz, 6H) | (APCI(+)) m/e 416 (M + H)⁺ |
| 256 | N-(imidazo[1,2-a]pyridin-7-ylmethyl)-2-{(5R)-2-oxo-5-[(propan-2-yloxy)methyl]-1,3-oxazolidin-3-yl}-1,3-thiazole-5-carboxamide | ¹H NMR (400 MHz, methanol-$d_4$) δ ppm 8.40 (d, J = 7.0 Hz, 1H), 8.04 (s, 1H), 7.80 (s, 1H), 7.53 (s, 1H), 7.45 (s, 1H), 6.92 (d, J = 7.0 Hz, 1H), 5.03-4.95 (m, 1H), 4.59 (s, 2H), 4.31 (t, J = 9.5 Hz, 1H), 4.13 (dd, J = 9.9, 5.7 Hz, 1H), 3.77 (dd, J = 11.2, 3.0 Hz, 1H), 3.71-3.58 (m, 2H), 1.13 (d, J = 6.1 Hz, 6H) | (APCI(+)) m/e 416 (M + H)⁺ |

Example 117

4-[(cyclopentylacetyl)amino]-N-(imidazo[1,2-a]pyridin-7-ylmethyl)benzamide

The title compound was prepared as described in Example 1A, substituting imidazo[1,2-a]pyridin-7-ylmethanamine for 3-methylbutan-1-amine and 4-(2-cyclopentylacetamido)benzoic acid for 4-nitrobenzoic acid. $^1$H NMR (400 MHz, DMSO-$d_6$) δ ppm 10.09 (s, 1H), 9.00-8.93 (m, 1H), 8.48 (dd, J=6.9, 0.9 Hz, 1H), 7.90-7.82 (m, 3H), 7.71-7.65 (m, 2H), 7.51 (d, J=1.2 Hz, 1H), 7.40-7.35 (m, 1H), 6.85 (dd, J=6.9, 1.7 Hz, 1H), 4.49 (d, J=5.9 Hz, 2H), 2.37-2.31 (m, 2H), 2.31-2.16 (m, 1H), 1.81-1.68 (m, 2H), 1.67-1.44 (m, 4H), 1.26-1.10 (m, 2H); MS (ESI(+)) m/e 377 (M+H)$^+$.

Example 118

2-cyclopentyl-N-(4-{[(imidazo[1,2-a]pyridin-7-ylmethyl)carbamoyl]amino}phenyl)acetamide

Example 118A

2-cyclopentyl-N-(4-nitrophenyl)acetamide

The title compound was prepared as described in Example 1A, substituting 4-nitroaniline for 3-methylbutan-1-amine and 2-cyclopentylacetic acid for 4-nitrobenzoic acid.

Example 118B

N-(4-aminophenyl)-2-cyclopentylacetamide

The title compound was prepared as described in Example 1B, substituting 2-cyclopentyl-N-(4-nitrophenyl)acetamide for N-isopentyl-4-nitrobenzamide.

Example 118C

2-cyclopentyl-N-(4-{[(imidazo[1,2-a]pyridin-7-ylmethyl)carbamoyl]amino}phenyl)acetamide The title compound was prepared as described in Example 1C, substituting N-(4-aminophenyl)-2-cyclopentylacetamide for 4-amino-N-isopentylbenzamide and imidazo[1,2-a]pyridin-7-ylmethanamine for imidazo[1,2-a]pyridin-6-amine $^1$H NMR (400 MHz, methanol-$d_4$) δ ppm 8.76-8.69 (m, 1H), 8.16 (dd, J=2.2, 0.8 Hz, 1H), 7.98 (d, J=2.2 Hz, 1H), 7.81-7.77 (m, 1H), 7.49-7.41 (m, 3H), 7.36-7.30 (m, 2H), 4.59 (s, 2H), 2.37-2.24 (m, 3H), 1.90-1.77 (m, 2H), 1.75-1.52 (m, 4H), 1.32-1.18 (m, 2H); MS (ESI(+)) m/e 392 (M+H)$^+$.

Example 119

N-(imidazo[1,2-a]pyridin-6-ylmethyl)-4-[1-(2-methylpropyl)-1H-pyrazol-4-yl]benzamide The title compound was prepared as described in Example 51A, substituting 4-bromo-N-(imidazo[1,2-a]pyridin-6-ylmethyl)benzamide for 4-bromoaniline. $^1$H NMR (400 MHz, DMSO-$d_6$) ppm 9.18 (t, J=5.7 Hz, 1 H), 8.75 (s, 1 H), 8.28 (s, 2 H), 8.02 (d, J=1.5 Hz, 1 H), 7.97 (s, 1 H), 7.89 (d, J=8.5 Hz, 2 H), 7.83-7.88 (m, 1 H), 7.74-7.80 (m, 1 H), 7.69 (d, J=8.3 Hz, 2 H), 4.56 (d, J=5.7 Hz, 2 H), 3.92 (d, J=7.2 Hz, 2 H), 2.13 (dq, J=13.6, 6.8 Hz, 1 H), 0.85 (d, J=6.6 Hz, 6 H); MS (ESI(+)) m/e 374 (M+H)$^+$.

Example 137

N-(imidazo[1,2-a]pyridin-6-ylmethyl)-2-[(3-methylbutanoyl)amino]-1,3-thiazole-5-carboxamide

Example 137A

2-(3-methylbutanamido)thiazole-5-carboxylic acid

The title compound was prepared as described in Example 52A, substituting 3-methylbutanoyl chloride for 2-cyclopentylacetyl chloride and methyl 2-aminothiazole-5-carboxylate for methyl 4-aminobenzoate.

Example 137B

N-(imidazo[1,2-a]pyridin-6-ylmethyl)-2-[(3-methylbutanoyl)amino]-1,3-thiazole-5-carboxamide The title compound was prepared as described in Example 1A, substituting imidazo[1,2-a]pyridin-6-ylmethanamine for 3-methylbutan-1-amine and 2-(3-methylbutanamido)thiazole-5-carboxylic acid for 4-nitrobenzoic acid. $^1$H NMR (400 MHz, DMSO-$d_6$) ppm 12.31 (s, 1 H), 9.05 (t, J=5.7 Hz, 1 H), 8.54 (s, 1 H), 7.97-8.11 (m, 2 H), 7.56-7.71 (m, 2 H), 7.34 (d, J=9.2 Hz, 1 H), 4.44 (d, J=5.7 Hz, 2 H), 2.33 (d, J=7.2 Hz, 2 H), 2.07 (dq, J=13.6, 6.7, 6.6 Hz, 1 H), 0.90 (d, J=6.6 Hz, 6 H); MS (ESI(+)) m/e 358 (M+H)$^+$.

Example 159

N-(imidazo[1,2-a]pyridin-6-ylmethyl)-4-{[1-(2-methylpropanoyl)piperidin-4-yl]oxy}benzamide

Example 159A tert-butyl 4-(4-(imidazo[1,2-a]pyridin-6-ylmethylcarbamoyl)phenoxy)piperidine-1-carboxylate The title compound was prepared as described in Example 1A, substituting imidazo[1,2-a]pyridin-6-ylmethanamine for 3-methylbutan-1-amine and 4-(1-(tert-butoxycarbonyl)piperidin-4-yloxy)benzoic acid for 4-nitrobenzoic acid.

Example 159B

N-(imidazo[1,2-a]pyridin-6-ylmethyl)-4-(piperidin-4-yloxy)benzamide

The title compound was prepared as described in Example 28A, substituting tert-butyl 4-(4-(imidazo[1,2-a]pyridin-6-ylmethylcarbamoyl)phenoxy)piperidine-1-carboxylate for tert-butyl 4-(4-(3-imidazo[1,2-a]pyridin-6-ylureido)phenyl)-5,6-dihydropyridine-1(2H)-carboxylate.

Example 159C

N-(imidazo[1,2-a]pyridin-6-ylmethyl)-4-{[1-(2-methylpropanoyl)piperidin-4-yl]oxy}benzamide The title compound was prepared as described in Example 1A, substituting N-(imidazo[1,2-a]pyridin-6-ylmethyl)-4-(piperidin-4-yloxy)benzamide for 3-methylbutan-1-amine and isobutyric acid for 4-nitrobenzoic acid. $^1$H NMR (400 MHz, methanol-$d_4$) δ ppm 8.79-8.74 (m, 1H), 8.23-8.19 (m, 1H), 8.04-7.97 (m, 2H), 7.94-7.81 (m, 3H), 7.09-7.03 (m, 2H), 4.81-4.72 (m, 1H), 4.69 (s, 2H), 3.91-3.77 (m, 2H), 3.62-3.48 (m, 2H), 3.04-2.92 (m, 1H), 2.12-1.86 (m, 2H), 1.87-1.61 (m, 2H), 1.11 (d, J=6.7 Hz, 6H); MS (ESI(+)) m/e 421 (M+H)$^+$.

TABLE 10

The following Examples were prepared essentially as described in Example 159, substituting the appropriate amine in Example 159A and the appropriate carboxylic acid in Example 159C.

| Ex | Name | $^1$H NMR | MS |
|---|---|---|---|
| 160 | 4-[(1-acetylpiperidin-4-yl)oxy]-N-(imidazo[1,2-a]pyridin-6-ylmethyl)benzamide | $^1$H NMR (400 MHz, methanol-d$_4$) δ ppm 8.80-8.75 (m, 1H), 8.21 (dd, J = 2.2, 0.7 Hz, 1H), 8.04-7.97 (m, 2H), 7.94-7.79 (m, 3H), 7.09-7.03 (m, 2H), 4.78-4.70 (m, 1H), 4.69 (s, 2H), 3.88-3.69 (m, 2H), 3.59-3.45 (m, 2H), 2.12 (s, 3H), 2.09-1.91 (m, 2H), 1.86-1.63 (m, 2H) | (ESI(+)) m/e 393 (M + H)$^+$ |
| 161 | 4-{[1-(cyclopropylcarbonyl)piperidin-4-yl]oxy}-N-(imidazo[1,2-a]pyridin-6-ylmethyl)benzamide | $^1$H NMR (400 MHz, methanol-d$_4$) δ ppm 8.79-8.75 (m, 1H), 8.21 (dd, J = 2.2, 0.7 Hz, 1H), 8.04-7.97 (m, 2H), 7.93-7.82 (m, 3H), 7.10-7.04 (m, 2H), 4.81-4.73 (m, 1H), 4.69 (s, 2H), 4.07-3.97 (m, 1H), 3.92-3.81 (m, 1H), 3.78-3.67 (m, 1H), 3.57-3.48 (m, 1H), 2.13-1.92 (m, 3H), 1.88-1.65 (m, 2H), 0.91-0.78 (m, 4H) | (ESI(+)) m/e 419 (M + H)$^+$ |
| 162 | N-(imidazo[1,2-a]pyridin-6-ylmethyl)-4-{[1-(tetrahydro-2H-pyran-4-ylcarbonyl)piperidin-4-yl]oxy}benzamide | $^1$H NMR (400 MHz, methanol-d$_4$) δ ppm 8.77 (m, 1H), 8.23-8.19 (m, 1H), 8.04-7.97 (m, 2H), 7.94-7.82 (m, 3H), 7.09-7.03 (m, 2H), 4.75 (m, 1H), 4.69 (s, 2H), 4.00-3.88 (m, 2H), 3.89-3.80 (m, 2H), 3.63-3.45 (m, 4H), 3.04-2.93 (m, 1H), 2.11-1.92 (m, 2H), 1.86-1.65 (m, 4H), 1.66-1.58 (m, 2H) | (ESI(+)) m/e 463 (M + H)$^+$ |
| 163 | 4-{[1-(1,4-dioxan-2-ylcarbonyl)piperidin-4-yl]oxy}-N-(imidazo[1,2-a]pyridin-6-ylmethyl)benzamide | $^1$H NMR (400 MHz, methanol-d$_4$) δ ppm 8.79-8.75 (m, 1H), 8.23-8.19 (m, 1H), 8.04-7.97 (m, 2H), 7.93-7.82 (m, 3H), 7.09-7.02 (m, 2H), 4.79-4.71 (m, 1H), 4.69 (s, 2H), 4.47-4.39 (m, 1H), 3.99-3.57 (m, 9H), 3.56-3.37 (m, 1H), 2.11-1.88 (m, 2H), 1.90-1.62 (m, 2H) | (ESI(+)) m/e 465 (M + H)$^+$ |
| 164 | N-(imidazo[1,2-a]pyridin-6-ylmethyl)-4-({1-[(2S)-tetrahydrofuran-2-ylcarbonyl]piperidin-4-yl}oxy)benzamide | $^1$H NMR (400 MHz, methanol-d$_4$) δ ppm 8.79-8.76 (m, 1H), 8.23-8.19 (m, 1H), 8.04-7.97 (m, 2H), 7.94-7.82 (m, 3H), 7.09-7.03 (m, 2H), 4.79-4.71 (m, 2H), 4.69 (s, 2H), 3.98-3.72 (m, 4H), 3.66-3.43 (m, 2H), 2.26-2.13 (m, 1H), 2.13-1.86 (m, 5H), 1.88-1.65 (m, 2H) | (ESI(+)) m/e 449 (M + H)$^+$ |
| 165 | N-(imidazo[1,2-a]pyridin-6-ylmethyl)-4-({1-[(2R)-tetrahydrofuran-2-ylcarbonyl]piperidin-4-yl}oxy)benzamide | $^1$H NMR (400 MHz, methanol-d$_4$) δ ppm 8.79-8.75 (m, 1H), 8.23-8.19 (m, 1H), 8.04-7.97 (m, 2H), 7.93-7.82 (m, 3H), 7.09-7.03 (m, 2H), 4.79-4.71 (m, 1H), 4.69 (s, 1H), 4.00-3.71 (m, 4H), 3.67-3.43 (m, 1H), 2.26-2.13 (m, 1H), 2.13-1.86 (m, 5H), 1.88-1.65 (m, 2H) | (ESI(+)) m/e 449 (M + H)$^+$ |
| 166 | 4-{[1-(2-hydroxy-2-methylpropanoyl)piperidin-4-yl]oxy}-N-(imidazo[1,2-a]pyridin-6-ylmethyl)benzamide | $^1$H NMR (400 MHz, methanol-d$_4$) δ ppm 8.79-8.75 (m, 1H), 8.21 (dd, J = 2.2, 0.7 Hz, 1H), 8.04-7.97 (m, 2H), 7.93-7.81 (m, 3H), 7.08-7.02 (m, 2H), 4.78-4.70 (m, 1H), 4.69 (s, 2H), 4.41-3.50 (m, 4H), 2.10-1.95 (m, 2H), 1.82-1.69 (m, 2H), 1.44 (s, 6H) | (ESI(+)) m/e 437 (M + H)$^+$ |
| 167 | N-(imidazo[1,2-a]pyridin-6-ylmethyl)-4-({1-[(propan-2-yloxy)acetyl]piperidin-4-yl}oxy)benzamide | $^1$H NMR (400 MHz, methanol-d$_4$) δ ppm 8.79-8.75 (m, 1H), 8.21 (dd, J = 2.2, 0.7 Hz, 1H), 8.04-7.97 (m, 2H), 7.93-7.82 (m, 3H), 7.09-7.03 (m, 2H), 4.80-4.72 (m, 1H), 4.69 (s, 2H), 4.19 (s, 2H), 3.87-3.73 (m, 2H), 3.73-3.62 (m, 1H), 3.59-3.45 (m, 2H), 2.11-1.93 (m, 2H), 1.87-1.68 (m, 2H), 1.19 (d, J = 6.1 Hz, 6H) | (ESI(+)) m/e 451 (M + H)$^+$ |
| 168 | 4-[(1-butanoylpiperidin-4-yl)oxy]-N-(imidazo[1,2-a]pyridin-6-ylmethyl)benzamide | $^1$H NMR (400 MHz, methanol-d$_4$) δ ppm 8.79-8.75 (m, 1H), 8.21 (dd, J = 2.2, 0.7 Hz, 1H), 8.04-7.97 (m, 2H), 7.96-7.81 (m, 3H), 7.08-7.02 (m, 2H), 4.78-4.70 (m, 1H), 4.69 (s, 2H), 3.90-3.73 (m, 2H), 3.59-3.46 (m, 2H), 2.40 (t, J = 7.5 Hz, 2H), 2.10-1.90 (m, 2H), 1.84-1.57 (m, 4H), 0.98 (t, J = 7.4 Hz, 3H) | (ESI(+)) m/e 421 (M + H)$^+$ |
| 169 | N-(imidazo[1,2-a]pyridin-6- | $^1$H NMR (400 MHz, methanol-d$_4$) δ ppm 8.80-8.75 (m, 1H), 8.21 (dd, J = 2.2, 0.7 Hz, | (ESI(+)) m/e |

TABLE 10-continued

The following Examples were prepared essentially as described in Example 159, substituting the appropriate amine in Example 159A and the appropriate carboxylic acid in Example 159C.

| Ex | Name | $^1$H NMR | MS |
|---|---|---|---|
|  | ylmethyl)-4-{[1-(3-methoxy-2-methylpropanoyl)piperidin-4-yl]oxy}benzamide | 1H), 8.04-7.97 (m, 2H), 7.94-7.82 (m, 3H), 7.09-7.03 (m, 2H), 4.80-4.71 (m, 1H), 4.69 (s, 2H), 4.01-3.71 (m, 2H), 3.71-3.41 (m, 3H), 3.38-3.31 (m, 1H), 3.30 (s, 3H), 3.26-3.16 (m, 1H), 2.12-1.88 (m, 2H), 1.87-1.61 (m, 2H), 1.06 (d, J = 6.8 Hz, 3H) | 451 (M + H)$^+$ |
| 170 | N-(imidazo[1,2-a]pyridin-6-ylmethyl)-4-{[1-(3,3,3-trifluoropropanoyl)piperidin-4-yl]oxy}benzamide | $^1$H NMR (400 MHz, methanol-d$_4$) δ ppm 8.79-8.75 (m, 1H), 8.21 (dd, J = 2.2, 0.7 Hz, 1H), 8.04-7.97 (m, 2H), 7.94-7.81 (m, 3H), 7.09-7.03 (m, 2H), 4.80-4.73 (m, 1H), 4.69 (s, 2H), 3.90-3.72 (m, 2H), 3.66-3.47 (m, 4H), 2.11-1.90 (m, 2H), 1.91-1.68 (m, 2H) | (ESI(+)) m/e 461 (M + H)$^+$ |
| 171 | N-(imidazo[1,2-a]pyridin-6-ylmethyl)-4-{[1-(tetrahydro-2H-pyran-4-ylacetyl)piperidin-4-yl]oxy}benzamide | $^1$H NMR (400 MHz, methanol-d$_4$) δ ppm 8.79-8.76 (m, 1H), 8.21 (dd, J = 2.1, 0.7 Hz, 1H), 8.04-7.97 (m, 2H), 7.93-7.82 (m, 3H), 7.09-7.03 (m, 2H), 4.78-4.71 (m, 1H), 4.68 (s, 2H), 3.97-3.74 (m, 4H), 3.59-3.48 (m, 2H), 3.48-3.38 (m, 2H), 2.37 (d, J = 7.0 Hz, 2H), 2.10-1.90 (m, 3H), 1.85-1.60 (m, 4H), 1.41-1.26 (m, 2H) | (ESI(+)) m/e 477 (M + H)$^+$ |
| 172 | 4-{[1-(cyclopropylacetyl)piperidin-4-yl]oxy}-N-(imidazo[1,2-a]pyridin-6-ylmethyl)benzamide | $^1$H NMR (400 MHz, methanol-d$_4$) δ ppm 8.79-8.75 (m, 1H), 8.21 (dd, J = 2.2, 0.7 Hz, 1H), 8.04-7.97 (m, 2H), 7.93-7.82 (m, 3H), 7.09-7.03 (m, 2H), 4.79-4.71 (m, 1H), 4.69 (s, 2H), 3.92-3.73 (m, 2H), 3.60-3.47 (m, 2H), 2.36 (d, J = 6.8 Hz, 2H), 2.10-1.91 (m, 2H), 1.86-1.65 (m, 2H), 1.08-0.94 (m, 1H), 0.58-0.47 (m, 2H), 0.23-0.16 (m, 2H) | (ESI(+)) m/e 433 (M + H)$^+$ |
| 173 | N-(imidazo[1,2-a]pyridin-6-ylmethyl)-4-{[1-(tetrahydrofuran-2-ylacetyl)piperidin-4-yl]oxy}benzamide | $^1$H NMR (400 MHz, methanol-d$_4$) δ ppm 8.80-8.75 (m, 1H), 8.22-8.19 (m, 1H), 8.04-7.97 (m, 2H), 7.92-7.81 (m, 3H), 7.09-7.03 (m, 2H), 4.79-4.70 (m, 1H), 4.69 (s, 2H), 4.29-4.18 (m, 1H), 3.94-3.66 (m, 4H), 3.65-3.45 (m, 2H), 2.76 (dd, J = 14.8, 7.6 Hz, 1H), 2.52 (dd, J = 14.8, 5.2 Hz, 1H), 2.18-1.67 (m, 7H), 1.69-1.53 (m, 1H) | (ESI(+)) m/e 463 (M + H)$^+$ |
| 411 | 4-[(1-acetylpiperidin-4-yl)oxy]-N-(imidazo[1,2-a]pyridin-7-ylmethyl)benzamide | $^1$H NMR (400 MHz, DMSO-d$_6$) δ ppm 8.96 (t, J = 5.9 Hz, 1H), 8.48 (d, J = 7.0 Hz, 1H), 7.88 (m, 3H), 7.51 (s, 1H), 7.37 (s, 1H), 7.07 (m, 2H), 6.85 (dd, J = 6.9, 1.6 Hz, 1H), 4.72 (m, 1H), 4.49 (d, J = 5.9 Hz, 2H), 3.85 (m, 1H), 3.68 (m, 1H), 3.50-3.15 (m, 2H), 2.02 (s, 3H), 2.03-1.85 (m 2H), 1.62 (m, 1H), 1.51 (m, 1H) | (ESI(+)) m/e 393 (M + H)$^+$ |
| 412 | N-(imidazo[1,2-a]pyridin-7-ylmethyl)-4-{[1-(2-methylpropanoyl)piperidin-4-yl]oxy}benzamide | $^1$H NMR (400 MHz, DMSO-d$_6$) δ ppm 8.96 (t, J = 5.9 Hz, 1H), 8.48 (dd, J = 6.9, 0.9 Hz, 1H), 7.88 (m, 3H), 7.51 (d, J = 1.2 Hz, 1H), 7.37 (s, 1H), 7.07 (m, 2H), 6.85 (dd, J = 6.9, 1.7 Hz, 1H), 4.73 (m, 1H), 4.49 (d, J = 5.9 Hz, 2H), 3.96-3.70 (m, 2H), 3.45-3.20 (m, 2H), 2.89 (m, 1H), 1.93 (m, 2H), 1.58 (m, 2H), 1.00 (d, J = 6.7 Hz, 6H) | (ESI(+)) m/e 421 (M + H)$^+$ |
| 413 | N-(imidazo[1,2-a]pyridin-7-ylmethyl)-4-({1-[(2S)-2-methylbutanoyl]piperidin-4-yl}oxy)benzamide | $^1$H NMR (400 MHz, DMSO-d$_6$) δ ppm 8.96 (t, J = 5.9 Hz, 1H), 8.48 (dd, J = 6.9, 0.9 Hz, 1H), 7.88 (m, 3H), 7.51 (s, 1H), 7.37 (s, 1H), 7.07 (m, 2H), 6.85 (dd, J = 6.9, 1.6 Hz, 1H), 4.74 (m, 1H), 4.49 (d, J = 5.9 Hz, 4.00-3.74 (m, 2H), 3.50-3.15 (m, 2H), 2.72 (m, 1H), 1.95 (m, 2H), 1.54 (m, 3H), 1.27 (m, 1H), 0.98 (d, J = 6.7 Hz, 3H), 0.81 (t, J = 7.4 Hz, 3H) | (ESI(+)) m/e 435 (M + H)$^+$ |
| 414 | 4-{[1-(cyclopropylacetyl)piperidin-4-yl]oxy}-N-(imidazo[1,2-a]pyridin-7- | $^1$H NMR (400 MHz, DMSO-d$_6$) δ ppm 8.95 (t, J = 5.9 Hz, 1H), 8.48 (dd, J = 6.9, 0.9 Hz, 1H), 7.88 (m, 3H), 7.51 (d, J = 1.2 Hz, 1H), 7.37 (s, 1H), 7.07 (m, 2H), 6.85 (dd, J = 7.0, 1.7 Hz, 1H), 4.73 (m, 1H), 4.49 (d, J = 5.9 Hz, 2H), 3.89 (m, 1H), 3.69 (m, 1H), | (ESI(+)) m/e 433 (M + H)$^+$ |

TABLE 10-continued

The following Examples were prepared essentially as described in Example 159, substituting the appropriate amine in Example 159A and the appropriate carboxylic acid in Example 159C.

| Ex | Name | ¹H NMR | MS |
|---|---|---|---|
|  | ylmethyl)benzamide | 3.40-3.15 (m, 2H), 2.28 (d, J = 6.7 Hz, 2H), 1.93 (m, 2H), 1.85-1.41 (m, 2H), 0.95 (m, 1H), 0.45 (m, 2H), 0.12 (m, 2H) |  |
| 415 | 4-[(1-benzoylpiperidin-4-yl)oxy]-N-(imidazo[1,2-a]pyridin-7-ylmethyl)benzamide | ¹H NMR (400 MHz, DMSO-d₆) δ ppm 8.96 (t, J = 5.9 Hz, 1H), 8.48 (dd, J = 6.9, 0.9 Hz, 1H), 7.90 (m, 3H), 7.51 (m, 1H), 7.47-7.37 (m, 5H), 7.36 (m, 1H), 7.07 (m, 2H), 6.84 (dd, J = 7.0, 1.7 Hz, 1H), 4.78 (m, 1H), 4.49 (d, J = 5.9 Hz, 2H), 4.00 (m, 1H), 3.55 (m, 1H), 3.45-3.15 (m, 2H), 2.00 (m, 2H), 1.64 (m, 2H) | (ESI(+)) m/e 455 (M + H)⁺ |
| 416 | N-(imidazo[1,2-a]pyridin-7-ylmethyl)-4-({1-[(propan-2-yloxy)acetyl]piperidin-4-yl}oxy)benzamide | ¹H NMR (400 MHz, DMSO-d₆) δ ppm 8.96 (t, J = 5.9 Hz, 1H), 8.48 (dd, J = 6.9, 0.9 Hz, 1H), 7.88 (m, 3H), 7.51 (d, J = 1.2 Hz, 1H), 7.37 (s, 1H), 7.07 (m, 2H), 6.85 (dd, J = 7.0, 1.7 Hz, 1H), 4.74 (m, 1H), 4.49 (d, J = 5.9 Hz, 2H), 4.10 (d, J = 1.1 Hz, 2H), 3.85 (m, 1H), 3.70 (m, 1H), 3.60 (m, 1H), 3.40-3.15 (m, 2H), 1.97 (m, 2H), 1.69-1.45 (m, 2H), 1.11 (d, J = 6.1 Hz, 6H) | (ESI(+)) m/e 451 (M + H)⁺ |
| 417 | 4-{[1-(2-hydroxy-2-methylpropanoyl)piperidin-4-yl]oxy}-N-(imidazo[1,2-a]pyridin-7-ylmethyl)benzamide | ¹H NMR (400 MHz, DMSO-d₆) δ ppm 8.96 (t, J = 5.9 Hz, 1H), 8.48 (dd, J = 6.9, 0.9 Hz, 1H), 7.88 (m, 3H), 7.51 (d, J = 1.2 Hz, 1H), 7.37 (s, 1H), 7.07 (m, 2H), 6.85 (dd, J = 7.0, 1.7 Hz, 1H), 5.42 (m, 1H), 4.73 (m, 1H), 4.49 (d, J = 5.9 Hz, 2H), 4.42-3.78 (m, 2H), 3.70-3.20 (m, 2H), 1.95 (m, 2H), 1.57 (m, 2H), 1.32 (s, 6H) | (ESI(+)) m/e 437 (M + H)⁺ |
| 418 | N-(imidazo[1,2-a]pyridin-7-ylmethyl)-4-({1-[(2R)-tetrahydrofuran-2-ylcarbonyl]piperidin-4-yl}oxy)benzamide | ¹H NMR (400 MHz, DMSO-d₆) δ ppm 8.96 (t, J = 5.9 Hz, 1H), 8.48 (dd, J = 6.9, 0.9 Hz, 1H), 7.88 (m, 3H), 7.51 (d, J = 1.2 Hz, 1H), 7.37 (s, 1H), 7.07 (m, 2H), 6.85 (dd, J = 7.0, 1.7 Hz, 1H), 4.79-4.64 (m, 2H), 4.49 (d, J = 5.9 Hz, 2H), 3.95-3.70 (m, 4H), 3.50-3.15 (m, 2H), 2.10-1.90 (m, 4H), 1.90-1.75 (m, 2H), 1.70-1.43 (m, 2H) | (ESI(+)) m/e 449 (M + H)⁺ |
| 419 | N-(imidazo[1,2-a]pyridin-7-ylmethyl)-4-({1-[(2S)-tetrahydrofuran-2-ylcarbonyl]piperidin-4-yl}oxy)benzamide | ¹H NMR (400 MHz, DMSO-d₆) δ ppm 8.96 (t, J = 5.9 Hz, 1H), 8.48 (dd, J = 6.9, 0.9 Hz, 1H), 7.88 (m, 3H), 7.51 (d, J = 1.2 Hz, 1H), 7.37 (s, 1H), 7.07 (m, 2H), 6.85 (dd, J = 6.9, 1.7 Hz, 1H), 4.79-4.64 (m, 2H), 4.49 (d, J = 5.9 Hz, 2H), 3.94-3.67 (m, 4H), 3.50-3.15 (m, 2H), 2.10-1.90 (m, 4H), 1.90-1.75 (m, 2H), 11.70-1.43 (m, 2H) | (ESI(+)) m/e 449 (M + H)⁺ |
| 420 | N-(imidazo[1,2-a]pyridin-7-ylmethyl)-4-{[1-(tetrahydro-2H-pyran-4-ylcarbonyl)piperidin-4-yl]oxy}benzamide | ¹H NMR (400 MHz, DMSO-d₆) δ ppm 8.96 (t, J = 5.9 Hz, 1H), 8.48 (dd, J = 6.9, 0.9 Hz, 1H), 7.88 (m, 3H), 7.51 (d, J = 1.2 Hz, 1H), 7.37 (s, 1H), 7.07 (m, 2H), 6.85 (dd, J = 7.0, 1.7 Hz, 1H), 4.73 (m, 1H), 4.49 (d, J = 5.9 Hz, 2H), 3.84 (m, 4H), 3.45-3.15 (m, 4H), 2.90 (m, 1H), 1.96 (m, 2H), 1.65-1.45 (m, 6H) | (ESI(+)) m/e 463 (M + H)⁺ |
| 421 | 4-{[1-(1,4-dioxan-2-ylcarbonyl)piperidin-4-yl]oxy}-N-(imidazo[1,2-a]pyridin-7-ylmethyl)benzamide | ¹H NMR (400 MHz, DMSO-d₆) δ ppm 8.96 (t, J = 6.0 Hz, 1H), 8.48 (dd, J = 6.9, 0.9 Hz, 1H), 7.89 (m, 3H), 7.51 (d, J = 1.2 Hz, 1H), 7.37 (d, J = 1.5 Hz, 1H), 7.07 (m, 2H), 6.85 (dd, J = 7.0, 1.7 Hz, 1H), 4.74 (m, 1H), 4.49 (d, J = 5.9 Hz, 2H), 4.35 (dd, J = 9.4, 2.8 Hz, 1H), 3.90-3.55 (m, 7H), 3.55-3.15 (m, 3H), 1.98 (m, 2H), 1.75-1.40 (m, 2H) | (ESI(+)) m/e 465 (M + H)⁺ |
| 422 | N-(imidazo[1,2-a]pyridin-7-ylmethyl)-4-{[1-(tetrahydro-2H-pyran-4-ylacetyl)piperidin-4-yl]oxy}benzamide | ¹H NMR (400 MHz, DMSO-d₆) δ ppm 8.95 (t, J = 5.9 Hz, 1H), 8.48 (d, J = 7.0 Hz, 1H), 7.89 (m, 3H), 7.51 (s, 1H), 7.37 (bs, 1H), 7.07 (m, 2H), 6.85 (dd, J = 6.9, 1.7 Hz, 1H), 4.72 (m, 1H), 4.49 (d, J = 5.9 Hz, 2H), 3.95-3.67 (m, 4H), 3.45-3.15 (m, 5H), 2.28 (m, 2H), 1.93 (m, 2H), 1.67-1.42 (m, 4H), 1.26-1.12 (m, 2H) | (ESI(+)) m/e 477 (M + H)⁺ |
| 423 | N-(imidazo[1,2-a]pyridin-7-ylmethyl)-4-{[1-(morpholin-4- | ¹H NMR (400 MHz, DMSO-d₆) δ ppm 8.96 (t, J = 5.9 Hz, 1H), 8.48 (d, J = 7.0 Hz, 1H), 7.89 (m, 3H), 7.51 (s, 1H), 7.37 (s, 1H), 7.07 (m, 2H), 6.85 (dd, J = 7.0, 1.6 Hz, 1H), | (ESI(+)) m/e 478 (M + H)⁺ |

TABLE 10-continued

The following Examples were prepared essentially as described in Example 159, substituting the appropriate amine in Example 159A and the appropriate carboxylic acid in Example 159C.

| Ex | Name | $^1$H NMR | MS |
|----|------|-----------|-----|
|    | ylacetyl)piperidin-4-yl]oxy}benzamide | 4.73 (m, 1H), 4.49 (d, J = 5.8 Hz, 2H), 3.86 (m, 2H), 3.57 (m, 4H), 3.50-3.20 (m, 2H), 3.20-3.05 (m, 2H), 2.40 (m, 4H), 2.08-1.89 (m, 2H), 1.70-1.41 (m, 2H) | |

Example 204

2-[1-(2-hydroxy-2-methylpropyl)-1H-pyrazol-4-yl]-N-(imidazo[1,2-a]pyridin-7-ylmethyl)-1,3-thiazole-5-carboxamide Example 204A 2-bromo-N-(imidazo[1,2-a]pyridin-7-ylmethyl)thiazole-5-carboxamide The title compound was prepared as described in Example 1A, substituting imidazo[1,2-a]pyridin-7-ylmethanamine for 3-methylbutan-1-amine and 2-bromothiazole-5-carboxylic acid for 4-nitrobenzoic acid.

Example 204B

2-[1-(2-hydroxy-2-methylpropyl)-1H-pyrazol-4-yl]-N-(imidazo[1,2-a]pyridin-7-ylmethyl)-1,3-thiazole-5-carboxamide The title compound was prepared as described in Example 51A, substituting 2-methyl-1-(3-(4,4,5,5-tetramethyl-1,3,2-dioxaborolan-2-yl)-1H-pyrrol-1-yl)propan-2-ol for 1-isobutyl-4-(4,4,5,5-tetramethyl-1,3,2-dioxaborolan-2-yl)-1H-pyrazole and 2-bromo-N-(imidazo[1,2-a]pyridin-7-ylmethyl)thiazole-5-carboxamide for 4-bromoaniline. $^1$H NMR (400 MHz, methanol-d$_4$) ppm 8.41 (d, J=7.05 Hz, 1 H) 8.27 (d, J=7.92 Hz, 2 H) 8.00 (s, 1 H) 7.80 (s, 1 H) 7.53 (s, 1 H) 7.47 (s, 1 H) 6.93 (dd, J=6.99, 1.36 Hz, 1 H) 4.61 (s, 2 H) 4.16 (s, 2 H) 1.20 (s, 6 H); MS (ESI)(+)) m/e 397 (M+H)$^+$.

Example 205

N-(imidazo[1,2-a]pyridin-7-ylmethyl)-2-[1-(2-methylpropyl)-1H-pyrazol-4-yl]-1,3-thiazole-5-carboxamide The title compound was prepared as described in Example 51A, substituting 2-bromo-N-(imidazo[1,2-a]pyridin-7-ylmethyl)thiazole-5-carboxamide for 4-bromoaniline. $^1$H NMR (400 MHz, methanol-d$_4$) ppm 8.40 (d, J=6.94 Hz, 1 H) 8.27 (d, J=7.48 Hz, 2 H) 8.00 (s, 1 H) 7.80 (s, 1 H) 7.53 (s, 1 H) 7.47 (s, 1 H) 6.93 (d, J=6.83 Hz, 1 H) 4.61 (s, 2 H) 4.01 (d, J=7.26 Hz, 2 H) 2.12-2.30 (m, 1 H) 0.93 (d, J=6.61 Hz, 6 H); MS (ESI)(+)) m/e 381 (M+H)$^+$.

Example 207 tert-butyl {4-[(imidazo[1,2-a]pyridin-7-ylmethyl)carbamoyl]phenyl}carbamate

The title compound was prepared as described in Example 1A, substituting imidazo[1,2-a]pyridin-7-ylmethanamine for 3-methylbutan-1-amine and 4-(tert-butoxycarbonylamino)benzoic acid for 4-nitrobenzoic acid. $^1$H NMR (300 MHz, DMSO-d$_6$) δ ppm 9.62 (s, 1H), 8.92 (t, J=6.0 Hz, 1H), 8.48 (dd, J=6.9, 0.9 Hz, 1H), 7.90-7.79 (m, 3H), 7.57-7.49 (m, 3H), 7.39-7.35 (m, 1H), 6.85 (dd, J=7.0, 1.6 Hz, 1H), 4.48 (d, J=5.8 Hz, 2H), 1.49 (s, 9H); MS (ESI(+)) m/e 367 (M+H)$^+$.

Example 208

N-(imidazo[1,2-a]pyridin-7-ylmethyl)-4-[(tetrahydro-2H-pyran-4-ylacetyl)amino]benzamide Example 208A tert-butyl {4-[(imidazo[1,2-a]pyridin-7-ylmethyl)carbamoyl]phenyl}carbamate The title compound was prepared as described in Example 1A, substituting imidazo[1,2-a]pyridin-7-ylmethanamine for 3-methylbutan-1-amine and 4-(tert-butoxycarbonylamino)benzoic acid for 4-nitrobenzoic acid.

Example 208B 4-amino-N-(imidazo[1,2-a]pyridin-7-ylmethyl)benzamide

The title compound was prepared as described in Example 28A, substituting tert-butyl {4-[(imidazo[1,2-a]pyridin-7-ylmethyl)carbamoyl]phenyl}carbamate for tert-butyl 4-(4-(3-imidazo[1,2-a]pyridin-6-ylureido)phenyl)-5,6-dihydropyridine-1(2H)-carboxylate.

Example 208C

N-(imidazo[1,2-a]pyridin-7-ylmethyl)-4-[(tetrahydro-2H-pyran-4-ylacetyl)amino]benzamide The title compound was prepared as described in Example 1A, substituting 4-amino-N-(imidazo[1,2-a]pyridin-7-ylmethyl)benzamide for 3-methylbutan-1-amine and 2-(tetrahydro-2H-pyran-4-yl)acetic acid for 4-nitrobenzoic acid. $^1$H NMR (400 MHz, methanol-d$_4$) δ ppm 8.74 (dd, J=7.0, 0.9 Hz, 1H), 8.17 (dd, J=2.2, 0.7 Hz, 1H), 7.98 (d, J=2.2 Hz, 1H), 7.91-7.84 (m, 2H), 7.81-7.78 (m, 1H), 7.75-7.68 (m, 2H), 7.49 (dd, J=7.0, 1.6 Hz, 1H), 4.79-4.74 (m, 2H), 3.98-3.89 (m, 2H), 3.50-3.38 (m, 2H), 2.38-2.32 (m, 2H), 2.20-2.02 (m, 1H), 1.74-1.61 (m, 2H), 1.47-1.28 (m, 2H); MS (ESI(+)) m/e 393 (M+H)$^+$.

TABLE 11

The following Examples were prepared essentially as described in Example 208, substituting the appropriate carboxylic acid in Example 208A and the appropriate carboxylic acid in Example 208C.

| Ex | Name | MS |
|---|---|---|
| 209 | N-(imidazo[1,2-a]pyridin-7-ylmethyl)-4-[(tetrahydrofuran-2-ylacetyl)amino]benzamide | (ESI(+)) m/e 379 (M + H)+ |
| 210 | N-(imidazo[1,2-a]pyridin-7-ylmethyl)-4-{[3-(tetrahydrofuran-2-yl)propanoyl]amino}benzamide | (ESI(+)) m/e 393 (M + H)+ |
| 211 | N-(imidazo[1,2-a]pyridin-7-ylmethyl)-4-{[(propan-2-yloxy)acetyl]amino}benzamide | (ESI(+)) m/e 367 (M + H)+ |
| 212 | 4-[(3-cyclopentylpropanoyl)amino]-N-(imidazo[1,2-a]pyridin-7-ylmethyl)benzamide | (ESI(+)) m/e 391 (M + H)+ |
| 213 | N-(imidazo[1,2-a]pyridin-7-ylmethyl)-4-[(4-methylpentanoyl)amino]benzamide | (ESI(+)) m/e 365 (M + H)+ |
| 214 | N-(imidazo[1,2-a]pyridin-7-ylmethyl)-4-[(tetrahydrofuran-3-ylacetyl)amino]benzamide | (ESI(+)) m/e 379 (M + H)+ |
| 305 | 4-[(cyclopentylacetyl)amino]-3-fluoro-N-(imidazo[1,2-a]pyridin-7-ylmethyl)benzamide | (ESI(+)) m/e 395 (M + H)+ |
| 463 | 4-[(cyclopentylacetyl)amino]-2-fluoro-N-(imidazo[1,2-a]pyridin-7-ylmethyl)benzamide | (ESI(+)) m/e 395 (M + H)+ |
| 867 | N-(imidazo[1,2-a]pyridin-7-ylmethyl)-4-{[(2-methoxyphenyl)acetyl]amino}benzamide | (ESI(+)) m/e 415 (M + H)+ |
| 868 | N-(imidazo[1,2-a]pyridin-7-ylmethyl)-4-[(phenylacetyl)amino]benzamide | (ESI(+)) m/e 385 (M + H)+ |
| 869 | 4-(benzoylamino)-N-(imidazo[1,2-a]pyridin-7-ylmethyl)benzamide | (ESI(+)) m/e 371 (M + H)+ |
| 870 | 2,5-difluoro-N-{4-[(imidazo[1,2-a]pyridin-7-ylmethyl)carbamoyl]phenyl}benzamide | (ESI(+)) m/e 407 (M + H)+ |
| 871 | 3,5-difluoro-N-{4-[(imidazo[1,2-a]pyridin-7-ylmethyl)carbamoyl]phenyl}benzamide | (ESI(+)) m/e 407 (M + H)+ |
| 872 | 3,4-difluoro-N-{4-[(imidazo[1,2-a]pyridin-7-ylmethyl)carbamoyl]phenyl}benzamide | (ESI(+)) m/e 407 (M + H)+ |
| 873 | 2,4-difluoro-N-{4-[(imidazo[1,2-a]pyridin-7-ylmethyl)carbamoyl]phenyl}benzamide | (ESI(+)) m/e 407 (M + H)+ |
| 874 | 2-fluoro-N-{4-[(imidazo[1,2-a]pyridin-7-ylmethyl)carbamoyl]phenyl}benzamide | (ESI(+)) m/e 389 (M + H)+ |
| 875 | N-{4-[(imidazo[1,2-a]pyridin-7-ylmethyl)carbamoyl]phenyl}-3-methoxybenzamide | (ESI(+)) m/e 401 (M + H)+ |
| 876 | 4-{[(2-fluorophenyl)acetyl]amino}-N-(imidazo[1,2-a]pyridin-7-ylmethyl)benzamide | (ESI(+)) m/e 403 (M + H)+ |
| 880 | N-{4-[(imidazo[1,2-a]pyridin-7-ylmethyl)carbamoyl]phenyl}-2-methoxybenzamide | (ESI(+)) m/e 401 (M + H)+ |
| 890 | 4-{[(2,5-difluorophenyl)acetyl]amino}-N-(imidazo[1,2-a]pyridin-7-ylmethyl)benzamide | (ESI(+)) m/e 421 (M + H)+ |
| 891 | 4-{[(2,4-difluorophenyl)acetyl]amino}-N-(imidazo[1,2-a]pyridin-7-ylmethyl)benzamide | (ESI(+)) m/e 421 (M + H)+ |
| 895 | 4-{[difluoro(phenyl)acetyl]amino}-N-(imidazo[1,2-a]pyridin-7-ylmethyl)benzamide | (ESI(+)) m/e 421 (M + H)+ |
| 896 | N-(imidazo[1,2-a]pyridin-7-ylmethyl)-4-[(2-methyl-2-phenylpropanoyl)amino]benzamide | (ESI(+)) m/e 413 (M + H)+ |

Example 215

4-[(4-cyanobenzyl)(cyclopentylacetyl)amino]-N-(imidazo[1,2-a]pyridin-6-ylmethyl)benzamide

Example 215A methyl 4-(4-cyanobenzylamino)benzoate

A solution of methyl 4-aminobenzoate (0.2 g, 1.323 mmol) and 4-formylbenzonitrile (0.177 g, 1.350 mmol) in methanol (2 ml) and dichloromethane (4 ml) was treated with acetic acid (0.379 ml, 6.62 mmol) followed by MP-cyanoborohydride (1.151 g, 2.65 mmol) and the reaction was slowly stirred at room temperature. After 16 hours, the mixture was filtered and concentrated and the concentrate was partitioned between 2 N sodium hydroxide and dichloromethane. The organic phase was concentrated to give the title compound with 30% of remaining 4-formylbenzonitrile.

Example 215B methyl 4-(N-(4-cyanobenzyl)-2-cyclopentylacetamido)benzoate

The title compound was prepared as described in Example 52A, substituting methyl 4-(4-cyanobenzylamino)benzoate for methyl 4-aminobenzoate.

Example 215C 4-(N-(4-cyanobenzyl)-2-cyclopentylacetamido)benzoic acid

The title compound was prepared as described in Example 4B, substituting methyl 4-(N-(4-cyanobenzyl)-2-cyclopentylacetamido)benzoate for methyl 4-(3-imidazo[1,2-a]pyridin-6-ylureido)benzoate.

Example 215D

4-[(4-cyanobenzyl)(cyclopentylacetyl)amino]-N-(imidazo[1,2-a]pyridin-6-ylmethyl)benzamide The title compound was prepared as described in Example 1A, substituting imidazo[1,2-a]pyridin-6-ylmethanamine for 3-methylbutan-1-amine and 4-(N-(4-cyanobenzyl)-2-cyclopentylacetamido)benzoic acid for 4-nitrobenzoic acid. $^1$H NMR (500 MHz, DMSO-$d_6$) δ ppm 9.08 (t, J=5.8 Hz, 1H), 8.47 (s, 1H), 7.94 (s, 1H), 7.90-7.85 (m, 2H), 7.79-7.74 (m, 2H), 7.56-7.49 (m, 2H), 7.43-7.37 (m, 2H), 7.36-7.30 (m, 2H), 7.21 (dd, J=9.3, 1.7 Hz, 1H), 4.98 (bs, 2H), 4.45 (d, J=5.8 Hz, 2H), 2.19-2.13 (m, 3H), 1.74-1.66 (m, 2H), 1.51-1.38 (m, 4H), 1.01-0.92 (m, 2H); MS (ESI(+)) m/e 492 (M+H)$^+$.

Example 216 tert-butyl 4-(4-{[(imidazo[1,2-a]pyridin-7-ylmethyl)carbamoyl]amino}phenyl)piperidine-1-carboxylate The title compound was prepared as described in Example 1C, substituting tert-butyl 4-(4-aminophenyl)piperidine-1-carboxylate for 4-amino-N-isopentylbenzamide and imidazo[1,2-a]pyridin-7-ylmethanamine for imidazo[1,2-a]pyridin-6-amine. $^1$H NMR (500 MHz, DMSO-$d_6$) δ ppm 8.56 (s, 1H), 8.51-8.45 (m, 1H), 7.88 (s, 1H), 7.52-7.49 (m, 1H), 7.39-7.36 (m, 1H), 7.35-7.30 (m, 2H), 7.12-7.07 (m, 2H), 6.83 (dd, J=7.0, 1.6 Hz, 1H), 6.67 (t, J=6.0 Hz, 1H), 4.32 (d, J=6.0 Hz, 2H), 4.10-4.00 (m, 2H), 2.89-2.65 (m, 2H), 2.62-2.54 (m, 1H), 1.75-1.66 (m, 2H), 1.49-1.37 (m, 11H); MS (ESI(+)) m/e 450 (M+H)$^+$.

Example 217 tert-butyl 4-{4-[(imidazo[1,2-a]pyridin-7-ylmethyl)carbamoyl]phenyl}piperidine-1-carboxylate The title compound was prepared as described in Example 1A, substituting imidazo[1,2-a]pyridin-7-ylmethanamine for 3-methylbutan-1-amine and 4-(1-(tert-butoxycarbonyl)piperidin-4-yl)benzoic acid for 4-nitrobenzoic acid. $^1$H NMR (300 MHz, DMSO-$d_6$) δ ppm 9.02 (t, J=6.0 Hz, 1H), 8.48 (dd, J=6.9, 0.9 Hz, 1H), 7.90-7.81 (m, 3H), 7.51 (d, J=1.2 Hz, 1H), 7.40-7.32 (m, 3H), 6.84 (dd, J=7.0, 1.7 Hz, 1H), 4.49 (d, J=5.9 Hz, 2H), 4.13-4.03 (m, 2H), 2.91-2.69 (m, 3H), 1.82-1.72 (m, 2H), 1.60-1.44 (m, 2H), 1.42 (s, 9H); MS (ESI(+)) m/e 435 (M+H)$^+$.

Example 220

1-(imidazo[1,2-a]pyridin-7-ylmethyl)-3-{4-[1-(tetrahydrofuran-2-ylcarbonyl)piperidin-4-yl]phenyl}urea

Example 220A 1-(imidazo[1,2-a]pyridin-7-ylmethyl)-3-(4-(piperidin-4-yl)phenyl)urea The title compound was prepared as described in Example 28A, substituting tert-butyl 4-(4-{[(imidazo[1,2-a]pyridin-7-ylmethyl)carbamoyl]amino}phenyl)piperidine-1-carboxylate for tert-butyl 4-(4-(3-imidazo[1,2-a]pyridin-6-ylureido)phenyl)-5,6-dihydropyridine-1(2H)-carboxylate.

Example 220B 1-(imidazo[1,2-a]pyridin-7-ylmethyl)-3-{4-[1-(tetrahydrofuran-2-ylcarbonyl)piperidin-4-yl]phenyl}urea The title compound was prepared as described in Example 1A, substituting 1-(imidazo[1,2-a]pyridin-7-ylmethyl)-3-(4-(piperidin-4-yl)phenyl)urea for 3-methylbutan-1-amine and tetrahydrofuran-2-carboxylic acid for 4-nitrobenzoic acid. $^1$H NMR (400 MHz, methanol-$d_4$) δ ppm 8.72 (d, J=7.0 Hz, 1H), 8.17-8.12 (m, 1H), 7.98-7.93 (m, 1H), 7.78 (bs, 1H), 7.48-7.41 (m, 1H), 7.35-7.28 (m, 2H), 7.18-7.12 (m, 2H), 4.81-4.72 (m, 1H), 4.67-4.55 (m, 3H), 4.19-4.08 (m, 1H), 4.01-3.91 (m, 1H), 3.90-3.81 (m, 1H), 3.24-3.09 (m, 1H), 2.85-2.67 (m, 2H), 2.30-2.14 (m, 1H), 2.09-1.79 (m, 5H), 1.73-1.46 (m, 2H); MS (ESI(+)) m/e 448 (M+H)$^+$.

TABLE 12

The following Examples were prepared essentially as described in Example 220, substituting the appropriate carboxylic acid in Example 220B.

| Ex | Name | MS |
|---|---|---|
| 221 | 1-(imidazo[1,2-a]pyridin-7-ylmethyl)-3-{4-[1-(tetrahydro-2H-pyran-4-ylcarbonyl)piperidin-4-yl]phenyl}urea | (ESI(+)) m/e 462 (M + H)+ |
| 222 | 1-{4-[1-(1,4-dioxan-2-ylcarbonyl)piperidin-4-yl]phenyl}-3-(imidazo[1,2-a]pyridin-7-ylmethyl)urea | (ESI(+)) m/e 464 (M + H)+ |
| 223 | 1-(imidazo[1,2-a]pyridin-7-ylmethyl)-3-{4-[1-(tetrahydro-2H-pyran-4-ylacetyl)piperidin-4-yl]phenyl}urea | (ESI(+)) m/e 476 (M + H)+ |
| 224 | 1-(imidazo[1,2-a]pyridin-7-ylmethyl)-3-{4-[1-(morpholin-4-ylacetyl)piperidin-4-yl]phenyl}urea | (ESI(+)) m/e 477 (M + H)+ |
| 225 | 1-(imidazo[1,2-a]pyridin-7-ylmethyl)-3-{4-[1-(tetrahydrofuran-2-ylacetyl)piperidin-4-yl]phenyl}urea | (ESI(+)) m/e 462 (M + H)+ |
| 226 | 1-{4-[1-(3-hydroxy-3-methylbutanoyl)piperidin-4-yl]phenyl}-3-(imidazo[1,2-a]pyridin-7-ylmethyl)urea | (ESI(+)) m/e 450 (M + H)+ |
| 227 | 1-{4-[1-(2-hydroxy-2-methylpropanoyl)piperidin-4-yl]phenyl}-3-(imidazo[1,2-a]pyridin-7-ylmethyl)urea | (ESI(+)) m/e 436 (M + H)+ |
| 228 | 1-(imidazo[1,2-a]pyridin-7-ylmethyl)-3-{4-[1-(2-methylpropanoyl)piperidin-4-yl]phenyl}urea | (ESI(+)) m/e 420 (M + H)+ |
| 229 | 1-[4-(1-benzoylpiperidin-4-yl)phenyl]-3-(imidazo[1,2-a]pyridin-7-ylmethyl)urea | (ESI(+)) m/e 454 (M + H)+ |
| 243 | 1-(4-{1-[(1,1-dioxidotetrahydro-2H-thiopyran-4-yl)carbonyl]piperidin-4-yl}phenyl)-3-(imidazo[1,2-a]pyridin-7-ylmethyl)urea | (ESI(+)) m/e 510 (M + H)+ |
| 286 | 1-(imidazo[1,2-a]pyridin-7-ylmethyl)-3-(4-{1-[(3S)-tetrahydrofuran-3-ylcarbonyl]piperidin-4-yl}phenyl)urea | (ESI(+)) m/e 448 (M + H)+ |
| 287 | 1-(imidazo[1,2-a]pyridin-7-ylmethyl)-3-(4-{1-[(3R)-tetrahydrofuran-3-ylcarbonyl]piperidin-4-yl}phenyl)urea | (ESI(+)) m/e 448 (M + H)+ |
| 288 | 1-(imidazo[1,2-a]pyridin-7-ylmethyl)-3-(4-{1-[(2S)-tetrahydrofuran-2-ylcarbonyl]piperidin-4-yl}phenyl)urea | (ESI(+)) m/e 448 (M + H)+ |
| 289 | 1-(imidazo[1,2-a]pyridin-7-ylmethyl)-3-(4-{1-[(2R)-tetrahydrofuran-2-ylcarbonyl]piperidin-4-yl}phenyl)urea | (ESI(+)) m/e 448 (M + H)+ |
| 709 | 1-[4-(1-butanoylpiperidin-4-yl)phenyl]-3-(imidazo[1,2-a]pyridin-7-ylmethyl)urea | (ESI(+)) m/e 420 (M + H)+ |
| 710 | 1-(imidazo[1,2-a]pyridin-7-ylmethyl)-3-(4-{1-[(2S)-2-methylbutanoyl]piperidin-4-yl}phenyl)urea | (ESI(+)) m/e 434 (M + H)+ |
| 711 | 1-(imidazo[1,2-a]pyridin-7-ylmethyl)-3-(4-{1-[(2-methylcyclopropyl)carbonyl]piperidin-4-yl}phenyl)urea | (ESI(+)) m/e 432 (M + H)+ |
| 712 | 1-{4-[1-(cyclopropylacetyl)piperidin-4-yl]phenyl}-3-(imidazo[1,2-a]pyridin-7-ylmethyl)urea | (ESI(+)) m/e 432 (M + H)+ |
| 713 | 1-(imidazo[1,2-a]pyridin-7-ylmethyl)-3-{4-[1-(3,3,3-trifluoropropanoyl)piperidin-4-yl]phenyl}urea | (ESI(+)) m/e 460 (M + H)+ |
| 714 | 1-(imidazo[1,2-a]pyridin-7-ylmethyl)-3-{4-[1-(4,4,4-trfluorobutanoyl)piperidin-4-yl]phenyl}urea | (ESI(+)) m/e 474 (M + H)+ |
| 715 | 1-(4-{1-[(4,4-difluorocyclohexyl)carbonyl]piperidin-4-yl}phenyl)-3-(imidazo[1,2-a]pyridin-7-ylmethyl)urea | (ESI(+)) m/e 496 (M + H)+ |
| 716 | 1-(imidazo[1,2-a]pyridin-7-ylmethyl)-3-{4-[1-(phenylacetyl)piperidin-4-yl]phenyl}urea | (ESI(+)) m/e 468 (M + H)+ |
| 719 | 1-{4-[1-(2-fluorobenzoyl)piperidin-4-yl]phenyl}-3-(imidazo[1,2-a]pyridin-7-ylmethyl)urea | (ESI(+)) m/e 472 (M + H)+ |
| 720 | 1-{4-[1-(3-fluorobenzoyl)piperidin-4-yl]phenyl}-3-(imidazo[1,2-a]pyridin-7-ylmethyl)urea | (ESI(+)) m/e 472 (M + H)+ |
| 721 | 1-{4-[1-(4-fluorobenzoyl)piperidin-4-yl]phenyl}-3-(imidazo[1,2-a]pyridin-7-ylmethyl)urea | (ESI(+)) m/e 472 (M + H)+ |

TABLE 12-continued

The following Examples were prepared essentially as described in
Example 220, substituting the appropriate carboxylic acid in Example 220B.

| Ex | Name | MS |
|---|---|---|
| 722 | 1-{4-[1-(2,4-difluorobenzoyl)piperidin-4-yl]phenyl}-3-(imidazo[1,2-a]pyridin-7-ylmethyl)urea | (ESI(+)) m/e 490 (M + H)+ |
| 723 | 1-{4-[1-(3,4-difluorobenzoyl)piperidin-4-yl]phenyl}-3-(imidazo[1,2-a]pyridin-7-ylmethyl)urea | (ESI(+)) m/e 490 (M + H)+ |
| 724 | 1-{4-[1-(3,5-difluorobenzoyl)piperidin-4-yl]phenyl}-3-(imidazo[1,2-a]pyridin-7-ylmethyl)urea | (ESI(+)) m/e 490 (M + H)+ |
| 725 | 1-{4-[1-(2,5-difluorobenzoyl)piperidin-4-yl]phenyl}-3-(imidazo[1,2-a]pyridin-7-ylmethyl)urea | (ESI(+)) m/e 490 (M + H)+ |
| 938 | 1-(4-{1-[2-chloropyridin-3-yl)carbonyl]piperidin-4-yl}phenyl)-3-(imidazo[1,2-a]pyridin-7-ylmethyl)urea | ESI(+) m/e 489 (M + H)+ |
| 939 | 1-(imidazo[1,2-a]pyridin-7-ylmethyl)-3-{4-[1-(3-methylbut-2-enoyl)piperidin-4-yl]phenyl}urea | ESI(+) m/e 432 (M + H)+ |
| 940 | 1-{4-[1-(3,3-dimethylbutanoyl)piperidin-4-yl]phenyl}-3-(imidazo[1,2-a]pyridin-7-ylmethyl)urea | ESI(+) m/e 448 (M + H)+ |
| 941 | 1-(imidazo[1,2-a]pyridin-7-ylmethyl)-3-(4-{1-[(2-methylcyclopent-1-en-1-yl)carbonyl]piperidin-4-yl}phenyl)urea | ESI(+) m/e 458 (M + H)+ |
| 942 | 1-{4-[1-(2-ethylbutanoyl)piperidin-4-yl]phenyl}-3-(imidazo[1,2-a]pyridin-7-ylmethyl)urea | ESI(+) m/e 448 (M + H)+ |
| 943 | 1-(4-{1-[4-fluorophenoxy)acetyl]piperidin-4-yl}phenyl)-3-(imidazo[1,2-a]pyridin-7-ylmethyl)urea | ESI(+) m/e 502 (M + H)+ |
| 944 | 1-{4-[1-(2,4-dimethoxybenzoyl)piperidin-4-yl]phenyl}-3-(imidazo[1,2-a]pyridin-7-ylmethyl)urea | ESI(+) m/e 514 (M + H)+ |
| 945 | 1-{4-[1-(cyclohex-3-en-1-ylcarbonyl)piperidin-4-yl]phenyl}-3-(imidazo[1,2-a]pyridin-7-ylmethyl)urea | ESI(+) m/e 458 (M + H)+ |
| 946 | 1-{4-[1-(2,5-dimethoxybenzoyl)piperidin-4-yl]phenyl}-3-(imidazo[1,2-a]pyridin-7-ylmethyl)urea | ESI(+) m/e 514 (M + H)+ |
| 947 | 1-(imidazo[1,2-a]pyridin-7-ylmethyl)-3-(4-{1-[(2-methoxyphenyl)acetyl]piperidin-4-yl}phenyl)urea | ESI(+) m/e 498 (M + H)+ |
| 948 | 1-{4-[1-(3-hydroxy-2-phenylpropanoyl)piperidin-4-yl]phenyl}-3-(imidazo[1,2-a]pyridin-7-ylmethyl)urea | ESI(+) m/e 498 (M + H)+ |
| 949 | 1-{4-[1-(2,6-dimethoxybenzoyl)piperidin-4-yl]phenyl}-3-(imidazo[1,2-a]pyridin-7-ylmethyl)urea | ESI(+) m/e 514 (M + H)+ |
| 950 | 1-{4-[1-(N,N-diethyl-beta-alanyl)piperidin-4-yl]phenyl}-3-(imidazo[1,2-a]pyridin-7-ylmethyl)urea | ESI(+) m/e 477 (M + H)+ |
| 951 | 1-(4-{1-[(2-chloro-6-methylpyridin-4-yl)carbonyl]piperidin-4-yl}phenyl)-3-(imidazo[1,2-a]pyridin-7-ylmethyl)urea | ESI(+) m/e 503 (M + H)+ |
| 952 | 1-(imidazo[1,2-a]pyridin-7-ylmethyl)-3-(4-{1-[(3-methoxyphenyl)acetyl]piperidin-4-yl}phenyl)urea | ESI(+) m/e 498 (M + H)+ |
| 953 | 1-(imidazo[1,2-a]pyridin-7-ylmethyl)-3-(4-{1-[(1-oxo-2,3-dihydro-1H-inden-4-yl)carbonyl]piperidin-4-yl}phenyl)urea | ESI(+) m/e 508 (M + H)+ |
| 954 | 1-{4-[1-(2-chloro-4-cyanobenzoyl)piperidin-4-yl]phenyl}-3-(imidazo[1,2-a]pyridin-7-ylmethyl)urea | ESI(+) m/e 513 (M + H)+ |
| 955 | 1-(imidazo[1,2-a]pyridin-7-ylmethyl)-3-(4-{1-[(2E)-2-methylbut-2-enoyl]piperidin-4-yl}phenyl)urea | ESI(+) m/e 432 (M + H)+ |
| 956 | 1-(imidazo[1,2-a]pyridin-7-ylmethyl)-3-{4-[1-(1H-indol-3-ylacetyl)piperidin-4-yl]phenyl}urea | ESI(+) m/e 507 (M + H)+ |
| 957 | 1-{4-[1-(2-hydroxy-3-methylbenzoyl)piperidin-4-yl]phenyl}-3-(imidazo[1,2-a]pyridin-7-ylmethyl)urea | ESI(+) m/e 484 (M + H)+ |
| 1011 | 1-(imidazo[1,2-a]pyridin-7-ylmethyl)-3-[4-(1-{[1-(propan-2-yl)-1H-pyrazol-3-yl]carbonyl}piperidin-4-yl)phenyl]urea | ESI(+) m/e 486 (M + H)+ |

TABLE 12-continued

The following Examples were prepared essentially as described in
Example 220, substituting the appropriate carboxylic acid in Example 220B.

| Ex | Name | MS |
|---|---|---|
| 1012 | 1-(4-{1-[(2S)-2,3-dihydro-1,4-benzodioxin-2-ylcarbonyl]piperidin-4-yl}phenyl)-3-(imidazo[1,2-a]pyridin-7-ylmethyl)urea | ESI(+)) m/e 512 (M + H)+ |
| 1013 | 1-(4-{1-[(3-cyclopropyl-1-methyl-1H-pyrazol-5-yl)carbonyl]piperidin-4-yl}phenyl)-3-(imidazo[1,2-a]pyridin-7-ylmethyl)urea | ESI(+)) m/e 497 (M + H)+ |
| 1014 | 1-(imidazo[1,2-a]pyridin-7-ylmethyl)-3-(4-{1-[(2-methyl-4,5,6,7-tetrahydro-2H-indazol-3-yl)carbonyl]piperidin-4-yl}phenyl)urea | ESI(+)) m/e 512 (M + H)+ |
| 1015 | 1-(imidazo[1,2-a]pyridin-7-ylmethyl)-3-{4-[1-(4,5,6,7-tetrahydro-2,1-benzoxazol-3-ylcarbonyl)piperidin-4-yl]phenyl}urea | ESI(+)) m/e 499 (M + H)+ |
| 1016 | 1-(4-{1-[2-chloro-5-fluoropyridin-4-yl)carbonyl]piperidin-4-yl}phenyl)-3-(imidazo[1,2-a]pyridin-7-ylmethyl)urea | ESI(+)) m/e 507 (M + H)+ |
| 1017 | 1-(4-{1-[(3-fluoro-6-methylpyridin-2-yl)carbonyl]piperidin-4-yl}phenyl)-3-(imidazo[1,2-a]pyridin-7-ylmethyl)urea | ESI(+)) m/e 487 (M + H)+ |
| 1018 | 1-(4-{1-[(2-chloro-3-fluoropyridin-4-yl)carbonyl]piperidin-4-yl}phenyl)-3-(imidazo[1,2-a]pyridin-7-ylmethyl)urea | ESI(+)) m/e 507 (M + H)+ |
| 1019 | 1-(4-{1-[(3-chloropyridin-2-yl)carbonyl]piperidin-4-yl}phenyl)-3-(imidazo[1,2-a]pyridin-7-ylmethyl)urea | ESI(+)) m/e 489 (M + H)+ |
| 1020 | 1-(imidazo[1,2-a]pyridin-7-ylmethyl)-3-[4-(1-{[1-(pyridin-2-yl)cyclopropyl]carbonyl}piperidin-4-yl)phenyl]urea | ESI(+)) m/e 495 (M + H)+ |
| 1021 | 1-(4-{1-[(1-cyclopentyl-1H-pyrazol-3-yl)carbonyl]piperidin-4-yl}phenyl)-3-(imidazo[1,2-a]pyridin-7-ylmethyl)urea | ESI(+)) m/e 512 (M + H)+ |
| 1022 | 1-[4-(1-{[1-(difluoromethyl)-1H-pyrazol-5-yl]carbonyl}piperidin-4-yl)phenyl]-3-(imidazo[1,2-a]pyridin-7-ylmethyl)urea | ESI(+)) m/e 494 (M + H)+ |
| 1023 | 1-{4-[1-(2,3-dihydro-1,4-benzodioxin-2-ylcarbonyl)piperidin-4-yl]phenyl}-3-(imidazo[1,2-a]pyridin-7-ylmethyl)urea | ESI(+)) m/e 512 (M + H)+ |
| 1024 | 1-{4-[1-(2,3-dihydro-1-benzofuran-1-ylcarbonyl)piperidin-4-yl]phenyl}-3-(imidazo[1,2-a]pyridin-7-ylmethyl)urea | ESI(+)) m/e 496 (M + H)+ |
| 1025 | 1-(imidazo[1,2-a]pyridin-7-ylmethyl)-3-(4-{1-[(4-methoxycyclohexyl)carbonyl]piperidin-4-yl}phenyl)urea | ESI(+)) m/e 490 (M + H)+ |
| 1026 | 1-{4-[1-(2,3-dihydro-1,4-benzodioxin-5-ylcarbonyl)piperidin-4-yl]phenyl}-3-(imidazo[1,2-a]pyridin-7-ylmethyl)urea | ESI(+)) m/e 512 (M + H)+ |
| 1027 | 1-(imidazo[1,2-a]pyridin-7-ylmethyl)-3-{4-[1-(isoquinolin-4-ylcarbonyl)piperidin-4-yl]phenyl}urea | ESI(+)) m/e 505 (M + H)+ |
| 1028 | 1-(imidazo[1,2-a]pyridin-7-ylmethyl)-3-(4-{1-[(2-methyl-1,3-benzoxazol-6-yl)carbonyl]piperidin-4-yl}phenyl)urea | ESI(+)) m/e 509 (M + H)+ |
| 1029 | 1-(4-{1-[(1-tert-butyl-3-methyl-1H-pyrazol-5-yl)carbonyl]piperidin-4-yl}phenyl)-3-(imidazo[1,2-a]pyridin-7-ylmethyl)urea | ESI(+)) m/e 514 (M + H)+ |
| 1030 | 1-(4-{1-[(1-cyanocyclopentyl)carbonyl]piperidin-4-yl}phenyl)-3-(imidazo[1,2-a]pyridin-7-ylmethyl)urea | ESI(+)) m/e 471 (M + H)+ |
| 1031 | 1-{4-[1-(cinnolin-4-ylcarbonyl)piperidin-4-yl]phenyl}-3-(imidazo[1,2-a]pyridin-7-ylmethyl)urea | ESI(+)) m/e 506 (M + H)+ |
| 1032 | 1-(imidazo[1,2-a]pyridin-7-ylmethyl)-3-{4-[1-(quinolin-7-ylcarbonyl)piperidin-4-yl]phenyl}urea | ESI(+)) m/e 505 (M + H)+ |
| 1033 | 1-{4-[1-(5-cyano-2-fluorobenzoyl)piperidin-4-yl]phenyl}-3-(imidazo[1,2-a]pyridin-7-ylmethyl)urea | ESI(+)) m/e 497 (M + H)+ |
| 1034 | 1-(4-{1-[(3-cyclopropyl-1,2-oxazol-5-yl)carbonyl]piperidin-4-yl}phenyl)-3-(imidazo[1,2-a]pyridin-7-ylmethyl)urea | ESI(+)) m/e 485 (M + H)+ |
| 1035 | 1-(imidazo[1,2-a]pyridin-7-ylmethyl)-3-{4-[1-(5,6,7,8-tetrahydroquinolin-3-ylcarbonyl)piperidin-4-yl]phenyl}urea | ESI(+)) m/e 509 (M + H)+ |
| 1036 | 1-{4-[1-(3,4-dihydro-2H-pyrano[2,3-b]pyridin-6-ylcarbonyl)piperidin-4-yl]phenyl}-3-(imidazo[1,2-a]pyridin-7-ylmethyl)urea | ESI(+)) m/e 511 (M + H)+ |

TABLE 12-continued

The following Examples were prepared essentially as described in
Example 220, substituting the appropriate carboxylic acid in Example 220B.

| Ex | Name | MS |
|---|---|---|
| 1037 | 1-(imidazo[1,2-a]pyridin-7-ylmethyl)-3-{4-[1-(isoquinolin-7-ylcarbonyl)piperidin-4-yl]phenyl}urea | ESI(+)) m/e 505 (M + H)$^+$ |
| 1038 | 1-(imidazo[1,2-a]pyridin-7-ylmethyl)-3-{4-[1-(quinoxalin-2-ylcarbonyl)piperidin-4-yl]phenyl}urea | ESI(+)) m/e 506 (M + H)$^+$ |
| 1039 | 1-(imidazo[1,2-a]pyridin-7-ylmethyl)-3-(4-{1-[(2E)-3-(2-methoxypyridin-3-yl)prop-2-enoyl]piperidin-4-yl}phenyl)urea | ESI(+)) m/e 511 (M + H)$^+$ |
| 1040 | 1-(imidazo[1,2-a]pyridin-7-ylmethyl)-3-(4-{1-[(2E)-3-(pyridin-2-yl)prop-2-enoyl]piperidin-4-yl}phenyl)urea | ESI(+)) m/e 481 (M + H)$^+$ |
| 1041 | 1-(4-{1-[(4-chloro-2,6-dimethylpyridin-3-yl)carbonyl]piperidin-4-yl}phenyl)-3-(imidazo[1,2-a]pyridin-7-ylmethyl)urea | ESI(+)) m/e XXX (M + H)$^+$ |
| 1042 | 1-(imidazo[1,2-a]pyridin-7-ylmethyl)-3-(4-{1-[(8-methylimidazo[1,2-a]pyridin-2-yl)carbonyl]piperidin-4-yl}phenyl)urea | ESI(+)) m/e 517 (M + H)$^+$ |
| 1043 | 1-(4-{1-[(2-ethoxypyridin-4-yl)carbonyl]piperidin-4-yl}phenyl)-3-(imidazo[1,2-a]pyridin-7-ylmethyl)urea | ESI(+)) m/e 499 (M + H)$^+$ |
| 4044 | 1-(imidazo[1,2-a]pyridin-7-ylmethyl)-3-(4-{1-[(1-methyl-4,5,6,7-tetrahydro-1H-indazol-3-yl)carbonyl]piperidin-4-yl}phenyl)urea | ESI(+)) m/e 512 (M + H)$^+$ |
| 1045 | 1-(imidazo[1,2-a]pyridin-7-ylmethyl)-3-(4-{1-[(4-methyl-4H-furo[3,2-b]pyrrol-5-yl)carbonyl]piperidin-4-yl}phenyl)urea | ESI(+)) m/e 497 (M + H)$^+$ |
| 1046 | 1-(imidazo[1,2-a]pyridin-7-ylmethyl)-3-(4-{1-[(2-methyl-2,3-dihydro-1-benzofuran-5-yl)carbonyl]piperidin-4-yl}phenyl)urea | ESI(+)) m/e 510 (M + H)$^+$ |
| 1047 | 1-(4-{1-[(4-chloro-1-ethyl-1H-pyrazol-5-yl)carbonyl]piperidin-4-yl}phenyl)-3-(imidazo[1,2-a]pyridin-7-ylmethyl)urea | ESI(+)) m/e 506 (M + H)$^+$ |
| 1048 | 1-{4-[1-(3-cyano-5-fluorobenzoyl)piperidin-4-yl]phenyl}-3-(imidazo[1,2-a]pyridin-7-ylmethyl)urea | ESI(+)) m/e 497 (M + H)$^+$ |
| 1049 | 1-(imidazo[1,2-a]pyridin-7-ylmethyl)-3-{4-[1-(isoquinolin-8-ylcarbonyl)piperidin-4-yl]phenyl}urea | ESI(+)) m/e 505 (M + H)$^+$ |
| 1050 | 1-(4-{1-[(4-cyanophenyl)acetyl]piperidin-4-yl}phenyl)-3-(imidazo[1,2-a]pyridin-7-ylmethyl)urea | ESI(+)) m/e 493 (M + H)$^+$ |
| 1051 | 1-(imidazo[1,2-a]pyridin-7-ylmethyl)-3-(4-{1-[(3-methoxythiophen-2-yl)carbonyl]piperidin-4-yl}phenyl)urea | ESI(+)) m/e 490 (M + H)$^+$ |
| 1052 | 1-{4-[1-(3-cyano-4-fluorobenzoyl)piperidin-4-yl]phenyl}-3-(imidazo[1,2-a]pyridin-7-ylmethyl)urea | ESI(+)) m/e 497 (M + H)$^+$ |
| 1053 | 1-(imidazo[1,2-a]pyridin-7-ylmethyl)-3-{4-[1-(4,5,6,7-tetrahydro-1,3-benzothiazol-2-ylcarbonyl)piperidin-4-yl]phenyl}urea | ESI(+)) m/e 515 (M + H)$^+$ |
| 1054 | 1-{4-[1-(1,3-benzothiazol-2-ylcarbonyl)piperidin-4-yl]phenyl}-3-(imidazo[1,2-a]pyridin-7-ylmethyl)urea | ESI(+)) m/e 511 (M + H)$^+$ |
| 1055 | 1-(4-{1-[(3-ethyl-1,2-oxazol-5-yl)carbonyl]piperidin-4-yl}phenyl)-3-(imidazo[1,2-a]pyridin-7-ylmethyl)urea | ESI(+)) m/e 473 (M + H)$^+$ |
| 1056 | 1-(imidazo[1,2-a]pyridin-7-ylmethyl)-3-[4-(1-{[3-methyl-1-(prop-2-en-1-yl)-1H-pyrazol-5-yl]carbonyl}piperidin-4-yl)phenyl]urea | ESI(+)) m/e 498 (M + H)$^+$ |
| 1057 | 1-{4-[1-(1,2,3-benzothiadiazol-5-ylcarbonyl)piperidin-4-yl]phenyl}-3-(imidazo[1,2-a]pyridin-7-ylmethyl)urea | ESI(+)) m/e 512 (M + H)$^+$ |
| 1058 | 1-(4-{1-[(2-ethyl-1,3-thiazol-4-yl)carbonyl]piperidin-4-yl}phenyl)-3-(imidazo[1,2-a]pyridin-7-ylmethyl)urea | ESI(+)) m/e 489 (M + H)$^+$ |
| 1059 | 1-(4-{1-[(5,6-dimethylpyridin-3-yl)carbonyl]piperidin-4-yl}phenyl)-3-(imidazo[1,2-a]pyridin-7-ylmethyl)urea | ESI(+)) m/e 483 (M + H)$^+$ |
| 1060 | 1-{4-[1-(1,3-benzothiazol-7-ylcarbonyl)piperidin-4-yl]phenyl}-3-(imidazo[1,2-a]pyridin-7-ylmethyl)urea | ESI(+)) m/e 511 (M + H)$^+$ |

TABLE 12-continued

The following Examples were prepared essentially as described in
Example 220, substituting the appropriate carboxylic acid in Example 220B.

| Ex | Name | MS |
|---|---|---|
| 1065 | 1-(4-{1-[2-(3-fluorophenoxy)propanoyl]piperidin-4-yl}phenyl)-3-(imidazo[1,2-a]pyridin-7-ylmethyl)urea | ESI(+)) m/e 517 (M + H)+ |
| 1066 | 1-(4-{1-[(3,5-difluoropyridin-2-yl)carbonyl]piperidin-4-yl}phenyl)-3-(imidazo[1,2-a]pyridin-7-ylmethyl)urea | ESI(+)) m/e 492 (M + H)+ |
| 1121 | 1-(4-{1-[(2-cyclopropyl-1,3-thiazol-5-yl)carbonyl]piperidin-4-yl}phenyl)-3-(imidazo[1,2-a]pyridin-7-ylmethyl)urea | ESI(+)) m/e 501 (M + H)+ |
| 1122 | 1-{4-[1-(1,3-benzothiazol-5-ylcarbonyl)piperidin-4-yl]phenyl}-3-(imidazo[1,2-a]pyridin-7-ylmethyl)urea | ESI(+)) m/e 511 (M + H)+ |
| 1123 | 1-(imidazo[1,2-a]pyridin-7-ylmethyl)-3-(4-{1-[(1-methyl-1H-indazol-6-yl)carbonyl]piperidin-4-yl}phenyl)urea | ESI(+)) m/e 508 (M + H)+ |
| 1124 | 1-(4-{1-[(4-chloro-1,3-dimethyl-1H-pyrazol-5-yl)carbonyl]piperidin-4-yl}phenyl)-3-(imidazo[1,2-a]pyridin-7-ylmethyl)urea | ESI(+)) m/e 506 (M + H)+ |
| 1125 | 1-(4-{1-[(5-ethylpyridin-2-yl)carbonyl]piperidin-4-yl}phenyl)-3-(imidazo[1,2-a]pyridin-7-ylmethyl)urea | ESI(+)) m/e 483 (M + H)+ |
| 1126 | 1-(4-{1-[(3-chloro-5-cyanopyridin-2-yl)carbonyl]piperidin-4-yl}phenyl)-3-(imidazo[1,2-a]pyridin-7-ylmethyl)urea | ESI(+)) m/e 514 (M + H)+ |
| 1127 | 1-(4-{1-[(1-cyano-3-methylcyclobutyl)carbonyl]piperidin-4-yl}phenyl)-3-(imidazo[1,2-a]pyridin-7-ylmethyl)urea | ESI(+)) m/e 471 (M + H)+ |
| 1128 | 1-(4-{1-[(1,5-diethyl-1H-1,2,3-triazol-4-yl)carbonyl]piperidin-4-yl}phenyl)-3-(imidazo[1,2-a]pyridin-7-ylmethyl)urea | ESI(+)) m/e 501 (M + H)+ |
| 1129 | 1-(imidazo[1,2-a]pyridin-7-ylmethyl)-3-{4-[1-(thieno[3,2-b]furan-5-ylcarbonyl)piperidin-4-yl]phenyl}urea | ESI(+)) m/e 500 (M + H)+ |
| 1130 | 1-(imidazo[1,2-a]pyridin-7-ylmethyl)-3-(4-{1-[(4-methoxythiophen-2-yl)carbonyl]piperidin-4-yl}phenyl)urea | ESI(+)) m/e 490 (M + H)+ |
| 1131 | 1-(4-{1-[(5-cyanothiophen-2-yl)carbonyl]piperidin-4-yl}phenyl)-3-(imidazo[1,2-a]pyridin-7-ylmethyl)urea | ESI(+)) m/e 485 (M + H)+ |
| 1132 | 1-(4-{1-[(5-cyclopropylpyridin-2-yl)carbonyl]piperidin-4-yl}phenyl)-3-(imidazo[1,2-a]pyridin-7-ylmethyl)urea | ESI(+)) m/e 495 (M + H)+ |
| 1133 | 1-{4-[1-(4-cyano-2,6-difluorobenzoyl)piperidin-4-yl]phenyl}-3-(imidazo[1,2-a]pyridin-7-ylmethyl)urea | ESI(+)) m/e 515 (M + H)+ |
| 1134 | 1-[4-(1-{[1-ethyl-3-(propan-2-yl)-1H-pyrazol-4-yl]carbonyl}piperidin-4-yl)phenyl]-3-(imidazo[1,2-a]pyridin-7-ylmethyl)urea | ESI(+)) m/e 514 (M + H)+ |
| 1135 | 1-{4-[1-(1-benzofuran-3-ylcarbonyl)piperidin-4-yl]phenyl}-3-(imidazo[1,2-a]pyridin-7-ylmethyl)urea | ESI(+)) m/e 494 (M + H)+ |
| 1136 | 1-(imidazo[1,2-a]pyridin-7-ylmethyl)-3-(4-{1-[(4-methoxy-5-methylpyridin-2-yl)carbonyl]piperidin-4-yl}phenyl)urea | ESI(+)) m/e 499 (M + H)+ |
| 1137 | 1-(4-{1-[(1-cyclopentyl-1H-pyrazol-5-yl)carbonyl]piperidin-4-yl}phenyl)-3-(imidazo[1,2-a]pyridin-7-ylmethyl)urea | ESI(+)) m/e 512 (M + H)+ |
| 1138 | 1-(4-{1-[(4-chloro-1,3-thiazol-5-yl)carbonyl]piperidin-4-yl}phenyl)-3-(imidazo[1,2-a]pyridin-7-ylmethyl)urea | ESI(+)) m/e 495 (M + H)+ |
| 1139 | 1-(4-{1-[(3-cyanothiophen-2-yl)carbonyl]piperidin-4-yl}phenyl)-3-(imidazo[1,2-a]pyridin-7-ylmethyl)urea | ESI(+)) m/e 485 (M + H)+ |
| 1140 | 1-(imidazo[1,2-a]pyridin-7-ylmethyl)-3-[4-(1-{[4-(propan-2-yl)pyrimidin-5-yl]carbonyl}piperidin-4-yl)phenyl]urea | ESI(+)) m/e 498 (M + H)+ |
| 1141 | 1-(imidazo[1,2-a]pyridin-7-ylmethyl)-3-(4-{1-[(1-methyl-5-propyl-1H-pyrazol-4-yl)carbonyl]piperidin-4-yl}phenyl)urea | ESI(+)) m/e 500 (M + H)+ |
| 1142 | 1-(4-{1-[2-(3-cyclopropyl-1H-pyrazol-1-yl)propanoyl]piperidin-4-yl}phenyl)-3-(imidazo[1,2-a]pyridin-7-ylmethyl)urea | ESI(+)) m/e 512 (M + H)+ |
| 1143 | 1-(imidazo[1,2-a]pyridin-7-ylmethyl)-3-{4-[1-(pyrazolo[1,5-a]pyridin-2-ylcarbonyl)piperidin-4-yl]phenyl}urea | ESI(+)) m/e 494 (M + H)+ |

TABLE 12-continued

The following Examples were prepared essentially as described in
Example 220, substituting the appropriate carboxylic acid in Example 220B.

| Ex | Name | MS |
|---|---|---|
| 1144 | 1-{4-[1-(1-benzofuran-5-ylcarbonyl)piperidin-4-yl]phenyl}-3-(imidazo[1,2-a]pyridin-7-ylmethyl)urea | ESI(+)) m/e 494 (M + H)+ |
| 1145 | 1-(imidazo[1,2-a]pyridin-7-ylmethyl)-3-[4-(1-{[2-(propan-2-yl)-1,3-oxazol-4-yl]carbonyl}piperidin-4-yl)phenyl]urea | ESI(+)) m/e 487 (M + H)+ |
| 1146 | 1-(imidazo[1,2-a]pyridin-7-ylmethyl)-3-(4-{1-[(1-methyl-1H-indazol-7-yl)carbonyl]piperidin-4-yl}phenyl)urea | ESI(+)) m/e 508 (M + H)+ |
| 1147 | 1-(imidazo[1,2-a]pyridin-7-ylmethyl)-3-(4-{1-[(2-methoxy-5-methylpyridin-3-yl)carbonyl]piperidin-4-yl}phenyl)urea | ESI(+)) m/e 499 (M + H)+ |
| 1148 | 1-(4-{1-[(5,6-dimethoxypyridin-2-yl)carbonyl]piperidin-4-yl}phenyl)-3-(imidazo[1,2-a]pyridin-7-ylmethyl)urea | ESI(+)) m/e 515 (M + H)+ |
| 1149 | 1-(imidazo[1,2-a]pyridin-7-ylmethyl)-3-(4-{1-[(2-methyl-2H-indazol-4-yl)carbonyl]piperidin-4-yl}phenyl)urea | ESI(+)) m/e 508 (M + H)+ |
| 1150 | 1-(4-{1-[(2-ethylpiperidin-1-yl)(oxo)acetyl]piperidin-4-yl}phenyl)-3-(imidazo[1,2-a]pyridin-7-ylmethyl)urea | ESI(+)) m/e 517 (M + H)+ |
| 1151 | 1-(imidazo[1,2-a]pyridin-7-ylmethyl)-3-(4-{1-[(2-methyl-2H-indazol-6-yl)carbonyl]piperidin-4-yl}phenyl)urea | ESI(+)) m/e 508 (M + H)+ |
| 1152 | 1-(imidazo[1,2-a]pyridin-7-ylmethyl)-3-(4-{1-[(1-methyl-1H-indazol-4-yl)carbonyl]piperidin-4-yl}phenyl)urea | ESI(+)) m/e 508 (M + H)+ |
| 1153 | 1-(imidazo[1,2-a]pyridin-7-ylmethyl)-3-[4-(1-{[2-(trifluoromethyl)furan-3-yl]carbonyl}piperidin-4-yl)phenyl]urea | ESI(+)) m/e 512 (M + H)+ |

Example 230

4-[1-(2-hydroxy-2-methylpropanoyl)piperidin-4-yl]-N-(imidazo[1,2-a]pyridin-7-ylmethyl)benzamide

Example 230A

N-(imidazo[1,2-a]pyridin-7-ylmethyl)-4-(piperidin-4-yl)benzamide

The title compound was prepared as described in Example 28A, substituting tert-butyl 4-{4-[(imidazo[1,2-a]pyridin-7-ylmethyl)carbamoyl]phenyl}piperidine-1-carboxylate for tert-butyl 4-(4-(3-imidazo[1,2-a]pyridin-6-ylureido)phenyl)-5,6-dihydropyridine-1(2H)-carboxylate.

Example 230B

4-[1-(2-hydroxy-2-methylpropanoyl)piperidin-4-yl]-N-(imidazo[1,2-a]pyridin-7-ylmethyl)benzamide The title compound was prepared as described in Example 1A, substituting N-(imidazo[1,2-a]pyridin-7-ylmethyl)-4-(piperidin-4-yl)benzamide for 3-methylbutan-1-amine and 2-hydroxy-2-methylpropanoic acid for 4-nitrobenzoic acid. $^1$H NMR (400 MHz, DMSO-$d_6$/$D_2O$, Temp=90° C.) δ ppm 8.77 (dd, J=6.9, 0.9 Hz, 1H), 8.22-8.18 (m, 1H), 8.02-7.98 (m, 1H), 7.88-7.81 (m, 2H), 7.77 (s, 1H), 7.44 (dd, J=6.9, 1.6 Hz, 1H), 7.40-7.34 (m, 2H), 4.76-4.64 (m, 4H), 2.98-2.82 (m, 3H), 1.89-1.81 (m, 2H), 1.65-1.48 (m, 2H), 1.38 (s, 6H); MS (ESI(+)) m/e 421 (M+H)+.

TABLE 13

The following Examples were prepared essentially as described in Example 230,
substituting the appropriate carboxylic acid in Example 230B.

| Ex | Name | MS |
|---|---|---|
| 231 | N-(imidazo[1,2-a]pyridin-7-ylmethyl)-4-[1-(tetrahydrofuran-3-ylcarbonyl)piperidin-4-yl]benzamide | (ESI(+)) m/e 443 (M + H)+ |
| 232 | N-(imidazo[1,2-a]pyridin-7-ylmethyl)-4-[1-(tetrahydro-2H-pyran-4-ylcarbonyl)piperidin-4-yl]benzamide | (ESI(+)) m/e 447 (M + H)+ |
| 233 | 4-[1-(1,4-dioxan-2-ylcarbonyl)piperidin-4-yl]-N-(imidazo[1,2-a]pyridin-7-ylmethyl)benzamide | (ESI(+)) m/e 445 (M + H)+ |
| 234 | 4-{1-[(1,1-dioxidotetrahydro-2H-thiopyran-4-yl)carbonyl]piperidin-4-yl}-N-(imidazo[1,2-a]pyridin-7-ylmethyl)benzamide | (ESI(+)) m/e 495 (M + H)+ |
| 235 | N-(imidazo[1,2-a]pyridin-7-ylmethyl)-4-[1-(tetrahydrofuran-2-ylacetyl)piperidin-4-yl]benzamide | (ESI(+)) m/e 447 (M + H)+ |

TABLE 13-continued

The following Examples were prepared essentially as described in Example 230, substituting the appropriate carboxylic acid in Example 230B.

| Ex | Name | MS |
|---|---|---|
| 236 | N-(imidazo[1,2-a]pyridin-7-ylmethyl)-4-[1-(tetrahydro-2H-pyran-4-ylacetyl)piperidin-4-yl]benzamide | (ESI(+)) m/e 461 (M + H)$^+$ |
| 237 | N-(imidazo[1,2-a]pyridin-7-ylmethyl)-4-{1-[(propan-2-yloxy)acetyl]piperidin-4-yl}benzamide | (ESI(+)) m/e 435 (M + H)$^+$ |
| 238 | N-(imidazo[1,2-a]pyridin-7-ylmethyl)-4-{1-[(2S)-2-methylbutanoyl]piperidin-4-yl}benzamide | (ESI(+)) m/e 419 (M + H)$^+$ |
| 239 | N-(imidazo[1,2-a]pyridin-7-ylmethyl)-4-[1-(2-methylpropanoyl)piperidin-4-yl]benzamide | (ESI(+)) m/e 405 (M + H)$^+$ |
| 308 | N-(imidazo[1,2-a]pyridin-7-ylmethyl)-4-{1-[(3S)-tetrahydrofuran-3-ylcarbonyl]piperidin-4-yl}benzamide | (ESI(+)) m/e 433 (M + H)$^+$ |
| 309 | N-(imidazo[1,2-a]pyridin-7-ylmethyl)-4-{1-[(3R)-tetrahydrofuran-3-ylcarbonyl]piperidin-4-yl}benzamide | (ESI(+)) m/e 433 (M + H)$^+$ |
| 310 | N-(imidazo[1,2-a]pyridin-7-ylmethyl)-4-{1-[(2R)-tetrahydrofuran-2-ylcarbonyl]piperidin-4-yl}benzamide | (ESI(+)) m/e 433 (M + H)$^+$ |
| 311 | N-(imidazo[1,2-a]pyridin-7-ylmethyl)-4-{1-[(2S)-tetrahydrofuran-2-ylcarbonyl]piperidin-4-yl}benzamide | (ESI(+)) m/e 433 (M + H)$^+$ |
| 312 | 4-[1-(cyclopropylacetyl)piperidin-4-yl]-N-(imidazo[1,2-a]pyridin-7-ylmethyl)benzamide | (ESI(+)) m/e 417 (M + H)$^+$ |
| 313 | 4-(1-acetylpiperidin-4-yl)-N-(imidazo[1,2-a]pyridin-7-ylmethyl)benzamide | (ESI(+)) m/e 377 (M + H)$^+$ |
| 437 | 4-(1-benzoylpiperidin-4-yl)-N-(imidazo[1,2-a]pyridin-7-ylmethyl)benzamide | (ESI(+)) m/e 439 (M + H)$^+$ |
| 44 | 4-{1-[(3,3-difluorocyclobutyl)carbonyl]piperidin-4-yl}-N-(imidazo[1,2-a]pyridin-7-ylmethyl)benzamide | (ESI(+)) m/e 453 (M + H)$^+$ |
| 441 | 4-{1-[(4,4-difluorocyclohexyl)carbonyl]piperidin-4-yl}-N-(imidazo[1,2-a]pyridin-7-ylmethyl)benzamide | (ESI(+)) m/e 481 (M + H)$^+$ |
| 484 | 4-[1-(furan-2-ylcarbonyl)piperidin-4-yl]-N-(imidazo[1,2-a]pyridin-7-ylmethyl)benzamide | (ESI(+)) m/e 429 (M + H)$^+$ |
| 498 | N-(imidazo[1,2-a]pyridin-7-ylmethyl)-4-[1-(pyridin-2-ylcarbonyl)piperidin-4-yl]benzamide | (ESI(+)) m/e 440 (M + H)$^+$ |
| 499 | 4-[1-(3,3-dimethylbutanoyl)piperidin-4-yl]-N-(imidazo[1,2-a]pyridin-7-ylmethyl)benzamide | (ESI(+)) m/e 433 (M + H)$^+$ |
| 500 | N-(imidazo[1,2-a]pyridin-7-ylmethyl)-4-[1-(4-methylbenzoyl)piperidin-4-yl]benzamide | (ESI(+)) m/e 453 (M + H)$^+$ |
| 501 | 4-[1-(2,2-dimethylbutanoyl)piperidin-4-yl]-N-(imidazo[1,2-a]pyridin-7-ylmethyl)benzamide | (ESI(+)) m/e 433 (M + H)$^+$ |
| 502 | 4-[1-(cyclohexylcarbonyl)piperidin-4-yl]-N-(imidazo[1,2-a]pyridin-7-ylmethyl)benzamide | (ESI(+)) m/e 445 (M + H)$^+$ |
| 503 | N-(imidazo[1,2-a]pyridin-7-ylmethyl)-4-[1-(thiophen-2-ylcarbonyl)piperidin-4-yl]benzamide | (ESI(+)) m/e 445 (M + H)$^+$ |
| 504 | N-(imidazo[1,2-a]pyridin-7-ylmethyl)-4-[1-(3,3,3-trifluoropropanoyl)piperidin-4-yl]benzamide | (ESI(+)) m/e 445 (M + H)$^+$ |
| 505 | 4-(1-butanoylpiperidin-4-yl)-N-(imidazo[1,2-a]pyridin-7-ylmethyl)benzamide | (ESI(+)) m/e 405 (M + H)$^+$ |
| 506 | 4-[1-(2,4-difluorobenzoyl)piperidin-4-yl]-N-(imidazo[1,2-a]pyridin-7-ylmethyl)benzamide | (ESI(+)) m/e 475 (M + H)$^+$ |
| 507 | N-(imidazo[1,2-a]pyridin-7-ylmethyl)-4-[1-(2-methylbenzoyl)piperidin-4-yl]benzamide | (ESI(+)) m/e 453 (M + H)$^+$ |
| 508 | 4-[1-(4-fluorobenzoyl)piperidin-4-yl]-N-(imidaz[1,2-a]pyridin-7-ylmethyl)benzamide | (ESI(+)) m/e 457 (M + H)$^+$ |

TABLE 13-continued

The following Examples were prepared essentially as described in Example 230, substituting the appropriate carboxylic acid in Example 230B.

| Ex | Name | MS |
|---|---|---|
| 509 | 4-[1-(2,2-dimethylpropanoyl)piperidin-4-yl]-N-(imidazo[1,2-a]pyridin-7-ylmethyl)benzamide | (ESI(+)) m/e 419 (M + H)+ |
| 510 | N-(imidazo[1,2-a]pyridin-7-ylmethyl)-4-{1-[(2E)-2-methylpent-2-enoyl]piperidin-4-yl}benzamide | (ESI(+)) m/e 431 (M + H)+ |
| 511 | N-(imidazo[1,2-a]pyridin-7-ylmethyl)-4-{1-[(1-methyl-1H-pyrazol-5-yl)carbonyl]piperidin-4-yl}benzamide | (ESI(+)) m/e 443 (M + H)+ |
| 512 | N-(imidazo[1,2-a]pyridin-7-ylmethyl)-4-{1-[(3-methyloxetan-3-yl)carbonyl]piperidin-4-yl}benzamide | (ESI(+)) m/e 433 (M + H)+ |
| 513 | 4-[1-(2-fluorobenzoyl)piperidin-4-yl]-N-(imidazo[1,2-a]pyridin-7-ylmethyl)benzamide | (ESI(+)) m/e 457 (M + H)+ |
| 514 | 4-{1-[(1-cyanocyclopropyl)carbonyl]piperidin-4-yl}-N-(imidazo[1,2-a]pyridin-7-ylmethyl)benzamide | (ESI(+)) m/e 428 (M + H)+ |
| 515 | 4-[1-(cyclopentylcarbonyl)piperidin-4-yl]-N-(imidazo[1,2-a]pyridin-7-ylmethyl)benzamide | (ESI(+)) m/e 431 (M + H)+ |
| 516 | 4-[1-(3-fluorobenzoyl)piperidin-4-yl]-N-(imidazo[1,2-a]pyridin-7-ylmethyl)benzamide | (ESI(+)) m/e 457 (M + H)+ |
| 517 | N-(imidazo[1,2-a]pyridin-7-ylmethyl)-4-{1-[(1-methyl-1H-pyrazol-4-yl)carbonyl]piperidin-4-yl}benzamide | (ESI(+)) m/e 443 (M + H)+ |
| 518 | N-(imidazo[1,2-a]pyridin-7-ylmethyl)-4-[1-(2-oxobutanoyl)piperidin-4-yl]benzamide | (ESI(+)) m/e 419 (M + H)+ |
| 519 | 4-{1-[(2,5-dimethylfuran-3-yl)carbonyl]piperidin-4-yl}-N-(imidazo[1,2-a]pyridin-7-ylmethyl)benzamide | (ESI(+)) m/e 457 (M + H)+ |
| 520 | 4-[1-(4-cyanobenzoyl)piperidin-4-yl]-N-(imidazo[1,2-a]pyridin-7-ylmethyl)benzamide | (ESI(+)) m/e 464 (M + H)+ |
| 521 | 4-[1-(3-cyanobenzoyl)piperidin-4-yl]-N-(imidazo[1,2-a]pyridin-7-ylmethyl)benzamide | (ESI(+)) m/e 464 (M + H)+ |
| 522 | 4-[1-(2,5-difluorobenzoyl)piperidin-4-yl]-N-(imidazo[1,2-a]pyridin-7-ylmethyl)benzamide | (ESI(+)) m/e 475 (M + H)+ |
| 523 | N-(imidazo[1,2-a]pyridin-7-ylmethyl)-4-[1-(pyrazin-2-ylcarbonyl)piperidin-4-yl]benzamide | (ESI(+)) m/e 441 (M + H)+ |
| 524 | N-(imidazo[1,2-a]pyridin-7-ylmethyl)-4-{1-[(3-methylthiophen-2-yl)carbonyl]piperidin-4-yl}benzamide | (ESI(+)) m/e 459 (M + H)+ |
| 525 | 4-{1-[(3,5-dimethyl-1,2-oxazol-4-yl)carbonyl]piperidin-4-yl}-N-(imidazo[1,2-a]pyridin-7-ylmethyl)benzamide | (ESI(+)) m/e 458 (M + H)+ |
| 526 | N-(imidazo[1,2-a]pyridin-7-ylmethyl)-4-[1-(3-methoxybenzoyl)piperidin-4-yl]benzamide | (ESI(+)) m/e 469 (M + H)+ |
| 527 | 4-[1-(3-chlorobenzoyl)piperidin-4-yl]-N-(imidazo[1,2-a]pyridin-7-ylmethyl)benzamide | (ESI(+)) m/e 473 (M + H)+ |
| 528 | N-(imidazo[1,2-a]pyridin-7-ylmethyl)-4-[1-(4-methoxybenzoyl)piperidin-4-yl]benzamide | (ESI(+)) m/e 469 (M + H)+ |
| 529 | 4-[1-(4-chlorobenzoyl)piperidin-4-yl]-N-(imidazo[1,2-a]pyridin-7-ylmethyl)benzamide | (ESI(+)) m/e 473 (M + H)+ |
| 530 | 4-[1-(3,5-difluorobenzoyl)piperidin-4-yl]-N-(imidazo[1,2-a]pyridin-7-ylmethyl)benzamide | (ESI(+)) m/e 475 (M + H)+ |
| 531 | 4-[1-(cyclopropylcarbonyl)piperidin-4-yl]-N-(imidazo[1,2-a]pyridin-7-ylmethyl)benzamide | (ESI(+)) m/e 403 (M + H)+ |
| 532 | N-(imidazo[1,2-a]pyridin-7-ylmethyl)-4-(1-propanoylpiperidin-4-yl)benzamide | (ESI(+)) m/e 391 (M + H)+ |
| 533 | N-(imidazo[1,2-a]pyridin-7-ylmethyl)-4-{1-[(1-methyl-1H-pyrrol-2-yl)carbonyl]piperidin-4-yl}benzamide | (ESI(+)) m/e 442 (M + H)+ |

TABLE 13-continued

The following Examples were prepared essentially as described in Example 230, substituting the appropriate carboxylic acid in Example 230B.

| Ex | Name | MS |
|---|---|---|
| 534 | N-(imidazo[1,2-a]pyridin-7-ylmethyl)-4-[1-(3-methylbutanoyl)piperidin-4-yl]benzamide | (ESI(+)) m/e 419 (M + H)+ |
| 535 | N-(imidazo[1,2-a]pyridin-7-ylmethyl)-4-[1-(pyridin-4-ylcarbonyl)piperidin-4-yl]benzamide | (ESI(+)) m/e 440 (M + H)+ |
| 536 | 4-[1-(2,3-dimethylbutanoyl)piperidin-4-yl]-N-(imidazo[1,2-a]pyridin-7-ylmethyl)benzamide | (ESI(+)) m/e 433 (M + H)+ |
| 537 | N-(imidazo[1,2-a]pyridin-7-ylmethyl)-4-[1-(pyridin-3-ylcarbonyl)piperidin-4-yl]benzamide | (ESI(+)) m/e 440 (M + H)+ |
| 538 | N-(imidazo[1,2-a]pyridin-7-ylmethyl)-4-{1-[(1-methylcyclopropyl)carbonyl]piperidin-4-yl}benzamide | (ESI(+)) m/e 417 (M + H)+ |
| 539 | N-(imidazo[1,2-a]pyridin-7-ylmethyl)-4-[1-(2-methoxybenzoyl)piperidin-4-yl]benzamide | (ESI(+)) m/e 469 (M + H)+ |
| 699 | 4-[1-(2-chlorobenzoyl)piperidin-4-yl]-N-(imidazo[1,2-a]pyridin-7-ylmethyl)benzamide | (ESI(+)) m/e 473 (M + H)+ |
| 700 | 4-[1-(2,6-difluorobenzoyl)piperidin-4-yl]-N-(imidazo[1,2-a]pyridin-7-ylmethyl)benzamide | (ESI(+)) m/e 475 (M + H)+ |
| 701 | 4-[1-(3,4-difluorobenzoyl)piperidin-4-yl]-N-(imidazo[1,2-a]pyridin-7-ylmethyl)benzamide | (ESI(+)) m/e 475 (M + H)+ |
| 702 | N-(imidazo[1,2-a]pyridin-7-ylmethyl)-4-{1-[3-(trifluoromethyl)benzoyl]piperidin-4-yl}benzamide | (ESI(+)) m/e 507 (M + H)+ |
| 703 | N-(imidazo[1,2-a]pyridin-7-ylmethyl)-4-{1-[3-(trifluoromethoxy)benzoyl]piperidin-4-yl}benzamide | (ESI(+)) m/e 523 (M + H)+ |
| 704 | N-(imidazo[1,2-a]pyridin-7-ylmethyl)-4-{1-[4-(trifluoromethoxy)benzoyl]piperidin-4-yl}benzamide | (ESI(+)) m/e 523 (M + H)+ |
| 705 | N-(imidazo[1,2-a]pyridin-7-ylmethyl)-4-{1-[4-(trifluoromethyl)benzoyl]piperidin-4-yl}benzamide | (ESI(+)) m/e 507 (M + H)+ |
| 706 | N-(imidazo[1,2-a]pyridin-7-ylmethyl)-4-{1-[2-(trifluoromethoxy)benzoyl]piperidin-4-yl}benzamide | (ESI(+)) m/e 523 (M + H)+ |
| 707 | N-(imidazo[1,2-a]pyridin-7-ylmethyl)-4-[1-(phenylacetyl)piperidin-4-yl]benzamide | (ESI(+)) m/e 453 (M + H)+ |
| 708 | N-(imidazo[1,2-a]pyridin-7-ylmethyl)-4-{1-[2-(trifluoromethyl)benzoyl]piperidin-4-yl}benzamide | (ESI(+)) m/e 507 (M + H)+ |
| 737 | 4-[1-(2-cyanobenzoyl)piperidin-4-yl]-N-(imidazo[1,2-a]pyridin-7-ylmethyl)benzamide | (ESI(-0) m/e 464 (M + H)+ |
| 913 | 4-{1-[(2-chloropyridin-3-yl)carbonyl]piperidin-4-yl}-N-(imidazo[1,2-a]pyridin-7-ylmethyl)benzamide | (ESI(+)) m/e 474 (M + H)+ |
| 914 | N-(imidazo[1,2-a]pyridin-7-ylmethyl)-4-[1-(3-methylbut-2-enoyl)piperidin-4-yl]benzamide | ESI(+)) m/e 417 (M + H)+ |
| 915 | 4-[1-(3-fluoro-4-methoxybenzoyl)piperidin-4-yl]-N-(imidazo[1,2-a]pyridin-7-ylmethyl)benzamide | ESI(+)) m/e 487 (M + H)+ |
| 916 | N-(imidazo[1,2-a]pyridin-7-ylmethyl)-4-{1-[(2-methylcyclopent-1-en-1-yl)carbonyl]piperidin-4-yl}benzamide | ESI(+)) m/e 443 (M + H)+ |
| 917 | 4-[1-(2-ethylbutanoyl)piperidin-4-yl]-N-(imidazo[1,2-a]pyridin-7-ylmethyl)benzamide | ESI(+)) m/e 433 (M + H)+ |
| 918 | 4-{1-[(4-fluorophenoxy)acetyl]piperidin-4-yl}-N-(imidazo[1,2-a]pyridin-7-ylmethyl)benzamide | ESI(+)) m/e 487 (M + H)+ |
| 919 | 4-[1-(3,5-dimethoxybenzoyl)piperidin-4-yl]-N-(imidazo[1,2-a]pyridin-7-ylmethyl)benzamide | ESI(+)) m/e 499 (M + H)+ |
| 920 | 4-[1-(cyclohex-3-en-1-ylcarbonyl)piperidin-4-yl]-N-(imidazo[1,2-a]pyridin-7-ylmethyl)benzamide | ESI(+)) m/e 443 (M + H)+ |

TABLE 13-continued

The following Examples were prepared essentially as described in Example 230, substituting the appropriate carboxylic acid in Example 230B.

| Ex | Name | MS |
|---|---|---|
| 921 | N-(imidazo[1,2-a]pyridin-7-ylmethyl)-4-{1-[(2-methoxyphenyl)acetyl]piperidin-4-yl}benzamide | ESI(+)) m/e 483 (M + H)+ |
| 922 | 4-[1-(3-hydroxy-2-phenylpropanoyl)piperidin-4-yl]-N-(imidazo[1,2-a]pyridin-7-ylmethyl)benzamide | ESI(+)) m/e 483 (M + H)+ |
| 923 | N-(imidazo[1,2-a]pyridin-7-ylmethyl)-4-[1-(3-methylbenzoyl)piperidin-4-yl]benzamide | ESI(+)) m/e 453 (M + H)+ |
| 924 | 4-[1-(2-acetylbenzoyl)piperidin-4-yl]-N-(imidazo[1,2-a]pyridin-7-ylmethyl)benzamide | ESI(+)) m/e 481 (M + H)+ |
| 925 | N-(imidazo[1,2-a]pyridin-7-ylmethyl)-4-{1-[2-(methoxymethyl)benzoyl]piperidin-4-yl}benzamide | ESI(+)) m/e 483 (M + H)+ |
| 926 | N-(imidazo[1,2-a]pyridin-7-ylmethyl)-4-[1-(2-phenylpropanoyl)piperidin-4-yl]benzamide | ESI(+)) m/e 467 (M + H)+ |
| 927 | 4-[1-(2,6-dimethoxybenzoyl)piperidin-4-yl]-N-(imidazo[1,2-a]pyridin-7-ylmethyl)benzamide | ESI(+)) m/e 499 (M + H)+ |
| 928 | 4-[1-(N,N-diethyl-beta-alanyl)piperidin-4-yl]-N-(imidazo[1,2-a]pyridin-7-ylmethyl)benzamide | ESI(+)) m/e 462 (M + H)+ |
| 929 | N-(imidazo[1,2-a]pyridin-7-ylmethyl)-4-(1-{[(2-methylpropyl)sulfonyl]acetyl}piperidin-4-yl)benzamide | ESI(+)) m/e 497 (M + H)+ |
| 930 | N-(imidazo[1,2-a]pyridin-7-ylmethyl)-4-[1-(2-phenoxypropanoyl)piperidin-4-yl]benzamide | ESI(+)) m/e 483 (M + H)+ |
| 931 | N-(imidazo[1,2-a]pyridin-7-ylmethyl)-4-[1-({[(1R,2S)-2-methylcyclohexyl]oxy}acetyl)piperidin-4-yl]benzamide | ESI(+)) m/e 489 (M + H)+ |
| 932 | 4-{1-[(2-chloro-6-methylpyridin-4-yl)carbonyl]piperidin-4-yl}-N-(imidazo[1,2-a]pyridin-7-ylmethyl)benzamide | ESI(+)) m/e 488 (M + H)+ |
| 933 | N-(imidazo[1,2-a]pyridin-7-ylmethyl)-4-{1-[(3-methoxyphenyl)acetyl]piperidin-4-yl}benzamide | ESI(+)) m/e 483 (M + H)+ |
| 934 | 4-[1-(2-chloro-4-cyanobenzoyl)piperidin-4-yl]-N-(imidazo[1,2-a]pyridin-7-ylmethyl)benzamide | ESI(+)) m/e 498 (M + H)+ |
| 935 | N-(imidazo[1,2-a]pyridin-7-ylmethyl)-4-{1-[(2E)-2-methylbut-2-enoyl]piperidin-4-yl}benzamide | ESI(+)) m/e 417 (M + H)+ |
| 936 | N-(imidazo[1,2-a]pyridin-7-ylmethyl)-4-{1-[(2-methoxy-5-methylphenyl)acetyl]piperidin-4-yl}benzamide | ESI(+)) m/e 497 (M + H)+ |
| 937 | 4-[1-(2-hydroxy-3-methylbenzoyl)piperidin-4-yl]-N-(imidazo[1,2-a]pyridin-7-ylmethyl)benzamide | ESI(+)) m/e 469 (M + H)+ |
| 959 | N-(imidazo[1,2-a]pyridin-7-ylmethyl)-4-(1-{[1-(propan-2-yl)-1H-pyrazol-3-yl]carbonyl}piperidin-4-yl)benzamide | ESI(+)) m/e 471 (M + H)+ |
| 960 | 4-{1-[(3-cyclopropyl-1-methyl-1H-pyrazol-5-yl)carbonyl]piperidin-4-yl}-N-(imidazo[1,2-a]pyridin-7-ylmethyl)benzamide | ESI(+)) m/e 483 (M + H)+ |
| 961 | N-(imidazo[1,2-a]pyridin-7-ylmethyl)-4-{1-[(2-methyl-4,5,6,7-tetrahydro-2H-indazol-3-yl)carbonyl]piperidin-4-yl}benzamide | ESI(+)) m/e 497 (M + H)+ |
| 962 | N-(imidazo[1,2-a]pyridin-7-ylmethyl)-4-(1-(4,5,6,7-tetrahydro-2,1-benzoxazol-3-ylcarbonyl)piperidin-4-yl]benzamide | ESI(+)) m/e 484 (M + H)+ |
| 963 | 4-{1-[(3-fluoro-6-methylpyridin-2-yl)carbonyl]piperidin-4-yl}-N-(imidazo[1,2-a]pyridin-7-ylmethyl)benzamide | ESI(+)) m/e 472 (M + H)+ |
| 964 | 4-{1-[(2-chloro-3-fluoropyridin-4-yl)carbonyl]piperidin-4-yl}-N-(imidazo[1,2-a]pyridin-7-ylmethyl)benzamide | ESI(+)) m/e 492 (M + H)+ |
| 965 | 4-{1-[(3-chloropyridin-2-yl)carbonyl]piperidin-4-yl}-N-(imidazo[1,2-a]pyridin-7-ylmethyl)benzamide | ESI(+)) m/e 474 (M + H)+ |
| 966 | N-(imidazo[1,2-a]pyridin-7-ylmethyl)-4-(1-{[1-(pyridin-2-yl)cyclopropyl]carbonyl}piperidin-4-yl)benzamide | ESI(+)) m/e 480 (M + H)+ |

TABLE 13-continued

The following Examples were prepared essentially as described in Example 230, substituting the appropriate carboxylic acid in Example 230B.

| Ex | Name | MS |
|---|---|---|
| 967 | 4-{1-[(1-cyclopentyl-1H-pyrazol-3-yl)carbonyl]piperidin-4-yl}-N-(imidazo[1,2-a]pyridin-7-ylmethyl)benzamide | ESI(+)) m/e 497 (M + H)+ |
| 968 | 4-{1-[2-(3-fluorophenoxy)propanoyl]piperidin-4-yl}-N-(imidazo[1,2-a]pyridin-7-ylmethyl)benzamide | ESI(+)) m/e 501 (M + H)+ |
| 969 | 4-(1-{[1-(difluoromethyl)-1H-pyrazol-5-yl]carbonyl}piperidin-4-yl)-N-(imidazo[1,2-a]pyridin-7-ylmethyl)benzamide | ESI(+)) m/e 479 (M + H)+ |
| 970 | 4-[1-(3,4-dihydro-2H-chromen-6-ylcarbonyl)piperidin-4-yl]-N-(imidazo[1,2-a]pyridin-7-ylmethyl)benzamide | ESI(+)) m/e 495 (M + H)+ |
| 971 | 4-{1-[(cyclohexyloxy)acetyl]piperidin-4-yl}-N-(imidazo[1,2-a]pyridin-7-ylmethyl)benzamide | ESI(+)) m/e 475 (M + H)+ |
| 972 | 4-{1-[(2-chloropyridin-3-yl)acetyl]piperidin-4-yl}-N-(imidazo[1,2-a]pyridin-7-ylmethyl)benzamide | ESI(+)) m/e 488 (M + H)+ |
| 973 | 4-{1-[(5-cyclopropyl-1,2-oxazol-3-yl)carbonyl]piperidin-4-yl}-N-(imidazo[1,2-a]pyridin-7-ylmethyl)benzamide | ESI(+)) m/e 470 (M + H)+ |
| 974 | 4-[1-(2H-chromen-3-ylcarbonyl)piperidin-4-yl]-N-(imidazo[1,2-a]pyridin-7-ylmethyl)benzamide | ESI(+)) m/e 493 (M + H)+ |
| 975 | 4-{1-[(3,5-difluoropyridin-2-yl)carbonyl]piperidin-4-yl}-N-(imidazo[1,2-a]pyridin-7-ylmethyl)benzamide | ESI(+)) m/e 476 (M + H)+ |
| 976 | 4-[1-(2,3-dihydro-1,4-benzodioxin-2-ylcarbonyl)piperidin-4-yl]-N-(imidazo[1,2-a]pyridin-7-ylmethyl)benzamide | ESI(+)) m/e 497 (M + H)+ |
| 977 | N-(imidazo[1,2-a]pyridin-7-ylmethyl)-4-{1-[(4-methoxycyclohexyl)carbonyl]piperidin-4-yl}benzamide | ESI(+)) m/e 475 (M + H)+ |
| 978 | 4-[1-(2,3-dihydro-1,4-benzodioxin-5-ylcarbonyl)piperidin-4-yl]-N-(imidazo[1,2-a]pyridin-7-ylmethyl)benzamide | ESI(+)) m/e 497 (M + H)+ |
| 979 | N-(imidazo[1,2-a]pyridin-7-ylmethyl)-4-[1-(isoquinolin-4-ylcarbonyl)piperidin-4-yl]benzamide | ESI(+)) m/e 490 (M + H)+ |
| 980 | N-(imidazo[1,2-a]pyridin-7-ylmethyl)-4-{1-[(2-methyl-1,3-benzoxazol-6-yl)carbonyl]piperidin-4-yl}benzamide | ESI(+)) m/e 494 (M + H)+ |
| 981 | 4-{1-[(1-tert-butyl-3-methyl-1H-pyrazol-5-yl)carbonyl]piperidin-4-yl}-N-(imidazo[1,2-a]pyridin-7-ylmethyl)benzamide | ESI(+)) m/e 499 (M + H)+ |
| 982 | 4-{1-[(1-cyanocyclopentyl)carbonyl]piperidin-4-yl}-N-(imidazo[1,2-a]pyridin-7-ylmethyl)benzamide | ESI(+)) m/e 456 (M + H)+ |
| 983 | N-(imidazo[1,2-a]pyridin-7-ylmethyl)-4-[1-(thieno[3,2-b]pyridin-2-ylcarbonyl)piperidin-4-yl]benzamide | ESI(+)) m/e 496 (M + H)+ |
| 984 | N-(imidazo[1,2-a]pyridin-7-ylmethyl)-4-[1-(quinolin-7-ylcarbonyl)piperidin-4-yl]benzamide | ESI(+)) m/e 490 (M + H)+ |
| 985 | 4-[1-(5-cyano-2-fluorobenzoyl)piperidin-4-yl]-N-(imidazo[1,2-a]pyridin-7-ylmethyl)benzamide | ESI(+)) m/e 482 (M + H)+ |
| 986 | N-(imidazo[1,2-a]pyridin-7-ylmethyl)-4-[1-(5,6,7,8-tetrahydroquinolin-3-ylcarbonyl)piperidin-4-yl]benzamide | ESI(+)) m/e 494 (M + H)+ |
| 987 | 4-[1-(3,4-dihydro-2H-pyrano[2,3-b]pyridin-6-ylcarbonyl)piperidin-4-yl]-N-(imidazo[1,2-a]pyridin-7-ylmethyl)benzamide | ESI(+)) m/e 496 (M + H)+ |
| 988 | N-(imidazo[1,2-a]pyridin-7-ylmethyl)-4-[1-(isoquinolin-7-ylcarbonyl)piperidin-4-yl]benzamide | ESI(+)) m/e 490 (M + H)+ |
| 989 | N-(imidazo[1,2-a]pyridin-7-ylmethyl)-4-[1-(quinoxalin-2-ylcarbonyl)piperidin-4-yl]benzamide | ESI(+)) m/e 491 (M + H)+ |
| 990 | N-(imidazo[1,2-a]pyridin-7-ylmethyl)-4-{1-[(2E)-3-(2-methoxypyridin-3-yl)prop-2-enoyl]piperidin-4-yl}benzamide | ESI(+)) m/e 496 (M + H)+ |
| 991 | -(imidazo[1,2-a]pyridin-7-ylmethyl)-4-{1-[(2E)-3-(pyridin-2-yl)prop-2-enoyl]piperidin-4-yl}benzamide | ESI(+)) m/e 466 (M + H)+ |

TABLE 13-continued

The following Examples were prepared essentially as described in Example 230, substituting the appropriate carboxylic acid in Example 230B.

| Ex | Name | MS |
|---|---|---|
| 992 | N-(imidazo[1,2-a]pyridin-7-ylmethyl)-4-{1-[(8-methylimidazo[1,2-a]pyridin-2-yl)carbonyl]piperidin-4-yl}benzamide | ESI(+)) m/e 493 (M + H)+ |
| 993 | 4-{1-[(2-ethoxypyridin-4-yl)carbonyl]piperidin-4-yl}-N-(imidazo[1,2-a]pyridin-7-ylmethyl)benzamide | ESI(+)) m/e 484 (M + H)+ |
| 994 | N-(imidazo[1,2-a]pyridin-7-ylmethyl)-4-{1-[(1-methyl-4,5,6,7-tetrahydro-1H-indazol-3-yl)carbonyl]piperidin-4-yl}benzamide | ESI(+)) m/e 497 (M + H)+ |
| 995 | N-(imidazo[1,2-a]pyridin-7-ylmethyl)-4-{1-[(4-methyl-4H-furo[3,2-b]pyrrol-5-yl)carbonyl]piperidin-4-yl}benzamide | ESI(+)) m/e 482 (M + H)+ |
| 996 | 4-[1-(3-cyano-5-fluorobenzoyl)piperidin-4-yl]-N-(imidazo[1,2-a]pyridin-7-ylmethyl)benzamide | ESI(+)) m/e 482 (M + H)+ |
| 997 | N-(imidazo[1,2-a]pyridin-7-ylmethyl)-4-[1-(isoquinolin-8-ylcarbonyl)piperidin-4-yl]benzamide | ESI(+)) m/e 490 (M + H)+ |
| 998 | 4-{1-[(4-cyanophenyl)acetyl]piperidin-4-yl}-N-(imidazo[1,2-a]pyridin-7-ylmethyl)benzamide | ESI(+)) m/e 478 (M + H)+ |
| 999 | 4-[1-(3-cyano-4-fluorobenzoyl)piperidin-4-yl]-N-(imidazo[1,2-a]pyridin-7-ylmethyl)benzamide | ESI(+)) m/e 482 (M + H)+ |
| 1000 | N-(imidazo[1,2-a]pyridin-7-ylmethyl)-4-[1-(4,5,6,7-tetrahydro-1,3-benzothiazol-2-ylcarbonyl)piperidin-4-yl]benzamide | ESI(+)) m/e 500 (M + H)+ |
| 1001 | 4-[1-(1,3-benzothiazol-2-ylcarbonyl)piperidin-4-yl]-N-(imidazo[1,2-a]pyridin-7-ylmethyl)benzamide | ESI(+)) m/e 496 (M + H)+ |
| 1002 | 4-{1-[(3-ethyl-1,2-oxazol-5-yl)carbonyl]piperidin-4-yl}-N-(imidazo[1,2-a]pyridin-7-ylmethyl)benzamide | ESI(+)) m/e 458 (M + H)+ |
| 1003 | N-(imidazo[1,2-a]pyridin-7-ylmethyl)-4-(1-{[3-methyl-1-(prop-2-en-1-yl)-1H-pyrazol-5-yl]carbonyl}piperidin-4-yl)benzamide | ESI(+)) m/e 483 (M + H)+ |
| 1004 | 4-[1-(1,2,3-benzothiadiazol-5-ylcarbonyl)piperidin-4-yl]-N-(imidazo[1,2-a]pyridin-7-ylmethyl)benzamide | ESI(+)) m/e 497 (M + H)+ |
| 1005 | 4-{1-[(2-ethyl-1,3-thiazol-4-yl)carbonyl]piperidin-4-yl}-N-(imidazo[1,2-a]pyridin-7-ylmethyl)benzamide | ESI(+)) m/e 474 (M + H)+ |
| 1006 | N-(imidazo[1,2-a]pyridin-7-ylmethyl)-4-(1-{[2-(propan-2-yl)pyrimidin-4-yl]carbonyl}piperidin-4-yl)benzamide | ESI(+)) m/e 483 (M + H)+ |
| 1007 | 4-{1-[(5,6-dimethylpyridin-3-yl)carbonyl]piperidin-4-yl}-N-(imidazo[1,2-a]pyridin-7-ylmethyl)benzamide | ESI(+)) m/e 468 (M + H)+ |
| 1008 | N-(imidazo[1,2-a]pyridin-7-ylmethyl)-4-(1-{[2-(propan-2-yl)tetrahydro-2H-pyran-4-yl]carbonyl}piperidin-4-yl)benzamide | ESI(+)) m/e 489 (M + H)+ |
| 1009 | N-(imidazo[1,2-a]pyridin-7-ylmethyl)-4-[1-(2-methoxy-6-methylbenzoyl)piperidin-4-yl]benzamide | ESI(+)) m/e 483 (M + H)+ |
| 1010 | 4-[1-(1,3-benzothiazol-7-ylcarbonyl)piperidin-4-yl]-N-(imidazo[1,2-a]pyridin-7-ylmethyl)benzamide | ESI(+)) m/e 496 (M + H)+ |
| 1061 | 4-{1-[(2-chloro-5-fluoropyridin-4-yl)carbonyl]piperidin-4-yl}-N-(imidazo[1,2-a]pyridin-7-ylmethyl)benzamide | ESI(+)) m/e 493 (M + H)+ |
| 1062 | 4-{1-[(3-cyclopropyl-1,2-oxazol-5-yl)carbonyl]piperidin-4-yl}-N-(imidazo[1,2-a]pyridin-7-ylmethyl)benzamide | ESI(+)) m/e 471 (M + H)+ |
| 1063 | N-(imidazo[1,2-a]pyridin-7-ylmethyl)-4-{1-[(3-methoxythiophen-2-yl)carbonyl]piperidin-4-yl}benzamide | ESI(+)) m/e 476 (M + H)+ |
| 1064 | N-(imidazo[1,2-a]pyridin-7-ylmethyl)-4-(1-{[2-methyl-5-(propan-2-yl)furan-3-yl]carbonyl}piperidin-4-yl)benzamide | ESI(+)) m/e 486 (M + H)+ |
| 1084 | 4-{1-[(2-cyclopropyl-1,3-thiazol-5-yl)carbonyl]piperidin-4-yl}-N-(imidazo[1,2-a]pyridin-7-ylmethyl)benzamide | ESI(+)) m/e 486 (M + H)+ |
| 1085 | 4-[1-(1,3-benzothiazol-5-ylcarbonyl)piperidin-4-yl]-N-(imidazo[1,2-a]pyridin-7-ylmethyl)benzamide | ESI(+)) m/e 496 (M + H)+ |

TABLE 13-continued

The following Examples were prepared essentially as described in Example 230, substituting the appropriate carboxylic acid in Example 230B.

| Ex | Name | MS |
|---|---|---|
| 1086 | N-(imidazo[1,2-a]pyridin-7-ylmethyl)-4-{1-[(1-methyl-1H-indazol-6-yl)carbonyl]piperidin-4-yl}benzamide | ESI(+)) m/e 493 (M + H)+ |
| 1087 | 4-{1-[(4-chloro-1,3-dimethyl-1H-pyrazol-5-yl)carbonyl]piperidin-4-yl}-N-(imidazo[1,2-a]pyridin-7-ylmethyl)benzamide | ESI(+)) m/e 491 (M + H)+ |
| 1088 | 4-{1-[(5-ethylpyridin-2-yl)carbonyl]piperidin-4-yl}-N-(imidazo[1,2-a]pyridin-7-ylmethyl)benzamide | ESI(+)) m/e 468 (M + H)+ |
| 1089 | 4-{1-[(3-chloro-5-cyanopyridin-2-yl)carbonyl]piperidin-4-yl}-N-(imidazo[1,2-a]pyridin-7-ylmethyl)benzamide | ESI(+)) m/e 499 (M + H)+ |
| 1090 | 4-{1-[(1-cyano-3-methylcyclobutyl)carbonyl]piperidin-4-yl}-N-(imidazo[1,2-a]pyridin-7-ylmethyl)benzamide | ESI(+)) m/e 456 (M + H)+ |
| 1091 | 4-{1-[(1,5-diethyl-1H-1,2,3-triazol-4-yl)carbonyl]piperidin-4-yl}-N-(imidazo[1,2-a]pyridin-7-ylmethyl)benzamide | ESI(+)) m/e 486 (M + H)+ |
| 1092 | N-(imidazo[1,2-a]pyridin-7-ylmethyl)-4-{1-[(4-methoxythiophen-2-yl)carbonyl]piperidin-4-yl}benzamide | ESI(+)) m/e 475 (M + H)+ |
| 1093 | 4-{1-[(5-cyanothiophen-2-yl)carbonyl]piperidin-4-yl}-N-(imidazo[1,2-a]pyridin-7-ylmethyl)benzamide | ESI(+)) m/e 470 (M + H)+ |
| 1094 | 4-{1-[(5-cyclopropylpyridin-2-yl)carbonyl]piperidin-4-yl}-N-(imidazo[1,2-a]pyridin-7-ylmethyl)benzamide | ESI(+)) m/e 480 (M + H)+ |
| 1095 | 4-[1-(4-cyano-2,6-difluorobenzoyl)piperidin-4-yl]-N-(imidazo[1,2-a]pyridin-7-ylmethyl)benzamide | ESI(+)) m/e 500 (M + H)+ |
| 1096 | 4-(1-{[1-ethyl-3-(propan-2-yl)-1H-pyrazol-4-yl]carbonyl}piperidin-4-yl)-N-(imidazo[1,2-a]pyridin-7-ylmethyl)benzamide | ESI(+)) m/e 499 (M + H)+ |
| 1097 | N-(imidazo[1,2-a]pyridin-7-ylmethyl)-4-(1-{[1-(propan-2-yl)-1H-pyrazol-3-yl]acetyl}piperidin-4-yl)benzamide | ESI(+)) m/e 485 (M + H)+ |
| 1098 | 4-[1-(1-benzofuran-3-ylcarbonyl)piperidin-4-yl]-N-(imidazo[1,2-a]pyridin-7-ylmethyl)benzamide | ESI(+)) m/e 479 (M + H)+ |
| 1099 | Example 1099 N-(imidazo[1,2-a]pyridin-7-ylmethyl)-4-{1-[(3-methyl-5,6,7,8-tetrahydroimidazo[1,5-a]pyridin-1-yl)carbonyl]piperidin-4-yl}benzamide | ESI(+)) m/e 497 (M + H)+ |
| 1100 | N-(imidazo[1,2-a]pyridin-7-ylmethyl)-4-{1-[(4-methoxy-5-methylpyridin-2-yl)carbonyl]piperidin-4-yl}benzamide | ESI(+)) m/e 484 (M + H)+ |
| 1101 | 4-{1-[(1-cyclopentyl-1H-pyrazol-5-yl)carbonyl]piperidin-4-yl}-N-(imidazo[1,2-a]pyridin-7-ylmethyl)benzamide | ESI(+)) m/e 497 (M + H)+ |
| 1102 | 4-{1-[(4-chloro-1,3-thiazol-5-yl)carbonyl]piperidin-4-yl}-N-(imidazo[1,2-a]pyridin-7-ylmethyl)benzamide | ESI(+)) m/e 480 (M + H)+ |
| 1103 | 4-{1-[(3-cyanothiophen-2-yl)carbonyl]piperidin-4-yl}-N-(imidazo[1,2-a]pyridin-7-ylmethyl)benzamide | ESI(+)) m/e 470 (M + H)+ |
| 1104 | N-(imidazo[1,2-a]pyridin-7-ylmethyl)-4-(1-{[4-(propan-2-yl)pyrimidin-5-yl]carbonyl}piperidin-4-yl)benzamide | ESI(+)) m/e 483 (M + H)+ |
| 1105 | N-(imidazo[1,2-a]pyridin-7-ylmethyl)-4-{1-[(1-methyl-5-propyl-1H-pyrazol-4-yl)carbonyl]piperidin-4-yl}benzamide | ESI(+)) m/e 485 (M + H)+ |
| 1106 | 4-{1-[2-(3-cyclopropyl-1H-pyrazol-1-yl)propanoyl]piperidin-4-yl}-N-(imidazo[1,2-a]pyridin-7-ylmethyl)benzamide | ESI(+)) m/e 497 (M + H)+ |
| 1107 | N-(imidazo[1,2-a]pyridin-7-ylmethyl)-4-{1-[(2-methyl-2,3-dihydro-1-benzofuran-7-yl)carbonyl]piperidin-4-yl}benzamide | ESI(+)) m/e 495 (M + H)+ |
| 1108 | N-(imidazo[1,2-a]pyridin-7-ylmethyl)-4-(1-{[2-(propan-2-yl)-1,3-thiazol-4-yl]carbonyl}piperidin-4-yl)benzamide | ESI(+)) m/e 488 (M + H)+ |
| 1109 | 4-(1-{[1-(difluoromethyl)-5-methyl-1H-pyrazol-3-yl]carbonyl}piperidin-4-yl)-N-(imidazo[1,2-a]pyridin-7-ylmethyl)benzamide | ESI(+)) m/e 493 (M + H)+ |

TABLE 13-continued

The following Examples were prepared essentially as described in Example 230, substituting the appropriate carboxylic acid in Example 230B.

| Ex | Name | MS |
|---|---|---|
| 1110 | 4-{1-[(4-cyanothiophen-2-yl)carbonyl]piperidin-4-yl}-N-(imidazo[1,2-a]pyridin-7-ylmethyl)benzamide | ESI(+)) m/e 470 (M + H)+ |
| 1111 | N-(imidazo[1,2-a]pyridin-7-ylmethyl)-4-[1-(pyrazolo[1,5-a]pyridin-2-ylcarbonyl)piperidin-4-yl]benzamide | ESI(+)) m/e 479 (M + H)+ |
| 1112 | 4-[1-(1-benzofuran-5-ylcarbonyl)piperidin-4-yl]-N-(imidazo[1,2-a]pyridin-7-ylmethyl)benzamide | ESI(+)) m/e 479 (M + H)+ |
| 1113 | N-(imidazo[1,2-a]pyridin-7-ylmethyl)-4-(1-{[2-(propan-2-yl)-1,3-oxazol-4-yl]carbonyl}piperidin-4-yl)benzamide | ESI(+)) m/e 472 (M + H)+ |
| 1114 | N-(imidazo[1,2-a]pyridin-7-ylmethyl)-4-{1-[(2-methoxy-5-methylpyridin-3-yl)carbonyl]piperidin-4-yl}benzamide | ESI(+)) m/e 484 (M + H)+ |
| 1115 | 4-{1-[(5,6-dimethoxypyridin-2-yl)carbonyl]piperidin-4-yl}-N-(imidazo[1,2-a]pyridin-7-ylmethyl)benzamide | ESI(+)) m/e 500 (M + H)+ |
| 1116 | N-(imidazo[1,2-a]pyridin-7-ylmethyl)-4-{1-[(2-methyl-2H-indazol-4-yl)carbonyl]piperidin-4-yl}benzamide | ESI(+)) m/e 493 (M + H)+ |
| 1117 | 4-{1-[(2-ethylpiperidin-1-yl)(oxo)acetyl]piperidin-4-yl}-N-(imidazo[1,2-a]pyridin-7-ylmethyl)benzamide | ESI(+)) m/e 502 (M + H)+ |
| 1118 | N-(imidazo[1,2-a]pyridin-7-ylmethyl)-4-{1-[(2-methyl-2H-indazol-6-yl)carbonyl]piperidin-4-yl}benzamide | ESI(+)) m/e 493 (M + H)+ |
| 1119 | N-(imidazo[1,2-a]pyridin-7-ylmethyl)-4-{1-[(1-methyl-1H-indazol-4-yl)carbonyl]piperidin-4-yl}benzamide | ESI(+)) m/e 493 (M + H)+ |
| 1120 | N-(imidazo[1,2-a]pyridin-7-ylmethyl)-4-(1-{[2-(trifluoromethyl)furan-3-yl]carbonyl}piperidin-4-yl)benzamide | ESI(+)) m/e 497 (M + H)+ |

Example 240

4-[(4-cyanobenzyl)(3-methoxypropanoyl)amino]-N-(imidazo[1,2-a]pyridin-6-ylmethyl)benzamide The title compound was prepared as described in Example 215, substituting 3-methoxypropanoyl chloride for 2-cyclopentylacetyl chloride in Example 215B. $^1$H NMR (400 MHz, DMSO-d$_6$) δ ppm 9.08 (t, J=5.8 Hz, 1H), 8.46 (dd, J=1.9, 0.9 Hz, 1H), 7.94 (dd, J=1.2, 0.6 Hz, 1H), 7.91-7.85 (m, 2H), 7.79-7.73 (m, 2H), 7.56-7.49 (m, 2H), 7.43-7.39 (m, 2H), 7.38-7.33 (m, 2H), 7.20 (dd, J=9.2, 1.7 Hz, 1H), 5.00 (bs, 2H), 4.45 (d, J=5.8 Hz, 2H), 3.54 (t, J=6.2 Hz, 2H), 3.17 (s, 3H), 2.43-2.35 (m, 2H); MS (ESI(+)) m/e 468 (M+H)+.

Example 241

5-(1-acetyl-1,2,3,6-tetrahydropyridin-4-yl)-N-(imidazo[1,2-a]pyridin-7-ylmethyl)thiophene-2-carboxamide

Example 241A 5-bromo-N-(imidazo[1,2-a]pyridin-7-ylmethyl)thiophene-2-carboxamide A solution of 5-bromothiophene-2-carboxylic acid (1.279 g, 6.18 mmol), imidazo[1,2-a]pyridin-7-ylmethanamine (1 g, 6.79 mmol), 1-hydroxybenzotriazole hydrate (1.041 g, 6.79 mmol) and N-methylmorpholine (1.698 ml, 15.44 mmol) in dimethylformamide (20 ml) at room temperature was treated with 1-(3-dimethylaminopropyl)-3-ethylcarbodiimide hydrochloride (2.131 g, 11.12 mmol). The mixture was stirred overnight and poured into a gently stirred round-bottom flask containing water (100 ml) and ethyl acetate (30 ml). The resulting bilayer suspension was stirred for several minutes, filtered and washed with water then minimal ethyl acetate to give the title compound after drying.

Example 241B tert-butyl 4-(5-(imidazo[1,2-a]pyridin-7-ylmethylcarbamoyl)thiophen-2-yl)-5,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline.

Example 241C

N-(imidazo[1,2-a]pyridin-7-ylmethyl)-5-(1,2,3,6-tetrahydropyridin-4-yl)thiophene-2-carboxamide The title compound was prepared as described in Example 28A, substituting tert-butyl 4-(5-(imidazo[1,2-a]pyridin-7-ylmethylcarbamoyl)thiophen-2-yl)-5,6-dihydropyridine-1(2H)-carboxylate for tert-butyl 4-(4-(3-imidazo[1,2-a]pyridin-6-ylureido)phenyl)-5,6-dihydropyridine-1(2H)-carboxylate.

Example 241D 5-(1-acetyl-1,2,3,6-tetrahydropyridin-4-yl)-N-(imidazo[1,2-a]pyridin-7-ylmethyl)thiophene-2-carboxamide The title compound was prepared as described in Example 52A, substituting acetyl chloride for 2-cyclopentylacetyl chloride and N-(imidazo[1,2-a]pyridin-7-ylmethyl)-5-(1,2,3,6-tetrahydropyridin-4-yl)thiophene-2-carboxamide for methyl 4-aminobenzoate. $^1$H NMR (400 MHz, DMSO-$d_6$) δ ppm 9.13-9.06 (m, 1H), 8.48 (d, J=7.0 Hz, 1H), 7.88 (s, 1H), 7.72 (d, J=3.9 Hz, 1H), 7.51 (d, J=1.2 Hz, 1H), 7.38 (s, 1H), 7.15 (t, J=4.2 Hz, 1H), 6.83 (dd, J=7.0, 1.6 Hz, 1H), 6.28-6.21 (m, 1H), 4.46 (d, J=5.9 Hz, 2H), 4.15-4.04 (m, 2H), 3.61 (dt, J=11.3, 5.6 Hz, 2H), 2.63-2.35 (m, 2H), 2.07-1.99 (m, 3H); MS (ESI)(+)) m/e 381 (M+H)$^+$.

Example 242

N-(imidazo[1,2-a]pyridin-7-ylmethyl)-5-[1-(methylsulfonyl)-1,2,3,6-tetrahydropyridin-4-yl]thiophene-2-carboxamide The title compound was prepared as described in Example 52A, substituting methanesulfonyl chloride for 2-cyclopentylacetyl chloride and N-(imidazo[1,2-a]pyridin-7-ylmethyl)-5-(1,2,3,6-tetrahydropyridin-4-yl)thiophene-2-carboxamide for methyl 4-aminobenzoate. $^1$H NMR (400 MHz, DMSO-$d_6$) δ ppm 9.15-9.07 (m, 1H), 8.48 (d, J=7.0 Hz, 1H), 7.88 (s, 1H), 7.73 (d, J=3.9 Hz, 1H), 7.51 (s, 1H), 7.38 (bs, 1H), 7.17 (d, J=3.9 Hz, 1H), 6.83 (d, J=7.0 Hz, 1H), 6.28 (bs, 1H), 4.49-4.43 (m, 2H), 3.88-3.82 (m, 2H), 3.29-3.07 (m, 2H), 2.93 (s, 3H), 2.65-2.41 (m, 2H); MS (ESI)(+)) m/e 417 (M+H)$^+$.

Example 246

5-[1-(cyclopropylsulfonyl)-1,2,3,6-tetrahydropyridin-4-yl]-N-(imidazo[1,2-a]pyridin-7-ylmethyl)thiophene-2-carboxamide The title compound was prepared as described in Example 52A, substituting cyclopropyl sulfonyl chloride for 2-cyclopentylacetyl chloride and N-(imidazo[1,2-a]pyridin-7-ylmethyl)-5-(1,2,3,6-tetrahydropyridin-4-yl)thiophene-2-carboxamide for methyl 4-aminobenzoate. $^1$H NMR (400 MHz, DMSO-$d_6$) δ ppm 9.10 (t, J=6.0 Hz, 1H), 8.48 (d, J=7.0 Hz, 1H), 7.88 (s, 1H), 7.73 (d, J=3.9 Hz, 1H), 7.51 (d, J=1.2 Hz, 1H), 7.38 (s, 1H), 7.17 (d, J=3.9 Hz, 1H), 6.83 (dd, J=7.0, 1.6 Hz, 1H), 6.28 (bs, 1H), 4.46 (d, J=5.9 Hz, 2H), 3.95-3.89 (m, 2H), 3.43 (t, J=5.7 Hz, 2H), 2.73-2.56 (m, 3H), 1.26-0.89 (m, 4H); MS (ESI)(+)) m/e 443 (M+H)$^+$.

Example 250

N-(imidazo[1,2-a]pyridin-7-ylmethyl)-5-[(4R)-2-oxo-4-(propan-2-yl)-1,3-oxazolidin-3-yl]thiophene-2-carboxamide A solution of 5-bromo-N-(imidazo[1,2-a]pyridin-7-ylmethyl)thiophene-2-carboxamide (84 mg, 0.25 mmol), (R)-4-isopropyloxazolidin-2-one (32 mg, 0.25 mmol), N,N-dimethylethane-1,2-diamine (2 mg, 0.025 mmol), copper(I) iodide (5 mg, 0.025 mmol) and potassium carbonate (121 mg, 0.88 mmol) in dioxane (1 ml) was stirred at 110° C. overnight. Concentration and reverse phase chromatography provided the title compound. $^1$H NMR (400 MHz, methanol-$d_4$) δ ppm 9.13 (t, J=5.3 Hz, 1H), 8.74 (d, J=5.5 Hz, 1H), 8.17 (s, 1H), 7.99 (s, 1H), 7.79 (s, 1H), 7.62 (d, J=4.1 Hz, 1H), 7.47 (d, J=7.0 Hz, 1H), 6.77 (d, J=4.2 Hz, 1H), 4.72 (s, 2H), 4.61-4.42 (m, 3H), 2.46 (ddd, J=10.2, 6.9, 3.5 Hz, 1H), 1.00 (d, J=7.0 Hz, 3H), 0.85 (d, J=6.8 Hz, 3H); (APCI(+)) m/e 385 (M+H)$^+$.

Example 257

N-(imidazo[1,2-a]pyridin-7-ylmethyl)-5-[1-(methoxyacetyl)piperidin-4-yl]thiophene-2-carboxamide

Example 257A tert-butyl 4-(5-(imidazo[1,2-a]pyridin-7-ylmethylcarbamoyl)thiophen-2-yl)piperidine-1-carboxylate The title compound was prepared as described in Example 1B, substituting tert-butyl 4-(5-(imidazo[1,2-a]pyridin-7-ylmethylcarbamoyl)thiophen-2-yl)-5,6-dihydropyridine-1(2H)-carboxylate for N-isopentyl-4-nitrobenzamide.

Example 257B

N-(imidazo[1,2-a]pyridin-7-ylmethyl)-5-(piperidin-4-yl)thiophene-2-carboxamide

The title compound was prepared as described in Example 28A, substituting tert-butyl 4-(5-(imidazo[1,2-a]pyridin-7-ylmethylcarbamoyl)thiophen-2-yl)piperidine-1-carboxylate for tert-butyl 4-(4-(3-imidazo[1,2-a]pyridin-6-ylureido)phenyl)-5,6-dihydropyridine-1(2H)-carboxylate.

Example 257C

N-(imidazo[1,2-a]pyridin-7-ylmethyl)-5-[1-(methoxyacetyl)piperidin-4-yl]thiophene-2-carboxamide The title compound was prepared as described in Example 1A, substituting N-(imidazo[1,2-a]pyridin-7-ylmethyl)-5-(piperidin-4-yl)thiophene-2-carboxamide for 3-methylbutan-1-amine and methoxyacetic acid for 4-nitrobenzoic acid. $^1$H NMR (400 MHz, methanol-$d_4$) δ ppm 8.39 (d, J=7.0 Hz, 1H), 7.79 (s, 1H), 7.60 (d, J=3.8 Hz, 1H), 7.53 (d, J=1.3 Hz, 1H), 7.44 (s, 1H), 6.96 (d, J=3.8 Hz, 1H), 6.92 (dd, J=7.1, 1.2 Hz, 1H), 4.58 (bs, 2H), 3.85-3.76 (m, 2H), 3.03 (tt, J=11.8, 3.8 Hz, 1H), 2.97-2.82 (m, 5H), 2.18-2.09 (m, 2H), 1.96 (s, 1H), 1.86-1.71 (m, 2H); MS (ESI(+)) m/e 413 (M+H)$^+$.

TABLE 14

The following Examples were prepared essentially as described in Example 257, substituting the appropriate carboxylic acid in Example 257C.

| Ex | Name | MS |
| --- | --- | --- |
| 258 | 5-(1-acetylpiperidin-4-yl)-N-(imidazo[1,2-a]pyridin-7-ylmethyl)thiophene-2-carboxamide | (ESI(+)) m/e 383 (M + H)$^+$ |

TABLE 14-continued

The following Examples were prepared essentially as described in Example 257, substituting the appropriate carboxylic acid in Example 257C.

| Ex | Name | MS |
|---|---|---|
| 259 | N-(imidazo[1,2-a]pyridin-7-ylmethyl)-5-[1-(2-methylpropanoyl)piperidin-4-yl]thiophene-2-carboxamide | (ESI(+)) m/e 411 (M + H)+ |
| 260 | 5-[1-(cyclopropylcarbonyl)piperidin-4-yl]-N-(imidazo[1,2-a]pyridin-7-ylmethyl)thiophene-2-carboxamide | (ESI(+)) m/e 409 (M + H)+ |
| 261 | N-(imidazo[1,2-a]pyridin-7-ylmethyl)-5-[1-(tetrahydrofuran-3-ylcarbonyl)piperidin-4-yl]thiophene-2-carboxamide | (ESI(+)) m/e 439 (M + H)+ |
| 262 | N-(imidazo[1,2-a]pyridin-7-ylmethyl)-5-[1-(tetrahydro-2H-pyran-4-ylacetyl)piperidin-4-yl]thiophene-2-carboxamide | (ESI(+)) m/e 467 (M + H)+ |
| 263 | N-(imidazo[1,2-a]pyridin-7-ylmethyl)-5-[1-(3-methylbutanoyl)piperidin-4-yl]thiophene-2-carboxamide | (ESI(+)) m/e 425 (M + H)+ |
| 264 | N-(imidazo[1,2-a]pyridin-7-ylmethyl)-5-[1-(1,2-oxazol-5-ylcarbonyl)piperidin-4-yl]thiophene-2-carboxamide | (ESI(+)) m/e 436 (M + H)+ |
| 879 | N-(imidazo[1,2-a]pyridin-7-ylmethyl)-5-{1-[2-methyl-2-(piperazin-1-yl)propanoyl]piperidin-4-yl}thiophene-2-carboxamide | (ESI(+)) m/e 495 (M + H)+ |
| 887 | 5-[1-(2,5-difluorobenzoyl)piperidin-4-yl]-N-(imidazo[1,2-a]pyridin-7-ylmethyl)thiophene-2-carboxamide | (ESI(+)) m/e 481 (M + H)+ |
| 888 | 5-[1-(2,4-difluorobenzoyl)piperidin-4-yl]-N-(imidazo[1,2-a]pyridin-7-ylmethyl)thiophene-2-carboxamide | (ESI(+)) m/e 481 (M + H)+ |

Example 266

5-[5-(hydroxymethyl)-2-oxo-1,3-oxazolidin-3-yl]-N-(imidazo[1,2-a]pyridin-7-ylmethyl)thiophene-2-carboxamide The title compound was prepared as described in Example 250, substituting 5-(hydroxymethyl)oxazolidin-2-one for (R)-4-isopropyloxazolidin-2-one. $^1$H NMR (400 MHz, methanol-d$_4$) δ ppm 9.10 (s, 1H), 8.74 (d, J=7.0 Hz, 1H), 8.17 (d, J=2.0 Hz, 1H), 7.98 (d, J=2.1 Hz, 1H), 7.78 (s, 1H), 7.60 (d, J=4.2 Hz, 1H), 7.52-7.41 (m, 1H), 6.60 (d, J=4.2 Hz, 1H), 4.84 (s, 1H), 4.71 (d, J=4.2 Hz, 2H), 4.16 (t, J=9.1 Hz, 1H), 3.98 (dd, J=8.9, 6.2 Hz, 1H), 3.88 (dd, J=12.7, 3.0 Hz, 1H), 3.69 (dd, J=12.7, 3.6 Hz, 1H); (APCI(+)) m/e 373 (M+H)+.

Example 267

5-[(4R)-4-hydroxy-2-oxopyrrolidin-1-yl]-N-(imidazo[1,2-a]pyridin-7-ylmethyl)thiophene-2-carboxamide The title compound was prepared as described in Example 250, substituting (R)-5-hydroxyoxazolidin-2-one for (R)-4-isopropyloxazolidin-2-one. $^1$H NMR (400 MHz, methanol-d$_4$) δ ppm 9.10 (t, J=6.1 Hz, 1H), 8.73 (d, J=6.9 Hz, 1H), 8.16 (d, J=1.8 Hz, 1H), 7.98 (d, J=2.0 Hz, 1H), 7.78 (s, 1H), 7.61 (d, J=4.2 Hz, 1H), 7.46 (d, J=7.7 Hz, 1H), 6.68 (d, J=4.2 Hz, 1H), 4.71 (s, 2H), 4.62 (t, J=5.7 Hz, 1H), 4.15 (dd, J=10.9, 5.3 Hz, 1H), 3.83 (d, J=10.9 Hz, 1H), 2.97 (dd, J=17.7, 6.2 Hz, 1H), 2.50 (d, J=18.2 Hz, 1H); (APCI(+)) m/e 357 (M+H)+.

Example 268

5-[(4S)-4-hydroxy-2-oxopyrrolidin-1-yl]-N-(imidazo[1,2-a]pyridin-7-ylmethyl)thiophene-2-carboxamide The title compound was prepared as described in Example 250, substituting (S)-5-hydroxyoxazolidin-2-one for (R)-4-isopropyloxazolidin-2-one. $^1$H NMR (400 MHz, methanol-d$_4$) δ ppm 9.10 (t, J=5.7 Hz, 1H), 8.74 (d, J=7.0 Hz, 1H), 8.17 (d, J=2.0 Hz, 1H), 7.98 (d, J=2.1 Hz, 1H), 7.78 (s, 1H), 7.61 (d, J=4.2 Hz, 1H), 7.46 (d, J=7.0 Hz, 1H), 6.68 (d, J=4.2 Hz, 1H), 4.71 (s, 2H), 4.62 (t, J=5.7 Hz, 1H), 4.15 (dd, J=10.9, 5.3 Hz, 1H), 3.83 (d, J=11.0 Hz, 1H), 2.97 (dd, J=17.6, 6.2 Hz, 1H), 2.50 (d, J=16.8 Hz, 1H); (APCI(+)) m/e 357 (M+H)+.

Example 271

N-(imidazo[1,2-a]pyridin-7-ylmethyl)-5-[1-(methylsulfonyl)piperidin-4-yl]thiophene-2-carboxamide The title compound was prepared as described in Example 52A, substituting methanesulfonyl chloride for 2-cyclopentylacetyl chloride and N-(imidazo[1,2-a]pyridin-7-ylmethyl)-5-(piperidin-4-yl)thiophene-2-carboxamide for methyl 4-aminobenzoate. $^1$H NMR (400 MHz, methanol-d$_4$) δ ppm 8.39 (d, J=7.0 Hz, 1H), 7.79 (s, 1H), 7.60 (d, J=3.8 Hz, 1H), 7.53 (d, J=1.3 Hz, 1H), 7.44 (s, 1H), 6.96 (d, J=3.8 Hz, 1H), 6.92 (dd, J=7.1, 1.2 Hz, 1H), 4.58 (bs, 2H), 3.85-3.76 (m, 2H), 3.03 (tt, J=11.8, 3.8 Hz, 1H), 2.97-2.82 (m, 5H), 2.18-2.09 (m, 2H), 1.96 (s, 1H), 1.86-1.71 (m, 2H); MS (ESI(+)) m/e 419 (M+H)+.

Example 274

N-(4-{[(imidazo[1,2-a]pyridin-6-ylmethyl)carbamoyl]amino}phenyl)-4-methylpentanamide Example 274A tert-butyl 4-(3-(imidazo[1,2-a]pyridin-6-ylmethyl)ureido)phenylcarbamate The title compound was prepared as described in Example 1C, substituting tert-butyl 4-aminophenylcarbamate for 4-amino-N-isopentylbenzamide and imidazo[1,2-a]pyridin-6-ylmethanamine for imidazo[1,2-a]pyridin-6-amine

Example 274B 1-(4-aminophenyl)-3-(imidazo[1,2-a]pyridin-6-ylmethyl)urea

The title compound was prepared as described in Example 28A, substituting tert-butyl 4-(3-(imidazo[1,2-a]pyridin-6-ylmethyl)ureido)phenylcarbamate for tert-butyl 4-(4-(3-imidazo[1,2-a]pyridin-6-ylureido)phenyl)-5,6-dihydropyridine-1(2H)-carboxylate.

Example 274C

N-(4-{[(imidazo[1,2-a]pyridin-6-ylmethyl)carbamoyl]amino}phenyl)-4-methylpentanamide The title compound was prepared as described in Example 1A, substituting 1-(4-aminophenyl)-3-(imidazo[1,2-a]pyridin-6-ylmethyl)urea for 3-methylbutan-1-amine and 4-methylpentanoic acid for 4-nitrobenzoic acid. $^1$H NMR (400 MHz, DMSO-$d_6$) δ ppm 9.70 (s, 1H), 8.50 (s, 1H), 8.43 (s, 1H), 7.94 (s, 1H), 7.53 (m, 2H), 7.43 (m, 2H), 7.30 (m, 2H), 7.21 (dd, J=9.2, 1.7 Hz, 1H), 6.61 (t, J=5.9 Hz, 1H), 4.28 (d, J=5.8 Hz, 2H), 2.26 (t, J=7.6 Hz, 2H), 1.60-1.40 (m, 3H), 0.89 (d, J=6.4 Hz, 6H); MS (ESI(+)) m/e 380 (M+H)$^+$.

TABLE 15

The following Examples were prepared essentially as described in Example 274, substituting the appropriate carboxylic acid in Example 274C.

| Ex | Name | $^1$H NMR | MS |
|---|---|---|---|
| 275 | 3-cyclopentyl-N-(4-{[(imidazo[1,2-a]pyridin-6-ylmethyl)carbamoyl]amino}phenyl)propanamide | $^1$H NMR (400 MHz, DMSO-$d_6$) δ ppm 9.69 (s, 1H), 8.48 (s, 1H), 8.43 (s, 1H), 7.94 (s, 1H), 7.53 (m, 2H), 7.43 (m, 2H), 7.30 (m, 2H), 7.20 (dd, J = 9.2, 1.7 Hz, 1H), 6.60 (t, J = 5.9 Hz, 1H), 4.28 (d, J = 5.8 Hz, 2H), 2.26 (t, J = 7.6 Hz, 2H), 1.75 (m, 3H), 1.66 – 1.39 (m, 6H), 1.08 (m, 2H) | (ESI(+)) m/e 406 (M + H)$^+$ |
| 276 | N-(4-{[(imidazo[1,2-a]pyridin-6-ylmethyl)carbamoyl]amino}phenyl)-2-(propan-2-yloxy)acetamide | $^1$H NMR (500 MHz, DMSO-$d_6$) δ ppm 9.36 (s, 1H), 8.53 (s, 1H), 8.43 (s, 1H), 7.94 (s, 1H), 7.53 (m, 2H), 7.49 (m, 2H), 7.33 (m, 2H), 7.21 (dd, J = 9.2, 1.7 Hz, 1H), 6.62 (t, J = 5.9 Hz, 1H), 4.28 (d, J = 5.9 Hz, 2H), 3.97 (s, 2H), 3.67 (m, 1H), 1.16 (d, J = 6.1 Hz, 6H) | (ESI(+)) m/e 382 (M + H)$^+$ |
| 277 | N-(4-{[(imidazo[1,2-a]pyridin-6-ylmethyl)carbamoyl]amino}phenyl)-2-(tetrahydrofuran-2-yl)acetamide | $^1$H NMR (400 MHz, DMSO-$d_6$) δ ppm 9.74 (s, 1H), 8.50 (s, 1H), 8.44 (d, J = 1.5 Hz, 1H), 7.96 (s, 1H), 7.54 (m, 2H), 7.44 (m, 2H), 7.31 (m, 2H), 7.22 (dd, J = 9.2, 1.7 Hz, 1H), 6.61 (t, J = 5.9 Hz, 1H), 4.28 (d, J = 5.9 Hz, 2H), 4.12 (m, 1H), 3.74 (m, 1H), 3.60 (m, 1H), 2.47 (m, 1H), 2.39 (m, 1H), 1.98 (m, 1H), 1.81 (m, 2H), 1.49 (m, 1H) | (ESI(+)) m/e 394 (M + H)$^+$ |
| 278 | N-(4-{[(imidazo[1,2-a]pyridin-6-ylmethyl)carbamoyl]amino}phenyl)-2-(tetrahydro-2H-pyran-4-yl)acetamide | $^1$H NMR (500 MHz, DMSO-$d_6$) δ ppm 9.72 (s, 1H), 8.50 (s, 1H), 8.43 (s, 1H), 7.94 (s, 1H), 7.53 (m, 2H), 7.43 (m, 2H), 7.31 (m, 2H), 7.21 (dd, J = 9.2, 1.7 Hz, 1H), 6.60 (t, J = 5.9 Hz, 1H), 4.28 (d, J = 5.9 Hz, 2H), 3.82 (m, 2H), 3.29 (m, 2H), 2.20 (d, J = 7.1 Hz, 2H), 2.01 (m, 1H), 1.57 (m, 2H), 1.25 (m, 2H) | (ESI(+)) m/e 408 (M + H)$^+$ |
| 279 | N-(4-{[(imidazo[1,2-a]pyridin-6-ylmethyl)carbamoyl]amino}phenyl)-3-phenylpropanamide | $^1$H NMR (400 MHz, DMSO-$d_6$) δ ppm 9.73 s, 1H), 8.49 (s, 1H), 8.42 (s, 1H), 7.94 (s, 1H), 7.53 (m, 2H), 7.42 (m, 2H), 7.35 – 7.15 (m, 8H), 6.60 (t, J = 5.9 Hz, 1H), 4.28 (d, J = 5.8 Hz, 2H), 2.89 (t, J = 7.3 Hz, 2H), 2.57 (t, J = 5.7 Hz, 2H) | (ESI(+)) m/e 414 (M + H)$^+$ |
| 280 | N-(4-{[(imidazo[1,2-a]pyridin-7-ylmethyl)carbamoyl]amino}phenyl)-4-methylpentanamide | $^1$H NMR (400 MHz, DMSO-$d_6$) δ ppm 9.69 (s, 1H), 8.52 (s, 1H), 8.47 (d, J = 7.0 Hz, 1H), 7.87 (s, 1H), 7.50 (bs, 1H), 7.42 (m, 2H), 7.37 (s, 1H), 7.30 (m, 2H), 6.82 (dd, J = 7.0, 1.5 Hz, 1H), 6.63 (t, J = 6.0 Hz, 1H), 4.31 (d, J = 5.9 Hz, 2H), 2.25 (t, J = 7.6 Hz, 2H), 1.60 – 1.41 (m, 3H), 0.88 (d, J = 6.4 Hz, 6H) | (ESI(+)) m/e 380 (M + H)$^+$ |
| 281 | 3-cyclopentyl-N-(4-{[(imidazo[1,2-a]pyridin-7-ylmethyl)carbamoyl]amino}phenyl)propanamide | $^1$H NMR (400 MHz, DMSO-$d_6$) δ ppm 9.69 (s, 1H), 8.53 (s, 1H), 8.48 (d, J = 6.9 Hz, 1H), 7.88 (bs, 1H), 7.52 (bs, 1H), 7.44 (m, 2H), 7.37 (s, 1H), 7.31 (m, 2H), 6.83 (dd, J = 6.9, 1.4 Hz, 1H), 6.64 (t, J = 6.0 Hz, 1H), 4.32 (d, J = 5.9 Hz, 2H), 2.27 (t, J = 7.6 Hz, 2H), 1.74 (m, 3H), 1.65 – 1.40 (m, 6H), 1.09 (m, 2H) | (ESI(+)) m/e 406 (M + H)$^+$ |
| 282 | N-(4-{[(imidazo[1,2-a]pyridin-7-ylmethyl)carbamoyl]amino}phenyl)-2-(propan-2-yloxy)acetamide | $^1$H NMR (400 MHz, DMSO-$d_6$) δ ppm 9.37 (s, 1H), 8.59 (s, 1H), 8.49 (m, 1H), 7.89 (s, 1H), 7.50 (m, 3H), 7.39 (s, 1H), 7.34 (m, 2H), 6.84 (dd, J = 6.9, 1.6 Hz, 1H), 6.68 (t, | (ESI(+)) m/e 382 (M + H)$^+$ |

TABLE 15-continued

The following Examples were prepared essentially as described in Example 274, substituting the appropriate carboxylic acid in Example 274C.

| Ex | Name | ¹H NMR | MS |
|---|---|---|---|
| | | J = 6.0 Hz, 1H), 4.33 (d, J = 6.0 Hz, 2H), 3.98 (s, 2H), 3.67 (m, 1H), 1.16 (d, J = 6.1 Hz, 6H) | |
| 283 | N-(4-{[(imidazo[1,2-a]pyridin-7-ylmethyl)carbamoyl]amino}phenyl)-2-(tetrahydrofuran-2-yl)acetamide | ¹H NMR (400 MHz, DMSO-$d_6$) δ ppm 9.73 (s, 1H), 8.54 (s, 1H), 8.48 (d, J = 7.0 Hz, 1H), 7.88 (s, 1H), 7.51 (s, 1H), 7.44 (m, 2H), 7.38 (bs, 1H), 7.32 (m, 2H), 6.83 (dd, J = 6.9, 1.6 Hz, 1H), 6.65 (t, J = 6.0 Hz, 1H), 4.32 (d, J = 5.9 Hz, 2H), 4.16 (m, 1H), 3.76 (m, 1H), 3.60 (m, 1H), 2.50 (m, 1H), 2.39 (m, 1H), 1.99 (m, 1H), 1.83 (m, 2H), 1.53 (m, 1H) | (ESI(+)) m/e 394 (M + H)⁺ |
| 284 | N-(4-{[(imidazo[1,2-a]pyridin-7-ylmethyl)carbamoyl]amino}phenyl)-2-(tetrahydro-2H-pyran-4-yl)acetamide | ¹H NMR (400 MHz, DMSO-$d_6$) δ ppm 9.72 (s, 1H), 8.53 (s, 1H), 8.48 (d, J = 6.9 Hz, 1H), 7.88 (bs, 1H), 7.51 (bs, 1H), 7.44 (m, 2H), 7.38 (bs, 1H), 7.32 (m, 2H), 6.83 (m, 1H), 6.65 (m, 1H), 4.32 (m, 2H), 3.82 (m, 2H), 3.33 (m, 2H), 2.20 (d, J = 7.1 Hz, 2H), 1.97 (m, 1H), 1.58 (m, 2H), 1.23 (m, 2H) | (ESI(+)) m/e 408 (M + H)⁺ |
| 285 | N-(4-{[(imidazo[1,2-a]pyridin-7-ylmethyl)carbamoyl]amino}phenyl)-3-phenylpropanamide | ¹H NMR (400 MHz, DMSO-$d_6$) δ ppm 9.74 (s, 1H), 8.54 (s, 1H), 8.49 (d, J = 6.9 Hz, 1H), 7.89 (bs, 1H), 7.52 (bs, 1H), 7.42 (m, 3H), 7.35 – 7.22 (m, 6H), 7.17 (m, 1H), 6.84 (d, J = 7.6 Hz, 1H), 6.65 (t, J = 6.0 Hz, 1H), 4.32 (d, J = 5.9 Hz, 2H), 2.90 (t, J = 7.7 Hz, 2H), 2.58 (t, J = 7.7 Hz, 2H) | (ESI(+)) m/e 414 (M + H)⁺ |

Example 290 tert-butyl 4-(3-fluoro-4-{[(imidazo[1,2-a]pyridin-7-ylmethyl)carbamoyl]amino}phenyl)-3,6-dihydropyridine-1(2H)-carboxylate

Example 290A 1-(4-bromo-2-fluorophenyl)-3-(imidazo[1,2-a]pyridin-7-ylmethyl)urea The title compound was prepared as described in Example 1C, substituting 4-bromo-2-fluoroaniline for 4-amino-N-isopentylbenzamide and imidazo[1,2-a]pyridin-7-ylmethanamine for imidazo[1,2-a]pyridin-6-amine.

Example 290B tert-butyl 4-(3-fluoro-4-{[(imidazo[1,2-a]pyridin-7-ylmethyl)carbamoyl]amino}phenyl)-3,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 1-(4-bromo-2-fluorophenyl)-3-(imidazo[1,2-a]pyridin-7-ylmethyl)urea for 4-bromoaniline. ¹H NMR (300 MHz, DMSO-$d_6$) δ ppm 8.53-8.46 (m, 2H), 8.09 (t, J=8.7 Hz, 1H), 7.91-7.88 (m, 1H), 7.54-7.50 (m, 1H), 7.42-7.37 (m, 1H), 7.33-7.24 (m, 1H), 7.21-7.08 (m, 2H), 6.83 (dd, J=7.0, 1.7 Hz, 1H), 6.17-6.10 (m, 1H), 4.35 (d, J=5.8 Hz, 2H), 4.01-3.94 (m, 2H), 3.55-3.47 (m, 2H), 2.46-2.36 (m, 2H), 1.42 (s, 9H); MS (ESI(+)) m/e 466 (M+H)⁺.

Example 291 tert-butyl (3S)-3-(4-{[(imidazo[1,2-a]pyridin-7-ylmethyl)carbamoyl]amino}phenoxy)pyrrolidine-1-carboxylate

Example 291A (S)-tert-butyl 3-(4-nitrophenoxy)pyrrolidine-1-carboxylate (S)-Tert-butyl 3-hydroxypyrrolidine-1-carboxylate (10 g, 53.4 mmol) was dissolved in 1-fluoro-4-nitrobenzene (13.94 g, 99 mmol). An aqueous solution of 5.9N potassium hydroxide (77 ml, 452 mmol) was added followed by addition of tetrabutylammonium bromide (2.238 g, 6.94 mmol). The reaction mixture was stirred at 40° C. for 24 hours and then cooled, diluted with water and extracted with ethyl acetate. The combined organic layers were dried with sodium sulfate, filtered and concentrated to give the title compound.

Example 291B (S)-tert-butyl 3-(4-aminophenoxy)pyrrolidine-1-carboxylate

The title compound was prepared as described in Example 1B, substituting (S)-tert-butyl 3-(4-nitrophenoxy)pyrrolidine-1-carboxylate for N-isopentyl-4-nitrobenzamide.

Example 291C tert-butyl (3S)-3-(4-{[(imidazo[1,2-a]pyridin-7-ylmethyl)carbamoyl]amino}phenoxy)pyrrolidine-1-carboxylate The title compound was prepared as described in Example 1C, substituting (S)-tert-butyl 3-(4-aminophenoxy)pyrrolidine-1-carboxylate for 4-amino-N-isopentylbenzamide and imidazo[1,2-a]pyridin-7-ylmethanamine for imidazo[1,2-a]pyridin-6-amine. $^1$H NMR (300 MHz, DMSO-d$_6$) δ ppm 8.51-8.44 (m, 2H), 7.88-7.86 (m, 1H), 7.53-7.49 (m, 1H), 7.40-7.27 (m, 3H), 6.86-6.80 (m, 3H), 6.63 (t, J=6.0 Hz, 1H), 4.93-4.84 (m, 1H), 4.32 (d, J=6.0 Hz, 2H), 3.55-3.28 (m, 4H), 2.16-1.94 (m, 2H), 1.42-1.36 (m, 9H); MS (ESI(+)) m/e 452 (M+H)$^+$.

Example 292 tert-butyl {2-fluoro-4-[(imidazo[1,2-a]pyridin-7-ylmethyl)carbamoyl]phenyl}carbamate The title compound was prepared as described in Example 1A, substituting imidazo[1,2-a]pyridin-7-ylmethanamine for 3-methylbutan-1-amine and 4-(tert-butoxycarbonylamino)-3-fluorobenzoic acid for 4-nitrobenzoic acid. $^1$H NMR (300 MHz, DMSO-d$_6$) δ ppm 9.26 (s, 1H), 9.08 (t, J=5.9 Hz, 1H), 8.48 (dd, J=6.9, 0.9 Hz, 1H), 7.91-7.78 (m, 2H), 7.76-7.68 (m, 2H), 7.52 (d, J=1.2 Hz, 1H), 7.39 (bs, 1H), 6.85 (dd, J=7.0, 1.7 Hz, 1H), 4.49 (d, J=5.8 Hz, 2H), 1.48 (s, 9H); MS (ESI(+)) m/e 385 (M+H)$^+$.

Example 297

2-(1-benzoyl-1,2,3,6-tetrahydropyridin-4-yl)-N-(imidazo[1,2-a]pyridin-7-ylmethyl)-1,3-thiazole-5-carboxamide Example 297A tert-butyl 4-(5-(imidazo[1,2-a]pyridin-7-ylmethylcarbamoyl)thiazol-2-yl)-5,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 2-bromo-N-(imidazo[1,2-a]pyridin-7-ylmethyl)thiazole-5-carboxamide for 4-bromoaniline.

Example 297B

N-(imidazo[1,2-a]pyridin-7-ylmethyl)-2-(1,2,3,6-tetrahydropyridin-4-yl)thiazole-5-carboxamide The title compound was prepared as described in Example 28A, substituting tert-butyl 4-(5-(imidazo[1,2-a]pyridin-7-ylmethylcarbamoyl)thiazol-2-yl)-5,6-dihydropyridine-1(2H)-carboxylate for tert-butyl 4-(4-(3-imidazo[1,2-a]pyridin-6-ylureido)phenyl)-5,6-dihydropyridine-1(2H)-carboxylate.

Example 297C 2-(1-benzoyl-1,2,3,6-tetrahydropyridin-4-yl)-N-(imidazo[1,2-a]pyridin-7-ylmethyl)-1,3-thiazole-5-carboxamide The title compound was prepared as described in Example 1A, substituting N-(imidazo[1,2-a]pyridin-7-ylmethyl)-2-(1,2,3,6-tetrahydropyridin-4-yl)thiazole-5-carboxamide for 3-methylbutan-1-amine and benzoic acid for 4-nitrobenzoic acid. $^1$H NMR (300 MHz, DMSO-d$_6$) ppm 9.27 (t, J=5.9 Hz, 1H), 8.50 (d, J=7.1 Hz, 1H), 8.41 (s, 1H), 7.89 (s, 1H), 7.38-7.56 (m, 7H), 6.85 (dd, J=6.8, 1.7 Hz, 1H), 6.56-6.89 (m, 1H), 4.49 (d, J=5.8 Hz, 2H), 4.08-4.40 (m, 2H), 3.74-3.92 (m, 1H), 3.44-3.66 (m, 1H), 2.66 (s, 2H); MS (ESI(+)) m/e 444 (M+H)$^+$.

Example 298

4-[1-(2-hydroxy-2-methylpropyl)-1H-pyrazol-4-yl]-N-(imidazo[1,2-a]pyridin-7-ylmethyl)benzamide Example 298A 4-bromo-N-(imidazo[1,2-a]pyridin-7-ylmethyl)benzamide The title compound was prepared as described in Example 1A, substituting imidazo[1,2-a]pyridin-7-ylmethanamine for 3-methylbutan-1-amine and 4-bromobenzoic acid for 4-nitrobenzoic acid.

Example 298B

4-[1-(2-hydroxy-2-methylpropyl)-1H-pyrazol-4-yl]-N-(imidazo[1,2-a]pyridin-7-ylmethyl)benzamide The title compound was prepared as described in Example 51A, substituting 1-(2-hydroxy-2-methylpropyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 4-bromo-N-(imidazo[1,2-a]pyridin-7-ylmethyl)benzamide for 4-bromoaniline. $^1$H NMR (300 MHz, DMSO-d$_6$) δ ppm 9.05 (t, J=5.9 Hz, 1H), 8.49 (dd, J=6.9, 0.9 Hz, 1H), 8.19 (d, J=0.8 Hz, 1H), 7.97 (d, J=0.7 Hz, 1H), 7.95-7.86 (m, 3H), 7.73-7.66 (m, 2H), 7.52 (d, J=1.2 Hz, 1H), 7.42-7.37 (m, 1H), 6.87 (dd, J=7.0, 1.7 Hz, 1H), 4.73 (s, 1H), 4.51 (d, J=5.8 Hz, 2H), 4.04 (s, 2H), 1.10 (s, 6H); MS (ESI(+)) m/e 390 (M+H)$^+$.

Example 299

N-(imidazo[1,2-a]pyridin-7-ylmethyl)-5-phenylthiophene-2-carboxamide

The title compound was prepared as described in Example 51A, substituting 4,4,5,5-tetramethyl-2-phenyl-1,3,2-dioxaborolane for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline. $^1$H NMR (300 MHz, DMSO-d$_6$) δ ppm 9.14 (t, J=6.0 Hz, 1H), 8.50 (dd, J=7.1, 0.7 Hz, 1H), 7.91-7.88 (m, 1H), 7.84 (d, J=3.9 Hz, 1H), 7.72 (dt, J=8.3, 2.4 Hz, 2H), 7.57 (d, J=3.9 Hz, 1H), 7.53 (d, J=1.2 Hz, 1H), 7.49-7.33 (m, 4H), 6.86 (dd, J=7.0, 1.7 Hz, 1H), 4.50 (d, J=5.8 Hz, 2H); MS (ESI(+)) m/e 334 (M+H).

Example 301 tert-butyl 3-{4-[(imidazo[1,2-a]pyridin-7-ylmethyl)carbamoyl]phenyl}pyrrolidine-1-carboxylate The title compound was prepared as described in Example 1A, substituting imidazo[1,2-a]pyridin-7-ylmethanamine for 3-methylbutan-1-amine and 4-(1-(tert-butoxycarbonyl)pyrrolidin-3-yl)benzoic acid for 4-nitrobenzoic acid. $^1$H NMR (400 MHz, DMSO-d$_6$) δ ppm 9.06 (t, J=5.9 Hz, 1H), 8.48 (dd, J=6.9, 0.9 Hz, 1H), 7.87 (m, 3H), 7.52 (d, J=1.2 Hz, 1H), 7.40 (m, 3H), 6.85 (dd, J=7.0, 1.7 Hz, 1H), 4.50 (d, J=5.9 Hz, 2H), 3.72 (dd, J=10.3, 7.5 Hz, 1H), 3.47 (m, 2H), 3.20 (m, 2H), 2.21 (m, 1H), 1.97 (m, 1H), 1.41 (m, 9H); (ESI(+)) m/e 421 (M+H)+.

Example 302 tert-butyl 3-(4-{[(imidazo[1,2-a]pyridin-7-ylmethyl)carbamoyl]amino}phenyl)pyrrolidine-1-carboxylate The title compound was prepared as described in Example 1C, substituting tert-butyl 3-(4-aminophenyl)pyrrolidine-1-carboxylate for 4-amino-N-isopentylbenzamide and imidazo[1,2-a]pyridin-7-ylmethanamine for imidazo[1,2-a]pyridin-6-amine. $^1$H NMR (400 MHz, DMSO-$d_6$) δ ppm 8.61 (s, 1H), 8.48 (dd, J=6.9, 0.9 Hz, 1H), 7.88 (d, J=1.1 Hz, 1H), 7.51 (d, J=1.2 Hz, 1H), 7.36 (m, 3H), 7.14 (m, 2H), 6.83 (dd, J=7.0, 1.7 Hz, 1H), 6.69 (t, J=6.0 Hz, 1H), 4.33 (d, J=6.0 Hz, 2H), 3.65 (dd, J=10.2, 7.5 Hz, 1H), 3.46 (m, 1H), 3.21 (m, 2H), 3.09 (m, 1H), 2.12 (m, 1H), 1.89 (m, 1H), 1.41 (m, 9H); (ESI(+)) m/e 436 (M+H)+.

Example 303

N-(4-{[(imidazo[1,2-a]pyridin-7-ylmethyl)carbamoyl]amino}phenyl)biphenyl-2-sulfonamide

Example 303A tert-butyl 4-(3-(imidazo[1,2-a]pyridin-7-ylmethyl)ureido)phenylcarbamate The title compound was prepared as described in Example 1C, substituting tert-butyl 4-aminophenylcarbamate for 4-amino-N-isopentylbenzamide and imidazo[1,2-a]pyridin-7-ylmethanamine for imidazo[1,2-a]pyridin-6-amine.

Example 303B 1-(4-aminophenyl)-3-(imidazo[1,2-a]pyridin-7-ylmethyl)urea

The title compound was prepared as described in Example 28A, substituting tert-butyl 4-(3-(imidazo[1,2-a]pyridin-7-ylmethyl)ureido)phenylcarbamate for tert-butyl 4-(4-(3-imidazo[1,2-a]pyridin-6-ylureido)phenyl)-5,6-dihydropyridine-1(2H)-carboxylate.

Example 303C

N-(4-{[(imidazo[1,2-a]pyridin-7-ylmethyl)carbamoyl]amino}phenyl)biphenyl-2-sulfonamide In a 4 mL vial was mixed 1-(4-aminophenyl)-3-(imidazo[1,2-a]pyridin-7-ylmethyl)urea (50 mg, 0.178 mmol) in anhydrous tetrahydrofuran (2 mL). To this mixture at room temperature was added 60% sodium hydride (24.88 mg, 0.622 mmol). The reaction was stirred about 30 minutes and biphenyl-2-sulfonyl chloride (53.9 mg, 0.213 mmol) was added. The reaction mixture stirred overnight at room temperature and was quenched with saturated ammonium chloride and water. The aqueous solution was extracted with dichloromethane and 10% methanol/dichloromethane. The organic layers were combined, concentrated and purified by normal phase chromatography to give the title compound. $^1$H NMR (400 MHz, DMSO-$d_6$) δ ppm 9.74 (bs, 1H), 8.56 (s, 1H), 8.47 (dd, J=6.9, 0.9 Hz, 1H), 7.95 (dd, J=7.8, 1.4 Hz, 1H), 7.87 (dd, J=1.2, 0.6 Hz, 1H), 7.62 (m, 1H), 7.54 (m, 1H), 7.51 (m, 1H), 7.38 (m, 4H), 7.30-7.20 (m, 5H), 6.82 (m, 3H), 6.66 (t, J=6.0 Hz, 1H), 4.30 (d, J=6.0 Hz, 2H); (ESI(+)) m/e 498 (M+H)+.

Example 306

1-{2-fluoro-4-[1-(2-methylpropanoyl)-1,2,3,6-tetrahydropyridin-4-yl]phenyl}-3-(imidazo[1,2-a]pyridin-7-ylmethyl)urea

Example 306A 1-(2-fluoro-4-(1,2,3,6-tetrahydropyridin-4-yl)phenyl)-3-(imidazo[1,2-a]pyridin-7-ylmethyl)urea The title compound was prepared as described in Example 28A, substituting tert-butyl 4-(3-fluoro-4-{[(imidazo[1,2-a]pyridin-7-ylmethyl)carbamoyl]amino}phenyl)-3,6-dihydropyridine-1(2H)-carboxylate for tert-butyl 4-(4-(3-imidazo[1,2-a]pyridin-6-ylureido)phenyl)-5,6-dihydropyridine-1(2H)-carboxylate.

Example 306B

1-{2-fluoro-4-[1-(2-methylpropanoyl)-1,2,3,6-tetrahydropyridin-4-yl]phenyl}-3-(imidazo[1,2-a]pyridin-7-ylmethyl)urea The title compound was prepared as described in Example 1A, substituting 1-(2-fluoro-4-(1,2,3,6-tetrahydropyridin-4-yl)phenyl)-3-(imidazo[1,2-a]pyridin-7-ylmethyl)urea for 3-methylbutan-1-amine and isobutyric acid for 4-nitrobenzoic acid. $^1$H NMR (300 MHz, methanol-$d_4$) δ ppm 8.74 (d, J=7.0 Hz, 1H), 8.19-8.15 (m, 1H), 8.00-7.96 (m, 1H), 7.92 (t, J=8.5 Hz, 1H), 7.81-7.77 (m, 1H), 7.50-7.44 (m, 1H), 7.28-7.16 (m, 2H), 6.17-6.11 (m, 1H), 4.61 (bs, 2H), 4.30-4.15 (m, 2H), 3.79 (t, J=5.7 Hz, 2H), 3.08-2.90 (m, 1H), 2.62-2.45 (m, 2H), 1.17-1.08 (m, 6H); MS (ESI(+)) m/e 436 (M+H)+.

Example 307

1-{2-fluoro-4-[1-(tetrahydrofuran-2-ylcarbonyl)-1,2,3,6-tetrahydropyridin-4-yl]phenyl}-3-(imidazo[1,2-a]pyridin-7-ylmethyl)urea The title compound was prepared as described in Example 1A, substituting 1-(2-fluoro-4-(1,2,3,6-tetrahydropyridin-4-yl)phenyl)-3-(imidazo[1,2-a]pyridin-7-ylmethyl)urea for 3-methylbutan-1-amine and tetrahydrofuran-2-carboxylic acid for 4-nitrobenzoic acid. $^1$H NMR (300 MHz, methanol-$d_4$) δ ppm 8.74 (d, J=7.0 Hz, 1H), 8.17 (d, J=2.2 Hz, 1H), 7.98 (d, J=2.2 Hz, 1H), 7.92 (t, J=8.5 Hz, 1H), 7.80 (bs, 1H), 7.47 (dd, J=7.0, 1.5 Hz, 1H), 7.28-7.16 (m, 2H), 6.17-6.09 (m, 1H), 4.84-4.70 (m, 1H), 4.61 (bs, 2H), 4.34-4.12 (m, 2H), 4.01-3.68 (m, 4H), 2.67-2.47 (m, 2H), 2.29-1.88 (m, 4H); MS (ESI(+)) m/e 464 (M+H)+.

Example 314 tert-butyl 4-{4-[2-(imidazo[1,2-a]pyridin-6-ylamino)-2-oxoethyl]phenyl}-3,6-dihydropyridine-1(2H)-carboxylate

Example 314A 2-(4-bromophenyl)-N-(imidazo[1,2-a]pyridin-6-yl)acetamide

The title compound was prepared as described in Example 1A, substituting imidazo[1,2-a]pyridin-6-amine for 3-methylbutan-1-amine and 2-(4-bromophenyl)acetic acid for 4-nitrobenzoic acid.

Example 314B tert-butyl 4-{4-[2-(imidazo[1,2-a]pyridin-6-ylamino)-2-oxoethyl]phenyl}-3,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 2-(4-bromophenyl)-N-(imidazo[1,2-a]pyridin-6-yl)acetamide for 4-bromoaniline. $^1$H NMR (300 MHz, DMSO-d$_6$) δ ppm 10.25 (s, 1H), 9.20-9.16 (m, 1H), 7.98-7.94 (m, 1H), 7.58-7.48 (m, 2H), 7.44-7.36 (m, 2H), 7.35-7.28 (m, 2H), 7.16 (dd, J=9.6, 2.0 Hz, 1H), 6.16-6.09 (m, 1H), 4.05-3.94 (m, 2H), 3.66 (s, 2H), 3.53 (t, J=5.7 Hz, 2H), 2.49-2.40 (m, 2H), 1.42 (s, 9H); MS (ESI(+)) m/e 433 (M+H)$^+$.

Example 315

N-(imidazo[1,2-a]pyridin-7-ylmethyl)-4-[1-(2-methylpropyl)-1H-pyrazol-4-yl]benzamide The title compound was prepared as described in Example 51A, substituting 4-bromo-N-(imidazo[1,2-a]pyridin-7-ylmethyl)benzamide for 4-bromoaniline. $^1$H NMR (300 MHz, DMSO-d$_6$) δ ppm 9.04 (t, J=5.9 Hz, 1H), 8.49 (dd, J=7.0, 0.9 Hz, 1H), 8.27 (s, 1H), 8.00-7.86 (m, 4H), 7.69 (d, J=8.4 Hz, 2H), 7.52 (d, J=1.2 Hz, 1H), 7.40 (d, J=1.5 Hz, 1H), 6.87 (dd, J=7.0, 1.7 Hz, 1H), 4.51 (d, J=5.9 Hz, 2H), 3.94 (d, J=7.1 Hz, 2H), 2.15 (dp, J=13.6, 6.8 Hz, 1H), 0.87 (d, J=6.7 Hz, 6H); MS (ESI(+)) m/e 374 (M+H)$^+$.

Example 318

N-(imidazo[1,2-a]pyridin-7-ylmethyl)-5-[3-(propan-2-yloxy)phenyl]thiophene-2-carboxamide The title compound was prepared as described in Example 51A, substituting 2-(3-isopropoxyphenyl)-4,4,5,5-tetramethyl-1,3,2-dioxaborolane for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline. $^1$H NMR (300 MHz, DMSO-d$_6$) δ ppm 9.04 (t, J=6.0 Hz, 1H), 8.49 (dd, J=7.0, 0.8 Hz, 1H), 8.19 (d, J=0.4 Hz, 1H), 7.89 (d, J=0.8 Hz, 1H), 7.86 (d, J=0.5 Hz, 1H), 7.75 (d, J=3.9 Hz, 1H), 7.52 (d, J=1.2 Hz, 1H), 7.40 (s, 1H), 7.24 (d, J=3.9 Hz, 1H), 6.85 (dd, J=7.0, 1.7 Hz, 1H), 4.48 (d, J=5.8 Hz, 2H), 4.13 (d, J=6.6 Hz, 2H), 3.09-2.83 (m, 4H), 2.47-2.40 (m, 1H), 2.14-1.96 (m, 1H), 1.88-1.69 (m, 1H), 1.69-1.54 (m, 1H), 1.37-1.14 (m, 1H).

Example 319

N-(imidazo[1,2-a]pyridin-7-ylmethyl)-2-[1-(tetrahydro-2H-pyran-4-ylcarbonyl)-1,2,3,6-tetrahydropyridin-4-yl]-1,3-thiazole-5-carboxamide The title compound was prepared as described in Example 1A, substituting N-(imidazo[1,2-a]pyridin-7-ylmethyl)-2-(1,2,3,6-tetrahydropyridin-4-yl)thiazole-5-carboxamide for 3-methylbutan-1-amine and tetrahydro-2H-pyran-4-carboxylic acid for 4-nitrobenzoic acid. $^1$H NMR (300 MHz, DMSO-d$_6$) ppm 9.26 (t, J=5.9 Hz, 1H), 8.50 (d, J=6.8 Hz, 1H), 8.40 (s, 1H), 7.89 (s, 1H), 7.52 (d, J=1.4 Hz, 1H), 7.42 (s, 1H), 6.84 (dd, J=7.1, 1.7 Hz, 1H), 6.72-6.79 (m, 1H), 4.49 (d, J=5.8 Hz, 2H), 4.32 (s, 1H), 4.16 (s, 1H), 3.81-3.89 (m, 2H), 3.73 (s, 2H), 3.36-3.47 (m, 1H), 2.83-3.05 (m, 1H), 2.65 (s, 1H), 2.38-2.54 (m, 2H), 1.50-1.69 (m, 4H); MS (ESI(+)) m/e 452 (M+H)$^+$.

Example 320

N-(imidazo[1,2-a]pyridin-7-ylmethyl)-2-[1-(2-methylpropanoyl)-1,2,3,6-tetrahydropyridin-4-yl]-1,3-thiazole-5-carboxamide The title compound was prepared as described in Example 1A, substituting N-(imidazo[1,2-a]pyridin-7-ylmethyl)-2-(1,2,3,6-tetrahydropyridin-4-yl)thiazole-5-carboxamide for 3-methylbutan-1-amine and isobutyric acid for 4-nitrobenzoic acid. $^1$H NMR (300 MHz, DMSO-d$_6$) ppm 9.26 (t, J=5.9 Hz, 1H), 8.50 (d, J=7.1 Hz, 1H), 8.40 (s, 1H), 7.89 (s, 1H), 7.53 (s, 1H), 7.42 (s, 1H), 6.84 (dd, J=7.1, 1.7 Hz, 1H), 6.76 (s, 1H), 4.49 (d, J=5.8 Hz, 2H), 4.29 (s, 1H), 4.16 (s, 1H), 3.62-3.74 (m, 2H), 2.81-3.03 (m, 1H), 2.60-2.69 (m, 1H), 2.50-2.58 (m, 1H), 1.02 (d, J=6.4 Hz, 6H); MS (ESI(+)) m/e 410 (M+H)$^+$.

Example 321

N-(imidazo[1,2-a]pyridin-7-ylmethyl)-4-({(3S)-1-[(2S)-2-methylbutanoyl]pyrrolidin-3-yl}oxy)benzamide

Example 321A (S)-tert-butyl 3-(4-(benzyloxycarbonyl)phenoxy)pyrrolidine-1-carboxylate To a stirred solution of (R)-tert-butyl 3-hydroxypyrrolidine-1-carboxylate (1 g, 5.34 mmol) in tetrahydrofuran (38.1 ml) was added benzyl 4-hydroxybenzoate (1.341 g, 5.87 mmol) and triphenylphpsphine polymer bound (4.45 g, 8.01 mmol). The reaction mixture was cooled to 0° C. and a solution of (E)-diisopropyl diazene-1,2-dicarboxylate (1.367 ml, 6.94 mmol) in tetrahydrofuran (5 mL) was added dropwise over 15 minutes. The reaction was allowed to stir at room temperature for 16 hours and the mixture was filtered. The solids were washed with dichloromethane, and the combined filtrates were concentrated and purified by normal phase chromatography to give the title compound.

Example 321B (S)-4-(1-(tert-butoxycarbonyl)pyrrolidin-3-yloxy)benzoic acid

The title compound was prepared as described in Example 1B, substituting (R)-tert-butyl 3-(4-(benzyloxycarbonyl)phenoxy)pyrrolidine-1-carboxylate for N-isopentyl-4-nitrobenzamide.

Example 321C (S)-tert-butyl 3-(4-(imidazo[1,2-a]pyridin-7-ylmethylcarbamoyl)phenoxy)pyrrolidine-1-carboxylate The title compound was prepared as described in Example 1A, substituting imidazo[1,2-a]pyridin-7-ylmethanamine for 3-methylbutan-1-amine and (S)-4-(1-(tert-butoxycarbonyl)pyrrolidin-3-yloxy)benzoic acid for 4-nitrobenzoic acid.

Example 321D (S)—N-(imidazo[1,2-a]pyridin-7-ylmethyl)-4-(pyrrolidin-3-yloxy)benzamide The title compound was prepared as described in Example 28A, substituting (S)-tert-butyl 3-(4-(imidazo[1,2-a]pyridin-7-ylmethylcarbamoyl)phenoxy)pyrrolidine-1-carboxylate for tert-butyl 4-(4-(3-imidazo[1,2-a]pyridin-6-ylureido)phenyl)-5,6-dihydropyridine-1 (2H)-carboxylate.

Example 321E

N-(imidazo[1,2-a]pyridin-7-ylmethyl)-4-({(3S)-1-[(2S)-2-methylbutanoyl]pyrrolidin-3-yl}oxy)benzamide The title compound was prepared as described in Example 1A, substituting (S)—N-(imidazo[1,2-a]pyridin-7-ylmethyl)-4-(pyrrolidin-3-yloxy)benzamide for 3-methylbutan-1-amine and (S)-2-methylbutanoic acid for 4-nitrobenzoic acid. $^1$H NMR (400 MHz, DMSO-$d_6$, Temp=90° C.) δ ppm 8.67-8.59 (m, 1H), 8.41 (d, J=6.9 Hz, 1H), 7.90-7.84 (m, 2H), 7.81 (s, 1H), 7.50-7.46 (m, 1H), 7.38 (s, 1H), 7.03-6.97 (m, 2H), 6.83 (dd, J=6.9, 1.7 Hz, 1H), 5.17-5.04 (m, 1H), 4.49 (d, J=5.9 Hz, 2H), 3.91-3.36 (m, 5H), 2.31-1.98 (m, 2H), 1.63-1.49 (m, 1H), 1.38-1.23 (m, 1H), 1.00 (d, J=6.7 Hz, 3H), 0.89-0.74 (m, 3H); MS (ESI(+)) m/e 421 (M+H)$^+$.

TABLE 16

The following Examples were prepared essentially as described in Example 321, substituting the appropriate carboxylic acid in Example 321E.

| Ex | Name | MS |
|---|---|---|
| 339 | N-(imidazo[1,2-a]pyridin-7-ylmethyl)-4-({(3S)-1-[(3R)-tetrahydrofuran-3-ylcarbonyl]pyrrolidin-3-yl}oxy)benzamide | (ESI(+)) m/e 435 (M + H)$^+$ |
| 340 | N-(imidazo[1,2-a]pyridin-7-ylmethyl)-4-({(3S)-1-[(2R)-tetrahydrofuran-2-ylcarbonyl]pyrrolidin-3-yl}oxy)benzamide | (ESI(+)) m/e 435 (M + H)$^+$ |
| 341 | N-(imidazo[1,2-a]pyridin-7-ylmethyl)-4-({(3S)-1-[(2S)-tetrahydrofuran-2-ylcarbonyl]pyrrolidin-3-yl}oxy)benzamide | (ESI(+)) m/e 435 (M + H)$^+$ |
| 342 | N-(imidazo[1,2-a]pyridin-7-ylmethyl)-4-{[(3S)-1-(tetrahydro-2H-pyran-4-ylcarbonyl)pyrrolidin-3-yl]oxy}benzamide | (ESI(+)) m/e 449 (M + H)$^+$ |
| 343 | N-(imidazo[1,2-a]pyridin-7-ylmethyl)-4-{[(3S)-1-(tetrahydro-2H-pyran-4-ylacetyl)pyrrolidin-3-yl]oxy}benzamide | (ESI(+)) m/e 463 (M + H)$^+$ |
| 346 | N-(imidazo[1,2-a]pyridin-7-ylmethyl)-4-({(3S)-1-[(3S)-tetrahydrofuran-3-ylcarbonyl]pyrrolidin-3-yl}oxy)benzamide | (ESI(+)) m/e 435 (M + H)$^+$ |
| 347 | 4-{[(3S)-1-(cyclopropylacetyl)pyrrolidin-3-yl]oxy}-N-(imidazo[1,2-a]pyridin-7-ylmethyl)benzamide | (ESI(+)) m/e 419 (M + H)$^+$ |
| 348 | 4-{[(3S)-1-(2-hydroxy-2-methylpropanoyl)pyrrolidin-3-yl]oxy}-N-(imidazo[1,2-a]pyridin-7-ylmethyl)benzamide | (ESI(+)) m/e 423 (M + H)$^+$ |
| 349 | N-(imidazo[1,2-a]pyridin-7-ylmethyl)-4-{[(3S)-1-(3-methoxy-2-methylpropanoyl)pyrrolidin-3-yl]oxy}benzamide | (ESI(+)) m/e 437 (M + H)$^+$ |
| 350 | 4-{[(3S)-1-butanoylpyrrolidin-3-yl]oxy}-N-(imidazo[1,2-a]pyridin-7-ylmethyl)benzamide | (ESI(+)) m/e 407 (M + H)$^+$ |
| 351 | N-(imidazo[1,2-a]pyridin-7-ylmethyl)-4-{[(3S)-1-(2-methylpropanoyl)pyrrolidin-3-yl]oxy}benzamide | (ESI(+)) m/e 407 (M + H)$^+$ |
| 352 | 4-{[(3S)-1-(cyclopropylcarbonyl)pyrrolidin-3-yl]oxy}-N-(imidazo[1,2-a]pyridin-7-ylmethyl)benzamide | (ESI(+)) m/e 405 (M + H)$^+$ |
| 353 | 4-{[(3S)-1-benzoylpyrrolidin-3-yl]oxy}-N-(imidazo[1,2-a]pyridin-7-ylmethyl)benzamide | (ESI(+)) m/e 441 (M + H)$^+$ |
| 354 | 4-{[(3S)-1-(3-hydroxy-3-methylbutanoyl)pyrrolidin-3-yl]oxy}-N-(imidazo[1,2-a]pyridin-7-ylmethyl)benzamide | (ESI(+)) m/e 437 (M + H)$^+$ |

Example 322 tert-butyl 4-[4-(imidazo[1,2-a]pyridin-7-ylcarbamoyl)phenyl]piperidine-1-carboxylate The title compound was prepared as described in Example 1A, substituting imidazo[1,2-a]pyridin-7-amine for 3-methylbutan-1-amine and 4-(1-(tert-butoxycarbonyl)piperidin-4-yl)benzoic acid for 4-nitrobenzoic acid. $^1$H NMR (300 MHz, DMSO-$d_6$) δ ppm 10.36 (s, 1H), 8.47 (d, J=7.3 Hz, 1H), 8.15-8.10 (m, 1H), 7.94-7.87 (m, 2H), 7.83 (s, 1H), 7.50-7.40 (m, 3H), 7.24 (dd, J=7.3, 2.1 Hz, 1H), 4.16-4.05 (m, 2H), 2.94-2.66 (m, 3H), 1.84-1.73 (m, 2H), 1.65-1.41 (m, 11H); MS (ESI(+)) m/e 421 (M+H)$^+$.

Example 323 tert-butyl 4-[4-(imidazo[1,2-a]pyridin-6-ylcarbamoyl)phenyl]piperidine-1-carboxylate The title compound was prepared as described in Example 1A, substituting imidazo[1,2-a]pyridin-6-amine for 3-methylbutan-1-amine and 4-(1-(tert-butoxycarbonyl)piperidin-4-yl)benzoic acid for 4-nitrobenzoic acid. $^1$H NMR (300 MHz, DMSO-$d_6$) δ ppm 10.27 (s, 1H), 9.36-9.31 (m, 1H), 8.03 (s, 1H), 7.95-7.88 (m, 2H), 7.60-7.52 (m, 2H), 7.47-7.35 (m, 3H), 4.15-4.04 (m, 2H), 2.95-2.66 (m, 3H), 1.83-1.73 (m, 2H), 1.65-1.45 (m, 2H), 1.42 (s, 9H); MS (ESI(+)) m/e 421 (M+H)$^+$.

Example 324

N-(imidazo[1,2-a]pyridin-7-ylmethyl)-5-{3-[(2-methylpropanoyl)amino]oxetan-3-yl}thiophene-2-carboxamide

Example 324A 5-(3-(1,1-dimethylethylsulfinamido)oxetan-3-yl)thiophene-2-carboxylic acid Butyllithium (6.16 ml, 15.41 mmol) was added dropwise to a stirred solution of diisopropylamine (1.919 ml, 13.69 mmol) in tetrahydrofuran (10 ml) at −78° C. The solution was allowed to warm to room temperature and then added dropwise by syringe to a stirred −78° C. solution of thiophene-2-carboxylic acid (0.877 g, 6.85 mmol) in tetrahydrofuran (30 ml). The resulting suspension was stirred for 40 minutes at −78° C. when a solution of 2-methyl-N-(oxetan-3-ylidene)propane-2-sulfinamide (1 g, 5.71 mmol) in tetrahydrofuran (10 ml) was added dropwise. After the addition was complete, the reaction mixture was allowed to warm to room temperature, quenched with saturated ammonium chloride and diluted with a water to dissolve the remaining solids. The aqueous solution was extracted with ethyl acetate, adjusted to pH 2 by addition of 1N aqueous hydrochloric acid and re-extracted with ethyl acetate and methylene chloride. The organic extracts were dried with magnesium sulfate, filtered, concentrated and purified by normal phase chromatography to give the title compound.

Example 324B 5-(3-(1,1-dimethylethylsulfinamido)oxetan-3-yl)-N-(imidazo[1,2-a]pyridin-7-ylmethyl)thiophene-2-carboxamide The title compound was prepared as described in Example 1A, substituting imidazo[1,2-a]pyridin-7-ylmethanamine for 3-methylbutan-1-amine and 5-(3-(1,1-dimethylethylsulfinamido)oxetan-3-yl)thiophene-2-carboxylic acid for 4-nitrobenzoic acid.

Example 324C 5-(3-aminooxetan-3-yl)-N-(imidazo[1,2-a]pyridin-7-ylmethyl)thiophene-2-carboxamide 5-(3-(1,1-Dimethylethylsulfinamido)oxetan-3-yl)-N-(imidazo[1,2-a]pyridin-7-ylmethyl)thiophene-2-carboxamide (432 mg, 1 mmol) in 10 ml methanol was treated with 4N aqueous HCl in dioxane (0.75 ml, 3 mmol) and the mixture was stirred for 2 hours. Concentration provided the title compound.

Example 324D

The title compound was prepared as described in Example 1A, substituting 5-(3-aminooxetan-3-yl)-N-(imidazo[1,2-a]pyridin-7-ylmethyl)thiophene-2-carboxamide for 3-methylbutan-1-amine and isobutyric acid for 4-nitrobenzoic acid. $^1$H NMR (300 MHz, DMSO-$d_6$) ppm 9.03-9.10 (m, 2H), 8.48 (d, J=7.1 Hz, 1H), 7.89 (s, 1H), 7.71 (d, J=4.0 Hz, 1H), 7.52 (d, J=1.2 Hz, 1H), 7.38 (s, 1H), 7.22 (d, J=4.0 Hz, 1H), 6.83 (dd, J=6.9, 1.8 Hz, 1H), 4.80 (d, J=6.7 Hz, 2H), 4.71 (d, J=6.7 Hz, 2H), 4.46 (d, J=6.0 Hz, 2H), 2.40-2.48 (m, 1H), 1.05 (d, J=7.1 Hz, 6H); MS (ESI(+)) m/e 399 (M+H)$^+$.

Example 325

5-[3-(benzoylamino)oxetan-3-yl]-N-(imidazo[1,2-a]pyridin-7-ylmethyl)thiophene-2-carboxamide The title compound was prepared as described in Example 1A, substituting 5-(3-aminooxetan-3-yl)-N-(imidazo[1,2-a]pyridin-7-ylmethyl)thiophene-2-carboxamide for 3-methylbutan-1-amine and benzoic acid for 4-nitrobenzoic acid. $^1$H NMR (300 MHz, DMSO-$d_6$) ppm 9.70 (s, 1H), 9.05 (t, J=5.9 Hz, 1H), 8.47 (d, J=6.8 Hz, 1H), 7.87-7.93 (m, 3H), 7.72 (d, J=3.7 Hz, 1H), 7.56-7.62 (m, 1H), 7.48-7.55 (m, 3H), 7.37 (s, 1H), 7.29 (d, J=3.7 Hz, 1H), 6.82 (dd, J=7.1, 1.7 Hz, 1H), 5.01 (d, J=6.8 Hz, 2H), 4.80 (d, J=7.1 Hz, 2H), 4.45 (d, J=5.8 Hz, 2H); MS (ESI(+)) m/e 433 (M+H)$^+$.

Example 326

N-(imidazo[1,2-a]pyridin-7-ylmethyl)-5-{3-[(tetrahydrofuran-3-ylacetyl)amino]oxetan-3-yl}thiophene-2-carboxamide The title compound was prepared as described in Example 1A, substituting 5-(3-aminooxetan-3-yl)-N-(imidazo[1,2-a]pyridin-7-ylmethyl)thiophene-2-carboxamide for 3-methylbutan-1-amine and 2-(tetrahydrofuran-3-yl)acetic acid for 4-nitrobenzoic acid. $^1$H NMR (300 MHz, DMSO-$d_6$) ppm 9.22 (s, 1H), 9.07 (t, J=6.0 Hz, 1H), 8.48 (d, J=7.1 Hz, 1H), 7.89 (s, 1H), 7.71 (d, J=3.6 Hz, 1H), 7.52 (d, J=1.2 Hz, 1H), 7.38 (s, 1H), 7.22 (d, J=4.0 Hz, 1H), 6.83 (dd, J=7.1, 1.6 Hz, 1H), 4.81 (d, J=6.7 Hz, 2H), 4.72 (d, J=6.7 Hz, 2H), 4.46 (d, J=6.0 Hz, 2H), 3.56-3.80 (m, 3H), 2.23-2.30 (m, 2H), 1.89-2.04 (m, 1H), 1.45-1.58 (m, 1H); MS (ESI(+)) m/e 441 (M+H)$^+$.

Example 327

N-(imidazo[1,2-a]pyridin-7-ylmethyl)-5-[3-(pentanoylamino)oxetan-3-yl]thiophene-2-carboxamide The title compound was prepared as described in Example 1A, substituting 5-(3-aminooxetan-3-yl)-N-(imidazo[1,2-a]pyridin-7-ylmethyl)thiophene-2-carboxamide for 3-methylbutan-1-amine and pentanoic acid for 4-nitrobenzoic acid. $^1$H NMR (300 MHz, DMSO-$d_6$) ppm 9.11 (s, 1H), 9.05 (t, J=5.9 Hz, 1H), 8.48 (dd, J=7.0, 0.8 Hz, 1H), 7.88 (s, 1H), 7.70 (d, J=4.1 Hz, 1H), 7.52 (d, J=1.4 Hz, 1H), 7.38 (s, 1H), 7.21 (d, J=3.7 Hz, 1H), 6.83 (dd, J=7.1, 1.7 Hz, 1H), 4.80 (d, J=6.8 Hz, 2H), 4.71 (d, J=6.8 Hz, 2H), 4.46 (d, J=5.8 Hz, 2H), 2.17 (t, J=7.5 Hz, 2H), 1.44-1.57 (m, 2H), 1.22-1.37 (m, 2H), 0.84-0.92 (m, 3H); MS (ESI(+)) m/e 413 (M+H)$^+$.

Example 328

1-(imidazo[1,2-a]pyridin-7-ylmethyl)-3-[4-({(3S)-1-[(2S)-2-methylbutanoyl]pyrrolidin-3-yl}oxy)phenyl]urea

Example 328A

(R)-tert-butyl 3-(4-nitrophenoxy)pyrrolidine-1-carboxylate (R)-Tert-butyl 3-hydroxypyrrolidine-1-carboxylate (10 g, 53.4 mmol) was dissolved in 1-fluoro-4-nitrobenzene (13.94 g, 99 mmol). An aqueous solution of 5.9N potassium hydroxide (77 ml, 452 mmol) was added followed by addition of tetrabutylammonium bromide (2.238 g, 6.94 mmol). The reaction mixture was stirred at 40° C. for 24 hours, cooled, diluted with water and extracted with ethyl acetate. The combined organic layers were dried with sodium sulfate, filtered and concentrated to give the title compound.

Example 328B

(R)-tert-butyl 3-(4-aminophenoxy)pyrrolidine-1-carboxylate

The title compound was prepared as described in Example 1B, substituting (R)-tert-butyl 3-(4-nitrophenoxy)pyrrolidine-1-carboxylate for N-isopentyl-4-nitrobenzamide.

Example 328C tert-butyl (3S)-3-(4-{[(imidazo[1,2-a]pyridin-7-ylmethyl)carbamoyl]amino}phenoxy)pyrrolidine-1-carboxylate The title compound was prepared as described in Example 1C, substituting (R)-tert-butyl 3-(4-aminophenoxy)pyrrolidine-1-carboxylate for 4-amino-N-isopentylbenzamide and imidazo[1,2-a]pyridin-7-ylmethanamine for imidazo[1,2-a]pyridin-6-amine.

Example 328D

(R)-1-(imidazo[1,2-a]pyridin-7-ylmethyl)-3-(4-(pyrrolidin-3-yloxy)phenyl)urea The title compound was prepared as described in Example 28A, substituting tert-butyl (3S)-3-(4-{[(imidazo[1,2-a]pyridin-7-ylmethyl)carbamoyl]amino}phenoxy)pyrrolidine-1-carboxylate for tert-butyl 4-(4-(3-imidazo[1,2-a]pyridin-6-ylureido)phenyl)-5,6-dihydropyridine-1(2H)-carboxylate.

Example 328E

1-(imidazo[1,2-a]pyridin-7-ylmethyl)-3-[4-({(3S)-1-[(2S)-2-methylbutanoyl]pyrrolidin-3-yl}oxy)phenyl]urea The title compound was prepared as described in Example 1A, substituting (R)-1-(imidazo[1,2-a]pyridin-7-ylmethyl)-3-(4-(pyrrolidin-3-yloxy)phenyl)urea for 3-methylbutan-1-amine and (S)-2-methylbutanoic acid for 4-nitrobenzoic acid. $^1$H NMR (400 MHz, methanol-$d_4$) δ ppm 8.76-8.70 (m, 1H), 8.19-8.12 (m, 1H), 8.00-7.94 (m, 1H), 7.81-7.75 (m, 1H), 7.46 (d, J=7.0 Hz, 1H), 7.34-7.25 (m, 2H), 6.92-6.82 (m, 2H), 5.07-4.95 (m, 1H), 4.58 (bs, 2H), 3.84-3.61 (m, 3H), 3.60-3.45 (m, 1H), 2.67-2.45 (m, 1H), 2.31-2.06 (m, 2H), 1.72-1.57 (m, 1H), 1.50-1.35 (m, 1H), 1.12-1.00 (m, 3H), 0.94-0.85 (m, 3H); MS (ESI(+)) m/e 436 (M+H)$^+$.

TABLE 17

The following Examples were prepared essentially as described in Example 328, substituting the appropriate alcohol in Example 328A and the appropriate carboxylic acid in Example 328E.

| Ex | Name | MS |
|---|---|---|
| 329 | 1-(4-{[(3R)-1-benzoylpyrrolidin-3-yl]oxy}phenyl)-3-(imidazo[1,2-a]pyridin-7-ylmethyl)urea | (ESI(+)) m/e 456 (M + H)$^+$ |
| 330 | 1-(imidazo[1,2-a]pyridin-7-ylmethyl)-3-(4-{[(3R)-1-(2-methylpropanoyl)pyrrolidin-3-yl]oxy}phenyl)urea | (ESI(+)) m/e 422 (M + H)$^+$ |
| 331 | 1-(4-{[(3R)-1-(cyclopropylcarbonyl)pyrrolidin-3-yl]oxy}phenyl)-3-(imidazo[1,2-a]pyridin-7-ylmethyl)urea | (ESI(+)) m/e 420 (M + H)$^+$ |
| 332 | 1-(4-{[(3R)-1-(cyclopropylacetyl)pyrrolidin-3-yl]oxy}phenyl)-3-(imidazo[1,2-a]pyridin-7-ylmethyl)urea | (ESI(+)) m/e 434 (M + H)$^+$ |
| 333 | 1-(imidazo[1,2-a]pyridin-7-ylmethyl)-3-(4-{[(3R)-1-(tetrahydro-2H-pyran-4-ylcarbonyl)pyrrolidin-3-yl]oxy}phenyl)urea | (ESI(+)) m/e 464 (M + H)$^+$ |

TABLE 17-continued

The following Examples were prepared essentially as described in Example 328, substituting the appropriate alcohol in Example 328A and the appropriate carboxylic acid in Example 328E.

| Ex | Name | MS |
|---|---|---|
| 334 | 1-(4-{[(3R)-1-(2-hydroxy-2-methylpropanoyl)pyrrolidin-3-yl]oxy}phenyl)-3-(imidazo[1,2-a]pyridin-7-ylmethyl)urea | (ESI(+)) m/e 438 (M + H)+ |
| 335 | 1-(imidazo[1,2-a]pyridin-7-ylmethyl)-3-[4-({(3R)-1-[(2R)-tetrahydrofuran-2-ylcarbonyl]pyrrolidin-3-yl}oxy)phenyl]urea | (ESI(+)) m/e 450 (M + H)+ |
| 336 | 1-(imidazo[1,2-a]pyridin-7-ylmethyl)-3-[4-({(3R)-1-[(2S)-tetrahydrofuran-2-ylcarbonyl]pyrrolidin-3-yl}oxy)phenyl]urea | (ESI(+)) m/e 450 (M + H)+ |
| 337 | 1-(imidazo[1,2-a]pyridin-7-ylmethyl)-3-(4-{[(3R)-1-(tetrahydrofuran-3-ylcarbonyl)pyrrolidin-3-yl]oxy}phenyl)urea | (ESI(+)) m/e 450 (M + H)+ |
| 338 | 1-(imidazo[1,2-a]pyridin-7-ylmethyl)-3-(4-{[(3R)-1-(tetrahydro-2H-pyran-4-ylacetyl)pyrrolidin-3-yl]oxy}phenyl)urea | (ESI(+)) m/e 478 (M + H)+ |
| 689 | 1-(4-{[(3R)-1-(2-fluorobenzoyl)pyrrolidin-3-yl]oxy}phenyl)-3-(imidazo[1,2-a]pyridin-7-ylmethyl)urea | (ESI(+)) m/e 474 (M + H)+ |
| 690 | 1-(4-{[(3R)-1-(3-fluorobenzoyl)pyrrolidin-3-yl]oxy}phenyl)-3-(imidazo[1,2-a]pyridin-7-ylmethyl)urea | (ESI(+)) m/e 474 (M + H)+ |
| 691 | 1-(4-{[(3R)-1-(4-fluorobenzoyl)pyrrolidin-3-yl]oxy}phenyl)-3-(imidazo[1,2-a]pyridin-7-ylmethyl)urea | (ESI(+)) m/e 474 (M + H)+ |
| 692 | 1-(4-{[(3R)-1-(2,4-difluorobenzoyl)pyrrolidin-3-yl]oxy}phenyl)-3-(imidazo[1,2-a]pyridin-7-ylmethyl)urea | (ESI(+)) m/e 492 (M + H)+ |
| 693 | 1-(imidazo[1,2-a]pyridin-7-ylmethyl)-3-[4-({(3R)-1-[4-(trifluoromethyl)benzoyl]pyrrolidin-3-yl}oxy)phenyl]urea | (ESI(+)) m/e 524 (M + H)+ |
| 694 | 1-(4-{[(3R)-1-(3,5-difluorobenzoyl)pyrrolidin-3-yl]oxy}phenyl)-3-(imidazo[1,2-a]pyridin-7-ylmethyl)urea | (ESI(+)) m/e 492 (M + H)+ |
| 695 | 1-(4-{[(3R)-1-(2-chlorobenzoyl)pyrrolidin-3-yl]oxy}phenyl)-3-(imidazo[1,2-a]pyridin-7-ylmethyl)urea | (ESI(+)) m/e 490 (M + H)+ |
| 696 | 1-(4-{[(3R)-1-(4-chlorobenzoyl)pyrrolidin-3-yl]oxy}phenyl)-3-(imidazo[1,2-a]pyridin-7-ylmethyl)urea | (ESI(+)) m/e 490 (M + H)+ |

Example 355

2-(4-benzoylpiperazin-1-yl)-N-(imidazo[1,2-a]pyridin-7-ylmethyl)-1,3-thiazole-5-carboxamide The title compound was prepared as in Example 53B, substituting phenyl(piperazin-1-yl)methanone for 4-cyanobenzylamine and 2-bromo-N-(imidazo[1,2-a]pyridin-7-ylmethyl)thiazole-5-carboxamide for 2-bromo-N-(imidazo[1,2-a]pyridin-6-yl)thiazole-5-carboxamide. $^1$H NMR (300 MHz, DMSO-d$_6$) ppm 8.86 (t, J=6.0 Hz, 1H), 8.48 (d, J=6.7 Hz, 1H), 7.90 (s, 1H), 7.89 (s, 1H), 7.52 (d, J=1.2 Hz, 1H), 7.41-7.50 (m, 5H), 7.37 (s, 1H), 6.82 (dd, J=7.1, 1.6 Hz, 1H), 4.43 (d, J=5.6 Hz, 2H), 3.41-3.82 (m, 8H); MS (ESI(+)) m/e 447 (M+H)+.

Example 356

N-(imidazo[1,2-a]pyridin-7-ylmethyl)-2-[4-(propan-2-yl)piperazin-1-yl]-1,3-thiazole-5-carboxamide The title compound was prepared as in Example 53B, substituting 1-isopropylpiperazine for 4-cyanobenzylamine and 2-bromo-N-(imidazo[1,2-a]pyridin-7-ylmethyl)thiazole-5-carboxamide for 2-bromo-N-(imidazo[1,2-a]pyridin-6-yl)thiazole-5-carboxamide. $^1$H NMR (300 MHz, DMSO-d$_6$) ppm 8.80 (t, J=5.9 Hz, 1H), 8.48 (d, J=7.1 Hz, 1H), 7.88 (s, 1H), 7.87 (s, 1H), 7.52 (d, J=1.4 Hz, 1H), 7.37 (s, 1H), 6.81 (dd, J=7.1, 1.7 Hz, 1H), 4.42 (d, J=6.1 Hz, 2H), 3.41-3.48 (m, 4H), 2.64-2.79 (m, 1H), 2.51-2.57 (m, 4H), 0.98 (d, J=6.4 Hz, 6H); MS (ESI(+)) m/e 385 (M+H)+.

Example 357

N-(imidazo[1,2-a]pyridin-7-ylmethyl)-2-[4-(2-methoxyethyl)piperazin-1-yl]-1,3-thiazole-5-carboxamide The title compound was prepared as in Example 53B, substituting 1-(2-methoxyethyl)piperazine for 4-cyanobenzylamine and 2-bromo-N-(imidazo[1,2-a]pyridin-7-ylmethyl)thiazole-5-carboxamide for 2-bromo-N-(imidazo[1,2-a]pyridin-6-yl)thiazole-5-carboxamide. $^1$H NMR (300 MHz, DMSO-d$_6$) ppm 8.82 (t, J=6.0 Hz, 1H), 8.48 (d, J=6.7 Hz, 1H), 7.88 (s, 1H), 7.88 (s, 1H), 7.52 (d, J=1.2 Hz, 1H), 7.37 (s, 1H), 6.81 (dd, J=7.1, 1.6 Hz, 1H), 4.43 (d, J=6.0 Hz, 2H), 3.42-3.48 (m, 6H), 3.24 (s, 3H), 2.51-2.56 (m, 6H); MS (ESI(+)) m/e 401 (M+H)+.

Example 358

N-(imidazo[1,2-a]pyridin-6-ylmethyl)-N'-(3-methylbutyl)benzene-1,4-dicarboxamide

Example 358A methyl 4-(imidazo[1,2-a]pyridin-6-ylmethylcarbamoyl)benzoate

The title compound was prepared as described in Example 1A, substituting imidazo[1,2-a]pyridin-6-ylmethanamine for 3-methylbutan-1-amine and 4-(methoxycarbonyl)benzoic acid for 4-nitrobenzoic acid.

Example 358B 4-(imidazo[1,2-a]pyridin-6-ylmethylcarbamoyl)benzoic acid

The title compound was prepared as described in Example 4B, substituting methyl 4-(imidazo[1,2-a]pyridin-6-ylmethylcarbamoyl)benzoate for methyl 4-(3-imidazo[1,2-a]pyridin-6-ylureido)benzoate.

Example 358C

N-(imidazo[1,2-a]pyridin-6-ylmethyl)-N'-(3-methylbutyl)benzene-1,4-dicarboxamide The title compound was prepared as described in Example 1A, substituting 3-methylbutan-1-amine for 3-methylbutan-1-amine and 4-(imidazo[1,2-a]pyridin-6-ylmethylcarbamoyl)benzoic acid for 4-nitrobenzoic acid. $^1$H NMR (300 MHz, DMSO-$d_6$) δ ppm 9.15 (t, J=5.8 Hz, 1H), 8.55-8.47 (m, 2H), 8.00-7.84 (m, 5H), 7.54 (dd, J=5.1, 4.1 Hz, 2H), 7.23 (dd, J=9.3, 1.7 Hz, 1H), 4.48 (d, J=5.8 Hz, 2H), 3.30-3.21 (m, 2H), 1.62 (dp, J=13.3, 6.6 Hz, 1H), 1.49-1.37 (m, 2H), 0.91 (d, J=6.6 Hz, 6H); MS (ESI(+)) m/e 365 (M+H)$^+$.

Example 359

N-(imidazo[1,2-a]pyridin-6-ylmethyl)-N'-[(3S)-tetrahydrofuran-3-ylmethyl]benzene-1,4-dicarboxamide The title compound was prepared as described in Example 1A, substituting (S)-(tetrahydrofuran-3-yl)methanamine for 3-methylbutan-1-amine and 4-(imidazo[1,2-a]pyridin-6-ylmethylcarbamoyl)benzoic acid for 4-nitrobenzoic acid. $^1$H NMR (300 MHz, DMSO-$d_6$) δ ppm 9.15 (t, J=5.8 Hz, 1H), 8.68 (t, J=5.7 Hz, 1H), 8.49 (bs, 1H), 8.03-7.85 (m, 5H), 7.58-7.50 (m, 2H), 7.23 (dd, J=9.1, 1.7 Hz, 1H), 4.49 (d, J=5.8 Hz, 2H), 3.80-3.56 (m, 4H), 3.48 (dd, J=8.5, 5.2 Hz, 1H), 3.28-3.17 (m, 1H), 2.03-1.87 (m, 1H), 1.68-1.46 (m, 1H), 1.37-1.09 (m, 1H); MS (ESI(+)) m/e 379 (M+H)$^+$.

Example 360

1-(imidazo[1,2-a]pyridin-6-ylmethyl)-3-[4-(1-propyl-1H-pyrazol-4-yl)phenyl]urea

Example 360A 1-(4-bromophenyl)-3-(imidazo[1,2-a]pyridin-6-ylmethyl)urea

The title compound was prepared as described in Example 3A, substituting 1-isocyanato-4-bromobenzene for 1-isocyanato-4-nitrobenzene and imidazo[1,2-a]pyridin-6-ylmethanamine for imidazo[1,2-a]pyridin-6-amine.

Example 360B 1-(imidazo[1,2-a]pyridin-6-ylmethyl)-3-[4-(1-propyl-1H-pyrazol-4-yl)phenyl]urea The title compound was prepared as described in Example 51A, substituting 1-propyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 1-(4-bromophenyl)-3-(imidazo[1,2-a]pyridin-6-ylmethyl)urea for 4-bromoaniline. $^1$H NMR (300 MHz, DMSO-$d_6$) δ ppm 8.59 (s, 1H), 8.44 (s, 1H), 8.04 (s, 1H), 7.95 (s, 1H), 7.76 (s, 1H), 7.57-7.50 (m, 2H), 7.48-7.32 (m, 4H), 7.21 (dd, J=9.2, 1.7 Hz, 1H), 6.65 (t, J=5.9 Hz, 1H), 4.30 (d, J=5.8 Hz, 2H), 4.04 (t, J=6.9 Hz, 2H), 1.87-1.73 (m, 2H), 0.84 (t, J=7.3 Hz, 3H); MS (ESI(+)) m/e 375 (M+H)$^+$.

Example 361

N-(imidazo[1,2-a]pyridin-7-ylmethyl)-2-phenyl-1,3-thiazole-5-carboxamide

The title compound was prepared as described in Example 51A, substituting phenyl boronic acid for 1-isobutyl-4-(4,4,5,5-tetramethyl-1,3,2-dioxaborolan-2-yl)-1H-pyrazole and 2-bromo-N-(imidazo[1,2-a]pyridin-7-ylmethyl)thiazole-5-carboxamide for 4-bromoaniline. $^1$H NMR (300 MHz, DMSO-$d_6$) δ ppm 9.34 (t, J=5.8 Hz, 1H), 8.56-8.48 (m, 2H), 8.05-7.95 (m, 2H), 7.90 (d, J=0.8 Hz, 1H), 7.60-7.49 (m, 4H), 7.45 (s, 1H), 6.87 (dd, J=7.0, 1.6 Hz, 1H), 4.52 (d, J=5.7 Hz, 2H); MS (ESI(+)) m/e 335 (M+H).

Example 362

1-(imidazo[1,2-a]pyridin-6-ylmethyl)-3-{4-[1-(2-methylpropyl)-1H-pyrazol-4-yl]phenyl}urea The title compound was prepared as described in Example 51A, substituting 1-(4-bromophenyl)-3-(imidazo[1,2-a]pyridin-6-ylmethyl)urea for 4-bromoaniline. $^1$H NMR (300 MHz, DMSO-$d_6$) δ ppm 8.59 (s, 1H), 8.44 (d, J=1.6 Hz, 1H), 8.03 (d, J=0.8 Hz, 1H), 7.97-7.93 (m, 1H), 7.77 (d, J=0.8 Hz, 1H), 7.57-7.50 (m, 2H), 7.44-7.35 (m, 4H), 7.21 (dd, J=9.2, 1.7 Hz, 1H), 6.65 (t, J=5.9 Hz, 1H), 4.30 (d, J=5.8 Hz, 2H), 3.90 (d, J=7.2 Hz, 2H), 2.19-2.06 (m, 1H), 0.85 (d, J=6.7 Hz, 6H); MS (ESI(+)) m/e 389 (M+H)$^+$.

Example 364 tert-butyl 3-(4-{[(imidazo[1,2-a]pyridin-7-ylmethyl)carbamoyl]amino}phenyl)azetidine-1-carboxylate The title compound was prepared as described in Example 1C, substituting tert-butyl 3-(4-aminophenyl)azetidine-1-carboxylate for 4-amino-N-isopentylbenzamide and imidazo[1,2-a]pyridin-7-ylmethanamine for imidazo[1,2-a]pyridin-6-amine. $^1$H NMR (500 MHz, DMSO-$d_6$) δ ppm 8.66 (s, 1H), 8.48 (m, 1H), 7.88 (s, 1H), 7.51 (d, J=1.2 Hz, 1H), 7.39 (m, 3H), 7.19 (m, 2H), 6.83 (dd, J=7.0, 1.6 Hz, 1H), 6.70 (t, J=6.0

Hz, 1H), 4.33 (d, J=6.0 Hz, 2H), 4.20 (m, 2H), 3.78 (m, 2H), 3.71 (m, 1H), 1.40 (s, 9H); (ESI(+)) m/e 422 (M+H)$^+$.

Example 365 tert-butyl 4-{4-[(imidazo[1,2-a]pyridin-7-ylmethyl)carbamoyl]phenoxy}piperidine-1-carboxylate

The title compound was prepared as described in Example 1A, substituting imidazo[1,2-a]pyridin-7-ylmethanamine for 3-methylbutan-1-amine and 4-(1-(tert-butoxycarbonyl)piperidin-4-yloxy)benzoic acid for 4-nitrobenzoic acid. $^1$H NMR (500 MHz, DMSO-d$_6$) δ ppm 8.95 (t, J=6.0 Hz, 1H), 8.48 (dd, J=6.9, 0.9 Hz, 1H), 7.88 (m, 3H), 7.51 (d, J=1.2 Hz, 1H), 7.37 (s, 1H), 7.06 (m, 2H), 6.85 (dd, J=7.0, 1.6 Hz, 1H), 4.67 (m, 1H), 4.49 (d, J=5.9 Hz, 2H), 3.67 (m, 2H), 3.18 (m, 2H), 1.92 (m, 2H), 1.52 (m, 2H), 1.41 (s, 9H); (ESI(+)) m/e 451 (M+H)$^+$.

Example 366 tert-butyl 4-(4-{[(imidazo[1,2-a]pyridin-7-ylmethyl)carbamoyl]amino}phenoxy)piperidine-1-carboxylate

The title compound was prepared as described in Example 1C, substituting tert-butyl 4-(4-aminophenoxy)piperidine-1-carboxylate for 4-amino-N-isopentylbenzamide and imidazo[1,2-a]pyridin-7-ylmethanamine for imidazo[1,2-a]pyridin-6-amine. $^1$H NMR (400 MHz, DMSO-d$_6$) δ ppm 8.47 (m, 2H), 7.88 (d, J=1.1 Hz, 1H), 7.51 (d, J=1.2 Hz, 1H), 7.37 (s, 1H), 7.30 (m, 2H), 6.85 (m, 3H), 6.62 (t, J=6.0 Hz, 1H), 4.42 (m, 1H), 4.32 (d, J=6.0 Hz, 2H), 3.64 (m, 2H), 3.15 (m, 2H), 1.86 (m, 2H), 1.51 (m, 2H), 1.40 (s, 9H); (ESI(+)) m/e 466 (M+H)$^+$.

Example 367

N-(imidazo[1,2-a]pyridin-7-ylmethyl)-4-[1-(2-methylpropanoyl)pyrrolidin-3-yl]benzamide

Example 367A

N-(imidazo[1,2-a]pyridin-7-ylmethyl)-4-(pyrrolidin-3-yl)benzamide

The title compound was prepared as described in Example 28A, substituting tert-butyl 3-{4-[(imidazo[1,2-a]pyridin-7-ylmethyl)carbamoyl]phenyl}pyrrolidine-1-carboxylate for tert-butyl 4-(4-(3-imidazo[1,2-a]pyridin-6-ylureido)phenyl)-5,6-dihydropyridine-1(2H)-carboxylate.

Example 367B

N-(imidazo[1,2-a]pyridin-7-ylmethyl)-4-[1-(2-methylpropanoyl)pyrrolidin-3-yl]benzamide

The title compound was prepared as described in Example 1A, substituting N-(imidazo[1,2-a]pyridin-7-ylmethyl)-4-(pyrrolidin-3-yl)benzamide for 3-methylbutan-1-amine and isobutyric acid for 4-nitrobenzoic acid. $^1$H NMR (400 MHz, DMSO-d$_6$) δ ppm 9.07 (m, 1H), 8.48 (d, J=7.0 Hz, 1H), 7.88 (m, 3H), 7.51 (d, J=1.2 Hz, 1H), 7.42 (m, 3H), 6.85 (dd, J=7.0, 1.6 Hz, 1H), 4.50 (d, J=5.9 Hz, 2H), 3.90-3.66 (m, 1H), 3.63-3.20 (m, 4H), 2.70 (m, 1H), 2.38-2.18 (m, 1H), 2.10-1.90 (m, 1H), 1.01 (m, 6H); (ESI(+)) m/e 391 (M+H)$^+$.

TABLE 18

The following Examples were prepared essentially as described in Example 367, substituting the appropriate carboxylic acid in Example 367B.

| Ex | Name | $^1$H NMR | MS |
|---|---|---|---|
| 368 | N-(imidazo[1,2-a]pyridin-7-ylmethyl)-4-{1-[(2S)-2-methylbutanoyl]pyrrolidin-3-yl}benzamide | $^1$H NMR (400 MHz, DMSO-d$_6$) δ ppm 9.07 (m, 1H), 8.48 (d, J = 7.0 Hz, 1H), 7.87 (m, 3H), 7.52 (d, J = 1.2 Hz, 1H), 7.41 (m, 3H), 6.85 (dd, J = 7.0, 1.6 Hz, 1H), 4.50 (d, J = 5.9 Hz, 2H), 3.90-3.66 (m, 1H), 3.63-3.20 (m, 4H), 2.51 (m, 1H), 2.38-2.18 (m, 1H), 2.10-1.90 (m, 1H), 1.57 (m, 1H), 1.34 (m, 1H), 1.01 (m, 3H), 0.86 (m, 3H) | (ESI(+)) m/e 405 (M + H)$^+$ |
| 369 | 4-[1-(cyclopropylacetyl)pyrrolidin-3-yl]-N-(imidazo[1,2-a]pyridin-7-ylmethyl)benzamide | $^1$H NMR (500 MHz, DMSO-d$_6$) δ ppm 9.07 (m, 1H), 8.48 (d, J = 7.0 Hz, 1H), 7.88 (m, 3H), 7.52 (d, J = 1.2 Hz, 1H), 7.42 (m, 3H), 6.85 (dd, J = 7.0, 1.6 Hz, 1H), 4.50 (d, J = 5.9 Hz, 2H), 3.88 (m, 1H), 3.61 (m, 1H), 3.60-3.20 (m, 3H), 2.35-2.15 (m, 3H), 2.10-1.88 (m, 1H), 1.99 (m, 1H), 0.44 (m, 2H), 0.12 (m, 2H) | (ESI(+)) m/e 403 (M + H)$^+$ |
| 370 | 4-(1-benzoylpyrrolidin-3-yl)-N-(imidazo[1,2-a]pyridin-7-ylmethyl)benzamide | $^1$H NMR (500 MHz, DMSO-d$_6$) δ ppm 9.07 (m, 1H), 8.48 (t, J = 6.2 Hz, 1H), 7.88 (m, 3H), 7.55 (m, 2H), 7.54-7.34 (m, 7H), 6.85 (m, 1H), 4.50 (m, 2H), 4.00 (m, 1H), 3.73 (m, 1H), 3.65-3.40 (m, 3H), 2.38-2.22 (m, 1H), 2.15-1.94 (m, 1H) | (ESI(+)) m/e 425 (M + H)$^+$ |
| 371 | N-(imidazo[1,2-a]pyridin-7-ylmethyl)-4-{1-[(propan-2-yloxy)acetyl]pyrrolidin-3-yl}benzamide | $^1$H NMR (500 MHz, DMSO-d$_6$) δ ppm 9.07 (m, 1H), 8.48 (d, J = 7.0 Hz, 1H), 7.89 (m, 3H), 7.52 (d, J = 1.2 Hz, 1H), 7.41 (m, 3H), 6.85 (dd, J = 7.0, 1.6 Hz, 1H), 4.51 (d, J = 5.9 Hz, 2H), 4.05 (d, J = 4.5 Hz, 2H), 3.95-3.81 (m, 1H), 3.70-3.55 (m, 2H), 3.55-3.20 (m, 3H), 2.38-2.18 (m, 1H), 2.08-1.88 (m, 1H), 1.11 (m, 6H) | (ESI(+)) m/e 421 (M + H)$^+$ |

TABLE 18-continued

The following Examples were prepared essentially as described in Example 367, substituting the appropriate carboxylic acid in Example 367B.

| Ex | Name | $^1$H NMR | MS |
|---|---|---|---|
| 372 | 4-[1-(2-hydroxy-2-methylpropanoyl)pyrrolidin-3-yl]-N-(imidazo[1,2-a]pyridin-7-ylmethyl)benzamide | $^1$H NMR (500 MHz, DMSO-d$_6$) δ ppm 9.07 (t, J = 6.0 Hz, 1H), 8.48 (d, J = 7.0 Hz, 1H), 7.88 (m, 3H), 7.52 (d, J = 1.2 Hz, 1H), 7.42 (m, 2H), 7.38 (m, 1H), 6.85 (dd, J = 7.0, 1.6 Hz, 1H), 5.15 (m, 1H), 4.50 (d, J = 5.9 Hz, 2H), 4.34 (m, 1H), 3.85-3.65 (m, 1H), 3.59 (m, 3H), 2.35-2.10 (m, 1H), 2.05-1.86 (m, 1H), 1.30 (m, 6H); ) | (ESI(+)) m/e 407 (M + H)$^+$ |
| 373 | N-(imidazo[1,2-a]pyridin-7-ylmethyl)-4-{1-[(2R)-tetrahydrofuran-2-ylcarbonyl]pyrrolidin-3-yl}benzamide | $^1$H NMR (500 MHz, DMSO-d$_6$) δ ppm 9.07 (m, 1H), 8.48 (d, J = 7.0 Hz, 1H), 7.88 (m, 3H), 7.52 (s, 1H), 7.45-7.35 (m, 3H), 6.85 (d, J = 7.1 Hz, 1H), 4.55 (m, 1H), 4.50 (m, 2H), 4.10-3.93 (m, 1H), 3.90-3.65 (m, 3H), 3.65-3.20 (m, 3H) 2.37-2.19 (m, 1H), 2.10-1.76 (m, 5H) | (ESI(+)) m/e 419 (M + H)$^+$ |
| 374 | N-(imidazo[1,2-a]pyridin-7-ylmethyl)-4-{1-[(2S)-tetrahydrofuran-2-ylcarbonyl]pyrrolidin-3-yl}benzamide | $^1$H NMR (500 MHz, DMSO-d$_6$) δ ppm 9.08 (m, 1H), 8.48 (m, 1H), 7.88 (m, 3H), 7.52 (s, 1H), 7.45-7.37 (m, 3H), 6.85 (dd, J = 7.0, 1.6 Hz, 1H), 4.55 (m, 1H), 4.50 (m, 2H), 4.10-3.93 (m, 1H), 3.90-3.65 (m, 3H), 3.65-3.20 (m, 3H) 2.37-2.19 (m, 1H), 2.10-1.75 (m, 5H) | (ESI(+)) m/e 419 (M + H)$^+$ |
| 375 | N-(imidazo[1,2-a]pyridin-7-ylmethyl)-4-{1-[(3S)-tetrahydrofuran-3-ylcarbonyl]pyrrolidin-3-yl}benzamide | $^1$H NMR (500 MHz, DMSO-d$_6$) δ ppm 9.08 (m, 1H), 8.48 (d, J = 7.0 Hz, 1H), 7.89 (m, 3H), 7.52 (s, 1H), 7.46 (m, 2H), 7.41 (m, 1H), 7.38 (m, 1H), 6.85 (d, J = 7.1 Hz, 1H), 4.51 (m, 2H), 4.10-3.93 (m, 1H), 3.95-3.80 (m, 2H), 3.65-3.20 (m, 6H), 2.36-2.20 (m, 1H), 2.14-1.85 (m, 4H) | (ESI(+)) m/e 419 (M + H)$^+$ |
| 376 | N-(imidazo[1,2-a]pyridin-7-ylmethyl)-4-[1-(tetrahydro-2H-pyran-4-ylcarbonyl)pyrrolidin-3-yl]benzamide | $^1$H NMR (500 MHz, DMSO-d$_6$) δ ppm 9.07 (m, 1H), 8.48 (d, J = 7.0 Hz, 1H), 7.88 (m, 3H), 7.51 (s, 1H), 7.45 (d, J = 8.0 Hz, 1H), 7.41 (m, 2H), 6.85 (m, 1H), 4.51 (d, J = 3.0 Hz, 2H), 3.88 (m, 3H), 3.75 (m, .55 (m, 2H), 3.55-3.20 (m, 3H), 2.71 (m, 1H), 2.39-2.19 (m, 1H), 2.10-1.85 (m, 1H), 1.59 (m, 4H) | (ESI(+)) m/e 433 (M + H)$^+$ |
| 377 | 4-[1-(1,4-dioxan-2-ylcarbonyl)pyrrolidin-3-yl]-N-(imidazo[1,2-a]pyridin-7-ylmethyl)benzamide | $^1$H NMR (500 MHz, DMSO-d$_6$) δ ppm 9.07 (m, 1H), 8.48 (d, J = 7.1 Hz, 1H), 7.89 (m, 3H), 7.52 (s, 1H), 7.43 (m, 2H), 7.38 (s, 1H), 6.85 (d, J = 7.1 Hz, 1H), 4.51 (dd, J = 5.8, 2.9 Hz, 2H), 4.27 (m, 2H), 4.15-4.00 (m, 1H), 3.90-3.70 (m, 4H), 3.70-3.20 (m, 5H); 2.39-2.19 (m, 1H), 2.15-1.88 (m, 1H) | (ESI(+)) m/e 435 (M + H)$^+$ |
| 378 | N-(imidazo[1,2-a]pyridin-7-ylmethyl)-4-[1-(tetrahydro-2H-pyran-4-ylacetyl)pyrrolidin-3-yl]benzamide | $^1$H NMR (500 MHz, DMSO-d$_6$) δ ppm 9.07 (m, 1H), 8.48 (d, J = 7.0 Hz, 1H), 7.88 (m, 3H), 7.52 (s, 1H), 7.42 (m, 2H), 7.38 (s, 1H), 6.85 (d, J = 7.1 Hz, 1H), 4.51 (m, 2H), 3.95 (m, 1H), 3.83 (m, 3H), 3.63 (m, 1H), 3.47 (m, 2H), 3.45-3.20 (m, 2H), 2.38-2.15 (m, 3H), 2.10-1.90 (m, 2H), 1.56 (m, 2H), 1.21 (m, 2H) | (ESI(+)) m/e 447 (M + H)$^+$ |
| 488 | N-(imidazo[1,2-a]pyridin-7-ylmethyl)-4-[1-(thiophen-2-ylcarbonyl)pyrrolidin-3-yl]benzamide | | (ESI(+)) m/e 431 (M + H)$^+$ |
| 562 | 4-[1-(4-fluorobenzoyl)pyrrolidin-3-yl]-N-(imidazo[1,2-a]pyridin-7-ylmethyl)benzamide | | (ESI(+)) m/e 443 (M + H)$^+$ |
| 580 | N-(imidazo[1,2-a]pyridin-7-ylmethyl)-4-{1- | | (ESI(+)) m/e 403 (M + H)$^+$ |

TABLE 18-continued

The following Examples were prepared essentially as described in Example 367, substituting the appropriate carboxylic acid in Example 367B.

| Ex | Name | $^1$H NMR | MS |
|---|---|---|---|
| | [(2-methylcyclopropyl)carbonyl]pyrrolidin-3-yl}benzamide | | |
| 581 | 4-[1-(cyclopentylacetyl)pyrrolidin-3-yl]-N-(imidazo[1,2-a]pyridin-7-ylmethyl)benzamide | | (ESI(+)) m/e 431 (M + H)$^+$ |
| 582 | N-(imidazo[1,2-a]pyridin-7-ylmethyl)-4-[1-(3-methylpentanoyl)pyrrolidin-3-yl]benzamide | | (ESI(+)) m/e 419 (M + H)$^+$ |
| 583 | 4-[1-(cyclopentylcarbonyl)pyrrolidin-3-yl]-N-(imidazo[1,2-a]pyridin-7-ylmethyl)benzamide | | (ESI(+)) m/e 417 (M + H)$^+$ |
| 584 | N-(imidazo[1,2-a]pyridin-7-ylmethyl)-4-{1-[(1-methylcyclopropyl)carbonyl]pyrrolidin-3-yl}benzamide | | (ESI(+)) m/e 403 (M + H)$^+$ |
| 585 | 4-[1-(2,2-dimethylpropanoyl)pyrrolidin-3-yl]-N-(imidazo[1,2-a]pyridin-7-ylmethyl)benzamide | | (ESI(+)) m/e 405 (M + H)$^+$ |
| 586 | N-(imidazo[1,2-a]pyridin-7-ylmethyl)-4-[1-(1,3-thiazol-5-ylcarbonyl)pyrrolidin-3-yl]benzamide | | (ESI(+)) m/e 432 (M + H)$^+$ |
| 587 | N-(imidazo[1,2-a]pyridin-7-ylmethyl)-4-[1-(2-methoxybenzoyl)pyrrolidin-3-yl]benzamide | | (ESI(+)) m/e 455 (M + H)$^+$ |
| 588 | N-(imidazo[1,2-a]pyridin-7-ylmethyl)-4-[1-(1,3-thiazol-4-ylcarbonyl)pyrrolidin-3-yl]benzamide | | (ESI(+)) m/e 432 (M + H)$^+$ |
| 589 | 4-[1-(2-fluorobenzoyl)pyrrolidin-3-yl]-N-(imidazo[1,2-a]pyridin-7-ylmethyl)benzamide | | (ESI(+)) m/e 443 (M + H)$^+$ |
| 590 | 4-[1-(furan-2-ylcarbonyl)pyrrolidin-3-yl]-N-(imidazo[1,2-a]pyridin-7-ylmethyl)benzamide | | (ESI(+)) m/e 415 (M + H)$^+$ |
| 591 | 4-[1-(3-fluorobenzoyl)pyrrolidin-3-yl]-N-(imidazo[1,2-a]pyridin-7-ylmethyl)benzamide | | (ESI(+)) m/e 443 (M + H)$^+$ |
| 592 | 4-[1-(2,4-difluorobenzoyl)pyrrolidin-3-yl]-N- | | (ESI(+)) m/e 461 (M + H)$^+$ |

TABLE 18-continued

The following Examples were prepared essentially as described in Example 367, substituting the appropriate carboxylic acid in Example 367B.

| Ex | Name | ¹H NMR | MS |
|---|---|---|---|
| | (imidazo[1,2-a]pyridin-7-ylmethyl)benzamide | | |
| 593 | N-(imidazo[1,2-a]pyridin-7-ylmethyl)-4-{1-[(1-methyl-1H-pyrazol-3-yl)carbonyl]pyrrolidin-3-yl}benzamide | | (ESI(+)) m/e 429 (M + H)⁺ |
| 594 | 4-[1-(2-chlorobenzoyl)pyrrolidin-3-yl]-N-(imidazo[1,2-a]pyridin-7-ylmethyl)benzamide | | (ESI(+)) m/e 459 (M + H)⁺ |
| 595 | N-(imidazo[1,2-a]pyridin-7-ylmethyl)-4-[1-(2-methylbenzoyl)pyrrolidin-3-yl]benzamide | | (ESI(+)) m/e 439 (M + H)⁺ |
| 596 | 4-[1-(4-chlorobenzoyl)pyrrolidin-3-yl]-N-(imidazo[1,2-a]pyridin-7-ylmethyl)benzamide | | (ESI(+)) m/e 459 (M + H)⁺ |
| 597 | 4-[1-(3-chlorobenzoyl)pyrrolidin-3-yl]-N-(imidazo[1,2-a]pyridin-7-ylmethyl)benzamide | | (ESI(+)) m/e 459 (M + H)⁺ |
| 598 | 4-[1-(2,2-dimethylbutanoyl)pyrrolidin-3-yl]-N-(imidazo[1,2-a]pyridin-7-ylmethyl)benzamide | | (ESI(+)) m/e 419 (M + H)⁺ |
| 599 | 4-[1-(3,5-difluorobenzoyl)pyrrolidin-3-yl]-N-(imidazo[1,2-a]pyridin-7-ylmethyl)benzamide | | (ESI(+)) m/e 461 (M + H)⁺ |
| 600 | N-(imidazo[1,2-a]pyridin-7-ylmethyl)-4-[1-(4-methylbenzoyl)pyrrolidin-3-yl]benzamide | | (ESI(+)) m/e 439 (M + H)⁺ |
| 601 | N-(imidazo[1,2-a]pyridin-7-ylmethyl)-4-[1-(3-methylbutanoyl)pyrrolidin-3-yl]benzamide | | (ESI(+)) m/e 405 (M + H)⁺ |
| 602 | 4-[1-(3,3-dimethylbutanoyl)pyrrolidin-3-yl]-N-(imidazo[1,2-a]pyridin-7-ylmethyl)benzamide | | (ESI(+)) m/e 419 (M + H)⁺ |
| 603 | 4-[1-(3-cyanobenzoyl)pyrrolidin-3-yl]-N-(imidazo[1,2-a]pyridin-7-ylmethyl)benzamide | | (ESI(+)) m/e 450 (M + H)⁺ |
| 604 | N-(imidazo[1,2-a]pyridin-7-ylmethyl)-4-[1-(3-methoxybenzoyl)pyrrolidin- | | (ESI(+)) m/e 455 (M + H)⁺ |

TABLE 18-continued

The following Examples were prepared essentially as described in Example 367, substituting the appropriate carboxylic acid in Example 367B.

| Ex | Name | $^1$H NMR | MS |
|---|---|---|---|
| 605 | N-(imidazo[1,2-a]pyridin-7-ylmethyl)-4-[1-(4-methoxybenzoyl)pyrrolidin-3-yl]benzamide | | (ESI(+)) m/e 455 (M + H)$^+$ |
| 606 | N-(imidazo[1,2-a]pyridin-7-ylmethyl)-4-{1-[(1-methyl-1H-pyrrol-2-yl)carbonyl]pyrrolidin-3-yl}benzamide | | (ESI(+)) m/e 428 (M + H)$^+$ |
| 607 | 4-[1-(cyclohexylacetyl)pyrrolidin-3-yl]-N-(imidazo[1,2-a]pyridin-7-ylmethyl)benzamide | | (ESI(+)) m/e 445 (M + H)$^+$ |
| 608 | N-(imidazo[1,2-a]pyridin-7-ylmethyl)-4-[1-(pyridin-4-ylcarbonyl)pyrrolidin-3-yl]benzamide | | (ESI(+)) m/e 426 (M + H)$^+$ |
| 609 | N-(imidazo[1,2-a]pyridin-7-ylmethyl)-4-[1-(pyridin-3-ylcarbonyl)pyrrolidin-3-yl]benzamide | | (ESI(+)) m/e 426 (M + H)$^+$ |
| 610 | 4-[1-(cyclohexylcarbonyl)pyrrolidin-3-yl]-N-(imidazo[1,2-a]pyridin-7-ylmethyl)benzamide | | (ESI(+)) m/e 431 (M + H)$^+$ |
| 611 | N-(imidazo[1,2-a]pyridin-7-ylmethyl)-4-[1-(pyridin-2-ylcarbonyl)pyrrolidin-3-yl]benzamide | | (ESI(+)) m/e 426 (M + H)$^+$ |
| 612 | 4-[1-(furan-3-ylcarbonyl)pyrrolidin-3-yl]-N-(imidazo[1,2-a]pyridin-7-ylmethyl)benzamide | | (ESI(+)) m/e 415 (M + H)$^+$ |
| 613 | N-(imidazo[1,2-a]pyridin-7-ylmethyl)-4-[1-(1,3-thiazol-2-ylcarbonyl)pyrrolidin-3-yl]benzamide | | (ESI(+)) m/e 432 (M + H)$^+$ |
| 614 | N-(imidazo[1,2-a]pyridin-7-ylmethyl)-4-{1-[(1-methylcyclohexyl)carbonyl]pyrrolidin-3-yl}benzamide | | (ESI(+)) m/e 445 (M + H)$^+$ |
| 615 | 4-[1-(2,3-dimethylbutanoyl)pyrrolidin-3-yl]-N-(imidazo[1,2-a]pyridin-7-ylmethyl)benzamide | | (ESI(+)) m/e 419 (M + H)$^+$ |

TABLE 18-continued

The following Examples were prepared essentially as described in Example 367, substituting the appropriate carboxylic acid in Example 367B.

| Ex | Name | $^1$H NMR | MS |
|---|---|---|---|
| 616 | N-(imidazo[1,2-a]pyridin-7-ylmethyl)-4-[1-(3-methylbenzoyl)pyrrolidin-3-yl]benzamide | | (ESI(+)) m/e 439 (M + H)$^+$ |
| 617 | N-(imidazo[1,2-a]pyridin-7-ylmethyl)-4-[1-(thiophen-3-ylcarbonyl)pyrrolidin-3-yl]benzamide | | (ESI(+)) m/e 431 (M + H)$^+$ |
| 618 | N-(imidazo[1,2-a]pyridin-7-ylmethyl)-4-{1-[3-(trifluoromethoxy)benzoyl]pyrrolidin-3-yl}benzamide | | (ESI(+)) m/e 509 (M + H)$^+$ |
| 619 | N-(imidazo[1,2-a]pyridin-7-ylmethyl)-4-{1-[(3-methylthiophen-2-yl)carbonyl]pyrrolidin-3-yl}benzamide | | (ESI(+)) m/e 445 (M + H)$^+$ |
| 620 | N-(imidazo[1,2-a]pyridin-7-ylmethyl)-4-{1-[3-(trifluoromethyl)benzoyl]pyrrolidin-3-yl}benzamide | | (ESI(+)) m/e 493 (M + H)$^+$ |
| 731 | N-(imidazo[1,2-a]pyridin-7-ylmethyl)-4-[1-(phenylacetyl)pyrrolidin-3-yl]benzamide | | (ESI(+)) m/e 439 (M + H)$^+$ |
| 732 | N-(imidazo[1,2-a]pyridin-7-ylmethyl)-4-[1-(2-methyl-2-phenylpropanoyl)pyrrolidin-3-yl]benzamide | | (ESI(+)) m/e 467 (M + H)$^+$ |
| 733 | 4-{1-[difluoro(phenyl)acetyl]pyrrolidin-3-yl}-N-(imidazo[1,2-a]pyridin-7-ylmethyl)benzamide | | (ESI(+)) m/e 475 (M + H)$^+$ |

Example 379

1-[4-(1-acetylpyrrolidin-3-yl)phenyl]-3-(imidazo[1,2-a]pyridin-7-ylmethyl)urea

Example 379A 1-(imidazo[1,2-a]pyridin-7-ylmethyl)-3-(4-(pyrrolidin-3-yl)phenyl)urea The title compound was prepared as described in Example 28A, substituting tert-butyl 3-(4-{[(imidazo[1,2-a]pyridin-7-ylmethyl)carbamoyl]amino}phenyl)pyrrolidine-1-carboxylate for tert-butyl 4-(4-(3-imidazo[1,2-a]pyridin-6-ylureido)phenyl)-5,6-dihydropyridine-1(2H)-carboxylate.

Example 379B

1-[4-(1-acetylpyrrolidin-3-yl)phenyl]-3-(imidazo[1,2-a]pyridin-7-ylmethyl)urea

The title compound was prepared as described in Example 1A, substituting 1-(imidazo[1,2-a]pyridin-7-ylmethyl)-3-(4-(pyrrolidin-3-yl)phenyl)urea for 3-methylbutan-1-amine and acetic acid for 4-nitrobenzoic acid. $^1$H NMR (500 MHz, DMSO-d$_6$) δ ppm 8.62 (d, J=6.4 Hz, 1H), 8.48 (d, J=7.0 Hz, 1H), 7.88 (s, 1H), 7.51 (s, 1H), 7.37 (m, 3H), 7.16 (m, 2H), 6.83 (dd, J=7.0, 1.6 Hz, 1H), 6.69 (m, 1H), 4.33 (d, J=6.0 Hz, 2H), 3.89-3.73 (m, 1H), 3.65-3.45 (m, 3H), 3.10 (m, 1H), 2.29-2.11 (m, 1H), 2.00-1.80 (m, 1H), 1.91 (s, 3H); (ESI(+)) m/e 378 (M+H)$^+$.

TABLE 19

The following Examples were prepared essentially as described in Example 379, substituting the appropriate carboxylic acid in Example 379B.

| Ex | Name | ¹H NMR | MS |
|---|---|---|---|
| 380 | 1-(imidazo[1,2-a]pyridin-7-ylmethyl)-3-{4-[1-(2-methylpropanoyl)pyrrolidin-3-yl]phenyl}urea | ¹H NMR (500 MHz, DMSO-d₆) δ ppm 8.62 (d, J = 6.5 Hz, 1H), 8.48 (d, J = 7.0 Hz, 1H), 7.88 (s, 1H), 7.51 (s, 1H), 7.36 (m, 3H), 7.16 (m, 2H), 6.83 (d, J = 7.1 Hz, 1H), 6.70 (m, 1H), 4.33 (d, J = 6.0 Hz, 2H), 3.80-3.65 (m, 1H), 3.60-3.48 (m, 1H), 3.45-3.20 (m, 2H), 3.13 (m, 1H), 2.68 (m, 1H), 2.30-2.10 (m, 1H), 2.05-1.80 (m, 1H), 1.00 (m, 6H) | (ESI(+)) m/e 406 (M + H)⁺ |
| 381 | 1-(imidazo[1,2-a]pyridin-7-ylmethyl)-3-(4-{1-[(2S)-2-methylbutanoyl]pyrrolidin-3-yl}phenyl)urea | ¹H NMR (500 MHz, DMSO-d₆) δ ppm 8.62 (d, J = 6.5 Hz, 1H), 8.48 (d, J = 7.0 Hz, 1H), 7.88 (s, 1H), 7.52 (s, 1H), 7.37 (m, 3H), 7.17 (m, 2H), 6.83 (dd, J = 7.0, 1.6 Hz, 1H), 6.69 (t, J = 6.0 Hz, 1H), 4.33 (d, J = 6.0 Hz, 2H), 3.95-3.75 (m, 1H), 3.70-3.45 (m, 2H), 3.45-3.20 (m, 1H), 3.20 (m, 1H), 2.30-2.11 (m, 1H), 2.05-1.80 (m, 1H), 1.55 (m, 1H), 1.25 (m, 2H), 0.96 (m, 3H), 0.87 (m, 3H) | (ESI(+)) m/e 420 (M + H)⁺ |
| 382 | 1-{4-[1-(cyclopropylacetyl)pyrrolidin-3-yl]phenyl}-3-(imidazo[1,2-a]pyridin-7-ylmethyl)urea | -¹H NMR (500 MHz, DMSO-d₆) δ ppm 8.62 (d, J = 4.1 Hz, 1H), 8.49 (d, J = 7.0 Hz, 1H), 7.89 (s, 1H), 7.52 (s, 1H), 7.37 (m, 3H), 7.16 (m, 2H), 6.84 (d, J = 7.1 Hz, 1H), 6.69 (t, J = 6.0 Hz, 1H), 4.33 (d, J = 6.0 Hz, 2H), 3.80 (m, 1H), 3.58 (m, 1H), 3.45 (m, 1H), 3.40-3.20 (m, 1H), 3.12 (m, 1H), 2.27-2.11 (m, 3H), 1.99-1.81 (m, 1H), 0.98 (m, 1H), 0.44 (m, 2H), 0.11 (m, 2H) | (ESI(+)) m/e 418 (M + H)⁺ |
| 383 | 1-[4-(1-benzoylpyrrolidin-3-yl)phenyl]-3-(imidazo[1,2-a]pyridin-7-ylmethyl)urea | ¹H NMR (500 MHz, DMSO-d₆) δ ppm 8.62 (m, 1H), 8.48 (d, J = 6.1 Hz, 1H), 7.88 (d, J = 3.0 Hz, 1H), 7.53 (m, 3H), 7.50-7.35 (m, 5H), 7.34 (d, 1H), 7.20 (d, J = 8.2 Hz, 1H), 7.13 (d, J = 8.2 Hz, 1H), 6.83 (m, 1H), 6.68 (m, 1H), 4.33 (d, J = 14.1 Hz, 2H), 3.68 (m, 1H), 3.60-3.45 (m, 2H), 3.40-3.20 (m, 2H), 2.29-2.13 (m, 1H) 2.07-1.90 (m, 1H) | (ESI(+)) m/e 440 (M + H)⁺ |
| 384 | 1-(imidazo[1,2-a]pyridin-7-ylmethyl)-3-(4-{1-[(propan-2-yloxy)acetyl]pyrrolidin-3-yl}phenyl)urea | -¹H NMR (500 MHz, DMSO-d₆) δ ppm 8.63 (d, J = 6.0 Hz, 1H), 8.48 (d, J = 7.0 Hz, 1H), 7.88 (s, 1H), 7.51 (s, 1H), 7.37 (m, 3H), 7.16 (m, 2H), 6.83 (dd, J = 7.0, 1.6 Hz, 1H), 6.70 (m, 1H), 4.33 (d, J = 6.0 Hz, 2H), 4.03 (d, J = 5.4 Hz, 2H), 3.90-3.74 (m, 1H), 3.68-3.52 (m, 2H), 3.47 (m, 1H), 3.40-3.20 (m, 1H), 3.16 (m, 1H), 2.29-2.11 (m, 1H), 2.00-1.73 (m, 1H), 1.10 (m, 6H) | (ESI(+)) m/e 436 (M + H)⁺ |
| 385 | 1-{4-[1-(2-hydroxy-2-methylpropanoyl)pyrrolidin-3-yl]phenyl}-3-(imidazo[1,2-a]pyridin-7-ylmethyl)urea | ¹H NMR (500 MHz, DMSO-d₆) δ ppm 8.65 (d, J = 6.0 Hz, 1H), 8.48 (d, J = 7.0 Hz, 1H), 7.88 (s, 1H), 7.51 (s, 1H), 7.37 (m, 3H), 7.16 (m, 2H), 6.83 (dd, J = 7.0, 1.6 Hz, 1H), 6.73 (m, 1H), 5.18 (bs, 1H), 4.33 (d, J = 6.0 Hz, 2H), 4.28 (m, 1H), 3.80-3.60 (m, 1H), 3.60-3.10 (m, 3H), 2.25-2.08 (m, 1H), 1.97-1.73 (m, 1H), 1.30 (m, 6H) | (ESI(+)) m/e 422 (M + H)⁺ |
| 386 | 1-(imidazo[1,2-a]pyridin-7-ylmethyl)-3-(4-{1-[(2R)-tetrahydrofuran-2-ylcarbonyl]pyrrolidin-3-yl}phenyl)urea | ¹H NMR (500 MHz, DMSO-d₆) δ ppm 8.62 (d, J = 5.7 Hz, 1H), 8.48 (d, J = 7.0 Hz, 1H), 7.88 (s, 1H), 7.51 (s, 1H), 7.37 (m, 3H), 7.16 (m, 2H), 6.83 (d, J = 6.2 Hz, 1H), 6.69 (t, J = 6.0 Hz, 1H), 4.53 (m, 1H), 4.33 (d, J = 6.0 Hz, 2H), 3.85-3.64 (m, 3H), 3.63-3.45 (m, 1H), 3.45-3.20 (m, 2H), 3.16 (m, 1H), 2.29-2.10 (m, 1H), 2.08-1.92 (m, 2H), 1.91-1.73 (m, 3H) | (ESI(+)) m/e 434 (M + H)⁺ |
| 387 | 1-(imidazo[1,2-a]pyridin-7-ylmethyl)-3-(4-{1-[(2S)-tetrahydrofuran-2-ylcarbonyl]pyrrolidin-3-yl}phenyl)urea | -¹H NMR (500 MHz, DMSO-d₆) δ ppm 8.62 (d, J = 5.6 Hz, 1H), 8.48 (d, J = 7.0 Hz, 1H), 7.88 (s, 1H), 7.51 (s, 1H), 7.36 (m, 3H), 7.16 (m, 2H), 6.83 (dd, J = 7.0, 1.6 Hz, 1H), 6.69 (t, J = 6.0 Hz, 1H), 4.53 (m, 1H), 4.33 (d, J = 6.0 Hz, 2H), 3.84-3.64 (m, 3H), 3.63-3.45 (m, 1H), 3.45-3.20 (m, 2H), 3.16 (m, 1H), 2.29-2.10 (m, 1H), 2.05-1.85 (m, 5H) | (ESI(+)) m/e 434 (M + H)⁺ |
| 388 | 1-(imidazo[1,2-a]pyridin-7- | ¹H NMR (500 MHz, DMSO-d₆) δ ppm 8.63 (d, J = 6.7 Hz, 1H), 8.48 (d, J = 7.0 Hz, | (ESI(+)) m/e |

TABLE 19-continued

The following Examples were prepared essentially as described in Example 379, substituting the appropriate carboxylic acid in Example 379B.

| Ex | Name | ¹H NMR | MS |
|---|---|---|---|
|  | ylmethyl)-3-(4-{1-[(3S)-tetrahydrofuran-3-ylcarbonyl]pyrrolidin-3-yl}phenyl)urea | 1H), 7.88 (s, 1H), 7.52 (s, 1H), 7.37 (m, 3H), 7.17 (m, 2H), 6.83 (dd, J = 7.0, 1.6 Hz, 1H), 6.70 (m, 1H), 4.33 (d, J = 6.0 Hz, 2H), 3.97-3.84 (m, 2H), 3.80-3.63 (m, 4H), 3.62-3.46 (m, 1H), 3.45-3.10 (m, 3H), 2.29-2.10 (m, 1H), 2.09-1.83 (m, 3H) | 434 (M + H)⁺ |
| 389 | 1-(imidazo[1,2-a]pyridin-7-ylmethyl)-3-{4-[1-(tetrahydro-2H-pyran-4-ylcarbonyl)pyrrolidin-3-yl]phenyl}urea | ¹H NMR (500 MHz, DMSO-d₆) δ ppm 8.62 (d, J = 7.5 Hz, 1H), 8.48 (d, J = 7.0 Hz, 1H), 7.88 (s, 1H), 7.51 (s, 1H), 7.36 (m, 3H), 7.16 (m, 2H), 6.83 (d, J = 7.1 Hz, 1H), 6.69 (t, J = 6.0 Hz, 1H), 4.33 (d, J = 6.0 Hz, 2H), 3.90-3.70 (m, 3H), 3.55 (m, 1H), 3.45-3.20 (m, 3H), 3.15 (m, 1H), 2.70 (m, 1H), 2.28-2.11 (m, 1H), 2.00-1.82 (m, 1H), 1.57 (m, 4H) | (ESI(+)) m/e 448 (M + H)⁺ |
| 390 | 1-{4-[1-(1,4-dioxan-2-ylcarbonyl)pyrrolidin-3-yl]phenyl}-3-(imidazo[1,2-a]pyridin-7-ylmethyl)urea | ¹H NMR (500 MHz, DMSO-d₆) δ ppm 8.62 (d, J = 7.5 Hz, 1H), 8.48 (d, J = 7.0 Hz, 1H), 7.88 (s, 1H), 7.51 (s, 1H), 7.37 (m, 3H), 7.16 (m, 2H), 6.83 (d, J = 7.1 Hz, 1H), 6.70 (t, J = 6.0 Hz, 1H), 4.33 (d, J = 6.0 Hz, 2H), 4.25 (m, 1H), 3.85-3.70 (m, 3H), 3.70-3.60 (m, 2H), 3.60-3.45 (m, 3H), 3.45-3.15 (m, 3H), 2.28-2.11 (m, 1H), 2.00-1.80 (m, 1H) | (ESI(+)) m/e 450 (M + H)⁺ |
| 391 | 1-(imidazo[1,2-a]pyridin-7-ylmethyl)-3-{4-[1-(tetrahydro-2H-pyran-4-ylacetyl)pyrrolidin-3-yl]phenyl}urea | -¹H NMR (400 MHz, DMSO-d₆) δ ppm 8.62 (d, J = 5.5 Hz, 1H), 8.48 (d, J = 7.0 Hz, 1H), 7.88 (s, 1H), 7.51 (s, 1H), 7.36 (m, 3H), 7.16 (m, 2H), 6.83 (dd, J = 7.0, 1.6 Hz, 1H), 6.69 (t, J = 6.0 Hz, 1H), 4.33 (d, J = 5.9 Hz, 2H), 3.90-3.72 (m, 3H), 3.67-3.40 (m, 2H), 3.27-3.08 (m, 2H), 3.14 (m, 1H), 2.28-2.10 (m, 3H), 2.00-1.80 (m, 3H), 1.59 (m, 2H), 1.17 (m, 2H) | (ESI(+)) m/e 462 (M + H)⁺ |
| 392 | 1-(imidazo[1,2-a]pyridin-7-ylmethyl)-3-{4-[1-(morpholin-4-ylacetyl)pyrrolidin-3-yl]phenyl}urea | -¹H NMR (400 MHz, DMSO-d₆) δ ppm 8.65 (d, J = 6.1 Hz, 1H), 8.48 (d, J = 6.9 Hz, 1H), 7.88 (s, 1H), 7.51 (d, J = 1.2 Hz, 1H), 736 (m, 3H), 7.16 (m, 2H), 6.83 (dd, J = 6.9, 1.7 Hz, 1H), 6.72 (td, J = 6.0, 2.3 Hz, 1H), 4.33 (d, J = 5.9 Hz, 2H), 3.74 (m, 1H), 3.55 (m, 4H), 3.45-3.20 (m, 2H), 3.17 (s, 2H), 3.13-3.03 (m, 2H), 2.44 (m, 4H), 2.30-2.10 (m, 1H), 2.00-1.80 (m, 1H) | (ESI(+)) m/e 463 (M + H)⁺ |

Example 393

N-(imidazo[1,2-a]pyridin-7-ylmethyl)-N'-(3-methylbutyl)benzene-1,4-dicarboxamide

Example 393A methyl 4-(imidazo[1,2-a]pyridin-7-ylmethylcarbamoyl)benzoate

The title compound was prepared as described in Example 1A, substituting imidazo[1,2-a]pyridin-7-ylmethanamine for 3-methylbutan-1-amine and 4-(methoxycarbonyl)benzoic acid for 4-nitrobenzoic acid.

Example 393B 4-(imidazo[1,2-a]pyridin-7-ylmethylcarbamoyl)benzoic acid

The title compound was prepared as described in Example 4B, substituting methyl 4-(imidazo[1,2-a]pyridin-7-ylmethylcarbamoyl)benzoate for methyl 4-(3-imidazo[1,2-a]pyridin-6-ylureido)benzoate.

Example 393C

N-(imidazo[1,2-a]pyridin-6-ylmethyl)-N'-(3-methylbutyl)benzene-1,4-dicarboxamide The title compound was prepared as described in Example 1A, substituting 3-methylbutan-1-amine for 3-methylbutan-1-amine and 4-(imidazo[1,2-a]pyridin-7-ylmethylcarbamoyl)benzoic acid for 4-nitrobenzoic acid. ¹H NMR (300 MHz, DMSO-d₆) δ ppm 9.25-9.11 (m, 1H), 8.57-8.37 (m, 2H), 8.04-7.81 (m, 5H), 7.51 (t, J=2.6 Hz, 1H), 7.41 (t, J=2.9 Hz, 1H), 6.87 (dd, J=7.0, 1.7 Hz, 1H), 4.58-4.38 (m, 2H), 3.29-3.25 (m, 2H), 1.71-1.56 (m, 1H), 1.53-1.31 (m, 2H), 0.91 (d, J=6.5 Hz, 6H); MS (ESI(+)) m/e 365 (M+H)⁺.

Example 394

N-(imidazo[1,2-a]pyridin-7-ylmethyl)-N'-[(3S)-tetrahydrofuran-3-ylmethyl]benzene-1,4-dicarboxamide The title compound was prepared as described in Example 1A, substituting (S)-(tetrahydrofuran-3-yl)methanamine for 3-methylbutan-1-amine and 4-(imidazo[1,2-a]pyridin-7-ylmethylcarbamoyl)benzoic acid for 4-nitrobenzoic acid. $^1$H NMR (300 MHz, DMSO-$d_6$) δ ppm 9.21 (t, J=5.9 Hz, 1H), 8.69 (t, J=5.7 Hz, 1H), 8.49 (dd, J=6.9, 0.9 Hz, 1H), 8.07-7.71 (m, 5H), 7.52 (d, J=1.2 Hz, 1H), 7.41 (s, 1H), 6.87 (dd, J=7.0, 1.7 Hz, 1H), 4.52 (d, J=5.9 Hz, 2H), 3.80-3.56 (m, 4H), 3.48 (dd, J=8.5, 5.2 Hz, 1H), 2.02-1.87 (m, 1H), 1.68-1.53 (m, 1H), 1.32-1.00 (m, 2H); MS (ESI(+)) m/e 379 (M+H)$^+$.

Example 396

4-{[(3-chloroimidazo[1,2-a]pyridin-6-yl)carbamoyl] amino}-N-(tetrahydro-2H-pyran-2-ylmethyl)benzamide A solution of 4-(3-imidazo[1,2-a]pyridin-6-ylureido)-N-((tetrahydro-2H-pyran-2-yl)methyl)benzamide (0.016 g, 0.041 mmol) in chloroform (0.813 ml) was treated with N-chlorosuccinimide (5.70 mg, 0.043 mmol) and the reaction mixture was stirred at room temperature for 16 hours. The reaction mixture was concentrated under a stream of nitrogen and purified using normal phase chromatography to give the title compound. $^1$H NMR (400 MHz, DMSO-$d_6$) δ ppm 9.11 (s, 1H), 9.02 (s, 1H), 8.89-8.85 (m, 1H), 8.35 (t, J=5.8 Hz, 1H), 7.85-7.79 (m, 2H), 7.69-7.60 (m, 2H), 7.58-7.52 (m, 2H), 7.19 (dd, J=9.5, 2.0 Hz, 1H), 3.91-3.83 (m, 1H), 3.46-3.19 (m, 4H), 1.80-1.73 (m, 1H), 1.66-1.57 (m, 1H), 1.49-1.36 (m, 3H), 1.26-1.09 (m, 1H); MS (ESI(+)) m/e 428 (M+H)$^+$.

Example 398

N-[(3-chloroimidazo[1,2-a]pyridin-6-yl)methyl]-4-[(tetrahydrofuran-3-ylacetyl)amino]benzamide The title compound was prepared as described in Example 396, substituting N-[(3-imidazo[1,2-a]pyridin-6-yl)methyl]-4-[(tetrahydrofuran-3-ylacetyl)amino]benzamide for 4-(3-imidazo[1,2-a]pyridin-6-ylureido)-N-((tetrahydro-2H-pyran-2-yl)methyl)benzamide. $^1$H NMR (300 MHz, DMSO-$d_6$) δ ppm 10.15 (s, 1H), 8.95 (t, J=5.8 Hz, 1H), 8.30-8.25 (m, 1H), 7.87-7.80 (m, 2H), 7.71-7.59 (m, 4H), 7.35 (dd, J=9.3, 1.7 Hz, 1H), 4.54 (d, J=5.8 Hz, 2H), 3.86-3.58 (m, 3H), 3.38-3.30 (m, 1H), 2.62-2.52 (m, 1H), 2.47-2.39 (m, 2H), 2.10-1.95 (m, 1H), 1.62-1.46 (m, 1H); MS (ESI(+)) m/e 413 (M+H)$^+$.

Example 399

5-(4-hydroxytetrahydro-2H-pyran-4-yl)-N-(imidazo [1,2-a]pyridin-7-ylmethyl)thiophene-2-carboxamide Example 399A 5-(4-hydroxytetrahydro-2H-pyran-4-yl)thiophene-2-carboxylic acid The title compound was prepared as described in Example 324A, substituting dihydro-2H-pyran-4(3H)-one for N-(oxetan-3-ylidene)propane-2-sulfinamide.

Example 399B 5-(4-hydroxytetrahydro-2H-pyran-4-yl)-N-(imidazo [1,2-a]pyridin-7-ylmethyl)thiophene-2-carboxamide The title compound was prepared as described in Example 1A, substituting imidazo[1,2-a]pyridin-7-ylmethanamine for 3-methylbutan-1-amine and 5-(4-hydroxytetrahydro-2H-pyran-4-yl)thiophene-2-carboxylic acid for 4-nitrobenzoic acid. $^1$H NMR (300 MHz, DMSO-$d_6$) ppm 8.99 (t, J=5.9 Hz, 1H), 8.48 (d, J=7.1 Hz, 1H), 7.88 (s, 1H), 7.66 (d, J=3.7 Hz, 1H), 7.52 (s, 1H), 7.37 (s, 1H), 7.02 (d, J=3.7 Hz, 1H), 6.83 (dd, J=7.0, 1.5 Hz, 1H), 5.67 (s, 1H), 4.46 (d, J=6.1 Hz, 2H), 3.63-3.77 (m, 4H), 1.89-2.04 (m, 2H), 1.69 (d, J=11.9 Hz, 2H); MS (ESI(+)) m/e 358 (M+H)$^+$.

Example 400

5-[3-hydroxy-1-(2-methylpropanoyl)azetidin-3-yl]-N-(imidazo[1,2-a]pyridin-7-ylmethyl)thiophene-2-carboxamide Example 400A 5-(1-(tert-butoxycarbonyl)-3-hydroxyazetidin-3-yl) thiophene-2-carboxylic acid The title compound was prepared as described in Example 324A, substituting tert-butyl 3-oxoazetidine-1-carboxylate for N-(oxetan-3-ylidene)propane-2-sulfinamide.

Example 400B tert-butyl 3-hydroxy-3-(5-(imidazo[1,2-a]pyridin-7-ylmethylcarbamoyl)thiophen-2-yl)azetidine-1-carboxylate The title compound was prepared as described in Example 1A, substituting imidazo[1,2-a]pyridin-7-ylmethanamine for 3-methylbutan-1-amine and 5-(1-(tert-butoxycarbonyl)-3-hydroxyazetidin-3-yl)thiophene-2-carboxylic acid for 4-nitrobenzoic acid.

Example 400C 5-(3-hydroxyazetidin-3-yl)-N-(imidazo[1,2-a]pyridin-7-ylmethyl)thiophene-2-carboxamide The title compound was prepared as described in Example 28A, substituting tert-butyl 3-hydroxy-3-(5-(imidazo[1,2-a]pyridin-7-ylmethylcarbamoyl)thiophen-2-yl)azetidine-1-carboxylate for tert-butyl 4-(4-(3-imidazo[1,2-a]pyridin-6-ylureido)phenyl)-5,6-dihydropyridine-1(2H)-carboxylate.

Example 400D

5-[3-hydroxy-1-(2-methylpropanoyl)azetidin-3-yl]-N-(imidazo[1,2-a]pyridin-7-ylmethyl)thiophene-2-carboxamide The title compound was prepared as described in Example 1A, substituting 5-(3-hydroxyazetidin-3-yl)-N-(imidazo[1,2-a]pyridin-7-ylmethyl)thiophene-2-carboxamide for 3-methylbutan-1-amine and isobutyric acid for 4-nitrobenzoic acid. $^1$H NMR (300 MHz, DMSO-$d_6$) ppm 9.06 (t, J=6.0 Hz, 1H), 8.49 (d, J=7.1 Hz, 1H), 7.89 (s, 1H), 7.72 (d, J=3.6 Hz, 1H), 7.52 (s, 1H), 7.38 (s, 1H), 7.18 (d, J=3.6 Hz, 1H), 6.90 (s, 1H), 6.83 (dd, J=6.9, 1.4 Hz, 1H), 4.47 (d, J=6.0 Hz, 2H), 4.41

(d, J=9.1 Hz, 1H), 4.32 (d, J=9.1 Hz, 1H), 4.05 (dd, J=17.5, 9.9 Hz, 2H), 2.46-2.57 (m, 1H), 1.00 (d, J=7.1 Hz, 6H); MS (ESI(+)) m/e 399 (M+H)$^+$.

Example 401

5-(1-benzoyl-3-hydroxyazetidin-3-yl)-N-(imidazo[1,2-a]pyridin-7-ylmethyl)thiophene-2-carboxamide The title compound was prepared as described in Example 1A, substituting 5-(3-hydroxyazetidin-3-yl)-N-(imidazo[1,2-a]pyridin-7-ylmethyl)thiophene-2-carboxamide for 3-methylbutan-1-amine and benzoic acid for 4-nitrobenzoic acid. $^1$H NMR (300 MHz, DMSO-d$_6$) ppm 9.05 (t, J=5.8 Hz, 1H), 8.48 (d, J=6.1 Hz, 1H), 7.88 (s, 1H), 7.73 (d, J=3.7 Hz, 1H), 7.66-7.71 (m, 2H), 7.43-7.54 (m, 4H), 7.38 (d, J=1.0 Hz, 1H), 7.26 (d, J=3.7 Hz, 1H), 6.93 (s, 1H), 6.83 (dd, J=7.1, 1.7 Hz, 1H), 4.46 (d, J=6.1 Hz, 2H), 4.23-4.63 (br. m, 4H); MS (ESI(+)) m/e 433 (M+H)$^+$.

Example 402 tert-butyl 3-{4-[(imidazo[1,2-a]pyridin-7-ylmethyl)carbamoyl]phenyl}azetidine-1-carboxylate The title compound was prepared as described in Example 1A, substituting imidazo[1,2-a]pyridin-7-ylmethanamine for 3-methylbutan-1-amine and 4-(1-(tert-butoxycarbonyl)azetidin-3-yl)benzoic acid for 4-nitrobenzoic acid. $^1$H NMR (400 MHz, DMSO-d$_6$) δ ppm 9.09 (t, J=5.9 Hz, 1H), 8.48 (dd, J=6.9, 0.9 Hz, 1H), 7.91 (m, 3H), 7.52 (d, J=1.2 Hz, 1H), 7.45 (m, 2H), 7.38 (s, 1H), 6.85 (dd, J=6.9, 1.7 Hz, 1H), 4.51 (d, J=5.9 Hz, 2H), 4.26 (m, 2H), 3.87 (m, 3H), 1.41 (s, 9H); (ESI(+)) m/e 407 (M+H)$^+$.

Example 403 tert-butyl 4-hydroxy-4-{5-[(imidazo[1,2-a]pyridin-7-ylmethyl)carbamoyl]thiophen-2-yl}piperidine-1-carboxylate

Example 403A 5-(1-(tert-butoxycarbonyl)-4-hydroxypiperidin-4-yl)thiophene-2-carboxylic acid The title compound was prepared as described in Example 324A, substituting tert-butyl 3-oxopiperidine-1-carboxylate for N-(oxetan-3-ylidene)propane-2-sulfinamide.

Example 403B tert-butyl 4-hydroxy-4-(5-(imidazo[1,2-a]pyridin-7-ylmethylcarbamoyl)thiophen-2-yl)piperidine-1-carboxylate The title compound was prepared as described in Example 1A, substituting imidazo[1,2-a]pyridin-7-ylmethanamine for 3-methylbutan-1-amine and 5-(1-(tert-butoxycarbonyl)-4-hydroxypiperidin-4-yl)thiophene-2-carboxylic acid for 4-nitrobenzoic acid. $^1$H NMR (300 MHz, DMSO-d$_6$) ppm 8.98 (t, J=5.9 Hz, 1H), 8.48 (d, J=7.1 Hz, 1H), 7.88 (s, 1H), 7.65 (d, J=4.1 Hz, 1H), 7.51 (d, J=1.0 Hz, 1H), 7.37 (s, 1H), 7.01 (d, J=3.7 Hz, 1H), 6.83 (dd, J=7.0, 1.5 Hz, 1H), 5.72 (s, 1H), 4.46 (d, J=5.8 Hz, 2H), 3.75-3.86 (m, 2H), 1.71-1.86 (m, 2H), 1.41 (s, 9H), 1.21-1.30 (m, 2H), 0.94 (d, J=5.8 Hz, 2H); MS (ESI(+)) m/e 457 (M+H)$^+$.

Example 404

1-(imidazo[1,2-a]pyridin-7-ylmethyl)-3-[5-(piperidin-1-ylcarbonyl)-1,3-thiazol-2-yl]urea

Example 404A ethyl 2-(3-(imidazo[1,2-a]pyridin-7-ylmethyl)ureido)thiazole-5-carboxylate The title compound was prepared as described in Example 1C, substituting ethyl 2-aminothiazole-5-carboxylate for 4-amino-N-isopentylbenzamide and imidazo[1,2-a]pyridin-7-ylmethanamine for imidazo[1,2-a]pyridin-6-amine.

Example 404B 2-(3-(imidazo[1,2-a]pyridin-7-ylmethyl)ureido)thiazole-5-carboxylic acid The title compound was prepared as described in Example 4B, substituting ethyl 2-(3-(imidazo[1,2-a]pyridin-7-ylmethyl)ureido)thiazole-5-carboxylate for methyl 4-(3-imidazo[1,2-a]pyridin-6-ylureido)benzoate.

Example 404C 1-(imidazo[1,2-a]pyridin-7-ylmethyl)-3-[5-(piperidin-1-ylcarbonyl)-1,3-thiazol-2-yl]urea The title compound was prepared as described in Example 1A, substituting piperidine for 3-methylbutan-1-amine and 2-(3-(imidazo[1,2-a]pyridin-7-ylmethyl)ureido)thiazole-5-carboxylic acid for 4-nitrobenzoic acid. $^1$H NMR (300 MHz, DMSO-d$_6$) ppm 10.91 (s, 1H), 8.49 (d, J=7.1 Hz, 1H), 7.89 (s, 1H), 7.62 (s, 1H), 7.52 (d, J=0.8 Hz, 1H), 7.39 (s, 1H), 7.11-7.18 (m, 1H), 6.83 (dd, J=6.9, 1.4 Hz, 1H), 4.39 (d, J=6.0 Hz, 2H), 3.54-3.61 (m, 4H), 1.47-1.67 (m, 6H); MS (ESI(+)) m/e 385 (M+H)$^+$.

Example 405

5-{3-hydroxy-1-[(2S)-2-methylbutanoyl]azetidin-3-yl}-N-(imidazo[1,2-a]pyridin-7-ylmethyl)thiophene-2-carboxamide The title compound was prepared as described in Example 1A, substituting 5-(3-hydroxyazetidin-3-yl)-N-(imidazo[1,2-a]pyridin-7-ylmethyl)thiophene-2-carboxamide for 3-methylbutan-1-amine and (S)-2-methylbutanoic acid for 4-nitrobenzoic acid. $^1$H NMR (300 MHz, DMSO-d$_6$) ppm 9.06 (t, J=5.9 Hz, 1H), 8.48 (d, J=7.1 Hz, 1H), 7.88 (s, 1H), 7.72 (d, J=4.1 Hz, 1H), 7.52 (d, J=1.4 Hz, 1H), 7.38 (s, 1H), 7.16 (dd, J=7.0, 3.9 Hz, 1H), 6.89 (s, 1H), 6.83 (dd, J=7.0, 1.5 Hz, 1H), 4.46 (d, J=6.1 Hz, 2H), 4.35-4.42 (m, 1H), 4.32 (d, J=8.8 Hz, 1H), 4.09 (dd, J=10.5, 4.4 Hz, 1H), 4.03 (d, J=10.2 Hz, 1H), 2.25-2.38 (m, 1H), 1.49 (s, 1H), 1.23-1.38 (m, 1H), 0.99 (d, J=6.8 Hz, 3H), 0.80-0.88 (m, 3H); MS (ESI(+)) m/e 413 (M+H)$^+$.

Example 406

5-[3-hydroxy-1-(tetrahydro-2H-pyran-4-ylacetyl)azetidin-3-yl]-N-(imidazo[1,2-a]pyridin-7-ylmethyl)thiophene-2-carboxamide The title compound was prepared as described in Example 1A, substituting 5-(3-hydroxyazetidin-3-yl)-N-(imidazo[1, 2-a]pyridin-7-ylmethyl)thiophene-2-carboxamide for 3-methylbutan-1-amine and 2-(tetrahydro-2H-pyran-4-yl)acetic acid for 4-nitrobenzoic acid. $^1$H NMR (400 MHz, DMSO-d$_6$) ppm 9.07 (t, J=6.0 Hz, 1H), 8.49 (d, J=7.0 Hz, 1H), 7.89 (s, 1H), 7.72 (d, J=4.0 Hz, 1H), 7.52 (d, J=1.2 Hz, 1H), 7.38 (s, 1H), 7.18 (d, J=4.0 Hz, 1H), 6.89 (s, 1H), 6.83 (dd, J=7.0, 1.5 Hz, 1H), 4.47 (d, J=5.8 Hz, 2H), 4.37 (d, J=9.2 Hz, 1H), 4.26-4.40 (m, 2H), 4.05-4.11 (m, 1H), 4.00-4.10 (m, 2H), 3.78-3.84 (m, 2H), 2.04-2.07 (m, 2H), 1.85-1.97 (m, 1H), 1.53-1.62 (m, 2H), 1.15-1.28 (m, 2H); MS (ESI(+)) m/e 455 (M+H)$^+$.

Example 407

2-{[(imidazo[1,2-a]pyridin-7-ylmethyl)carbamoyl]amino}-N-(3-methylbutyl)-1,3-thiazole-5-carboxamide The title compound was prepared as described in Example 1A, substituting 3-methylbutan-1-amine for 3-methylbutan-1-amine and 2-(3-(imidazo[1,2-a]pyridin-7-ylmethyl)ureido)thiazole-5-carboxylic acid for 4-nitrobenzoic acid. $^1$H NMR (300 MHz, DMSO-d$_6$) ppm 8.49 (d, J=7.8 Hz, 1H), 8.21 (t, J=5.9 Hz, 1H), 7.88-7.89 (m, J=1.4 Hz, 1H), 7.87 (s, 1H), 7.52 (d, J=1.4 Hz, 1H), 7.39 (s, 1H), 7.18 (t, J=5.8 Hz, 1H), 6.83 (dd, J=6.8, 1.7 Hz, 1H), 4.38 (d, J=6.1 Hz, 2H), 3.16-3.25 (m, 2H), 1.52-1.67 (m, 1H), 1.38 (q, J=6.9 Hz, 2H), 0.83-0.91 (m, 7H); MS (ESI(+)) m/e 387 (M+H)$^+$.

Example 408

N-(imidazo[1,2-a]pyridin-7-ylmethyl)-5-(3-{[(2S)-2-methylbutanoyl]amino}oxetan-3-yl)thiophene-2-carboxamide The title compound was prepared as described in Example 1A, substituting 5-(3-aminooxetan-3-yl)-N-(imidazo[1,2-a]pyridin-7-ylmethyl)thiophene-2-carboxamide for 3-methylbutan-1-amine and (S)-2-methylbutanoic acid for 4-nitrobenzoic acid. $^1$H NMR (300 MHz, DMSO-d$_6$) ppm 9.11 (s, 1H), 9.05 (t, J=5.9 Hz, 1H), 8.48 (d, J=7.8 Hz, 1H), 7.88 (s, 1H), 7.71 (d, J=3.7 Hz, 1H), 7.52 (s, 1H), 7.38 (s, 1H), 7.22 (d, J=3.7 Hz, 1H), 6.83 (dd, J=7.1, 1.7 Hz, 1H), 4.77-4.83 (m, 2H), 4.72 (dd, J=6.4, 4.4 Hz, 2H), 4.46 (d, J=5.8 Hz, 2H), 2.19-2.29 (m, 1H), 1.46-1.66 (m, 1H), 1.26-1.43 (m, 1H), 1.03 (d, J=6.8 Hz, 3H), 0.85 (t, J=7.3 Hz, 3H); MS (ESI(+)) m/e 413 (M+H)$^+$.

Example 409

N-(imidazo[1,2-a]pyridin-7-ylmethyl)-1-[1-(3-methylbutanoyl)piperidin-4-yl]-1H-pyrazole-3-carboxamide Example 409A 1-(4-hydroxypiperidin-1-yl)-3-methylbutan-1-one The title compound was prepared as described in Example 52A, substituting 3-methylbutanoyl chloride for 2-cyclopentylacetyl chloride and piperidin-4-ol for methyl 4-aminobenzoate.

Example 409B ethyl 1-(1-(3-methylbutanoyl)piperidin-4-yl)-1H-pyrazole-3-carboxylate A solution of 1-(hydroxypiperidin-1-yl)-3-methylbutan-1-one (793 mg, 4.28 mmol), ethyl 1H-pyrazole-4-carboxylate (500 mg, 3.57 mmol) and cyanomethylenetributylphosphorane (1.03 g, 4.28 mmol) in toluene (20 ml) was stirred overnight at 85° C. The solvent was removed and the crude mixture was purified by normal phase chromatography to give the title compound.

Example 409C 1-(1-(3-methylbutanoyl)piperidin-4-yl)-1H-pyrazole-3-carboxylic acid The title compound was prepared as described in Example 4B, substituting ethyl 1-(1-(3-methylbutanoyl)piperidin-4-yl)-1H-pyrazole-3-carboxylate for methyl 4-(3-imidazo[1,2-a]pyridin-6-ylureido)benzoate.

Example 409D

N-(imidazo[1,2-a]pyridin-7-ylmethyl)-1-[1-(3-methylbutanoyl)piperidin-4-yl]-1H-pyrazole-3-carboxamide The title compound was prepared as described in Example 1A, substituting imidazo[1,2-a]pyridin-7-ylmethanamine for 3-methylbutan-1-amine and 1-(1-(3-methylbutanoyl)piperidin-4-yl)-1H-pyrazole-3-carboxylic acid for 4-nitrobenzoic acid. $^1$H NMR (300 MHz, DMSO-d$_6$) δ ppm 9.10 (t, J=6.0 Hz, 1H), 8.50 (dd, J=7.0, 0.9 Hz, 1H), 7.93-7.86 (m, 1H), 7.57-7.47 (m, 2H), 7.41 (s, 1H), 6.92 (d, J=2.0 Hz, 1H), 6.85 (dd, J=7.0, 1.7 Hz, 1H), 5.45-5.28 (m, 1H), 4.57-4.43 (m, 3H), 3.99 (d, J=14.0 Hz, 1H), 3.20-3.03 (m, 1H), 2.70-2.53 (m, 1H), 2.32-2.11 (m, 3H), 2.09-1.68 (m, 4H), 0.91 (d, J=6.6 Hz, 6H); MS (ESI(+)) m/e 408 (M+H).

Example 424

1-{4-[(1-acetylazetidin-3-yl)oxy]phenyl}-3-(imidazo[1,2-a]pyridin-7-ylmethyl)urea Example 424A tert-butyl 3-(4-(3-(imidazo[1,2-a]pyridin-7-ylmethyl)ureido)phenoxy)azetidine-1-carboxylate The title compound was prepared as described in Example 1C, substituting tert-butyl 3-(4-aminophenoxy)azetidine-1-carboxylate for 4-amino-N-isopentylbenzamide and imidazo[1,2-a]pyridin-7-ylmethanamine for imidazo[1,2-a]pyridin-6-amine.

Example 424B 1-(4-(azetidin-3-yloxy)phenyl)-3-(imidazo[1,2-a]pyridin-7-ylmethyl)urea The title compound was prepared as described in Example 28A, substituting tert-butyl 3-(4-(3-(imidazo[1,2-a]pyridin-7-ylmethyl)ureido)phenoxy)azetidine-1-carboxylate for tert-butyl 4-(4-(3-imidazo[1,2-a]pyridin-6-ylureido)phenyl)-5,6-dihydropyridine-1(2H)-carboxylate.

Example 424C

1-{4-[(1-acetylazetidin-3-yl)oxy]phenyl}-3-(imidazo[1,2-a]pyridin-7-ylmethyl)urea The title compound was prepared as described in Example 1A, substituting 1-(4-(azetidin-3-yloxy)phenyl)-3-(imidazo

[1,2-a]pyridin-7-ylmethyl)urea for 3-methylbutan-1-amine and acetic acid for 4-nitrobenzoic acid. ¹H NMR (400 MHz, DMSO-d₆) δ ppm 8.50 (m, 2H), 7.88 (s, 1H), 7.51 (d, J=1.2 Hz, 1H), 7.37 (m, 1H), 7.33 (m, 2H), 6.83 (dd, J=6.9, 1.6 Hz, 1H), 6.74 (m, 2H), 6.63 (t, J=6.0 Hz, 1H), 4.93 (m, 1H), 4.51 (m, 1H), 4.32 (d, J=6.0 Hz, 2H), 4.24 (m, 1H), 4.04 (dd, J=9.6, 4.1 Hz, 1H), 3.72 (dd, J=10.5, 4.0 Hz, 1H), 1.78 (s, 3H); (ESI(+)) m/e 380 (M+H)⁺.

TABLE 20

The following Examples were prepared essentially as described in Example 424, substituting the appropriate carboxylic acid in Example 424C.

| Ex | Name | ¹H NMR | MS |
|---|---|---|---|
| 425 | 1-(imidazo[1,2-a]pyridin-7-ylmethyl)-3-(4-{[1-(2-methylpropanoyl)azetidin-3-yl]oxy}phenyl)urea | ¹H NMR (400 MHz, DMSO-d₆) δ ppm 8.49 (m, 2H), 7.88 (s, 1H), 7.51 (d, J = 1.2 Hz, 1H), 7.37 (m, 1H), 7.33 (m, 2H), 6.83 (dd, J = 6.9, 1.7 Hz, 1H), 6.75 (m, 2H), 6.63 (t, J = 6.0 Hz, 1H), 4.95 (m, 1H), 4.57 (dd, J = 9.4, 6.4 Hz, 1H), 4.32 (d, J = 6.0 Hz, 2H), 4.25 (dd, J = 10.5, 6.5 Hz, 1H), 4.08 (dd, J = 9.4, 3.9 Hz, 1H), 3.73 (dd, J = 10.5, 4.0 Hz, 1H), 2.47 (m, 1H), 0.97 (m, 6H) | (ESI(+)) m/e 408 (M + H)⁺ |
| 426 | 1-(imidazo[1,2-a]pyridin-7-ylmethyl)-3-[4-({1-[(2S)-2-methylbutanoyl]azetidin-3-yl}oxy)phenyl]urea | ¹H NMR (400 MHz, DMSO-d₆) δ ppm 8.49 (m, 2H), 7.88 (d, J = 1.1 Hz, 1H), 7.51 (d, J = 1.2 Hz, 1H), 7.37 (m, 1H), 7.33 (m, 2H), 6.83 (dd, J = 6.9, 1.6 Hz, 1H), 6.75 (m, 2H), 6.64 (t, J = 6.0 Hz, 1H), 4.95 (m, 1H), 4.56 (dd, J = 9.4, 6.5 Hz, 1H), 4.32 (d, J = 6.0 Hz, 2H), 4.26 (m, 1H), 4.08 (m, 1H), 3.74 (m, 1H), 2.28 (m, 1H), 1.47 (m, 1H), 1.28 (m, 1H), 0.95 (m, 3H), 0.81 (m, 3H) | (ESI(+)) m/e 422 (M + H)⁺ |
| 427 | 1-(4-{[1-(cyclopropylacetyl)azetidin-3-yl]oxy}phenyl)-3-(imidazo[1,2-a]pyridin-7-ylmethyl)urea | ¹H NMR (400 MHz, DMSO-d₆) δ ppm 8.49 (m, 2H), 7.90 (s, 1H), 7.54 (d, J = 1.2 Hz, 1H), 7.39 (s, 1H), 7.33 (m, 2H), 6.86 (dd, J = 7.0, 1.6 Hz, 1H), 6.74 (m, 2H), 6.64 (t, J = 6.0 Hz, 1H), 4.94 (m, 1H), 4.50 (dd, J = 9.6, 6.6 Hz, 1H), 4.33 (d, J = 6.0 Hz, 2H), 4.26 (dd, J = 10.5, 6.5 Hz, 1H), 4.03 (dd, J = 9.4, 3.9 Hz, 1H), 3.74 (dd, J = 10.5, 3.9 Hz, 1H), 2.02 (d, J = 6.8 Hz, 2H), 0.92 (m, 1H), 0.43 (m, 2H), 0.10 (m, 2H) | (ESI(+)) m/e 420 (M + H)⁺ |
| 428 | 1-{4-[(1-benzoylazetidin-3-yl)oxy]phenyl}-3-(imidazo[1,2-a]pyridin-7-ylmethyl)urea | ¹H NMR (400 MHz, DMSO-d₆) δ ppm 8.49 (m, 2H), 7.88 (s, 1H), 7.65 (m, 2H), 7.52 (m, 2H), 7.45 (m, 2H), 7.37 (m, 1H), 7.33 (m, 2H), 6.83 (dd, J = 6.9, 1.6 Hz, 1H), 6.75 (m, 2H), 6.63 (t, J = 6.0 Hz, 1H), 5.00 (m, 1H), 4.67 (m, 1H), 4.51 (m, 1H), 4.32 (d, J = 6.0 Hz, 2H), 4.26 (m, 1H), 3.97 (m, 1H) | (ESI(+)) m/e 442 (M + H)⁺ |
| 429 | 1-(imidazo[1,2-a]pyridin-7-ylmethyl)-3-[4-({1-[(propan-2-yloxy)acetyl]azetidin-3-yl}oxy)phenyl]urea | ¹H NMR (400 MHz, DMSO-d₆) δ ppm 8.49 (m, 2H), 7.88 (s, 1H), 7.51 (d, J = 1.2 Hz, 1H), 7.37 (s, 1H), 7.33 (m, 2H), 6.83 (dd, J = 6.9, 1.6 Hz, 1H), 6.74 (m, 2H), 6.64 (t, J = 6.0 Hz, 1H), 4.96 (m, 1H), 4.60 (dd, J = 10.1, 6.4 Hz, 1H), 4.30 (m, 3H), 4.11 (dd, J = 10.1, 3.9 Hz, 1H), 3.94 (s, 2H), 3.77 (dd, J = 10.7, 3.8 Hz, 1H), 3.58 (m, 1H), 1.09 (d, J = 6.1 Hz, 6H) | (ESI(+)) m/e 438 (M + H)⁺ |
| 430 | 1-(4-{[1-(2-hydroxy-2-methylpropanoyl)azetidin-3-yl]oxy}phenyl)-3-(imidazo[1,2-a]pyridin-7-ylmethyl)urea | ¹H NMR (400 MHz, DMSO-d₆) δ ppm 8.48 (m, 2H), 7.88 (s, 1H), 7.51 (s, 1H), 7.38 (s, 1H), 7.33 (m, 2H), 6.83 (dd, J = 6.9, 1.6 Hz, 1H), 6.74 (m, 2H), 6.63 (t, J = 6.0 Hz, 1H), 5.13 (s, 1H), 4.91 (m, 1H), 4.78 (m, 1H), 4.32 (d, J = 6.0 Hz, 3H), 4.26 (m, 1H), 3.73 (m, 1H), 1.25 (s, 6H) | (ESI(+)) m/e 424 (M + H)⁺ |
| 431 | 1-(imidazo[1,2-a]pyridin-7-ylmethyl)-3-[4-({1-[(2R)-tetrahydrofuran-2-ylcarbonyl]azetidin-3-yl}oxy)phenyl]urea | ¹H NMR (400 MHz, DMSO-d₆) δ ppm 8.49 (m, 2H), 7.88 (s, 1H), 7.51 (d, J = 1.2 Hz, 1H), 7.37 (s, 1H), 7.33 (m, 2H), 6.83 (dd, J = 6.9, 1.6 Hz, 1H), 6.74 (m, 2H), 6.63 (t, J = 6.0 Hz, 1H), 4.95 (m, 1H), 4.66 (m, 1H), 4.31 (m, 4H), 4.13 (m, 1H), 3.75 (m, 3H), 2.03 (m, 1H), 1.93 (m, 1H), 1.81 (m, 2H) | (ESI(+)) m/e 436 (M + H)⁺ |
| 432 | 1-(imidazo[1,2-a]pyridin-7-ylmethyl)-3-[4-({1-[(2S)- | -¹H NMR (400 MHz, DMSO-d₆) δ ppm 8.49 (m, 2H), 7.88 (s, 1H), 7.51 (d, J = 1.2 Hz, 1H), 7.37 (s, 1H), 7.33 (m, 2H), 6.83 (dd, J = 6.9, 1.6 Hz, 1H), 6.74 (m, 2H), 6.64 (t, J = 6.0 Hz, 1H), 4.95 (m, 1H), 4.66 (m, 1H), | (ESI(+)) m/e 436 (M + H)⁺ |

TABLE 20-continued

The following Examples were prepared essentially as described in Example 424, substituting the appropriate carboxylic acid in Example 424C.

| Ex | Name | ¹H NMR | MS |
|---|---|---|---|
| | tetrahydrofuran-2-ylcarbonyl]azetidin-3-yl}oxy)phenyl]urea | 4.3123 (m, 4H), 4.13 (m, 1H), 3.75 (m, 3H), 2.03 (m, 1H), 1.93 (m, 1H), 1.81 (m, 2H) | |
| 433 | 1-(imidazo[1,2-a]pyridin-7-ylmethyl)-3-(4-{[1-(tetrahydro-2H-pyran-4-ylcarbonyl)azetidin-3-yl]oxy}phenyl)urea | ¹H NMR (400 MHz, DMSO-$d_6$) δ ppm 8.48 (m, 2H), 7.88 (d, J = 1.1 Hz, 1H), 7.51 (d, J = 1.2 Hz, 1H), 7.37 (s, 1H), 7.33 (m, 2H), 6.83 (dd, J = 6.9, 1.7 Hz, 1H), 6.74 (m, 2H), 6.64 (t, J = 6.0 Hz, 1H), 4.95 (m, 1H), 4.60 (dd, J = 9.4, 6.5 Hz, 1H), 4.32 (d, J = 6.0 Hz, 3H), 4.26 (m, 1H), 4.11 (dd, J = 9.5, 3.8 Hz, 1H), 3.84 (m, 2H), 3.74 (dd, J = 10.6, 3.9 Hz, 1H), 3.36-3.26 (m, 2H), 1.57 (m, 4H) | (ESI(+)) m/e 450 (M + H)⁺ |
| 434 | 1-(4-{[1-(1,4-dioxan-2-ylcarbonyl)azetidin-3-yl]oxy}phenyl)-3-(imidazo[1,2-a]pyridin-7-ylmethyl)urea | ¹H NMR (400 MHz, DMSO-$d_6$) δ ppm 8.48 (d, 2H), 7.88 (s, 1H), 7.51 (s, 1H), 7.37 (s, 1H), 7.33 (m, 2H), 6.83 (dd, J = 6.9, 1.6 Hz, 1H), 6.74 (m, 2H), 6.64 (t, J = 6.0 Hz, 1H), 4.96 (m, 1H), 4.69 (m, 1H), 4.30 (m, 3H), 4.18 (m, 2H), 3.76 (m, 3H), 3.65-3.45 (m, 4H) | (ESI(+)) m/e 452 (M + H)⁺ |
| 435 | 1-(imidazo[1,2-a]pyridin-7-ylmethyl)-3-(4-{[1-(tetrahydro-2H-pyran-4-ylacetyl)azetidin-3-yl]oxy}phenyl)urea | ¹H NMR (400 MHz, DMSO-$d_6$) δ ppm 8.51 (s, 1H), 8.48 (dd, J = 6.9, 0.9 Hz, 1H), 7.88 (d, J = 1.1 Hz, 1H), 7.51 (d, J = 1.2 Hz, 1H), 7.37 (s, 1H), 7.33 (m, 2H), 6.83 (dd, J = 6.9, 1.7 Hz, 1H), 6.74 (m, 2H), 6.64 (t, J = 6.0 Hz, 1H), 4.94 (m, 1H), 4.52 (m, 1H), 4.32 (d, J = 6.0 Hz, 2H), 4.25 (m, 1H), 4.04 (dd, J = 9.5, 3.9 Hz, 1H), 3.76 (m, 3H), 3.27 (m, 2H), 2.02 (d, J = 1.9 Hz, 2H), 1.87 (m, 1H), 1.54 (m, 2H), 1.19 (m, 2H) | (ESI(+)) m/e 464 (M + H)⁺ |

Example 436 tert-butyl (3R)-3-{4-[(imidazo[1,2-a]pyridin-7-ylmethyl)carbamoyl]phenoxy}pyrrolidine-1-carboxylate The title compound was prepared as described in Example 321A-C, substituting (S)-tert-butyl 3-hydroxypyrrolidine-1-carboxylate for (R)-tert-butyl 3-hydroxypyrrolidine-1-carboxylate in Example 321A. ¹H NMR (400 MHz, methanol-$d_4$) δ ppm 8.41-8.35 (m, 1H), 7.91-7.83 (m, 2H), 7.81-7.76 (m, 1H), 7.52 (d, J=1.4 Hz, 1H), 7.47-7.43 (m, 1H), 7.06-6.98 (m, 2H), 6.93 (dd, J=7.1, 1.5 Hz, 1H), 5.12-5.05 (m, 1H), 4.62 (bs, 2H), 3.68-3.39 (m, 4H), 2.25-2.13 (m, 2H), 1.49-1.43 (m, 9H); MS (ESI(+)) m/e 437 (M+H)⁺.

Example 438

1-[4-(1-benzoyl-1,2,3,6-tetrahydropyridin-4-yl)-2-fluorophenyl]-3-(imidazo[1,2-a]pyridin-7-ylmethyl)urea Example 438A 1-(2-fluoro-4-(1,2,3,6-tetrahydropyridin-4-yl)phenyl)-3-(imidazo[1,2-a]pyridin-7-ylmethyl)urea The title compound was prepared as described in Example 28A, substituting tert-butyl 4-(3-fluoro-4-{[(imidazo[1,2-a]pyridin-7-ylmethyl)carbamoyl]amino}phenyl)-3,6-dihydropyridine-1(2H)-carboxylate for tert-butyl 4-(4-(3-imidazo[1,2-a]pyridin-6-ylureido)phenyl)-5,6-dihydropyridine-1(2H)-carboxylate.

Example 438B

1-[4-(1-benzoyl-1,2,3,6-tetrahydropyridin-4-yl)-2-fluorophenyl]-3-(imidazo[1,2-a]pyridin-7-ylmethyl)urea The title compound was prepared as described in Example 1A, substituting 1-(2-fluoro-4-(1,2,3,6-tetrahydropyridin-4-yl)phenyl)-3-(imidazo[1,2-a]pyridin-7-ylmethyl)urea for 3-methylbutan-1-amine and benzoic acid for 4-nitrobenzoic acid. ¹H NMR (400 MHz, methanol-$d_4$) δ ppm 8.77-8.70 (m, 1H), 8.19-8.15 (m, 1H), 8.00-7.96 (m, 1H), 7.95-7.88 (m, 1H), 7.80 (s, 1H), 7.53-7.41 (m, 6H), 7.30-7.15 (m, 2H), 6.26-5.95 (m, 1H), 4.61 (bs, 2H), 4.41-4.31 (m, 1H), 4.17-4.08 (m, 1H), 4.02-3.93 (m, 1H), 3.69-3.59 (m, 1H), 2.67-2.52 (m, 2H); MS (ESI(+)) m/e 470 (M+H)⁺.

Example 439

1-{2-fluoro-4-[1-(tetrahydro-2H-pyran-4-ylacetyl)-1,2,3,6-tetrahydropyridin-4-yl]phenyl}-3-(imidazo[1,2-a]pyridin-7-ylmethyl)urea The title compound was prepared as described in Example 1A, substituting 1-(2-fluoro-4-(1,2,3,6-tetrahydropyridin-4-yl)phenyl)-3-(imidazo[1,2-a]pyridin-7-ylmethyl)urea for 3-methylbutan-1-amine and 2-(tetrahydro-2H-pyran-4-yl)

acetic acid for 4-nitrobenzoic acid. ¹H NMR (400 MHz, methanol-d₄) δ ppm 8.74 (dd, J=7.0, 0.9 Hz, 1H), 8.18-8.15 (m, 1H), 7.98 (d, J=2.2 Hz, 1H), 7.92 (t, J=8.5 Hz, 1H), 7.82-7.78 (m, 1H), 7.47 (dd, J=7.0, 1.6 Hz, 1H), 7.28-7.15 (m, 2H), 6.16-6.10 (m, 1H), 4.61 (bs, 2H), 4.25-4.16 (m, 2H), 3.96-3.87 (m, 2H), 3.83-3.72 (m, 2H), 3.48-3.37 (m, 2H), 2.61-2.54 (m, 1H), 2.53-2.46 (m, 1H), 2.45-2.34 (m, 2H), 2.11-1.97 (m, 1H), 1.73-1.62 (m, 2H), 1.42-1.27 (m, 2H); MS (ESI(+)) m/e 492 (M+H)⁺.

Example 442

1-(imidazo[1,2-a]pyridin-7-ylmethyl)-3-(4-{[1-(2-methylpropanoyl)piperidin-4-yl]oxy}phenyl)urea

Example 442A 1-(imidazo[1,2-a]pyridin-7-ylmethyl)-3-(4-(piperidin-4-yloxy)phenyl)urea The title compound was prepared as described in Example 28A, substituting tert-butyl 4-(4-{[(imidazo[1,2-a]pyridin-7-ylmethyl)carbamoyl]amino}phenoxy)piperidine-1-carboxylate for tert-butyl 4-(4-(3-imidazo[1,2-a]pyridin-6-ylureido)phenyl)-5,6-dihydropyridine-1(2H)-carboxylate.

Example 442B 1-(imidazo[1,2-a]pyridin-7-ylmethyl)-3-(4-{[1-(2-methylpropanoyl)piperidin-4-yl]oxy}phenyl)urea The title compound was prepared as described in Example 1A, substituting 1-(imidazo[1,2-a]pyridin-7-ylmethyl)-3-(4-(piperidin-4-yloxy)phenyl)urea for 3-methylbutan-1-amine and isobutyric acid for 4-nitrobenzoic acid. ¹H NMR (500 MHz, DMSO-d₆) δ ppm 8.48 (m, 2H), 7.88 (s, 1H), 7.51 (s, 1H), 7.37 (s, 1H), 7.31 (m, 2H), 6.87 (m, 2H), 6.83 (dd, J=7.0, 1.6 Hz, 1H), 6.62 (t, J=6.0 Hz, 1H), 4.48 (m, 1H), 4.32 (d, J=6.0 Hz, 2H), 3.85 (m, 1H), 3.74 (m, 1H), 3.35 (m, 1H), 3.22 (m, 1H), 2.88 (m, 1H), 1.88 (m, 2H), 1.49 (m, 2H), 0.99 (d, J=6.7 Hz, 6H); (ESI(+)) m/e 436 (M+H)⁺.

TABLE 21

| | | | |
|---|---|---|---|
| The following Examples were prepared essentially as described in Example 442, substituting the appropriate carboxylic acid in Example 442B. | | | |
| Ex | Name | ¹H NMR | MS |
| 443 | 1-(imidazo[1,2-a]pyridin-7-ylmethyl)-3-[4-({1-[(2S)-2-methylbutanoyl]piperidin-4-yl}oxy)phenyl]urea | ¹H NMR (500 MHz, DMSO-d₆) δ ppm 8.48 (m, 2H), 7.88 (s, 1H), 7.51 (s, 1H), 7.37 (s, 1H), 7.31 (m, 2H), 6.87 (m, 2H), 6.83 (dd, J = 7.0, 1.6 Hz, 1H), 6.65 (t, J = 6.0 Hz, 1H), 4.49 (m, 1H), 4.32 (d, J = 6.0 Hz, 2H), 3.84 (m, 2H), 3.26 (m, 2H), 2.72 (m, 1H), 1.90 (m, 2H), 1.51 (m, 3H), 1.29 (m, 1H), 0.97 (d, J = 6.7 Hz, 3H), 0.81 (t, J = 7.4 Hz, 3H) | (ESI(+)) m/e 450 (M + H)⁺ |
| 444 | 1-(4-{[1-(cyclopropylacetyl)piperidin-4-yl]oxy}phenyl)-3-(imidazo[1,2-a]pyridin-7-ylmethyl)urea | ¹H NMR (500 MHz, DMSO-d₆) δ ppm 8.48 (m, 2H), 7.88 (s, 1H), 7.51 (s, 1H), 7.37 (s, 1H), 7.31 (m, 2H), 6.87 (m, 2H), 6.83 (dd, J = 7.0, 1.6 Hz, 1H), 6.62 (t, J = 6.0 Hz, 1H), 4.47 (m, 1H), 4.32 (d, J = 6.0 Hz, 2H), 3.85 (m, 1H), 3.66 (m, 1H), 3.30 (m, 1H), 3.22 (m, 1H), 2.26 (d, J = 6.8 Hz, 2H), 1.91 (m, 2H), 1.50 (m, 2H), 0.95 (m, 1H), 0.44 (m, 2H), 0.11 (m, 2H) | (ESI(+)) m/e 448 (M + H)⁺ |
| 445 | 1-{4-[(1-benzoylpiperidin-4-yl)oxy]phenyl}-3-(imidazo[1,2-a]pyridin-7-ylmethyl)urea | ¹H NMR (500 MHz, DMSO-d₆) δ ppm 8.48 (m, 2H), 7.88 (s, 1H), 7.51 (s, 1H), 7.44 (m, 3H), 7.40 (m, 2H), 7.37 (m, 1H), 7.31 (m, 2H), 6.87 (m, 2H), 6.83 (dd, J = 7.0, 1.6 Hz, 1H), 6.63 (t, J = 6.0 Hz, 1H), 4.52 (m, 1H), 4.31 (d, J = 6.0 Hz, 2H), 3.96 (m, 1H), 3.52 (m, 1H), 3.45-3.20 (m, 2H), 1.91 (m, 2H), 1.59 (m, 2H) | (ESI(+)) m/e 470 (M + H)⁺ |
| 446 | 1-(imidazo[1,2-a]pyridin-7-ylmethyl)-3-[4-({1-[(propan-2-yloxy)acetyl]piperidin-4-yl}oxy)phenyl]urea | ¹H NMR (400 MHz, DMSO-d₆) δ ppm 8.48 (m, 2H), 7.88 (m, 1H), 7.51 (d, J = 1.2 Hz, 1H), 7.37 (m, 1H), 7.31 (m, 2H), 6.87 (m, 2H), 6.83 (dd, J = 7.0, 1.6 Hz, 1H), 6.64 (m, 1H), 4.49 (m, 1H), 4.32 (d, J = 6.0 Hz, 2H), 4.08 (s, 2H), 3.82 (m, 1H), 3.67 (m, 1H), 3.59 (m, 1H), 3.40-3.15 (m, 2H), 1.90 (m, 2H), 1.52 (m, 2H), 1.10 (d, J = 6.1 Hz, 6H) | (ESI(+)) m/e 466 (M + H)⁺ |
| 447 | 1-(4-{[1-(2-hydroxy-2-methylpropanoyl)piperidin-4-yl]oxy}phenyl)-3-(imidazo[1,2-a]pyridin-7-ylmethyl)urea | ¹H NMR (500 MHz, DMSO-d₆) δ ppm 8.48 (m, 2H), 7.88 (s, 1H), 7.52 (d, J = 1.2 Hz, 1H), 7.38 (s, 1H), 7.30 (m, 2H), 6.87 (m, 2H), 6.83 (dd, J = 7.0, 1.6 Hz, 1H), 6.62 (t, J = 6.0 Hz, 1H), 5.39 (s, 1H), 4.48 (m, 1H), 4.32 (d, J = 6.0 Hz, 2H), 4.10-3.40 (m, 2H), 3.40-3.15 (m, 2H), 1.90 (m, 2H), 1.54 (m, 2H), 1.31 (s, 6H) | (ESI(+)) m/e 452 (M + H)⁺ |
| 448 | 1-(imidazo[1,2-a]pyridin-7-ylmethyl)-3-[4-({1-[(2R)-tetrahydrofuran-2- | ¹H NMR (500 MHz, DMSO-d₆) δ ppm 8.49 (m, 2H), 7.90 (s, 1H), 7.54 (d, J = 1.2 Hz, 1H), 7.39 (s, 1H), 7.31 (m, 2H), 6.86 (m, 3H), 6.62 (t, J = 6.0 Hz, 1H), 4.67 (m, 1H), 4.48 (m, 1H), 4.32 (d, J = 6.0 Hz, | (ESI(+)) m/e 464 (M + H)⁺ |

TABLE 21-continued

The following Examples were prepared essentially as described in Example 442, substituting the appropriate carboxylic acid in Example 442B.

| Ex | Name | $^1$H NMR | MS |
|---|---|---|---|
|  | ylcarbonyl]piperidin-4-yl}oxy)phenyl]urea | 2H), 3.78 (m, 4H), 3.45-3.15 (m, 2H), 2.10-1.75 (m, 6H), 1.53 (m, 2H) | |
| 449 | 1-(imidazo[1,2-a]pyridin-7-ylmethyl)-3-[4-({1-[(2S)-tetrahydrofuran-2-ylcarbonyl]piperidin-4-yl}oxy)phenyl]urea | $^1$H NMR (500 MHz, DMSO-d$_6$) δ ppm 8.48 (m, 2H), 7.89 (s, 1H), 7.52 (d, J = 1.2 Hz, 1H), 7.38 (s, 1H), 7.31 (m, 2H), 6.87 (m, 2H), 6.83 (dd, J = 7.0, 1.6 Hz, 1H), 6.62 (t, J = 6.0 Hz, 1H), 4.67 (m, 1H), 4.48 (m, 1H), 4.32 (d, J = 6.0 Hz, 2H), 3.78 (m, 4H), 3.45-3.16 (m, 2H), 2.09-1.92 (m, 2H), 2.09-1.92 (m, 4H), 1.53 (m, 2H) | (ESI(+)) m/e 464 (M + H)$^+$ |
| 450 | 1-(imidazo[1,2-a]pyridin-7-ylmethyl)-3-(4-{[1-(tetrahydro-2H-pyran-4-ylcarbonyl)piperidin-4-yl]oxy}phenyl)urea | $^1$H NMR (500 MHz, DMSO-d$_6$) δ ppm 8.48 (m, 2H), 7.88 (s, 1H), 7.51 (d, J = 1.2 Hz, 1H), 7.38 (s, 1H), 7.31 (m, 2H), 6.87 (m, 2H), 6.83 (dd, J = 7.0, 1.6 Hz, 1H), 6.62 (t, J = 6.0 Hz, 1H), 4.48 (m, 1H), 4.32 (d, J = 6.0 Hz, 2H), 3.88-3.71 (m, 4H), 3.38 (m, 2H), 3.34-3.16 (m, 1H), 3.22 (m, 1H), 2.89 (m, 1H), 1.91 (m, 2H), 1.67-1.40 (m, 6H) | (ESI(+)) m/e 478 (M + H)$^+$ |
| 451 | 1-(imidazo[1,2-a]pyridin-7-ylmethyl)-3-(4-{[1-(tetrahydro-2H-pyran-4-ylacetyl)piperidin-4-yl]oxy}phenyl)urea | $^1$H NMR (500 MHz, DMSO-d$_6$) δ ppm 8.48 (m, 2H), 7.88 (s, 1H), 7.52 (bs, 1H), 7.38 (bs, 1H), 7.31 (m, 2H), 6.87 (m, 2H), 6.83 (dd, J = 7.0, 1.5 Hz, 1H), 6.62 (t, J = 6.0 Hz, 1H), 4.47 (m, 1H), 4.32 (d, J = 6.0 Hz, 2H), 3.89-3.75 (m, 3H), 3.70 (m, 1H), 3.40-3.17 (m, 4H), 2.26 (m, 2H), 1.89 (m, 3H), 1.60-1.40 (m, 4H), 1.19 (m, 2H) | (ESI(+)) m/e 492 (M + H)$^+$ |
| 726 | 1-(4-{[1-(3-fluorobenzoyl)piperidin-4-yl]oxy}phenyl)-3-(imidazo[1,2-a]pyridin-7-ylmethyl)urea | | (ESI(+)) m/e 488 (M + H)$^+$ |
| 727 | 1-(4-{[1-(2,4-difluorobenzoyl)piperidin-4-yl]oxy}phenyl)-3-(imidazo[1,2-a]pyridin-7-ylmethyl)urea | | (ESI(+)) m/e 506 (M + H)$^+$ |
| 728 | 1-(4-{[1-(2,5-difluorobenzoyl)piperidin-4-yl]oxy}phenyl)-3-(imidazo[1,2-a]pyridin-7-ylmethyl)urea | | (ESI(+)) m/e 506 (M + H)$^+$ |
| 729 | 1-(4-{[1-(3,4-difluorobenzoyl)piperidin-4-yl]oxy}phenyl)-3-(imidazo[1,2-a]pyridin-7-ylmethyl)urea | | (ESI(+)) m/e 506 (M + H)$^+$ |
| 730 | 1-(4-{[1-(3,5-difluorobenzoyl)piperidin-4-yl]oxy}phenyl)-3-(imidazo[1,2-a]pyridin-7-ylmethyl)urea | | (ESI(+)) m/e 506 (M + H)$^+$ |

Example 452

1-(imidazo[1,2-a]pyridin-7-ylmethyl)-3-{4-[1-(2-methylpropanoyl)azetidin-3-yl]phenyl}urea

Example 452A 1-(4-(azetidin-3-yl)phenyl)-3-(imidazo[1,2-a]pyridin-7-ylmethyl)urea The title compound was prepared as described in Example 28A, substituting tert-butyl 3-(4-(3-(imidazo[1,2-a]pyridin-7-ylmethyl)ureido)phenyl)azetidine-1-carboxylate for tert-butyl 4-(4-(3-imidazo[1,2-a]pyridin-6-ylureido)phenyl)-5,6-dihydropyridine-1(2H)-carboxylate.

Example 452B 1-(imidazo[1,2-a]pyridin-7-ylmethyl)-3-{4-[1-(2-methylpropanoyl)azetidin-3-yl]phenyl}urea The title compound was prepared as described in Example 1A, substituting 1-(4-(azetidin-3-yl)phenyl)-3-(imidazo[1,2-a]pyridin-7-ylmethyl)urea for 3-methylbutan-1-amine and isobutyric acid for 4-nitrobenzoic acid. $^1$H NMR (500 MHz, DMSO-$d_6$) δ ppm 8.66 (s, 1H), 8.48 (d, J=7.0 Hz, 1H), 7.88 (s, 1H), 7.51 (s, 1H), 7.39 (m, 3H), 7.22 (m, 2H), 6.83 (dd, J=7.0, 1.6 Hz, 1H), 6.70 (t, J=6.0 Hz, 1H), 4.52 (m, 1H), 4.33 (d, J=6.0 Hz, 2H), 4.20 (m, 1H), 4.08 (dd, J=8.5, 5.3 Hz, 1H), 3.76 (m, 2H), 2.49 (m, 1H), 0.99 (d, J=6.8 Hz, 6H); (ESI(+)) m/e 392 (M+H)$^+$.

TABLE 22

The following Examples were prepared essentially as described in Example 452, substituting the appropriate carboxylic acid in Example 452B.

| Ex | Name | $^1$H NMR | MS |
|---|---|---|---|
| 453 | 1-(imidazo[1,2-a]pyridin-7-ylmethyl)-3-(4-{1-[(2S)-2-methylbutanoyl]azetidin-3-yl}phenyl)urea | $^1$H NMR (500 MHz, DMSO-$d_6$) δ ppm 8.66 (s, 1H), 8.48 (d, J = 7.0 Hz, 1H), 7.88 (s, 1H), 7.52 (s, 1H), 7.40 (m, 3H), 7.22 (m, 2H), 6.84 (dd, J = 7.0, 1.6 Hz, 1H), 6.70 (m, 1H), 4.52 (m, 1H), 4.33 (d, J = 6.0 Hz, 2H), 4.21 (m, 1H), 4.06 (m, 1H), 3.76 (m, 2H), 2.27 (m, 1H), 1.50 (m, 1H), 1.30 (m, 1H), 0.98 (d, J = 6.8 Hz, 3H), 0.84 (t, J = 7.4 Hz, 3H) | (ESI(+)) m/e 406 (M + H)$^+$ |
| 454 | 1-{4-[1-(cyclopropylacetyl)azetidin-3-yl]phenyl}-3-(imidazo[1,2-a]pyridin-7-ylmethyl)urea | $^1$H NMR (500 MHz, DMSO-$d_6$) δ ppm 8.66 (s, 1H), 8.49 (d, J = 7.0 Hz, 1H), 7.89 (s, 1H), 7.53 (d, J = 1.2 Hz, 1H), 7.40 (m, 3H), 7.22 (m, 2H), 6.85 (dd, J = 7.0, 1.6 Hz, 1H), 6.70 (t, J = 6.0 Hz, 1H), 4.45 (m, 1H), 4.33 (d, J = 6.0 Hz, 2H), 4.20 (m, 1H), 4.04 (m, 1H), 3.75 (m, 2H), 2.02 (d, J = 6.8 Hz, 2H), 0.94 (m, 1H), 0.44 (m, 2H), 0.11 (m, 2H) | (ESI(+)) m/e 404 (M + H)$^+$ |
| 455 | 1-[4-(1-benzoylazetidin-3-yl)phenyl]-3-(imidazo[1,2-a]pyridin-7-ylmethyl)urea | $^1$H NMR (500 MHz, DMSO-$d_6$) δ ppm 8.68 (s, 1H), 8.48 (d, J = 7.0 Hz, 1H), 7.88 (s, 1H), 7.68 (m, 2H), 7.52 (m, 2H), 7.46 (m, 2H), 7.40 (m, 3H), 7.26 (m, 2H), 6.83 (dd, J = 7.0, 1.6 Hz, 1H), 6.72 (t, J = 6.0 Hz, 1H), 464 (m, 1H), 4.44 (m, 1H), 4.33 (d, J = 6.0 Hz, 2H), 4.27 (m, 1H), 3.98 (m, 1H), 3.85 (m, 1H) | (ESI(+)) m/e 426 (M + H)$^+$ |
| 456 | 1-(imidazo[1,2-a]pyridin-7-ylmethyl)-3-(4-{1-[(propan-2-yloxy)acetyl]azetidin-3-yl}phenyl)urea | $^1$H NMR (500 MHz, DMSO-$d_6$) δ ppm 8.67 (s, 1H), 8.48 (d, J = 7.0 Hz, 1H), 7.88 (s, 1H), 7.51 (d, J = 1.2 Hz, 1H), 7.40 (m, 3H), 7.22 (m, 2H), 6.83 (dd, J = 7.0, 1.6 Hz, 1H), 6.71 (t, J = 6.0 Hz, 1H), 4.56 (m, 1H), 4.33 (d, J = 6.0 Hz, 2H), 4.24 (m, 1H), 4.13 (m, 1H), 3.95 (s, 2H), 3.79 (m, 2H), 3.59 (m, 1H), 1.10 (d, J = 6.1 Hz, 6H) | (ESI(+)) m/e 422 (M + H)$^+$ |
| 457 | 1-{4-[1-(2-hydroxy-2-methylpropanoyl)azetidin-3-yl]phenyl}-3-(imidazo[1,2-a]pyridin-7-ylmethyl)urea | $^1$H NMR (500 MHz, DMSO-$d_6$) δ ppm 8.66 (s, 1H), 8.50 (d, J = 7.0 Hz, 1H), 7.90 (s, 1H), 7.54 (d, J = 1.2 Hz, 1H), 7.40 (m, 3H), 7.21 (m, 2H), 6.86 (dd, J = 7.0, 1.6 Hz, 1H), 6.70 (t, J = 6.0 Hz, 1H), 5.09 (s, 1H), 4.75 (m, 1H), 4.32 (m, 3H), 4.22 (m, 1H), 3.74 (m, 2H), 1.27 (s, 6H) | (ESI(+)) m/e 408 (M + H)$^+$ |
| 458 | 1-(imidazo[1,2-a]pyridin-7-ylmethyl)-3-(4-{1-[(2R)-tetrahydrofuran-2-ylcarbonyl]azetidin-3-yl}phenyl)urea | $^1$H NMR (500 MHz, DMSO-$d_6$) δ ppm 8.73 (s, 1H), 8.48 (d, J = 7.0 Hz, 1H), 7.88 (s, 1H), 7.51 (s, 1H), 7.40 (m, 3H), 7.22 (m, 2H), 6.83 (dd, J = 7.0, 1.6 Hz, 1H), 6.78 (t, J = 6.0 Hz, 1H), 4.60 (m, 1H), 4.37 (m, 1H), 4.33 (d, J = 6.0 Hz, 2H), 4.24 (m, 1H), 4.16 (m, 1H), 3.86-3.69 (m, 4H), 2.04 (m, 1H), 1.96 (m, 1H), 1.82 (m, 2H) | (ESI(+)) m/e 420 (M + H)$^+$ |
| 459 | 1-(imidazo[1,2-a]pyridin-7-ylmethyl)-3-(4-{1-[(2S)-tetrahydrofuran- | $^1$H NMR (500 MHz, DMSO-$d_6$) δ ppm 8.66 (s, 1H), 8.48 (d, J = 7.0 Hz, 1H), 7.88 (s, 1H), 7.51 (s, 1H), 7.40 (m, 3H), 7.22 (m, 2H), 6.83 (dd, J = 7.0, 1.6 Hz, 1H), 6.74-6.67 (m, 1H), 4.60 (m, 1H), 4.37 (m, 1H), | (ESI(+)) m/e 420 (M + H)$^+$ |

TABLE 22-continued

The following Examples were prepared essentially as described in Example 452, substituting the appropriate carboxylic acid in Example 452B.

| Ex | Name | $^1$H NMR | MS |
|---|---|---|---|
|  | 2-ylcarbonyl]azetidin-3-yl}phenyl)urea | 4.33 (d, J = 6.0 Hz, 2H), 4.23 (m, 1H), 4.15 (m, 1H), 3.85-3.69 (m, 4H), 2.04 (m, 1H), 1.96 (m, 1H), 1.81 (m, 2H) |  |
| 460 | 1-(imidazo[1,2-a]pyridin-7-ylmethyl)-3-{4-[1-(tetrahydro-2H-pyran-4-ylcarbonyl)azetidin-3-yl]phenyl}urea | $^1$H NMR (500 MHz, DMSO-d$_6$) δ ppm 8.67 (s, 1H), 8.48 (d, J = 7.0 Hz, 1H), 7.88 (s, 1H), 7.51 (d, J = 1.1 Hz, 1H), 7.40 (m, 3H), 7.22 (m, 2H), 6.83 (dd, J = 7.0, 1.6 Hz, 1H), 6.71 (t, J = 6.0 Hz, 1H), 4.54 (m, 1H), 4.33 (d, J = 6.0 Hz, 2H), 4.21 (m, 1H), 4.13 (m, 1H), 3.85 (m, 2H), 3.77 (m, 2H), 3.40-3.25 (m, 2H), 2.50 (m, 1H), 1.58 (m, 4H) | (ESI(+)) m/e 434 (M + H)$^+$ |
| 461 | 1-(imidazo[1,2-a]pyridin-7-ylmethyl)-3-{4-[1-(tetrahydro-2H-pyran-4-ylacetyl)azetidin-3-yl]phenyl}urea | $^1$H NMR (500 MHz, DMSO-d$_6$) δ ppm 8.70 (s, 1H), 8.48 (d, J = 7.0 Hz, 1H), 7.88 (s, 1H), 7.51 (s, 1H), 7.40 (m, 3H), 7.21 (m, 2H), 6.83 (dd, J = 7.0, 1.6 Hz, 1H), 6.75 (t, J = 6.0 Hz, 1H), 4.47 (m, 1H), 4.33 (d, J = 6.0 Hz, 2H), 4.19 (m, 1H), 4.05 (m, 1H), 3.85-3.69 (m, 4H), 3.28 (m, 2H), 2.03 (d, J = 1.8 Hz, 2H), 1.90 (m, 1H), 1.57 (m, 2H), 1.21 (m, 2H) | (ESI(+)) m/e 448 (M + H)$^+$ |

Example 462

4-[(cyclopentylacetyl)amino]-2-fluoro-N-(imidazo[1,2-a]pyridin-6-ylmethyl)benzamide

Example 462A methyl 4-(2-cyclopentylacetamido)-2-fluorobenzoate

The title compound was prepared as described in Example 52A, substituting 2-cyclopentylacetyl chloride for 2-cyclopentylacetyl chloride and methyl 4-amino-2-fluorobenzoate for methyl 4-aminobenzoate.

Example 462B 4-(2-cyclopentylacetamido)-2-fluorobenzoic acid

The title compound was prepared as described in Example 4B, substituting methyl 4-(2-cyclopentylacetamido)-2-fluorobenzoate for methyl 4-(3-imidazo[1,2-a]pyridin-6-ylureido)benzoate.

Example 462C

4-[(cyclopentylacetyl)amino]-2-fluoro-N-(imidazo[1,2-a]pyridin-6-ylmethyl)benzamide The title compound was prepared as described in Example 1A, substituting imidazo[1,2-a]pyridin-6-ylmethanamine for 3-methylbutan-1-amine and 4-(2-cyclopentylacetamido)-2-fluorobenzoic acid for 4-nitrobenzoic acid. $^1$H NMR (501 MHz, DMSO-d$_6$) δ ppm 10.24 (s, 1H), 8.70-8.63 (m, 1H), 8.46 (s, 1H), 7.95 (s, 1H), 7.74-7.62 (m, 2H), 7.58-7.50 (m, 2H), 7.32 (dd, J=8.5, 1.9 Hz, 1H), 7.24 (dd, J=9.2, 1.7 Hz, 1H), 4.45 (d, J=5.9 Hz, 2H), 2.37-2.31 (m, 2H), 2.31-2.15 (m, 1H), 1.81-1.69 (m, 2H), 1.67-1.45 (m, 4H), 1.25-1.12 (m, 2H); MS (ESI(+)) m/e 395 (M+H)$^+$.

Example 464

N-(imidazo[1,2-a]pyridin-7-ylmethyl)-5-[6-(morpholin-4-yl)pyridin-3-yl]thiophene-2-carboxamide The title compound was prepared as described in Example 51A, substituting 4-(5-(4,4,5,5-tetramethyl-1,3,2-dioxaborolan-2-yl)pyridin-2-yl)morpholine for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline. $^1$H NMR (500 MHz, DMSO-d$_6$) δ ppm 9.34 (t, J=6.0 Hz, 1H), 8.87 (d, J=7.0 Hz, 1H), 8.51 (d, J=2.5 Hz, 1H), 8.33 (d, J=2.2 Hz, 1H), 8.15 (d, J=2.1 Hz, 1H), 7.90 (dd, J=8.9, 2.6 Hz, 1H), 7.85 (d, J=3.9 Hz, 1H), 7.81 (s, 1H), 7.50-7.44 (m, 2H), 6.94 (d, J=9.0 Hz, 1H), 4.67 (d, J=5.9 Hz, 2H), 3.75-3.66 (m, 4H), 3.57-3.49 (m, 4H); MS (ESI(+)) m/e 420 (M+H).

Example 467

N-(imidazo[1,2-a]pyridin-7-ylmethyl)-5-[1-(3-methylbutanoyl)pyrrolidin-3-yl]thiophene-2-carboxamide

Example 467A tert-butyl 3-(5-(imidazo[1,2-a]pyridin-7-ylmethylcarbamoyl)thiophen-2-yl)pyrrolidine-1-carboxylate The title compound was prepared as described in Example 1A, substituting imidazo[1,2-a]pyridin-7-ylmethanamine for 3-methylbutan-1-amine and 5-(1-(tert-butoxycarbonyl)pyrrolidin-3-yl)thiophene-2-carboxylic acid for 4-nitrobenzoic acid.

Example 467B

N-(imidazo[1,2-a]pyridin-7-ylmethyl)-5-(pyrrolidin-3-yl)thiophene-2-carboxamide

The title compound was prepared as described in Example 28A, substituting tert-butyl 3-(5-(imidazo[1,2-a]pyridin-7-ylmethylcarbamoyl)thiophen-2-yl)pyrrolidine-1-carboxylate for tert-butyl 4-(4-(3-imidazo[1,2-a]pyridin-6-ylureido)phenyl)-5,6-dihydropyridine-1(2H)-carboxylate.

Example 467C

N-(imidazo[1,2-a]pyridin-7-ylmethyl)-5-[1-(3-methylbutanoyl)pyrrolidin-3-yl]thiophene-2-carboxamide The title compound was prepared as described in Example 1A, substituting N-(imidazo[1,2-a]pyridin-7-ylmethyl)-5-(pyrrolidin-3-yl)thiophene-2-carboxamide for 3-methylbutan-1-amine and 3-methylbutanoic acid for 4-nitrobenzoic acid. $^1$H NMR (300 MHz, DMSO-$d_6$) ppm 9.02 (t, J=5.4 Hz, 1H), 8.48 (d, J=6.8 Hz, 1H), 7.88 (s, 1H), 7.68 (dd, J=3.9, 2.2 Hz, 1H), 7.52 (d, J=1.4 Hz, 1H), 7.37 (s, 1H), 7.02 (dd, J=8.1, 3.7 Hz, 1H), 6.82 (dd, J=7.0, 1.5 Hz, 1H), 4.46 (d, J=5.8 Hz, 2H), 3.22-3.94 (m, 5H), 2.21-2.42 (m, 1H), 2.10-2.17 (m, 2H), 1.86-2.09 (m, 2H), 0.86-0.95 (m, 6H); MS (ESI(+)) m/e 411 (M+H)$^+$.

TABLE 23

The following Examples were prepared essentially as described in Example 467, using an appropriate carboxylic acid in Example 467C.

| Ex | Name | MS |
| --- | --- | --- |
| 540 | N-(imidazo[1,2-a]pyridin-7-ylmethyl)-5-[1-(3,3,3-trifluoropropanoyl)pyrrolidin-3-yl]thiophene-2-carboxamide | (ESI(+)) m/e 437 (M + H)$^+$ |
| 541 | N-(imidazo[1,2-a]pyridin-7-ylmethyl)-5-[1-(2-methylpropanoyl)pyrrolidin-3-yl]thiophene-2-carboxamide | (ESI(+)) m/e 397 (M + H)$^+$ |
| 542 | 5-(1-benzoylpyrrolidin-3-yl)-N-(imidazo[1,2-a]pyridin-7-ylmethyl)thiophene-2-carboxamide | (ESI(+)) m/e 431 (M + H)$^+$ |
| 717 | 5-[1-(cyclopropylcarbonyl)pyrrolidin-3-yl]-N-(imidazo[1,2-a]pyridin-7-ylmethyl)thiophene-2-carboxamide | (ESI(+)) m/e 395 (M + H)$^+$ |
| 718 | N-(imidazo[1,2-a]pyridin-7-ylmethyl)-5-[1-(4-methylbenzoyl)pyrrolidin-3-yl]thiophene-2-carboxamide | (ESI(+)) m/e 445 (M + H)$^+$ |
| 756 | 5-[1-(cyclopropylacetyl)pyrrolidin-3-yl]-N-(imidazo[1,2-a]pyridin-7-ylmethyl)thiophene-2-carboxamide | (ESI(+)) m/e 409 (M + H)$^+$ |
| 757 | 5-[1-(2-chlorobenzoyl)pyrrolidin-3-yl]-N-(imidazo[1,2-a]pyridin-7-ylmethyl)thiophene-2-carboxamide | (ESI(+)) m/e 465 (M + H)$^+$ |
| 758 | 5-{1-[(4-fluorophenyl)acetyl]pyrrolidin-3-yl}-N-(imidazo[1,2-a]pyridin-7-ylmethyl)thiophene-2-carboxamide | (ESI(+)) m/e 463 (M + H)$^+$ |
| 759 | N-(imidazo[1,2-a]pyridin-7-ylmethyl)-5-[1-(3-methoxybenzoyl)pyrrolidin-3-yl]thiophene-2-carboxamide | (ESI(+)) m/e 461 (M + H)$^+$ |
| 760 | N-(imidazo[1,2-a]pyridin-7-ylmethyl)-5-[1-(2-methoxybenzoyl)pyrrolidin-3-yl]thiophene-2-carboxamide | (ESI(+)) m/e 461 (M + H)$^+$ |
| 761 | 5-{1-[(3-fluorophenyl)acetyl]pyrrolidin-3-yl}-N-(imidazo[1,2-a]pyridin-7-ylmethyl)thiophene-2-carboxamide | (ESI(+)) m/e 463 (M + H)$^+$ |
| 762 | 5-[1-(3-fluorobenzoyl)pyrrolidin-3-yl]-N-(imidazo[1,2-a]pyridin-7-ylmethyl)thiophene-2-carboxamide | (ESI(+)) m/e 449 (M + H)$^+$ |
| 763 | 5-[1-(4-fluorobenzoyl)pyrrolidin-3-yl]-N-(imidazo[1,2-a]pyridin-7-ylmethyl)thiophene-2-carboxamide | (ESI(+)) m/e 449 (M + H)$^+$ |
| 764 | 5-{1-[(3,5-difluorophenyl)acetyl]pyrrolidin-3-yl}-N-(imidazo[1,2-a]pyridin-7-ylmethyl)thiophene-2-carboxamide | (ESI(+)) m/e 481 (M + H)$^+$ |
| 765 | 5-{1-[(2-fluorophenyl)acetyl]pyrrolidin-3-yl}-N-(imidazo[1,2-a]pyridin-7-ylmethyl)thiophene-2-carboxamide | (ESI(+)) m/e 463 (M + H)$^+$ |
| 766 | 5-[1-(4-cyanobenzoyl)pyrrolidin-3-yl]-N-(imidazo[1,2-a]pyridin-7-ylmethyl)thiophene-2-carboxamide | (ESI(+)) m/e 456 (M + H)$^+$ |
| 767 | N-(imidazo[1,2-a]pyridin-7-ylmethyl)-5-{1-[(3-methyloxetan-3-yl)carbonyl]pyrrolidin-3-yl}thiophene-2-carboxamide | (ESI(+)) m/e 425 (M + H)$^+$ |
| 768 | 5-[1-(3,5-difluorobenzoyl)pyrrolidin-3-yl]-N-(imidazo[1,2-a]pyridin-7-ylmethyl)thiophene-2-carboxamide | (ESI(+)) m/e 467 (M + H)$^+$ |
| 769 | 5-[1-(cyclopentylcarbonyl)pyrrolidin-3-yl]-N-(imidazo[1,2-a]pyridin-7-ylmethyl)thiophene-2-carboxamide | (ESI(+)) m/e 421 (M + H)$^+$ |
| 770 | 5-[1-(4-chlorobenzoyl)pyrrolidin-3-yl]-N-(imidazo[1,2-a]pyridin-7-ylmethyl)thiophene-2-carboxamide | (ESI(+)) m/e 465 (M + H)$^+$ |

TABLE 23-continued

The following Examples were prepared essentially as described in Example 467, using an appropriate carboxylic acid in Example 467C.

| Ex | Name | MS |
|---|---|---|
| 771 | N-(imidazo[1,2-a]pyridin-7-ylmethyl)-5-{1-[(1-methyl-1H-pyrrol-2-yl)carbonyl]pyrrolidin-3-yl}thiophene-2-carboxamide | (ESI(+)) m/e 434 (M + H)$^+$ |
| 772 | 5-[1-(2,4-difluorobenzoyl)pyrrolidin-3-yl]-N-(imidazo[1,2-a]pyridin-7-ylmethyl)thiophene-2-carboxamide | (ESI(+)) m/e 467 (M + H)$^+$ |
| 773 | N-(imidazo[1,2-a]pyridin-7-ylmethyl)-5-[1-(pyridin-4-ylcarbonyl)pyrrolidin-3-yl]thiophene-2-carboxamide | (ESI(+)) m/e 432 (M + H)$^+$ |
| 774 | N-(imidazo[1,2-a]pyridin-7-ylmethyl)-5-[1-(pyridin-2-ylcarbonyl)pyrrolidin-3-yl]thiophene-2-carboxamide | (ESI(+)) m/e 432 (M + H)$^+$ |
| 775 | N-(imidazo[1,2-a]pyridin-7-ylmethyl)-5-{1-[(1-methyl-1H-pyrazol-4-yl)carbonyl]pyrrolidin-3-yl}thiophene-2-carboxamide | (ESI(+)) m/e 435 (M + H)$^+$ |
| 776 | 5-[1-(2-fluorobenzoyl)pyrrolidin-3-yl]-N-(imidazo[1,2-a]pyridin-7-ylmethyl)thiophene-2-carboxamide | (ESI(+)) m/e 449 (M + H)$^+$ |
| 777 | N-(imidazo[1,2-a]pyridin-7-ylmethyl)-5-{1-[(2E)-2-methylpent-2-enoyl]pyrrolidin-3-yl}thiophene-2-carboxamide | (ESI(+)) m/e 423 (M + H)$^+$ |
| 778 | 5-{1-[(2,5-dimethylfuran-3-yl)carbonyl]pyrrolidin-3-yl}-N-(imidazo[1,2-a]pyridin-7-ylmethyl)thiophene-2-carboxamide | (ESI(+)) m/e 449 (M + H)$^+$ |
| 779 | 5-[1-(3-chlorobenzoyl)pyrrolidin-3-yl]-N-(imidazo[1,2-a]pyridin-7-ylmethyl)thiophene-2-carboxamide | (ESI(+)) m/e 465 (M + H)$^+$ |
| 780 | N-(imidazo[1,2-a]pyridin-7-ylmethyl)-5-(1-propanoylpyrrolidin-3-yl)thiophene-2-carboxamide | (ESI(+)) m/e 383 (M + H)$^+$ |
| 781 | 5-{1-[(1-cyanocyclopropyl)carbonyl]pyrrolidin-3-yl}-N-(imidazo[1,2-a]pyridin-7-ylmethyl)thiophene-2-carboxamide | (ESI(+)) m/e 420 (M + H)$^+$ |
| 782 | 5-(1-butanoylpyrrolidin-3-yl)-N-(imidazo[1,2-a]pyridin-7-ylmethyl)thiophene-2-carboxamide | (ESI(+)) m/e 397 (M + H)$^+$ |
| 783 | 5-[1-(furan-2-ylcarbonyl)pyrrolidin-3-yl]-N-(imidazo[1,2-a]pyridin-7-ylmethyl)thiophene-2-carboxamide | (ESI(+)) m/e 421 (M + H)$^+$ |
| 784 | N-(imidazo[1,2-a]pyridin-7-ylmethyl)-5-[1-(4-methoxybenzoyl)pyrrolidin-3-yl]thiophene-2-carboxamide | (ESI(+)) m/e 461 (M + H)$^+$ |
| 785 | 5-[1-(2,5-difluorobenzoyl)pyrrolidin-3-yl]-N-(imidazo[1,2-a]pyridin-7-ylmethyl)thiophene-2-carboxamide | (ESI(+)) m/e 467 (M + H)$^+$ |
| 786 | N-(imidazo[1,2-a]pyridin-7-ylmethyl)-5-[1-(thiophen-2-ylcarbonyl)pyrrolidin-3-yl]thiophene-2-carboxamide | (ESI(+)) m/e 437 (M + H)$^+$ |
| 787 | 5-[1-(2,2-dimethylpropanoyl)pyrrolidin-3-yl]-N-(imidazo[1,2-a]pyridin-7-ylmethyl)thiophene-2-carboxamide | (ESI(+)) m/e 411 (M + H)$^+$ |
| 788 | 5-[1-(3,3-dimethylbutanoyl)pyrrolidin-3-yl]-N-(imidazo[1,2-a]pyridin-7-ylmethyl)thiophene-2-carboxamide | (ESI(+)) m/e 425 (M + H)$^+$ |
| 791 | 5-[1-(2,2-dimethylbutanoyl)pyrrolidin-3-yl]-N-(imidazo[1,2-a]pyridin-7-ylmethyl)thiophene-2-carboxamide | (ESI(+)) m/e 425 (M + H)$^+$ |
| 792 | N-(imidazo[1,2-a]pyridin-7-ylmethyl)-5-[1-(pyrazin-2-ylcarbonyl)pyrrolidin-3-yl]thiophene-2-carboxamide | (ESI(+)) m/e 433 (M + H)$^+$ |
| 793 | N-(imidazo[1,2-a]pyridin-7-ylmethyl)-5-{1-[(3-methylthiophen-2-yl)carbonyl]pyrrolidin-3-yl}thiophene-2-carboxamide | (ESI(+)) m/e 451 (M + H)$^+$ |
| 794 | N-(imidazo[1,2-a]pyridin-7-ylmethyl)-5-[1-(2-methylbenzoyl)pyrrolidin-3-yl]thiophene-2-carboxamide | (ESI(+)) m/e 445 (M + H)$^+$ |
| 795 | N-(imidazo[1,2-a]pyridin-7-ylmethyl)-5-{1-[(1-methylcyclopropyl)carbonyl]pyrrolidin-3-yl}thiophene-2-carboxamide | (ESI(+)) m/e 409 (M + H)$^+$ |
| 796 | N-(imidazo[1,2-a]pyridin-7-ylmethyl)-5-[1-(4,4,4-trifluorobutanoyl)pyrrolidin-3-yl]thiophene-2-carboxamide | (ESI(+)) m/e 451 (M + H)$^+$ |
| 797 | 5-{1-[(3,5-dimethyl-1,2-oxazol-4-yl)carbonyl]pyrrolidin-3-yl}-N-(imidazo[1,2-a]pyridin-7-ylmethyl)thiophene-2-carboxamide | (ESI(+)) m/e 450 (M + H)$^+$ |

TABLE 23-continued

The following Examples were prepared essentially as described in Example 467, using an appropriate carboxylic acid in Example 467C.

| Ex | Name | MS |
|----|------|-----|
| 798 | N-(imidazo[1,2-a]pyridin-7-ylmethyl)-5-[1-(pyridin-3-ylcarbonyl)pyrrolidin-3-yl]thiophene-2-carboxamide | (ESI(+)) m/e 432 (M + H)$^+$ |
| 799 | N-(imidazo[1,2-a]pyridin-7-ylmethyl)-5-{1-[(1-methyl-1H-pyrazol-5-yl)carbonyl]pyrrolidin-3-yl}thiophene-2-carboxamide | (ESI(+)) m/e 435 (M + H)$^+$ |
| 800 | 5-[1-(2,3-dimethylbutanoyl)pyrrolidin-3-yl]-N-(imidazo[1,2-a]pyridin-7-ylmethyl)thiophene-2-carboxamide | (ESI(+)) m/e 425 (M + H)$^+$ |

Example 468

N-(imidazo[1,2-a]pyridin-7-ylmethyl)-5-{1-[(2-methylpropanoyl)amino]cyclobutyl}thiophene-2-carboxamide Example 468A 5-(1-(1,1-dimethylethylsulfinamido)cyclobutyl)thiophene-2-carboxylic acid The title compound was prepared as described in Example 324A, substituting N-cyclobutylidene-2-methylpropane-2-sulfinamide for N-(oxetan-3-ylidene)propane-2-sulfinamide.

Example 468B 5-(1-(1,1-dimethylethylsulfinamido)cyclobutyl)-N-(imidazo[1,2-a]pyridin-7-ylmethyl)thiophene-2-carboxamide The title compound was prepared as described in Example 1A, substituting imidazo[1,2-a]pyridin-7-ylmethanamine for 3-methylbutan-1-amine and 5-(1-(1,1-dimethylethylsulfinamido)cyclobutyl)thiophene-2-carboxylic acid for 4-nitrobenzoic acid.

Example 468C 5-(1-aminocyclobutyl)-N-(imidazo[1,2-a]pyridin-7-ylmethyl)thiophene-2-carboxamide The title compound was prepared in Example 324C, substituting 5-(1-(1,1-dimethylethylsulfinamido)cyclobutyl)-N-(imidazo[1,2-a]pyridin-7-ylmethyl)thiophene-2-carboxamide for 5-(3-(1,1-dimethylethylsulfinamido)oxetan-3-yl)-N-(imidazo[1,2-a]pyridin-7-ylmethyl)thiophene-2-carboxamide.

Example 468D

The title compound was prepared as described in Example 1A, substituting 5-(1-aminocyclobutyl)-N-(imidazo[1,2-a]pyridin-7-ylmethyl)thiophene-2-carboxamide for 3-methylbutan-1-amine and isobutyric acid for 4-nitrobenzoic acid. $^1$H NMR (300 MHz, DMSO-d$_6$) ppm 8.97 (t, J=5.9 Hz, 1H), 8.53 (s, 1H), 8.48 (d, J=7.1 Hz, 1H), 7.88 (s, 1H), 7.63 (d, J=3.7 Hz, 1H), 7.52 (d, J=1.4 Hz, 1H), 7.38 (s, 1H), 7.04 (d, J=3.7 Hz, 1H), 6.82 (dd, J=6.8, 1.7 Hz, 1H), 4.45 (d, J=5.8 Hz, 2H), 2.36-2.48 (m, 5H), 1.86-2.01 (m, 2H), 0.99 (d, J=6.8 Hz, 6H); MS (ESI(+)) m/e 397 (M+H)$^+$.

Example 469

N-(imidazo[1,2-a]pyridin-7-ylmethyl)-5-{1-[(3-methylbutanoyl)amino]cyclobutyl}thiophene-2-carboxamide The title compound was prepared as described in Example 1A, substituting 5-(1-aminocyclobutyl)-N-(imidazo[1,2-a]pyridin-7-ylmethyl)thiophene-2-carboxamide for 3-methylbutan-1-amine and 3-methylbutanoic acid for 4-nitrobenzoic acid. $^1$H NMR (300 MHz, DMSO-d$_6$) ppm 8.97 (t, J=5.9 Hz, 1H), 8.59 (s, 1H), 8.48 (d, J=7.8 Hz, 1H), 7.88 (s, 1H), 7.63 (d, J=4.1 Hz, 1H), 7.51 (d, J=1.0 Hz, 1H), 7.37 (s, 1H), 7.05 (d, J=3.7 Hz, 1H), 6.82 (dd, J=7.1, 1.7 Hz, 1H), 4.45 (d, J=5.8 Hz, 2H), 2.39-2.47 (m, 4H), 1.83-2.03 (m, 5H), 0.87 (d, J=6.4 Hz, 6H); MS (ESI(+)) m/e 411 (M+H)$^+$.

Example 470

N-(imidazo[1,2-a]pyridin-7-ylmethyl)-5-(1-{[(2S)-2-methylbutanoyl]amino}cyclobutyl)thiophene-2-carboxamide The title compound was prepared as described in Example 1A, substituting 5-(1-aminocyclobutyl)-N-(imidazo[1,2-a]pyridin-7-ylmethyl)thiophene-2-carboxamide for 3-methylbutan-1-amine and (S)-2-methylbutanoic acid for 4-nitrobenzoic acid. $^1$H NMR (300 MHz, DMSO-d$_6$) ppm 8.97 (t, J=6.1 Hz, 1H), 8.57 (s, 1H), 8.47 (d, J=7.1 Hz, 1H), 7.88 (s, 1H), 7.63 (d, J=4.1 Hz, 1H), 7.51 (d, J=1.4 Hz, 1H), 7.37 (s, 1H), 7.04 (d, J=3.7 Hz, 1H), 6.82 (dd, J=7.0, 1.5 Hz, 1H), 4.45 (d, J=5.8 Hz, 2H), 2.37-2.49 (m, 4H), 2.13-2.26 (m, 1H), 1.84-2.01 (m, 2H), 1.40-1.59 (m, 1H), 1.20-1.36 (m, 1H), 0.97 (d, J=6.8 Hz, 3H), 0.82 (t, J=7.3 Hz, 3H); MS (ESI(+)) m/e 411 (M+H).

Example 471

5-[1-(benzoylamino)cyclobutyl]-N-(imidazo[1,2-a]pyridin-7-ylmethyl)thiophene-2-carboxamide The title compound was prepared as described in Example 1A, substituting 5-(1-aminocyclobutyl)-N-(imidazo[1,2-a]pyridin-7-ylmethyl)thiophene-2-carboxamide for 3-methylbutan-1-amine and benzoic acid for 4-nitrobenzoic acid. $^1$H NMR (300 MHz, DMSO-d$_6$) ppm 9.17 (s, 1H), 8.98 (t, J=5.9 Hz, 1H), 8.46 (d, J=6.1 Hz, 1H), 7.84-7.90 (m, 3H), 7.65 (d, J=4.1 Hz, 1H), 7.43-7.57 (m, 4H), 7.37 (s, 1H), 7.14 (d, J=4.1 Hz, 1H), 6.81 (dd, J=6.8, 1.7 Hz, 1H), 4.44 (d, J=6.1 Hz, 2H), 2.61-2.73 (m, 2H), 2.50-2.60 (m, 2H), 1.91-2.07 (m, 2H); MS (ESI(+)) m/e 431 (M+H).

Example 472

N-(imidazo[1,2-a]pyridin-7-ylmethyl)-5-{1-[(3,3,3-trifluoropropanoyl)amino]cyclobutyl}thiophene-2-carboxamide The title compound was prepared as described in Example 1A, substituting 5-(1-aminocyclobutyl)-N-(imidazo[1,2-a]pyridin-7-ylmethyl)thiophene-2-carboxamide for 3-methylbutan-1-amine and 3,3,3-trifluoropropanoic acid for 4-nitrobenzoic acid. $^1$H NMR (300 MHz, DMSO-$d_6$) ppm 9.08 (s, 1H), 9.00 (t, J=5.9 Hz, 1H), 8.48 (d, J=7.8 Hz, 1H), 7.88 (s, 1H), 7.65 (d, J=3.7 Hz, 1H), 7.52 (s, 1H), 7.38 (s, 1H), 7.07 (d, J=3.7 Hz, 1H), 6.83 (dd, J=6.8, 1.7 Hz, 1H), 4.46 (d, J=5.8 Hz, 2H), 3.19-3.36 (m, 2H), 2.43-2.53 (m, 4H), 1.86-2.03 (m, 2H); MS (ESI(+)) m/e 437 (M+H)$^+$.

Example 473

N-(1-{5-[(imidazo[1,2-a]pyridin-7-ylmethyl)carbamoyl]thiophen-2-yl}cyclobutyl)tetrahydro-2H-pyran-4-carboxamide The title compound was prepared as described in Example 1A, substituting 5-(1-aminocyclobutyl)-N-(imidazo[1,2-a]pyridin-7-ylmethyl)thiophene-2-carboxamide for 3-methylbutan-1-amine and tetrahydro-2H-pyran-4-carboxylic acid for 4-nitrobenzoic acid. $^1$H NMR (300 MHz, DMSO-$d_6$) ppm 8.97 (t, J=6.1 Hz, 1H), 8.60 (s, 1H), 8.48 (d, J=7.1 Hz, 1H), 7.88 (s, 1H), 7.63 (d, J=3.7 Hz, 1H), 7.51 (d, J=1.0 Hz, 1H), 7.37 (s, 1H), 7.04 (d, J=3.7 Hz, 1H), 6.82 (dd, J=7.0, 1.5 Hz, 1H), 4.45 (d, J=5.8 Hz, 2H), 3.81-3.89 (m, 2H), 3.24-3.36 (m, 2H), 2.33-2.48 (m, 5H), 1.84-2.00 (m, 2H), 1.47-1.65 (m, 4H); MS (ESI(+)) m/e 439 (M+H)$^+$.

Example 474 tert-butyl 3-{4-[(imidazo[1,2-a]pyridin-7-ylmethyl)carbamoyl]phenoxy}azetidine-1-carboxylate The title compound was prepared as described in Example 1A, substituting imidazo[1,2-a]pyridin-7-ylmethanamine for 3-methylbutan-1-amine and 4-(1-(tert-butoxycarbonyl)azetidin-3-yloxy)benzoic acid for 4-nitrobenzoic acid. $^1$H NMR (500 MHz, DMSO-$d_6$) δ ppm 8.98 (t, J=5.9 Hz, 1H), 8.48 (d, J=7.0 Hz, 1H), 7.89 (m, 3H), 7.51 (d, J=1.1 Hz, 1H), 7.37 (s, 1H), 6.92 (m, 2H), 6.84 (dd, J=7.0, 1.6 Hz, 1H), 5.06 (m, 1H), 4.49 (d, J=5.9 Hz, 2H), 4.33 (m, 2H), 3.80 (m, 2H), 1.39 (s, 9H); MS (ESI(+)) m/e 423 (M+H)$^+$.

Example 485

N-(imidazo[1,2-a]pyridin-7-ylmethyl)-5-[1-(piperidin-4-ylmethyl)-1H-pyrazol-4-yl]thiophene-2-carboxamide

Example 485A tert-butyl 4-((4-(5-((imidazo[1,2-a]pyridin-7-ylmethyl)carbamoyl)thiophen-2-yl)-1H-pyrazol-1-yl)methyl)piperidine-1-carboxylate The title compound was prepared as described in Example 51A, substituting tert-butyl 4-((4-(4,4,5,5-tetramethyl-1,3,2-dioxaborolan-2-yl)-1H-pyrazol-1-yl)methyl)piperidine-1-carboxylate for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline.

Example 485B

N-(imidazo[1,2-a]pyridin-7-ylmethyl)-5-[1-(piperidin-4-ylmethyl)-1H-pyrazol-4-yl]thiophene-2-carboxamide The title compound was prepared as described in Example 28A, substituting tert-butyl 4-((4-(5-((imidazo[1,2-a]pyridin-7-ylmethyl)carbamoyl)thiophen-2-yl)-1H-pyrazol-1-yl)methyl)piperidine-1-carboxylate for tert-butyl 4-(4-(3-imidazo[1,2-a]pyridin-6-ylureido)phenyl)-5,6-dihydropyridine-1(2H)-carboxylate. $^1$H NMR (300 MHz, methanol-$d_4$) δ 8.76 (dd, J=7.1, 0.9 Hz, 1H), 8.19 (dd, J=2.2, 0.7 Hz, 1H), 8.07 (s, 1H), 8.00 (d, J=2.2 Hz, 1H), 7.83 (d, J=0.6 Hz, 2H), 7.72 (d, J=3.8 Hz, 1H), 7.49 (dd, J=7.0, 1.6 Hz, 1H), 7.22 (d, J=3.9 Hz, 1H), 4.75 (s, 2H), 4.15 (d, J=7.0 Hz, 2H), 3.48-3.36 (m, 2H), 3.08-2.91 (m, 2H), 2.37-2.15 (m, 1H), 1.85 (d, J=14.0 Hz, 2H), 1.63-1.43 (m, 2H); MS (ESI(+)) m/e 421 (M+H)$^+$.

Example 486

1-(imidazo[1,2-a]pyridin-7-ylmethyl)-3-{4-[1-(2-methylpropyl)-1H-pyrazol-4-yl]phenyl}urea

Example 486A 1-(4-bromophenyl)-3-(imidazo[1,2-a]pyridin-7-ylmethyl)urea

To a solution of imidazo[1,2-a]pyridin-7-ylmethanamine (500 mg, 3.40 mmol) in dichloromethane (17 ml) at room temperature was added 1-bromo-4-isocyanatobenzene (680 mg, 3.40 mmol) as a single portion. The resulting suspension was stirred overnight and then filtered with dichloromethane washes to give the title compound.

Example 486B 1-(imidazo[1,2-a]pyridin-7-ylmethyl)-3-{4-[1-(2-methylpropyl)-1H-pyrazol-4-yl]phenyl}urea The title compound was prepared as described in Example 51A, substituting substituting 1-isobutyl-4-(4,4,5,5-tetramethyl-1,3,2-dioxaborolan-2-yl)-1H-pyrazole for 1-propyl-4-(4,4,5,5-tetramethyl-1,3,2-dioxaborolan-2-yl)-1H-pyrazole and 1-(4-bromophenyl)-3-(imidazo[1,2-a]pyridin-7-ylmethyl)urea for 4-bromoaniline. $^1$H NMR (300 MHz, DMSO-$d_6$) δ ppm 8.62 (s, 1H), 8.48 (dd, J=6.9, 0.9 Hz, 1H), 8.02 (d, J=0.8 Hz, 1H), 7.88 (dd, J=1.2, 0.7 Hz, 1H), 7.77 (d, J=0.8 Hz, 1H), 7.54-7.34 (m, 6H), 6.84 (dd, J=7.0, 1.7 Hz, 1H), 6.69 (t, J=6.0 Hz, 1H), 4.34 (d, J=5.9 Hz, 2H), 3.90 (d, J=7.1 Hz, 2H), 2.21-2.04 (m, 1H), 0.86 (d, J=6.7 Hz, 6H). MS (ESI(+)) m/e 389 (M+H)$^+$.

Example 487

1-(imidazo[1,2-a]pyridin-7-ylmethyl)-3-[4-(1-propyl-1H-pyrazol-4-yl)phenyl]urea

The title compound was prepared as described in Example 51A, substituting 1-propyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 1-(4-bromophenyl)-3-(imidazo[1,2-a]pyridin-7-ylmethyl)urea for 4-bromoaniline. $^1$H NMR (300 MHz, DMSO-d$_6$) δ 8.62 (s, 1H), 8.48 (dd, J=6.9, 0.9 Hz, 1H), 8.04 (d, J=0.8 Hz, 1H), 7.90-7.86 (m, 1H), 7.76 (d, J=0.8 Hz, 1H), 7.51 (d, J=1.2 Hz, 1H), 7.46-7.35 (m, 5H), 6.84 (dd, J=7.0, 1.7 Hz, 1H), 6.69 (t, J=6.0 Hz, 1H), 4.34 (d, J=5.9 Hz, 2H), 4.04 (t, J=6.9 Hz, 2H), 1.91-1.73 (m, 2H), 1.26-1.05 (m, 1H), 0.85 (t, J=7.4 Hz, 3H); MS (ESI(+)) m/e 375 (M+H)$^+$.

Example 489

N-(imidazo[1,2-a]pyridin-7-ylmethyl)-4-phenoxybenzamide

The title compound was prepared as described in Example 1A, substituting imidazo[1,2-a]pyridin-7-ylmethanamine for 3-methylbutan-1-amine and 4-phenoxybenzoic acid for 4-nitrobenzoic acid. $^1$H NMR (400 MHz, DMSO-d$_6$) δ ppm 9.05 (t, J=5.9 Hz, 1H), 8.48 (dd, J=6.9, 0.9 Hz, 1H), 7.95 (m, 2H), 7.89 (s, 1H), 7.52 (d, J=1.2 Hz, 1H), 7.44 (m, 2H), 7.38 (s, 1H), 7.22 (m, 1H), 7.14-6.98 (m, 4H), 6.85 (dd, J=7.0, 1.7 Hz, 1H), 4.50 (d, J=5.9 Hz, 2H); MS (ESI(+)) m/e 344 (M+H)$^+$.

Example 490

N-(imidazo[1,2-a]pyridin-7-ylmethyl)-4-[1-(2-methylpropanoyl)azetidin-3-yl]benzamide

Example 490A 4-(azetidin-3-yl)-N-(imidazo[1,2-a]pyridin-7-ylmethyl)benzamide The title compound was prepared as described in Example 28A, substituting tert-butyl 3-{4-[(imidazo[1,2-a]pyridin-7-ylmethyl)carbamoyl]phenyl}azetidine-1-carboxylate for tert-butyl 4-(4-(3-imidazo[1,2-a]pyridin-6-ylureido)phenyl)-5,6-dihydropyridine-1(2H)-carboxylate.

Example 490B

N-(imidazo[1,2-a]pyridin-7-ylmethyl)-4-[1-(2-methylpropanoyl)azetidin-3-yl]benzamide The title compound was prepared as described in Example 1A, substituting -(azetidin-3-yl)-N-(imidazo[1,2-a]pyridin-7-ylmethyl)benzamide for 3-methylbutan-1-amine and 2-methylpropanoic acid for 4-nitrobenzoic acid. $^1$H NMR (500 MHz, DMSO-d$_6$) δ ppm 9.10 (t, J=5.9 Hz, 1H), 8.48 (d, J=7.0 Hz, 1H), 7.91 (m, 3H), 7.52 (d, J=1.0 Hz, 1H), 7.48 (m, 2H), 7.38 (s, 1H), 6.85 (dd, J=7.0, 1.7 Hz, 1H), 4.58 (t, J=8.6 Hz, 1H), 4.51 (d, J=5.9 Hz, 2H), 4.26 (t, J=9.0 Hz, 1H), 4.18 (dd, J=8.4, 6.0 Hz, 1H), 3.92 (m, 1H), 3.84 (m, 1H), 3.17 (d, J=5.0 Hz, 1H), 1.00 (dd, J=6.8, 1.6 Hz, 6H); MS (ESI(+)) m/e 377 (M+H)$^+$.

TABLE 24

The following Examples were prepared essentially as described in Example 490, using an appropriate carboxylic acid in Example 490B.

| Ex | Name | MS |
|---|---|---|
| 547 | N-(imidazo[1,2-a]pyridin-7-ylmethyl)-4-{1-[(2S)-2-methylbutanoyl]azetidin-3-yl}benzamide | (ESI(+)) m/e 391 (M + H)$^+$ |
| 548 | 4-[1-(cyclopropylacetyl)azetidin-3-yl]-N-(imidazo[1,2-a]pyridin-7-ylmethyl)benzamide | (ESI(+)) m/e 389 (M + H)$^+$ |
| 549 | 4-(1-benzoylazetidin-3-yl)-N-(imidazo[1,2-a]pyridin-7-ylmethyl)benzamide | (ESI(+)) m/e 411 (M + H)$^+$ |
| 550 | 4-[1-(2-hydroxy-2-methylpropanoyl)azetidin-3-yl]-N-(imidazo[1,2-a]pyridin-7-ylmethyl)benzamide | (ESI(+)) m/e 393 (M + H)$^+$ |
| 551 | N-(imidazo[1,2-a]pyridin-7-ylmethyl)-4-[1-(tetrahydro-2H-pyran-4-ylacetyl)azetidin-3-yl]benzamide | (ESI(+)) m/e 433 (M + H)$^+$ |
| 552 | N-(imidazo[1,2-a]pyridin-7-ylmethyl)-4-[1-(thiophen-2-ylcarbonyl)azetidin-3-yl]benzamide | (ESI(+)) m/e 417 (M + H)$^+$ |
| 628 | N-(imidazo[1,2-a]pyridin-7-ylmethyl)-4-{1-[(2-methylcyclopropyl)carbonyl]azetidin-3-yl}benzamide | (ESI(+)) m/e 389 (M + H)$^+$ |
| 629 | 4-[1-(cyclopentylacetyl)azetidin-3-yl]-N-(imidazo[1,2-a]pyridin-7-ylmethyl)benzamide | (ESI(+)) m/e 417 (M + H)$^+$ |
| 630 | N-(imidazo[1,2-a]pyridin-7-ylmethyl)-4-[1-(3-methylpentanoyl)azetidin-3-yl]benzamide | (ESI(+)) m/e 405 (M + H)$^+$ |
| 631 | 4-[1-(cyclopentylcarbonyl)azetidin-3-yl]-N-(imidazo[1,2-a]pyridin-7-ylmethyl)benzamide | (ESI(+)) m/e 403 (M + H)$^+$ |

TABLE 24-continued

The following Examples were prepared essentially as described in Example 490, using an appropriate carboxylic acid in Example 490B.

| Ex | Name | MS |
|---|---|---|
| 632 | N-(imidazo[1,2-a]pyridin-7-ylmethyl)-4-{1-[(1-methylcyclopropyl)carbonyl]azetidin-3-yl}benzamide | (ESI(+)) m/e 389 (M + H)$^+$ |
| 633 | 4-[1-(2,2-dimethylpropanoyl)azetidin-3-yl]-N-(imidazo[1,2-a]pyridin-7-ylmethyl)benzamide | (ESI(+)) m/e 391 (M + H)$^+$ |
| 634 | N-(imidazo[1,2-a]pyridin-7-ylmethyl)-4-[1-(1,3-thiazol-5-ylcarbonyl)azetidin-3-yl]benzamide | (ESI(+)) m/e 418 (M + H)$^+$ |
| 635 | N-(imidazo[1,2-a]pyridin-7-ylmethyl)-4-[1-(pyrazin-2-ylcarbonyl)azetidin-3-yl]benzamide | (ESI(+)) m/e 413 (M + H)$^+$ |
| 636 | N-(imidazo[1,2-a]pyridin-7-ylmethyl)-4-[1-(2-methoxybenzoyl)azetidin-3-yl]benzamide | (ESI(+)) m/e 441 (M + H)$^+$ |
| 637 | N-(imidazo[1,2-a]pyridin-7-ylmethyl)-4-[1-(1,3-thiazol-4-ylcarbonyl)azetidin-3-yl]benzamide | (ESI(+)) m/e 418 (M + H)$^+$ |
| 638 | 4-[1-(2-fluorobenzoyl)azetidin-3-yl]-N-(imidazo[1,2-a]pyridin-7-ylmethyl)benzamide | (ESI(+)) m/e 429 (M + H)$^+$ |
| 639 | 4-[1-(furan-2-ylcarbonyl)azetidin-3-yl]-N-(imidazo[1,2-a]pyridin-7-ylmethyl)benzamide | (ESI(+)) m/e 401 (M + H)$^+$ |
| 640 | 4-[1-(3-fluorobenzoyl)azetidin-3-yl]-N-(imidazo[1,2-a]pyridin-7-ylmethyl)benzamide | (ESI(+)) m/e 429 (M + H)$^+$ |
| 641 | 4-[1-(2,4-difluorobenzoyl)azetidin-3-yl]-N-(imidazo[1,2-a]pyridin-7-ylmethyl)benzamide | (ESI(+)) m/e 447 (M + H)$^+$ |
| 642 | N-(imidazo[1,2-a]pyridin-7-ylmethyl)-4-{1-[(1-methyl-1H-pyrazol-3-yl)carbonyl]azetidin-3-yl}benzamide | (ESI(+)) m/e 415 (M + H)$^+$ |
| 643 | 4-[1-(2-chlorobenzoyl)azetidin-3-yl]-N-(imidazo[1,2-a]pyridin-7-ylmethyl)benzamide | (ESI(+)) m/e 445 (M + H)$^+$ |
| 644 | N-(imidazo[1,2-a]pyridin-7-ylmethyl)-4-[1-(2-methylbenzoyl)azetidin-3-yl]benzamide | (ESI(+)) m/e 425 (M + H)$^+$ |
| 645 | 4-[1-(4-chlorobenzoyl)azetidin-3-yl]-N-(imidazo[1,2-a]pyridin-7-ylmethyl)benzamide | (ESI(+)) m/e 445 (M + H)$^+$ |
| 646 | 4-[1-(3-chlorobenzoyl)azetidin-3-yl]-N-(imidazo[1,2-a]pyridin-7-ylmethyl)benzamide | (ESI(+)) m/e 445 (M + H)$^+$ |
| 647 | 4-[1-(2,2-dimethylbutanoyl)azetidin-3-yl]-N-(imidazo[1,2-a]pyridin-7-ylmethyl)benzamide | (ESI(+)) m/e 405 (M + H)$^+$ |
| 648 | 4-[1-(3,5-difluorobenzoyl)azetidin-3-yl]-N-(imidazo[1,2-a]pyridin-7-ylmethyl)benzamide | (ESI(+)) m/e 447 (M + H)$^+$ |
| 649 | 4-[1-(4-fluorobenzoyl)azetidin-3-yl]-N-(imidazo[1,2-a]pyridin-7-ylmethyl)benzamide | (ESI(+)) m/e 429 (M + H)$^+$ |
| 650 | N-(imidazo[1,2-a]pyridin-7-ylmethyl)-4-[1-(4-methylbenzoyl)azetidin-3-yl]benzamide | (ESI(+)) m/e 425 (M + H)$^+$ |
| 651 | N-(imidazo[1,2-a]pyridin-7-ylmethyl)-4-[1-(3-methylbutanoyl)azetidin-3-yl]benzamide | (ESI(+)) m/e 391 (M + H)$^+$ |
| 652 | 4-[1-(3,3-dimethylbutanoyl)azetidin-3-yl]-N-(imidazo[1,2-a]pyridin-7-ylmethyl)benzamide | (ESI(+)) m/e 405 (M + H)$^+$ |
| 653 | 4-[1-(3-cyanobenzoyl)azetidin-3-yl]-N-(imidazo[1,2-a]pyridin-7-ylmethyl)benzamide | (ESI(+)) m/e 436 (M + H)$^+$ |
| 654 | N-(imidazo[1,2-a]pyridin-7-ylmethyl)-4-[1-(3-methoxybenzoyl)azetidin-3-yl]benzamide | (ESI(+)) m/e 441 (M + H)$^+$ |
| 655 | N-(imidazo[1,2-a]pyridin-7-ylmethyl)-4-[1-(4-methoxybenzoyl)azetidin-3-yl]benzamide | (ESI(+)) m/e 441 (M + H)$^+$ |

TABLE 24-continued

The following Examples were prepared essentially as described in Example 490, using an appropriate carboxylic acid in Example 490B.

| Ex | Name | MS |
|---|---|---|
| 565 | N-(imidazo[1,2-a]pyridin-7-ylmethyl)-4-{1-[(1-methyl-1H-pyrrol-2-yl)carbonyl]azetidin-3-yl}benzamide | (ESI(+)) m/e 414 (M + H)$^+$ |
| 657 | 4-[1-(cyclohexylacetyl)azetidin-3-yl]-N-(imidazo[1,2-a]pyridin-7-ylmethyl)benzamide | (ESI(+)) m/e 431 (M + H)$^+$ |
| 658 | N-(imidazo[1,2-a]pyridin-7-ylmethyl)-4-[1-(pyridin-4-ylcarbonyl)azetidin-3-yl]benzamide | (ESI(+)) m/e 412 (M + H)$^+$ |
| 659 | N-(imidazo[1,2-a]pyridin-7-ylmethyl)-4-[1-(pyridin-3-ylcarbonyl)azetidin-3-yl]benzamide | (ESI(+)) m/e 412 (M + H)$^+$ |
| 660 | 4-[1-(cyclohexylcarbonyl)azetidin-3-yl]-N-(imidazo[1,2-a]pyridin-7-ylmethyl)benzamide | (ESI(+)) m/e 417 (M + H)$^+$ |
| 661 | N-(imidazo[1,2-a]pyridin-7-ylmethyl)-4-[1-(pyridin-2-ylcarbonyl)azetidin-3-yl]benzamide | (ESI(+)) m/e 412 (M + H)$^+$ |
| 662 | 4-[1-(furan-3-ylcarbonyl)azetidin-3-yl]-N-(imidazo[1,2-a]pyridin-7-ylmethyl)benzamide | (ESI(+)) m/e 401 (M + H)$^+$ |
| 663 | N-(imidazo[1,2-a]pyridin-7-ylmethyl)-4-[1-(pyrimidin-4-ylcarbonyl)azetidin-3-yl]benzamide | (ESI(+)) m/e 413 (M + H)$^+$ |
| 664 | N-(imidazo[1,2-a]pyridin-7-ylmethyl)-4-[1-(1,3-thiazol-2-ylcarbonyl)azetidin-3-yl]benzamide | (ESI(+)) m/e 418 (M + H)$^+$ |
| 665 | N-(imidazo[1,2-a]pyridin-7-ylmethyl)-4-{1-[(1-methylcyclohexyl)carbonyl]azetidin-3-yl}benzamide | (ESI(+)) m/e 431 (M + H)$^+$ |
| 666 | 4-[1-(2,3-dimethylbutanoyl)azetidin-3-yl]-N-(imidazo[1,2-a]pyridin-7-ylmethyl)benzamide | (ESI(+)) m/e 405 (M + H)$^+$ |
| 667 | N-(imidazo[1,2-a]pyridin-7-ylmethyl)-4-[1-(3-methylbenzoyl)azetidin-3-yl]benzamide | (ESI(+)) m/e 425 (M + H)$^+$ |
| 668 | N-(imidazo[1,2-a]pyridin-7-ylmethyl)-4-[1-(thiophen-3-ylcarbonyl)azetidin-3-yl]benzamide | (ESI(+)) m/e 417 (M + H)$^+$ |
| 669 | N-(imidazo[1,2-a]pyridin-7-ylmethyl)-4-{1-[3-(trifluoromethoxy)benzoyl]azetidin-3-yl}benzamide | (ESI(+)) m/e 495 (M + H)$^+$ |
| 670 | N-(imidazo[1,2-a]pyridin-7-ylmethyl)-4-{1-[(3-methylthiophen-2-yl)carbonyl]azetidin-3-yl}benzamide | (ESI(+)) m/e 431 (M + H)$^+$ |
| 671 | N-(imidazo[1,2-a]pyridin-7-ylmethyl)-4-{1-[3-(trifluoromethyl)benzoyl]azetidin-3-yl}benzamide | (ESI(+)) m/e 479 (M + H)$^+$ |

Example 491 tert-butyl 4-{4-[(3-chloroimidazo[1,2-a]pyridin-6-yl)carbamoyl]phenyl}piperidine-1-carboxylate A solution of tert-butyl 4-(4-(imidazo[1,2-a]pyridin-6-ylcarbamoyl)phenyl)piperidine-1-carboxylate (0.015 g, 0.036 mmol) in chloroform (0.618 ml) and methanol (0.095 ml) was treated with N-chlorosuccinimide (5.24 mg, 0.039 mmol) and the reaction was stirred at ambient temperature for 16 hours. The reaction mixture was concentrated under a stream of warm nitrogen. The residue was purified by normal phase flash chromatography to provide the title compound. $^1$H NMR (500 MHz, methanol-d$_4$) δ ppm 9.23 (s, 1H), 7.93 (d, J=8.3 Hz, 2H), 7.62-7.51 (m, 3H), 7.42 (d, J=8.3 Hz, 2H), 4.27-4.19 (m, 2H), 2.96-2.76 (m, 3H), 1.90-1.82 (m, 2H), 1.70-1.57 (m, 2H), 1.48 (s, 9H); MS (ESI(+)) m/e 455 (M+H)$^+$.

Example 492

N-(imidazo[1,2-a]pyridin-7-ylmethyl)-4-{[(3R)-1-(2-methylpropanoyl)pyrrolidin-3-yl]oxy}benzamide Example 492A (R)—N-(imidazo[1,2-a]pyridin-7-ylmethyl)-4-(pyrrolidin-3-yloxy)benzamide The title compound was prepared as described in Example 28A, substituting tert-butyl (3R)-3-{4-[(imidazo[1,2-a]pyridin-7-ylmethyl)carbamoyl]phenoxy}pyrrolidine-1-carboxylate for tert-butyl 4-(4-(3-imidazo[1,2-a]pyridin-6-ylureido)phenyl)-5,6-dihydropyridine-1(2H)-carboxylate.

Example 492B

N-(imidazo[1,2-a]pyridin-7-ylmethyl)-4-{[(3R)-1-(2-methylpropanoyl)pyrrolidin-3-yl]oxy}benzamide The title compound was prepared as described in Example 1A, substituting (R)—N-(imidazo[1,2-a]pyridin-7-ylmethyl)-4-(pyrrolidin-3-yloxy)benzamide for 3-methylbutan-1-amine and isobutyric acid for 4-nitrobenzoic acid. $^1$H NMR (500 MHz, methanol-d$_4$) δ ppm 8.75 (d, J=7.0 Hz, 1H), 8.17 (d, J=2.2 Hz, 1H), 7.99 (d, J=2.2 Hz, 1H), 7.94-7.86 (m, 2H), 7.80 (bs, 1H), 7.48 (dd, J=7.0, 1.6 Hz, 1H), 7.11-7.01 (m, 2H), 5.23-5.11 (m, 1H), 4.76 (s, 2H), 3.92-3.47 (m, 4H), 2.87-2.64 (m, 1H), 2.36-2.16 (m, 2H), 1.16-1.01 (m, 6H); MS (ESI(+)) m/e 407 (M+H)$^+$.

Example 493

4-{[(3R)-1-benzoylpyrrolidin-3-yl]oxy}-N-(imidazo[1,2-a]pyridin-7-ylmethyl)benzamide The title compound was prepared as described in Example 1A, substituting (R)—N-(imidazo[1,2-a]pyridin-7-ylmethyl)-4-(pyrrolidin-3-yloxy)benzamide for 3-methylbutan-1-amine and benzoic acid for 4-nitrobenzoic acid. $^1$H NMR (500 MHz, methanol-d$_4$) δ ppm 8.74 (t, J=6.6 Hz, 1H), 8.20-8.14 (m, 1H), 8.01-7.96 (m, 1H), 7.92 (d, J=8.7 Hz, 1H), 7.85 (d, J=8.6 Hz, 1H), 7.82-7.76 (m, 1H), 7.59-7.39 (m, 6H), 7.10 (d, J=8.6 Hz, 1H), 7.00 (d, J=8.6 Hz, 1H), 5.24-5.07 (m, 1H), 4.75 (d, J=12.3 Hz, 2H), 3.99-3.70 (m, 3H), 3.66-3.56 (m, 1H), 2.39-2.19 (m, 2H); MS (ESI(+)) m/e 441 (M+H)$^+$.

Example 494

N-(imidazo[1,2-a]pyridin-7-ylmethyl)-4-({(3R)-1-[(3S)-tetrahydrofuran-3-ylcarbonyl]pyrrolidin-3-yl}oxy)benzamide The title compound was prepared as described in Example 1A, substituting (R)—N-(imidazo[1,2-a]pyridin-7-ylmethyl)-4-(pyrrolidin-3-yloxy)benzamide for 3-methylbutan-1-amine and (S)-tetrahydrofuran-3-carboxylic acid for 4-nitrobenzoic acid. $^1$H NMR (500 MHz, methanol-d$_4$) δ ppm 8.75 (d, J=7.0 Hz, 1H), 8.19-8.15 (m, 1H), 8.01-7.97 (m, 1H), 7.93-7.86 (m, 2H), 7.82-7.77 (m, 1H), 7.51-7.45 (m, 1H), 7.10-7.01 (m, 2H), 5.23-5.12 (m, 1H), 4.75 (s, 2H), 4.05-3.92 (m, 1H), 3.94-3.63 (m, 7H), 3.57-3.34 (m, 1H), 2.40-2.29 (m, 1H), 2.27-1.97 (m, 3H); MS (ESI(+)) m/e 435 (M+H)$^+$.

Example 495

N-(imidazo[1,2-a]pyridin-7-ylmethyl)-4-({(3R)-1-[(2S)-2-methylbutanoyl]pyrrolidin-3-yl}oxy)benzamide The title compound was prepared as described in Example 1A, substituting (R)—N-(imidazo[1,2-a]pyridin-7-ylmethyl)-4-(pyrrolidin-3-yloxy)benzamide for 3-methylbutan-1-amine and (S)-2-methylbutanoic acid for 4-nitrobenzoic acid. $^1$H NMR (500 MHz, methanol-d$_4$) δ ppm 8.75 (d, J=7.0 Hz, 1H), 8.17 (d, J=2.2 Hz, 1H), 7.99 (d, J=2.2 Hz, 1H), 7.94-7.86 (m, 2H), 7.82-7.77 (m, 1H), 7.48 (d, J=7.1 Hz, 1H), 7.10-7.00 (m, 2H), 5.22-5.11 (m, 1H), 4.76 (s, 2H), 3.91-3.49 (m, 4H), 2.70-2.49 (m, 1H), 2.35-2.17 (m, 2H), 1.73-1.59 (m, 1H), 1.50-1.36 (m, 1H), 1.14-1.03 (m, 3H), 0.93-0.86 (m, 3H); MS (ESI(+)) m/e 421 (M+H)$^+$.

Example 496

1-(imidazo[1,2-a]pyridin-7-ylmethyl)-3-(4-phenoxyphenyl)urea

The title compound was prepared as described in Example 1C, substituting 4-phenoxyaniline for 4-amino-N-isopentylbenzamide and imidazo[1,2-a]pyridin-7-ylmethanamine for imidazo[1,2-a]pyridin-6-amine. $^1$H NMR (400 MHz, DMSO-d$_6$) δ ppm 8.68 (s, 1H), 8.49 (dd, J=6.9, 0.9 Hz, 1H), 7.88 (t, J=0.9 Hz, 1H), 7.52 (d, J=1.2 Hz, 1H), 7.44 (m, 2H), 7.39 (m, 1H), 7.34 (m, 2H), 7.07 (m, 1H), 6.93 (m, 4H), 6.84 (dd, J=7.0, 1.7 Hz, 1H), 6.70 (t, J=6.0 Hz, 1H), 4.34 (d, J=6.0 Hz, 2H); MS (ESI(+)) m/e 359 (M+H)$^+$.

Example 497

5-[1-(2-methylpropyl)-1H-pyrazol-4-yl]-N-([1,2,4]triazolo[1,5-a]pyridin-7-ylmethyl)thiophene-2-carboxamide

Example 497A 5-(1-isobutyl-1H-pyrazol-4-yl)thiophene-2-carboxylic acid

The title compound was prepared as described in Example 51A, substituting 5-bromothiophene-2-carboxylic acid for 4-bromoaniline.

Example 497B

5-[1-(2-methylpropyl)-1H-pyrazol-4-yl]-N-([1,2,4]triazolo[1,5-a]pyridin-7-ylmethyl)thiophene-2-carboxamide The title compound was prepared as described in Example 1A, substituting [1,2,4]triazolo[1,5-a]pyridin-7-ylmethanamine for 3-methylbutan-1-amine and 5-(1-isobutyl-1H-pyrazol-4-yl)thiophene-2-carboxylic acid for 4-nitrobenzoic acid. $^1$H NMR (300 MHz, DMSO-d$_6$) δ ppm 9.11 (t, J=6.0 Hz, 1H), 8.90 (dd, J=7.1, 1.0 Hz, 1H), 8.46 (s, 1H), 8.15 (d, J=0.9 Hz, 1H), 7.81 (s, 1H), 7.75 (d, J=3.9 Hz, 1H), 7.71-7.64 (m, 1H), 7.23 (d, J=3.8 Hz, 1H), 7.16 (dd, J=7.1, 1.8 Hz, 1H), 4.58 (d, J=5.8 Hz, 2H), 3.93 (d, J=7.1 Hz, 2H), 2.20-2.04 (m, 1H), 0.86 (d, J=6.6 Hz, 6H); MS (ESI(+)) m/e 381 (M+H)$^+$.

Example 543

N-(imidazo[1,2-a]pyridin-7-ylmethyl)-2-[1-(2-methylpropanoyl)piperidin-4-yl]-1,3-thiazole-5-carboxamide

Example 543A 2-bromo-N-(imidazo[1,2-a]pyridin-7-ylmethyl)thiazole-5-carboxamide The title compound was prepared as described in Example 1A, substituting imidazo[1,2-a]pyridin-7-ylmethanamine for 3-methylbutan-1-amine and 2-bromothiazole-5-carboxylic acid for 4-nitrobenzoic acid.

Example 543B tert-butyl 4-(5-((imidazo[1,2-a]pyridin-7-ylmethyl)carbamoyl)thiazol-2-yl)-5,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 2-bromo-N-(imidazo[1,2-a]pyridin-7-ylmethyl)thiazole-5-carboxamide for 4-bromoaniline.

Example 543C tert-butyl 4-(5-((imidazo[1,2-a]pyridin-7-ylmethyl)carbamoyl)thiazol-2-yl)piperidine-1-carboxylate The title compound was prepared as described in Example 1B, substituting tert-butyl 4-(5-((imidazo[1,2-a]pyridin-7-ylmethyl)carbamoyl)thiazol-2-yl)-5,6-dihydropyridine-1(2H)-carboxylate for N-isopentyl-4-nitrobenzamide.

Example 543D

N-(imidazo[1,2-a]pyridin-7-ylmethyl)-2-(piperidin-4-yl)thiazole-5-carboxamide

The title compound was prepared as described in Example 28A, substituting tert-butyl 4-(5-((imidazo[1,2-a]pyridin-7-ylmethyl)carbamoyl)thiazol-2-yl)piperidine-1-carboxylate for tert-butyl 4-(4-(3-imidazo[1,2-a]pyridin-6-ylureido)phenyl)-5,6-dihydropyridine-1(2H)-carboxylate.

Example 543E

N-(imidazo[1,2-a]pyridin-7-ylmethyl)-2-[1-(2-methylpropanoyl)piperidin-4-yl]-1,3-thiazole-5-carboxamide The title compound was prepared as described in Example 1A, substituting N-(imidazo[1,2-a]pyridin-7-ylmethyl)-2-(piperidin-4-yl)thiazole-5-carboxamide for 3-methylbutan-1-amine and isobutyric acid for 4-nitrobenzoic acid. $^1$H NMR (500 MHz, DMSO-$d_6$) ppm 9.23 (t, J=6.0 Hz, 1H), 8.49 (d, J=7.0 Hz, 1H), 8.33 (s, 1H), 7.89 (bs, 1H), 7.52 (d, J=1.0 Hz, 1H), 7.40 (bs, 1H), 6.84 (dd, J=7.0, 1.7 Hz, 1H), 4.48 (d, J=6.1 Hz, 2H), 4.44 (d, J=13.4 Hz, 1H), 4.02 (d, J=13.1 Hz, 1H), 3.34-3.27 (m, 1H), 3.19 (t, J=11.9 Hz, 1H), 2.95-2.84 (m, 1H), 2.72 (t, J=12.1 Hz, 1H), 2.13-2.02 (m, 2H), 1.68-1.43 (m, 2H), 1.04-0.96 (m, 6H); MS (ESI(+)) m/e 412 (M+H)$^+$.

Example 544

N-(imidazo[1,2-a]pyridin-7-ylmethyl)-2-[1-(3-methylbutanoyl)piperidin-4-yl]-1,3-thiazole-5-carboxamide The title compound was prepared as described in Example 1A, substituting N-(imidazo[1,2-a]pyridin-7-ylmethyl)-2-(piperidin-4-yl)thiazole-5-carboxamide for 3-methylbutan-1-amine and 3-methylbutanoic acid for 4-nitrobenzoic acid. $^1$H NMR (400 MHz, DMSO-$d_6$) 9.23 (t, J=5.9 Hz, 1H), 8.49 (dd, J=6.9, 0.9 Hz, 1H), 8.33 (s, 1H), 7.92-7.87 (m, 1H), 7.53 (d, J=1.2 Hz, 1H), 7.40 (d, J=1.6 Hz, 1H), 6.84 (dd, J=6.9, 1.7 Hz, 1H), 4.51-4.41 (m, 3H), 3.96 (d, J=13.8 Hz, 1H), 3.34-3.24 (m, 1H), 3.16 (t, J=11.7 Hz, 1H), 2.71 (t, J=12.2 Hz, 1H), 2.21 (dd, J=7.0, 2.3 Hz, 2H), 2.10-2.00 (m, 2H), 1.61 (qd, J=12.7, 4.3 Hz, 1H), 1.49 (qd, J=12.5, 4.4 Hz, 1H), 0.90 (d, J=6.6 Hz, 6H); MS (ESI(+)) m/e 426 (M+H)$^+$.

Example 545

2-(1-benzoylpiperidin-4-yl)-N-(imidazo[1,2-a]pyridin-7-ylmethyl)-1,3-thiazole-5-carboxamide The title compound was prepared as described in Example 1A, substituting N-(imidazo[1,2-a]pyridin-7-ylmethyl)-2-(piperidin-4-yl)thiazole-5-carboxamide for 3-methylbutan-1-amine and benzoic acid for 4-nitrobenzoic acid. $^1$H NMR (500 MHz, DMSO-$d_6$) ppm 9.24 (t, J=5.9 Hz, 1H), 8.49 (d, J=7.0 Hz, 1H), 8.34 (s, 1H), 7.89 (s, 1H), 7.53 (d, J=1.1 Hz, 1H), 7.43 (ddd, J=9.6, 6.8, 3.7 Hz, 6H), 6.84 (dd, J=7.0, 1.6 Hz, 1H), 4.48 (d, J=5.9 Hz, 2H), 4.48 (d, J=5.9 Hz, 1H), 3.72-3.58 (m, 1H), 3.26-3.13 (m, 1H), 3.06-2.91 (m, 1H), 2.17-1.95 (m, 2H), 1.72-1.62 (m, 2H); MS (ESI(+)) m/e 446 (M+H)$^+$.

Example 546

4-[(cyclopentylacetyl)amino]-N-([1,2,4]triazolo[1,5-a]pyridin-7-ylmethyl)benzamide The title compound was prepared as described in Example 1A, substituting [1,2,4]triazolo[1,5-a]pyridin-7-ylmethanamine for 3-methylbutan-1-amine and 4-(2-cyclopentylacetamido)benzoic acid for 4-nitrobenzoic acid. $^1$H NMR (500 MHz, methanol-$d_4$) δ ppm 8.78-8.72 (m, 1H), 8.40 (s, 1H), 7.90-7.83 (m, 2H), 7.75-7.67 (m, 3H), 7.25 (dd, J=7.0, 1.8 Hz, 1H), 4.75-4.69 (m, 2H), 2.44-2.25 (m, 3H), 1.95-1.76 (m, 2H), 1.78-1.50 (m, 4H), 1.35-1.17 (m, 2H); MS (ESI(+)) m/e 378 (M+H)$^+$.

Example 553

5-[4-hydroxy-1-(3-methylbutanoyl)piperidin-4-yl]-N-(imidazo[1,2-a]pyridin-7-ylmethyl)thiophene-2-carboxamide

Example 553A 5-(4-hydroxypiperidin-4-yl)-N-(imidazo[1,2-a]pyridin-7-ylmethyl)thiophene-2-carboxamide The title compound was prepared as described in Example 28A, substituting tert-butyl 4-hydroxy-4-(5-(imidazo[1,2-a]pyridin-7-ylmethylcarbamoyl)thiophen-2-yl)piperidine-1-carboxylate for tert-butyl 4-(4-(3-imidazo[1,2-a]pyridin-6-ylureido)phenyl)-5,6-dihydropyridine-1(2H)-carboxylate.

Example 553B

5-[3-hydroxy-1-(2-methylpropanoyl)azetidin-3-yl]-N-(imidazo[1,2-a]pyridin-7-ylmethyl)thiophene-2-carboxamide The title compound was prepared as described in Example 1A, substituting 5-(4-hydroxypiperidin-4-yl)-N-(imidazo[1,2-a]pyridin-7-ylmethyl)thiophene-2-carboxamide for 3-methylbutan-1-amine and 2-methylpropanoic acid for 4-nitrobenzoic acid. $^1$H NMR (300 MHz, DMSO-$d_6$) ppm 8.98 (t, J=6.0 Hz, 1H), 8.48 (dd, J=6.9, 0.9 Hz, 1H), 7.90-7.87 (m, 1H), 7.65 (d, J=3.8 Hz, 1H), 7.51 (d, J=1.2 Hz, 1H), 7.37 (s, 1H), 7.00 (d, J=3.8 Hz, 1H), 6.83 (dd, J=7.0, 1.7 Hz, 1H), 5.76

(s, 1H), 4.46 (d, J=5.9 Hz, 2H), 4.33-4.23 (m, 1H), 3.81-3.71 (m, 1H), 2.99-2.85 (m, 1H), 2.21 (d, J=7.0 Hz, 2H), 2.07-1.91 (m, 1H), 1.86-1.71 (m, 4H), 0.94-0.87 (m, 6H); MS (ESI(+)) m/e 441 (M+H)$^+$.

Example 554

5-[4-hydroxy-1-(2-methylpropanoyl)piperidin-4-yl]-N-(imidazo[1,2-a]pyridin-7-ylmethyl)thiophene-2-carboxamide The title compound was prepared as described in Example 1A, substituting 5-(4-hydroxypiperidin-4-yl)-N-(imidazo[1,2-a]pyridin-7-ylmethyl)thiophene-2-carboxamide for 3-methylbutan-1-amine and isobutyric acid for 4-nitrobenzoic acid. $^1$H NMR (300 MHz, DMSO-d$_6$) ppm 8.98 (s, 1H), 8.48 (d, J=7.0 Hz, 1H), 7.88 (s, 1H), 7.65 (d, J=3.8 Hz, 1H), 7.51 (d, J=1.1 Hz, 1H), 7.37 (s, 1H), 7.01 (d, J=3.8 Hz, 1H), 6.83 (dd, J=7.0, 1.7 Hz, 1H), 5.77 (s, 1H), 4.46 (d, J=5.6 Hz, 2H), 4.33-4.22 (m, 1H), 3.88-3.74 (m, 1H), 2.98-2.82 (m, 2H), 1.82 (s, 4H), 1.05-0.96 (m, 6H); MS (ESI(+)) m/e 427 (M+H)$^+$.

Example 555

5-[1-(3,3-dimethylbutanoyl)-4-hydroxypiperidin-4-yl]-N-(imidazo[1,2-a]pyridin-7-ylmethyl)thiophene-2-carboxamide The title compound was prepared as described in Example 1A, substituting 5-(4-hydroxypiperidin-4-yl)-N-(imidazo[1,2-a]pyridin-7-ylmethyl)thiophene-2-carboxamide for 3-methylbutan-1-amine and 3,3-dimethylbutanoic acid for 4-nitrobenzoic acid. $^1$H NMR (300 MHz, DMSO-d$_6$) ppm 8.98 (t, J=5.8 Hz, 1H), 8.48 (dd, J=6.9, 0.9 Hz, 1H), 7.91-7.86 (m, 1H), 7.65 (d, J=3.8 Hz, 1H), 7.52 (d, J=1.2 Hz, 1H), 7.37 (s, 1H), 7.00 (d, J=3.8 Hz, 1H), 6.83 (dd, J=7.0, 1.7 Hz, 1H), 5.76 (s, 1H), 4.46 (d, J=6.0 Hz, 2H), 4.38-4.28 (m, 1H), 3.89-3.78 (m, 1H), 2.97-2.85 (m, 1H), 2.38-2.13 (m, 3H), 1.86-1.71 (m, 4H), 0.99 (s, 9H); MS (ESI(+)) m/e 455 (M+H)$^+$.

Example 556

5-(1-benzoyl-4-hydroxypiperidin-4-yl)-N-(imidazo[1,2-a]pyridin-7-ylmethyl)thiophene-2-carboxamide The title compound was prepared as described in Example 1A, substituting 5-(4-hydroxypiperidin-4-yl)-N-(imidazo[1,2-a]pyridin-7-ylmethyl)thiophene-2-carboxamide for 3-methylbutan-1-amine and benzoic acid for 4-nitrobenzoic acid. $^1$H NMR (300 MHz, DMSO-d$_6$) ppm 8.98 (s, 1H), 8.48 (d, J=6.2 Hz, 1H), 7.88 (s, 1H), 7.66 (d, J=3.8 Hz, 1H), 7.53-7.35 (m, 7H), 7.06 (d, J=3.8 Hz, 1H), 6.83 (d, J=7.0 Hz, 1H), 5.83 (s, 1H), 4.46 (d, J=5.9 Hz, 3H), 4.52-4.26 (m, 1H), 1.93 (s, 5H); MS (ESI(+)) m/e 461 (M+H)$^+$.

Example 557

N-(imidazo[1,2-a]pyridin-7-ylmethyl)-4-[1-(propan-2-ylsulfonyl)azetidin-3-yl]benzamide

Example 557A tert-butyl 3-(4-((imidazo[1,2-a]pyridin-7-ylmethyl)carbamoyl)phenyl)azetidine-1-carboxylate The title compound was prepared as described in Example 1A, substituting imidazo[1,2-a]pyridin-7-ylmethanamine for 3-methylbutan-1-amine and 4-(1-(tert-butoxycarbonyl)azetidin-3-yl)benzoic acid for 4-nitrobenzoic acid.

Example 557B 4-(azetidin-3-yl)-N-(imidazo[1,2-a]pyridin-7-ylmethyl)benzamide The title compound was prepared as described in Example 28A, substituting tert-butyl 3-(4-((imidazo[1,2-a]pyridin-7-ylmethyl)carbamoyl)phenyl)azetidine-1-carboxylate for tert-butyl 4-(4-(3-imidazo[1,2-a]pyridin-6-ylureido)phenyl)-5,6-dihydropyridine-1(2H)-carboxylate.

Example 557C

N-(imidazo[1,2-a]pyridin-7-ylmethyl)-4-[1-(propan-2-ylsulfonyl)azetidin-3-yl]benzamide In a 4 mL vial was mixed 4-(azetidin-3-yl)-N-(imidazo[1,2-a]pyridin-7-ylmethyl)benzamide bis(2,2,2-trifluoroacetate) (60 mg, 0.112 mmol) in anhydrous tetrahydrofuran (2 mL) at room temperature. To this mixture was added in portions 60% sodium hydride in mineral oil (22.45 mg, 0.561 mmol). This heterogeneous mixture was stirred 1 hour. To this was added propane-2-sulfonyl chloride (0.015 mL, 0.135 mmol) at and reaction mixture was stirred for 3 hours. The mixture was quenched with water, and product was extracted with 10% methanol/dichloromethane. The organic layers were combined, concentrated and purified by normal phase chromatography to give the title compound. $^1$H NMR (400 MHz, DMSO-d$_6$) δ ppm 9.07 (m, 1H), 8.47 (d, J=7.0 Hz, 1H), 7.90 (m, 3H), 7.48 (m, 3H), 7.37 (s, 1H), 6.84 (m, 1H), 4.50 (d, J=5.9 Hz, 2H), 4.22 (m, 2H), 3.93 (m, 3H), 3.48 (m, 1H), 1.25 (d, J=5.9 Hz, 6H); MS (ESI(+)) m/e 413 (M+H)$^+$.

Example 558

N-(imidazo[1,2-a]pyridin-7-ylmethyl)-4-{[1-(2-methylpropanoyl)azetidin-3-yl]oxy}benzamide

Example 558A 4-(azetidin-3-yloxy)-N-(imidazo[1,2-a]pyridin-7-ylmethyl)benzamide The title compound was prepared as described in Example 28A, substituting tert-butyl 3-{4-[(imidazo[1,2-a]pyridin-7-ylmethyl)carbamoyl]phenoxy}azetidine-1-carboxylate for tert-butyl 4-(4-(3-imidazo[1,2-a]pyridin-6-ylureido)phenyl)-5,6-dihydropyridine-1(2H)-carboxylate.

Example 558B

N-(imidazo[1,2-a]pyridin-7-ylmethyl)-4-{[1-(2-methylpropanoyl)azetidin-3-yl]oxy}benzamide The title compound was prepared as described in Example 1A, substituting 4-(azetidin-3-yloxy)-N-(imidazo[1,2-a]pyridin-7-ylmethyl)benzamide for 3-methylbutan-1-amine and isobutyric acid for 4-nitrobenzoic acid. $^1$H NMR (400 MHz, DMSO-d$_6$) δ ppm 8.99 (t, J=5.9 Hz, 1H), 8.48 (dd, J=6.9, 0.9 Hz, 1H), 7.90 (m, 3H), 7.51 (d, J=1.2 Hz, 1H), 7.37 (s, 1H), 6.95 (m, 2H), 6.85 (dd, J=6.9, 1.7 Hz, 1H), 5.11 (m, 1H), 4.64 (dd, J=9.5, 6.4 Hz, 1H), 4.49 (d, J=5.8 Hz, 2H), 4.32 (dd, J=10.4, 6.3 Hz, 1H), 4.09 (m, 1H), 3.78 (dd, J=10.6, 3.9 Hz, 1H), 2.48 (m, 1H), 0.98 (t, J=6.7 Hz, 6H); MS (ESI(+)) m/e 393 (M+H)⁺.

Example 559

N-(imidazo[1,2-a]pyridin-7-ylmethyl)-4-({1-[(2S)-2-methylbutanoyl]azetidin-3-yl}oxy)benzamide The title compound was prepared as described in Example 1A, substituting 4-(azetidin-3-yloxy)-N-(imidazo[1,2-a]pyridin-7-ylmethyl)benzamide for 3-methylbutan-1-amine and (2S)-2-methylbutyric acid for 4-nitrobenzoic acid. ¹H NMR (400 MHz, DMSO-d₆) δ ppm 8.99 (t, J=5.9 Hz, 1H), 8.48 (dd, J=6.9, 0.9 Hz, 1H), 7.90 (m, 3H), 7.51 (d, J=1.2 Hz, 1H), 7.37 (s, 1H), 6.95 (m, 2H), 6.85 (dd, J=6.9, 1.6 Hz, 1H), 5.11 (dd, J=6.4, 3.5 Hz, 1H), 4.63 (dd, J=9.5, 6.5 Hz, 1H), 4.49 (d, J=5.9 Hz, 2H), 4.33 (m, 1H), 4.11 (m, 1H), 3.79 (m, 1H), 2.29 (m, 1H), 1.50 (m, 1H), 1.28 (m, 1H), 0.97 (t, J=6.0 Hz, 3H), 0.82 (m, 3H); MS (ESI(+)) m/e 407 (M+H)⁺.

Example 560

4-{[1-(cyclopropylacetyl)azetidin-3-yl]oxy}-N-(imidazo[1,2-a]pyridin-7-ylmethyl)benzamide The title compound was prepared as described in Example 1A, substituting 4-(azetidin-3-yloxy)-N-(imidazo[1,2-a]pyridin-7-ylmethyl)benzamide for 3-methylbutan-1-amine and cyclopropylacetic acid for 4-nitrobenzoic acid. ¹H NMR (500 MHz, DMSO-d₆) δ ppm 8.99 (t, J=5.9 Hz, 1H), 8.48 (dd, J=6.9, 0.9 Hz, 1H), 7.90 (m, 3H), 7.51 (d, J=1.2 Hz, 1H), 7.37 (s, 1H), 6.94 (m, 2H), 6.85 (dd, J=7.0, 1.7 Hz, 1H), 5.10 (m, 1H), 4.57 (dd, J=9.5, 6.5 Hz, 1H), 4.49 (d, J=5.9 Hz, 2H), 4.33 (dd, J=10.6, 6.5 Hz, 1H), 4.08 (dd, J=9.6, 3.8 Hz, 1H), 3.78 (dd, J=10.6, 3.9 Hz, 1H), 2.03 (d, J=6.8 Hz, 2H), 0.91 (m, 1H), 0.44 (m, 2H), 0.10 (m, 2H); MS (ESI(+)) m/e 405 (M+H)⁺.

Example 561

4-[(1-benzoylazetidin-3-yl)oxy]-N-(imidazo[1,2-a]pyridin-7-ylmethyl)benzamide

The title compound was prepared as described in Example 1A, substituting 4-(azetidin-3-yloxy)-N-(imidazo[1,2-a]pyridin-7-ylmethyl)benzamide for 3-methylbutan-1-amine and benzoic acid for 4-nitrobenzoic acid. ¹H NMR (400 MHz, DMSO-d₆) δ ppm 8.99 (t, J=5.9 Hz, 1H), 8.48 (dd, J=6.9, 0.9 Hz, 1H), 7.90 (m, 3H), 7.66 (m, 2H), 7.59-7.42 (m, 4H), 7.37 (s, 1H), 6.95 (m, 2H), 6.84 (dd, J=6.9, 1.7 Hz, 1H), 5.17 (m, 1H), 4.71 (m, 1H), 4.57 (m, 1H), 4.49 (d, J=5.9 Hz, 2H), 4.33 (m, 1H), 4.02 (m, 1H); MS (ESI(+)) m/e 427 (M+H)⁺.

Example 563 tert-butyl 4-{4-[([1,2,4]triazolo[1,5-a]pyridin-7-ylmethyl)carbamoyl]phenyl}piperidine-1-carboxylate The title compound was prepared as described in Example 1A, substituting [1,2,4]triazolo[1,5-a]pyridin-7-ylmethanamine for 3-methylbutan-1-amine and 4-(1-(tert-butoxycarbonyl)piperidin-4-yl)benzoic acid for 4-nitrobenzoic acid. ¹H NMR (300 MHz, DMSO-d₆) δ ppm 9.11 (t, J=5.9 Hz, 1H), 8.89 (dd, J=7.0, 0.9 Hz, 1H), 8.44 (s, 1H), 7.89-7.83 (m, 2H), 7.67-7.65 (m, 1H), 7.40-7.34 (m, 2H), 7.15 (dd, J=7.0, 1.8 Hz, 1H), 4.62-4.57 (m, 2H), 4.14-4.03 (m, 2H), 2.91-2.67 (m, 3H), 1.82-1.71 (m, 2H), 1.60-1.37 (m, 1H); MS (ESI(+)) m/e 436 (M+H)⁺.

Example 564

2-cyclopentyl-N-(4-{[(([1,2,4]triazolo[1,5-a]pyridin-7-ylmethyl)carbamoyl]amino}phenyl)acetamide The title compound was prepared as described in Example 1C, substituting N-(4-aminophenyl)-2-cyclopentylacetamide for 4-amino-N-isopentylbenzamide and [1,2,4]triazolo[1,5-a]pyridin-7-ylmethanamine for imidazo[1,2-a]pyridin-6-amine ¹H NMR (300 MHz, DMSO-d₆) δ ppm 9.68 (s, 1H), 8.89 (d, J=7.0 Hz, 1H), 8.64 (s, 1H), 8.45 (s, 1H), 7.65 (s, 1H), 7.47-7.41 (m, 2H), 7.34-7.28 (m, 2H), 7.14 (dd, J=7.0, 1.8 Hz, 1H), 6.78 (t, J=6.0 Hz, 1H), 4.42 (d, J=6.0 Hz, 2H), 2.29-2.15 (m, 3H), 1.79-1.68 (m, 2H), 1.66-1.43 (m, 4H), 1.24-1.11 (m, 2H); MS (ESI(+)) m/e 393 (M+H)⁺.

Example 565 tert-butyl 4-(4-{[([1,2,4]triazolo[1,5-a]pyridin-7-ylmethyl)carbamoyl]amino}phenyl)piperidine-1-carboxylate The title compound was prepared as described in Example 1C, substituting tert-butyl 4-(4-aminophenyl)piperidine-1-carboxylate for 4-amino-N-isopentylbenzamide and [1,2,4]triazolo[1,5-a]pyridin-7-ylmethanamine for imidazo[1,2-a]pyridin-6-amine ¹H NMR (300 MHz, DMSO-d₆) δ ppm 8.89 (d, J=7.0 Hz, 1H), 8.66 (s, 1H), 8.45 (s, 1H), 7.64 (s, 1H), 7.36-7.30 (m, 2H), 7.14 (dd, J=7.0, 1.8 Hz, 1H), 7.12-7.07 (m, 2H), 6.80 (t, J=6.0 Hz, 1H), 4.43 (d, J=6.0 Hz, 2H), 4.10-4.00 (m, 2H), 2.90-2.63 (m, 2H), 2.66-2.54 (m, 1H), 1.75-1.67 (m, 2H), 1.49-1.35 (s, 11H); MS (ESI(+)) m/e 451 (M+H)⁺.

Example 566

N-(imidazo[1,2-a]pyridin-7-ylmethyl)-4-(piperidin-1-ylcarbonyl)benzamide

The title compound was prepared as described in Example 1A, substituting piperidine for 3-methylbutan-1-amine and 4-(imidazo[1,2-a]pyridin-7-ylmethylcarbamoyl)benzoic acid for 4-nitrobenzoic acid. ¹H NMR (500 MHz, DMSO-d₆) δ ppm 9.18 (t, J=5.9 Hz, 1H), 8.49 (d, J=7.0 Hz, 1H), 7.96 (m, 2H), 7.89 (s, 1H), 7.52 (d, J=1.2 Hz, 1H), 7.47 (m, 2H), 7.40 (s, 1H), 6.86 (dd, J=7.0, 1.7 Hz, 1H), 4.52 (d, J=5.9 Hz, 2H), 3.59 (m, 2H), 3.24 (m, 2H), 1.66-1.38 (m, 6H); MS (ESI(+)) m/e 363 (M+H)⁺.

Example 567

4-[1-(ethylsulfonyl)azetidin-3-yl]-N-(imidazo[1,2-a]pyridin-7-ylmethyl)benzamide The title compound was prepared as described in Example 557C, substituting ethane sulfonyl chloride for propane-2-sulfonyl chloride. ¹H NMR (500 MHz, DMSO-d₆) δ ppm 9.10 (t, J=6.0 Hz, 1H), 8.49 (dd, J=6.9, 0.9 Hz, 1H), 7.93 (m, 2H), 7.88 (m, 1H), 7.52 (d, J=1.2 Hz, 1H), 7.49 (m, 2H), 7.39 (s, 1H), 6.86 (dd, J=7.0, 1.6 Hz, 1H), 4.51 (d, J=5.9 Hz, 2H), 4.23 (m, 2H), 3.95 (m, 3H), 3.19 (q, J=7.3 Hz, 2H), 1.25 (t, J=7.3 Hz, 3H); MS (ESI(+)) m/e 399 (M+H)⁺.

Example 568

4-[1-(cyclopropylsulfonyl)azetidin-3-yl]-N-(imidazo[1,2-a]pyridin-7-ylmethyl)benzamide The title compound was prepared as described in Example 557C, substituting cyclopropane sulfonyl chloride for propane-2-sulfonyl chloride. $^1$H NMR (500 MHz, DMSO-$d_6$) δ ppm 9.10 (t, J=6.0 Hz, 1H), 8.49 (dd, J=6.9, 0.9 Hz, 1H), 7.93 (m, 2H), 7.88 (m, 1H), 7.52 (d, J=1.1 Hz, 1H), 7.50 (m, 2H), 7.39 (s, 1H), 6.86 (dd, J=7.0, 1.6 Hz, 1H), 4.51 (d, J=5.9 Hz, 2H), 4.26 (t, J=7.7 Hz, 2H), 3.99 (m, 3H), 2.85 (m, 1H), 1.06 (m, 2H), 0.97 (m, 2H); MS (ESI(+)) m/e 411 (M+H)$^+$.

Example 569

N-(imidazo[1,2-a]pyridin-7-ylmethyl)-4-[1-(phenylsulfonyl)azetidin-3-yl]benzamide The title compound was prepared as described in Example 557C, substituting benzene sulfonyl chloride for propane-2-sulfonyl chloride. $^1$H NMR (500 MHz, DMSO-$d_6$) δ ppm 9.04 (t, J=5.9 Hz, 1H), 8.47 (m, 1H), 7.92-7.82 (m, 4H), 7.75 (m, 4H), 7.51 (d, J=1.2 Hz, 1H), 7.36 (s, 1H), 7.97 (m, 2H), 6.83 (dd, J=7.0, 1.6 Hz, 1H), 4.47 (d, J=5.9 Hz, 2H), 4.16 (m, 2H), 3.79 (m, 1H), 3.67 (m, 2H); MS (ESI(+)) m/e 447 (M+H)$^+$.

Example 570 propan-2-yl 4-{5-[(imidazo[1,2-a]pyridin-7-ylmethyl)carbamoyl]thiophen-2-yl}piperidine-1-carboxylate To a suspension N-(imidazo[1,2-a]pyridin-7-ylmethyl)-5-(piperidin-4-yl)thiophene-2-carboxamide (0.103 g, 0.249 mmol) in dichloromethane (2 ml) was added N-methylmorpholine (0.110 ml, 0.997 mmol) followed by isopropylchloroformate (0.374 ml, 0.374 mmol). A second portion of isopropylchloroformate (0.4 ml) was added and after 1 hour the mixture was directly purified by normal phase chromatography to give the title compound. $^1$H NMR (500 MHz, DMSO-$d_6$) δ ppm 9.05 (t, J=6.0 Hz, 1H), 8.51 (d, J=7.0 Hz, 1H), 7.92 (s, 1H), 7.68 (d, J=3.8 Hz, 1H), 7.56 (d, J=1.2 Hz, 1H), 7.40 (d, J=1.4 Hz, 1H), 6.96 (d, J=3.8 Hz, 1H), 6.88 (dd, J=7.0, 1.7 Hz, 1H), 4.78 (hept, J=6.2 Hz, 1H), 4.47 (d, J=5.9 Hz, 2H), 4.05 (d, J=12.9 Hz, 2H), 3.10-2.97 (m, 1H), 2.98-2.81 (m, 2H), 2.01-1.88 (m, 2H), 1.57-1.38 (m, 2H), 1.19 (d, J=6.2 Hz, 6H); MS (ESI(+)) m/e 427 (M+H)$^+$.

Example 571

2-methylpropyl 4-{5-[(imidazo[1,2-a]pyridin-7-ylmethyl)carbamoyl]thiophen-2-yl}piperidine-1-carboxylate The title compound was prepared as described in Example 570, substituting isobutyl carbonochloridate for isopropyl carbonochloridate. $^1$H NMR (300 MHz, DMSO-$d_6$) δ 8.99 (t, J=6.0 Hz, 1H), 8.48 (dd, J=7.0, 0.9 Hz, 1H), 7.88 (t, J=1.0 Hz, 1H), 7.67 (d, J=3.9 Hz, 1H), 7.51 (d, J=1.1 Hz, 1H), 7.37 (s, 1H), 6.96 (d, J=3.1 Hz, 1H), 6.82 (dd, J=7.0, 1.8 Hz, 1H), 4.46 (d, J=5.8 Hz, 2H), 4.06 (d, J=13.3 Hz, 2H), 3.79 (d, J=6.6 Hz, 2H), 3.13-2.97 (m, 1H), 2.97-2.80 (m, 2H), 2.03-1.77 (m, 3H), 1.48 (qd, J=12.5, 4.2 Hz, 2H), 0.89 (d, J=6.7 Hz, 6H); MS (ESI(+)) m/e 441 (M+H)$^+$.

Example 572

N-(imidazo[1,2-a]pyridin-7-ylmethyl)-5-[1-(3,3,3-trifluoropropanoyl)piperidin-4-yl]thiophene-2-carboxamide The title compound was prepared as described in Example 52A, substituting 3,3,3-trifluoropropanoyl chloride for 2-cyclopentylacetyl chloride and N-(imidazo[1,2-a]pyridin-7-ylmethyl)-5-(piperidin-4-yl)thiophene-2-carboxamide for methyl 4-aminobenzoate. $^1$H NMR (300 MHz, DMSO-$d_6$) δ ppm 9.00 (t, J=6.0 Hz, 1H), 8.48 (dd, J=6.9, 1.0 Hz, 1H), 7.88 (t, J=1.0 Hz, 1H), 7.67 (d, J=3.8 Hz, 1H), 7.51 (d, J=1.3 Hz, 1H), 7.40-7.33 (m, 1H), 6.96 (dd, J=3.7, 0.8 Hz, 1H), 6.83 (dd, J=7.0, 1.7 Hz, 1H), 4.46 (d, J=6.3 Hz, 2H), 3.90 (d, J=13.8 Hz, 1H), 3.66 (q, J=11.0 Hz, 2H), 3.23-3.04 (m, 2H), 2.71 (td, J=12.8, 2.6 Hz, 1H), 2.07-1.88 (m, 2H), 1.71-1.31 (m, 2H); MS (ESI(+)) m/e 451 (M+H)$^+$.

Example 573

N-(imidazo[1,2-a]pyridin-7-ylmethyl)-5-{1-[(2-methylpropyl)sulfonyl]piperidin-4-yl}thiophene-2-carboxamide The title compound was prepared as described in Example 52A, substituting 2-methylpropane-1-sulfonyl chloride for 2-cyclopentylacetyl chloride and N-(imidazo[1,2-a]pyridin-7-ylmethyl)-5-(piperidin-4-yl)thiophene-2-carboxamide for methyl 4-aminobenzoate. $^1$H NMR (400 MHz, DMSO-$d_6$) δ ppm 9.01 (t, J=6.0 Hz, 1H), 8.48 (d, J=6.9 Hz, 1H), 7.89 (s, 1H), 7.68 (d, J=3.8 Hz, 1H), 7.52 (d, J=1.1 Hz, 1H), 7.38 (s, 1H), 6.98 (d, J=3.8 Hz, 1H), 6.83 (dd, J=7.0, 1.7 Hz, 1H), 4.46 (d, J=6.0 Hz, 2H), 3.71-3.59 (m, 2H), 2.99 (tt, J=11.6, 3.6 Hz, 1H), 2.94-2.82 (m, 4H), 2.20-2.08 (m, 1H), 2.08-1.97 (m, 2H), 1.62 (qd, J=12.6, 4.1 Hz, 2H), 1.04 (d, J=6.7 Hz, 6H); MS (ESI(+)) m/e 461 (M+H)$^+$.

Example 574

N-(imidazo[1,2-a]pyridin-7-ylmethyl)-5-[1-(4,4,4-trifluorobutanoyl)piperidin-4-yl]thiophene-2-carboxamide The title compound was prepared as described in Example 1A, substituting N-(imidazo[1,2-a]pyridin-7-ylmethyl)-5-(piperidin-4-yl)thiophene-2-carboxamide for 3-methylbutan-1-amine and 4,4,4-trifluorobutanoic acid for 4-nitrobenzoic acid. $^1$H NMR (400 MHz, DMSO-$d_6$) δ ppm 9.00 (t, J=6.0 Hz, 1H), 8.48 (d, J=6.8 Hz, 1H), 7.89 (s, 1H), 7.68 (d, J=3.8 Hz, 1H), 7.52 (d, J=1.2 Hz, 1H), 7.41-7.34 (m, 1H), 6.96 (d, J=3.8 Hz, 1H), 6.83 (dd, J=7.0, 1.7 Hz, 1H), 4.54-4.38 (m, 3H), 4.02-3.88 (m, 1H), 3.12 (tdt, J=11.3, 7.9, 3.1 Hz, 2H), 2.76-2.41 (m, 5H), 2.06-1.88 (m, 2H), 1.58 (qd, J=12.3, 4.0 Hz, 1H), 1.42 (qd, J=12.5, 4.2 Hz, 1H); MS (ESI(+)) m/e 465 (M+H)$^+$.

Example 575

N-[(3-chloroimidazo[1,2-a]pyridin-7-yl)methyl]-4-[1-(2-methylpropanoyl)piperidin-4-yl]benzamide A solution of N-(imidazo[1,2-a]pyridin-7-ylmethyl)-4-(1-isobutyrylpiperidin-4-yl)benzamide (0.025 g, 0.062 mmol) in chloroform (1.030 ml) was treated with N-chlorosuccinimide (9.49 mg, 0.071 mmol) and the reaction was stirred at ambient temperature for 16 hours. The reaction was concen-

Example 576

N-(imidazo[1,2-a]pyridin-7-ylmethyl)-5-{1-[(4-methyltetrahydro-2H-pyran-4-yl)methyl]-1H-pyrazol-4-yl}thiophene-2-carboxamide The title compound was prepared as described in Example 51A, substituting 1-((4-methyltetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline. $^1$H NMR (300 MHz, DMSO-$d_6$) δ ppm 9.02 (t, J=6.0 Hz, 1H), 8.49 (dd, J=7.1, 1.0 Hz, 1H), 8.13 (s, 1H), 7.89 (t, J=1.0 Hz, 1H), 7.81 (s, 1H), 7.74 (d, J=3.8 Hz, 1H), 7.52 (d, J=1.3 Hz, 1H), 7.43-7.36 (m, 1H), 7.23 (d, J=3.8 Hz, 1H), 6.85 (dd, J=7.1, 1.7 Hz, 1H), 4.48 (d, J=5.9 Hz, 2H), 4.04 (s, 2H), 3.68 (dt, J=11.8, 4.6 Hz, 2H), 3.52 (ddd, J=11.9, 9.1, 3.0 Hz, 2H), 1.51 (ddd, J=13.4, 9.2, 4.2 Hz, 2H), 1.24 (dt, J=13.4, 4.0 Hz, 2H), 0.96 (s, 3H); MS (ESI(+)) m/e 436 (M+H)$^+$.

Example 577

5-[1-(2-cyano-2-methylpropyl)-1H-pyrazol-4-yl]-N-(imidazo[1,2-a]pyridin-7-ylmethyl)thiophene-2-carboxamide The title compound was prepared as described in Example 51A, substituting 2,2-dimethyl-3-(4-(4,4,5,5-tetramethyl-1,3,2-dioxaborolan-2-yl)-1H-pyrazol-1-yl)propanenitrile and 5-bromo-N-(imidazo[1,2-a]pyridin-7-ylmethyl)thiophene-2-carboxamide for 4-bromoaniline. $^1$H NMR (300 MHz, DMSO-$d_6$) δ 9.05 (t, J=6.0 Hz, 1H), 8.49 (dd, J=6.8, 1.0 Hz, 1H), 8.19 (d, J=0.7 Hz, 1H), 7.92 (s, 1H), 7.90-7.88 (m, 1H), 7.76 (d, J=3.8 Hz, 1H), 7.52 (d, J=1.1 Hz, 1H), 7.43-7.36 (m, 1H), 7.27 (d, J=3.8 Hz, 1H), 6.85 (dd, J=6.9, 1.7 Hz, 1H), 4.48 (d, J=5.7 Hz, 2H), 4.35 (s, 2H), 1.35 (s, 6H); MS (ESI(+)) m/e 405 (M+H)$^+$.

Example 578

4-chloro-N-(imidazo[1,2-a]pyridin-7-ylmethyl)-5-[1-(2-methylpropyl)-1H-pyrazol-4-yl]thiophene-2-carboxamide

Example 578A 1-(5-bromo-4-chlorothiophen-2-yl)ethanone

2-Bromo-3-chlorothiophene (10.7 g, 51.5 mmol) was dissolved in dichloromethane (73.5 ml). The flask was equipped with a desiccant filled drying tube and the solution was chilled in an ice bath. Acetyl chloride (6.06 g, 77 mmol) was added followed by addition of aluminum trichloride (8.24 g, 61.8 mmol) over about 2 minutes (reaction bubbled vigorously as aluminum trichloride was added). The reaction mixture was stirred overnight, allowing to warm to room temperature, and then added cautiously and with stirring to a 1-L beaker containing ~200 mL sat sodium bicarbonate. The mixture was stirred for 30 minutes and diluted with dichloromethane (~100 mL). The layers were separated and the organic layer was washed with aqueous saturated sodium bicarbonate, water, and brine. The combined organic layers were dried with sodium sulfate, filtered, and concentrated to give a crude solid. This material was recrystallized from hot hexanes to give the title compound.

Example 578B 5-bromo-4-chlorothiophene-2-carboxylic acid

Sodium hydroxide (50% in water) (5.82 ml, 110 mmol) was added to water (15 ml), and the mixture was chilled to 0° C. Bromine solution (1.669 ml, 32.6 mmol) was added, followed by dropwise addition of a solution of 1-(5-bromo-4-chlorothiophen-2-yl)ethanone (2.4 g, 10.02 mmol) in dioxane (18 ml). The mixture was stirred for 1.5 hours at room temperature, washed with dichloromethane, and then the aqueous phase was adjusted to pH 1 using 4N aqueous HCl. The precipitated solid was collected by filtration to give the title compound.

Example 578C 4-chloro-5-(1-isobutyl-1H-pyrazol-4-yl)thiophene-2-carboxylic acid The title compound was prepared as described in Example 51A, substituting 5-bromo-4-chlorothiophene-2-carboxylic acid for 4-bromoaniline.

Example 578D 4-chloro-N-(imidazo[1,2-a]pyridin-7-ylmethyl)-5-[1-(2-methylpropyl)-1H-pyrazol-4-yl]thiophene-2-carboxamide The title compound was prepared as described in Example 1A, substituting imidazo[1,2-a]pyridin-7-ylmethanamine for 3-methylbutan-1-amine and 4-chloro-5-(1-isobutyl-1H-pyrazol-4-yl)thiophene-2-carboxylic acid for 4-nitrobenzoic acid. $^1$H NMR (500 MHz, DMSO-$d_6$) ppm 9.17 (t, J=5.9 Hz, 1H), 8.50 (d, J=7.0 Hz, 1H), 8.31 (s, 1H), 7.93-7.88 (m, 2H), 7.83 (s, 1H), 7.53 (d, J=1.1 Hz, 1H), 7.42 (s, 1H), 6.85 (dd, J=7.0, 1.6 Hz, 1H), 4.49 (d, J=5.9 Hz, 2H), 3.98 (d, J=7.2 Hz, 2H), 2.20-2.08 (m, 1H), 0.86 (d, J=6.7 Hz, 6H); MS (ESI(+)) m/e 414 (M+H)$^+$.

Example 579

4-chloro-N-(imidazo[1,2-a]pyridin-7-ylmethyl)-5-{1-[(3R)-tetrahydrofuran-3-ylmethyl]-1H-pyrazol-4-yl}thiophene-2-carboxamide The title compound was prepared as described in Example 1A, substituting imidazo[1,2-a]pyridin-7-ylmethanamine for 3-methylbutan-1-amine and (R)-4-chloro-5-(1-((tetrahydrofuran-3-yl)methyl)-1H-pyrazol-4-yl)thiophene-2-carboxylic acid for 4-nitrobenzoic acid. $^1$H NMR (500 MHz, DMSO-$d_6$) ppm 9.17 (t, J=6.0 Hz, 1H), 8.50 (d, J=7.0 Hz, 1H), 8.28 (s, 1H), 7.93-7.88 (m, 2H), 7.83 (s, 1H), 7.53 (d, J=1.2 Hz, 1H), 7.42 (s, 1H), 6.85 (dd, J=7.0, 1.7 Hz, 1H), 4.49 (d, J=5.9 Hz, 2H), 4.28-4.15 (m, 3H), 3.78-3.72 (m, 1H), 3.67-3.61 (m, Trated under a stream of warm nitrogen. The residue was purified by normal phase chromatography to give the title compound. $^1$H NMR (500 MHz, methanol-$d_4$) δ ppm 8.67 (d, J=7.0 Hz, 1H), 8.11 (s, 1H), 7.89-7.83 (m, 2H), 7.81 (s, 1H), 7.57 (dd, J=7.1, 1.5 Hz, 1H), 7.43-7.37 (m, 2H), 4.80-4.75 (m, 2H), 4.75-4.67 (m, 1H), 4.25-4.16 (m, 1H), 3.28-3.18 (m, 1H), 3.07-2.88 (m, 2H), 2.79-2.66 (m, 1H), 2.02-1.85 (m, 2H), 1.75-1.53 (m, 2H), 1.17-1.08 (m, 6H); MS (ESI(+)) m/e 439 (M+H)$^+$.

1H), 1.98-1.90 (m, 1H), 1.84-1.70 (m, 2H), 1.65-1.57 (m, 1H); MS (ESI(+)) m/e 442 (M+H)+.

Example 621

5-[1-(2-hydroxy-2-methylpropyl)-1H-pyrazol-4-yl]-N-([1,2,4]triazolo[1,5-a]pyridin-6-ylmethyl)thiophene-2-carboxamide Example 621A N-([1,2,4]triazolo[1,5-a]pyridin-6-ylmethyl)-5-bromothiophene-2-carboxamide The title compound was prepared as described in Example 1A, substituting [1,2,4]triazolo[1,5-a]pyridin-6-ylmethanamine for 3-methylbutan-1-amine and 5-bromothiophene-2-carboxylic acid for 4-nitrobenzoic acid.

Example 621B

5-[1-(2-hydroxy-2-methylpropyl)-1H-pyrazol-4-yl]-N-([1,2,4]triazolo[1,5-a]pyridin-6-ylmethyl)thiophene-2-carboxamide The title compound was prepared as described in Example 51A, substituting 2-methyl-1-(4-(4,4,5,5-tetramethyl-1,3,2-dioxaborolan-2-yl)-1H-pyrazol-1-yl)propan-2-ol for 1-isobutyl-4-(4,4,5,5-tetramethyl-1,3,2-dioxaborolan-2-yl)-1H-pyrazole and N-([1,2,4]triazolo[1,5-a]pyridin-6-ylmethyl)-5-bromothiophene-2-carboxamide for 4-bromoaniline. $^1$H NMR (300 MHz, DMSO-$d_6$) δ ppm 9.03 (t, J=5.9 Hz, 1H), 8.88 (s, 1H), 8.48 (s, 1H), 8.04 (d, J=0.5 Hz, 1H), 7.84 (dd, J=9.2, 0.7 Hz, 1H), 7.79 (d, J=0.5 Hz, 1H), 7.71 (d, J=3.9 Hz, 1H), 7.66 (dd, J=9.2, 1.7 Hz, 1H), 7.22 (d, J=3.9 Hz, 1H), 4.72 (s, 1H), 4.54 (d, J=5.8 Hz, 2H), 4.03 (s, 2H), 1.08 (s, 6H); MS (ESI(+)) m/e 397 (M+H)+.

Example 622

5-{1-[(4-methyltetrahydro-2H-pyran-4-yl)methyl]-1H-pyrazol-4-yl}-N-([1,2,4]triazolo[1,5-a]pyridin-6-ylmethyl)thiophene-2-carboxamide The title compound was prepared as described in Example 51A, substituting 1-((4-methyltetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and N-([1,2,4]triazolo[1,5-a]pyridin-6-ylmethyl)-5-bromothiophene-2-carboxamide for 4-bromoaniline. $^1$H NMR (300 MHz, DMSO-$d_6$) δ ppm 9.03 (t, J=5.9 Hz, 1H), 8.88 (s, 1H), 8.48 (s, 1H), 8.04 (d, J=0.5 Hz, 1H), 7.84 (dd, J=9.2, 0.7 Hz, 1H), 7.79 (d, J=0.5 Hz, 1H), 7.71 (d, J=3.9 Hz, 1H), 7.66 (dd, J=9.2, 1.7 Hz, 1H), 7.22 (d, J=3.9 Hz, 1H), 4.72 (s, 1H), 4.54 (d, J=5.8 Hz, 2H), 4.03 (s, 2H), 1.08 (s, 6H); MS (ESI(+)) m/e 437 (M+H)+.

Example 623

N-(imidazo[1,2-a]pyridin-7-ylmethyl)-4-[1-(methylsulfonyl)azetidin-3-yl]benzamide The title compound was prepared as described in Example 557C, substituting methane sulfonyl chloride for propane-2-sulfonyl chloride. $^1$H NMR (400 MHz, DMSO-$d_6$) δ ppm 9.11 (t, J=6.0 Hz, 1H), 8.49 (m, 1H), 7.91 (m, 2H), 7.88 (m, 1H), 7.52 (m, 2H), 7.49 (m, 1H), 7.39 (s, 1H), 6.86 (dd, J=7.0, 1.7 Hz, 1H), 4.51 (d, J=5.9 Hz, 2H), 4.23 (m, 2H), 3.95 (m, 3H), 3.08 (s, 3H); MS (ESI(+)) m/e 385 (M+H)+.

Example 624

N-(imidazo[1,2-a]pyridin-7-ylmethyl)-4-[1-(methylsulfonyl)pyrrolidin-3-yl]benzamide The title compound was prepared as described in Example 557C, substituting methane sulfonyl chloride for propane-2-sulfonyl chloride and N-(imidazo[1,2-a]pyridin-7-ylmethyl)-4-(pyrrolidin-3-yl)benzamide for 4-(azetidin-3-yl)-N-(imidazo[1,2-a]pyridin-7-ylmethyl)benzamide. $^1$H NMR (400 MHz, DMSO-$d_6$) δ ppm 9.07 (t, J=5.9 Hz, 1H), 8.48 (dd, J=6.9, 0.9 Hz, 1H), 7.88 (m, 3H), 7.52 (d, J=1.2 Hz, 1H), 7.45 (m, 2H), 7.38 (m, 1H), 6.85 (dd, J=6.9, 1.7 Hz, 1H), 4.51 (d, J=5.9 Hz, 2H), 3.73 (dd, J=9.6, 7.5 Hz, 1H), 3.47 (m, 2H), 3.35 (m, 1H), 3.19 (t, J=9.6 Hz, 1H), 2.97 (s, 3H), 2.31 (m, 1H), 2.02 (m, 1H); MS (ESI(+)) m/e 399 (M+H)+.

Example 625

4-[1-(ethylsulfonyl)pyrrolidin-3-yl]-N-(imidazo[1,2-a]pyridin-7-ylmethyl)benzamide The title compound was prepared as described in Example 557C, substituting ethane sulfonyl chloride for propane-2-sulfonyl chloride and N-(imidazo[1,2-a]pyridin-7-ylmethyl)-4-(pyrrolidin-3-yl)benzamide for 4-(azetidin-3-yl)-N-(imidazo[1,2-a]pyridin-7-ylmethyl)benzamide. $^1$H NMR (400 MHz, DMSO-$d_6$) δ ppm 9.07 (t, J=5.9 Hz, 1H), 8.48 (dd, J=6.9, 0.9 Hz, 1H), 7.88 (m, 3H), 7.52 (d, J=1.2 Hz, 1H), 7.45 (m, 2H), 7.38 (s, 1H), 6.85 (dd, J=6.9, 1.7 Hz, 1H), 4.50 (d, J=5.9 Hz, 2H), 3.75 (dd, J=9.5, 7.5 Hz, 1H), 3.50 (m, 2H), 3.38 (m, 1H), 3.26-3.12 (m, 3H), 2.32 (m, 1H), 2.03 (m, 1H), 1.24 (t, J=7.3 Hz, 3H); MS (ESI(+)) m/e 413 (M+H)+.

Example 626

4-[1-(cyclopropylsulfonyl)pyrrolidin-3-yl]-N-(imidazo[1,2-a]pyridin-7-ylmethyl)benzamide The title compound was prepared as described in Example 557C, substituting cyclopropane sulfonyl chloride for propane-2-sulfonyl chloride and N-(imidazo[1,2-a]pyridin-7-ylmethyl)-4-(pyrrolidin-3-yl)benzamide for 4-(azetidin-3-yl)-N-(imidazo[1,2-a]pyridin-7-ylmethyl)benzamide. $^1$H NMR (400 MHz, DMSO-$d_6$) δ ppm 9.07 (t, J=5.9 Hz, 1H), 8.48 (dd, J=6.9, 0.9 Hz, 1H), 7.88 (m, 3H), 7.51 (d, J=1.2 Hz, 1H), 7.45 (m, 2H), 7.38 (m, 1H), 6.85 (dd, J=6.9, 1.7 Hz, 1H), 4.50 (d, J=5.9 Hz, 2H), 3.79 (dd, J=9.7, 7.5 Hz, 1H), 3.53 (m, 2H), 3.43 (m, 1H), 3.23 (m, 1H), 2.78 (m, 1H), 2.34 (m, 1H), 2.01 (m, 1H), 0.98 (m, 4H); MS (ESI(+)) m/e 425 (M+H)+.

Example 627

N-(imidazo[1,2-a]pyridin-7-ylmethyl)-4-[1-(phenylsulfonyl)pyrrolidin-3-yl]benzamide The title compound was prepared as described in Example 557C, substituting benzene sulfonyl chloride for propane-2-sulfonyl chloride and N-(imidazo[1,2-a]pyridin-7-ylmethyl)-4-(pyrrolidin-3-yl)benzamide for 4-(azetidin-3-yl)-N-(imidazo[1,2-a]pyridin-7-ylmethyl)benzamide. $^1$H NMR (400 MHz, DMSO-$d_6$) δ ppm 9.04 (t, J=5.9 Hz, 1H), 8.48 (dd, J=6.9, 0.9 Hz, 1H), 7.87 (m, 3H), 7.81 (m, 2H), 7.74 (m, 1H), 7.66 (m, 2H), 7.51 (d, J=1.2 Hz, 1H), 7.37 (m, 1H), 7.25 (m, 2H), 6.84 (dd, J=6.9, 1.7 Hz, 1H), 4.49 (d, J=5.9 Hz, 2H), 3.72 (dd, J=9.8, 7.5 Hz, 1H), 3.46 (m, 1H), 3.26 (m, 2H), 3.11 (m, 1H), 2.17 (m, 1H), 1.78 (m, 1H); MS (ESI(+)) m/e 461 (M+H)+.

Example 672

N-(imidazo[1,2-a]pyridin-7-ylmethyl)-4-[1-(propan-2-ylsulfonyl)pyrrolidin-3-yl]benzamide The title compound was prepared as described in Example 557C, substituting propane-2-sulfonyl chloride for propane-2-sulfonyl chloride and N-(imidazo[1,2-a]pyridin-7-ylmethyl)-4-(pyrrolidin-3-yl)benzamide for 4-(azetidin-3-yl)-N-(imidazo[1,2-a]pyridin-7-ylmethyl)benzamide. $^1$H NMR (501 MHz, DMSO-$d_6$) δ ppm 9.04 (t, J=6.0 Hz, 1H), 8.47 (d, J=6.9 Hz, 1H), 7.87 (m, 3H), 7.50 (d, J=1.2 Hz, 1H), 7.43 (m, 2H), 7.37 (s, 1H), 6.84 (dd, J=7.0, 1.6 Hz, 1H), 4.49 (d, J=5.9 Hz, 2H), 3.77 (m, 1H), 3.52 (m, 2H), 3.42 (m, 2H), 3.25 (m, 1H), 2.30 (m, 1H), 2.04 (m, 1H), 1.25 (dd, J=6.8, 1.4 Hz, 6H); MS (ESI(+)) m/e 427 (M+H)+.

Example 673

1-(imidazo[1,2-a]pyridin-7-ylmethyl)-3-{4-[1-(2-methoxyethyl)-1H-pyrazol-4-yl]phenyl}urea The title compound was prepared as described in Example 51A, substituting 1-(2-methoxyethyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 1-(4-bromophenyl)-3-(imidazo[1,2-a]pyridin-7-ylmethyl)urea for 4-bromoaniline. $^1$H NMR (500 MHz, DMSO-$d_6$) δ ppm 8.66 (s, 1H), 8.50 (d, J=7.0 Hz, 1H), 8.01 (s, 1H), 7.90 (s, 1H), 7.77 (s, 1H), 7.54 (s, 1H), 7.40 (m, 5H), 6.87 (dd, J=7.0, 1.6 Hz, 1H), 6.71 (t, J=6.0 Hz, 1H), 4.34 (d, J=6.0 Hz, 2H), 4.23 (t, J=5.3 Hz, 2H), 3.69 (t, J=5.3 Hz, 2H), 3.23 (s, 3H); MS (ESI(+)) m/e 391 (M+H)+.

Example 674

1-(imidazo[1,2-a]pyridin-7-ylmethyl)-3-{4-[1-(tetrahydrofuran-2-ylmethyl)-1H-pyrazol-4-yl]phenyl}urea The title compound was prepared as described in Example 51A, substituting 1-(tetrahydrofuran-2-ylmethyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 1-(4-bromophenyl)-3-(imidazo[1,2-a]pyridin-7-ylmethyl)urea for 4-bromoaniline. $^1$H NMR (500 MHz, DMSO-$d_6$) δ ppm 8.64 (s, 1H), 8.47 (d, J=7.0 Hz, 1H), 8.00 (s, 1H), 7.87 (s, 1H), 7.77 (s, 1H), 7.50 (d, J=1.2 Hz, 1H), 7.40 (m, 5H), 6.83 (dd, J=7.0, 1.6 Hz, 1H), 6.70 (t, J=6.0 Hz, 1H), 4.33 (d, J=6.0 Hz, 2H), 4.13 (m, 3H), 3.74 (m, 1H), 3.62 (m, 1H), 1.91 (m, 1H), 1.76 (m, 2H), 1.60 (m, 1H); MS (ESI(+)) m/e 417 (M+H)+.

Example 675

1-(imidazo[1,2-a]pyridin-7-ylmethyl)-3-{4-[1-(tetrahydro-2H-pyran-4-ylmethyl)-1H-pyrazol-4-yl]phenyl}urea The title compound was prepared as described in Example 51A, substituting 1-(tetrahydro-2H-pyran-4-ylmethyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 1-(4-bromophenyl)-3-(imidazo[1,2-a]pyridin-7-ylmethyl)urea for 4-bromoaniline. $^1$H NMR (500 MHz, DMSO-$d_6$) δ ppm 8.64 (s, 1H), 8.47 (d, J=7.0 Hz, 1H), 8.02 (s, 1H), 7.87 (s, 1H), 7.77 (d, J=0.8 Hz, 1H), 7.50 (d, J=1.2 Hz, 1H), 7.40 (m, 5H), 6.83 (dd, J=7.0, 1.6 Hz, 1H), 6.70 (t, J=6.0 Hz, 1H), 4.32 (d, J=5.9 Hz, 2H), 3.98 (d, J=7.1 Hz, 2H), 3.81 (m, 2H), 3.23 (m, 2H), 2.05 (m, 1H), 1.40 (m, 2H), 1.23 (m, 2H); MS (ESI(+)) m/e 431 (M+H)+.

Example 676

5-[1-(1,4-dioxan-2-ylmethyl)-1H-pyrazol-4-yl]-N-([1,2,4]triazolo[1,5-a]pyridin-6-ylmethyl)thiophene-2-carboxamide The title compound was prepared as described in Example 51A, substituting 1-((1,4-dioxan-2-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and N-([1,2,4]triazolo[1,5-a]pyridin-6-ylmethyl)-5-bromothiophene-2-carboxamide for 4-bromoaniline. $^1$H NMR (300 MHz, DMSO-$d_6$) δ ppm 9.03 (t, J=5.9 Hz, 1H), 8.90-8.85 (m, 1H), 8.48 (s, 1H), 8.12 (s, 1H), 7.84 (dd, J=9.2, 0.8 Hz, 1H), 7.82 (d, J=0.6 Hz, 1H), 7.71 (d, J=3.9 Hz, 1H), 7.66 (dd, J=9.2, 1.7 Hz, 1H), 7.22 (d, J=3.9 Hz, 1H), 4.54 (d, J=5.8 Hz, 2H), 4.20-4.12 (m, 2H), 3.95-3.83 (m, 1H), 3.74 (dd, J=11.4, 2.5 Hz, 2H), 3.68-3.60 (m, 1H), 3.59-3.39 (m, 2H), 3.29-3.21 (m, 1H); MS (ESI(+)) m/e 425 (M+H)+.

Example 677

5-[1-(2-fluorobenzoyl)piperidin-4-yl]-N-(imidazo[1,2-a]pyridin-7-ylmethyl)thiophene-2-carboxamide The title compound was prepared as described in Example 52A, substituting 2-fluorobenzoyl chloride for 2-cyclopentylacetyl chloride and N-(imidazo[1,2-a]pyridin-7-ylmethyl)-5-(piperidin-4-yl)thiophene-2-carboxamide for methyl 4-aminobenzoate. $^1$H NMR (300 MHz, DMSO-$d_6$) δ ppm 9.00 (t, J=6.0 Hz, 1H), 8.48 (dd, J=7.0, 0.8 Hz, 1H), 7.91-7.85 (m, 1H), 7.67 (d, J=3.8 Hz, 1H), 7.55-7.35 (m, 4H), 7.34-7.25 (m, 2H), 6.98 (dd, J=3.8, 0.5 Hz, 1H), 6.83 (dd, J=7.0, 1.7 Hz, 1H), 4.60 (d, J=13.2 Hz, 1H), 4.46 (d, J=5.9 Hz, 2H), 3.45 (d, J=12.7 Hz, 1H), 3.28-3.08 (m, 2H), 2.93 (td, J=12.8, 2.5 Hz, 1H), 2.00 (dd, J=43.2, 12.5 Hz, 2H), 1.68-1.39 (m, 2H); MS (ESI(+)) m/e 463 (M+H)+.

Example 678 tert-butyl 4-{4-[(imidazo[1,2-a]pyrazin-6-ylmethyl)carbamoyl]phenyl}piperidine-1-carboxylate The title compound was prepared as described in Example 1A, substituting imidazo[1,2-a]pyrazin-6-ylmethanamine for 3-methylbutan-1-amine and 4-(1-(tert-butoxycarbonyl)piperidin-4-yl)benzoic acid for 4-nitrobenzoic acid. $^1$H NMR (500 MHz, methanol-$d_4$) δ ppm 9.00-8.96 (m, 1H), 8.51-8.46 (m, 1H), 8.04-8.00 (m, 1H), 7.89-7.81 (m, 2H), 7.81-7.77 (m, 1H), 7.39-7.32 (m, 2H), 4.68 (s, 2H), 4.27-4.16 (m, 2H), 2.97-2.70 (m, 3H), 1.92-1.78 (m, 2H), 1.71-1.50 (m, 2H), 1.48 (s, 9H); MS (ESI(+)) m/e 436 (M+H)+.

Example 679

4-[(cyclopentylacetyl)amino]-N-(imidazo[1,2-a]pyrazin-6-ylmethyl)benzamide

The title compound was prepared as described in Example 1A, substituting imidazo[1,2-a]pyrazin-6-ylmethanamine for 3-methylbutan-1-amine and 4-(2-cyclopentylacetamido)benzoic acid for 4-nitrobenzoic acid. $^1$H NMR (500 MHz, methanol-$d_4$) δ ppm 9.19 (d, J=0.9 Hz, 1H), 8.65 (d, J=1.2 Hz, 1H), 8.20 (d, J=1.1 Hz, 1H), 8.03 (d, J=1.5 Hz, 1H), 7.90-7.83 (m, 2H), 7.73-7.66 (m, 2H), 4.74 (s, 2H), 2.44-2.22 (m, 3H), 1.92-1.76 (m, 2H), 1.76-1.49 (m, 4H), 1.35-1.14 (m, 2H); MS (ESI(+)) m/e 378 (M+H)$^+$.

Example 680 tert-butyl 4-(4-{[(imidazo[1,2-a]pyrazin-6-ylmethyl)carbamoyl]amino}phenyl)piperidine-1-carboxylate The title compound was prepared as described in Example 1C, substituting tert-butyl 4-(4-aminophenyl)piperidine-1-carboxylate for 4-amino-N-isopentylbenzamide and imidazo[1,2-a]pyrazin-6-ylmethanamine for imidazo[1,2-a]pyridin-6-amine $^1$H NMR (500 MHz, methanol-$d_4$) δ ppm 8.99-8.95 (m, 1H), 8.48-8.44 (m, 1H), 8.02 (s, 1H), 7.81-7.77 (m, 1H), 7.33-7.26 (m, 2H), 7.15-7.09 (m, 2H), 4.49 (s, 2H), 4.22-4.14 (m, 2H), 2.92-2.73 (m, 2H), 2.74-2.58 (m, 1H), 1.82-1.74 (m, 2H), 1.61-1.41 (m, 11H); MS (ESI(+)) m/e 451 (M+H)$^+$.

Example 681

2-cyclopentyl-N-(4-{[(imidazo[1,2-a]pyrazin-6-ylmethyl)carbamoyl]amino}phenyl)acetamide The title compound was prepared as described in Example 1C, substituting N-(4-aminophenyl)-2-cyclopentylacetamide for 4-amino-N-isopentylbenzamide and imidazo[1,2-a]pyrazin-6-ylmethanamine for imidazo[1,2-a]pyridin-6-amine $^1$H NMR (500 MHz, methanol-$d_4$) δ ppm 9.17-9.13 (m, 1H), 8.60 (s, 1H), 8.18 (s, 1H), 7.99 (d, J=1.5 Hz, 1H), 7.46-7.40 (m, 2H), 7.35-7.29 (m, 2H), 4.56 (bs, 2H), 2.37-2.23 (m, 3H), 1.90-1.77 (m, 2H), 1.77-1.49 (m, 4H), 1.34-1.17 (m, 2H); MS (ESI(+)) m/e 393 (M+H)$^+$.

Example 682

N-(imidazo[1,2-a]pyridin-7-ylmethyl)-4-[1-(phenylsulfonyl)piperidin-4-yl]benzamide A solution of N-(imidazo[1,2-a]pyridin-7-ylmethyl)-4-(piperidin-4-yl)benzamide (0.05 g, 0.150 mmol) in tetrahydrofuran (1.246 ml) was treated with sodium hydride (0.018 g, 0.449 mmol) in 3 portions. The reaction was stirred at ambient temperature for 45 minutes and became a partially homogeneous solution. Benzenesulfonyl chloride (0.021 ml, 0.164 mmol) was added and the mixture was stirred for 16 hours. The reaction was treated with 0.1 mL water and was concentrated under a stream of nitrogen. Reverse-phase chromatography provided the title compound. $^1$H NMR (500 MHz, methanol-$d_4$) δ ppm 8.73 (dd, J=7.0, 0.9 Hz, 1H), 8.15 (dd, J=2.2, 0.8 Hz, 1H), 7.97 (d, J=2.2 Hz, 1H), 7.89-7.75 (m, 5H), 7.73-7.59 (m, 3H), 7.46 (dd, J=7.0, 1.6 Hz, 1H), 7.37-7.31 (m, 2H), 4.75 (s, 2H), 3.96-3.88 (m, 2H), 2.67-2.52 (m, 1H), 2.48-2.37 (m, 2H), 1.95-1.72 (m, 4H); MS (ESI(+)) m/e 475 (M+H)$^+$.

Example 683

N-(imidazo[1,2-a]pyridin-7-ylmethyl)-4-[1-(propan-2-ylsulfonyl)piperidin-4-yl]benzamide The title compound was prepared as described in Example 682, substituting propane-2-sulfonyl chloride for benzenesulfonyl chloride. $^1$H NMR (500 MHz, methanol-$d_4$) δ ppm 8.75 (d, J=7.0 Hz, 1H), 8.17 (d, J=2.2 Hz, 1H), 7.99 (d, J=2.2 Hz, 1H), 7.89-7.83 (m, 2H), 7.80 (s, 1H), 7.49 (dd, J=7.0, 1.6 Hz, 1H), 7.43-7.37 (m, 2H), 4.77 (s, 2H), 3.95-3.87 (m, 2H), 3.38-3.29 (m, 1H), 3.12-3.00 (m, 2H), 2.89-2.75 (m, 1H), 1.95-1.86 (m, 2H), 1.82-1.68 (m, 2H), 1.34 (d, J=6.8 Hz, 6H); MS (ESI(+)) m/e 417 (M+H)$^+$.

Example 684

4-[1-(cyclopropylsulfonyl)piperidin-4-yl]-N-(imidazo[1,2-a]pyridin-7-ylmethyl)benzamide The title compound was prepared as described in Example 682, substituting cyclopropanesulfonyl chloride for benzenesulfonyl chloride. $^1$H NMR (500 MHz, methanol-$d_4$) δ ppm 8.75 (dd, J=7.0, 0.9 Hz, 1H), 8.19-8.15 (m, 1H), 7.98 (d, J=2.2 Hz, 1H), 7.90-7.84 (m, 2H), 7.80 (s, 1H), 7.48 (dd, J=7.0, 1.6 Hz, 1H), 7.45-7.38 (m, 2H), 4.77 (s, 2H), 3.92-3.84 (m, 2H), 3.07-2.96 (m, 2H), 2.86-2.73 (m, 1H), 2.57-2.46 (m, 1H), 2.00-1.91 (m, 2H), 1.88-1.73 (m, 2H), 1.13-0.99 (m, 4H); MS (ESI(+)) m/e 439 (M+H)$^+$.

Example 685

5-{(1R)-1-[(cyclopropylcarbonyl)amino]-3-methylbutyl}-N-(imidazo[1,2-a]pyridin-7-ylmethyl)thiophene-2-carboxamide Example 685A tert-butyl 5-formylthiophene-2-carboxylate 5-Formylthiophene-2-carboxylic acid (5.3 g, 33.9 mmol) was taken up in tetrahydrofuran (100 ml) and boc-anhydride (16.30 g, 74.7 mmol) was added, followed by N,N-dimethylaminopyridine (0.829 g, 6.79 mmol). The mixture was stirred overnight at room temperature, during which time the reaction became a dark, purplish color. It was diluted with saturated sodium bicarbonate and extracted with ether. The organic layers were dried over sodium sulfate, concentrated then purified by normal phase chromatography to give the title compound.

Example 685B (S,E)-tert-butyl 5-(((tert-butylsulfinyl)imino)methyl)thiophene-2-carboxylate tert-Butyl 5-formylthiophene-2-carboxylate (2 g, 9.42 mmol) and (S)-2-methylpropane-2-sulfinamide (1.370 g, 11.31 mmol) were dissolved in dichloromethane (100 ml). The mixture was chilled in an ice bath, and then tetraethoxytitanium (8.7 ml, 41.5 mmol) was added. The mixture was allowed to warm to room temperature overnight with stirring. The mixture was poured into a large Erlenmeyer flask with 200 mL dichloromethane and was diluted with 18 mL H$_2$O. After vigorous stirring for 30 minutes the suspension was filtered through diatomaceous earth and the filtrate was concentrated. Purification using normal phase chromatography provided the title compound.

Example 685C tert-butyl 5-((R)-1-((S)-1,1-dimethylethylsulfinamido)-3-methylbutyl)thiophene-2-carboxylate and tert-butyl 5-((S)-1-((S)-1,1-dimethylethylsulfinamido)-3-methylbutyl)thiophene-2-carboxylate (S,E)-tert-Butyl 5-((tert-butylsulfinylimino)methyl)thiophene-2-carboxylate (1 g, 3.17 mmol) was dissolved in dichloromethane (15.85 ml) and chilled to −45° C. in an acetone bath to which dry ice had been added to achieve the desired temperature. Isobutylmagnesium bromide (2.0M in diethyl ether; 3.17 ml, 6.34 mmol) was added dropwise over ~5 minutes. The mixture was stirred for 4 hours keeping the temperature between −40° C. and −50° C. by periodic addition of dry ice and then warmed to room temperature overnight. The mixture was quenched with saturated ammonium chloride (exothermic, bubbling) and extracted with dichloromethane (three times; considerable emulsion formed). The organic extracts were dried with sodium sulfate, filtered, concentrated and chromatographed to provide both tert-butyl 5-((R)-1-((S)-1,1-dimethylethylsulfinamido)-3-methylbutyl)thiophene-2-carboxylate and tert-butyl 5-((S)-1-((S)-1,1-dimethylethylsulfinamido)-3-methylbutyl)thiophene-2-carboxylate as separate compounds.

Example 685D (R)-tert-butyl 5-(1-amino-3-methylbutyl)thiophene-2-carboxylate

The title compound was prepared as described in Example 324C, substituting tert-butyl 5-((R)-1-((S)-1,1-dimethylethylsulfinamido)-3-methylbutyl)thiophene-2-carboxylate for tert-butyl 5-((R)-1-((S)-1,1-dimethylethylsulfinamido)-3-methylbutyl)thiophene-2-carboxylate.

Example 685E (R)-5-(1-(cyclopropanecarboxamido)-3-methylbutyl)thiophene-2-carboxylic acid The title compound was prepared as described in Example 1A, substituting (R)-tert-butyl 5-(1-amino-3-methylbutyl)thiophene-2-carboxylate for 3-methylbutan-1-amine and cyclopropanecarboxylic acid for 4-nitrobenzoic acid followed by acidic deprotection as described in Example 28A, substituting (R)-tert-butyl 5-(1-(cyclopropanecarboxamido)-3-methylbutyl)thiophene-2-carboxylate for tert-butyl 4-(4-(3-imidazo[1,2-a]pyridin-6-ylureido)phenyl)-5,6-dihydropyridine-1(2H)-carboxylate.

Example 685F

5-{(1R)-1-[(cyclopropylcarbonyl)amino]-3-methylbutyl}-N-(imidazo[1,2-a]pyridin-7-ylmethyl)thiophene-2-carboxamide The title compound was prepared as described in Example 1A, substituting imidazo[1,2-a]pyridin-7-ylmethanamine for 3-methylbutan-1-amine and (R)-5-(1-(cyclopropanecarboxamido)-3-methylbutyl)thiophene-2-carboxylic acid for 4-nitrobenzoic acid. $^1$H NMR (300 MHz, DMSO-$d_6$) ppm 9.00 (t, J=6.0 Hz, 1H), 8.55 (d, J=8.4 Hz, 1H), 8.48 (d, J=7.4 Hz, 1H), 7.88 (d, J=1.1 Hz, 1H), 7.64 (d, J=3.8 Hz, 1H), 7.52 (d, J=1.2 Hz, 1H), 7.37 (s, 1H), 6.98 (d, J=3.8 Hz, 1H), 6.82 (dd, J=7.0, 1.7 Hz, 1H), 5.11 (td, J=8.8, 5.0 Hz, 1H), 4.46 (d, J=5.9 Hz, 2H), 1.80-1.52 (m, 4H), 0.95-0.83 (m, 6H), 0.75-0.59 (m, 4H); MS (ESI(+)) m/e 411 (M+H)$^+$.

Example 686

N-(imidazo[1,2-a]pyridin-7-ylmethyl)-5-{(1R)-3-methyl-1-[(tetrahydrofuran-3-ylacetyl)amino]butyl}thiophene-2-carboxamide The title compound was described as in Example 685, substituting 2-(tetrahydrofuran-3-yl)acetic acid for cyclopropanecarboxylic acid in Example 685E. $^1$H NMR (300 MHz, DMSO-$d_6$) ppm 9.00 (t, J=6.0 Hz, 1H), 8.48 (d, J=7.0 Hz, 1H), 8.39 (d, J=8.5 Hz, 1H), 7.88 (s, 1H), 7.64 (d, J=3.7 Hz, 1H), 7.52 (d, J=1.2 Hz, 1H), 7.37 (s, 1H), 6.97 (d, J=3.8 Hz, 1H), 6.82 (dd, J=7.0, 1.7 Hz, 1H), 5.16-5.05 (m, 1H), 4.45 (d, J=5.9 Hz, 2H), 3.76-3.51 (m, 3H), 3.29-3.21 (m, 1H), 2.29-2.16 (m, 3H), 2.02-1.86 (m, 1H), 1.78-1.40 (m, 4H), 0.99-0.77 (m, 6H); MS (ESI(+)) m/e 455 (M+H)$^+$.

Example 687

5-{(1S)-1-[(cyclopropylcarbonyl)amino]-3-methylbutyl}-N-(imidazo[1,2-a]pyridin-7-ylmethyl)thiophene-2-carboxamide The title compound was described as in Example 685, substituting butyl 5-((S)-1-((S)-1,1-dimethylethylsulfinamido)-3-methylbutyl)thiophene-2-carboxylate for tert-butyl 5-((R)-1-((S)-1,1-dimethylethylsulfinamido)-3-methylbutyl)thiophene-2-carboxylate in Example 685D. $^1$H NMR (300 MHz, DMSO-$d_6$) ppm 9.04-8.96 (m, 1H), 8.55 (d, J=8.4 Hz, 1H), 8.48 (dd, J=7.0, 0.9 Hz, 1H), 7.88 (s, 1H), 7.64 (d, J=3.8 Hz, 1H), 7.52 (d, J=1.1 Hz, 1H), 7.37 (s, 1H), 6.98 (d, J=3.8 Hz, 1H), 6.83 (dd, J=7.0, 1.7 Hz, 1H), 5.17-5.05 (m, 1H), 4.46 (d, J=5.9 Hz, 2H), 1.77-1.44 (m, 4H), 1.01-0.77 (m, 6H), 0.66 (d, J=7.2 Hz, 4H); MS (ESI(+)) m/e 411 (M+H)$^+$.

Example 688

N-(imidazo[1,2-a]pyridin-7-ylmethyl)-2-(1-phenylpiperidin-4-yl)-1,3-thiazole-5-carboxamide Example 688A ethyl 2-(piperidin-4-yl)thiazole-5-carboxylate Ethyl 3-ethoxyacrylate (1.50 g, 10.38 mml) was dissolved in dioxane/water and chilled to −10° C. N-Bromosuccinimide (2.03 g, 11.42 mmol) was added and the mixture was stirred 1 hour at room temperature. tert-Butyl 4-carbamothioylpiperidine-1-carboxylate (2.54 g, 10.38 mmol) was added and the mixture was heated at 100° C. for 1 hour. The reaction mixture was poured into 25 mL saturated ammonium hydroxide and extracted with dichloromethane. The combined organic layers were washed with brine, dried with sodium sulfate, filtered, and concentrated. Normal phase chromatography provided the title compound.

Example 688B ethyl 2-(1-phenylpiperidin-4-yl)thiazole-5-carboxylate

Ethyl 2-(piperidin-4-yl)thiazole-5-carboxylate (100 mg, 0.416 mmol), 2,2'-bis(diphenylphosphino)-1,1'-binaphthalene (21 mg, 0.033 mmol), bis(dibenzylideneacetone)palladium(0) (15 mg, 0.017 mmol) and cesium carbonate (678 mg, 2.081 mmol) were placed in a pressure tube capped with a septum and degassed with nitrogen by passing a stream through the vessel for 30 minutes. Separately, bromobenzene (68.6 mg, 0.437 mmol) was dissolved in toluene (2 ml) and the solution was degassed by bubbling nitrogen for 30 minutes. The bromobenzene solution was added to the solid mixture and the sealed tube was heated to 100° C. overnight. The mixture was partitioned between dichloromathane and water and the combined organic layers were concentrated and purified by normal phase chromatography to give the title compound.

Example 688C lithium 2-(1-phenylpiperidin-4-yl)thiazole-5-carboxylate

A solution of ethyl 2-(1-phenylpiperidin-4-yl)thiazole-5-carboxylate (31 mg, 0.098 mmol) in 1 ml of 1:1 tetrahydrofuran/methanol was treated with 1M LiOH (0.11 ml, 0.11 mol) and stirred at 65° C. for 3 hours. The mixture was taken to dryness and used directly in the next step.

Example 688D

N-(imidazo[1,2-a]pyridin-7-ylmethyl)-2-(1-phenylpiperidin-4-yl)-1,3-thiazole-5-carboxamide Lithium 2-(1-phenylpiperidin-4-yl)thiazole-5-carboxylate (28.8 mg, 0.098 mmol), imidazo[1,2-a]pyridin-7-ylmethanamine (17.31 mg, 0.118 mmol), 4-methylmorpholine (49.6 mg, 0.490 mmol) and 2-(3H-[1,2,3]triazolo[4,5-b]pyridin-3-yl)-1,1,3,3-tetramethylisouronium hexafluorophosphate(V) (55.9 mg, 0.147 mmol) were combined in a vial with dichloromethane (2.5 ml) and the reaction was stirred overnight. The mixture was partitioned between dichloromethane and saturated sodium bicarbonate. The organic layers were dried with sodium sulfate, filtered, and concentrated. Trituration of the crude material with dichloromethane provided the title compound. $^1$H NMR (300 MHz, DMSO-d$_6$) ppm 9.21 (t, J=5.9 Hz, 1H), 8.49 (dd, J=7.0, 0.9 Hz, 1H), 8.34 (s, 1H), 7.91-7.88 (m, 1H), 7.52 (d, J=1.2 Hz, 1H), 7.43-7.38 (m, 1H), 7.26-7.16 (m, 2H), 7.01-6.93 (m, 2H), 6.84 (dd, J=7.0, 1.7 Hz, 1H), 6.81-6.72 (m, 1H), 4.48 (d, J=5.9 Hz, 2H), 3.81-3.73 (m, 2H), 3.24-3.01 (m, 1H), 2.90-2.78 (m, 2H), 2.19-2.09 (m, 2H), 1.90-1.73 (m, 2H); MS (ESI(+)) m/e 418 (M+H)$^+$.

Example 697

N-(imidazo[1,2-a]pyridin-7-ylmethyl)-2-[1-(pyridin-2-yl)piperidin-4-yl]-1,3-thiazole-5-carboxamide The title compound was prepared as described in Example 688, substituting 2-bromopyridine for bromobenzene in Example 688B. $^1$H NMR (400 MHz, DMSO-d$_6$) ppm 9.21 (t, J=5.9 Hz, 1H), 8.49 (dd, J=6.9, 0.9 Hz, 1H), 8.33 (s, 1H), 8.13-8.09 (m, 1H), 7.89 (s, 1H), 7.55-7.48 (m, 2H), 7.40 (s, 1H), 6.86 (d, J=8.7 Hz, 1H), 6.83 (dd, J=7.0, 1.6 Hz, 1H), 6.61 (dd, J=6.9, 5.1 Hz, 1H), 4.48 (d, J=5.9 Hz, 2H), 4.40-4.32 (m, 2H), 3.03-2.92 (m, 2H), 2.14-2.05 (m, 2H), 1.68 (qd, J=12.5, 3.9 Hz, 2H); MS (ESI(+)) m/e 419 (M+H)$^+$.

Example 698

5-{1-[(4-fluorotetrahydro-2H-pyran-4-yl)methyl]-1H-pyrazol-4-yl}-N-(imidazo[1,2-a]pyridin-7-ylmethyl)thiophene-2-carboxamide The title compound was prepared as described in Example 51A, substituting 1-((4-fluorotetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline. $^1$H NMR (300 MHz, DMSO-d$_6$) δ ppm 9.03 (t, J=6.0 Hz, 1H), 8.49 (d, J=7.1 Hz, 1H), 8.11 (s, 1H), 7.89 (s, 1H), 7.85 (s, 1H), 7.75 (d, J=3.9 Hz, 1H), 7.52 (d, J=1.2 Hz, 1H), 7.40 (s, 1H), 7.26 (d, J=3.9 Hz, 1H), 6.85 (dd, J=7.0, 1.6 Hz, 1H), 4.48 (d, J=5.9 Hz, 2H), 4.42 (d, J=21.4 Hz, 2H), 3.74 (ddd, J=11.4, 4.6, 2.9 Hz, 2H), 3.51 (td, J=11.3, 2.0 Hz, 2H), 1.92-1.64 (m, 2H), 1.55 (t, J=11.8 Hz, 2H); MS (ESI(+)) m/e 440 (M+H)$^+$.

Example 734

N-(imidazo[1,2-a]pyridin-7-ylmethyl)-5-{1-[(4-methyltetrahydro-2H-pyran-4-yl)methyl]-1H-pyrazol-4-yl}furan-2-carboxamide

Example 734A 5-bromo-N-(imidazo[1,2-a]pyridin-7-ylmethyl)furan-2-carboxamide The title compound was prepared as described in Example 1A, substituting imidazo[1,2-a]pyridin-7-ylmethanamine for 3-methylbutan-1-amine and 5-bromofuran-2-carboxylic acid for 4-nitrobenzoic acid.

Example 734B

N-(imidazo[1,2-a]pyridin-7-ylmethyl)-5-{1-[(4-methyltetrahydro-2H-pyran-4-yl)methyl]-1H-pyrazol-4-yl}furan-2-carboxamide The title compound was prepared as described in Example 51A, substituting 1-((4-methyltetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and bromide for 4-bromoaniline. $^1$H NMR (300 MHz, DMSO-d$_6$) δ ppm 8.89 (t, J=6.1 Hz, 1H), 8.49 (dd, J=7.0, 0.9 Hz, 1H), 8.13 (d, J=0.5 Hz, 1H), 7.91-7.86 (m, 2H), 7.52 (d, J=1.2 Hz, 1H), 7.40 (s, 1H), 7.17 (d, J=3.6 Hz, 1H), 6.85 (dd, J=7.0, 1.7 Hz, 1H), 6.67 (d, J=3.5 Hz, 1H), 4.49 (d, J=6.0 Hz, 2H), 4.07 (s, 2H), 3.68 (dt, J=11.5, 4.5 Hz, 2H), 3.51 (ddd, J=11.9, 9.3, 3.0 Hz, 2H), 1.51 (ddd, J=13.4, 9.2, 4.2 Hz, 2H), 1.33-1.15 (m, 2H), 0.96 (s, 3H); MS (ESI(+)) m/e 420 (M+H)$^+$.

Example 735

5-[1-(2-fluorobenzoyl)piperidin-4-yl]-N-(imidazo[1,2-a]pyridin-7-ylmethyl)furan-2-carboxamide

Example 735A tert-butyl 4-(5-((imidazo[1,2-a]pyridin-7-ylmethyl)carbamoyl)furan-2-yl)-5,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline.

Example 735B tert-butyl 4-(5-((imidazo[1,2-a]pyridin-7-ylmethyl)carbamoyl)furan-2-yl)piperidine-1-carboxylate The title compound was prepared as described in Example 1B, substituting tert-butyl 4-(5-((imidazo[1,2-a]pyridin-7-ylmethyl)carbamoyl)furan-2-yl)-5,6-dihydropyridine-1(2H)-carboxylate for N-isopentyl-4-nitrobenzamide.

Example 735C

N-(imidazo[1,2-a]pyridin-7-ylmethyl)-5-(piperidin-4-yl)furan-2-carboxamide

The title compound was prepared as described in Example 28A, substituting tert-butyl 4-(5-((imidazo[1,2-a]pyridin-7-ylmethyl)carbamoyl)furan-2-yl)piperidine-1-carboxylate for tert-butyl 4-(4-(3-imidazo[1,2-a]pyridin-6-ylureido)phenyl)-5,6-dihydropyridine-1(2H)-carboxylate.

Example 735D

5-[1-(2-fluorobenzoyl)piperidin-4-yl]-N-(imidazo[1,2-a]pyridin-7-ylmethyl)furan-2-carboxamide The title compound was prepared as described in Example 1A, substituting N-(imidazo[1,2-a]pyridin-7-ylmethyl)-5-(piperidin-4-yl)furan-2-carboxamide for 3-methylbutan-1-amine and 2-fluorobenzoic acid for 4-nitrobenzoic acid. $^1$H NMR (300 MHz, DMSO-$d_6$) δ ppm 8.85 (t, J=6.1 Hz, 1H), 8.47 (dd, J=7.0, 0.8 Hz, 1H), 7.92-7.83 (m, 1H), 7.55-7.45 (m, 2H), 7.41 (td, J=7.5, 1.5 Hz, 1H), 7.37 (s, 1H), 7.34-7.25 (m, 2H), 7.06 (d, J=3.4 Hz, 1H), 6.83 (dd, J=7.0, 1.7 Hz, 1H), 6.33 (dd, J=3.5, 0.7 Hz, 1H), 4.53 (d, J=13.4 Hz, 1H), 4.44 (d, J=6.0 Hz, 2H), 3.44 (d, J=13.0 Hz, 1H), 3.19 (t, J=12.8 Hz, 1H), 3.11-2.90 (m, 2H), 2.09 (d, J=11.0 Hz, 1H), 1.94 (d, J=11.9 Hz, 1H), 1.73-1.42 (m, 2H); MS (ESI(+)) m/e 447 (M+H)$^+$.

Example 736

N-(imidazo[1,2-a]pyridin-7-ylmethyl)-5-[1-(2-methylpropanoyl)piperidin-4-yl]furan-2-carboxamide The title compound was prepared as described in Example 1A, substituting N-(imidazo[1,2-a]pyridin-7-ylmethyl)-5-(piperidin-4-yl)furan-2-carboxamide for 3-methylbutan-1-amine and isobutyric acid for 4-nitrobenzoic acid. $^1$H NMR (300 MHz, DMSO-$d_6$) δ ppm 8.84 (t, J=6.1 Hz, 1H), 8.47 (dd, J=7.0, 0.8 Hz, 1H), 7.94-7.82 (m, 1H), 7.51 (d, J=1.2 Hz, 1H), 7.42-7.33 (m, 1H), 7.05 (d, J=3.4 Hz, 1H), 6.83 (dd, J=7.0, 1.7 Hz, 1H), 6.31 (dd, J=3.4, 0.6 Hz, 1H), 4.44 (d, J=6.0 Hz, 3H), 4.06-3.90 (m, 1H), 3.21-3.07 (m, 1H), 3.07-2.77 (m, 2H), 2.77-2.59 (m, 1H), 2.06-1.90 (m, 2H), 1.61-1.37 (m, 2H), 0.99 (d, J=6.7 Hz, 6H); MS (ESI(+)) m/e 395 (M+H)$^+$.

Example 738

N-(imidazo[1,2-a]pyridin-7-ylmethyl)-5-[1-(2,2,2-trifluoroethyl)-1H-pyrazol-4-yl]furan-2-carboxamide The title compound was prepared as described in Example 51A, substituting 4-(4,4,5,5-tetramethyl-1,3,2-dioxaborolan-2-yl)-1-(2,2,2-trifluoroethyl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (400 MHz, DMSO-$d_6$) ppm 9.21 (t, J=5.9 Hz, 1H), 8.49 (dd, J=6.9, 0.9 Hz, 1H), 8.33 (s, 1H), 8.13-8.09 (m, 1H), 7.89 (s, 1H), 7.55-7.48 (m, 2H), 7.40 (s, 1H), 6.86 (d, J=8.7 Hz, 1H), 6.83 (dd, J=7.0, 1.6 Hz, 1H), 6.61 (dd, J=6.9, 5.1 Hz, 1H), 4.48 (d, J=5.9 Hz, 2H), 4.40-4.32 (m, 2H), 3.03-2.92 (m, 2H), 2.14-2.05 (m, 2H), 1.68 (qd, J=12.5, 3.9 Hz, 2H); MS (ESI (+)) m/e 390 (M+H)$^+$.

Example 739

2-cyclopentyl-N-{4-[(imidazo[1,2-a]pyridin-7-ylacetyl)amino]phenyl}acetamide

The title compound was prepared as described in Example 1A, substituting N-(4-aminophenyl)-2-cyclopentylacetamide for 3-methylbutan-1-amine and 2-(imidazo[1,2-a]pyridin-7-yl)acetic acid for 4-nitrobenzoic acid. $^1$H NMR (500 MHz, methanol-$d_4$) δ ppm 8.75 (dd, J=6.9, 1.0 Hz, 1H), 8.21-8.16 (m, 1H), 8.01 (d, J=2.1 Hz, 1H), 7.89 (s, 1H), 7.55-7.45 (m, 5H), 3.99 (s, 2H), 2.39-2.24 (m, 3H), 1.91-1.76 (m, 2H), 1.78-1.46 (m, 4H), 1.39-1.15 (m, 2H); MS (ESI(+)) m/e 377 (M+H)$^+$.

Example 740

N-(imidazo[1,2-a]pyridin-7-ylmethyl)-5-[1-(2-methylpropyl)-1H-pyrazol-4-yl]furan-2-carboxamide The title compound was prepared as described in Example 51A, substituting 5-bromo-N-(imidazo[1,2-a]pyridin-7-ylmethyl)furan-2-carboxamide for 4-bromoaniline. $^1$H NMR (300 MHz, DMSO-$d_6$) ppm 8.88 (t, J=6.1 Hz, 1H), 8.49 (dd, J=7.0, 0.9 Hz, 1H), 8.15 (s, 1H), 7.90-7.86 (m, 2H), 7.52 (d, J=1.2 Hz, 1H), 7.40 (s, 1H), 7.17 (d, J=3.5 Hz, 1H), 6.85 (dd, J=7.0, 1.7 Hz, 1H), 6.65 (d, J=3.5 Hz, 1H), 4.49 (d, J=6.1 Hz, 2H), 3.95 (d, J=7.2 Hz, 2H), 2.21-2.05 (m, 1H), 0.85 (d, J=6.7 Hz, 6H); MS (ESI(+)) m/e 364 (M+H)$^+$.

Example 741

5-(1-benzyl-1H-pyrazol-4-yl)-N-(imidazo[1,2-a]pyridin-7-ylmethyl)furan-2-carboxamide The title compound was prepared as described in Example 51A, substituting 1-benzyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (400 MHz, DMSO-$d_6$) ppm 8.92 (t, J=6.1 Hz, 1H), 8.49 (dd, J=6.9, 0.9 Hz, 1H), 8.27 (d, J=0.7 Hz, 1H), 7.93 (d, J=0.7 Hz, 1H), 7.89 (t, J=0.9 Hz, 1H), 7.52 (d, J=1.2 Hz, 1H), 7.41-7.23 (m, 6H), 7.17 (d, J=3.5 Hz, 1H), 6.85 (dd, J=7.0, 1.7 Hz, 1H), 6.68 (d, J=3.5 Hz, 1H), 5.39 (s, 2H), 4.49 (d, J=6.1 Hz, 2H); MS (ESI(+)) m/e 398 (M+H)$^+$.

Example 742

N-(imidazo[1,2-a]pyridin-7-ylmethyl)-5-{1-[(2S)-tetrahydrofuran-2-ylmethyl]-1H-pyrazol-4-yl}furan-2-carboxamide The title compound was prepared as described in Example 51A, substituting (S)-1-((tetrahydrofuran-2-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (400 MHz, DMSO-$d_6$) ppm 8.94 (t, J=6.1 Hz, 1H), 8.49 (dd, J=6.9, 0.9 Hz, 1H), 8.15 (s, 1H), 7.89 (s, 2H), 7.52 (d, J=1.2 Hz, 1H), 7.40 (s, 1H), 7.17 (d, J=3.5 Hz, 1H), 6.86 (dd, J=7.0, 1.7 Hz, 1H), 6.68 (d, J=3.5 Hz, 1H), 4.49 (d, J=6.1 Hz, 2H), 4.28-4.09 (m, 3H), 3.78-3.69 (m, 1H), 3.68-3.55 (m, 1H), 2.01-1.88 (m, 1H), 1.85-1.66 (m, 2H), 1.66-1.54 (m, 1H); MS (ESI(+)) m/e 392 (M+H)$^+$.

Example 743

N-(imidazo[1,2-a]pyridin-7-ylmethyl)-5-{1-[(2R)-tetrahydrofuran-2-ylmethyl]-1H-pyrazol-4-yl}furan-2-carboxamide The title compound was prepared as described in Example 51A, substituting (R)-1-((tetrahydrofuran-2-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (400 MHz, DMSO-d$_6$) ppm 8.94 (t, J=6.1 Hz, 1H), 8.49 (dd, J=6.9, 0.9 Hz, 1H), 8.15 (s, 1H), 7.89 (s, 2H), 7.52 (d, J=1.2 Hz, 1H), 7.40 (s, 1H), 7.17 (d, J=3.5 Hz, 1H), 6.86 (dd, J=7.0, 1.7 Hz, 1H), 6.68 (d, J=3.5 Hz, 1H), 4.49 (d, J=6.1 Hz, 2H), 4.28-4.07 (m, 3H), 3.78-3.69 (m, 1H), 3.68-3.59 (m, 1H), 2.01-1.88 (m, 1H), 1.85-1.66 (m, 2H), 1.66-1.54 (m, 1H); MS (ESI(+)) m/e 392 (M+H)$^+$.

Example 744

N-(imidazo[1,2-a]pyridin-7-ylmethyl)-5-[1-(2-methylpropanoyl)-1,2,3,6-tetrahydropyridin-4-yl]furan-2-carboxamide Example 744A tert-butyl 4-(5-((imidazo[1,2-a]pyridin-7-ylmethyl)carbamoyl)furan-2-yl)-5,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline.

Example 744B

N-(imidazo[1,2-a]pyridin-7-ylmethyl)-5-(1,2,3,6-tetrahydropyridin-4-yl)furan-2-carb oxamide The title compound was prepared as described in Example 28A, substituting tert-butyl 4-(5-((imidazo[1,2-a]pyridin-7-ylmethyl)carbamoyl)furan-2-yl)-5,6-dihydropyridine-1(2H)-carboxylate for tert-butyl 4-(4-(3-imidazo[1,2-a]pyridin-6-ylureido)phenyl)-5,6-dihydropyridine-1(2H)-carboxylate.

Example 744C

N-(imidazo[1,2-a]pyridin-7-ylmethyl)-5-[1-(2-methylpropanoyl)-1,2,3,6-tetrahydropyridin-4-yl]furan-2-carboxamide The title compound was prepared as described in Example 1A, substituting N-(imidazo[1,2-a]pyridin-7-ylmethyl)-5-(1,2,3,6-tetrahydropyridin-4-yl)furan-2-carboxamide for 3-methylbutan-1-amine and isobutyric acid for 4-nitrobenzoic acid. $^1$H NMR (400 MHz, DMSO-d$_6$) ppm 9.00 (t, J=5.3 Hz, 1H), 8.49 (dd, J=7.0, 0.7 Hz, 1H), 7.89 (s, 1H), 7.52 (d, J=1.2 Hz, 1H), 7.39 (s, 1H), 7.13 (d, J=3.5 Hz, 1H), 6.84 (dd, J=7.0, 1.7 Hz, 1H), 6.58 (d, J=3.0 Hz, 1H), 6.53 (s, 1H), 4.47 (d, J=6.1 Hz, 2H), 4.25 (s, 1H), 4.13 (s, 1H), 3.66 (dd, J=12.2, 6.1 Hz, 2H), 3.01-2.82 (m, 1H), 2.47 (bs, 1H), 2.36 (bs, 1H), 1.09-0.86 (m, 6H); MS (ESI(+)) m/e 393 (M+H)$^+$.

Example 745

N-(imidazo[1,2-a]pyridin-7-ylmethyl)-5-[1-(3-methylbutanoyl)-1,2,3,6-tetrahydropyridin-4-yl]furan-2-carboxamide The title compound was prepared as described in Example 1A, substituting N-(imidazo[1,2-a]pyridin-7-ylmethyl)-5-(1,2,3,6-tetrahydropyridin-4-yl)furan-2-carboxamide for 3-methylbutan-1-amine and 3-methylbutanoic acid for 4-nitrobenzoic acid. $^1$H NMR (400 MHz, DMSO-d$_6$) ppm 9.00 (dd, J=8.8, 5.7 Hz, 1H), 8.49 (dd, J=7.0, 0.5 Hz, 1H), 7.89 (s, 1H), 7.52 (d, J=1.2 Hz, 1H), 7.39 (s, 1H), 7.13 (dd, J=3.4, 2.1 Hz, 1H), 6.84 (dd, J=7.0, 1.7 Hz, 1H), 6.58 (dd, J=6.2, 3.5 Hz, 1H), 6.52 (d, J=15.2 Hz, 1H), 4.47 (d, J=6.1 Hz, 2H), 4.17 (dd, J=21.3, 2.5 Hz, 2H), 3.74-3.53 (m, 2H), 2.45 (bs, 1H), 2.37 (bs, 1H), 2.27 (d, J=7.0 Hz, 1H), 2.22 (d, J=6.9 Hz, 1H), 2.06-1.94 (m, 1H), 0.91 (dd, J=6.5, 5.3 Hz, 6H); MS (ESI(+)) m/e 407 (M+H)$^+$.

Example 746

5-(1-benzoyl-1,2,3,6-tetrahydropyridin-4-yl)-N-(imidazo[1,2-a]pyridin-7-ylmethyl)furan-2-carboxamide The title compound was prepared as described in Example 1A, substituting N-(imidazo[1,2-a]pyridin-7-ylmethyl)-5-(1,2,3,6-tetrahydropyridin-4-yl)furan-2-carboxamide for 3-methylbutan-1-amine and benzoic acid for 4-nitrobenzoic acid. $^1$H NMR (400 MHz, DMSO-d$_6$) ppm 8.62 (t, J=5.4 Hz, 1H), 8.44-8.39 (m, 1H), 7.81 (s, 1H), 7.51-7.35 (m, 7H), 7.08 (d, J=3.5 Hz, 1H), 6.82 (dd, J=7.0, 1.6 Hz, 1H), 6.53 (d, J=3.5 Hz, 1H), 6.50-6.43 (m, 1H), 4.47 (d, J=6.1 Hz, 2H), 4.20 (d, J=2.1 Hz, 2H), 3.64 (t, J=5.3 Hz, 2H), 2.52-2.46 (m, 2H); MS (ESI(+)) m/e 427 (M+H)$^+$.

Example 747

N-(imidazo[1,2-a]pyridin-7-ylmethyl)-5-[4-(2-methylpropyl)phenyl]furan-2-carboxamide The title compound was prepared as described in Example 51A, substituting 4-isobutylphenylboronic acid for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (300 MHz, DMSO-d$_6$) δ ppm 9.08 (t, J=6.1 Hz, 1H), 8.49 (dd, J=6.9, 0.8 Hz, 1H), 7.92-7.87 (m, 1H), 7.87-7.79 (m, 2H), 7.52 (d, J=1.2 Hz, 1H), 7.45-7.38 (m, 1H), 7.25 (d, J=8.3 Hz, 2H), 7.21 (d, J=3.6 Hz, 1H), 7.04 (d, J=3.6 Hz, 1H), 6.87 (dd, J=7.0, 1.7 Hz, 1H), 4.51 (d, J=6.0 Hz, 2H), 2.49-2.46 (m, 2H), 1.86 (dp, J=13.4, 6.8 Hz, 1H), 0.87 (d, J=6.6 Hz, 6H); MS (ESI(+)) m/e 374 (M+H)$^+$.

Example 748

N-(imidazo[1,2-a]pyridin-7-ylmethyl)-5-{1-[(2S)-2-methylbutanoyl]-1,2,3,6-tetrahydropyridin-4-yl}furan-2-carboxamide The title compound was prepared as described in Example 1A, substituting N-(imidazo[1,2-a]pyridin-7-ylmethyl)-5-(1, 2,3,6-tetrahydropyridin-4-yl)furan-2-carboxamide for 3-methylbutan-1-amine and (2S)-2-methylbutanoic acid for 4-nitrobenzoic acid. $^1$H NMR (400 MHz, DMSO-d$_6$) ppm 9.00 (t, J=5.0 Hz, 1H), 8.49 (dd, J=7.0, 0.6 Hz, 1H), 7.89 (s, 1H), 7.52 (d, J=1.1 Hz, 1H), 7.39 (s, 1H), 7.13 (d, J=3.5 Hz, 1H), 6.84 (dd, J=7.0, 1.6 Hz, 1H), 6.61-6.56 (m, 1H), 6.53 (d, J=9.8 Hz, 1H), 4.47 (d, J=6.1 Hz, 2H), 4.35-4.07 (m, 2H), 3.75-3.58 (m, 2H), 2.90-2.62 (m, 1H), 2.48-2.30 (m, 2H), 1.57 (dt, J=24.3, 8.8 Hz, 1H), 1.32 (dt, J=13.1, 6.8 Hz, 1H), 0.99 (dd, J=9.6, 6.8 Hz, 3H), 0.81 (q, J=7.1 Hz, 3H); MS (ESI(+)) m/e 407 (M+H)$^+$.

Example 749

5-[1-(3,3-dimethylbutanoyl)-1,2,3,6-tetrahydropyridin-4-yl]-N-(imidazo[1,2-a]pyridin-7-ylmethyl)furan-2-carboxamide The title compound was prepared as described in Example 1A, substituting N-(imidazo[1,2-a]pyridin-7-ylmethyl)-5-(1,2,3,6-tetrahydropyridin-4-yl)furan-2-carboxamide for 3-methylbutan-1-amine and 3,3-dimethylbutanoic acid for 4-nitrobenzoic acid. $^1$H NMR (400 MHz, DMSO-d$_6$) ppm 9.00 (t, J=6.1 Hz, 1H), 8.49 (dd, J=7.0, 0.7 Hz, 1H), 7.89 (s, 1H), 7.52 (d, J=1.2 Hz, 1H), 7.39 (s, 1H), 7.13 (t, J=3.4 Hz, 1H), 6.84 (dd, J=7.0, 1.7 Hz, 1H), 6.57 (dd, J=6.1, 3.6 Hz, 1H), 6.51 (d, J=23.1 Hz, 1H), 4.47 (d, J=6.0 Hz, 2H), 4.19 (dd, J=31.4, 2.4 Hz, 2H), 3.73-3.62 (m, 2H), 2.41 (d, J=31.8 Hz, 2H), 2.28 (d, J=17.4 Hz, 2H), 0.99 (d, J=7.2 Hz, 9H); MS (ESI(+)) m/e 421 (M+H)$^+$.

Example 750

5-[1-(cyclopropylacetyl)-1,2,3,6-tetrahydropyridin-4-yl]-N-(imidazo[1,2-a]pyridin-7-ylmethyl)furan-2-carboxamide The title compound was prepared as described in Example 1A, substituting N-(imidazo[1,2-a]pyridin-7-ylmethyl)-5-(1,2,3,6-tetrahydropyridin-4-yl)furan-2-carboxamide for 3-methylbutan-1-amine and cyclopropylacetic acid for 4-nitrobenzoic acid. $^1$H NMR (400 MHz, DMSO-d$_6$) ppm 9.05-8.93 (m, 1H), 8.49 (dd, J=7.0, 0.8 Hz, 1H), 7.90-7.87 (m, 1H), 7.52 (d, J=1.2 Hz, 1H), 7.39 (bs, 1H), 7.13 (d, J=3.5 Hz, 1H), 6.84 (dd, J=7.0, 1.6 Hz, 1H), 6.58 (dd, J=6.9, 3.5 Hz, 1H), 6.55-6.48 (m, 1H), 4.47 (d, J=6.1 Hz, 2H), 4.15 (d, J=8.4 Hz, 2H), 3.63 (dt, J=18.3, 5.7 Hz, 2H), 2.48-2.35 (m, 2H), 2.35-2.27 (m, 2H), 1.03-0.91 (m, 1H), 0.49-0.41 (m, 2H), 0.12 (dq, J=10.2, 5.0 Hz, 2H); MS (ESI(+)) m/e 405 (M+H)$^+$.

Example 751

N-(imidazo[1,2-a]pyridin-7-ylmethyl)-2-{1-[(2-methylpropyl)sulfonyl]pyrrolidin-3-yl}-1,3-thiazole-5-carboxamide

Example 751A tert-butyl 3-(5-formylthiazol-2-yl)pyrrolidine-1-carboxylate tert-Butyl 3-carbamothioylpyrrolidine-1-carboxylate (5 g, 21.71 mmol), 2-chloromalonaldehyde (3.70 g, 34.7 mmol) and magnesium carbonate (1.830 g, 21.71 mmol) were combined in dioxane (100 ml). The mixture was heated to 60° C. for 3 hours, stirred overnight at room temperature and then filtered through a pad of diatomaceous earth, rinsing with dichloromethane. The filtrate was concentrated in vacuo and then purified by normal phase chromatography to provide the title compound.

Example 751B 2-(1-(tert-butoxycarbonyl)pyrrolidin-3-yl)thiazole-5-carboxylic acid tert-Butyl 3-(5-formylthiazol-2-yl)pyrrolidine-1-carboxylate (3.65 g, 12.93 mmol) was suspended in water (35 ml) and t-butanol (60 ml). Sodium dihydrogenphosphate (2.094 g, 17.45 mmol) was added, followed by 2-methylbut-2-ene (5.34 ml, 50.4 mmol). After 5 minutes, sodium chlorite (2.92 g, 32.3 mmol) was added in portions over about 5 minutes (mildly exothermic). The reaction was stirred for 1 hour at room temperature, then additional 2-methyl-2-butene (2 mL) was added. After stirring for 2 hours at room temperature, the reaction was concentrated and water (100 mL) was added. The mixture was adjusted to pH 2 by addition of 1N hydrochloric acid, then extracted dichloromethane. The organic extracts were dried over sodium sulfate, filtered and concentrated to provide the title compound.

Example 751C tert-butyl 3-(5-(imidazo[1,2-a]pyridin-7-ylmethylcarbamoyl)thiazol-2-yl)pyrrolidine-1-carboxylate The title compound was prepared as described in Example 688D, substituting 2-(1-(tert-butoxycarbonyl)pyrrolidin-3-yl)thiazole-5-carboxylic acid for lithium 2-(1-phenylpiperidin-4-yl)thiazole-5-carboxylate.

Example 751D

N-(imidazo[1,2-a]pyridin-7-ylmethyl)-2-(pyrrolidin-3-yl)thiazole-5-carboxamide

The title compound was prepared as described in Example 28A, substituting tert-butyl 3-(5-(imidazo[1,2-a]pyridin-7-ylmethylcarbamoyl)thiazol-2-yl)pyrrolidine-1-carboxylate for tert-butyl 4-(4-(3-imidazo[1,2-a]pyridin-6-ylureido)phenyl)-5,6-dihydropyridine-1(2H)-carboxylate.

Example 751E

N-(imidazo[1,2-a]pyridin-7-ylmethyl)-2-{1-[(2-methylpropyl)sulfonyl]pyrrolidin-3-yl}-1,3-thiazole-5-carboxamide N-(imidazo[1,2-a]pyridin-7-ylmethyl)-2-(pyrrolidin-3-yl)thiazole-5-carboxamide, 2.7-trifluoroacetic acid (150 mg, 0.236 mmol) was dissolved in N,N-dimethylformamide (0.7 mL). Triethylamine (0.3 mL, 2.152 mmol) was added, followed by 2-methylpropane-1-sulfonyl chloride (74.0 mg, 0.472 mmol) and the reaction was stirred overnight at room temperature. The reaction mixture was diluted with water and extracted with ethyl acetate. The organic extracts were dried with sodium sulfate, filtered, and concentrated and purified by normal phase chromatography to give the title compound. $^1$H NMR (300 MHz, DMSO-d$_6$) ppm 9.24 (t, J=5.9 Hz, 1H), 8.49 (d, J=7.0 Hz, 1H), 8.35 (s, 1H), 7.89 (s, 1H), 7.52 (d, J=1.2 Hz, 1H), 7.41 (s, 1H), 6.83 (dd, J=7.0, 1.7 Hz, 1H), 4.48 (d, J=5.9 Hz, 2H), 3.91 (p, J=7.2 Hz, 1H), 3.74 (dd, J=9.8, 7.3

Hz, 1H), 3.51-3.35 (m, 3H), 2.99 (d, J=6.6 Hz, 2H), 2.46-2.33 (m, 1H), 2.24-2.03 (m, 2H), 1.03 (d, J=6.7 Hz, 6H); MS (ESI(+)) m/e 448 (M+H)+.

Example 752

N-(imidazo[1,2-a]pyridin-7-ylmethyl)-2-[1-(phenylsulfonyl)pyrrolidin-3-yl]-1,3-thiazole-5-carboxamide The title compound was prepared as described in Example 682, substituting N-(imidazo[1,2-a]pyridin-7-ylmethyl)-2-(pyrrolidin-3-yl)thiazole-5-carboxamide for N-(imidazo[1,2-a]pyridin-7-ylmethyl)-4-(piperidin-4-yl)benzamide. $^1$H NMR (300 MHz, DMSO-d$_6$) ppm 9.20 (t, J=5.9 Hz, 1H), 8.50 (dd, J=7.0, 0.9 Hz, 1H), 8.21 (s, 1H), 7.89 (t, J=0.9 Hz, 1H), 7.84-7.77 (m, 2H), 7.74-7.65 (m, 1H), 7.65-7.57 (m, 2H), 7.52 (d, J=1.2 Hz, 1H), 7.40 (bs, 1H), 6.83 (dd, J=7.0, 1.7 Hz, 1H), 4.47 (d, J=5.9 Hz, 2H), 3.80-3.59 (m, 2H), 3.44-3.31 (m, 3H), 2.32-2.17 (m, 1H), 2.06-1.93 (m, 1H); MS (ESI(+)) m/e 468 (M+H)+.

Example 753

N-(imidazo[1,2-a]pyridin-7-ylmethyl)-5-{1-[(2-methylpropyl)sulfonyl]-1,2,3,6-tetrahydropyridin-4-yl}furan-2-carboxamide The title compound was prepared as described in Example 682, substituting 2-methylpropane sulfonyl chloride for benzenesulfonyl chloride and N-(imidazo[1,2-a]pyridin-7-ylmethyl)-5-(1,2,3,6-tetrahydropyridin-4-yl)furan-2-carboxamide for N-(imidazo[1,2-a]pyridin-7-ylmethyl)-4-(piperidin-4-yl)benzamide. $^1$H NMR (300 MHz, DMSO-d$_6$) ppm 9.04-8.96 (m, 1H), 8.48 (dd, J=6.9, 0.9 Hz, 1H), 7.89-7.87 (m, 1H), 7.52 (d, J=1.2 Hz, 1H), 7.39 (s, 1H), 7.13 (d, J=3.5 Hz, 1H), 6.84 (dd, J=7.0, 1.7 Hz, 1H), 6.62-6.57 (m, 1H), 6.56-6.51 (m, 1H), 4.47 (d, J=6.1 Hz, 2H), 3.97-3.91 (m, 2H), 3.40 (t, J=5.7 Hz, 2H), 2.97 (d, J=6.5 Hz, 2H), 2.54-2.48 (m, 2H), 2.19-2.05 (m, 1H), 1.07-1.01 (m, 6H); MS (ESI(+)) m/e 443 (M+H)+.

Example 754

N-(imidazo[1,2-a]pyrazin-6-ylmethyl)-5-[1-(2-methylpropyl)-1H-pyrazol-4-yl]thiophene-2-carboxamide The title compound was prepared as described in Example 1A, substituting imidazo[1,2-a]pyrazin-6-ylmethanamine for 3-methylbutan-1-amine and 5-(1-isobutyl-1H-pyrazol-4-yl)thiophene-2-carboxylic acid for 4-nitrobenzoic acid. $^1$H NMR (300 MHz, DMSO-d$_6$) δ ppm 9.10-9.01 (m, 2H), 8.53 (d, J=1.3 Hz, 1H), 8.18-8.16 (m, 1H), 8.14 (d, J=0.5 Hz, 1H), 7.83-7.79 (m, 2H), 7.76 (d, J=3.9 Hz, 1H), 7.22 (d, J=3.9 Hz, 1H), 4.54 (d, J=5.7 Hz, 2H), 3.92 (d, J=7.2 Hz, 2H), 2.13 (dp, J=13.6, 6.7 Hz, 1H), 0.85 (d, J=6.7 Hz, 6H); MS (ESI(+)) m/e 381 (M+H)+.

Example 755 tert-butyl 4-[(4-{5-[(imidazo[1,2-a]pyridin-7-ylmethyl)carbamoyl]thiophen-2-yl}-1H-pyrazol-1-yl)methyl]-4-methylpiperidine-1-carboxylate The title compound was prepared as described in Example 51A, substituting tert-butyl 4-methyl-4-((4-(4,4,5,5-tetramethyl-1,3,2-dioxaborolan-2-yl)-1H-pyrazol-1-yl)methyl)piperidine-1-carboxylate for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline. $^1$H NMR (300 MHz, DMSO-d$_6$) δ ppm 9.02 (t, J=6.0 Hz, 1H), 8.49 (dd, J=7.0, 0.8 Hz, 1H), 8.13 (s, 1H), 7.91-7.86 (m, 1H), 7.81 (d, J=0.4 Hz, 1H), 7.74 (d, J=3.9 Hz, 1H), 7.52 (d, J=1.2 Hz, 1H), 7.40 (s, 1H), 7.23 (d, J=3.8 Hz, 1H), 6.84 (dd, J=7.0, 1.7 Hz, 1H), 4.48 (d, J=5.8 Hz, 2H), 4.02 (s, 2H), 3.65-3.50 (m, 2H), 3.19-3.02 (m, 2H), 1.47-1.34 (m, 11H), 1.30-1.15 (m, 2H), 0.93 (s, 3H); MS (ESI(+)) m/e 535 (M+H)+.

Example 789

N-(imidazo[1,2-a]pyridin-7-ylmethyl)-5-{1-[(4-methylpiperidin-4-yl)methyl]-1H-pyrazol-4-yl}thiophene-2-carboxamide The title compound was prepared as described in Example 28A, substituting tert-butyl 4-[(4-{5-[(imidazo[1,2-a]pyridin-7-ylmethyl)carbamoyl]thiophen-2-yl}-1H-pyrazol-1-yl)methyl]-4-methylpiperidine-1-carboxylate for tert-butyl 4-(4-(3-imidazo[1,2-a]pyridin-6-ylureido)phenyl)-5,6-dihydropyridine-1(2H)-carboxylate. $^1$H NMR (500 MHz, DMSO-d$_6$) δ ppm 14.80 (s, 1H), 9.65 (t, J=6.0 Hz, 1H), 9.20 (s, 1H), 8.99 (s, 1H), 8.91 (d, J=7.0 Hz, 1H), 8.36 (d, J=2.0 Hz, 1H), 8.21 (s, 1H), 8.17 (d, J=2.1 Hz, 1H), 7.96 (d, J=3.9 Hz, 1H), 7.86 (s, 1H), 7.84 (s, 1H), 7.51 (dd, J=7.0, 1.4 Hz, 1H), 7.28 (d, J=3.8 Hz, 1H), 4.64 (d, J=5.8 Hz, 2H), 4.10 (s, 2H), 3.19-3.12 (m, 2H), 3.04-2.96 (m, 2H), 1.74-1.59 (m, 2H), 1.57-1.46 (m, 2H), 0.96 (s, 3H); MS (ESI(+)) m/e 435 (M+H)+.

Example 790

5-{1-[(4-fluorotetrahydro-2H-pyran-4-yl)methyl]-1H-pyrazol-4-yl}-N-(imidazo[1,2-a]pyridin-7-ylmethyl)furan-2-carboxamide The title compound was prepared as described in Example 51A, substituting 1-((4-fluorotetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (500 MHz, DMSO-d$_6$) δ ppm 8.97 (t, J=6.1 Hz, 1H), 8.50 (dd, J=13.4, 3.5 Hz, 1H), 8.16 (s, 1H), 7.94 (s, 1H), 7.92 (s, 1H), 7.56 (d, J=1.1 Hz, 1H), 7.43 (s, 1H), 7.18 (d, J=3.5 Hz, 1H), 6.89 (dd, J=7.0, 1.5 Hz, 1H), 6.71 (d, J=6.4 Hz, 1H), 4.51 (d, J=6.1 Hz, 2H), 4.46 (d, J=21.9 Hz, 2H), 3.81-3.70 (m, 2H), 3.56-3.45 (m, 2H), 1.89-1.68 (m, 2H), 1.53 (t, J=11.7 Hz, 2H); MS (ESI(+)) m/e 424 (M+H)+.

Example 801

N-(imidazo[1,2-a]pyridin-7-ylmethyl)-5-[1-(phenylsulfonyl)-1,2,3,6-tetrahydropyridin-4-yl]furan-2-carboxamide The title compound was prepared as described in Example 682, substituting N-(imidazo[1,2-a]pyridin-7-ylmethyl)-5-(1,2,3,6-tetrahydropyridin-4-yl)furan-2-carboxamide for N-(imidazo[1,2-a]pyridin-7-ylmethyl)-4-(piperidin-4-yl)benzamide. $^1$H NMR (300 MHz, DMSO-d$_6$) ppm 8.97 (t, J=6.1 Hz, 1H), 8.47 (d, J=6.5 Hz, 1H), 7.88 (s, 1H), 7.85-7.78 (m, 2H), 7.75-7.68 (m, 1H), 7.69-7.60 (m, 2H), 7.51 (d, J=1.2 Hz, 1H), 7.37 (s, 1H), 7.10 (d, J=3.5 Hz, 1H), 6.82 (dd, J=7.0, 1.7 Hz, 1H), 6.54 (d, J=3.5 Hz, 1H), 6.46-6.43 (m, 1H), 4.46

(d, J=6.1 Hz, 2H), 3.79-3.74 (m, 2H), 3.28-3.21 (m, 2H), 2.45 (s, 2H); MS (ESI(+)) m/e 463 (M+H)+.

Example 802

2-[1-(2-fluorobenzoyl)piperidin-4-yl]-N-(imidazo[1,2-a]pyridin-7-ylmethyl)-1,3-thiazole-5-carboxamide The title compound was prepared as described in Example 52A, substituting 2-fluorobenzoyl chloride for 2-cyclopentylacetyl chloride and N-(imidazo[1,2-a]pyridin-7-ylmethyl)-2-(piperidin-4-yl)thiazole-5-carboxamide for methyl 4-aminobenzoate. $^1$H NMR (400 MHz, DMSO-$d_6$) ppm 9.23 (t, J=5.9 Hz, 1H), 8.49 (d, J=6.9 Hz, 1H), 8.34 (s, 1H), 7.89 (s, 1H), 7.56-7.36 (m, 4H), 7.35-7.25 (m, 2H), 6.84 (dd, J=7.0, 1.7 Hz, 1H), 4.61-4.52 (m, 1H), 4.48 (d, J=5.9 Hz, 2H), 3.51-3.39 (m, 1H), 3.42-3.34 (m, 1H), 3.23 (t, J=12.1 Hz, 1H), 3.01 (td, J=12.7, 2.9 Hz, 1H), 2.21-2.13 (m, 1H), 2.08-1.97 (m, 1H), 1.77-1.54 (m, 2H); MS (ESI(+)) m/e 464 (M–H)+.

Example 803

5-[1-(2-fluorobenzoyl)-1,2,3,6-tetrahydropyridin-4-yl]-N-(imidazo[1,2-a]pyridin-7-ylmethyl)furan-2-carboxamide The title compound was prepared as described in Example 1A, substituting N-(imidazo[1,2-a]pyridin-7-ylmethyl)-5-(1,2,3,6-tetrahydropyridin-4-yl)furan-2-carboxamide for 3-methylbutan-1-amine and 2-fluorobenzoic acid for 4-nitrobenzoic acid. $^1$H NMR (400 MHz, DMSO-$d_6$) ppm 8.66-8.58 (m, 1H), 8.45-8.39 (m, 1H), 7.81 (s, 1H), 7.54-7.44 (m, 2H), 7.43-7.36 (m, 2H), 7.31-7.21 (m, 2H), 7.08 (d, J=3.5 Hz, 1H), 6.82 (dd, J=6.9, 1.7 Hz, 1H), 6.53 (d, J=3.4 Hz, 1H), 6.48 (bs, 1H), 4.47 (d, J=6.1 Hz, 2H), 4.41-3.34 (m, 4H), 2.52-2.37 (m, 2H); MS (ESI(+)) m/e 445 (M+H)+.

Example 804

2-[1-(2-fluorobenzoyl)pyrrolidin-3-yl]-N-(imidazo[1,2-a]pyridin-7-ylmethyl)-1,3-thiazole-5-carboxamide The title compound was prepared as described in Example 1A, substituting N-(imidazo[1,2-a]pyridin-7-ylmethyl)-2-(pyrrolidin-3-yl)thiazole-5-carboxamide for 3-methylbutan-1-amine and 2-fluorobenzoic acid for 4-nitrobenzoic acid. $^1$H NMR (400 MHz, DMSO-$d_6$) ppm 8.95-8.88 (m, 1H), 8.43 (d, J=7.0 Hz, 1H), 8.32-8.17 (m, 1H), 7.82 (s, 1H), 7.53-7.35 (m, 4H), 7.30-7.19 (m, 2H), 6.85-6.78 (m, 1H), 4.50-4.44 (m, 2H), 4.05-3.23 (m, 5H), 2.45-2.11 (m, 2H); MS (ESI(+)) m/e 450 (M+H)+.

Example 805

N-(imidazo[1,2-a]pyridin-7-ylmethyl)-2-[1-(2-methylpropanoyl)pyrrolidin-3-yl]-1,3-thiazole-5-carboxamide The title compound was prepared as described in Example 1A, substituting N-(imidazo[1,2-a]pyridin-7-ylmethyl)-2-(pyrrolidin-3-yl)thiazole-5-carboxamide for 3-methylbutan-1-amine and isobutyric acid for 4-nitrobenzoic acid. $^1$H NMR (300 MHz, DMSO-$d_6$) ppm 9.28-9.19 (m, 1H), 8.49 (dd, J=6.9, 0.9 Hz, 1H), 8.34 (d, J=2.4 Hz, 1H), 7.91-7.87 (m, 1H), 7.52 (d, J=1.2 Hz, 1H), 7.41 (s, 1H), 6.83 (dd, J=7.0, 1.7 Hz, 1H), 4.48 (d, J=5.9 Hz, 2H), 4.11-3.33 (m, 5H), 3.17 (d, J=5.2 Hz, 1H), 2.74-2.59 (m, 1H), 2.46-2.00 (m, 6H), 1.03-0.97 (m, 1H); MS (ESI(+)) m/e 398 (M+H)+.

Example 806

N-(imidazo[1,2-a]pyridin-7-ylmethyl)-2-[1-(3-methylbutanoyl)pyrrolidin-3-yl]-1,3-thiazole-5-carboxamide The title compound was prepared as described in Example 1A, substituting N-(imidazo[1,2-a]pyridin-7-ylmethyl)-2-(pyrrolidin-3-yl)thiazole-5-carboxamide for 3-methylbutan-1-amine and 3-methylbutanoic acid for 4-nitrobenzoic acid. $^1$H NMR (300 MHz, DMSO-$d_6$) ppm 9.28-9.19 (m, 1H), 8.49 (d, J=7.0 Hz, 1H), 8.34 (d, J=2.4 Hz, 1H), 7.91-7.87 (m, 1H), 7.52 (d, J=1.2 Hz, 1H), 7.43-7.38 (m, 1H), 6.83 (dd, J=7.0, 1.7 Hz, 1H), 4.48 (d, J=5.9 Hz, 2H), 3.97-3.72 (m, 2H), 3.70-3.46 (m, 2H), 3.17 (d, J=5.1 Hz, 1H), 2.45-1.91 (m, 5H), 0.94-0.86 (m, 6H); MS (ESI(+)) m/e 412 (M+H)+.

Example 807

2-(1-benzoylpyrrolidin-3-yl)-N-(imidazo[1,2-a]pyridin-7-ylmethyl)-1,3-thiazole-5-carboxamide The title compound was prepared as described in Example 1A, substituting N-(imidazo[1,2-a]pyridin-7-ylmethyl)-2-(pyrrolidin-3-yl)thiazole-5-carboxamide for 3-methylbutan-1-amine and benzoic acid for 4-nitrobenzoic acid. $^1$H NMR (400 MHz, DMSO-$d_6$) ppm 8.94-8.87 (m, 1H), 8.43 (d, J=6.9 Hz, 1H), 8.27 (s, 1H), 8.23-8.16 (m, 1H), 7.82 (s, 1H), 7.52-7.38 (m, 6H), 6.81 (dd, J=6.9, 1.7 Hz, 1H), 4.47 (d, J=5.8 Hz, 2H), 3.94-3.84 (m, 2H), 3.76-3.53 (m, 3H), 2.44-2.34 (m, 1H), 2.24-2.14 (m, 1H); MS (ESI(+)) m/e 432 (M+H)+.

Example 808 tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate

Example 808A tert-butyl 4-(2-(4-(4,4,5,5-tetramethyl-1,3,2-dioxaborolan-2-yl)-1H-pyrazol-1-yl)ethyl)piperazine-1-carboxylate 4-(4,4,5,5-Tetramethyl-1,3,2-dioxaborolan-2-yl)-1H-pyrazole (0.500 g, 2.58 mmol), tert-butyl 4-(2-hydroxyethyl)piperazine-1-carboxylate (0.593 g, 2.58 mmol) and 2-(tributylphosphoranylidene)acetonitrile (0.746 g, 3.09 mmol) were stirred together in toluene (10 ml) at 85° C. overnight. The reaction was concentrated and purified by normal phase chromatography to give the title compound.

Example 808B tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate The title compound was prepared as described in Example 51A, substituting tert-butyl 4-(2-(4-(4,4,5,5-tetramethyl-1,3,2-dioxaborolan-2-yl)-1H-pyrazol-1-yl)ethyl)piperazine-1-carboxylate for 1-isobutyl-4-(4,4,5,5-tetramethyl-1,3,2-dioxaborolan-2-yl)-1H-pyrazole and 5-bromo-N-(imidazo[1, 2-a]pyridin-7-ylmethyl)thiophene-2-carboxamide for 4-bromoaniline. $^1$H NMR (300 MHz, DMSO-d$_6$) δ ppm 9.02 (t, J=6.0 Hz, 1H), 8.53-8.45 (m, 1H), 8.16 (s, 1H), 7.89 (d, J=0.7 Hz, 1H), 7.79 (d, J=0.5 Hz, 1H), 7.74 (d, J=3.8 Hz, 1H), 7.52 (d, J=1.2 Hz, 1H), 7.39 (s, 1H), 7.22 (d, J=3.9 Hz, 1H), 6.84 (dd, J=7.0, 1.6 Hz, 1H), 4.48 (d, J=5.9 Hz, 2H), 4.23 (t, J=6.5 Hz, 2H), 3.29-3.25 (m, 2H), 2.74 (t, J=6.6 Hz, 2H), 2.42-2.33 (m, 4H), 1.38 (s, 9H); MS (ESI(+)) m/e 536 (M+H)$^+$.

Example 809

N-(imidazo[1,2-a]pyridin-7-ylmethyl)-5-{1-[2-(piperazin-1-yl)ethyl]-1H-pyrazol-4-yl}thiophene-2-carboxamide The title compound was prepared as described in Example 28A, substituting tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate for tert-butyl 4-(4-(3-imidazo[1,2-a]pyridin-6-ylureido)phenyl)-5,6-dihydropyridine-1(2H)-carboxylate. $^1$H NMR (300 MHz, DMSO-d$_6$) δ ppm 9.34 (t, J=5.9 Hz, 1H), 8.94 (s, 2H), 8.87 (d, J=7.0 Hz, 1H), 8.33 (dd, J=2.1, 0.7 Hz, 1H), 8.22 (d, J=0.8 Hz, 1H), 8.15 (d, J=2.1 Hz, 1H), 7.87 (d, J=0.8 Hz, 1H), 7.82 (d, J=3.9 Hz, 1H), 7.79 (s, 1H), 7.47 (dd, J=7.0, 1.5 Hz, 1H), 7.27 (d, J=3.8 Hz, 1H), 4.65 (d, J=5.9 Hz, 2H), 4.43-4.34 (m, 2H), 3.22-3.16 (m, 6H), 2.98-2.89 (m, 4H); MS (ESI(+)) m/e 436 (M+H)$^+$.

Example 810

5-{1-[(4-fluorotetrahydro-2H-pyran-4-yl)methyl]-1H-pyrazol-4-yl}-N-([1,2,4]triazolo[1,5-a]pyridin-6-ylmethyl)furan-2-carboxamide Example 810A N-([1,2,4]triazolo[1,5-a]pyridin-6-ylmethyl)-5-bromofuran-2-carboxamide The title compound was prepared as described in Example 1A, substituting [1,2,4]triazolo[1,5-a]pyridin-6-ylmethanamine for 3-methylbutan-1-amine and 5-bromofuran-2-carboxylic acid for 4-nitrobenzoic acid.

Example 810B

5-{1-[(4-fluorotetrahydro-2H-pyran-4-yl)methyl]-1H-pyrazol-4-yl}-N-([1,2,4]triazolo[1,5-a]pyridin-6-ylmethyl)furan-2-carboxamide The title compound was prepared as described in Example 51A, substituting 1-((4-fluorotetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and N-([1,2,4]triazolo[1,5-a]pyridin-6-ylmethyl)-5-bromofuran-2-carboxamide for 4-bromoaniline. $^1$H NMR (300 MHz, DMSO-d$_6$) δ ppm 8.93 (t, J=6.0 Hz, 1H), 8.90-8.85 (m, 1H), 8.48 (s, 1H), 8.13 (s, 1H), 7.92 (d, J=0.5 Hz, 1H), 7.84 (dd, J=9.2, 0.7 Hz, 1H), 7.66 (dd, J=9.2, 1.7 Hz, 1H), 7.16 (d, J=3.6 Hz, 1H), 6.70 (d, J=3.5 Hz, 1H), 4.56 (d, J=6.0 Hz, 2H), 4.45 (d, J=21.8 Hz, 2H), 3.82-3.66 (m, 2H), 3.51 (td, J=11.2, 2.0 Hz, 2H), 1.92-1.63 (m, 2H), 1.60-1.42 (m, 2H); MS (ESI(+)) m/e 425 (M+H)$^+$.

Example 811

N-(imidazo[1,2-a]pyrazin-6-ylmethyl)-4-[1-(2-methylpropanoyl)piperidin-4-yl]benzamide Example 811A N-(imidazo[1,2-a]pyrazin-6-ylmethyl)-4-(piperidin-4-yl)benzamide The title compound was prepared as described in Example 28A, substituting tert-butyl 4-{4-[(imidazo[1,2-a]pyrazin-6-ylmethyl)carbamoyl]phenyl}piperidine-1-carboxylate for tert-butyl 4-(4-(3-imidazo[1,2-a]pyridin-6-ylureido)phenyl)-5,6-dihydropyridine-1(2H)-carboxylate.

Example 811B

N-(imidazo[1,2-a]pyrazin-6-ylmethyl)-4-[1-(2-methylpropanoyl)piperidin-4-yl]benzamide The title compound was prepared as described in Example 1A, substituting N-(imidazo[1,2-a]pyrazin-6-ylmethyl)-4-(piperidin-4-yl)benzamide for 3-methylbutan-1-amine and isobutyric acid for 4-nitrobenzoic acid. $^1$H NMR (500 MHz, methanol-d$_4$) δ ppm 9.24 (s, 1H), 8.72-8.68 (m, 1H), 8.27-8.23 (m, 1H), 8.11-8.07 (m, 1H), 7.88-7.82 (m, 2H), 7.41-7.35 (m, 2H), 4.76 (s, 2H), 4.75-4.66 (m, 1H), 4.24-4.15 (m, 1H), 3.29-3.18 (m, 1H), 3.06-2.85 (m, 2H), 2.78-2.64 (m, 1H), 2.02-1.84 (m, 2H), 1.74-1.52 (m, 2H), 1.17-1.07 (m, 6H); MS (ESI(+)) m/e 406 (M+H)$^+$.

Example 812

4-[1-(4-fluorobenzoyl)piperidin-4-yl]-N-(imidazo[1,2-a]pyrazin-6-ylmethyl)benzamide The title compound was prepared as described in Example 1A, substituting N-(imidazo[1,2-a]pyrazin-6-ylmethyl)-4-(piperidin-4-yl)benzamide for 3-methylbutan-1-amine and 4-fluorobenzoic acid for 4-nitrobenzoic acid. $^1$H NMR (500 MHz, methanol-d$_4$) δ ppm 9.29-9.25 (m, 1H), 8.72 (d, J=1.4 Hz, 1H), 8.27 (d, J=1.7 Hz, 1H), 8.12 (d, J=1.7 Hz, 1H), 7.89-7.83 (m, 2H), 7.55-7.45 (m, 2H), 7.44-7.38 (m, 2H), 7.25-7.16 (m, 2H), 4.87-4.84 (m, 1H), 4.77 (s, 2H), 3.90-3.79 (m, 1H), 3.33-3.19 (m, 1H), 3.03-2.89 (m, 2H), 2.07-1.61 (m, 4H); MS (ESI(+)) m/e 458 (M+H)$^+$.

Example 813

4-[1-(2,5-difluorobenzoyl)piperidin-4-yl]-N-(imidazo[1,2-a]pyrazin-6-ylmethyl)benzamide The title compound was prepared as described in Example 1A, substituting N-(imidazo[1,2-a]pyrazin-6-ylmethyl)-4-(piperidin-4-yl)benzamide for 3-methylbutan-1-amine and 2,5-difluorobenzoic acid for 4-nitrobenzoic acid. $^1$H NMR (500 MHz, methanol-d$_4$) δ ppm 9.23 (s, 1H), 8.69 (s, 1H), 8.24 (d, J=1.6 Hz, 1H), 8.07 (d, J=1.6 Hz, 1H), 7.89-7.83 (m, 2H), 7.43-7.36 (m, 2H), 7.31-7.15 (m, 3H), 4.84-4.73 (m, 3H), 3.71-3.62 (m, 1H), 3.36-3.24 (m, 1H), 3.04-2.90 (m, 2H), 2.04-1.95 (m, 1H), 1.92-1.61 (m, 3H); MS (ESI(+)) m/e 476 (M+H)$^+$.

Example 814

N-(imidazo[1,2-a]pyrazin-6-ylmethyl)-4-{1-[(1-methylcyclopropyl)carbonyl]piperidin-4-yl}benzamide The title compound was prepared as described in Example 1A, substituting N-(imidazo[1,2-a]pyrazin-6-ylmethyl)-4-(piperidin-4-yl)benzamide for 3-methylbutan-1-amine and 1-methylcyclopropanecarboxylic acid for 4-nitrobenzoic acid. $^1$H NMR (500 MHz, methanol-$d_4$) δ ppm 9.28 (s, 1H), 8.73 (s, 1H), 8.28 (d, J=1.7 Hz, 1H), 8.13 (d, J=1.7 Hz, 1H), 7.89-7.83 (m, 2H), 7.42-7.36 (m, 2H), 4.78 (s, 2H), 4.62-4.53 (m, 2H), 3.20-2.70 (m, 3H), 1.97-1.89 (m, 2H), 1.72-1.57 (m, 2H), 1.33 (s, 3H), 0.96-0.89 (m, 2H), 0.71-0.58 (m, 2H); MS (ESI(+)) m/e 418 (M+H)$^+$.

Example 815

N-(imidazo[1,2-a]pyrazin-6-ylmethyl)-4-[1-(3,3,3-trifluoropropanoyl)piperidin-4-yl]benzamide The title compound was prepared as described in Example 1A, substituting N-(imidazo[1,2-a]pyrazin-6-ylmethyl)-4-(piperidin-4-yl)benzamide for 3-methylbutan-1-amine and 3,3,3-trifluoropropanoic acid for 4-nitrobenzoic acid. $^1$H NMR (500 MHz, methanol-$d_4$) δ ppm 9.22 (d, J=1.4 Hz, 1H), 8.68 (d, J=1.4 Hz, 1H), 8.23 (d, J=1.9 Hz, 1H), 8.06 (d, J=1.6 Hz, 1H), 7.89-7.82 (m, 2H), 7.42-7.34 (m, 2H), 4.81-4.65 (m, 3H), 4.11-3.99 (m, 1H), 3.62-3.44 (m, 2H), 3.37-3.21 (m, 1H), 3.01-2.86 (m, 1H), 2.85-2.71 (m, 1H), 1.99-1.85 (m, 2H), 1.85-1.54 (m, 2H); MS (ESI(+)) m/e 446 (M+H)$^+$.

Example 816

N-(imidazo[1,2-a]pyrazin-6-ylmethyl)-4-[1-(3-methylbutanoyl)piperidin-4-yl]benzamide The title compound was prepared as described in Example 1A, substituting N-(imidazo[1,2-a]pyrazin-6-ylmethyl)-4-(piperidin-4-yl)benzamide for 3-methylbutan-1-amine and 3-methylbutanoic acid for 4-nitrobenzoic acid. $^1$H NMR (500 MHz, methanol-$d_4$) δ ppm 99.24 (d, J=1.4 Hz, 1H), 8.70 (d, J=1.4 Hz, 1H), 8.25 (d, J=1.7 Hz, 1H), 8.09 (d, J=1.7 Hz, 1H), 7.89-7.82 (m, 2H), 7.41-7.34 (m, 2H), 4.79-4.66 (m, 3H), 4.19-4.07 (m, 1H), 3.30-3.16 (m, 1H), 3.00-2.85 (m, 1H), 2.80-2.63 (m, 1H), 2.36-2.29 (m, 2H), 2.17-2.00 (m, 1H), 2.01-1.84 (m, 2H), 1.75-1.50 (m, 2H), 0.99 (d, J=6.6 Hz, 6H); MS (ESI(+)) m/e 420 (M+H)$^+$.

Example 817

N-(imidazo[1,2-a]pyrazin-6-ylmethyl)-4-[1-(propan-2-ylsulfonyl)piperidin-4-yl]benzamide The title compound was prepared as described in Example 682, substituting propane-2-sulfonyl chloride for benzenesulfonyl chloride and N-(imidazo[1,2-a]pyrazin-6-ylmethyl)-4-(piperidin-4-yl)benzamide for N-(imidazo[1,2-a]pyridin-7-ylmethyl)-4-(piperidin-4-yl)benzamide. $^1$H NMR (500 MHz, methanol-$d_4$) δ ppm 9.21 (d, J=1.4 Hz, 1H), 8.67 (d, J=1.4 Hz, 1H), 8.22 (d, J=1.6 Hz, 1H), 8.05 (d, J=1.6 Hz, 1H), 7.89-7.82 (m, 2H), 7.40-7.35 (m, 2H), 4.85-4.79 (m, 1H), 4.75 (s, 2H), 3.96-3.85 (m, 2H), 3.12-3.00 (m, 1H), 2.88-2.74 (m, 1H), 1.95-1.85 (m, 2H), 1.84-1.65 (m, 2H), 1.33 (d, J=6.8 Hz, 6H); MS (ESI(+)) m/e 442 (M+H)$^+$.

Example 818

N-(imidazo[1,2-a]pyridin-7-ylmethyl)-5-[1-(2-methylpropyl)-1H-pyrazol-5-yl]furan-2-carboxamide The title compound was prepared as described in Example 51A, substituting 1-isobutyl-5-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (300 MHz, DMSO-$d_6$) δ ppm 9.03 (t, J=6.1 Hz, 1H), 8.49 (dd, J=7.0, 0.7 Hz, 1H), 7.89 (s, 1H), 7.54-7.51 (m, 2H), 7.41 (s, 1H), 7.30 (d, J=3.6 Hz, 1H), 6.96 (d, J=3.6 Hz, 1H), 6.85 (dd, J=7.0, 1.6 Hz, 1H), 6.76 (d, J=1.9 Hz, 1H), 4.50 (d, J=6.0 Hz, 2H), 4.22 (d, J=7.3 Hz, 2H), 2.04 (dp, J=13.8, 6.8 Hz, 1H), 0.81 (d, J=6.7 Hz, 6H); MS (ESI(+)) m/e 364 (M+H)$^+$.

Example 819

N-(imidazo[1,2-a]pyrazin-6-ylmethyl)-5-[1-(2-methylpropyl)-1H-pyrazol-4-yl]furan-2-carboxamide

Example 819A 5-(1-isobutyl-1H-pyrazol-4-yl)furan-2-carboxylic acid

The title compound was prepared as described in Example 51A, substituting 5-bromofuran-2-carboxylic acid for 4-bromoaniline.

Example 819B

N-(imidazo[1,2-a]pyrazin-6-ylmethyl)-5-[1-(2-methylpropyl)-1H-pyrazol-4-yl]furan-2-carboxamide The title compound was prepared as described in Example 1A, substituting imidazo[1,2-a]pyrazin-6-ylmethanamine for 3-methylbutan-1-amine and 5-(1-isobutyl-1H-pyrazol-4-yl)furan-2-carboxylic acid for 4-nitrobenzoic acid. $^1$H NMR (300 MHz, DMSO-$d_6$) ppm 9.05-9.02 (m, 1H), 8.90 (t, J=6.0 Hz, 1H), 8.52 (d, J=1.4 Hz, 1H), 8.19-8.14 (m, 2H), 7.90-7.88 (m, 1H), 7.80 (d, J=1.0 Hz, 1H), 7.17 (d, J=3.5 Hz, 1H), 6.65 (d, J=3.5 Hz, 1H), 4.56 (d, J=5.9 Hz, 2H), 3.96 (d, J=7.1 Hz, 2H), 2.20-2.07 (m, 1H), 0.85 (d, J=6.7 Hz, 6H); MS (ESI(+)) m/e 365 (M+H)$^+$.

Example 820

5-[1-(2-methylpropyl)-1H-pyrazol-4-yl]-N-([1,2,4]triazolo[1,5-a]pyridin-6-ylmethyl)furan-2-carboxamide The title compound was prepared as described in Example 1A, substituting [1,2,4]triazolo[1,5-a]pyridin-6-ylmethanamine for 3-methylbutan-1-amine and 5-(1-isobutyl-1H-pyrazol-4-yl)furan-2-carboxylic acid for 4-nitrobenzoic acid. $^1$H NMR (300 MHz, DMSO-$d_6$) ppm 8.94-8.85 (m, 2H), 8.48 (s, 1H), 8.14 (s, 1H), 7.87 (s, 1H), 7.84 (d, J=9.1 Hz, 1H), 7.66 (dd, J=9.1, 1.7 Hz, 1H), 7.16 (d, J=3.5 Hz, 1H), 6.64 (d, J=3.5

Hz, 1H), 4.56 (d, J=6.0 Hz, 2H), 3.95 (d, J=7.1 Hz, 2H), 2.21-1.97 (m, 1H), 0.90-0.76 (m, 6H); MS (ESI(+)) m/e 365 (M+H)+.

Example 821

N-(imidazo[1,2-a]pyridin-7-ylmethyl)-5-[1-(3-methylbutyl)-1H-pyrazol-5-yl]furan-2-carboxamide The title compound was prepared as described in Example 51A, substituting 1-isopentyl-1H-pyrazol-5-ylboronic acid for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (300 MHz, DMSO-d$_6$) δ ppm 9.03 (t, J=6.1 Hz, 1H), 8.49 (dd, J=7.0, 0.8 Hz, 1H), 7.89 (s, 1H), 7.58-7.43 (m, 2H), 7.43-7.37 (m, 1H), 7.30 (d, J=3.5 Hz, 1H), 6.95 (d, J=3.6 Hz, 1H), 6.85 (dd, J=7.0, 1.7 Hz, 1H), 6.73 (d, J=1.9 Hz, 1H), 4.50 (d, J=6.0 Hz, 2H), 4.44-4.36 (m, 2H), 1.68-1.38 (m, 3H), 0.84 (d, J=6.4 Hz, 6H); MS (ESI(+)) m/e 378 (M+H)+.

Example 822

5-{1-[(4-methyltetrahydro-2H-pyran-4-yl)methyl]-1H-pyrazol-4-yl}-N-([1,2,4]triazolo[1,5-a]pyridin-6-ylmethyl)furan-2-carboxamide The title compound was prepared as described in Example 51A, substituting 1-((4-methyltetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and N-([1,2,4]triazolo[1,5-a]pyridin-6-ylmethyl)-5-bromofuran-2-carboxamide for 4-bromoaniline. $^1$H NMR (300 MHz, DMSO-d$_6$) δ ppm 8.95-8.83 (m, 2H), 8.48 (s, 1H), 8.15-8.09 (m, 1H), 7.88 (d, J=0.4 Hz, 1H), 7.83 (dd, J=9.2, 0.7 Hz, 1H), 7.66 (dd, J=9.2, 1.7 Hz, 1H), 7.16 (d, J=3.5 Hz, 1H), 6.66 (d, J=3.5 Hz, 1H), 4.56 (d, J=6.0 Hz, 2H), 4.06 (s, 2H), 3.68 (dt, J=11.4, 4.5 Hz, 2H), 3.51 (ddd, J=11.9, 9.3, 2.9 Hz, 2H), 1.50 (ddd, J=13.4, 9.2, 4.2 Hz, 2H), 1.31-1.17 (m, 2H), 0.96 (s, 3H); MS (ESI(+)) m/e 421 (M+H)+.

Example 823

N-(imidazo[1,2-a]pyridin-7-ylmethyl)-5-{[(2R)-2-(methoxymethyl)pyrrolidin-1-yl]carbonyl}thiophene-2-carboxamide

Example 823A

Methyl 5-(imidazo[1,2-a]pyridin-7-ylmethylcarbamoyl)thiophene-2-carboxylate

The title compound was prepared as described in Example 688D, substituting 5-(methoxycarbonyl)thiophene-2-carboxylic acid for lithium 2-(1-phenylpiperidin-4-yl)thiazole-5-carboxylate.

Example 823B

Lithium 5-(imidazo[1,2-a]pyridin-7-ylmethylcarbamoyl)thiophene-2-carboxylate

The title compound was prepared as described in Example 688C, substituting methyl 5-(imidazo[1,2-a]pyridin-7-ylmethylcarbamoyl)thiophene-2-carboxylate for ethyl 2-(1-phenylpiperidin-4-yl)thiazole-5-carboxylate.

Example 823C

N-(imidazo[1,2-a]pyridin-7-ylmethyl)-5-{[(2R)-2-(methoxymethyl)pyrrolidin-1-yl]carbonyl}thiophene-2-carboxamide The title compound was prepared as described in Example 1A, substituting), (R)-2-(methoxymethyl)pyrrolidine for 3-methylbutan-1-amine and lithium 5-(imidazo[1,2-a]pyridin-7-ylmethylcarbamoyl)thiophene-2-carboxylate for 4-nitrobenzoic acid. $^1$H NMR (300 MHz, DMSO-d$_6$) ppm 9.23 (t, J=6.0 Hz, 1H), 8.49 (dd, J=6.9, 0.9 Hz, 1H), 7.90-7.88 (m, 1H), 7.79 (d, J=4.0 Hz, 1H), 7.60 (d, J=4.0 Hz, 1H), 7.52 (d, J=1.2 Hz, 1H), 7.42-7.39 (m, 1H), 6.85 (dd, J=7.0, 1.7 Hz, 1H), 4.49 (d, J=5.9 Hz, 2H), 4.35-4.23 (m, 1H), 3.78-3.65 (m, 2H), 3.26 (s, 3H), 2.02-1.81 (m, 4H); MS (ESI(+)) m/e 399 (M+H)+.

Example 824

N-(imidazo[1,2-a]pyridin-7-ylmethyl)-5-{[2-(2-methylpropyl)pyrrolidin-1-yl]carbonyl}thiophene-2-carboxamide The title compound was prepared as described in Example 1A, substituting), 2-isobutylpyrrolidine for 3-methylbutan-1-amine and lithium 5-(imidazo[1,2-a]pyridin-7-ylmethylcarbamoyl)thiophene-2-carboxylate for 4-nitrobenzoic acid. $^1$H NMR (300 MHz, DMSO-d$_6$) ppm 9.23 (t, J=6.0 Hz, 1H), 8.49 (dd, J=6.9, 0.9 Hz, 1H), 7.90-7.88 (m, 1H), 7.79 (d, J=4.0 Hz, 1H), 7.60 (d, J=4.0 Hz, 1H), 7.52 (d, J=1.2 Hz, 1H), 7.42-7.39 (m, 1H), 6.85 (dd, J=7.0, 1.7 Hz, 1H), 4.49 (d, J=5.9 Hz, 2H), 4.35-4.23 (m, 1H), 3.78-3.65 (m, 2H), 3.26 (s, 3H), 2.02-1.81 (m, 4H); MS (ESI(+)) m/e 411 (M+H)+.

Example 825

5-[1-(2,2-dimethylpropyl)-1H-pyrazol-4-yl]-N-(imidazo[1,2-a]pyridin-7-ylmethyl)furan-2-carboxamide The title compound was prepared as described in Example 51A, substituting 1-neopentyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline. $^1$H NMR (300 MHz, DMSO-d$_6$) δ ppm 8.89 (t, J=6.1 Hz, 1H), 8.49 (dd, J=7.0, 0.9 Hz, 1H), 8.11 (d, J=0.5 Hz, 1H), 7.95-7.83 (m, 2H), 7.52 (d, J=1.2 Hz, 1H), 7.46-7.34 (m, 1H), 7.17 (d, J=3.4 Hz, 1H), 6.85 (dd, J=7.0, 1.7 Hz, 1H), 6.66 (d, J=3.5 Hz, 1H), 4.49 (d, J=6.0 Hz, 2H), 3.95 (s, 2H), 0.92 (s, 9H); MS (ESI(+)) m/e 378 (M+H)+.

Example 826

4-[1-(2-fluorobenzoyl)piperidin-4-yl]-N-(imidazo[1,2-a]pyrazin-6-ylmethyl)benzamide The title compound was prepared as described in Example 1A, substituting N-(imidazo[1,2-a]pyrazin-6-ylmethyl)-4-(piperidin-4-yl)benzamide for 3-methylbutan-1-amine and 2-fluorobenzoic acid for 4-nitrobenzoic acid. $^1$H NMR (300 MHz, DMSO-d$_6$) δ ppm 9.08-9.00 (m, 2H), 8.49 (d, J=1.4 Hz, 1H), 8.16-8.13 (m, 1H), 7.92-7.85 (m, 2H), 7.79 (d, J=1.0 Hz, 1H), 7.57-7.23 (m, 6H), 4.74-4.61 (m, 1H), 4.57 (d, J=5.7 Hz, 2H), 3.54-3.43 (m, 1H), 3.24-3.14 (m, 1H), 3.00-2.79 (m, 2H), 1.97-1.84 (m, 1H), 1.82-1.47 (m, 3H); MS (ESI(+)) m/e 458 (M+H)⁺.

Example 827

5-[1-(2-fluorobenzoyl)piperidin-4-yl]-N-(imidazo[1,2-a]pyrazin-6-ylmethyl)thiophene-2-carboxamide

Example 827A tert-butyl 4-(5-(ethoxycarbonyl)thiophen-2-yl)-5,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and ethyl 5-bromothiophene-2-carboxylate for 4-bromoaniline.

Example 827B tert-butyl 4-(5-(ethoxycarbonyl)thiophen-2-yl)piperidine-1-carboxylate The title compound was prepared as described in Example 1B, substituting tert-butyl 4-(5-(ethoxycarbonyl)thiophen-2-yl)-5,6-dihydropyridine-1(2H)-carboxylate for N-isopentyl-4-nitrobenzamide.

Example 827C 5-(1-(tert-butoxycarbonyl)piperidin-4-yl)thiophene-2-carboxylic acid In a 250 mL round bottom flask was mixed tert-butyl 4-(5-(ethoxycarbonyl)thiophen-2-yl)piperidine-1-carboxylate (5.00 g, 14.73 mmol) in tetrahydrofuran (50 ml). Aqueous 4N NaOH (38.41 ml, 73.6 mmol) solution was added along with some methanol (10 ml) to get a single phase solution. The mixture was stirred overnight at room temperature. The solvents were removed to give a white slurry that was diluted with water and adjusted to pH of 5 with 1N aqueous hydrochloric acid. Filtration provided the title compound.

Example 827D tert-butyl 4-(5-((imidazo[1,2-a]pyrazin-6-ylmethyl)carbamoyl)thiophen-2-yl)piperidine-1-carboxylate The title compound was prepared as described in Example 1A, substituting imidazo[1,2-a]pyrazin-6-ylmethanamine for 3-methylbutan-1-amine and 5-(1-(tert-butoxycarbonyl)piperidin-4-yl)thiophene-2-carboxylic acid for 4-nitrobenzoic acid.

Example 827E

N-(imidazo[1,2-a]pyrazin-6-ylmethyl)-5-(piperidin-4-yl)thiophene-2-carboxamide

The title compound was prepared as described in Example 28A, substituting tert-butyl 4-(5-((imidazo[1,2-a]pyrazin-6-ylmethyl)carbamoyl)thiophen-2-yl)piperidine-1-carboxylate for tert-butyl 4-(4-(3-imidazo[1,2-a]pyridin-6-ylureido)phenyl)-5,6-dihydropyridine-1(2H)-carboxylate.

Example 827F

5-[1-(2-fluorobenzoyl)piperidin-4-yl]-N-(imidazo[1,2-a]pyrazin-6-ylmethyl)thiophene-2-carboxamide The title compound was prepared as described in Example 52A, substituting 2-fluorobenzoyl chloride for 2-cyclopentylacetyl chloride and N-(imidazo[1,2-a]pyrazin-6-ylmethyl)-5-(piperidin-4-yl)thiophene-2-carboxamide for methyl 4-aminobenzoate. ¹H NMR (400 MHz, DMSO-d₆) δ ppm 9.05 (m, 2H), 8.50 (d, J=1.5 Hz, 1H), 8.16 (s, 1H), 7.80 (d, J=1.0 Hz, 1H), 7.69 (d, J=3.7 Hz, 1H), 7.50 (m, 1H), 7.43 (m, 1H), 7.31 (m, 2H), 6.98 (d, J=3.8 Hz, 1H), 4.60 (m, 1H), 4.52 (d, J=5.8 Hz, 2H), 3.45 (m, 1H), 3.18 (m, 2H), 2.93 (m, 1H), 2.12-1.85 (m, 2H), 1.52 (m, 2H); MS (ESI(+)) m/e 464 (M+H)⁺.

Example 828

5-[1-(4-fluorobenzoyl)piperidin-4-yl]-N-(imidazo[1,2-a]pyrazin-6-ylmethyl)thiophene-2-carboxamide The title compound was prepared as described in Example 52A, substituting 4-fluorobenzoyl chloride for 2-cyclopentylacetyl chloride and N-(imidazo[1,2-a]pyrazin-6-ylmethyl)-5-(piperidin-4-yl)thiophene-2-carboxamide for methyl 4-aminobenzoate. ¹H NMR (400 MHz, DMSO-d₆) δ ppm 9.05 (m, 2H), 8.51 (d, J=1.4 Hz, 1H), 8.16 (t, J=0.8 Hz, 1H), 7.80 (d, J=1.0 Hz, 1H), 7.70 (d, J=3.8 Hz, 1H), 7.49 (m, 2H), 7.28 (m, 2H), 6.99 (dd, J=3.7, 0.8 Hz, 1H), 4.54 (m, 1H), 4.52 (d, J=5.8 Hz, 2H), 3.65 (m, 1H), 3.15 (m, 2H), 2.93 (m, 1H), 1.97 (m, 2H), 1.59 (m, 2H); MS (ESI(+)) m/e 464 (M+H)⁺.

Example 829

5-[1-(2,4-difluorobenzoyl)piperidin-4-yl]-N-(imidazo[1,2-a]pyrazin-6-ylmethyl)thiophene-2-carboxamide The title compound was prepared as described in Example 52A, substituting 2,4-difluorobenzoyl chloride for 2-cyclopentylacetyl chloride and N-(imidazo[1,2-a]pyrazin-6-ylmethyl)-5-(piperidin-4-yl)thiophene-2-carboxamide for methyl 4-aminobenzoate. ¹H NMR (400 MHz, DMSO-d₆) δ ppm 9.05 (m, 2H), 8.50 (d, J=1.4 Hz, 1H), 8.16 (s, 1H), 7.80 (d, J=1.0 Hz, 1H), 7.69 (d, J=3.8 Hz, 1H), 7.52 (m, 1H), 7.37 (td, J=9.7, 2.4 Hz, 1H), 7.19 (td, J=8.5, 2.5 Hz, 1H), 6.98 (d, J=3.8 Hz, 1H), 4.58 (m, 1H), 4.52 (d, J=5.8 Hz, 2H), 3.43 (m, 1H), 3.17 (m, 2H), 2.92 (m, 1H), 2.00 (m, 2H), 1.52 (m, 2H); MS (ESI(+)) m/e 482 (M+H)⁺.

Example 830

5-[1-(2,5-difluorobenzoyl)piperidin-4-yl]-N-(imidazo[1,2-a]pyrazin-6-ylmethyl)thiophene-2-carboxamide The title compound was prepared as described in Example 52A, substituting 2,5-difluorobenzoyl chloride for 2-cyclopentylacetyl chloride and N-(imidazo[1,2-a]pyrazin-6-ylmethyl)-5-(piperidin-4-yl)thiophene-2-carboxamide for methyl 4-aminobenzoate. ¹H NMR (400 MHz, DMSO-d₆) δ ppm 9.04 (m, 2H), 8.51 (d, J=1.5 Hz, 1H), 8.16 (s, 1H), 7.80 (d, J=1.1 Hz, 1H), 7.70 (d, J=3.8 Hz, 1H), 7.56 (m, 1H), 7.36

(m, 2H), 6.98 (d, J=3.8 Hz, 1H), 4.57 (m, 1H), 4.52 (d, J=5.8 Hz, 2H), 3.46 (m, 1H), 3.17 (m, 2H), 2.93 (m, 1H), 2.02 (m, 2H), 1.55 (m, 2H); MS (ESI(+)) m/e 482 (M+H)+.

Example 831

5-[1-(2-fluorobenzoyl)piperidin-4-yl]-N-([1,2,4]triazolo[1,5-a]pyridin-6-ylmethyl)thiophene-2-carboxamide

Example 831A tert-butyl 4-(5-(([1,2,4]triazolo[1,5-a]pyridin-6-ylmethyl)carbamoyl)thiophen-2-yl)piperidine-1-carboxylate The title compound was prepared as described in Example 1A, substituting [1,2,4]triazolo[1,5-a]pyridin-6-ylmethanamine for 3-methylbutan-1-amine and 5-(1-(tert-butoxycarbonyl)piperidin-4-yl)thiophene-2-carboxylic acid for 4-nitrobenzoic acid.

Example 831B

N-([1,2,4]triazolo[1,5-a]pyridin-6-ylmethyl)-5-(piperidin-4-yl)thiophene-2-carboxamide The title compound was prepared as described in Example 28A, substituting tert-butyl 4-(5-(([1,2,4]triazolo[1,5-a]pyridin-6-ylmethyl)carbamoyl)thiophen-2-yl)piperidine-1-carboxylate for tert-butyl 4-(4-(3-imidazo[1,2-a]pyridin-6-ylureido)phenyl)-5,6-dihydropyridine-1(2H)-carboxylate.

Example 831C

5-[1-(2-fluorobenzoyl)piperidin-4-yl]-N-([1,2,4]triazolo[1,5-a]pyridin-6-ylmethyl)thiophene-2-carboxamide The title compound was prepared as described in Example 52A, substituting 2-fluorobenzoyl chloride for 2-cyclopentylacetyl chloride and N-([1,2,4]triazolo[1,5-a]pyridin-6-ylmethyl)-5-(piperidin-4-yl)thiophene-2-carboxamide for methyl 4-aminobenzoate. $^1$H NMR (400 MHz, DMSO-$d_6$) δ ppm 9.03 (t, J=5.9 Hz, 1H), 8.86 (d, J=1.5 Hz, 1H), 8.48 (s, 1H), 7.83 (dd, J=9.1, 0.9 Hz, 1H), 7.64 (m, 2H), 7.50 (m, 1H), 7.42 (m, 1H), 7.31 (m, 2H), 6.97 (dd, J=3.7, 0.8 Hz, 1H), 4.60 (m, 1H), 4.53 (d, J=5.8 Hz, 2H), 3.45 (m, 1H), 3.17 (m, 2H), 2.93 (m, 1H), 2.07 (m, 1H), 1.93 (m, 1H), 1.54 (m, 2H); MS (ESI(+)) m/e 464 (M+H)+.

Example 832

5-[1-(3-fluorobenzoyl)piperidin-4-yl]-N-([1,2,4]triazolo[1,5-a]pyridin-6-ylmethyl)thiophene-2-carboxamide The title compound was prepared as described in Example 52A, substituting 3-fluorobenzoyl chloride for 2-cyclopentylacetyl chloride and N-([1,2,4]triazolo[1,5-a]pyridin-6-ylmethyl)-5-(piperidin-4-yl)thiophene-2-carboxamide for methyl 4-aminobenzoate. $^1$H NMR (400 MHz, DMSO-$d_6$) δ ppm 9.02 (t, J=5.9 Hz, 1H), 8.86 (d, J=1.5 Hz, 1H), 8.48 (s, 1H), 7.83 (dd, J=9.1, 0.9 Hz, 1H), 7.66 (m, 2H), 7.50 (m, 1H), 7.34-7.22 (m, 3H), 6.98 (d, J=3.8 Hz, 1H), 4.55 (m, 1H), 4.53 (d, J=5.8 Hz, 2H), 3.56 (m, 1H), 3.13 (m, 2H), 2.91 (m, 1H), 1.97 (m, 2H), 1.60 (m, 2H); MS (ESI(+)) m/e 464 (M+H)+.

Example 833

5-[1-(4-fluorobenzoyl)piperidin-4-yl]-N-([1,2,4]triazolo[1,5-a]pyridin-6-ylmethyl)thiophene-2-carboxamide The title compound was prepared as described in Example 52A, substituting 4-fluorobenzoyl chloride for 2-cyclopentylacetyl chloride and N-([1,2,4]triazolo[1,5-a]pyridin-6-ylmethyl)-5-(piperidin-4-yl)thiophene-2-carboxamide for methyl 4-aminobenzoate. $^1$H NMR (400 MHz, DMSO-$d_6$) δ ppm 9.02 (t, J=5.9 Hz, 1H), 8.86 (d, J=1.5 Hz, 1H), 8.48 (s, 1H), 7.83 (dd, J=9.1, 0.9 Hz, 1H), 7.64 (m, 2H), 7.47 (m, 2H), 7.27 (m, 2H), 6.98 (dd, J=3.7, 0.8 Hz, 1H), 4.55 (m, 1H), 4.53 (d, J=5.8 Hz, 2H), 3.62 (m, 1H), 3.14 (m, 2H), 2.91 (m, 1H), 1.97 (m, 2H), 1.58 (m, 2H); MS (ESI(+)) m/e 464 (M+H)+.

Example 834

5-[1-(2,4-difluorobenzoyl)piperidin-4-yl]-N-([1,2,4]triazolo[1,5-a]pyridin-6-ylmethyl)thiophene-2-carboxamide The title compound was prepared as described in Example 52A, substituting 2,4-difluorobenzoyl chloride for 2-cyclopentylacetyl chloride and N-([1,2,4]triazolo[1,5-a]pyridin-6-ylmethyl)-5-(piperidin-4-yl)thiophene-2-carboxamide for methyl 4-aminobenzoate. $^1$H NMR (400 MHz, DMSO-$d_6$) δ ppm 9.02 (t, J=5.9 Hz, 1H), 8.86 (m, 1H), 8.48 (s, 1H), 7.83 (dd, J=9.1, 0.9 Hz, 1H), 7.64 (m, 2H), 7.52 (m, 1H), 7.36 (td, J=9.7, 2.4 Hz, 1H), 7.19 (m, 1H), 6.97 (dd, J=3.8, 0.8 Hz, 1H), 4.57 (m, 1H), 4.53 (d, J=5.8 Hz, 2H), 3.46 (m, 1H), 3.18 (m, 2H), 2.92 (m, 1H), 2.07 (m, 1H), 1.93 (m, 1H), 1.52 (m, 2H); MS (ESI(+)) m/e 482 (M+H)+.

Example 835

5-[1-(2,5-difluorobenzoyl)piperidin-4-yl]-N-([1,2,4]triazolo[1,5-a]pyridin-6-ylmethyl)thiophene-2-carboxamide The title compound was prepared as described in Example 52A, substituting 2,5-difluorobenzoyl chloride for 2-cyclopentylacetyl chloride and N-([1,2,4]triazolo[1,5-a]pyridin-6-ylmethyl)-5-(piperidin-4-yl)thiophene-2-carboxamide for methyl 4-aminobenzoate. $^1$H NMR (400 MHz, DMSO-$d_6$) δ ppm 9.02 (t, J=5.9 Hz, 1H), 8.86 (d, J=1.5 Hz, 1H), 8.48 (s, 1H), 7.83 (dd, J=9.1, 0.9 Hz, 1H), 7.64 (m, 2H), 7.37 (m, 3H), 6.97 (dd, J=3.7, 0.8 Hz, 1H), 4.57 (m, 1H), 4.53 (d, J=5.8 Hz, 2H), 3.46 (m, 1H), 3.19 (m, 2H), 2.93 (m, 1H), 2.13 (m, 1H), 1.92 (m, 1H), 1.54 (m, 2H); MS (ESI(+)) m/e 482 (M+H)+.

Example 836

5-[1-(3,5-difluorobenzoyl)piperidin-4-yl]-N-([1,2,4]triazolo[1,5-a]pyridin-6-ylmethyl)thiophene-2-carboxamide The title compound was prepared as described in Example 52A, substituting 3,5-difluorobenzoyl chloride for 2-cyclopentylacetyl chloride and N-([1,2,4]triazolo[1,5-a]pyridin-6-ylmethyl)-5-(piperidin-4-yl)thiophene-2-carboxamide for methyl 4-aminobenzoate. $^1$H NMR (400 MHz, DMSO-$d_6$) δ ppm 9.02 (t, J=5.9 Hz, 1H), 8.86 (d, J=1.5 Hz, 1H), 8.48 (s, 1H), 7.83 (dd, J=9.1, 0.9 Hz, 1H), 7.64 (m, 2H), 7.34 (tt, J=9.4, 2.4 Hz, 1H), 7.19 (m, 2H), 6.98 (dd, J=3.8, 0.8 Hz, 1H), 4.55 (m, 1H), 4.53 (d, J=5.8 Hz, 2H), 3.55 (m, 1H), 3.15 (m, 2H), 2.90 (m, 1H), 2.03 (m, 1H), 1.90 (m, 1H), 1.61 (m, 2H); MS (ESI(+)) m/e 482 (M+H)+.

Example 837

N-(imidazo[1,2-a]pyrazin-6-ylmethyl)-5-[1-(2-methylpropanoyl)piperidin-4-yl]thiophene-2-carboxamide The title compound was prepared as described in Example 1A, substituting N-(imidazo[1,2-a]pyrazin-6-ylmethyl)-5-(piperidin-4-yl)thiophene-2-carboxamide for 3-methylbutan-1-amine and isobutyric acid for 4-nitrobenzoic acid. $^1$H NMR (400 MHz, DMSO-$d_6$) δ ppm 9.03 (m, 2H), 8.50 (d, J=1.4 Hz, 1H), 8.16 (m, 1H), 7.80 (d, J=1.0 Hz, 1H), 7.69 (d, J=3.8 Hz, 1H), 6.96 (dd, J=3.7, 0.8 Hz, 1H), 4.52 (d, J=5.8 Hz, 2H), 4.49 (m, 1H), 4.02 (m, 1H), 3.13 (m, 2H), 2.90 (m, 1H), 2.64 (m, 1H), 1.99 (m, 2H), 1.43 (m, 2H), 1.00 (m, 6H); MS (ESI(+)) m/e 412 (M+H)+.

Example 838

N-(imidazo[1,2-a]pyrazin-6-ylmethyl)-5-[1-(3-methylbutanoyl)piperidin-4-yl]thiophene-2-carboxamide The title compound was prepared as described in Example 1A, substituting N-(imidazo[1,2-a]pyrazin-6-ylmethyl)-5-(piperidin-4-yl)thiophene-2-carboxamide for 3-methylbutan-1-amine and 3-methylbutanoic acid for 4-nitrobenzoic acid. $^1$H NMR (400 MHz, DMSO-$d_6$) δ ppm 9.03 (m, 2H), 8.50 (d, J=1.4 Hz, 1H), 8.16 (s, 1H), 7.80 (d, J=1.0 Hz, 1H), 7.69 (d, J=3.8 Hz, 1H), 6.96 (dd, J=3.7, 0.8 Hz, 1H), 4.52 (d, J=5.8 Hz, 2H), 4.49 (m, 1H), 3.96 (m, 1H), 3.10 (m, 2H), 2.64 (m, 1H), 2.21 (d, J=7.0 Hz, 2H), 1.99 (m, 3H), 1.43 (m, 2H), 0.90 (d, J=6.6 Hz, 6H); MS (ESI(+)) m/e 426 (M+H)+.

Example 839

N-(imidazo[1,2-a]pyrazin-6-ylmethyl)-5-{1-[(1-methylcyclopropyl)carbonyl]piperidin-4-yl}thiophene-2-carboxamide The title compound was prepared as described in Example 1A, substituting N-(imidazo[1,2-a]pyrazin-6-ylmethyl)-5-(piperidin-4-yl)thiophene-2-carboxamide for 3-methylbutan-1-amine and (1-methylcyclopropyl)carboxylic acid for 4-nitrobenzoic acid. $^1$H NMR (400 MHz, DMSO-$d_6$) δ ppm 9.03 (m, 2H), 8.50 (d, J=1.4 Hz, 1H), 8.16 (d, J=0.9 Hz, 1H), 7.80 (d, J=1.0 Hz, 1H), 7.69 (d, J=3.8 Hz, 1H), 6.97 (dd, J=3.7, 0.8 Hz, 1H), 4.52 (d, J=5.8 Hz, 2H), 4.33 (m, 2H), 3.11 (m, 1H), 2.93 (m, 2H), 1.99 (m, 2H), 1.47 (m, 2H), 1.23 (s, 3H), 0.80 (m, 2H), 0.54 (m, 2H); MS (ESI(+)) m/e 424 (M+H)+.

Example 840

N-(imidazo[1,2-a]pyrazin-6-ylmethyl)-5-[1-(4,4,4-trifluorobutanoyl)piperidin-4-yl]thiophene-2-carboxamide The title compound was prepared as described in Example 1A, substituting N-(imidazo[1,2-a]pyrazin-6-ylmethyl)-5-(piperidin-4-yl)thiophene-2-carboxamide for 3-methylbutan-1-amine and 4,4,4-trifluorobutanoic acid for 4-nitrobenzoic acid. $^1$H NMR (400 MHz, DMSO-$d_6$) δ ppm 9.03 (m, 2H), 8.50 (d, J=1.4 Hz, 1H), 8.16 (s, 1H), 7.80 (d, J=1.0 Hz, 1H), 7.69 (d, J=3.8 Hz, 1H), 6.96 (dd, J=3.7, 0.8 Hz, 1H), 4.52 (d, J=5.8 Hz, 2H), 4.47 (m, 1H), 3.94 (m, 1H), 3.13 (m, 2H), 2.66 (m, 3H), 2.50 (m, 2H), 1.97 (m, 2H), 1.57 (m, 1H), 1.41 (m, 1H); MS (ESI(+)) m/e 466 (M+H)+.

Example 841

N-(imidazo[1,2-a]pyrazin-6-ylmethyl)-5-[1-(tetrahydro-2H-pyran-4-ylcarbonyl)piperidin-4-yl]thiophene-2-carboxamide The title compound was prepared as described in Example 1A, substituting N-(imidazo[1,2-a]pyrazin-6-ylmethyl)-5-(piperidin-4-yl)thiophene-2-carboxamide for 3-methylbutan-1-amine and tetrahydro-2H-pyran-4-ylcarboxylic acid for 4-nitrobenzoic acid. $^1$H NMR (400 MHz, DMSO-$d_6$) δ ppm 9.03 (m, 2H), 8.50 (d, J=1.4 Hz, 1H), 8.16 (s, 1H), 7.80 (d, J=1.0 Hz, 1H), 7.69 (d, J=3.8 Hz, 1H), 6.96 (dd, J=3.7, 0.8 Hz, 1H), 4.52 (d, J=5.8 Hz, 2H), 4.47 (m, 1H), 4.07 (m, 1H), 3.84 (m, 2H), 3.40 (m, 2H), 3.13 (m, 2H), 2.89 (m, 1H), 2.64 (m, 1H), 1.98 (m, 2H), 1.77-1.30 (m, 6H); MS (ESI(+)) m/e 454 (M+H)+.

Example 842

5-[1-(2-methylpropanoyl)piperidin-4-yl]-N-([1,2,4]triazolo[1,5-a]pyridin-6-ylmethyl)thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and isobutyric acid for 4-nitrobenzoic acid. $^1$H NMR (400 MHz, DMSO-$d_6$) δ ppm 9.01 (t, J=5.9 Hz, 1H), 8.86 (s, 1H), 8.47 (s, 1H), 7.83 (d, J=9.1 Hz, 1H), 7.64 (m, 2H), 6.96 (d, J=3.8 Hz, 1H), 4.52 (d, J=5.8 Hz, 2H), 4.47 (m, 1H), 4.02 (m, 1H), 3.12 (m, 2H), 2.88 (m, 1H), 2.63 (m, 1H), 1.99 (m, 2H), 1.43 (m, 2H), 1.00 (m, 6H); MS (ESI(+)) m/e 412 (M+H)+.

Example 843

5-[1-(3-methylbutanoyl)piperidin-4-yl]-N-([1,2,4]triazolo[1,5-a]pyridin-6-ylmethyl)thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and 3-methylbutanoic acid for 4-nitrobenzoic acid. $^1$H NMR (400 MHz, DMSO-$d_6$) δ ppm 9.01 (t, J=5.9 Hz, 1H), 8.86 (d, J=1.5 Hz, 1H), 8.47 (s, 1H), 7.83 (dd, J=9.1, 0.9 Hz, 1H), 7.64 (m, 2H), 6.95 (dd, J=3.7, 0.8 Hz, 1H), 4.52 (d, J=5.8 Hz, 2H), 4.48 (m, 1H), 3.96 (m, 1H), 3.10 (m, 2H), 2.63 (m, 1H), 2.21 (m, 2H), 1.98 (m, 3H), 1.43 (m, 2H), 0.90 (d, J=6.6 Hz, 6H); MS (ESI(+)) m/e 426 (M+H)+.

Example 844

5-{1-[(2S)-2-methylbutanoyl]piperidin-4-yl}-N-([1,2,4]triazolo[1,5-a]pyridin-6-ylmethyl)thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and (2S)-2-methylbutanoic acid for 4-nitrobenzoic acid. $^1$H NMR (400 MHz, DMSO-d$_6$) δ ppm 9.01 (t, J=5.9 Hz, 1H), 8.86 (d, J=1.5 Hz, 1H), 8.47 (s, 1H), 7.83 (dd, J=9.1, 0.9 Hz, 1H), 7.64 (m, 2H), 6.95 (d, J=3.8 Hz, 1H), 4.52 (d, J=5.8 Hz, 2H), 4.49 (m, 1H), 4.05 (m, 1H), 3.13 (m, 2H), 2.69 (m, 2H), 1.99 (m, 2H), 1.61-1.18 (m, 4H), 0.98 (m, 3H), 0.82 (m, 3H); MS (ESI(+)) m/e 426 (M+H)$^+$.

Example 845

5-{1-[(1-methylcyclopropyl)carbonyl]piperidin-4-yl}-N-([1,2,4]triazolo[1,5-a]pyridin-6-ylmethyl) thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and (1-methylcyclopropyl)carboxylic acid for 4-nitrobenzoic acid. $^1$H NMR (400 MHz, DMSO-d$_6$) δ ppm 9.01 (t, J=5.9 Hz, 1H), 8.86 (d, J=1.5 Hz, 1H), 8.47 (s, 1H), 7.83 (dd, J=9.1, 0.9 Hz, 1H), 7.64 (m, 2H), 6.96 (dd, J=3.7, 0.9 Hz, 1H), 4.53 (d, J=5.8 Hz, 2H), 4.33 (m, 2H), 3.10 (m, 1H), 2.92 (m, 2H), 1.98 (m, 2H), 1.47 (m, 2H), 1.23 (s, 3H), 0.80 (m, 2H), 0.53 (m, 2H); MS (ESI(+)) m/e 424 (M+H)$^+$.

Example 846

N-([1,2,4]triazolo[1,5-a]pyridin-6-ylmethyl)-5-[1-(3,3,3-trifluoropropanoyl)piperidin-4-yl]thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and 3,3,3-trifluoropropanoic acid for 4-nitrobenzoic acid. $^1$H NMR (400 MHz, DMSO-d$_6$) δ ppm 9.02 (t, J=5.9 Hz, 1H), 8.86 (m, 1H), 8.48 (s, 1H), 7.83 (dd, J=9.1, 0.9 Hz, 1H), 7.65 (m, 2H), 6.95 (dd, J=3.7, 0.9 Hz, 1H), 4.53 (d, J=5.8 Hz, 2H), 4.45 (m, 1H), 3.90 (m, 1H), 3.66 (m, 2H), 3.13 (m, 2H), 2.70 (m, 1H), 1.97 (m, 2H), 1.57 (m, 1H), 1.42 (m, 1H); MS (ESI(+)) m/e 452 (M+H)$^+$.

Example 847

N-([1,2,4]triazolo[1,5-a]pyridin-6-ylmethyl)-5-[1-(4,4,4-trifluorobutanoyl)piperidin-4-yl]thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and 4,4,4-trifluorobutanoic acid for 4-nitrobenzoic acid. $^1$H NMR (400 MHz, DMSO-d$_6$) δ ppm 9.01 (t, J=5.8 Hz, 1H), 8.86 (m, 1H), 8.48 (s, 1H), 7.83 (dd, J=9.1, 0.9 Hz, 1H), 7.64 (m, 2H), 6.95 (dd, J=3.7, 0.8 Hz, 1H), 4.53 (d, J=5.8 Hz, 2H), 4.47 (m, 1H), 3.94 (m, 1H), 3.12 (m, 2H), 2.65 (m, 3H), 2.50 (m, 2H), 1.96 (m, 2H), 1.57 (m, 1H), 1.41 (m, 1H); MS (ESI(+)) m/e 466 (M+H)$^+$.

Example 848

5-{1-[(4,4-difluorocyclohexyl)carbonyl]piperidin-4-yl}-N-([1,2,4]triazolo[1,5-a]pyridin-6-ylmethyl) thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and (4,4-difluorocyclohexyl)carboxylic acid for 4-nitrobenzoic acid. $^1$H NMR (400 MHz, DMSO-d$_6$) δ ppm 9.01 (t, J=5.8 Hz, 1H), 8.86 (m, 1H), 8.48 (s, 1H), 7.83 (dd, J=9.1, 0.9 Hz, 1H), 7.64 (m, 2H), 6.96 (dd, J=3.7, 0.8 Hz, 1H), 4.53 (d, J=5.8 Hz, 2H), 4.48 (m, 1H), 4.06 (m, 1H), 3.13 (m, 2H), 2.82 (m, 1H), 2.65 (m, 1H), 2.10-1.80 (m, 6H), 1.80-1.30 (m, 6H); MS (ESI(+)) m/e 488 (M+H)$^+$.

Example 849

5-[1-(tetrahydro-2H-pyran-4-ylcarbonyl)piperidin-4-yl]-N-([1,2,4]triazolo[1,5-a]pyridin-6-ylmethyl) thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and tetrahydro-2H-pyran-4-ylcarboxylic acid for 4-nitrobenzoic acid. $^1$H NMR (400 MHz, DMSO-d$_6$) δ ppm 9.01 (t, J=5.9 Hz, 1H), 8.86 (m, 1H), 8.48 (s, 1H), 7.83 (dd, J=9.1, 0.9 Hz, 1H), 7.64 (m, 2H), 6.95 (dd, J=3.7, 0.8 Hz, 1H), 4.53 (d, J=5.8 Hz, 2H), 4.48 (m, 1H), 4.06 (m, 1H), 3.84 (m, 2H), 3.38 (m, 2H), 3.12 (m, 2H), 2.89 (m, 1H), 2.64 (m, 1H), 1.98 (m, 2H), 1.65-1.30 (m, 6H); MS (ESI(+)) m/e 454 (M+H)$^+$.

Example 850

5-[1-(2-hydroxy-2-methylpropanoyl)piperidin-4-yl]-N-([1,2,4]triazolo[1,5-a]pyridin-6-ylmethyl) thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and 2-hydroxy-2-methylpropanoic acid for 4-nitrobenzoic acid. $^1$H NMR (400 MHz, DMSO-d$_6$) δ ppm 9.01 (t, J=5.8 Hz, 1H), 8.86 (m, 1H), 8.47 (s, 1H), 7.83 (dd, J=9.1, 0.9 Hz, 1H), 7.64 (m, 2H), 6.95 (dd, J=3.7, 0.8 Hz, 1H), 5.39 (s, 1H), 5.00-4.30 (m, 2H), 4.53 (d, J=5.8 Hz, 2H), 3.10 (m, 1H), 3.10-2.60 (m, 2H), 1.96 (m, 2H), 1.50 (m, 2H), 1.32 (s, 6H); MS (ESI(+)) m/e 428 (M+H)$^+$.

Example 851

5-{1-[(1-methylpiperidin-4-yl)carbonyl]piperidin-4-yl}-N-([1,2,4]triazolo[1,5-a]pyridin-6-ylmethyl) thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and (1-methylpiperidin-4-yl)carboxylic acid for 4-nitrobenzoic acid. $^1$H NMR (400 MHz, DMSO-d$_6$) δ ppm 9.02 (t, J=5.8 Hz, 1H), 8.85 (s, 1H), 8.47 (s, 1H), 7.83 (d, J=9.1 Hz, 1H), 7.64 (m, 2H), 6.95 (d, J=3.8 Hz, 1H), 4.53 (d, J=5.8 Hz, 2H), 4.48 (m, 1H), 4.00 (m, 1H), 3.04 (m, 4H), 2.80-2.57 (m, 4H), 2.13 (s, 3H), 2.07-1.80 (m, 4H), 1.81-0.93 (m, 4H); MS (ESI(+)) m/e 467 (M+H)$^+$.

Example 852

5-[1-(2-cyanobenzoyl)piperidin-4-yl]-N-([1,2,4]triazolo[1,5-a]pyridin-6-ylmethyl)thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and 2-cyanobenzoic acid for 4-nitrobenzoic acid. $^1$H NMR (400 MHz, DMSO-$d_6$) δ ppm 9.02 (t, J=5.8 Hz, 1H), 8.86 (m, 1H), 8.47 (s, 1H), 7.95 (m, 1H), 7.82 (m, 2H), 7.70-7.57 (m, 4H), 6.96 (dd, J=3.7, 0.8 Hz, 1H), 4.61 (m, 1H), 4.52 (d, J=5.8 Hz, 2H), 3.35 (m, 1H), 3.14 (m, 2H), 2.97 (m, 1H), 2.09 (m, 1H), 1.89 (m, 1H), 1.60 (m, 2H); MS (ESI(+)) m/e 471 (M+H)$^+$.

Example 853

5-[1-(pyridin-2-ylcarbonyl)piperidin-4-yl]-N-([1,2,4]triazolo[1,5-a]pyridin-6-ylmethyl)thiophene-2-carboxamide The title compound was prepared as described in Example 1A, substituting N-([1,2,4]triazolo[1,5-a]pyridin-6-ylmethyl)-5-(piperidin-4-yl)thiophene-2-carboxamide for 3-methylbutan-1-amine and pyridin-2-ylcarboxylic acid for 4-nitrobenzoic acid. $^1$H NMR (400 MHz, DMSO-$d_6$) δ ppm 9.03 (t, J=5.8 Hz, 1H), 8.86 (m, 1H), 8.59 (m, 1H), 8.48 (s, 1H), 7.92 (td, J=7.7, 1.7 Hz, 1H), 7.83 (dd, J=9.1, 0.9 Hz, 1H), 7.64 (m, 2H), 7.57 (dt, J=7.7, 1.1 Hz, 1H), 7.47 (m, 1H), 6.97 (dd, J=3.7, 0.8 Hz, 1H), 4.58 (m, 1H), 4.53 (d, J=5.8 Hz, 2H), 3.72 (m, 1H), 3.17 (m, 2H), 2.93 (m, 1H), 2.08 (m, 1H), 1.91 (m, 1H), 1.58 (m, 2H); MS (ESI(+)) m/e 447 (M+H)$^+$.

Example 854

2-cyclopentyl-N-{4-[(imidazo[1,2-a]pyridin-6-ylacetyl)amino]phenyl}acetamide

The title compound was prepared as described in Example 1A, substituting N-(4-aminophenyl)-2-cyclopentylacetamide for 3-methylbutan-1-amine and 2-(imidazo[1,2-a]pyridin-6-yl)acetic acid for 4-nitrobenzoic acid. $^1$H NMR (400 MHz, DMSO-$d_6$) δ ppm 10.12 (bs, 1H), 9.77 (bs, 1H), 8.47-8.44 (m, 1H), 7.94 (s, 1H), 7.58-7.43 (m, 6H), 7.19 (dd, J=9.2, 1.7 Hz, 1H), 3.64 (bs, 2H), 2.30-2.19 (m, 3H), 1.82-1.65 (m, 2H), 1.66-1.43 (m, 4H), 1.26-1.08 (m, 2H); MS (ESI(+)) m/e 377 (M+H)$^+$.

Example 855 tert-butyl 4-{4-[(imidazo[1,2-b]pyridazin-6-ylmethyl)carbamoyl]phenyl}piperidine-1-carboxylate The title compound was prepared as described in Example 1A, substituting imidazo[1,2-b]pyridazin-6-ylmethanamine for 3-methylbutan-1-amine and 4-(1-(tert-butoxycarbonyl)piperidin-4-yl)benzoic acid for 4-nitrobenzoic acid. $^1$H NMR (400 MHz, DMSO-$d_6$) δ ppm 9.15 (t, J=5.9 Hz, 1H), 8.24 (s, 1H), 8.07 (d, J=9.3 Hz, 1H), 7.88-7.82 (m, 2H), 7.75 (d, J=1.2 Hz, 1H), 7.41-7.34 (m, 2H), 7.20 (d, J=9.3 Hz, 1H), 4.63 (d, J=5.8 Hz, 2H), 4.13-4.03 (m, 2H), 2.91-2.67 (m, 3H), 1.80-1.72 (m, 2H), 1.61-1.44 (m, 2H), 1.42 (s, 9H); MS (ESI(+)) m/e 436 (M+H)$^+$.

Example 856

4-[(cyclopentylacetyl)amino]-N-(imidazo[1,2-b]pyridazin-6-ylmethyl)benzamide

The title compound was prepared as described in Example 1A, substituting imidazo[1,2-b]pyridazin-6-ylmethanamine for 3-methylbutan-1-amine and 4-(2-cyclopentylacetamido)benzoic acid for 4-nitrobenzoic acid. $^1$H NMR (400 MHz, methanol-$d_4$) δ ppm 8.38 (d, J=1.9 Hz, 1H), 8.28 (dd, J=9.4, 0.7 Hz, 1H), 8.07 (d, J=1.9 Hz, 1H), 7.90-7.84 (m, 2H), 7.79-7.66 (m, 3H), 4.91-4.79 (m, 2H), 2.43-2.25 (m, 3H), 1.92-1.78 (m, 2H), 1.79-1.50 (m, 4H), 1.33-1.18 (m, 2H); MS (ESI(+)) m/e 378 (M+H)$^+$.

Example 857

5-(1-benzyl-3-cyclopropyl-1H-pyrazol-5-yl)-N-(imidazo[1,2-a]pyridin-7-ylmethyl)thiophene-2-carboxamide Example 857A methyl 5-(3-cyclopropylpropioloyl)thiophene-2-carboxylate Methyl 5-(chlorocarbonyl)thiophene-2-carboxylate (500 mg, 2.443 mmol) was dissolved in triethylamine (5 mL) and the suspension was degassed with nitrogen. Copper(I) iodide (40 mg, 0.210 mmol) and bistriphenylphosphine palladium (II) chloride (40 mg, 0.057 mmol) were added followed by ethynylcyclopropane (162 mg, 2.443 mmol). The mixture was stirred overnight, diluted with methanol and concentrated to dryness. The crude material was partitioned between dichloromethane and water. The organic extracts were dried with sodium sulfate, filtered, concentrated and purified by normal phase chromatography to afford the title compound.

Example 857B methyl 5-(1-benzyl-3-cyclopropyl-1H-pyrazol-5-yl)thiophene-2-carboxylate Methyl 5-(3-cyclopropylpropioloyl)thiophene-2-carboxylate (100 mg, 0.427 mmol) was dissolved in N,N-dimethylformamide (2 mL), and the solution was cooled to 0° C. Benzylhydrazine hydrochloride (74.5 mg, 0.470 mmol) was added followed by potassium carbonate (77 mg, 0.555 mmol). The mixture was stirred at 0° C. until the ice bath melted and was stirred overnight at room temperature. The solution was partitioned between water and ethyl acetate. The organic extract was dried with sodium sulfate, filtered, concentrated and purified by normal phase chromatography to afford the title compound.

Example 857C 5-(1-benzyl-3-cyclopropyl-1H-pyrazol-5-yl)thiophene-2-carboxylic acid The title compound was prepared as described in Example 4B, substituting methyl 5-(1-benzyl-3-cyclopropyl-1H-pyrazol-5-yl)thiophene-2-carboxylate for methyl 4-(3-imidazo[1,2-a]pyridin-6-ylureido)benzoate.

Example 857D 5-(1-benzyl-3-cyclopropyl-1H-pyrazol-5-yl)-N-(imidazo[1,2-a]pyridin-7-ylmethyl)thiophene-2-carboxamide The title compound was prepared as described in Example 1A, substituting imidazo[1,2-a]pyridin-7-ylmethanamine for 3-methylbutan-1-amine and 5-(1-benzyl-3-cyclopropyl-1H-pyrazol-5-yl)thiophene-2-carboxylic acid for 4-nitrobenzoic acid. $^1$H NMR (300 MHz, DMSO-$d_6$) δ ppm 9.04 (t, J=5.9

Hz, 1H), 8.49 (dd, J=7.0, 0.9 Hz, 1H), 7.91-7.87 (m, 1H), 7.74 (d, J=3.9 Hz, 1H), 7.52 (d, J=1.2 Hz, 1H), 7.42-7.24 (m, 5H), 7.23-7.15 (m, 2H), 6.84 (dd, J=7.0, 1.7 Hz, 1H), 6.38 (s, 1H), 5.44 (bs, 2H), 4.47 (d, J=5.9 Hz, 2H), 1.94-1.81 (m, 1H), 0.97-0.86 (m, 2H), 0.72-0.59 (m, 2H); MS (ESI(+)) m/e 454 (M+H)$^+$.

Example 858

5-[1-(2,2-dimethylpropyl)-1H-pyrazol-4-yl]-N-(imidazo[1,2-a]pyrazin-6-ylmethyl)thiophene-2-carboxamide

Example 858A 5-bromo-N-(imidazo[1,2-a]pyrazin-6-ylmethyl)thiophene-2-carboxamide The title compound was prepared as described in Example 1A, substituting imidazo[1,2-a]pyrazin-6-ylmethanamine for 3-methylbutan-1-amine and 5-bromothiophene-2-carboxylic acid for 4-nitrobenzoic acid.

Example 858B

The title compound was prepared as described in Example 51A, substituting 1-neopentyl-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyrazin-6-ylmethyl)thiophene-2-carboxamide for 4-bromoaniline. $^1$H NMR (300 MHz, DMSO-d$_6$) δ ppm 9.10-8.99 (m, 2H), 8.53 (d, J=1.3 Hz, 1H), 8.17 (d, J=0.9 Hz, 1H), 8.10 (d, J=0.5 Hz, 1H), 7.82-7.78 (m, 2H), 7.76 (d, J=3.8 Hz, 1H), 7.23 (d, J=3.9 Hz, 1H), 4.54 (d, J=5.7 Hz, 2H), 3.92 (s, 2H), 0.92 (s, 9H); MS (ESI(+)) m/e 395 (M+H)$^+$.

Example 859

5-[1-(propan-2-ylsulfonyl)piperidin-4-yl]-N-([1,2,4]triazolo[1,5-a]pyridin-6-ylmethyl)thiophene-2-carboxamide The title compound was prepared as described in Example 682, substituting propane-2-sulfonyl chloride for benzenesulfonyl chloride and N-([1,2,4]triazolo[1,5-a]pyridin-6-ylmethyl)-5-(piperidin-4-yl)thiophene-2-carboxamide for N-(imidazo[1,2-a]pyridin-7-ylmethyl)-4-(piperidin-4-yl)benzamide. $^1$H NMR (400 MHz, DMSO-d$_6$) δ ppm 9.03 (t, J=5.8 Hz, 1H), 8.86 (d, J=1.5 Hz, 1H), 8.48 (s, 1H), 7.83 (dd, J=9.1, 0.9 Hz, 1H), 7.64 (m, 2H), 6.97 (dd, J=3.7, 0.9 Hz, 1H), 4.53 (d, J=5.8 Hz, 2H), 3.71 (m, 2H), 3.25 (m, 1H), 3.02 (m, 3H), 2.00 (m, 2H), 1.56 (m, 2H), 1.22 (d, J=6.8 Hz, 6H); MS (ESI(+)) m/e 448 (M+H)$^+$.

Example 860

5-[1-(phenylsulfonyl)piperidin-4-yl]-N-([1,2,4]triazolo[1,5-a]pyridin-6-ylmethyl)thiophene-2-carboxamide The title compound was prepared as described in Example 682, substituting N-([1,2,4]triazolo[1,5-a]pyridin-6-ylmethyl)-5-(piperidin-4-yl)thiophene-2-carboxamide for N-(imidazo[1,2-a]pyridin-7-ylmethyl)-4-(piperidin-4-yl)benzamide. $^1$H NMR (400 MHz, DMSO-d$_6$) δ ppm 9.01 (t, J=5.9 Hz, 1H), 8.85 (s, 1H), 8.47 (s, 1H), 7.83 (d, J=9.1 Hz, 1H), 7.81-7.69 (m, 3H), 7.71-7.55 (m, 4H), 6.90 (d, J=3.8 Hz, 1H), 4.51 (d, J=5.8 Hz, 2H), 3.73 (m, 2H), 2.84 (m, 1H), 2.37 (m, 2H), 1.99 (m, 2H), 1.61 (m, 2H); MS (ESI(+)) m/e 482 (M+H)$^+$.

Example 861

N-(imidazo[1,2-a]pyrazin-6-ylmethyl)-5-{1-[(4-methyltetrahydro-2H-pyran-4-yl)methyl]-1H-pyrazol-4-yl}thiophene-2-carboxamide The title compound was prepared as described in Example 51A, substituting 1-((4-methyltetrahydro-2H-pyran-4-yl)methyl)-4-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyrazin-6-ylmethyl)thiophene-2-carboxamide for 4-bromoaniline. $^1$H NMR (300 MHz, DMSO-d$_6$) δ ppm 9.09-9.01 (m, 2H), 8.53 (d, J=1.4 Hz, 1H), 8.18-8.15 (m, 1H), 8.13 (d, J=0.5 Hz, 1H), 7.83-7.79 (m, 2H), 7.76 (d, J=3.9 Hz, 1H), 7.23 (d, J=3.9 Hz, 1H), 4.54 (d, J=5.7 Hz, 2H), 4.04 (s, 2H), 3.68 (dt, J=11.4, 4.5 Hz, 2H), 3.51 (ddd, J=11.8, 9.2, 2.9 Hz, 2H), 1.50 (ddd, J=13.4, 9.1, 4.1 Hz, 2H), 1.33-1.18 (m, 2H), 0.96 (s, 3H); MS (ESI(+)) m/e 437 (M+H)$^+$.

Example 862 tert-butyl 4-{4-[(imidazo[1,2-a]pyridin-6-ylacetyl)amino]phenyl}piperidine-1-carboxylate The title compound was prepared as described in Example 1A, substituting tert-butyl 4-(4-aminophenyl)piperidine-1-carboxylate for 3-methylbutan-1-amine and 2-(imidazo[1,2-a]pyridin-6-yl)acetic acid for 4-nitrobenzoic acid. $^1$H NMR (300 MHz, DMSO-d$_6$) δ ppm 10.14 (s, 1H), 8.52 (s, 1H), 8.01 (d, J=1.3 Hz, 1H), 7.65-7.58 (m, 2H), 7.54-7.47 (m, 2H), 7.31 (dd, J=9.2, 1.7 Hz, 1H), 7.20-7.13 (m, 2H), 4.11-3.99 (m, 2H), 3.68 (s, 2H), 2.89-2.54 (m, 3H), 1.76-1.66 (m, 2H), 1.53-1.32 (m, 11H); MS (ESI(+)) m/e 435 (M+H)$^+$.

Example 863

N-{4-[1-(2-fluorobenzoyl)piperidin-4-yl]phenyl}-2-(imidazo[1,2-a]pyridin-6-yl)acetamide

Example 863A 2-(imidazo[1,2-a]pyridin-6-yl)-N-(4-(piperidin-4-yl)phenyl)acetamide The title compound was prepared as described in Example 28A, substituting tert-butyl 4-{4-[(imidazo[1,2-a]pyridin-6-ylacetyl)amino]phenyl}piperidine-1-carboxylate for tert-butyl 4-(4-(3-imidazo[1,2-a]pyridin-6-ylureido)phenyl)-5,6-dihydropyridine-1(2H)-carboxylate.

Example 863B

N-{4-[1-(2-fluorobenzoyl)piperidin-4-yl]phenyl}-2-(imidazo[1,2-a]pyridin-6-yl)acetamide The title compound was prepared as described in Example 1A, substituting 2-(imidazo[1,2-a]pyridin-6-yl)-N-(4-(piperidin-4-yl)phenyl)acetamide for 3-methylbutan-1-amine and 2-fluorobenzoic acid for 4-nitrobenzoic acid. $^1$H NMR (400 MHz, methanol-d$_4$) δ ppm 8.77 (s, 1H), 8.21 (d, J=2.2 Hz, 1H), 8.03 (d, J=2.1 Hz, 1H), 8.01-7.94 (m, 1H), 7.93-7.87

(m, 1H), 7.55-7.35 (m, 4H), 7.33-7.26 (m, 1H), 7.25-7.17 (m, 3H), 4.83-4.74 (m, 1H), 3.91 (s, 2H), 3.68-3.58 (m, 1H), 3.30-3.18 (m, 1H), 3.02-2.78 (m, 2H), 2.01-1.91 (m, 1H), 1.87-1.50 (m, 3H); MS (ESI(+)) m/e 457 (M+H)$^+$.

Example 864

N-(imidazo[1,2-a]pyrazin-6-ylmethyl)-4-[1-(phenylsulfonyl)piperidin-4-yl]benzamide The title compound was prepared as described in Example 682, substituting N-(imidazo[1,2-a]pyrazin-6-ylmethyl)-4-(piperidin-4-yl)benzamide for N-(imidazo[1,2-a]pyridin-7-ylmethyl)-4-(piperidin-4-yl)benzamide. $^1$H NMR (400 MHz, methanol-$d_4$) δ ppm 9.04-8.96 (m, 1H), 8.51 (s, 1H), 8.05 (s, 1H), 7.85-7.79 (m, 5H), 7.73-7.66 (m, 1H), 7.67-7.59 (m, 2H), 7.35-7.28 (m, 2H), 4.72-4.67 (m, 2H), 3.96-3.88 (m, 2H), 2.63-2.51 (m, 1H), 2.48-2.37 (m, 2H), 1.93-1.85 (m, 2H), 1.86-1.72 (m, 2H); MS (ESI(+)) m/e 476 (M+H)$^+$.

Example 865

2-(imidazo[1,2-a]pyridin-6-yl)-N-{4-[1-(2-methylpropanoyl)piperidin-4-yl]phenyl}acetamide The title compound was prepared as described in Example 1A, substituting 2-(imidazo[1,2-a]pyridin-6-yl)-N-(4-(piperidin-4-yl)phenyl)acetamide for 3-methylbutan-1-amine and isobutyric acid for 4-nitrobenzoic acid. $^1$H NMR (400 MHz, methanol-$d_4$) δ ppm 8.77 (d, J=1.4 Hz, 1H), 8.21 (dd, J=2.2, 0.7 Hz, 1H), 8.03 (d, J=2.2 Hz, 1H), 8.01-7.94 (m, 1H), 7.93-7.87 (m, 1H), 7.53-7.47 (m, 2H), 7.23-7.17 (m, 2H), 4.73-4.64 (m, 1H), 4.21-4.13 (m, 1H), 3.91 (s, 2H), 3.27-3.14 (m, 1H), 2.99 (hept, J=6.7 Hz, 1H), 2.88-2.74 (m, 1H), 2.76-2.63 (m, 1H), 1.96-1.81 (m, 2H), 1.71-1.45 (m, 2H), 1.16-1.07 (m, 6H); MS (ESI(+)) m/e 405 (M+H)$^+$.

Example 866

N-{4-[1-(2,4-difluorobenzoyl)piperidin-4-yl]phenyl}-2-(imidazo[1,2-a]pyridin-6-yl)acetamide The title compound was prepared as described in Example 1A, substituting 2-(imidazo[1,2-a]pyridin-6-yl)-N-(4-(piperidin-4-yl)phenyl)acetamide for 3-methylbutan-1-amine and 2,4-difluorobenzoic acid for 4-nitrobenzoic acid. $^1$H NMR (400 MHz, methanol-$d_4$) δ ppm 8.77 (d, J=1.4 Hz, 1H), 8.23-8.18 (m, 1H), 8.03 (d, J=2.2 Hz, 1H), 8.01-7.94 (m, 1H), 7.93-7.87 (m, 1H), 7.54-7.42 (m, 3H), 7.25-7.19 (m, 2H), 7.13-7.05 (m, 2H), 4.84-4.74 (m, 2H), 3.91 (s, 2H), 3.68-3.59 (m, 1H), 3.30-3.20 (m, 1H), 3.02-2.79 (m, 1H), 2.00-1.91 (m, 1H), 1.88-1.52 (m, 3H); MS (ESI(+)) m/e 475 (M+H)$^+$.

Example 877

N-(imidazo[1,2-a]pyridin-7-ylmethyl)-4-{[2-(2-methylpropyl)pyrrolidin-1-yl]carbonyl}benzamide Example 877A methyl 4-((imidazo[1,2-a]pyridin-7-ylmethyl)carbamoyl)benzoate The title compound was prepared as described in Example 1A, substituting imidazo[1,2-a]pyridin-7-ylmethanamine for 3-methylbutan-1-amine and 4-(methoxycarbonyl)benzoic acid for 4-nitrobenzoic acid.

Example 877B 4-((imidazo[1,2-a]pyridin-7-ylmethyl)carbamoyl)benzoic acid

The title compound was prepared as described in Example 4B, substituting methyl 4-((imidazo[1,2-a]pyridin-7-ylmethyl)carbamoyl)benzoate for methyl 4-(3-imidazo[1,2-a]pyridin-6-ylureido)benzoate.

Example 877C

N-(imidazo[1,2-a]pyridin-7-ylmethyl)-4-{[2-(2-methylpropyl)pyrrolidin-1-yl]carbonyl}benzamide The title compound was prepared as described in Example 1A, substituting 2-isobutylpyrrolidine for 3-methylbutan-1-amine and 4-(imidazo[1,2-a]pyridin-7-ylmethylcarbamoyl)benzoic acid for 4-nitrobenzoic acid. $^1$H NMR (300 MHz, DMSO-$d_6$) δ ppm 9.17 (t, J=5.9 Hz, 1H), 8.49 (dd, J=6.9, 0.9 Hz, 1H), 7.95 (d, J=8.2 Hz, 2H), 7.89 (d, J=1.2 Hz, 1H), 7.56 (d, J=8.0 Hz, 2H), 7.52 (d, J=1.2 Hz, 1H), 7.40 (s, 1H), 6.86 (dd, J=7.0, 1.7 Hz, 1H), 4.52 (d, J=5.9 Hz, 2H), 4.25-4.14 (m, 1H), 3.58-3.51 (m, 1H), 3.51-3.38 (m, 1H), 2.09-1.53 (m, 5H), 1.33-1.17 (m, 2H), 0.94 (d, J=6.4 Hz, 6H); MS (ESI(+)) m/e 405 (M+H)$^+$.

Example 878

N-(imidazo[1,2-a]pyridin-7-ylmethyl)-4-{[(2R)-2-(methoxymethyl)pyrrolidin-1-yl]carbonyl}benzamide The title compound was prepared as described in Example 1A, substituting (2R)-2-(methoxymethyl)pyrrolidine for 3-methylbutan-1-amine and 4-(imidazo[1,2-a]pyridin-7-ylmethylcarbamoyl)benzoic acid for 4-nitrobenzoic acid. $^1$H NMR (300 MHz, DMSO-$d_6$) δ ppm 9.18 (t, J=4.8 Hz, 1H), 8.49 (dd, J=7.0, 0.9 Hz, 1H), 7.95 (d, J=8.3 Hz, 2H), 7.88 (s, 1H), 7.57 (d, J=7.7 Hz, 2H), 7.52 (d, J=1.2 Hz, 1H), 7.40 (s, 1H), 6.86 (dd, J=7.0, 1.6 Hz, 1H), 4.52 (d, J=5.9 Hz, 2H), 3.62-2.88 (br m, 8H), 2.05-1.64 (br m, 4H); MS (ESI(+) m/e 393 (M+H)$^+$.

Example 881

N-(imidazo[1,2-a]pyridin-7-ylmethyl)-4-(phenylsulfonyl)benzamide

The title compound was prepared as described in Example 1A, substituting imidazo[1,2-a]pyridin-7-ylmethanamine for 3-methylbutan-1-amine and 4-(phenylsulfonyl)benzoic acid for 4-nitrobenzoic acid. $^1$H NMR (400 MHz, DMSO-$d_6$) δ ppm 9.53 (t, J=5.9 Hz, 1H), 8.83 (d, J=6.9 Hz, 1H), 8.30 (d, J=2.1 Hz, 1H), 8.16-8.07 (m, 5H), 8.03-7.97 (m, 2H), 7.80-7.61 (m, 4H), 7.46 (dd, J=6.9, 1.6 Hz, 1H), 4.68 (d, J=5.8 Hz, 2H); MS (ESI(+)) m/e 392 (M+H)$^+$.

Example 882

4-(phenylsulfonyl)-N-([1,2,4]triazolo[1,5-a]pyridin-6-ylmethyl)benzamide

The title compound was prepared as described in Example 1A, substituting [1,2,4]triazolo[1,5-a]pyridin-6-ylmethanamine for 3-methylbutan-1-amine and 4-(phenylsulfonyl)benzoic acid for 4-nitrobenzoic acid. $^1$H NMR (400 MHz, DMSO-d$_6$) δ ppm 9.32 (t, J=5.8 Hz, 1H), 8.92-8.87 (m, 1H), 8.49-8.46 (m, 1H), 8.07 (m, 4H), 8.01-7.95 (m, 2H), 7.85-7.78 (m, 1H), 7.75-7.67 (m, 1H), 7.68-7.60 (m, 3H), 4.57 (d, J=5.7 Hz, 2H); MS (ESI(+)) m/e 393 (M+H)$^+$.

Example 889

N-(imidazo[1,2-a]pyridin-7-ylmethyl)-5-{1-[2-(piperazin-1-yl)ethyl]-1H-pyrazol-4-yl}furan-2-carboxamide

Example 889A tert-butyl 4-(2-(4-(5-((imidazo[1,2-a]pyrazin-6-ylmethyl)carbamoyl)furan-2-yl)-1H-pyrazol-1-yl)ethyl)piperazine-1-carboxylate The title compound was prepared as described in Example 51A, substituting tert-butyl 4-(2-(4-(4,4,5,5-tetramethyl-1,3,2-dioxaborolan-2-yl)-1H-pyrazol-1-yl)ethyl)piperazine-1-carboxylate for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)furan-2-carboxamide for 4-bromoaniline.

Example 889B

N-(imidazo[1,2-a]pyridin-7-ylmethyl)-5-{1-[2-(piperazin-1-yl)ethyl]-1H-pyrazol-4-yl}furan-2-carboxamide The title compound was prepared as described in Example 28A, substituting tert-butyl 4-(2-(4-(5-((imidazo[1,2-a]pyrazin-6-ylmethyl)carbamoyl)furan-2-yl)-1H-pyrazol-1-yl)ethyl)piperazine-1-carboxylate for tert-butyl 4-(4-(3-imidazo[1,2-a]pyridin-6-ylureido)phenyl)-5,6-dihydropyridine-1(2H)-carboxylate. $^1$H NMR (300 MHz, DMSO-d$_6$) δ ppm 9.70 (s, 2H), 9.28 (t, J=6.1 Hz, 1H), 8.87 (d, J=6.7 Hz, 1H), 8.33 (s, 2H), 8.15 (d, J=2.1 Hz, 1H), 8.00 (s, 1H), 7.82 (s, 1H), 7.49 (dd, J=7.0, 1.5 Hz, 1H), 7.26 (d, J=3.5 Hz, 1H), 6.72 (d, J=3.5 Hz, 1H), 4.73-4.59 (m, 4H), 3.66-3.56 (m, 2H), 3.41 (d, J=11.4 Hz, 8H); MS (ESI(+)) m/e 420 (M+H)$^+$.

Example 892

5-(3-cyclopropyl-1-methyl-1H-pyrazol-5-yl)-N-(imidazo[1,2-a]pyridin-7-ylmethyl)thiophene-2-carboxamide The title compound was prepared as described in Example 857, substituting methylhydrazine for benzylhydrazine in Example 857B. $^1$H NMR (300 MHz, DMSO-d$_6$) δ 9.04 (t, J=6.0 Hz, 1H), 8.49 (dd, J=7.0, 0.9 Hz, 1H), 7.89 (s, 1H), 7.73 (d, J=3.9 Hz, 1H), 7.52 (d, J=1.2 Hz, 1H), 7.40 (s, 1H), 7.30 (d, J=3.8 Hz, 1H), 6.85 (dd, J=7.0, 1.7 Hz, 1H), 6.32 (s, 1H), 4.47 (d, J=5.9 Hz, 2H), 3.84 (s, 3H), 1.97-1.84 (m, 1H), 1.04-0.89 (m, 2H), 0.75-0.63 (m, 2H); MS (ESI(+)) m/e 378 (M+H)$^+$.

Example 893

5-[3-cyclopropyl-1-(2-methoxyethyl)-1H-pyrazol-5-yl]-N-(imidazo[1,2-a]pyridin-7-ylmethyl)thiophene-2-carboxamide The title compound was prepared as described in Example 857, substituting (2-methoxyethyl)hydrazine for benzylhydrazine in Example 857B. $^1$H NMR (300 MHz, DMSO-d$_6$) δ ppm 9.04 (t, J=6.0 Hz, 1H), 8.49 (dd, J=7.0, 1.0 Hz, 1H), 7.89 (s, 1H), 7.73 (d, J=3.9 Hz, 1H), 7.52 (d, J=1.2 Hz, 1H), 7.40 (s, 1H), 7.31 (d, J=3.8 Hz, 1H), 6.85 (dd, J=7.0, 1.7 Hz, 1H), 6.31 (s, 1H), 4.47 (d, J=5.9 Hz, 2H), 4.33 (t, J=5.5 Hz, 2H), 3.73 (t, J=5.5 Hz, 2H), 3.24 (s, 3H), 2.00-1.87 (m, 1H), 1.01-0.92 (m, 2H), 0.72-0.63 (m, 2H); MS (ESI(+)) m/e 422 (M+H)$^+$.

Example 894

N-(imidazo[1,2-a]pyrazin-6-ylmethyl)-5-{1-[2-(piperazin-1-yl)ethyl]-1H-pyrazol-4-yl}thiophene-2-carboxamide See Example 894A tert-butyl 4-(2-(4-(5-((imidazo[1,2-a]pyrazin-6-ylmethyl)carbamoyl)thiophen-2-yl)-1H-pyrazol-1-yl)ethyl)piperazine-1-carboxylate The title compound was prepared as described in Example 51A, substituting tert-butyl 4-(2-(4-(4,4,5,5-tetramethyl-1,3,2-dioxaborolan-2-yl)-1H-pyrazol-1-yl)ethyl)piperazine-1-carboxylate for 1-isobutyl-4-(4,4,5,5-tetramethyl-1,3,2-dioxaborolan-2-yl)-1H-pyrazole and 5-bromo-N-(imidazo[1,2-a]pyrazin-6-ylmethyl)thiophene-2-carboxamide for 4-bromoaniline.

Example 894B

N-(imidazo[1,2-a]pyrazin-6-ylmethyl)-5-{1-[2-(piperazin-1-yl)ethyl]-1H-pyrazol-4-yl}thiophene-2-carboxamide The title compound was prepared as described in Example 28A, substituting tert-butyl 4-(2-(4-(5-((imidazo[1,2-a]pyrazin-6-ylmethyl)carbamoyl)thiophen-2-yl)-1H-pyrazol-1-yl)ethyl)piperazine-1-carboxylate for tert-butyl 4-(4-(3-imidazo[1,2-a]pyridin-6-ylureido)phenyl)-5,6-dihydropyridine-1(2H)-carboxylate. $^1$H NMR (300 MHz, DMSO-d$_6$) δ ppm 9.52 (s, 2H), 9.28-9.17 (m, 2H), 8.68 (d, J=1.2 Hz, 1H), 8.36-8.30 (m, 1H), 8.27 (d, J=0.4 Hz, 1H), 8.05 (d, J=1.4 Hz, 1H), 7.91 (d, J=0.5 Hz, 1H), 7.81 (d, J=3.9 Hz, 1H), 7.27 (d, J=3.9 Hz, 1H), 4.71-4.48 (m, 2H), 4.07 (s, 8H), 3.37 (s, 4H); MS (ESI(+)) m/e 437 (M+H)$^+$.

Example 897

N-(imidazo[1,2-a]pyrazin-6-ylmethyl)-4-(phenylsulfonyl)benzamide

The title compound was prepared as described in Example 1A, substituting imidazo[1,2-a]pyrazin-6-ylmethanamine for 3-methylbutan-1-amine and 4-(phenylsulfonyl)benzoic acid for 4-nitrobenzoic acid. $^1$H NMR (400 MHz, DMSO-d$_6$) δ ppm 9.38 (t, J=5.8 Hz, 1H), 9.11 (s, 1H), 8.61-8.57 (m, 1H), 8.18 (s, 1H), 8.16-8.03 (m, 4H), 8.04-7.97 (m, 2H), 7.93-7.89 (m, 1H), 7.76-7.68 (m, 1H), 7.70-7.61 (m, 2H), 4.60 (d, J=5.7 Hz, 2H); MS (ESI(+)) m/e 393 (M+H)$^+$.

Example 898

N-(imidazo[1,2-a]pyridin-6-ylmethyl)-4-(phenylsulfonyl)benzamide

The title compound was prepared as described in Example 1A, substituting imidazo[1,2-a]pyridin-6-ylmethanamine for 3-methylbutan-1-amine and 4-(phenylsulfonyl)benzoic acid for 4-nitrobenzoic acid. $^{1}$H NMR (400 MHz, DMSO-d$_{6}$) δ ppm 9.47 (t, J=5.8 Hz, 1H), 8.82 (s, 1H), 8.35-8.30 (m, 1H), 8.19-8.14 (m, 1H), 8.12-8.08 (m, 4H), 8.05-7.88 (m, 4H), 7.76-7.68 (m, 1H), 7.68-7.60 (m, 2H), 4.61 (d, J=5.8 Hz, 2H); MS (ESI(+)) m/e 392 (M+H)$^{+}$.

Example 899

N-(imidazo[1,2-a]pyridin-7-ylmethyl)-5-[1-(2-methylpropyl)-1H-pyrazol-5-yl]thiophene-2-carboxamide The title compound was prepared as described in Example 51A, substituting 1-isobutyl-5-(4,4,5,5-tetramethyl-1,3,2-dioxaborolan-2-yl)-1H-pyrazole for 1-isobutyl-4-(4,4,5,5-tetramethyl-1,3,2-dioxaborolan-2-yl)-1H-pyrazole and 5-bromo-N-(imidazo[1,2-a]pyridin-7-ylmethyl)thiophene-2-carboxamide for 4-bromoaniline. $^{1}$H NMR (500 MHz, DMSO-d$_{6}$) δ ppm 9.24 (t, J=5.9 Hz, 1H), 8.51 (dd, J=7.0, 0.7 Hz, 1H), 7.90 (d, J=0.8 Hz, 1H), 7.87 (d, J=3.9 Hz, 1H), 7.57-7.49 (m, 2H), 7.43 (s, 1H), 7.39 (d, J=3.9 Hz, 1H), 6.87 (dd, J=7.0, 1.6 Hz, 1H), 6.56 (d, J=1.9 Hz, 1H), 4.51 (d, J=5.9 Hz, 2H), 4.08 (d, J=7.4 Hz, 2H), 2.09 (dp, J=13.8, 6.9 Hz, 1H), 0.80 (d, J=6.7 Hz, 6H); MS (ESI(+)) m/e 380 (M+H)$^{+}$.

Example 900 tert-butyl 4-{4-[(imidazo[1,2-a]pyridin-7-ylacetyl)amino]phenyl}piperidine-1-carboxylate The title compound was prepared as described in Example 1A, substituting tert-butyl 4-(4-aminophenyl)piperidine-1-carboxylate for 3-methylbutan-1-amine and 2-(imidazo[1,2-a]pyridin-7-yl)acetic acid for 4-nitrobenzoic acid. $^{1}$H NMR (400 MHz, DMSO-d$_{6}$) δ ppm 10.16 (s, 1H), 8.55 (d, J=6.9 Hz, 1H), 7.97 (s, 1H), 7.65-7.53 (m, 2H), 7.53-7.47 (m, 2H), 7.20-7.13 (m, 2H), 7.01-6.95 (m, 1H), 4.09-4.00 (m, 2H), 3.72 (s, 2H), 2.87-2.55 (m, 3H), 1.76-1.67 (m, 2H), 1.50-1.35 (m, 11H); MS (ESI(+)) m/e 435 (M+H)$^{+}$.

Example 901

N-[(3-chloroimidazo[1,2-a]pyrazin-6-yl)methyl]-4-[(cyclopentylacetyl)amino]benzamide The title compound was prepared as described in Example 396, substituting 4-(2-cyclopentylacetamido)-N-(imidazo[1,2-a]pyrazin-6-ylmethyl)benzamide for 4-(3-imidazo[1,2-a]pyridin-6-ylureido)-N-((tetrahydro-2H-pyran-2-yl)methyl)benzamide. $^{1}$H NMR (400 MHz, DMSO-d$_{6}$) δ ppm 10.07 (s, 1H), 9.09 (s, 1H), 8.95 (t, J=5.7 Hz, 1H), 8.28 (s, 1H), 7.95 (s, 1H), 7.87-7.81 (m, 2H), 7.69-7.63 (m, 2H), 4.61 (d, J=5.6 Hz, 2H), 2.38-2.12 (m, 3H), 1.80-1.64 (m, 2H), 1.66-1.40 (m, 4H), 1.25-1.09 (m, 2H); MS (ESI(+)) m/e 412 (M+H)$^{+}$.

Example 902

N-{4-[1-(2,4-difluorobenzoyl)piperidin-4-yl]phenyl}-2-(imidazo[1,2-a]pyridin-7-yl)acetamide Example 902A 2-(imidazo[1,2-a]pyridin-7-yl)-N-(4-(piperidin-4-yl)phenyl)acetamide The title compound was prepared as described in Example 28A, substituting tert-butyl 4-{4-[(imidazo[1,2-a]pyridin-7-ylacetyl)amino]phenyl}piperidine-1-carboxylate for tert-butyl 4-(4-(3-imidazo[1,2-a]pyridin-6-ylureido)phenyl)-5,6-dihydropyridine-1(2H)-carboxylate.

Example 902B

N-{4-[1-(2,4-difluorobenzoyl)piperidin-4-yl]phenyl}-2-(imidazo[1,2-a]pyridin-7-yl)acetamide The title compound was prepared as described in Example 1A, substituting 2-(imidazo[1,2-a]pyridin-7-yl)-N-(4-(piperidin-4-yl)phenyl)acetamide for 3-methylbutan-1-amine and 2,4-difluorobenzoic acid for 4-nitrobenzoic acid. $^{1}$H NMR (400 MHz, DMSO-d$_{6}$) δ ppm 10.29 (s, 1H), 8.84 (d, J=6.9 Hz, 1H), 8.31 (d, J=1.9 Hz, 1H), 8.14 (d, J=2.1 Hz, 1H), 7.89 (s, 1H), 7.56-7.47 (m, 3H), 7.47-7.40 (m, 1H), 7.42-7.31 (m, 1H), 7.23-7.15 (m, 3H), 4.68-4.60 (m, 1H), 3.95 (bs, 2H), 3.58-3.44 (m, 1H), 3.26-3.09 (m, 1H), 2.94-2.70 (m, 2H), 1.94-1.81 (m, 1H), 1.79-1.40 (m, 3H); MS (ESI(+)) m/e 475 (M+H)$^{+}$.

Example 903

2-(imidazo[1,2-a]pyridin-7-yl)-N-{4-[1-(2-methylpropanoyl)piperidin-4-yl]phenyl}acetamide The title compound was prepared as described in Example 1A, substituting 2-(imidazo[1,2-a]pyridin-7-yl)-N-(4-(piperidin-4-yl)phenyl)acetamide for 3-methylbutan-1-amine and isobutyric acid for 4-nitrobenzoic acid. $^{1}$H NMR (400 MHz, DMSO-d$_{6}$) δ ppm 10.28 (s, 1H), 8.84 (d, J=6.9 Hz, 1H), 8.34-8.28 (m, 1H), 8.18-8.14 (m, 1H), 7.89 (s, 1H), 7.55-7.43 (m, 3H), 7.22-7.16 (m, 2H), 4.60-4.50 (m, 1H), 4.09-4.00 (m, 1H), 3.96 (s, 2H), 3.18-3.01 (m, 1H), 2.96-2.82 (m, 1H), 2.79-2.67 (m, 1H), 2.63-2.50 (m, 1H), 1.87-1.70 (m, 2H), 1.57-1.30 (m, 2H), 1.07-0.93 (m, 6H); MS (ESI(+)) m/e 405 (M+H)$^{+}$.

Example 904

1-[(3-chloroimidazo[1,2-a]pyridin-7-yl)methyl]-3-{4-[1-(2-methylpropanoyl)piperidin-4-yl]phenyl}urea The title compound was prepared as described in Example 396, substituting 1-(imidazo[1,2-a]pyridin-7-ylmethyl)-3-(4-(1-isobutyrylpiperidin-4-yl)phenyl)urea for 4-(3-imidazo[1,2-a]pyridin-6-ylureido)-N-((tetrahydro-2H-pyran-2-yl)methyl)benzamide. $^{1}$H NMR (400 MHz, DMSO-d$_{6}$) δ ppm 8.31 (bs, 1H), 8.24 (d, J=7.0 Hz, 1H), 7.58 (s, 1H), 7.46 (s, 1H), 7.35-7.29 (m, 2H), 7.12-7.02 (m, 3H), 6.62-6.55 (m, 1H), 4.38 (d, J=6.0 Hz, 2H), 4.36-4.19 (m, 2H), 2.93-2.62 (m, 4H), 1.85-1.77 (m, 2H), 1.53-1.37 (m, 2H), 1.03 (d, J=6.7 Hz, 6H); MS (ESI(+)) m/e 454 (M+H)$^{+}$.

Example 905

N-{4-[1-(2-fluorobenzoyl)piperidin-4-yl]phenyl}-2-(imidazo[1,2-a]pyridin-7-yl)acetamide The title compound was prepared as described in Example 1A, substituting 2-(imidazo[1,2-a]pyridin-7-yl)-N-(4-(piperidin-4-yl)phenyl)acetamide for 3-methylbutan-1-amine and 2-fluorobenzoic acid for 4-nitrobenzoic acid. $^{1}$H NMR (400 MHz, methanol-d$_{4}$) δ ppm 8.75 (d, J=7.0 Hz, 1H), 8.18 (d, J=2.2 Hz, 1H), 8.00 (d, J=2.2 Hz, 1H), 7.89 (s, 1H), 7.56-7.35 (m, 5H), 7.33-7.25 (m, 1H), 7.25-7.17 (m, 3H), 4.83-4.74 (m, 1H), 3.99 (s, 2H), 3.68-3.59 (m, 1H), 3.31-3.18 (m, 1H), 3.03-2.76 (m, 2H), 2.00-1.92 (m, 1H), 1.87-1.51 (m, 3H); MS (ESI(+)) m/e 457 (M+H)+.

Example 906

N-(imidazo[1,2-a]pyridin-7-ylmethyl)-5-[1-methyl-3-(2-methylpropyl)-1H-pyrazol-5-yl]thiophene-2-carboxamide The title compound was prepared as described in Example 857, substituting 4-methylpent-1-yne for ethynylcyclopropane in Example 857A and methylhydrazine for benzylhydrazine in Example 857B. $^1$H NMR (400 MHz, DMSO-d$_6$) δ ppm 9.05 (t, J=5.9 Hz, 1H), 8.49 (dd, J=6.9, 0.9 Hz, 1H), 7.89 (s, 1H), 7.74 (d, J=3.9 Hz, 1H), 7.52 (d, J=1.2 Hz, 1H), 7.40 (s, 1H), 7.35 (d, J=3.8 Hz, 1H), 6.85 (dd, J=6.9, 1.7 Hz, 1H), 6.46 (s, 1H), 4.48 (d, J=5.9 Hz, 2H), 3.75 (s, 3H), 2.54-2.51 (m, 2H), 1.96-1.84 (m, 1H), 0.94 (d, J=6.6 Hz, 6H); MS (ESI(+)) m/e 394 (M+H)+.

Example 907

5-[1-benzyl-3-(2-methylpropyl)-1H-pyrazol-5-yl]-N-(imidazo[1,2-a]pyridin-7-ylmethyl)thiophene-2-carboxamide The title compound was prepared as described in Example 857, substituting 4-methylpent-1-yne for ethynylcyclopropane in Example 857A. $^1$H NMR (300 MHz, DMSO-d$_6$) δ ppm 9.05 (t, J=5.8 Hz, 1H), 8.49 (dd, J=7.0, 0.9 Hz, 1H), 7.89 (s, 1H), 7.76 (d, J=3.9 Hz, 1H), 7.52 (d, J=1.2 Hz, 1H), 7.42-7.38 (m, 2H), 7.37-7.23 (m, 3H), 7.17-7.11 (m, 2H), 6.85 (dd, J=7.0, 1.7 Hz, 1H), 6.56 (s, 1H), 5.35 (bs, 2H), 4.48 (d, J=5.9 Hz, 2H), 2.49-2.45 (m, 2H), 1.87-1.74 (m, 1H), 0.87 (d, J=6.6 Hz, 6H); MS (ESI(+)) m/e 470 (M+H)+.

Example 908

4-[(cyclopentylacetyl)amino]-2-fluoro-N-(imidazo[1,2-a]pyrazin-6-ylmethyl)benzamide The title compound was prepared as described in Example 1A, substituting imidazo[1,2-a]pyrazin-6-ylmethanamine for 3-methylbutan-1-amine and 4-(2-cyclopentylacetamido)-2-fluorobenzoic acid for 4-nitrobenzoic acid. $^1$H NMR (400 MHz, DMSO-d$_6$) δ ppm 10.27 (s, 1H), 9.13 (s, 1H), 8.73-8.65 (m, 1H), 8.59-8.56 (m, 1H), 8.24 (s, 1H), 7.94-7.91 (m, 1H), 7.75-7.67 (m, 2H), 7.34 (dd, J=8.5, 1.9 Hz, 1H), 4.59 (d, J=5.8 Hz, 2H), 2.37-2.32 (m, 2H), 2.32-2.16 (m, 1H), 1.82-1.68 (m, 2H), 1.67-1.44 (m, 4H), 1.26-1.10 (m, 2H); MS (ESI(+)) m/e 396 (M+H)+.

Example 909

N-(2,5-difluorobenzyl)-N'-(imidazo[1,2-a]pyridin-7-ylmethyl)benzene-1,4-dicarboxamide The title compound was prepared as described in Example 1A, substituting 2,5-difluorobenzyl amine for 3-methylbutan-1-amine and 4-(imidazo[1,2-a]pyridin-7-ylmethylcarbamoyl)benzoic acid for 4-nitrobenzoic acid. $^1$H NMR (400 MHz, DMSO-d$_6$) δ ppm 9.42 (t, J=5.9 Hz, 1H), 9.20 (t, J=5.8 Hz, 1H), 8.83 (d, J=6.9 Hz, 1H), 8.29 (d, J=2.0 Hz, 1H), 8.10 (d, J=2.0 Hz, 1H), 8.04-8.00 (m, 4H), 7.78 (s, 1H), 7.45 (dd, J=6.9, 1.6 Hz, 1H), 7.32-7.12 (m, 3H), 4.69 (d, J=5.8 Hz, 2H), 4.52 (d, J=5.7 Hz, 2H); MS (ESI(+)) m/e 421 (M+H)+.

Example 910

N-(imidazo[1,2-a]pyridin-7-ylmethyl)-4-{[2-(propan-2-yl)pyrrolidin-1-yl]carbonyl}benzamide The title compound was prepared as described in Example 1A, substituting (propan-2-yl)pyrrolidine for 3-methylbutan-1-amine and 4-(imidazo[1,2-a]pyridin-7-ylmethylcarbamoyl)benzoic acid for 4-nitrobenzoic acid. $^1$H NMR (400 MHz, DMSO-d$_6$) δ ppm 9.44-9.36 (m, 1H), 8.86 (d, J=6.9 Hz, 1H), 8.31 (d, J=2.1 Hz, 1H), 8.14 (d, J=2.1 Hz, 1H), 8.01-7.95 (m, 2H), 7.80 (s, 1H), 7.65-7.59 (m, 2H), 7.49 (d, J=7.6 Hz, 1H), 4.69 (d, J=5.8 Hz, 2H), 4.15-4.05 (m, 1H), 3.47-3.19 (m, 2H), 2.39-2.26 (m, 1H), 1.96-1.57 (m, 4H), 0.93-0.85 (m, 6H); MS (ESI(+)) m/e 391 (M+H)+.

Example 911

N-{4-[5-(2,2-dimethylpropyl)-1,3,4-oxadiazol-2-yl]phenyl}-2-(imidazo[1,2-a]pyridin-7-yl)acetamide Example 911A N'-(3,3-dimethylbutanoyl)-4-nitrobenzohydrazide A suspension of 4-nitrobenzohydrazide (0.500 g, 2.76 mmol), and 4-methylmorpholine (0.455 ml, 4.14 mmol) were stirred in dichloromethane (20 ml). 3,3-Dimethylbutanoyl chloride (0.422 ml, 3.04 mmol) was added and the reaction mixture was stirred for 2 hours. Normal phase chromatography of the crude reaction mixture gave the title compound.

Example 911B 2-neopentyl-5-(4-nitrophenyl)-1,3,4-oxadiazole

A mixture of N'-(3,3-dimethylbutanoyl)-4-nitrobenzohydrazide (0.556 g, 1.991 mmol) and methyl N-(triethylammoniumsulfonyl)carbamate (0.572 g, 2.389 mmol) in tetrahydrofuran (10 ml) was heated to 120° C. in a microwave for 45 minutes. The crude reaction mixture was concentrated and purified by normal phase chromatography to give the title compound.

Example 911C 4-(5-neopentyl-1,3,4-oxadiazol-2-yl)aniline

The title compound was prepared as described in Example 1B, substituting 2-neopentyl-5-(4-nitrophenyl)-1,3,4-oxadiazole for tert-butyl 4-(4-(1-(benzyloxycarbonyl)azetidine-3-carboxamido)phenoxy)piperidine-1-carboxylate.

Example 911D

N-{4-[5-(2,2-dimethylpropyl)-1,3,4-oxadiazol-2-yl]phenyl}-1-(pyridazin-3-yl)azetidine-3-carboxamide The title compound was prepared as described in Example 1A, substituting 4-(5-neopentyl-1,3,4-oxadiazol-2-yl)aniline for tert-butyl 4-(4-aminophenoxy)piperidine-1-carboxylate and 2-(imidazo[1,2-a]pyridin-7-yl)acetic acid for 1-(benzyloxycarbonyl)azetidine-3-carboxylic acid. $^1$H NMR (400 MHz, DMSO-d$_6$) δ ppm 10.55 (s, 1H), 8.49 (d, J=7.0 Hz, 1H), 7.96-7.89 (m, 3H), 7.86-7.79 (m, 2H), 7.53 (d, J=1.1 Hz, 1H), 7.49 (s, 1H), 6.88 (dd, J=7.0, 1.6 Hz, 1H), 3.77 (s, 2H), 2.82 (s, 2H), 1.02 (s, 9H); MS (ESI(+)) m/e 390 (M+H)⁺.

Example 912 tert-butyl 4-(3-fluoro-4-{[(imidazo[1,2-a]pyridin-7-ylmethyl)carbamoyl]amino}phenyl)piperidine-1-carboxylate

Example 912A tert-butyl 4-(4-amino-3-fluorophenyl)-5,6-dihydropyridine-1(2H)-carboxylate The title compound was prepared as described in Example 51A, substituting tert-butyl 4-(4,4,5,5-tetramethyl-1,3,2-dioxaborolan-2-yl)-5,6-dihydropyridine-1(2H)-carboxylate for 1-isobutyl-4-(4,4,5,5-tetramethyl-1,3,2-dioxaborolan-2-yl)-1H-pyrazole and 4-bromo-2-fluoroaniline for 4-bromoaniline.

Example 912B tert-butyl 4-(4-amino-3-fluorophenyl)piperidine-1-carboxylate

The title compound was prepared as described in Example 1B, substituting tert-butyl 4-(4-amino-3-fluorophenyl)-5,6-dihydropyridine-1(2H)-carboxylate for N-isopentyl-4-nitrobenzamide.

Example 912C tert-butyl 4-(3-fluoro-4-{[(imidazo[1,2-a]pyridin-7-ylmethyl)carbamoyl]amino}phenyl)piperidine-1-carboxylate The title compound was prepared as described in Example 1C, substituting tert-butyl 4-(4-amino-3-fluorophenyl)piperidine-1-carboxylate for 4-amino-N-isopentylbenzamide and imidazo[1,2-a]pyridin-7-ylmethanamine for imidazo[1,2-a]pyridin-6-amine. ¹H NMR (400 MHz, DMSO-d₆) δ ppm 8.49 (d, J=7.0 Hz, 1H), 8.37 (d, J=2.3 Hz, 1H), 7.97 (t, J=8.5 Hz, 1H), 7.88 (s, 1H), 7.52 (d, J=1.2 Hz, 1H), 7.39 (s, 1H), 7.12-7.04 (m, 2H), 7.00-6.94 (m, 1H), 6.82 (dd, J=7.0, 1.6 Hz, 1H), 4.35 (d, J=5.9 Hz, 2H), 4.10-4.01 (m, 2H), 2.89-2.56 (m, 3H), 1.77-1.68 (m, 2H), 1.41 (s, 11H); MS (ESI(+)) m/e 468 (M+H)⁺.

Example 958

N-(imidazo[1,2-a]pyridin-7-ylmethyl)-4-[1-(pyrrolidin-1-ylcarbonyl)piperidin-4-yl]benzamide The title compound was prepared as described in Example 1068, substituting pyrrolidine-1-carbonyl chloride for piperidine-1-carbonyl chloride. ¹H NMR (400 MHz, DMSO-d₆) δ ppm 9.28-9.21 (m, 1H), 8.85 (d, J=7.0 Hz, 1H), 8.31 (d, J=2.1 Hz, 1H), 8.13 (d, J=2.1 Hz, 1H), 7.91-7.85 (m, 2H), 7.77 (s, 1H), 7.47 (dd, J=7.0, 1.6 Hz, 1H), 7.43-7.36 (m, 2H), 4.67 (d, J=5.8 Hz, 2H), 3.83-3.75 (m, 2H), 3.35-3.23 (m, 4H), 2.85-2.72 (m, 3H), 1.81-1.69 (m, 6H), 1.71-1.53 (m, 2H); MS (ESI(+)) m/e 432 (M+H)⁺.

Example 1067 tert-butyl 4-{3-fluoro-4-[(imidazo[1,2-a]pyridin-7-ylacetyl)amino]phenyl}piperidine-1-carboxylate The title compound was prepared as described in Example 1A, substituting tert-butyl 4-(4-amino-3-fluorophenyl)piperidine-1-carboxylate for 3-methylbutan-1-amine and 2-(imidazo[1,2-a]pyridin-7-yl)acetic acid hydrochloride for 4-nitrobenzoic acid. ¹H NMR (400 MHz, DMSO-d₆) δ ppm 9.97 (s, 1H), 8.58 (d, J=6.9 Hz, 1H), 8.00 (s, 1H), 7.77-7.67 (m, 2H), 7.58 (d, J=1.4 Hz, 1H), 7.15 (dd, J=12.2, 1.9 Hz, 1H), 7.06-6.99 (m, 2H), 4.10-4.01 (m, 2H), 3.82 (bs, 2H), 2.94-2.58 (m, 3H), 1.78-1.69 (m, 2H), 1.53-1.36 (m, 11H); MS (ESI(+)) m/e 453 (M+H)⁺.

Example 1068

N-(imidazo[1,2-a]pyridin-7-ylmethyl)-4-[1-(piperidin-1-ylcarbonyl)piperidin-4-yl]benzamide A solution of piperidine-1-carbonyl chloride (0.033 g, 0.224 mmol) in N-methyl-2-pyrrolidinone (1 mL) was treated with N-(imidazo[1,2-a]pyridin-7-ylmethyl)-4-(piperidin-4-yl)benzamide (0.05 g, 0.150 mmol) and triethylamine (0.042 ml, 0.299 mmol) and the reaction mixture was stirred at room temperature for 18 hours. The mixture was purified by reverse-phase HPLC to give the title compound. ¹H NMR (400 MHz, DMSO-d₆) δ ppm 9.24 (t, J=5.9 Hz, 1H), 8.84 (d, J=7.0 Hz, 1H), 8.30 (d, J=2.1 Hz, 1H), 8.13 (d, J=2.1 Hz, 1H), 7.91-7.84 (m, 2H), 7.76 (s, 1H), 7.50-7.44 (m, 1H), 7.42-7.36 (m, 2H), 4.67 (d, J=5.8 Hz, 2H), 3.71-3.62 (m, 2H), 3.16-3.10 (m, 4H), 2.89-2.68 (m, 3H), 1.81-1.72 (m, 2H), 1.68-1.44 (m, 8H); MS (ESI(+)) m/e 446 (M+H)⁺.

Example 1069

1-[4-(1-benzoylpiperidin-4-yl)-2-fluorophenyl]-3-(imidazo[1,2-a]pyridin-7-ylmethyl)urea

Example 1069A 1-(2-fluoro-4-(piperidin-4-yl)phenyl)-3-(imidazo[1,2-a]pyridin-7-ylmethyl)urea The title compound was prepared as described in Example 28A, substituting tert-butyl 4-(3-fluoro-4-{[(imidazo[1,2-a]pyridin-7-ylmethyl)carbamoyl]amino}phenyl)piperidine-1-carboxylate for tert-butyl 4-(4-(3-imidazo[1,2-a]pyridin-6-ylureido)phenyl)-5,6-dihydropyridine-1(2H)-carboxylate.

Example 1069B

1-[4-(1-benzoylpiperidin-4-yl)-2-fluorophenyl]-3-(imidazo[1,2-a]pyridin-7-ylmethyl)urea The title compound was prepared as described in Example 1A, substituting 1-(2-fluoro-4-(piperidin-4-yl)phenyl)-3-(imidazo[1,2-a]pyridin-7-ylmethyl)urea for 3-methylbutan-1-amine and benzoic acid for 4-nitrobenzoic acid. ¹H NMR (400 MHz, methanol-d₄) δ ppm 8.73 (d, J=7.0 Hz, 1H), 8.16 (d, J=2.1 Hz, 1H), 7.99-7.95 (m, 1H), 7.85-7.77 (m, 2H), 7.50-7.39 (m, 6H), 7.11-6.99 (m, 2H), 4.84-4.72 (m, 1H), 4.60 (bs, 2H), 3.93-3.73 (m, 1H), 3.29-3.15 (m, 1H), 3.00-2.76 (m, 2H), 2.03-1.84 (m, 1H), 1.83-1.53 (m, 3H); MS (ESI(+)) m/e 472 (M+H)⁺.

TABLE 25

The following Examples were prepared essentially as described in Example 1069, substituting an appropriate carboxylic acid in Example 1069B.

| Ex | Name | MS |
|---|---|---|
| 1070 | 1-{4-[1-(2,2-dimethylpropanoyl)piperidin-4-yl]-2-fluorophenyl}-3-(imidazo[1,2-a]pyridin-7-ylmethyl)urea | (ESI(+)) m/e 452 (M + H)$^+$ |
| 1071 | 1-{4-[1-(3,3-dimethylbutanoyl)piperidin-4-yl]-2-fluorophenyl}-3-(imidazo[1,2-a]pyridin-7-ylmethyl)urea | (ESI(+)) m/e 466 (M + H)$^+$ |
| 1072 | 1-{2-fluoro-4-[1-(4-methylpentanoyl)piperidin-4-yl]phenyl}-3-(imidazo[1,2-a]pyridin-7-ylmethyl)urea | (ESI(+)) m/e 466 (M + H)$^+$ |
| 1073 | 1-(2-fluoro-4-{1-[(2S)-2-methylbutanoyl]piperidin-4-yl}phenyl)-3-(imidazo[1,2-a]pyridin-7-ylmethyl)urea | (ESI(+)) m/e 452 (M + H)$^+$ |
| 1074 | 1-{2-fluoro-4-[1-(tetrahydro-2H-pyran-4-ylcarbonyl)piperidin-4-yl]phenyl}-3-(imidazo[1,2-a]pyridin-7-ylmethyl)urea | (ESI(+)) m/e 480 (M + H)$^+$ |
| 1075 | 1-{2-fluoro-4-[1-(pyridin-2-ylcarbonyl)piperidin-4-yl]phenyl}-3-(imidazo[1,2-a]pyridin-7-ylmethyl)urea | (ESI(+)) m/e 473 (M + H)$^+$ |
| 1076 | 1-{4-[1-(2-cyanobenzoyl)piperidin-4-yl]-2-fluorophenyl}-3-(imidazo[1,2-a]pyridin-7-ylmethyl)urea | (ESI(+)) m/e 497 (M + H)$^+$ |
| 1078 | 1-{2-fluoro-4-[1-(2-methylpropanoyl)piperidin-4-yl]phenyl}-3-(imidazo[1,2-a]pyridin-7-ylmethyl)urea | (ESI(+)) m/e 438 (M + H)$^+$ |

Example 1077

4-{4-[(imidazo[1,2-a]pyridin-7-ylmethyl)carbamoyl]phenyl}-N,N-dimethylpiperidine-1-carboxamide The title compound was prepared as described in Example 1068, substituting N,N-dimethylamine-1-carbonyl chloride for piperidine-1-carbonyl chloride. $^1$H NMR (400 MHz, methanol-d$_4$) δ ppm 8.75 (d, J=7.0 Hz, 1H), 8.19-8.15 (m, 1H), 8.01-7.97 (m, 1H), 7.89-7.83 (m, 2H), 7.80 (s, 1H), 7.51-7.46 (m, 1H), 7.44-7.38 (m, 2H), 4.77 (s, 2H), 3.85-3.76 (m, 2H), 2.98-2.77 (m, 9H), 1.90-1.81 (m, 2H), 1.81-1.66 (m, 2H); MS (ESI(+)) m/e 406 (M+H)$^+$.

Example 1079

4-[(cyclopentylacetyl)amino]-N-[(7-fluoroimidazo[1,2-a]pyridin-6-yl)methyl]benzamide The title compound was prepared as described in Example 1A, substituting (7-fluoroimidazo[1,2-a]pyridin-6-yl)methanamine for 3-methylbutan-1-amine and 4-(2-cyclopentylacetamido)benzoic acid for 4-nitrobenzoic acid. $^1$H NMR (400 MHz, DMSO-d$_6$) δ ppm 10.08 (s, 1H), 8.87 (t, J=5.5 Hz, 1H), 8.56 (d, J=7.3 Hz, 1H), 7.96 (s, 1H), 7.88-7.82 (m, 2H), 7.71-7.64 (m, 2H), 7.52 (d, J=1.2 Hz, 1H), 7.46-7.39 (m, 1H), 4.49 (d, J=5.5 Hz, 2H), 2.36-2.30 (m, 2H), 2.31-2.15 (m, 1H), 1.81-1.68 (m, 2H), 1.68-1.43 (m, 4H), 1.26-1.10 (m, 2H); MS (ESI(+)) m/e 395 (M+H)$^+$.

Example 1080

N-[(7-fluoroimidazo[1,2-a]pyridin-6-yl)methyl]-5-[1-(2-methylpropyl)-1H-pyrazol-4-yl]thiophene-2-carboxamide The title compound was prepared as described in Example 1A, substituting (7-fluoroimidazo[1,2-a]pyridin-6-yl)methanamine for 3-methylbutan-1-amine and 5-(1-isobutyl-1H-pyrazol-4-yl)thiophene-2-carboxylic acid for 4-nitrobenzoic acid. $^1$H NMR (300 MHz, DMSO-d$_6$) δ ppm 8.93 (t, J=5.5 Hz, 1H), 8.58 (d, J=7.7 Hz, 1H), 8.14 (d, J=0.8 Hz, 1H), 7.98 (s, 1H), 7.80 (d, J=0.8 Hz, 1H), 7.73 (d, J=3.8 Hz, 1H), 7.53 (d, J=1.3 Hz, 1H), 7.44 (d, J=11.0 Hz, 1H), 7.21 (d, J=3.8 Hz, 1H), 4.48 (d, J=5.5 Hz, 2H), 3.92 (d, J=7.2 Hz, 2H), 2.21-2.05 (m, 1H), 0.85 (d, J=6.7 Hz, 6H); MS (ESI(+)) m/e 398 (M+H)$^+$.

Example 1081

N-[4-(1-benzoylpiperidin-4-yl)-2-fluorophenyl]-2-(imidazo[1,2-a]pyridin-7-yl)acetamide

Example 1081A

N-(2-fluoro-4-(piperidin-4-yl)phenyl)-2-(imidazo[1,2-a]pyridin-7-yl)acetamide

The title compound was prepared as described in Example 28A, substituting tert-butyl 4-{3-fluoro-4-[(imidazo[1,2-a]pyridin-7-ylacetyl)amino]phenyl}piperidine-1-carboxylate for tert-butyl 4-(4-(3-imidazo[1,2-a]pyridin-6-ylureido)phenyl)-5,6-dihydropyridine-1(2H)-carboxylate.

Example 1081B

N-[4-(1-benzoylpiperidin-4-yl)-2-fluorophenyl]-2-(imidazo[1,2-a]pyridin-7-yl)acetamide The title compound was prepared as described in Example 1A, substituting N-(2-fluoro-4-(piperidin-4-yl)phenyl)-2-(imidazo[1,2-a]pyridin-7-yl)acetamide for 3-methylbutan-1-amine and benzoic acid for 4-nitrobenzoic acid. $^1$H NMR (400 MHz, methanol-d$_4$) δ ppm 8.75 (dd, J=6.9, 0.9 Hz, 1H), 8.19 (dd, J=2.2, 0.8 Hz, 1H), 8.00 (d, J=2.2 Hz, 1H), 7.91 (s, 1H), 7.78 (t, J=8.2 Hz, 1H), 7.53-7.38 (m, 6H), 7.16-7.04 (m, 2H), 4.83-4.69 (m, 1H), 4.06 (s, 2H), 3.91-3.79 (m, 1H), 3.30-3.14 (m, 1H), 3.03-2.81 (m, 2H), 2.07-1.54 (m, 4H); MS (ESI(+)) m/e 457 (M+H)$^+$.

What is claimed is:

1. A compound of Formula (IA), or a therapeutically acceptable salt thereof,

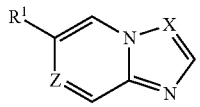

Formula (IA)

wherein

X is N or CY$^1$;

Y$^1$ is independently selected from the group consisting of hydrogen, OH, CN, F, Cl, Br, and I;

R$^1$ is independently selected from the group consisting of NHC(O)NHR$^3$, NHC(O)NH(CH$_2$)$_m$R$^{3x}$, CH$_2$NHC(O)NHR$^3$, NHC(O)R$^3$, NHC(O)(CH$_2$)$_n$R$^3$, C(O)NH(CH$_2$)$_n$R$^3$, NHC(O)(CH$_2$)$_m$R$^{3x}$, C(O)NH(CH$_2$)$_m$R$^{3x}$, CH$_2$C(O)NHR$^3$, and CH$_2$NHC(O)R$^3$; and Z is CH, C—F, C—Cl, C—Br, C—I or N; or X is N or CY$^1$;

Y$^1$ is independently selected from the group consisting of hydrogen, alkyl, alkoxy, haloalkyl, hydroxyalkyl, OH, CN, F, Cl, Br, and I;

R$^1$ is hydrogen, F, Cl, Br, or I;

Z is CR$^2$; and

R$^2$ is independently selected from the group consisting of NHC(O)NHR$^3$, NHC(O)NH(CH$_2$)$_m$R$^{3x}$, CH$_2$NHC(O)NHR$^3$, NHC(O)R$^3$, NHC(O)(CH$_2$)$_n$R$^3$, C(O)NH(CH$_2$)$_n$R$^3$, NHC(O)(CH$_2$)$_m$R$^{3x}$, C(O)NH(CH$_2$)$_m$R$^{3x}$, CH$_2$C(O)NHR$^3$, and CH$_2$NHC(O)R$^3$; and R$^3$ is independently selected from the group consisting of furanyl, thienyl, pyrrolyl, imidazolyl, pyrazolyl, triazolyl, tetrazolyl, isoxazolyl, thiazolyl, isothiazolyl, thiadiazolyl, oxadiazolyl, and oxatriazolyl; wherein each R$^3$ furanyl, thienyl, pyrrolyl, imidazolyl, pyrazolyl, triazolyl, tetrazolyl, isoxazolyl, thiazolyl, isothiazolyl, thiadiazolyl, oxadiazolyl, and oxatriazolyl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, CO(O)R$^4$, OC(O)R$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NR$^4$C(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^{3x}$ is independently selected from the group consisting of furanyl, thienyl, pyrrolyl, imidazolyl, pyrazolyl, triazolyl, tetrazolyl, isoxazolyl, thiazolyl, isothiazolyl, thiadiazolyl, oxadiazolyl, and oxatriazolyl; wherein each R$^{3x}$ furanyl, thienyl, pyrrolyl, imidazolyl, pyrazolyl, triazolyl, tetrazolyl, isoxazolyl, thiazolyl, isothiazolyl, thiadiazolyl, oxadiazolyl, and oxatriazolyl is substituted with one, two, three or four substituents independently selected from the group consisting of R$^4$, OR$^4$, SR$^4$, S(O)R$^4$, SO$_2$R$^4$, C(O)R$^4$, CO(O)R$^4$, OC(O)R$^4$, OC(O)OR$^4$, NH$_2$, NHR$^4$, N(R$^4$)$_2$, NHC(O)R$^4$, NR$^4$C(O)R$^4$, NHS(O)$_2$R$^4$, NR$^4$S(O)$_2$R$^4$, NHC(O)OR$^4$, NHC(O)NH$_2$, NHC(O)NHR$^4$, NHC(O)N(R$^4$)$_2$, NR$^4$C(O)NHR$^4$, NR$^4$C(O)N(R$^4$)$_2$, C(O)NH$_2$, C(O)NHR$^4$, C(O)N(R$^4$)$_2$, C(O)NHOH, C(O)NHOR$^4$, C(O)NHSO$_2$R$^4$, C(O)NR$^4$SO$_2$R$^4$, SO$_2$NH$_2$, SO$_2$NHR$^4$, SO$_2$N(R$^4$)$_2$, C(O)H, C(O)OH, C(N)NH$_2$, C(N)NHR$^4$, C(N)N(R$^4$)$_2$, CNOH, CNOCH$_3$, OH, CN, N$_3$, NO$_2$, F, Cl, Br and I;

R$^4$, at each occurrence, is independently selected from the group consisting of alkyl, alkenyl, alkynyl, aryl, cycloalkyl, cycloalkenyl, and 3-12 membered heterocyclyl; wherein each R$^4$ alkyl, alkenyl, and alkynyl is optionally substituted with one, two, three or four substituents independently selected from the group consisting of R$^5$, OR$^5$, SR$^5$, S(O)R$^5$, SO$_2$R$^5$, C(O)R$^5$, CO(O)R$^5$, OC(O)R$^5$, OC(O)OR$^5$, NH$_2$, NHR$^5$, N(R$^5$)$_2$, NHC(O)R$^5$, NR$^5$C(O)R$^5$, NHS(O)$_2$R$^5$, N R$^5$S(O)$_2$R$^5$, NHC(O)OR$^5$, NR$^5$C(O)OR$^5$, NHC(O)NH$_2$, NHC(O)NHR$^5$, NHC(O)N(R$^5$)$_2$, NR$^5$C(O)NHR$^5$, NR$^5$C(O)N(R$^5$)$_2$, C(O)NH$_2$, C(O)NHR$^5$, C(O)N(R$^5$)$_2$, C(O)NHOH, C(O)NHOR$^5$, C(O)NHSO$_2$R$^5$, C(O)NR$^5$SO$_2$R$^5$, SO$_2$NH$_2$, SO$_2$NHR$^5$, SO$_2$N(R$^5$)$_2$, C(O)H, C(O)OH, C(N)NH$_2$, C(N)NHR$^5$, C(N)N(R$^5$)$_2$, CNOH, CNOCH$_3$, OH, CN, N$_3$, NO$_2$, F, Cl, Br and I; wherein each R$^4$ aryl, cycloalkyl, cycloalkenyl, and 3-12 membered heterocyclyl is optionally substituted with one, two, three or four substituents independently selected from the group consisting of R$^6$, OR$^6$, SR$^6$, S(O)R$^6$, SO$_2$R$^6$, C(O)R$^6$, CO(O)R$^6$, C(O)C(O)R$^6$, OC(O)R$^6$, OC(O)OR$^6$, NH$_2$, NHR$^6$, N(R$^6$)$_2$, NHC(O)R$^6$, NR$^6$C(O)R$^6$, NHS(O)$_2$R$^6$, NR$^6$S(O)$_2$R$^6$, NHC(O)OR$^6$, NR$^6$C(O)OR$^6$, NHC(O)NH$_2$, NHC(O)NHR$^6$, NHC(O)N(R$^6$)$_2$, NR$^6$C(O)NHR$^6$, NR$^6$C(O)N(R$^6$)$_2$, C(O)NH$_2$, C(O)NHR$^6$, C(O)N(R$^6$)$_2$, C(O)NHOH, C(O)NHOR$^6$, C(O)NHSO$_2$R$^6$, C(O)NR$^6$SO$_2$R$^6$, SO$_2$NH$_2$, SO$_2$NHR$^6$, SO$_2$N(R$^6$)$_2$, C(O)H, C(O)OH, C(N)NH$_2$, C(N)NHR$^6$, C(N)N(R$^6$)$_2$, CNOH, CNOCH$_3$, OH, CN, N$_3$, NO$_2$, F, Cl, Br and I;

R$^5$, at each occurrence, is independently selected from the group consisting of alkyl, alkenyl, alkynyl, aryl, heterocyclyl, cycloalkyl, and cycloalkenyl; wherein each R$^5$ alkyl, alkenyl, and alkynyl is optionally substituted with one, two, three or four substituents independently selected from the group consisting of R$^7$, OR$^7$, SR$^7$, S(O)R$^7$, SO$_2$R$^7$, C(O)R$^7$, CO(O)R$^7$, OC(O)R$^7$, OC(O)OR$^7$, NH$_2$, NHR$^7$, N(R$^7$)$_2$, NHC(O)R$^7$, NR$^7$C(O)R$^7$, NHS(O)$_2$R$^7$, N R$^7$S(O)$_2$R$^7$, NHC(O)OR$^7$, NR$^7$C(O)OR$^7$, NHC(O)NH$_2$, NHC(O)NHR$^7$, NHC(O)N(R$^7$)$_2$, NR$^7$C(O)NHR$^7$, NR$^7$C(O)N(R$^7$)$_2$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, C(O)H, C(O)OH, C(N)NH$_2$, C(N)NHR$^7$, C(N)N(R$^7$)$_2$, CNOH, CNOCH$_3$, OH, CN, N$_3$, NO$_2$, F, Cl, Br and I; wherein each R$^5$ aryl, cycloalkyl, cycloalkenyl, and heterocyclyl is optionally substituted with one, two, three or four substituents independently selected from the group consisting of R$^8$, OR$^8$, SR$^8$, S(O)R$^8$, SO$_2$R$^8$, C(O)R$^8$, CO(O)R$^8$, OC(O)R$^8$, OC(O)OR$^8$, NH$_2$, NHR$^8$, N(R$^8$)$_2$, NHC(O)R$^8$, NR$^8$C(O)R$^8$, NHS(O)$_2$ R$^8$, NR$^8$S(O)$_2$R$^8$, NHC(O)OR$^8$, NR$^8$C(O)R$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, SO$_2$NH$_2$, SO$_2$NHR$^8$, SO$_2$N(R$^8$)$_2$, C(O)H, C(O)OH, C(N)NH$_2$, C(N)NHR$^8$, C(N)N(R$^8$)$_2$, CNOH, CNOCH$_3$, OH, CN, N$_3$, NO$_2$, F, Cl, Br and I;

R$^6$, at each occurrence, is independently selected from the group consisting of alkyl, alkenyl, alkynyl, aryl, heterocyclyl, cycloalkyl, and cycloalkenyl; wherein each R$^6$ alkyl, alkenyl, and alkynyl is optionally substituted with one, two, three or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, N R$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, C(O)H, C(O)OH, C(N)NH$_2$, C(N)NHR$^9$, C(N)N(R$^9$)$_2$, CNOH, CNOCH$_3$, OH, CN, N$_3$, NO$_2$, F, Cl, Br and I; wherein each R$^6$ aryl, cycloalkyl, cycloalkenyl, and heterocyclyl is optionally substituted with one, two, three or four substituents independently selected from the group consisting of R$^{10}$, OR$^{10}$, SR$^{10}$, S(O)R$^{10}$, SO$_2$R$^{10}$, C(O)R$^{10}$, CO(O)R$_{10}$, OC(O)R$_{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$, NHC(O)N(R$^{10}$)$_2$, NR$^{10}$C(O)NHR$^{10}$, NR$^{10}$C(O)N(R$^{10}$)$_2$, C(O)NH$_2$, C(O)NHR$^{10}$, C(O)N(R$^{10}$, C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$, SO$_2$N(R$^{10}$, C(O)H, C(O)OH, C(N)NH$_2$, C(N)NHR$^{10}$, C(N)N(R$^{10}$)$_2$, CNOH, CNOCH$_3$, OH, CN, N$_3$, NO$_2$, F, Cl, Br and I;

R$^7$, at each occurrence, is independently selected from the group consisting of alkyl, alkenyl, alkynyl, aryl, heterocyclyl, cycloalkyl, and cycloalkenyl; wherein each R$^7$ alkyl, alkenyl, and alkynyl is optionally substituted with one, two, three or four substituents independently selected from the group consisting of aryl, alkoxy, OH, CN, N$_3$, NO$_2$, F, Cl, Br and I; wherein each R$^7$ aryl, cycloalkyl, cycloalkenyl, and heterocyclyl is optionally substituted with one, two, three or four substituents independently selected from the group consisting of OH, CN, N$_3$, NO$_2$, F, Cl, Br and I;

R$^8$, at each occurrence, is independently selected from the group consisting of alkyl, alkenyl, and alkynyl;

R$^9$, at each occurrence, is independently selected from the group consisting of alkyl, alkenyl, alkynyl, aryl, heterocyclyl, cycloalkyl, and cycloalkenyl; wherein each R$^9$ alkyl, alkenyl, and alkynyl is optionally substituted with one, two, three or four substituents independently selected from the group consisting of aryl, alkoxy, OH, CN, NO$_2$, F, Cl, Br and I; wherein each R$^9$ aryl, cycloalkyl, cycloalkenyl, and heterocyclyl is optionally substituted with one, two, three or four substituents independently selected from the group consisting of R$^{11}$, OR$^{11}$, C(O)R$_{11}$, CO(O)R$^{11}$, OC(O)R$^{11}$, NH$_2$, NHR$^{11}$, N(R$^{11}$)$_2$, NHC(O)R$^{11}$, NR$^{11}$C(O)R$^{11}$, C(O)NH$_2$, C(O)NHR$^{11}$, C(O)N(R$^{11}$)$_2$, C(O)H, C(O)OH, COH, CN, NO$_2$, F, Cl, Br and I;

R$^{10}$, at each occurrence, is independently selected from the group consisting of aryl, heterocyclyl, cycloalkyl, cycloalkenyl, alkyl, alkenyl, and alkynyl; wherein each R$^{10}$ alkyl, alkenyl, and alkynyl is optionally substituted with one, two, three or four substituents independently selected from the group consisting of alkoxy, F, Cl, Br and I;

R$^{11}$, at each occurrence, is independently selected from the group consisting of aryl, heterocyclyl, cycloalkyl, cycloalkenyl, alkyl, alkenyl, and alkynyl;

m is 4, 5, or 6; and n is 1or 2;

with the provisos that when X is CY$^1$ and Y$^1$ is hydrogen; and R$^3$ is thiazolyl; the R$^3$ thiazolyl is substituted with one substituent;

when X is CY$^1$ and Y$^1$ is hydrogen; R$^1$ is C(O)NH(CH$_2$)$_n$R$^3$; n is 1; R$^2$ is hydrogen; and R$^3$ is furanyl; the R$^3$ furanyl is not substituted with benzyl, or 3-fluorophenyl methyl; and when X is CY$^1$ and Y$^1$ is hydrogen; R$^1$ is C(O)NH(CH$_2$)$_n$R$^3$; n is 1; R$^2$ is hydrogen; and R$^3$ is thienyl; the R$^3$ thienyl is not substituted with phenoxy, 3-fluorophenoxy, or 3-chlorophenoxy.

2. The compound of claim 1, or a therapeutically acceptable salt thereof, wherein R$^1$ is NHC(O)NHR$^3$; and R$^2$ is hydrogen.

3. The compound of claim 1, or a therapeutically acceptable salt thereof, wherein R$^1$ is CH$_2$NHC(O)R$^3$; and R$^2$ is hydrogen.

4. The compound of claim 1, or a therapeutically acceptable salt thereof, wherein R$^1$ is hydrogen; and R$^2$ is CH$_2$NHC(O)NHR$^3$.

5. The compound of claim 1, or a therapeutically acceptable salt thereof, wherein R$^1$ is hydrogen; and R$^2$ is CH$_2$NHC(O)R$^3$.

6. The compound of any one of claims 1-5, or a therapeutically acceptable salt thereof, wherein R$^3$ is thienyl; wherein each R$^3$ thienyl is substituted with one, two, or three substituents independently selected from the group consisting of R$^4$, C(O)R$^4$, NHR$^4$, NHC(O)R$^4$, NR$^4$C(O)R$^4$, NHC(O)OR$^4$, NR$^4$C(O)NHR$^4$, C(O)NHR$^4$, F, Cl, Br and I.

7. The compound of claim 1, selected from the group consisting of

2-[(4-cyanobenzyl)(3-methylbutanoyl)amino]-N-(imidazo[1,2-a]pyridin-6-yl)-1,3-thiazole-5-carboxamide;

2-[(4-cyanobenzyl)(3-methoxypropanoyl)amino]-N-(imidazo[1,2-a]pyridin-6-yl)-1,3-thiazole-5-carboxamide;

2-[(4-cyanobenzyl)(3-methylbutanoyl)amino]-N-(imidazo[1,2-a]pyridin-6-ylmethyl)-1,3-thiazole-5-carboxamide;

2-[(4-cyanobenzyl)(3-methoxypropanoyl)amino]-N-(imidazo[1,2-a]pyridin-6-ylmethyl)-1,3-thiazole-5-carboxamide;

2-[(4-cyanobenzyl)(3-methoxypropanoyl)amino]-N-(imidazo[1,2-a]pyridin-7-ylmethyl)-1,3-thiazole-5-carboxamide;

N-(imidazo[1,2-a]pyridin-6-ylmethyl)-2-[(3-methoxypropanoyl)(3-methylbutyl)amino]-1,3-thiazole-5-carboxamide;

N-(imidazo[1,2-a]pyridin-6-ylmethyl)-5-[1-(2-methylpropyl)-1H-pyrazol-4-yl]thiophene-2-carboxamide;

N-(imidazo[1,2-a]pyridin-6-ylmethyl)-2-(1,2,4,5-tetrahydro-3H-3-benzazepin-3-yl)-1,3-thiazole-5-carboxamide;

N-(imidazo[1,2-a]pyridin-6-ylmethyl)-2-(3-phenylpyrrolidin-1-yl)-1,3-thiazole-5-carboxamide;

N-(imidazo[1,2-a]pyridin-6-ylmethyl)-2-[(3-methylbutyl)amino]-1,3-thiazole-5-carboxamide;

2-(1,3-dihydro-2H-isoindol-2-yl)-N-(imidazo[1,2-a]pyridin-6-ylmethyl)-1,3-thiazole-5-carboxamide;

2-(3,4-dihydroisoquinolin-2(1H)-yl)-N-(imidazo[1,2-a]pyridin-6-ylmethyl)-1,3-thiazole-5-carboxamide;

N-(imidazo[1,2-a]pyridin-6-ylmethyl)-24{[2-(propan-2-yloxy)ethyl]carbamoyl}(tetrahydrofuran-2-ylmethyl)amino]-1,3-thiazole-5-carboxamide;

N-(imidazo[1,2-a]pyridin-6-ylmethyl)-2-[2-oxo-4-(tetrahydrofuran-3-yl)-1,3-oxazolidin-3-yl]-1,3-thiazole-5-carboxamide;

N-(imidazo[1,2-a]pyridin-6-ylmethyl)-5-[1-(2-methylpropyl)-1H-pyrazol-4-yl]furan-2-carboxamide;

N-(imidazo[1,2-a]pyridin-7-ylmethyl)-2-[(3-methoxypropanoyl)(tetrahydrofuran-2-ylmethyl)amino]-1,3-thiazole-5-carboxamide;
N-(imidazo[1,2-a]pyridin-6-ylmethyl)-2-(2-oxo-5-phenyl-1,3-oxazolidin-3-yl)-1,3-thiazole-5-carboxamide;
N-(imidazo[1,2-a]pyridin-6-ylmethyl)-2-{[(2-methyl-1,3-thiazol-5-yl)acetyl](tetrahydrofuran-2-ylmethyl)amino}-1,3-thiazole-5-carboxamide;
N-(imidazo[1,2-a]pyridin-6-ylmethyl)-2-{[(2-methyl-1,3-thiazol-4-yl)acetyl](tetrahydrofuran-2-ylmethyl)amino}-1,3-thiazole-5-carboxamide;
N-(imidazo[1,2-a]pyridin-6-ylmethyl)-2-{[(3-methyl-1,2-oxazol-5-yl)acetyl](tetrahydrofuran-2-ylmethyl)amino}-1,3-thiazole-5-carboxamide;
2-{[3-(3-chloro-1,2-oxazol-5-yl)propanoyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-{[3-(3-methoxy-1,2-oxazol-5-yl)propanoyl](tetrahydrofuran-2-ylmethyl)amino}-1,3-thiazole-5-carboxamide;
2-{[(3,5-dimethyl-1,2-oxazol-4-yl)acetyl](tetrahydrofuran-2-ylmethyl)amino}-N-(imidazo[1,2-a]pyridin-6-ylmethyl)-1,3-thiazole-5-carboxamide;
2-{[3-(3,5-dimethyl-1,2-oxazol-4-yl)propanoyl](tetrahydrofuran-2-ylmethyl)amino}-N-(imidazo[1,2-a]pyridin-6-ylmethyl)-1,3-thiazole-5-carboxamide;
N-(imidazo[1,2-a]pyridin-6-ylmethyl)-2-{[3-(1-methyl-1H-pyrazol-4-yl)propanoyl](tetrahydrofuran-2-ylmethyl)amino}-1,3-thiazole-5-carboxamide;
N-(imidazo[1,2-a]pyridin-6-ylmethyl)-2-{[3-(4-methyl-1,3-thiazol-5-yl)propanoyl](tetrahydrofuran-2-ylmethyl)amino}-1,3-thiazole-5-carboxamide;
N-(imidazo[1,2-a]pyridin-6-ylmethyl)-2-[(tetrahydrofuran-2-ylmethyl)(1H-tetrazol-5-ylacetyl)amino]-1,3-thiazole-5-carboxamide;
N-(imidazo[1,2-a]pyridin-6-ylmethyl)-2-{[3-(1,2-oxazol-5-yl)propanoyl](tetrahydrofuran-2-ylmethyl)amino}-1,3-thiazole-5-carboxamide;
N-(imidazo[1,2-a]pyridin-6-ylmethyl)-2-[(1,2-oxazol-3-ylacetyl)(tetrahydrofuran-2-ylmethyl)amino]-1,3-thiazole-5-carboxamide;
N-(imidazo[1,2-a]pyridin-6-ylmethyl)-2-{[3-(1,2-oxazol-4-yl)propanoyl](tetrahydrofuran-2-ylmethyl)amino}-1,3-thiazole-5-carboxamide;
N-(imidazo[1,2-a]pyridin-6-ylmethyl)-2-{(tetrahydrofuran-2-ylmethyl)[3-(1,3-thiazol-2-yl)propanoyl]amino}-1,3-thiazole-5-carboxamide;
N-(imidazo[1,2-a]pyridin-6-ylmethyl)-2-[(3-methylbutanoyl)amino]-1,3-thiazole-5-carboxamide;
N-(imidazo[1,2-a]pyridin-7-ylmethyl)-2-{[(2-methoxyethyl)carbamoyl](tetrahydrofuran-2-ylmethyl)amino}-1,3-thiazole-5-carboxamide;
N-(imidazo[1,2-a]pyridin-6-ylmethyl)-2-[(3-methoxypropanoyl)(tetrahydrofuran-3-ylmethyl)amino]-1,3-thiazole-5-carboxamide;
N-(imidazo[1,2-a]pyridin-6-ylmethyl)-2-[tetrahydrofuran-3-ylmethyl)(tetrahydro-2H-pyran-4-ylcarbonyl)amino]-1,3-thiazole-5-carboxamide;
N-(imidazo[1,2-a]pyridin-6-ylmethyl)-2-{[(2-methoxyethyl)carbamoyl](tetrahydrofuran-3-ylmethyl)amino}-1,3-thiazole-5-carboxamide;
N-(imidazo[1,2-a]pyridin-6-ylmethyl)-2-[(3-methoxypropanoyl)(tetrahydro-2H-pyran-4-ylmethyl)amino]-1,3-thiazole-5-carboxamide;
N-(imidazo[1,2-a]pyridin-6-ylmethyl)-2-[(tetrahydrofuran-3-ylcarbonyl)(tetrahydro-2H-pyran-4-ylmethyl)amino]-1,3-thiazole-5-carboxamide;
N-(imidazo[1,2-a]pyridin-6-ylmethyl)-2-[(tetrahydro-2H-pyran-4-ylcarbonyl)(tetrahydro-2H-pyran-4-ylmethyl)amino]-1,3-thiazole-5-carboxamide;
N-(imidazo[1,2-a]pyridin-6-ylmethyl)-2-{(3-methoxypropanoyl)[(2R)-tetrahydrofuran-2-ylmethyl]amino}-1,3-thiazole-5-carboxamide;
N-(imidazo[1,2-a]pyridin-6-ylmethyl)-2-{(tetrahydrofuran-3-ylcarbonyl)[(2R)-tetrahydrofuran-2-ylmethyl]amino}-1,3-thiazole-5-carboxamide;
N-(imidazo[1,2-a]pyridin-6-ylmethyl)-2-{[(2R)-tetrahydrofuran-2-ylmethyl](tetrahydro-2H-pyran-4-ylcarbonyl)amino}-1,3-thiazole-5-carboxamide;
N-(imidazo[1,2-a]pyridin-6-ylmethyl)-2-{(3-methoxypropanoyl)[(2S)-tetrahydrofuran-2-ylmethyl]amino}-1,3-thiazole-5-carboxamide;
N-(imidazo[1,2-a]pyridin-6-ylmethyl)-2-{(tetrahydrofuran-3-ylcarbonyl)[(2S)-tetrahydrofuran-2-ylmethyl]amino}-1,3-thiazole-5-carboxamide;
N-(imidazo[1,2-a]pyridin-6-ylmethyl)-2-{[(2S)-tetrahydrofuran-2-ylmethyl](tetrahydro-2H-pyran-4-ylcarbonyl)amino}-1,3-thiazole-5-carboxamide;
N-(imidazo[1,2-a]pyridin-6-ylmethyl)-2-{[(2-methoxyethyl)carbamoyl](tetrahydro-2H-pyran-4-ylmethyl)amino}-1,3-thiazole-5-carboxamide;
N-(imidazo[1,2-a]pyridin-6-ylmethyl)-2-[{[2-(propan-2-yloxy)ethyl]carbamoyl}(tetrahydro-2H-pyran-4-ylmethyl)amino]-1,3-thiazole-5-carboxamide;
N-(imidazo[1,2-a]pyridin-6-ylmethyl)-2-{[(2-methoxyethyl)carbamoyl][(2R)-tetrahydrofuran-2-ylmethyl]amino}-1,3-thiazole-5-carboxamide;
N-(imidazo[1,2-a]pyridin-6-ylmethyl)-2-{[2-(propan-2-yloxy)ethyl]carbamoyl}[(2R)-tetrahydrofuran-2-ylmethyl]amino)-1,3-thiazole-5-carboxamide;
N-(imidazo[1,2-a]pyridin-6-ylmethyl)-2-{[(2-methoxyethyl)carbamoyl][(2S)-tetrahydrofuran-2-ylmethyl]amino}-1,3-thiazole-5-carboxamide;
N-(imidazo[1,2-a]pyridin-6-ylmethyl)-2-({[2-(propan-2-yloxy)ethyl]carbamoyl}[(2S)-tetrahydrofuran-2-ylmethyl]amino)-1,3-thiazole-5-carboxamide;
N-(imidazo[1,2-a]pyridin-6-ylmethyl)-2-[{[2-(propan-2-yloxy)ethyl]carbamoyl}(tetrahydrofuran-3-ylmethyl)amino]-1,3-thiazole-5-carboxamide;
2-[5-(4-chlorophenyl)-2-oxo-1,3-oxazolidin-3-yl]-N-(imidazo[1,2-a]pyridin-6-ylmethyl)-1,3-thiazole-5-carboxamide;
N-(imidazo[1,2-a]pyridin-7-ylmethyl)-5-[1-(2-methylpropyl)-1H-pyrazol-4-yl]thiophene-2-carboxamide;
N-(imidazo[1,2-a]pyridin-6-ylmethyl)-5-[1-(2-methylpropanoyl)-1H-pyrazol-4-yl]thiophene-2-carboxamide;
5-[1-(2-hydroxy-2-methylpropyl)-1H-pyrazol-4-yl]-N-(imidazo[1,2-a]pyridin-6-ylmethyl)thiophene-2-carboxamide;
N-(imidazo[1,2-a]pyridin-6-ylmethyl)-5-{1-[(3-methyloxetan-3-yl)methyl]-1H-pyrazol-4-yl}thiophene-2-carboxamide;
5-[1-(cyclobutylmethyl)-1H-pyrazol-4-yl]-N-(imidazo[1,2-a]pyridin-6-ylmethyl)thiophene-2-carboxamide;
5-[1-(cyclohexylmethyl)-1H-pyrazol-4-yl]-N-(imidazo[1,2-a]pyridin-6-ylmethyl)thiophene-2-carboxamide;
5-{1-[(2R)-2-hydroxybutyl]-1H-pyrazol-4-yl}-N-(imidazo[1,2-a]pyridin-6-ylmethyl)thiophene-2-carboxamide;
N-(imidazo[1,2-a]pyridin-7-ylmethyl)-2-[(4R)-2-oxo-4-(propan-2-yl)-1,3-oxazolidin-3-yl]-1,3-thiazole-5-carboxamide;

5-[1-(2-hydroxy-2-methylpropyl)-1H-pyrazol-4-yl]-N-(imidazo[1,2-a]pyridin-7-ylmethyl)thiophene-2-carboxamide;

N-(imidazo[1,2-a]pyridin-6-ylmethyl)-2-{[(1-methyl-1H-pyrazol-4-yl)acetyl](tetrahydrofuran-2-ylmethyl)amino}-1,3-thiazole-5-carboxamide;

2-{[(1,3-dimethyl-1H-pyrazol-4-yl)acetyl](tetrahydrofuran-2-ylmethyl)amino}-N-(imidazo[1,2-a]pyridin-6-ylmethyl)-1,3-thiazole-5-carboxamide;

N-(imidazo[1,2-a]pyridin-7-ylmethyl)-2-[(4S)-2-oxo-4-(propan-2-yl)-1,3-oxazolidin-3-yl]-1,3-thiazole-5-carboxamide;

N-(imidazo[1,2-a]pyridin-6-ylmethyl)-5-[1-(tetrahydro-2H-pyran-2-ylmethyl)-1H-pyrazol-4-yl]thiophene-2-carboxamide;

2-{(4R)-4-[(benzyloxy)methyl]-2-oxo-1,3-oxazolidin-3-yl}-N-(imidazo[1,2-a]pyridin-7-ylmethyl)-1,3-thiazole-5-carboxamide;

2-{(4S)-4-[(benzyloxy)methyl]-2-oxo-1,3-oxazolidin-3-yl}-N-(imidazo[1,2-a]pyridin-7-ylmethyl)-1,3-thiazole-5-carboxamide;

N-(imidazo[1,2-a]pyridin-6-ylmethyl)-2-{[3-(1-methyl-1H-pyrrol-2-yl)propanoyl](tetrahydrofuran-2-ylmethyl)amino}-1,3-thiazole-5-carboxamide;

2-{[(1,5-dimethyl-1H-pyrazol-3-yl)acetyl](tetrahydrofuran-2-ylmethyl)amino}-N-(imidazo[1,2-a]pyridin-6-ylmethyl)-1,3-thiazole-5-carboxamide;

N-(imidazo[1,2-a]pyridin-6-ylmethyl)-2-[(tetrahydrofuran-2-ylmethyl)(1,3-thiazol-4-ylacetyl)amino]-1,3-thiazole-5-carboxamide;

N-(imidazo[1,2-a]pyridin-7-ylmethyl)-2-{(1,2-oxazol-3-ylacetyl)[(2R)-tetrahydrofuran-2-ylmethyl]amino}-1,3-thiazole-5-carboxamide;

N-(imidazo[1,2-a]pyridin-7-ylmethyl)-2-{[(5-methyl-1,2-oxazol-3-yl)acetyl][(2R)-tetrahydrofuran-2-ylmethyl]amino}-1,3-thiazole-5-carboxamide;

N-(imidazo[1,2-a]pyridin-7-ylmethyl)-2-{[3-(1,2-oxazol-5-yl)propanoyl][(2R)-tetrahydrofuran-2-ylmethyl]amino}-1,3-thiazole-5-carboxamide;

N-(imidazo[1,2-a]pyridin-7-ylmethyl)-2-{[3-(1,2-oxazol-4-yl)propanoyl][(2R)-tetrahydrofuran-2-ylmethyl]amino}-1,3-thiazole-5-carboxamide;

N-(imidazo[1,2-a]pyridin-7-ylmethyl)-2-{[(2R)-tetrahydrofuran-2-ylmethyl](1,3-thiazol-4-ylacetyl)amino}-1,3-thiazole-5-carboxamide;

2-{[(1,5-dimethyl-1H-pyrazol-3-yl)acetyl][(2R)-tetrahydrofuran-2-ylmethyl]amino}-N-(imidazo[1,2-a]pyridin-7-ylmethyl)-1,3-thiazole-5-carboxamide;

N-(imidazo[1,2-a]pyridin-7-ylmethyl)-2-{[3-(1-methyl-1H-pyrazol-4-yl)propanoyl][(2R)-tetrahydrofuran-2-ylmethyl]amino}-1,3-thiazole-5-carboxamide;

2-{[(3,5-dimethyl-1,2-oxazol-4-yl)acetyl][(2R)-tetrahydrofuran-2-ylmethyl]amino}-N-(imidazo[1,2-a]pyridin-7-ylmethyl)-1,3-thiazole-5-carboxamide;

N-(imidazo[1,2-a]pyridin-6-ylmethyl)-5-[1-(tetrahydrofuran-3-ylmethyl)-1H-pyrazol-4-yl]thiophene-2-carboxamide;

N-(imidazo[1,2-a]pyridin-6-ylmethyl)-5-[1-(tetrahydro-2H-pyran-4-ylmethyl)-1H-pyrazol-4-yl]thiophene-2-carboxamide;

N-(imidazo[1,2-a]pyridin-7-ylmethyl)-2-{[(1-methyl-1H-pyrazol-4-yl)acetyl][(2R)-tetrahydrofuran-2-ylmethyl]amino}-1,3-thiazole-5-carboxamide;

N-(imidazo[1,2-a]pyridin-7-ylmethyl)-2-{[3-(1-methyl-1H-pyrrol-2-yl)propanoyl][(2R)-tetrahydrofuran-2-ylmethyl]amino}-1,3-thiazole-5-carboxamide;

2-[1-(2-hydroxy-2-methylpropyl)-1H-pyrazol-4-yl]-N-(imidazo[1,2-a]pyridin-7-ylmethyl)-1,3-thiazole-5-carboxamide;

N-(imidazo[1,2-a]pyridin-7-ylmethyl)-2-[1-(2-methylpropyl)-1H-pyrazol-4-yl]-1,3-thiazole-5-carboxamide;

N-(imidazo[1,2-a]pyridin-6-ylmethyl)-5-[1-(tetrahydro-2H-pyran-3-ylmethyl)-1H-pyrazol-4-yl]thiophene-2-carboxamide;

2-{5-[(benzyloxy)methyl]-2-oxo-1,3-oxazolidin-3-yl}-N-(imidazo[1,2-a]pyridin-7-ylmethyl)-1,3-thiazole-5-carboxamide;

N-(imidazo[1,2-a]pyridin-6-ylmethyl)-5-[1-(tetrahydrofuran-2-ylmethyl)-1H-pyrazol-4-yl]thiophene-2-carboxamide;

5-(1-acetyl-1,2,3,6-tetrahydropyridin-4-yl)-N-(imidazo[1,2-a]pyridin-7-ylmethyl)thiophene-2-carboxamide;

N-(imidazo[1,2-a]pyridin-7-ylmethyl)-5-[1-(methylsulfonyl)-1,2,3,6-tetrahydropyridin-4-yl]thiophene-2-carboxamide;

2-[(2S)-2-(hydroxymethyl)-5-oxopyrrolidin-1-yl]-N-(imidazo[1,2-a]pyridin-7-ylmethyl)-1,3-thiazole-5-carboxamide;

N-(imidazo[1,2-a]pyridin-7-ylmethyl)-2-[(4R)-4-methyl-2-oxo-1,3-oxazolidin-3-yl]-1,3-thiazole-5-carboxamide;

5-[1-(cyclopropylsulfonyl)-1,2,3,6-tetrahydropyridin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydro-2H-pyran-2-ylmethyl)-1H-pyrazol-4-yl]thiophene-2-carboxamide;

N-(imidazo[1,2-a]pyridin-7-ylmethyl)-5-[1-(tetrahydrofuran-2-ylmethyl)-1H-pyrazol-4-yl]thiophene-2-carboxamide;

N-(imidazo[1,2-a]pyridin-7-ylmethyl)-2-{2-oxo-5-[(propan-2-yloxy)methyl]-1,3-oxazolidin-3-yl}-1,3-thiazole-5-carboxamide;

N-(imidazo[1,2-a]pyridin-7-ylmethyl)-5-[(4R)-2-oxo-4-(propan-2-yl)-1,3-oxazolidin-3-yl]thiophene-2-carboxamide;

2-[5-(hydroxymethyl)-2-oxo-1,3-oxazolidin-3-yl]-N-(imidazo[1,2-a]pyridin-7-ylmethyl)-1,3-thiazole-5-carboxamide;

N-(imidazo[1,2-a]pyridin-7-ylmethyl)-5-[1-(tetrahydrofuran-3-ylmethyl)-1H-pyrazol-4-yl]thiophene-2-carboxamide;

N-(imidazo[1,2-a]pyridin-7-ylmethyl)-5-[1-(tetrahydro-2H-pyran-3-ylmethyl)-1H-pyrazol-4-yl]thiophene-2-carboxamide;

N-(imidazo[1,2-a]pyridin-7-ylmethyl)-5-{1-[(3-methyloxetan-3-yl)methyl]-1H-pyrazol-4-yl}thiophene-2-carboxamide;

N-(imidazo[1,2-a]pyridin-7-ylmethyl)-2-{(5S)-2-oxo-5-[(propan-2-yloxy)methyl]-1,3-oxazolidin-3-yl}-1,3-thiazole-5-carboxamide;

N-(imidazo[1,2-a]pyridin-7-ylmethyl)-2-{(5R)-2-oxo-5-[(propan-2-yloxy)methyl]-1,3-oxazolidin-3-yl}-1,3-thiazole-5-carboxamide;

N-(imidazo[1,2-a]pyridin-7-ylmethyl)-5-[1-(methoxyacetyl)piperidin-4-yl]thiophene-2-carboxamide;

5-(1-acetylpiperidin-4-yl)-N-(imidazo[1,2-a]pyridin-7-ylmethyl)thiophene-2-carboxamide;

N-(imidazo[1,2-a]pyridin-7-ylmethyl)-5-[1-(2-methylpropanoyl)piperidin-4-yl]thiophene-2-carboxamide;

5-[1-(cyclopropylcarbonyl)piperidin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydrofuran-3-ylcarbonyl)piperidin-4-yl]thiophene-2-carboxamide;

N-(imidazo[1,2-a]pyridin-7-ylmethyl)-5-[1-(tetrahydro-2H-pyran-4-ylacetyl)piperidin-4-yl]thiophene-2-carboxamide;

N-(imidazo[1,2-a]pyridin-7-ylmethyl)-5-[1-(3-methylbutanoyl)piperidin-4-yl]thiophene-2-carboxamide;

N-(imidazo[1,2-a]pyridin-7-ylmethyl)-5-[1-(1,2-oxazol-5-ylcarbonyl)piperidin-4-yl]thiophene-2-carboxamide;

N-(imidazo[1,2-a]pyridin-7-ylmethyl)-5-[1-(tetrahydro-2H-pyran-4-ylmethyl)-1H-pyrazol-4-yl]thiophene-2-carboxamide;

5-[5-(hydroxymethyl)-2-oxo-1,3-oxazolidin-3-yl]-N-(imidazo[1,2-a]pyridin-7-ylmethyl)thiophene-2-carboxamide;

5-[(4R)-4-hydroxy-2-oxopyrrolidin-1-yl]-N-(imidazo[1,2-a]pyridin-7-ylmethyl)thiophene-2-carboxamide;

5-[(4S)-4-hydroxy-2-oxopyrrolidin-1-yl]-N-(imidazo[1,2-a]pyridin-7-ylmethyl)thiophene-2-carboxamide;

N-(imidazo[1,2-a]pyridin-7-ylmethyl)-5-[1-(2-methoxyethyl)-1H-pyrazol-4-yl]thiophene-2-carboxamide;

N-(imidazo[1,2-a]pyridin-7-ylmethyl)-5-[1-(methylsulfonyl)piperidin-4-yl]thiophene-2-carboxamide;

5-[1-(cyclohexylmethyl)-5-ethyl-1H-pyrazol-4-yl]-N-(imidazo[1,2-a]pyridin-7-ylmethyl)thiophene-2-carboxamide;

N-(imidazo[1,2-a]pyridin-7-ylmethyl)-5-{1-[(1-methoxy-3,3-dimethylcyclohexyl)methyl]-5-methyl-1H-pyrazol-4-yl}thiophene-2-carboxamide;

N-(imidazo[1,2-a]pyridin-7-ylmethyl)-5-(1-propyl-1H-pyrazol-4-yl)thiophene-2-carboxamide;

N-(imidazo[1,2-a]pyridin-7-ylmethyl)-5-{1-[2-(morpholin-4-yl)ethyl]-1H-pyrazol-4-yl}thiophene-2-carboxamide;

5-(1-ethyl-1H-pyrazol-4-yl)-N-(imidazo[1,2-a]pyridin-7-ylmethyl)thiophene-2-carboxamide;

5-[1-(1,1-dioxidotetrahydrothiophen-3-yl)-1H-pyrazol-4-yl]-N-(imidazo[1,2-a]pyridin-7-ylmethyl)thiophene-2-carboxamide;

2-(1-benzoyl-1,2,3,6-tetrahydropyridin-4-yl)-N-(imidazo[1,2-a]pyridin-7-ylmethyl)-1,3-thiazole-5-carboxamide;

N-(imidazo[1,2-a]pyridin-7-ylmethyl)-5-phenylthiophene-2-carboxamide;

N-(imidazo[1,2-a]pyridin-7-ylmethyl)-5-{1-[2-(methylsulfonyl)ethyl]-1H-pyrazol-4-yl}thiophene-2-carboxamide;

5-{1-[(2R)-2-hydroxypropyl]-1H-pyrazol-4-yl}-N-(imidazo[1,2-a]pyridin-7-ylmethyl)thiophene-2-carboxamide;

5-[1-(1,4-dioxan-2-ylmethyl)-1H-pyrazol-4-yl]-N-(imidazo[1,2-a]pyridin-7-ylmethyl)thiophene-2-carboxamide;

5-[1-(2-hydroxyethyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[3-(propan-2-yloxy)phenyl]thiophene-2-carboxamide;

N-(imidazo[1,2-a]pyridin-7-ylmethyl)-2-[1-(tetrahydro-2H-pyran-4-ylcarbonyl)-1,2,3,6-tetrahydropyridin-4-yl]-1,3-thiazole-5-carboxamide;

N-(imidazo[1,2-a]pyridin-7-ylmethyl)-2-[1-(2-methylpropanoyl)-1,2,3,6-tetrahydropyridin-4-yl]-1,3-thiazole-5-carboxamide;

N-(imidazo[1,2-a]pyridin-7-ylmethyl)-5-{3-[(2-methylpropanoyl)amino]oxetan-3-yl}thiophene-2-carboxamide;

5-[3-(benzoylamino)oxetan-3-yl]-N-(imidazo[1,2-a]pyridin-7-ylmethyl)thiophene-2-carboxamide;

N-(imidazo[1,2-a]pyridin-7-ylmethyl)-5-{3-[(tetrahydrofuran-3-ylacetyl)amino]oxetan-3-yl}thiophene-2-carboxamide;

N-(imidazo[1,2-a]pyridin-7-ylmethyl)-5-[3-(pentanoylamino)oxetan-3-yl]thiophene-2-carboxamide;

5-{1-[(1,1-dioxidotetrahydro-2H-thiopyran-3-yl)methyl]-1H-pyrazol-4-yl}-N-(imidazo[1,2-a]pyridin-7-ylmethyl)thiophene-2-carboxamide;

N-(imidazo[1,2-a]pyridin-7-ylmethyl)-5-(1-methyl-1H-pyrazol-4-yl)thiophene-2-carboxamide;

2-(4-benzoylpiperazin-1-yl)-N-(imidazo[1,2-a]pyridin-7-ylmethyl)-1,3-thiazole-5-carboxamide;

N-(imidazo[1,2-a]pyridin-7-ylmethyl)-2-[4-(propan-2-yl)piperazin-1-yl]-1,3-thiazole-5-carboxamide;

N-(imidazo[1,2-a]pyridin-7-ylmethyl)-2-[4-(2-methoxyethyl)piperazin-1-yl]-1,3-thiazole-5-carboxamide;

N-(imidazo[1,2-a]pyridin-7-ylmethyl)-2-phenyl-1,3-thiazole-5-carboxamide;

N-(imidazo[1,2-a]pyridin-7-ylmethyl)-5-(1-methyl-1H-pyrazol-5-yl)thiophene-2-carboxamide;

N-(imidazo[1,2-a]pyridin-7-ylmethyl)-5-{1-[(2R)-tetrahydrofuran-2-ylmethyl]-1H-pyrazol-4-yl}thiophene-2-carboxamide;

N-(imidazo[1,2-a]pyridin-7-ylmethyl)-5-{1-[(2S)-tetrahydrofuran-2-ylmethyl]-1H-pyrazol-4-yl}thiophene-2-carboxamide;

5-(4-hydroxytetrahydro-2H-pyran-4-yl)-N-(imidazo[1,2-a]pyridin-7-ylmethyl)thiophene-2-carboxamide;

5-[3-hydroxy-1-(2-methylpropanoyl)azetidin-3-yl]-N-(imidazo[1,2-a]pyridin-7-ylmethyl)thiophene-2-carboxamide;

5-(1-benzoyl-3-hydroxyazetidin-3-yl)-N-(imidazo[1,2-a]pyridin-7-ylmethyl)thiophene-2-carboxamide;

tert-butyl 4-hydroxy-4-{5-[(imidazo[1,2-a]pyridin-7-ylmethyl)carbamoyl]thiophen-2-yl}piperidine-1-carboxylate;

1-(imidazo[1,2-a]pyridin-7-ylmethyl)-3-[5-(piperidin-1-ylcarbonyl)-1,3-thiazol-2-yl]urea;

5-{3-hydroxy-1-[(2S)-2-methylbutanoyl]azetidin-3-yl}-N-(imidazo[1,2-a]pyridin-7-ylmethyl)thiophene-2-carboxamide;

5-[3-hydroxy-1-(tetrahydro-2H-pyran-4-ylacetyl)azetidin-3-yl]-N-(imidazo[1,2-a]pyridin-7-ylmethyl)thiophene-2-carboxamide;

2-{[(imidazo[1,2-a]pyridin-7-ylmethyl)carbamoyl]amino}-N-(3-methylbutyl)-1,3-thiazole-5-carboxamide;

N-(imidazo[1,2-a]pyridin-7-ylmethyl)-5-(3-{[(2S)-2-methylbutanoyl]amino}oxetan-3-yl)thiophene-2-carboxamide;

N-(imidazo[1,2-a]pyridin-7-ylmethyl)-1-[1-(3-methylbutanoyl)piperidin-4-yl]-1H-pyrazole-3-carboxamide;

N-(imidazo[1,2-a]pyridin-7-ylmethyl)-5-[1-(tetrahydro-2H-pyran-4-yl)-1H-pyrazol-4-yl]thiophene-2-carboxamide;

N-(imidazo[1,2-a]pyridin-7-ylmethyl)-5-[6-(morpholin-4-yl)pyridin-3-yl]thiophene-2-carboxamide;

N-(imidazo[1,2-a]pyridin-7-ylmethyl)-5-{1-[(2-methyltetrahydro-2H-pyran-2-yl)methyl]-1H-pyrazol-4-yl}thiophene-2-carboxamide;

tert-butyl 4-[(4-{5-[(imidazo[1,2-a]pyridin-7-ylmethyl)carbamoyl]thiophen-2-yl}-1H-pyrazol-1-yl)methyl]piperidine-1-carboxylate;

N-(imidazo[1,2-a]pyridin-7-ylmethyl)-5-[1-(3-methylbutanoyl)pyrrolidin-3-yl]thiophene-2-carboxamide;

N-(imidazo[1,2-a]pyridin-7-ylmethyl)-5-{1-[(2-methylpropanoyl)amino]cyclobutyl}thiophene-2-carboxamide;

N-(imidazo[1,2-a]pyridin-7-ylmethyl)-5-{1-[(3-methylbutanoyl)amino]cyclobutyl}thiophene-2-carboxamide;

N-(imidazo[1,2-a]pyridin-7-ylmethyl)-5-(1-{[(2S)-2-methylbutanoyl]amino}cyclobutyl)thiophene-2-carboxamide;

5-[1-(benzoylamino)cyclobutyl]-N-(imidazo[1,2-a]pyridin-7-ylmethyl)thiophene-2-carboxamide;

N-(imidazo[1,2-a]pyridin-7-ylmethyl)-5-{1-[(3,3,3-trifluoropropanoyl)amino]cyclobutyl}thiophene-2-carboxamide;

N-(1-{5-[(imidazo[1,2-a]pyridin-7-ylmethyl)carbamoyl]thiophen-2-yl}cyclobutyl)tetrahydro-2H-pyran-4-carboxamide;

5-[1-(cyclobutylmethyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[1-(tetrahydrofuran-2-ylmethyl)-1H-pyrazol-4-yl]furan-2-carboxamide;

N-(imidazo[1,2-a]pyridin-7-ylmethyl)-5-[1-(tetrahydro-2H-pyran-2-ylmethyl)-1H-pyrazol-4-yl]furan-2-carboxamide;

N-(imidazo[1,2-a]pyridin-7-ylmethyl)-5-[1-(tetrahydrofuran-3-ylmethyl)-1H-pyrazol-4-yl]furan-2-carboxamide;

N-(imidazo[1,2-a]pyridin-7-ylmethyl)-5-[1-(tetrahydro-2H-pyran-3-ylmethyl)-1H-pyrazol-4-yl]furan-2-carboxamide;

N-(imidazo[1,2-a]pyridin-7-ylmethyl)-5-[1-(tetrahydro-2H-pyran-4-ylmethyl)-1H-pyrazol-4-yl]furan-2-carboxamide;

5-[1-(cyclobutylmethyl)-1H-pyrazol-4-yl]-N-(imidazo[1,2-a]pyridin-7-ylmethyl)furan-2-carboxamide;

N-(imidazo[1,2-a]pyridin-7-ylmethyl)-5-{1-[(3-methyloxetan-3-yl)methyl]-1H-pyrazol-4-yl}furan-2-carboxamide;

N-(imidazo[1,2-a]pyridin-7-ylmethyl)-5-[1-(piperidin-4-ylmethyl)-1H-pyrazol-4-yl]thiophene-2-carboxamide;

5-[1-(2-methylpropyl)-1H-pyrazol-4-yl]-N-([1,2,4]triazolo[1,5-a]pyridin-7-ylmethyl)thiophene-2-carboxamide;

N-(imidazo[1,2-a]pyridin-7-ylmethyl)-5-[1-(3,3,3-trifluoropropanoyl)pyrrolidin-3-yl]thiophene-2-carboxamide;

N-(imidazo[1,2-a]pyridin-7-ylmethyl)-5-[1-(2-methylpropanoyl)pyrrolidin-3-yl]thiophene-2-carboxamide;

5-(1-benzoylpyrrolidin-3-yl)-N-(imidazo[1,2-a]pyridin-7-ylmethyl)thiophene-2-carboxamide;

N-(imidazo[1,2-a]pyridin-7-ylmethyl)-2-[1-(2-methylpropanoyl)piperidin-4-yl]-1,3-thiazole-5-carboxamide;

N-(imidazo[1,2-a]pyridin-7-ylmethyl)-2-[1-(3-methylbutanoyl)piperidin-4-yl]-1,3-thiazole-5-carboxamide;

2-(1-benzoylpiperidin-4-yl)-N-(imidazo[1,2-a]pyridin-7-ylmethyl)-1,3-thiazole-5-carboxamide;

5-[4-hydroxy-1-(3-methylbutanoyl)piperidin-4-yl]-N-(imidazo[1,2-a]pyridin-7-ylmethyl)thiophene-2-carboxamide;

5-[4-hydroxy-1-(2-methylpropanoyl)piperidin-4-yl]-N-(imidazo[1,2-a]pyridin-7-ylmethyl)thiophene-2-carboxamide;

5-[1-(3,3-dimethylbutanoyl)-4-hydroxypiperidin-4-yl]-N-(imidazo[1,2-a]pyridin-7-ylmethyl)thiophene-2-carboxamide;

5-(1-benzoyl-4-hydroxypiperidin-4-yl)-N-(imidazo[1,2-a]pyridin-7-ylmethyl)thiophene-2-carboxamide;

propan-2-yl 4-{5-[(imidazo[1,2-a]pyridin-7ylmethyl)carbamoyl]thiophen-2-yl}piperidine-1-carboxylate;

2-methylpropyl 4-{5-[(imidazo[1,2-a]pyridin-7-ylmethyl)carbamoyl]thiophen-2-yl}piperidine-1-carboxylate;

N-(imidazo[1,2-a]pyridin-7-ylmethyl)-5-[1-(3,3,3-trifluoropropanoyl)piperidin-4-yl]thiophene-2-carboxamide;

N-(imidazo[1,2-a]pyridin-7-ylmethyl)-5-{1-[(2-methylpropyl)sulfonyl]piperidin-4-yl}thiophene-2-carboxamide;

N-(imidazo[1,2-a]pyridin-7-ylmethyl)-5-[1-(4,4,4-trifluorobutanoyl)piperidin-4-yl]thiophene-2-carboxamide;

N-(imidazo[1,2-a]pyridin-7-ylmethyl)-5-{1-[(4-methyltetrahydro-2H-pyran-4-yl)methyl]-1H-pyrazol-4-yl}thiophene-2-carboxamide;

5-[1-(2-cyano-2-methylpropyl)-1H-pyrazol-4-yl]-N-(imidazo[1,2-a]pyridin-7-ylmethyl)thiophene-2-carboxamide;

4-chloro-N-(imidazo[1,2-a]pyridin-7-ylmethyl)-5-[1-(2-methylpropyl)-1H-pyrazol-4-yl]thiophene-2-carboxamide;

4-chloro-N-(imidazo[1,2-a]pyridin-7-ylmethyl)-5-{1-[(3R)-tetrahydrofuran-3-ylmethyl]-1H-pyrazol-4-yl}thiophene-2-carboxamide;

5-[1-(2-hydroxy-2-methylpropyl)-1H-pyrazol-4-yl]-N-([1,2,4]triazolo[1,5-a]pyridin-6-ylmethyl)thiophene-2-carboxamide;

5-{1-[(4-methyltetrahydro-2H-pyran-4-yl)methyl]-1H-pyrazol-4-yl}-N-([1,2,4]triazolo[1,5-a]pyridin-6-ylmethyl)thiophene-2-carboxamide;

5-[1-(1,4-dioxan-2-ylmethyl)-1H-pyrazol-4-yl]-N-([1,2,4]triazolo[1,5-a]pyridin-6-ylmethyl)thiophene-2-carboxamide;

5-[1-(2-fluorobenzoyl)piperidin-4-yl]-N-(imidazo[1,2-a]pyridin-7-ylmethyl)thiophene-2-carboxamide;

5-{(1R)-1-[(cyclopropylcarbonyl)amino]-3-methylbutyl}-N-(imidazo[1,2-a]pyridin-7-ylmethyl)thiophene-2-carboxamide;

N-(imidazo[1,2-a]pyridin-7-ylmethyl)-5-{(1R)-3-methyl-1-[(tetrahydrofuran-3-ylacetyl)amino]butyl}thiophene-2-carboxamide;

5-{(1S)-1-[(cyclopropylcarbonyl)amino]-3-methylbutyl}-N-(imidazo[1,2-a]pyridin-7-ylmethyl)thiophene-2-carboxamide;

N-(imidazo[1,2-a]pyridin-7-ylmethyl)-2(1-phenylpiperidin-4-yl)-1,3-thiazole-5-carboxamide;

N-(imidazo[1,2-a]pyridin-7-ylmethyl)-2-[1-(pyridin-2-yl)piperidin-4-yl]-1,3-thiazole-5-carboxamide;

5-{1-[(4-fluorotetrahydro-2H-pyran-4-yl)methyl]-1H-pyrazol-4-yl}-N-(imidazo[1,2-a]pyridin-7-ylmethyl)thiophene-2-carboxamide;

5-[1-(cyclopropylcarbonyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(4-methylbenzoyl)pyrrolidin-3-yl]thiophene-2-carboxamide;

N-(imidazo[1,2-a]pyridin-7-ylmethyl)-5-{1-[(4-methyltetrahydro-2H-pyran-4-yl)methyl]-1H-pyrazol-4-yl}furan-2-carboxamide;

5-[1-(2-fluorobenzoyl)piperidin-4-yl]-N-(imidazo[1,2-a]pyridin-7-ylmethyl)furan-2-carboxamide;

N-(imidazo[1,2-a]pyridin-7-ylmethyl)-5-[1-(2-methylpropanoyl)piperidin-4-yl]furan-2-carboxamide;

N-(imidazo[1,2-a]pyridin-7-ylmethyl)-5-[1-(2,2,2-trifluoroethyl)-1H-pyrazol-4-yl]furan-2-carboxamide;
N-(imidazo[1,2-a]pyridin-7-ylmethyl)-5-[1-(2-methylpropyl)-1H-pyrazol-4-yl]furan-2-carboxamide;
5-(1-benzyl-1H-pyrazol-4-yl)-N-(imidazo[1,2-a]pyridin-7-ylmethyl)furan-2-carboxamide;
N-(imidazo[1,2-a]pyridin-7-ylmethyl)-5-{1-[(2S)-tetrahydrofuran-2-ylmethyl]-1H-pyrazol-4-yl}furan-2-carboxamide;
N-(imidazo[1,2-a]pyridin-7-ylmethyl)-5-{1-[(2R)-tetrahydrofuran-2-ylmethyl]-1H-pyrazol-4-yl}furan-2-carboxamide;
N-(imidazo[1,2-a]pyridin-7-ylmethyl)-5-[1-(2-methylpropanoyl)-1,2,3,6-tetrahydropyridin-4-yl]furan-2-carboxamide;
N-(imidazo[1,2-a]pyridin-7-ylmethyl)-5-[1-(3-methylbutanoyl)-1,2,3,6-tetrahydropyridin-4-yl]furan-2-carboxamide;
5-(1-benzoyl-1,2,3,6-tetrahydropyridin-4-yl)-N-(imidazo[1,2-a]pyridin-7-ylmethyl)furan-2-carboxamide;
N-(imidazo[1,2-a]pyridin-7-ylmethyl)-5-[4-(2-methylpropyl)phenyl]furan-2-carboxamide;
N-(imidazo[1,2-a]pyridin-7-ylmethyl)-5-{1-[(2S)-2-methylbutanoyl]-1,2,3,6-tetrahydropyridin-4-yl}furan-2-carboxamide;
5-[1-(3,3-dimethylbutanoyl)-1,2,3,6-tetrahydropyridin-4-yl]-N-(imidazo[1,2-a]pyridin-7-ylmethyl)furan-2-carboxamide;
5-[1-(cyclopropylacetyl)-1,2,3,6-tetrahydropyridin-4-yl]-N-(imidazo[1,2-a]pyridin-7-ylmethyl)furan-2-carboxamide;
N-(imidazo[1,2-a]pyridin-7-ylmethyl)-2-{1-[(2-methylpropyl)sulfonyl]pyrrolidin-3-yl}-1,3-thiazole-5-carboxamide;
N-(imidazo[1,2-a]pyridin-7-ylmethyl)-2-[1-(phenylsulfonyl)pyrrolidin-3-yl]-1,3-thiazole-5-carboxamide;
N-(imidazo[1,2-a]pyridin-7-ylmethyl)-5-{1-[(2-methylpropyl)sulfonyl]-1,2,3,6-tetrahydropyridin-4-yl}furan-2-carboxamide;
N-(imidazo[1,2-a]pyrazin-6-ylmethyl)-5-[1-(2-methylpropyl)-1H-pyrazol-4-yl]thiophene-2-carboxamide;
tert-butyl 4-[(4-{5-[(imidazo[1,2-a]pyridin-7-ylmethyl)carbamoyl]thiophen-2-yl}-1H-pyrazol-1-yl)methyl]-4-methylpiperidine-1-carboxylate;
5-[1-(cyclopropylacetyl)pyrrolidin-3-yl]-N-(imidazo[1,2-a]pyridin-7-ylmethyl)thiophene-2-carboxamide;
5-[1-(2-chlorobenzoyl)pyrrolidin-3-yl]-N-(imidazo[1,2-a]pyridin-7-ylmethyl)thiophene-2-carboxamide;
5-{1-[(4-fluorophenyl)acetyl]pyrrolidin-3-yl}-N-(imidazo[1,2-a]pyridin-7-ylmethyl)thiophene-2-carboxamide;
N-(imidazo[1,2-a]pyridin-7-ylmethyl)-5-[1-(3-methoxybenzoyl)pyrrolidin-3-yl]thiophene-2-carboxamide;
N-(imidazo[1,2-a]pyridin-7-ylmethyl)-5-[1-(2-methoxybenzoyl)pyrrolidin-3-yl]thiophene-2-carboxamide;
5-{1-[(3-fluorophenyl)acetyl]pyrrolidin-3-yl}-N-(imidazo[1,2-a]pyridin-7-ylmethyl)thiophene-2-carboxamide;
5-[1-(3-fluorobenzoyl)pyrrolidin-3-yl]-N-(imidazo[1,2-a]pyridin-7-ylmethyl)thiophene-2-carboxamide;
5-[1-(4-fluorobenzoyl)pyrrolidin-3-yl]-N-(imidazo[1,2-a]pyridin-7-ylmethyl)thiophene-2-carboxamide;
5-{1-[(3,5-difluorophenyl)acetyl]pyrrolidin-3-yl}-N-(imidazo[1,2-a]pyridin-7-ylmethyl)thiophene-2-carboxamide;
5-{1-[(2-fluorophenyl)acetyl]pyrrolidin-3-yl}-N-(imidazo[1,2-a]pyridin-7-ylmethyl)thiophene-2-carboxamide;
5-[1-(4-cyanobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(3-methyloxetan-3-yl)carbonyl]pyrrolidin-3-yl}thiophene-2-carboxamide;
5-[1-(3,5-difluorobenzoyl)pyrrolidin-3-yl]-N-(imidazo[1,2-a]pyridin-7-ylmethyl)thiophene-2-carboxamide;
5-[1-(cyclopentylcarbonyl)pyrrolidin-3-yl]-N-(imidazo[1,2-a]pyridin-7-ylmethyl)thiophene-2-carboxamide;
5-[1-(4-chlorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(1-methyl-1H-pyrrol-2-yl)carbonyl]pyrrolidin-3-yl}thiophene-2-carboxamide;
5-[1-(2,4-difluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(pyridin-4-ylcarbonyl)pyrrolidin-3-yl]thiophene-2-carboxamide;
N-(imidazo[1,2-a]pyridin-7-ylmethyl)-5-[1-(pyridin-2-ylcarbonyl)pyrrolidin-3-yl]thiophene-2-carboxamide;
N-(imidazo[1,2-a]pyridin-7-ylmethyl)-5-{1-[(1-methyl-1H-pyrazol-4-yl)carbonyl]pyrrolidin-3-yl}thiophene-2-carboxamide;
5-[1-(2-fluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(2E)-2-methylpent-2-enoyl]pyrrolidin-3-yl}thiophene-2-carboxamide;
5-{1-[(2,5-dimethylfuran-3-yl)carbonyl]pyrrolidin-3-yl}-N-(imidazo[1,2-a]pyridin-7-ylmethyl)thiophene-2-carboxamide;
5-[1-(3-chlorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-(1-propanoylpyrrolidin-3-yl)thiophene-2-carboxamide;
5-{1-[(1-cyanocyclopropyl)carbonyl]pyrrolidin-3-yl}-N-(imidazo[1,2-a]pyridin-7-ylmethyl)thiophene-2-carboxamide;
5-(1-butanoylpyrrolidin-3-yl)-N-(imidazo[1,2-a]pyridin-7-ylmethyl)thiophene-2-carboxamide;
5-[1-(furan-2-ylcarbonyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(4-methoxybenzoyl)pyrrolidin-3-yl]thiophene-2-carboxamide;
5-[1-(2,5-difluorobenzoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(thiophen-2-ylcarbonyl)pyrrolidin-3-yl]thiophene-2-carboxamide;
5-[1-(2,2-dimethylpropanoyl)pyrrolidin-3-yl]-N-(imidazo[1,2-a]pyridin-7-ylmethyl)thiophene-2-carboxamide;
5-[1-(3,3-dimethylbutanoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-{1-[(4-methylpiperidin-4-yl)methyl]-1H-pyrazol-4-yl}thiophene-2-carboxamide;
5-{1-[(4-fluorotetrahydro-2H-pyran-4-yl)methyl]-1H-pyrazol-4-yl}-N-(imidazo[1,2-a]pyridin-7-ylmethyl)furan-2-carboxamide;
5-[1-(2,2-dimethylbutanoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(pyrazin-2-ylcarbonyl)pyrrolidin-3-yl]thiophene-2-carboxamide;

N-(imidazo[1,2-a]pyridin-7-ylmethyl)-5-{1-[(3-methylthiophen-2-yl)carbonyl]pyrrolidin-3-yl}thiophene-2-carboxamide;
N-(imidazo[1,2-a]pyridin-7-ylmethyl)-5-[1-(2-methylbenzoyl)pyrrolidin-3-yl]thiophene-2-carboxamide;
N-(imidazo[1,2-a]pyridin-7-ylmethyl)-5-{1-[(1-methylcyclopropyl)carbonyl]pyrrolidin-3-yl}thiophene-2-carboxamide;
N-(imidazo[1,2-a]pyridin-7-ylmethyl)-5-[1-(4,4,4-trifluorobutanoyl)pyrrolidin-3-yl]thiophene-2-carboxamide;
5-{1-[(3,5-dimethyl-1,2-oxazol-4-yl)carbonyl]pyrrolidin-3-yl}-N-(imidazo[1,2-a]pyridin-7-ylmethyl)thiophene-2-carboxamide;
N-(imidazo[1,2-a]pyridin-7-ylmethyl)-5-[1-(pyridin-3-ylcarbonyl)pyrrolidin-3-yl]thiophene-2-carboxamide;
N-(imidazo[1,2-a]pyridin-7-ylmethyl)-5-{1-[(1-methyl-1H-pyrazol-5-yl)carbonyl]pyrrolidin-3-yl}thiophene-2-carboxamide;
5-[1-(2,3-dimethylbutanoyl)pyrrolidin-3-yl]-N-(imidazo[1,2-a]pyridin-7-ylmethyl)thiophene-2-carboxamide;
N-(imidazo[1,2-a]pyridin-7-ylmethyl)-5-[1-(phenylsulfonyl)-1,2,3,6-tetrahydropyridin-4-yl]furan-2-carboxamide;
2-[1-(2-fluorobenzoyl)piperidin-4-yl]-N-(imidazo[1,2-a]pyridin-7-ylmethyl)-1,3-thiazole-5-carboxamide;
5-[1-(2-fluorobenzoyl)-1,2,3,6-tetrahydropyridin-4-yl]-N-(imidazo[1,2-a]pyridin-7-ylmethyl)furan-2-carboxamide;
2-[1-(2-fluorobenzoyl)pyrrolidin-3-yl]-N-(imidazo[1,2-a]pyridin-7-ylmethyl)-1,3-thiazole-5-carboxamide;
N-(imidazo[1,2-a]pyridin-7-ylmethyl)-2-[1-(2-methylpropanoyl)pyrrolidin-3-yl]-1,3-thiazole-5-carboxamide;
N-(imidazo[1,2-a]pyridin-7-ylmethyl)-2-[1-(3-methylbutanoyl)pyrrolidin-3-yl]-1,3-thiazole-5-carboxamide;
2-(1-benzoylpyrrolidin-3-yl)-N-(imidazo[1,2-a]pyridin-7-ylmethyl)-1,3-thiazole-5-carboxamide;
tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate;
N-(imidazo[1,2-a]pyridin-7-ylmethyl)-5-{1-[2-(piperazin-1-yl)ethyl]-1H-pyrazol-4-yl}thiophene-2-carboxamide;
5-{1-[(4-fluorotetrahydro-2H-pyran-4-yl)methyl]-1H-pyrazol-4-yl}-N-([2,4]triazolo[1,5-a]pyridin-6-ylmethyl)furan-2-carboxamide;
N-(imidazo[1,2-a]pyridin-7-ylmethyl)-5-[1-(2-methylpropyl)-1H-pyrazol-5-yl]furan-2-carboxamide;
N-(imidazo[1,2-a]pyrazin-6-ylmethyl)-5-[1-(2-methylpropyl)-1H-pyrazol-4-yl]furan-2-carboxamide;
5-[1-(2-methylpropyl)-1H-pyrazol-4-yl]-N-([1,2,4]triazolo[1,5-a]pyridin-6-ylmethyl)furan-2-carboxamide;
N-(imidazo[1,2-a]pyridin-7-ylmethyl)-5-[1-(3-methylbutyl)-1H-pyrazol-5-yl]furan-2-carboxamide;
5-{1-[(4-methyltetrahydro-2H-pyran-4-yl)methyl]-1H-pyrazol-4-yl}-N-([1,2,4]triazolo[1,5-a]pyridin-6-ylmethyl)furan-2-carboxamide;
N-(imidazo[1,2-a]pyridin-7-ylmethyl)-5-{[(2R)-2-(methoxymethyl)pyrrolidin-1-yl]carbonyl}thiophene-2-carboxamide;
N-(imidazo[1,2-a]pyridin-7-ylmethyl)-5-{[2-(2-methylpropyl)pyrrolidin-1-yl]carbonyl}thiophene-2-carboxamide;
5-[1-(2,2-dimethylpropyl)-1H-pyrazol-4-yl]-N-(imidazo[1,2-a]pyridin-7-ylmethyl)furan-2-carboxamide;
5-[1-(2-fluorobenzoyl)piperidin-4-yl]-N-(imidazo[1,2-a]pyrazin-6-ylmethyl)thiophene-2-carboxamide;
5-[1-(4-fluorobenzoyl)piperidin-4-yl]-N-(imidazo[1,2-a]pyrazin-6-ylmethyl)thiophene-2-carboxamide;
5-[1-(2,4-difluorobenzoyl)piperidin-4-yl]-N-(imidazo[1,2-a]pyrazin-6-ylmethyl)thiophene-2-carboxamide;
5-[1-(2,5-difluorobenzoyl)piperidin-4-yl]-N-(imidazo[1,2-a]pyrazin-6-ylmethyl)thiophene-2-carboxamide;
5-[1-(2-fluorobenzoyl)piperidin-4-yl]-N-([1,2,4]triazolo[1,5-a]pyridin-6-ylmethyl)thiophene-2-carboxamide;
5-[1-(3-fluorobenzoyl)piperidin-4-yl]-N-([1,2,4]triazolo[1,5-a]pyridin-6-ylmethyl)thiophene-2-carboxamide;
5-[1-(4-fluorobenzoyl)piperidin-4-yl]-N-([1,2,4]triazolo[1,5-a]pyridin-6-ylmethyl)thiophene-2-carboxamide;
5-[1-(2,4-difluorobenzoyl)piperidin-4-yl]-N-([1,2,4]triazolo[1,5-a]pyridin-6-ylmethyl)thiophene-2-carboxamide;
5-[1-(2,5-difluorobenzoyl)piperidin-4-yl]-N-([1,2,4]triazolo[1,5-a]pyridin-6-ylmethyl)thiophene-2-carboxamide;
5-[1-(3,5-difluorobenzoyl)piperidin-4-yl]-N-([1,2,4]triazolo[1,5-a]pyridin-6-ylmethyl)thiophene-2-carboxamide;
N-(imidazo[1,2-a]pyrazin-6-ylmethyl)-5-[1-(2-methylpropanoyl)piperidin-4-yl]thiophene-2-carboxamide;
N-(imidazo[1,2-a]pyrazin-6-ylmethyl)-5-[1-(3-methylbutanoyl)piperidin-4-yl]thiophene-2-carboxamide;
N-(imidazo[1,2-a]pyrazin-6-ylmethyl)-5-{1-[(1-methylcyclopropyl)carbonyl]piperidin-4-yl}thiophene-2-carboxamide;
N-(imidazo[1,2-a]pyrazin-6-ylmethyl)-5-[1-(4,4,4-trifluorobutanoyl)piperidin-4-yl]thiophene-2-carboxamide;
N-(imidazo[1,2-a]pyrazin-6-ylmethyl)-5-[1-(tetrahydro-2H-pyran-4-ylcarbonyl)piperidin-4-yl]thiophene-2-carboxamide;
5-[1-(2-methylpropanoyl)piperidin-4-yl]-N-([1,2,4]triazolo[1,5-a]pyridin-6-ylmethyl)thiophene-2-carboxamide;
5-[1-(3-methylbutanoyl)piperidin-4-yl]-N-([1,2,4]triazolo[1,5-a]pyridin-6-ylmethyl)thiophene-2-carboxamide;
5-{1-[(2S)-2-methylbutanoyl]piperidin-4-yl}-N-([1,2,4]triazolo[1,5-a]pyridin-6-ylmethyl)thiophene-2-carboxamide;
5-{1-[(1-methylcyclopropyl)carbonyl]piperidin-4-yl}-N-([1,2,4]triazolo[1,5-a]pyridin-6-ylmethyl)thiophene-2-carboxamide;
N-([1,2,4]triazolo[1,5-a]pyridin-6-ylmethyl)-5-[1-(3,3,3-trifluoropropanoyl)piperidin-4-yl]thiophene-2-carboxamide;
N-([1,2,4]triazolo[1,5-a]pyridin-6-ylmethyl)-5-[1-(4,4,4-trifluorobutanoyl)piperidin-4-yl]thiophene-2-carboxamide;
5-{1-[(4,4-difluorocyclohexyl)carbonyl]piperidin-4-yl}-N-([1,2,4]triazolo[1,5-a]pyridin-6-ylmethyl)thiophene-2-carboxamide;
5-[1-(tetrahydro-2H-pyran-4-ylcarbonyl)piperidin-4-yl]-N-([1,2,4]triazolo[1,5-a]pyridin-6-ylmethyl)thiophene-2-carboxamide;
5-[1-(2-hydroxy-2-methylpropanoyl)piperidin-4-yl]-N-([1,2,4]triazolo[1,5-a]pyridin-6-ylmethyl)thiophene-2-carboxamide;
5-{1-[(1-methylpiperidin-4-yl)carbonyl]piperidin-4-yl}-N-([1,2,4]triazolo[1,5-a]pyridin-6-ylmethyl)thiophene-2-carboxamide;

5-[1-(2-cyanobenzoyl)piperidin-4-yl]-N-([1,2,4]triazolo[1,5-a]pyridin-6-ylmethyl)thiophene-2-carboxamide;
5-[1-(pyridin-2-ylcarbonyl)piperidin-4-yl]-N-([1,2,4]triazolo[1,5-a]pyridin-6-ylmethyl)thiophene-2-carboxamide;
5-(1-benzyl-3-cyclopropyl-1H-pyrazol-5-yl)-N-(imidazo[1,2-a]pyridin-7-ylmethyl)thiophene-2-carboxamide;
5-[1-(2,2-dimethylpropyl)-1H-pyrazol-4-yl]-N-(imidazo[1,2-a]pyrazin-6-ylmethyl)thiophene-2-carboxamide;
5-[1-(propan-2-ylsulfonyl)piperidin-4-yl]-N-([1,2,4]triazolo[1,5-a]pyridin-6-ylmethyl)thiophene-2-carboxamide;
5-[1-(phenylsulfonyl)piperidin-4-yl]-N-([1,2,4]triazolo[1,5-a]pyridin-6-ylmethyl)thiophene-2-carboxamide;
N-(imidazo[1,2-a]pyrazin-6-ylmethyl)-5-{1-[(4-methyltetrahydro-2H-pyran-4-yl)methyl]-1H-pyrazol-4-yl}thiophene-2-carboxamide;
N-(imidazo[1,2-a]pyridin-7-ylmethyl)-5-{1-[2-methyl-2-(piperazin-1-yl)propanoyl]piperidin-4-yl}thiophene-2-carboxamide;
5-[1-(2,2-dimethylpropyl)-1H-pyrazol-4-yl]-N-(imidazo[1,2-a]pyridin-7-ylmethyl)thiophene-2-carboxamide;
N-(imidazo[1,2-a]pyridin-7-ylmethyl)-5-[1-(tricyclo[3.3.1.1~3,7~]dec-1-ylmethyl)-1H-pyrazol-4-yl]thiophene-2-carboxamide;
5-(1-benzyl-1H-pyrazol-4-yl)-N-(imidazo[1,2-a]pyridin-7-ylmethyl)thiophene-2-carboxamide;
N-(imidazo[1,2-a]pyridin-7-ylmethyl)-5-[1-(2-oxatricyclo[3.3.1.1~3,7~]dec-1-ylmethyl)-1H-pyrazol-4-yl]thiophene-2-carboxamide;
5-[1-(2,5-difluorobenzoyl)piperidin-4-yl]-N-(imidazo[1,2-a]pyridin-7-ylmethyl)thiophene-2-carboxamide;
5-[1-(2,4-difluorobenzoyl)piperidin-4-yl]-N-(imidazo[1,2-a]pyridin-7-ylmethyl)thiophene-2-carboxamide;
N-(imidazo[1,2-a]pyridin-7-ylmethyl)-5-{1-[2-(piperazin-1-yl)ethyl]-1H-pyrazol-4-yl}furan-2-carboxamide;
5-(3-cyclopropyl-1-methyl-1H-pyrazol-5-yl)-N-(imidazo[1,2-a]pyridin-7-ylmethyl)thiophene-2-carboxamide;
5-[3-cyclopropyl-1-(2-methoxyethyl)-1H-pyrazol-5-yl]-N-(imidazo[1,2-a]pyridin-7-ylmethyl)thiophene-2-carboxamide;
N-(imidazo[1,2-a]pyrazin-6-ylmethyl)-5-{1-[2-(piperazin-1-yl)ethyl]-1H-pyrazol-4-yl}thiophene-2-carboxamide;
N-(imidazo[1,2-a]pyridin-7-ylmethyl)-5-[1-(2-methylpropyl)-1H-pyrazol-5-yl]thiophene-2-carboxamide;
N-(imidazo[1,2-a]pyridin-7-ylmethyl)-5-[1-methyl-3-(2-methylpropyl)-1H-pyrazol-5-yl]thiophene-2-carboxamide;
5-[1-benzyl-3-(2-methylpropyl)-1H-pyrazol-5-yl]-N-(imidazo[1,2-a]pyridin-7-ylmethyl)thiophene-2-carboxamide;
N-[(7-fluoroimidazo[1,2-a]pyridin-6-yl)methyl]-5-[1-(2-methylpropyl)-1H-pyrazol-4-yl]thiophene-2-carboxamide;
5-{1[2,2-dimethyl-3-(piperazin-1-yl)propyl]-1H-pyrazol-4-yl}-N-(imidazo[1,2-a]pyridin-7-ylmethyl)thiophene-2-carboxamide;
5-[1-(3-amino-2,2-dimethylpropyl)-1H-pyrazol-4-yl]-N-(imidazo[1,2-a]pyridin-7-ylmethyl)thiophene-2-carboxamide; and pharmaceutically acceptable salts thereof.

8. A composition comprising an excipient and a therapeutically effective amount of a compound of claim 1, or pharmaceutically acceptable salts thereof.

9. A compound of Formula (VIA), or a therapeutically acceptable salt thereof,

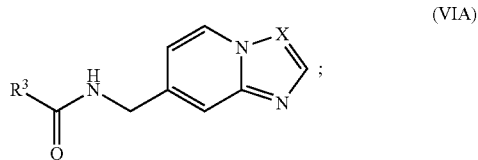

wherein
X is N or $CY^1$;
$Y^1$ is independently selected from the group consisting of hydrogen, OH, CN, F, Cl, Br, and I;
$R^3$ is independently selected from the group consisting of furanyl, thienyl, pyrrolyl, imidazolyl, pyrazolyl, triazolyl, tetrazolyl, isoxazolyl, thiazolyl, isothiazolyl, thiadiazolyl, oxadiazolyl, and oxatriazolyl; wherein each $R^3$ furanyl, thienyl, pyrrolyl, imidazolyl, pyrazolyl, triazolyl, tetrazolyl, isoxazolyl, thiazolyl, isothiazolyl, thiadiazolyl, oxadiazolyl, and oxatriazolyl is substituted with one, two, three or four substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $NHS(O)_2R^4$, $NR^4S(O)_2R^4$, $NHC(O)OR^4$, $NR^4C(O)OR^4$, $NHC(O)NH_2$, $NHC(O)NHR^4$, $NHC(O)N(R^4)_2$, $NR^4C(O)NHR^4$, $NR^4C(O)N(R^4)_2$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $C(O)H$, $C(O)OH$, $C(N)NH_2$, $C(N)NHR^4$, $C(N)N(R^4)_2$, CNOH, $CNOCH_3$, OH, CN, $N_3$, $NO_2$, F, Cl, Br and I;
$R^4$, at each occurrence, is independently selected from the group consisting of alkyl, alkenyl, alkynyl, aryl, cycloalkyl, cycloalkenyl, and 3-12 membered heterocyclyl; wherein each $R^4$ alkyl, alkenyl, and alkynyl is optionally substituted with one, two, three or four substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $N R^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $C(N)NH_2$, $C(N)NHR^5$, $C(N)N(R^5)_2$, CNOH, $CNOCH_3$, OH, CN, $N_3$, $NO_2$, F, Cl, Br and I; wherein each $R^4$ aryl, cycloalkyl, cycloalkenyl, and 3-12 membered heterocyclyl is optionally substituted with one, two, three or four substituents independently selected from the group consisting of $R^6$, $OR^6$, $SR^6$, $S(O)R^6$, $SO_2R^6$, $C(O)R^6$, $CO(O)R^6$, $C(O)C(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $C(N)NH_2$, $C(N)NHR^6$, $C(N)N(R^6)_2$, CNOH, $CNOCH_3$, OH, CN, $N_3$, $NO_2$, F, Cl, Br and I;
$R^5$, at each occurrence, is independently selected from the group consisting of alkyl, alkenyl, alkynyl, aryl, heterocyclyl, cycloalkyl, and cycloalkenyl; wherein each $R^5$ alkyl, alkenyl, and alkynyl is optionally substituted with one, two, three or four substituents independently selected from the group consisting of $R^7$, $OR^7$, $SR^7$, $S(O)R^7$, $SO_2R^7$, $C(O)R^7$, $CO(O)R^7$, $OC(O)R^7$, $OC(O)OR^7$, $NH_2$, $NHR^7$, $N(R^7)_2$, $NHC(O)R^7$, $NR^7C(O)R^7$, $NHS(O)_2R^7$, $N R^7S(O)_2R^7$, $NHC(O)OR^7$, $NR^7C(O)OR^7$, $NHC(O)NH_2$, $NHC(O)NHR^7$, $NHC(O)N(R^7)_2$, $NR^7C(O)NHR^7$, $NR^7C(O)N(R^7)_2$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $C(O)H$, $C(O)OH$, $C(N)NH_2$, $C(N)NHR^7$, $C(N)N(R^7)_2$, CNOH, $CNOCH_3$, OH, CN, $N_3$, $NO_2$, F, Cl, Br and I; wherein each $R^5$ aryl, cycloalkyl, cycloalkenyl, and heterocyclyl is optionally substituted with one, two, three or four substituents independently selected from the group consisting of $R^8$, $OR^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2 R^8$, $NR^8S(O)_2R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $SO_2NH_2$, $SO_2NHR^8$, $SO_2N(R^8)_2$, $C(O)H$, $C(O)OH$, $C(N)NH_2$, $C(N)NHR^8$, $C(N)N(R^8)_2$, CNOH, $CNOCH_3$, OH, CN, $N_3$, $NO_2$, F, Cl, Br and I;

$R^6$, at each occurrence, is independently selected from the group consisting of alkyl, alkenyl, alkynyl, aryl, heterocyclyl, cycloalkyl, and cycloalkenyl; wherein each $R^6$ alkyl, alkenyl, and alkynyl is optionally substituted with one, two, three or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $N R^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $C(O)H$, $C(O)OH$, $C(N)NH_2$, $C(N)NHR^9$, $C(N)N(R^9)_2$, CNOH, $CNOCH_3$, OH, CN, $N_3$, $NO_2$, F, Cl, Br and I; wherein each $R^6$ aryl, cycloalkyl, cycloalkenyl, and heterocyclyl is optionally substituted with one, two, three or four substituents independently selected from the group consisting of $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$,$)NHC(O)N(R^{10}_2$, $NR^{10}C(O)NHR^{10}$,$)$ $NR^{10}C(O)N(R^{10})_2$, $C(O)NH_2$, $C(O)NHR^{10}$,$)C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, CNOH, $CNOCH_3$, OH, CN, $N_3$, $NO_2$, F, Cl, Br and I;

$R^7$, at each occurrence, is independently selected from the group consisting of alkyl, alkenyl, alkynyl, aryl, heterocyclyl, cycloalkyl, and cycloalkenyl; wherein each $R^7$ alkyl, alkenyl, and alkynyl is optionally substituted with one, two, three or four substituents independently selected from the group consisting of aryl, alkoxy, OH, CN, $N_3$, $NO_2$, F, Cl, Br and I; wherein each $R^7$ aryl, cycloalkyl, cycloalkenyl, and heterocyclyl is optionally substituted with one, two, three or four substituents independently selected from the group consisting of OH, CN, $N_3$, $NO_2$, F, Cl, Br and I;

$R^8$, at each occurrence, is independently selected from the group consisting of alkyl, alkenyl, and alkynyl;

$R^9$, at each occurrence, is independently selected from the group consisting of alkyl, alkenyl, alkynyl, aryl, heterocyclyl, cycloalkyl, and cycloalkenyl; wherein each $R^9$ alkyl, alkenyl, and alkynyl is optionally substituted with one, two, three or four substituents independently selected from the group consisting of aryl, alkoxy, OH, CN, $NO_2$, F, Cl, Br and I; wherein each $R^9$ aryl, cycloalkyl, cycloalkenyl, and heterocyclyl is optionally substituted with one, two, three or four substituents independently selected from the group consisting of $R^{11}$, $OR^{11}$, $C(O)R^{11}$, $CO(O)R^{11}$, $NH_2$, $NHR^{11}$, $N(R^{11})_2$, $NHC(O)R^{11}$, $C(O)R^{11}$, $C(O)NH_2$, $C(O)NHR^{11}$, $C(O)N(R^{11})_2$, $C(O)H$, $C(O)OH$, COH, CN, $NO_2$, F, Cl, Br and I;

$R^{10}$, at each occurrence, is independently selected from the group consisting of aryl, heterocyclyl, cycloalkyl, cycloalkenyl, alkyl, alkenyl, and alkynyl; wherein each $R^{10}$ alkyl, alkenyl, and alkynyl is optionally substituted with one, two, three or four substituents independently selected from the group consisting of alkoxy, F, Cl, Br and I; and $R^{11}$, at each occurrence, is independently selected from the group consisting of aryl, heterocyclyl, cycloalkyl, cycloalkenyl, alkyl, alkenyl, and alkynyl;

with the proviso that when X is $CY^1$ and $Y^1$ is hydrogen; and $R^3$ is thiazolyl; the $R^3$ thiazolyl is substituted with one substituent.

10. The compound claim 9, or a therapeutically acceptable salt thereof, wherein $R^3$ is thienyl; wherein each $R^3$ thienyl is substituted with one, two, or three substituents independently selected from the group consisting of $R^4$, $C(O)R^4$, $NHR^4$, $NHC(O)R^4$, $NR^4C(O)R^4$, $NHC(O)OR^4$, $NR^4C(O)NHR^4$, $C(O)NHR^4$, F, Cl, Br and I.

11. The compound of claim 1, selected from the group consisting of:

N-(imidazo[1,2-a]pyridin-6-ylmethyl)-5-[1-(2-methylpropyl)-1H-pyrazol-4-yl]thiophene-2-carboxamide;

N-(imidazo[1,2-a]pyridin-7-ylmethyl)-5-[1-(2-methylpropyl)-1H-pyrazol-4-yl]thiophene-2-carboxamide;

N-(imidazo[1,2-a]pyridin-6-ylmethyl)-5-[1-(2-methylpropanoyl)-1H-pyrazol-4-yl]thiophene-2-carboxamide;

5-[1-(2-hydroxy-2-methylpropyl)-1H-pyrazol-4-yl]-N-(imidazo[1,2-a]pyridin-6-ylmethyl)thiophene-2-carboxamide;

N-(imidazo[1,2-a]pyridin-6-ylmethyl)-5-{1-[(3-methyloxetan-3-yl)methyl]-1H-pyrazol-4-yl}thiophene-2-carboxamide;

5-[1-(cyclobutylmethyl)-1H-pyrazol-4-yl]-N-(imidazo[1,2-a]pyridin-6-ylmethyl)thiophene-2-carboxamide;

5-[1-(cyclohexylmethyl)-1H-pyrazol-4-yl]-N-(imidazo[1,2-a]pyridin-6-ylmethyl)thiophene-2-carboxamide;

5-{1-[(2R)-2-hydroxybutyl]-1H-pyrazol-4-yl}-N-(imidazo[1,2-a]pyridin-6-ylmethyl)thiophene-2-carboxamide;

5-[1-(2-hydroxy-2-methylpropyl)-1H-pyrazol-4-yl]-N-(imidazo[1,2-a]pyridin-7-ylmethyl)thiophene-2-carboxamide;

N-(imidazo[1,2-a]pyridin-6-ylmethyl)-5-[1-(tetrahydro-2H-pyran-2-ylmethyl)-1H-pyrazol-4-yl]thiophene-2-carboxamide;

N-(imidazo[1,2-a]pyridin-6-ylmethyl)-5-[1-(tetrahydrofuran-3-ylmethyl)-1H-pyrazol-4-yl]thiophene-2-carboxamide;

N-(imidazo[1,2-a]pyridin-6-ylmethyl)-5-[1-(tetrahydro-2H-pyran-4-ylmethyl)-1H-pyrazol-4-yl]thiophene-2-carboxamide;

N-(imidazo[1,2-a]pyridin-6-ylmethyl)-5-[1-(tetrahydro-2H-pyran-3-ylmethyl)-1H-pyrazol-4-yl]thiophene-2-carboxamide;

N-(imidazo[1,2-a]pyridin-6-ylmethyl)-5-[1-(tetrahydrofuran-2-ylmethyl)-1H-pyrazol-4-yl]thiophene-2-carboxamide;

5-(1-acetyl-1,2,3,6-tetrahydropyridin-4-yl)-N-(imidazo[1,2-a]pyridin-7-ylmethyl)thiophene-2-carboxamide;

N-(imidazo[1,2-a]pyridin-7-ylmethyl)-5-[1-(methylsulfonyl)-1,2,3,6-tetrahydropyridin-4-yl]thiophene-2-carboxamide;

5-[1-(cyclopropylsulfonyl)-1,2,3,6-tetrahydropyridin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydro-2H-pyran-2-ylmethyl)-1H-pyrazol-4-yl]thiophene-2-carboxamide;

N-(imidazo[1,2-a]pyridin-7-ylmethyl)-5-[1-(tetrahydrofuran-2-ylmethyl)-1H-pyrazol-4-yl]thiophene-2-carboxamide;

N-(imidazo[1,2-a]pyridin-7-ylmethyl)-5-[(4R)-2-oxo-4-(propan-2-yl)-1,3-oxazolidin-3-yl]thiophene-2-carboxamide;

N-(imidazo[1,2-a]pyridin-7-ylmethyl)-5-[1-(tetrahydrofuran-3-ylmethyl)-1H-pyrazol-4-yl]thiophene-2-carboxamide;

N-(imidazo[1,2-a]pyridin-7-ylmethyl)-5-[1-(tetrahydro-2H-pyran-3-ylmethyl)-1H-pyrazol-4-yl]thiophene-2-carboxamide;

N-(imidazo[1,2-a]pyridin-7-ylmethyl)-5-{1-[(3-methyloxetan-3-yl)methyl]-1H-pyrazol-4-yl}thiophene-2-carboxamide;

N-(imidazo[1,2-a]pyridin-7-ylmethyl)-5-[1-(methoxyacetyl)piperidin-4-yl]thiophene-2-carboxamide;

5-(1-acetylpiperidin-4-yl)-N-(imidazo[1,2-a]pyridin-7-ylmethyl)thiophene-2-carboxamide;

N-(imidazo[1,2-a]pyridin-7-ylmethyl)-5-[1-(2-methylpropanoyl)piperidin-4-yl]thiophene-2-carboxamide;

5-[1-(cyclopropylcarbonyl)piperidin-4-yl]-N-(imidazo[1,2-a]pyridin-7-ylmethyl)thiophene-2-carboxamide;

N-(imidazo[1,2-a]pyridin-7-ylmethyl)-5-[1-(tetrahydrofuran-3-ylcarbonyl)piperidin-4-yl]thiophene-2-carboxamide;

N-(imidazo[1,2-a]pyridin-7-ylmethyl)-5-[1-(tetrahydro-2H-pyran-4-ylacetyl)piperidin-4-yl]thiophene-2-carboxamide;

N-(imidazo[1,2-a]pyridin-7-ylmethyl)-5-[1-(3-methylbutanoyl)piperidin-4-yl]thiophene-2-carboxamide;

N-(imidazo[1,2-a]pyridin-7-ylmethyl)-5-[1-(1,2-oxazol-5-ylcarbonyl)piperidin-4-yl]thiophene-2-carboxamide;

N-(imidazo[1,2-a]pyridin-7-ylmethyl)-5-[1-(tetrahydro-2H-pyran-4-ylmethyl)-1H-pyrazol-4-yl]thiophene-2-carboxamide;

5-[5-(hydroxymethyl)-2-oxo-1,3-oxazolidin-3-yl]-N-(imidazo[1,2-a]pyridin-7-ylmethyl)thiophene-2-carboxamide;

5-[(4R)-4-hydroxy-2-oxopyrrolidin-1-yl]-N-(imidazo[1,2-a]pyridin-7-ylmethyl)thiophene-2-carboxamide;

5-[(4S)-4-hydroxy-2-oxopyrrolidin-1-yl]-N-(imidazo[1,2-a]pyridin-7-ylmethyl)thiophene-2-carboxamide;

N-(imidazo[1,2-a]pyridin-7-ylmethyl)-5-[1-(2-methoxyethyl)-1H-pyrazol-4-yl]thiophene-2-carboxamide;

N-(imidazo[1,2-a]pyridin-7-ylmethyl)-5-[1-(methylsulfonyl)piperidin-4-yl]thiophene-2-carboxamide;

5-[1-(cyclohexylmethyl)-5-ethyl-1H-pyrazol-4-yl]-N-(imidazo[1,2-a]pyridin-7-ylmethyl)thiophene-2-carboxamide;

N-(imidazo[1,2-a]pyridin-7-ylmethyl)-5-{1-[(1-methoxy-3,3-dimethylcyclohexyl)methyl]-5-methyl-1H-pyrazol-4-yl}thiophene-2-carboxamide;

N-(imidazo[1,2-a]pyridin-7-ylmethyl)-5-(1-propyl-1H-pyrazol-4-yl)thiophene-2-carboxamide;

N-(imidazo[1,2-a]pyridin-7-ylmethyl)-5-{1-[2-(morpholin-4-yl)ethyl]-1H-pyrazol-4-yl}thiophene-2-carboxamide;

5-(1-ethyl-1H-pyrazol-4-yl)-N-(imidazo[1,2-a]pyridin-7-ylmethyl)thiophene-2-carboxamide;

5-[1-(1,1-dioxidotetrahydrothiophen-3-yl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-phenylthiophene-2-carboxamide;

N-(imidazo[1,2-a]pyridin-7-ylmethyl)-5-{1-[2-(methylsulfonyl)ethyl]-1H-pyrazol-4-yl}thiophene-2-carboxamide;

5-{1-[(2R)-2-hydroxypropyl]-1H-pyrazol-4-yl}-N-(imidazo[1,2-a]pyridin-7-ylmethyl)thiophene-2-carboxamide;

5-[1-(1,4-dioxan-2-ylmethyl)-1H-pyrazol-4-yl]-N-(imidazo[1,2-a]pyridin-7-ylmethyl)thiophene-2-carboxamide;

5-[1-(2-hydroxyethyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[3-(propan-2-yloxy)phenyl]thiophene-2-carboxamide;

N-(imidazo[1,2-a]pyridin-7-ylmethyl)-5-{3-[(2-methylpropanoyl)amino]oxetan-3-yl}thiophene-2-carboxamide;

5-[3-(benzoylamino)oxetan-3-yl]-N-(imidazo[1,2-a]pyridin-7-ylmethyl)thiophene-2-carboxamide;

N-(imidazo[1,2-a]pyridin-7-ylmethyl)-5-{3-[(tetrahydrofuran-3-ylacetyl)amino]oxetan-3-yl}thiophene-2-carboxamide;

N-(imidazo[1,2-a]pyridin-7-ylmethyl)-5[3-(pentanoylamino)oxetan-3-yl]thiophene-2-carboxamide;

5-{1-[(1,1-dioxidotetrahydro-2H-thiopyran-3-yl)methyl]-1H-pyrazol-4-yl}-N-(imidazo[1,2-a]pyridin-7-ylmethyl)thiophene-2-carboxamide;

N-(imidazo[1,2-a]pyridin-7-ylmethyl)-5-(1-methyl-1H-pyrazol-4-yl)thiophene-2-carboxamide;

N-(imidazo[1,2-a]pyridin-7-ylmethyl)-5-(1-methyl-1H-pyrazol-5-yl)thiophene-2-carboxamide;

N-(imidazo[1,2-a]pyridin-7-ylmethyl)-5-{1-[(2R)-tetrahydrofuran-2-ylmethyl]-1H-pyrazol-4-yl}thiophene-2-carboxamide;

N-(imidazo[1,2-a]pyridin-7-ylmethyl)-5-{1-[(2S)-tetrahydrofuran-2-ylmethyl]-1H-pyrazol-4-yl}thiophene-2-carboxamide;

5-(4-hydroxytetrahydro-2H-pyran-4-yl)-N-(imidazo[1,2-a]pyridin-7-ylmethyl)thiophene-2-carboxamide;

5-[3-hydroxy-1-(2-methylpropanoyl)azetidin-3-yl]-N-(imidazo[1,2-a]pyridin-7-ylmethyl)thiophene-2-carboxamide;

5-(1-benzoyl-3-hydroxyazetidin-3-yl)-N-(imidazo[1,2-a]pyridin-7-ylmethyl)thiophene-2-carboxamide;

tert-butyl 4-hydroxy-4-{5-[(imidazo[1,2-a]pyridin-7-ylmethyl)carbamoyl]thiophen-2-yl}piperidine-1-carboxylate;

5-{3-hydroxy-1-[(2S)-2-methylbutanoyl]azetidin-3-yl}-N-(imidazo[1,2-a]pyridin-7-ylmethyl)thiophene-2-carboxamide;

5-[3-hydroxy-1-(tetrahydro-2H-pyran-4-ylacetyl)azetidin-3-yl]-N-(imidazo[1,2-a]pyridin-7-ylmethyl)thiophene-2-carboxamide;

N-(imidazo[1,2-a]pyridin-7-ylmethyl)-5-(3-{[(2S)-2-methylbutanoyl]amino}oxetan-3-yl)thiophene-2-carboxamide;

N-(imidazo[1,2-a]pyridin-7-ylmethyl)-5-[1-(tetrahydro-2H-pyran-4-yl)-1H-pyrazol-4-yl]thiophene-2-carboxamide;

N-(imidazo[1,2-a]pyridin-7-ylmethyl)-5-[6-(morpholin-4-yl)pyridin-3-yl]thiophene-2-carboxamide;

N-(imidazo[1,2-a]pyridin-7-ylmethyl)-5-{1-[(2-methyltetrahydro-2H-pyran-2-yl)methyl]-1H-pyrazol-4-yl}thiophene-2-carboxamide;

tert-butyl 4-[(4-{5-[(imidazo[1,2-a]pyridin-7-ylmethyl)carbamoyl]thiophen-2-yl}-1H-pyrazol-1-yl)methyl]piperidine-1-carboxylate;

N-(imidazo[1,2-a]pyridin-7-ylmethyl)-5-[1-(3-methylbutanoyl)pyrrolidin-3-yl]thiophene-2-carboxamide;

N-(imidazo[1,2-a]pyridin-7-ylmethyl)-5-{1-[(2-methylpropanoyl)amino]cyclobutyl}thiophene-2-carboxamide;

N-(imidazo[1,2-a]pyridin-7-ylmethyl)-5-{1-[(3-methylbutanoyl)amino]cyclobutyl}thiophene-2-carboxamide;

N-(imidazo[1,2-a]pyridin-7-ylmethyl)-5-(1-{[(2S)-2-methylbutanoyl]amino}cyclobutyl)thiophene-2-carboxamide;

5-[1-(benzoylamino)cyclobutyl]-N-(imidazo[1,2-a]pyridin-7-ylmethyl)thiophene-2-carboxamide;

N-(imidazo[1,2-a]pyridin-7-ylmethyl)-5-{1-[(3,3,3-trifluoropropanoyl)amino]cyclobutyl}thiophene-2-carboxamide;

N-(1-{5-[(imidazo[1,2-a]pyridin-7-ylmethyl)carbamoyl]thiophen-2-yl}cyclobutyl)tetrahydro-2H-pyran-4-carboxamide;

5-[1-(cyclobutylmethyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[1-(piperidin-4-ylmethyl)-1H-pyrazol-4-yl]thiophene-2-carboxamide;

5-[1-(2-methylpropyl)-1H-pyrazol-4-yl]-N-([1,2,4]triazolo[1,5-a]pyridin-7-ylmethyl)thiophene-2-carboxamide;

N-(imidazo[1,2-a]pyridin-7-ylmethyl)-5-[1-(3,3,3-trifluoropropanoyl)pyrrolidin-3-yl]thiophene-2-carboxamide;

N-(imidazo[1,2-a]pyridin-7-ylmethyl)-5-[1-(2-methylpropanoyl)pyrrolidin-3-yl]thiophene-2-carboxamide;

5-(1-benzoylpyrrolidin-3-yl)-N-(imidazo[1,2-a]pyridin-7-ylmethyl)thiophene-2-carboxamide;

5-[4-hydroxy-1-(3-methylbutanoyl)piperidin-4-yl]-N-(imidazo[1,2-a]pyridin-7-ylmethyl)thiophene-2-carboxamide;

5-[4-hydroxy-1-(2-methylpropanoyl)piperidin-4-yl]-N-(imidazo[1,2-a]pyridin-7-ylmethyl)thiophene-2-carboxamide;

5-[1-(3,3-dimethylbutanoyl)-4-hydroxypiperidin-4-yl]-N-(imidazo[1,2-a]pyridin-7-ylmethyl)thiophene-2-carboxamide;

5-(1-benzoyl-4-hydroxypiperidin-4-yl)-N-(imidazo[1,2-a]pyridin-7-ylmethyl)thiophene-2-carboxamide;

propan-2-yl 4-{5-[(imidazo[1,2-a]pyridin-7-ylmethyl)carbamoyl]thiophen-2-yl}piperidine-1-carboxylate;

2-methylpropyl 4-{5-[(imidazo[1,2-a]pyridin-7-ylmethyl)carbamoyl]thiophen-2-yl}piperidine-1-carboxylate;

N-(imidazo[1,2-a]pyridin-7-ylmethyl)-5-[1-(3,3,3-trifluoropropanoyl)piperidin-4-yl]thiophene-2-carboxamide;

N-(imidazo[1,2-a]pyridin-7-ylmethyl)-5-{1-[(2-methylpropyl)sulfonyl]piperidin-4-yl}thiophene-2-carboxamide;

N-(imidazo[1,2-a]pyridin-7-ylmethyl)-5-[1-(4,4,4-trifluorobutanoyl)piperidin-4-yl]thiophene-2-carboxamide;

N-(imidazo[1,2-a]pyridin-7-ylmethyl)-5-{1-[(4-methyltetrahydro-2H-pyran-4-yl)methyl]-1H-pyrazol-4-yl}thiophene-2-carboxamide;

5-[1-(2-cyano-2-methylpropyl)-1H-pyrazol-4-yl]-N-(imidazo[1,2-a]pyridin-7-ylmethyl)thiophene-2-carboxamide;

4-chloro-N-(imidazo[1,2-a]pyridin-7-ylmethyl)-5-[1-(2-methylpropyl)-1H-pyrazol-4-yl]thiophene-2-carboxamide;

4-chloro-N-(imidazo[1,2-a]pyridin-7-ylmethyl)-5-{1-[(3R)-tetrahydrofuran-3-ylmethyl]-1H-pyrazol-4-yl}thiophene-2-carboxamide;

5-[1-(2-hydroxy-2-methylpropyl)-1H-pyrazol-4-yl]-N-([1,2,4]triazolo[1,5-a]pyridin-6-ylmethyl)thiophene-2-carboxamide;

5-{1-[(4-methyltetrahydro-2H-pyran-4-yl)methyl]-1H-pyrazol-4-yl}-N-([1,2,4]triazolo[1,5-a]pyridin-6-ylmethyl)thiophene-2-carboxamide;

5-[1-(1,4-dioxan-2-ylmethyl)-1H-pyrazol-4-yl]-N-([1,2,4]triazolo[1,5-a]pyridin-6-ylmethyl)thiophene-2-carboxamide;

5-[1-(2-fluorobenzoyl)piperidin-4-yl]-N-(imidazo[1,2-a]pyridin-7-ylmethyl)thiophene-2-carboxamide;

5-{(1R)-1-[(cyclopropylcarbonyl)amino]-3-methylbutyl}-N-(imidazo[1,2-a]pyridin-7-ylmethyl)thiophene-2-carboxamide;

N-(imidazo[1,2-a]pyridin-7-ylmethyl)-5-{(1R)-3-methyl-1-[(tetrahydrofuran-3-ylacetyl)amino]butyl}thiophene-2-carboxamide;

5-{(1S)-1-[(cyclopropylcarbonyl)amino]-3-methylbutyl}-N-(imidazo[1,2-a]pyridin-7-ylmethyl)thiophene-2-carboxamide;

5-{1-[(4-fluorotetrahydro-2H-pyran-4-yl)methyl]-1H-pyrazol-4-yl}-N-(imidazo[1,2-a]pyridin-7-ylmethyl)thiophene-2-carboxamide;

5-[1-(cyclopropylcarbonyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(4-methylbenzoyl)pyrrolidin-3-yl]thiophene-2-carboxamide;

N-(imidazo[1,2-a]pyrazin-6-ylmethyl)-5-[1-(2-methylpropyl)-1H-pyrazol-4-yl]thiophene-2-carboxamide;

tert-butyl 4-[(4-{5-[(imidazo[1,2-a]pyridin-7-ylmethyl)carbamoyl]thiophen-2-yl}-1H-pyrazol-1-yl)methyl]-4-methylpiperidine-1-carboxylate;

5-[1-(cyclopropylacetyl)pyrrolidin-3-yl]-N-(imidazo[1,2-a]pyridin-7-ylmethyl)thiophene-2-carboxamide;

5-[1-(2-chlorobenzoyl)pyrrolidin-3-yl]-N-(imidazo[1,2-a]pyridin-7-ylmethyl)thiophene-2-carboxamide;

5-{1-[(4-fluorophenyl)acetyl]pyrrolidin-3-yl}-N-(imidazo[1,2-a]pyridin-7-ylmethyl)thiophene-2-carboxamide;

N-(imidazo[1,2-a]pyridin-7-ylmethyl)-5-[1-(3-methoxybenzoyl)pyrrolidin-3-yl]thiophene-2-carboxamide;

N-(imidazo[1,2-a]pyridin-7-ylmethyl)-5-[1-(2-methoxybenzoyl)pyrrolidin-3-yl]thiophene-2-carboxamide;

5-{1-[(3-fluorophenyl)acetyl]pyrrolidin-3-yl}-N-(imidazo[1,2-a]pyridin-7-ylmethyl)thiophene-2-carboxamide;

5-[1-(3-fluorobenzoyl)pyrrolidin-3-yl]-N-(imidazo[1,2-a]pyridin-7-ylmethyl)thiophene-2-carboxamide;

5-[1-(4-fluorobenzoyl)pyrrolidin-3-yl]-N-(imidazo[1,2-a]pyridin-7-ylmethyl)thiophene-2-carboxamide;

5-{1-[(3,5-difluorophenyl)acetyl]pyrrolidin-3-yl}-N-(imidazo[1,2-a]pyridin-7-ylmethyl)thiophene-2-carboxamide;

5-{1-[(2-fluorophenyl)acetyl]pyrrolidin-3-yl}-N-(imidazo[1,2-a]pyridin-7-ylmethyl)thiophene-2-carboxamide;

5-[1-(4-cyanobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(3-methyloxetan-3-yl)carbonyl]pyrrolidin-3-yl }thiophene-2-carboxamide;

5-[1-(3,5-difluorobenzoyl)pyrrolidin-3-yl]-N-(imidazo[1,2-a]pyridin-7-ylmethyl)thiophene-2-carboxamide;

5-[1-(cyclopentylcarbonyl)pyrrolidin-3-yl]-N-(imidazo[1,2-a]pyridin-7-ylmethyl)thiophene-2-carboxamide;

5-[1-(4-chlorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(1-methyl-1H-pyrrol-2-yl)carbonyl]pyrrolidin-3-yl}thiophene-2-carboxamide;

5-[1-(2,4-difluorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(pyridin-4-ylcarbonyl)pyrrolidin-3-yl]thiophene-2-carboxamide;

N-(imidazo[1,2-a]pyridin-7-ylmethyl)-5-[1-(pyridin-2-ylcarbonyl)pyrrolidin-3-yl]thiophene-2-carboxamide;

N-(imidazo[1,2-a]pyridin-7-ylmethyl)-5-{1-[(1-methyl-1H-pyrazol-4-yl)carbonyl]pyrrolidin-3-yl}thiophene-2-carboxamide;

5-[1-(2-fluorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(2E)-2-methylpent-2-enoyl]pyrrolidin-3-yl}thiophene-2-carboxamide;

5-{1-[(2,5-dimethylfuran-3-yl)carbonyl]pyrrolidin-3-yl}-N-(imidazo[1,2-a]pyridin-7-ylmethyl)thiophene-2-carboxamide;

5-[1-(3-chlorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-(1-propanoylpyrrolidin-3-yl)thiophene-2-carboxamide;

5-{1-[(1-cyanocyclopropyl)carbonyl]pyrrolidin-3-yl}-N-(imidazo[1,2-a]pyridin-7-ylmethyl)thiophene-2-carboxamide;

5-(1-butanoylpyrrolidin-3-yl)-N-(imidazo[1,2-a]pyridin-7-ylmethyl)thiophene-2-carboxamide;

5-[1-(furan-2-ylcarbonyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(4-methoxybenzoyl)pyrrolidin-3-yl]thiophene-2-carboxamide;

5-[1-(2,5-difluorobenzoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(thiophen-2-ylcarbonyl)pyrrolidin-3-yl]thiophene-2-carboxamide;

5-[1-(2,2-dimethylpropanoyl)pyrrolidin-3-yl]-N-(imidazo[1,2-a]pyridin-7-ylmethyl)thiophene-2-carboxamide;

5-[1-(3,3-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-{1-[(4-methylpiperidin-4-yl)methyl]-1H-pyrazol-4-yl}thiophene-2-carboxamide;

5-[1-(2,3-dimethylbutanoyl)pyrrolidin-3-yl]-N-(imidazo[1,2-a]pyridin-7-ylmethyl)thiophene-2-carboxamide;

N-(imidazo[1,2-a]pyridin-7-ylmethyl)-5-[1-(pyrazin-2-ylcarbonyl)pyrrolidin-3-yl]thiophene-2-carboxamide;

N-(imidazo[1,2-a]pyridin-7-ylmethyl)-5-{1-[(3-methylthiophen-2-yl)carbonyl]pyrrolidin-3-yl}thiophene-2-carboxamide;

N-(imidazo[1,2-a]pyridin-7-ylmethyl)-5-[1-(2-methylbenzoyl)pyrrolidin-3-yl]thiophene-2-carboxamide;

N-(imidazo[1,2-a]pyridin-7-ylmethyl)-5-{1-[(1-methylcyclopropyl)carbonyl]pyrrolidin-3-yl}thiophene-2-carboxamide;

N-(imidazo[1,2-a]pyridin-7-ylmethyl)-5-[1-(4,4,4-trifluorobutanoyl)pyrrolidin-3-yl]thiophene-2-carboxamide;

5-{1-[(3,5-dimethyl-1,2-oxazol-4-yl)carbonyl]pyrrolidin-3-yl}-N-(imidazo[1,2-a]pyridin-7-ylmethyl)thiophene-2-carboxamide;

N-(imidazo[1,2-a]pyridin-7-ylmethyl)-5-[1-(pyridin-3-ylcarbonyl)pyrrolidin-3-yl]thiophene-2-carboxamide;

N-(imidazo[1,2-a]pyridin-7-ylmethyl)-5-{1-[(1-methyl-1H-pyrazol-5-yl)carbonyl]pyrrolidin-3-yl}thiophene-2-carboxamide;

5-[1-(2,3-dimethylbutanoyl)pyrrolidin-3-yl]-N-(imidazo[1,2-a]pyridin-7-ylmethyl)thiophene-2-carboxamide;

tert-butyl 4-[2-(4-{5-[(imidazo[1,2-a]pyridin-7-ylmethyl)carbamoyl]thiophen-2-yl}-1H-pyrazol-1-yl)ethyl]piperazine-1-carboxylate;

N-(imidazo[1,2-a]pyridin-7-ylmethyl)-5-{1-[2-(piperazin-1-yl)ethyl]-1H-pyrazol-4-yl}thiophene-2-carboxamide;

N-(imidazo[1,2-a]pyridin-7-ylmethyl)-5-{[(2R)-2-(methoxymethyl)pyrrolidin-1-yl]carbonyl}thiophene-2-carboxamide;

N-(imidazo[1,2-a]pyridin-7-ylmethyl)-5-{[2-(2-methylpropyl)pyrrolidin-1-yl]carbonyl}thiophene-2-carboxamide;

5-[1-(2-fluorobenzoyl)piperidin-4-yl]-N-(imidazo[1,2-a]pyrazin-6-ylmethyl)thiophene-2-carboxamide;

5-[1-(4-fluorobenzoyl)piperidin-4-yl]-N-(imidazo[1,2-a]pyrazin-6-ylmethyl)thiophene-2-carboxamide;

5-[1-(2,4-difluorobenzoyl)piperidin-4-yl]-N-(imidazo[1,2-a]pyrazin-6-ylmethyl)thiophene-2-carboxamide;

5-[1-(2,5-difluorobenzoyl)piperidin-4-yl]-N-(imidazo[1,2-a]pyrazin-6-ylmethyl)thiophene-2-carboxamide;

5-[1-(2-fluorobenzoyl)piperidin-4-yl]-N-([1,2,4]triazolo[1,5-a]pyridin-6-ylmethyl)thiophene-2-carboxamide;

5-[1-(3-fluorobenzoyl)piperidin-4-yl]-N-([1,2,4]triazolo[1,5-a]pyridin-6-ylmethyl)thiophene-2-carboxamide;

5-[1-(4-fluorobenzoyl)piperidin-4-yl]-N-([1,2,4]triazolo[1,5-a]pyridin-6-ylmethyl)thiophene-2-carboxamide;

5-[1-(2,4-difluorobenzoyl)piperidin-4-yl]-N-([1,2,4]triazolo[1,5-a]pyridin-6-ylmethyl)thiophene-2-carboxamide;

5-[1-(2,5-difluorobenzoyl)piperidin-4-yl]-N-([1,2,4]triazolo[1,5-a]pyridin-6-ylmethyl)thiophene-2-carboxamide;

5-[1-(3,5-difluorobenzoyl)piperidin-4-yl]-N-([1,2,4]triazolo[1,5-a]pyridin-6-ylmethyl)thiophene-2-carboxamide;

N-(imidazo[1,2-a]pyrazin-6-ylmethyl)-5-[1-(2-methylpropanoyl)piperidin-4-yl]thiophene-2-carboxamide;

N-(imidazo[1,2-a]pyrazin-6-ylmethyl)-5-[1-(3-methylbutanoyl)piperidin-4-yl]thiophene-2-carboxamide;

N-(imidazo[1,2-a]pyrazin-6-ylmethyl)-5-{1-[(1-methylcyclopropyl)carbonyl]piperidin-4-yl}thiophene-2-carboxamide;

N-(imidazo[1,2-a]pyrazin-6-ylmethyl)-5-[1-(4,4-trifluorobutanoyl)piperidin-4-yl]thiophene-2-carboxamide;

N-(imidazo[1,2-a]pyrazin-6-ylmethyl)-5-[1-(tetrahydro-2H-pyran-4-ylcarbonyl)piperidin-4-yl]thiophene-2-carboxamide;

5-[1-(2-methylpropanoyl)piperidin-4-yl]-N-([1,2,4]triazolo[1,5-a]pyridin-6-ylmethyl)thiophene-2-carboxamide;

5-[1-(3-methylbutanoyl)piperidin-4-yl]-N-([1,2,4]triazolo[1,5-a]pyridin-6-ylmethyl)thiophene-2-carboxamide;

5-{1-[(2S)-2-methylbutanoyl]piperidin-4-yl}-N-([1,2,4]triazolo[1,5-a]pyridin-6-ylmethyl)thiophene-2-carboxamide;

5-{1-[(1-methylcyclopropyl)carbonyl]piperidin-4-yl}-N-([1,2,4]triazolo[1,5-a]pyridin-6-ylmethyl)thiophene-2-carboxamide;

N-([1,2,4]triazolo[1,5-a]pyridin-6-ylmethyl)-5-[1-(3,3,3-trifluoropropanoyl)piperidin-4-yl]thiophene-2-carboxamide;

N-([1,2,4]triazolo[1,5-a]pyridin-6-ylmethyl)-5-[1-(4,4,4-trifluorobutanoyl)piperidin-4-yl]thiophene-2-carboxamide;

5-{1-[(4,4-difluorocyclohexyl)carbonyl]piperidin-4-yl}-N-([1,2,4]triazolo[1,5-a]pyridin-6-ylmethyl)thiophene-2-carboxamide;

5-[1-(tetrahydro-2H-pyran-4-ylcarbonyl)piperidin-4-yl]-N-([1,2,4]triazolo[1,5-a]pyridin-6-ylmethyl)thiophene-2-carboxamide;

5-[1-(2-hydroxy-2-methylpropanoyl)piperidin-4-yl]-N-([1,2,4]triazolo[1,5-a]pyridin-6-ylmethyl)thiophene-2-carboxamide;

5-{1-[(1-methylpiperidin-4-yl)carbonyl]piperidin-4-yl}-N-([1,2,4]triazolo[1,5-a]pyridin-6-ylmethyl)thiophene-2-carboxamide;

5-[1-(2-cyanobenzoyl)piperidin-4-yl]-N-([1,2,4]triazolo[1,5-a]pyridin-6-ylmethyl)thiophene-2-carboxamide;

5-[1-(pyridin-2-ylcarbonyl)piperidin-4-yl]-N-([1,2,4]triazolo[1,5-a]pyridin-6-ylmethyl)thiophene-2-carboxamide;

5-(1-benzyl-3-cyclopropyl-1H-pyrazol-5-yl)-N-(imidazo[1,2-a]pyridin-7-ylmethyl)thiophene-2-carboxamide;

5-[1-(2,2-dimethylpropyl)-1H-pyrazo 1-4-yl]-N-(imidazo[1,2-a]pyrazin-6-ylmethyl)thiophene-2-carboxamide;

5-[1-(propan-2-ylsulfonyl)piperidin-4-yl]-N-([1,2,4]triazolo[1,5-a]pyridin-6-ylmethyl)thiophene-2-carboxamide;

5-[1-(phenylsulfonyl)piperidin-4-yl]-N-([1,2,4]triazolo[1,5-a]pyridin-6-ylmethyl)thiophene-2-carboxamide;

N-(imidazo[1,2-a]pyrazin-6-ylmethyl)-5-{1-[(4-methyltetrahydro-2H-pyran-4-yl)methyl]-1H-pyrazol-4-yl}thiophene-2-carboxamide;

N-(imidazo[1,2-a]pyridin-7-ylmethyl)-5-{1-[2-methyl-2-(piperazin-1-yl)propanoyl]piperidin-4-yl}thiophene-2-carboxamide;

5-[1-(2,2-dimethylpropyl)-1H-pyrazol-4-yl]-N-(imidazo[1,2-a]pyridin-7-ylmethyl)thiophene-2-carboxamide;

N-(imidazo[1,2-a]pyridin-7-ylmethyl)-5-[1-(tricyclo[3.3.1.1~3,7~]dec-1-ylmethyl)-1H-pyrazol-4-yl]thiophene-2-carboxamide;

5-(1-benzyl-1H-pyrazol-4-yl)-N-(imidazo[1,2-a]pyridin-7-ylmethyl)thiophene-2-carboxamide;

N-(imidazo[1,2-a]pyridin-7-ylmethyl)-5-[1-(2-oxatricyclo[3.3.1.1~3,7~]dec-1-ylmethyl)-1H-pyrazol-4-yl]thiophene-2-carboxamide;

5-[1-(2,5-difluorobenzoyl)piperidin-4-yl]-N-(imidazo[1,2-a]pyridin-7-ylmethyl)thiophene-2-carboxamide;

5-[1-(2,4-difluorobenzoyl)piperidin-4-yl]-N-(imidazo[1,2-a]pyridin-7-ylmethyl)thiophene-2-carboxamide;

5-(3-cyclopropyl-1-methyl-1H-pyrazol-5-yl)-N-(imidazo[1,2-a]pyridin-7-ylmethyl)thiophene-2-carboxamide;

5-[3-cyclopropyl-1-(2-methoxyethyl)-1H-pyrazol-5-yl]-N-(imidazo[1,2-a]pyridin-7-ylmethyl)thiophene-2-carboxamide;

N-(imidazo[1,2-a]pyrazin-6-ylmethyl)-5-{1-[2-(piperazin-1-yl)ethyl]-1H-pyrazol-4-yl}thiophene-2-carboxamide;

N-(imidazo[1,2-a]pyridin-7-ylmethyl)-5-[(2-methylpropyl)-1H-pyrazol-5-yl]thiophene-2-carboxamide;

N-(imidazo[1,2-a]pyridin-7-ylmethyl)-5-[1-methyl-3-(2-methylpropyl)-1H-pyrazol-5-yl]thiophene-2-carboxamide;

5-[1-benzyl-3-(2-methylpropyl)-1H-pyrazol-5-yl]-N-(imidazo[1,2-a]pyridin-7-ylmethyl)thiophene-2-carboxamide;

N-[(7-fluoroimidazo[1,2-a]pyridin-6-yl)methyl]-5-[1-(2-methylpropyl)-1H-pyrazol-4-yl]thiophene-2-carboxamide;

5-{1-[2,2-dimethyl-3-(piperazin-1-yl)propyl]-1H-pyrazol-4-yl}-N-(imidazo[1,2-a]pyridin-7-ylmethyl)thiophene-2-carboxamide;

5-[1-(3-amino-2,2-dimethylpropyl)-1H-pyrazol-4-yl]-N-(imidazo[1,2-a]pyridin-7-ylmethyl)thiophene-2-carboxamide;

and pharmaceutically acceptable salts thereof.

12. The compound of claim 1, which is N-(imidazo[1,2-a]pyridin-6-ylmethyl)-2-{[3-(1,2-oxazol-5-yl)propanoyl](tetrahydrofuran-2-ylmethyl)amino}-1,3-thiazole-5-carboxamide, or a pharmaceutically acceptable salt thereof.

13. The compound of claim 1, which is N-(imidazo[1,2-a]pyridin-7-ylmethyl)-5-{1-[(1-methyl-1H-pyrazol-5-yl)carbonyl]pyrrolidin-3-yl}thiophene-2-carboxamide, or a pharmaceutically acceptable salt thereof.

14. The compound of claim 1, which is N-(imidazo[1,2-a]pyridin-7-ylmethyl)-5-{1-[(4-methylpiperidin-4-yl)methyl]-1H-pyrazol-4-yl}thiophene-2-carboxamide, or a pharmaceutically acceptable salt thereof.

15. The compound of claim 1, which is 2-{[(3,5-dimethyl-1,2-oxazol-4-yl)acetyl][(2R)-tetrahydrofuran-2-ylmethyl]amino}-N-(imidazo[1,2-a]pyridin-7-ylmethyl)-1,3-thiazole-5-carboxamide, or a pharmaceutically acceptable salt thereof.

16. The compound of claim 1, which is 5-[1-(3,5-difluorobenzoyl)piperidin-4-yl]-N-([1,2,4]triazolo[1,5-a]pyridin-6-ylmethyl)thiophene-2-carboxamide, or a pharmaceutically acceptable salt thereof.

17. The compound of claim 1, which is N-(imidazo[1,2-a]pyridin-7-ylmethyl)-5-[1-(tetrahydrofuran-2-ylmethyl)-1H-pyrazol-4-yl]thiophene-2-carboxamide, or a pharmaceutically acceptable salt thereof.

18. The compound of claim 1, which is N-(imidazo[1,2-a]pyridin-7-ylmethyl)-5-{1-[(2-methylpropyl)sulfonyl]piperidin-4-yl}thiophene-2-carboxamide or a pharmaceutically acceptable salt thereof.

\* \* \* \* \*